United States Patent
Kotian et al.

(10) Patent No.: US 11,559,515 B2
(45) Date of Patent: Jan. 24, 2023

(54) INDOLE COMPOUNDS AND ANALOGUES THEREOF

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); Weihe Zhang, Vestavia Hills, AL (US); Lakshminarayana Vogeti, Lawrence, KS (US); Minwan Wu, Vestavia Hills, AL (US); Venkat R. Chintareddy, Vestavia Hills, AL (US); Krishnan Raman, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 17/003,552

(22) Filed: Aug. 26, 2020

(65) Prior Publication Data
US 2021/0260035 A1 Aug. 26, 2021

Related U.S. Application Data

(63) Continuation of application No. 16/073,934, filed as application No. PCT/US2017/015953 on Feb. 1, 2017, now Pat. No. 10,849,883.

(Continued)

(51) Int. Cl.
| | |
|---|---|
| C07D 401/14 | (2006.01) |
| A61K 31/416 | (2006.01) |
| C07D 231/56 | (2006.01) |
| C07D 403/04 | (2006.01) |
| C07D 209/42 | (2006.01) |
| C07D 209/12 | (2006.01) |
| C07D 403/06 | (2006.01) |
| C07D 403/12 | (2006.01) |
| C07D 401/06 | (2006.01) |
| C07D 487/04 | (2006.01) |
| C07D 209/48 | (2006.01) |
| C07D 209/40 | (2006.01) |
| C07D 401/04 | (2006.01) |
| C07D 471/04 | (2006.01) |
| C07D 401/12 | (2006.01) |
| C07D 405/12 | (2006.01) |
| A61P 13/10 | (2006.01) |
| C07D 209/30 | (2006.01) |

(Continued)

(52) U.S. Cl.
CPC .............. *A61K 31/416* (2013.01); *A61P 9/00* (2018.01); *A61P 13/00* (2018.01); *A61P 13/10* (2018.01); *A61P 21/04* (2018.01); *A61P 25/28* (2018.01); *A61P 37/06* (2018.01); *C07D 209/12* (2013.01); *C07D 209/30* (2013.01); *C07D 209/40* (2013.01); *C07D 209/42* (2013.01); *C07D 209/48* (2013.01); *C07D 231/56* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01); *C07D 405/12* (2013.01); *C07D 471/04* (2013.01); *C07D 487/04* (2013.01)

(58) Field of Classification Search
CPC .... C07D 209/30; C07D 401/04; C07D 41/06; C07D 401/14; C07D 403/04; C07D 403/06; C07D 403/12; A61K 31/404; A61K 31/4155; A61K 31/4439; A61K 31/454; A61K 31/501; A61K 31/506
See application file for complete search history.

(56) References Cited

U.S. PATENT DOCUMENTS

| 10,849,883 B2 | 12/2020 | Kotian et al. |
| 2002/0151540 A1 | 10/2002 | Lai et al. |

(Continued)

FOREIGN PATENT DOCUMENTS

| CA | 2872000 A1 | 11/2013 |
| CA | 2882724 A1 | 1/2014 |

(Continued)

OTHER PUBLICATIONS

Abdel-Rahman et al., "Amino Acid Derivatives, VII [1]: Synthesis and Antiviral Evaluation of a-Amino Acid Esters Bearing an Indazole Side Chain," Monatshefte Fuer Chemie, 139(3):289-297 (2008).
Brogan et al., "Organization of a small molecule probe that restores e-cadherin expression," Bioorganic and Medical Chemistry Letters, 25: 4260-4264 (2015).

(Continued)

*Primary Examiner* — Jeffrey H Murray
(74) *Attorney, Agent, or Firm* — Dana M. Gordon; Laura A. Wzorek; Foley Hoag LLP

(57) ABSTRACT

Disclosed are compounds of formula I, and pharmaceutically acceptable salts thereof. The compounds are inhibitors of the complement system. Also provided are pharmaceutical compositions comprising a compound of formula I, and methods involving use of the compounds and compositions in the treatment and prevention of diseases and conditions characterized by aberrant complement system activity.

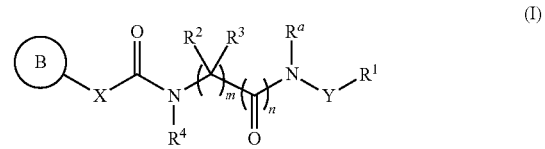

19 Claims, No Drawings

Related U.S. Application Data

(60) Provisional application No. 62/289,653, filed on Feb. 1, 2016.

(51) Int. Cl.
  *A61P 21/04* (2006.01)
  *A61P 25/28* (2006.01)
  *A61P 9/00* (2006.01)
  *A61P 37/06* (2006.01)
  *A61P 13/00* (2006.01)

(56) References Cited

U.S. PATENT DOCUMENTS

| | | |
|---|---|---|
| 2014/0275080 A1 | 9/2014 | Flynn et al. |
| 2015/0105367 A1 | 4/2015 | Flynn et al. |
| 2018/0179185 A1 | 6/2018 | Wiles et al. |
| 2018/0179186 A1 | 6/2018 | Wiles et al. |
| 2018/0186782 A1 | 7/2018 | Wiles et al. |
| 2018/0201580 A1 | 7/2018 | Wiles et al. |

FOREIGN PATENT DOCUMENTS

| | | | |
|---|---|---|---|
| JP | 2005/516979 A | 6/2005 | |
| JP | 2007/8914 A | 1/2007 | |
| WO | WO-1995/022524 A1 | 8/1995 | |
| WO | WO-9811066 A1 | 3/1998 | |
| WO | WO-1998009957 A1 | 3/1998 | |
| WO | WO-2001038584 A2 | 5/2001 | |
| WO | WO-2004/065353 A1 | 8/2004 | |
| WO | WO-2004/087743 A2 | 10/2004 | |
| WO | WO2007115231 * | 11/2007 | ........... C07K 14/715 |
| WO | WO-2009/106980 A2 | 9/2009 | |
| WO | WO-2010/045580 A1 | 4/2010 | |
| WO | WO-2012/065062 A1 | 5/2012 | |
| WO | WO-2012093101 A1 | 7/2012 | |
| WO | WO-2014002051 A2 | 1/2014 | |
| WO | WO-2014002058 A2 | 1/2014 | |
| WO | WO-2015/002230 A1 | 1/2015 | |
| WO | WO-2015/130854 A1 | 9/2015 | |
| WO | WO-2016/205010 A1 | 12/2016 | |
| WO | WO-2017/035411 A1 | 3/2017 | |
| WO | WO-2017/035413 A2 | 3/2017 | |
| WO | WO-2017/035415 A1 | 3/2017 | |
| WO | WO-2017/035418 A1 | 3/2017 | |

OTHER PUBLICATIONS

CAS Registry Nos. 1299415-01-2; 1299253-94-3; 1216606-76-6; 1211085-00-5; 1210941-98-2; 924192-99-4.

Chen et al., "Methyl Pyropheophorbide-a Analogues: Potential Fluorescent Probes for the Peripheral-Type Benzodiazepine Receptor. Effect of Central Metal in Photosensitizing Efficacy," Journal of Medicinal Chemistry 48: 3692-3695 (2005).

Extended European Search Report for EP Application No. 17748044.9 dated Jul. 30, 2019.

Hays, "Trapping of peptide-based surrogates in an artificially created channel of cytochrome c peroxidase," Protein Science, 12(2):278-287 (2003).

International Preliminary Search Report on Patentability for International Application No. PCT/US2017/015953 dated Aug. 7, 2018.

International Search Report and Written Opinion for International Application No. PCT/US2017/015953 dated May 18, 2017.

Martin et al., "Effect of heterocyclic capping groups on the self-assembly of a dipeptide hydrogel," Soft Matter, 12(10):2700-2707 (2016).

Paul et al., "Regioselective solid-phase synthesis of N-mono-hydroxylated and N-mono-methylated acylpolyamine spider toxins using an 2-(ortho-nitrophenyl) ethanal-modified resin," Organic and Biomolecular Chemistry, 13: 4473-4485 (2015).

PubChem: Substance Record for SID: 115755424, (Mar. 28, 2011).

Written Opinion from the Intellectual Property Office of Singapore for International Application No. 11201805940Q dated Sep. 10, 2019.

Extended European Search Report for EP Application No. 21173901.6 dated Nov. 18, 2021.

* cited by examiner

INDOLE COMPOUNDS AND ANALOGUES THEREOF

CROSS-REFERENCES TO RELATED APPLICATIONS

This application is a continuation of U.S. application Ser. No. 16/073,934, filed Jul. 30, 2018; which is the U.S. national stage of International Patent Application No. PCT/US2017/015953, filed Feb. 1, 2017; which claims the benefit of priority to U.S. Provisional Patent Application Ser. No. 62/289,653, filed Feb. 1, 2016.

BACKGROUND OF THE INVENTION

The complement system is a branch of an organism's immune system that enhances the ability of antibodies and phagocytic cells to destroy and remove foreign particles (e.g., pathogens) from the organism. The complement system comprises a set of plasma proteins that act together to attack extracellular forms of pathogens and induce a series of inflammatory responses to help fight infection. Complement activation can occur through several pathways. For example, complement activation can occur spontaneously in response to certain pathogens or by antibody binding to a pathogen. When complement proteins are activated a cascade is triggered by which one complement protein induces the activation of the next protein in the sequence. The activation of a small number of complement proteins at the start of the pathway is hugely amplified by each successive enzymatic reaction, resulting in the rapid generation of a disproportionately large complement response. (Marrides, S. *Pharmacological Reviews* 1998, Vol. 50, pages 59-88). In healthy organisms there are regulatory mechanisms to prevent uncontrolled complement activation.

When activated, complement proteins can bind to a pathogen, opsonizing them for engulfment by phagocytes bearing receptors for complement. Then, small fragments of some complement proteins act as chemoattractants to recruit more phagocytes to the site of complement activation, and also to activate these phagocytes. Next, the complement proteins create holes or pores in the invading organisms, leading to their destruction. While complement plays an important role in protecting the body from foreign organisms, it can also destroy healthy cells and tissue. The inappropriate activation of complement is implicated in a long list of disease pathologies (Morgan, B. *Eur J Clin Invest* 1994, Vol. 24, pages 219-228) affecting the immune, renal, cardiovascular, and neurological systems.

SUMMARY OF THE INVENTION

In certain aspects, the invention provides compounds of formula (I), and pharmaceutically acceptable salts thereof:

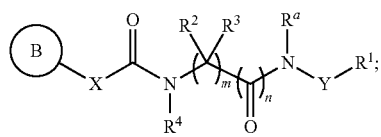

wherein, independently for each occurrence:
$R^1$ represents optionally substituted aryl, heteroaryl, cycloalkyl, heterocycloalkyl, alkyl, or alkenyl;
$R^2$ and $R^3$ each independently represent H, F, or optionally substituted alkyl, alkenyl, alkynyl, alkoxyalkyl, haloalkyl, hydroxyalkyl, (alkylthio)alkyl, aralkyl, heteroaralkyl, cycloalkyl, (cycloalkyl)alkyl, heterocycloalkyl, or (heterocycloalkyl)alkyl;
or $R^2$ and $R^3$, taken together with the carbon atom to which they are bonded, form an optionally substituted cycloalkyl or heterocycloalkyl ring;
$R^4$ represents H or optionally substituted alkyl, alkenyl, alkynyl, cycloalkyl, (cycloalkyl)alkyl, heterocycloalkyl, (heterocycloalkyl)alkyl, aralkyl, heteroaralkyl, hydroxyalkyl, or haloalkyl;
X represents NH, $CH_2$, CHF, $CF_2$, $CH(C_1-C_6)$alkyl, or $C((C_1-C_6)alkyl)_2$;
Y is absent or represents $CH_2$, C(O), $CR^{15}R^{16}$, $S(O)_2$, or optionally substituted $(C_3-C_7)$cycloalkylene, arylene, or heteroarylene;
$R^a$ represents H or optionally substituted $(C_1-C_6)$alkyl, (heterocycloalkyl)alkyl, or $(C_3-C_7)$cycloalkyl;
m is an integer from 1-6;
n is 0 or 1;
$R^{15}$ and $R^{16}$ are each independently selected from the group consisting of H, hydroxy, halogen, $-C(O)OR^{17}$, $-C(O)NR^{17}R^{18}$, $-NR^{17}R^{18}$, alkyl, hydroxyalkyl, haloalkyl, alkoxyalkyl, aryl, aralkyl, heteroaryl, heteroaralkyl, cycloalkyl, (cycloalkyl)alkyl, heterocycloalkyl, and (heterocycloalkyl)alkyl, wherein alkyl, aryl, aralkyl, heteroaryl, heteroaralkyl, cycloalkyl, (cycloalkyl)alkyl, heterocycloalkyl, and (heterocycloalky-l)alkyl are optionally substituted with one or more substituents selected from the group consisting of $-CN$, $-OR^{17}$, $-NR^{17}R^{18}$, halo, and alkyl;
or $R^{15}$ and $R^{16}$ may be taken together with the intervening atom to form an optionally substituted carbocyclic or heterocyclic ring;
$R^{17}$ and $R^{18}$ are each independently selected from the group consisting of H, alkyl, haloalkyl, hydroxyalkyl, alkoxyalkyl, aryl, aralkyl, heteroaryl, heteroaralkyl, cycloalkyl, (cycloalkyl)alkyl, heterocycloalkyl, and (heterocycloalkyl)alkyl;
or $R^{17}$ and $R^{18}$, when attached to the same atom, may be taken together with the intervening atom to form an optionally substituted heterocyclic ring;

Ⓑ represents

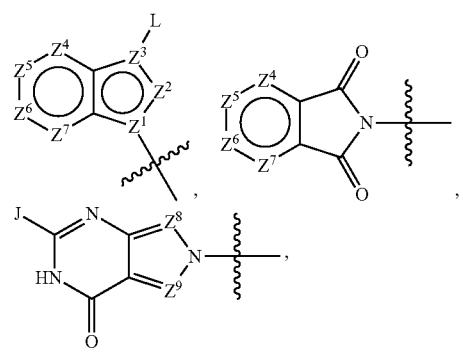

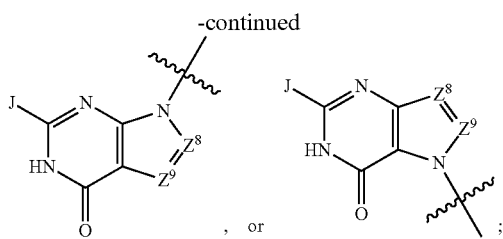
, or ;

$Z^1$ and $Z^3$ each independently represent C or N;

$Z^2$ represents N, CH, or CF;

$Z^4$ represents N or $CR^8$;

$Z^5$ represents N or $CR^5$;

$Z^6$ represents N or $CR^6$;

$Z^7$ represents N or $CR^9$;

$Z^8$ and $Z^9$ each independently represent N or $CR^{19}$;

$R^5$ and $R^6$ each independently represent H, halogen, —CN, —NO$_2$, —OR$^{13}$, —NR$^{13}$R$^{14}$, —C(O)R$^{13}$, —C(O)OR$^{13}$, —C(O)NR$^{13}$R$^{14}$, —OC(O)R$^{13}$, —NR$^{13}$C(O)R$^{14}$, —OC(O)NR$^{13}$R$^{14}$, —OC(O)OR$^{13}$, —NR$^{13}$C(O)OR$^{14}$, —NR$^{13}$C(O)NR$^{13}$R$^{14}$, —OS(O)$_p$(R$^{13}$), —NR$^{13}$S(O)$_p$(R$^{14}$), or optionally substituted alkyl, alkenyl, alkynyl, haloalkyl, aralkyl, heteroaralkyl, heteroaryl, aryl, cycloalkyl, (cycloalkyl)alkyl, heterocycloalkyl, or (heterocycloalkyl)alkyl;

L represents —H, —CN, —C(O)R$^7$, —CH(OH)R$^7$, or —S(O)$_p$(alkyl);

$R^7$, independently for each occurrence, represents H, NH$_2$, CH$_3$, OH, CF$_3$, CH$_2$OH, (C$_1$-C$_6$)alkyl, hydroxy (C$_1$-C$_6$)alkyl, (C$_1$-C$_6$)alkoxy(C$_1$-C$_6$)alkyl, halo(C$_1$-C$_6$) alkyl, NH(C$_1$-C$_6$)alkyl, N((C$_1$-C$_6$)alkyl)$_2$;

$R^8$ and $R^9$ each independently represent H, halogen, —OR$^{13}$, —NR$^{13}$R$^{14}$, —C(O)R$^{13}$, —C(O)OR$^{13}$, —C(O)NR$^{13}$R$^{14}$, —OC(O)R$^{13}$, —NR$^{13}$C(O)R$^{14}$, —OC(O)NR$^{13}$R$^{14}$, —OC(O)OR$^{13}$, —NR$^{13}$C(O)OR$^{14}$, —NR$^{13}$C(O)NR$^{13}$R$^{14}$, —OS(O)$_p$(R$^{13}$), —NR$^{13}$S(O)$_p$(R$^{14}$), or optionally substituted alkyl, alkenyl, alkynyl, haloalkyl, aralkyl, heteroaralkyl, heteroaryl, or aryl;

or $R^5$ and $R^8$, or $R^5$ and $R^6$, or $R^6$ and $R^9$ may be taken together with the intervening atoms to form an optionally substituted heterocyclic or carbocyclic ring;

$R^{13}$ and $R^{14}$, independently for each occurrence, represent H or optionally substituted alkyl, alkenyl, alkynyl, aryl, aralkyl, heteroaryl, heteroaralkyl, cycloalkyl, (cycloalkyl)alkyl, heterocycloalkyl, or (heterocycloalkyl)alkyl; or, when $R^{13}$ and RH are attached to the same atom, $R^{13}$ and $R^{14}$ taken together with the atom may form an optionally substituted heterocyclic ring;

$R^{19}$, independently for each occurrence, represents H, F, CN, —C(O)R$^7$, —CH(OH)R$^7$, or S(O)$_p$(alkyl);

J represents H or NH$_2$; and p is 0, 1, or 2;

wherein, if $Z^1$ is N, or if

Ⓑ represents

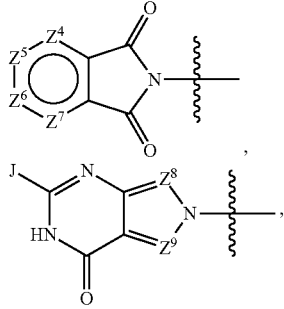
,

,

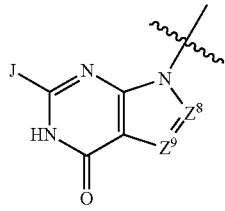
, or

, then X represents CH$_2$.

In certain aspects, the invention provides a pharmaceutical composition, comprising a compound of the invention, or a pharmaceutically acceptable salt thereof; and a pharmaceutically acceptable carrier.

In certain aspects, the invention provides a method of treating or preventing a disease or condition characterized by aberrant complement system activity. The method comprises the step of administering to a subject in need thereof a therapeutically effective amount of a compound of the invention, or a pharmaceutically acceptable salt thereof, thereby treating or preventing the disease or condition characterized by aberrant complement system activity. In certain embodiments, the disease or condition characterized by aberrant complement system activity is an immunological disorder. In certain embodiments, the disease or condition characterized by aberrant complement system activity is a disease of the central nervous system. In certain embodiments, the disease or condition characterized by aberrant complement system activity is a neurodegenerative disease or neurological disease. In certain embodiments, the disease or condition characterized by aberrant complement system activity is a renal disease. In certain embodiments, the disease or condition characterized by aberrant complement system activity is a cardiovascular disease. In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

DETAILED DESCRIPTION

Inhibitors of the complement system have been reported and are useful in therapeutic methods and compositions suitable for use in treating or preventing various immunological disorders, eurodegenerative diseases, and diseases of the central nervous system. Provided herein are compounds of formula (I) that are useful treating or preventing a disease or condition characterized by aberrant complement system activity.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, isobutyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of cycloalkylalkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulthydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflouromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

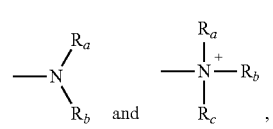

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; Rd represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$.

In certain embodiments, the term "amino" refers to $NH_2$.

In certain embodiments, the term "alkylamino" refers to —NH(alkyl).

In certain embodiments, the term "dialkylamino" refers to —N(alkyl)$_2$.

The term "amido", as used herein, means —NHC(=O)—, wherein the amido group is bound to the parent molecular moiety through the nitrogen. Examples of amido include alkylamido such as $CH_3C$(=O)N(H)— and $CH_3CH_2C$(=O)N(H)—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

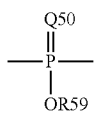

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

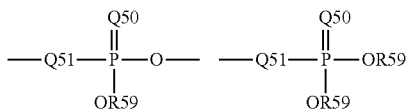

wherein Q50 and R59, each independently, are defined above, and Q51 represents 0, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an N3 group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurom-ethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to CN.

The term "halo" is a term of art and as used herein refers to F, Cl, —Br, or I.

The term "haloalkyl" as used herein refers to an alkyl group, as defined herein, wherein some or all of the hydrogens are replaced with halogen atoms.

The term "hydroxy" is a term of art and as used herein refers to OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si-$) group (i.e., (hydrocarbyl)$_3Si$), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2nd ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's Pharmaceutical Sciences by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds of Formula (I), or pharmaceutically acceptable salts thereof:

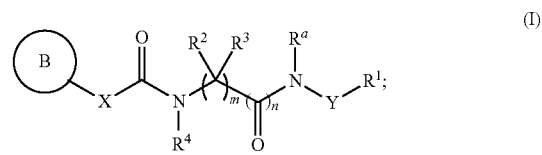

wherein, independently for each occurrence:

$R^1$ represents optionally substituted aryl, heteroaryl, cycloalkyl, heterocycloalkyl, alkyl, or alkenyl;

$R^2$ and $R^3$ each independently represent H, F, or optionally substituted alkyl, alkenyl, alkynyl, alkoxyalkyl, haloalkyl, hydroxyalkyl, (alkylthio)alkyl, aralkyl, heteroaralkyl, cycloalkyl, (cycloalkyl)alkyl, heterocycloalkyl, or (heterocycloalkyl)alkyl;

or $R^2$ and $R^3$, taken together with the carbon atom to which they are bonded, form an optionally substituted cycloalkyl or heterocycloalkyl ring;

$R^4$ represents H or optionally substituted alkyl, alkenyl, alkynyl, cycloalkyl, (cycloalkyl)alkyl, heterocycloalkyl, (heterocycloalkyl)alkyl, aralkyl, heteroaralkyl, hydroxyalkyl, or haloalkyl;

X represents NH, $CH_2$, CHF, $CF_2$, $CH(C_1-C_6)$alkyl, or $C((C_1-C_6)$alkyl$)_2$;

Y is absent or represents $CH_2$, C(O), $CR^{15}R^{16}$, $S(O)_2$, or optionally substituted $(C_3-C_7)$cycloalkylene, arylene, or heteroarylene;

$R^a$ represents H or optionally substituted $(C_1-C_6)$alkyl, (heterocycloalkyl)alkyl, or $(C_3-C_7)$cycloalkyl;

m is an integer from 1-6;

n is 0 or 1;

$R^{15}$ and $R^{16}$ are each independently selected from the group consisting of H, hydroxy, halogen, —C(O)$OR^{17}$, —$OR^{17}$, —C(O)$NR^{17}R^{18}$, —$NR^{17}R^{18}$, alkyl, hydroxyalkyl, haloalkyl, alkoxyalkyl, aryl, aralkyl, heteroaryl, heteroaralkyl, cycloalkyl, (cycloalkyl)alkyl, heterocycloalkyl, and (heterocycloalkyl)alkyl, wherein alkyl, aryl, aralkyl, heteroaryl, heteroaralkyl, cycloalkyl, (cycloalkyl)alkyl, heterocycloalkyl, and (heterocycloalkyl)alkyl are optionally substituted with one or more substituents selected from the group consisting of —CN, —$OR^{17}$, —$NR^{17}R^{18}$, halo, and alkyl;

or $R^{15}$ and $R^{16}$ may be taken together with the intervening atom to form an optionally substituted carbocyclic or heterocyclic ring;

$R^{17}$ and $R^{18}$ are each independently selected from the group consisting of H, alkyl, haloalkyl, hydroxyalkyl, alkoxyalkyl, aryl, aralkyl, heteroaryl, heteroaralkyl, cycloalkyl, (cycloalkyl)alkyl, heterocycloalkyl, and (heterocycloalkyl)alkyl;

or $R^{17}$ and $R^{18}$, when attached to the same atom, may be taken together with the intervening atom to form an optionally substituted heterocyclic ring;

represents

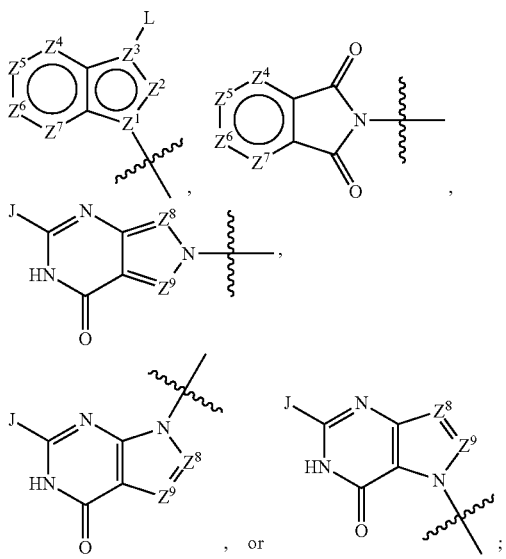

Z¹ and Z³ each independently represent C or N;
Z² represents N, CH, or CF;
$Z^4$ represents N or $CR^8$;
$Z^5$ represents N or $CR^5$;
$Z^6$ represents N or $CR^6$;
$Z^7$ represents N or $CR^9$;
$Z^8$ and $Z^9$ each independently represent N or $CR^{19}$;
$R^5$ and $R^6$ each independently represent H, halogen, —CN, —NO$_2$, —OR$^{13}$, —NR$^{13}$R$^{14}$, —C(O)R$^{13}$, —C(O)OR$^{13}$, —C(O)NR$^{13}$R$^{14}$, —OC(O)R$^{13}$, —NR$^{13}$C(O)R$^{14}$, —OC(O)NR$^{13}$R$^{14}$, —OC(O)OR$^{13}$, —NR$^{13}$C(O)OR$^{14}$, —NR$^{13}$C(O)NR$^{13}$R$^{14}$, —OS(O)$_p$(R$^{13}$), —NR$^{13}$S(O)$_p$(R$^{14}$), or optionally substituted alkyl, alkenyl, alkynyl, haloalkyl, aralkyl, heteroaralkyl, heteroaryl, aryl, cycloalkyl, (cycloalkyl)alkyl, heterocycloalkyl, or (heterocycloalkyl)alkyl;
L represents —H, —CNc, —C(O)R$^7$, —CH(OH)R$^7$, or —S(O)$_p$(alkyl);
$R^7$, independently for each occurrence, represents H, NH$_2$, CH$_3$, OH, CF$_3$, CH$_2$OH, (C$_1$-C$_6$)alkyl, hydroxy(C$_1$-C$_6$)alkyl, (C$_1$-C$_6$)alkoxy(C$_1$-C$_6$)alkyl, halo(C$_1$-C$_6$)alkyl, NH(C$_1$-C$_6$)alkyl, N((C$_1$-C$_6$)alkyl)$_2$;
$R^8$ and $R^9$ each independently represent H, halogen, —OR$^{13}$, —NR$^{13}$R$^{14}$, —C(O)R$^{13}$, —C(O)OR$^{13}$, —C(O)NR$^{13}$R$^{14}$, —OC(O)R$^{13}$, —NR$^{13}$C(O)R$^{14}$, —OC(O)NR$^{13}$R$^{14}$, —OC(O)OR$^{13}$, —NR$^{13}$C(O)OR$^{14}$, —NR$^{13}$C(O)NR$^{13}$R$^{14}$, —OS(O)$_p$(R$^{13}$), —NR$^{13}$S(O)$_p$(R$^{14}$), or optionally substituted alkyl, alkenyl, alkynyl, haloalkyl, aralkyl, heteroaralkyl, heteroaryl, or aryl;
or $R^5$ and $R^8$, or $R^5$ and $R^6$, or $R^6$ and $R^9$ may be taken together with the intervening atoms to form an optionally substituted heterocyclic or carbocyclic ring;
$R^{13}$ and $R^{14}$, independently for each occurrence, represent H or optionally substituted alkyl, alkenyl, alkynyl, aryl, aralkyl, heteroaryl, heteroaralkyl, cycloalkyl, (cycloalkyl)alkyl, heterocycloalkyl, or (heterocycloalkyl)alkyl; or, when $R^{13}$ and $R^{14}$ are attached to the same atom, $R^{13}$ and $R^{14}$ taken together with the atom may form an optionally substituted heterocyclic ring;
$R^{19}$, independently for each occurrence, represents H, F, CN, —C(O)R$^7$, —CH(OH)R$^7$, or —S(O)$_p$(alkyl);
J represents H or NH$_2$; and
p is 0, 1, or 2;
wherein, if $Z^1$ is N, or if

represents

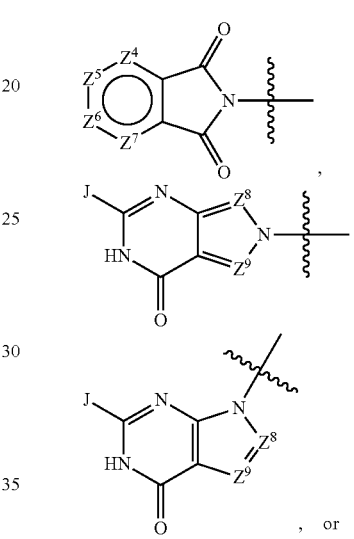

then X represents CH$_2$.

In preferred embodiments, n is 1.

In certain embodiments, $R^1$ represents aryl or heteroaryl, optionally substituted by one or more substituents independently selected from the group consisting of halogen, —CN, alkoxy, haloalkoxy, alkyl, haloalkyl, alkenyl, dialkylamino, heterocycloalkyl, aryl, and heteroaryl.

In certain embodiments, $R^1$ represents aryl or heteroaryl, optionally substituted by one or more substituents independently selected from the group consisting of halogen, alkoxy, haloalkoxy, alkyl, haloalkyl, alkenyl, dialkylamino, aryl, and heteroaryl.

In embodiments in which $R^1$ represents aryl or heteroaryl substituted by one or more substituents including an aryl or heteroaryl substituent, the aryl or heteroaryl substituent may be further substituted by one or more substituents selected from the group consisting of alkyl and halogen.

In certain embodiments, $R^1$ represents aryl or heteroaryl, optionally substituted by one or more substituents independently selected from the group consisting of halogen, alkoxy, haloalkoxy, alkyl, haloalkyl, alkenyl, and dialkylamino.

In certain embodiments, $R^1$ represents aryl or heteroaryl, substituted by one or more substituents, at least one of which is halogen. For example, $R^1$ may represent phenyl, substituted by a chloro and a fluoro group.

In other embodiments, $R^1$ represents phenyl, pyridinyl, pyrazinyl, or pyrimidinyl, optionally substituted by one or more substituents selected from the group consisting of halogen, alkoxy (e.g., methoxy), haloalkoxy (e.g., trifluoromethoxy), alkyl (e.g., methyl), haloalkyl (e.g., trifluoromethyl), alkenyl (e.g., vinyl), and dialkylamino (e.g., dimethylamino).

In alternative embodiments, $R^1$ is optionally substituted alkyl or alkenyl. For example, $R^1$ may be $(C_1-C_6)$alkyl or $(C_2-C_6)$alkenyl, optionally substituted by halogen, hydroxy, alkoxy, or haloalkoxy.

In other embodiments, $R^1$ is optionally substituted cycloalkyl or heterocycloalkyl. For example, $R^1$ may be cycloalkyl or heterocycloalkyl, optionally substituted by one or more substituents selected from the group consisting of halo, hydroxy, $(C_1-C_6)$alkyl, $(C_1-C_6)$alkoxy, and halo$(C_1-C_6)$alkyl. In some embodiments, $R^1$ is a heterocycloalkyl that is fused at two adjacent positions to an aryl or heteroaryl ring (e.g., a tetrahydroquinolinyl group).

In certain embodiments, $R^1$ is optionally substituted heteroaryl and Y is absent; or, $R^1$ is optionally substituted aryl and Y is $CH_2$.

In certain embodiments, Y is absent or represents $CH_2$.

In certain embodiments, Y is absent. Alternatively, Y is $CH_2$.

Alternatively, Y can be optionally substituted $(C_3-C_7)$cycloalkylene. For example, Y can be cyclopropylene substituted by fluoro.

In other alternative embodiments, Y can be optionally substituted arylene or heteroarylene. For example, Y can be phenylene or pyridinylene, optionally substituted by halo or alkyl.

In alternative embodiments, Y is $CR^{15}R^{16}$. In certain such embodiments, $R^{15}$ and $R^{16}$ are selected from the group consisting of H, alkyl, hydroxyalkyl, haloalkyl, alkoxyalkyl, aralkyl, heteroaralkyl, (cycloalkyl)alkyl, and (heterocycloalkyl)alkyl, wherein alkyl, aryl, aralkyl, heteroaryl, heteroaralkyl, cycloalkyl, (cycloalkyl)alkyl, heterocycloalkyl, and (heterocycloalkyl)alkyl are optionally substituted with one or more substituents selected from the group consisting of —CN, —$OR^{17}$, —$NR^{17}R^{18}$, halo, and alkyl, and further wherein $R^{17}$ and $R^{18}$ are each independently selected from the group consisting of H and alkyl.

Alternatively, Y is $CR^{15}R^{16}$ and $R^{15}$ and $R^{16}$ are taken together with the intervening atom to form an optionally substituted carbocyclic or heterocyclic ring, e.g., a cyclopropyl ring.

In certain embodiments, Y represents $CH(C_1-C_6)$alkyl. Alternatively, Y represents $CH(C_1-C_6)$alkyl, wherein the $(C_1-C_6)$alkyl is substituted by hydroxy, alkoxy, or di(alkyl)amino.

In certain embodiments, $R^2$ and $R^3$ each independently represent H or optionally substituted alkyl, alkenyl, alkynyl, alkoxyalkyl, haloalkyl, hydroxyalkyl, (alkylthio)alkyl, aralkyl, heteroaralkyl, cycloalkyl, (cycloalkyl)alkyl, heterocycloalkyl, or (heterocycloalkyl)alkyl.

In certain embodiments, $R^2$ is H and $R^3$ represents H or optionally substituted alkyl, alkoxyalkyl, hydroxyalkyl, (alkylthio)alkyl, aralkyl, heteroaralkyl, cycloalkyl, or (cycloalkyl)alkyl.

In certain embodiments, both $R^2$ and $R^3$ represent H.

Alternatively, both $R^2$ and $R^3$ may represent alkyl, e.g., methyl.

In further embodiments, $R^2$ and $R^3$, taken together with the intervening atom, form an optionally substituted carbocyclic or heterocyclic ring.

In certain embodiments, $R^4$ represents H or optionally substituted alkyl, cycloalkyl, (cycloalkyl)alkyl, heterocycloalkyl, aralkyl, hydroxyalkyl, or haloalkyl; preferably $R^4$ represents H or optionally substituted alkyl or cycloalkyl.

In certain embodiments, $R^4$ represents H or alkyl, alkenyl, alkynyl, cycloalkyl, (cycloalkyl)alkyl, heterocycloalkyl, (heterocycloalkyl)alkyl, aralkyl, heteroaralkyl, hydroxyalkyl, or haloalkyl, each optionally substituted by one or more substituents independently selected from the group consisting of halo, alkoxy, alkyl, hydroxy, hydroxyalkyl, haloalkyl, $NH_2$, —NH(alkyl), —N(alkyl)$_2$, —C(O)O(alkyl), —C(O)NH$_2$, —S(O)$_2$(alkyl), —NHS(O)$_2$(alkyl), and —NHC(O)(O(alkyl)).

In exemplary embodiments, $R^4$ represents

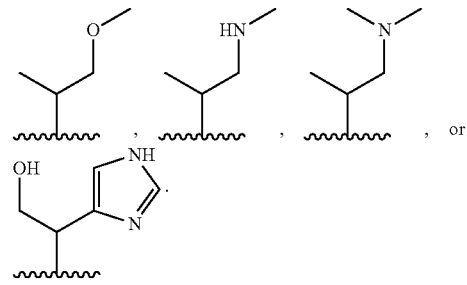

In certain embodiments, $R^a$ represents $(C_1-C_6)$alkyl, (heterocycloalkyl)alkyl, or $(C_3-C_7)$cycloalkyl, optionally substituted by hydroxy or dialkylamino.

In certain embodiments, $R^a$ represents H, $(C_1-C_6)$alkyl, or $(C_3-C_7)$cycloalkyl. In further embodiments, $R^a$ represents H. Alternatively, in some embodiments, $R^a$ represents $(C_1-C_6)$alkyl.

In certain embodiments, m is an integer from 1-4. In some embodiments, m is 1 or 2. Preferably, m is 1.

In certain embodiments,

represents

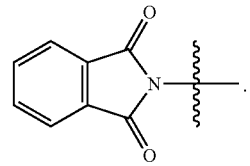 [SMILES: *N1C(=O)c2ccccc2C1=O]

Alternatively,

represents

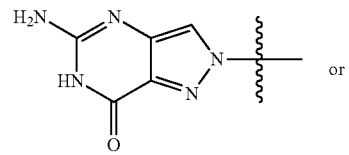

or

-continued

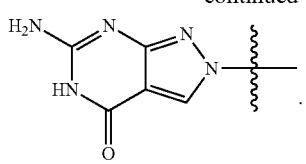

In further embodiments,

represents

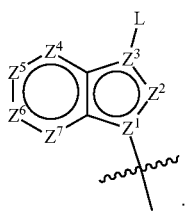

In some embodiments,

may represent

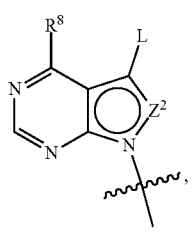

wherein $R^8$, L, and $Z^2$ are as defined above. For example,

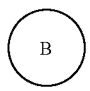

may represent

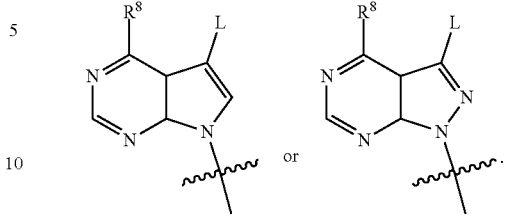

In certain such embodiments, $R^8$ is preferably H, $NH_2$, or Cl. In further such embodiments, L represents H or CN.

In certain embodiments, L represents $C(O)R^7$.

In certain embodiments, the compound of Formula (I) has the structure of Formula (Ia):

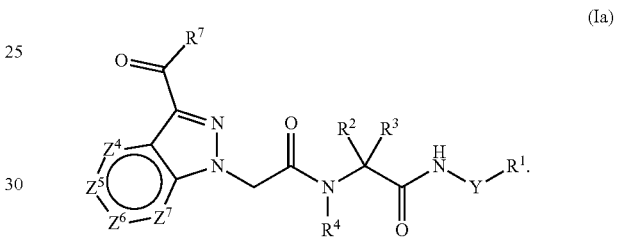

(Ia)

In certain embodiments, the compound of Formula (I) has the structure of Formula (Ib):

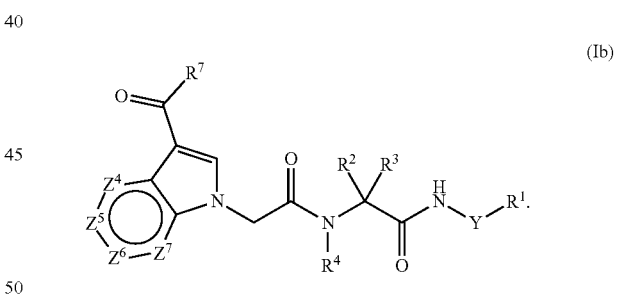

(Ib)

In certain embodiments, the compound of Formula (I) has the structure of Formula (Ic):

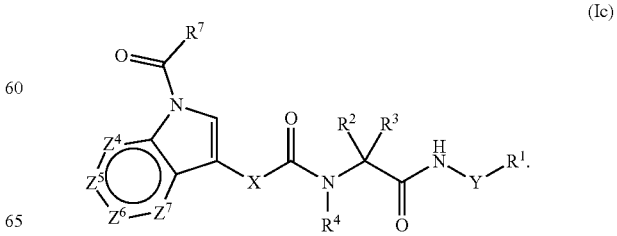

(Ic)

In certain embodiments, the compound of Formula (I) has the structure of Formula (Id):

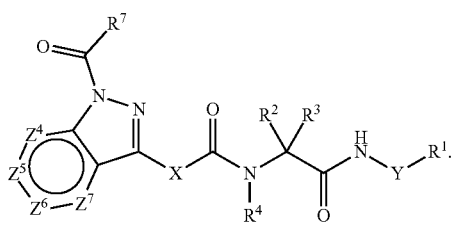

(Id)

In certain embodiments of the compounds of formulae (Ic) or (Id), X is NH.

In certain embodiments of the compounds of formula (I), if $Z^1$ is N, then X is $CH_2$. In further embodiments, $Z^1$ is C, then X is NH.

In certain embodiments of the compounds of formulae (Ia), (Ib), (Ic), or (Id), $Z^4$ represents $CR^8$, $Z^5$ represents $CR^5$, $Z^6$ represents $CR^6$, and $Z^7$ represents $CR^9$.

In certain embodiments, $Z^4$ and $Z^7$ each represent CH.

In certain embodiments, $Z^5$ represents $CR^5$ and $Z^6$ represents $CR^6$; and $R^5$ and $R^6$ each independently represent H, halogen, —$NR^{13}R^{14}$, —$C(O)R^{13}$, —$C(O)OR^{13}$, —$C(O)NHR^{14}$, —$NHC(O)NR^{13}R^{14}$, —$NHS(O)_2(R^{14})$, or optionally substituted alkyl, alkenyl, alkynyl, heteroaryl, or aryl.

In certain such embodiments, $R^{13}$ and $R^{14}$, independently for each occurrence, represent H or optionally substituted aryl, aralkyl, heteroaryl, heteroaralkyl, cycloalkyl, or (cycloalkyl)alkyl.

In further embodiments, $R^5$ and $R^6$ each independently represent H or alkyl, alkenyl, alkynyl, heteroaryl, or aryl, optionally substituted with one or more substituents selected from the group consisting of aryl, heteroaryl, silyl, alkyl, amino, alkylamino, dialkylamino, —C(O)(alkyl), heterocycloalkyl, and halogen. Alternatively, $R^5$ and $R^6$ each independently represent H or alkyl, alkenyl, alkynyl, heteroaryl, or aryl, optionally substituted with one or more substituents selected from the group consisting of aryl, heteroaryl, silyl, alkyl, amino, alkylamino, dialkylamino, —C(O)(alkyl), and halogen.

In certain embodiments, $R^{13}$ and $R^{14}$, independently for each occurrence, represent H or alkyl, alkenyl, alkynyl, aryl, aralkyl, heteroaryl, heteroaralkyl, cycloalkyl, (cycloalkyl)alkyl, heterocycloalkyl, or (heterocycloalkyl)alkyl, optionally substituted by one or more substituents independently selected from halo, alkoxy, alkyl, hydroxy, hydroxyalkyl, haloalkyl, —$NH_2$, —NH(alkyl), —N(alkyl)$_2$, —C(O)O(alkyl), —$C(O)NH_2$, —$S(O)_2$(alkyl), —$NHS(O)_2$(alkyl), and —NHC(O)(O(alkyl)).

In certain embodiments, $R^5$ and $R^6$ each independently represent H, halogen, —$OR^{13}$, —$NR^{13}R^{14}$, —$C(O)R^{13}$, —$C(O)OR^{13}$, —$C(O)NR^{13}R^{14}$, —$OC(O)R^{13}$, —$NR^{13}C(O)R^{14}$, —$OC(O)NR^{13}R^{14}$, —$OC(O)OR^{13}$, —$NR^{13}C(O)OR^{14}$, —$NR^{13}C(O)NR^{13}R^{14}$, —$OS(O)_p(R^{13})$, —$NR^{13}S(O)_p(R^{14})$, or optionally substituted alkyl, alkenyl, alkynyl, haloalkyl, aralkyl, heteroaralkyl, heteroaryl, aryl, cycloalkyl, (cycloalkyl)alkyl, heterocycloalkyl, or (heterocycloalkyl)alkyl.

In certain embodiments, $R^5$, $R^6$, $R^8$, and $R^9$ each independently represent H or alkyl, alkenyl, alkynyl, haloalkyl, aralkyl, heteroaralkyl, heteroaryl, aryl, cycloalkyl, (cycloalkyl)alkyl, heterocycloalkyl, or (heterocycloalkyl)alkyl, optionally substituted with one or more substituents selected from the group consisting of aryl, heteroaryl, silyl, alkyl, amino, alkylamino, dialkylamino, —C(O)(alkyl), hydroxy, alkoxy, aryloxy, heteroaryloxy, and halogen.

In certain embodiments, $R^5$, $R^6$, $R^8$, and $R^9$ each independently represent H or alkyl, alkenyl, alkynyl, heteroaryl, or aryl, optionally substituted with one or more substituents selected from the group consisting of aryl, heteroaryl, silyl, alkyl, amino, alkylamino, dialkylamino, —C(O)(alkyl), hydroxy, alkoxy, aryloxy, heteroaryloxy, and halogen.

In certain embodiments, $R^5$, $R^6$, $R^8$, and $R^9$ each independently represent H or —$CH(OH)R^{50}$, —$CH(NH_2)R^{50}$, —$CH(OR^{51})R^{50}$, —$CH(NHR^{51})R^{50}$, —$C(NH_2)(R^{51})(R^{50})$, —$C(OH)(R^{51})(R^{50})$, and —$NH(CO)CR^5R^6R^{50}$; wherein for each occurrence $R^{50}$ and $R^{51}$ are each independently selected from alkyl, alkenyl, alkynyl, haloalkyl, aralkyl, heteroaralkyl, heteroaryl, aryl, cycloalkyl, (cycloalkyl)alkyl, heterocycloalkyl, and (heterocycloalkyl)alkyl.

In certain embodiments, $R^5$, $R^6$, and $R^8$ are each H.

In certain embodiments, $R^5$, $R^6$, and $R^9$ are each H.

In certain embodiments, $R^5$, $R^8$, and $R^9$ are each H.

In certain embodiments, $R^6$, $R^8$, and $R^9$ are each H.

In certain embodiments, $R^7$ represents $NH_2$, $CH_3$, or $CF_3$.

In certain embodiments, $R^7$ represents $NH_2$.

In certain embodiments, the compound of the invention is selected from the group consisting of the following table of compounds, or a pharmaceutically acceptable salt thereof:

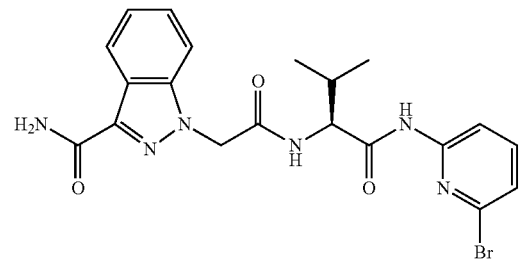

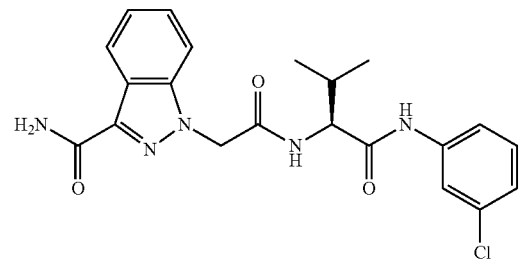

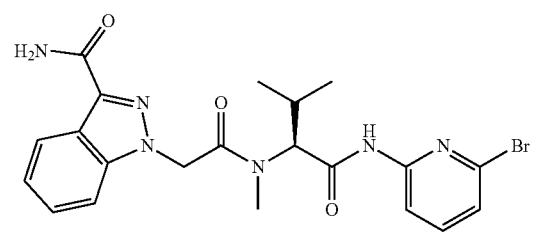

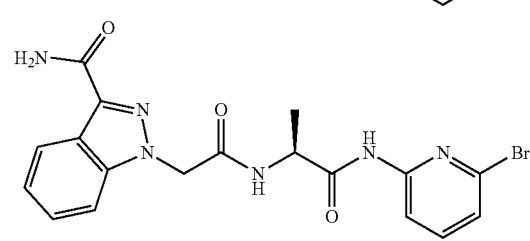

21
-continued
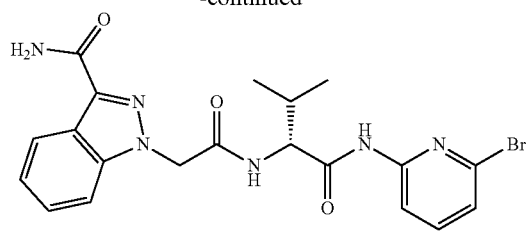
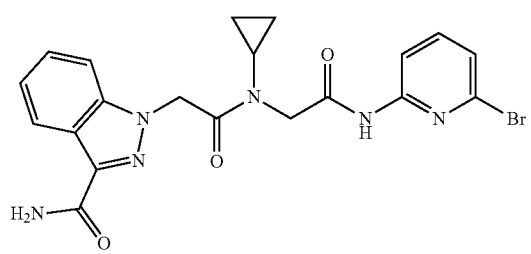
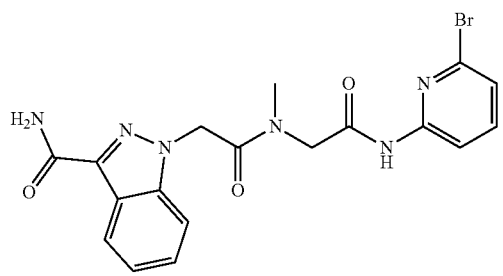
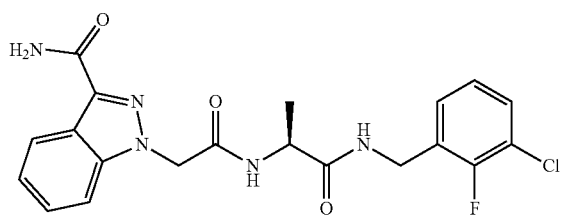
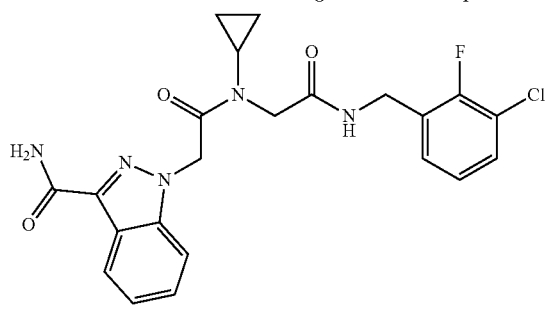
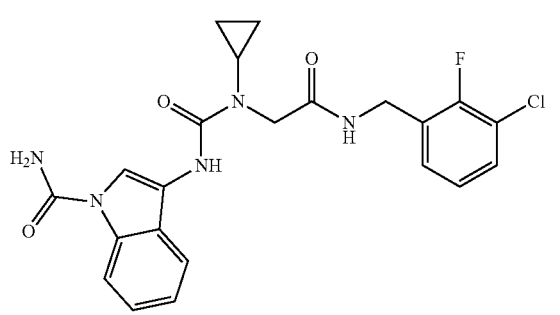
22
-continued
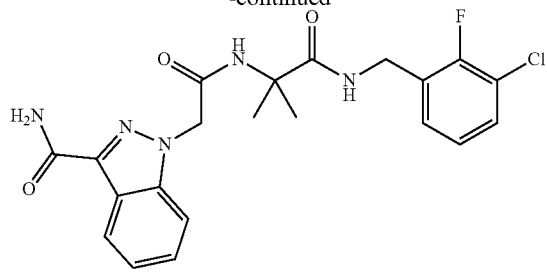
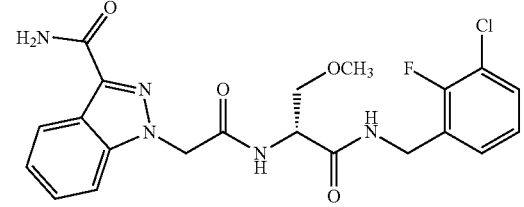
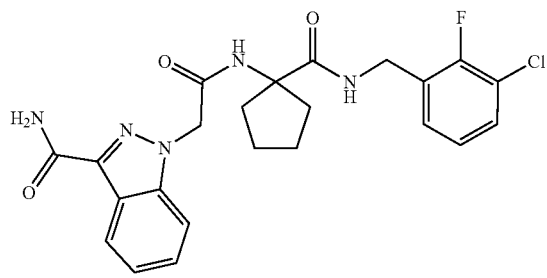
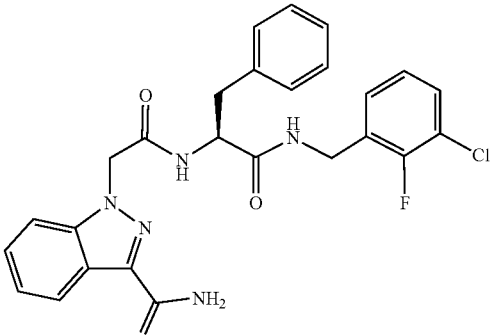
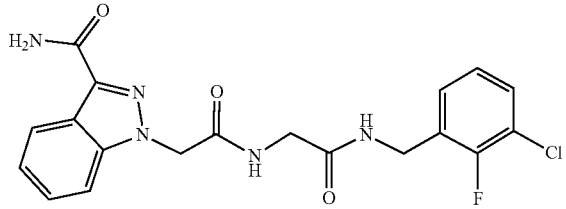
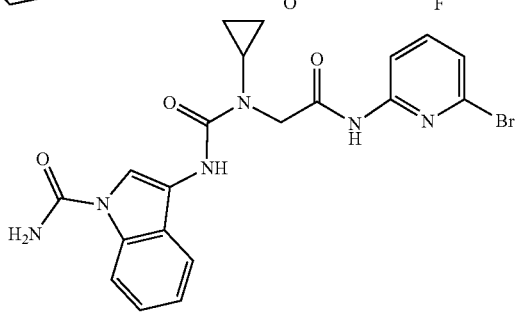

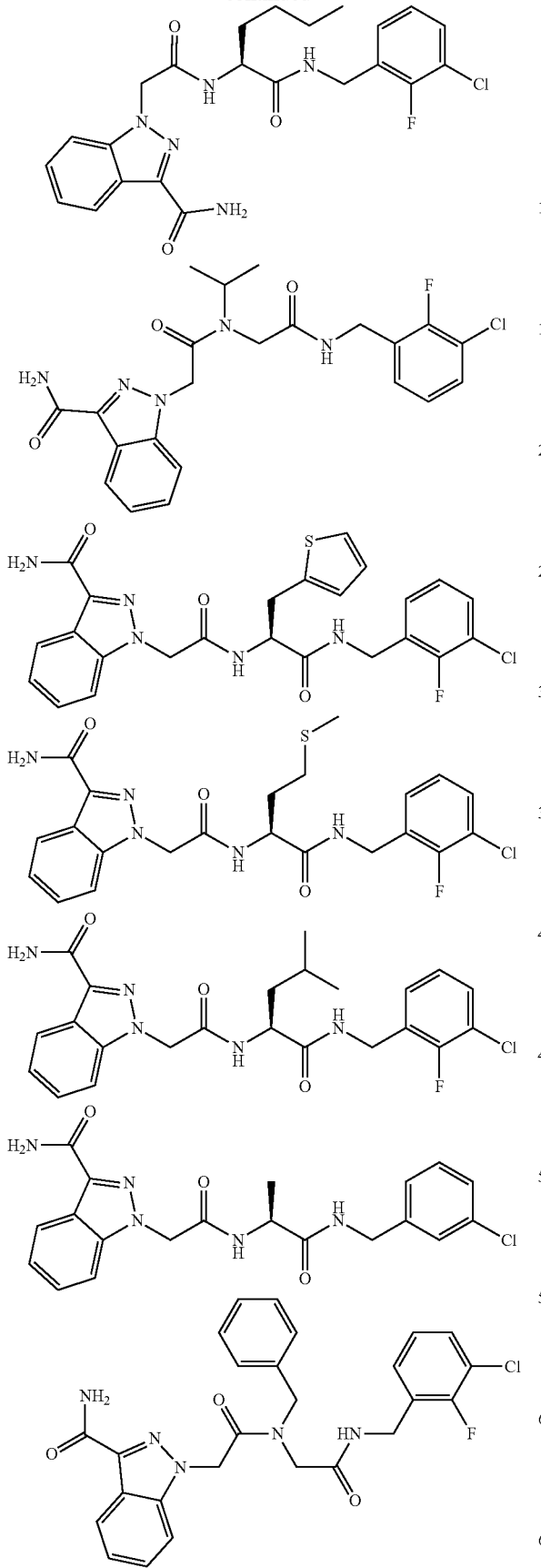
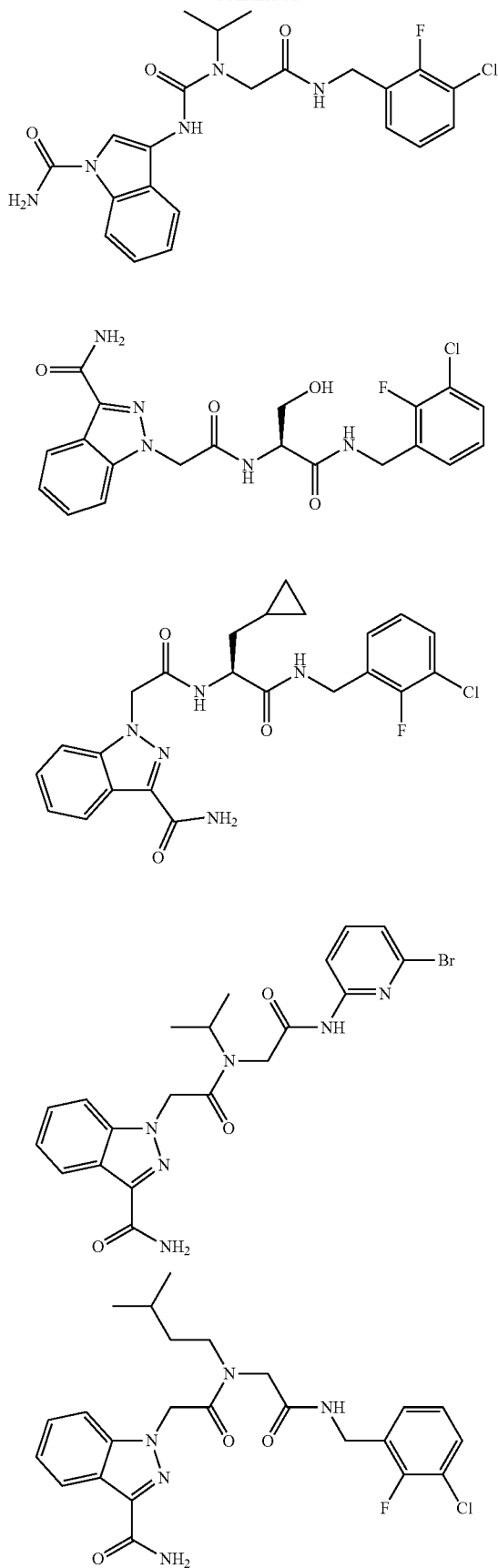

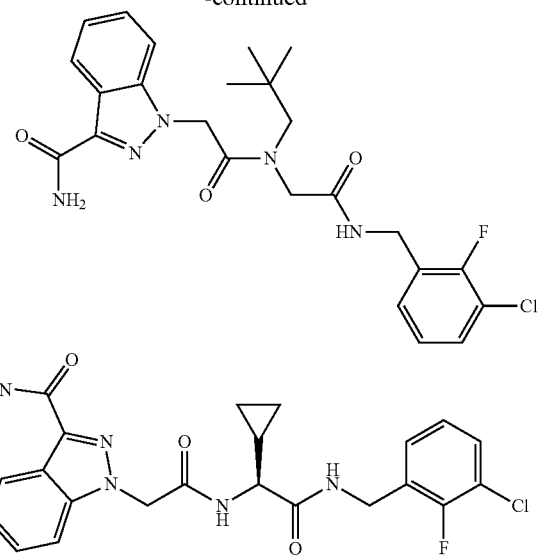
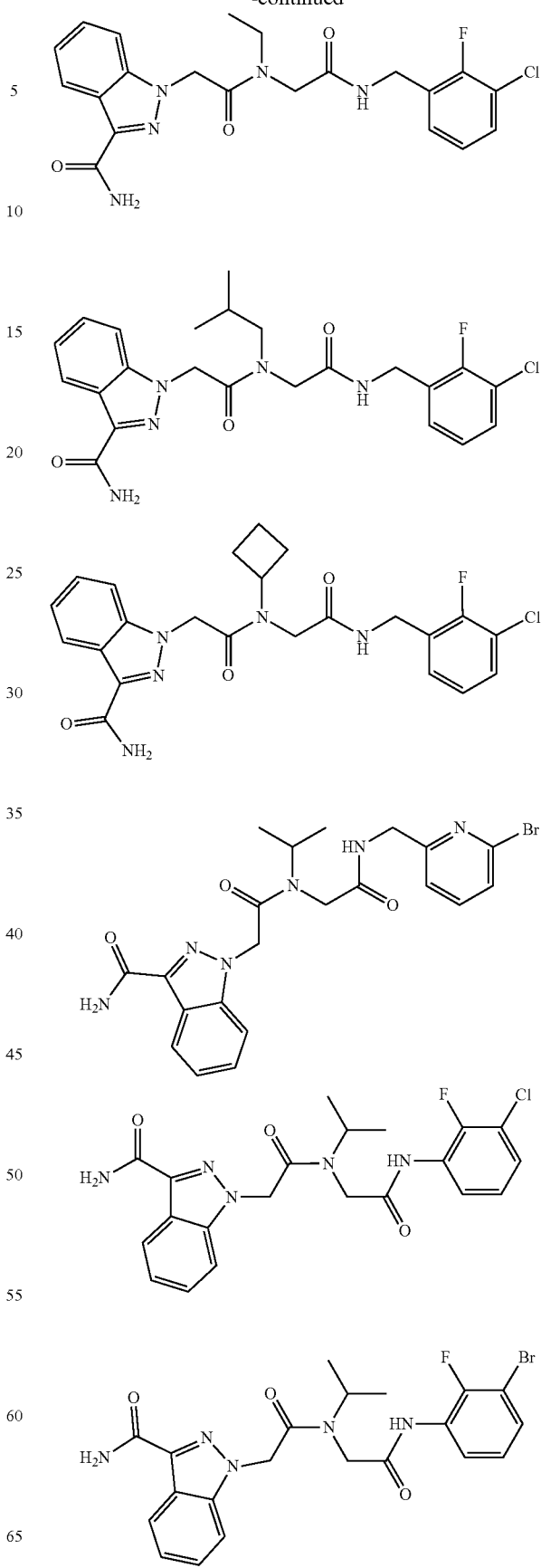

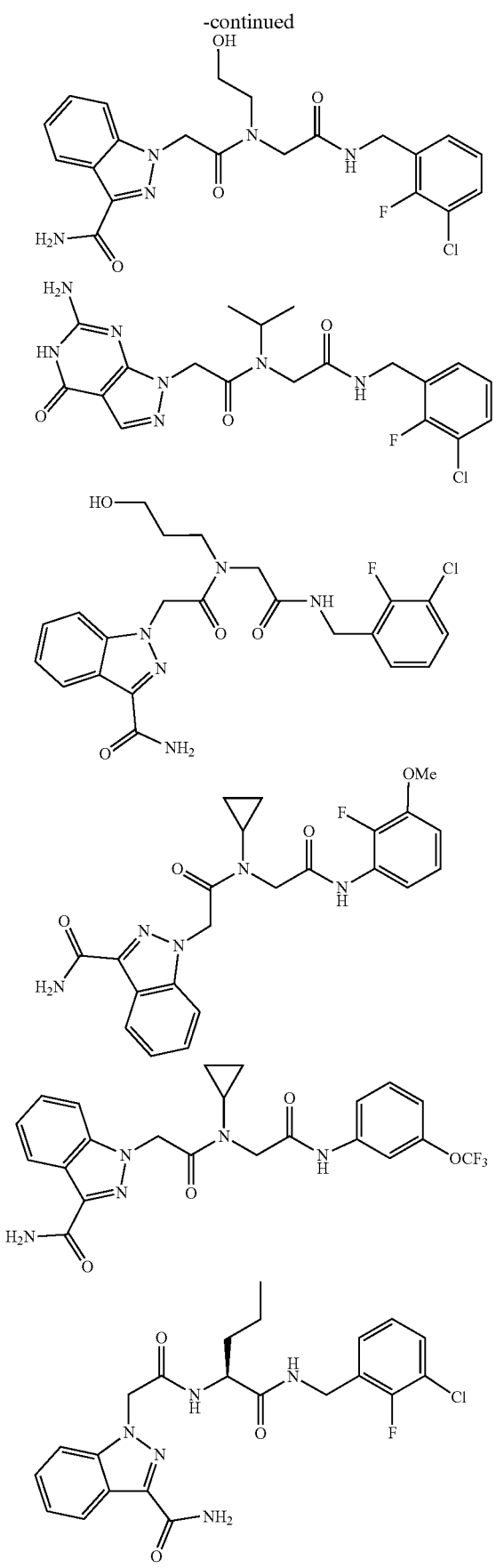

-continued

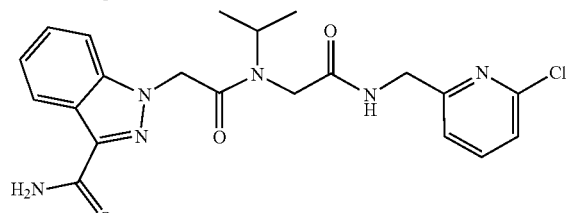
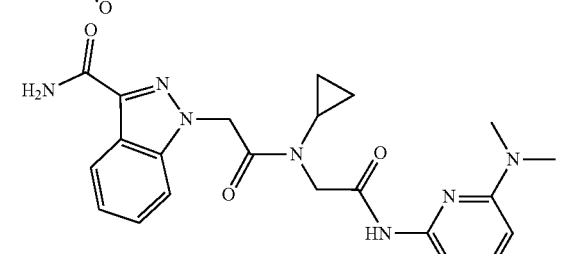
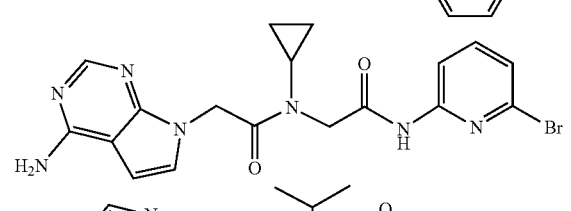
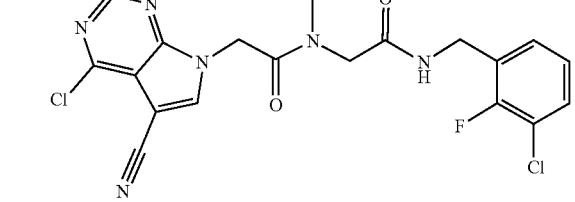
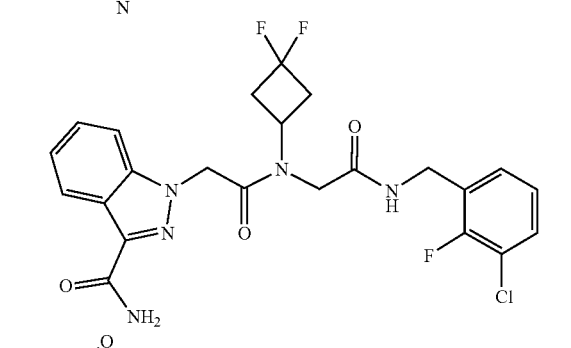
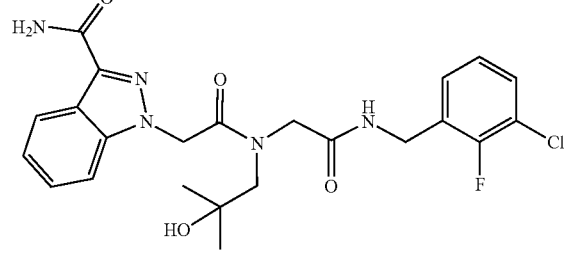
-continued
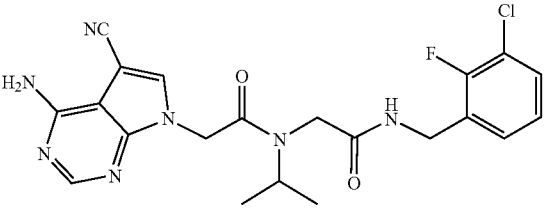
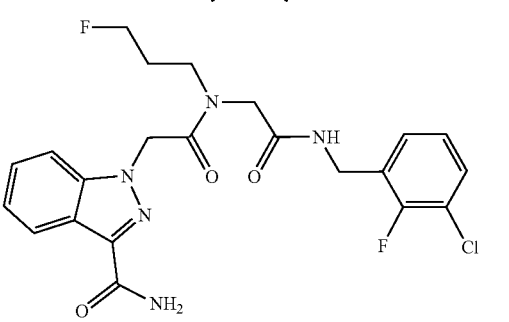
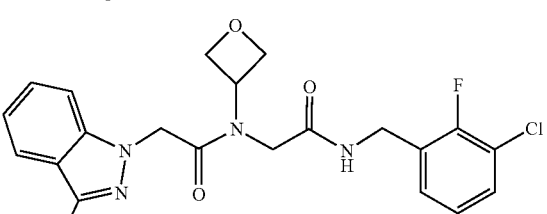
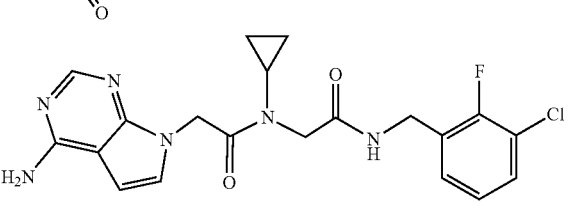
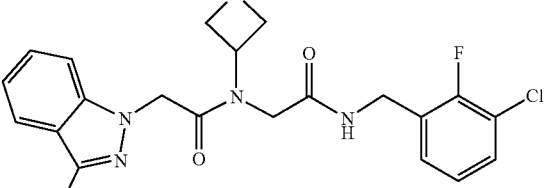
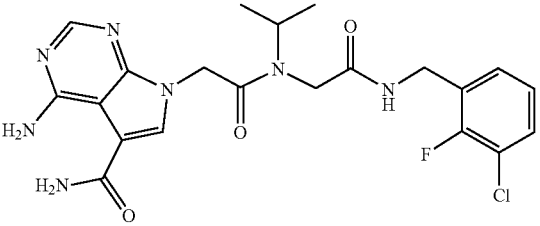
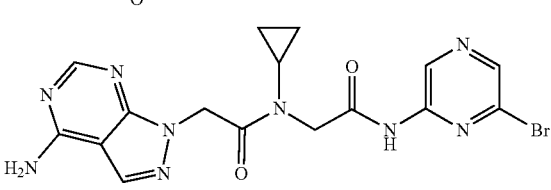

-continued
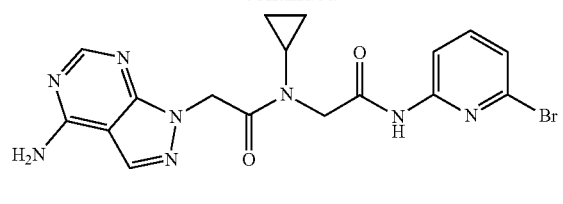
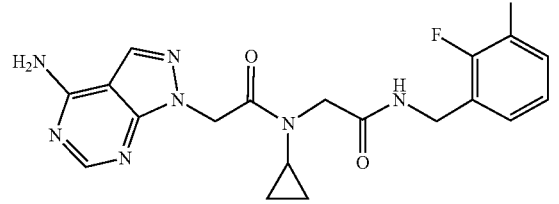
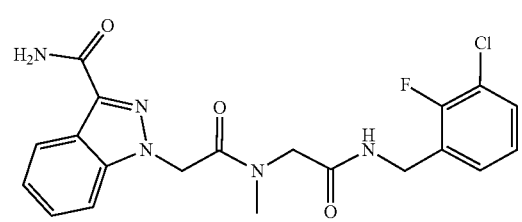
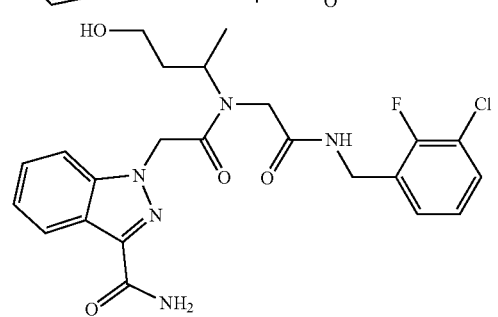
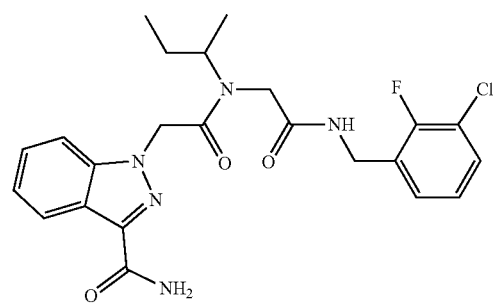
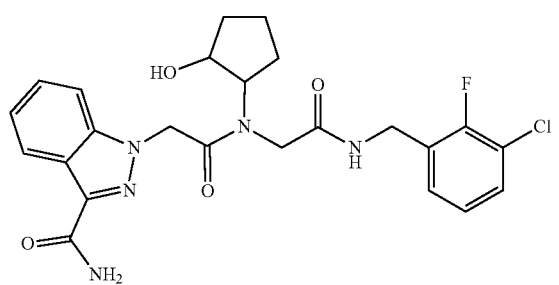
-continued
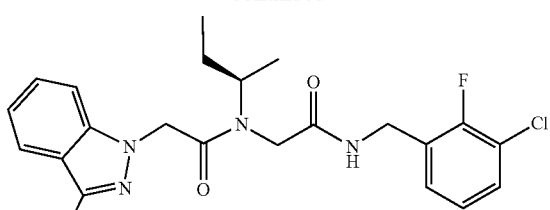
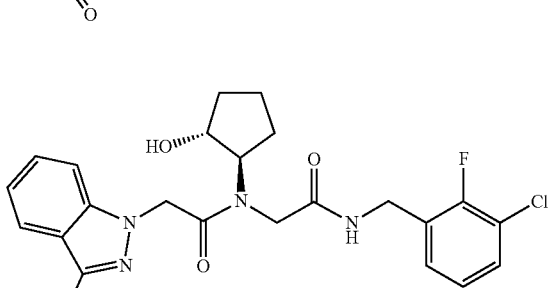
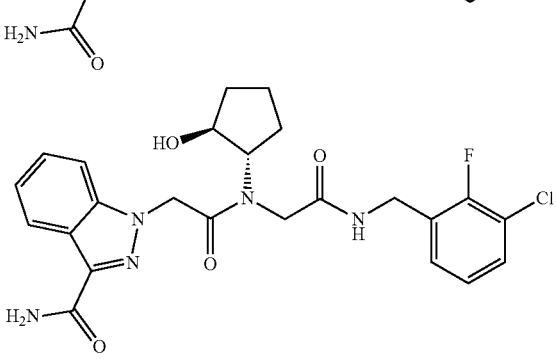
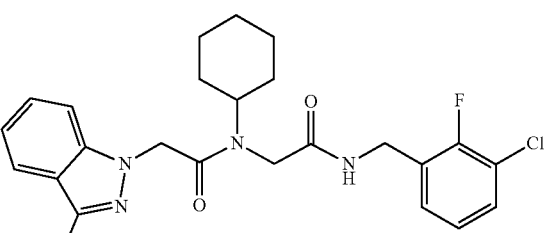
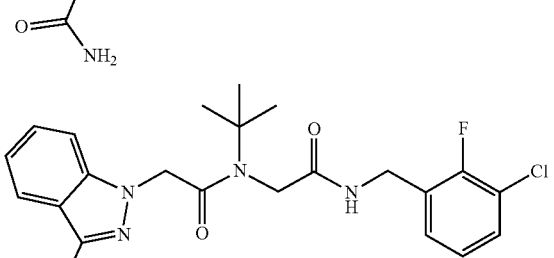
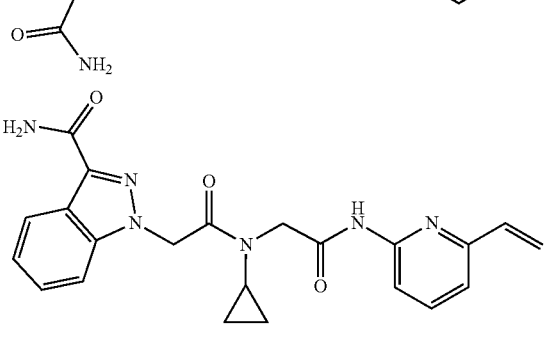

33
-continued
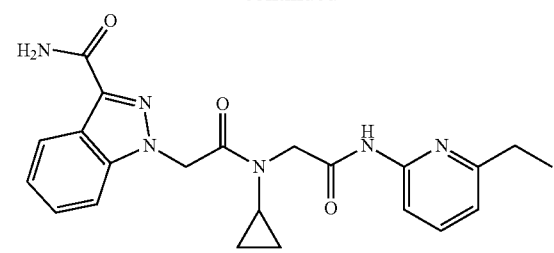
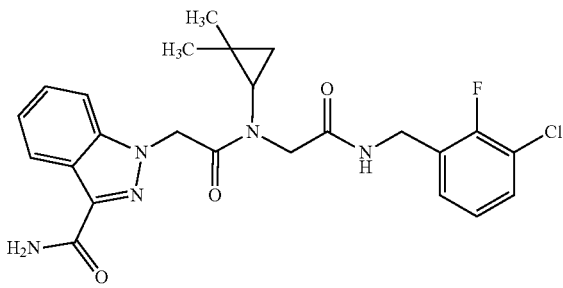
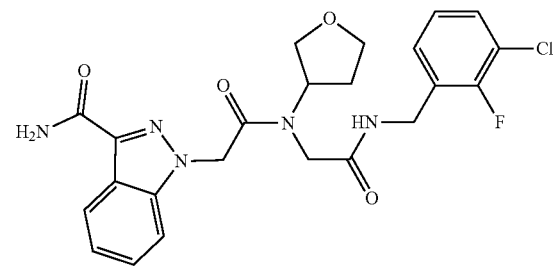
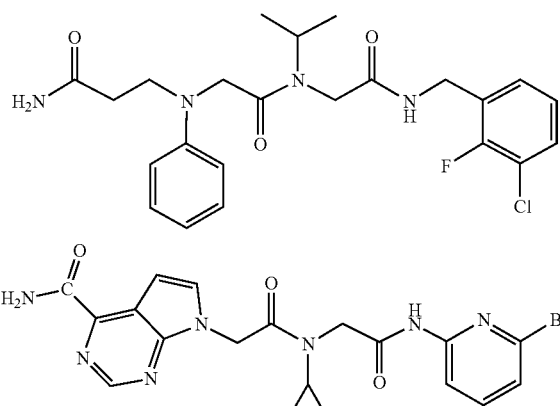
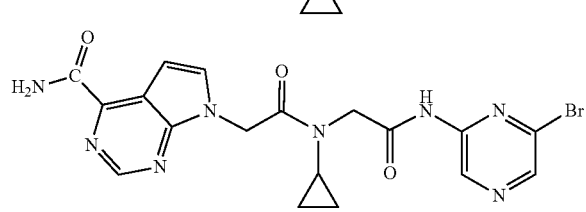
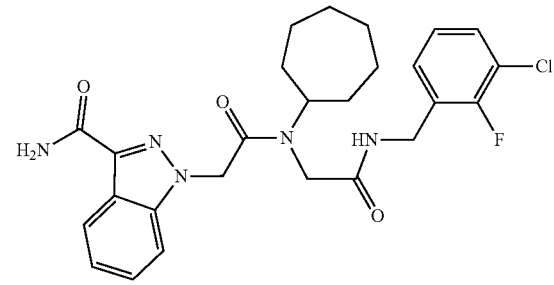
34
-continued
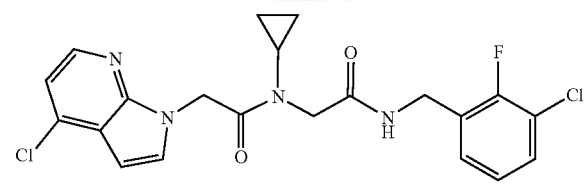
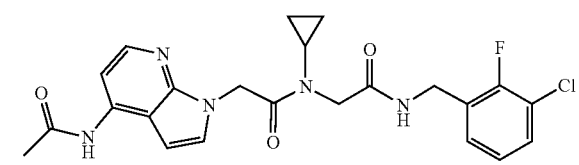
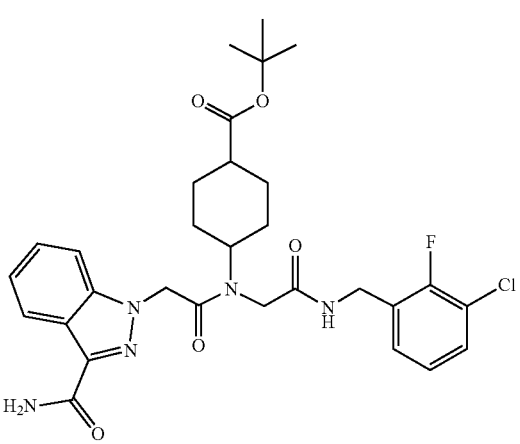
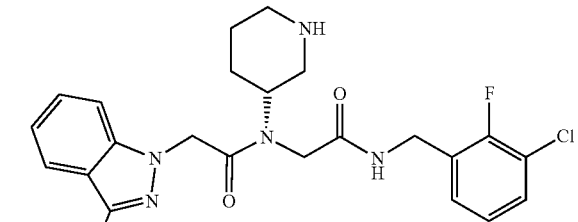
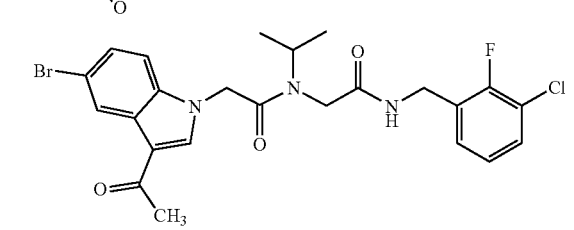
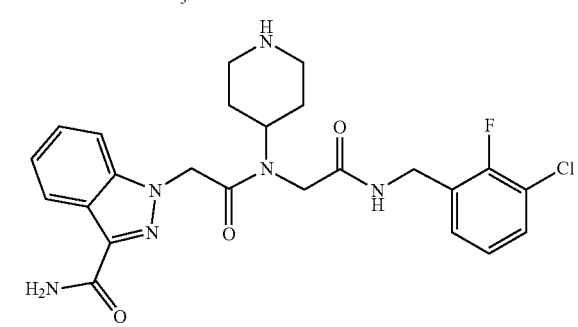

35
-continued
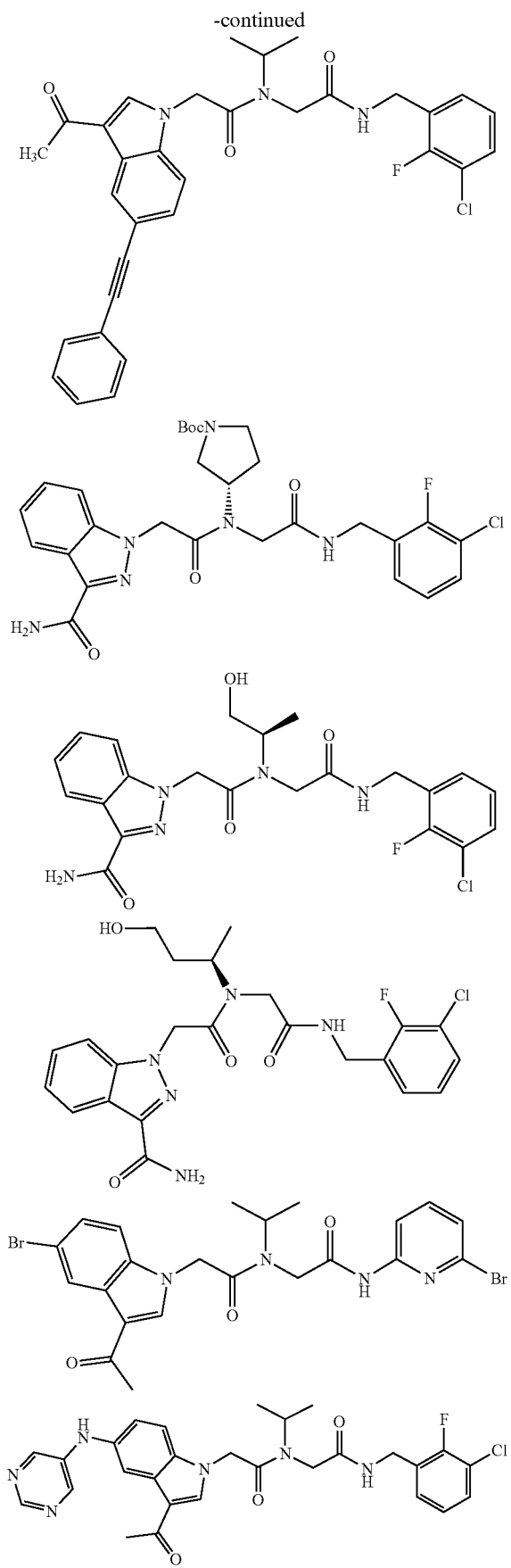
36
-continued
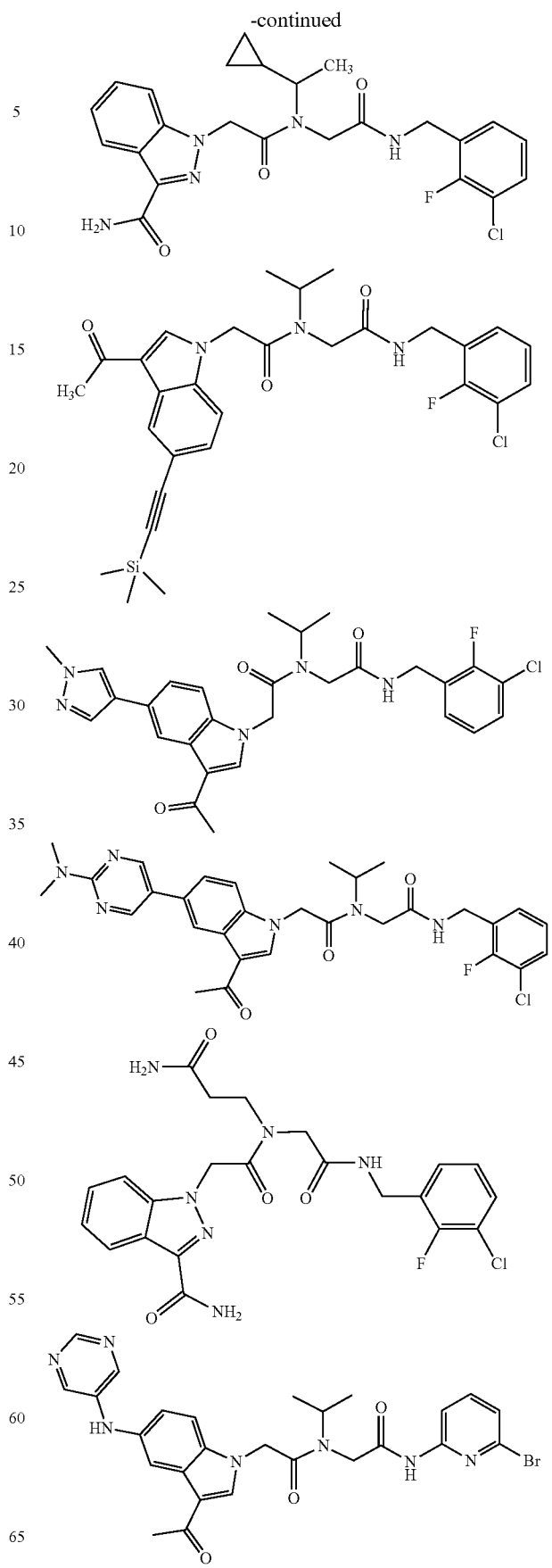

| 37 | 38 |
|---|---|
| -continued | -continued |
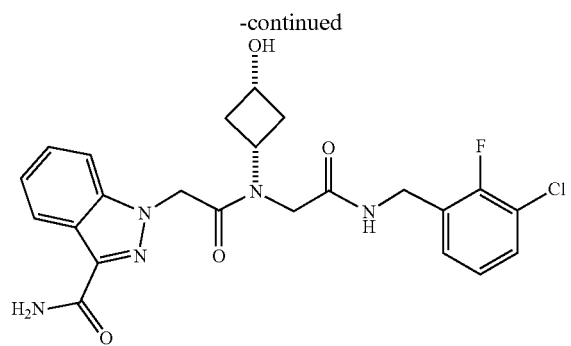
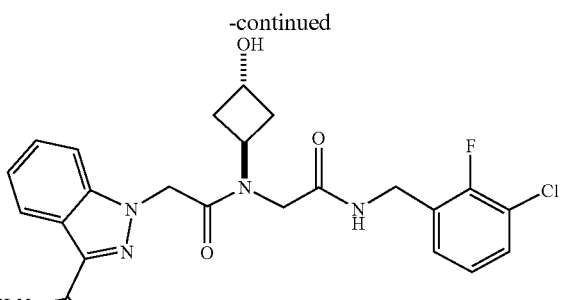
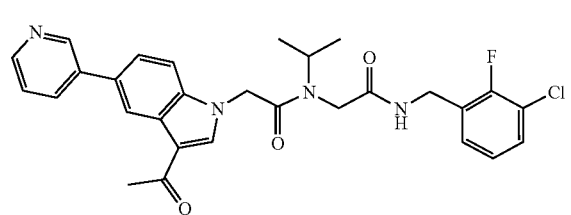
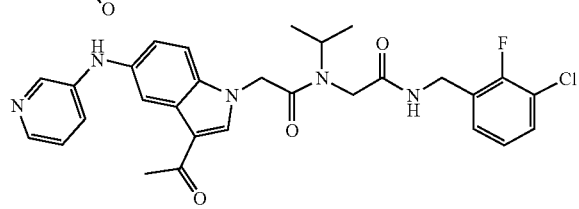
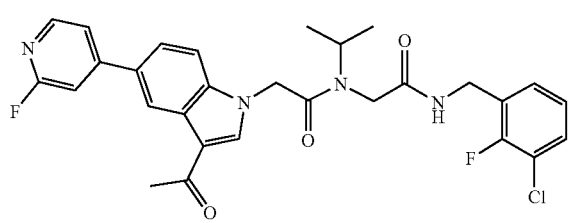
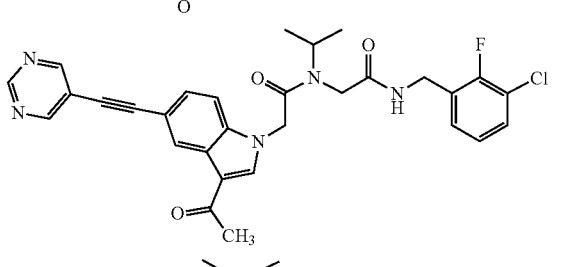
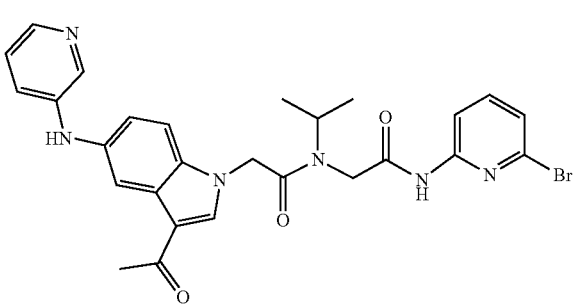
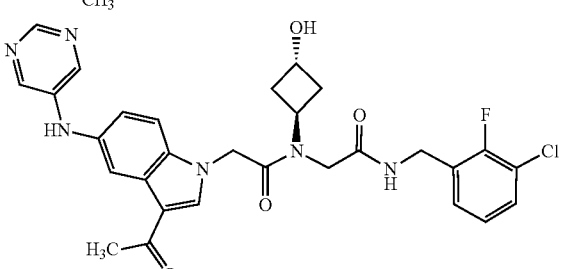
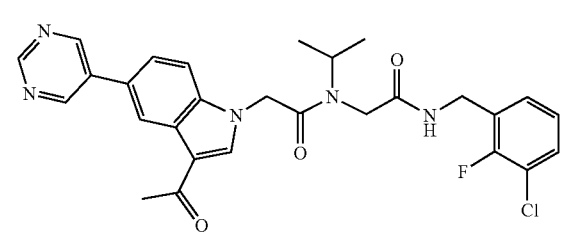
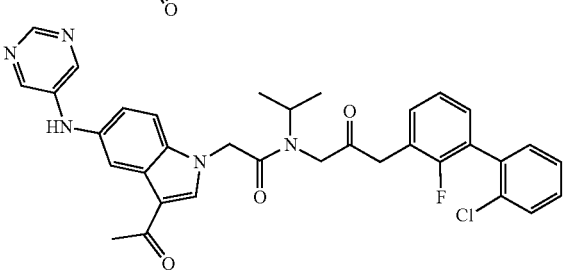
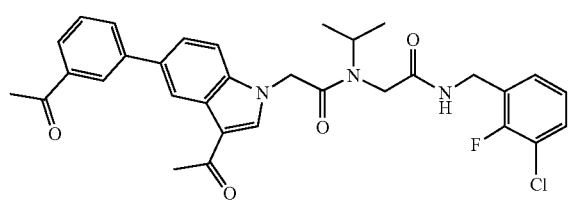
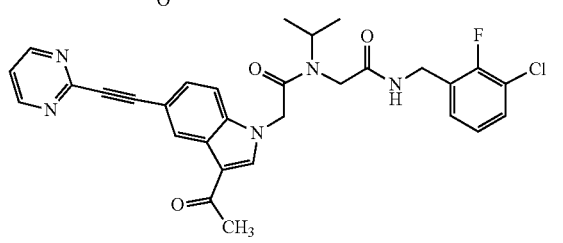

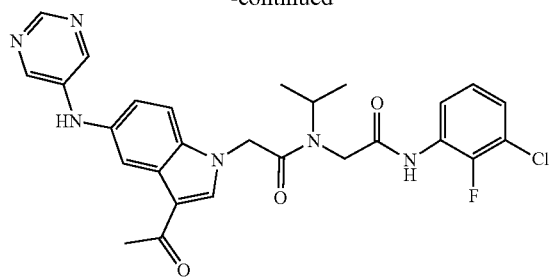
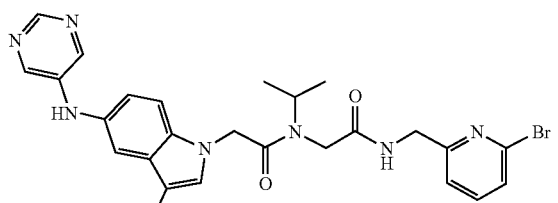
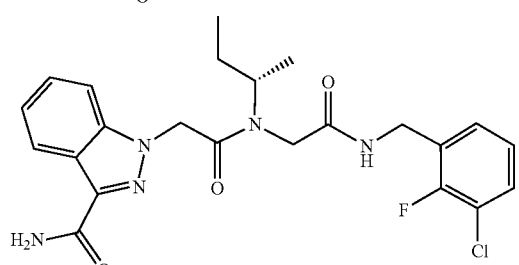
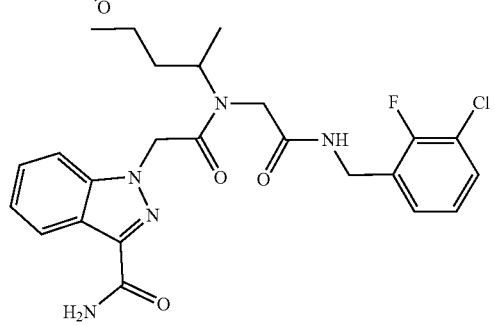
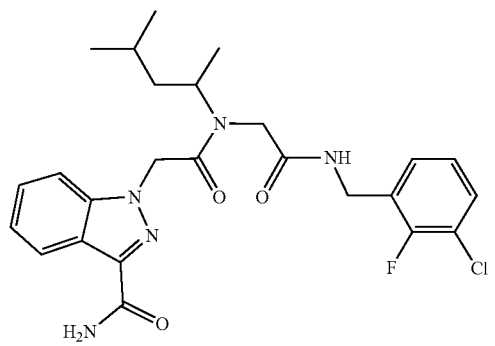
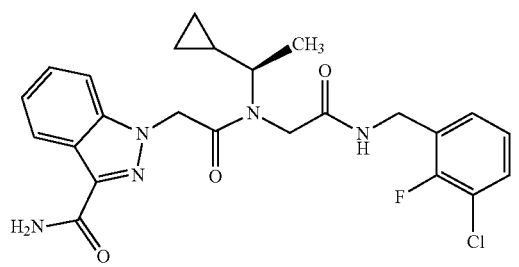
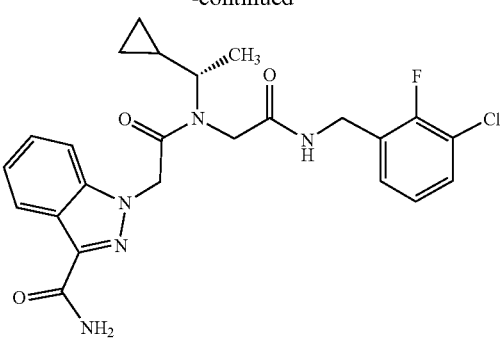
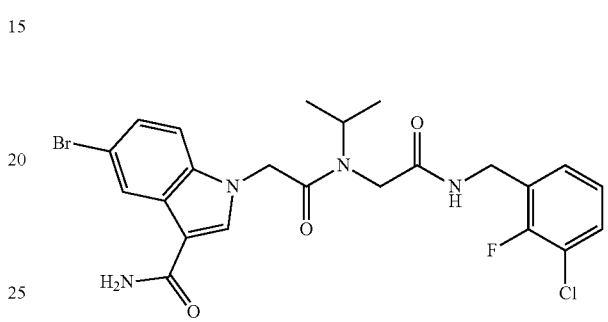
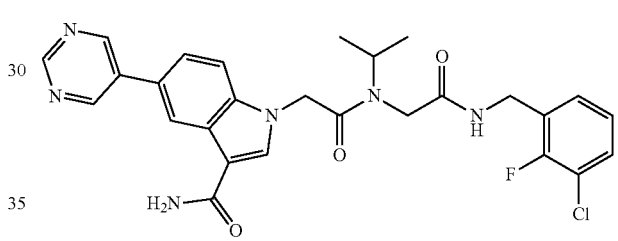
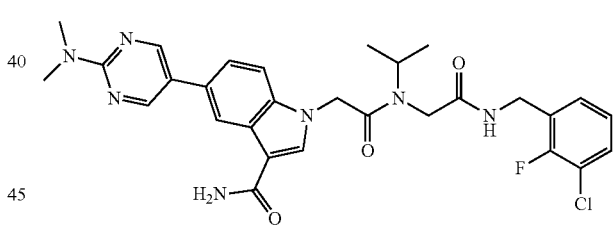
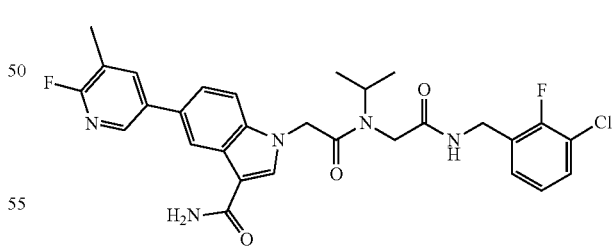
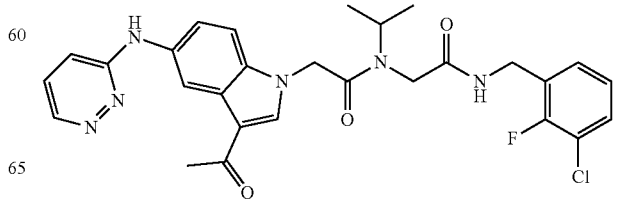

41
-continued
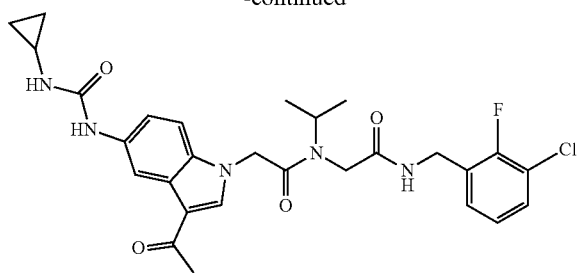
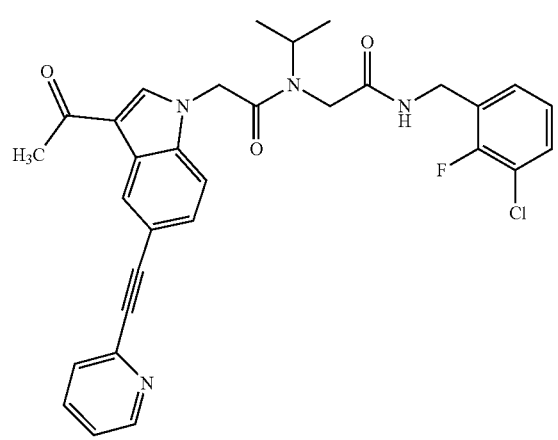
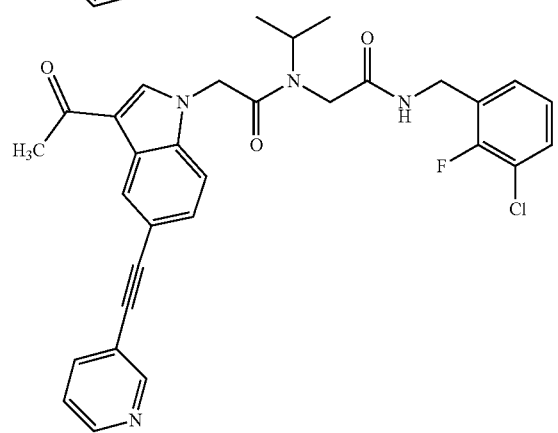
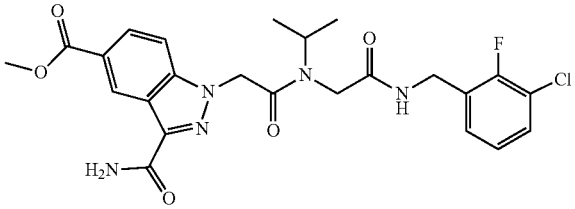
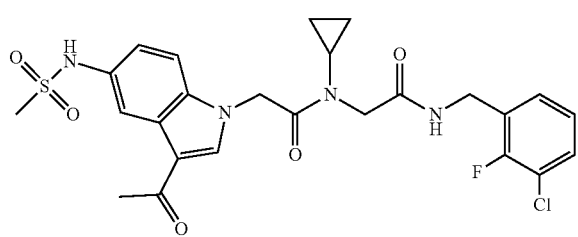
42
-continued
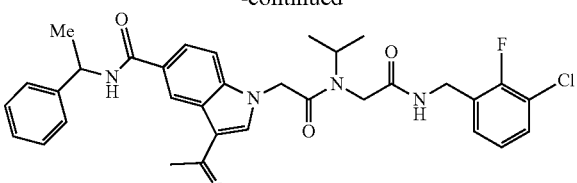
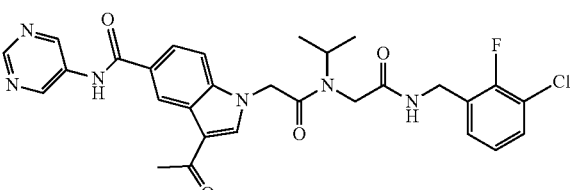
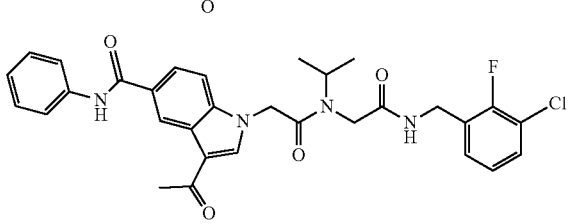
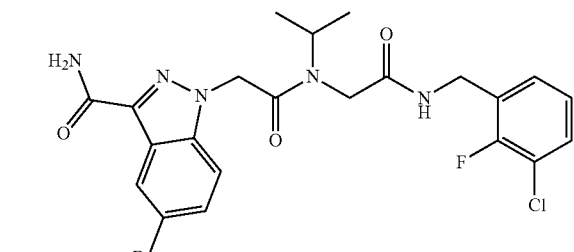
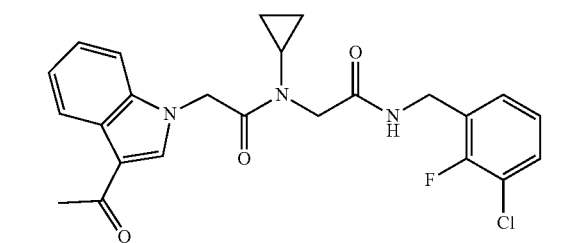
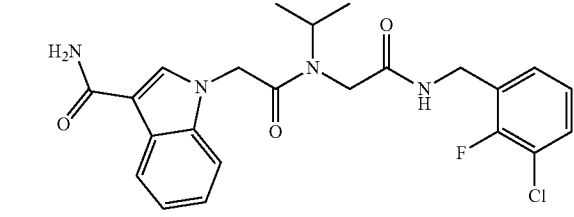
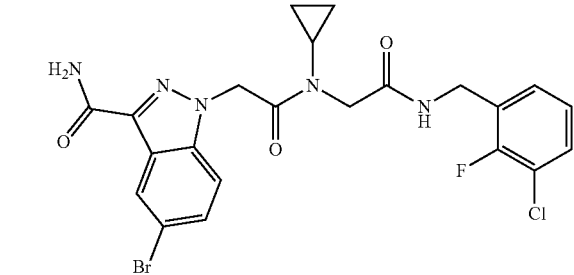

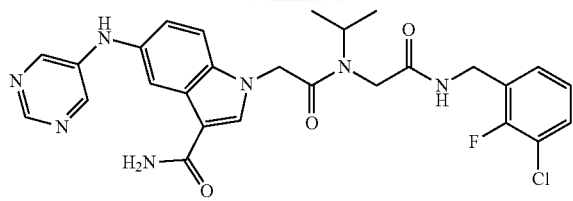
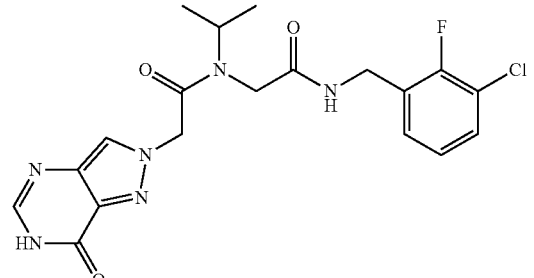
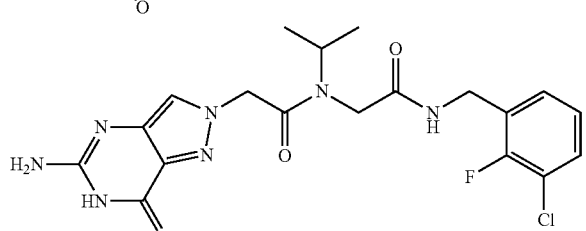
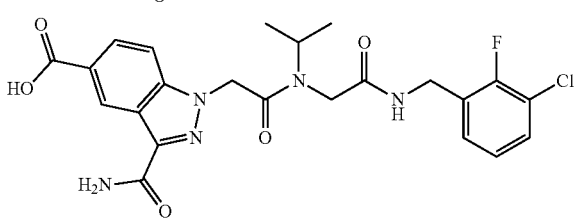
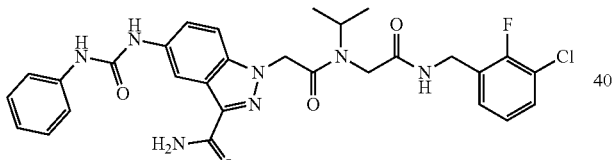
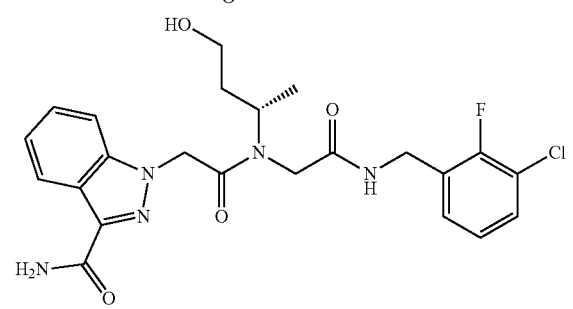
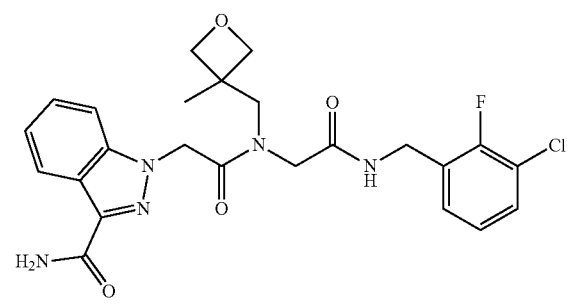
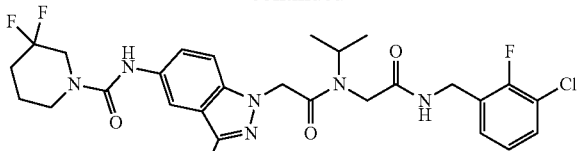
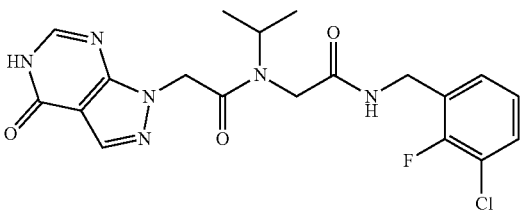
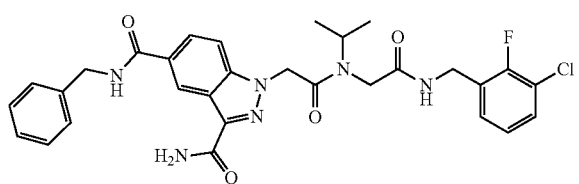
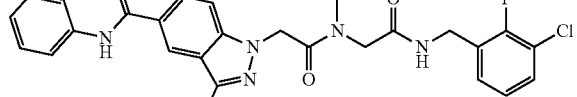
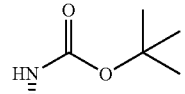
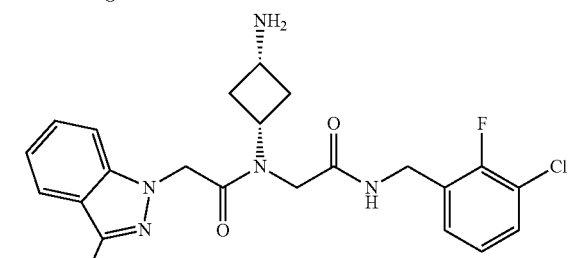
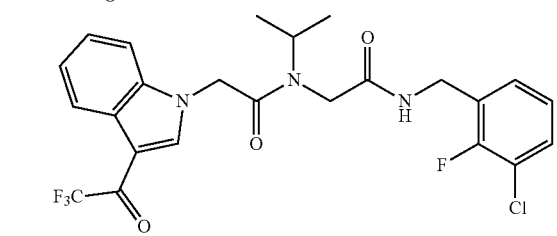

45
-continued
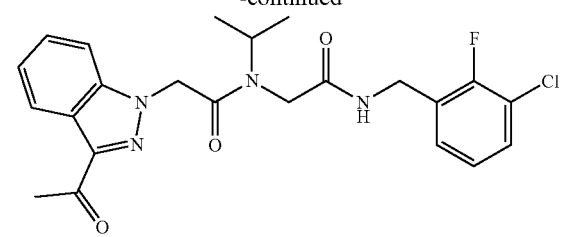
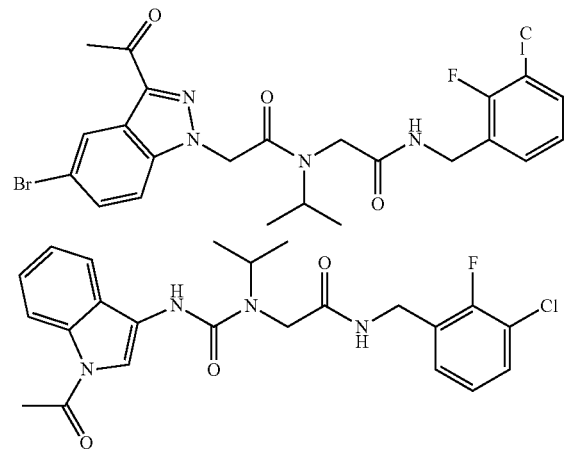
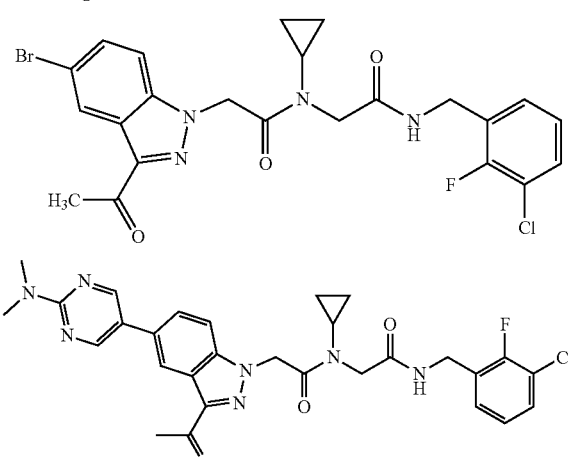
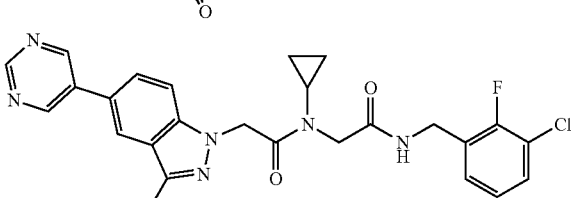
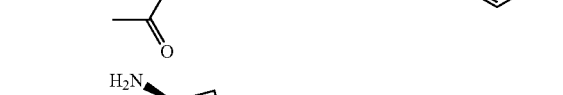
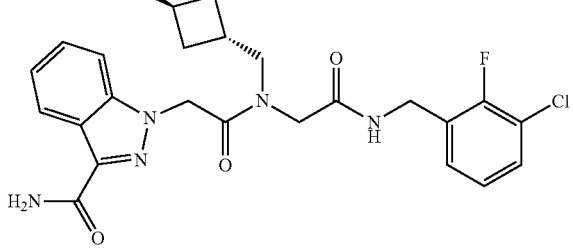
46
-continued
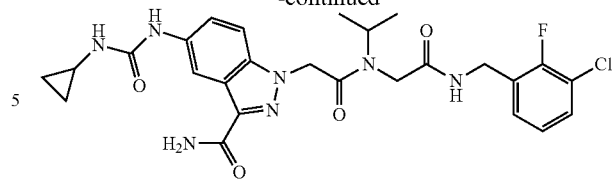
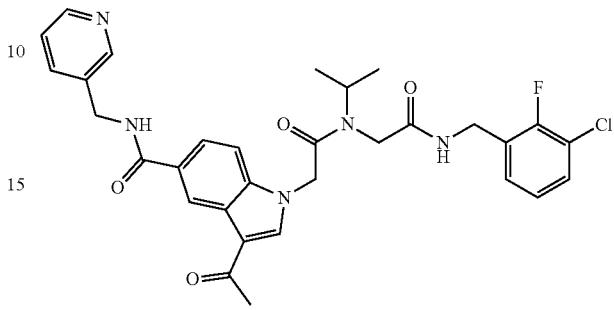
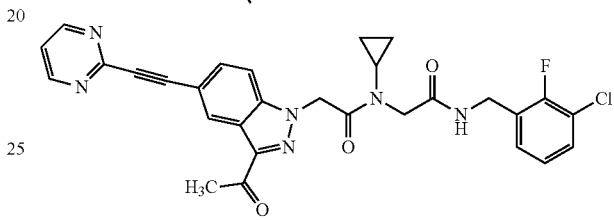
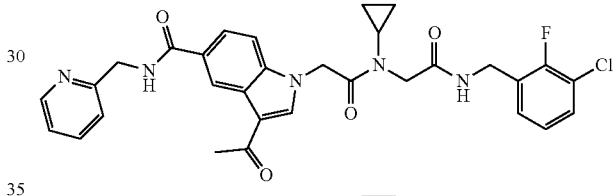
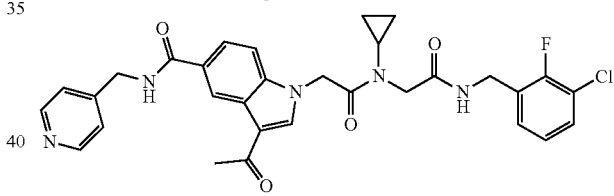
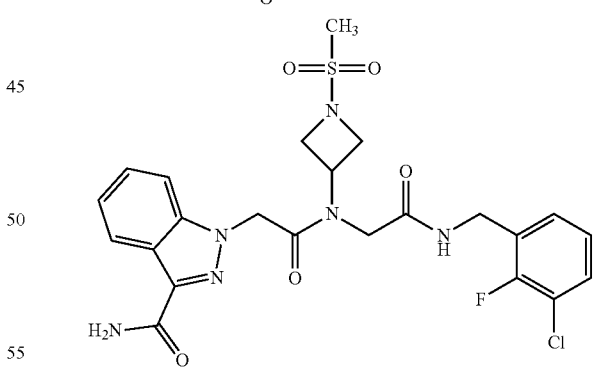
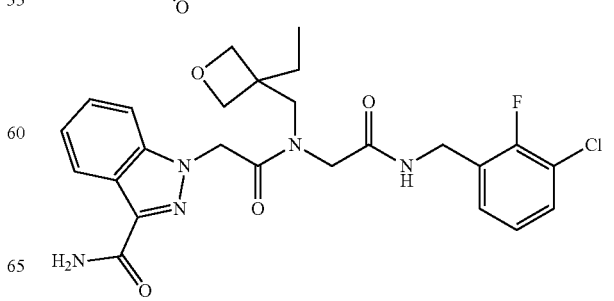

47
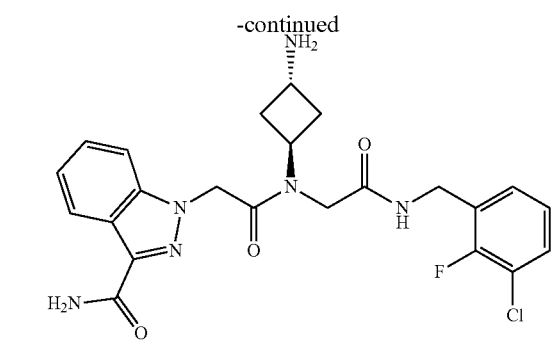
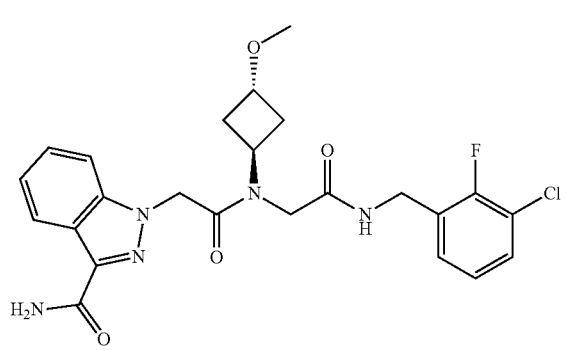
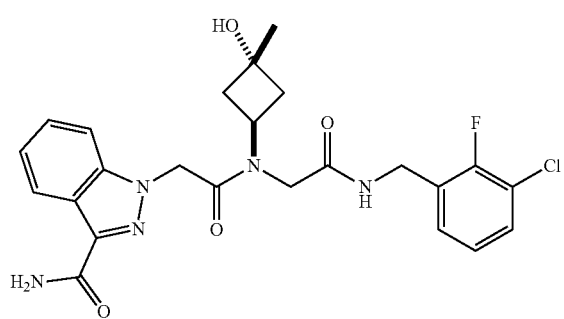
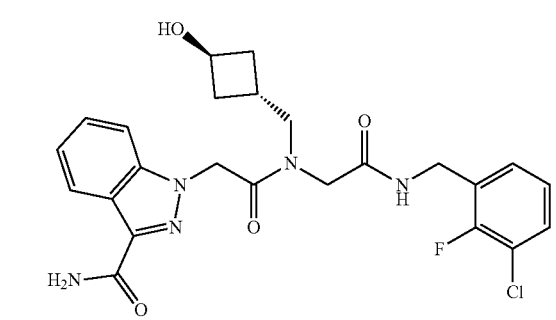
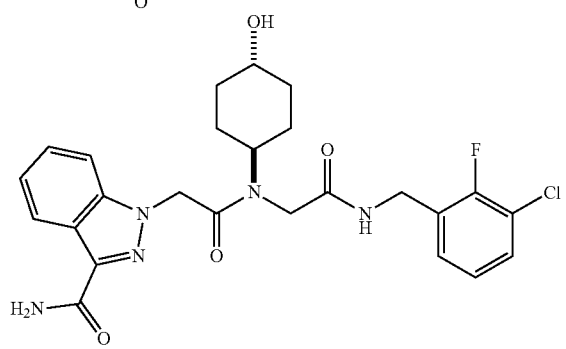
48
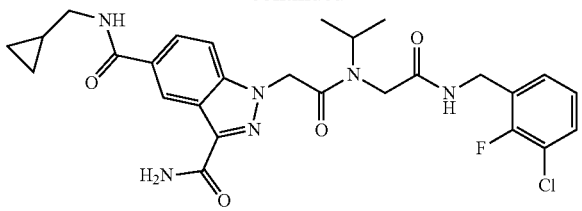
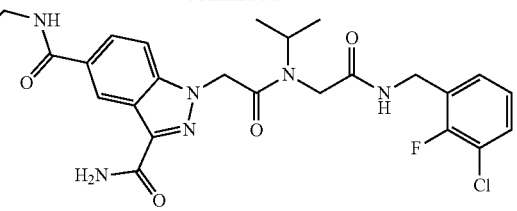
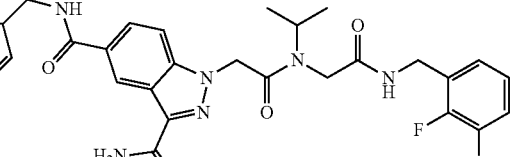
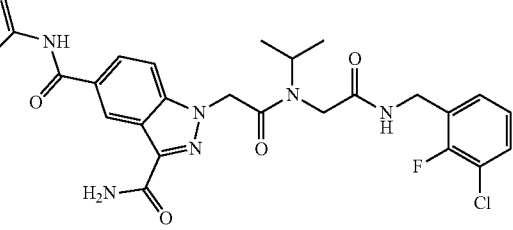
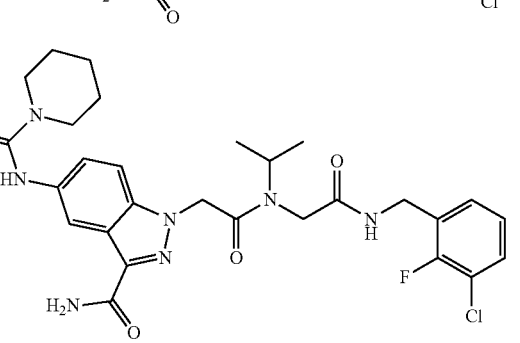
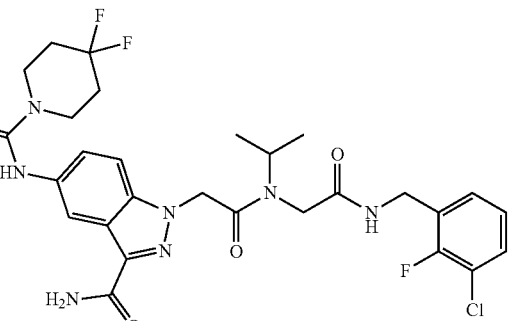
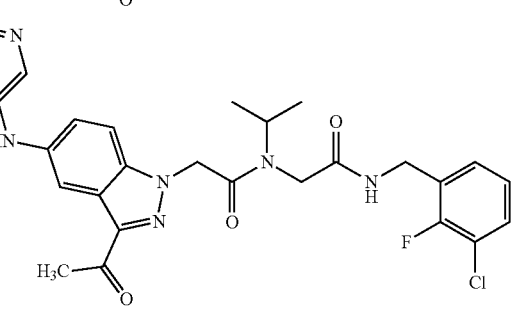

49
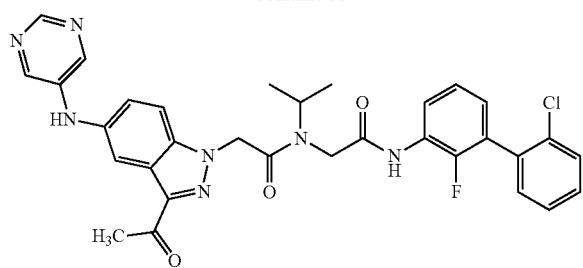
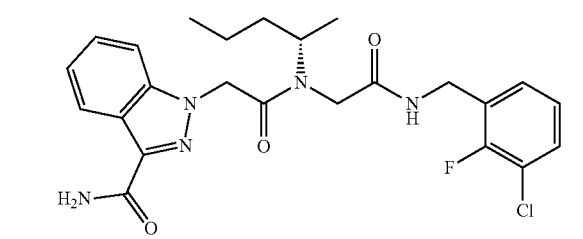
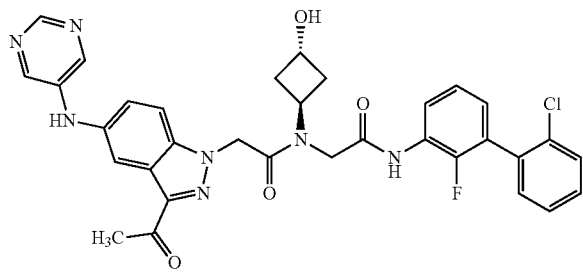
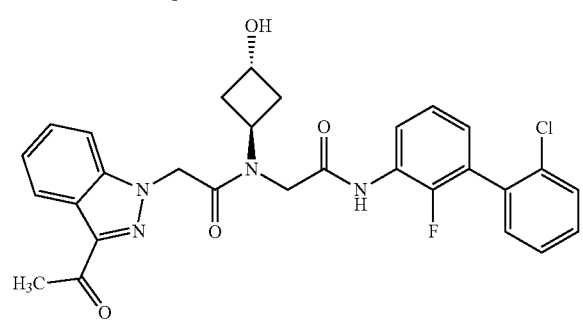
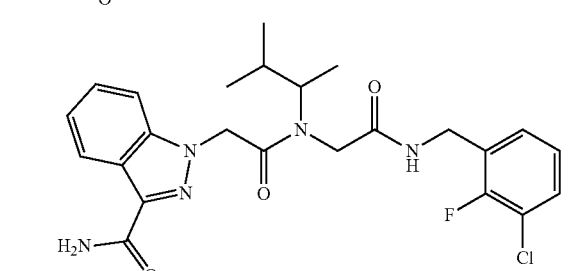
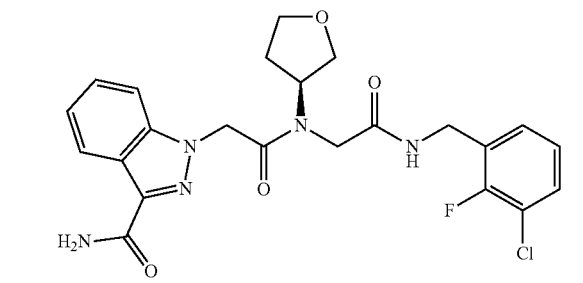
50
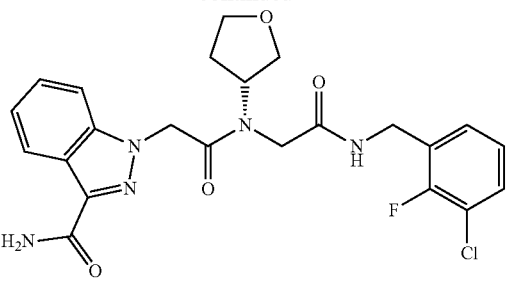
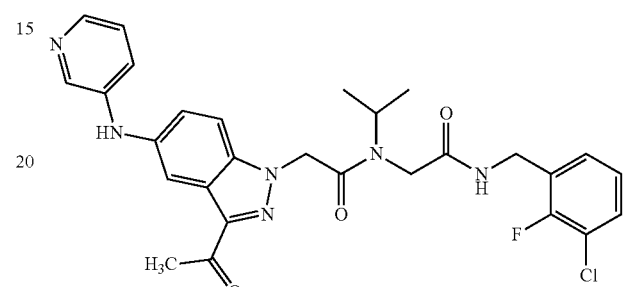
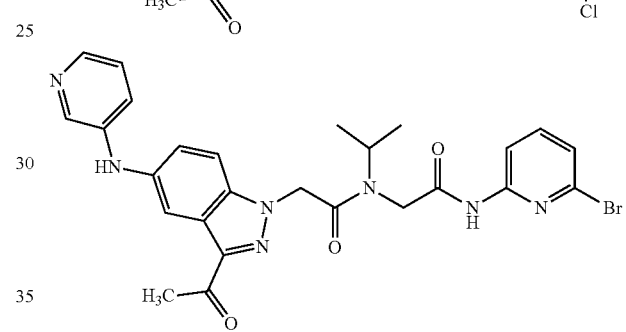
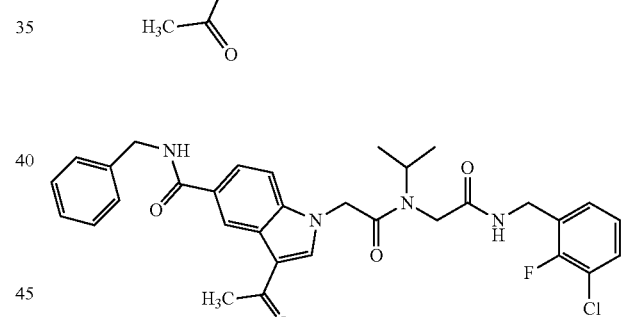
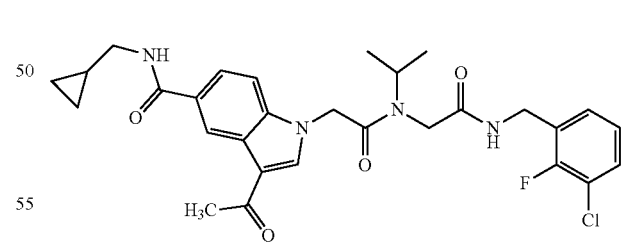
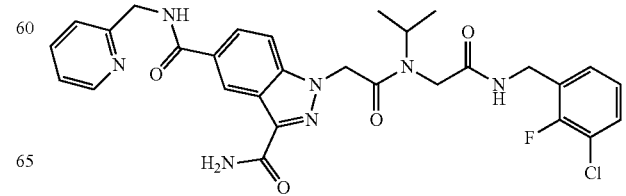

51
-continued
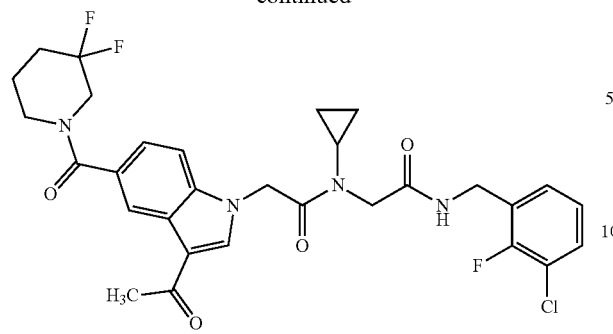
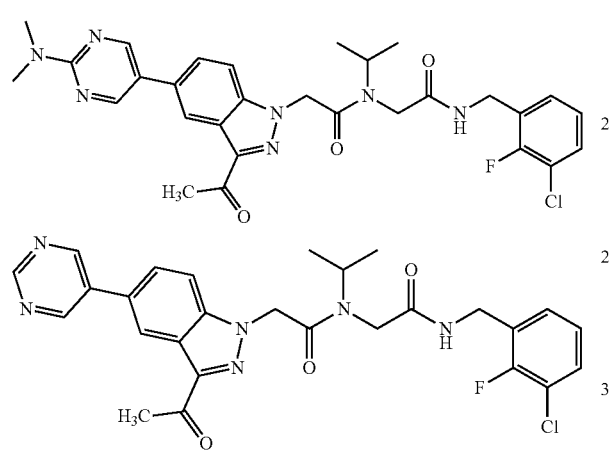
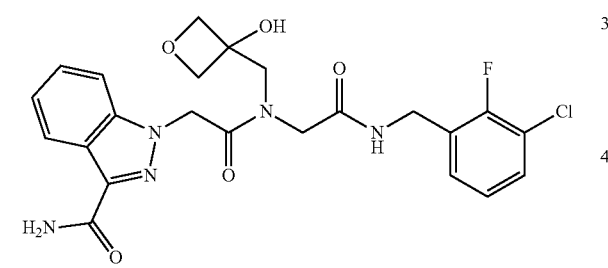
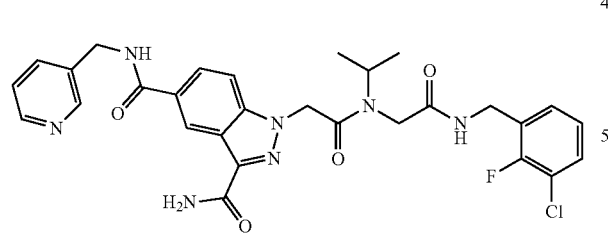
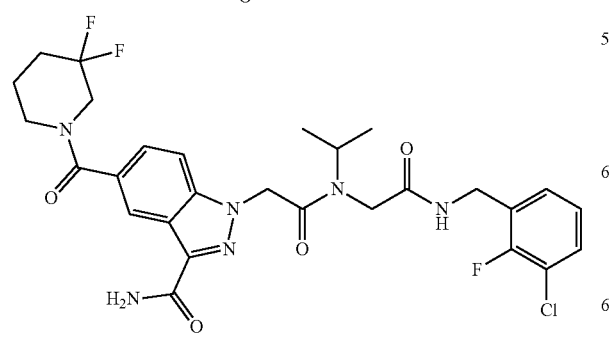
52
-continued
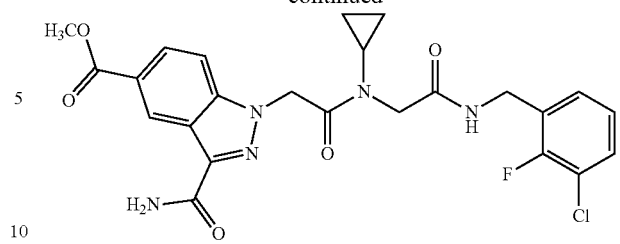
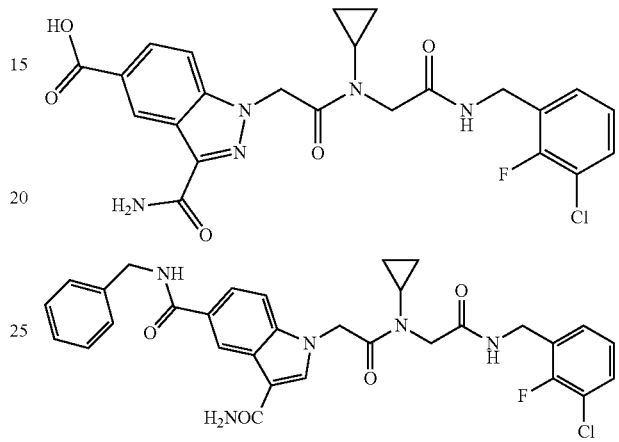
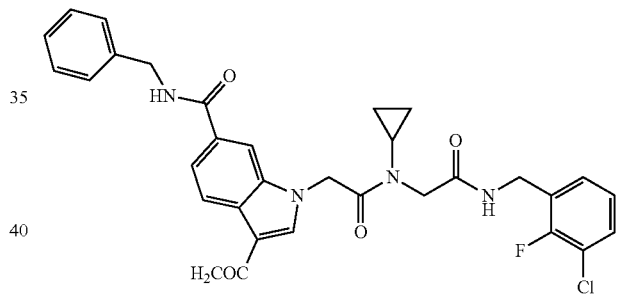
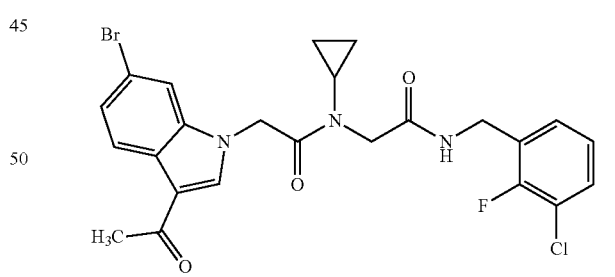
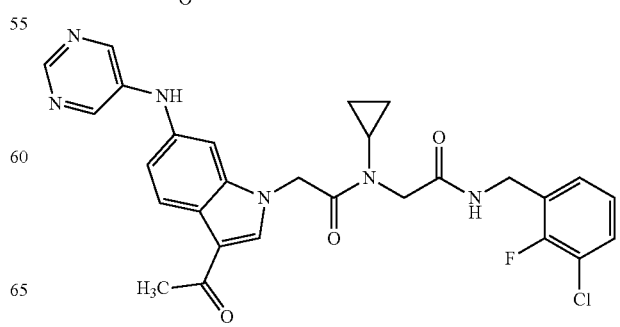

53
-continued
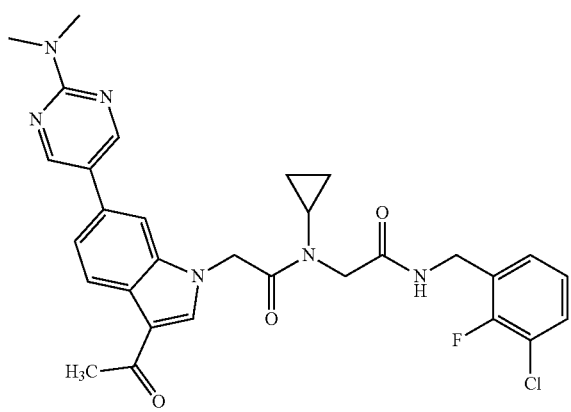
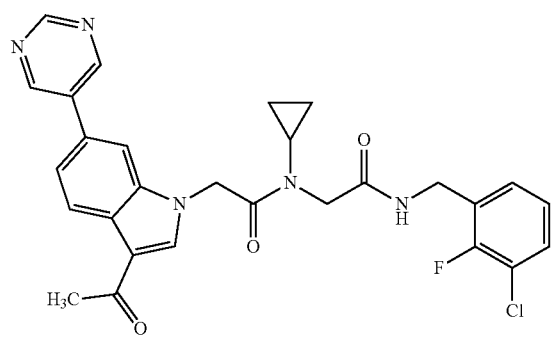
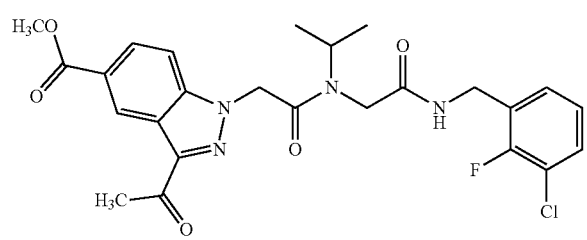
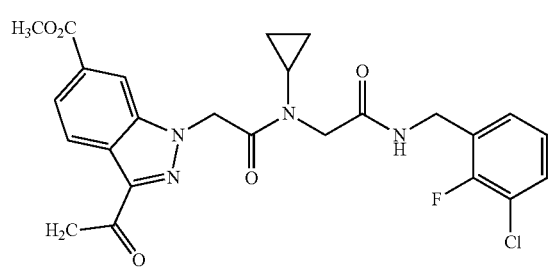
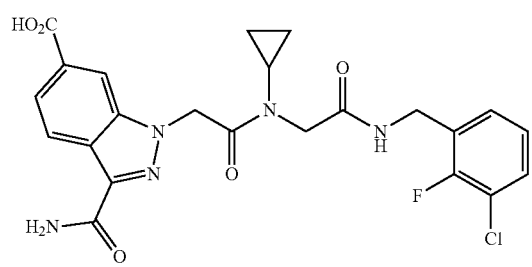
54
-continued
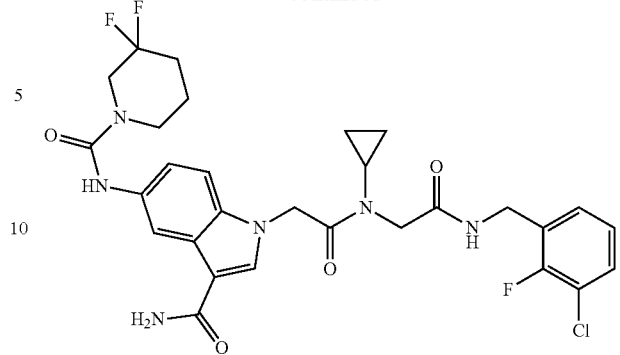
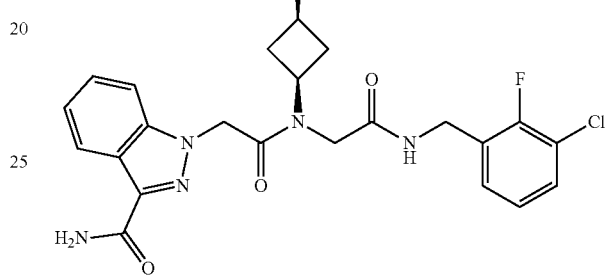
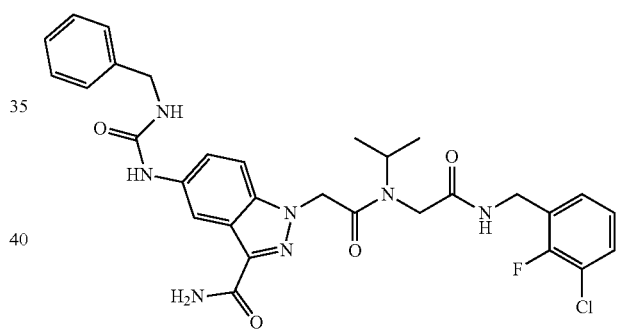
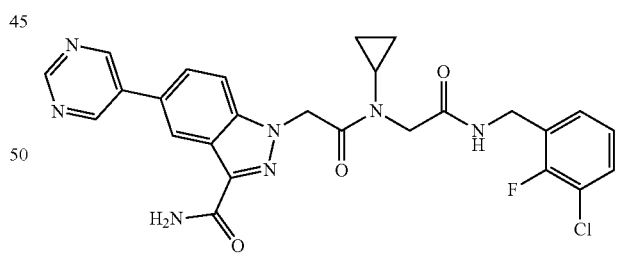
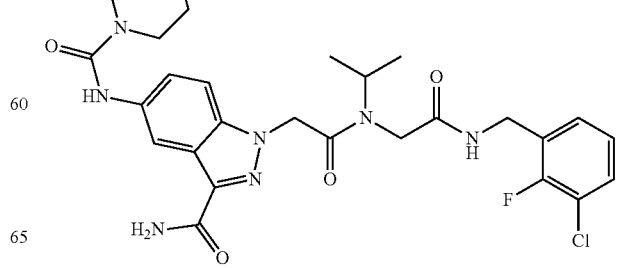

55
-continued
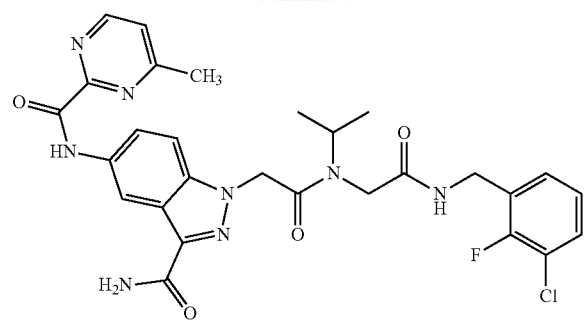
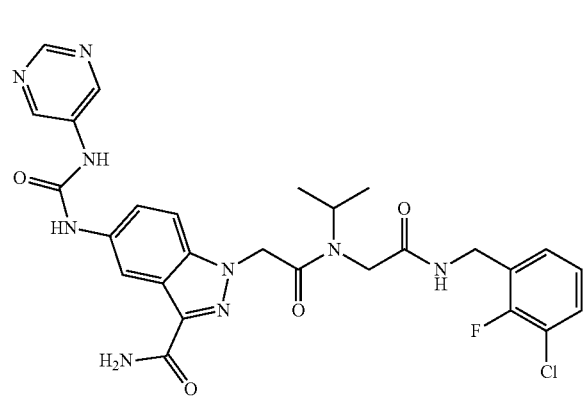
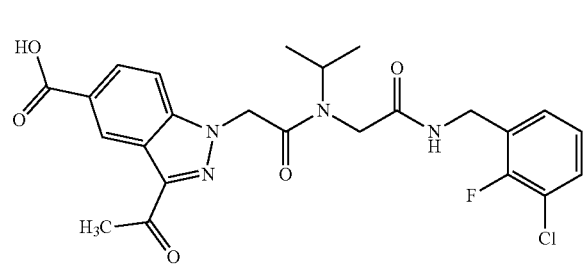
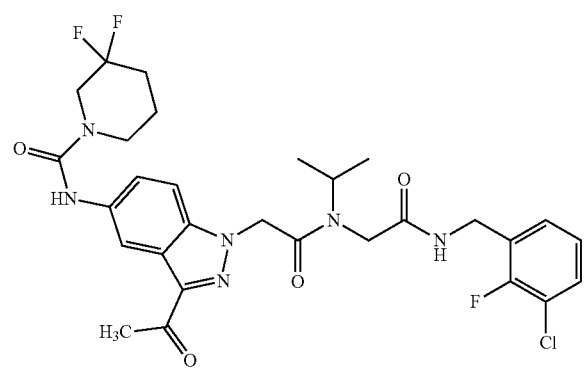
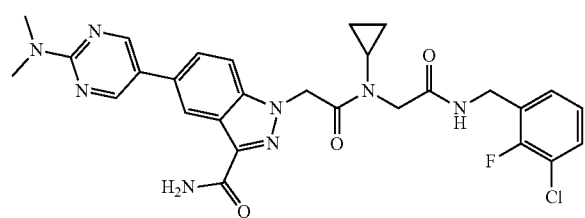
56
-continued
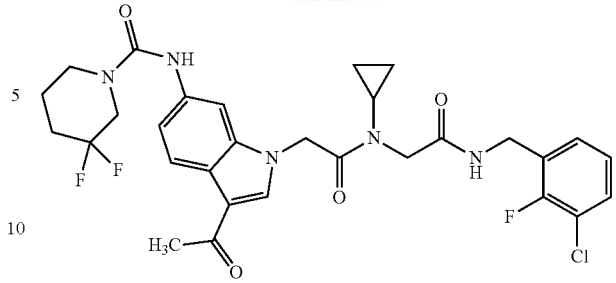
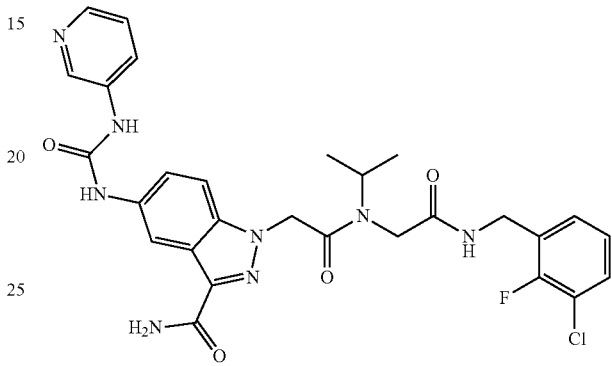
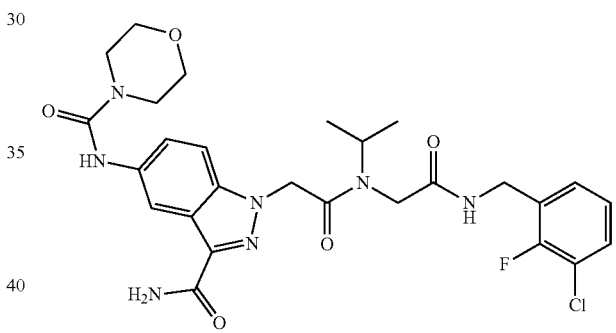
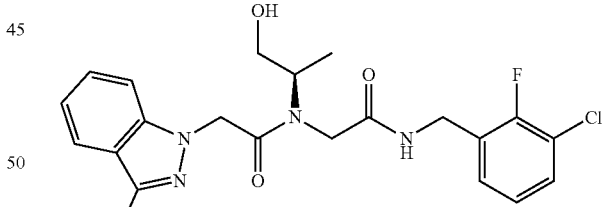
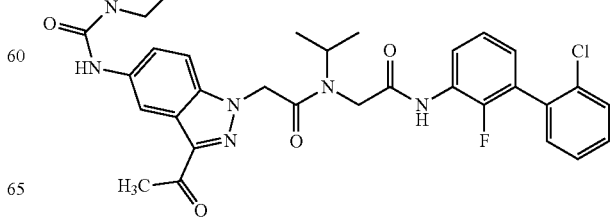

57
-continued
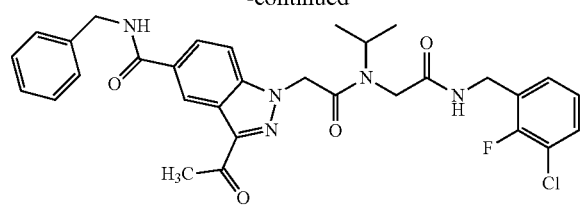
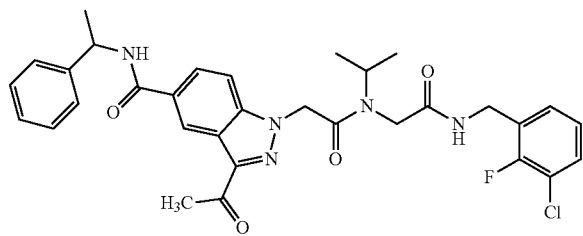
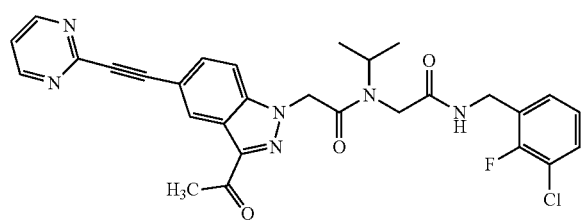
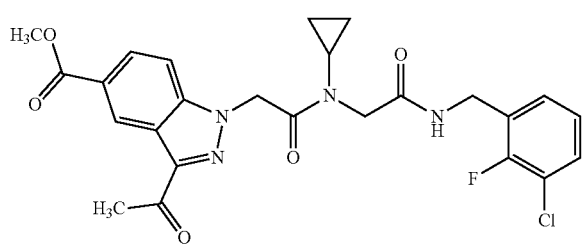
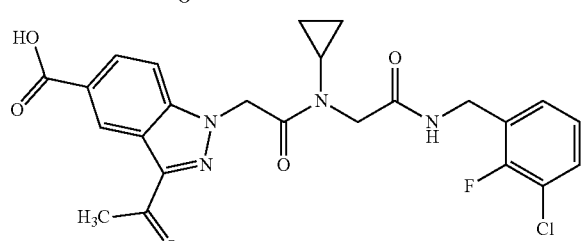
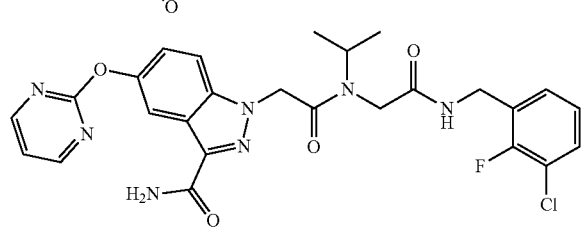
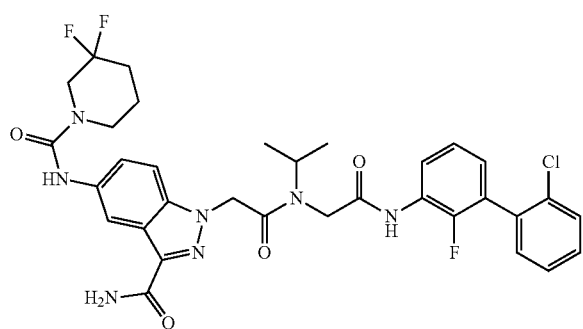
58
-continued
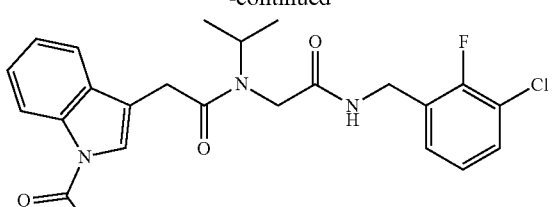
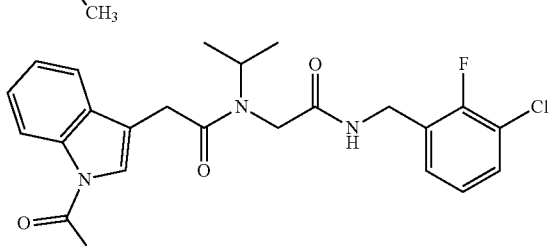
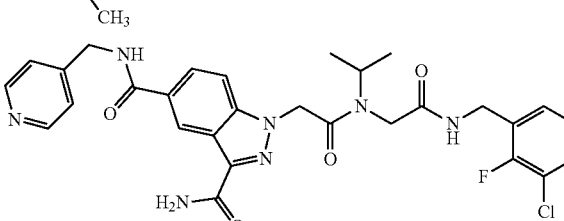
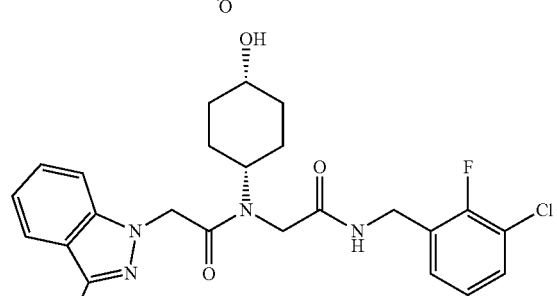
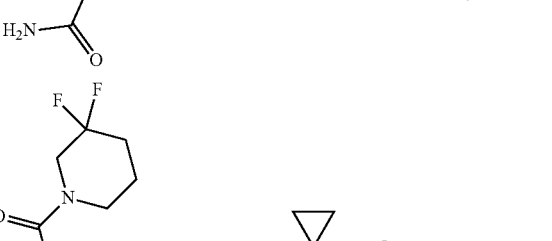
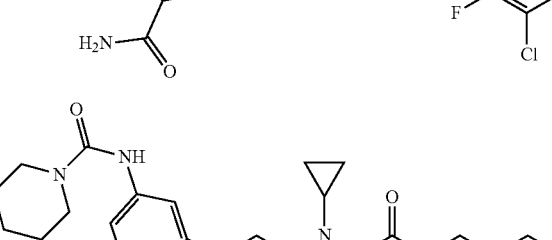
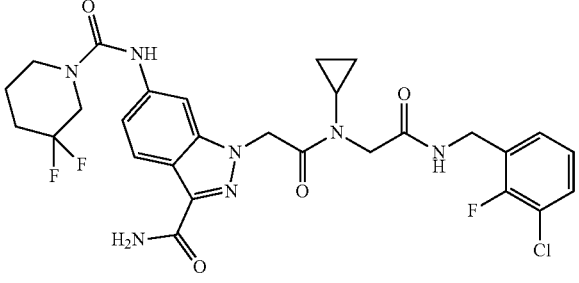

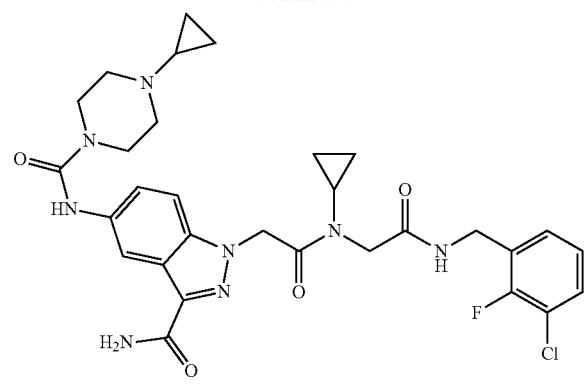
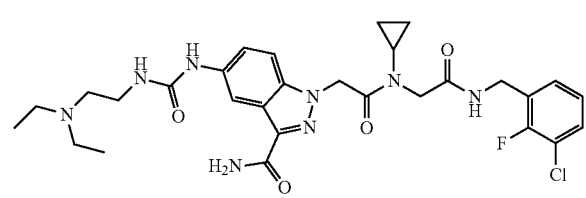
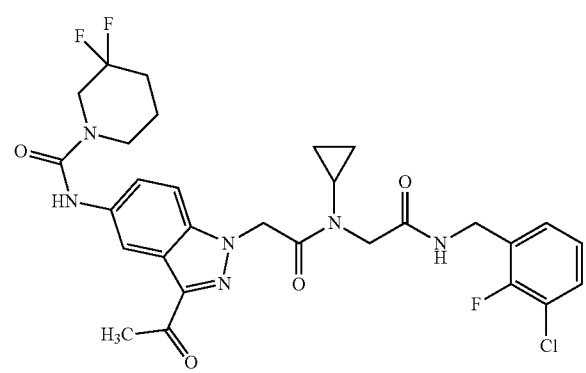
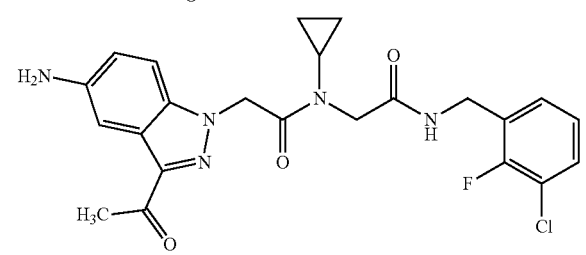
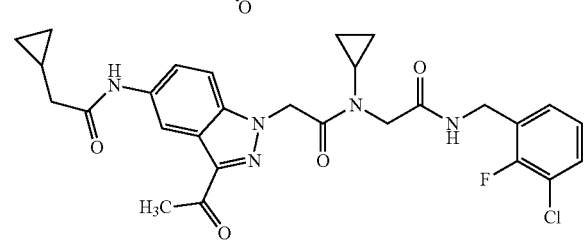
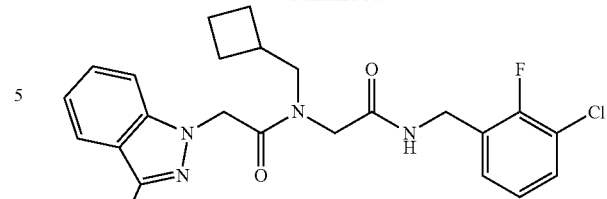
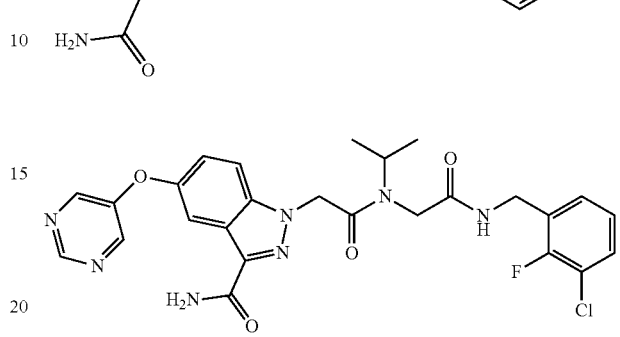
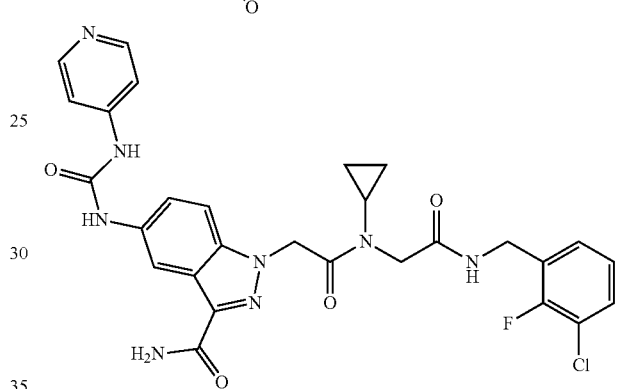
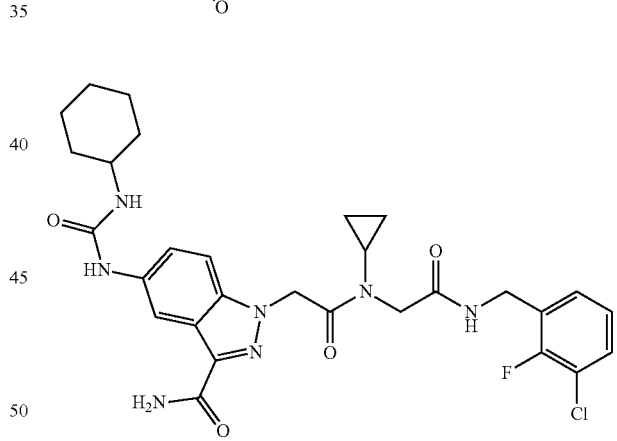
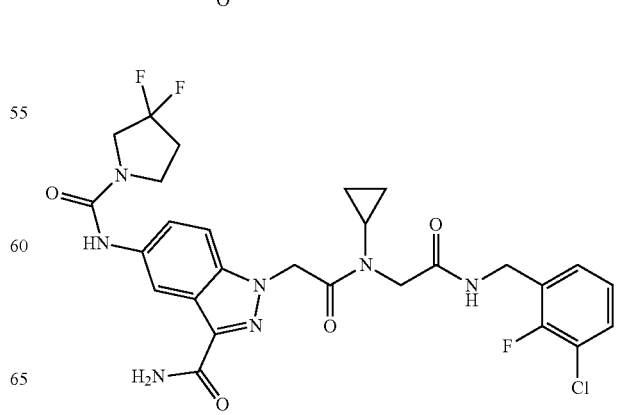

61
-continued
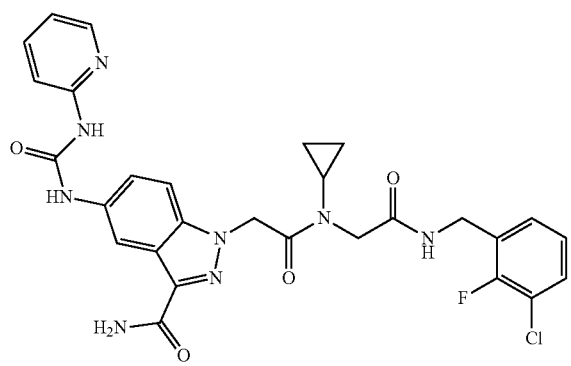
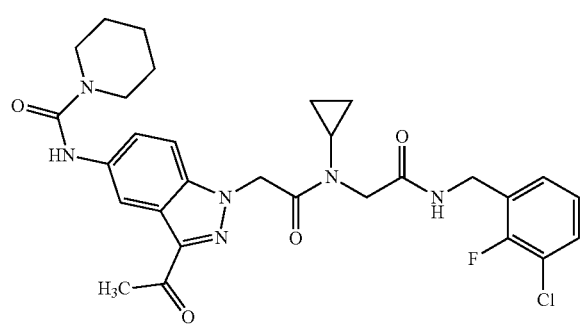
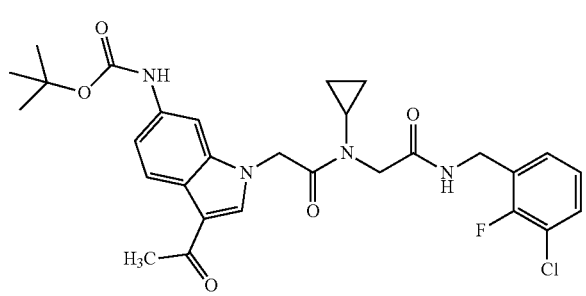
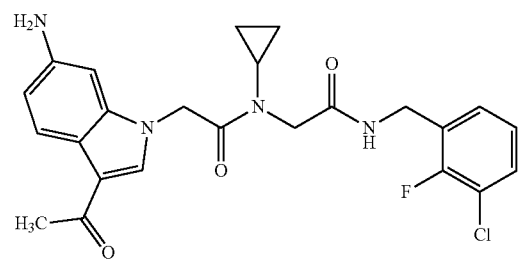
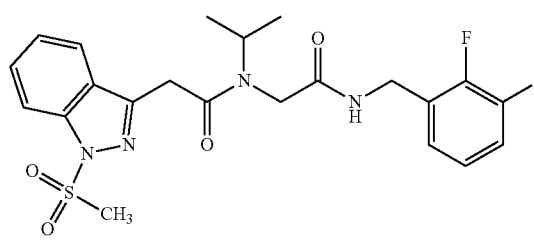
62
-continued
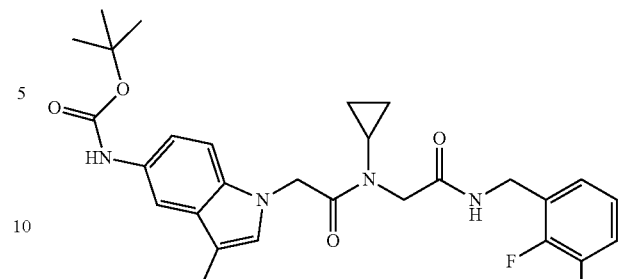
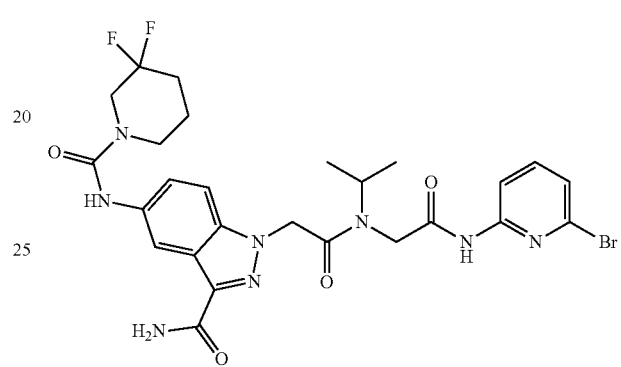
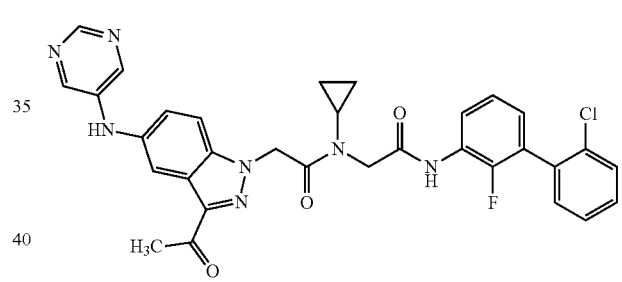
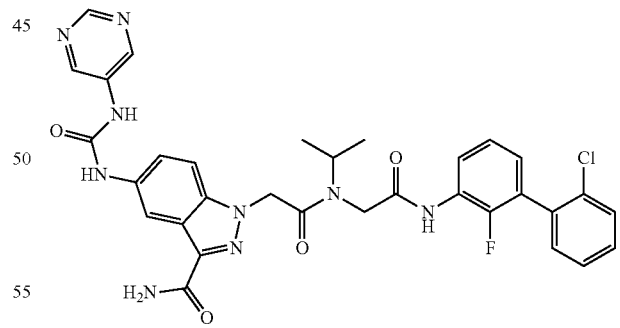
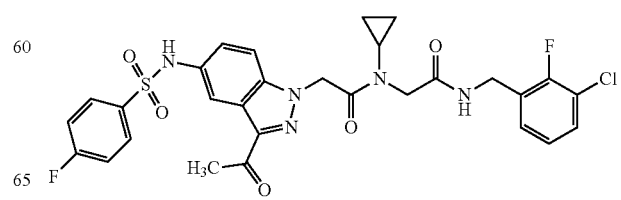

-continued
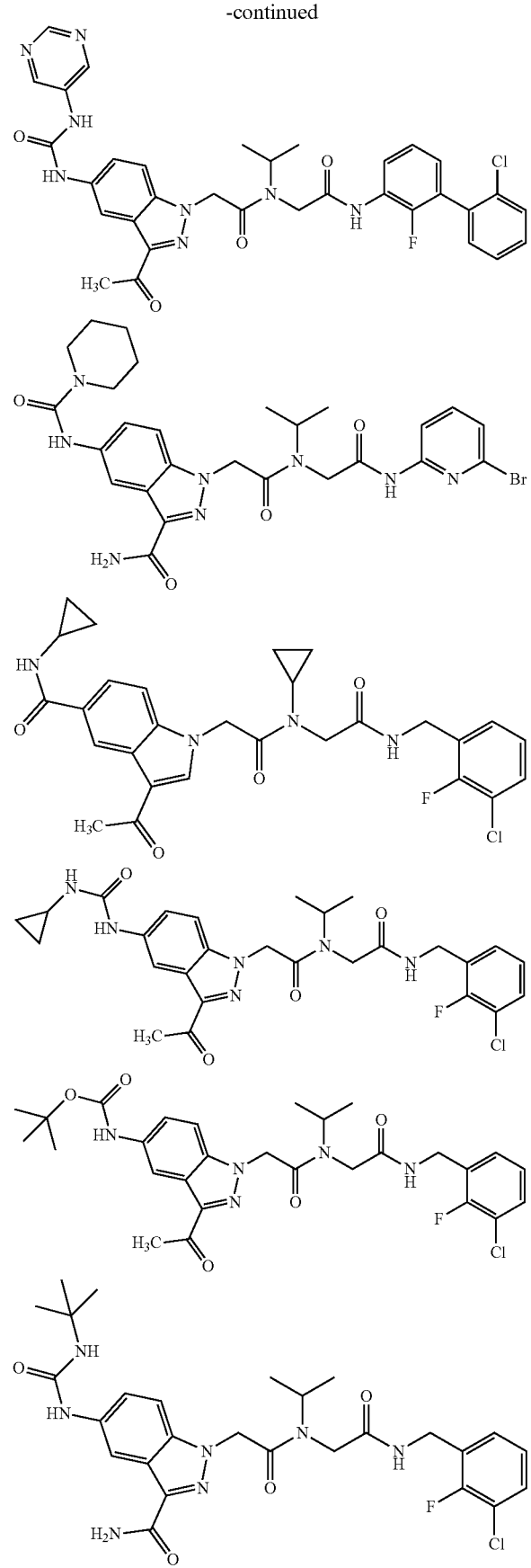
-continued
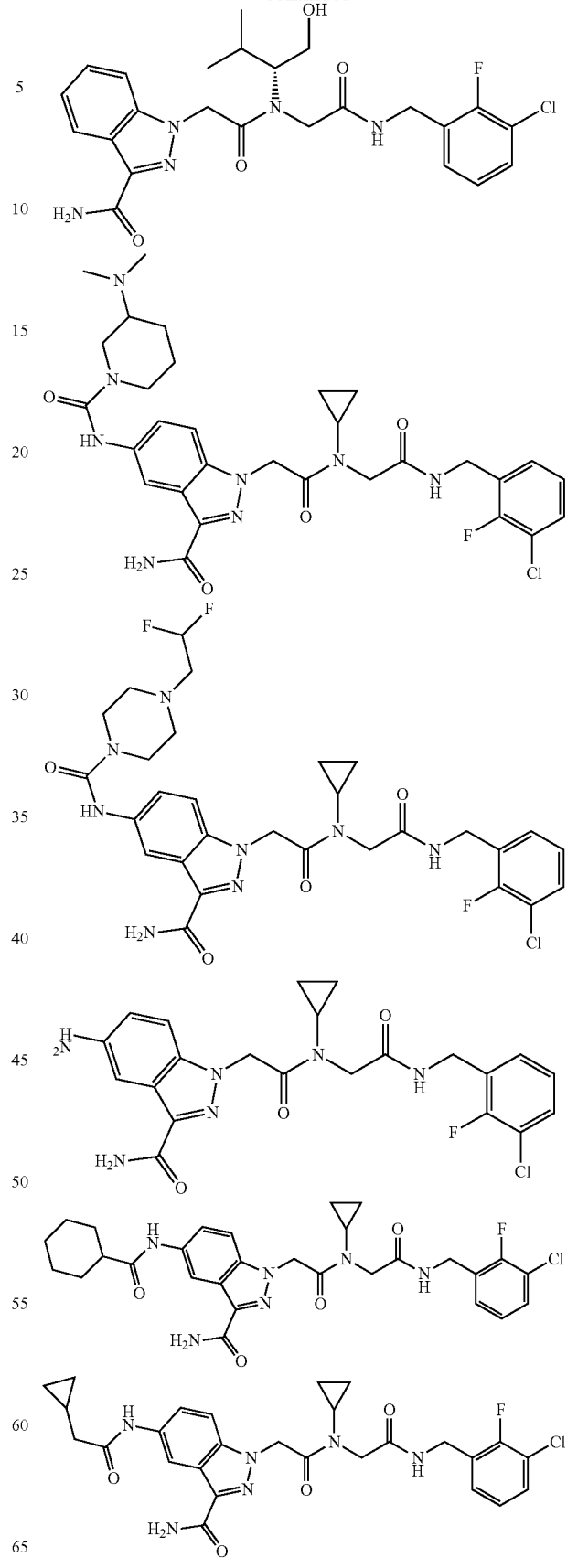

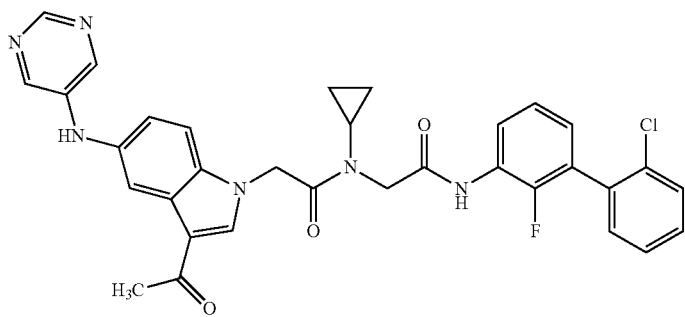
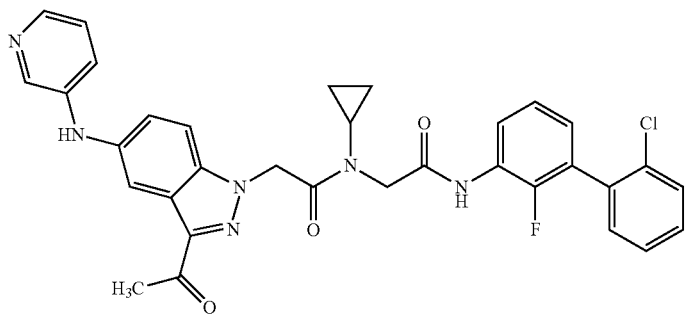
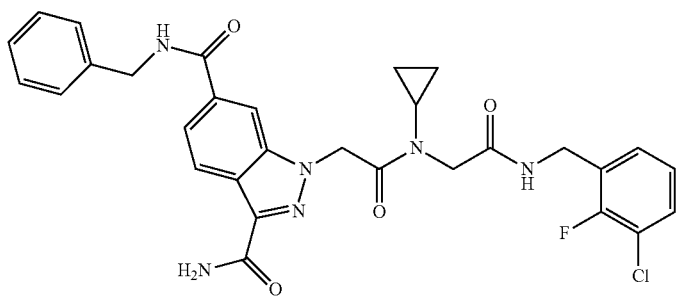
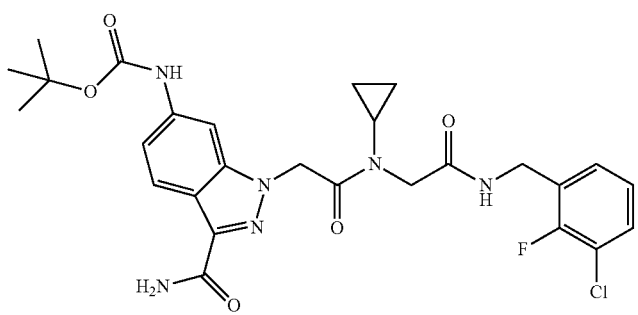
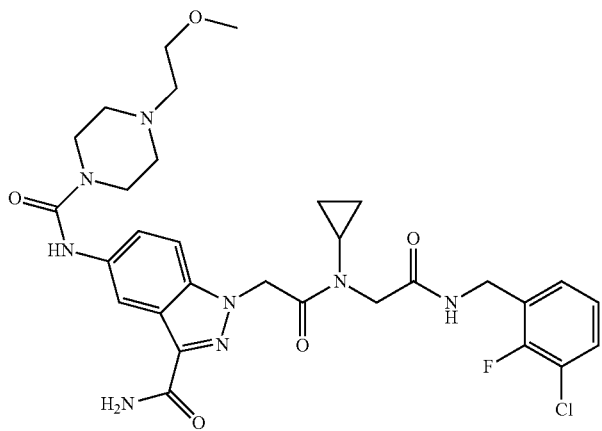

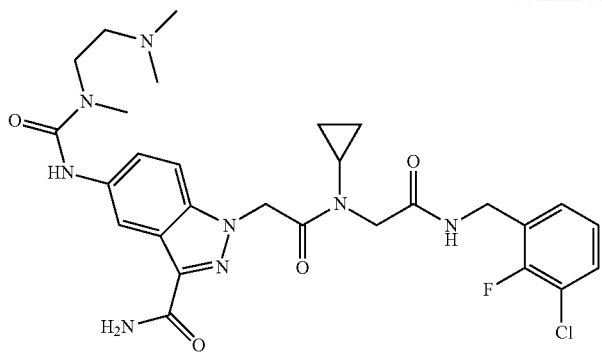
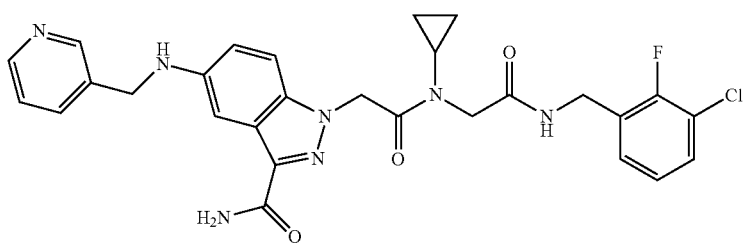
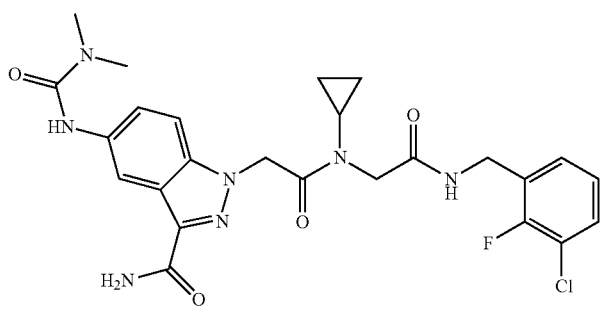
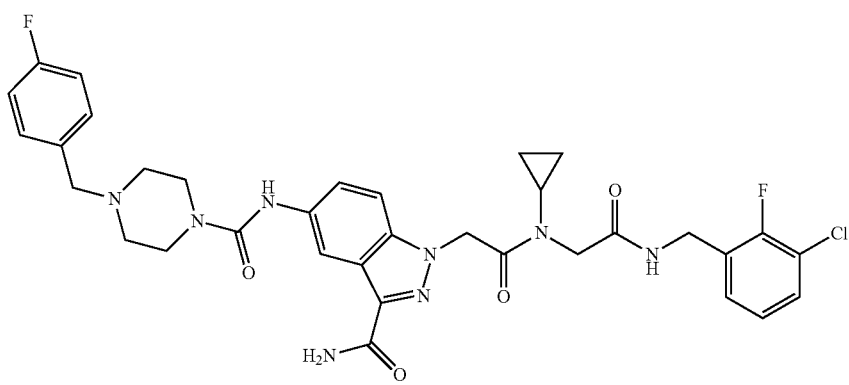
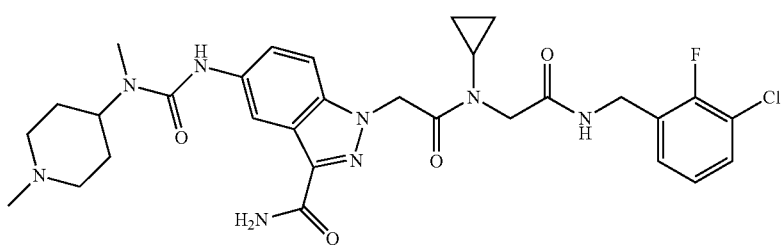

-continued
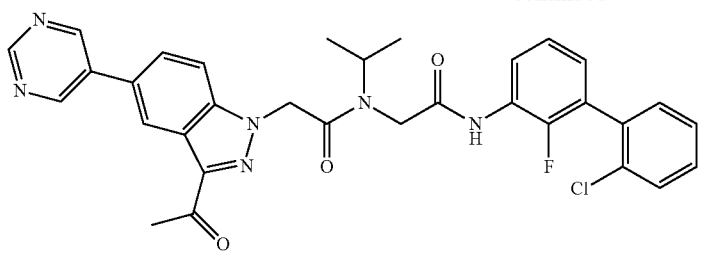
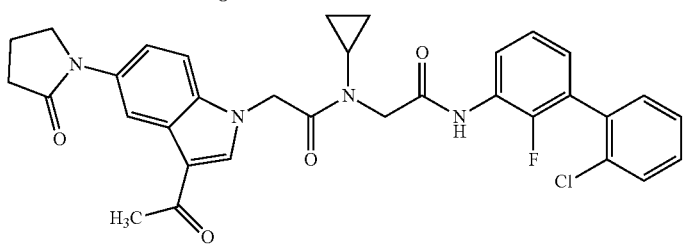
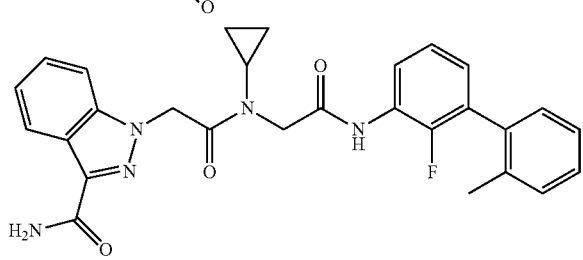
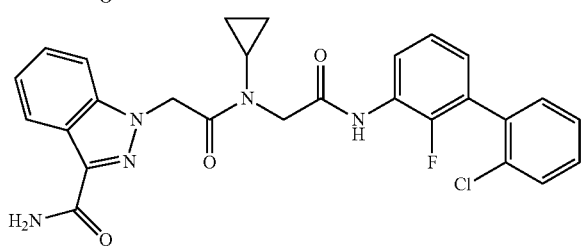
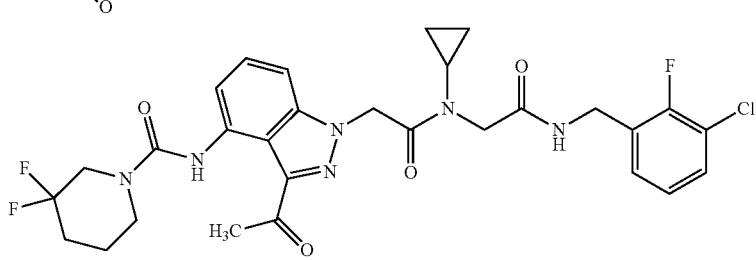
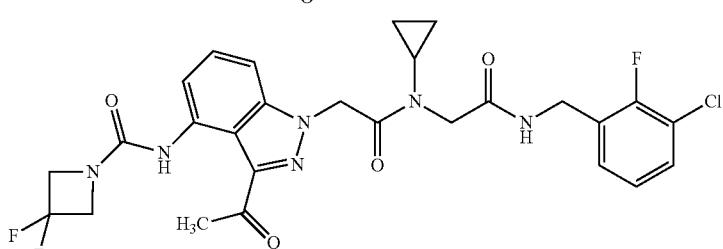
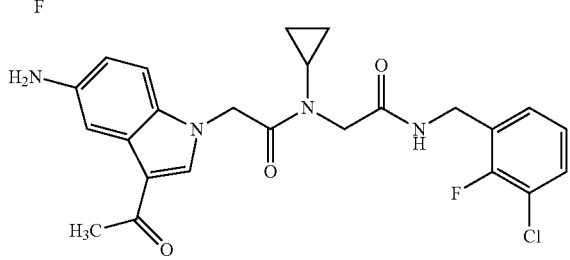

-continued
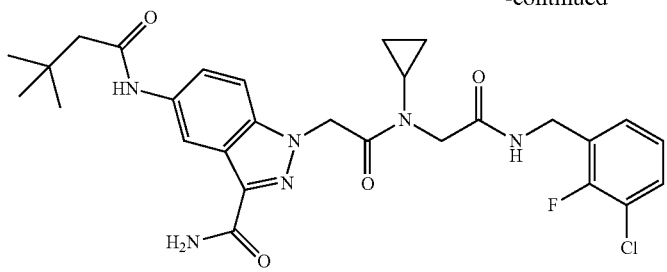
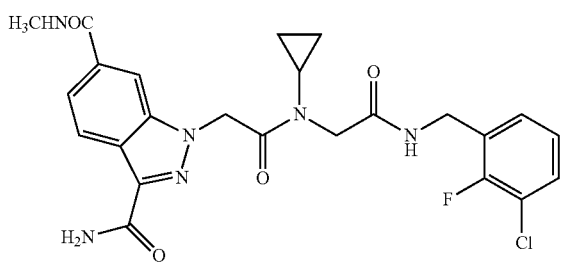
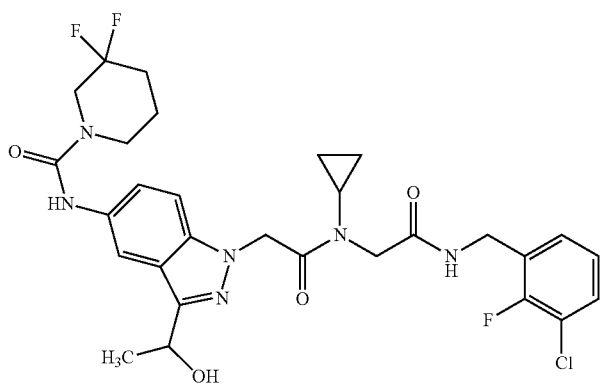
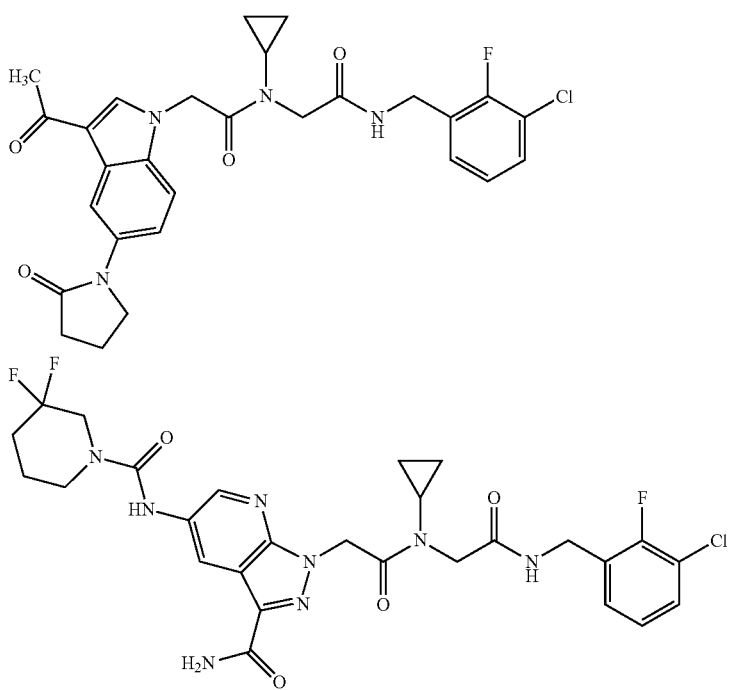

-continued
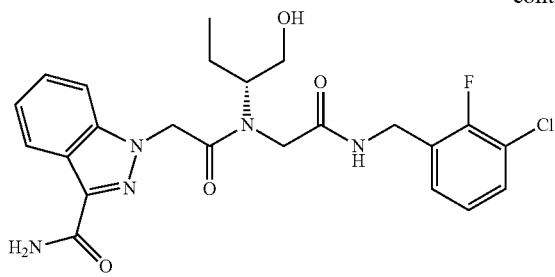
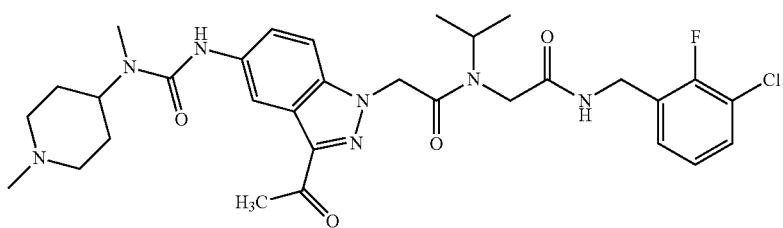
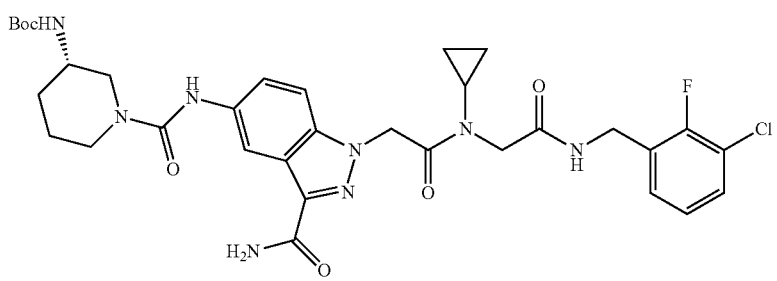
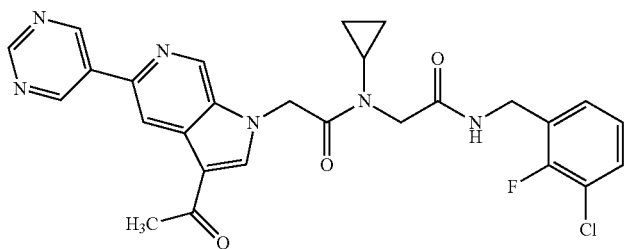
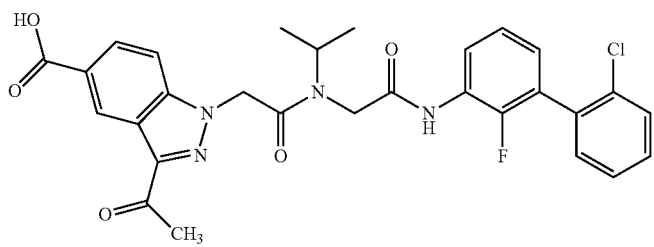
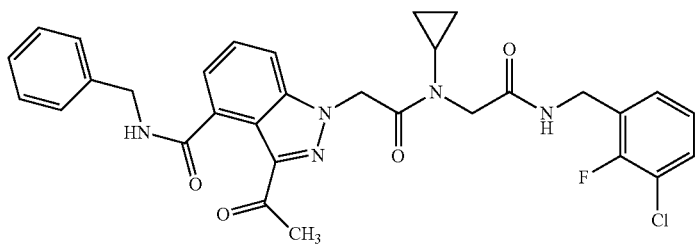

-continued
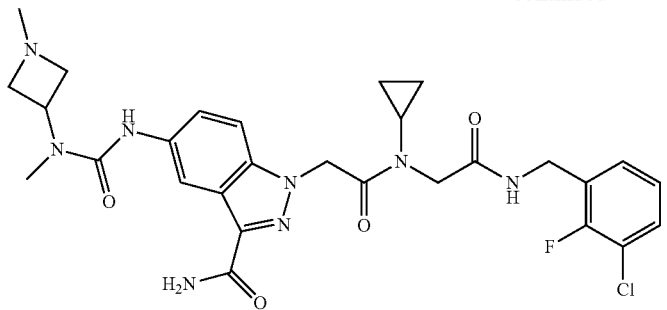
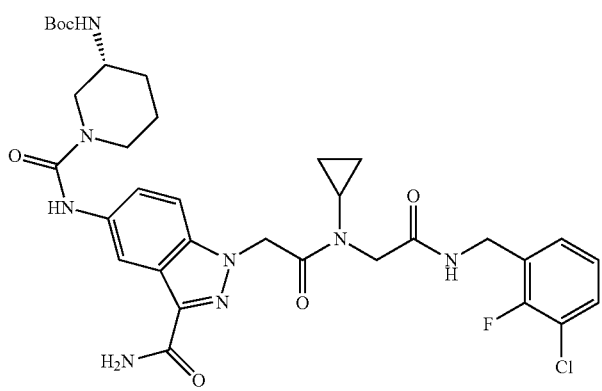
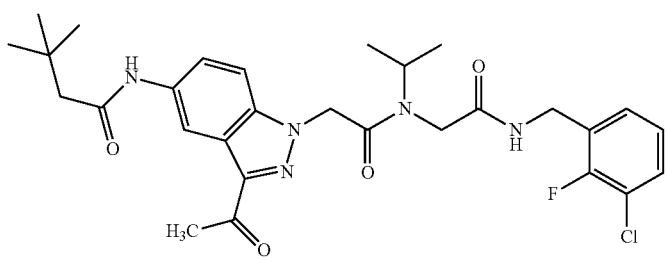
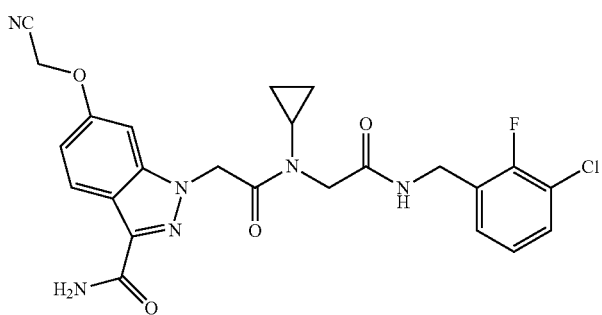
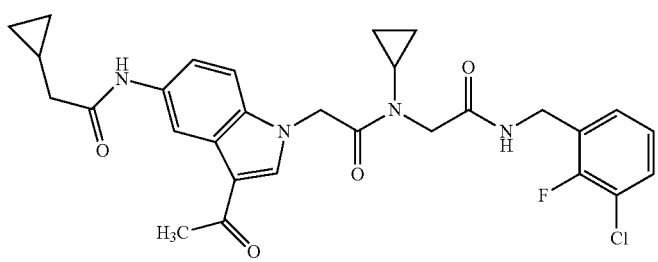

-continued
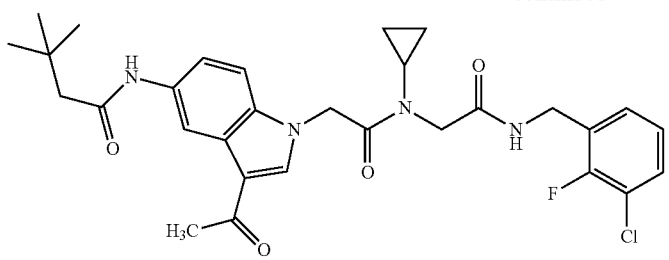
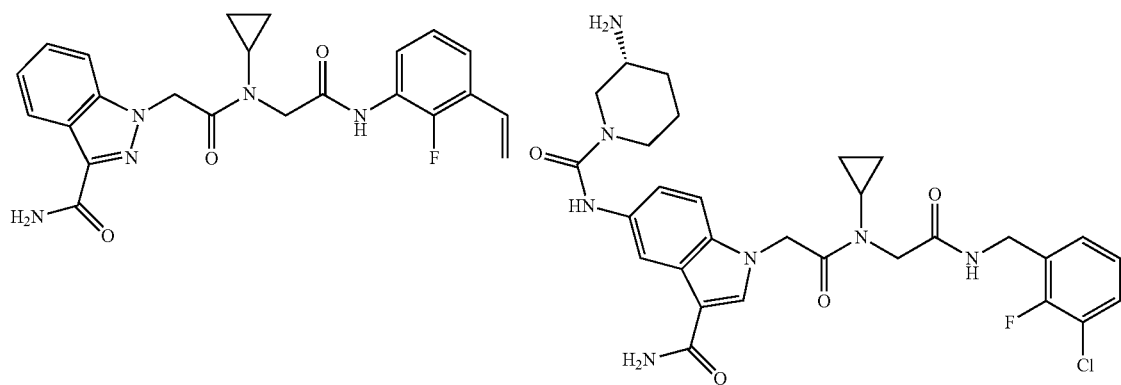
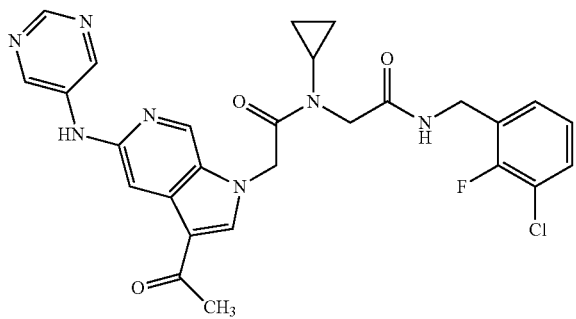
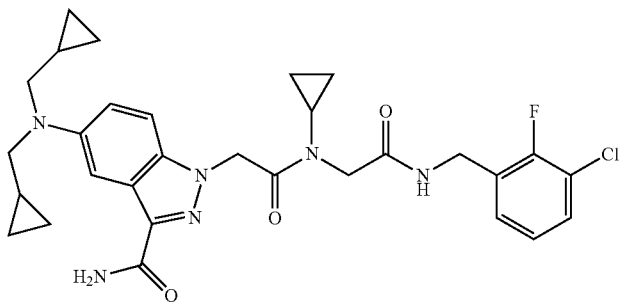
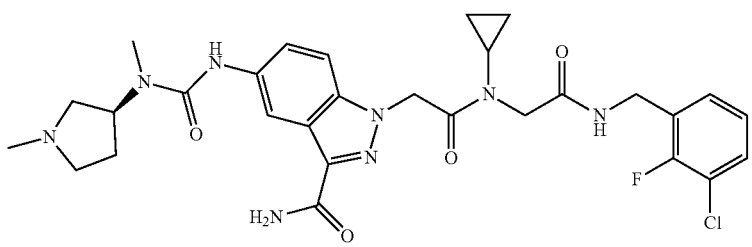

-continued
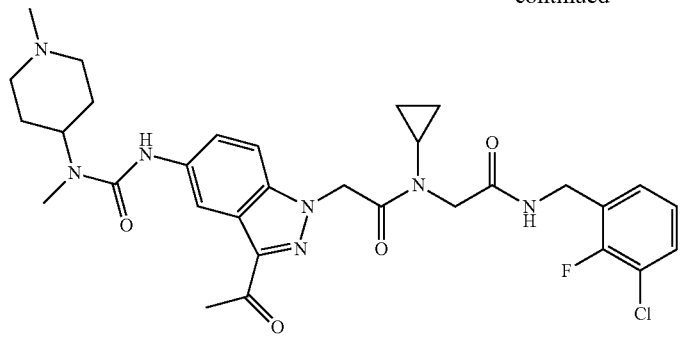
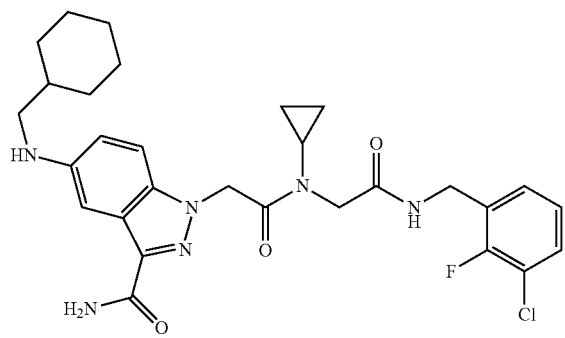
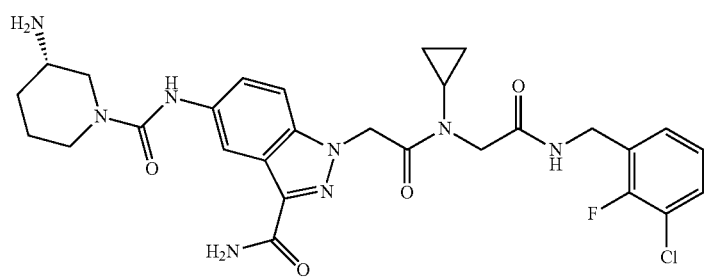
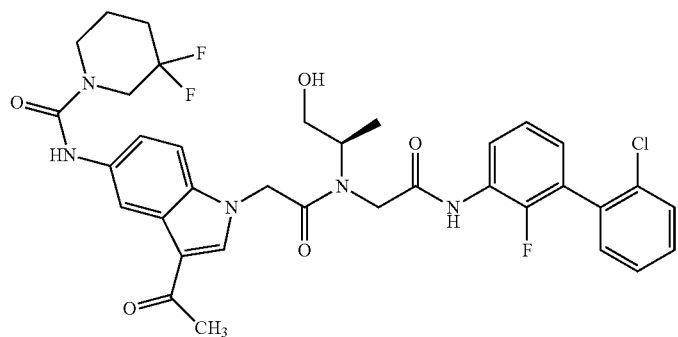
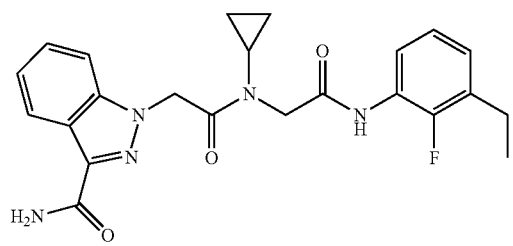

-continued
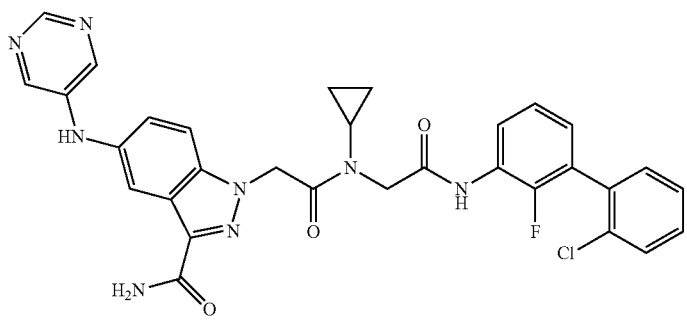
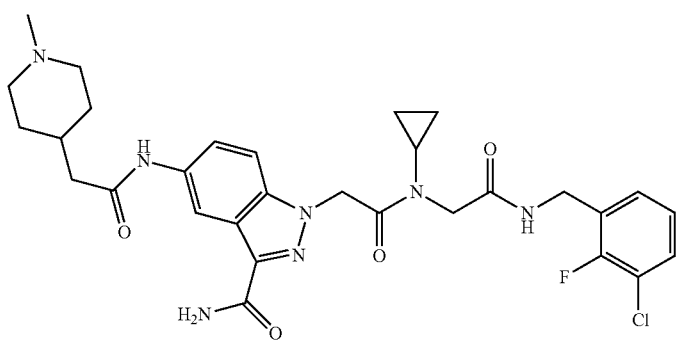
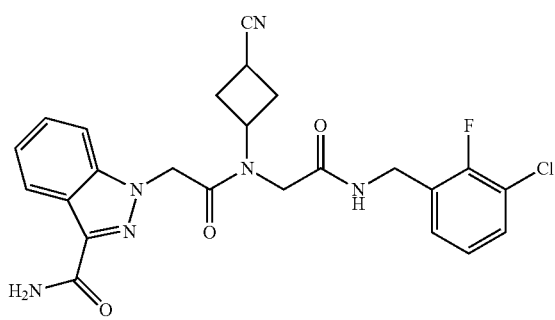
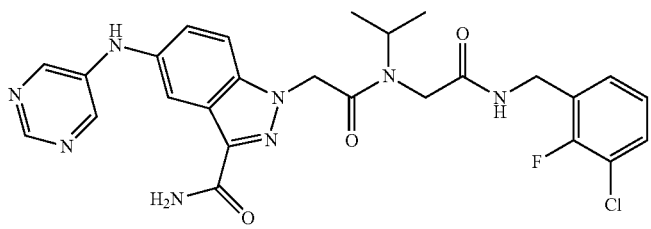
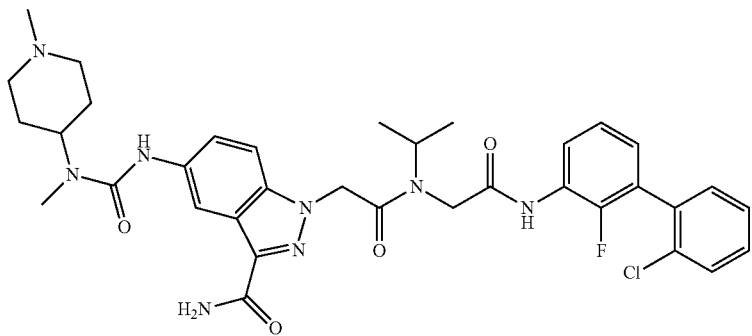

-continued
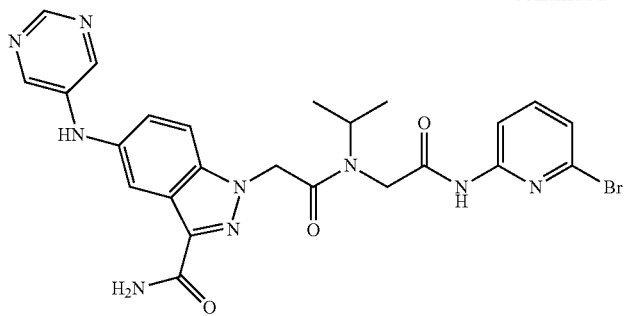
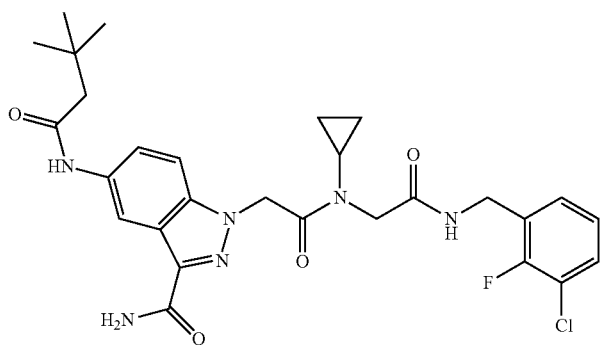
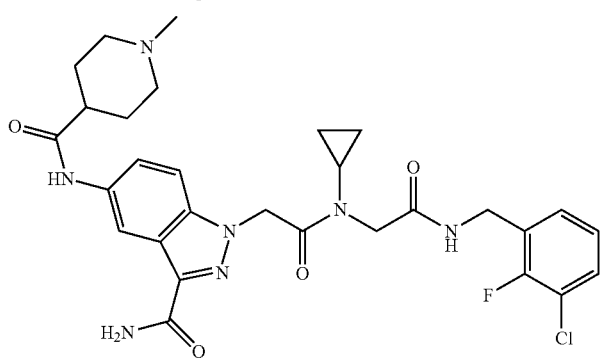
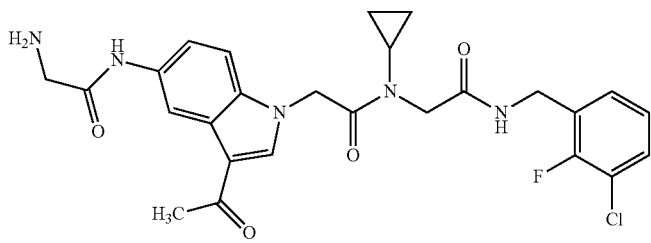
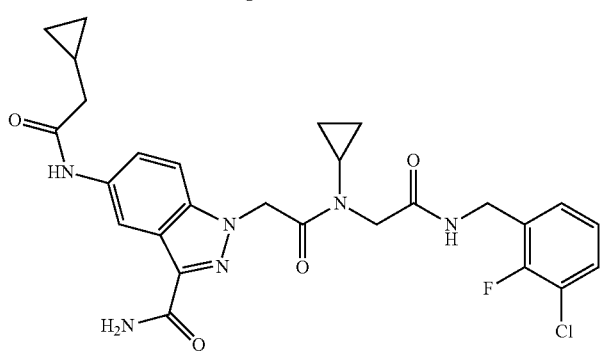

85
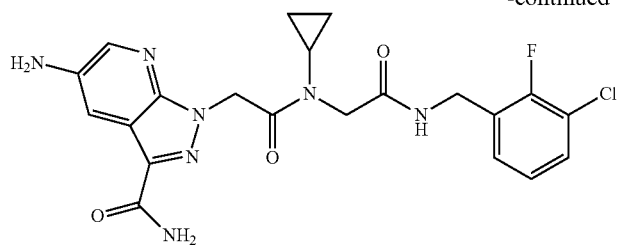
-continued
86
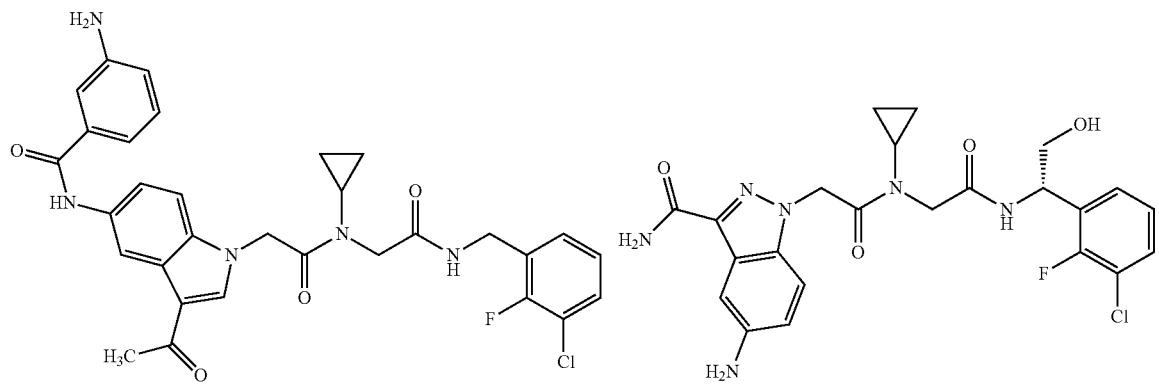
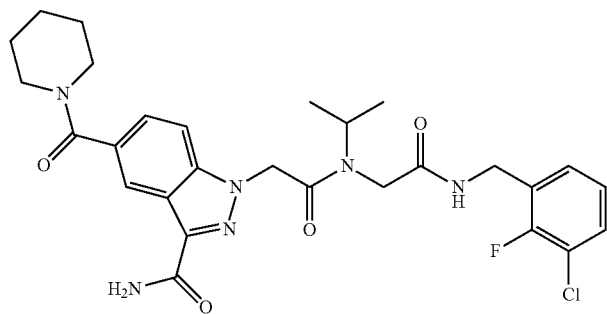
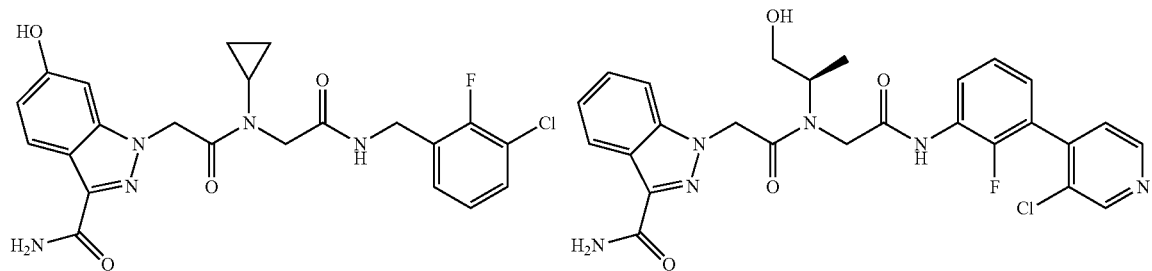
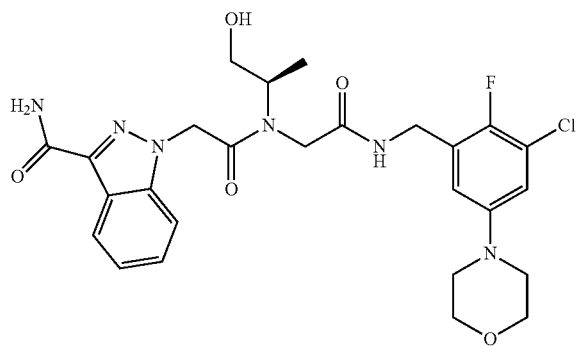

87
-continued
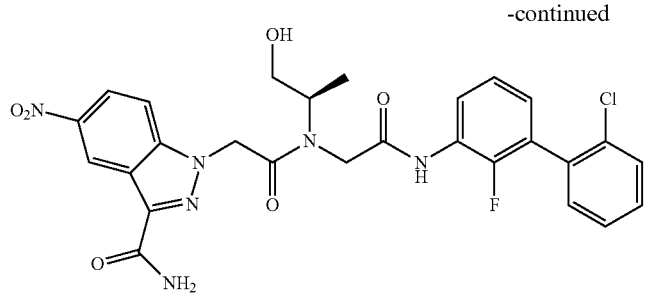
88
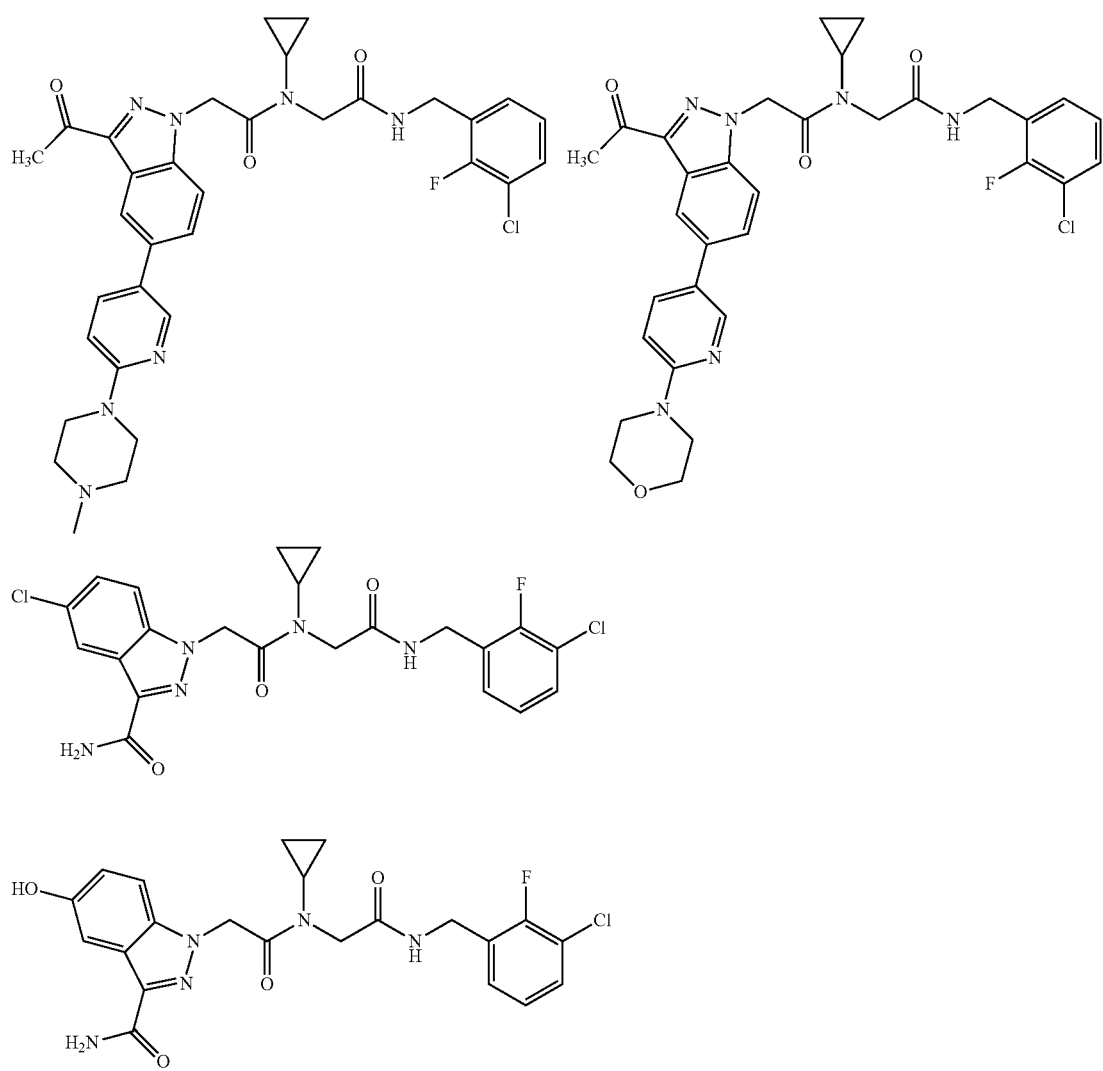
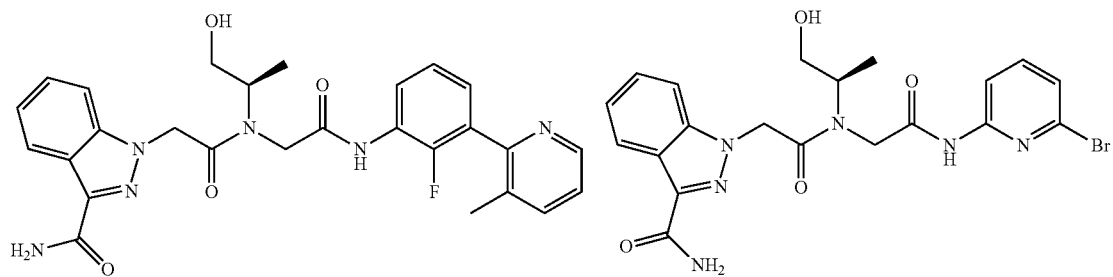

-continued
89
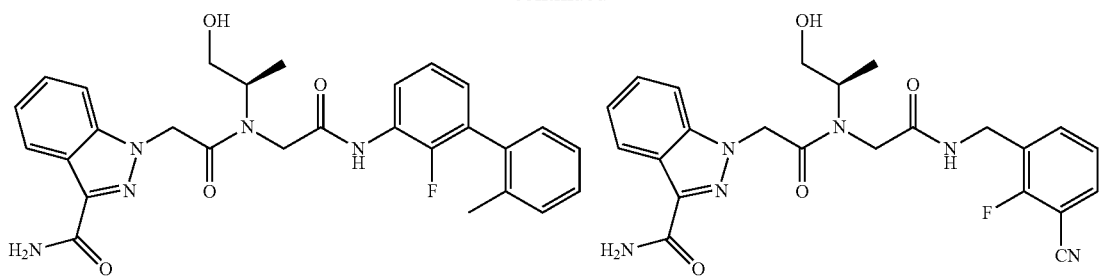
90
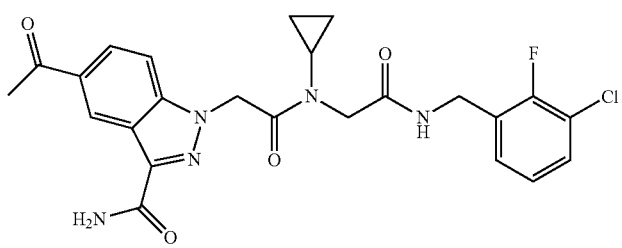
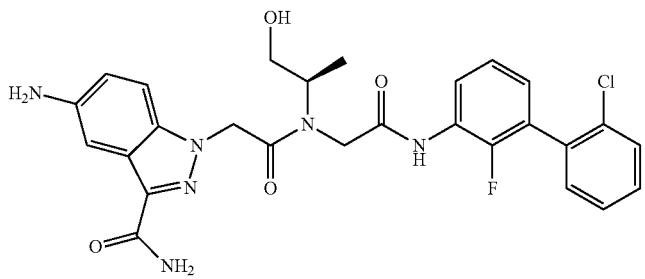
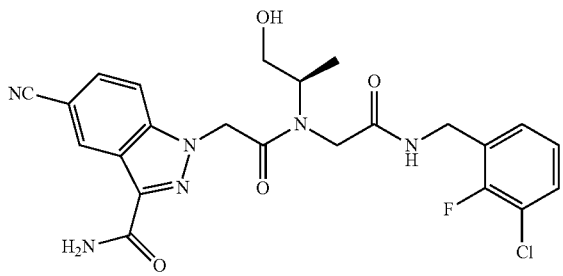
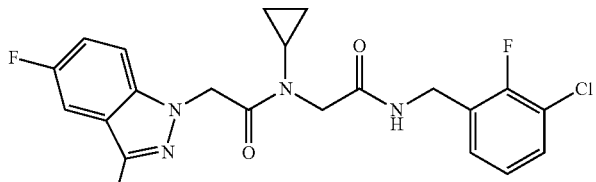
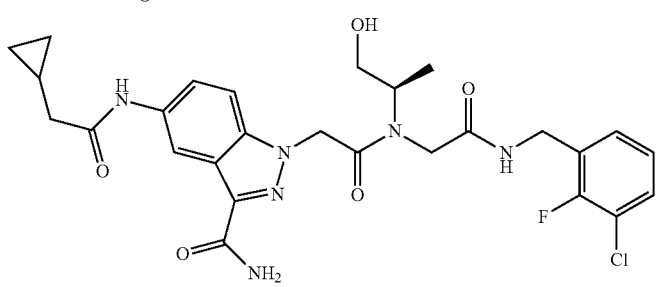

-continued
| 91 | 92 |
|---|---|
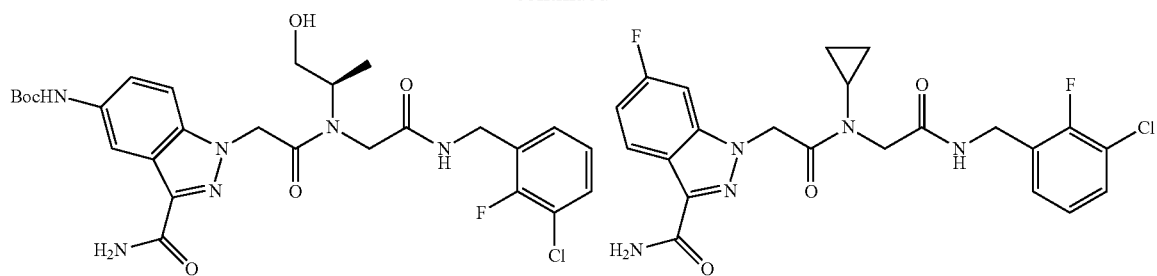
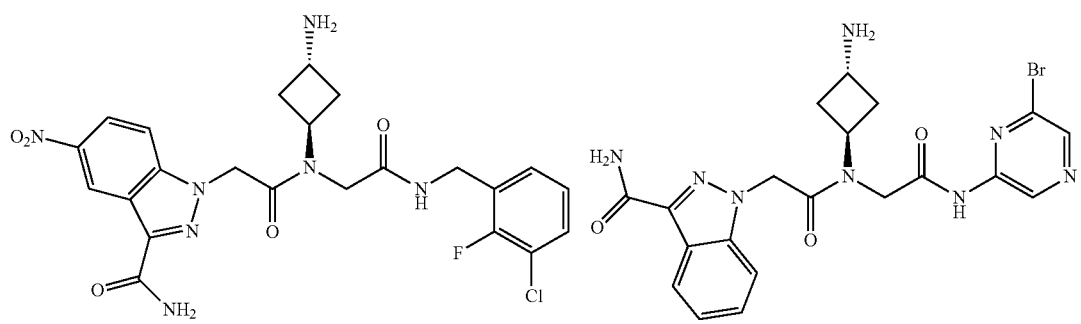
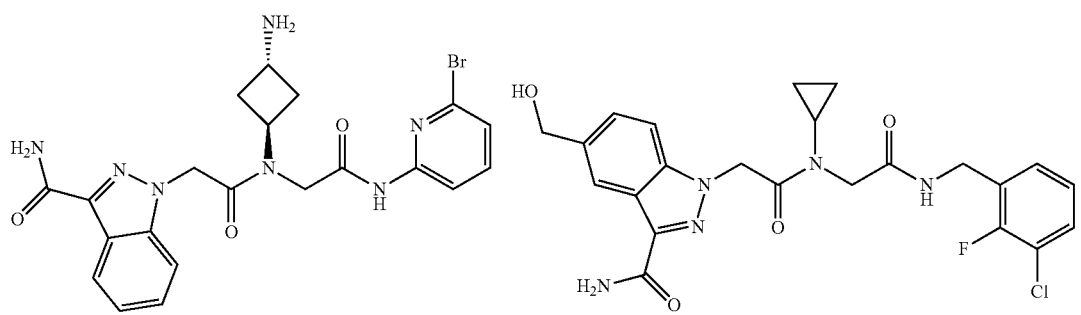
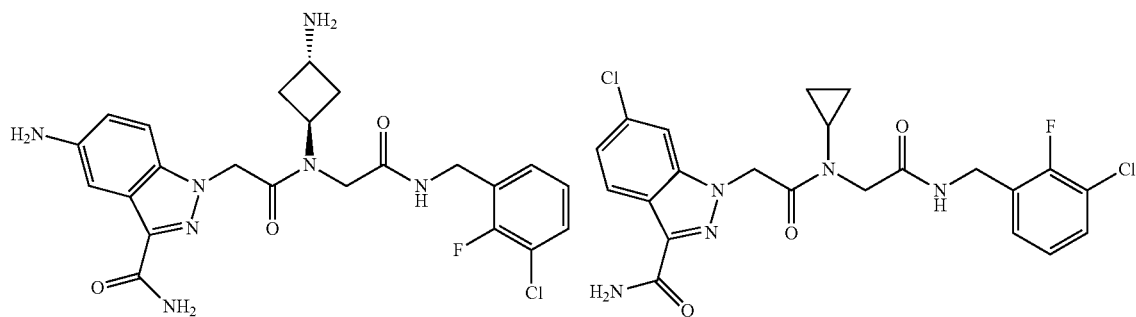
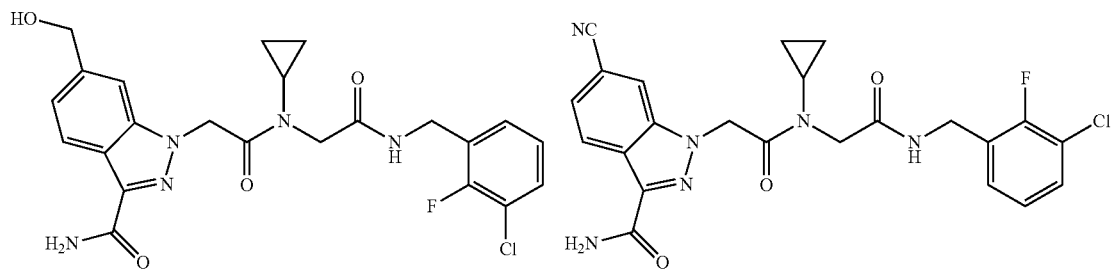

-continued
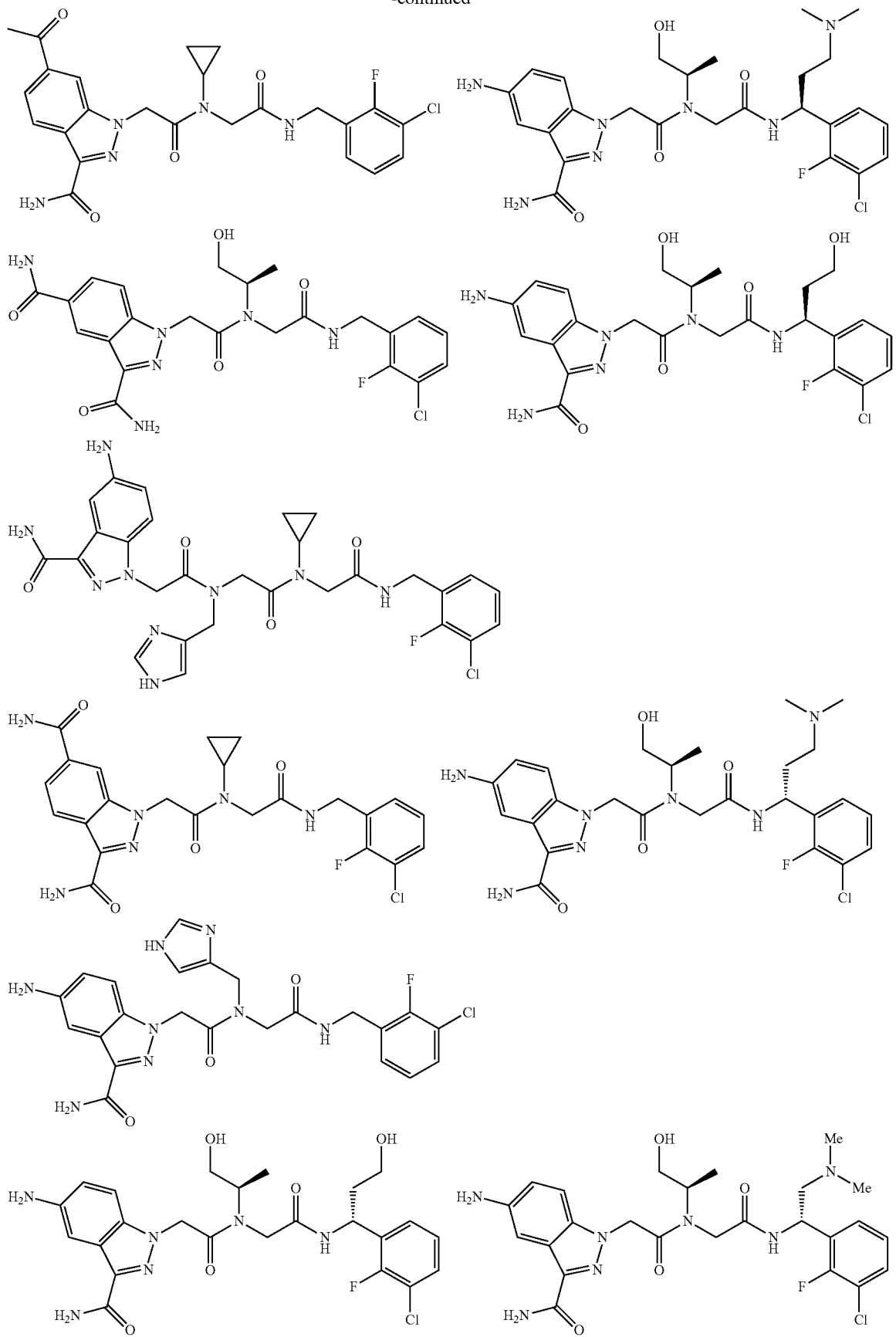

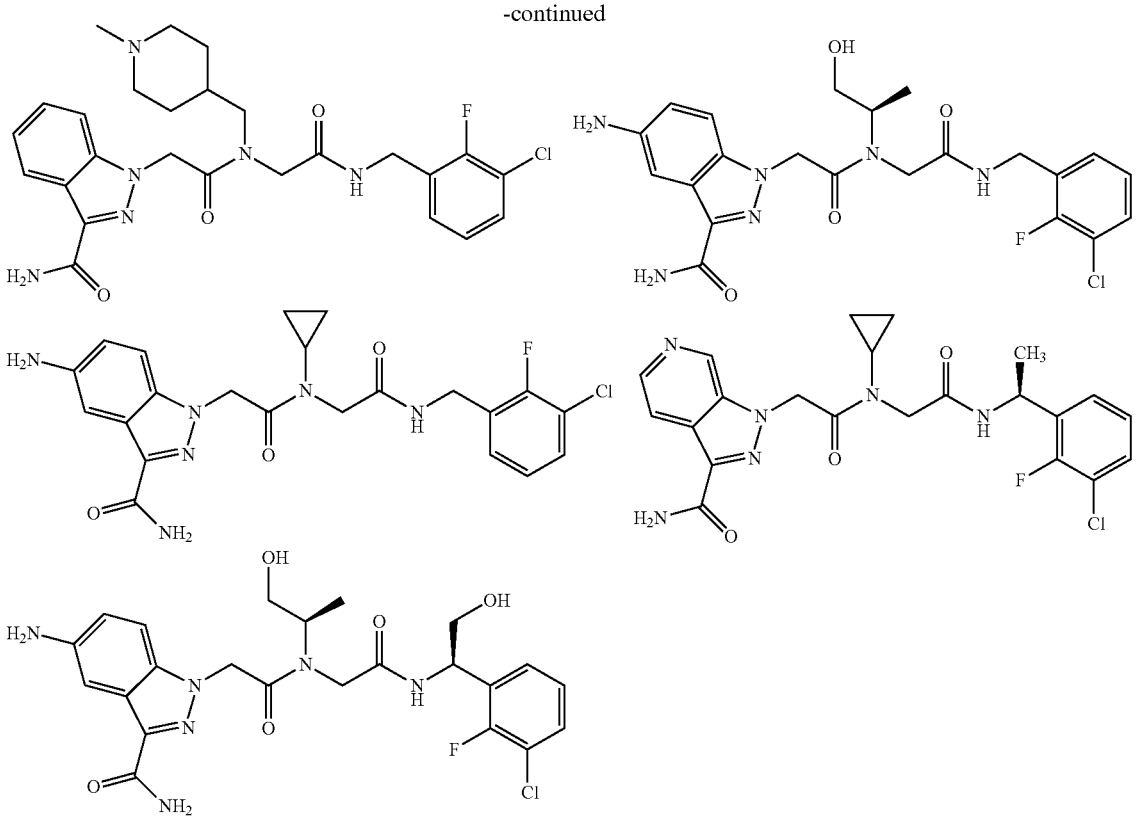

Pharmaceutical Compositions

The invention provides pharmaceutical compositions, each comprising one or more compounds of the invention and a pharmaceutically acceptable carrier. In certain embodiments, the pharmaceutical composition comprises a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant complement system activity.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds that useful for treating or preventing a disease or condition characterized by aberrant complement system activity.

In certain aspects, the invention provides a compound of the invention, or a pharmaceutically acceptable salt thereof, for use as a medicament.

In certain aspects, the invention provides methods of treating or preventing a disease or condition characterized by aberrant complement system activity. The method includes the step of administering to a subject in need thereof a therapeutically effective amount of a compound of the invention, or a pharmaceutically acceptable salt thereof, thereby treating or preventing the disease or condition characterized by aberrant complement system activity. By reducing complement system activity in the subject, the disease or condition characterized by aberrant complement system activity is treated.

Alternatively, in certain aspects, the invention provides a compound of the invention, or a pharmaceutically acceptable salt thereof, for treatment of a disease or condition characterized by aberrant complement system activity.

Alternatively, in certain aspects, the invention provides the use of a compound of the invention, or a pharmaceutically acceptable salt thereof, for the manufacture of a medicament for use in treatment of a disease or condition characterized by aberrant complement system activity.

As used herein, a "disease or condition characterized by aberrant complement system activity" refers to any disease or condition in which it is desirable to reduce complement system activity. For example, it may be desirable to reduce complement system activity in the setting of inappropriate activation or hyperactivation of the complement system.

In certain embodiments, the disease or condition characterized by aberrant complement system activity is an immunological disorder.

In certain embodiments, the disease or condition characterized by aberrant complement system activity is a disease of the central nervous system.

In certain embodiments, the disease or condition characterized by aberrant complement system activity is a renal disease.

In certain embodiments, the disease or condition characterized by aberrant complement system activity is a cardiovascular disease.

In certain embodiments, the disease or condition characterized by aberrant complement system activity is a neurodegenerative disease or neurological disease In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

In certain embodiments, the disease or condition is paroxysmal nocturnal hemoglobinuria.

In certain embodiments, the disease or condition is atypical hemolytic uremic syndrome.

In certain embodiments, the disease or condition is organ transplant rejection.

In certain embodiments, the disease or condition is myasthenia gravis.

In certain embodiments, the disease or condition is neuromyelitis optica.

In certain embodiments, the disease or condition is membranoproliferative glomerulonephritis.

In certain embodiments, the disease or condition is dense-deposit disease.

In certain embodiments, the disease or condition is cold agglutinin disease.

In certain embodiments, the disease or condition is catastrophic antiphospholipid syndrome.

In other embodiments, the the disease or condition characterized by aberrant complement system activity is adult respiratory distress syndrome, myocardial infarct, lung inflammation, hyperacute rejection (transplantation rejection), sepsis, cardiopulmonary bypass, burns, asthma, restenosis, multiple organ dysfunction syndrome, Guillain-Barré syndrome, hemorrhagic shock, paroxysmal nocturnal hemoglobinuria, glomerulonephritis, systemic lupus erythematosus, rheumatoid arthritis, infertility, Alzheimer's disease, organ rejection (transplantation), myasthenia gravis, multiple sclerosis, platelet storage, or hemodialysis.

Formulations, Routes of Administration, and Dosing

The compounds of the invention can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or an active salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful for treating or preventing ischemia, blood loss, or reperfusion injury.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to a mammal to treat or prevent a disease or condition characterized by aberrant complement system activity. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Scheme 1

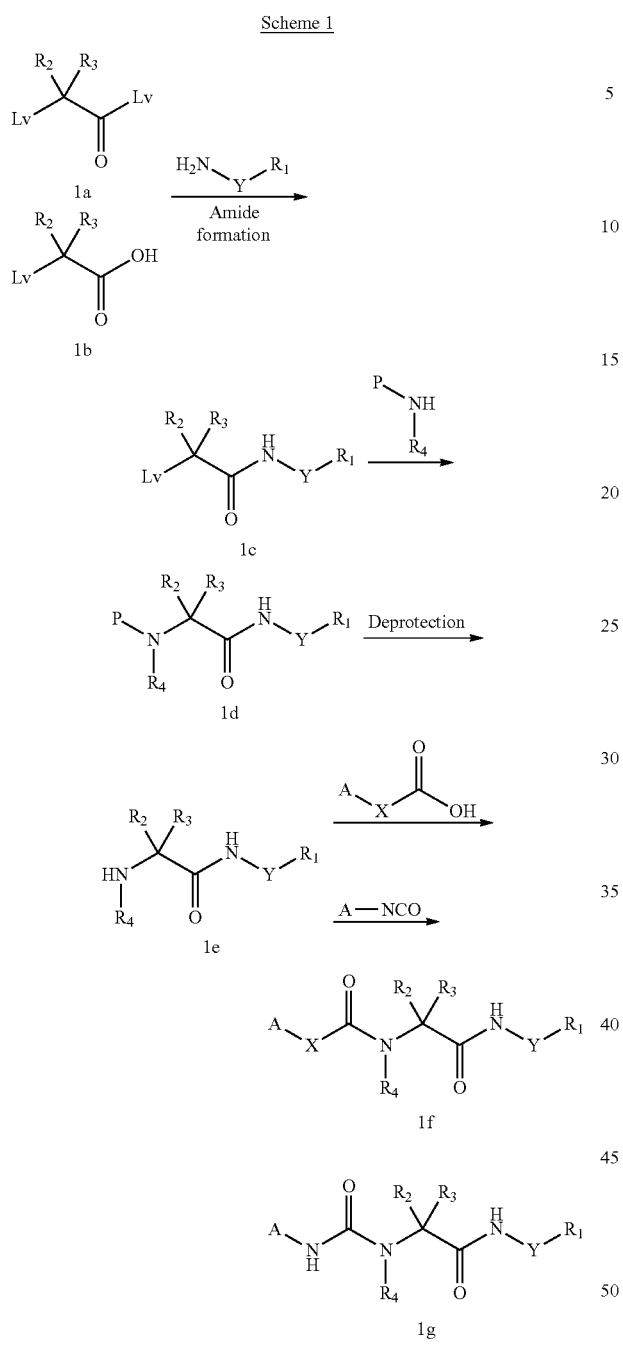

Scheme 2

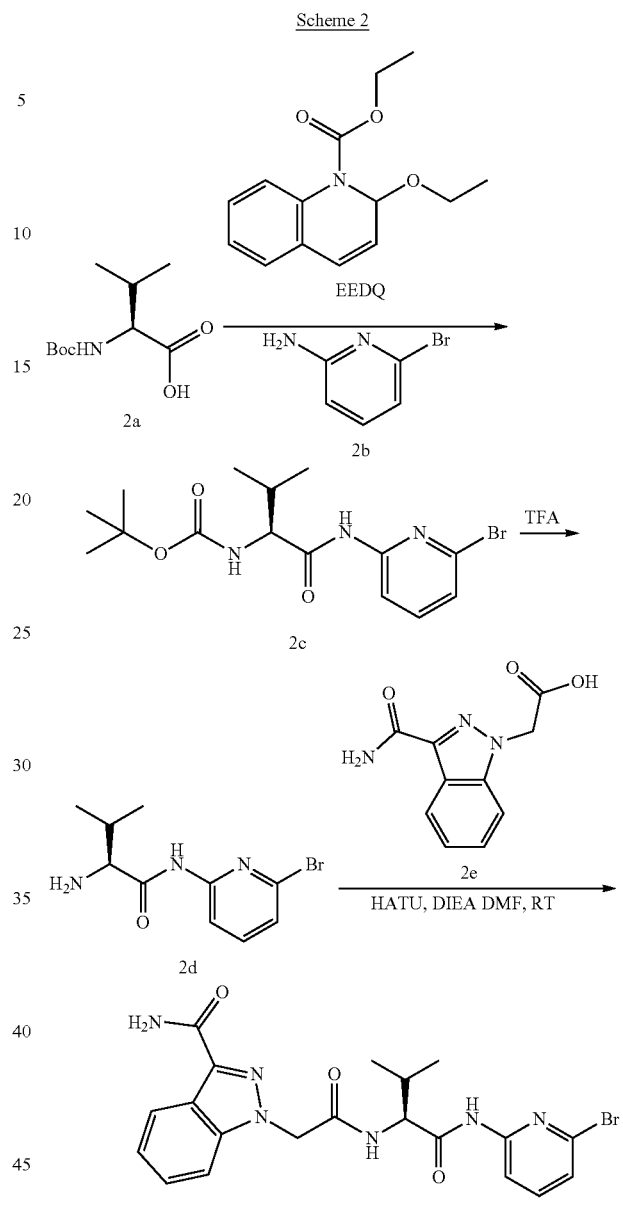

Preparation of (S)-1-(2-((1-((6-bromopyridin-2-yl)amino)-3-methyl-1-oxobutan-2-yl)-amino)-2-oxoethyl)-1H-indazole-3-carboxamide (2f)

Step-1: Preparation of (S)-tert-butyl (1-((6-bromopyridin-2-yl)amino)-3-methyl-1-oxobutan-2-yl) carbamate (2c)

Scheme 1 depicts general synthesis of compounds of type (1f) and/or (1 g). These compounds were prepared in a manner wherein (1a) or (1b) consisting of an activated carbonyl compound bearing a leaving group (Lv) upon reacting with free or protected amine under coupling conditions yields (1c). The compound (1d) was prepared by reaction of free or protected amine with (1c); the protecting group was removed using standard conditions to form (1e). In the final step, compound (1e) was coupled with activated carbonyl group using a coupling reagent to form amide compounds (1f), subsequently substituted urea compounds (1g) were prepared from (1e) using structurally diverse isocyanate.

To a solution of Boc-L-valine (2a) (1.32 g, 6.07 mmol) and 6-bromopyridin-2-amine (2b) (1.0 g, 5.78 mmol) in THF (20 mL) was added ethyl 2-ethoxyquinoline-1(2H)-carboxylate (EEDQ, 1.43 g, 5.78 mmol). The resulting mixture was refluxed for 4 days, cooled to room temperature, diluted with EtOAc (100 mL), washed with $KHSO_4$ (1 N, 2×30 mL) and brine (20 mL). The organic layer was dried, concentrated in vacuum and the residue obtained was purified by flash column chromatography [silica gel (12 g), eluting with EtOAc (0-50%) in hexane] to afford (S)-tert-butyl 1-(6-bromopyridin-2-ylamino)-3-methyl-1-oxobutan-2-ylcarbamate (2c) (121 mg, 0.325 mmol, 6% yield) as a semi-solid; $^1$H NMR (300 MHz, DMSO-$d_6$) δ 10.78 (s, 1H), 8.09 (d, J=8.1 Hz, 1H), 7.73 (t, J=7.9 Hz, 1H), 7.34 (d, J=7.7 Hz, 1H), 6.98 (d, J=8.4 Hz, 1H), 4.06-3.94 (m, 1H), 2.05-1.92 (m, 1H), 1.37 (s, 9H), 0.93-0.86 (m, 6H); MS (ES+): 394.4 (M+Na).

Step-2: Preparation of (S)-2-amino-N-(6-bromopyridin-2-yl)-3-methylbutanamide (2d)

To a stirred solution of (S)-tert-butyl 1-(6-bromopyridin-2-ylamino)-3-methyl-1-oxobutan-2-ylcarbamate (2c) (120 mg, 0.322 mmol) in DCM (10 mL) was added TFA (368 mg, 3.22 mmol) at room temperature and stirred for 16 h. The reaction mixture was concentrated in vacuum to remove DCM and excess TFA to furnish (S)-2-amino-N-(6-bromopyridin-2-yl)-3-methylbutanamide (2d) which was used as such in the next step without further purification; MS (ES+): 273.3 (M+1).

Step-3: Preparation of (S)-1-(2-((1-((6-bromopyridin-2-yl)amino)-3-methyl-1-oxobutan-2-yl)amino)-2-oxoethyl)-1H-indazole-3-carboxamide (2f)

To the above TFA salt of (S)-2-amino-N-(6-bromopyridin-2-yl)-3-methylbutanamide (2d) (120 mg, 0.441 mmol) in DMF (4 mL) was added 2-(3-carbamoyl-1H-indazol-1-yl)acetic acid (2e) (116 mg, 0.529 mmol, prepared according to procedure reported by Altmann, Eva et al; in PCT Int. Appl., WO 2012/093101), DIPEA (0.308 mL, 1.764 mmol), HATU (201 mg, 0.529 mmol) and stirred at room temperature overnight. The reaction mixture was diluted with EtOAc (100 mL), washed with water (3×), brine, dried, filtered and concentrated in vacuum to dryness. The residue obtained was purified by flash column chromatography [silica gel (12 g) eluting with 0-60% EtOAc/MeOH (9:1) in hexane] to furnish (S)-1-(2-((1-((6-bromopyridin-2-yl)amino)-3-methyl-1-oxobutan-2-yl)amino)-2-oxoethyl)-1H-indazole-3-carboxamide (2f) (38 mg, 18% yield) as a white solid; $^1$H NMR (300 MHz, DMSO-$d_6$) δ 11.01 (s, 1H), 8.57 (d, J=8.1 Hz, 1H), 8.13 (dd, J=21.3, 8.2 Hz, 2H), 7.81-7.56 (m, 3H), 7.39 (dd, J=23.5, 7.5 Hz, 3H), 7.25 (t, J=7.5 Hz, 1H), 5.41-5.23 (m, 2H), 4.46 (t, J=7.2 Hz, 1H), 2.15-2.00 (m, 1H), 1.00-0.83 (m, 7H); MS (ES+): 496.4 (M+Na).

Scheme 3

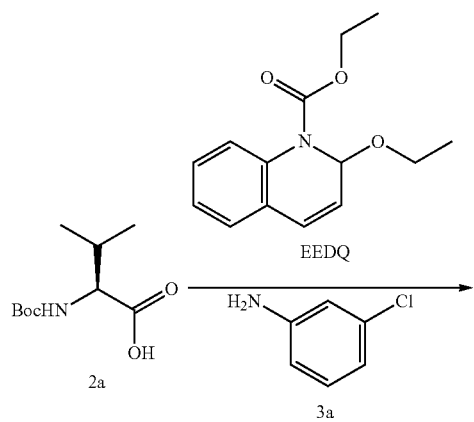

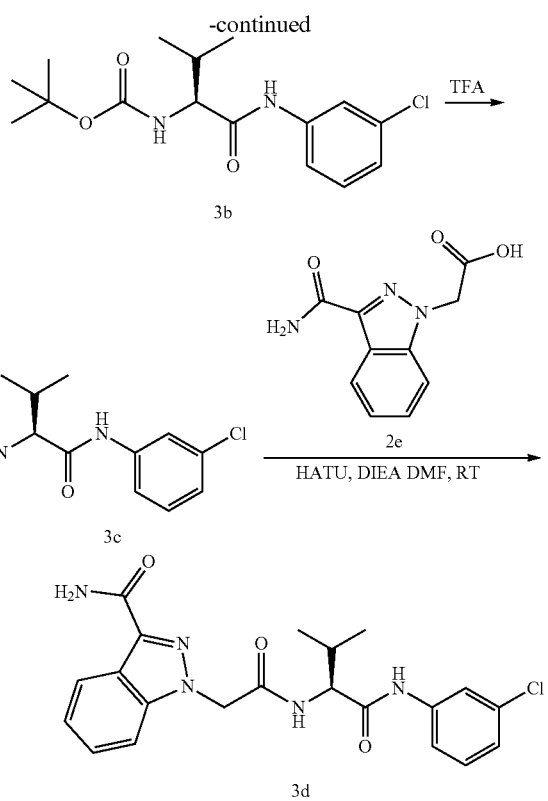

Preparation of (S)-1-(2-((1-((3-chlorophenyl)amino)-3-methyl-1-oxobutan-2-yl)-amino)-2-oxoethyl)-1H-indazole-3-carboxamide (3d)

Step-1: Preparation of (S)-tert-butyl-(3-chlorophenylamino)-3-methyl-1-oxobutan-2-ylcarbamate (3b)

Reaction of Boc-L-valine (2a) (1.73 g, 7.84 mmol) with 3-chloroaniline (3a) (1.0 g, 7.84 mmol) according to the procedure reported in step-1 of Scheme 2 gave after workup and purification (S)-tert-butyl 1-(3-chlorophenylamino)-3-methyl-1-oxobutan-2-ylcarbamate (3b) (1.72 g, 5.26 mmol, 67% yield) as a white solid; $^1$H NMR (300 MHz, DMSO-$d_6$) δ 10.20 (s, 1H), 7.84 (s, 1H), 7.46 (d, J=8.0 Hz, 1H), 7.34 (t, J=8.0 Hz, 1H), 7.11 (d, J=7.4 Hz, 1H), 6.99 (d, J=8.1 Hz, 1H), 3.89 (t, J=7.7 Hz, 1H), 2.09-1.80 (m, 1H), 1.39 (s, 9H), 0.89 (d, J=6.4 Hz, 6H); MS (ES+): 349.4 (M+Na).

Step-2: Preparation of (S)-2-amino-N-(3-chlorophenyl)-3-methylbutanamide (3c)

Reaction of (S)-tert-butyl 1-(3-chlorophenylamino)-3-methyl-1-oxobutan-2-ylcarbamate (3b) (750 mg, 2.30 mmol) with TFA (2.62 g, 22.95 mmol) according to the procedure reported in step-2 of Scheme 2 gave after workup and purification by chromatography [silica (12 g) eluting with EtOAc/MeOH (9:1) in hexane from 0 to 60%] (S)-2-amino-N-(3-chlorophenyl)-3-methylbutanamide (3c) (355 mg, 1.57 mmol, 68% yield) as a white solid; $^1$H NMR (300 MHz, DMSO-$d_6$) δ 7.86-7.78 (m, 1H), 7.49 (d, J=7.9 Hz, 1H), 7.39 (t, J=7.9 Hz, 1H), 7.18 (d, J=7.8 Hz, 1H), 3.66 (d, J=5.6 Hz, 1H), 2.21-2.05 (m, 1H), 0.97 (t, J=7.1 Hz, 6H); MS (ES+): 227.3 (M+1).

Step-3: Preparation of (S)-1-(2-((1-((3-chlorophenyl)amino)-3-methyl-1-oxobutan-2-yl)amino)-2-oxoethyl)-1H-indazole-3-carboxamide (3d)

Reaction of (S)-2-amino-N-(3-chlorophenyl)-3-methylbutanamide (3c) (145 mg, 0.64 mmol) with 2-(3-carbamoyl-1H-indazol-1-yl)acetic acid (2e) according to the procedure reported in step-3 of Scheme 2 gave after workup and purification by chromatography [silica (12 g), eluting with 0-60% EtOAc/MeOH (9:1) in hexane] (S)-1-(2-((1-((3-chlorophenyl)amino)-3-methyl-1-oxobutan-2-yl)-amino)-2-oxoethyl)-1H-indazole-3-carboxamide (3d) (50 mg, 0.117 mmol, 18% yield) as a yellow solid; $^1$H NMR (300 MHz, DMSO-$d_6$) δ 10.38 (s, 1H), 8.69 (d, J=8.3 Hz, 1H), 8.18 (d, J=7.9 Hz, 1H), 7.83 (s, 1H), 7.76-7.59 (m, 2H), 7.52-7.31 (m, 4H), 7.26 (t, J=7.2 Hz, 1H), 7.13 (d, J=7.7 Hz, 1H), 5.43-5.22 (m, 2H), 4.33 (t, J=7.5 Hz, 1H), 2.22-1.86 (m, 1H), 0.95 (t, J=6.5 Hz, 6H); MS (ES+): 450.4 (M+Na)

Preparation of (S)-1-(2-((1-((6-bromopyridin-2-yl)amino)-3-methyl-1-oxobutan-2-yl)(methyl)amino)-2-oxoethyl)-1H-indazole-3-carboxamide (4d)

Step-1: Preparation of (5)-tert-butyl(1-((6-bromopyridin-2-yl)amino)-3-methyl-1-oxobutan-2-yl)(methyl)carbamate (4b)

Reaction of (S)-2-(tert-butoxycarbonyl)methyl)amino)-3-methylbutanoic acid (4a) (500 mg, 2.16 mmol) with 6-bromopyridin-2-amine (2b) (374 mg, 2.16 mmol) according to the procedure reported in step-1 of Scheme 2 gave after workup and purification by chromatography on silica gel (12 g) of (5)-tert-butyl (1-((6-bromopyridin-2-yl)amino)-3-methyl-1-oxobutan-2-yl)(methyl)carbamate (4b) (135 mg, 0.35 mmol, 16% yield) as a semi-solid; $^1$H NMR (300 MHz, DMSO-$d_6$) δ 10.92 (s, 1H), 8.08 (d, J=8.1 Hz, 1H), 7.74 (t, J=7.9 Hz, 1H), 7.36 (d, J=8.0 Hz, 1H), 2.85 (s, 3H), 2.75 (s, 1H), 2.21-2.07 (m, 1H), 1.40 (s, 9H), 0.93-0.83 (m, 6H); MS (ES+): 410.4 (M+Na); (ES$^-$), 386.3 (M−1).

Step-2: Preparation of (S)—N-(6-bromopyridin-2-yl)-3-methyl-2-(methylamino)butanamide (4c)

Reaction of (5)-tert-butyl (1-((6-bromopyridin-2-yl)amino)-3-methyl-1-oxobutan-2-yl)(methyl)carbamate (4b) (125 mg, 0.32 mmol) with TFA (369 mg, 3.24 mmol) according to the procedure reported in step-2 of Scheme 2 gave after workup (S)—N-(6-bromopyridin-2-yl)-3-methyl-2-(methylamino)butanamide (4c) as a TFA salt which was used as such in next step without further purification; MS (ES+): 288.3 (M+1).

Step-3: Preparation of (S)-1-(2-((1-((6-bromopyridin-2-yl)amino)-3-methyl-1-oxobutan-2-yl)(methyl)amino)-2-oxoethyl)-1H-indazole-3-carboxamide (4d)

Reaction of above TFA salt of (S)—N-(6-bromopyridin-2-yl)-3-methyl-2-(methylamino)butanamide (4c) (99 mg, 0.247 mmol) with 2-(3-carbamoyl-1H-indazol-1-yl)acetic acid (2e) (65.1 mg, 0.297 mmol) according to the procedure reported in step-3 of Scheme 2 gave after workup and purification by chromatography [silica (12 g), eluting with 0-60% EtOAc/MeOH (9:1) in hexane] (S)-1-(2-((1-((6-bromopyridin-2-yl)amino)-3-methyl-1-oxobutan-2-yl)(methyl)amino)-2-oxoethyl)-1H-indazole-3-carboxamide (4d) (53 mg, 0.11 mmol, 44% yield) as a white solid; $^1$H NMR (300 MHz, DMSO-$d_6$) δ 10.92 (s, 1H), 8.25-8.02 (m, 2H), 7.87-7.65 (m, 1H), 7.65-7.50 (m, 2H), 7.46-7.31 (m, 3H), 7.31-7.18 (m, 1H), 5.78-5.44 (m, 2H), 4.84 (d, J=10.8 Hz, 1H), 3.27-2.88 (m, 3H), 2.44-2.09 (m, 1H), 1.12-0.79 (m, 6H); MS (ES+): 488.4 (M+1).

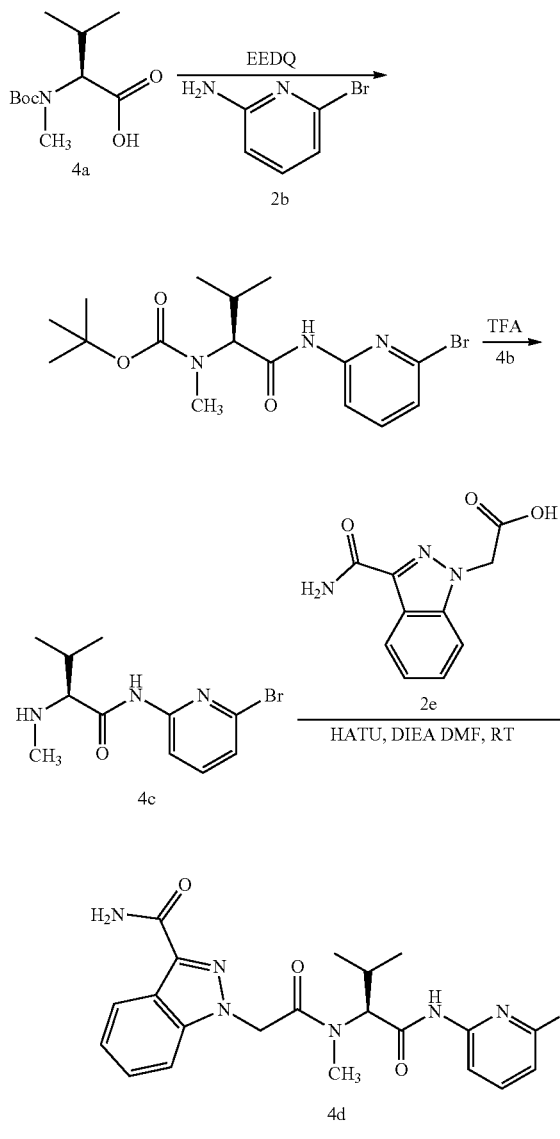

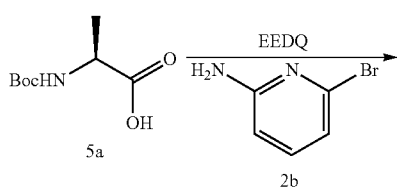

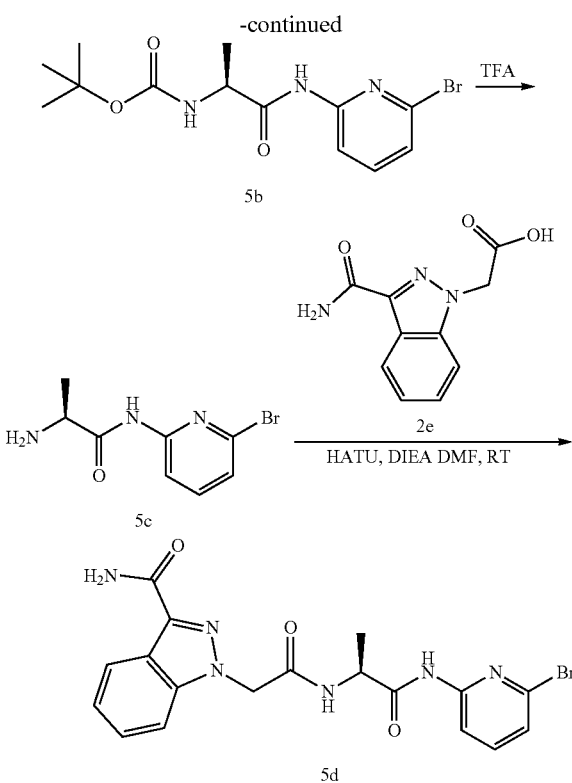

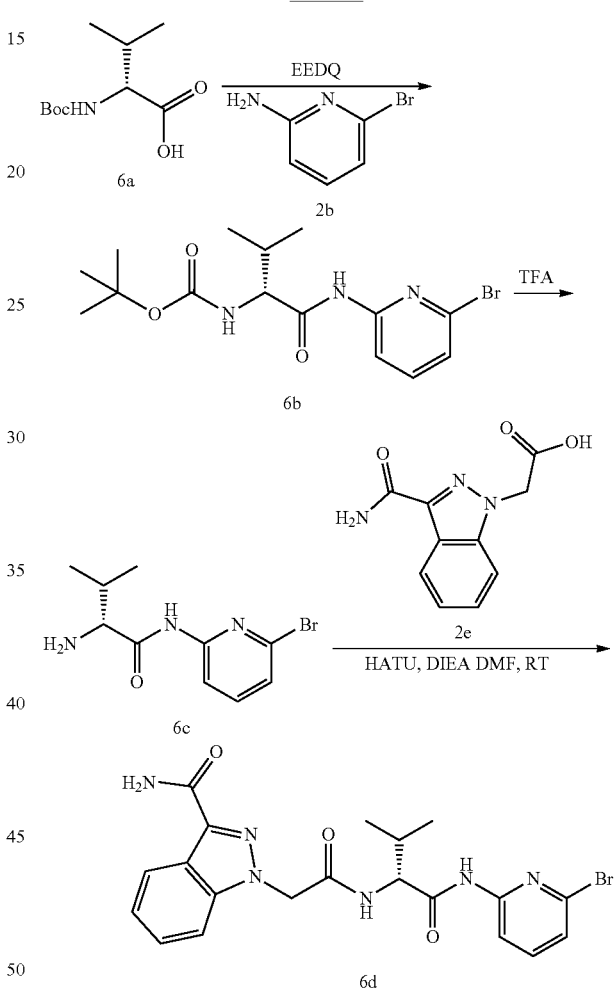

step-3 of Scheme 2 gave after workup and purification by chromatography [silica (12 g), eluting with 0-60% EtOAc/MeOH (9:1) in hexane] (S)-1-(2-((1-(((6-bromopyridin-2-yl)amino)-1-oxopropan-2-yl)-amino)-2-oxoethyl)-1H-indazole-3-carboxamide (5d) (18 mg, 12% yield) as a white solid; $^1$H NMR (300 MHz, DMSO-$d_6$) δ 10.96 (s, 1H), 8.75 (d, J=6.9 Hz, 1H), 8.16 (d, J=8.2 Hz, 1H), 8.07 (d, J=8.2 Hz, 1H), 7.79-7.56 (m, 3H), 7.47-7.30 (m, 3H), 7.30-7.18 (m, 1H), 5.26 (s, 2H), 4.71-4.36 (m, 1H), 1.34 (d, J=7.1 Hz, 3H); MS (ES+): 467.4 (M+Na).

Preparation of (S)-1-(2-((1-(((6-bromopyridin-2-yl)amino)-1-oxopropan-2-yl)-amino)-2-oxoethyl)-1H-indazole-3-carboxamide (5d)

Step-1: Preparation of (5)-tert-butyl (1-((6-bromopyridin-2-yl)amino)-1-oxopropan-2-yl)carbamate (5b)

Reaction of (S)-2-(tert-butoxycarbonylamino)propanoic acid (5a) (1.15 g, 6.07 mmol) with 6-bromopyridin-2-amine (2b) (1.0 g, 5.78 mmol) according to the procedure reported in step-1 of Scheme 2 gave after workup and purification by chromatography (5)-tert-butyl (1-((6-bromopyridin-2-yl)amino)-1-oxopropan-2-yl)carbamate (5b) (250 mg, 0.73 mmol, 13% yield) as a clear oil; MS (ES−): 342.4 (M−1).

Step-2: Preparation of (S)-2-amino-N-(6-bromopyridin-2-yl)propanamide) (5c)

Reaction of (5)-tert-butyl (1-((6-bromopyridin-2-yl)amino)-1-oxopropan-2-yl)carbamate (5b) (225 mg, 0.65 mmol) with TFA (745 mg, 6.54 mmol) according to the procedure reported in step-2 of Scheme 2 gave after workup (S)-2-amino-N-(6-bromopyridin-2-yl)propanamide) (5c) as TFA salt which was used in next step without further purification; MS (ES+): 245.2 (M+1).

Step-3: Preparation of (S)-1-(2-((1-(((6-bromopyridin-2-yl)amino)-1-oxopropan-2-yl)-amino)-2-oxoethyl)-1H-indazole-3-carboxamide (5d)

Reaction of above TFA salt of (S)-2-amino-N-(6-bromopyridin-2-yl)propanamide) (5c) (125 mg, 0.35 mmol) with 2-(3-carbamoyl-1H-indazol-1-yl)acetic acid (2e) (92 mg, 0.419 mmol) according to the procedure reported in

Preparation of (R)-1-(2-((1-(((6-bromopyridin-2-yl)amino)-3-methyl-1-oxobutan-2-yl)-amino)-2-oxoethyl)-1H-indazole-3-carboxamide (6d)

Step-1: Preparation of (R)-tert-butyl (1-((6-bromopyridin-2-yl)amino)-3-methyl-1-oxobutan-2-yl)carbamate (6b)

Reaction of (R)-2-((tert-butoxycarbonyl)amino)-3-methylbutanoic acid (6a) (1.0 g, 4.6 mmol) with 6-bromopyridin-2-amine (2b) (1.0 g, 5.80 mmol) according to the procedure reported in step-1 of Scheme 2 gave after workup and purification by chromatography (R)-tert-butyl (1-((6-bromopyridin-2-yl)amino)-3-methyl-1-oxobutan-2-yl)carbamate (6b) (523 mg, 31% yield) as a white semi-solid; ¹H NMR (300 MHz, DMSO-$d_6$) δ 10.78 (s, 1H), 8.09 (d, J=8.2 Hz, 1H), 7.83-7.66 (m, 1H), 7.34 (d, J=7.6 Hz, 1H), 6.97 (d, J=8.4 Hz, 1H), 4.03 (t, J=7.8 Hz, 1H), 2.07-1.87 (m, 1H), 1.40 (s, 9H), 0.92-0.84 (m, 6H); MS (ES+): 394.4 (M+Na).

Step-2: Preparation of (R)-2-amino-N-(6-bromopyridin-2-yl)-3-methylbutanamide (6c)

Reaction of (R)-tert-butyl (1-((6-bromopyridin-2-yl)amino)-3-methyl-1-oxobutan-2-yl)carbamate (6b) (490 mg, 1.32 mmol) with TFA (750 mg, 6.58 mmol) according to the procedure reported in step-2 of Scheme 2 gave after workup and purification by flash column chromatography [silica (12 g), eluting with MeOH in CHCl₃ 0 to 20%] to give (R)-2-amino-N-(6-bromopyridin-2-yl)-3-methylbutanamide (6c) (185 mg, 0.680 mmol, 52% yield) as a white solid; ¹H NMR (300 MHz, DMSO-$d_6$) δ 8.13 (d, J=8.1 Hz, 1H), 7.74 (t, J=7.9 Hz, 1H), 7.34 (d, J=7.7 Hz, 1H), 3.22 (d, J=5.2 Hz, 1H), 2.02-1.85 (m, 1H), 0.91 (d, J=6.8 Hz, 3H), 0.82 (d, J=6.8 Hz, 3H); MS (ES+): 272.3 (M+1).

Step-3: Preparation of (R)-tert-butyl (1-((6-bromopyridin-2-yl)amino)-3-methyl-1-oxobutan-2-yl)carbamate (6b)

Reaction of (R)-2-amino-N-(6-bromopyridin-2-yl)-3-methylbutanamide (6c) (91 mg, 0.33 mmol) with 2-(3-carbamoyl-1H-indazol-1-yl)acetic acid (2e) (88 mg, 0.4 mmol) according to the procedure reported in step-3 of Scheme 2 gave after workup and purification by chromatography [silica (12 g), eluting with CMA80 in CHCl₃ 0 to 40%] to give (R)-tert-butyl (1-((6-bromopyridin-2-yl)amino)-3-methyl-1-oxobutan-2-yl)carbamate (6b) (65 mg, 0.14 mmol, 41% yield) as a white solid; ¹H NMR (300 MHz, DMSO-$d_6$) δ 11.12-10.90 (m, 1H), 8.58 (d, J=7.8 Hz, 1H), 8.14 (dd, J=21.5, 8.0 Hz, 2H), 7.84-7.53 (m, 3H), 7.50-7.10 (m, 4H), 5.43-5.19 (m, 2H), 4.57-4.34 (m, 1H), 2.18-2.00 (m, 1H), 0.94 (s, 6H); MS (ES+): 473.4 (M+1).

Scheme 7

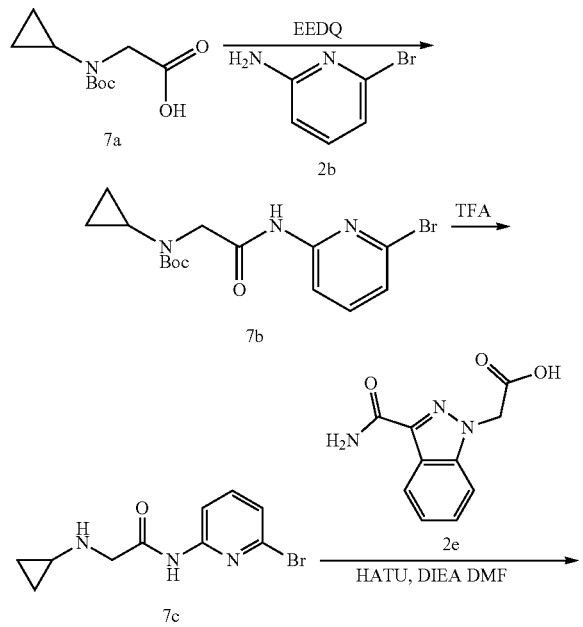

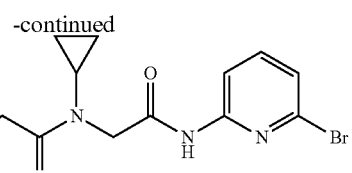

7d

Preparation of 1-(2-((2-(((6-bromopyridin-2-yl)amino)-2-oxoethyl)(cyclopropyl)amino)-2-oxoethyl)-1H-indazole-3-carboxamide (7d)

Step-1: Preparation of tert-butyl (2-((6-bromopyridin-2-yl)amino)-2-oxoethyl)(cyclopropyl) carbamate (7b)

Reaction of 2-((tert-butoxycarbonyl)(cyclopropyl)amino)acetic acid (7a) (0.5 g, 2.32 mmol) with 6-bromopyridin-2-amine (2b) (0.4 g, 2.32 mmol) according to the procedure reported in step-1 of Scheme 2 gave after workup and purification by chromatography [silica (12 g), eluting with MeOH in CHCl₃ from 0-20%] tert-butyl (2-((6-bromopyridin-2-yl)amino)-2-oxoethyl)(cyclopropyl) carbamate (7b) contaminated with 6-bromopyridin-2-amine (2b).

Step-2: Preparation of N-(6-bromopyridin-2-yl)-2-(cyclopropylamino)acetamide (7c)

Reaction of tert-butyl (2-((6-bromopyridin-2-yl)amino)-2-oxoethyl)(cyclopropyl) carbamate (7b) from above step-1 with TFA (0.9 mL, 11.61 mmol) according to the procedure reported in step-2 of Scheme 2 gave after workup N-(6-bromopyridin-2-yl)-2-(cyclopropylamino)acetamide (7c) as a TFA salt; MS (ES+): 272.3 (M+2).

Step-3: Preparation of 1-(2-((2-(((6-bromopyridin-2-yl)amino)-2-oxoethyl)(cyclopropyl)amino)-2-oxoethyl)-1H-indazole-3-carboxamide (7d)

Reaction of N-(6-bromopyridin-2-yl)-2-(cyclopropylamino)acetamide (7c) TFA salt from above step-2 (90 mg, 0.33 mmol) with 2-(3-carbamoyl-1H-indazol-1-yl)acetic acid (2e) (88 mg, 0.4 mmol) according to the procedure reported in step-3 of Scheme 2 gave after workup and purification by chromatography [silica (12 g), eluting with CMA80 in CHCl₃ 0 to 40%] 1-(2-((2-(((6-bromopyridin-2-yl)amino)-2-oxoethyl)(cyclopropyl)amino)-2-oxoethyl)-1H-indazole-3-carboxamide (7d) (24 mg, 0.051 mmol, 15% yield for three steps) as a white solid.

¹H NMR (300 MHz, DMSO-$d_6$) δ 10.96 (s, 1H), 8.17 (d, J=8.1 Hz, 1H), 8.02 (d, J=8.1 Hz, 1H), 7.81-7.59 (m, 3H), 7.51-7.18 (m, 4H), 5.70 (s, 2H), 4.18 (s, 2H), 3.15-3.05 (m, 1H), 1.15-0.77 (m, 4H); MS (ES+): 471.4 (M+1).

Scheme 8

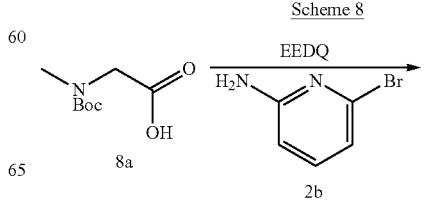

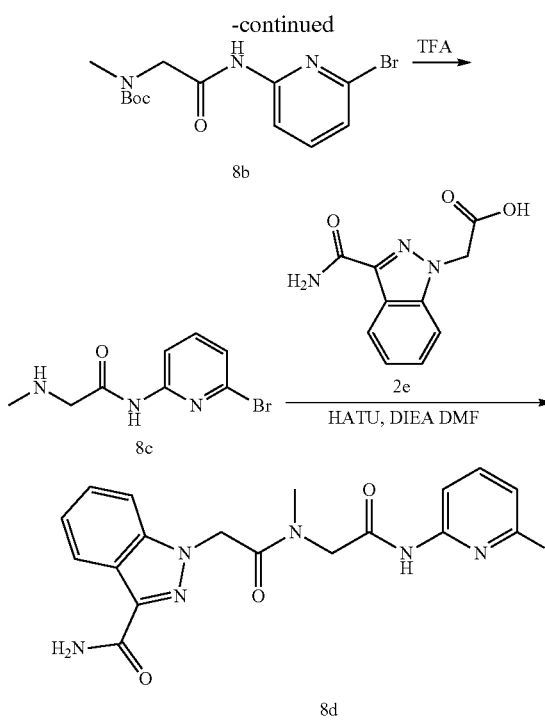

1H-indazol-1-yl)acetic acid (2e) (88 mg, 0.4 mmol) according to the procedure reported in step-3 of Scheme 2 gave after workup and purification by chromatography [silica (12 g), eluting with CMA80 in CHCl₃ 0 to 30%] 1-(2-((2-((6-bromopyridin-2-yl)amino)-2-oxoethyl)(methyl)amino)-2-oxoethyl)-1H-indazole-3-carboxamide (8d) (67 mg, 0.15 mmol, 41% yield for three steps) as a yellow solid; $^1$H NMR (300 MHz, DMSO-d$_6$) δ 11.30-10.84 (2 s at 11.22, 10.94, 1H), 8.23-8.00 (m, 2H), 7.87-7.56 (m, 3H), 7.49-7.21 (m, 4H), 5.54 (2 s at 5.61, 5.46, 2H), 4.34 (2 s at 4.47, 4.20, 2H), 3.04 (2 s at 3.23, 2.85, 3H); MS (ES+): 467.4 (M+Na).

Scheme 9

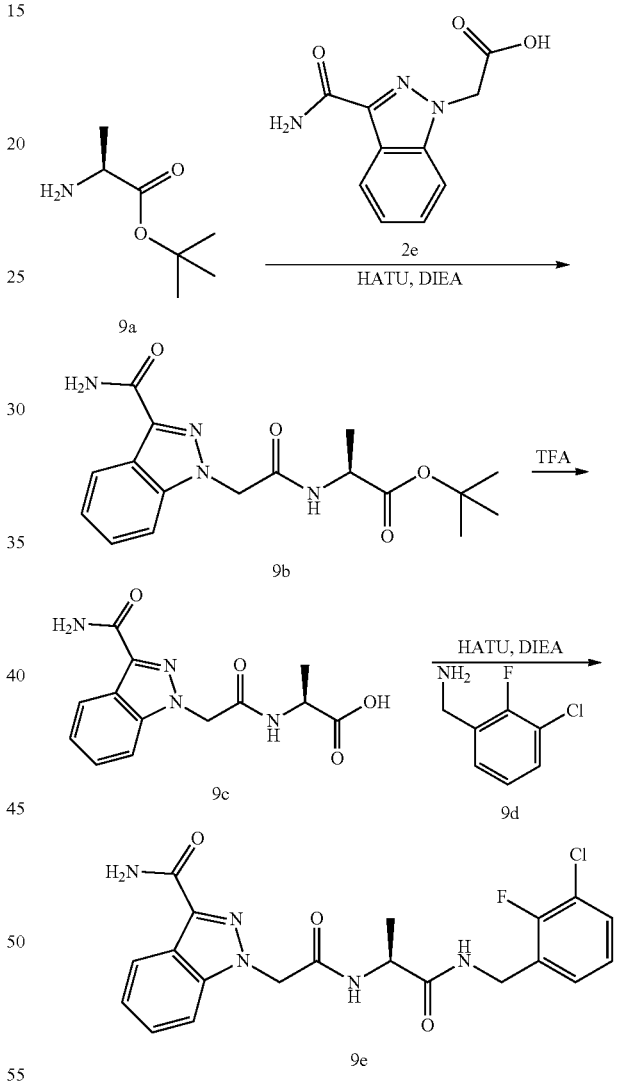

Preparation of 1-(2-((2-((6-bromopyridin-2-yl)amino)-2-oxoethyl)(methyl)amino)-2-oxoethyl)-1H-indazole-3-carboxamide (8d)

Step-1: Preparation of tert-butyl (2-((6-bromopyridin-2-yl)amino)-2-oxoethyl)(methyl)carbamate (8b)

Reaction of 2-((tert-butoxycarbonyl)(methyl)amino)acetic acid (8a) (2 g, 10.57 mmol) with 6-bromopyridin-2-amine (2b) (1.52 g, 8.81 mmol) according to the procedure reported in step-1 of Scheme 2 gave after workup and purification by chromatography [silica gel (24 g), eluting with EtOAc (0-50%) in hexane] tert-butyl (2-((6-bromopyridin-2-yl)amino)-2-oxoethyl)(methyl)carbamate (8b) (685 mg, 1.99 mmol, 23% yield) as a white solid; $^1$H NMR (300 MHz, DMSO-d$_6$) δ 10.90 (d, 1H), 8.06 (t, J=7.8 Hz, 1H), 7.74 (td, J=8.0, 3.6 Hz, 1H), 7.34 (d, J=7.7 Hz, 1H), 4.01 (d, J=7.5 Hz, 2H), 2.84 (d, J=8.0 Hz, 3H), 1.35 (d, J=27.9 Hz, 9H); MS (ES+): 344.3 (M+1).

Step-2: Preparation of N-(6-bromopyridin-2-yl)-2-(methylamino)acetamide (8c)

Reaction of tert-butyl (2-((6-bromopyridin-2-yl)amino)-2-oxoethyl)(methyl)carbamate (8b) (650 mg, 1.89 mmol) with TFA (0.73 mL, 9.44 mmol) according to the procedure reported in step-2 of Scheme 2 gave after workup and purification by chromatography [silica (12 g), eluting with MeOH in CHCl₃ 0 to 20%] N-(6-bromopyridin-2-yl)-2-(methylamino)acetamide (8c) (285 mg, 1.17 mmol, 62% yield) as an off white solid; $^1$H NMR (300 MHz, DMSO-d$_6$) δ 11.38 (s, 1H), 8.93 (s, 2H), 8.05 (d, J=7.9 Hz, 1H), 7.81 (t, J=8.0 Hz, 1H), 7.51-7.32 (m, 1H), 3.98 (s, 2H), 2.62 (s, 3H); MS (ES+): 244.3 (M+1).

Step-3: Preparation of 1-(2-((2-((6-bromopyridin-2-yl)amino)-2-oxoethyl)(methyl)amino)-2-oxoethyl)-1H-indazole-3-carboxamide (8d)

Reaction of N-(6-bromopyridin-2-yl)-2-(methylamino)acetamide (8c) (90 mg, 0.37 mmol) with 2-(3-carbamoyl- Preparation of (S)-1-(2-((1-((3-chloro-2-fluorobenzyl)amino)-1-oxopropan-2-yl)amino)-2-oxoethyl)-1H-indazole-3-carboxamide (9e)

Step-1: Preparation of (S)-tert-butyl 2-(2-(3-carbamoyl-1H-indazol-1-yl)acetamido)propanoate (9b)

Reaction of (5)-tert-butyl 2-aminopropanoate (9a) (767 mg, 4.22 mmol) with 2-(3-carbamoyl-1H-indazol-1-yl)acetic acid (2e) (1.02 g, 4.64 mmol) according to the procedure reported in step-3 of Scheme 2 gave after workup and purification by chromatography [silica (40 g), eluting with CMA80 in CHCl₃ 0 to 40%] (S)-tert-butyl 2-(2-(3-carbamoyl-1H-indazol-1-yl)acetamido)propanoate (9b) (965 mg, 2.79 mmol, 66% yield) as a white solid; $^1$H NMR (300 MHz, DMSO-d₆) δ 8.73 (d, J=7.1 Hz, 1H), 8.17 (d, J=8.2 Hz, 1H), 7.77-7.57 (m, 2H), 7.49-7.33 (m, 2H), 7.26 (t, J=7.5 Hz, 1H), 5.22 (s, 2H), 4.23-4.06 (m, 1H), 1.38 (s, 9H), 1.30 (d, J=7.3 Hz, 3H); MS (ES+): 369.5 (M+Na); 345.4 (M−1).

Step-2: Preparation of (S)-2-(2-(3-carbamoyl-1H-indazol-1-yl)acetamido)propanoic acid (9c)

Reaction of (S)-tert-butyl 2-(2-(3-carbamoyl-1H-indazol-1-yl)acetamido)propanoate (9b) (900 mg, 2.6 mmol) with TFA (1.2 mL, 15.59 mmol) according to the procedure reported in step-2 of Scheme 2 gave after workup (S)-2-(2-(3-carbamoyl-1H-indazol-1-yl)acetamido)propanoic acid (9c) (750 mg, 2.58 mmol, 99% yield) as a TFA salt which was used in the next step without further purification.

Step-3: Preparation of (S)-1-(2-((1-((3-chloro-2-fluorobenzyl)amino)-1-oxopropan-2-yl)amino)-2-oxoethyl)-1H-indazole-3-carboxamide (9e)

Reaction of (S)-2-(2-(3-carbamoyl-1H-indazol-1-yl)acetamido)propanoic acid (9c) (100 mg, 0.35 mmol) TFA salt from above step-2 with 3-chloro-2-fluorobenzylamine (9d) (66.0 mg, 0.413 mmol), according to the procedure reported in step-3 of Scheme 2 gave after workup and purification by [silica (12 g), eluting with CMA80 in CHCl₃ from 0 to 50%] (S)-1-(2-((1-((3-chloro-2-fluorobenzyl)amino)-1-oxopropan-2-yl)amino)-2-oxoethyl)-1H-indazole-3-carboxamide (9e) (22 mg, 0.05 mmol, 15% yield) as a white solid; $^1$H NMR (300 MHz, DMSO-d₆) δ 8.68 (d, J=7.2 Hz, 1H), 8.64-8.57 (m, 1H), 8.17 (d, J=8.0 Hz, 1H), 7.72 (s, 1H), 7.64 (d, J=8.6 Hz, 1H), 7.57-7.33 (m, 3H), 7.34-7.19 (m, 2H), 7.19-7.06 (m, 1H), 5.25 (s, 2H), 4.44-4.20 (m, 3H), 1.28 (d, J=6.9 Hz, 3H); MS (ES+): 454.4 (M+Na); 430.4 (M−1).

Scheme 10

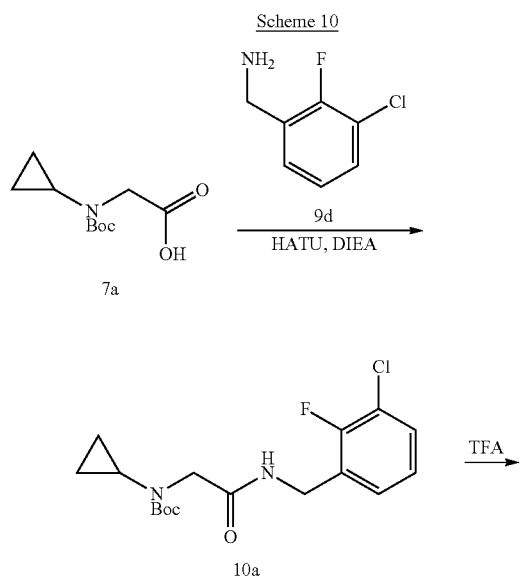

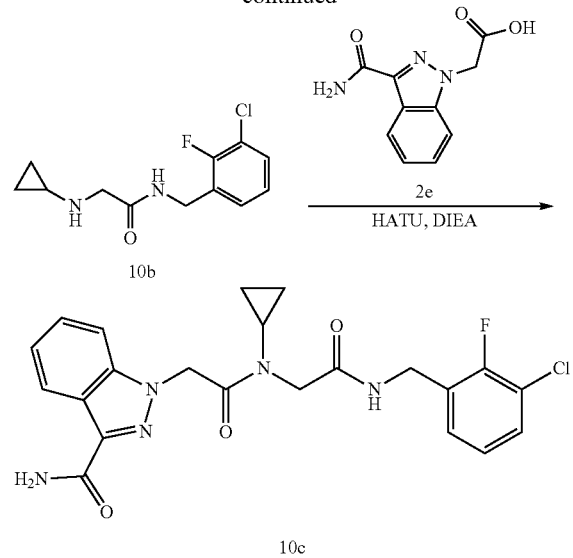

Preparation of 1-(2-((2-((3-chloro-2-fluorobenzyl)amino)-2-oxoethyl)(cyclopropyl)amino)-2-oxoethyl)-1H-indazole-3-carboxamide (10c)

Step-1: Preparation of tert-butyl (2-((3-chloro-2-fluorobenzyl)amino)-2-oxoethyl)(cyclopropyl)carbamate (10a)

Reaction of 2-((tert-butoxycarbonyl)(cyclopropyl)amino) acetic acid (7a) (250 mg, 1.16 mmol) with 3-chloro-2-fluorobenzylamine (9d) (185 mg, 1.16 mmol) according to the procedure reported in step-3 of Scheme 2 gave after workup and purification by chromatography [silica (40 g), eluting with EtOAc in hexane 0 to 50%] tert-butyl (2-((3-chloro-2-fluorobenzyl)amino)-2-oxoethyl)(cyclopropyl)carbamate (10a) (365 mg, 1.02 mmol, 88% yield) as a clear oil; $^1$H NMR (300 MHz, DMSO-d₆) δ 8.42 (t, J=5.9 Hz, 1H), 7.53-7.42 (m, 1H), 7.34-7.23 (m, 1H), 7.22-7.11 (m, 1H), 4.33 (d, J=5.7 Hz, 2H), 3.76 (s, 2H), 2.67-2.54 (m, 1H), 1.46-1.10 (m, 9H), 0.68-0.43 (m, 4H); MS (ES+): 379.4 (M+Na).

Step-2: Preparation of N-(3-chloro-2-fluorobenzyl)-2-(cyclopropylamino)acetamide (10b)

Reaction of tert-butyl (2-((3-chloro-2-fluorobenzyl)amino)-2-oxoethyl)(cyclopropyl)carbamate (10a) (365 mg, 1.02 mmol) with TFA (0.54 mL, 6.97 mmol) according to the procedure reported in step-2 of Scheme 2 gave after workup N-(3-chloro-2-fluorobenzyl)-2-(cyclopropylamino) acetamide (10b) (265 mg, 0.715 mmol, 61.5% yield) as a TFA salt, which was used in the next step without further purification; MS (ES+) 257.3 (M+1).

Step-3: Preparation of 1-(2-((2-((3-chloro-2-fluorobenzyl)amino)-2-oxoethyl)(cyclopropyl)amino)-2-oxoethyl)-1H-indazole-3-carboxamide (10c)

Reaction of N-(3-chloro-2-fluorobenzyl)-2-(cyclopropylamino)acetamide (10b) (150 mg, 0.41 mmol) TFA salt from above step-2 with 2-(3-carbamoyl-1H-indazol-1-yl)acetic acid (2e) (106 mg, 0.49 mmol) according to the procedure reported in step-3 of Scheme 2 gave after workup and purification by [silica (12 g), eluting with CMA80 in CHCl₃ from 0 to 40%] 1-(2-((2-(((3-chloro-2-fluorobenzyl)amino)-2-oxoethyl)(cyclopropyl)amino)-2-oxoethyl)-1H-indazole-3-carboxamide (10c) (85 mg, 0.19 mmol, 46% yield) as a white solid; $^1$H NMR (300 MHz, DMSO-d₆) δ 8.51 (t, J=5.8 Hz, 1H), 8.18 (d, J=8.1 Hz, 1H), 7.74 (s, 1H), 7.64 (d, J=8.5 Hz, 1H), 7.52-7.33 (m, 3H), 7.31-7.16 (m, 2H), 7.16-7.05 (m, 1H), 5.67 (s, 2H), 4.33 (d, J=5.5 Hz, 2H), 3.98 (s, 2H), 3.14-2.99 (m, 1H), 1.08-0.95 (m, 2H), 0.95-0.86 (m, 2H); $^{19}$F NMR (282 MHz, DMSO) δ −121.33; MS (ES+): 458.5 (M+1); 456.5 (M−1).

Scheme 11

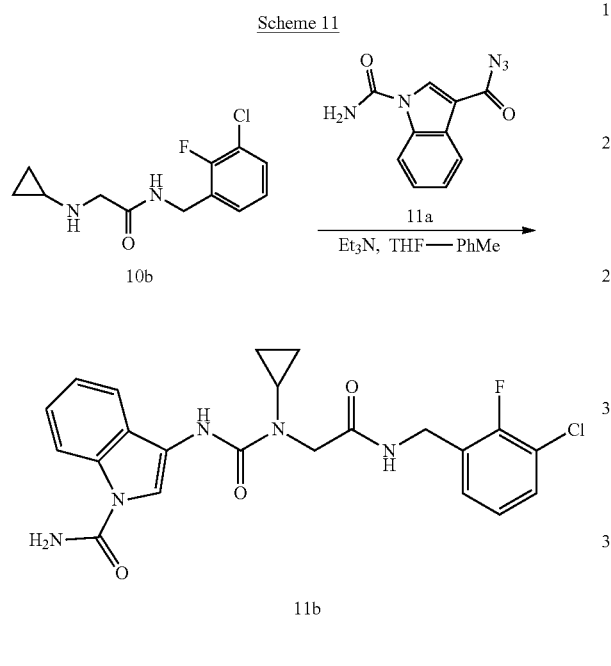

Preparation of 3-(3-(2-(3-chloro-2-fluorobenzylamino)-2-oxoethyl)-3-cyclopropylureido)-1H-indole-1-carboxamide (11b)

A suspension of 1-carbamoyl-1H-indole-3-carbonyl azide (11a) (50 mg, 0.22 mmol, prepared according to procedure reported by Altmann, Eva et al; in PCT Int. Appl., WO 2012/093101) in toluene (10 mL) was refluxed for 1.5 h. The resulting clear solution was cooled to room temperature and added a solution of N-(3-chloro-2-fluorobenzyl)-2-(cyclopropylamino)acetamide (10b) (56.0 mg, 0.22 mmol) in THF (5 mL), and triethylamine (0.061 µL, 0.44 mmol). The reaction mixture was stirred at room temperature for 3 h and concentrated in vacuum. The residue obtained was purified by flash column chromatography [Silica gel (24 g) eluting with CMA80 in CHCl₃ 0 to 40%] to afford 3-(3-(2-(3-chloro-2-fluorobenzylamino)-2-oxoethyl)-3-cyclopropylureido)-1H-indole-1-carboxamide (11b) (42 mg, 0.092 mmol, 42% yield) as a white solid; $^1$H NMR (300 MHz, DMSO-d₆) δ 8.47 (t, J=5.9 Hz, 1H), 8.33-8.23 (m, 2H), 8.03 (s, 1H), 7.67 (d, J=7.7 Hz, 1H), 7.55-7.39 (m, 1H), 7.37-7.23 (m, 2H), 7.23-7.14 (m, 2H), 4.36 (d, J=5.7 Hz, 2H), 3.99 (s, 2H), 2.99-2.84 (m, 1H), 1.01-0.88 (m, 2H), 0.80 (d, J=3.8 Hz, 2H); $^{19}$F NMR (282 MHz, DMSO-d₆) δ −121.33 (t, J=6.9 Hz); MS (ES+) 458.5 (M+1).

Scheme 12

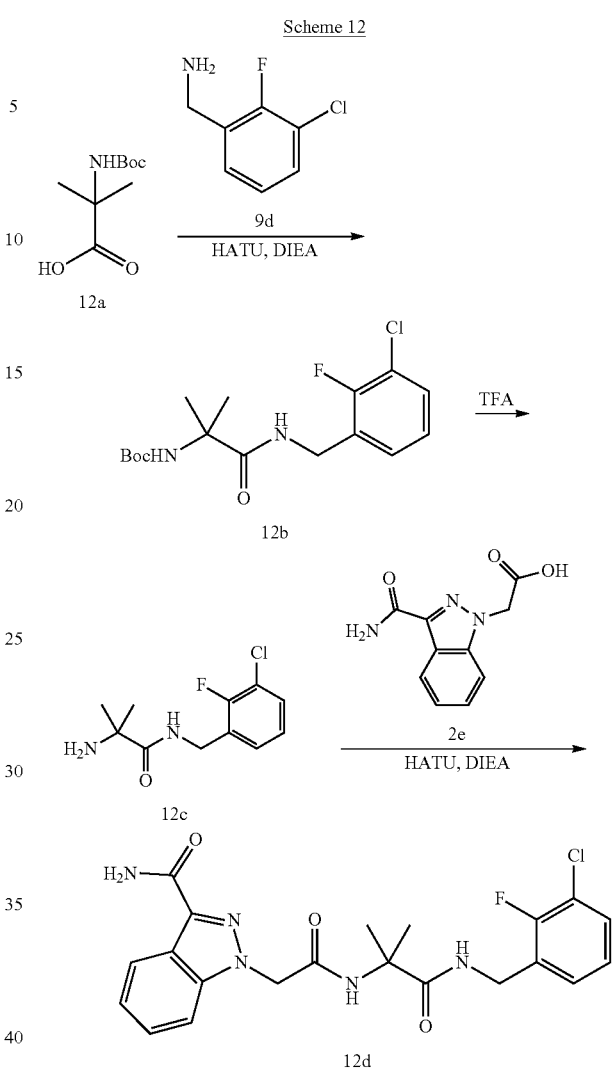

Preparation of 1-(2-(1-(3-chloro-2-fluorobenzylamino)-2-methyl-1-oxopropan-2-ylamino)-2-oxoethyl)-1H-indazole-3-carboxamide (12d)

Step-1: Preparation of tert-butyl 2-(2-(3-chloro-2-fluorophenyl)propan-2-ylamino)-2-oxoethylcarbamate (12b)

Reaction of 2-(tert-butoxycarbonylamino)-2-methylpropanoic acid (12a) (650 mg, 3.2 mmol) with 3-chloro-2-fluorobenzylamine (9d) (425 mg, 2.67 mmol) according to the procedure reported in step-3 of Scheme 2 gave after workup and purification by chromatography [silica (12 g), eluting with EtOAc in hexane from 0-50%] tert-butyl 2-(2-(3-chloro-2-fluorophenyl)propan-2-ylamino)-2-oxoethylcarbamate (12b) (752 mg, 2.18 mmol, 82% yield) as a white solid; $^1$H NMR (300 MHz, DMSO-d₆) δ 8.16 (s, 1H), 7.51-7.28 (m, 2H), 7.18-7.04 (m, 1H), 6.99 (s, 1H), 4.29 (d, J=5.5 Hz, 2H), 1.46-1.33 (m, 9H), 1.30 (s, 6H); $^{19}$F NMR (282 MHz, DMSO-d₆) δ −121.85; MS (ES+): 345.4 (M+1), 367.4 (M+Na).

Step-2: Preparation of 2-amino-N-(2-(3-chloro-2-fluorophenyl)propan-2-yl)acetamide (12c)

Reaction of tert-butyl 2-(2-(3-chloro-2-fluorophenyl)propan-2-ylamino)-2-oxoethylcarbamate (12b) (700 mg, 2.030 mmol) with TFA (0.94 mL, 12.18 mmol) according to the procedure reported in step-2 of Scheme 2 gave after workup 2-amino-N-(2-(3-chloro-2-fluorophenyl)propan-2-yl)acetamide (12c) TFA salt (725 mg, 2.02 mmol, 100% yield) as a semi-solid, which was used in the next step without further purification; $^1$H NMR (300 MHz, DMSO-$d_6$) 8.93 (t, J=5.6 Hz, 1H), 8.21 (s, 2H), 7.50 (td, J=7.4, 2.1 Hz, 1H), 7.31-7.14 (m, 2H), 4.40 (d, J=5.5 Hz, 2H), 1.48 (s, 6H); $^{19}$F NMR (282 MHz, DMSO) δ −73.40, −121.12; MS (ES+): 245.3 (M+1).

Step-3: Preparation of 1-(2-(1-(3-chloro-2-fluorobenzylamino)-2-methyl-1-oxopropan-2-ylamino)-2-oxoethyl)-1H-indazole-3-carboxamide (12d)

Reaction of 2-amino-N-(2-(3-chloro-2-fluorophenyl)propan-2-yl)acetamide (12c) (300 mg, 0.836 mmol) TFA salt from above step-2 with 2-(3-carbamoyl-1H-indazol-1-yl)acetic acid (2e) (220 mg, 1.0 mmol) according to the procedure reported in step-3 of Scheme 2 gave after workup and purification by [silica (12 g), eluting with CMA80 in CHCl$_3$ from 0 to 40%] 1-(2-(1-(3-chloro-2-fluorobenzylamino)-2-methyl-1-oxopropan-2-ylamino)-2-oxoethyl)-1H-indazole-3-carboxamide (12d) (185 mg, 0.42 mmol, 50% yield) as a white solid; $^1$H NMR (300 MHz, DMSO-$d_6$) δ 8.58 (s, 1H), 8.36 (t, J=5.9 Hz, 1H), 8.19 (d, J=8.1 Hz, 1H), 7.69 (s, 1H), 7.62-7.53 (m, 1H), 7.46-7.32 (m, 3H), 7.30-7.14 (m, 2H), 6.92 (t, J=7.9 Hz, 1H), 5.24 (s, 2H), 4.32 (d, J=5.6 Hz, 2H), 1.41 (s, 6H); $^{19}$F NMR (282 MHz, DMSO-$d_6$) δ −121.89; MS (ES+) 446.5 (M+1), 468.5 (M+Na).

Scheme 13

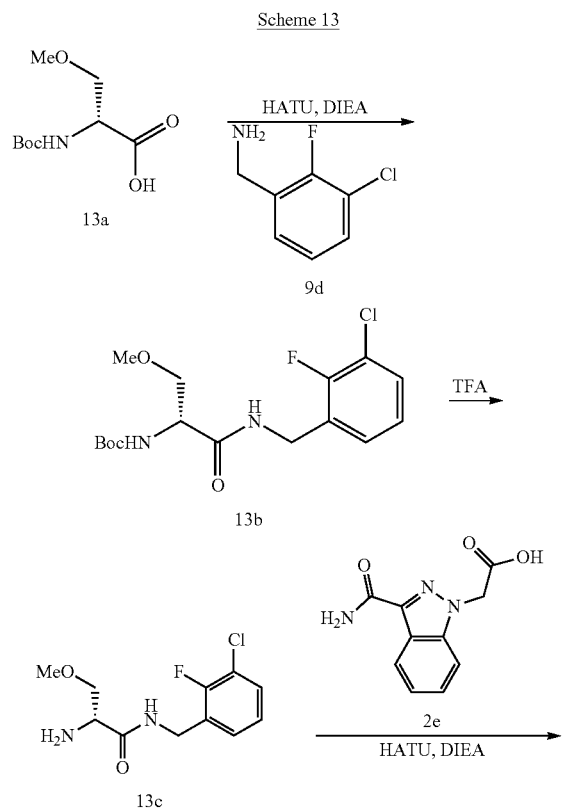

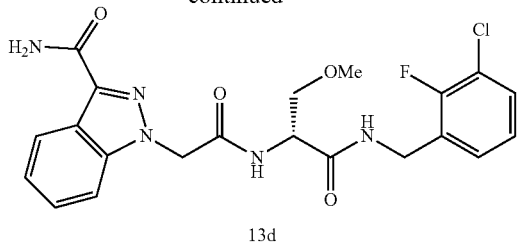

13d

Preparation of (R)-1-(2-((1-((3-chloro-2-fluorobenzyl)amino)-3-methoxy-1-oxopropan-2-yl)amino)-2-oxoethyl)-1H-indazole-3-carboxamide (13d)

Step-1: Preparation of (R)-tert-butyl (1-((3-chloro-2-fluorobenzyl)amino)-3-methoxy-1-oxopropan-2-yl)carbamate (13b)

Reaction of (R)-2-((tert-butoxycarbonyl)amino)-3-methoxypropanoic acid (13a) (382 mg, 1.74 mmol) with 3-chloro-2-fluorobenzylamine (9d) (232 mg, 1.45 mmol) according to the procedure reported in step-3 of Scheme 2 gave after workup (R)-tert-butyl (1-((3-chloro-2-fluorobenzyl)amino)-3-methoxy-1-oxopropan-2-yl)carbamate (13b) which was used as such in next step; MS (ES+): 383.4 (M+Na).

Step-2: Preparation of (R)-2-amino-N-(3-chloro-2-fluorobenzyl)-3-methoxypropanamide (13c)

Reaction of (R)-tert-butyl (1-((3-chloro-2-fluorobenzyl)amino)-3-methoxy-1-oxopropan-2-yl)carbamate (13b) (525 mg, 1.45 mmol) with TFA (2.02 mL, 26.2 mmol) according to the procedure reported in step-2 of Scheme 2 gave after workup (R)-2-amino-N-(3-chloro-2-fluorobenzyl)-3-methoxypropanamide (13c) TFA salt (379 mg, 1.45 mmol, 100% yield) which was used in the next step without further purification; MS (ES+): 261.3 (M+1).

Step-3: Preparation of (R)-1-(2-((1-((3-chloro-2-fluorobenzyl)amino)-3-methoxy-1-oxopropan-2-yl)amino)-2-oxoethyl)-1H-indazole-3-carboxamide (13d)

Reaction of (R)-2-amino-N-(3-chloro-2-fluorobenzyl)-3-methoxypropanamide (13c) (379 mg, 1.45 mmol) TFA salt from above step-2 with 2-(3-carbamoyl-1H-indazol-1-yl)acetic acid (2e) (382 mg, 1.75 mmol) according to the procedure reported in step-3 of Scheme 2 gave after workup and purification by chromatography [silica (24 g), eluting with MeOH in CHCl$_3$ from 0 to 40%] (R)-1-(2-((1-((3-chloro-2-fluorobenzyl)amino)-3-methoxy-1-oxopropan-2-yl)amino)-2-oxoethyl)-1H-indazole-3-carboxamide (13d) (32 mg, 5% yield) as a white solid; $^1$H NMR (300 MHz, DMSO-$d_6$) δ 8.78-8.66 (m, 2H), 8.18 (dt, J=8.2, 1.0 Hz, 1H), 7.72 (s, 1H, D$_2$O exchangeable), 7.64 (d, J=8.5 Hz, 1H), 7.54-7.35 (m, 3H, 1H, D$_2$O exchangeable), 7.31-7.22 (m, 2H), 7.20-7.10 (m, 1H), 5.30 (d, J=2.3 Hz, 2H), 4.57-4.47 (m, 1H), 4.46-4.28 (m, 2H), 3.65-3.50 (m, 2H), 3.28 (s, 3H); $^{19}$F NMR (282 MHz, DMSO-$d_6$) δ −121.28; MS (ES+): 484.5 (M+Na); (ES−) 496.4 (M+Cl).

Scheme 14

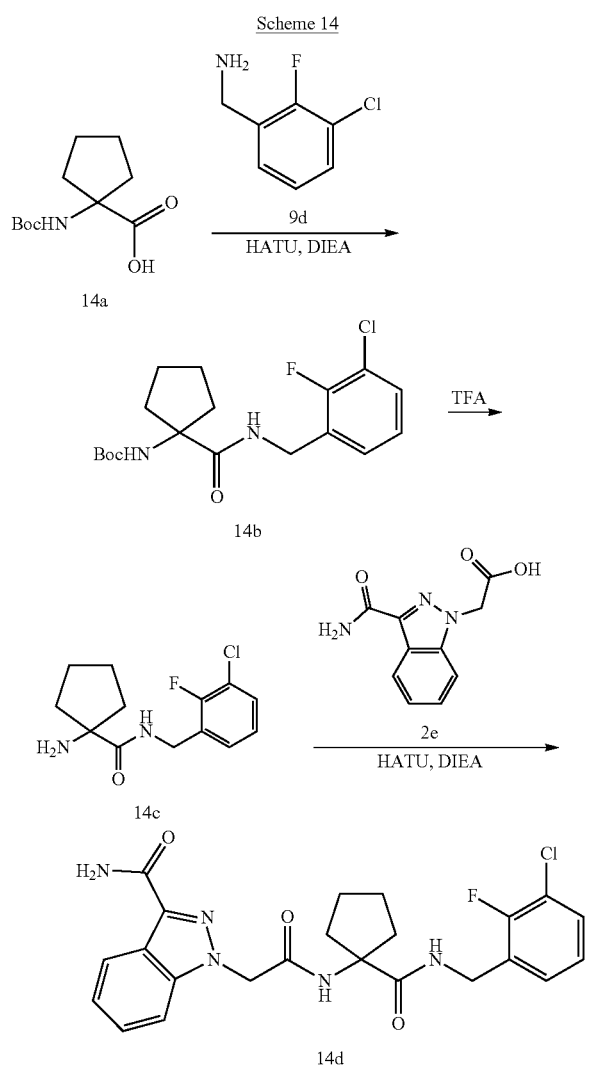

Preparation of 1-(2-((1-((3-chloro-2-fluorobenzyl)carbamoyl)cyclopentyl)amino)-2-oxoethyl)-1H-indazole-3-carboxamide (14d)

Step-1: Preparation of tert-butyl(1-((3-chloro-2-fluorobenzyl)carbamoyl)cyclopentyl)carbamate (14b)

Reaction of 1-((tert-butoxycarbonyl)amino)cyclopentanecarboxylic acid (14a) (650 mg, 2.85 mmol) with 3-chloro-2-fluorobenzylamine (9d) (379 mg, 2.37 mmol) according to the procedure reported in step-3 of Scheme 2 gave after workup and purification by chromatography [silica gel (12 g), eluting with EtOAc in hexane, 0-50%] tert-butyl (1-((3-chloro-2-fluorobenzyl)carbamoyl)cyclopentyl)carbamate (14b) (650 mg, 1.73 mmol, 74% yield) as a white solid; $^1$H NMR (300 MHz, DMSO-$d_6$) 8.15-8.06 (m, 1H), 7.43 (t, J=7.1 Hz, 1H), 7.35 (t, J=7.1 Hz, 1H), 7.19-7.06 (m, 2H), 4.31 (d, J=5.9 Hz, 2H), 2.07-1.92 (m, 2H), 1.89-1.71 (m, 3H), 1.65-1.55 (m, 3H), 1.38 (s, 9H); MS (ES+): 371.4 (M+1), 393.4 (M+Na).

Step-2: Preparation of 1-amino-N-(3-chloro-2-fluorobenzyl)cyclopentanecarboxamide (14c)

Reaction of tert-butyl (1-((3-chloro-2-fluorobenzyl)carbamoyl)cyclopentyl)carbamate (14b) (650 mg, 1.75 mmol) with TFA (1.35 mL, 17.53 mmol) according to the procedure reported in step-2 of Scheme 2 gave after workup 1-amino-N-(3-chloro-2-fluorobenzyl)cyclopentanecarboxamide (14c) TFA salt (675 mg, 1.75 mmol, 100% yield) as a clear oil which was used in the next step without further purification; $^1$H NMR (300 MHz, DMSO-$d_6$) δ 8.86 (t, J=5.2 Hz, 1H), 8.17 (s, 2H), 7.50 (t, J=7.4 Hz, 1H), 7.32-7.13 (m, 2H), 4.40 (d, J=5.2 Hz, 2H), 4.13 (s, 1H), 2.10 (s, 2H), 1.86 (d, J=15.6 Hz, 6H); $^{19}$F NMR (282 MHz, DMSO) δ −73.25 (TFA); −121.06; MS (ES+): 271.3 (M+1).

Step-3: Preparation of 1-(2-((1-((3-chloro-2-fluorobenzyl)carbamoyl)cyclopentyl)amino)-2-oxoethyl)-1H-indazole-3-carboxamide (14d)

Reaction of 1-amino-N-(3-chloro-2-fluorobenzyl)cyclopentanecarboxamide (14c) (117 mg, 0.53 mmol) TFA salt from above step-2 with 2-(3-carbamoyl-1H-indazol-1-yl)acetic acid (2e) (116 mg, 0.53 mmol) according to the procedure reported in step-3 of Scheme 2 gave after workup and purification by chromatography [silica (12 g), eluting with CMA80 in CHCl$_3$ 0 to 40%] 1-(2-((1-((3-chloro-2-fluorobenzyl)carbamoyl)cyclopentyl)amino)-2-oxoethyl)-1H-indazole-3-carboxamide (14d) (62 mg, 0.13 mmol, 30% yield) as a white solid; $^1$H NMR (300 MHz, DMSO-$d_6$) δ 8.63 (s, 1H), 8.37 (t, J=5.9 Hz, 1H), 8.17 (d, J=8.1 Hz, 1H), 7.65 (s, 1H), 7.57 (d, J=8.5 Hz, 1H), 7.45-7.31 (m, 3H), 7.31-7.20 (m, 1H), 7.20-7.09 (m, 1H), 6.91 (t, J=7.9 Hz, 1H), 5.25 (s, 2H), 4.33 (d, J=5.7 Hz, 2H), 2.15-1.97 (m, 2H), 1.96-1.80 (m, 2H), 1.77-1.59 (m, 4H); $^{19}$F NMR (282 MHz, DMSO-$d_6$) δ −121.99; MS (ES+): 472.5 (M+1).

Scheme 15

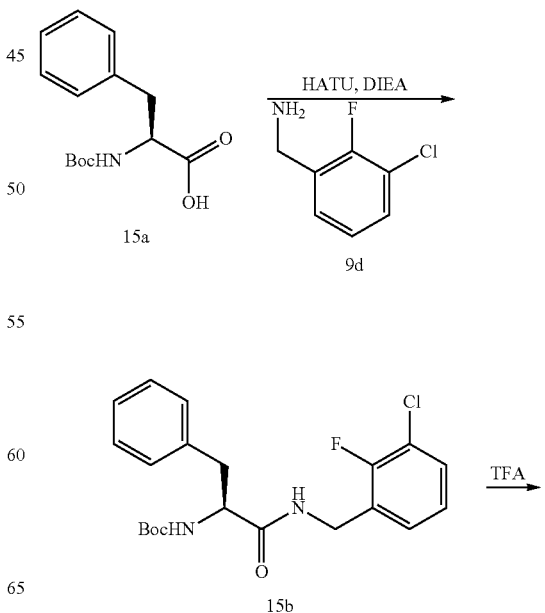

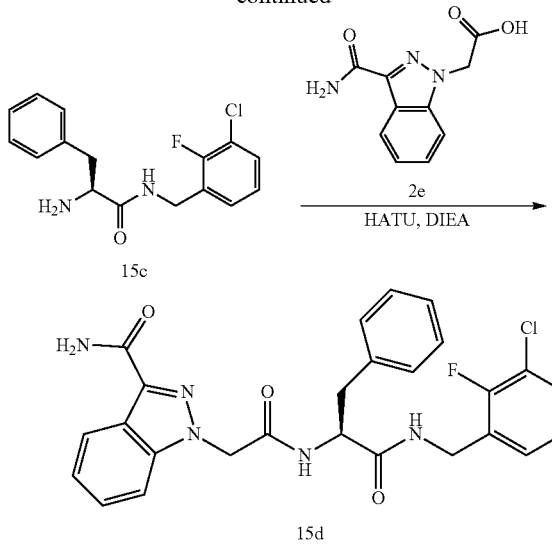

δ 8.79-8.67 (m, 2H), 8.15 (dt, J=8.2, 1.0 Hz, 1H), 7.65 (s, 1H), 7.47 (td, J=7.5, 1.9 Hz, 1H), 7.42-7.35 (m, 3H), 7.30-7.19 (m, 6H), 7.14-7.00 (m, 2H), 5.31-5.08 (m, 2H), 4.64-4.53 (m, 1H), 4.44-4.21 (m, 2H), 3.11-2.97 (m, 1H), 2.92-2.75 (m, 1H); $^{19}$F NMR (282 MHz, DMSO-$d_6$) δ −121.21; MS (ES+): 530.5 (M+Na); (ES−): 506.5 (M−1), 542.4 (M+Cl).

Scheme 16

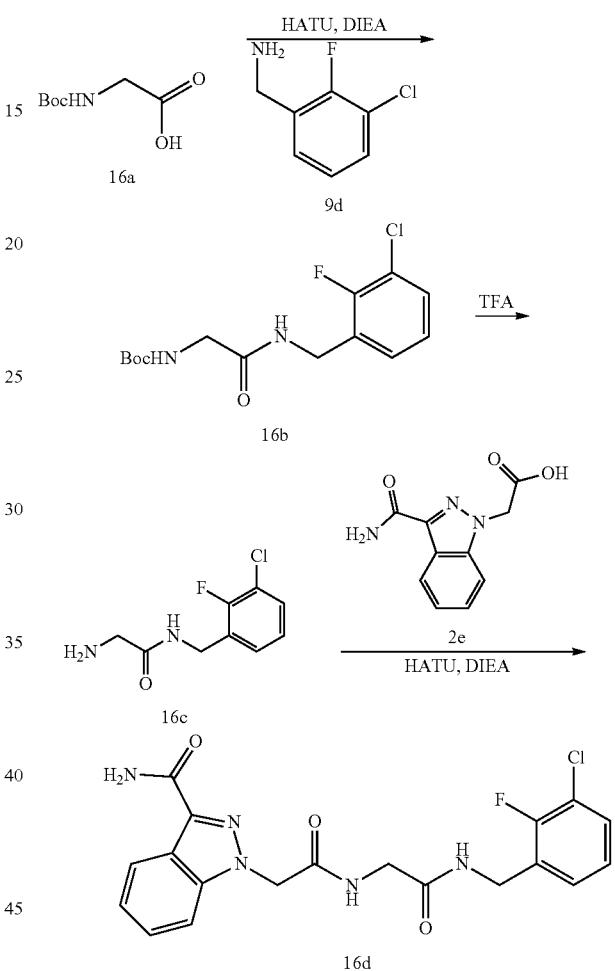

Preparation of (S)-1-(2-((1-((3-chloro-2-fluorobenzyl)amino)-1-oxo-3-phenylpropan-2-yl)-amino)-2-oxoethyl)-1H-indazole-3-carboxamide (15d)

Step-1: Preparation of (S)-tert-butyl (1-((3-chloro-2-fluorobenzyl)amino)-1-oxo-3-phenylpropan-2-yl) carbamate (15b)

Reaction of (S)-2-((tert-butoxycarbonyl)amino)-3-phenylpropanoic acid (15a) (475 mg, 1.79 mmol) with 3-chloro-2-fluorobenzylamine (9d) (238 mg, 1.49 mmol) according to the procedure reported in step-3 of Scheme 2 gave after workup (5)-tert-butyl (1-((3-chloro-2-fluorobenzyl)amino)-1-oxo-3-phenylpropan-2-yl)carbamate (15b) which was used as such in the next step; MS (ES−): 441.4 (M+Cl).

Step-2: Preparation of (S)-2-amino-N-(3-chloro-2-fluorobenzyl)-3-phenylpropanamide (15c)

Reaction of (5)-tert-butyl (1-((3-chloro-2-fluorobenzyl)amino)-1-oxo-3-phenylpropan-2-yl)carbamate (15b) (607 mg, 1.5 mmol) with TFA according to the procedure reported in step-2 of Scheme 2 gave after workup (S)-2-amino-N-(3-chloro-2-fluorobenzyl)-3-phenylpropanamide (15c) TFA salt (458 mg, 1.49 mmol, 83%) which was used in next step without further purification; MS (ES+): 307.4 (M+1), (ES−) 305.2 (M−1).

Step-3: Preparation of (S)-1-(2-((1-((3-chloro-2-fluorobenzyl)amino)-1-oxo-3-phenylpropan-2-yl)-amino)-2-oxoethyl)-1H-indazole-3-carboxamide (15d)

Reaction of (S)-2-amino-N-(3-chloro-2-fluorobenzyl)-3-phenylpropanamide (15c) (458 mg, 1.49 mmol) TFA salt from above step-2 with 2-(3-carbamoyl-1H-indazol-1-yl) acetic acid (2e) (393 mg, 1.79 mmol) according to the procedure reported in step-3 of Scheme 2 gave after workup and purification by chromatography [silica (24 g), eluting with MeOH in CHCl$_3$ 0 to 40%] (S)-1-(2-((1-((3-chloro-2-fluorobenzyl)amino)-1-oxo-3-phenylpropan-2-yl)-amino)-2-oxoethyl)-1H-indazole-3-carboxamide (15d) (66 mg, 13% yield) as an off-white solid; $^1$H NMR (300 MHz, DMSO-$d_6$)

Preparation of 1-(2-((2-((3-chloro-2-fluorobenzyl) amino)-2-oxoethyl)amino)-2-oxoethyl)-1H-indazole-3-carboxamide (16d)

Step-1: Preparation of tert-butyl (2-((3-chloro-2-fluorobenzyl)amino)-2-oxoethyl)carbamate (16b)

Reaction of 2-((tert-butoxycarbonyl)amino)acetic acid (16a) (4 g, 22.83 mmol) with 3-chloro-2-fluorobenzylamine (9d) (3.31 g, 20.76 mmol) according to the procedure reported in step-3 of Scheme 2 gave after workup and purification by chromatography [silica (80 g), eluting with EtOAc in hexane from 0 to 60%] tert-butyl (2-((3-chloro-2-fluorobenzyl)amino)-2-oxoethyl)carbamate (16b) (4.09 g, 12.91 mmol, 62% yield) as a white solid; $^1$H NMR (300 MHz, DMSO-$d_6$) δ 8.37 (t, J=5.8 Hz, 1H), 7.53-7.41 (m, 1H), 7.35-7.23 (m, 1H), 7.24-7.12 (m, 1H), 7.05 (t, J=6.0

Hz, 1H), 4.33 (d, J=5.8 Hz, 2H), 3.57 (d, 2H), 1.38 (s, 9H); $^{19}$F NMR (282 MHz, DMSO) δ −121.38; MS (ES+): 339.4 (M+Na)

Step-2: Preparation of 2-amino-N-(3-chloro-2-fluorobenzyl)acetamide (16c)

Reaction of tert-butyl (2-((3-chloro-2-fluorobenzyl)amino)-2-oxoethyl)carbamate (16b) (4.08 g, 12.88 mmol) with TFA (4.96 mL, 64.4 mmol) according to the procedure reported in step-2 of Scheme 2 gave after workup 2-amino-N-(3-chloro-2-fluorobenzyl)acetamide (16c) TFA salt (9.07 mmol, 70% yield) as a white solid, which was used in the next step without further purification; $^1$H NMR (300 MHz, DMSO-d$_6$) δ 8.94 (t, J=5.7 Hz, 1H), 8.04 (s, 3H), 7.56-7.45 (m, 1H), 7.40-7.29 (m, 1H), 7.27-7.15 (m, 1H), 4.41 (d, J=5.7 Hz, 2H), 3.62 (s, 2H); $^{19}$F NMR (282 MHz, DMSO-d$_6$) δ −73.32, −120.87; MS (ES$^+$) 217.2 (M+1).

Step-3: Preparation of 1-(2-((2-((3-chloro-2-fluorobenzyl)amino)-2-oxoethyl)amino)-2-oxoethyl)-1H-indazole-3-carboxamide (16d) Reaction of 2-amino-N-(3-chloro-2-fluorobenzyl)acetamide (16c)

(160 mg, 0.48 mmol) TFA salt from above step-2 with 2-(3-carbamoyl-1H-indazol-1-yl)acetic acid (2e) (127 mg, 0.58 mmol) according to the procedure reported in step-3 of Scheme 2 gave after workup and purification by chromatography [silica (12 g), eluting with CMA80 in CHCl$_3$ 0 to 40%] 1-(2-((2-((3-chloro-2-fluorobenzyl)amino)-2-oxoethyl)amino)-2-oxoethyl)-1H-indazole-3-carboxamide (16d) (120 mg, 0.29 mmol, 59% yield) as a white solid; $^1$H NMR (300 MHz, DMSO-d$_6$) δ 8.59 (t, J=5.7 Hz, 1H), 8.54 (t, J=5.7 Hz, 1H), 8.18 (d, J=8.0 Hz, 1H), 7.75-7.61 (m, 2H), 7.54-7.34 (m, 3H), 7.33-7.20 (m, 2H), 7.20-7.10 (m, 1H), 5.26 (s, 2H), 4.36 (d, J=5.6 Hz, 2H), 3.82 (d, J=5.5 Hz, 2H); $^{19}$F NMR (282 MHz, DMSO-d$_6$) δ −121.23; MS (ES+): 418.5 (M+1), 440.4 (M+Na); 416.3 (M−1).

Preparation of 3-(3-(2-(((6-bromopyridin-2-yl)amino)-2-oxoethyl)-3-cyclopropylureido)-1H-indole-1-carboxamide (17a)

Reaction of N-(6-bromopyridin-2-yl)-2-(cyclopropylamino)acetamide (7c) with 1-carbamoyl-1H-indole-3-carbonyl azide (11a) (50 mg, 0.22 mmol) according to the procedure reported in Scheme 11 gave after workup and purification by flash column chromatography (Silica gel, 24 g eluting with CHCl$_3$-CMA80 0-40%) 3-(3-(2-(((6-bromopyridin-2-yl)amino)-2-oxoethyl)-3-cyclopropylureido)-1H-indole-1-carboxamide (17a) (108 mg, 0.23 mmol, 76% yield) as a white solid; $^1$H NMR (300 MHz, DMSO-d$_6$) δ 10.95 (s, 1H), 8.35-8.22 (m, 2H), 8.07 (d, J=8.2 Hz, 1H), 8.02 (s, 1H), 7.78-7.64 (m, 2H), 7.42 (s, 2H), 7.34 (d, J=7.7 Hz, 1H), 7.31-7.15 (m, 2H), 4.19 (s, 2H), 3.06-2.89 (m, 1H), 1.05-0.87 (m, 2H), 0.85-0.72 (m, 2H); MS (ES+): 471.4 (M+1), 493.4 (M+Na).

Scheme 18

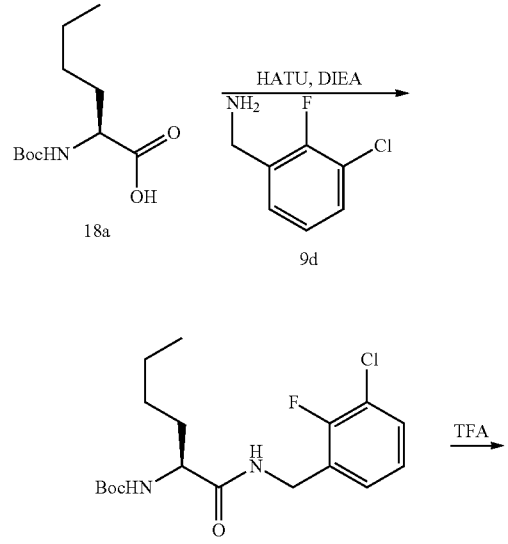

Scheme 17

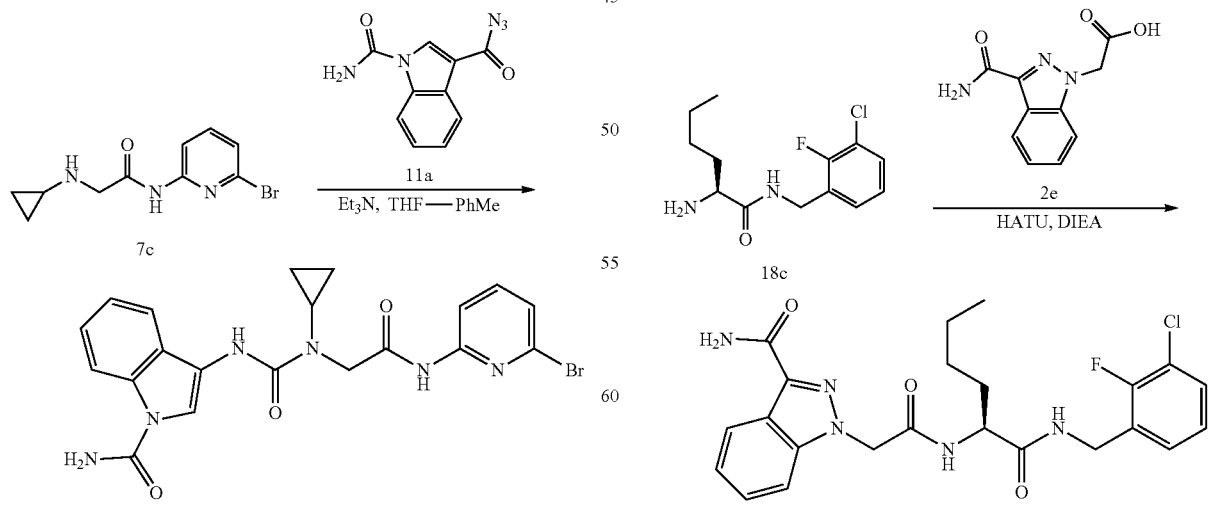

Preparation of (S)-1-(2-((1-((3-chloro-2-fluorobenzyl)amino)-1-oxohexan-2-yl)-amino)-2-oxoethyl)-1H-indazole-3-carboxamide (18d)

Step-1: Preparation of (5)-tert-butyl (1-((3-chloro-2-fluorobenzyl)amino)-1-oxohexan-2-yl)carbamate (18b)

Reaction of (S)-2-((tert-butoxycarbonyl)amino)hexanoic acid (18a) (0.42 g, 1.8 mmol) with 3-chloro-2-fluorobenzylamine (9d) (0.239 g, 1.5 mmol) according to the procedure reported in step-3 of Scheme 2 gave after workup (5)-tert-butyl (1-((3-chloro-2-fluorobenzyl)amino)-1-oxohexan-2-yl)carbamate (18b) which was used as such in the next step.

Step-2: Preparation of (S)-2-amino-N-(3-chloro-2-fluorobenzyl)hexanamide (18c)

Reaction of (5)-tert-butyl (1-((3-chloro-2-fluorobenzyl)amino)-1-oxohexan-2-yl)carbamate (18b) (0.56 g, 1.5 mmol) with TFA (2.08 mL, 26.9 mmol) according to the procedure reported in step-2 of Scheme 2 gave after workup (S)-2-amino-N-(3-chloro-2-fluorobenzyl)hexanamide (18c) TFA salt (9.07 mmol, 70% yield) which was used as such in the next step; MS (ES+): 273.4 (M+1).

Step-3: Preparation of (S)-1-(2-((1-((3-chloro-2-fluorobenzyl)amino)-1-oxohexan-2-yl)amino)-2-oxoethyl)-1H-indazole-3-carboxamide (18d)

Reaction of (S)-2-amino-N-(3-chloro-2-fluorobenzyl)hexanamide (18c) (408 mg, 1.5 mmol) TFA salt from above step-2 with 2-(3-carbamoyl-1H-indazol-1-yl)acetic acid (2e) (393 mg, 1.8 mmol) according to the procedure reported in step-3 of Scheme 2 gave after workup gave (S)-1-(2-((1-((3-chloro-2-fluorobenzyl)amino)-1-oxohexan-2-yl)amino)-2-oxoethyl)-1H-indazole-3-carboxamide (18d) (56 mg, 0.12 mmol, 8% yield) as an off-white solid; $^1$H NMR (300 MHz, DMSO-$d_6$) δ 8.76-8.62 (m, 2H, $D_2O$ exchangeable), 8.24 (d, J=8.1 Hz, 1H), 7.76 (s, 1H, $D_2O$ exchangeable), 7.69 (d, J=8.6 Hz, 1H), 7.60-7.42 (m, 3H), 7.32 (t, J=7.7 Hz, 2H), 7.20 (t, J=7.8 Hz, 1H), 5.32 (s, 2H), 4.53-4.26 (m, 3H), 1.81-1.56 (m, 2H), 1.31 (s, 4H), 0.96-0.86 (m, 3H); $^{19}$F NMR (282 MHz, DMSO-$d_6$) δ −121.09; MS (ES+): 496.5 (M+Na), 472.5 (M−1).

Scheme 19

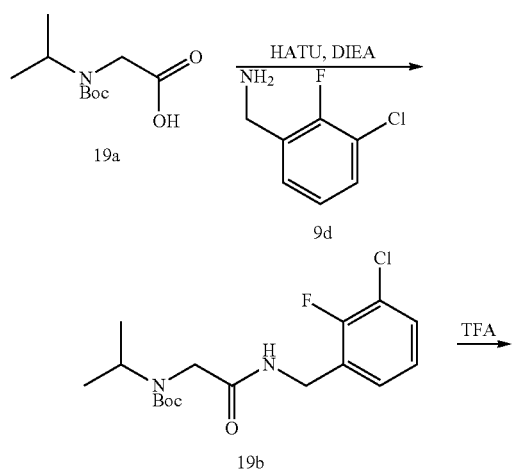

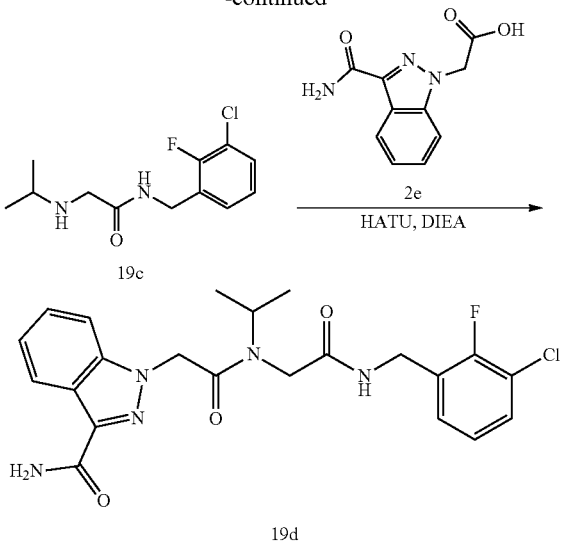

Preparation of 1-(2-((2-((3-chloro-2-fluorobenzyl)amino)-2-oxoethyl)(isopropyl)amino)-2-oxoethyl)-1H-indazole-3-carboxamide (19d)

Step-1: Preparation of tert-butyl (2-((3-chloro-2-fluorobenzyl)amino)-2-oxoethyl)(isopropyl)carbamate (19b)

Reaction of 2-((tert-butoxycarbonyl)(isopropyl)amino)acetic acid (19a) (300 mg, 1.38 mmol) with 3-chloro-2-fluorobenzylamine (9d) (200 mg, 1.26 mmol) according to the procedure reported in step-3 of Scheme 2 gave after workup and purification by chromatography [silica (12 g), eluting with EtOAc in hexane 0 to 60%] tert-butyl (2-((3-chloro-2-fluorobenzyl)amino)-2-oxoethyl)(isopropyl)carbamate (19b) (395 mg, 1.1 mmol, 88% yield) as a white solid; $^1$H NMR (300 MHz, DMSO-$d_6$) δ 8.35 (s, 1H), 7.47 (t, J=7.5 Hz, 1H), 7.37-7.25 (m, 1H), 7.23-7.10 (m, 1H), 4.32 (d, J=5.7 Hz, 2H), 4.28-3.95 (m, 1H), 3.75-3.57 (m, 2H), 1.40 (s, 3H), 1.26 (s, 6H), 1.12-0.95 (m, 6H); MS (ES$^+$) 381.4 (M+Na).

Step-2: Preparation of N-(3-chloro-2-fluorobenzyl)-2-(isopropylamino)acetamide (19c)

Reaction of tert-butyl (2-((3-chloro-2-fluorobenzyl)amino)-2-oxoethyl)(isopropyl)carbamate (19b) (340 mg, 0.95 mmol) with TFA (0.37 mL, 4.74 mmol) according to the procedure reported in step-2 of Scheme 2 gave after workup N-(3-chloro-2-fluorobenzyl)-2-(isopropylamino)acetamide (19c) TFA salt (348 mg, 0.93 mmol, 99% yield) as a white solid, which was used in the next step without further purification; $^1$H NMR (300 MHz, DMSO-$d_6$) δ 9.04 (t, J=5.7 Hz, 1H), 8.81 (s, 2H), 7.57-7.46 (m, 1H), 7.40-7.30 (m, 1H), 7.26-7.16 (m, 1H), 4.42 (d, J=5.6 Hz, 2H), 3.78-3.77 (m, 2H), 3.37-3.20 (m, 1H), 1.20 (d, J=6.5 Hz, 6H); $^{19}$F NMR (282 MHz, DMSO-$d_6$) δ −73.83 (TFA peak), −120.79; MS (ES+) 259.4 (M+1).

Step-3: Preparation of 1-(2-((2-((3-chloro-2-fluorobenzyl)amino)-2-oxoethyl)(isopropyl)amino)-2-oxoethyl)-1H-indazole-3-carboxamide (19d)

Reaction of N-(3-chloro-2-fluorobenzyl)-2-(isopropylamino)acetamide (19c) (160 mg, 0.43 mmol) TFA salt from above step-2 with 2-(3-carbamoyl-1H-indazol-1-yl)acetic acid (2e) (113 mg, 0.52 mmol) according to the procedure reported in step-3 of Scheme 2 gave after workup and purification by chromatography [silica (12 g), eluting with CMA80 in CHCl$_3$ 0 to 40%] 1-(2-((2-((3-chloro-2-fluorobenzyl)amino)-2-oxoethyl)(isopropyl)amino)-2-oxoethyl)-1H-indazole-3-carboxamide (19d) (115 mg, 0.25 mmol, 58% yield) as a white solid; $^1$H NMR (300 MHz, DMSO-d$_6$) δ 8.83, 8.36 (2t, J=5.7 Hz, 1H), 8.18 (d, J=8.0 Hz, 1H), 7.71 (s, 1H), 7.63-7.47 (m, 2H), 7.47-7.31 (m, 3H), 7.29-6.99 (m, 2H), 5.59, 5.45 (2s, 2H), 4.61-4.39 (m, 2H), 4.36-4.10 (m, 2H), 3.91-3.75 (m, 1H), 1.23, 0.99 (2dd, J=72.0, 6.4 Hz, 6H); $^{19}$F NMR (282 MHz, DMSO-d$_6$) δ −120.94, −121.48; MS (ES+): 460.5 (M+1); (ES−): 458.5 (M−1); (based on NMR the compound is a mixture of rotamers with 2:3 ratio)

Scheme 20

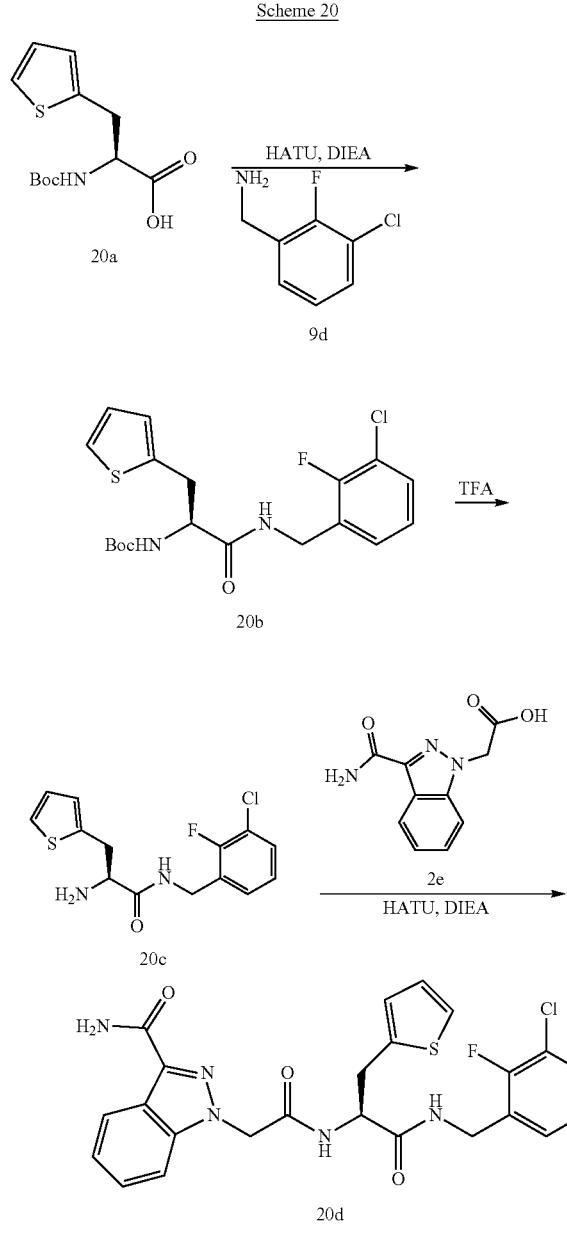

Preparation of (S)-1-(2-((1-((3-chloro-2-fluorobenzyl)amino)-1-oxo-3-(thiophen-2-yl)propan-2-yl)amino)-2-oxoethyl)-1H-indazole-3-carboxamide (20d)

Step-1: Preparation of (S)-tert-butyl (1-((3-chloro-2-fluorobenzyl)amino)-1-oxo-3-(thiophen-2-yl)propan-2-yl)carbamate (20b)

Reaction of (S)-2-((tert-butoxycarbonyl)amino)-3-(thiophen-2-yl)propanoic acid (20a) (428 mg, 1.58 mmol) with 3-chloro-2-fluorobenzylamine (9d) (252 mg, 1.58 mmol) according to the procedure reported in step-3 of Scheme 2 gave after workup (5)-tert-butyl (1-((3-chloro-2-fluorobenzyl)amino)-1-oxo-3-(thiophen-2-yl)propan-2-yl)carbamate (20b) which was used as such in the next step; MS (ES−): 448.4 (M+Cl).

Step-2: Preparation of (S)-2-amino-N-(3-chloro-2-fluorobenzyl)-3-(thiophen-2-yl)propanamide (20c)

Reaction of (S)-tert-butyl(1-((3-chloro-2-fluorobenzyl)amino)-1-oxo-3-(thiophen-2-yl)propan-2-yl)carbamate (20b) (652 mg, 1.58 mmol) with TFA (2.19 mL, 28.4 mmol) according to the procedure reported in step-2 of Scheme 2 gave after workup (S)-2-amino-N-(3-chloro-2-fluorobenzyl)-3-(thiophen-2-yl)propanamide (20c) TFA salt which was used in next step without further purification; MS (ES+): 313.3 (M+1).

Step-3: Preparation of (S)-1-(2-((1-((3-chloro-2-fluorobenzyl)amino)-1-oxo-3-(thiophen-2-yl)propan-2-yl)-amino)-2-oxoethyl)-1H-indazole-3-carboxamide (20d)

Reaction of (S)-2-amino-N-(3-chloro-2-fluorobenzyl)-3-phenylpropanamide (15c) (494 mg, 1.58 mmol) TFA salt from above step-2 with 2-(3-carbamoyl-1H-indazol-1-yl) acetic acid (2e) (415 mg, 1.9 mmol) according to the procedure reported in step-3 of Scheme 2 gave after workup (S)-1-(2-((1-((3-chloro-2-fluorobenzyl)amino)-1-oxo-3-(thiophen-2-yl)propan-2-yl)amino)-2-oxoethyl)-1H-indazole-3-carboxamide (20d) (86 mg, 11% yield) as an off-white solid; $^1$H NMR (300 MHz, DMSO-d$_6$) δ 8.91-8.70 (m, 2H), 8.17 (dt, J=8.2, 1.0 Hz, 1H), 7.67 (s, 1H), 7.55-7.35 (m, 5H), 7.30-7.21 (m, 1H), 7.17-7.04 (m, 2H), 6.98-6.92 (m, 1H), 6.92-6.87 (m, 1H), 5.37-5.09 (m, 2H), 4.66-4.50 (m, 1H), 4.46-4.22 (m, 2H), 3.33-3.21 (m, 1H), 3.17-2.99 (m, 1H); $^{19}$F NMR (282 MHz, DMSO-d$_6$) δ −121.19; MS (ES+): 514.53 (M+1), 536.5 (M+Na), 512.5 (M−1).

Scheme 21

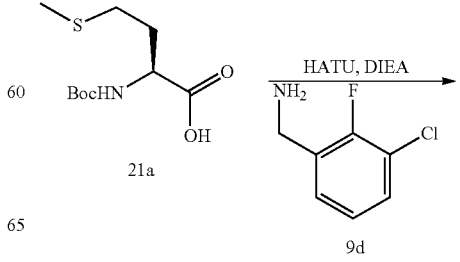

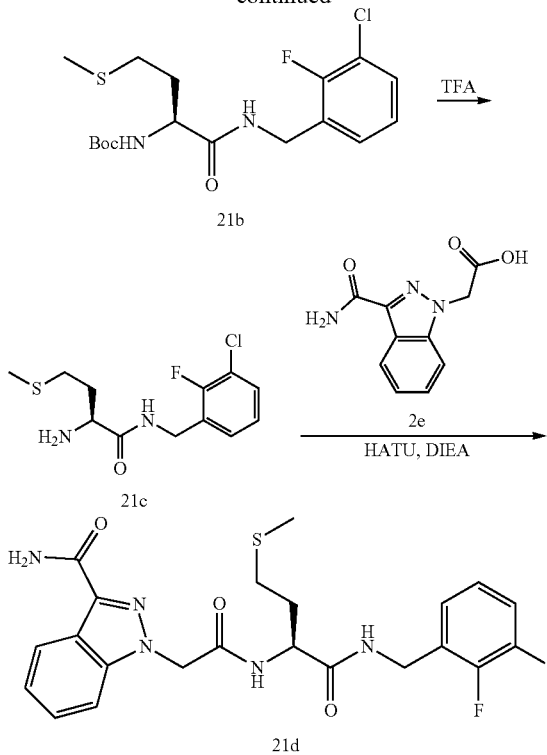

Preparation of (S)-1-(2-((1-((3-chloro-2-fluorobenzyl)amino)-4-(methylthio)-1-oxobutan-2-yl)-amino)-2-oxoethyl)-1H-indazole-3-carboxamide (21d)

Step-1: Preparation of (S)-tert-butyl (1-((3-chloro-2-fluorobenzyl)amino)-4-(methylthio)-1-oxobutan-2-yl)carbamate (21b)

Reaction of (S)-2-((tert-butoxycarbonyl)amino)-4-(methylthio)butanoic acid (21a) (391 mg, 1.57 mmol) with 3-chloro-2-fluorobenzylamine (9d) (250 mg, 1.57 mmol) according to the procedure reported in step-3 of Scheme 2 gave after workup (S)-tert-butyl (1-((3-chloro-2-fluorobenzyl)amino)-4-(methylthio)-1-oxobutan-2-yl)carbamate (21b) which was used as such in the next step; MS (ES−): 391.4 (M−1).

Step-2: Preparation of (S)-2-amino-N-(3-chloro-2-fluorobenzyl)-4-(methylthio)butanamide (21c)

Reaction of (5)-tert-butyl (1-((3-chloro-2-fluorobenzyl)amino)-4-(methylthio)-1-oxobutan-2-yl)carbamate (21b) from above step with TFA (3 mL) according to the procedure reported in step-2 of Scheme 2 gave after workup (S)-2-amino-N-(3-chloro-2-fluorobenzyl)-4-(methylthio)butanamide (21c) TFA salt which was used in next step without further purification; MS (ES+): 291.3 (M+1).

Step-3: Preparation of (S)-1-(2-((1-((3-chloro-2-fluorobenzyl)amino)-4-(methylthio)-1-oxobutan-2-yl)-amino)-2-oxoethyl)-1H-indazole-3-carboxamide (21d)

Reaction of (S)-2-amino-N-(3-chloro-2-fluorobenzyl)-4-(methylthio)butanamide (21c) (0.254 g, 0.931 mmol) TFA salt from above step-2 with 2-(3-carbamoyl-1H-indazol-1-yl)acetic acid (2e) (136 mg, 0.62 mmol) according to the procedure reported in step-3 of Scheme 2 gave after workup and purification by flash column chromatography [silica gel (24 g), eluting with CMA80 in CHCl$_3$ 0 to 40%] (5)-1-(2-((1-((3-chloro-2-fluorobenzyl)amino)-4-(methylthio)-1-oxobutan-2-yl)amino)-2-oxoethyl)-1H-indazole-3-carboxamide (21d) (33 mg, 0.067 mmol, 11% yield) as a white solid; $^1$H NMR (300 MHz, DMSO-d$_6$) δ 8.75-8.60 (m, 2H), 8.17 (d, J=8.1 Hz, 1H), 7.71 (s, 1H), 7.63 (d, J=8.5 Hz, 1H), 7.58-7.35 (m, 3H), 7.31-7.20 (m, 2H), 7.15 (q, J=8.8, 7.8 Hz, 1H), 5.27 (s, 2H), 4.47-4.27 (m, 3H), 2.48-2.36 (m, 2H), 2.04 (s, 1H), 2.02 (s, 2H), 2.01-1.67 (m, 2H); $^{19}$F NMR (282 MHz, DMSO-d$_6$) δ −121.12 (d, J=7.1 Hz); MS (ES+): 492.5 (M+1); MS (ES−): 490.5 (M−1); 526.5 (M+Cl).

Scheme 22

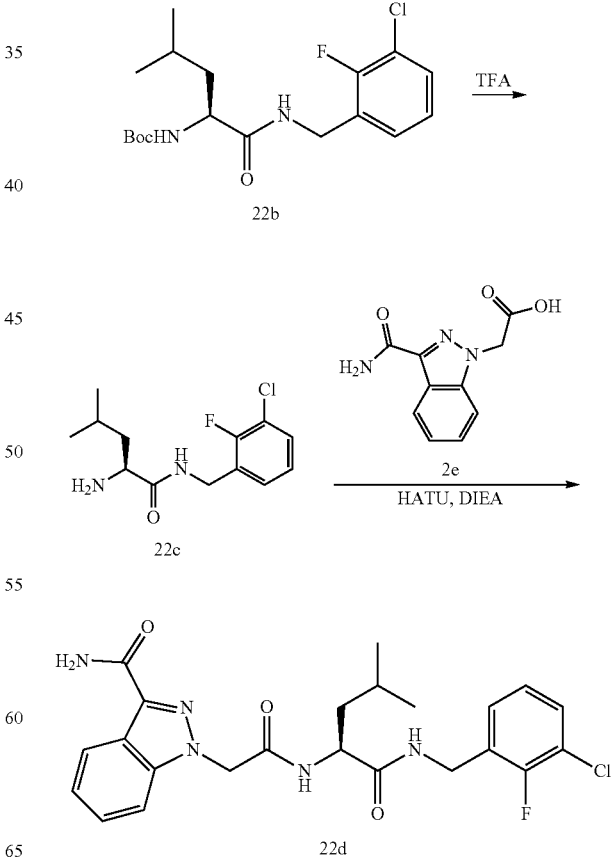

Preparation of (S)-1-(2-((1-((3-chloro-2-fluorobenzyl)amino)-4-methyl-1-oxopentan-2-yl)amino)-2-oxoethyl)-1H-indazole-3-carboxamide (22d)

Step-1: Preparation of (S)-tert-butyl (1-((3-chloro-2-fluorobenzyl)amino)-4-methyl-1-oxopentan-2-yl)carbamate (22b)

Reaction of (S)-2-((tert-butoxycarbonyl)amino)-4-methylpentanoic acid (22a) (362 mg, 1.57 mmol) with 3-chloro-2-fluorobenzylamine (9d) (250 mg, 1.57 mmol) according to the procedure reported in step-3 of Scheme 2 gave after workup (5)-tert-butyl (1-((3-chloro-2-fluorobenzyl)amino)-4-methyl-1-oxopentan-2-yl)carbamate (22b) which was used as such in the next step; MS (ES+): 395.4 (M+Na).

Step-2: Preparation of (S)-2-amino-N-(3-chloro-2-fluorobenzyl)-4-methylpentanamide (22c)

Reaction of (5)-tert-butyl (1-((3-chloro-2-fluorobenzyl)amino)-4-methyl-1-oxopentan-2-yl)carbamate (22b) from above step with TFA (3 mL) according to the procedure reported in step-2 of Scheme 2 gave after workup (S)-2-amino-N-(3-chloro-2-fluorobenzyl)-4-methylpentanamide (22c) TFA salt which was used in next step without further purification; MS (ES+): 273.4 (M+1).

Step-3: Preparation of (S)-1-(2-((1-chloro-2-fluorobenzyl)amino)-4-methyl-1-oxopentan-2-yl)-amino)-2-oxoethyl)-1H-indazole-3-carboxamide (22d)

Reaction of (S)-2-amino-N-(3-chloro-2-fluorobenzyl)-4-methylpentanamide (22c) (0.25 g, 0.93 mmol) TFA salt from above step-2 with 2-(3-carbamoyl-1H-indazol-1-yl)acetic acid (2e) (136 mg, 0.62 mmol) according to the procedure reported in step-3 of Scheme 2 gave after workup and purification by flash column chromatography [silica gel (24 g), eluting with CMA80 in CHCl$_3$; 0 to 40%] (S)-1-(2-((1-((3-chloro-2-fluorobenzyl)amino)-4-methyl-1-oxopentan-2-yl)-amino)-2-oxoethyl)-1H-indazole-3-carboxamide (22d) (65 mg, 0.14 mmol, 22% yield) as a pale white solid; $^1$H NMR (300 MHz, DMSO-d$_6$) δ 8.69 (t, J=5.8 Hz, 1H), 8.62 (d, J=8.0 Hz, 1H), 8.17 (d, J=8.1 Hz, 1H), 7.70 (s, 1H), 7.61 (d, J=8.5 Hz, 1H), 7.52-7.35 (m, 3H), 7.32-7.19 (m, 2H), 7.13 (t, J=7.9 Hz, 1H), 5.25 (s, 2H), 4.42-4.24 (m, 3H), 1.70-1.54 (m, 1H), 1.55-1.42 (m, 2H), 0.90 (d, J=6.4 Hz, 3H), 0.83 (d, J=6.4 Hz, 3H); $^{19}$F NMR (282 MHz, DMSO-d$_6$) δ −121.23; MS (ES+) 474.5 (M+1), 496.5 (M+Na); MS (ES−) 508.5

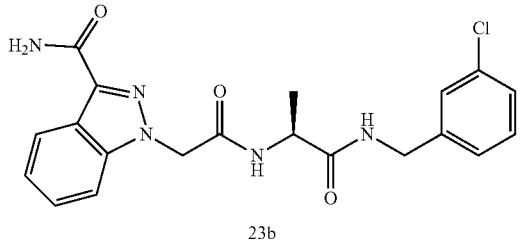

Preparation of (S)-1-(2-((1-((3-chlorobenzyl)amino)-1-oxopropan-2-yl)-amino)-2-oxoethyl)-1H-indazole-3-carboxamide (23b)

Reaction of (S)-2-(2-(3-carbamoyl-1H-indazol-1-yl)acetamido)propanoic acid (9c) (200 mg, 0.69 mmol) TFA salt with (3-chlorophenyl)methanamine (23a) (98 mg, 0.69 mmol), according to the procedure reported in step-3 of Scheme 2 gave after workup (S)-1-(2-((1-((3-chlorobenzyl)amino)-1-oxopropan-2-yl)-amino)-2-oxoethyl)-1H-indazole-3-carboxamide (23b) (126 mg, 0.3 mmol, 44% yield) as a yellow solid; $^1$H NMR (300 MHz, DMSO-d$_6$) δ 8.67 (d, J=7.4 Hz, 1H), 8.59 (t, J=6.0 Hz, 1H), 8.17 (d, J=8.1 Hz, 1H), 7.72 (s, 1H), 7.64 (d, J=8.5 Hz, 1H), 7.47-7.15 (m, 7H), 5.41-5.16 (m, 2H), 4.43-4.23 (m, 3H), 1.29 (d, J=7.0 Hz, 3H); MS (ES+): 414.5 (M+1); ES(−): 412.4 (M−1).

-continued

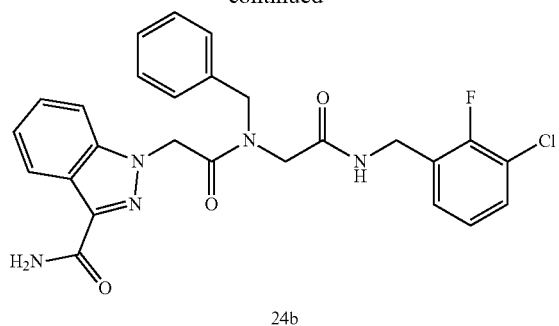

24b

Preparation of 1-(2-(benzyl(2-((3-chloro-2-fluorobenzyl)amino)-2-oxoethyl)amino)-2-oxoethyl)-1H-indazole-3-carboxamide (24b)

Step-1: Preparation of 2-(benzylamino)-N-(3-chloro-2-fluorobenzyl)acetamide (24a)

To a solution of 2-amino-N-(3-chloro-2-fluorobenzyl)acetamide (16c) (320 mg, 1.48 mmol) in THF (10 mL) was added benzaldehyde (143 mg, 1.343 mmol) and acetic acid (0.12 mL, 2.01 mmol). The resulting mixture was stirred for 50 min, NaBH$_4$ (102 mg, 2.69 mmol) was added and stirred at room temperature overnight. The reaction was quenched with aqueous NaHCO$_3$ (2N, 20 mL), stirred for 30 min- and diluted with EtOAc (100 mL). The organic layer was separated washed with brine, dried, filtered and concentrated in vacuum to afford 2-(benzylamino)-N-(3-chloro-2-fluorobenzyl)acetamide (24a) (240 mg, 0.78 mmol, 58% yield). which was used in the next step without further purification. MS (ES+): 307.3 (M+1)

Step-2: Preparation of 1-(2-(benzyl(2-((3-chloro-2-fluorobenzyl)amino)-2-oxoethyl)amino)-2-oxoethyl)-1H-indazole-3-carboxamide (24b)

Reaction of 2-(benzylamino)-N-(3-chloro-2-fluorobenzyl)acetamide (24a) (240 mg, 0.78 mmol) with 2-(3-carbamoyl-1H-indazol-1-yl)acetic acid (2e) (171 mg, 0.78 mmol) according to the procedure reported in step-3 of Scheme 2 gave after workup and purification by chromatography [silica (12 g), eluting with CMA80 in CHCl$_3$; 0 to 40%] 1-(2-(benzyl(2-((3-chloro-2-fluorobenzyl)amino)-2-oxoethyl)amino)-2-oxoethyl)-1H-indazole-3-carboxamide (24b) (38 mg, 0.075 mmol, 10% yield) as a white solid; $^1$H NMR (300 MHz, DMSO-d$_6$) δ 8.79 and 8.52 (2t, J=5.9 Hz, 1H), 8.25-8.11 (m, 1H), 7.80-7.66 (m, 1H), 7.66-7.56 (m, 1H), 7.56-7.36 (m, 5H), 7.34-7.10 (m, 6H), 5.58 (s, 2H), 4.83 and 4.46 (2s, 2H), 4.43 and 4.34 (2d, J=5.6 Hz, 2H), 4.21 and 3.95 (s, 2H); $^{19}$F NMR (282 MHz, DMSO-d$_6$) δ −121.06, −121.35; MS (ES+): 508.5 (M+1); (ES−) 506.5 (M−1); (based on NMR the compound is a mixture of rotamers 2:1 ratio)

Scheme 25

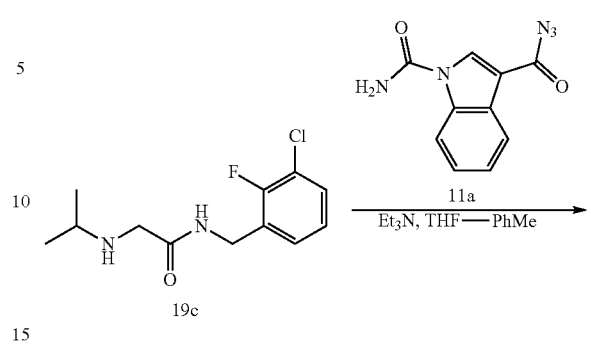

Preparation of 3-(3-(2-((3-chloro-2-fluorobenzyl)amino)-2-oxoethyl)-3-isopropylureido)-1H-indole-1-carboxamide (25a)

Reaction of N-(3-chloro-2-fluorobenzyl)-2-(isopropylamino)acetamide (19c) (90 mg, 0.35 mmol) with 1-carbamoyl-1H-indole-3-carbonyl azide (11a) (80 mg, 0.35 mmol) according to the procedure reported in Scheme 11 gave after workup and purification by flash column chromatography (Silica gel, 24 g eluting with CMA80 in CHCl$_3$ from 0-30%) 3-(3-(2-((3-chloro-2-fluorobenzyl)amino)-2-oxoethyl)-3-isopropylureido)-1H-indole-1-carboxamide (25a) (9 mg, 6% yield) as a yellow solid; $^1$H NMR (300 MHz, DMSO-d$_6$) δ 8.92 (s, 1H, D20 exchangeable), 8.82-8.70 (m, 1H, D$_2$O exchangeable), 8.30-8.22 (m, 1H), 7.98 (s, 1H), 7.62 (d, J=7.7 Hz, 1H), 7.54-7.32 (m, 4H, 2H, D$_2$O exchangeable), 7.30-7.21 (m, 1H), 7.20-7.11 (m, 2H), 4.56-4.33 (m, 3H), 3.97 (s, 2H), 1.10 (d, J=6.6 Hz, 6H); $^{19}$F NMR (282 MHz, DMSO-d$_6$) δ −121.07; MS (ES+): 460.5 (M+1), 482.49 (M+Na); MS (ES−): 458.44 (M−1).

Scheme 26

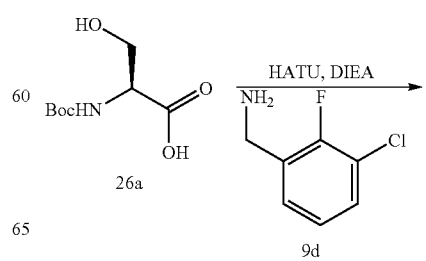

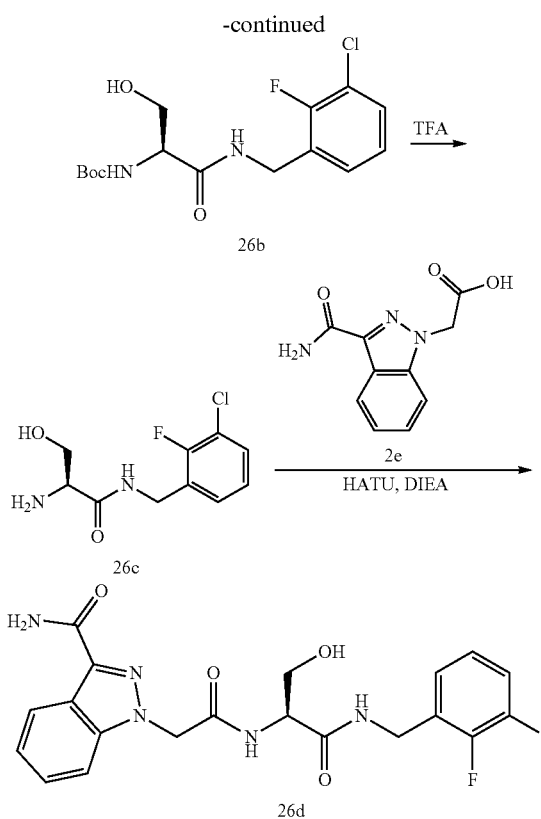

from above step-2 with 2-(3-carbamoyl-1H-indazol-1-yl) acetic acid (2e) (416 mg, 1.9 mmol) according to the procedure reported in step-3 of Scheme 2 gave after workup and purification by flash column chromatography [silica gel (24 g), eluting with CMA80 in CHCl$_3$; 0 to 100%] (S)-1-(2-((1-((3-chloro-2-fluorobenzyl)amino)-3-hydroxy-1-oxo-propan-2-yl)amino)-2-oxoethyl)-1H-indazole-3-carboxamide (26d) (16 mg, 2% yield) as an off white solid; $^1$H NMR (300 MHz, DMSO-d$_6$) δ 8.67-8.57 (m, 2H, D$_2$O exchangeable), 8.18 (dt, J=8.2, 1.0 Hz, 1H), 7.73 (s, 1H, D$_2$O exchangeable), 7.64 (dt, J=8.6, 0.9 Hz, 1H), 7.52-7.37 (m, 3H), 7.33-7.22 (m, 2H), 7.17-7.09 (m, 1H), 5.40-5.22 (m, 2H), 5.13 (t, J=5.3 Hz, 1H, D$_2$O exchangeable), 4.42-4.29 (m, 3H), 3.70-3.59 (m, 2H); $^1$H NMR (300 MHz, DMSO-d$_6$ D$_2$O) δ 8.17-8.09 (m, 1H), 7.62-7.55 (m, 1H), 7.46-7.36 (m, 2H), 7.34-7.17 (m, 2H), 7.06 (t, J=7.9 Hz, 1H), 5.40-5.14 (m, 2H), 4.32 (s, 2H), 4.28 (t, J=5.4 Hz, 1H), 3.76-3.54 (m, 2H); MS (ES+): 448.5 (M+1), 470.5 (M+Na); MS (ES−): 446.4 (M−1), 482.4 (M+Cl).

Preparation of (S)-1-(2-((1-((3-chloro-2-fluorobenzyl)amino)-3-hydroxy-1-oxopropan-2-yl)amino)-2-oxoethyl)-1H-indazole-3-carboxamide (26d)

Step-1: Preparation of (S)-tert-butyl (1-((3-chloro-2-fluorobenzyl)amino)-3-hydroxy-1-oxopropan-2-yl)carbamate (26b)

Reaction of (S)-2-((tert-butoxycarbonyl)amino)-3-hydroxypropanoic acid (26a) (389 mg, 1.9 mmol) with 3-chloro-2-fluorobenzylamine (9d) (252 mg, 1.58 mmol) according to the procedure reported in step-3 of Scheme 2 gave after workup (5)-tert-butyl (1-((3-chloro-2-fluorobenzyl)amino)-3-hydroxy-1-oxopropan-2-yl)carbamate (26b) which was used as such in the next step; MS (ES+): 369.4 (M+Na), MS (ES−): 381.3 (M+Cl).

Step-2: Preparation of (S)-2-amino-N-(3-chloro-2-fluorobenzyl)-3-hydroxypropanamide (26c)

Reaction of (5)-tert-butyl (1-((3-chloro-2-fluorobenzyl)amino)-3-hydroxy-1-oxopropan-2-yl)carbamate (26b) (548 mg, 1.58 mmol) from above step with TFA (2.19 mL, 28.4 mmol) according to the procedure reported in step-2 of Scheme 2 gave after workup (S)-2-amino-N-(3-chloro-2-fluorobenzyl)-3-hydroxypropanamide (26c) TFA salt which was used in next step without further purification; MS (ES+): 247.3 (M+1).

Step-3: Preparation of (S)-1-(2-((1-((3-chloro-2-fluorobenzyl)amino)-3-hydroxy-1-oxopropan-2-yl)amino)-2-oxoethyl)-1H-indazole-3-carboxamide (26d)

Reaction of (S)-2-amino-N-(3-chloro-2-fluorobenzyl)-3-hydroxypropanamide (26c) (390 g, 1.58 mmol) TFA salt

Scheme 27

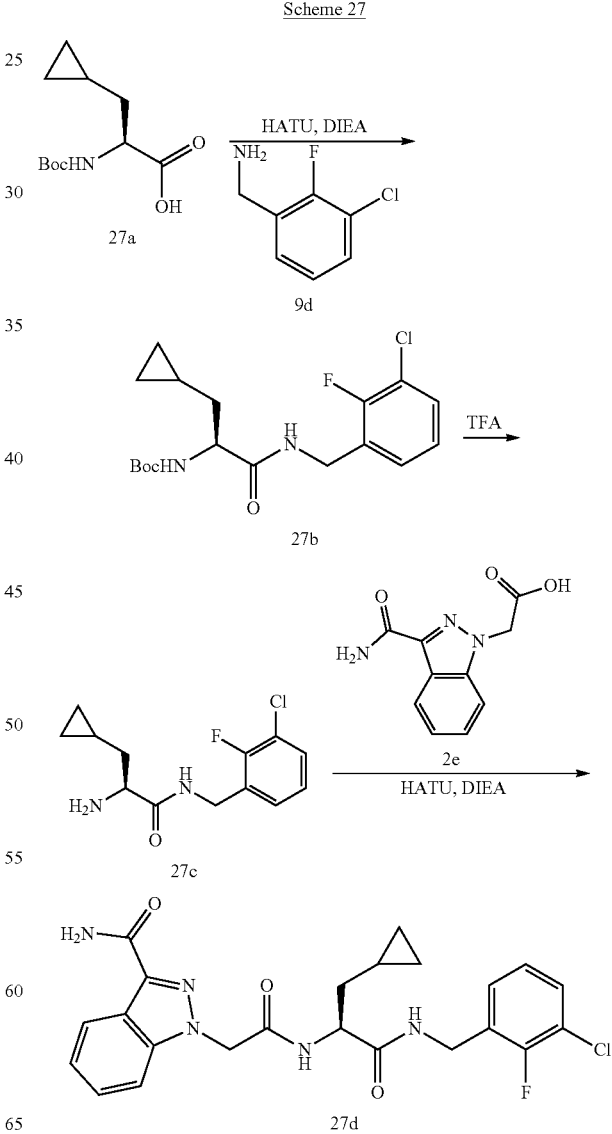

Preparation of (S)-1-(2-((1-((3-chloro-2-fluorobenzyl)amino)-3-cyclopropyl-1-oxopropan-2-yl)amino)-2-oxoethyl)-1H-indazole-3-carboxamide (27d)

Step-1: Preparation of (S)-tert-butyl (1-((3-chloro-2-fluorobenzyl)amino)-3-cyclopropyl-1-oxopropan-2-yl)carbamate (27b)

Reaction of (S)-2-((tert-butoxycarbonyl)amino)-3-cyclopropylpropanoic acid (27a) (575 mg, 2.51 mmol, prepared according to method reported by Hendricks, Robert Than et al; in U.S. Pat. Appl. Publ., 20110230462) according to the procedure reported in step-3 of Scheme 2 gave after workup (S)-tert-butyl(1-((3-chloro-2-fluorobenzyl)amino)-3-cyclopropyl-1-oxopropan-2-yl)carbamate (27b) which was used as such in the next step; MS (ES+): 393.3 (M+Na); MS (ES−): 405.4 (M+Cl).

Step-2: Preparation of (S)-2-amino-N-(3-chloro-2-fluorobenzyl)-3-cyclopropylpropanamide (27c)

Reaction of (5)-tert-butyl (1-((3-chloro-2-fluorobenzyl)amino)-3-cyclopropyl-1-oxopropan-2-yl)carbamate (27b) (930 mg, 2.51 mmol) from above step with TFA (3.48 mL, 45.1 mmol) according to the procedure reported in step-2 of Scheme 2 gave after workup (S)-2-amino-N-(3-chloro-2-fluorobenzyl)-3-cyclopropylpropanamide (27c) TFA salt which was used in next step without further purification; MS (ES+): 271.3 (M+1).

Step-3: Preparation of (S)-1-(2-((1-((3-chloro-2-fluorobenzyl)amino)-3-cyclopropyl-1-oxopropan-2-yl)amino)-2-oxoethyl)-1H-indazole-3-carboxamide (27d)

Reaction of (S)-2-amino-N-(3-chloro-2-fluorobenzyl)-3-cyclopropylpropanamide (27c) (679 g, 2.51 mmol) TFA salt from above step-2 with 2-(3-carbamoyl-1H-indazol-1-yl)acetic acid (2e) (660 mg, 3.01 mmol) according to the procedure reported in step-3 of Scheme 2 gave after workup (5)-1-(2-((1-((3-chloro-2-fluorobenzyl)amino)-3-cyclopropyl-1-oxopropan-2-yl-amino)-2-oxoethyl)-1H-indazole-3-carboxamide (27d) (93 mg, 8% yield) as an off-white solid; $^1$H NMR (300 MHz, DMSO-$d_6$) δ 8.73-8.56 (m, 2H), 8.17 (d, J=8.1 Hz, 1H), 7.69 (s, 1H), 7.63 (d, J=8.4 Hz, 1H), 7.52-7.36 (m, 3H), 7.25 (t, J=7.4 Hz, 2H), 7.13 (t, J=7.9 Hz, 1H), 5.26 (s, 2H), 4.45-4.25 (m, 3H), 1.73-1.36 (m, 2H), 0.79-0.63 (m, 1H), 0.46-0.25 (m, 2H), 0.15-0.01 (m, 2H); $^{19}$F NMR (282 MHz, DMSO-$d_6$) δ 120.97; MS (ES+): 472.5 (M+1), 494.5 (M+Na); (ES−): 470.4 (M−1), 506.5 (M+Cl).

Scheme 28

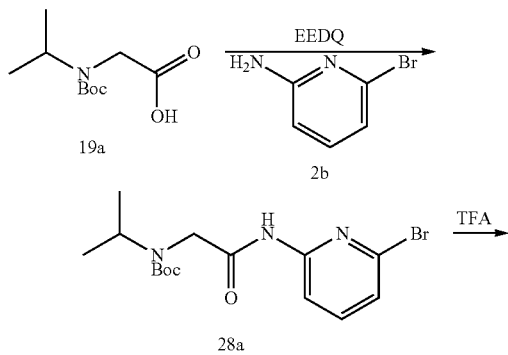

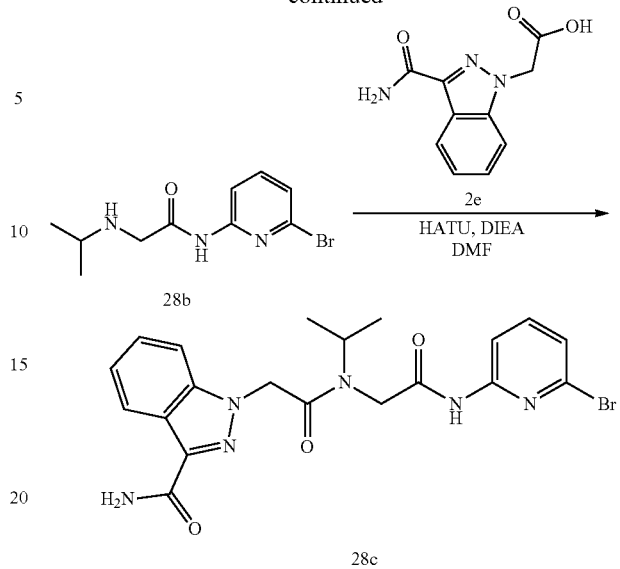

Preparation of 1-(2-((2-((6-bromopyridin-2-yl)amino)-2-oxoethyl)(isopropyl)amino)-2-oxoethyl)-1H-indazole-3-carboxamide (28c)

Step-1: Preparation of tert-butyl (2-((6-bromopyridin-2-yl)amino)-2-oxoethyl)(isopropyl)carbamate (28a)

Reaction of 2-((tert-butoxycarbonyl)(isopropyl)amino) acetic acid (19a) (0.65 g, 2.99 mmol) with 6-bromopyridin-2-amine (2b) (0.78 g, 4.49 mmol) according to the procedure reported in step-1 of Scheme 2 gave after workup and purification by chromatography [silica (12 g), eluting with MeOH in CHCl$_3$ from 0-20%] tert-butyl (2-((6-bromopyridin-2-yl)amino)-2-oxoethyl)(isopropyl)carbamate (28a) which was used in the next step without further purification.

Step-2: Preparation of N-(6-bromopyridin-2-yl)-2-(isopropylamino)acetamide (28b)

Reaction of tert-butyl (2-((6-bromopyridin-2-yl)amino)-2-oxoethyl)(isopropyl)carbamate (28a) from above step-1 with TFA (1.15 mL, 14.96 mmol) according to the procedure reported in step-2 of Scheme 2 gave after workup and purification by chromatography [silica (12 g), eluting with CMA80 in CHCl$_3$ 0 to 20%] N-(6-bromopyridin-2-yl)-2-(isopropylamino)acetamide (28b) (340 mg, 1.25 mmol, 42%) which was used in the next step without further purification; MS (ES+): 272.3 (M+1).

Step-3: Preparation of 1-(2-((2-((6-bromopyridin-2-yl)amino)-2-oxoethyl)(isopropyl)amino)-2-oxoethyl)-1H-indazole-3-carboxamide (28c)

Reaction of N-(6-bromopyridin-2-yl)-2-(isopropylamino) acetamide (28b) (100 mg, 0.26 mmol) with 2-(3-carbamoyl-1H-indazol-1-yl)acetic acid (2e) (62 mg, 0.29 mmol) according to the procedure reported in step-3 of Scheme 2 gave after workup and purification by chromatography [silica (12 g), eluting with CMA80 in CHCl$_3$ 0 to 40%] 1-(2-((2-((6-bromopyridin-2-yl)amino)-2-oxoethyl)(isopropyl)amino)-2-oxoethyl)-1H-indazole-3-carboxamide (28c)

(70 mg, 0.15 mmol, 57% yield) as a white solid; $^1$H NMR (300 MHz, DMSO-$d_6$) δ 11.17 and 10.77 (2s, 1H), 8.24-7.95 (m, 2H), 7.87-7.54 (m, 3H), 7.51-7.14 (m, 4H), 5.62 and 5.46 (2s, 2H), 4.606-4.332 (m, 1H), 4.43 and 4.03 (2s, 2H), 1.25 (d, J=6.3 Hz, 3H), 1.04 (d, J=6.8 Hz, 3H); MS (ES+): 473.4 (M+1); (based on NMR the compound is a mixture of rotamers with 1.2:1 ratio)

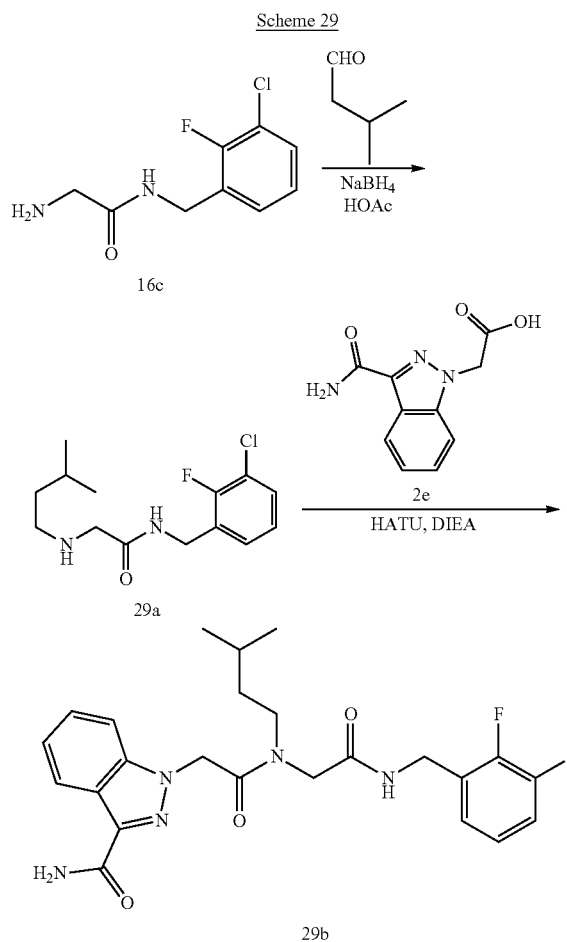

Preparation of 1-(2-((2-((3-chloro-2-fluorobenzyl) amino)-2-oxoethyl)(isopentyl)amino)-2-oxoethyl)-1H-indazole-3-carboxamide (29b)

Step-1: Preparation of N-(3-chloro-2-fluorobenzyl)-2-(isopentylamino)acetamide (29a)

Reaction of 2-amino-N-(3-chloro-2-fluorobenzyl)acetamide (16c) (337 mg, 1.56 mmol) with isovaleraldehyde (147 mg, 1.711 mmol) according to the procedure reported in step-1 of Scheme 24 gave after work and purification by flash column chromatography [silica (12 g), eluting with EtOAc in hexane 0 to 60%] N-(3-chloro-2-fluorobenzyl)-2-(isopentylamino)acetamide (29a) (120 mg, 0.42 mmol, 27% yield) as a clear oil; $^1$H NMR (300 MHz, DMSO-$d_6$) δ 8.34 (t, J=5.8 Hz, 1H), 7.52-7.39 (m, 1H), 7.32-7.23 (m, 1H), 7.21-7.11 (m, 1H), 4.36 (d, J=5.9 Hz, 2H), 3.11 (s, 2H), 2.48-2.39 (m, 2H), 1.66-1.43 (m, 1H), 1.36-1.16 (m, 3H), 0.82 (d, J=6.6 Hz, 6H); $^{19}$F NMR (282 MHz, DMSO-$d_6$) δ −121.38; MS (ES+): 287.4 (M+1); (ES−): 285.3 (M−1).

Step-2: Preparation of N-(3-chloro-2-fluorobenzyl)-2-(isopentylamino)acetamide (29a)

Reaction of N-(3-chloro-2-fluorobenzyl)-2-(isopentylamino)acetamide (29a) (100 mg, 0.35 mmol) with 2-(3-carbamoyl-1H-indazol-1-yl)acetic acid (2e) (84 mg, 0.384 mmol) according to the procedure reported in step-3 of Scheme 2 gave after workup and purification by chromatography [silica (12 g), eluting with CMA80 in CHCl$_3$ 0 to 40%] N-(3-chloro-2-fluorobenzyl)-2-(isopentylamino)acetamide (29a) (100 mg, 0.21 mmol, 59% yield) as a white solid; $^1$H NMR (300 MHz, DMSO-$d_6$) δ 8.85 and 8.49 (2t, J=5.6 Hz, 1H), 8.18 (d, J=8.1 Hz, 1H), 7.76-7.66 (m, 1H), 7.62-7.47 (m, 2H), 7.47-7.33 (m, 3H), 7.29-7.09 (m, 2H), 5.56 and 5.47 (2s, 2H), 4.46 and 4.34 (2d, J=5.4 Hz, 2H), 4.23 and 3.94 (2s, 2H), 3.52-3.39 (m, 1H), 3.30-3.15 (m, 1H), 1.66-1.37 (m, 2H), 1.37-1.15 (m, 1H), 0.93 and 0.80 (2d, J=6.4 Hz, 6H); $^{19}$F NMR (282 MHz, DMSO-$d_6$) δ −120.92, −121.31; MS (ES+): 473.4 (M+1); (based on NMR the compound is a mixture of rotamers with 3:2 ratio).

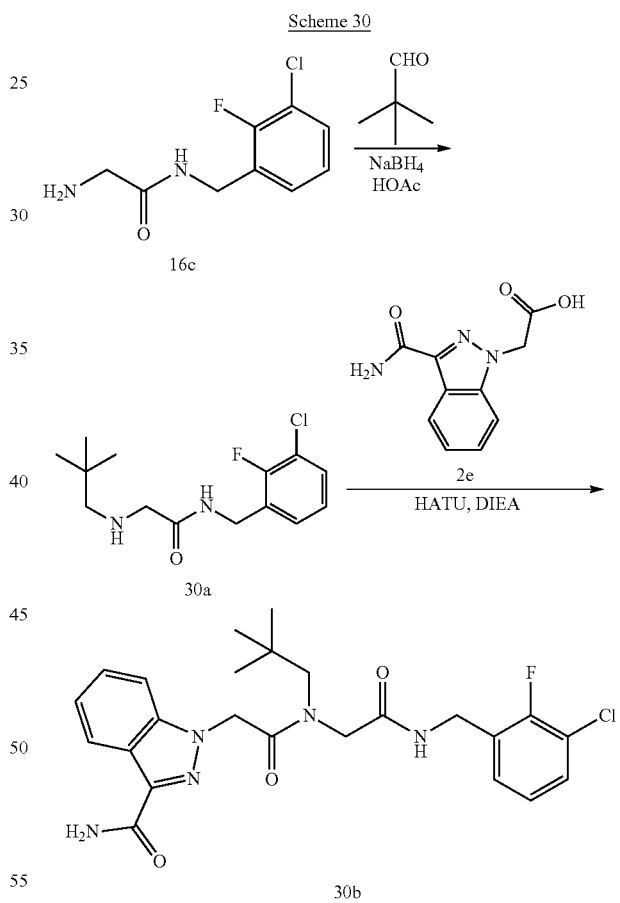

Preparation of 1-(2-((2-((3-chloro-2-fluorobenzyl) amino)-2-oxoethyl)(neopentyl)amino)-2-oxoethyl)-1H-indazole-3-carboxamide (30b)

Step-1: Preparation of N-(3-chloro-2-fluorobenzyl)-2-(neopentylamino)acetamide (30a)

Reaction of 2-amino-N-(3-chloro-2-fluorobenzyl)acetamide (16c) (300 mg, 1.39 mmol) with trimethylacetaldehyde (131 mg, 1.523 mmol) according to the procedure reported in step-1 of Scheme 24 gave after work and purification by flash column chromatography [silica (12 g), eluting with EtOAc in hexane 0 to 60%] N-(3-chloro-2-fluorobenzyl)-2-(neopentylamino)acetamide (30a) (200 mg, 0.7 mmol, 50% yield) as a clear oil; $^1$H NMR (300 MHz, DMSO-$d_6$) δ 8.55 (d, J=5.5 Hz, 1H), 7.79 (t, J=7.5 Hz, 1H), 7.60 (t, J=7.1 Hz, 1H), 7.50 (t, J=7.8 Hz, 1H), 4.69 (d, J=5.9 Hz, 2H), 3.44 (s, 2H), 2.90-2.74 (m, 2H), 2.41 (s, 1H), 1.16 (d, J=2.9 Hz, 9H); $^{19}$F NMR (282 MHz, DMSO-$d_6$) δ -121.08; MS (ES+): 287.4 (M+1); (ES-) 285.3 (M-1).

Step-2: Preparation of 1-(2-((2-(((3-chloro-2-fluorobenzyl)amino)-2-oxoethyl)(neopentyl)amino)-2-oxoethyl)-1H-indazole-3-carboxamide (30b)

Reaction of N-(3-chloro-2-fluorobenzyl)-2-(neopentylamino)acetamide (30a) (130 mg, 0.45 mmol) with 2-(3-carbamoyl-1H-indazol-1-yl)acetic acid (2e) (109 mg, 0.5 mmol) according to the procedure reported in step-3 of Scheme 2 gave after workup and purification by chromatography [silica (12 g), eluting with CMA80 in CHCl$_3$ 0 to 40%] 1-(2-((2-(((3-chloro-2-fluorobenzyl)amino)-2-oxoethyl)(neopentyl)amino)-2-oxoethyl)-1H-indazole-3-carboxamide (30b) (100 mg, 0.21 mmol, 45% yield) as a white solid; $^1$H NMR (300 MHz, DMSO-$d_6$) δ 8.83 (t, J=5.7 Hz, 1H), 8.18 (d, J=8.1 Hz, 1H), 7.81-7.58 (m, 1H), 7.57-7.46 (m, 2H), 7.46-7.31 (m, 3H), 7.30-7.15 (m, 2H), 5.61-5.37 (m, 2H), 4.47 (d, J=5.4 Hz, 2H), 4.32 (s, 2H), 3.04 (s, 2H), 1.14-0.71 (m, 9H); $^{19}$F NMR (282 MHz, DMSO-$d_6$) δ -120.96; MS (ES+): 488.5 (M+1); (ES-): 486.5 (M-1).

Scheme 31

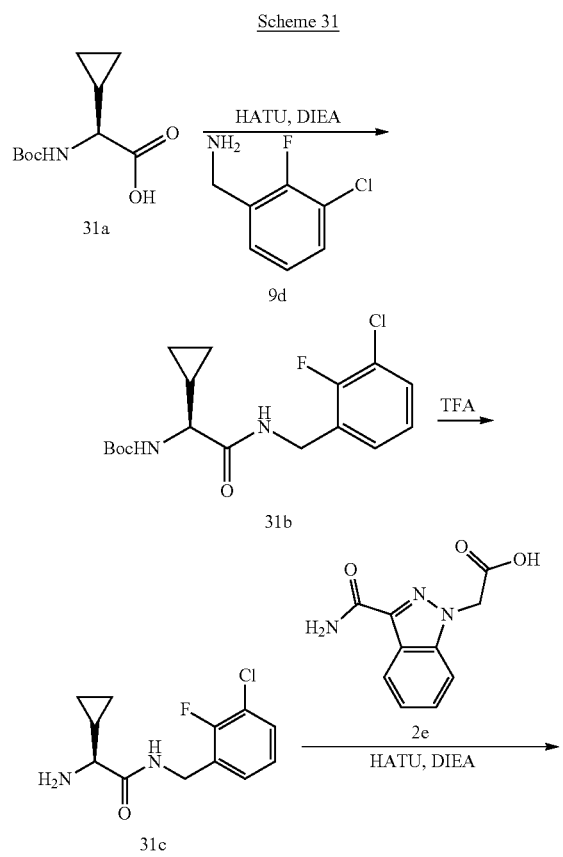

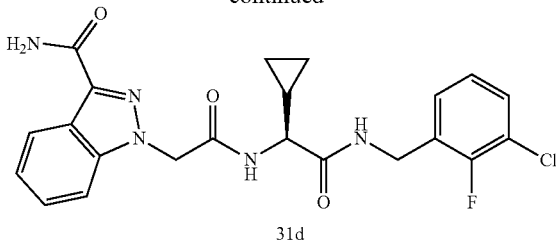

Preparation of (S)-1-(2-((2-(((3-chloro-2-fluorobenzyl)amino)-1-cyclopropyl-2-oxoethyl)amino)-2-oxoethyl)-1H-indazole-3-carboxamide (31d)

Step-1: Preparation of (S)-tert-butyl (2-((3-chloro-2-fluorobenzyl)amino)-1-cyclopropyl-2-oxoethyl)carbamate (31b)

Reaction of (S)-2-((tert-butoxycarbonyl)amino)-2-cyclopropylacetic acid (31a) (232 mg, 1.08 mmol, prepared according to method reported by Hendricks, Robert Than et al; in U.S. Pat. Appl. Publ., 2011/0230462) with 3-chloro-2-fluorobenzylamine (9d) (172 mg, 1.08 mmol) according to the procedure reported in step-3 of Scheme 2 gave after workup (5)-tert-butyl (2-((3-chloro-2-fluorobenzyl)amino)-1-cyclopropyl-2-oxoethyl)carbamate (31b) which was used as such in the next step; MS (ES-): 391.3 (M+Cl).

Step-2: Preparation of (S)-2-amino-N-(3-chloro-2-fluorobenzyl)-2-cyclopropylacetamide (31c)

Reaction of (5)-tert-butyl (2-((3-chloro-2-fluorobenzyl)amino)-1-cyclopropyl-2-oxoethyl)carbamate (31b) (378 mg, 1.06 mmol) from above step-1 with TFA (1.5 mL, 19.07 mmol) according to the procedure reported in step-2 of Scheme 2 gave after workup (S)-2-amino-N-(3-chloro-2-fluorobenzyl)-2-cyclopropylacetamide (31c) TFA salt which was used in next step without further purification; MS (ES+): 257.3 (M+1).

Step-3: Preparation of (S)-1-(2-((2-(((3-chloro-2-fluorobenzyl)amino)-1-cyclopropyl-2-oxoethyl)amino)-2-oxoethyl)-1H-indazole-3-carboxamide (31d)

Reaction of (S)-2-amino-N-(3-chloro-2-fluorobenzyl)-2-cyclopropylacetamide (31c) (272 mg, 1.06 mmol) TFA salt from above step-2 with 2-(3-carbamoyl-1H-indazol-1-yl)acetic acid (2e) (279 mg, 1.27 mmol) according to the procedure reported in step-3 of Scheme 2 gave after workup and purification by flash column chromatography [silica gel (24 g), eluting with CMA80 in CHCl$_3$; 0 to 30%] (S)-1-(2-((2-(((3-chloro-2-fluorobenzyl)amino)-1-cyclopropyl-2-oxoethyl)amino)-2-oxoethyl)-1H-indazole-3-carboxamide (31d) (21 mg, 0.046 mmol, 4% yield) as an off-white solid; $^1$H NMR (300 MHz, DMSO-$d_6$) δ 8.80 (d, J=7.8 Hz, 1H, D$_2$O exchangeable), 8.62 (t, J=5.8 Hz, 1H, D$_2$O exchangeable), 8.17 (d, J=8.1 Hz, 1H), 7.81-7.60 (m, 2H), 7.54-7.36 (m, 3H), 7.32-7.20 (m, 2H), 7.14 (t, J=7.9 Hz, 1H), 5.27 (s, 2H), 4.49-4.24 (m, 2H), 3.77 (t, J=8.1 Hz, 1H), 1.17-1.00 (m, 1H), 0.59-0.41 (m, 3H), 0.37-0.22 (m, 1H); $^{19}$F NMR (282 MHz, DMSO-$d_6$) δ -121.16; MS (ES+): 480.5 (M+Na); (ES-): 456.4 (M-1), 492.4 (M+Cl).

Scheme 32

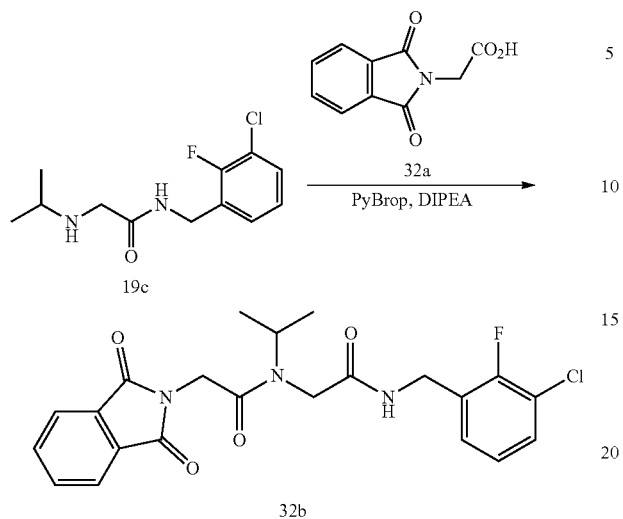

Preparation of N-(2-((3-chloro-2-fluorobenzyl)amino)-2-oxoethyl)-2-(1,3-dioxoisoindolin-2-yl)-N-isopropylacetamide (32b)

To solution of N-(3-chloro-2-fluorobenzyl)-2-(isopropylamino)acetamide (19c) (195 mg, 0.75 mmol), N-ethyl-N-isopropylpropan-2-amine (0.66 mL, 3.77 mmol), 2-(1,3-dioxoisoindolin-2-yl)acetic acid (32a) (186 mg, 0.9 mmol), in DMF (6 mL) was added bromo-tris-pyrrolidino phosphoniumhexafluorophosphate (PyBrop, 422 mg, 0.9 mmol) and stirred at room temperature for 14 h. The reaction mixture was diluted with brine (100 mL) and extracted with EtOAc (3×100 mL). The organic layers were combined, dried, filtered and evaporated to dryness. The residue obtained was purified by flash column chromatography [silica gel (24 g), eluting with MeOH in CHCl$_3$ 0-100%] to afford N-(2-((3-chloro-2-fluorobenzyl)amino)-2-oxoethyl)-2-(1,3-dioxoisoindolin-2-yl)-N-isopropylacetamide (32b) (103 mg, 0.23 mmol, 31% yield) as a white solid; $^1$H NMR (300 MHz, DMSO-d$_6$) δ 8.73 & 8.34 (2t, J=5.9 Hz, 1H), 7.97-7.82 (m, 4H), 7.55-7.33 (m, 2H), 7.28-7.06 (m, 1H), 4.64-4.17 (m, 5H), 4.13 & 3.81 (2s, 2H), 1.20 & 0.96 (2d, J=6.6 Hz, 6H); $^{19}$F NMR (282 MHz, DMSO-d$_6$) δ −121.07, −121.49 (based on NMR the compound is a mixture of two rotamers with ~1:1 ratio); MS (ES+): 446.5 (M+1), 468.4 (M+Na); (ES−) 444.5 (M−1); Analysis calculated for C$_{22}$H$_{21}$ClFN$_3$O$_4$: C, 59.26; H, 4.75; N, 9.42; Found: C, 58.86; H, 4.84; N, 9.36.

Scheme 33

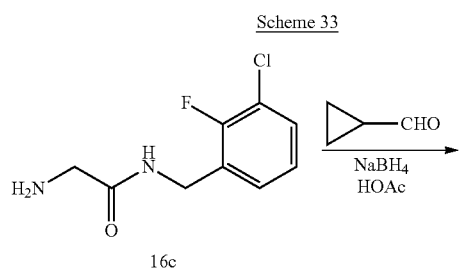

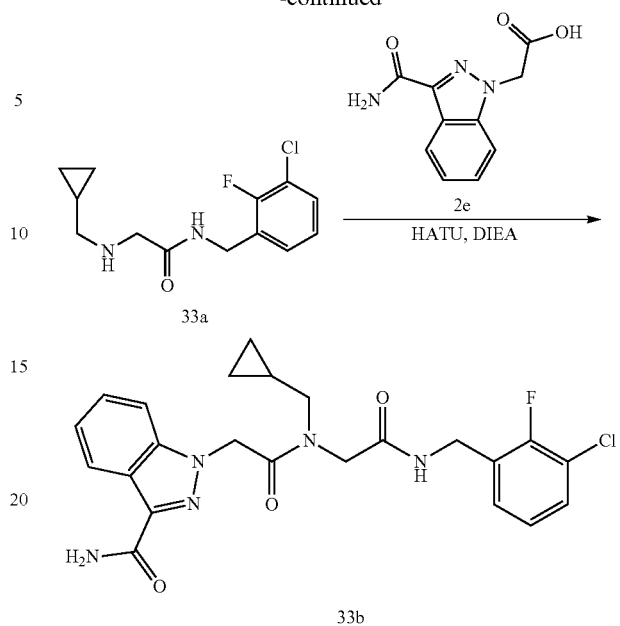

Preparation of 1-(2-((2-((3-chloro-2-fluorobenzyl)amino)-2-oxoethyl)(cyclopropylmethyl)amino)-2-oxoethyl)-1H-indazole-3-carboxamide (33b)

Step-1: Preparation of N-(3-chloro-2-fluorobenzyl)-2-((cyclopropylmethyl)amino)acetamide (33a)

Reaction of 2-amino-N-(3-chloro-2-fluorobenzyl)acetamide (16c) (250 mg, 1.15 mmol) with cyclopropanecarbaldehyde (89 mg, 1.27 mmol) according to the procedure reported in step-1 of Scheme 24 gave after workup and purification by flash column chromatography N-(3-chloro-2-fluorobenzyl)-2-((cyclopropylmethyl)amino)acetamide (33a) (190 mg, 38% yield); MS (ES+): 271.3 (M+1).

Step-2: Preparation of 1-(2-((2-((3-chloro-2-fluorobenzyl)amino)-2-oxoethyl)(cyclopropylmethyl)amino)-2-oxoethyl)-1H-indazole-3-carboxamide (33b)

Reaction of N-(3-chloro-2-fluorobenzyl)-2-((cyclopropylmethyl)amino)acetamide (33a) (190 mg, 0.7 mmol) with 2-(3-carbamoyl-1H-indazol-1-yl)acetic acid (2e) (169 mg, 0.77 mmol) according to the procedure reported in step-3 of Scheme 2 gave after workup and purification by chromatography [silica (12 g), eluting with CMA80 in CHCl$_3$ 0 to 60%] 1-(2-((2-(3-chloro-2-fluorobenzyl)amino)-2-oxoethyl)(cyclopropylmethyl)amino)-2-oxoethyl)-1H-indazole-3-carboxamide (33b) (41 mg, 0.087 mmol, 12% yield) as a white solid; $^1$H NMR (300 MHz, DMSO-d$_6$) (a mixture of two rotamers) δ 8.96-8.39 (m, 1H), 8.18 (d, J=7.5 Hz, 1H), 7.87-7.66 (m, 1H), 7.62-7.03 (m, 7H), 5.54 (2s, 2H), 4.57-3.98 (m, 4H), 3.46-3.39 (m, 1H), 3.22-2.99 (m, 1H), 1.22-0.69 (m, 1H), 0.62-0.04 (m, 4H); $^{19}$F NMR (282 MHz, DMSO-d$_6$) δ −120.74, 121.14; MS (ES+): 472.5 (M+1), 494.5 (M+Na); 470.6 (M−1).

Scheme 34

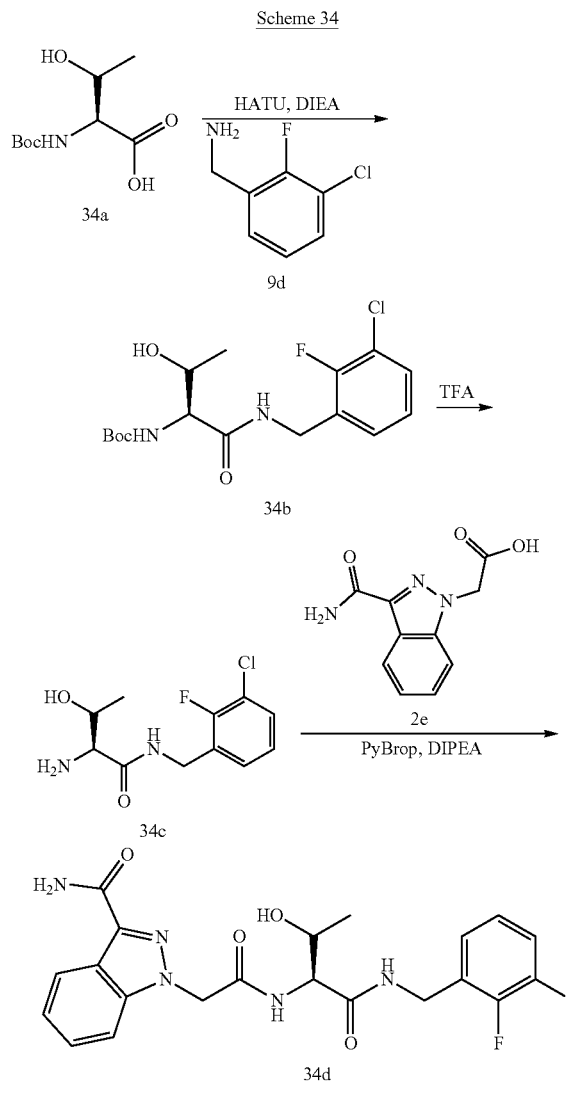

(791 mg, 2.19 mmol) from above step-1 with TFA (3.04 mL, 39.5 mmol) according to the procedure reported in step-2 of Scheme 2 gave after workup (2S,3R)-2-amino-N-(3-chloro-2-fluorobenzyl)-3-hydroxybutanamide (34c) TFA salt which was used in next step without further purification.

Step-3: Preparation of 1-(2-(((2S,3R)-1-((3-chloro-2-fluorobenzyl)amino)-3-hydroxy-1-oxobutan-2-yl)amino)-2-oxoethyl)-1H-indazole-3-carboxamide (34d)

Reaction of (2S,3R)-2-amino-N-(3-chloro-2-fluorobenzyl)-3-hydroxybutanamide (34c) (680 mg, 2.61 mmol) TFA salt from above step-2 with 2-(3-carbamoyl-1H-indazol-1-yl)acetic acid (2e) (572 mg, 2.61 mmol) according to the procedure reported in Scheme 32 gave after workup 1-(2-(((2 S,3R)-1-((3-chloro-2-fluorobenzyl)amino)-3-hydroxy-1-oxobutan-2-yl)amino)-2-oxoethyl)-1H-indazole-3-carboxamide (34d) (28 mg, 0.061 mmol, 2% yield) as an off-white solid; $^1$H NMR (300 MHz, DMSO-$d_6$) δ 8.50 (t, J=5.8 Hz, 1H, D20 exchangeable), 8.39 (d, J=8.3 Hz, 1H, $D_2O$ exchangeable), 8.17 (d, J=8.1 Hz, 1H), 7.71 (s, 1H, $D_2O$ exchangeable), 7.62 (d, J=8.5 Hz, 1H), 7.52-7.36 (m, 3H), 7.34-7.22 (m, 2H), 7.18-7.05 (m, 1H), 5.36 (s, 2H), 5.07 (d, J=4.7 Hz, 1H, $D_2O$ exchangeable), 4.37 (t, J=4.7 Hz, 2H), 4.20 (dd, J=8.3, 3.9 Hz, 1H), 4.13-4.02 (m, 1H), 1.07 (d, J=6.2 Hz, 3H); $^{19}$F NMR (282 MHz, DMSO-$d_6$) δ −121.36; MS (ES+): 484.5 (M+Na); (ES−) 460.5 (M−1), 496.4 (M+Cl).

Scheme 35

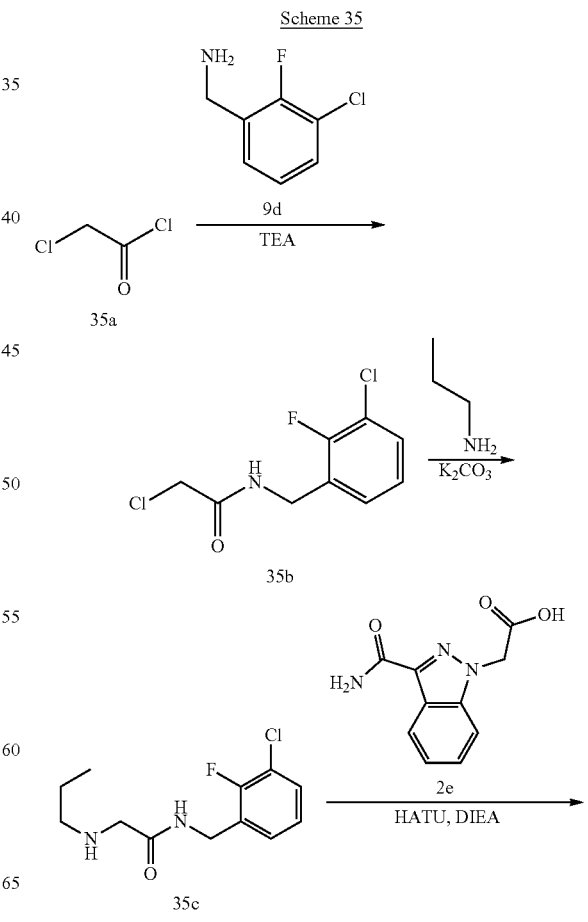

Preparation of 1-(2-(((2S,3R)-1-((3-chloro-2-fluorobenzyl)amino)-3-hydroxy-1-oxobutan-2-yl)amino)-2-oxoethyl)-1H-indazole-3-carboxamide (34d)

Step-1: Preparation of tert-butyl ((2S,3R)-1-((3-chloro-2-fluorobenzyl)amino)-3-hydroxy-1-oxobutan-2-yl)carbamate (34b)

Reaction of (2S,3R)-2-((tert-butoxycarbonyl)amino)-3-hydroxybutanoic acid (34a) (481 mg, 2.19 mmol) with 3-chloro-2-fluorobenzylamine (9d) (350 mg, 2.19 mmol) according to the procedure reported in step-3 of Scheme 2 gave after workup tert-butyl ((2S,3R)-1-((3-chloro-2-fluorobenzyl)amino)-3-hydroxy-1-oxobutan-2-yl)carbamate (34b) which was used as such in the next step.

Step-2: Preparation of (2S,3R)-2-amino-N-(3-chloro-2-fluorobenzyl)-3-hydroxybutanamide (34c)

Reaction of tert-butyl ((2 S,3R)-1-((3-chloro-2-fluorobenzyl)amino)-3-hydroxy-1-oxobutan-2-yl)carbamate (34b)

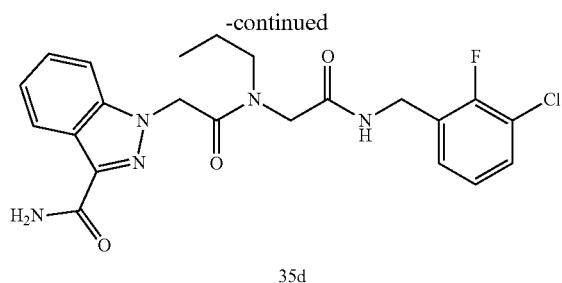

35d

Preparation of 1-(2-((2-((3-chloro-2-fluorobenzyl)amino)-2-oxoethyl)(propyl)amino)-2-oxoethyl)-1H-indazole-3-carboxamide (35d)

Step-1: Preparation of 2-chloro-N-(3-chloro-2-fluorobenzyl)acetamide (35b)

To a solution of 2-chloroacetyl chloride (35a) (1.04 g, 9.21 mmol) and triethylamine (1.93 mL, 13.81 mmol) in THF (10 mL) at 0° C. was added (3-chloro-2-fluorophenyl)methanamine (9d) (1.47 g, 9.21 mmol). The reaction mixture was stirred at room temperature overnight, quenched with water (20 mL) and extracted with DCM (3×20 mL). The organic layers were combined, dried, filtered and concentrated in vacuum to dryness. The residue obtained was purified by chromatography [silica (24 g), eluting with EtOAc/MeOH (9:1) in hexane 0 to 40%] to afford 2-chloro-N-(3-chloro-2-fluorobenzyl)acetamide (35b) (1.2 g, 5.08 mmol, 55% yield) as a white solid; $^1$H NMR (300 MHz, DMSO-$d_6$) δ 8.81 (t, J=5.2 Hz, 1H), 7.50 (td, J=7.8, 1.8 Hz, 1H), 7.35-7.26 (m, 1H), 7.25-7.15 (m, 1H), 4.37 (d, J=5.8 Hz, 2H), 4.13 (s, 2H); $^{19}$F NMR (282 MHz, DMSO) δ -121.08; MS (ES+) 236.2 (M+1); 234.1 (M-2).

Step-2: Preparation of N-(3-chloro-2-fluorobenzyl)-2-(propylamino)acetamide (35c)

To a solution of 2-chloro-N-(3-chloro-2-fluorobenzyl)acetamide (35b) (600 mg, 2.54 mmol) in CH$_3$CN (10 mL) was added propan-1-amine (300 mg, 5.08 mmol), K$_2$CO$_3$ (878 mg, 6.35 mmol) and heated at 60° C. for 5 h. The inorganic solid was removed by filtration and filtrate was concentrated in vacuum to dryness. The residue obtained was purified by chromatography [silica (12 g), eluting with EtOAc/MeOH (9:1) in hexane 0 to 60%] to give N-(3-chloro-2-fluorobenzyl)-2-(propylamino)acetamide (35c) (468 mg, 1.81 mmol, 71% yield) as a yellow oil; $^1$H NMR (300 MHz, DMSO-$d_6$) δ 8.35 (t, J=5.9 Hz, 1H), 7.53-7.39 (m, 1H), 7.34-7.22 (m, 1H), 7.22-7.11 (m, 1H), 4.37 (d, J=6.0 Hz, 2H), 3.12 (s, 2H), 2.41 (t, J=7.1 Hz, 2H), 2.16 (s, 1H), 1.50-1.29 (m, 2H), 0.84 (t, J=7.4 Hz, 3H); $^{19}$F NMR (282 MHz, DMSO) δ -121.68; MS (ES+) 259.4 (M+1); 257.3 (M-1).

Step-3: Preparation of 1-(2-((2-((3-chloro-2-fluorobenzyl)amino)-2-oxoethyl)(propyl)amino)-2-oxoethyl)-1H-indazole-3-carboxamide (35d)

Reaction of N-(3-chloro-2-fluorobenzyl)-2-(propylamino)acetamide (35c) (130 mg, 0.50 mmol) with 2-(3-carbamoyl-1H-indazol-1-yl)acetic acid (2e) (121 mg, 0.55 mmol) according to the procedure reported in step-3 of Scheme 2 gave after workup 1-(2-((2-((3-chloro-2-fluorobenzyl)amino)-2-oxoethyl)(propyl)amino)-2-oxoethyl)-1H-indazole-3-carboxamide (35d) (155 mg, 0.34 mmol, 67% yield) as a white solid; $^1$H NMR (300 MHz, DMSO-$d_6$) (a mixture of two rotamers) δ 8.84 and 8.48 (2t, J=5.8 Hz, 1H), 8.23-8.13 (m, 1H), 7.71 (d, J=8.3 Hz, 1H), 7.61-7.03 (m, 7H), 5.56 and 5.47 (2s, 2H), 4.46 and 4.33 (2d, J=5.7 Hz, 2H), 4.24 and 3.95 (2s, 2H), 3.49-3.38 (m, 1H), 3.25-3.13 (m, 1H), 1.53 (m, 2H), 0.93 and 0.77 (2t, J=7.3 Hz, 3H); $^{19}$F NMR (282 MHz, DMSO-$d_6$) δ -121.25, 121.63; MS (ES+) 482.5 (M+Na); 458.4 (M-1).

Scheme 36

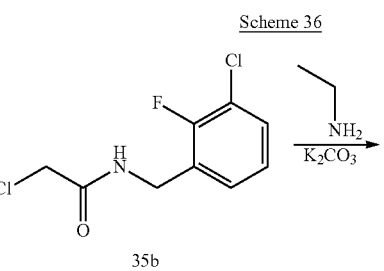

35b

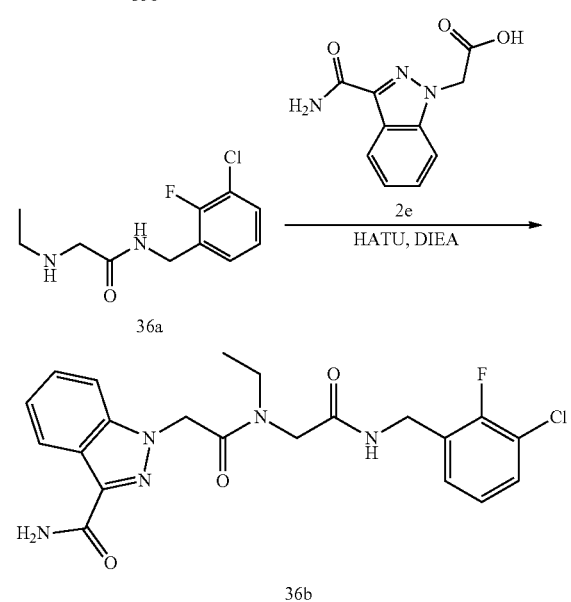

36b

Preparation of 1-(2-((2-((3-chloro-2-fluorobenzyl)amino)-2-oxoethyl)(ethyl)amino)-2-oxoethyl)-1H-indazole-3-carboxamide (36b)

Step-1: Preparation of N-(3-chloro-2-fluorobenzyl)-2-(ethylamino)acetamide (36a)

Reaction of 2-chloro-N-(3-chloro-2-fluorobenzyl)acetamide (35b) (600 mg, 2.54 mmol) with ethanamine hydrochloride (415 mg, 5.08 mmol) according to the procedure reported in step-2 of Scheme 35 gave after workup N-(3-chloro-2-fluorobenzyl)-2-(ethylamino)acetamide (36a) (494 mg, 2.02 mmol, 79% yield) as a yellow oil; $^1$H NMR (300 MHz, DMSO-$d_6$) δ 8.39 (t, J=5.8 Hz, 1H), 7.53-7.40 (m, 1H), 7.33-7.23 (m, 1H), 7.23-7.13 (m, 1H), 4.37 (d, J=5.9 Hz, 2H), 3.14 (s, 2H), 2.50 (q, J=7.1 Hz, 2H), 2.25 (s, 1H), 1.00 (t, J=7.1 Hz, 3H); $^{19}$F NMR (282 MHz, DMSO-$d_6$) δ -121.72; MS (ES+) 245.3 (M+1); 243.2 (M-1).

Step-2: Preparation of 1-(2-((2-((3-chloro-2-fluorobenzyl)amino)-2-oxoethyl)(ethyl)amino)-2-oxoethyl)-1H-indazole-3-carboxamide (36b)

Reaction of N-(3-chloro-2-fluorobenzyl)-2-(ethylamino)acetamide (36a) (174 mg, 0.71 mmol) with 2-(3-carbamoyl-1H-indazol-1-yl)acetic acid (2e) (171 mg, 0.78 mmol) according to the procedure reported in step-3 of Scheme 2 gave after workup 1-(2-((2-((3-chloro-2-fluorobenzyl)amino)-2-oxoethyl)(ethyl)amino)-2-oxoethyl)-1H-indazole-3-carboxamide (36b) (69 mg, 0.156 mmol, 22% yield) as a white solid; $^1$H NMR (300 MHz, DMSO-$d_6$) (a mixture of two rotamers) δ 8.85 and 8.49 (2t, J=5.5 Hz, 1H), 8.18 (d, J=8.1 Hz, 1H), 7.71 (d, J=7.4 Hz, 1H), 7.62-7.09 (m, 7H), 5.57 and 5.45 (2s, 2H), 4.46 and 4.34 (2d, J=5.5 Hz, 2H), 4.24 and 3.95 (2s, 2H), 3.56-3.24 (m, 2H), 1.23 and 0.97 (2t, J=7.1 Hz, 3H); $^{19}$F NMR (282 MHz, DMSO-$d_6$) δ −121.28, 121.65; MS (ES+) 468.5 (M+Na); 444.5 (M−1); [based on NMR, this compound is a mixture of rotamers with 1:1 ratio]

Scheme 37

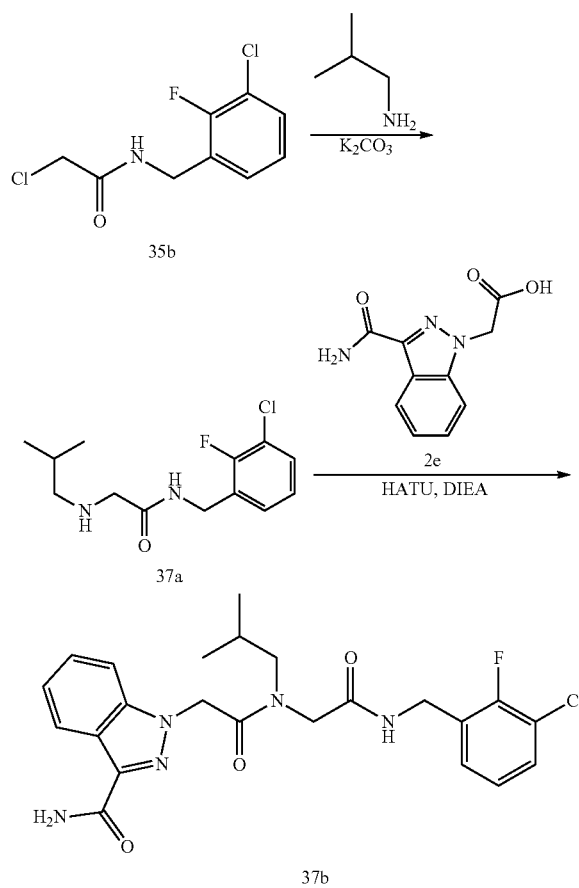

Preparation of 1-(2-((2-((3-chloro-2-fluorobenzyl)amino)-2-oxoethyl)(isobutyl)amino)-2-oxoethyl)-1H-indazole-3-carboxamide (37b)

Step-1: Preparation of N-(3-chloro-2-fluorobenzyl)-2-(isobutylamino)acetamide (37a)

Reaction of 2-chloro-N-(3-chloro-2-fluorobenzyl)acetamide (35b) (200 mg, 0.85 mmol) with isobutylamine (124 mg, 1.7 mmol), according to the procedure reported in step-2 of Scheme 35 gave after workup N-(3-chloro-2-fluorobenzyl)-2-(isobutylamino)acetamide (37a) (50 mg, 0.18 mmol, 22% yield) as a yellow oil; MS (ES+): 273.4 (M+1); (ES−) 271.3 (M−1)

Step-2: Preparation of 1-(2-((2-((3-chloro-2-fluorobenzyl)amino)-2-oxoethyl)(isobutyl)amino)-2-oxoethyl)-1H-indazole-3-carboxamide (37b)

Reaction of N-(3-chloro-2-fluorobenzyl)-2-(isobutylamino)acetamide (37a) (54 mg, 0.2 mmol) with 2-(3-carbamoyl-1H-indazol-1-yl)acetic acid (2e) (48 mg, 0.22 mmol) according to the procedure reported in step-3 of Scheme 2 gave after workup and purification by column chromatography [silica (12 g), eluting with CMA80 in CHCl$_3$ from 0 to 40%] to give 1-(2-((2-((3-chloro-2-fluorobenzyl)amino)-2-oxoethyl)(isobutyl)amino)-2-oxoethyl)-1H-indazole-3-carboxamide (37b) (48 mg, 0.1 mmol, 51% yield) as a white solid; $^1$H NMR (300 MHz, DMSO-$d_6$) δ 8.84 and 8.48 (2t, J=5.6 Hz, 1H), 8.18 (d, J=8.2 Hz, 1H), 7.78-7.65 (m, 1H), 7.59-7.00 (m, 7H), 5.54 and 5.50 (2s, 2H), 4.53-3.86 (m, 4H), 3.34-2.97 (m, 2H), 2.10-1.65 (m, 1H), 0.99 and 0.79 (2d, J=6.6 Hz, 6H); $^{19}$F NMR (282 MHz, DMSO-$d_6$) δ −121.22, 121.64; MS (ES+): 474.5 (M+1); (ES−): 472.4 (M−1); [based on NMR, this compound is a mixture of rotamers with 3:2 ratio]

Scheme 38

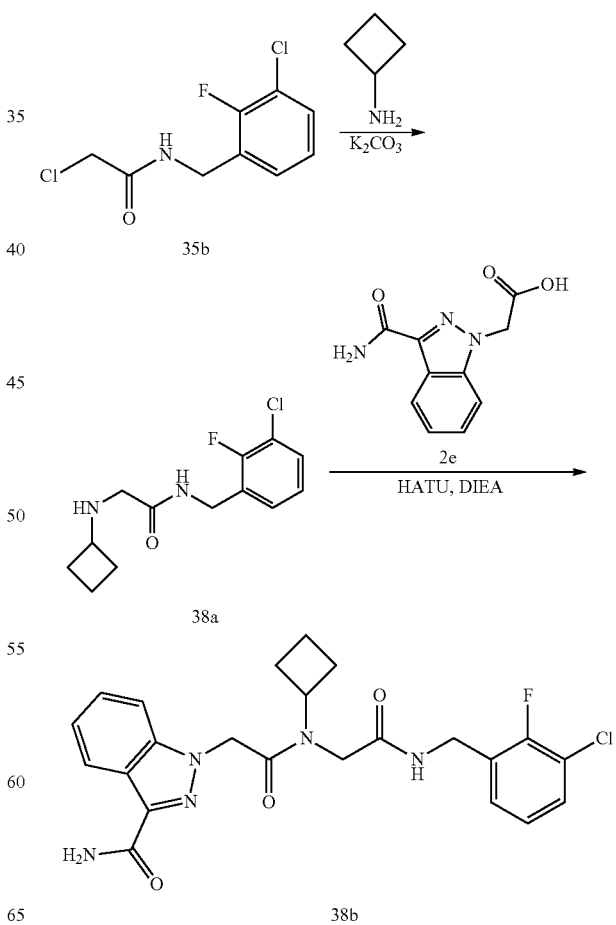

Preparation of 1-(2-((2-((3-chloro-2-fluorobenzyl)
amino)-2-oxoethyl)(cyclobutyl)amino)-2-oxoethyl)-
1H-indazole-3-carboxamide (38b)

Step-1: Preparation of N-(3-chloro-2-fluorobenzyl)-
2-(cyclobutylamino)acetamide (38a)

Reaction of 2-chloro-N-(3-chloro-2-fluorobenzyl)acetamide (35b) (530 mg, 2.25 mmol) with cyclobutanamine (319 mg, 4.49 mmol), according to the procedure reported in step-2 of Scheme 35 gave after workup and purification by chromatography [silica (12 g), eluting with EtOAc/MeOH (9:1) in hexane 0 to 60%] N-(3-chloro-2-fluorobenzyl)-2-(cyclobutylamino)acetamide (38a) (523 mg, 1.93 mmol, 86% yield) as a yellow oil; $^1$H NMR (300 MHz, DMSO-$d_6$) δ 8.33 (t, J=5.9 Hz, 1H), 7.52-7.39 (m, 1H), 7.32-7.23 (m, 1H), 7.23-7.14 (m, 1H), 4.34 (d, J=6.0 Hz, 2H), 3.18-3.07 (m, 1H), 3.05 (s, 2H), 2.37 (s, 1H), 2.11-1.96 (m, 2H), 1.75-1.44 (m, 4H); $^{19}$F NMR (282 MHz, DMSO-$d_6$) δ −121.68; MS (ES+): 271.4 (M+1); (ES−): 269.3 (M−1);

Step-2: Preparation of 1-(2-((2-((3-chloro-2-fluorobenzyl)amino)-2-oxoethyl)(cyclobutyl)amino)-2-oxoethyl)-1H-indazole-3-carboxamide (38b)

Reaction of N-(3-chloro-2-fluorobenzyl)-2-(cyclobutylamino)acetamide (38a) (210 mg, 0.78 mmol) with 2-(3-carbamoyl-1H-indazol-1-yl)acetic acid (2e) (187 mg, 0.85 mmol) according to the procedure reported in step-3 of Scheme 2 gave after workup 1-(2-((2-((3-chloro-2-fluorobenzyl)amino)-2-oxoethyl)(cyclobutyl)amino)-2-oxoethyl)-1H-indazole-3-carboxamide (38b) (298 mg, 0.63 mmol, 81% yield) as an off white solid; $^1$H NMR (300 MHz, DMSO-$d_6$) δ 8.87 and 8.43 (2t, J=5.8 Hz, 1H), 8.18 (d, J=7.6 Hz, 1H), 7.71 (s, 1H), 7.62-7.02 (m, 7H), 5.56 and 5.42 (s, 2H), 4.75-4.50 (m, 1H), 4.49-4.02 (m, 4H), 2.30-2.09 (m, 2H), 2.03-1.86 (m, 2H), 1.74-1.46 (m, 2H); $^{19}$F NMR (282 MHz, DMSO-$d_6$) δ −121.23, 121.61; MS (ES+): 494.5 (M+Na); ES(−): 470.4 (M−1); [based on NMR, this compound is a mixture of rotamers with 2:3 ratio].

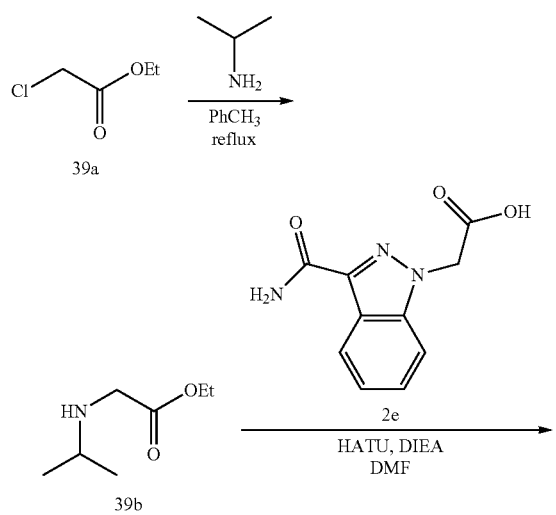

Scheme 39

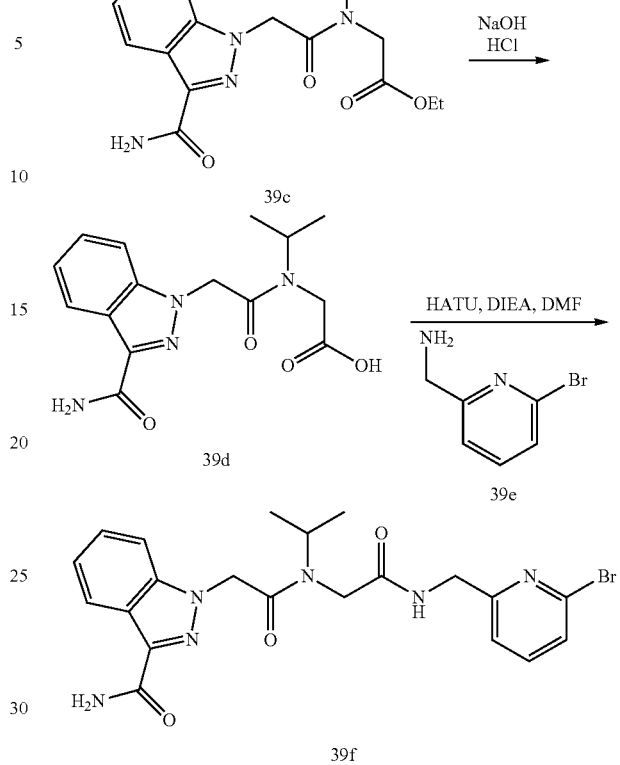

Preparation of 1-(2-((2-(((6-bromopyridin-2-yl)methyl)amino)-2-oxoethyl)(isopropyl)amino)-2-oxoethyl)-1H-indazole-3-carboxamide (39f)

Step-1: Preparation of ethyl 2-(isopropylamino)acetate (39b)

A stirred solution of propan-2-amine (22.94 mL, 269 mmol) and ethyl 2-chloroacetate (39a) (19.21 mL, 180 mmol) in toluene (200 mL) was heated at reflux for 2 h, cooled to room temperature, diluted with brine (300 mL) and with extracted with EtOAc (2×300 mL). The organic layers combined were, dried, filtered and evaporated to dryness. The residue obtained was purified by flash column chromatography [Silica gel, 80 g eluting with EtOAc in hexanes from 0-30%) to afford ethyl 2-(isopropylamino)acetate (39b) (18.78 g, 129 mmol, 72% yield) as a yellow semi-solid; MS (ES+): 146.2 (M+1); (ES−) 180.1 (M+Cl).

Step-2: Preparation of ethyl 2-(2-(3-carbamoyl-1H-indazol-1-yl)-N-isopropylacetamido)acetate (39c)

Reaction of ethyl 2-(isopropylamino)acetate (39b) (4.42 g, 30.4 mmol) with 2-(3-carbamoyl-1H-indazol-1-yl)acetic acid (2e) (4.00 g, 18.25 mmol) according to the procedure reported in step-3 of Scheme 2 gave after workup ethyl 2-(2-(3-carbamoyl-1H-indazol-1-yl)-N-isopropylacetamido)acetate (39c) as an dark yellow oil which was used as such in the next step.

Step-3: Preparation of 2-(2-(3-carbamoyl-1H-indazol-1-yl)-N-isopropylacetamido)acetic acid (39d)

To a solution of ethyl 2-(2-(3-carbamoyl-1H-indazol-1-yl)-N-isopropylacetamido)acetate (39c) (3.00 g, 8.66 mmol)

in of acetonitrile (30 mL) at room temperature was added sodium hydroxide (0.762 g, 19.05 mmol) in 30 mL of $H_2O$) and stirred overnight. Acetonitrile was removed by evaporation vacuum and the aqueous layer was basified with 1 N NaOH, washed with ether. The basic aqueous layer was acidified with ice-cold 1 N HCl and the solid obtained was collected by filtration, dried in vacuum to afford 2-(2-(3-carbamoyl-1H-indazol-1-yl)-N-isopropylacetamido)acetic acid (39d) (1.53 g, 4.81 mmol, 55.5% yield) as a yellow solid; MS (ES+): 341.4 (M+Na); (ES−) 317.4 (M−1).

Step-4: Preparation of 1-(2-((2-(((6-bromopyridin-2-yl)methyl)amino)-2-oxoethyl)(isopropyl)amino)-2-oxoethyl)-1H-indazole-3-carboxamide (39f)

Reaction of 2-(2-(3-carbamoyl-1H-indazol-1-yl)-N-isopropylacetamido)acetic acid (39d) (0.15 g, 0.47 mmol) with (6-bromopyridin-2-yl)methanamine (39e) (0.115 g, 0.613 mmol), according to the procedure reported in step-3 of Scheme 2 gave after workup and purification by flash column chromatography [Silica gel, 24 g eluting with MeOH in $CHCl_3$ 0-100%) 1-(2-((2-(((6-bromopyridin-2-yl)methyl)amino)-2-oxoethyl)(isopropyl)amino)-2-oxoethyl)-1H-indazole-3-carboxamide (39f) (65 mg, 0.13 mmol, 28% yield) as an off-white solid, which was mixture of rotamers from NMR analysis; $^1H$ NMR (300 MHz, DMSO-$d_6$) δ 8.92 & 8.46 (2t, J=6.1 Hz, 1H), 8.23-8.12 (m, 1H), 7.78-7.18 (m, 8H), 5.59 & 5.46 (2s, 2H), 4.63-4.50 (m, 1H), 4.46 (d, J=5.7 Hz) & 4.31 (d, J=6.1 Hz) (2d, 2H), 4.25 & 3.85 (2s, 2H), 1.25 (d, J=6.2 Hz) & 1.02 (dd, J=6.8, 2.0 Hz) (d &dd, 6H); $^1H$ NMR (300 MHz, DMSO-$d_6$/$D_2O$) δ 8.17-8.09 (m, 1H), 7.69 (t, J=7.7 Hz, 1H), 7.61-7.33 (m, 4H), 7.31-7.16 (m, 1H), 5.57 (s) & 5.42 (s) (2s, 2H), 4.59-4.46 (m, 1H), 4.43 (s) & 4.29 (2s, 2H), 4.19 (s, 1H), 1.22 (d, J=6.4 Hz) & 1.00 (d, J=6.8 Hz) (2d, 6H); MS (ES+): 487.5, 489.5 (M+2), 509.5, 511.5 (M+Na); (ES−): 485.4, 487.5 (M−1), 521.4, 523.4 (M+Cl).

Scheme 40

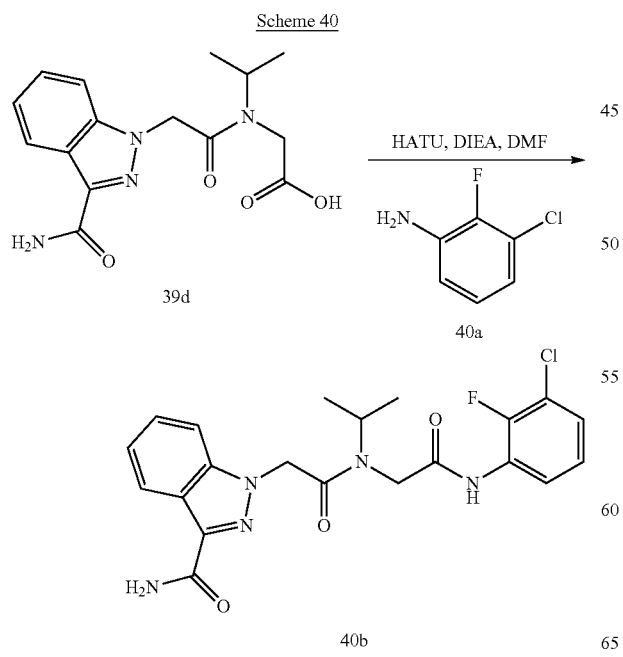

Preparation of 1-(2-((2-((3-chloro-2-fluorophenyl)amino)-2-oxoethyl)(isopropyl)amino)-2-oxoethyl)-1H-indazole-3-carboxamide (40b)

Reaction of 2-(2-(3-carbamoyl-1H-indazol-1-yl)-N-isopropylacetamido)acetic acid (39d) (0.15 g, 0.47 mmol) with 3-chloro-2-fluoroaniline (40a) (0.089 g, 0.613 mmol) according to the procedure reported in step-3 of Scheme 2 gave after workup and purification by flash column chromatography [Silica gel, 24 g eluting with MeOH in $CHCl_3$ 0-30%) 1-(2-((2-((3-chloro-2-fluorophenyl)amino)-2-oxoethyl)(isopropyl)amino)-2-oxoethyl)-1H-indazole-3-carboxamide (40b) (51 mg, 0.11 mmol, 24% yield) as an off-white solid; $^1H$ NMR (300 MHz, DMSO-$d_6$) δ 10.34 & 9.86 (2s, 1H), 8.29-8.10 (m, 1H), 8.02-7.51 (m, 3H), 7.51-7.06 (m, 5H), 5.63 & 5.48 (s, 2H), 4.79-3.92 (m, 3H), 1.26 (d, J=6.6 Hz) & 1.06 (d, J=6.8 Hz) (2d, 6H); $^{19}F$ NMR (282 MHz, DMSO-$d_6$) δ −126.60; (based on NMR the compound is a mixture of rotamers with ~2:3 ratio); MS (ES+): 446.5 (M+1); MS (ES−): 444.4 (M−1), 480.4 (M+Cl).

Scheme 41

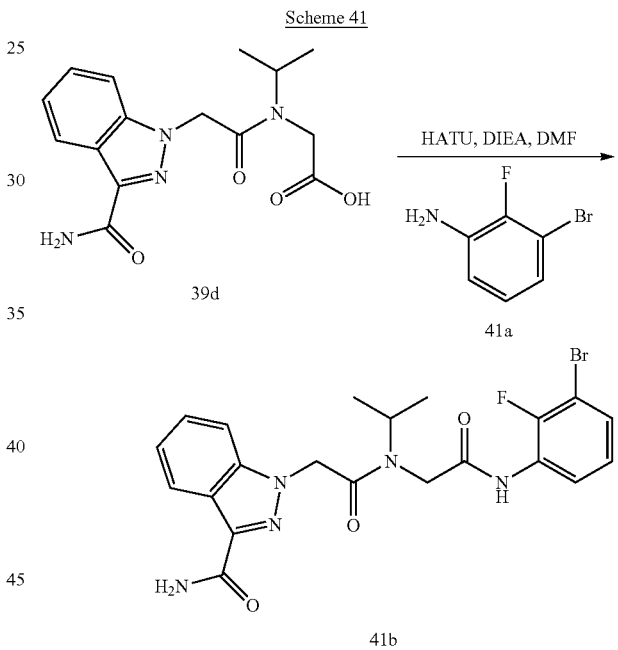

Preparation of 1-(2-((2-((3-bromo-2-fluorophenyl)amino)-2-oxoethyl)(isopropyl)amino)-2-oxoethyl)-1H-indazole-3-carboxamide (41b)

Reaction of 2-(2-(3-carbamoyl-1H-indazol-1-yl)-N-isopropylacetamido)acetic acid (39d) (0.15 g, 0.47 mmol) with 3-bromo-2-fluoroaniline (41a) (90 mg, 0.47 mmol) according to the procedure reported in step-3 of Scheme 2 gave after workup and purification by flash column chromatography [Silica gel, 24 g eluting with MeOH in $CHCl_3$ from 0-100%) 1-(2-((2-((3-bromo-2-fluorophenyl)amino)-2-oxoethyl)(isopropyl)amino)-2-oxoethyl)-1H-indazole-3-carboxamide (41b) (48 mg, 0.1 mmol, 21% yield) as an off-white solid; $^1H$ NMR (300 MHz, DMSO-$d_6$) δ 10.34 & 9.85 (2s, 1H), 8.28-7.02 (m, 9H), 5.63 & 5.49 (2s, 2H), 4.83-3.91 (m, 3H), 1.26 (d, J=6.5 Hz) 1.06 (d, J=6.9 Hz) (2d, 6H); $^{19}F$ NMR (282 MHz, DMSO-$d_6$) δ −118.22 (d, J=3.7

Hz); (based on NMR the compound is a mixture of rotamers with ~2:3 ratio); MS (ES+): 490.4, 492.5 (M+2); MS (ES−): 488.3, 490.3 (M−2).

Step-2: Preparation of 1-(2-((2-((3-chloro-2-fluorobenzyl)amino)-2-oxoethyl)(2-hydroxy ethyl)amino)-2-oxo ethyl)-1H-indazole-3-carboxamide (42b)

Reaction of N-(3-chloro-2-fluorobenzyl)-2-((2-hydroxy ethyl)amino)acetamide (42a) (210 mg, 0.81 mmol) with 2-(3-carbamoyl-1H-indazol-1-yl)acetic acid (2e) (194 mg, 0.89 mmol) according to the procedure reported in step-3 of Scheme 2 gave after workup 1-(2-(2-((3-chloro-2-fluorobenzyl)amino)-2-oxo ethyl)(2-hydroxy ethyl)amino)-2-oxo ethyl)-1H-indazole-3-carboxamide (42b) (128 mg, 0.28 mmol, 34% yield) as a white solid; $^1$H NMR (300 MHz, DMSO-$d_6$) δ 8.87 and 8.57 (2t, J=5.8 Hz, 1H), 8.18 (d, J=8.1 Hz, 1H), 7.78-7.64 (m, 1H), 7.60-7.00 (m, 7H), 5.66 and 5.43 (2s, 2H), 5.24 and 4.76 2 (2t, J=5.1 Hz, 1H), 4.49-4.32 (m, 2H), 4.00 (s, 1H), 3.72-3.55 (m, 3H), 3.51-3.39 (m, 1H), 3.34-3.26 (m, 1H); $^{19}$F NMR (282 MHz, DMSO-$d_6$) δ −121.33, 121.63; MS (ES−): 460.5 (M−1); [based on NMR, this compound is a mixture of two rotamers with 2:5 ratio].

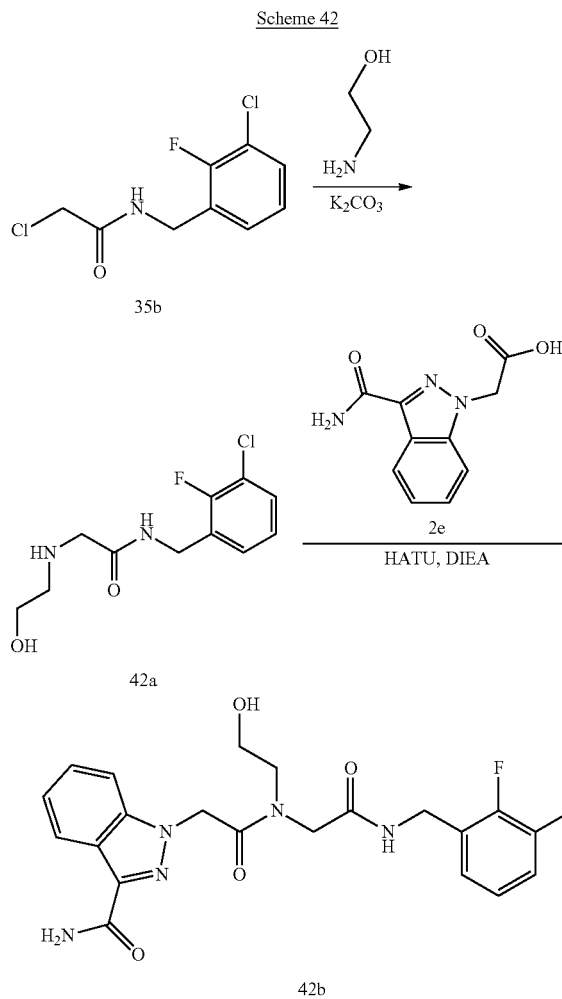

Scheme 42

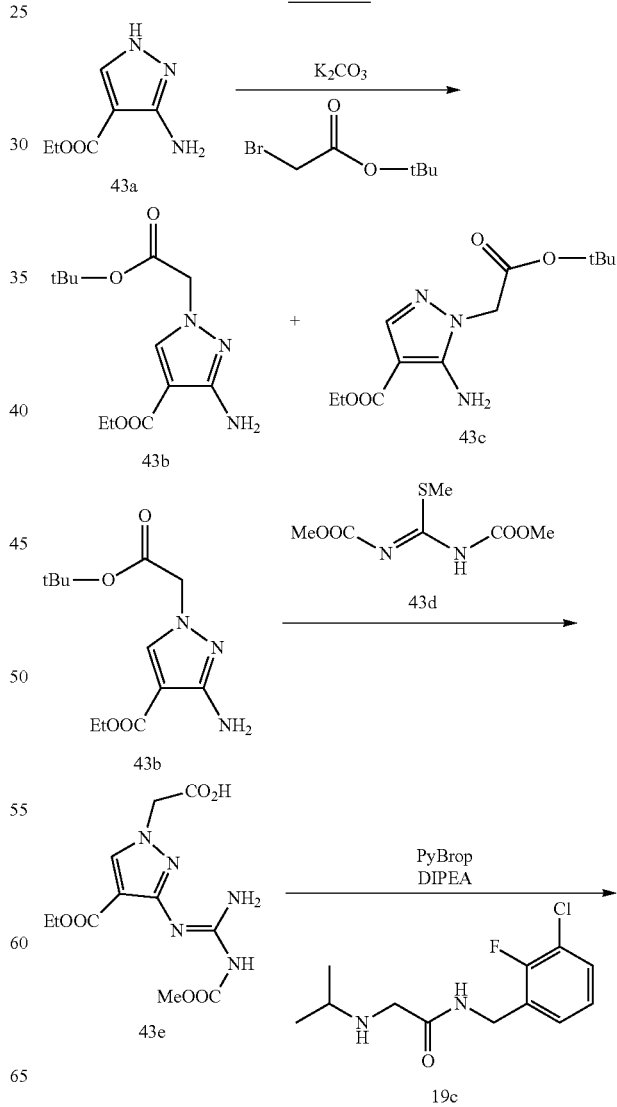

Scheme 43

Preparation of 1-(2-((2-((3-chloro-2-fluorobenzyl)amino)-2-oxoethyl)(2-hydroxyethyl)amino)-2-oxo-ethyl)-1H-indazole-3-carboxamide (42b)

Step-1: Preparation of N-(3-chloro-2-fluorobenzyl)-2-((2-hydroxyethyl)amino)acetamide (42a)

Reaction of 2-chloro-N-(3-chloro-2-fluorobenzyl)acetamide (35b) (500 mg, 2.12 mmol) with 2-aminoethanol (259 mg, 4.24 mmol) according to the procedure reported in step-2 of Scheme 35 gave after workup and purification by chromatography [silica (12 g), eluting with EtOAc/MeOH (9:1) in hexane 0 to 60%] N-(3-chloro-2-fluorobenzyl)-2-((2-hydroxyethyl)amino)acetamide (42a) (402 mg, 1.54 mmol, 73% yield) as a clear oil; $^1$H NMR (300 MHz, DMSO-$d_6$) δ 8.45 (t, J=6.0 Hz, 1H), 7.53-7.40 (m, 1H), 7.33-7.23 (m, 1H), 7.23-7.11 (m, 1H), 4.54 (s, 1H), 4.36 (d, J=6.0 Hz, 2H), 3.52-3.40 (m, 2H), 3.16 (s, 3H), 2.55 (t, J=5.6 Hz, 2H); $^{19}$F NMR (282 MHz, DMSO-$d_6$) δ −73.53 (TFA peak), −121.72; MS (ES+): 261.3 (M+1), 283.3 (M+Na); (ES−): 259.3 (M−1).

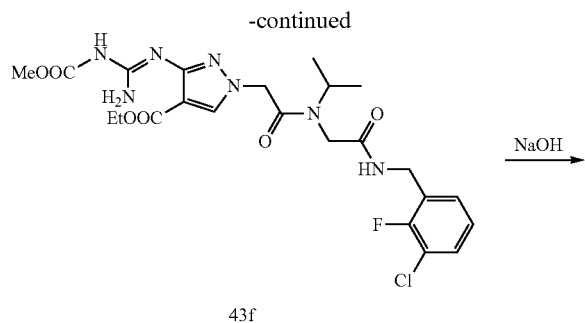

43f

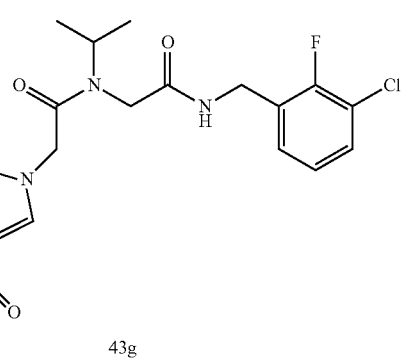

43g

Preparation of 2-(6-amino-4-oxo-4,5-dihydro-2H-pyrazolo[3,4-d]pyrimidin-2-yl)-N-(2-(3-chloro-2-fluorobenzylamino)-2-oxoethyl)-N-isopropylacetamide (43 g)

Step-1: Preparation of ethyl 3-amino-1-(2-(tert-butoxy)-2-oxoethyl)-1H-pyrazole-4-carboxylate (43c)

To a solution of ethyl 3-amino-1H-pyrazole-4-carboxylate (43a) (5 g, 31.6 mmol) and tert-butyl 2-bromoacetate (5.60 mL, 37.9 mmol) in DMF (20 mL) was added Potassium carbonate (6.55 g, 47.4 mmol) and stirred at room temperature overnight. The reaction mixture was diluted with EtOAc (200 mL), washed with water (2×100 mL), brine (100 mL), dried, filtered and concentrated in vacuum. The residue was purified by flash column chromatography on silica gel eluting with hexanes/EtOAc (1:0 to 2:1) to afford ethyl 3-amino-1-(2-(tert-butoxy)-2-oxoethyl)-1H-pyrazole-4-carboxylate (43b) as a (1.16 g, 14%) as a yellow solid; $^1$H NMR (300 MHz, DMSO-$d_6$) δ 7.93 (s, 1H), 5.37 (s, 2H), 4.69 (s, 2H), 4.17 (q, J=7.1 Hz, 2H), 1.42 (s, 9H), 1.24 (t, J=7.1 Hz, 3H); MS (ES+: 270.4 (M+1) and 292.4 (M+Na); and ethyl 5-amino-1-(2-(tert-butoxy)-2-oxoethyl)-1H-pyrazole-4-carboxylate (43c) (1.56 g, 18%) as a brown gum. $^1$H NMR (300 MHz, DMSO-$d_6$) δ 7.45 (s, 1H), 6.38 (s, 2H), 4.70 (s, 2H), 4.16 (q, J=7.1 Hz, 2H), 1.41 (s, 9H), 1.24 (t, J=7.1 Hz, 3H); MS (ES$^-$): 268.3 (M−1) and 304.3 (M+Cl).

Step-2: Preparation of (E)-2-(3-(amino(methoxycarbonylamino)methyleneamino)-4-(ethoxycarbonyl)-1H-pyrazol-1-yl)acetic acid (43e)

A mixture of ethyl 3-amino-1-(2-(tert-butoxy)-2-oxoethyl)-1H-pyrazole-4-carboxylate (43b) (571 mg, 2.12 mmol) and (Z)-(methoxycarbonylamino)(methylthio)methylenecarbamic acid methyl ester (43d) (646 mg) in acetic acid (5 mL) was heated with stirring at 100° C. overnight. The reaction mixture was cooled to room temperature and triturated with CHCl$_3$ followed by filtration, washing with CHCl$_3$, and drying under vacuum to afford (E)-2-(3-(amino(methoxy carbonylamino)methyleneamino)-4-(ethoxy carbonyl)-1H-pyrazol-1-yl)acetic acid (43e) (290 mg, 44%) as a white solid; $^1$H NMR (300 MHz, DMSO-$d_6$) δ 11.81 (bs, 1H), 8.34 (s, 1H), 8.07 (s, 1H), 4.97 (s, 2H), 4.28 (q, J=7.1 Hz, 2H), 3.54 (s, 3H), 1.30 (t, J=7.1 Hz, 3H); MS (ES+): 314 (M+1), Step-3: Preparation of (E)-ethyl 3-(amino(methoxycarbonylamino)methyleneamino)-1-(2-((2-(3-chloro-2-fluorobenzylamino)-2-oxoethyl)(isopropyl)amino)-2-oxoethyl)-1H-pyrazole-4-carboxylate (43f)

Reaction of (E)-2-(3-(amino(methoxycarbonylamino)methyleneamino)-4-(ethoxycarbonyl)-1H-pyrazol-1-yl)acetic acid (43e) (80 mg, 0.26 mmol) with N-(3-chloro-2-fluorobenzyl)-2-(isopropylamino)acetamide (19c) (79 mg, 0.306 mmol) according to the procedure reported in step-3 of Scheme-2 gave after workup and purification by flash column chromatography on silica gel eluting with CHCl$_3$/MeOH (1:0 to 19:1) to give (E)-ethyl 3-(amino(methoxy carbonylamino)methyleneamino)-1-(2-((2-(3-chloro-2-fluorobenzylamino)-2-oxoethyl)(isopropyl)amino)-2-oxoethyl)-1H-pyrazole-4-carboxylate (43f) (64 mg, 45%) as an off-white solid; $^1$H NMR ((300 MHz, DMSO-$d_6$) (as a mixture of two rotamers): δ 11.60 (s, 1H), 8.75 & 8.33 (2t, 1H), 8.26 (s, 1H), 8.22 (s, 1H), 8.06 (d, J=13.5 Hz, 1H), 7.59-7.05 (m, 3H), 5.25 & 5.05 (2s, 2H), 4.64-4.50 & 4.17-3.98 (2m, 1H), 4.46-4.22 (m, 4H), 4.07 & 3.83 (2s, 2H), 3.54 (s, 3H), 1.35-0.92 (m, 9H); $^{19}$F NMR (282 MHz, DMSO-$d_6$) δ −121.28, −121.69; MS (ES+): 554.6 (M+1) & 556.6 (M+3); MS (ES−): 588.6 and 590.6 (M+Cl).

Step-4: Preparation of 2-(6-amino-4-oxo-4,5-dihydro-2H-pyrazolo[3,4-d]pyrimidin-2-yl)-N-(2-(3-chloro-2-fluorobenzylamino)-2-oxoethyl)-N-isopropylacetamide (43 g)

To a solution of (E)-ethyl 3-(amino(methoxycarbonylamino)methyleneamino)-1-(2-((2-(3-chloro-2-fluorobenzylamino)-2-oxoethyl)(isopropyl)amino)-2-oxoethyl)-1H-pyrazole-4-carboxylate (43f) (54 mg, 0.097 mmol) in MeOH (8 mL) was added with 1 N aqueous sodium hydroxide (0.49 mL, 0.98 mmol) and refluxed for 2.5 h. The reaction mixture was cooled to room temperature concentrated in vacuum to remove MeOH, diluted with water (10 mL) and acidified with 4 N HCl. The solid obtained was collected by filtration, dried under vacuum to afford 2-(6-amino-4-oxo-4,5-dihydro-2H-pyrazolo[3,4-d]pyrimidin-2-yl)-N-(2-(3-chloro-2-fluorobenzylamino)-2-oxoethyl)-N-isopropylacetamide (43 g) (15 mg, 34%) as a white solid; $^1$H NMR (300 MHz, DMSO-$d_6$) (a mixture of two rotamers) 610.35 & 10.33 (2s, 1H), 8.74 & 8.36 (2t, 1H), 8.14 & 8.13 (2s, 1H), 7.60-7.07 (m, 3H), 6.20 (bs, 2H), 5.21 & 5.03 (2s, 2H), 4.41 (d, J=5.6 Hz) & 4.33 (d, J=5.7 Hz) (2d, 2H), 4.64-4.48 & 4.21-4.05 (2m, 1H), 4.10 & 3.83 (2s, 2H), 1.15 (d, J=6.4 Hz) & 0.97 (d, J=6.8 Hz) (2d, 6H); $^{19}$F NMR (282 MHz, DMSO-$d_6$) δ −121.35, −121.73. MS (ES+): 450.5 (M+1).

Scheme 44

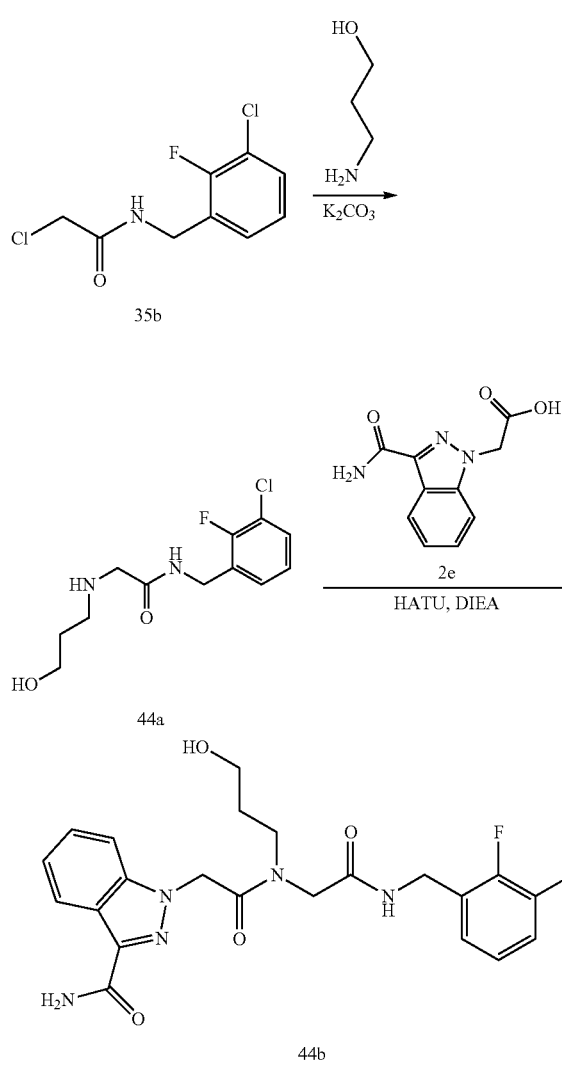

Preparation of 1-(2-((2-((3-chloro-2-fluorobenzyl) amino)-2-oxoethyl)(3-hydroxypropyl)amino)-2-oxo-ethyl)-1H-indazole-3-carboxamide (44b)

Step-1: Preparation of N-(3-chloro-2-fluorobenzyl)-2-((3-hydroxypropyl)amino)acetamide (44a)

Reaction of 2-chloro-N-(3-chloro-2-fluorobenzyl)acet-amide (35b) (500 mg, 2.12 mmol) with 2-aminoethanol (318 mg, 4.24 mmol) according to the procedure reported in step-2 of Scheme 35 gave after workup and purification by chromatography [silica (12 g), eluting with EtOAc/MeOH (9:1) in hexane 0 to 60%] N-(3-chloro-2-fluorobenzyl)-2-((3-hydroxypropyl)amino)acetamide (44a) (494 mg, 2.02 mmol, 73% yield) as a clear oil; $^1$H NMR (300 MHz, DMSO-d$_6$) δ 8.38 (t, J=6.1 Hz, 1H), 7.52-7.42 (m, 1H), 7.33-7.23 (m, 1H), 7.19 (td, J=7.8, 1.0 Hz, 1H), 4.37 (d, J=5.8 Hz, 2H), 4.14 (s, 1H), 3.45 (t, J=6.3 Hz, 2H), 3.18 (s, 2H), 3.13 (s, 2H), 2.56-2.52 (m, 1H), 1.61-1.49 (m, 2H); MS (ES$^+$) 275.4 (M+1); MS (ES$^-$), 273.3 (M-1).

Step-2: Preparation of 1-(2-((2-((3-chloro-2-fluorobenzyl)amino)-2-oxoethyl)(3-hydroxypropyl) amino)-2-oxoethyl)-1H-indazole-3-carboxamide (44b)

Reaction of N-(3-chloro-2-fluorobenzyl)-2-((3-hydroxy-propyl)amino)acetamide (44a) (120 mg, 0.44 mmol) with 2-(3-carbamoyl-1H-indazol-1-yl)acetic acid (2e) (105 mg, 0.48 mmol) according to the procedure reported in step-3 of Scheme 2 gave after workup 1-(2-((2-((3-chloro-2-fluo-robenzyl)amino)-2-oxoethyl)(3-hydroxypropyl)amino)-2-oxoethyl)-1H-indazole-3-carboxamide (44b) (59 mg, 0.12 mmol, 28% yield) as a white solid; $^1$H NMR (300 MHz, DMSO-d$_6$) (a mixture of two rotamers) δ 8.86 (t, J=5.5 Hz) & 8.51 (t, J=5.9 Hz) (2t, 1H), 8.18 (d, J=8.1 Hz, 1H), 7.72 (d, J=7.1 Hz, 1H), 7.60-7.06 (m, 7H), 5.63 & 5.45 (2s, 2H), 4.82-4.29 (m, 3H), 4.26 & 3.94 (2s, 2H), 3.65-3.48 (m, 2H), 3.35-3.23 (m, 2H), 1.89-1.46 (m, 2H); $^{19}$F NMR (282 MHz, DMSO) δ -121.30, 121.64; MS (ES+) 476.5 (M+1); MS (ES$^-$), 510.5 (M+Cl); HPLC, Rt 4.005 min, 93.5338% [based on NMR, this compound is a mixture of two rotamers 2:5 ratio].

Scheme 45

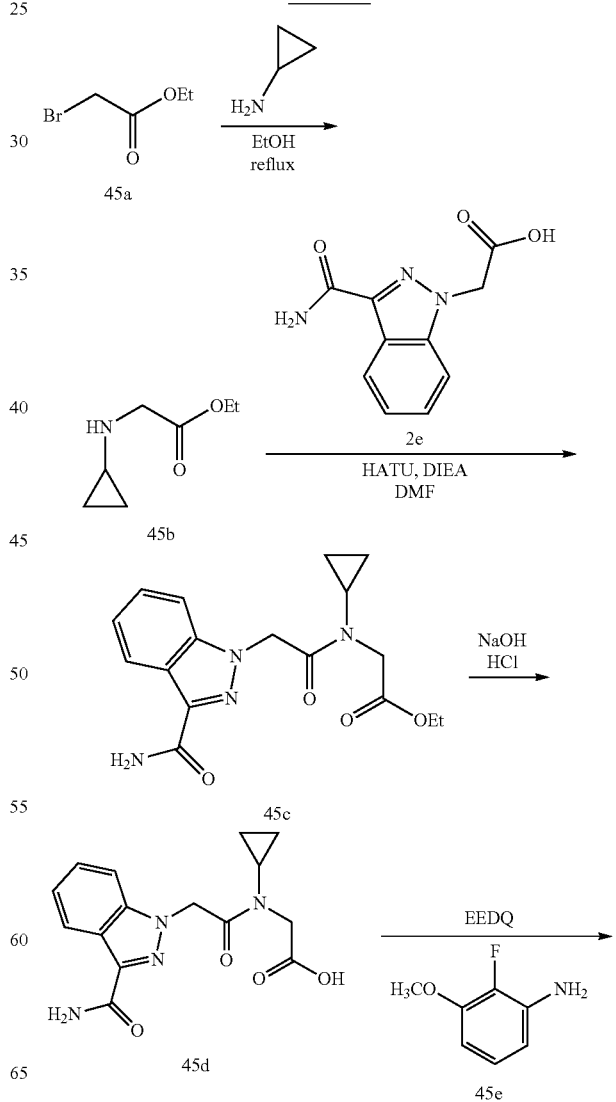

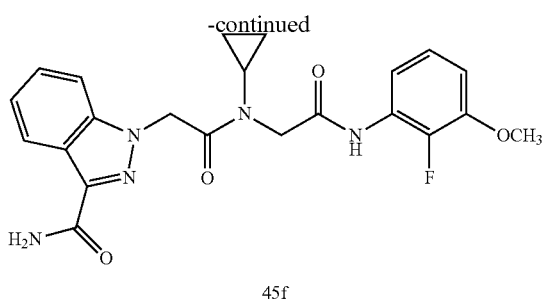

45f

Preparation of 1-(2-(cyclopropyl(2-((2-fluoro-3-methoxyphenyl)amino)-2-oxoethyl)amino)-2-oxoethyl)-1H-indazole-3-carboxamide (45f)

Step-1: Preparation of ethyl 2-(cyclopropylamino)acetate (45b)

Reaction of ethyl 2-bromoacetate (45a) (10 g, 59.9 mmol) with cyclopropylamine (16.88 mL, 240 mmol) in ethanol (80 mL) at room temperature according to the procedure reported in step-1 of Scheme 39 gave after workup ethyl 2-(cyclopropylamino)acetate (45b) (7.2 g, 50.3 mmol, 84% yield) as light orange colored liquid; $^1$H NMR (300 MHz, DMSO-$d_6$) δ 4.09 (q, J=7.1 Hz, 2H), 3.30 (s, 2H), 2.60 (s, 1H), 2.23-2.09 (m, 1H), 1.19 (t, J=7.1 Hz, 3H), 0.37-0.28 (m, 2H), 0.24-0.17 (m, 2H); MS (ES+) 144.2 (M+1).

Step-2: Preparation of ethyl 2-(2-(3-carbamoyl-1H-indazol-1-yl)-N-cyclopropylacetamido)acetate (45c)

Reaction of ethyl 2-(cyclopropylamino)acetate (45b) (1.57 g, 10.95 mmol) with 2-(3-carbamoyl-1H-indazol-1-yl) acetic acid (2e) (2 g, 9.12 mmol) according to the procedure reported in step-3 of Scheme 2 gave after workup ethyl 2-(2-(3-carbamoyl-1H-indazol-1-yl)-N-cyclopropylacetamido)acetate (45c) (2 g, 5.81 mmol, 64% yield) as off-white solid; $^1$H NMR (300 MHz, DMSO-$d_6$) δ 8.22-8.14 (m, 1H), 7.71 (s, 1H), 7.66-7.59 (m, 1H), 7.47-7.35 (m, 2H), 7.26 (ddd, J=7.9, 6.9, 0.9 Hz, 1H), 5.69 (s, 2H), 4.16-3.99 (m, 4H), 3.15-3.02 (m, 1H), 1.31-1.21 (m, 2H), 1.17 (t, J=7.1 Hz, 3H), 1.03-0.88 (m, 2H); MS (ES+): 345.5 (M+1), 367.4 (M+Na), MS (ES−): 379.5 (M+Cl).

Step-3: Preparation of 2-(2-(3-carbamoyl-1H-indazol-1-yl)-N-cyclopropylacetamido)acetic acid (45d)

Hydrolysis ester of ethyl 2-(2-(3-carbamoyl-1H-indazol-1-yl)-N-cyclopropylacetamido)acetate (45c) (1.8 g, 5.23 mmol) according to the procedure reported in step-3 of Scheme 39 gave after workup 2-(2-(3-carbamoyl-1H-indazol-1-yl)-N-cyclopropylacetamido)acetic acid (45d) (1.5 g, 4.74 mmol, 91% yield) as light orange colored foam; $^1$H NMR (300 MHz, DMSO-$d_6$) δ 12.76 (s, 1H), 8.18 (dt, J=8.1, 1.0 Hz, 1H), 7.73 (s, 1H), 7.64 (dt, J=8.6, 0.9 Hz, 1H), 7.47-7.36 (m, 2H), 7.26 (ddd, J=8.0, 6.8, 0.9 Hz, 1H), 5.68 (s, 2H), 4.00 (s, 2H), 3.12-2.99 (m, 1H), 1.06-0.86 (m, 4H).

Step-4: Preparation of 1-(2-(cyclopropyl(2-((2-fluoro-3-methoxyphenyl)amino)-2-oxoethyl)amino)-2-oxoethyl)-1H-indazole-3-carboxamide (45f)

Reaction of 2-(2-(3-carbamoyl-1H-indazol-1-yl)-N-cyclopropylacetamido)acetic acid (45d) (0.12 g, 0.38 mmol) with 2-fluoro-3-methoxyaniline (0.054 g, 0.379 mmol) (45e) (54 mg, 0.379 mmol), according to the procedure reported in step-1 of Scheme 2 gave after workup and purification by flash column chromatography [Silica gel, 12 g eluting with MeOH/EtOAc (9:1) in hexane 0-100%] 1-(2-(cyclopropyl (2-((2-fluoro-3-methoxyphenyl)amino)-2-oxoethyl)amino)-2-oxoethyl)-1H-indazole-3-carboxamide (45f) (70 mg, 0.159 mmol, 42% yield) as a white solid; $^1$H NMR (300 MHz, DMSO-$d_6$) δ 9.83 (s, 1H), 8.18 (dt, J=8.1, 1.0 Hz, 1H), 7.74 (s, 1H), 7.66 (d, J=8.5 Hz, 1H), 7.59-7.34 (m, 3H), 7.32-7.20 (m, 1H), 7.06 (td, J=8.3, 1.8 Hz, 1H), 6.98-6.86 (m, 1H), 5.70 (s, 2H), 4.20 (s, 2H), 3.82 (s, 3H), 3.11 (s, 1H), 1.05-0.91 (m, 4H); $^{19}$F NMR (282 MHz, DMSO-$d_6$) δ −147.62; MS (ES+): 440.5 (M+1), 462.5 (M+Na), MS (ES−): 438.5 (M−1).

Scheme 46

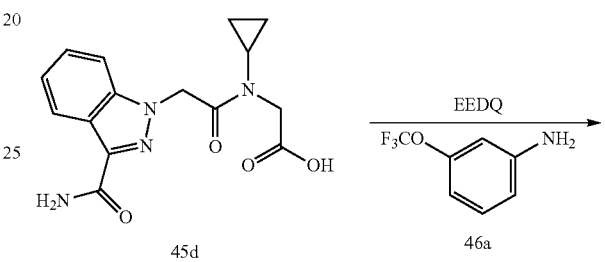

45d

46a

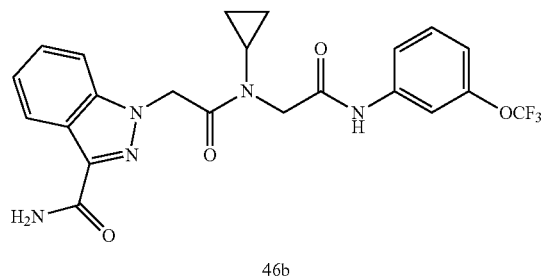

46b

Preparation of 1-(2-(cyclopropyl(2-oxo-2-((3-(trifluoromethoxy)phenyl)amino)ethyl)amino)-2-oxoethyl)-1H-indazole-3-carboxamide (46b)

Reaction of 2-(2-(3-carbamoyl-1H-indazol-1-yl)-N-cyclopropylacetamido)acetic acid (45d) (0.12 g, 0.38 mmol) with 23-(trifluoromethoxy)aniline (46a) (67 mg, 0.379 mmol) according to the procedure reported in step-1 of Scheme 2 gave after workup and purification by flash column chromatography [Silica gel, 12 g eluting with MeOH/EtOAc (9:1) in hexane 0-100%] 1-(2-(cyclopropyl (2-oxo-2-((3-(trifluoromethoxy)phenyl)amino)ethyl) amino)-2-oxoethyl)-1H-indazole-3-carboxamide (46b) (65 mg, 0.137 mmol, 36% yield) as a white solid; $^1$H NMR (300 MHz, DMSO-$d_6$) δ 10.38 (s, 1H), 8.22-8.12 (m, 1H), 7.80-7.71 (m, 2H), 7.70-7.61 (m, 1H), 7.52-7.33 (m, 4H), 7.30-7.20 (m, 1H), 7.09-6.95 (m, 1H), 5.71 (s, 2H), 4.15 (s, 2H), 3.18-3.06 (m, 1H), 1.11-0.89 (m, 4H); $^{19}$F NMR (282 MHz, DMSO-$d_6$) δ −56.72; MS (ES+): 476.5 (M+1), 498.5 (M+Na), MS (ES−): 474.5 (M−1).

Scheme 47

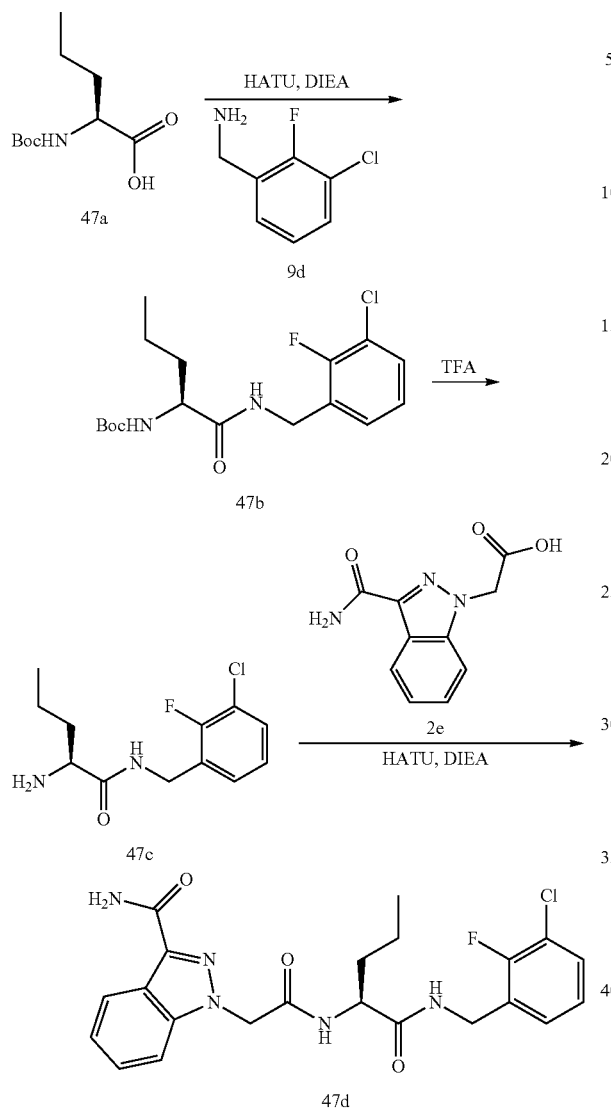

Preparation of (S)-1-(2-((1-((3-chloro-2-fluorobenzyl)amino)-1-oxopentan-2-yl)-amino)-2-oxoethyl)-1H-indazole-3-carboxamide (47d)

Step-1: Preparation of (5)-tert-butyl (1-((3-chloro-2-fluorobenzyl)amino)-1-oxopentan-2-yl)carbamate (47b)

Reaction of (S)-2-((tert-butoxycarbonyl)amino)pentanoic acid (47a) (412 mg, 1.9 mmol) with 3-chloro-2-fluorobenzylamine (9d) (252 mg, 1.58 mmol) according to the procedure reported in step-3 of Scheme 2 gave after workup (5)-tert-butyl (1-((3-chloro-2-fluorobenzyl)amino)-1-oxopentan-2-yl)carbamate (47b) which was used as such in the next step. MS (ES+): 381.45 (M+Na); (ES−): 393.34 (M+Cl).

Step-2: Preparation of (S)-2-amino-N-(3-chloro-2-fluorobenzyl)pentanamide (47c)

Reaction of (5)-tert-butyl (1-((3-chloro-2-fluorobenzyl)amino)-1-oxopentan-2-yl)carbamate (47b) (567 mg, 1.58 mmol) with TFA (2.19 mL, 28.4 mmol) according to the procedure reported in step-2 of Scheme 2 gave after workup (S)-2-amino-N-(3-chloro-2-fluorobenzyl)pentanamide (47c) which was used as such in the next step; MS (ES+): 259.4 (M+1).

Step-3: Preparation of (S)-1-(2-((1-((3-chloro-2-fluorobenzyl)amino)-1-oxopentan-2-yl)-amino)-2-oxoethyl)-1H-indazole-3-carboxamide (47d)

Reaction of (S)-2-amino-N-(3-chloro-2-fluorobenzyl)pentanamide (47c) (409 mg, 1.58 mmol) TFA salt from above step-2 with 2-(3-carbamoyl-1H-indazol-1-yl)acetic acid (2e) (416 mg, 1.9 mmol) according to the procedure reported in step-3 of Scheme 2 gave after workup and purification by chromatography [silica (24 g), eluting with MeOH in $CHCl_3$ from 0 to 50%] (5)-1-(2-((1-((3-chloro-2-fluorobenzyl)amino)-1-oxopentan-2-yl)-amino)-2-oxoethyl)-1H-indazole-3-carboxamide (47d) (12 mg, 0.026 mmol, 2% yield) as an off-white solid; $^1$H NMR (300 MHz, DMSO-$d_6$) δ 8.65 (t, J=5.8 Hz, 1H), 8.59 (d, J=7.9 Hz, 1H), 8.17 (dt, J=8.2, 1.1 Hz, 1H), 7.70 (s, 1H), 7.66-7.59 (m, 1H), 7.53-7.37 (m, 3H), 7.31-7.21 (m, 2H), 7.19-7.09 (m, 1H), 5.26 (s, 2H), 4.38-4.20 (m, 3H), 1.66-1.53 (m, 2H), 1.33-1.26 (m, 2H), 0.86 (t, J=7.4 Hz, 3H); $^{19}$F NMR (282 MHz, DMSO-$d_6$) δ −121.48; MS (ES+): 460.47 (M+1), 482.5 (M+Na); (ES−): 458.40 (M−1), 494.41 (M+Cl).

Scheme 48

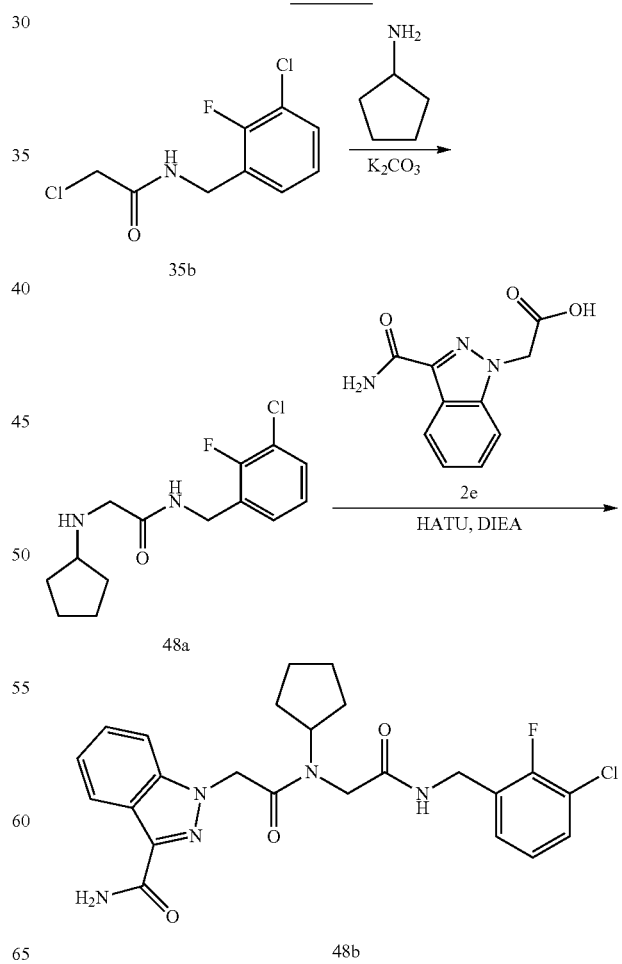

Preparation of 1-(2-((2-((3-chloro-2-fluorobenzyl)amino)-2-oxoethyl)(cyclopentyl)amino)-2-oxoethyl)-1H-indazole-3-carboxamide (48b)

Step-1: Preparation of N-(3-chloro-2-fluorobenzyl)-2-(cyclopentylamino)acetamide (48a)

Reaction of 2-chloro-N-(3-chloro-2-fluorobenzyl)acetamide (35b) (500 mg, 2.12 mmol) with cyclopentylamine (216 mg, 2.54 mmol) according to the procedure reported in step-2 of Scheme 35 gave after workup and purification by chromatography [silica (12 g), eluting with EtOAc/MeOH (9:1) in hexane 0 to 60%] N-(3-chloro-2-fluorobenzyl)-2-(cyclopentylamino)acetamide (48a) as a clear oil which was used as such in next step; MS (ES+): 285.4 (M+1); MS (ES−): 283.3 (M−1).

Step-2: Preparation of 1-(2-((2-((3-chloro-2-fluorobenzyl)amino)-2-oxoethyl)(cyclopentyl)amino)-2-oxoethyl)-1H-indazole-3-carboxamide (48b)

Reaction of N-(3-chloro-2-fluorobenzyl)-2-(cyclopentylamino)acetamide (48a) (240 mg, 0.84 mmol) with 2-(3-carbamoyl-1H-indazol-1-yl)acetic acid (2e) (203 mg, 0.93 mmol) according to the procedure reported in step-3 of Scheme 2 gave after workup 1-(2-((2-((3-chloro-2-fluorobenzyl)amino)-2-oxoethyl)(cyclopentyl)amino)-2-oxoethyl)-1H-indazole-3-carboxamide (48b) (315 mg, 0.65 mmol, 77% yield) as a white solid; $^1$H NMR (300 MHz, DMSO-$d_6$) δ 8.84 (t, J=5.6 Hz) and 8.40 (t, J=5.8 Hz) (2t, 1H), 8.18 (d, J=8.1 Hz, 1H), 7.71 (s, 1H), 7.64-7.00 (m, 7H), 5.63 & 5.45 (2s, 2H), 4.67-4.24 (m, 3H), 4.19 & 3.82 (2s, 2H), 2.06-1.84 (m, 1H), 1.75-1.28 (m, 7H); $^{19}$F NMR (282 MHz, DMSO) δ −121.17, 121.71; MS (ES$^+$) 486.6 (M+1); MS (ES$^-$), 484.4 (M−1); HPLC, Rt 7.134 min, 96.7156% [based on NMR, this compound is a mixture of two rotamers 1:1 ratio].

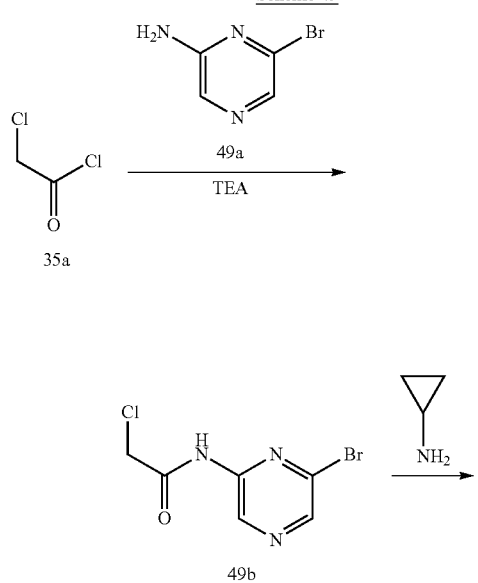

Scheme 49

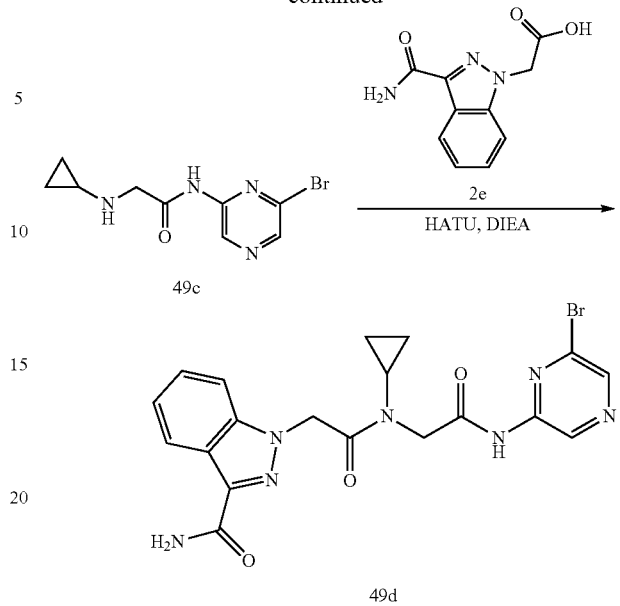

Preparation of 1-(2-((2-((6-bromopyrazin-2-yl)amino)-2-oxoethyl)(cyclopropyl)amino)-2-oxoethyl)-1H-indazole-3-carboxamide (49d)

Step-1: Preparation of N-(6-bromopyrazin-2-yl)-2-chloroacetamide (49b)

Reaction of 2-chloroacetyl chloride (35a) (0.24 mL, 3 mmol) with 6-bromopyrazin-2-amine (49a) (350 mg, 2.01 mmol) according to the procedure reported in step-1 of Scheme 35 gave after workup N-(6-bromopyrazin-2-yl)-2-chloroacetamide (49b) (45 mg, 1.8 mmol, 89% yield) as a dark orange solid; $^1$H NMR (300 MHz, DMSO-$d_6$) δ 11.51 (s, 1H), 9.28 (d, J=0.6 Hz, 1H), 8.60 (d, J=0.6 Hz, 1H), 4.39 (s, 2H); MS (ES+): 250.2, 252.2 (M, M+2), MS (ES−): 248.1, 250.1 (M−2, M).

Step-2: Preparation of N-(6-bromopyrazin-2-yl)-2-(cyclopropylamino)acetamide (49c)

Reaction of N-(6-bromopyrazin-2-yl)-2-chloroacetamide (49b) (480 mg, 1.92 mmol) with Cyclopropylamine (0.34 mL, 4.79 mmol) according to the procedure reported in step-2 of Scheme 35 gave after workup and purification by column chromatography [silica gel (24 g), eluting with EtOAc in hexane 0 to 100%] N-(6-bromopyrazin-2-yl)-2-(cyclopropylamino)acetamide (49c) (33 mg, 1.22 mmol, 64% yield) as an orange colored solid; $^1$H NMR (300 MHz, DMSO-$d_6$) δ 9.33 (s, 1H), 8.55 (s, 1H), 4.00 (s, 1H), 3.43 (s, 2H), 2.24-2.10 (m, 1H), 0.41-0.30 (m, 2H), 0.29-0.18 (m, 2H); MS (ES−): 269.2, 271.2 (M−2, M).

Step-3: Preparation of 1-(2-((2-((6-bromopyrazin-2-yl)amino)-2-oxoethyl)(cyclopropyl)amino)-2-oxoethyl)-1H-indazole-3-carboxamide (49d)

Reaction of N-(6-bromopyrazin-2-yl)-2-(cyclopropylamino)acetamide (49c) (90 mg, 0.33 mmol) with 2-(3-carbamoyl-1H-indazol-1-yl)acetic acid (2e) (73 mg, 0.33 mmol) according to the procedure reported in step-3 of Scheme 2 gave after workup 1-(2-((2-((6-bromopyrazin-2-yl)amino)-2-oxoethyl)(cyclopropyl)amino)-2-oxoethyl)-1H-indazole-3-carboxamide (49d) (110 mg, 0.23 mmol, 70% yield) as white solid; $^1$H NMR (300 MHz, DMSO-$d_6$) δ 11.29 (s, 1H), 9.25 (s, 1H), 8.54 (s, 1H), 8.17 (d, J=8.2, 1H), 7.72 (s, 1H), 7.69-7.64 (m, 1H), 7.50-7.34 (m, 2H), 7.25 (d, J=7.9, 1H), 5.71 (s, 2H), 4.22 (s, 2H), 3.20-3.06 (m, 1H), 1.14-0.84 (m, 4H); MS (ES+): 472.4, 474.5 (M+1, M+3), MS (ES−): 470.4, 472.4.

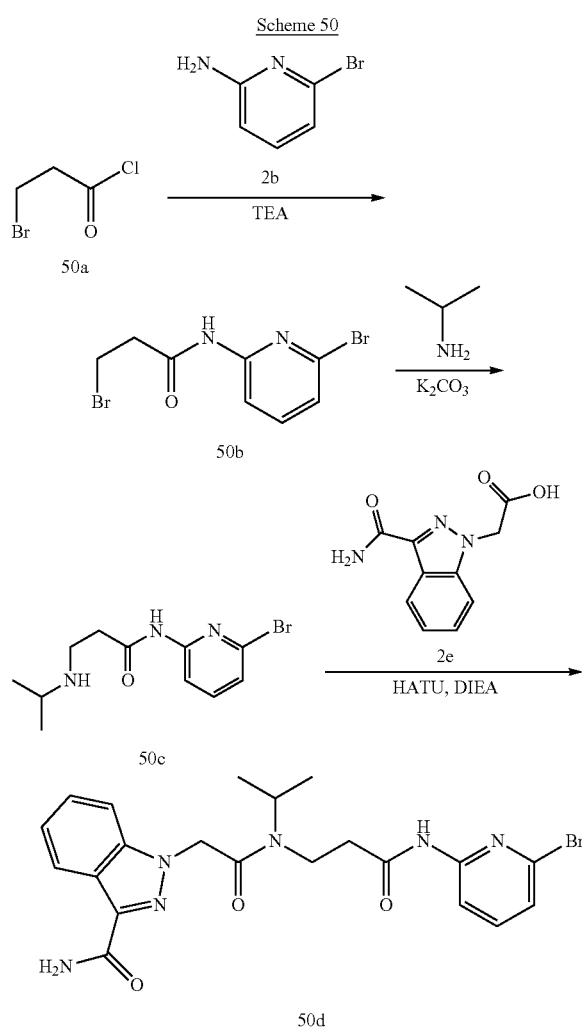

Preparation of 1-(2-((3-((6-bromopyridin-2-yl)amino)-3-oxopropyl)(isopropyl)amino)-2-oxoethyl)-1H-indazole-3-carboxamide (50d)

Step-1: Preparation of 3-bromo-N-(6-bromopyridin-2-yl)propanamide (50b)

Reaction of 3-bromopropanoyl chloride (50a) (1 g, 5.83 mmol) with 6-bromopyridin-2-amine (2b) (1.01 g, 5.83 mmol) according to the procedure reported in step-1 of Scheme 35 gave after workup and purification by flash column chromatography [silica (24 g), eluting with EtOAc/MeOH (9:1) in hexane 0 to 40%] to give 3-bromo-N-(6-bromopyridin-2-yl)propanamide (50b) (1.26 g, 4.09 mmol, 70.1% yield) as a white solid; MS (ES+): 307.2 (M+1).

Step-2: Preparation of N-(6-bromopyridin-2-yl)-3-(isopropylamino)propanamide (50c)

Reaction of 3-bromo-N-(6-bromopyridin-2-yl)propanamide (50b) (520 mg, 1.69 mmol) with propan-2-amine (299 mg, 5.07 mmol) according to the procedure reported in step-2 of Scheme 35 gave after workup and purification by flash column chromatography [silica (12 g), eluting with EtOAc/MeOH (9:1) in hexane 0 to 60%] N-(6-bromopyridin-2-yl)-3-(isopropylamino)propanamide (50c) (321 mg, 1.12 mmol, 66% yield) as a clear oil; MS (ES+): 286.3 (M+1); MS (ES−): 284.3 (M−1).

Step-3: Preparation of 1-(2-((3-((6-bromopyridin-2-yl)amino)-3-oxopropyl)(isopropyl)amino)-2-oxoethyl)-1H-indazole-3-carboxamide (50d)

Reaction of N-(6-bromopyridin-2-yl)-3-(isopropylamino)propanamide (50c) (230 mg, 0.8 mmol) with 2-(3-carbamoyl-1H-indazol-1-yl)acetic acid (2e) (194 mg, 0.88 mmol) according to the procedure reported in step-3 of Scheme 2 gave after workup and purification by flash column chromatography [silica (12 g), eluting with CMA80 in CHCl$_3$ 0 to 40%] 1-(2-((3-((6-bromopyridin-2-yl)amino)-3-oxopropyl)(isopropyl)amino)-2-oxoethyl)-1H-indazole-3-carboxamide (50d) (325 mg, 0.67 mmol, 83% yield) as an off white solid; $^1$H NMR (300 MHz, DMSO-$d_6$) δ 11.06 & 10.82 (2s, 1H), 8.28-7.99 (m, 2H), 7.86-7.54 (m, 3H), 7.49-7.20 (m, 4H), 5.60 & 5.55 (2s, 2H), 4.41-4.12 (m, 1H), 3.71 (t, J=7.1 Hz) & 3.48-3.40 (M) (t & m, 2H), 2.90 (t, J=7.1 Hz) & 2.63-2.60 (m) (t & m, 2H), 1.25 (d, J=6.5 Hz) & 1.15 (d, J=6.8 Hz) (2d, 6H); MS (ES+): 487.4 (M+1); [based on NMR, this compound is a mixture of two rotamers with 4:5 ratio].

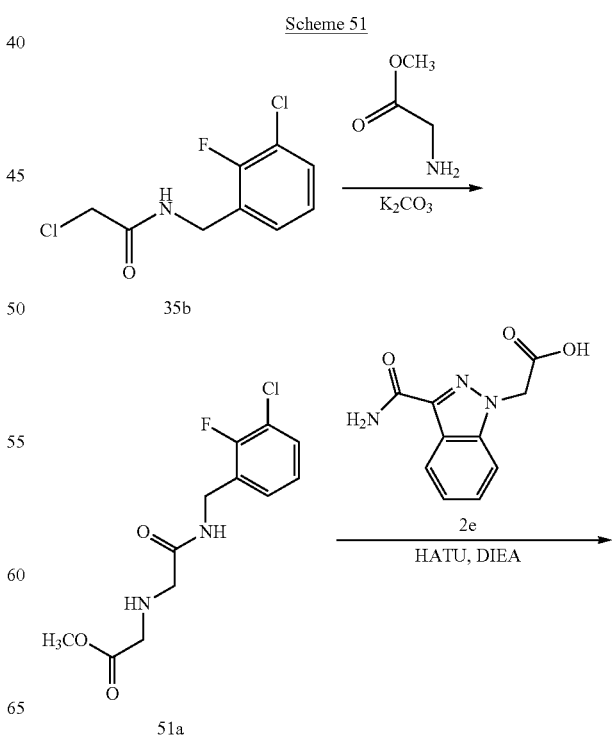

-continued

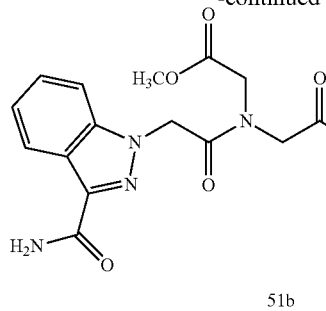

51b

Preparation of methyl 2-(2-(3-carbamoyl-1H-indazol-1-yl)-N-(2-((3-chloro-2-fluorobenzyl)amino)-2-oxoethyl)acetamido)acetate (51b)

Step-1: Preparation of methyl 2-((2-((3-chloro-2-fluorobenzyl)amino)-2-oxoethyl)amino)acetate (51a)

Reaction of 2-chloro-N-(3-chloro-2-fluorobenzyl)acetamide (35b) (500 mg, 2.12 mmol) with methyl 2-aminoacetate (266 mg, 2.12 mmol) according to the procedure reported in step-2 of Scheme 35 gave after workup and purification by flash column chromatography [silica (12 g), eluting with EtOAc/MeOH (9:1) in hexane 0 to 60%] methyl 2-((2-((3-chloro-2-fluorobenzyl)amino)-2-oxoethyl)amino)acetate (51a) (293 mg, 1.02 mmol, 48% yield) as a clear oil; MS (ES+) 311.3 (M+Na)

Step-2: Preparation of 2-(2-(3-carbamoyl-1H-indazol-1-yl)-N-(2-((3-chloro-2-fluorobenzyl)amino)-2-oxoethyl)acetamido)acetate (51b)

Reaction of methyl 2-((2-((3-chloro-2-fluorobenzyl)amino)-2-oxoethyl)amino)acetate (51a) (200 mg, 0.69 mmol) with 2-(3-carbamoyl-1H-indazol-1-yl)acetic acid (2e) (167 mg, 0.76 mmol) according to the procedure reported in step-3 of Scheme 2 gave after workup and purification by flash column chromatography [silica (12 g), eluting with CMA80 in CHCl₃ 0 to 60%] 2-(2-(3-carbamoyl-1H-indazol-1-yl)-N-(2-((3-chloro-2-fluorobenzyl)amino)-2-oxoethyl)acetamido)acetate (51b) (36 mg, 0.073 mmol, 11% yield) as a white solid; $^1$H NMR (300 MHz, DMSO-$d_6$) δ 8.82 (t, J=5.8 Hz) and 8.53 (t, J=5.3 Hz) (2t, 1H), 8.18 (d, J=7.5 Hz, 1H), 7.74 (s, 1H), 7.52-7.09 (m, 7H), 5.54 and 5.51 (2s, 2H), 4.57-4.28 (m, 4H), 4.08 and 3.99 (2s, 2H), 3.75 and 3.61 (2s, 3H); $^{19}$F NMR (282 MHz, DMSO) δ −121.32, −121.61; MS (ES+): 490.5 (M+1), 512.5 (M+Na); MS (ES−): 488.4 (M−1); [based on NMR, this compound is a mixture of two rotamers with 5:4 ratio].

Scheme 52

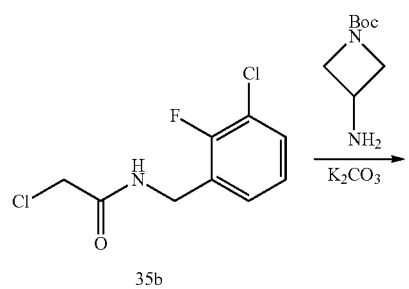

-continued

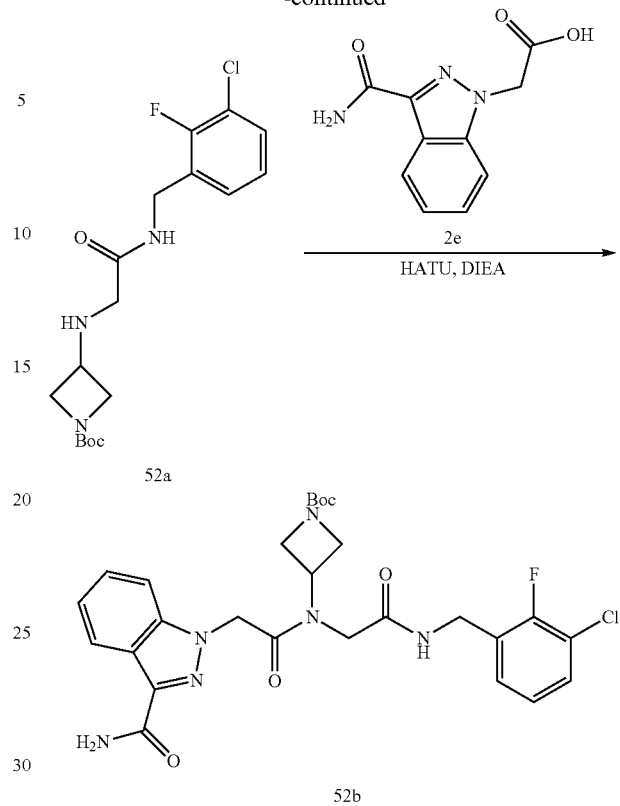

Preparation of tert-butyl 3-(2-(3-carbamoyl-1H-indazol-1-yl)-N-(2-((3-chloro-2-fluorobenzyl)amino)-2-oxoethyl)acetamido)azetidine-1-carboxylate (52b)

Step-1: Preparation of tert-butyl 3-((2-((3-chloro-2-fluorobenzyl)amino)-2-oxoethyl)amino)azetidine-1-carboxylate (52a)

Reaction of 2-chloro-N-(3-chloro-2-fluorobenzyl)acetamide (35b) (925 mg, 3.92 mmol) with tert-butyl 3-aminoazetidine-1-carboxylate (710 mg, 4.12 mmol) according to the procedure reported in step-2 of Scheme 35 gave after workup and purification by flash column chromatography [silica (12 g), eluting with EtOAc/MeOH (9:1) in hexane 0 to 60%] tert-butyl 3-((2-((3-chloro-2-fluorobenzyl)amino)-2-oxoethyl)amino)azetidine-1-carboxylate (52a) (785 mg, 2.11 mmol, 51% yield) as a clear oil; MS (ES+) 372.4 (M+1); MS (ES−): 370.4 (M−1).

Step-2: Preparation of tert-butyl 3-(2-(3-carbamoyl-1H-indazol-1-yl)-N-(2-((3-chloro-2-fluorobenzyl)amino)-2-oxoethyl)acetamido)azetidine-1-carboxylate (52b)

Reaction of tert-butyl 3-((2-((3-chloro-2-fluorobenzyl)amino)-2-oxoethyl)amino)azetidine-1-carboxylate (52a) (440 mg, 1.18 mmol) with 2-(3-carbamoyl-1H-indazol-1-yl)acetic acid (2e) (285 mg, 1.3 mmol) according to the procedure reported in step-3 of Scheme 2 gave after workup and purification by flash column chromatography [silica (12 g), eluting with CMA80 in CHCl₃ 0 to 60%] tert-butyl 3-(2-(3-carbamoyl-1H-indazol-1-yl)-N-(2-((3-chloro-2- fluorobenzyl)amino)-2-oxoethyl)acetamido)azetidine-1-carboxylate (52b) (325 mg, 0.57 mmol, 48% yield) as a white solid; $^1$H NMR (300 MHz, DMSO-d$_6$) δ 8.93 (t, J=5.6 Hz) and 8.59 (t, J=5.8 Hz) (2t, 1H), 8.18 (d, J=8.1 Hz, 1H), 7.69 (d, J=8.7 Hz, 1H), 7.59-7.02 (m, 7H), 5.60 & 5.43 (2s, 2H), 5.12-4.74 (m, 1H), 4.48 (d, J=5.4 Hz) & 4.33 (d, J=5.6 Hz) (2d, 2H), 4.39 & 4.10 (2s, 2H), 4.16 (t, J=8.7 Hz) & 4.01-3.76 (m) (t & m, 4H), 1.39 & 1.35 (2s, 9H); $^{19}$F NMR (282 MHz, DMSO) δ −121.26, 121.61; MS (ES+) 573.7 (M+1); [based on NMR, this compound is a mixture of two rotamers 1:1 ratio].

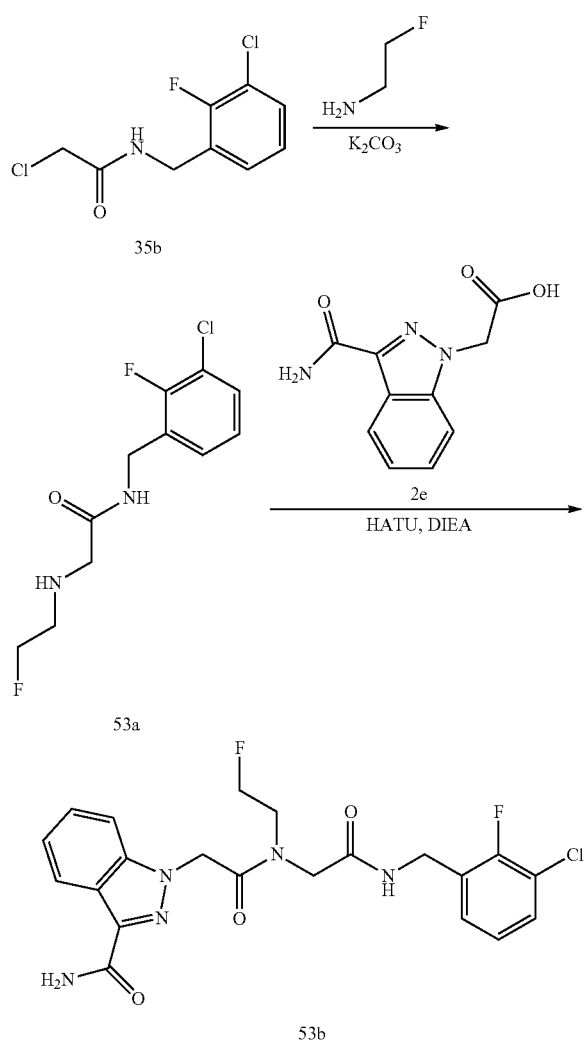

Scheme 53

Preparation of 1-(2-((2-((3-chloro-2-fluorobenzyl)amino)-2-oxoethyl)(2-fluoroethyl)amino)-2-oxoethyl)-1H-indazole-3-carboxamide (53b)

Step-1: Preparation of N-(3-chloro-2-fluorobenzyl)-2-((2-fluoroethyl)amino)acetamide (53a)

Reaction of 2-chloro-N-(3-chloro-2-fluorobenzyl)acetamide (35b) (500 mg, 2.12 mmol) with tert-fluoroethanamine hydrochloride (422 mg, 4.24 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((2-fluoroethyl)amino)acetamide (53a) (224 mg, 0.85 mmol, 40% yield) as a clear oil; $^1$H NMR (300 MHz, DMSO-d$_6$) δ 8.39 (t, J=5.9 Hz, 1H), 7.53-7.44 (m, 1H), 7.31-7.23 (m, 1H), 7.23-7.13 (m, 1H), 4.60-4.50 (m, 1H), 4.41-4.32 (m, 3H), 3.19 (s, 2H), 2.82 (t, J=5.0 Hz, 1H), 2.72 (t, J=5.0 Hz, 1H), 2.47-2.37 (m, 1H); $^{19}$F NMR (282 MHz, DMSO) δ −121.69; MS (ES+) 263.4 (M+1); 261.3 (M−1);

Step-2: Preparation of 1-(2-((2-((3-chloro-2-fluorobenzyl)amino)-2-oxoethyl)(2-fluoroethyl)amino)-2-oxoethyl)-1H-indazole-3-carboxamide (53b)

Reaction of N-(3-chloro-2-fluorobenzyl)-2-((2-fluoroethyl)amino)acetamide (53a) (178 mg, 0.68 mmol) with 2-(3-carbamoyl-1H-indazol-1-yl)acetic acid (2e) (163 mg, 0.745 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)(2-fluoroethyl)amino)-2-oxoethyl)-1H-indazole-3-carboxamide (53b) (162 mg, 0.349 mmol, 51.5% yield) as a white solid; $^1$H NMR (300 MHz, DMSO-d$_6$) δ 8.84 (t, J=5.7 Hz) and 8.54 (t, J=5.8 Hz) (2t, 1H), 8.18 (d, J=7.5 Hz, 1H), 7.74 (s, 1H), 7.57-7.07 (m, 7H), 5.59 & 5.48 (2s, 2H), 4.88-4.62 (m, 1H), 4.61-4.29 (m, 3H), 4.35 & 4.03 (2s, 2H), 3.97-3.80 (m, 1H), 3.62 (t, J=4.8 Hz) and 3.53 (t, J=4.9 Hz) (2t, 1H); MS (ES+): 464.5 (M+1); MS (ES−), 462.4 (M−1); [based on NMR, this compound is a mixture of two rotamers with 1:1 ratio].

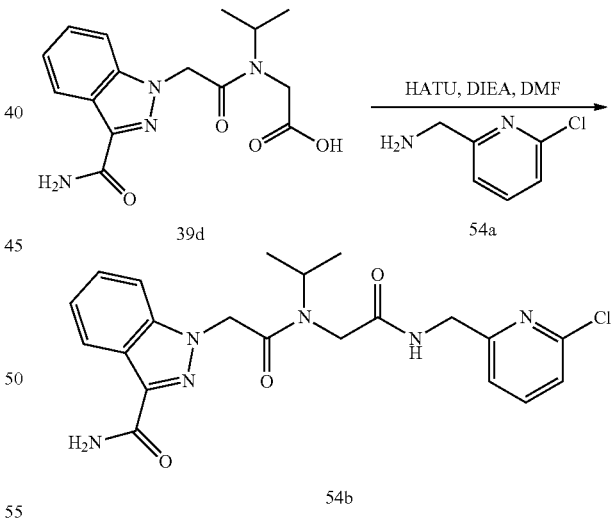

Scheme 54

Preparation of 1-(2-((2-(((6-chloropyridin-2-yl)methyl)amino)-2-oxoethyl)(isopropyl)amino)-2-oxoethyl)-1H-indazole-3-carboxamide (54b)

Reaction of 2-(2-(3-carbamoyl-1H-indazol-1-yl)-N-isopropylacetamido)acetic acid (39d) (0.15 g, 0.47 mmol) with (6-chloropyridin-2-yl)methanamine (54a) (122 mg, 0.57 mmol) according to the procedure reported in step-3 of Scheme 2 gave after workup and purification by flash column chromatography [Silica gel, 24 g eluting with MeOH in CHCl₃ from 0-50%) 1-(2-((2-(((6-chloropyridin-2-yl)methyl)amino)-2-oxoethyl)(isopropyl)amino)-2-oxoethyl)-1H-indazole-3-carboxamide (54b) (101 mg, 0.23 mmol, 48% yield) as an off-white solid; ¹H NMR (300 MHz, DMSO-d₆) δ 8.93 (t, J=6.0 Hz) & 8.47 (t, J=6.1 Hz) (2t, 1H), 8.22-8.13 (m, 1H), 7.85 (t, J=7.8 Hz, 1H), 7.69 (d, J=4.4 Hz, 1H), 7.61 (d, J=7.9 Hz, 1H), 7.53 (dt, J=8.5, 1.0 Hz, 1H), 7.46-7.30 (m, 3H), 7.31-7.16 (m, 1H), 5.60 & 5.47 (2s, 2H), 4.62-4.50 (m, 1H), 4.47 (d, J=5.8 Hz & 4.32 (d, J=6.0 Hz) (2d, 2H), 4.23 & 3.86 (2s, 2H), 1.25 (d, J=6.5 Hz) & 1.02 (d, J=6.8 Hz) (2d, 6H); (based on NMR the compound is a mixture of two rotamers ~1:2 ratio); MS (ES+): 443.5 (M+1), 465.5 (M+Na); (ES−): 441.4 (M−1), 477.4 (M+Cl).

Scheme 55

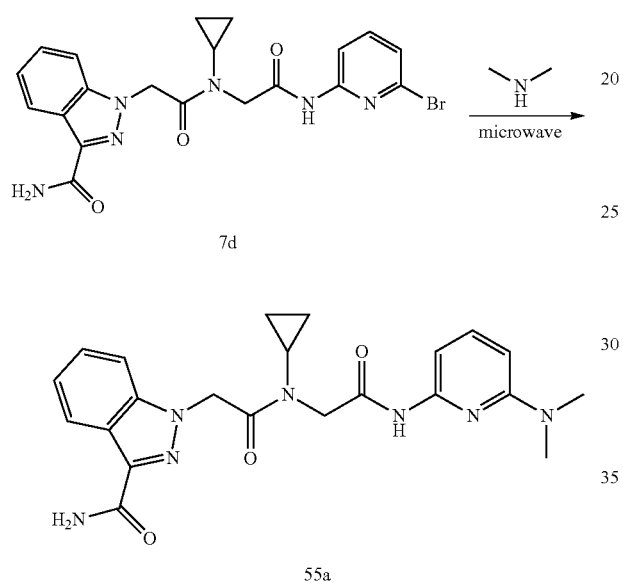

7d

55a

Preparation of 1-(2-(cyclopropyl(2-((6-(dimethylamino)pyridin-2-yl)-amino)-2-oxoethyl)amino)-2-oxoethyl)-1H-indazole-3-carboxamide (55a)

To a solution of 1-(2-((2-((6-bromopyridin-2-yl)amino)-2-oxoethyl)(cyclopropyl)amino)-2-oxoethyl)-1H-indazole-3-carboxamide (7d) (105 mg, 0.22 mmol) in dioxane (1 mL) was added aqueous dimethylamine (0.56 mL, 4.46 mmol) and heated under microwave irradiation at 150° C. for 3 h. The reaction mixture was cooled to room temperature, diluted with water (50 mL) and extracted with EtOAc (2×40 mL). The organic layers were combined washed with brine, dried, filtered and concentrated in vacuum. The residue obtained was purified by chromatography [silica gel (12 g), eluting with EtOAc/MeOH (9:1) in hexane 0 to 100%] to afford 1-(2-(cyclopropyl(2-((6-(dimethylamino)pyridin-2-yl)-amino)-2-oxoethyl)amino)-2-oxoethyl)-1H-indazole-3-carboxamide (55a) (55 mg, 0.13 mmol, 57% yield) as a white solid; ¹H NMR (300 MHz, DMSO-d₆) δ 10.00 (s, 1H), 8.21-8.11 (m, 1H), 7.76 (s, 1H), 7.66 (d, J=8.5 Hz, 1H), 7.52-7.34 (m, 3H), 7.30-7.15 (m, 2H), 6.31 (d, J=8.3 Hz, 1H), 5.70 (s, 2H), 4.19 (s, 2H), 3.17-3.05 (m, 1H), 2.98 (s, 6H), 1.08-0.86 (m, 4H); MS (ES+): 436.6 (M+1); (ES−): 470.5 (M+Cl).

Scheme 56

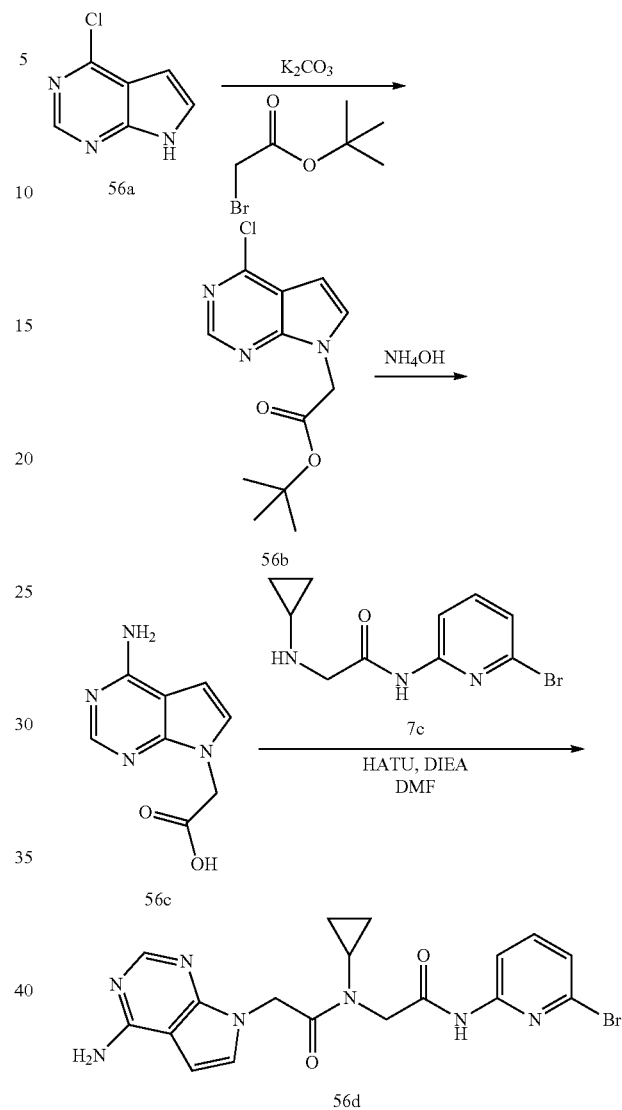

56a

56b

56c

56d

Preparation of 2-(4-amino-7H-pyrrolo[2,3-d]pyrimidin-7-yl)-N-(2-((6-bromopyridin-2-yl)amino)-2-oxoethyl)-N-cyclopropylacetamide (56d)

Step-1: Preparation of tert-butyl 2-(4-chloro-7H-pyrrolo[2,3-d]pyrimidin-7-yl)acetate (56b)

Reaction of 4-chloro-7H-pyrrolo[2,3-d]pyrimidine (56a) (1.5 g, 9.77 mmol) in acetonitrile (60 mL) with tert-butyl 2-bromoacetate (2.16 mL, 14.65 mmol) using Potassium carbonate (2.7 g, 19.54 mmol) as base according to the procedure reported step-2 of Scheme 35 gave after workup and purification by flash column chromatography [silica gel (40 g), eluting with EtOAc in hexanes 0 to 50%] tert-butyl 2-(4-chloro-7H-pyrrolo[2,3-d]pyrimidin-7-yl)acetate (56b) (2.2 g, 8.22 mmol, 84% yield) as white solid; ¹H NMR (300 MHz, DMSO-d₆) δ 8.65 (s, 1H), 7.75 (d, J=3.6 Hz, 1H), 6.68 (d, J=3.6 Hz, 1H), 5.09 (s, 2H), 1.41 (s, 9H); MS (ES+) 268.4 (M+1), MS (ES−) 302.3 (M+Cl).

Step-2: Preparation of 2-(4-amino-7H-pyrrolo[2,3-d]pyrimidin-7-yl)acetic acid (56c)

Reaction of tert-butyl 2-(4-chloro-7H-pyrrolo[2,3-d]pyrimidin-7-yl)acetate (56b) (512 mg, 1.91 mmol) with aqueous conc. ammonium hydroxide (1.5 mL, 38.3 mmol) under micro irradiation according to the procedure reported Scheme 55 gave after workup 2-(4-amino-7H-pyrrolo[2,3-d]pyrimidin-7-yl)acetic acid (56c) (312 mg, 1.62 mmol, 85% yield) as a white solid; $^1$H NMR (300 MHz, DMSO-$d_6$) δ 7.98 (s, 1H), 7.02 (d, J=3.4 Hz, 1H), 6.82 (s, 2H), 6.43 (d, J=3.5 Hz, 1H), 4.45 (s, 2H); MS (ES+): 193.2 (M+1); (ES−): 191.2 (M−1).

Step-3: Preparation of 2-(4-amino-7H-pyrrolo[2,3-d]pyrimidin-7-yl)-N-(2-((6-bromopyridin-2-yl)amino)-2-oxoethyl)-N-cyclopropylacetamide (56d)

Reaction of N-(6-bromopyridin-2-yl)-2-(cyclopropylamino)acetamide (7c) (8 mg, 0.3 mmol) with 2-(4-amino-7H-pyrrolo[2,3-d]pyrimidin-7-yl)acetic acid (56c) (57 mg, 0.3 mmol) according to the procedure reported in step-3 of Scheme 2 gave after workup and purification by chromatography [silica (12 g), eluting with CMA80 in CHCl$_3$ 0 to 40%] 2-(4-amino-7H-pyrrolo[2,3-d]pyrimidin-7-yl)-N-(2-((6-bromopyridin-2-yl)amino)-2-oxoethyl)-N-cyclopropylacetamide (56d) (22 mg, 0.05 mmol, 17% yield) as a white solid; $^1$H NMR (300 MHz, DMSO-$d_6$) δ 10.93 (s, 1H), 8.07-7.95 (m, 2H), 7.72 (t, J=8.0 Hz, 1H), 7.32 (d, J=7.7, 0.7 Hz, 1H), 7.07 (d, J=3.5 Hz, 1H), 6.95 (s, 2H), 6.51 (d, J=3.5 Hz, 1H), 5.27 (s, 2H), 4.16 (s, 2H), 3.11-2.95 (m, 1H), 1.02-0.85 (m, 4H); MS (ES+): 444.5, 446.4 (M+1, M+3), MS (ES−): 442.3, 444.4.

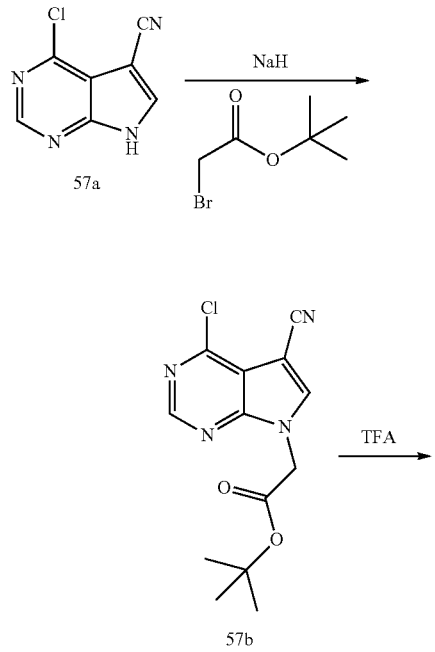

Scheme 57

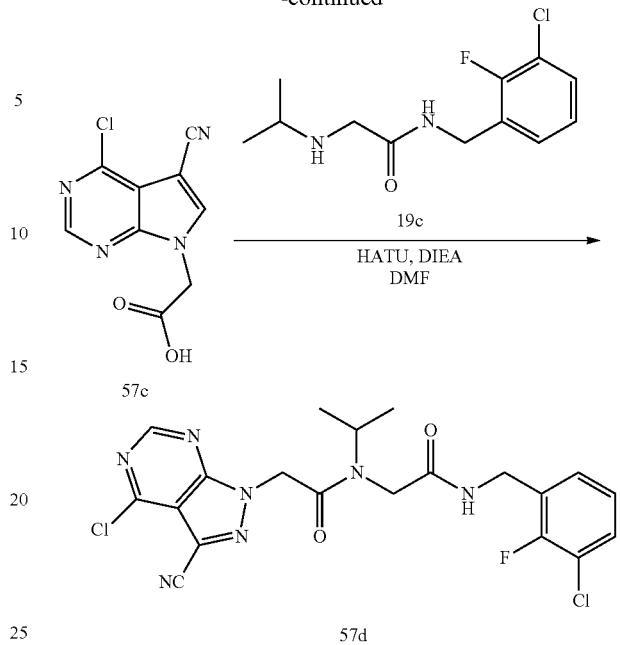

Preparation of N-(2-((3-chloro-2-fluorobenzyl)amino)-2-oxoethyl)-2-(4-chloro-5-cyano-7H-pyrrolo[2,3-d]pyrimidin-7-yl)-N-isopropylacetamide (57d)

Step-1: Preparation of tert-butyl 2-(4-chloro-5-cyano-7H-pyrrolo[2,3-d]pyrimidin-7-yl)acetate (57b)

To a solution of 4-chloro-7H-pyrrolo[2,3-d]pyrimidine-5-carbonitrile (57a) (811 mg, 4.54 mmol) in DMF (10 mL) was added at room temperature, NaH (60% in mineral oil, 218 mg, 5.45 mmol) stirred for 5 mins followed by the addition of tert-butyl 2-bromoacetate (0.81 mL, 5.45 mmol). The reaction mixture was stirred for 2 h quenched with EtOAc (50 mL) and brine (75 mL). The organic layer was separated washed with water (50 mL), dried, filtered and concentrated in vacuum. The residue obtained was purified by flash column chromatography [silica gel (24 g), eluting with MeOH in CHCl$_3$ 0 to 30%] to afford tert-butyl 2-(4-chloro-5-cyano-7H-pyrrolo[2,3-d]pyrimidin-7-yl)acetate (57b) (989 mg, 3.38 mmol, 74% yield) as an off-white solid; $^1$H NMR (300 MHz, DMSO-$d_6$) δ 8.86 (s, 1H), 8.71 (s, 1H), 5.18 (s, 2H), 1.42 (s, 9H); MS (ES+): 293.4 (M+1), 315.3 (M+Na); (ES−): 291.3 (M−1), 327.4 (M+Cl).

Step-2: Preparation of 2-(4-chloro-5-cyano-7H-pyrrolo[2,3-d]pyrimidin-7-yl)acetic acid (57c)

Reaction of tert-butyl 2-(4-chloro-5-cyano-7H-pyrrolo[2,3-d]pyrimidin-7-yl)acetate (57b) (500 mg, 1.71 mmol) with TFA (1.32 mL, 17.08 mmol) according to the procedure reported in step-2 of Scheme 2 gave after workup 2-(4-chloro-5-cyano-7H-pyrrolo[2,3-d]pyrimidin-7-yl)acetic acid (57c) (310 mg, 1.31 mmol, 77% yield) which was used as such in the next step without further purification; MS (ES+): 237.3 (M+1); (ES−): 235.2 (M−1)

Step-3: Preparation of N-(2-((3-chloro-2-fluorobenzyl)amino)-2-oxoethyl)-2-(4-chloro-5-cyano-7H-pyrrolo[2,3-d]pyrimidin-7-yl)-N-isopropylacetamide (57d)

Reaction of N-(3-chloro-2-fluorobenzyl)-2-(isopropylamino)acetamide (19c) (387 mg, 1.5 mmol) with 2-(4-chloro-5-cyano-7H-pyrrolo[2,3-d]pyrimidin-7-yl)acetic acid (57c) (295 mg, 1.25 mmol) according to the procedure reported in step-3 of Scheme 2 gave after workup and purification by chromatography [First column: Silica gel (24 g), eluting with MeOH in CHCl$_3$ 0-100%; Second column: Silica gel (24 g) eluting with EtOAc/MeOH (9:1) in hexanes 0-100%] N-(2-((3-chloro-2-fluorobenzyl)amino)-2-oxoethyl)-2-(4-chloro-5-cyano-7H-pyrrolo[2,3-d]pyrimidin-7-yl)-N-isopropylacetamide (57d) (115 mg, 0.241 mmol, 19% yield) as a white solid; $^1$H NMR (300 MHz, DMSO-d$_6$) δ 8.82 & 8.82 (2s, 1H), 8.79 & 8.33 (2t, 1H), 8.64 & 8.61 (2s, 1H), 7.57-7.33 (m, 2H), 7.30-7.03 (m, 1H), 5.46 & 5.33 (2s, 2H), 4.62-4.47 & 4.26-4.20 (2m, 1H), 4.44 (d, J=5.6 Hz) & 4.30 (d, J=5.8 Hz) (2d, 2H), 4.18 & 3.84 (2s, 2H), 1.24 (d, J=6.4 Hz) & 0.98 (d, J=6.8 Hz) (2d, 6H); $^{19}$F NMR (282 MHz, DMSO-d$_6$) δ −121.27, −121.63; [based on NMR the compound is a mixture of two rotamers ~2:3 ratio]; MS (ES+): 477.5 (M+1); (ES−): 475.5, 477.5 (M−1).

Scheme 58

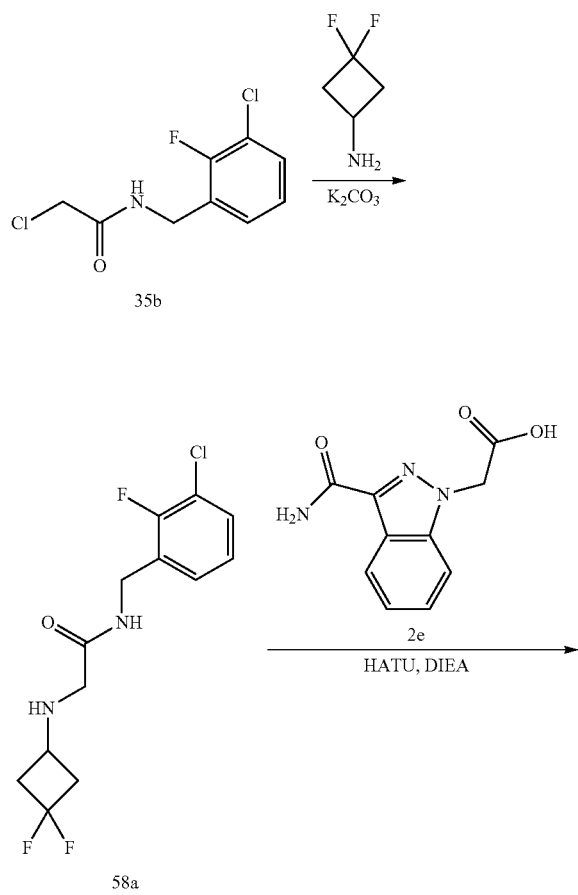

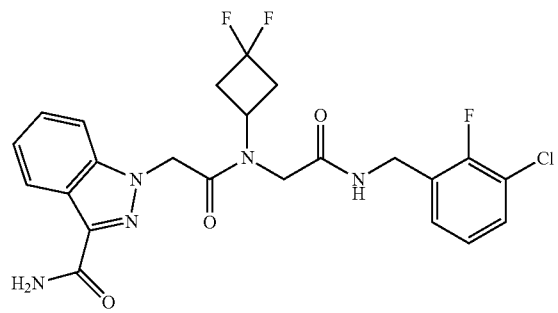

58b

Preparation of 1-(2-((2-((3-chloro-2-fluorobenzyl)amino)-2-oxoethyl)(3,3-difluorocyclobutyl)amino)-2-oxoethyl)-1H-indazole-3-carboxamide (58b)

Step-1: Preparation of N-(3-chloro-2-fluorobenzyl)-2-((3,3-difluorocyclobutyl)amino)acetamide (58a)

Reaction of 2-chloro-N-(3-chloro-2-fluorobenzyl)acetamide (35b) (500 mg, 2.12 mmol) with 3,3-difluorocyclobutanamine hydrochloride (502 mg, 3.49 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((3,3-difluorocyclobutyl)amino)acetamide (58a) (110 mg, 0.36 mmol, 17%) as a clear oil; $^1$H NMR (300 MHz, DMSO-d$_6$) δ 8.39 (t, J=6.0 Hz, 1H), 7.52-7.43 (m, 1H), 7.33-7.24 (m, 1H), 7.24-7.14 (m, 1H), 4.35 (d, J=5.9 Hz, 2H), 3.17-3.03 (m, 3H), 2.80-2.61 (m, 3H), 2.41-2.22 (m, 2H); MS (ES+): 307.3, 309.3 (M+1, M+3)

Step-2: Preparation of tert-butyl 1-(2-((2-((3-chloro-2-fluorobenzyl)amino)-2-oxoethyl)(3,3-difluorocyclobutyl)amino)-2-oxoethyl)-1H-indazole-3-carboxamide (58b)

Reaction of N-(3-chloro-2-fluorobenzyl)-2-((3,3-difluorocyclobutyl)amino)acetamide (58a) (110 mg, 0.36 mmol) with 2-(3-carbamoyl-1H-indazol-1-yl)acetic acid (2e) (86 mg, 0.4 mmol) according to the procedure reported in step-3 of Scheme 2 gave after workup and purification by flash column chromatography [silica (12 g), eluting with CMA80 in CHCl$_3$ 0 to 60%] tert-butyl 1-(2-((2-((3-chloro-2-fluorobenzyl)amino)-2-oxoethyl)(3,3-difluorocyclobutyl)amino)-2-oxoethyl)-1H-indazole-3-carboxamide (58b) (115 mg, 0.23 mmol, 63% yield) as a white solid; $^1$H NMR (300 MHz, DMSO-d$_6$) δ 8.90 (t, J=5.9 Hz) and 8.57 (t, J=6.6 Hz) (2t, 1H), 8.18 (d, J=8.0 Hz, 1H), 7.79-7.63 (m, 1H), 7.56-7.07 (m, 7H), 5.65 and 5.43 (2s, 2H), 4.64-4.02 (m, 5H), 3.12-2.85 (m, 2H), 2.80-2.65 (m, 2H); $^{19}$F NMR (282 MHz, DMSO-d$_6$) δ −82.66, −99.20, −121.23, −121.60; MS (ES$^{-1}$): 508.5 (M+1); MS (ES$^-$): 506.5 (M−1); [based on NMR, this compound is a mixture of two rotamers 5:1 ratio].

Scheme 59

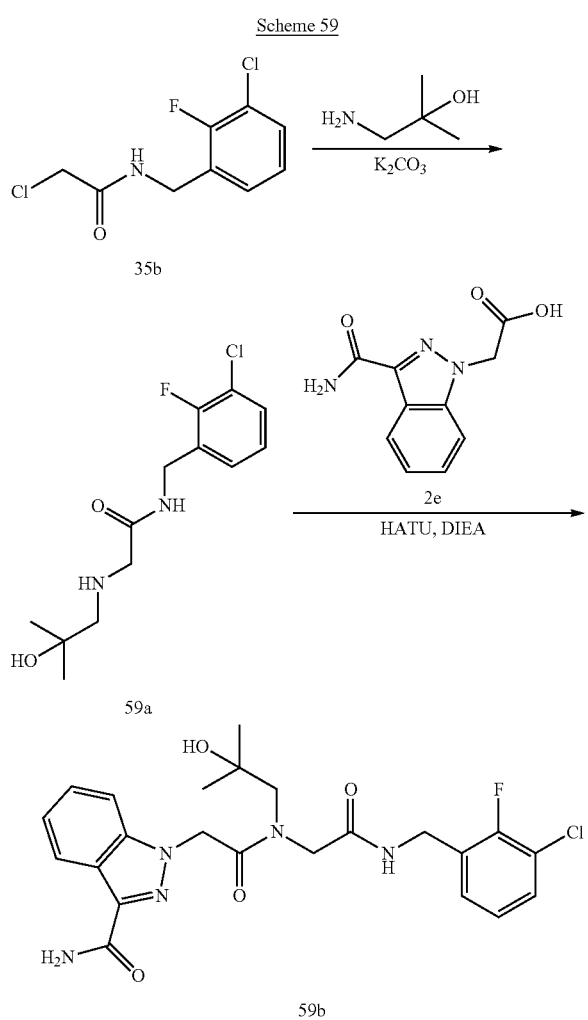

mmol) with 2-(3-carbamoyl-1H-indazol-1-yl)acetic acid (2e) (167 mg, 0.76 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)(2-hydroxy-2-methylpropyl)amino)-2-oxoethyl)-1H-indazole-3-carboxamide (59b) (239 mg, 0.49 mmol, 70% yield) as a white solid; $^1$H NMR (300 MHz, DMSO-d$_6$) δ 8.83 (t, J=5.6 Hz and 8.49 (t, J=5.9 Hz) (2t, 1H), 8.18 (d, J=8.1 Hz, 1H), 7.71 (d, J=11.8 Hz, 1H), 7.57-7.01 (m, 7H), 5.69 and 5.44 (2s, 2H), 5.08 and 4.59 (2s, 1H), 4.52-4.28 (m, 3H), 4.07 (s, 1H), 3.50 and 3.20 (2s, 2H), 1.24 and 1.03 (2s, 6H); $^{19}$F NMR (282 MHz, DMSO) δ −121.34, −121.67; MS (ES+): 490.5 (M+1); MS (ES−): 488.5 (M−1); [based on NMR, this compound is a mixture of two rotamers with 1:1 ratio].

Scheme 60

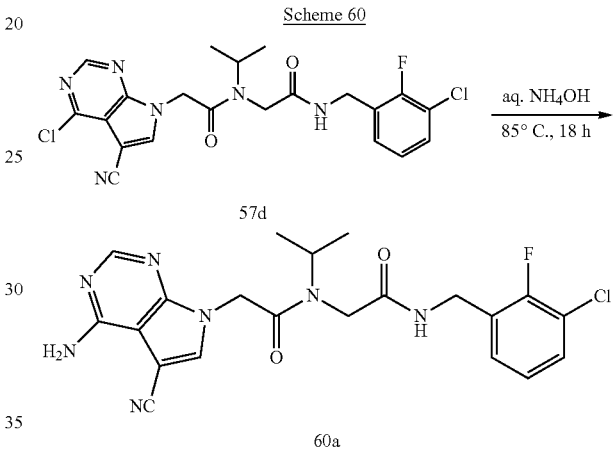

Preparation of 2-(4-amino-5-cyano-7H-pyrrolo[2,3-d]pyrimidin-7-yl)-N-(2-((3-chloro-2-fluorobenzyl)amino)-2-oxoethyl)-N-isopropylacetamide (60a)

To a solution of N-(2-((3-chloro-2-fluorobenzyl)amino)-2-oxoethyl)-2-(4-chloro-5-cyano-7H-pyrrolo[2,3-d]pyrimidin-7-yl)-N-isopropylacetamide (57d) (80 mg, 0.17 mmol) in dioxane (3 mL) was added aqueous ammonium hydroxide (1.83 mL, 46.9 mmol) and heated at 85° C. for 18 h. The reaction was cooled to room temperature and excess solvent was removed under reduced pressure. The residue obtained was triturated with CHCl$_3$ and the solid obtained was collected by filtration, rinsed with MeOH, evaporated to dryness to afford 2-(4-amino-5-cyano-7H-pyrrolo[2,3-d]pyrimidin-7-yl)-N-(2-((3-chloro-2-fluorobenzyl)amino)-2-oxoethyl)-N-isopropylacetamide (60a) (36 mg, 0.079 mmol, 47% yield) as a white solid; $^1$H NMR (300 MHz, DMSO-d$_6$) δ 8.77 (t, J=5.8 Hz) and 8.31 (t, J=5.9 Hz) (2t, 1H), 8.18 and 8.18 (2s, 1H), 8.07 and 8.06 (2s, 1H), 7.57-7.33 (m, 2H), 7.28-7.06 (m, 1H), 6.84 (s, 2H), 5.25 and 5.12 (2s, 2H), 4.63-4.48 and 4.26-4.19 (2m, 1H), 4.43 (d, J=5.6 Hz) and 4.31 (d, J=5.8 Hz) (2d, 2H), 4.15 and 3.83 (2s, 2H), 1.21 (d, J=6.4 Hz) and 0.97 (d, J=6.8 Hz) (2d, 6H); $^{19}$F NMR (282 MHz, DMSO-d$_6$) δ −121.31, −121.67. [based on NMR the compound is a mixture of two rotamers 1:1 ratio]; MS (ES+): 458.5 (M+1), 480.5 (M+Na); (ES−): 456.4 (M−1), 492.5 (M+Cl).

Preparation of 1-(2-((2-((3-chloro-2-fluorobenzyl)amino)-2-oxoethyl)(2-hydroxy-2-methylpropyl)amino)-2-oxoethyl)-1H-indazole-3-carboxamide (59b)

Step-1: Preparation of N-(3-chloro-2-fluorobenzyl)-2-((2-hydroxy-2-methylpropyl)amino)acetamide (59a)

Reaction of 2-chloro-N-(3-chloro-2-fluorobenzyl)acetamide (35b) (500 mg, 2.12 mmol) with 1-amino-2-methylpropan-2-ol (378 mg, 4.24 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((2-hydroxy-2-methylpropyl)amino)acetamide (59a) (200 mg, 0.69 mmol, 33%) as a clear oil; MS (ES+) 289.4 (M+1); (ES−) 287.3.

Step-2: Preparation of 1-(2-((2-((3-chloro-2-fluorobenzyl)amino)-2-oxoethyl)(2-hydroxy-2-methylpropyl)amino)-2-oxoethyl)-1H-indazole-3-carboxamide (59b)

Reaction of N-(3-chloro-2-fluorobenzyl)-2-((2-hydroxy-2-methylpropyl)amino)acetamide (59a) (200 mg, 0.69

Scheme 61

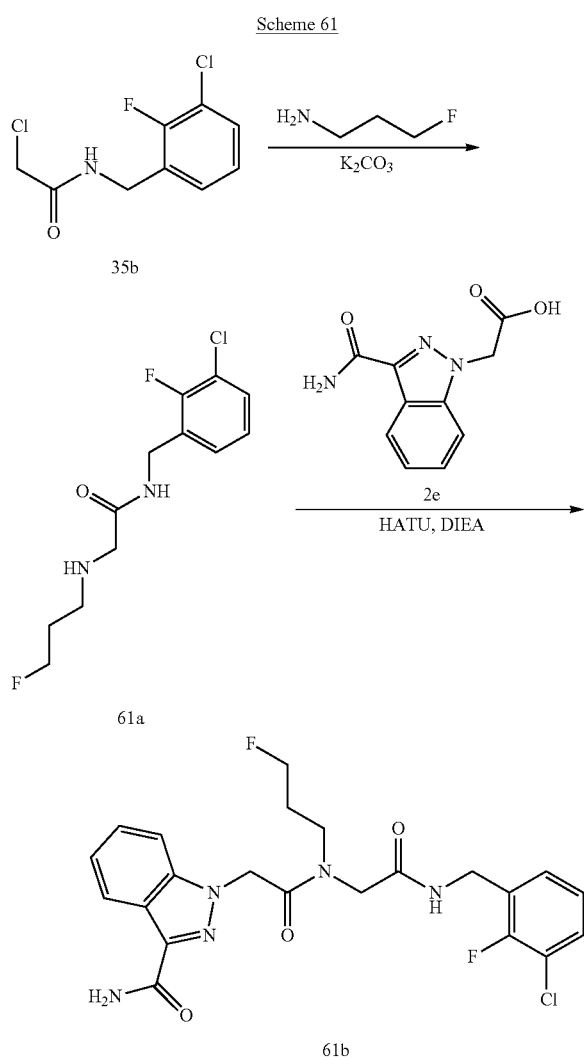

Preparation of 1-(2-((2-((3-chloro-2-fluorobenzyl)amino)-2-oxoethyl)(3-fluoropropyl)amino)-2-oxoethyl)-1H-indazole-3-carboxamide (61b)

Step-1: Preparation of N-(3-chloro-2-fluorobenzyl)-2-((3-fluoropropyl)amino)acetamide (61a)

Reaction of 2-chloro-N-(3-chloro-2-fluorobenzyl)acetamide (35b) (494 mg, 2.09 mmol) with 3-fluoropropan-1-amine hydrochloride (250 mg, 2.201 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((3-fluoropropyl)amino)acetamide (61a) (287 mg, 1.04 mmol, 47%) as a clear oil; MS (ES+): 277.4, 279.3 (M+1, M+3); (ES-): 275.3

Step-2: Preparation of 1-(2-((2-((3-chloro-2-fluorobenzyl)amino)-2-oxoethyl)(3-fluoropropyl)amino)-2-oxoethyl)-1H-indazole-3-carboxamide (61b)

Reaction of N-(3-chloro-2-fluorobenzyl)-2-((3-fluoropropyl)amino)acetamide (61a) (144 mg, 0.52 mmol) with 2-(3-carbamoyl-1H-indazol-1-yl)acetic acid (2e) (125 mg, 0.57 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)(3-fluoropropyl)amino)-2-oxoethyl)-1H-indazole-3-carboxamide (61b) (145 mg, 0.30 mmol, 58% yield) as a white solid; $^1$H NMR (300 MHz, DMSO-d$_6$) δ 8.87 (t, J=5.7 Hz) and 8.52 (t, J=5.9 Hz) (2t, 1H), 8.18 (d, J=8.1 Hz, 1H), 7.78-7.66 (m, 1H), 7.61-7.07 (m, 7H), 5.58 and 5.45 (2s, 2H), 4.70 and 4.54 (2t, J=5.6 Hz, 1H), 4.51-4.30 (m, 3H), 4.27 and 3.97 (2s, 2H), 3.62 (t, J=7.1 Hz) and 3.39-3.33 (t & m, 2H), 2.17-1.96 and 1.90-1.68 (2m, 2H); $^{19}$F NMR (282 MHz, DMSO) δ −121.27, −121.62; MS (ES+) 478.5 (M+1); MS (ES−), 476.5 (M−1); [based on NMR, this compound is a mixture of two rotamers with 5:4 ratio].

Scheme 62

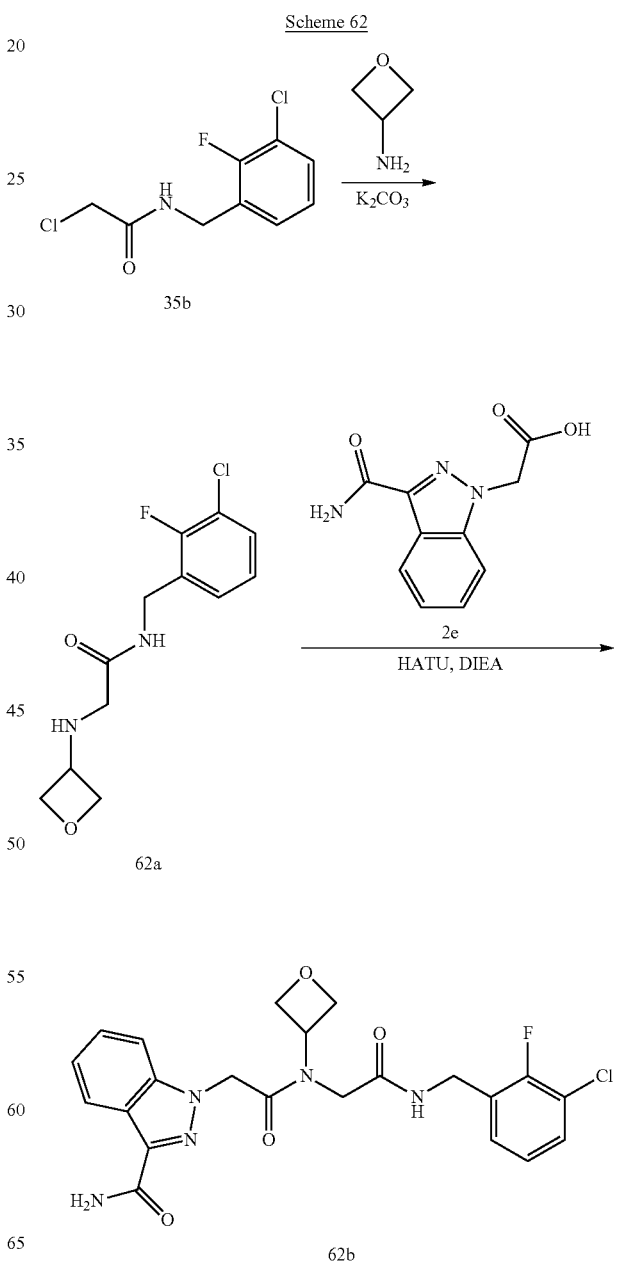

185

Preparation of 1-(2-((2-((3-chloro-2-fluorobenzyl)amino)-2-oxoethyl)(oxetan-3-yl)amino)-2-oxoethyl)-1H-indazole-3-carboxamide (62b)

Step-1: Preparation of N-(3-chloro-2-fluorobenzyl)-2-(oxetan-3-ylamino)acetamide (62a)

Reaction of 2-chloro-N-(3-chloro-2-fluorobenzyl)acetamide (35b) (500 mg, 2.12 mmol) with oxetan-3-amine (310 mg, 4.24 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(oxetan-3-ylamino)acetamide (62a) (365 mg, 1.34 mmol, 63% yield) as a yellow oil; MS (ES+) 273.3, 275.3 (M+1, M+3); (ES−): 271.3 (M−1)

Step-2: Preparation of 1-(2-((2-((3-chloro-2-fluorobenzyl)amino)-2-oxoethyl)(oxetan-3-yl)amino)-2-oxoethyl)-1H-indazole-3-carboxamide (62b)

Reaction of N-(3-chloro-2-fluorobenzyl)-2-(oxetan-3-ylamino)acetamide (62a) (200 mg, 0.73 mmol) with 2-(3-carbamoyl-1H-indazol-1-yl)acetic acid (2e) (177 mg, 0.81 mmol) according to the procedure reported in step-3 of Scheme 2 gave after workup and purification by flash column chromatography [silica (12 g), eluting with CMA80 in CHCl₃ 0 to 60%] 1-(2-((2-((3-chloro-2-fluorobenzyl)amino)-2-oxoethyl)(oxetan-3-yl)-amino)-2-oxoethyl)-1H-indazole-3-carboxamide (62b) (192 mg, 0.41 mmol, 55% yield) as a white solid; $^1$H NMR (300 MHz, DMSO-$d_6$) δ 8.94 (t, J=5.7 Hz) and 8.59 (t, J=5.8 Hz) (2t, 1H), 8.17 (d, J=8.2 Hz, 1H), 7.68 (d, J=14.5 Hz, 1H), 7.57-7.05 (m, 7H), 5.58 and 5.44 (2s, 2H), 5.12 (t, J=7.4 Hz, 1H), 4.80 (t, J=7.2 Hz) and 4.69 (t, J=6.7 Hz (2t, 2H), 4.58 (t, J=7.2 Hz, 1H), 4.54-4.45 (m, 2H), 4.43 and 4.24 (2s, 2H), 4.34 (d, J=5.6 Hz, 1H); $^{19}$F NMR (282 MHz, DMSO) δ −121.26, −121.67; MS (ES+): 474.5 (M+1); MS (ES−): 472.4 (M−1); [based on NMR, this compound is a mixture of two rotamers with 5:4 ratio].

Scheme 63

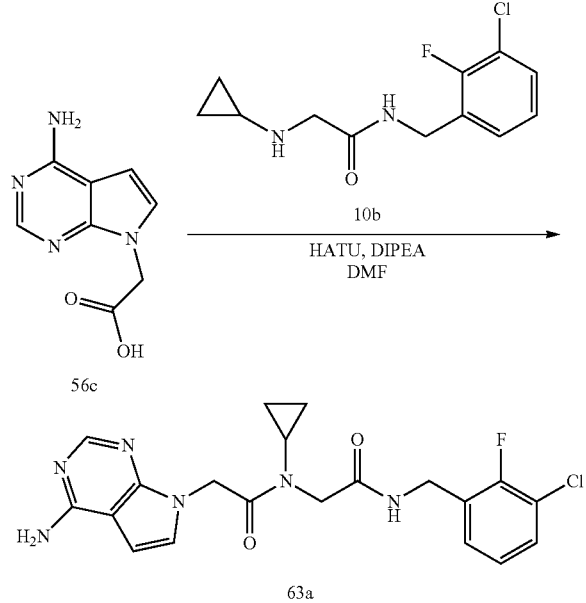

186

Preparation of 2-(4-amino-7H-pyrrolo[2,3-d]pyrimidin-7-yl)-N-(2-((3-chloro-2-fluorobenzyl)amino)-2-oxoethyl)-N-cyclopropylacetamide (63a)

Reaction of N-(3-chloro-2-fluorobenzyl)-2-(cyclopropylamino)acetamide (10b) (85 mg, 0.33 mmol) with 2-(4-amino-7H-pyrrolo[2,3-d]pyrimidin-7-yl)acetic acid (56c) (64 mg, 0.33 mmol) according to the procedure reported in step-3 of Scheme 2 gave after workup and purification by chromatography [silica (12 g), eluting with CMA80 in CHCl₃ 0 to 40%] 2-(4-amino-7H-pyrrolo[2,3-d]pyrimidin-7-yl)-N-(2-((3-chloro-2-fluorobenzyl)amino)-2-oxoethyl)-N-cyclopropylacetamide (63a) (42 mg, 0.097 mmol, 29% yield) as a white solid; $^1$H NMR (300 MHz, DMSO-$d_6$) δ 8.44 (t, J=5.9 Hz, 1H), 8.01 (s, 1H), 7.47 (td, J=7.6, 1.8 Hz, 1H), 7.28-7.19 (m, 1H), 7.15 (td, J=7.8, 1.0 Hz, 1H), 7.06 (d, J=3.5 Hz, 1H), 6.96 (s, 2H), 6.52 (d, J=3.5 Hz, 1H), 5.25 (s, 2H), 4.33 (d, J=5.7 Hz, 2H), 3.96 (s, 2H), 3.07-2.94 (m, 1H), 1.01-0.82 (m, 4H); $^{19}$F NMR (282 MHz, DMSO-$d_6$) δ −121.62; MS (ES+): 431.5 & 433.4 (M+1), MS (ES−): 429.5 (M−1).

Scheme 64

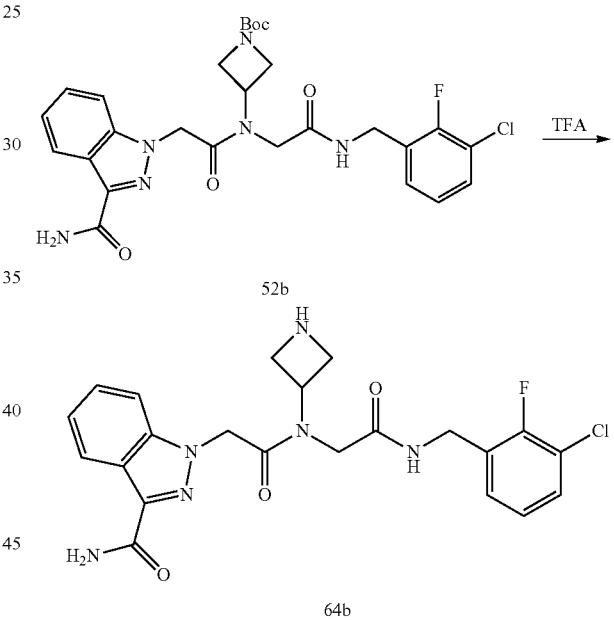

Preparation of 1-(2-(azetidin-3-yl(2-((3-chloro-2-fluorobenzyl)amino)-2-oxoethyl)amino)-2-oxoethyl)-1H-indazole-3-carboxamide (64b)

Reaction of tert-butyl 3-(2-(3-carbamoyl-1H-indazol-1-yl)-N-(2-((3-chloro-2-fluorobenzyl)amino)-2-oxoethyl)acetamido)azetidine-1-carboxylate (52b) (236 mg, 0.41 mmol) with TFA (0.19 mL, 2.47 mmol) according to the procedure reported in step-2 of Scheme 2 gave after workup and purification by chromatography [silica (12 g), eluting with CMA80 in CHCl₃ 0 to 60%] 1-(2-(azetidin-3-yl(2-((3-chloro-2-fluorobenzyl)amino)-2-oxoethyl)amino)-2-oxoethyl)-1H-indazole-3-carboxamide (64b) (112 mg, 0.24 mmol, 58% yield) as a white solid; $^1$H NMR (300 MHz, DMSO-$d_6$) δ 8.94 (t, J=5.7 Hz) and 8.51 (t, J=6.0 Hz) (2t, 1H), 8.17 (d, J=8.2 Hz, 1H), 7.68 (bs, 1H), 7.52-7.22 (m, 7H), 5.55 and 5.41 (2s, 2H), 4.91 (m, 1H), 4.47 (d, J=5.3 Hz)

and 4.33 (d, J=5.5 Hz) (2d, 2H), 4.42 and 4.18 (2s, 2H), 3.62 (d, J=7.2 Hz, 2H), 3.41 (d, J=7.6 Hz, 2H), 3.35 (s, 1H); $^{19}$F NMR (282 MHz, DMSO) δ −121.28, −121.64; MS (ES+) 473.5 (M+1); MS (ES−), 471.4 (M−1); [based on NMR, this compound is a mixture of two rotamers 1:1 ratio].

Scheme 65

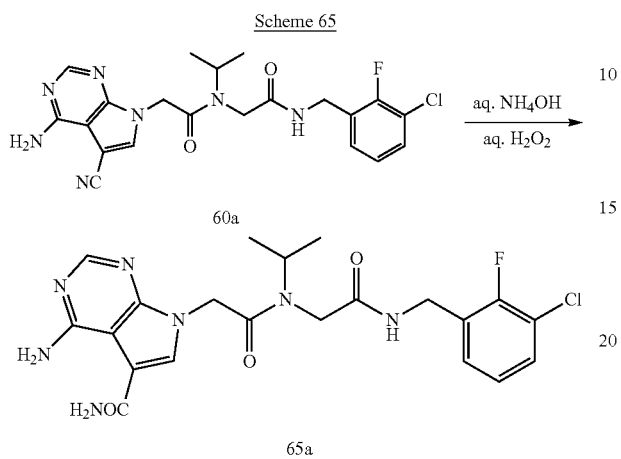

Preparation of 4-amino-7-(2-((2-((3-chloro-2-fluorobenzyl)amino)-2-oxoethyl)(isopropyl)amino)-2-oxoethyl)-7H-pyrrolo[2,3-d]pyrimidine-5-carboxamide (65a)

To a solution of 2-(4-amino-5-cyano-7H-pyrrolo[2,3-d]pyrimidin-7-yl)-N-(2-((3-chloro-2-fluorobenzyl)amino)-2-oxoethyl)-N-isopropylacetamide (60a) (32 mg, 0.07 mmol) in ethanol (5 mL) was added aq. ammonium hydroxide (0.54 mL, 13.98 mmol) followed by aq. hydrogen peroxide (35%, 0.122 mL, 1.398 mmol) and stirred at room temperature for 16 h. Excess solvent was removed under reduced pressure and the residue obtained was purified by flash column chromatography [Silica gel (12 g), eluting with MeOH in CHCl$_3$ 0-50%) to afford 4-amino-7-(2-((2-((3-chloro-2-fluorobenzyl)amino)-2-oxoethyl)(isopropyl)amino)-2-oxoethyl)-7H-pyrrolo[2,3-d]pyrimidine-5-carboxamide (65a) (14 mg, 0.029 mmol, 42% yield) as a white solid; $^{1}$H NMR (300 MHz, DMSO-d$_6$) δ 8.79 (t, J=5.7 Hz) and 8.35 (t, J=5.9 Hz) (2t, 1H), 8.04 and 8.04 (2s, 1H), 7.90 and 7.88 (2s, 1H), 7.58-7.35 (m, 2H), 7.34-7.07 (m, 3H), 5.21 and 5.08 (2s, 2H), 4.63-4.51 and 4.28-4.23 (2m, 1H), 4.43 (d, J=5.6 Hz) and 4.31 (d, J=5.8 Hz) (2d, 2H), 4.17 and 3.84 (2s, 2H), 1.20 (d, J=6.4 Hz) and 0.97 (d, J=6.8 Hz) (2d, 6H); $^{19}$F NMR (282 MHz, DMSO-d$_6$) δ −121.32, −121.70. [based on NMR the compound is a mixture of two rotamers 1:1 ratio]; MS (ES+): 476.5 (M+1), 498.5 (M+Na); (ES−): 474.5 (M−1), 510.3 (M+Cl).

Scheme 66

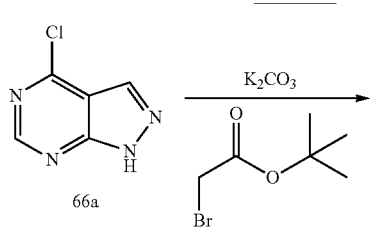

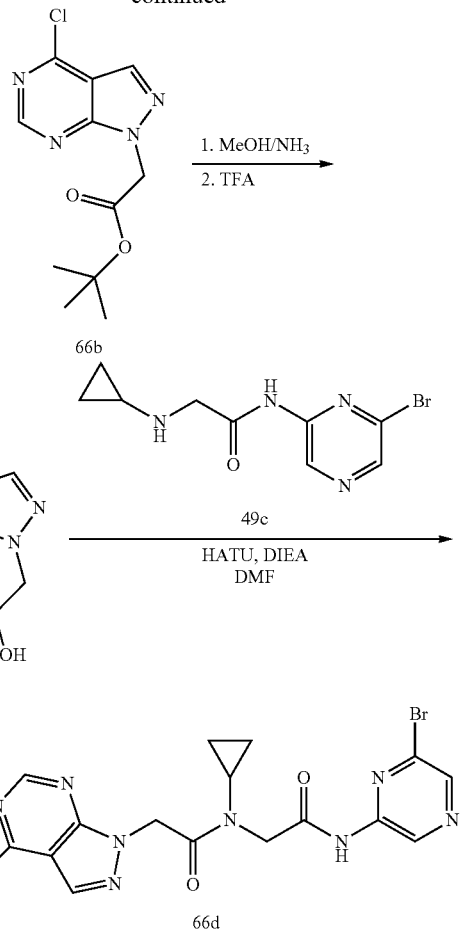

Preparation of 2-(4-amino-1H-pyrazolo[3,4-d]pyrimidin-1-yl)-N-(2-((6-bromopyrazin-2-yl)amino)-2-oxoethyl)-N-cyclopropylacetamide (66d)

Step-1: Preparation of tert-butyl 2-(4-chloro-1H-pyrazolo[3,4-d]pyrimidin-1-yl)acetate (66b)

Reaction of 4-chloro-1H-pyrazolo[3,4-d]pyrimidine (66a) (6.82 g, 44.16 mmol) with tert-butyl 2-bromoacetate (7.82 mL, 52.96 mmol) using potassium carbonate (9.14 g, 66.13 mmol) as base according to the procedure reported step-2 of Scheme 35 gave after workup and purification by flash column chromatography [silica gel (40 g), eluting with EtOAc in hexanes 0 to 60%] tert-butyl 2-(4-chloro-1H-pyrazolo[3,4-d]pyrimidin-1-yl)acetate (66b) (4.5 g, 16.75 mmol, 38% yield) as white solid.

Step-2: Preparation of 2-(4-amino-1H-pyrazolo[3,4-d]pyrimidin-1-yl)acetic acid (66c)

A solution of tert-butyl 2-(4-chloro-1H-pyrazolo[3,4-d]pyrimidin-1-yl)acetate (66b) (300 mg, 1.12 mmol) in methanolic ammonia (3.72 mL, 11.16 mmol) was stirred at room temperature for 2d, concentrated in vacuum and the residue was purified by chromatography [silica gel (12 g), eluting with EtOAc/MeOH (9:1) in hexanes 0 to 100%] afforded intermediate product. This material was dissolved in DCM (5 mL), added TFA (0.86 mL, 11.16 mmol) and stirred at room temperature for 4d. The solvent was removed under vacuum and resultant residue was suspended in toluene (10 mL) and evaporated. The solid was dried under vacuum to afford 2-(4-amino-1H-pyrazolo[3,4-d]pyrimidin-1-yl)acetic acid (66c) (0.14 g, 0.73 mmol, 65% yield) as an off-white solid; $^1$H NMR (300 MHz, DMSO-d$_6$) δ 9.24 (s, 1H), 8.64 (s, 1H), 8.39 (s, 1H), 8.32 (s, 1H), 5.16 (s, 2H); MS (ES+) 194.2 (M+1).

Step-3: Preparation of 2-(4-amino-1H-pyrazolo[3,4-d]pyrimidin-1-yl)-N-(2-((6-bromopyrazin-2-yl)amino)-2-oxoethyl)-N-cyclopropylacetamide (66d)

Reaction of N-(6-bromopyrazin-2-yl)-2-(cyclopropylamino)acetamide (49c) (70 mg, 0.26 mmol) with 2-(4-amino-1H-pyrazolo[3,4-d]pyrimidin-1-yl)acetic acid (66c) (50 mg, 0.26 mmol) according to the procedure reported in step-3 of Scheme 2 gave after workup and purification by chromatography [silica (12 g), eluting with CMA80 in CHCl$_3$ 0 to 40%] 2-(4-amino-1H-pyrazolo[3,4-d]pyrimidin-1-yl)-N-(2-((6-bromopyrazin-2-yl)amino)-2-oxoethyl)-N-cyclopropylacetamide (66d) (62 mg, 0.14 mmol, 54% yield) as a white solid; $^1$H NMR (300 MHz, DMSO-d$_6$) δ 11.27 (s, 1H), 9.25 (s, 1H), 8.54 (s, 1H), 8.15 (s, 1H), 8.08 (s, 1H), 7.87-7.54 (m, 2H), 5.45 (s, 2H), 4.19 (s, 2H), 3.14-3.02 (m, 1H), 1.02-0.88 (m, 4H); MS (ES+): 446.4 & 448.4 (M+1), 468.4 & 470.4 (M+Na).

Scheme 67

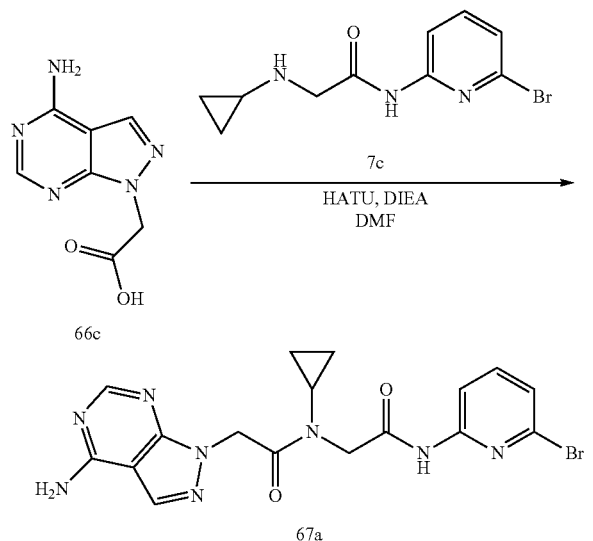

Preparation of 2-(4-amino-1H-pyrazolo[3,4-d]pyrimidin-1-yl)-N-(2-((6-bromopyridin-2-yl)amino)-2-oxoethyl)-N-cyclopropylacetamide (67a)

Reaction of N-(6-bromopyrazin-2-yl)-2-(cyclopropylamino)acetamide (7c) (70 mg, 0.26 mmol) with 2-(4-amino-1H-pyrazolo[3,4-d]pyrimidin-1-yl)acetic acid (66c) (50 mg, 0.26 mmol) according to the procedure reported in step-3 of Scheme 2 gave after workup and purification by chromatography [silica (12 g), eluting with CMA80 in CHCl$_3$ 0 to 40%] 2-(4-amino-1H-pyrazolo[3,4-d]pyrimidin-1-yl)-N-(2-((6-bromopyridin-2-yl)amino)-2-oxoethyl)-N-cyclopropylacetamide (67a) (68 mg, 0.153 mmol, 59% yield) as a white solid; $^1$H NMR (300 MHz, DMSO-d$_6$) δ 10.93 (s, 1H), 8.15 (s, 1H), 8.08 (s, 1H), 8.02 (d, J=8.1 Hz, 1H), 7.86-7.53 (m, 3H), 7.33 (dd, J=7.7, 0.7 Hz, 1H), 5.43 (s, 2H), 4.15 (s, 2H), 3.12-3.00 (m, 1H), 1.01-0.86 (m, 4H); MS (ES+); 445.4 & 447.4 (M+1), 467.4 & 469.5 (M+Na), MS (ES-): 443.4 & 445.4 (M-1).

Scheme 68

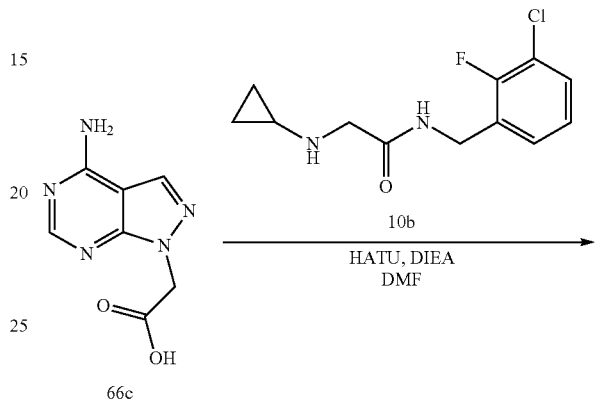

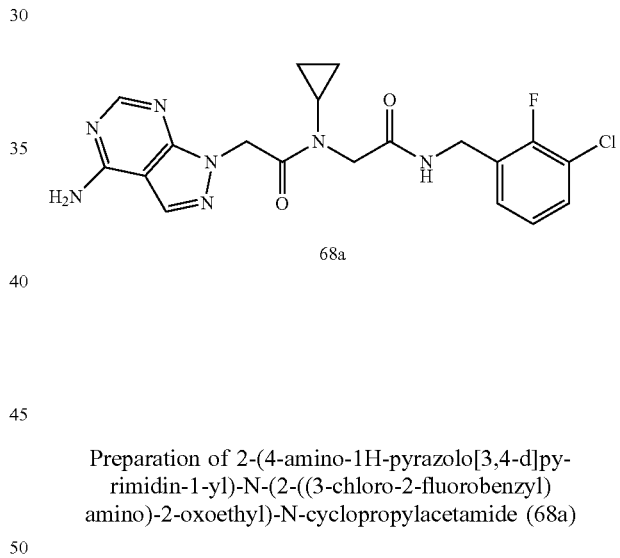

Preparation of 2-(4-amino-1H-pyrazolo[3,4-d]pyrimidin-1-yl)-N-(2-((3-chloro-2-fluorobenzyl)amino)-2-oxoethyl)-N-cyclopropylacetamide (68a)

Reaction of N-(3-chloro-2-fluorobenzyl)-2-(cyclopropylamino)acetamide (10b) (70 mg, 0.27 mmol) with 2-(4-amino-1H-pyrazolo[3,4-d]pyrimidin-1-yl)acetic acid (66c) (53 mg, 0.27 mmol) according to the procedure reported in step-3 of Scheme 2 gave after workup and purification by chromatography [silica (12 g), eluting with CMA80 in CHCl$_3$ 0 to 40%] 2-(4-amino-1H-pyrazolo[3,4-d]pyrimidin-1-yl)-N-(2-((3-chloro-2-fluorobenzyl)amino)-2-oxoethyl)-N-cyclopropylacetamide (68a) (85 mg, 0.2 mmol, 72% yield) as a white solid; $^1$H NMR (300 MHz, DMSO-d$_6$) δ 8.45 (t, J=5.8 Hz, 1H), 8.14 (s, 1H), 8.08 (s, 1H), 7.88-7.52 (m, 2H), 7.47 (td, J=7.6, 1.8 Hz, 1H), 7.27-7.19 (m, 1H), 7.19-7.10 (m, 1H), 5.42 (s, 2H), 4.32 (d, J=5.7 Hz, 2H), 3.95 (s, 2H), 3.09-2.95 (m, 1H), 0.99-0.82 (m, 4H); $^{19}$F NMR (282 MHz, DMSO-d$_6$) δ −121.62; MS (ES+): 432.5 & 433.5 (M+1), 454.4 (M+23), MS (ES-): 430.4 & 432.4 (M-1).

191

Scheme 69

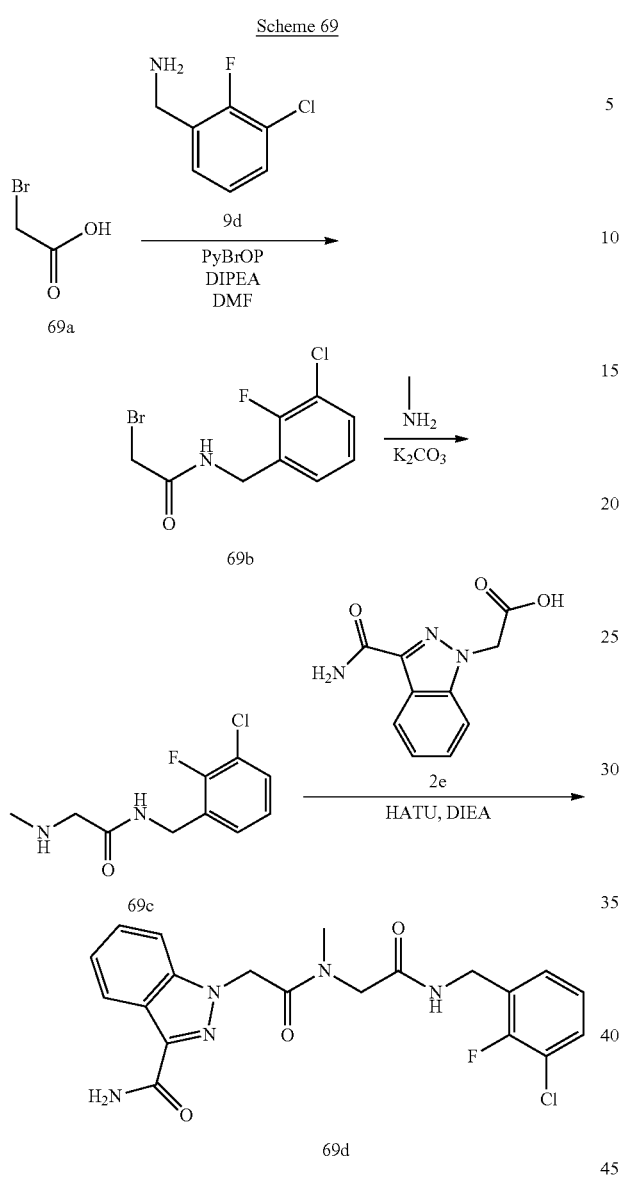

Preparation of 1-(2-((2-((3-chloro-2-fluorobenzyl)
amino)-2-oxoethyl)(methyl)amino)-2-oxoethyl)-1H-
indazole-3-carboxamide (69d)

Step-1: Preparation of 2-bromo-N-(3-chloro-2-fluo-
robenzyl)acetamide (69b)

Reaction of 2-bromoacetic acid (69a) (2.09 g, 15.04 mmol) with 3-chloro-2-fluorobenzylamine (9d) (2.0 g, 12.53 mmol) according to the procedure reported in Scheme 32 gave after workup and purification by flash column chromatography [silica gel (40 g), eluting with EtOAc in hexanes 0-100%] 2-bromo-N-(3-chloro-2-fluorobenzyl)acetamide (69b) (2.58 g, 9.21 mmol, 74% yield) as a yellow solid; $^1$H NMR (300 MHz, DMSO-$d_6$) δ 8.86 (t, J=5.9 Hz, 1H, D$_2$O exchangeable), 7.51 (ddd, J=7.9, 7.2, 1.8 Hz, 1H), 7.36-7.27 (m, 1H), 7.26-7.16 (m, 1H), 4.44-4.27 (m, 2H), 3.91 (s, 2H); $^{19}$F NMR (282 MHz, DMSO-$d_6$) δ -121.04; MS (ES+): 280.2, 282.2 (M+2); (ES-): 278.2, 280.2 (M-2).

192

Step-2: Preparation of N-(3-chloro-2-fluorobenzyl)-
2-(methylamino)acetamide (69c)

Reaction of 2-bromo-N-(3-chloro-2-fluorobenzyl)acetamide (69b) (300 mg, 1.07 mmol) with methylamine (2M in MeOH) (0.962 mL, 1.925 mmol) in ethanol (20 mL) according to the procedure reported in step-2 of Scheme 35 gave after workup N-(3-chloro-2-fluorobenzyl)-2-(methylamino) acetamide (69c) (217 mg, 0.94 mmol, 88% yield) as a yellow oil which was used as such in the next step; MS (ES-): 229.2 (M-1).

Step-3: Preparation of 1-(2-((2-((3-chloro-2-fluo-
robenzyl)amino)-2-oxoethyl)(methyl)amino)-2-oxo-
ethyl)-1H-indazole-3-carboxamide (69d)

Reaction of N-(3-chloro-2-fluorobenzyl)-2-(methylamino)acetamide (69c) (217 mg, 0.94 mmol) with 2-(3-carbamoyl-1H-indazol-1-yl)acetic acid (2e) (572 mg, 2.61 mmol) according to the procedure reported in step-3 of Scheme 2 gave after workup and purification by flash column chromatography [Silica gel (24 g), eluting with MeOH in CHCl$_3$ 0-50%) 1-(2-((2-((3-chloro-2-fluorobenzyl)amino)-2-oxo ethyl)(methyl)amino)-2-oxoethyl)-1H-indazole-3-carboxamide (69d) (139 mg, 34% yield) as a pale yellow solid; $^1$H NMR (300 MHz, DMSO-$d_6$) δ 8.93-8.78 & 8.59-8.45 (2m, 1H), 8.18 (d, J=8.1 Hz, 1H), 7.79-7.58 (m, 2H), 7.58-7.33 (m, 3H), 7.34-7.05 (m, 3H), 5.57 & 5.44 (2s, 2H), 4.46 (d, J=5.1 Hz) & 4.35 (d, J=5.6 Hz) (2d, 2H), 4.25 & 4.00 (2s, 2H), 3.19 & 2.81 (s, 3H) $^{19}$F NMR (282 MHz, DMSO-$d_6$) δ -121.40, -121.64 [based on NMR the compound is a mixture of two rotamers ~2:3 ratio]; MS (ES+): 432.5 (M+1).

Scheme 70

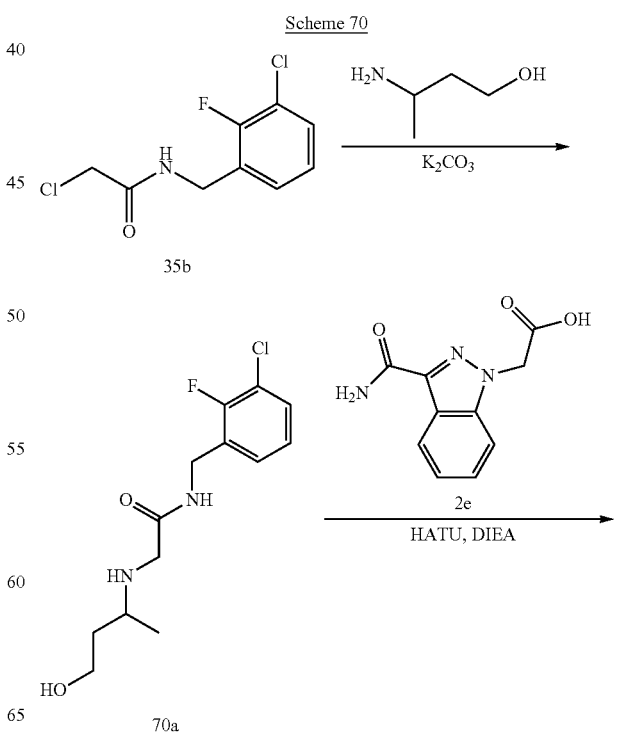

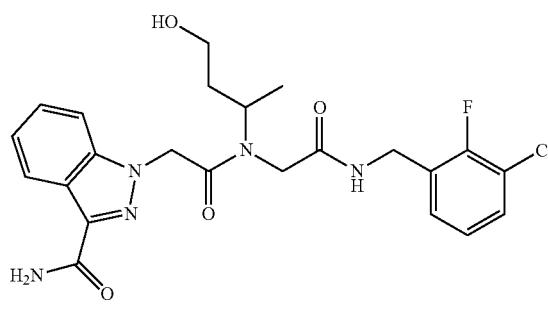

70b

Preparation of 1-(2-((2-((3-chloro-2-fluorobenzyl)amino)-2-oxoethyl)(4-hydroxybutan-2-yl)amino)-2-oxoethyl)-1H-indazole-3-carboxamide (70b)

Step-1: Preparation of N-(3-chloro-2-fluorobenzyl)-2-((4-hydroxybutan-2-yl)amino)acetamide (70a)

Reaction of 2-chloro-N-(3-chloro-2-fluorobenzyl)acetamide (35b) (494 mg, 2.09 mmol) with 3-aminobutan-1-ol (378 mg, 4.24 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((4-hydroxybutan-2-yl)amino)acetamide (70a) (200 mg, 0.69 mmol, 33%) as a clear oil; MS (ES+) 289.4 (M+1); (ES−) 287.3 (M−1).

Step-2: Preparation of 1-(2-((2-((3-chloro-2-fluorobenzyl)amino)-2-oxoethyl)(4-hydroxybutan-2-yl)amino)-2-oxoethyl)-1H-indazole-3-carboxamide (70b)

Reaction of N-(3-chloro-2-fluorobenzyl)-2-((4-hydroxybutan-2-yl)amino)acetamide (70a) (200 mg, 0.69 mmol) with 2-(3-carbamoyl-1H-indazol-1-yl)acetic acid (2e) (167 mg, 0.76 mmol) according to the procedure reported in step-3 of Scheme 2 gave after workup and purification by flash column chromatography [silica (12 g), eluting with CMA80 in CHCl$_3$ 0 to 60%] followed by prep-HPLC [C$_{18}$ column, MeOH in water 0-100%] 1-(2-((2-((3-chloro-2-fluorobenzyl)amino)-2-oxoethyl)(4-hydroxybutan-2-yl)amino)-2-oxoethyl)-1H-indazole-3-carboxamide (70b) (102 mg, 0.21 mmol, 30% yield) as a white solid; $^1$H NMR (300 MHz, DMSO-d$_6$) δ 8.83 (t, J=5.5 Hz) and 8.40 (t, J=5.8 Hz) (2t, 1H), 8.18 (d, J=7.9 Hz, 1H), 7.72 (d, J=6.5 Hz, 1H), 7.58-7.00 (m, 7H), 5.79-5.40 (m, 2H), 4.57-3.41 (m, 7H) 3.31 (t, J=6.5 Hz, 1H), 1.80-1.41 (m, 2H), 1.25 (d, J=6.5 Hz) & 0.98 (d, J=6.8 Hz) (2d, 3H); $^{19}$F NMR (282 MHz, DMSO) δ −74.30 (TFA peak), −121.26, −121.77; MS (ES$^+$) 490.5 (M+1); MS (ES$^−$), 488.4 (M−1); [based on NMR, this compound is a mixture of two rotamers 4:5 ratio].

Scheme 71

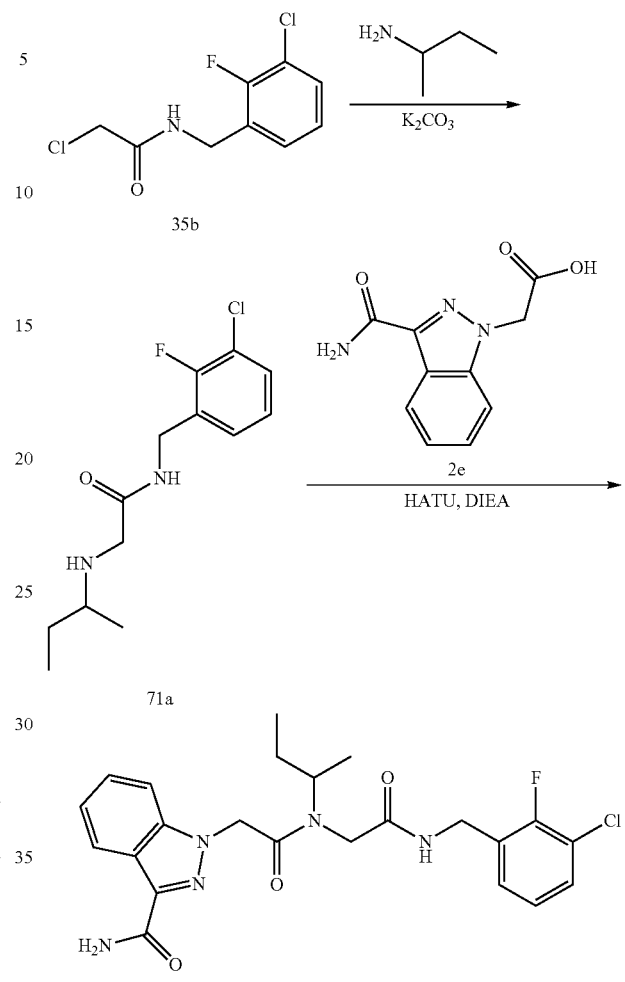

Preparation of 1-(2-(sec-butyl(2-((3-chloro-2-fluorobenzyl)amino)-2-oxoethyl)amino)-2-oxoethyl)-1H-indazole-3-carboxamide (71b)

Step-1: Preparation of 2-(sec-butylamino)-N-(3-chloro-2-fluorobenzyl)acetamide (71a)

Reaction of 2-chloro-N-(3-chloro-2-fluorobenzyl)acetamide (35b) (500 mg, 2.12 mmol) with butan-2-amine (775 mg, 10.59 mmol) according to the procedure reported in step-2 of Scheme 35 gave after workup and purification by flash column chromatography [silica (12 g), eluting with EtOAc/MeOH (9:1) in hexane 0 to 60%] 2-(sec-butylamino)-N-(3-chloro-2-fluorobenzyl)acetamide (71a) (170 mg, 0.62 mmol, 29%) as a yellow oil; MS (ES+): 273.4 (M+1); MS (ES−): 271.3 (M−1).

Step-2: Preparation of 1-(2-(sec-butyl(2-((3-chloro-2-fluorobenzyl)amino)-2-oxoethyl)amino)-2-oxoethyl)-1H-indazole-3-carboxamide (71b)

Reaction of 2-(sec-butylamino)-N-(3-chloro-2-fluorobenzyl)acetamide (71a) (170 mg, 0.62 mmol) with 2-(3-carbamoyl-1H-indazol-1-yl)acetic acid (2e) (150 mg, 0.69 mmol) according to the procedure reported in step-3 of Scheme 2 gave after workup and purification by flash column chromatography [silica (12 g), eluting with CMA80 in CHCl₃ 0 to 60%] 1-(2-(sec-butyl(2-((3-chloro-2-fluorobenzyl)amino)-2-oxoethyl)amino)-2-oxoethyl)-1H-indazole-3-carboxamide (71b) (178 mg, 0.38 mmol, 60% yield) as a white solid; $^1$H NMR (300 MHz, DMSO-d₆) δ 8.82 (t, J=5.7 Hz) and 8.36 (t, J=5.9 Hz) (2t, 1H), 8.18 (d, J=8.1 Hz, 1H), 7.77-7.67 (m, 1H), 7.60-7.02 (m, 7H), 5.66-5.39 (m, 2H), 4.57-3.71 (m, 5H), 1.69-1.28 (m, 2H), 1.26-0.61 (m, 6H); $^{19}$F NMR (282 MHz, DMSO-d₆) δ −121.19, −121.76; MS (ES+) 474.5 (M+1); MS (ES−), 472.5 (M−1); [based on NMR, this compound is a mixture of two rotamers 2:1 ratio].

reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((2-hydroxycyclopentyl) amino)acetamide (72a) (158 mg, 0.53 mmol, 36%) as a yellow oil; MS (ES+): 301.3; (ES−): 299.3 (M−1).

Step-2: Preparation of 1-(2-((2-((3-chloro-2-fluorobenzyl)amino)-2-oxoethyl)(2-hydroxycyclopentyl)amino)-2-oxoethyl)-1H-indazole-3-carboxamide (72b)

Reaction of N-(3-chloro-2-fluorobenzyl)-2-((2-hydroxycyclopentyl)amino)acetamide (72a) (158 mg, 0.53 mmol) with 2-(3-carbamoyl-1H-indazol-1-yl)acetic acid (2e) (127 mg, 0.58 mmol) according to the procedure reported in step-3 of Scheme 2 gave after workup and purification by flash column chromatography [silica (12 g), eluting with CMA80 in CHCl₃ 0 to 60%] 1-(2-((2-((3-chloro-2-fluorobenzyl)amino)-2-oxoethyl)(2-hydroxycyclopentyl) amino)-2-oxoethyl)-1H-indazole-3-carboxamide (72b) (128 mg, 0.26 mmol, 49% yield) as an off white solid; $^1$H NMR (300 MHz, DMSO-d₆) δ 8.87 (t, J=5.7 Hz) and 8.47 (t, J=5.9 Hz) (2t, 1H), 8.18 (d, J=8.1 Hz, 1H), 7.77-7.64 (m, 1H), 7.60-6.99 (m, 7H), 5.69 and 5.43 (2s, 1H), 5.36 (d, J=4.7 Hz) and 4.75 (d, J=4.8 Hz) (2d, 2H), 4.50-3.70 (m, 6H), 2.04-1.28 (m, 6H); $^{19}$F NMR (282 MHz, DMSO-d₆) δ −121.22, −121.68; MS (ES+) 502.6 (M+1); MS (ES−): 500.5 (M−1); [based on NMR, this compound is a mixture of two rotamers 1:3 ratio].

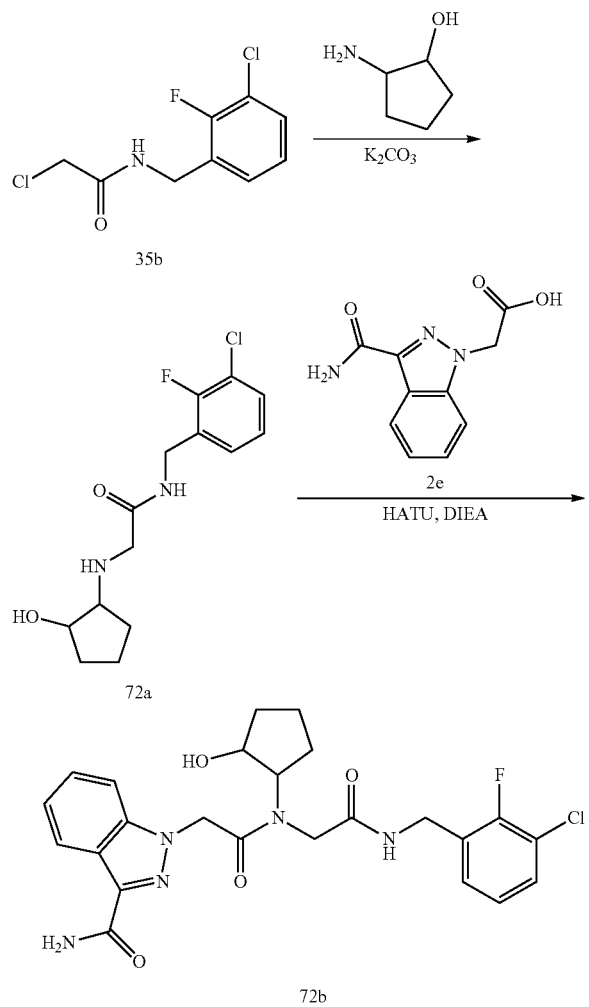

Scheme 72

72a

72b

Preparation of 1-(2-((2-((3-chloro-2-fluorobenzyl) amino)-2-oxoethyl)(2-hydroxycyclopentyl)amino)-2-oxoethyl)-1H-indazole-3-carboxamide (72b)

Step-1: Preparation of N-(3-chloro-2-fluorobenzyl)-2-((2-hydroxycyclopentyl)amino)acetamide (72a)

Reaction of 2-chloro-N-(3-chloro-2-fluorobenzyl)acetamide (35b) (350 mg, 1.48 mmol) with 2-aminocyclopentanol (375 mg, 3.71 mmol) according to the procedure

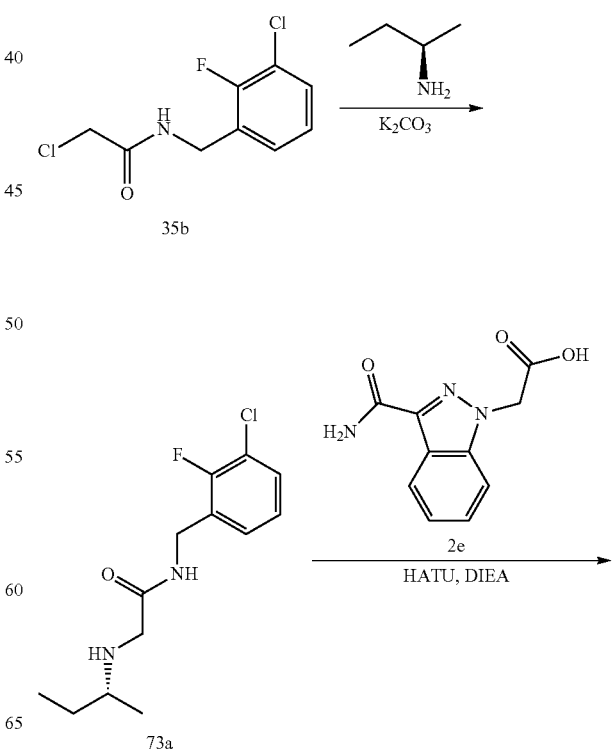

Scheme 73

35b

73a

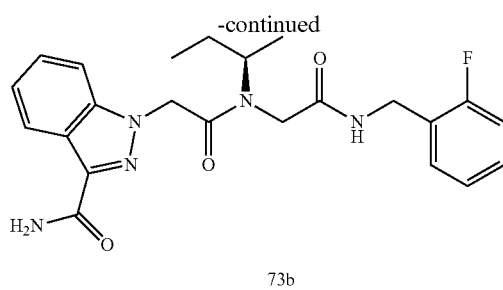

73b

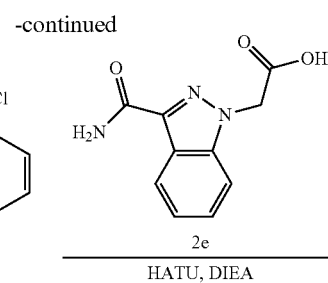

74a

Preparation of (R)-1-(2-(sec-butyl(2-((3-chloro-2-fluorobenzyl)amino)-2-oxoethyl)amino)-2-oxo-ethyl)-1H-indazole-3-carboxamide (73b)

Step-1: Preparation of (R)-2-(sec-butylamino)-N-(3-chloro-2-fluorobenzyl)acetamide (73a)

Reaction of 2-chloro-N-(3-chloro-2-fluorobenzyl)acetamide (35b) (200 mg, 0.85 mmol) with (R)-butan-2-amine (155 mg, 2.12 mmol) according to the procedure reported in step-2 of Scheme 35 gave after workup and purification by flash column chromatography [silica (12 g), eluting with EtOAc/MeOH (9:1) in hexane 0 to 60%] (R)-2-(sec-butylamino)-N-(3-chloro-2-fluorobenzyl)acetamide (73a) (100 mg, 0.37 mmol, 43%) as a yellow oil; MS (ES+): 273.3 (M+1); MS (ES−): 271.3 (M−1).

Step-2: Preparation of (R)-1-(2-(sec-butyl(2-((3-chloro-2-fluorobenzyl)amino)-2-oxoethyl)amino)-2-oxoethyl)-1H-indazole-3-carboxamide (73b)

Reaction of (R)-2-(sec-butylamino)-N-(3-chloro-2-fluorobenzyl)acetamide (73a) (100 mg, 0.37 mmol) with 2-(3-carbamoyl-1H-indazol-1-yl)acetic acid (2e) (88 mg, 0.4 mmol) according to the procedure reported in step-3 of Scheme 2 gave after workup and purification by flash column chromatography [silica (12 g), eluting with CMA80 in CHCl₃ 0 to 60%] (R)-1-(2-(sec-butyl(2-((3-chloro-2-fluorobenzyl)amino)-2-oxo ethyl)amino)-2-oxo ethyl)-1H-indazole-3-carboxamide (73b) (101 mg, 0.21 mmol, 58% yield) as a white solid; $^1$H NMR (300 MHz, DMSO-d₆) δ 8.82 (t, J=5.5 Hz) and 8.36 (t, J=5.7 Hz) (2t, 1H), 8.19 (d, J=8.1 Hz, 1H), 7.82-7.65 (m, 1H), 7.59-7.01 (m, 7H), 5.68-5.39 (m, 2H), 4.55-3.71 (m, 5H), 1.67-1.28 (m, 2H), 1.26-0.65 (m, 6H); $^{19}$F NMR (282 MHz, DMSO-d₆) δ −121.19, −121.76; MS (ES+) 474.6 (M+1); 496.5 (M+Na); MS (ES−), 472.5 (M−1); [based on NMR, this compound is a mixture of rotamers 1:3 ratio].

Scheme 74

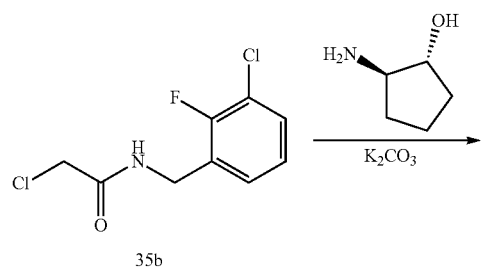

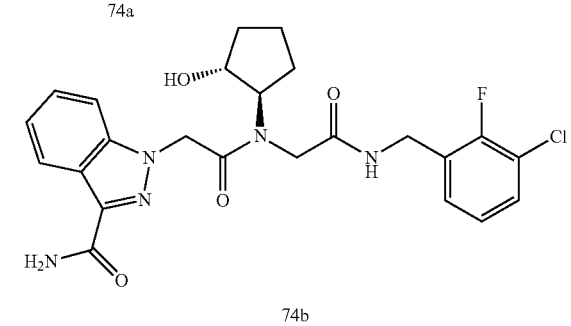

74b

Preparation of 1-(2-((2-((3-chloro-2-fluorobenzyl)amino)-2-oxoethyl)((1R,2R)-2-hydroxycyclopentyl)amino)-2-oxoethyl)-1H-indazole-3-carboxamide (74b)

Step-1: Preparation of N-(3-chloro-2-fluorobenzyl)-2-(((1R,2R)-2-hydroxycyclopentyl)amino)acetamide (74a)

Reaction of 2-chloro-N-(3-chloro-2-fluorobenzyl)acetamide (35b) (350 mg, 1.48 mmol) with (1R,2R)-2-aminocyclopentanol (510 mg, 3.71 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(((1R,2R)-2-hydroxycyclopentyl)amino)acetamide (74a) (312 mg, 1.04 mmol, 70%) as a yellow oil; MS (ES+): 301.3 (M+1); MS (ES−): 299.3 (M−1).

Step-2: Preparation of 1-(2-((2-((3-chloro-2-fluorobenzyl)amino)-2-oxoethyl)((1R,2R)-2-hydroxycyclopentyl)amino)-2-oxoethyl)-1H-indazole-3-carboxamide (74b)

Reaction of N-(3-chloro-2-fluorobenzyl)-2-(((1R,2R)-2-hydroxycyclopentyl)amino)acetamide (74a) (135 mg, 0.55 mmol) with 2-(3-carbamoyl-1H-indazol-1-yl)acetic acid (2e) (132 mg, 0.6 mmol) according to the procedure reported in step-3 of Scheme 2 gave after workup and purification by flash column chromatography [silica (12 g), eluting with CMA80 in CHCl₃ 0 to 60%] 1-(2-((2-((3-chloro-2-fluorobenzyl)amino)-2-oxoethyl)((1R,2R)-2-hydroxycyclopentyl)amino)-2-oxoethyl)-1H-indazole-3-carboxamide (74b) (95 mg, 0.189 mmol, 34.5% yield) as a white solid; $^1$H NMR (300 MHz, DMSO-d$_6$) δ 8.87 (t, J=5.8 Hz) and 8.47 (t, J=5.9 Hz) (2t, 1H), 8.18 (d, J=8.1 Hz, 1H), 7.71 (d, J=6.5 Hz, 1H), 7.58-7.00 (m, 7H), 5.69 and 5.43 (2s, 2H), 5.37 (d, J=4.7 Hz) and 4.76 (d, J=4.8 Hz) (2d, 1H), 4.52-3.71 (m, 6H), 2.03-1.37 (m, 6H); $^{19}$F NMR (282 MHz, DMSO-d$_6$) δ −121.22, −121.68; MS (ES+) 502.6 (M+1); 524.5 (M+Na); [based on NMR, this compound is a mixture of two rotamers 2:7 ratio].

cyclopentanol (510 mg, 3.71 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(((1S,2S)-2-hydroxycyclopentyl)amino)acetamide (75a) (285 mg, 0.95 mmol, 64%) as a yellow oil; MS (ES+): 301.4 (M+1); MS (ES−): 299.4 (M−1).

Step-2: Preparation of 1-(2-((2-((3-chloro-2-fluorobenzyl)amino)-2-oxoethyl)((1S,2S)-2-hydroxycyclopentyl)amino)-2-oxoethyl)-1H-indazole-3-carboxamide (75b)

Reaction of N-(3-chloro-2-fluorobenzyl)-2-(((1S,2S)-2-hydroxycyclopentyl)amino)acetamide (75a) (165 mg, 0.55 mmol) with 2-(3-carbamoyl-1H-indazol-1-yl)acetic acid (2e) (132 mg, 0.6 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)((1S,2S)-2-hydroxycyclopentyl)amino)-2-oxoethyl)-1H-indazole-3-carboxamide (75b) (185 mg, 0.369 mmol, 67.2% yield) as a white solid; $^1$H NMR (300 MHz, DMSO-d$_6$) δ 8.88 (t, J=5.6 Hz) and 8.48 (t, J=5.7 Hz) (2s, 1H), 8.18 (d, J=8.1 Hz, 1H), 7.78-7.63 (m, 1H), 7.57-6.99 (m, 7H), 5.69 and 5.44 (2s, 2H), 5.37 (d, J=4.6 Hz) and 4.76 (d, J=4.7 Hz) (2d, 1H), 4.51-3.72 (m, 6H), 2.03-1.45 (m, 6H); $^{19}$F NMR (282 MHz, DMSO-d$_6$) δ −121.21, −121.67; MS (ES+): 524.5 (M+Na); (ES−): 500.5 (M−1); [based on NMR, this compound is a mixture of two rotamers 2:7 ratio].

Scheme 75

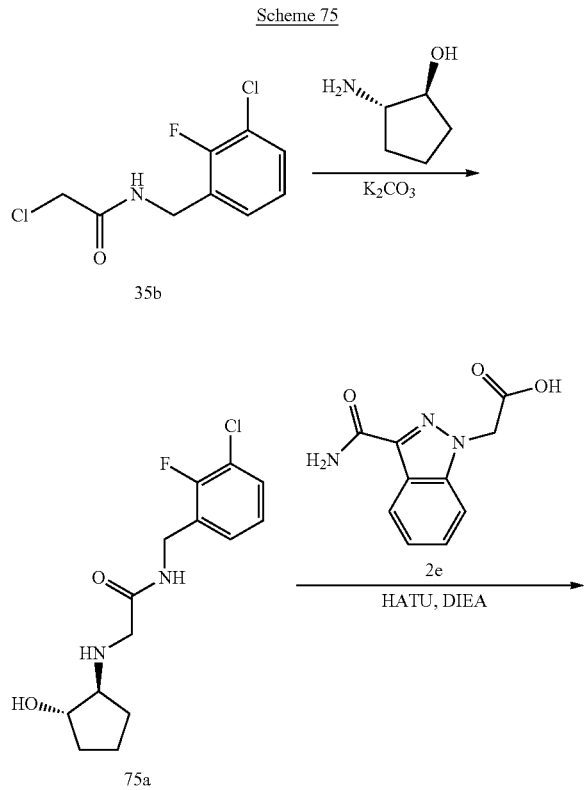

Preparation of 1-(2-((2-((3-chloro-2-fluorobenzyl)amino)-2-oxoethyl)((1S,2S)-2-hydroxycyclopentyl)amino)-2-oxoethyl)-1H-indazole-3-carboxamide (75b)

Step-1: Preparation of N-(3-chloro-2-fluorobenzyl)-2-(((1S,2S)-2-hydroxycyclopentyl)amino)acetamide (75a)

Reaction of 2-chloro-N-(3-chloro-2-fluorobenzyl)acetamide (35b) (350 mg, 1.48 mmol) with (1S,2S)-2-amino- Scheme 76

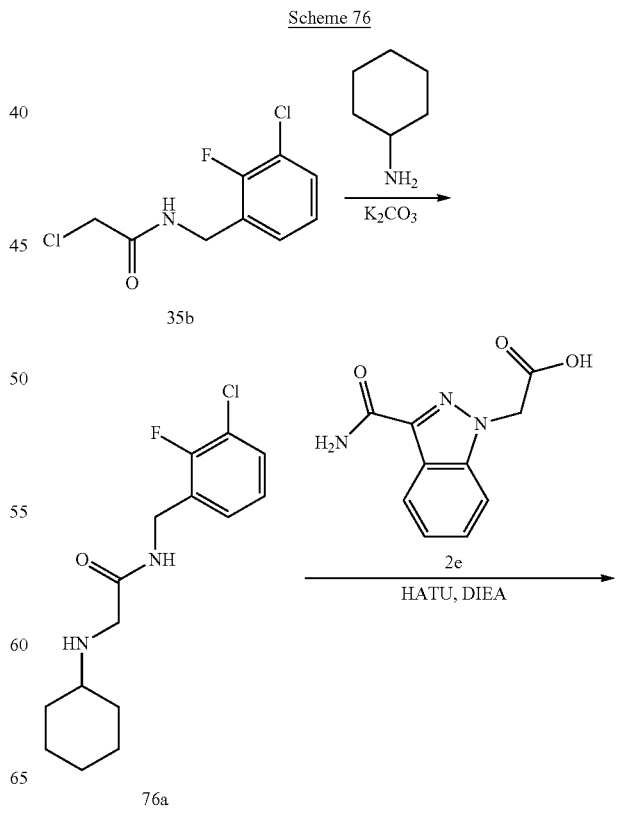

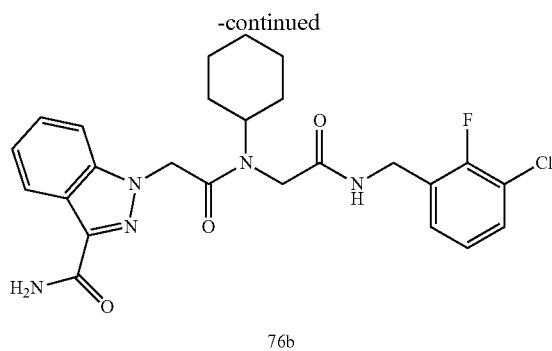

76b

Preparation of 1-(2-((2-((3-chloro-2-fluorobenzyl)amino)-2-oxoethyl)(cyclohexyl)amino)-2-oxoethyl)-1H-indazole-3-carboxamide (76b)

Step-1: Preparation of N-(3-chloro-2-fluorobenzyl)-2-(cyclohexylamino)acetamide (76a)

Reaction of 2-chloro-N-(3-chloro-2-fluorobenzyl)acetamide (35b) (400 mg, 1.69 mmol) with cyclohexanamine (840 mg, 8.87 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(cyclohexylamino)acetamide (76a) (331 mg, 1.11 mmol, 65%) as a yellow oil; MS (ES+): 299.4 (M+1); MS (ES−): 297.3 (M−1).

Step-2: Preparation of 1-(2-((2-((3-chloro-2-fluorobenzyl)amino)-2-oxoethyl)(cyclohexyl)amino)-2-oxoethyl)-1H-indazole-3-carboxamide (76b)

Reaction of N-(3-chloro-2-fluorobenzyl)-2-(cyclohexylamino)acetamide (76a) (145 mg, 0.49 mmol) with 2-(3-carbamoyl-1H-indazol-1-yl)acetic acid (2e) (117 mg, 0.53 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)(cyclohexyl)amino)-2-oxoethyl)-1H-indazole-3-carboxamide (76b) (176 mg, 0.352 mmol, 72.5% yield) as a white solid; $^1$H NMR (300 MHz, DMSO-d$_6$) δ 8.82 (t, J=5.7 Hz) and 8.33 (t, J=5.8 Hz) (2t, 1H), 8.18 (d, J=8.1 Hz, 1H), 7.76-7.65 (m, 1H), 7.64-7.02 (m, 7H), 5.60 and 5.47 (2s, 2H), 4.46 (d, J=5.5 Hz) and 4.32 (d, J=5.7 Hz) (2d, 2H), 4.24-3.70 (m, 3H), 1.90-0.93 (m, 10H); $^{19}$F NMR (282 MHz, DMSO-d$_6$) δ −121.11, −121.68; MS (ES+): 500.5 (M+1); MS (ES−): 498.5 (M−1); [based on NMR, this compound is a mixture of two rotamers with 1:1 ratio].

Scheme 77

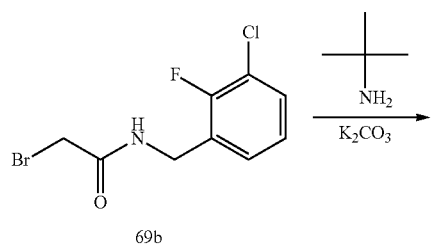

69b

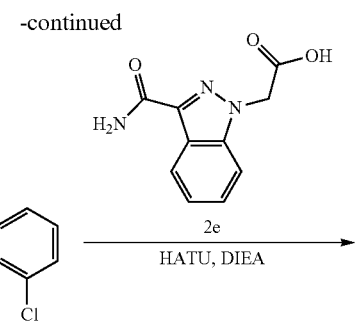

2e

HATU, DIEA

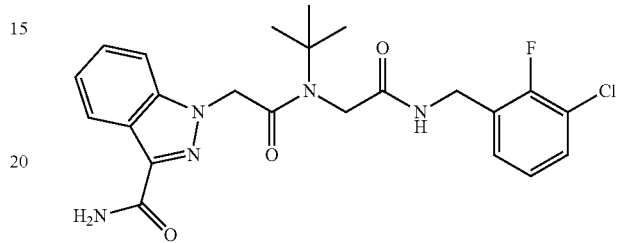

77b

Preparation of 1-(2-(tert-butyl(2-((3-chloro-2-fluorobenzyl)amino)-2-oxoethyl)amino)-2-oxoethyl)-1H-indazole-3-carboxamide (77b)

Step-1: Preparation of 2-(tert-butylamino)-N-(3-chloro-2-fluorobenzyl)acetamide (77a)

Reaction of 2-bromo-N-(3-chloro-2-fluorobenzyl)acetamide (69b) (300 mg, 1.07 mmol) with 2-methylpropan-2-amine (0.2 mL, 1.93 mmol) according to the procedure reported in step-2 of Scheme 35 gave after workup 2-(tert-butylamino)-N-(3-chloro-2-fluorobenzyl)acetamide (77a) (226 mg, 0.83 mmol, 77%) as a yellow oil which was used as such without further purification; $^1$H NMR (300 MHz, DMSO-d$_6$) δ 8.38 (t, J=5.9 Hz, 1H), 7.51-7.43 (m, 1H), 7.30-7.23 (m, 1H), 7.22-7.15 (m, 1H), 4.36 (d, J=6.1 Hz, 2H), 3.09 (s, 2H), 2.28 (s, 1H), 1.00 (s, 9H); $^{19}$F NMR (282 MHz, DMSO-d$_6$) δ −121.72; MS (ES+): 273.4 (M+1); MS (ES−): 271.3 (M−1).

Step-2: Preparation of 1-(2-(tert-butyl(2-((3-chloro-2-fluorobenzyl)amino)-2-oxoethyl)amino)-2-oxoethyl)-1H-indazole-3-carboxamide (77b)

Reaction of 2-(tert-butylamino)-N-(3-chloro-2-fluorobenzyl)acetamide (77a) (210 mg, 0.77 mmol) with 2-(3-carbamoyl-1H-indazol-1-yl)acetic acid (2e) (203 mg, 0.92 mmol) according to the procedure reported in step-3 of Scheme 2 gave after workup and purification by flash column chromatography [silica (12 g), eluting with MeOH in CHCl$_3$ 0 to 50%] 1-(2-(tert-butyl(2-((3-chloro-2-fluorobenzyl)amino)-2-oxoethyl)amino)-2-oxoethyl)-1H-indazole-3-carboxamide (77b) (37 mg, 0.078 mmol, 10% yield) as a white solid; $^1$H NMR (300 MHz, DMSO-d$_6$) δ 8.81 (t, J=5.7 Hz, 1H, D$_2$O exchangeable), 8.18 (dt, J=8.3, 1.0 Hz, 1H), 7.76 (s, 1H, D$_2$O exchangeable), 7.60-7.48 (m, 2H), 7.47-7.33 (m, 3H), 7.31-7.16 (m, 2H), 5.39 (s, 2H), 4.47 (d, J=5.5 Hz, 2H), 4.25 (s, 2H), 1.29 (s, 9H); $^{19}$F NMR (282 MHz, DMSO-d$_6$) δ −121.23; MS (ES+): 474.5 (M+1), 496.4 (M+Na); MS (ES−): 508.6 (M+Cl).

Scheme 78

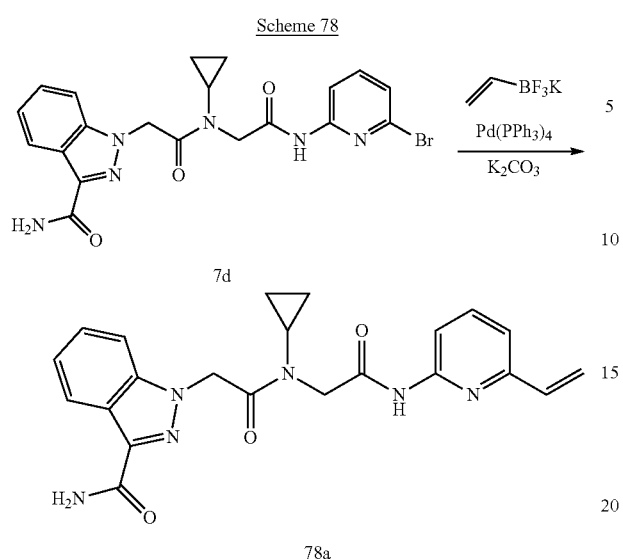

Preparation of 1-(2-(cyclopropyl(2-oxo-2-((6-vinylpyridin-2-yl)amino)ethyl)amino)-2-oxoethyl)-1H-indazole-3-carboxamide (78a)

To a degassed solution of 1-(2-((2-((6-bromopyridin-2-yl)amino)-2-oxoethyl)(cyclopropyl)amino)-2-oxoethyl)-1H-indazole-3-carboxamide (170 mg, 0.36 mmol) in dioxane (5 mL) was added potassium vinyltrifluoroborate (97 mg, 0.72 mmol), tetrakistriphenylphosphine Palladium (0) (42 mg, 0.036 mmol), degassed solution of potassium carbonate (100 mg, 0.72 mmol) in water (0.5 mL). The reaction mixture was stirred under argon atmosphere for 16 h, quenched with water (30 mL) and EtOAc (40 mL). The organic layers was separated and aqueous layer was extracted with EtOAc (20 mL). The organic layers were combined washed with brine, dried, filtered and concentrated in vacuum. The residue was purified by flash column chromatography [silica gel (12 g), eluting with EtOAc-MeOH (9:1) in hexane 0 to 100%] to afford 1-(2-(cyclopropyl(2-oxo-2-((6-vinylpyridin-2-yl)amino)ethyl)amino)-2-oxoethyl)-1H-indazole-3-carboxamide (78a) (80 mg, 0.191 mmol, 53% yield) as an off-white solid; $^1$H NMR (300 MHz, DMSO-$d_6$) δ 10.57 (s, 1H), 8.17 (d, J=8.1 Hz, 1H), 7.91 (d, J=8.2 Hz, 1H), 7.81-7.70 (m, 2H), 7.67 (d, J=8.5 Hz, 1H), 7.50-7.33 (m, 2H), 7.31-7.13 (m, 2H), 6.72 (dd, J=17.4, 10.8 Hz, 1H), 6.19 (dd, J=17.5, 1.8 Hz, 1H), 5.70 (s, 2H), 5.46 (dd, J=10.7, 1.7 Hz, 1H), 4.21 (s, 2H), 3.20-3.05 (m, 1H), 1.10-0.84 (m, 4H); MS (ES+): 419.5 (M+1); (ES−) 453.4.5 (M+Cl).

Scheme 79

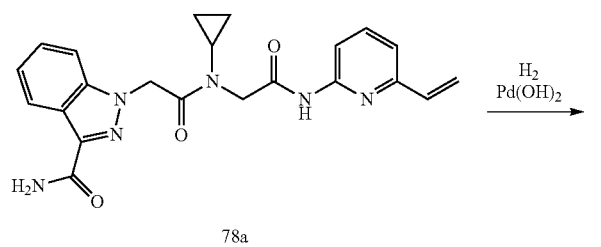

Preparation of 1-(2-(cyclopropyl(2-((6-ethylpyridin-2-yl)amino)-2-oxoethyl)amino)-2-oxoethyl)-1H-indazole-3-carboxamide (79a)

A solution of 1-(2-(cyclopropyl(2-oxo-2-((6-vinylpyridin-2-yl)amino)ethyl)amino)-2-oxoethyl)-1H-indazole-3-carboxamide (78a) (35 mg, 0.084 mmol) in EtOAc (5 mL) containing PdOH$_2$ (12 mg, 0.084 mmol) was hydrogenated at atmospheric pressure for 16 h. The reaction mixture was filtered over a Celite pad to remove catalyst and filtrate was concentrated in vacuum. The residue was purified by flash chromatography [silica gel (4 g), eluting with CMA80 in CHCl$_3$ 0 to 40%] to afford 1-(2-(cyclopropyl(2-((6-ethylpyridin-2-yl)amino)-2-oxoethyl)amino)-2-oxoethyl)-1H-indazole-3-carboxamide (79a) (18 mg, 0.043 mmol, 51% yield) as a white solid; $^1$H NMR (300 MHz, DMSO-$d_6$) δ 10.53 (s, 1H), 8.17 (d, J=8.1, 1.0 Hz, 1H), 7.83 (d, J=8.5 Hz, 1H), 7.76 (s, 1H), 7.72-7.62 (m, 2H), 7.48-7.35 (m, 2H), 7.30-7.20 (m, 1H), 6.96 (d, J=7.5 Hz, 1H), 5.70 (s, 2H), 4.19 (s, 2H), 3.17-3.05 (m, 1H), 2.65 (q, J=7.6 Hz, 2H), 1.19 (t, J=7.6 Hz, 3H), 1.07-0.87 (m, 4H); MS (ES+): 421.5 (M+1); (ES−): 419.5 (M−1).

Scheme 80

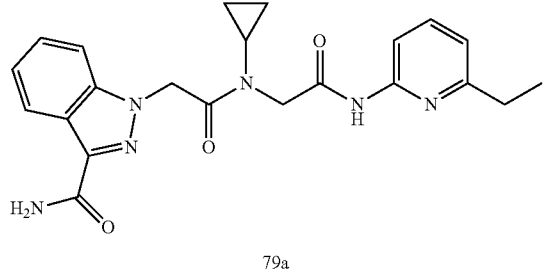

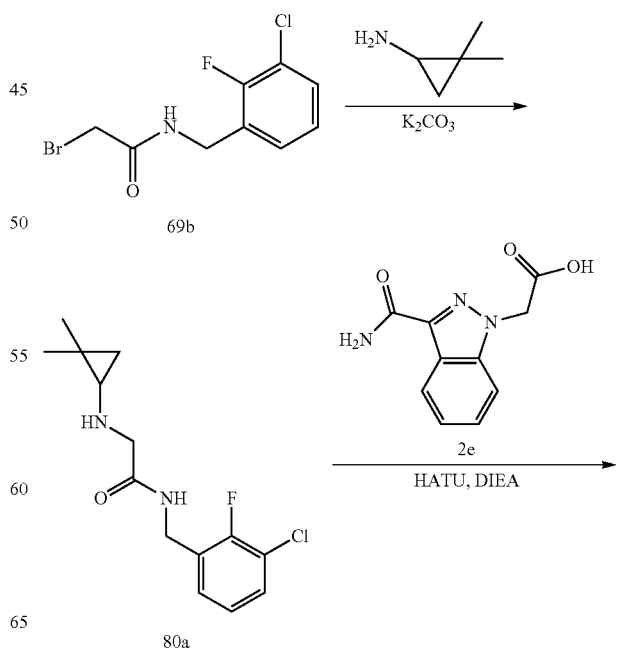

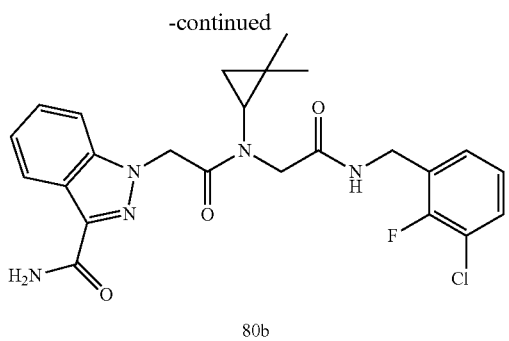

80b

Preparation of 1-(2-((2-((3-chloro-2-fluorobenzyl)amino)-2-oxoethyl)(2,2-dimethylcyclopropyl)amino)-2-oxoethyl)-1H-indazole-3-carboxamide (80b)

Step-1: Preparation of N-(3-chloro-2-fluorobenzyl)-2-((2,2-dimethylcyclopropyl)amino)acetamide (80a)

Reaction of 2-bromo-N-(3-chloro-2-fluorobenzyl)acetamide (69b) (300 mg, 1.07 mmol) with 2,2-dimethylcyclopropanamine (182 mg, 2.14 mmol) according to the procedure reported in step-2 of Scheme 35 gave after workup N-(3-chloro-2-fluorobenzyl)-2-((2,2-dimethylcyclopropyl)amino)acetamide (80a) (305 mg, 1.07 mmol, 100%) as a yellow oil which was used as such without further purification; MS (ES+): 285.4 (M+1); MS (ES−): 283.3 (M−1).

Step-2: Preparation of 1-(2-((2-((3-chloro-2-fluorobenzyl)amino)-2-oxoethyl)(2,2-dimethylcyclopropyl)amino)-2-oxoethyl)-1H-indazole-3-carboxamide (80b)

Reaction of N-(3-chloro-2-fluorobenzyl)-2-((2,2-dimethylcyclopropyl)amino)acetamide (80a) (305 mg, 1.07 mmol) with 2-(3-carbamoyl-1H-indazol-1-yl)acetic acid (2e) (282 mg, 1.29 mmol) according to the procedure reported in step-3 of Scheme 2 gave after workup and purification by flash column chromatography [silica (24 g), eluting with MeOH in CHCl$_3$ 0 to 50%] 1-(2-((2-((3-chloro-2-fluorobenzyl)amino)-2-oxoethyl)(2,2-dimethylcyclopropyl)amino)-2-oxoethyl)-1H-indazole-3-carboxamide (80b) (68 mg, 0.14 mmol, 1% yield) as a white solid in the form of mixture of two rotamers; $^1$H NMR (300 MHz, DMSO-d$_6$) (a mixture of two rotamers) δ 8.83 (J=5.7 Hz) & 8.50 (J=5.8 Hz (2t, 1H), 8.22-8.16 (m, 1H), 7.73 & 7.70 (2s, 1H), 7.58-7.36 (m, 4H), 7.32-7.19 (m, 2H), 7.11 (td, J=7.8, 1.0 Hz, 1H), 5.74-5.25 (m, 2H), 4.37-4.30 (m, 2H), 4.17-3.81 (m, 2H), 2.96 (dd, J=8.0, 4.5 Hz, 1H), 1.28 & 0.96 (2s, 3H), 1.18 & 0.91 (2s, 3H), 0.87-0.74 (m, 2H); $^{19}$F NMR (282 MHz, DMSO-d$_6$) δ −121.23, −121.56; MS (ES+): 486.5 (M+1), 508.5 (M+Na); MS (ES−): 484.5 (M−1), 520.5 (M+Cl).

Scheme 81

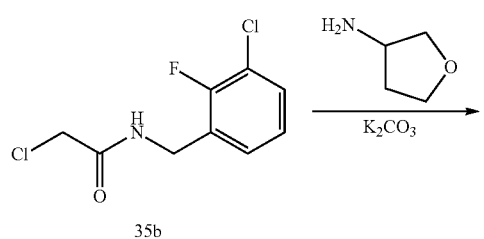

35b

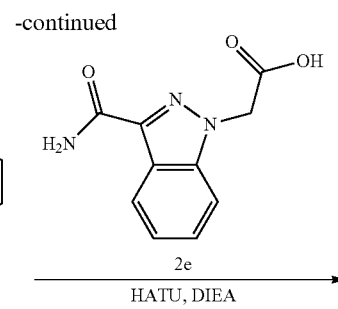

81a

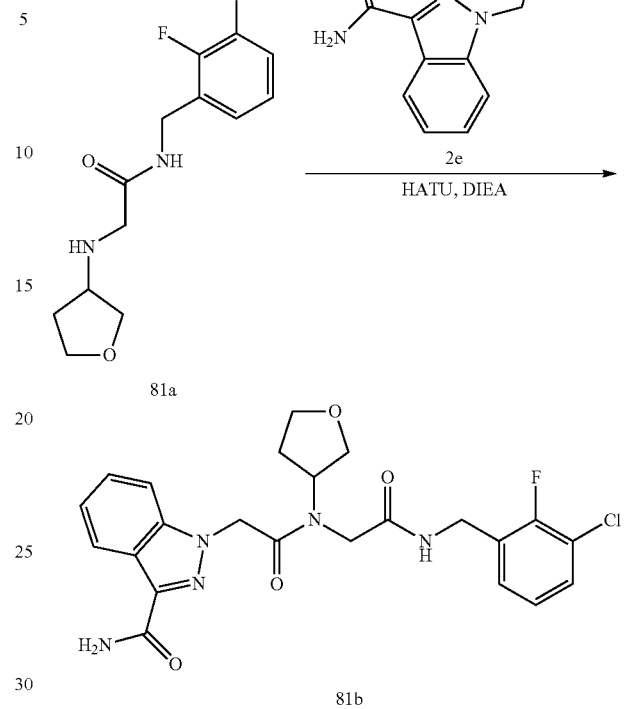

81b

Preparation of 1-(2-((2-((3-chloro-2-fluorobenzyl)amino)-2-oxoethyl)(tetrahydrofuran-3-yl)amino)-2-oxoethyl)-1H-indazole-3-carboxamide (81b)

Step-1: Preparation of N-(3-chloro-2-fluorobenzyl)-2-((tetrahydrofuran-3-yl)amino)acetamide (81a)

Reaction of 2-chloro-N-(3-chloro-2-fluorobenzyl)acetamide (35b) (300 mg, 1.27 mmol) with tetrahydrofuran-3-amine (332 mg, 3.81 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((tetrahydrofuran-3-yl)amino)acetamide (81a) (152 mg, 0.53 mmol, 42% yield) as a clear oil; $^1$H NMR (300 MHz, DMSO-d$_6$) δ $^1$H NMR (300 MHz, DMSO-d$_6$) δ 8.37 (t, J=6.0 Hz, 1H, D$_2$O exchangeable), 7.48 (td, J=7.8, 1.8 Hz, 1H), 7.33-7.24 (m, 1H), 7.24-7.12 (m, 1H), 4.36 (d, J=6.0 Hz, 2H), 3.83-3.55 (m, 3H), 3.46-3.36 (m, 1H), 3.30-3.18 (m, 1H), 3.14 (s, 2H), 2.35 (s, 1H, D$_2$O exchangeable), 1.95-1.80 (m, 1H), 1.72-1.55 (m, 1H); MS (ES+), 287.3 (M+1); (ES−): 285.3 (M−1).

Step-2: Preparation of 1-(2-((2-((3-chloro-2-fluorobenzyl)amino)-2-oxoethyl)(tetrahydrofuran-3-yl)amino)-2-oxoethyl)-1H-indazole-3-carboxamide (81b)

Reaction of N-(3-chloro-2-fluorobenzyl)-2-((tetrahydrofuran-3-yl)-amino)acetamide (81a) (110 mg, 0.38 mmol) with 2-(3-carbamoyl-1H-indazol-1-yl)acetic acid (2e) (93 mg, 0.42 mmol) according to the procedure reported in step-3 of Scheme 2 gave after workup and purification by flash column chromatography [silica (12 g), eluting with CMA80 in CHCl₃ 0 to 60%] 1-(2-((2-((3-chloro-2-fluorobenzyl)amino)-2-oxoethyl)(tetrahydrofuran-3-yl)amino)-2-oxoethyl)-1H-indazole-3-carboxamide (81b) (136 mg, 0.28 mmol, 73% yield) as a white solid; $^1$H NMR (300 MHz, DMSO-d₆) δ 8.89 (t, J=5.6 Hz) and 8.49 (t, J=5.8 Hz) (2t, 1H), 8.25-8.09 (m, 1H), 7.70 (s, 1H), 7.61-7.00 (m, 7H), 5.75-5.56 (m) and 5.40 (s) (2H), 4.95-4.71 (m, 1H), 4.47 (d, J=5.6 Hz) and 4.31 (d, J=5.5 Hz) (2d, 2H), 4.25 (s) and 4.03-3.73 (m) (4H), 3.63-3.48 (m, 2H), 2.17-1.62 (m, 2H); $^{19}$F NMR (282 MHz, DMSO-d₆) δ −121.27, −121.73; MS (ES+) 488.5 (M+1); 510.5 (M+Na); MS (ES−), 486.5 (M−1); [based on NMR, this compound is a mixture of two rotamers 1:1 ratio].

Scheme 82

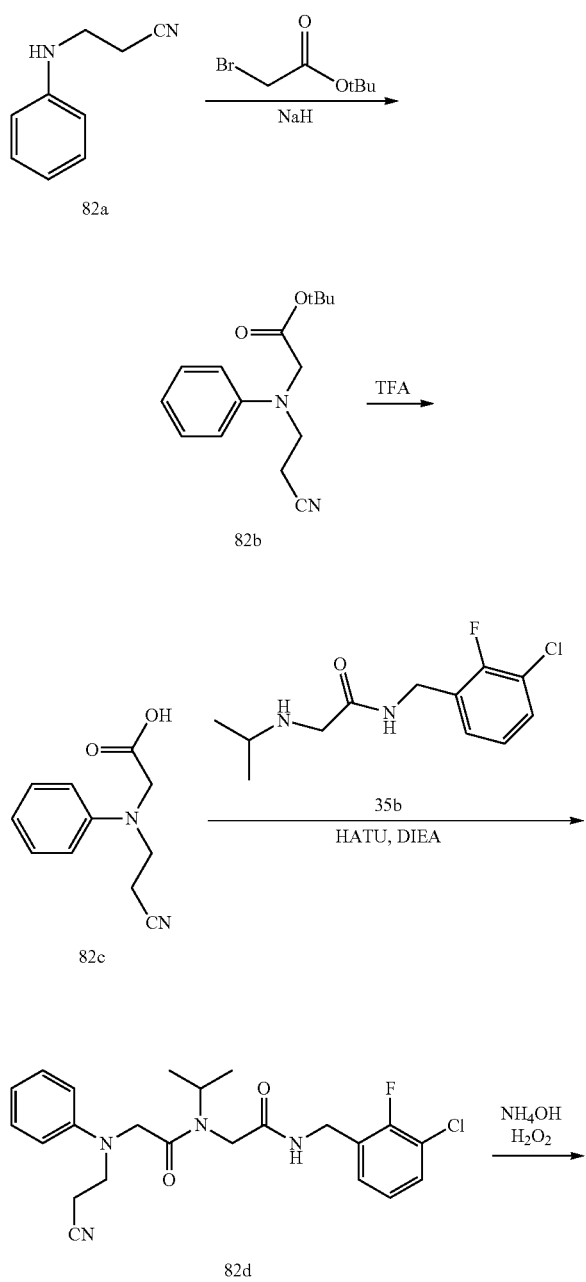

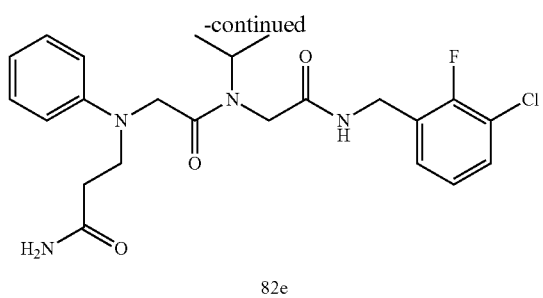

82e

Preparation of 3-((2-((2-((3-chloro-2-fluorobenzyl)amino)-2-oxoethyl)(isopropyl)amino)-2-oxoethyl)(phenyl)amino)propanamide (82e)

Step-1: Preparation of tert-butyl 2-((2-cyanoethyl)(phenyl)amino)acetate (82b)

Reaction of 3-(phenylamino)propanenitrile (82a) (1.0 g, 6.84 mmol) with tert-butyl 2-bromoacetate (1.11 mL, 7.52 mmol) using sodium hydride (0.274 g, 6.84 mmol) as a base according to the procedure reported in step-1 of Scheme 57 gave after workup and purification by flash column chromatography [silica (40 g), eluting with EtOAc in hexane 0 to 50%] tert-butyl 2-((2-cyanoethyl)(phenyl)amino)acetate (82b) (148 mg, 0.57 mmol, 8% yield) as a colorless oil; $^1$H NMR (300 MHz, DMSO-d₆) δ 7.24-7.11 (m, 2H), 6.76-6.51 (m, 3H), 4.09 (s, 2H), 3.70 (t, J=6.9 Hz, 2H), 2.74 (t, J=6.8 Hz, 2H), 1.39 (s, 9H); MS (ES+): 283.5 (M+Na).

Step-2: Preparation of 2-((2-cyanoethyl)(phenyl)amino)acetic acid (82c)

Reaction of tert-butyl 2-((2-cyanoethyl)(phenyl)amino)acetate (82b) (141 mg, 0.542 mmol) with TFA (0.42 mL, 5.42 mmol) according to the procedure reported in step-2 of Scheme 2 gave after workup 2-((2-cyanoethyl)(phenyl)amino)acetic acid (82c) which was used as such in the next step; MS (ES+): 205.3 (M+1); MS (ES−): 203.3 (M−1).

Step-3: Preparation of N-(2-((3-chloro-2-fluorobenzyl)amino)-2-oxoethyl)-2-((2-cyanoethyl)(phenyl)amino)-N-isopropylacetamide (82d)

Reaction of 2-((2-cyanoethyl)(phenyl)amino)acetic acid (82c) (110 mg, 0.544 mmol) with N-(3-chloro-2-fluorobenzyl)-2-(isopropylamino)acetamide (35b) (141 mg, 0.54 mmol) according to the procedure reported in step-3 of Scheme 2 gave after workup N-(2-((3-chloro-2-fluorobenzyl)amino)-2-oxoethyl)-2-((2-cyanoethyl)(phenyl)amino)-N-isopropylacetamide (82d) which was used as such in the next step; MS (ES−): 443.5 (M−1).

Step-4: Preparation of 3-((2-((2-((3-chloro-2-fluorobenzyl)amino)-2-oxoethyl)(isopropyl)amino)-2-oxoethyl)(phenyl)amino)propanamide (82e)

Reaction of N-(2-((3-chloro-2-fluorobenzyl)amino)-2-oxoethyl)-2-((2-cyanoethyl)(phenyl)amino)-N-isopropylacetamide (82d) (242 mg, 0.54 mmol) in ethanol (5 mL) using aq. NH₄OH (2.12 mL, 54.4 mmol) and H₂O₂ (aq. 35%, 0.95 mL, 10.88 mmol) according to the procedure reported in Scheme 65 gave after workup and purification by flash column chromatography [First column: silica gel (24 g), eluting with MeOH in CHCl₃ 0-30%; Second column: Silica gel (12 g), eluting with MeOH in CHCl₃ 0-10%] 3-((2-((2-((3-chloro-2-fluorobenzyl)amino)-2-oxoethyl)(isopropyl)amino)-2-oxoethyl)(phenyl)amino)propanamide (82e) (53 mg, 0.11 mmol, 21% yield) as an off-white solid in the form of mixture of two rotamers; ¹H NMR (300 MHz, DMSO-d₆) δ 8.70 (t, J=5.8 Hz) and 8.28 (t, J=6.0 Hz) (2t, 1H), 7.56-7.31 (m, 3H), 7.30-7.15 (m, 1H), 7.15-7.03 (m, 2H), 6.82 (bs, 1H), 6.70-6.49 (m, 3H), 4.67-4.52 and 4.19-4.05 (m, 1H), 4.46-4.30 (m, 2H), 4.30 and 4.14 (2s, 2H), 4.01 and 3.79 (2s, 2H), 3.57-3.44 (m, 2H), 2.41-2.31 (m, 2H), 1.18 (d, J=6.4 Hz) and 0.97 (d, J=6.8 Hz) (2d, 6H); ¹⁹F NMR (282 MHz, DMSO-d₆) δ -121.30, -121.90; MS (ES+): 463.5 (M+1), 485.5 (M+Na); MS (ES-): 461.5 (M-1), 497.5 (M+Cl).

Preparation of 7-(2-((2-(((6-bromopyridin-2-yl)amino)-2-oxoethyl)(cyclopropyl)amino)-2-oxo-ethyl)-7H-pyrrolo[2,3-d]pyrimidine-4-carboxamide (83d)

Step-1: Preparation of tert-butyl 2-(4-cyano-7H-pyrrolo[2,3-d]pyrimidin-7-yl)acetate (83a)

To a degassed solution of tert-butyl 2-(4-chloro-7H-pyrrolo[2,3-d]pyrimidin-7-yl)acetate (56b) (0.54 g, 2.02 mmol) in DMA (10 mL) was added dicyanozinc (237 mg, 2.02 mmol), 1,1'-binaphthyl-2-yldi-tert-butylphosphine (80 mg, 0.20 mmol), palladium(II)trifluoroacetate (34 mg, 0.10 mmol), Zn (66 mg, 1.01 mmol) and heated at 95° C. for 16 h. Mixture was cooled to room temperature, diluted with EtOAc (20 mL), filtered over Celite pad and washed with EtOAc (2×15 mL). The combined filtrate was washed with water (2×40 mL), brine, dried, filtered and concentrated in vacuum. The residue obtained was purified by flash column chromatography [silica gel (24 g), eluting with EtOAc in hexanes 0 to 100%] to afford tert-butyl 2-(4-cyano-7H-pyrrolo[2,3-d]pyrimidin-7-yl)acetate (83a) (80 mg, 0.31 mmol, 15% yield) as white solid; ¹H NMR (300 MHz, DMSO-d₆) δ 9.00 (s, 1H), 8.01 (d, J=3.7 Hz, 1H), 6.90 (d, J=3.7 Hz, 1H), 5.14 (s, 2H), 1.41 (s, 9H); MS (ES-): 257.3 (M-1).

Step-2: Preparation of tert-butyl 2-(4-carbamoyl-7H-pyrrolo[2,3-d]pyrimidin-7-yl)acetate (83b)

Reaction of tert-butyl 2-(4-cyano-7H-pyrrolo[2,3-d]pyrimidin-7-yl)acetate (83a) (350 mg, 1.36 mmol) in ethanol (10 mL) using aq. NH₄OH (1.06 mL, 27.1 mmol) and H₂O₂ (aq. 35%, 0.42 mL, 13.55 mmol) according to the procedure reported in Scheme 65 gave after workup tert-butyl 2-(4-carbamoyl-7H-pyrrolo[2,3-d]pyrimidin-7-yl)acetate (83b) (360 mg, 1.30 mmol, 96% yield) as a white solid; ¹H NMR (300 MHz, DMSO-d₆) δ 8.87 (s, 1H), 8.33 (s, 1H), 7.88 (s, 1H), 7.76 (d, J=3.6 Hz, 1H), 7.07 (d, J=3.5 Hz, 1H), 5.09 (s, 2H), 1.41 (s, 9H); MS (ES+): 277.4 (M+1): MS (ES-): 275.3 (M-1).

Step-3: Preparation of 2-(4-carbamoyl-7H-pyrrolo[2,3-d]pyrimidin-7-yl)acetic acid (83c)

Reaction of tert-butyl 2-(4-carbamoyl-7H-pyrrolo[2,3-d]pyrimidin-7-yl)acetate (83b) (340 mg, 1.23 mmol) with TFA (0.95 mL, 12.31 mmol) according to the procedure reported in step-2 of Scheme 2 gave after workup 2-(4-carbamoyl-7H-pyrrolo[2,3-d]pyrimidin-7-yl)acetic acid (83c) which was used as such in the next step; MS (ES+): 221.3 (M+1); MS (ES-): 219.2 (M-1).

Step-4: Preparation of 7-(2-((2-(((6-bromopyridin-2-yl)amino)-2-oxoethyl)(cyclopropyl)amino)-2-oxo-ethyl)-7H-pyrrolo[2,3-d]pyrimidine-4-carboxamide (83d)

Reaction of N-(6-bromopyridin-2-yl)-2-(cyclopropylamino)acetamide (7c) (70 mg, 0.26 mmol) with 2-(4-carbamoyl-7H-pyrrolo[2,3-d]pyrimidin-7-yl)acetic acid (83c) (57 mg, 0.26 mmol) according to the procedure reported in step-3 of Scheme 2 gave after workup and purification by flash column chromatography [silica gel (12 g), eluting with CMA80 in CHCl₃ 0 to 40%] 7-(2-((2-(((6-bromopyridin-2-yl)amino)-2-oxoethyl)(cyclopropyl)amino)-2-oxoethyl)-7H-pyrrolo[2,3-d]pyrimidine-4-car-

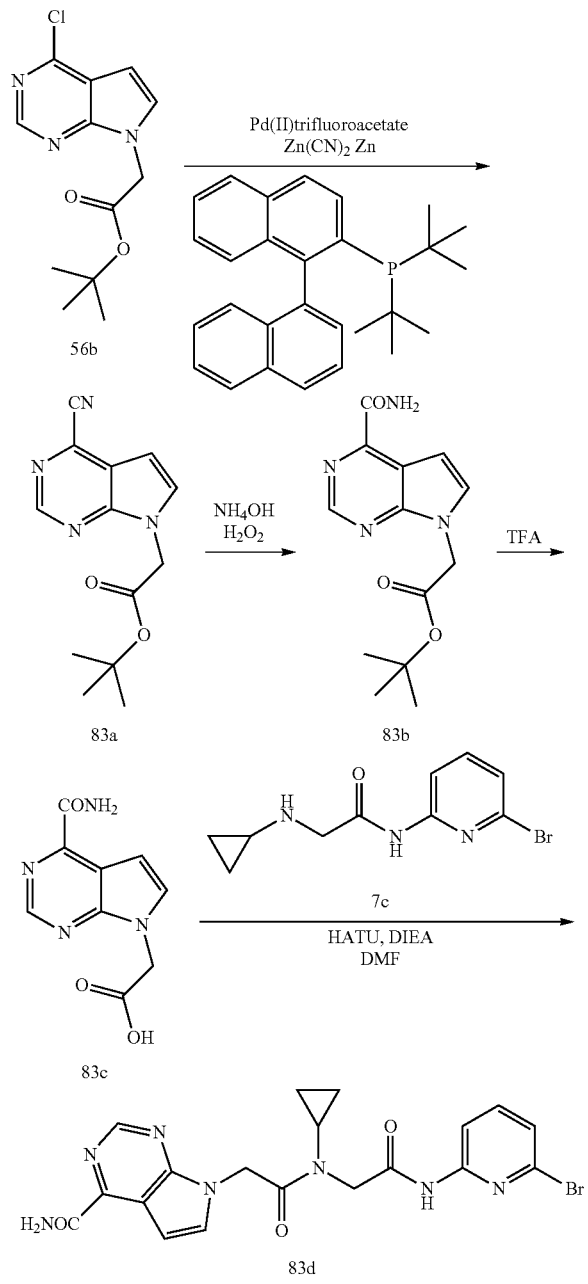

Scheme 83 boxamide (83d) (60 mg, 0.13 mmol, 49% yield) as a white solid; ¹H NMR (300 MHz, DMSO-d₆) δ 10.94 (s, 1H), 8.86 (s, 1H), 8.31 (s, 1H), 8.01 (d, J=8.1 Hz, 1H), 7.86 (s, 1H), 7.77-7.65 (m, 2H), 7.32 (dd, J=7.7, 0.7 Hz, 1H), 7.05 (d, J=3.5 Hz, 1H), 5.50 (s, 2H), 4.17 (s, 2H), 3.14-3.02 (m, 1H), 1.04-0.89 (m, 4H); MS (ES+): 472.5, 474.5 (M+1); MS (ES−); 470.4, 472.4 (M−1).

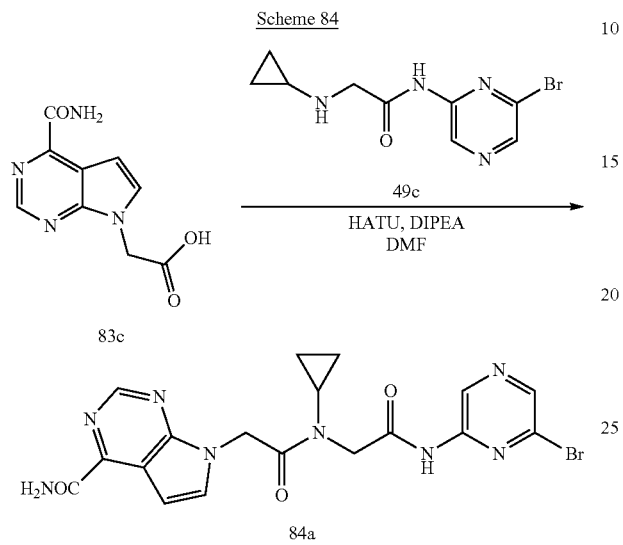

Preparation of 7-(2-((2-((6-bromopyrazin-2-yl)amino)-2-oxoethyl)(cyclopropyl)amino)-2-oxoethyl)-7H-pyrrolo[2,3-d]pyrimidine-4-carboxamide (84a)

Reaction of N-(6-bromopyrazin-2-yl)-2-(cyclopropylamino)acetamide (49c) (70 mg, 0.26 mmol) with 2-(4-carbamoyl-7H-pyrrolo[2,3-d]pyrimidin-7-yl)acetic acid (83c) (57 mg, 0.26 mmol) according to the procedure reported in step-3 of Scheme 2 gave after workup and purification by flash column chromatography [silica gel (12 g), eluting with CMA80 in CHCl₃ 0 to 40%] 7-(2-((2-((6-bromopyrazin-2-yl)amino)-2-oxoethyl)(cyclopropyl)amino)-2-oxoethyl)-7H-pyrrolo[2,3-d]pyrimidine-4-carboxamide (84a) (55 mg, 0.12 mmol, 45% yield) as a white solid; ¹H NMR (300 MHz, DMSO-d₆) δ 11.28 (s, 1H), 9.24 (s, 1H), 8.86 (s, 1H), 8.54 (s, 1H), 8.31 (s, 1H), 7.85 (s, 1H), 7.72 (d, J=3.5 Hz, 1H), 7.05 (d, J=3.5 Hz, 1H), 5.51 (s, 2H), 4.22 (s, 2H), 3.15-3.05 (m, 1H), 1.06-0.92 (m, 4H); MS (ES+): 473.4 and 475.4 (M+1); MS (ES−): 471.3 and 473.3 (M−1).

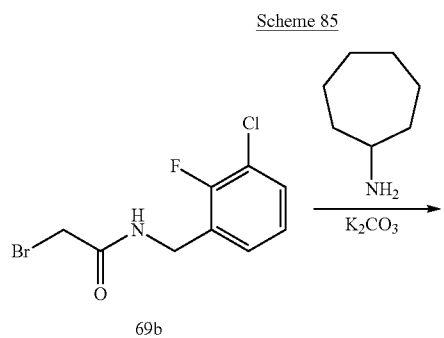

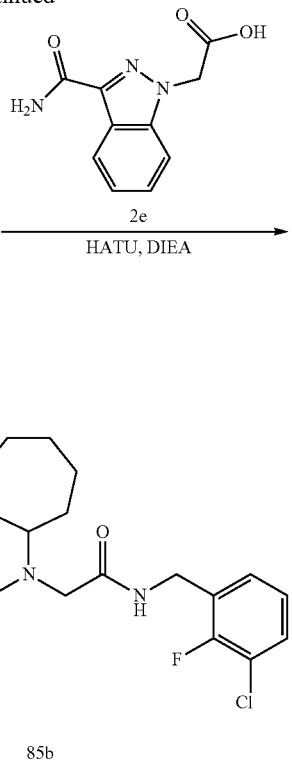

Preparation of 1-(2-((2-((3-chloro-2-fluorobenzyl)amino)-2-oxoethyl)(cycloheptyl)amino)-2-oxoethyl)-1H-indazole-3-carboxamide (85b)

Step-1: Preparation of N-(3-chloro-2-fluorobenzyl)-2-(cycloheptylamino)acetamide (85a)

Reaction of 2-bromo-N-(3-chloro-2-fluorobenzyl)acetamide (69b) (313 mg, 1.12 mmol) with cycloheptanamine (0.17 mL, 1.34 mmol) according to the procedure reported in step-2 of Scheme 35 gave after workup N-(3-chloro-2-fluorobenzyl)-2-(cycloheptylamino)acetamide (85a) as a yellow oil which was used as such without further purification; MS (ES+): 313.4 (M+1); MS (ES−): 311.4 (M−1), 347.4 (M+Cl).

Step-2: Preparation of 1-(2-((2-((3-chloro-2-fluorobenzyl)amino)-2-oxoethyl)(cycloheptyl)amino)-2-oxoethyl)-1H-indazole-3-carboxamide (85b)

Reaction of N-(3-chloro-2-fluorobenzyl)-2-(cycloheptylamino)acetamide (85a) (347 mg, 1.12 mmol) with 2-(3-carbamoyl-1H-indazol-1-yl)acetic acid (2e) (365 mg, 1.66 mmol) according to the procedure reported in step-3 of Scheme 2 gave after workup and purification by flash column chromatography [silica (40 g), eluting with MeOH in CHCl₃ 0 to 10%] 1-(2-((2-((3-chloro-2-fluorobenzyl)amino)-2-oxoethyl)(cycloheptyl)amino)-2-oxoethyl)-1H-indazole-3-carboxamide (85b) (136 mg, 0.27 mmol, 24% yield) as an off-white solid as a mixture of two rotamers; ¹H NMR (300 MHz, DMSO-d₆) δ 8.85 (t, J=5.8 Hz) & 8.37 (t, J=5.9 Hz) (2t, 1H), 8.23-8.13 (m, 1H), 7.70 (s, 1H), 7.65-7.35 (m, 5H), 7.32-6.96 (m, 2H), 5.59 & 5.46 (s, 2H), 4.46 (d, J=5.6 Hz) & 4.31 (d, J=5.7 Hz) (2d, 2H), 4.27-4.21 &

3.98-3.87 (m, 1H), 4.19 & 3.82 (2s, 2H), 1.69-1.40 (m, 11H), 1.36-1.23 (m, 1H); $^{19}$F NMR (282 MHz, DMSO-d$_6$) δ −121.10, −121.72; MS (ES+): 514.8 and 516.7 (M+1), 536.7 and 538.6 (M+Na); MS (ES−): 512.3, 514.6 (M−1), 548.5 (M+Cl).

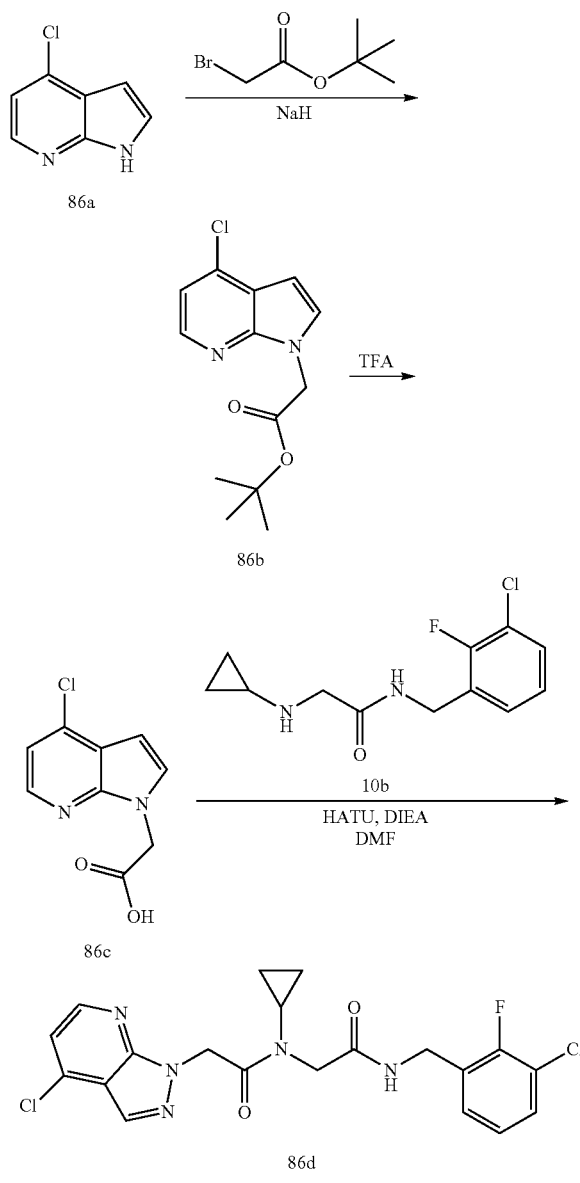

Preparation of 2-(4-chloro-1H-pyrrolo[2,3-b]pyridin-1-yl)-N-(2-((3-chloro-2-fluorobenzyl)amino)-2-oxoethyl)-N-cyclopropylacetamide (86d)

Step-1: Preparation of tert-butyl 2-(4-chloro-1H-pyrrolo[2,3-b]pyridin-1-yl)acetate (86b)

Reaction of 4-chloro-1H-pyrrolo[2,3-b]pyridine (86a) (2.0 g, 13.11 mmol) with tert-butyl 2-bromoacetate (2.32 mL, 15.73 mmol) according to the procedure reported in step-1 of Scheme 56 gave after workup and purification by flash column chromatography [silica (40 g), eluting with EtOAc in hexane 0 to 50%] tert-butyl 2-(4-chloro-1H-pyrrolo[2,3-b]pyridin-1-yl)acetate (86b) (3 g, 11.25 mmol, 86% yield) as a colorless oil; $^1$H NMR (300 MHz, DMSO-d$_6$) δ 8.21 (d, J=5.2 Hz, 1H), 7.66 (d, J=3.6 Hz, 1H), 7.26 (d, J=5.2 Hz, 1H), 6.56 (d, J=3.6 Hz, 1H), 5.05 (s, 2H), 1.40 (s, 9H).

Step-2: Preparation of 2-(4-chloro-1H-pyrrolo[2,3-b]pyridin-1-yl)acetic acid (86c)

Reaction of tert-butyl 2-(4-chloro-1H-pyrrolo[2,3-b]pyridin-1-yl)acetate (86b) (1.5 g, 5.62 mmol) with TFA (4.33 mL, 56.2 mmol) according to the procedure reported in step-2 of Scheme 2 gave after workup 2-(4-chloro-1H-pyrrolo[2,3-b]pyridin-1-yl)acetic acid (86c) (940 mg, 4.46 mmol, 79% yield) as light orange solid; $^1$H NMR (300 MHz, DMSO-d$_6$) δ 13.08 (s, 1H), 8.20 (d, J=5.2 Hz, 1H), 7.67 (d, J=3.6 Hz, 1H), 7.26 (d, J=5.2 Hz, 1H), 6.56 (d, J=3.6 Hz, 1H), 5.06 (s, 2H); MS (ES+): 211.2 (M+1); (ES−) 209.1 (M−1).

Step-3: Preparation of 2-(4-chloro-1H-pyrrolo[2,3-b]pyridin-1-yl)-N-(2-((3-chloro-2-fluorobenzyl)amino)-2-oxoethyl)-N-cyclopropylacetamide (86d)

Reaction of 2-(4-chloro-1H-pyrrolo[2,3-b]pyridin-1-yl) acetic acid (86c) (330 mg, 1.57 mmol) with N-(3-chloro-2-fluorobenzyl)-2-(cyclopropylamino)acetamide (10b) (402 mg, 1.57 mmol) according to the procedure reported in step-3 of Scheme 2 gave after workup and purification by flash column [silica gel (24 g), eluting with MeOH-EtOAc (1:9) in hexanes 0 to 70%] 2-(4-chloro-1H-pyrrolo[2,3-b]pyridin-1-yl)-N-(2-((3-chloro-2-fluorobenzyl)amino)-2-oxoethyl)-N-cyclopropylacetamide (86d) (580 mg, 1.29 mmol, 82% yield) as a white solid; $^1$H NMR (300 MHz, DMSO-d$_6$) δ 8.45 (t, J=5.8 Hz, 1H), 8.18 (d, J=5.2 Hz, 1H), 7.61 (d, J=3.6 Hz, 1H), 7.47 (td, J=7.6, 1.8 Hz, 1H), 7.29-7.18 (m, 2H), 7.18-7.10 (m, 1H), 6.56 (d, J=3.5 Hz, 1H), 5.44 (s, 2H), 4.33 (d, J=5.7 Hz, 2H), 3.97 (s, 2H), 3.09-2.98 (m, 1H), 1.05-0.87 (m, 4H); $^{19}$F NMR (282 MHz, DMSO-d$_6$) δ −121.61; MS (ES−): 447.3 and 449.5 (M−1), 483.4 and 485.4 (M+Cl).

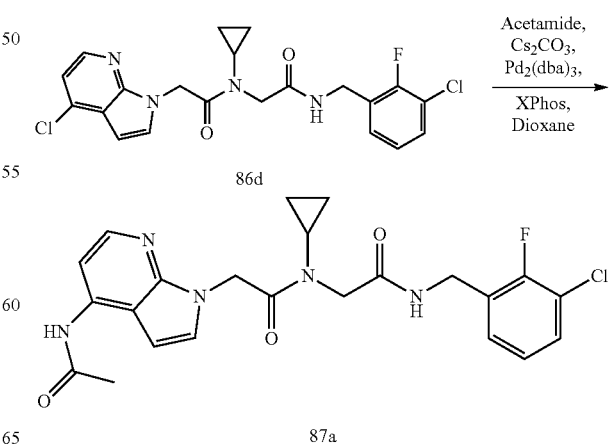

215

Preparation of 2-(4-acetamido-1H-pyrrolo[2,3-b]pyridin-1-yl)-N-(2-((3-chloro-2-fluorobenzyl)amino)-2-oxoethyl)-N-cyclopropylacetamide (87a)

To a degassed solution of 2-(4-chloro-1H-pyrrolo[2,3-b]pyridin-1-yl)-N-(2-((3-chloro-2-fluorobenzyl)amino)-2-oxoethyl)-N-cyclopropylacetamide (86d) (300 mg, 0.67 mmol) in dioxane (10 mL) was added cesium carbonate (326 mg, 1.0 mmol), acetamide (79 mg, 1.34 mmol), dicyclohexyl(2',4',6'-triisopropylbiphenyl-2-yl)phosphine (32 mg, 0.067 mmol), $Pd_2(dba)_3$ (31 mg, 0.033 mmol) and heated at 80° C. for 16 h. The mixture was cooled to room temperature, diluted with EtOAc (5 mL), filtered over Celite pad and pad was washed with EtOAc (2×5 mL). The filtrate was washed with water (2×30 mL), brine, dried, filtered and concentrated in vacuum. The residue was purified by flash column chromatography [silica gel (12 g), eluting with CMA80 in $CHCl_3$ 0 to 40%] to afford 2-(4-acetamido-1H-pyrrolo[2,3-b]pyridin-1-yl)-N-(2-((3-chloro-2-fluorobenzyl)amino)-2-oxoethyl)-N-cyclopropylacetamide (87a) (105 mg, 0.22 mmol, 33% yield) as a white solid; $^1H$ NMR (300 MHz, DMSO-$d_6$) δ 10.05 (s, 1H), 8.44 (t, J=5.9 Hz, 1H), 8.06 (d, J=5.4 Hz, 1H), 7.83 (d, J=5.4 Hz, 1H), 7.51-7.41 (m, 1H), 7.35 (d, J=3.6 Hz, 1H), 7.27-7.07 (m, 2H), 6.82 (d, J=3.6 Hz, 1H), 5.37 (s, 2H), 4.33 (d, J=5.8 Hz, 2H), 3.97 (s, 2H), 3.09-2.97 (m, 1H), 2.20 (s, 3H), 1.03-0.84 (m, 4H); $^{19}F$ NMR (282 MHz, DMSO-$d_6$) δ −121.62; MS (ES+) 472.5 (M+1); MS (ES−): 470.5 (M−1), 506.5 (M+Cl).

Scheme 88

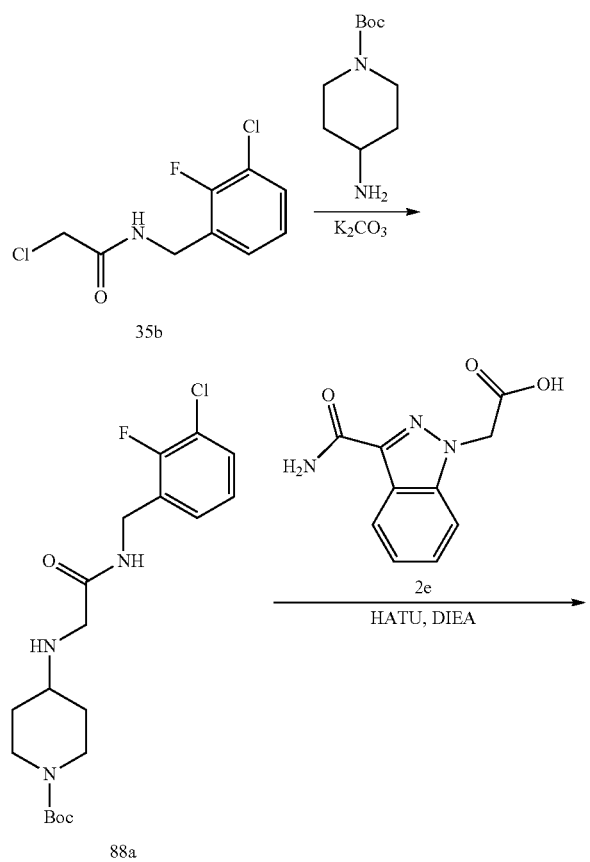

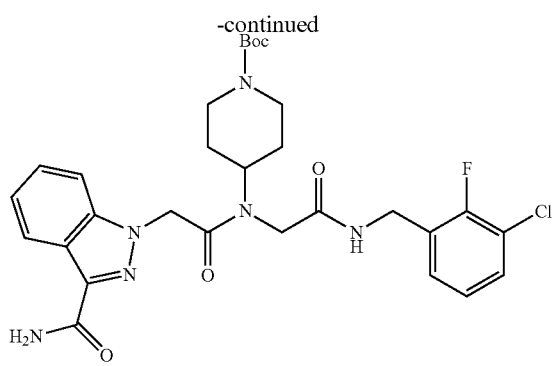

88b

Preparation of tert-butyl 4-(2-(3-carbamoyl-1H-indazol-1-yl)-N-(2-((3-chloro-2-fluorobenzyl)amino)-2-oxoethyl)acetamido)piperidine-1-carboxylate (88b)

Step-1: Preparation of tert-butyl 4-((2-((3-chloro-2-fluorobenzyl)amino)-2-oxoethyl)amino)piperidine-1-carboxylate (88a)

Reaction of 2-chloro-N-(3-chloro-2-fluorobenzyl)acetamide (35b) (500 mg, 5.3 mmol) with tert-butyl 4-aminopiperidine-1-carboxylate (1.06 g, 5.3 mmol) according to the procedure reported in step-2 of Scheme 35 gave after workup and purification by flash column chromatography [silica (12 g), eluting with EtOAc/MeOH (9:1) in hexane 0 to 60%] tert-butyl 4-((2-((3-chloro-2-fluorobenzyl)amino)-2-oxoethyl)amino)piperidine-1-carboxylate (88a) (762 mg, 1.91 mmol, 90%) as a clear oil. $^1H$ NMR (300 MHz, DMSO-$d_6$) δ 8.38 (t, J=6.1 Hz, 1H), 7.53-7.40 (m, 1H), 7.34-7.23 (m, 1H), 7.23-7.14 (m, 1H), 4.36 (d, J=6.0 Hz, 2H), 3.79 (d, J=13.1 Hz, 2H), 3.16 (s, 2H), 2.87-2.63 (m, 2H), 2.48-2.40 (m, 1H), 2.27 (s, 1H), 1.79-1.64 (m, 2H), 1.38 (s, 9H), 1.20-1.01 (m, 2H); MS (ES+): 400.5 (M+1); MS (ES−): 398.4 (M−1).

Step-2: Preparation of tert-butyl 4-(2-(3-carbamoyl-1H-indazol-1-yl)-N-(2-((3-chloro-2-fluorobenzyl)amino)-2-oxoethyl)acetamido)piperidine-1-carboxylate (88b)

Reaction of tert-butyl 4-((2-((3-chloro-2-fluorobenzyl)amino)-2-oxoethyl)amino)piperidine-1-carboxylate (88a) (660 mg, 1.65 mmol) with 2-(3-carbamoyl-1H-indazol-1-yl)acetic acid (2e) (398 mg, 1.82 mmol) according to the procedure reported in step-3 of Scheme 2 gave after workup and purification by flash column chromatography [silica (12 g), eluting with CMA80 in $CHCl_3$ 0 to 60%] tert-butyl 4-(2-(3-carbamoyl-1H-indazol-1-yl)-N-(2-((3-chloro-2-fluorobenzyl)amino)-2-oxoethyl)acetamido)piperidine-1-carboxylate (88b) (442 mg, 0.74 mmol, 45% yield) as a white solid; NMR (300 MHz, DMSO-$d_6$) δ 8.78 (t, J=5.7 Hz) and 8.36 (t, J=5.8 Hz) (2t, 1H), 8.18 (m, 1H), 7.71 (m, 1H), 7.60-7.06 (m, 7H), 5.67 and 5.48 (2s, 2H), 4.46 (d, J=3.7 Hz) and 4.31 (d, J=4.9 Hz) (2d, 2H), 4.21 and 3.86 (2s, 2H), 4.37-3.90 (m, 3H), 2.77 (m, 2H), 1.40 (m, 13H); $^{19}F$ NMR (282 MHz, DMSO) δ −121.12, −121.67; MS (ES+): 623.6 & 625.7 (M+Na); [based on NMR, this compound is a mixture of rotamers 2:1 ratio].

Scheme 89

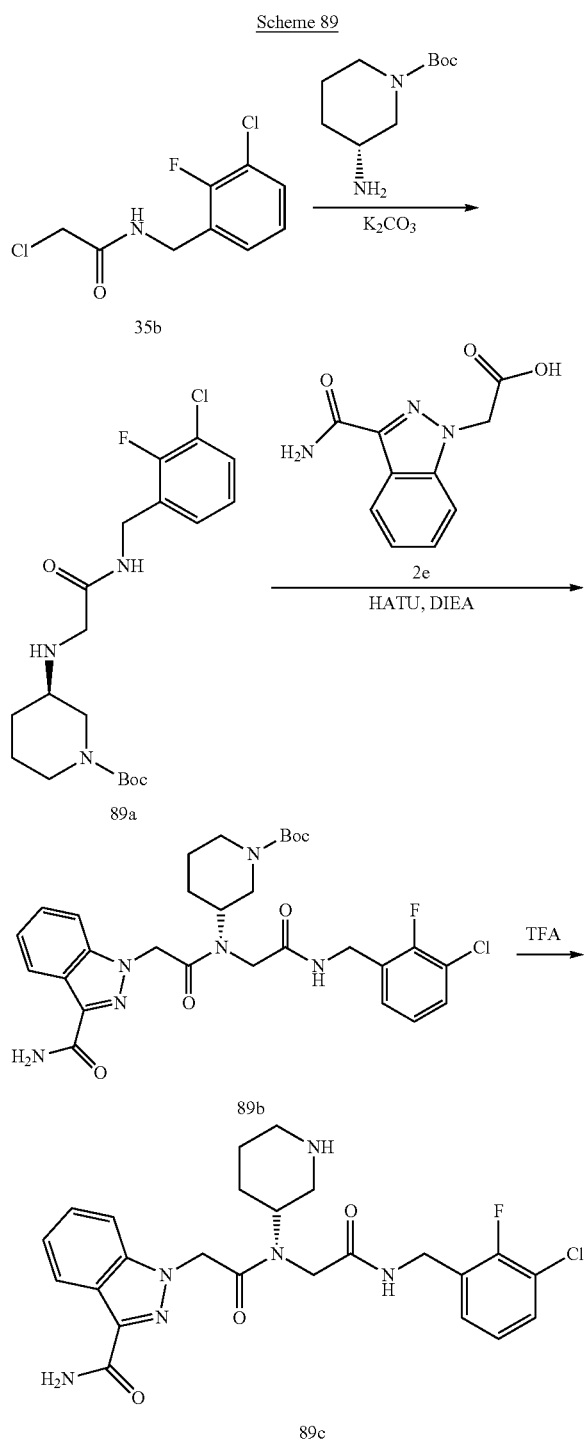

Preparation of (R)-1-(2-((2-((3-chloro-2-fluorobenzyl)amino)-2-oxoethyl)(piperidin-3-yl)amino)-2-oxoethyl)-1H-indazole-3-carboxamide (89c)

Step-1: Preparation of (R)-tert-butyl 3-((2-((3-chloro-2-fluorobenzyl)amino)-2-oxoethyl)amino)piperidine-1-carboxylate (89a)

Reaction of 2-chloro-N-(3-chloro-2-fluorobenzyl)acetamide (35b) (500 mg, 5.3 mmol) with (R)-tert-butyl 3-aminopiperidine-1-carboxylate (1.06 g, 5.3 mmol) according to the procedure reported in step-2 of Scheme 35 gave after workup and purification by flash column chromatography [silica (12 g), eluting with EtOAc/MeOH (9:1) in hexane 0 to 60%] (R)-tert-butyl 3-((2-((3-chloro-2-fluorobenzyl)amino)-2-oxoethyl)amino)piperidine-1-carboxylate (89a) (850 mg, 2.13 mmol, 100%) as a yellow oil; MS (ES+): 400.5 (M+1); MS (ES−): 398.4 (M−1).

Step-2: Preparation of (R)-tert-butyl 3-(2-(3-carbamoyl-1H-indazol-1-yl)-N-(2-((3-chloro-2-fluorobenzyl)amino)-2-oxoethyl)acetamido)piperidine-1-carboxylate (89b)

Reaction of (R)-tert-butyl 3-((2-((3-chloro-2-fluorobenzyl)amino)-2-oxoethyl)amino)piperidine-1-carboxylate (89a) (710 mg, 1.78 mmol) with 2-(3-carbamoyl-1H-indazol-1-yl)acetic acid (2e) (428 mg, 1.95 mmol) according to the procedure reported in step-3 of Scheme 2 gave after workup and purification by flash column chromatography [silica (12 g), eluting with CMA80 in CHCl$_3$ 0 to 60%] (R)-tert-butyl 3-(2-(3-carbamoyl-1H-indazol-1-yl)-N-(2-((3-chloro-2-fluorobenzyl)amino)-2-oxoethyl)acetamido)piperidine-1-carboxylate (89b) (520 mg, 0.87 mmol, 49% yield) as a white solid. MS (ES+): 602.6 (M+1).

Step-3: Preparation of (R)-1-(2-((2-((3-chloro-2-fluorobenzyl)amino)-2-oxoethyl)(piperidin-3-yl)amino)-2-oxoethyl)-1H-indazole-3-carboxamide (89c)

Reaction of (R)-tert-butyl 3-(2-(3-carbamoyl-1H-indazol-1-yl)-N-(2-((3-chloro-2-fluorobenzyl)amino)-2-oxoethyl)acetamido)piperidine-1-carboxylate (89b) (495 mg, 0.82 mmol) with TFA (0.32 mL, 4.12 mmol) according to the procedure reported in step-2 of Scheme 2 gave after workup and purification by flash column chromatography [silica (12 g), eluting with CMA80 in CHCl$_3$ 0 to 60%] (R)-1-(2-((2-((3-chloro-2-fluorobenzyl)amino)-2-oxoethyl)(piperidin-3-yl)-amino)-2-oxoethyl)-1H-indazole-3-carboxamide (89c) (300 mg, 0.6 mmol, 73% yield) as a white solid; $^1$H NMR (300 MHz, DMSO-d$_6$) δ 8.82 (t, J=5.6 Hz) and 8.37 (t, J=5.9H) (2t, 1H), 8.18 (d, J=8.1 Hz, 1H), 7.78-7.64 (m, 1H), 7.63-7.03 (m, 7H), 5.75-5.51 (m) and 5.45 (s) (2H), 4.52-4.38 (m, 1H), 4.31 (d, J=5.7 Hz) and 4.22 (d, J=4.6 Hz) (2d, 2H), 4.17-4.04 and 3.85-3.75 (2m, 1H), 3.89 and 3.17 (2s, 2H), 3.12-2.65 (m, 2H), 2.45-2.18 (m, 2H), 1.96-1.25 (m, 4H); $^{19}$F NMR (282 MHz, DMSO-d$_6$) δ −73.45 (TFA peak), −121.17, −121.70; MS (ES+) 501.5 (M+1); 499.5 (M−1); [based on NMR, this compound is a mixture of rotamers 2:1 ratio].

Scheme 90

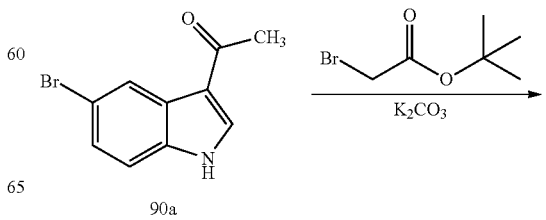

1H), 8.32 (d, J=2.0 Hz, 1H), 7.54 (d, J=8.8, 1H), 7.40 (dd, J=8.7, 2.0 Hz, 1H), 5.15 (s, 2H), 2.44 (s, 3H); MS (ES+): 296.2, 298.2 (M+2); (ES−) 294.2, 296.2 (M−2).

Step-3: Preparation of 2-(3-acetyl-5-bromo-1H-indol-1-yl)-N-(2-((3-chloro-2-fluorobenzyl)amino)-2-oxoethyl)-N-isopropylacetamide (90d)

Reaction of 2-(3-acetyl-5-bromo-1H-indol-1-yl)acetic acid (90c) (1.6 g, 5.4 mmol) with N-(3-chloro-2-fluorobenzyl)-2-(isopropylamino)acetamide (19c) (1.4 g, 5.4 mmol) according to the procedure reported in step-3 of Scheme 2 gave after workup and purification by flash column [silica gel (40 g), eluting with MeOH in $CHCl_3$ 0-100%] 2-(3-acetyl-5-bromo-1H-indol-1-yl)-N-(2-((3-chloro-2-fluorobenzyl)amino)-2-oxoethyl)-N-isopropylacetamide (90d) (1.67 g, 3.11 mmol, 58% yield) as a pale yellow solid as of mixture of two rotamers; $^1$H NMR (300 MHz, DMSO-$d_6$) δ 8.83 (t, J=5.7 Hz, 1H), 8.36-8.28 (m, 2H, another triplet of amide proton of one of the two rotamers were overlapped in this region), 7.56-7.29 (m, 4H), 7.22 (td, J=7.9, 1.1 Hz) & 6.99 (td, J=7.9, 1.1 Hz) (2td, 1H), 5.37 & 5.18 (2s, 2H), 4.65-4.51 & 4.27-4.18 (2m, 1H), 4.47 (d, J=5.6 Hz) & 4.33 (d, J=5.8 Hz) (2d, 2H), 4.17 & 3.84 (2s, 2H), 2.44 & 2.42 (2s, 3H), 1.25 (d, J=6.4 Hz) & 0.99 (d, J=6.8 Hz) (2d, 6H); $^{19}$F NMR (282 MHz, DMSO-$d_6$) δ −121.19, −121.76; MS (ES+): 536.49 and 538.49 (M+1), 558.5 and 560.5 (M+Na); (ES−): 534.36 and 536.41 (M−1), 570.4 and 572.4 (M+Cl).

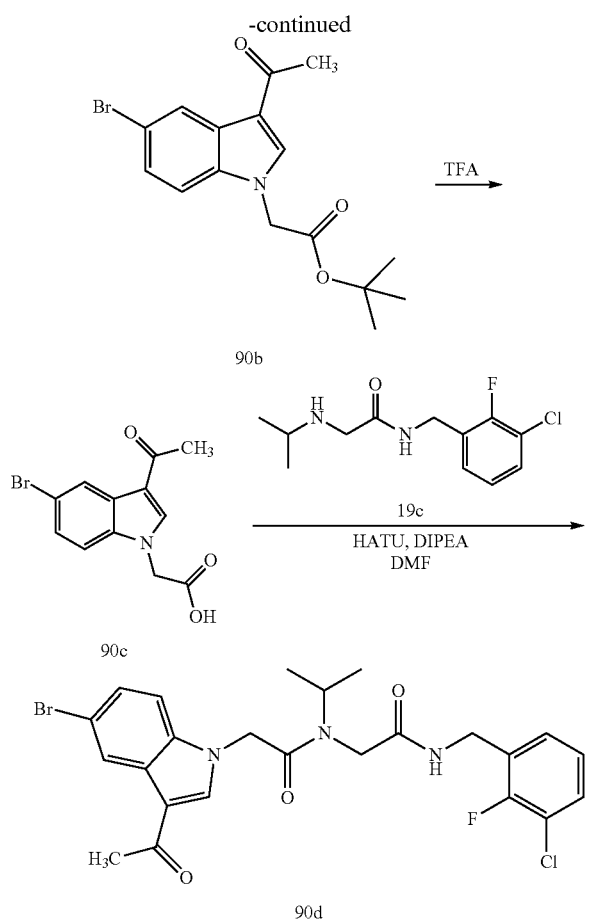

Preparation of 2-(3-acetyl-5-bromo-1H-indol-1-yl)-N-(2-((3-chloro-2-fluorobenzyl)amino)-2-oxoethyl)-N-isopropylacetamide (90d)

Step-1: Preparation of tert-butyl 2-(3-acetyl-5-bromo-1H-indol-1-yl)acetate (90b)

Reaction of 1-(5-bromo-1H-indol-3-yl)ethanone (90a) (prepared according to the procedure reported By Denis, Jean-Noeel et al in PCT Int. Appl., WO 2013/014102, 8.24 g, 34.6 mmol) with tert-butyl 2-bromoacetate (6.14 mL, 41.5 mmol) according to the procedure reported in step-1 of Scheme 56 gave after workup tert-butyl 2-(3-acetyl-5-bromo-1H-indol-1-yl)acetate (90b) (11.26 g, 32.0 mmol, 92% yield) as an off-white solid; $^1$H NMR (300 MHz, DMSO-$d_6$) δ 8.38 (s, 1H), 8.35-8.29 (m, 1H), 7.54-7.36 (m, 2H), 5.14 (s, 2H), 2.44 (s, 3H), 1.43 (s, 9H); MS (ES+): 352.2, 354.3 (M+2), 374.4, 376.3 (M+Na); (ES−): 350.3, 352.3 (M−2), 386.3, 388.3 (M+Cl).

Step-2: Preparation of 2-(3-acetyl-5-bromo-1H-indol-1-yl)acetic acid (90c)

Reaction of tert-butyl 2-(3-acetyl-5-bromo-1H-indol-1-yl)acetate (90b) (11.15 g, 31.7 mmol) with TFA (48.8 mL, 633 mmol) according to the procedure reported in step-2 of Scheme 2 gave after workup 2-(3-acetyl-5-bromo-1H-indol-1-yl)acetic acid (90c) (11.38 g, 38.4 mmol, 88% yield) as a pink solid in the form of TFA adduct; $^1$H NMR (300 MHz, DMSO-$d_6$) δ 13.33 (bs, 1H, $D_2O$ exchangeable), 8.40 (s, Scheme 91

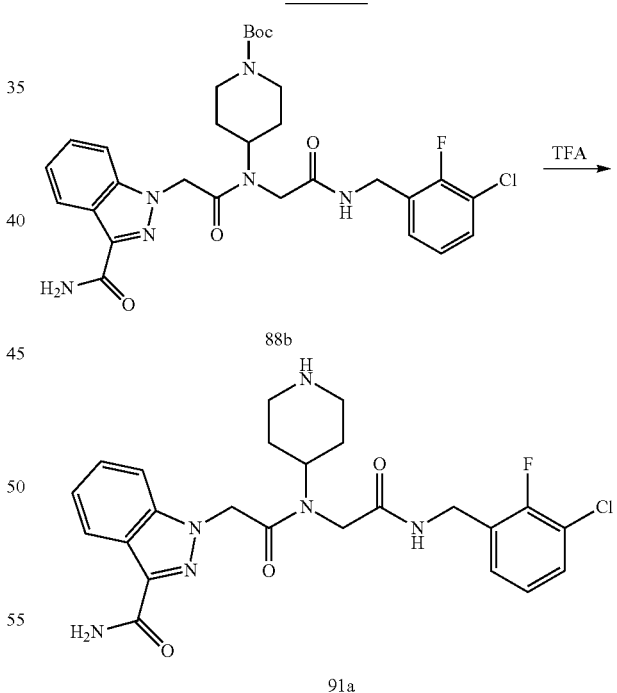

Preparation of 1-(2-((2-((3-chloro-2-fluorobenzyl)amino)-2-oxoethyl)(piperidin-4-yl)-amino)-2-oxoethyl)-1H-indazole-3-carboxamide (91a)

Reaction of tert-butyl 4-(2-(3-carbamoyl-1H-indazol-1-yl)-N-(2-((3-chloro-2-fluorobenzyl)amino)-2-oxoethyl)acetamido)piperidine-1-carboxylate (88b) (500 mg, 0.92 mmol) with TFA (0.35 mL, 4.58 mmol) according to the procedure reported in step-2 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)(piperidin-4-yl)-amino)-2-oxoethyl)-1H-indazole-3-carboxamide (91a) (386 mg, 0.77 mmol, 84% yield) as a white solid; $^1$H NMR (300 MHz, DMSO-d$_6$) δ 8.89 (t, J=5.6 Hz) and 8.42 (t, J=5.9 Hz) (2t, 1H), 8.23-8.12 (m, 1H), 7.77-7.64 (m, 1H), 7.64-7.04 (m, 7H), 5.65 and 5.44 (s, 2H), 4.47 (d, J=5.4 Hz) and 4.32 (d, J=5.7 Hz) (2d, 2H), 4.21 and 3.84 (2s, 2H), 4.32-4.30 and 4.12-3.95 (2m, 1H), 3.22-3.01 (m, 2H), 2.85-2.69 and 2.69-2.56 (2m, 2H), 1.94-1.40 (m, 4H); $^{19}$F NMR (282 MHz, DMSO) δ −73.53 (TFA peak), −121.18, −121.66; MS (ES+): 501.6 (M+1); 499.5 (M−1); [based on NMR, this compound is a mixture of rotamers 3:2 ratio].

Scheme 92

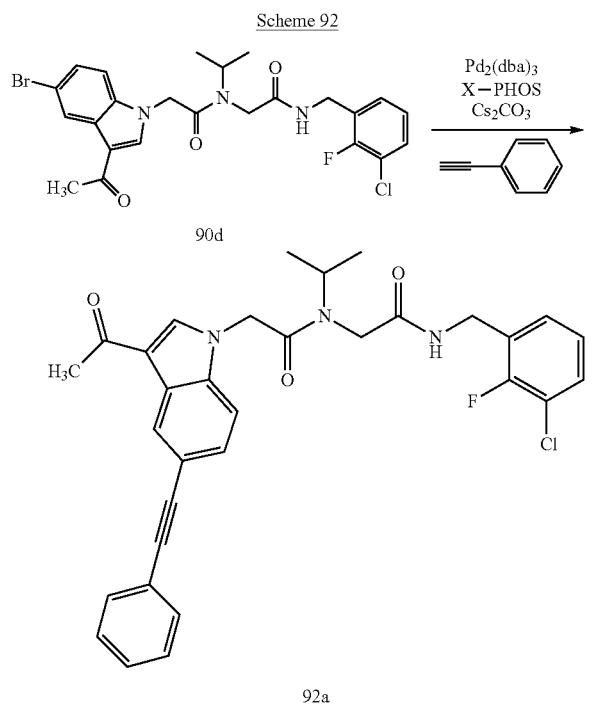

90d

92a

Preparation of 2-(3-acetyl-5-(phenylethynyl)-1H-indol-1-yl)-N-(2-((3-chloro-2-fluorobenzyl)amino)-2-oxoethyl)-N-isopropylacetamide (92a)

A solid mixture of 2-(3-acetyl-5-bromo-1H-indol-1-yl)-N-(2-((3-chloro-2-fluorobenzyl)amino)-2-oxoethyl)-N-isopropylacetamide (90d) (113 mg, 0.21 mmol), Cs$_2$CO$_3$ (69 mg, 0.21 mmol), dicyclohexyl(2',4',6'-triisopropylbiphenyl-2-yl)phosphine (X-PHOS, 20 mg, 0.04 mmol), Pd$_2$(dba)$_3$ (19 mg, 0.02 mmol) was purged with positive flow of nitrogen for 10 min, then added phenylacetylene (0.023 mL, 0.21 mmol) and anhydrous toluene (10 mL) under a positive flow of nitrogen. The reaction flask was heated at 90° C. for 8 h. The reaction mixture was diluted with EtOAc (50 mL), filtered through a Celite pad, subsequently pad was rinsed with EtOAc (3×20 mL). The filtrate was washed with brine, dried, filtered and evaporated to dryness. The residue was purified by flash column chromatography [silica gel (24 g), eluting with MeOH in CHCl$_3$ 0 to 20%] to afford 2-(3-acetyl-5-(phenylethynyl)-1H-indol-1-yl)-N-(2-((3-chloro-2-fluorobenzyl)amino)-2-oxoethyl)-N-isopropylacetamide (92a) (63 mg, 54% yield) as a brown solid as a mixture of two rotamers; $^1$H NMR (300 MHz, DMSO-d$_6$) δ 8.84 (t, J=5.7 Hz) and 8.43-8.26 (m) (3H), 7.63-7.34 (m, 9H), 7.30-6.96 (m, 1H), 5.39 & 5.21 (2s, 2H), 4.67-4.53 & 4.32-4.19 (2m, 1H), 4.48 (d, J=5.9 Hz) & 4.34 (d, J=5.8 Hz) (2d, 2H), 4.19 & 3.86 (2s, 2H), 2.46 & 2.44 (2s, 3H), 1.26 (d, J=6.4 Hz) & 1.01 (d, J=6.8 Hz) (2d, 6H); $^{19}$F NMR (282 MHz, DMSO-d$_6$) δ −121.18, −121.77; MS (ES+): 558.7 & 560.6 (M+1); (ES−): 556.6 & 558.6 (M−1).

Scheme 93

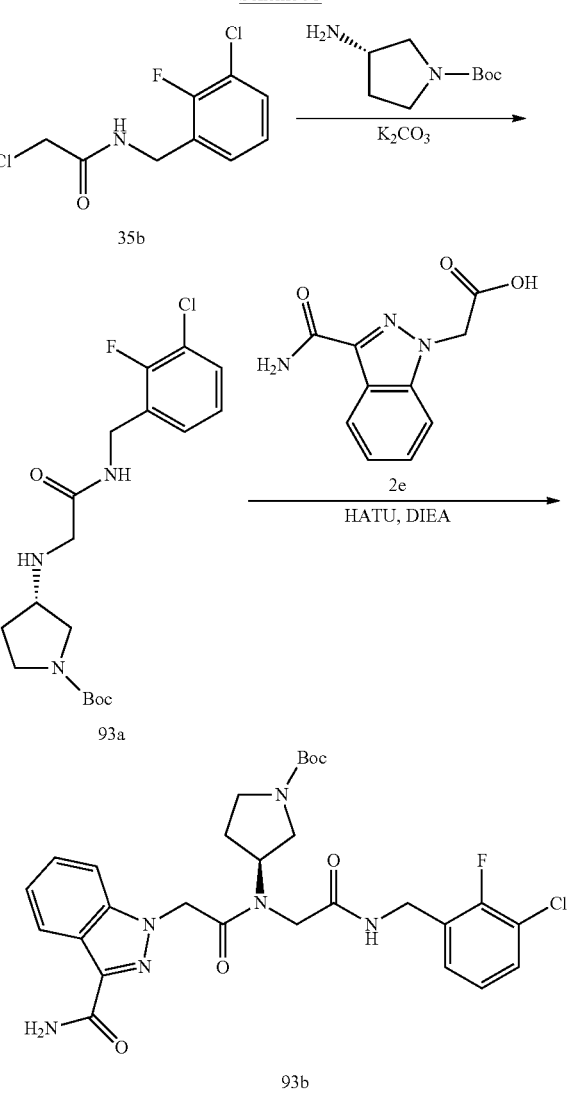

35b

93a

93b

Preparation of (S)-tert-butyl 3-(2-(3-carbamoyl-1H-indazol-1-yl)-N-(2-((3-chloro-2-fluorobenzyl)amino)-2-oxoethyl)acetamido)pyrrolidine-1-carboxylate (93b)

Step-1: Preparation of (S)-tert-butyl 3-((2-((3-chloro-2-fluorobenzyl)amino)-2-oxoethyl)amino)pyrrolidine-1-carboxylate (93a)

Reaction of 2-chloro-N-(3-chloro-2-fluorobenzyl)acetamide (35b) (350 mg, 1.48 mmol) with (S)-tert-butyl 3-aminopyrrolidine-1-carboxylate (690 mg, 3.71 mmol) according to the procedure reported in step-2 of Scheme 35 gave after workup and purification by flash column chromatography [silica (12 g), eluting with EtOAc/MeOH (9:1) in hexane 0 to 60%] (5)-tert-butyl 3-((2-((3-chloro-2-fluorobenzyl)amino)-2-oxoethyl)amino)pyrrolidine-1-carboxylate (93a) (500 mg, 1.3 mmol, 87%) as a yellow oil; MS (ES+): 386.5 (M+1).

Step-2: Preparation of (S)-tert-butyl 3-(2-(3-carbamoyl-1H-indazol-1-yl)-N-(2-((3-chloro-2-fluorobenzyl)amino)-2-oxoethyl)acetamido)pyrrolidine-1-carboxylate (93b)

Reaction of (5)-tert-butyl 3-((2-((3-chloro-2-fluorobenzyl)amino)-2-oxoethyl)amino)pyrrolidine-1-carboxylate (93a) (300 mg, 0.78 mmol) with 2-(3-carbamoyl-1H-indazol-1-yl)acetic acid (2e) (187 mg, 0.86 mmol) according to the procedure reported in step-3 of Scheme 2 gave after workup and purification by flash column chromatography [silica (12 g), eluting with CMA80 in CHCl$_3$ 0 to 60%] (5)-tert-butyl 3-(2-(3-carbamoyl-1H-indazol-1-yl)-N-(2-((3-chloro-2-fluorobenzyl)amino)-2-oxoethyl)acetamido)pyrrolidine-1-carboxylate (93b) (352 mg, 0.6 mmol, 77% yield) as a white solid; $^1$H NMR (300 MHz, DMSO-d$_6$) δ 8.83 (t, J=5.6 Hz) and 8.44 (t, J=5.0 Hz) (2t, 1H), 8.22-8.13 (m, 1H), 7.77-7.65 (m, 1H), 7.64-7.01 (m, 7H), 5.70 and 5.42 (2s, 2H), 4.84-4.63 (m, 1H), 4.47 (d, J=5.1 Hz) and 4.31 (d, J=5.7 Hz) (2d, 2H), 4.26 and 3.91 (2s, 2H), 3.46-2.95 (m, 2H), 2.19-1.80 (m, 2H), 1.41 and 1.37 (2s, 9H), 0.89-0.77 (m, 2H); $^{19}$F NMR (282 MHz, DMSO-d$_6$) δ −121.24, −121.68; MS (ES+): 587.6 (M+1); MS (ES−): 585.6 (M−1); [based on NMR, this compound is a mixture of rotamers]

Scheme 94

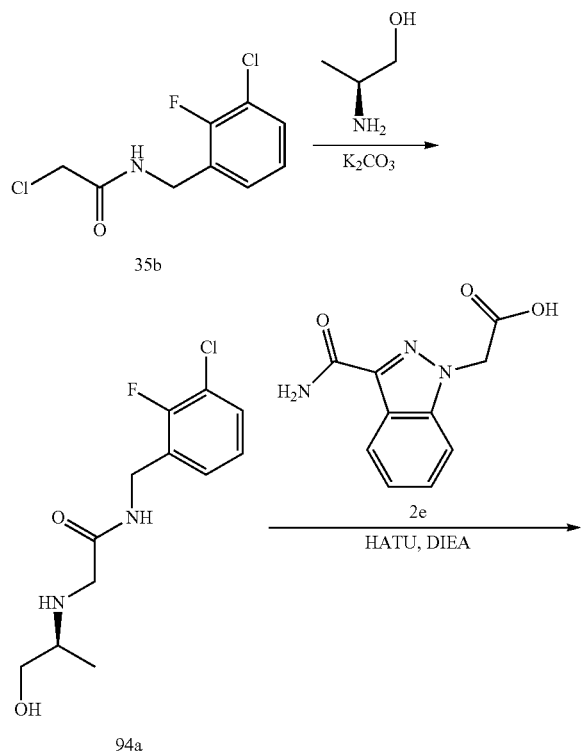

94a

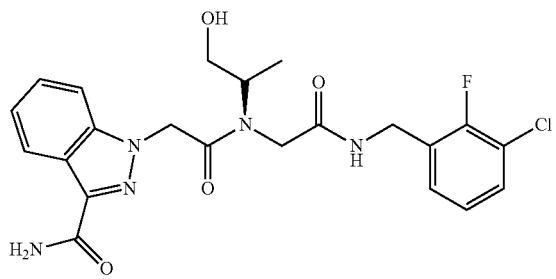

94b

Preparation of (S)-1-(2-((2-((3-chloro-2-fluorobenzyl)amino)-2-oxoethyl)(1-hydroxypropan-2-yl)amino)-2-oxoethyl)-1H-indazole-3-carboxamide (94b)

Step-1: Preparation of (S)—N-(3-chloro-2-fluorobenzyl)-2-((1-hydroxypropan-2-yl)amino)acetamide (94a)

Reaction of 2-chloro-N-(3-chloro-2-fluorobenzyl)acetamide (35b) (350 mg, 1.48 mmol) with (S)-2-aminopropan-1-ol (278 mg, 3.71 mmol) according to the procedure reported in step-2 of Scheme 35 gave after workup and purification by flash column chromatography [silica (12 g), eluting with EtOAc/MeOH (9:1) in hexane 0 to 60%] (S)—N-(3-chloro-2-fluorobenzyl)-2-((1-hydroxypropan-2-yl)amino)acetamide (94a) (200 mg, 0.73 mmol, 49%) as a yellow oil; MS (ES+): 275.4, 277.4 (M+1, M+3).

Step-2: Preparation of (S)-1-(2-((2-((3-chloro-2-fluorobenzyl)amino)-2-oxoethyl)(1-hydroxypropan-2-yl)amino)-2-oxoethyl)-1H-indazole-3-carboxamide (94b)

Reaction of (S)—N-(3-chloro-2-fluorobenzyl)-2-((1-hydroxypropan-2-yl)amino)acetamide (94a) (200 mg, 0.73 mmol) with 2-(3-carbamoyl-1H-indazol-1-yl)acetic acid (2e) (176 mg, 0.8 mmol) according to the procedure reported in step-3 of Scheme 2 gave after workup and purification by flash column chromatography [silica (12 g), eluting with CMA80 in CHCl$_3$ 0 to 60%] (S)-1-(2-((2-((3-chloro-2-fluorobenzyl)amino)-2-oxo ethyl)(1-hydroxy propan-2-yl)amino)-2-oxoethyl)-1H-indazole-3-carboxamide (94b) (210 mg, 0.44 mmol, 61% yield) as a white solid; $^1$H NMR (300 MHz, DMSO-d$_6$) δ 8.90-8.46 (m, 1H), 8.25-8.12 (m, 1H), 7.72 (s, 1H), 7.60-6.89 (m, 7H), 5.83-5.31 (m, 3H), 4.86-4.11 (m, 4H), 4.00-3.72 (m, 1H), 3.55-3.39 (m, 1H), 3.32-3.13 (m, 1H), 1.17-0.88 (m, 3H); $^{19}$F NMR (282 MHz, DMSO) δ −121.26, −121.65; MS (ES+): 476.5 (M+1); (ES−): 474.5 (M−1); [based on NMR, this compound is a mixture of rotamers]

Scheme 95

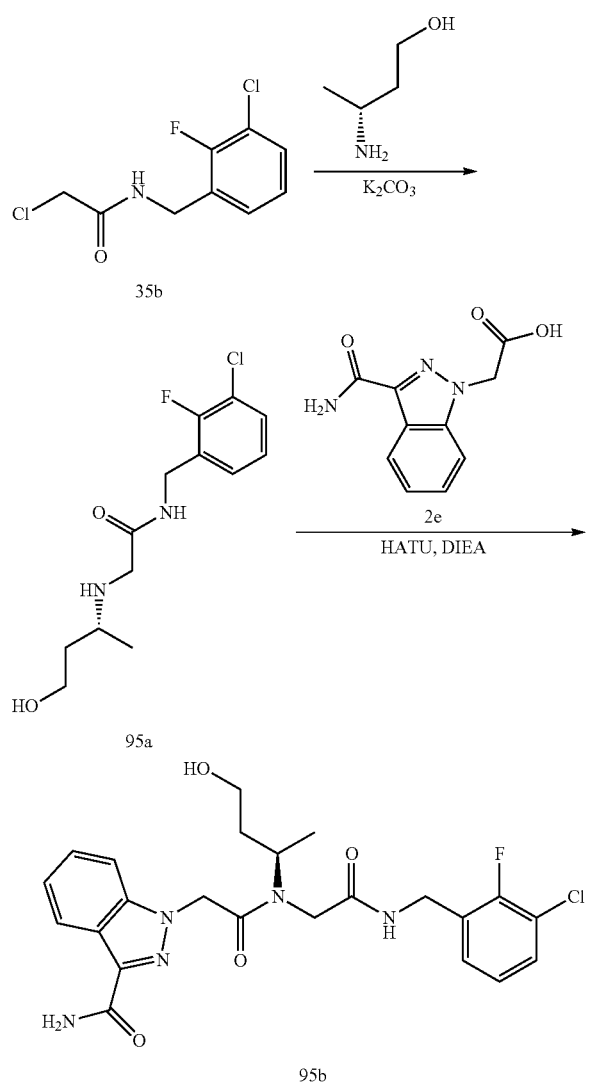

Preparation of (R)-1-(2-((2-((3-chloro-2-fluorobenzyl)amino)-2-oxoethyl)(4-hydroxybutan-2-yl)amino)-2-oxoethyl)-1H-indazole-3-carboxamide (95b)

Step-1: Preparation of (R)—N-(3-chloro-2-fluorobenzyl)-2-((4-hydroxybutan-2-yl)amino)acetamide (95a)

Reaction of 2-chloro-N-(3-chloro-2-fluorobenzyl)acetamide (35b) (500 mg, 2.12 mmol) with (R)-3-aminobutan-1-ol (378 mg, 4.24 mmol) according to the procedure reported in step-2 of Scheme 35 gave after workup and purification by flash column chromatography [silica (12 g), eluting with EtOAc/MeOH (9:1) in hexane 0 to 60%] (R)—N-(3-chloro-2-fluorobenzyl)-2-((4-hydroxybutan-2-yl)amino)acetamide (95a) (150 mg, 0.52 mmol, 25%) as a yellow oil; MS (ES+): 289.4 (M+1); MS (ES-): 287.3 (M-1).

Step-2: Preparation of (R)-1-(2-((2-((3-chloro-2-fluorobenzyl)amino)-2-oxoethyl)(4-hydroxy butan-2-yl)amino)-2-oxo ethyl)-1H-indazole-3-carboxamide (95b)

Reaction of (R)—N-(3-chloro-2-fluorobenzyl)-2-((4-hydroxybutan-2-yl)amino)acetamide (95a) (150 mg, 0.52 mmol) with 2-(3-carbamoyl-1H-indazol-1-yl)acetic acid (2e) (125 mg, 0.57 mmol) according to the procedure reported in step-3 of Scheme 2 gave after workup and purification by flash column chromatography [silica (12 g), eluting with CMA80 in CHCl₃ 0 to 60%] (R)-1-(2-((2-((3-chloro-2-fluorobenzyl)amino)-2-oxoethyl)(4-hydroxybutan-2-yl)amino)-2-oxoethyl)-1H-indazole-3-carboxamide (95b) (43 mg, 0.088 mmol, 17% yield) as a white solid; $^1$H NMR (300 MHz, DMSO-d$_6$) δ 8.90-8.46 (m, 1H), 8.25-8.12 (m, 1H), 7.72 (s, 1H), 7.60-6.89 (m, 7H), 5.83-5.31 and 4.86-4.11 and 4.00-3.72 (3m, 8H), 3.55-3.39 and 3.32-3.13 (2m, 2H), 1.17-0.88 (m, 3H); $^{19}$F NMR (282 MHz, DMSO) δ -121.26, -121.77; MS (ES+): 490.5 (M+1); (ES-): 488.5 (M-1); [based on NMR, this compound is a mixture of rotamers 1:1 ratio].

Scheme 96

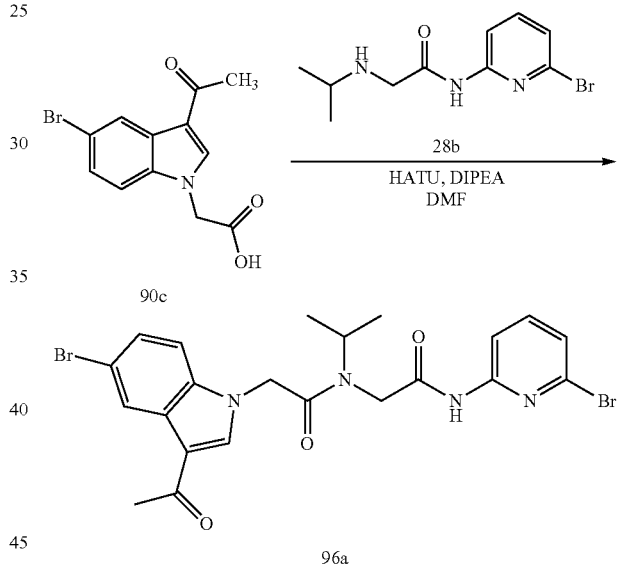

Preparation of 2-(3-acetyl-5-bromo-1H-indol-1-yl)-N-(2-((6-bromopyridin-2-yl)amino)-2-oxoethyl)-N-isopropylacetamide (96a)

Reaction of N-(6-bromopyridin-2-yl)-2-(isopropylamino)acetamide (28b) (1.1 g, 4.05 mmol) with 2-(3-acetyl-5-bromo-1H-indol-1-yl)acetic acid (90c) (1.2 g, 4.05 mmol) according to the procedure reported in step-3 of Scheme 2 gave after workup 2-(3-acetyl-5-bromo-1H-indol-1-yl)-N-(2-((6-bromopyridin-2-yl)amino)-2-oxoethyl)-N-isopropylacetamide (96a) (1.5 g, 2.73 mmol, 67% yield) as a white solid; $^1$H NMR (300 MHz, DMSO-d$_6$) (as a mixture of rotamers) δ 11.20 and 10.81 (2s, 1H), 8.36-8.28 (m, 2H), 8.17 and 8.01 (2d, J=8.1 Hz, 1H), 7.81 and 7.70 (2t, J=8.0 Hz, 1H), 7.48-7.27 (m, 3H), 5.41 and 5.20 (2s, 2H), 4.69-4.55 and 4.32-4.20 (2m, 1H), 4.42 and 4.04 (2s, 2H), 2.44 and 2.43 (2s, 3H), 1.26 and 1.03 (2d, J=6.4 Hz, 6H); MS (ES+): 551.4, 553.4 (M+1); MS (ES-): 583.4, 585.4 (M+Cl).

Scheme 97

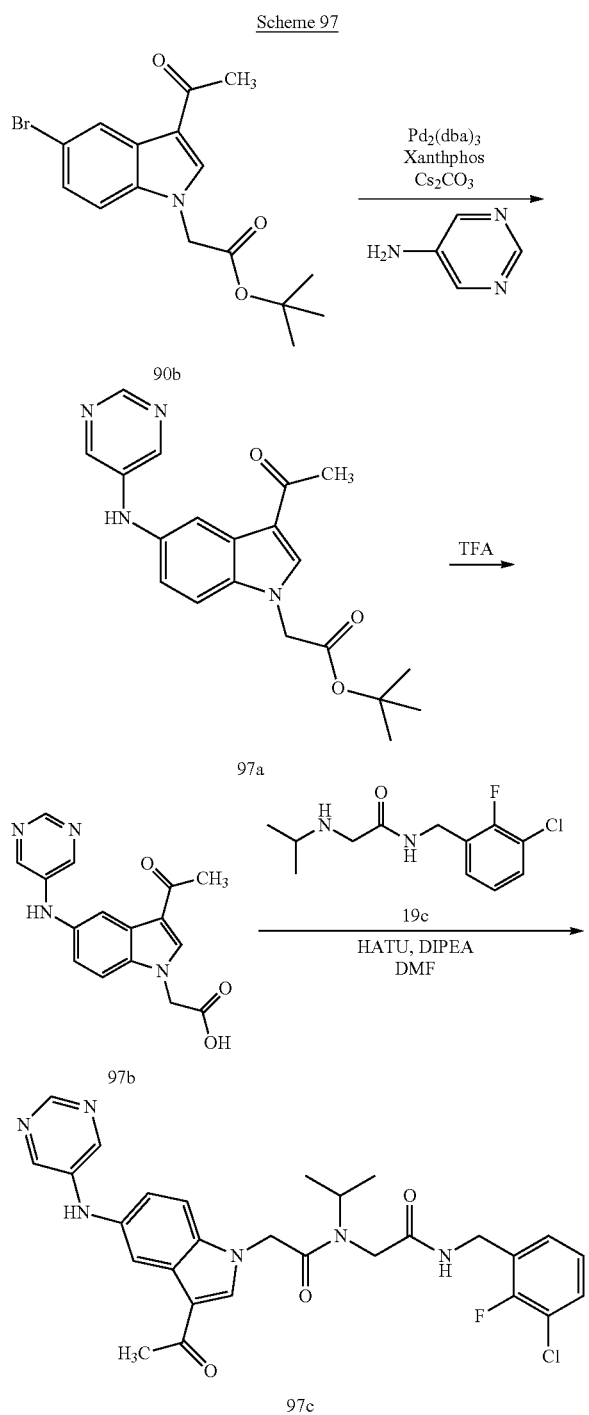

Preparation of 2-(3-acetyl-5-(pyrimidin-5-ylamino)-1H-indol-1-yl)-N-(2-((3-chloro-2-fluorobenzyl)amino)-2-oxoethyl)-N-isopropylacetamide (97c)

Step-1: Preparation of tert-butyl 2-(3-acetyl-5-(pyrimidin-5-ylamino)-1H-indol-1-yl)acetate (97a)

To a degassed DMF (12 mL) in a sealed reactor were added tert-butyl 2-(3-acetyl-5-bromo-1H-indol-1-yl)acetate (90b) (1.05 g, 2.98 mmol), cesium carbonate (1.94 g, 5.96 mmol), pyrimidin-5-amine (340 mg, 3.58 mmol), $Pd_2(dba)_3$ (273 mg, 0.3 mmol), (9,9-dimethyl-9H-xanthene-4,5-diyl)bis(diphenylphosphine) (Xanthphos, 172 mg, 0.3 mmol) and heated with stirring at 100° C. for 16 h. The mixture was cooled to room temperature, diluted with EtOAc (30 mL) and filtered over Celite pad. The pad was washed with EtOAc (2×15 mL) and combined filtrate was concentrated to give a crude residue which was purified by flash column chromatography [silica gel (40 g), eluting with CMA80 in $CHCl_3$ 0 to 20%] to afford tert-butyl 2-(3-acetyl-5-(pyrimidin-5-ylamino)-1H-indol-1-yl)acetate (97a) (0.34 g, 0.93 mmol, 31% yield) as light yellow solid; MS (ES+): 367.5 (M+1), MS (ES−): 401.4 (M+Cl).

Step-2: Preparation of 2-(3-acetyl-5-(pyrimidin-5-ylamino)-1H-indol-1-yl)acetic acid (97b)

Reaction of tert-butyl 2-(3-acetyl-5-(pyrimidin-5-ylamino)-1H-indol-1-yl)acetate (97a) (340 mg, 0.93 mmol) with TFA (1.43 mL, 18.56 mmol) according to the procedure reported in step-2 of Scheme 2 gave after workup 2-(3-acetyl-5-(pyrimidin-5-ylamino)-1H-indol-1-yl)acetic acid (97b) (250 mg, 0.81 mmol, 87% yield) as light orange solid. $^1$H NMR showed product as mixture of rotamers and data is corresponding to the major rotamer; $^1$H NMR (300 MHz, DMSO-$d_6$) δ 13.7-13.1 (bs, 1H, $D_2O$ exchangeable), 8.67-8.51 (m, 2H), 8.48 (s, 2H), 8.31 (s, 1H), 8.01 (d, J=2.2 Hz, 1H), 7.48 (d, J=8.8 Hz, 1H), 7.18-7.07 (m, 1H), 5.11 (s, 2H), 2.41 (s, 3H); MS (ES+) 311.4 (M+1), MS (ES−) 309.3 (M−1).

Step-3: Preparation of 2-(3-acetyl-5-(pyrimidin-5-ylamino)-1H-indol-1-yl)-N-(2-((3-chloro-2-fluorobenzyl)amino)-2-oxoethyl)-N-isopropylacetamide (97c)

Reaction of 2-(3-acetyl-5-(pyrimidin-5-ylamino)-1H-indol-1-yl)acetic acid (97b) (80 mg, 0.26 mmol) with N-(3-chloro-2-fluorobenzyl)-2-(isopropylamino)acetamide (19c) (67 mg, 0.26 mmol) according to the procedure reported in step-3 of Scheme 2 gave after workup and purification by flash column [silica gel (12 g), eluting with CMA-80 in $CHCl_3$ 0-100%] 2-(3-acetyl-5-(pyrimidin-5-ylamino)-1H-indol-1-yl)-N-(2-((3-chloro-2-fluorobenzyl)amino)-2-oxoethyl)-N-isopropylacetamide (97c) (68 mg, 0.12 mmol, 48% yield) as an off-white solid; $^1$H NMR (300 MHz, DMSO-$d_6$) (as a mixture of two rotamers) δ 8.83 and 8.35 (2t, J=5.8 Hz, 1H), 8.57 and 8.56 (2s, 1H), 8.49 (s, 1H), 8.47 (s, 2H), 8.25 and 8.20 (2s, 1H), 8.00 (d, J=2.2 Hz, 1H), 7.57-7.34 (m, 3H), 7.25-6.96 (m, 2H), 5.34 and 5.15 (2s, 2H), 4.69-4.51 and 4.28-4.21 (2m, 1H), 4.47 and 4.34 (2d, J=5.6 Hz, 2H), 4.18 and 3.85 (2s, 2H), 2.41 and 2.40 (2s, 3H), 1.25 and 1.00 (2d, J=6.8 Hz, 6H); $^{19}$F NMR (282 MHz, DMSO-$d_6$) (as a mixture of two rotamers) δ −121.18 and −121.77; MS (ES+): 551.6 (M+1), MS (ES−): 549.5 (M−1).

Scheme 98

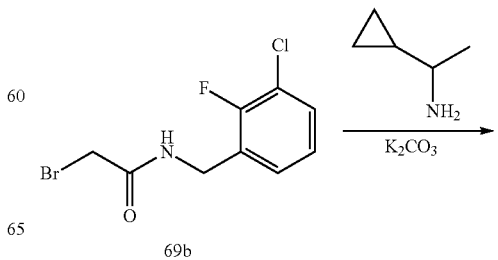

0.13-0.02 (m) (5H); $^{19}$F NMR (282 MHz, DMSO-$d_6$) δ −121.19, −121.75; MS (ES+): 486.5 (M+1), 508.5 (M+Na); (ES−) 484.5 (M−1), 520.5 (M+Cl).

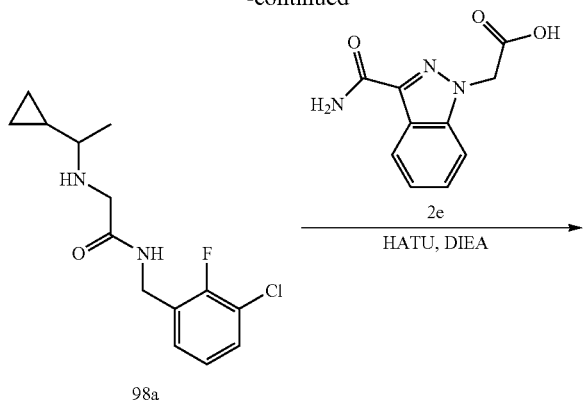

98a

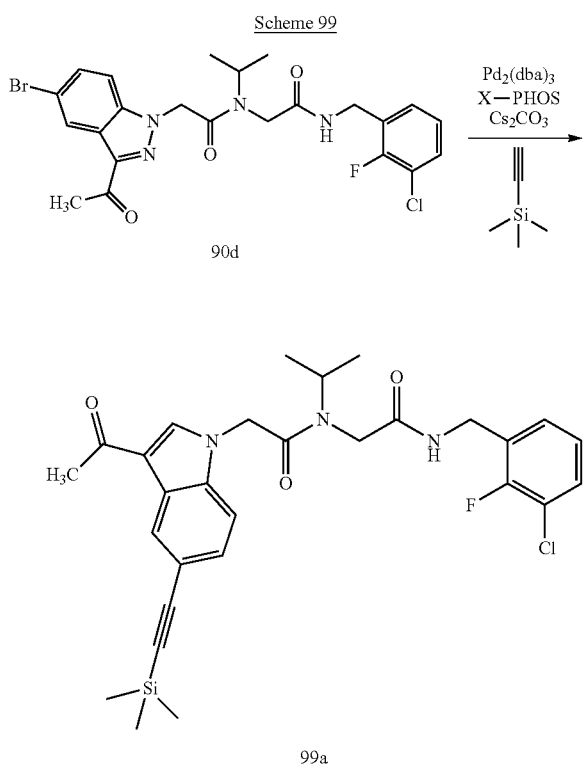

Preparation of 1-(2-((2-((3-chloro-2-fluorobenzyl)amino)-2-oxoethyl)(1-cyclopropylethyl)amino)-2-oxoethyl)-1H-indazole-3-carboxamide (98b)

Step-1: Preparation of N-(3-chloro-2-fluorobenzyl)-2-((1-cyclopropylethyl)amino)acetamide (98a)

Reaction of 2-bromo-N-(3-chloro-2-fluorobenzyl)acetamide (69b) (307 mg, 1.09 mmol) with 1-cyclopropylethanamine (93 mg, 1.09 mmol) according to the procedure reported in step-2 of Scheme 35 gave after workup N-(3-chloro-2-fluorobenzyl)-2-((1-cyclopropylethyl)amino)acetamide (98a) as a yellow oil which was used as such without further purification; MS (ES+): 285.4 (M+1); MS (ES−): 283.3 (M−1).

Step-2: Preparation of 1-(2-((2-((3-chloro-2-fluorobenzyl)amino)-2-oxoethyl)(1-cyclopropylethyl)amino)-2-oxoethyl)-1H-indazole-3-carboxamide (98b)

Reaction of N-(3-chloro-2-fluorobenzyl)-2-((1-cyclopropylethyl)amino)acetamide (98a) (312 mg, 1.1 mmol) with 2-(3-carbamoyl-1H-indazol-1-yl)acetic acid (2e) (288 mg, 1.32 mmol) according to the procedure reported in step-3 of Scheme 2 gave after workup and purification by flash column chromatography [silica (40 g), eluting with MeOH in CHCl$_3$ 0 to 10%] 1-(2-((2-((3-chloro-2-fluorobenzyl)amino)-2-oxoethyl)(1-cyclopropylethyl)amino)-2-oxoethyl)-1H-indazole-3-carboxamide (98b) (115 mg, 0.24 mmol, 22% yield) as a pale yellow solid as a mixture of two rotamers; $^1$H NMR (300 MHz, DMSO-$d_6$) δ 8.82 (t, J=5.7 Hz) and 8.30 (t, J=5.9 Hz) (2t, 1H), 8.22-8.13 (m, 1H), 7.74 and 7.70 (2s, 1H), 7.61-7.33 (m, 5H), 7.30-7.00 (m, 2H), 5.76-5.35 (m, 2H), 4.54-4.21 (m) and 3.96 (s) (4H), 3.80-3.46 (m, 1H), 1.27 (d, J=6.4 Hz) and 1.02 (d, J=6.8 Hz) (2d, 3H), 0.93-0.76 (m) and 0.64-0.37 (m) and 0.31-0.14 (m) and

Preparation of 2-(3-acetyl-5-((trimethylsilyl)ethynyl)-1H-indol-1-yl)-N-(2-((3-chloro-2-fluorobenzyl)amino)-2-oxoethyl)-N-isopropylacetamide (99a)

Reaction of 2-(3-acetyl-5-bromo-1H-indol-1-yl)-N-(2-((3-chloro-2-fluorobenzyl)amino)-2-oxoethyl)-N-isopropylacetamide (90d) (504 mg, 0.94 mmol) with ethynyltrimethylsilane (0.13 mL, 0.94 mmol) according to the procedure reported in scheme 92 gave after workup and purification by flash column chromatography [silica gel (40 g), eluting with MeOH in CHCl$_3$ 0 to 100%; second column: silica gel (12 g), eluting with MeOH/EtOAc (9:1) in hexanes 0 to 100%] 2-(3-acetyl-5-((trimethylsily)ethynyl)-1H-indol-1-yl)-N-(2-((3-chloro-2-fluorobenzyl)amino)-2-oxoethyl)-N-isopropylacetamide (99a) (21 mg, 0.038 mmol, 4% yield) as a yellow solid as a mixture of two rotamers; $^1$H NMR (300 MHz, DMSO-$d_6$) δ 8.84 (t, J=5.8 Hz) and 8.42-8.22 (m) (3H), 7.62-6.96 (m, 5H), 5.37 and 5.19 (2s, 2H), 4.65-4.52 and 4.26-4.21 (2m, 1H), 4.47 (d, J=5.6 Hz) and 4.32 (d, J=5.7 Hz) (2d, 2H), 4.17 and 3.84 (2s, 2H), 2.44 and 2.42 (2s, 3H), 1.25 (d, J=6.4 Hz) and 0.99 (d, J=6.8 Hz) (2d, 6H), 0.40-0.08 (m, 9H); $^{19}$F NMR (282 MHz, DMSO-$d_6$) δ −121.20, −121.77 (d, J=4.0 Hz); MS (ES+): 554.6 & 556.6 (M+1), 576.6 & 578.7 (M+Na); MS (ES−): 588.5 & 590.6 (M+Cl).

Scheme 100

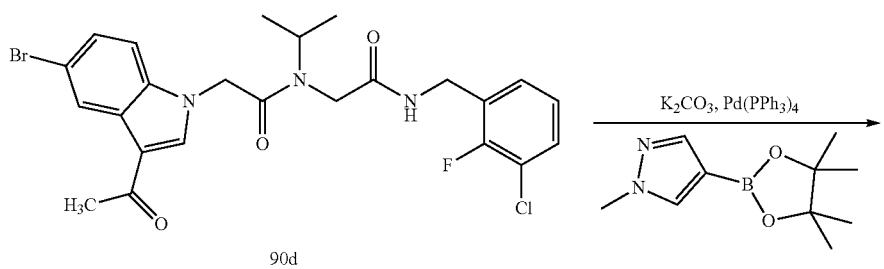

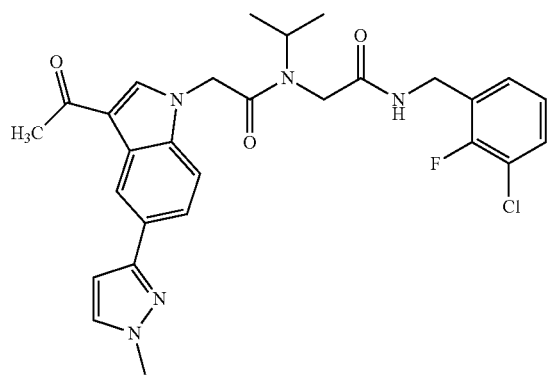

Preparation of 2-(3-acetyl-5-(1-methyl-1H-pyrazol-3-yl)-1H-indol-1-yl)-N-(2-((3-chloro-2-fluorobenzyl)amino)-2-oxoethyl)-N-isopropylacetamide (100a)

To a degassed solution of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol), 1-methyl-4-(4,4,5,5-tetramethyl-1,3,2-dioxaborolan-2-yl)-1H-pyrazole (70 mg, 0.335 mmol) in dioxane (4 mL) was added a solution of $K_2CO_3$ (1.12 mL, 0.56 mmol) in water (1 mL) followed by tetrakistriphenylphosphine Palladium(0) (32 mg, 0.028 mmol) and heated at 80° C. for 4 h. The mixture was cooled to room temperature and diluted with EtOAc (50 mL) and water (60 mL). The organic layer was separated washed with brine, dried, filtered and concentrated in vacuum. The residue obtained was purified by flash column chromatography [silica gel (12 g), eluting with CMA80 in $CHCl_3$ 0 to 30%] to afford 2-(3-acetyl-5-(1-methyl-1H-pyrazol-3-yl)-1H-indol-1-yl)-N-(2-((3-chloro-2-fluorobenzyl)amino)-2-oxoethyl)-N-isopropylacetamide (100a) (85 mg, 0.16 mmol, 57% yield) as a white solid; $^1$H NMR (300 MHz, DMSO-$d_6$) (a mixture of two rotamers in 2:1 ratio) δ 8.83 and 8.35 (2t, J=6.0 Hz, 1H), 8.31-8.27 (m, 1H), 8.24 and 8.19 (2s, 1H), 8.10 (s, 1H), 7.83-7.76 (m, 1H), 7.55-7.35 (m, 4H), 7.26-7.17 and 7.05-6.96 (2m, 1H), 5.34 and 5.16 (2s, 2H), 4.65-4.52 and 4.30-4.21 (2m, 1H), 4.48 and 4.34 (2d, J=5.6 Hz, 2H), 4.18 and 3.85 (2s, 2H), 3.88 and 3.87 (2s, 3H), 2.44 and 2.42 (2s, 3H), 1.25 and 1.00 (2d, J=6.4 Hz, 6H); NMR (282 MHz, DMSO-$d_6$) (a mixture of two rotamers) δ −121.19 and −121.79; MS (ES+): 538.6 (M+1), 560.6 (M+Na); MS (ES): 536.6 (M−1).

Scheme 101

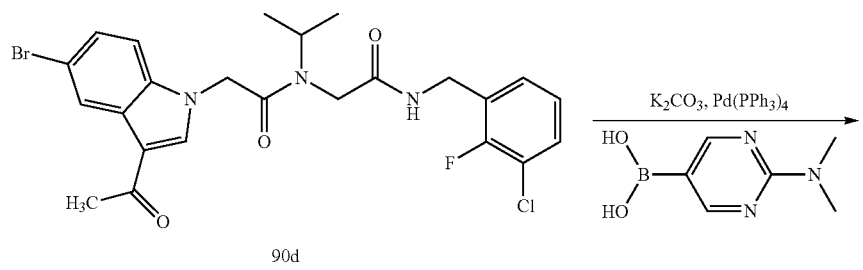

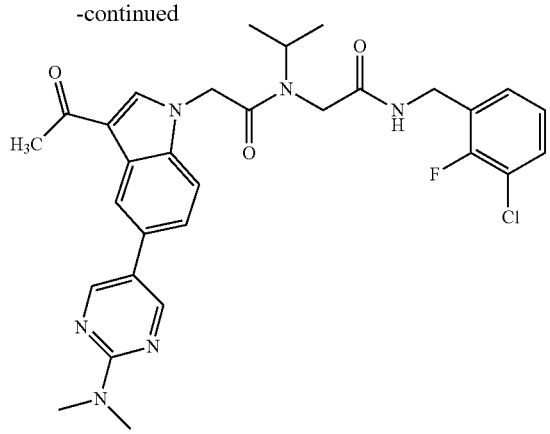

101a

Preparation of 2-(3-acetyl-5-(2-(dimethylamino)pyrimidin-5-yl)-1H-indol-1-yl)-N-(2-((3-chloro-2-fluorobenzyl)amino)-2-oxoethyl)-N-isopropylacetamide (101a)

Reaction of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol) with (2-(dimethylamino)pyrimidin-5-yl)boronic acid (56 mg, 0.34 mmol) according the procedure reported in Scheme 100 gave after workup and purification by flash column chromatography [silica gel (12 g), eluting with CMA80 in $CHCl_3$ 0 to 30%] 2-(3-acetyl-5-(2-(dimethylamino)pyrimidin-5-yl)-1H-indol-1-yl)-N-(2-((3-chloro-2-fluorobenzyl)amino)-2-oxoethyl)-N-isopropylacetamide (101a) (26 mg, 0.045 mmol, 16% yield) as a white solid; $^1$H NMR (300 MHz, DMSO-$d_6$) (mixture of rotamers) 8.83 and 8.35 (2t, J=5.2 Hz, 1H), 8.65 and 8.646 (2s, 2H), 8.31 and 8.26 (2s, 1H), 7.60-7.47 (m, 2H), 7.47-7.36 (m, 2H), 7.28-7.16 and 7.07-6.95 (2m, 2H), 5.38 and 5.20 (2s, 2H), 4.65-4.53 and 4.29-4.22 (2m, 1H), 4.48 and 4.33 (2d, J=5.6 Hz, 2H), 4.19 and 3.85 (2s, 2H), 3.25-3.10 (m, 6H), 2.45 and 2.44 (2s, 3H), 1.26 and 1.00 (d, J=6.8 Hz, 6H); $^{19}$F NMR (282 MHz, DMSO-$d_6$) (a mixture of two rotamers) δ −121.18 and −121.78; MS (ES+): 579.7 (M+1), 601.7 (M+Na), MS (ES−): 577.6 (M−1).

Scheme 102

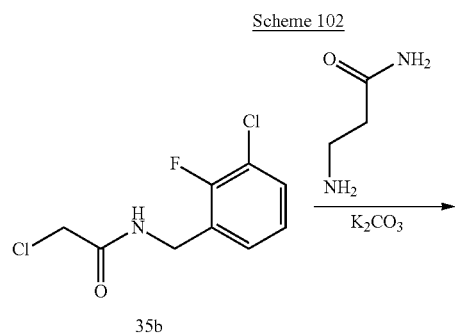

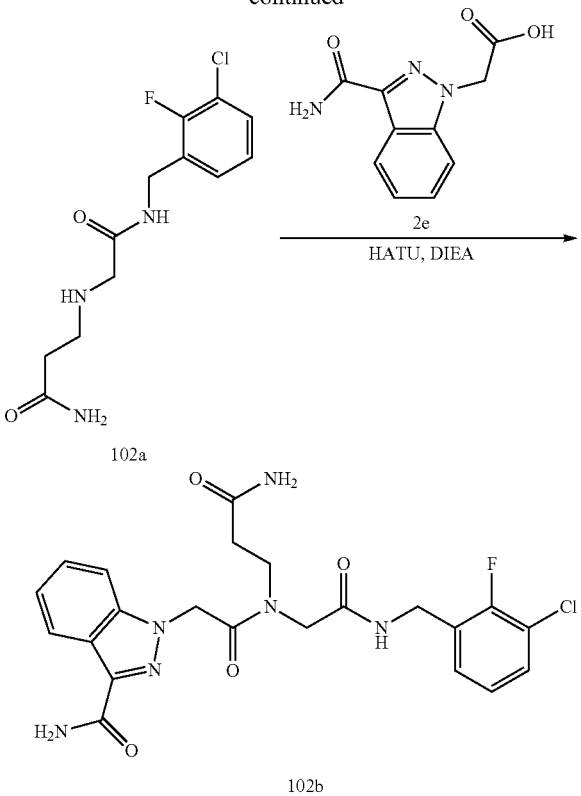

Preparation of 1-(2-((3-amino-3-oxopropyl)(2-((3-chloro-2-fluorobenzyl)amino)-2-oxoethyl)amino)-2-oxoethyl)-1H-indazole-3-carboxamide (102b)

Step-1: Preparation of 3-((2-((3-chloro-2-fluorobenzyl)amino)-2-oxoethyl)amino)propanamide (102a)

Reaction of 2-chloro-N-(3-chloro-2-fluorobenzyl)acetamide (35b) (350 mg, 1.48 mmol) with 3-aminopropanamide hydrochloride (462 mg, 3.71 mmol) according to the procedure reported in step-2 of Scheme 35 gave after workup and purification by flash column chromatography [silica (12 g), eluting with EtOAc/MeOH (9:1) in hexane 0 to 60%] 3-((2-((3-chloro-2-fluorobenzyl)amino)-2-oxo-ethyl)amino)propanamide (102a) (168 mg, 0.77 mmol, 52%) as a yellow oil; MS (ES+): 288.4 (M+1), 310.3 (M+Na); (ES−): 286.3 (M−1).

Step-2: Preparation of 1-(2-((3-amino-3-oxopropyl)(2-((3-chloro-2-fluorobenzyl)amino)-2-oxoethyl)amino)-2-oxoethyl)-1H-indazole-3-carboxamide (102b)

Reaction of 3-((2-((3-chloro-2-fluorobenzyl)amino)-2-oxoethyl)amino)propanamide (102a) (168 mg, 0.77 mmol) with 2-(3-carbamoyl-1H-indazol-1-yl)acetic acid (2e) (200 mg, 0.7 mmol) according to the procedure reported in step-3 of Scheme 2 gave after workup and trituration of crude residue with MeOH (5 mL) 1-(2-((3-amino-3-oxopropyl)(2-((3-chloro-2-fluorobenzyl)amino)-2-oxoethyl)amino)-2-oxoethyl)-1H-indazole-3-carboxamide (102b) (158 mg, 0.32 mmol, 47% yield) as a white solid; $^1$H NMR (300 MHz, DMSO-$d_6$) δ 8.89 (t, J=5.5 Hz) and 8.56 (t, J=5.8 Hz) (2t, 1H), 8.24-8.08 (m, 1H), 7.78-7.65 (m, 1H), 7.64-6.85 (m, 9H), 5.70 and 5.412 (s, 2H), 4.47 (d, J=5.5 Hz) and 4.38-4.24 (m) and 3.95 (s) (4H), 3.74 (t, J=6.3 Hz) and 3.41 (t, J=7.0 Hz) (2t, 2H), 2.28 (t, J=7.1 Hz, 1H); $^{19}$F NMR (282 MHz, DMSO-$d_6$) δ −121.36, −121.65; MS (ES+) 489.5 (M+1); (ES−): 487.4 (M−1); [based on NMR, this compound is a mixture of two rotamers 4:5 ratio].

CMA80 in CHCl$_3$ 0 to 30%] 2-(3-acetyl-5-(pyrimidin-5-ylamino)-1H-indol-1-yl)-N-(2-((6-bromopyridin-2-yl)amino)-2-oxoethyl)-N-isopropylacetamide (103a) (45 mg, 0.080 mmol, 35% yield) as an off-white solid as a mixture of rotamers; $^1$H NMR (300 MHz, DMSO-$d_6$) δ 11.20 and 10.83 (2s, 1H), 8.56 and 8.55 (2s, 1H), 8.50 and 8.49 (2s, 1H), 8.47 and 8.46 (2s, 2H), 8.25 and 8.24 (2s, 1H), 8.21-7.97 (m, 2H), 7.81 and 7.70 (2t, J=8.0 Hz, 1H), 7.48-7.27 (m, 2H), 7.17-7.07 (m, 1H), 5.37 and 5.18 (2s, 2H), 4.71-4.59 and 4.36-4.23 (2m, 1H), 4.43 and 4.05 (2s, 2H), 2.42 and 2.40 (2s, 3H), 1.26 and 1.04 (2d, J=6.8 Hz, 6H); MS (ES+): 564.5, 566.5 (M+1), MS (ES−): 562.5, 564.5 (M−1), 598.5, 600.5 (M+Cl).

Scheme 104

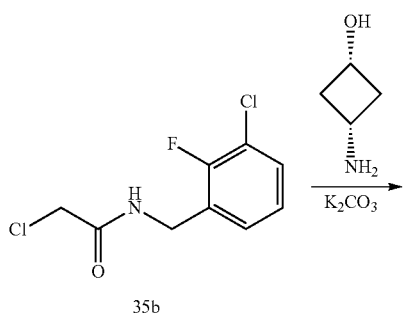

35b

Scheme 103

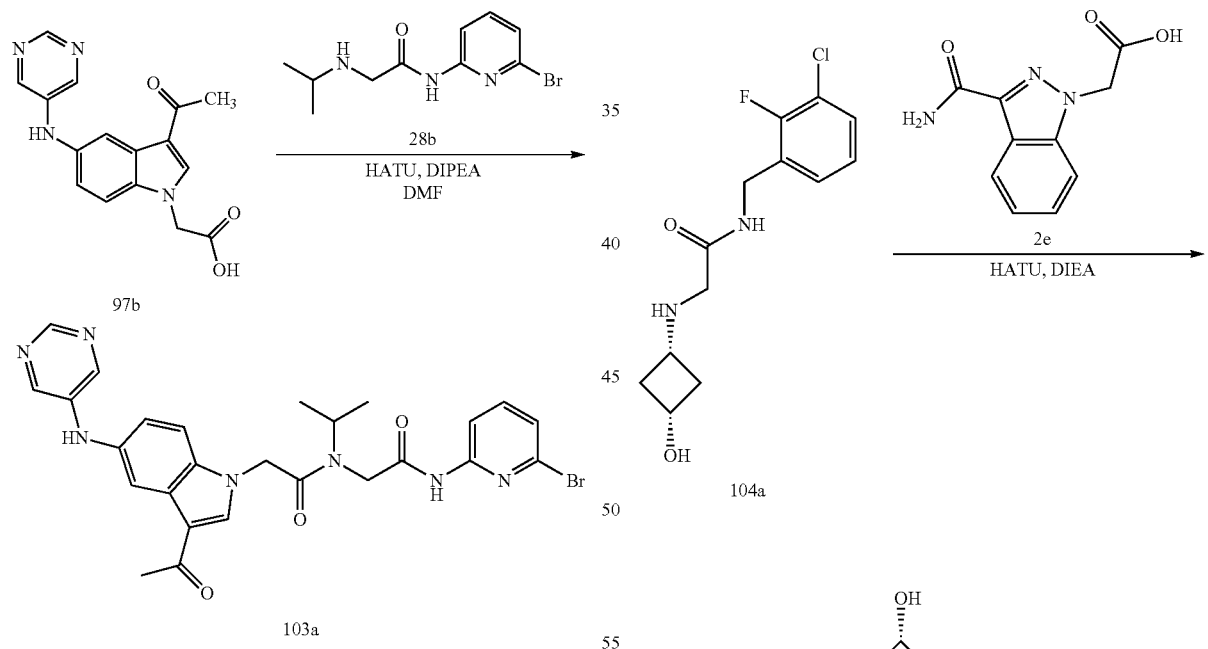

97b

103a

Preparation of 2-(3-acetyl-5-(pyrimidin-5-ylamino)-1H-indol-1-yl)-N-(2-((6-bromopyridin-2-yl)amino)-2-oxoethyl)-N-isopropylacetamide (103a)

Reaction of N-(6-bromopyridin-2-yl)-2-(isopropylamino)acetamide (28b) (61 mg, 0.23 mmol) with 2-(3-acetyl-5-(pyrimidin-5-ylamino)-1H-indol-1-yl)acetic acid (97b) (70 mg, 0.23 mmol) according to the procedure reported in step-3 of Scheme 2 gave after workup and purification by flash column chromatography [silica gel (12 g), eluting with

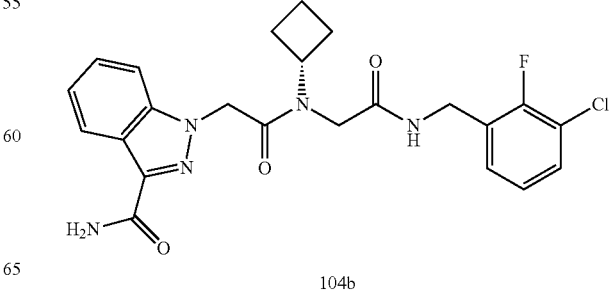

104b

Preparation of 1-(2-((2-((3-chloro-2-fluorobenzyl)amino)-2-oxoethyl)((cis)-3-hydroxycyclobutyl)amino)-2-oxoethyl)-1H-indazole-3-carboxamide (104b)

Step-1: Preparation of N-(3-chloro-2-fluorobenzyl)-2-(((cis)-3-hydroxycyclobutyl)amino)acetamide (104a)

Reaction of 2-chloro-N-(3-chloro-2-fluorobenzyl)acetamide (35b) (350 mg, 1.48 mmol) with (cis)-3-aminocyclobutanol hydrochloride (458 mg, 3.71 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(((cis)-3-hydroxycyclobutyl)amino)acetamide (104a) (250 mg, 0.87 mmol, 59%) as a yellow oil; MS (ES+): 287.3 (M+1); MS (ES−): 285.3 (M−1).

Step-2: Preparation of 1-(2-((2-((3-chloro-2-fluorobenzyl)amino)-2-oxoethyl)((cis-3-hydroxycyclobutyl)amino)-2-oxoethyl)-1H-indazole-3-carboxamide (104b)

Reaction of N-(3-chloro-2-fluorobenzyl)-2-(((cis)-3-hydroxycyclobutyl)amino)acetamide (104a) (250 mg, 0.87 mmol) with 2-(3-carbamoyl-1H-indazol-1-yl)acetic acid (2e) (210 mg, 0.96 mmol) according to the procedure reported in step-3 of Scheme 2 gave after workup and purification by flash column chromatography [silica (12 g), eluting with CMA-80 in CHCl₃ 0 to 60%] 1-(2-((2-((3-chloro-2-fluorobenzyl)amino)-2-oxoethyl)((cis)-3-hydroxycyclobutyl)amino)-2-oxoethyl)-1H-indazole-3-carboxamide (104b) (245 mg, 0.5 mmol, 58% yield) as a white solid; $^1$H NMR (300 MHz, DMSO-$d_6$) δ 8.88 (t, J=5.7 Hz) and 8.44 (t, J=5.9 Hz) (2t, 1H), 8.24-8.09 (m, 1H), 7.70 (s, 1H), 7.59-7.04 (m, 7H), 5.53 and 5.40 (2s, 2H), 5.20-5.06 (m, 1H), 4.47 (d, J=5.5 Hz) and 4.34 (d, J=5.7 Hz) (2d, 2H), 4.30 and 4.04 (2s, 2H), 4.19-4.05 (m, 1H), 3.88-3.68 (m, 1H), 2.70-2.55 (m, 1H), 2.39-2.25 (m, 1H), 2.13-1.90 (m, 1H), 1.85-1.70 (m, 1H); $^{19}$F NMR (282 MHz, DMSO-$d_6$) δ −121.26, −121.59; MS (ES+); 488.5 (M+1); (ES−): 486.5 (M−1); [based on NMR, this compound is a mixture of rotamers 4:5 ratio]

Scheme 105

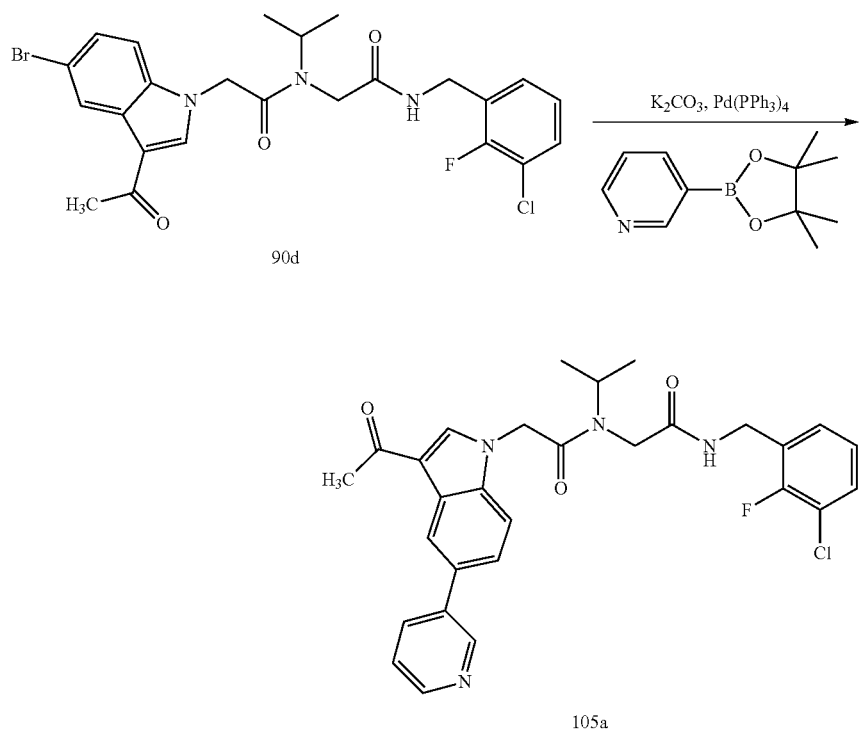

105a

Preparation of 2-(3-acetyl-5-(pyridin-3-yl)-1H-indol-1-yl)-N-(2-((3-chloro-2-fluorobenzyl)amino)-2-oxoethyl)-N-isopropylacetamide (105a)

Reaction of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol) with pyridin-3-ylboronic acid (34 mg, 0.28 mmol) according the procedure reported in Scheme 100 gave after workup and purification by flash column chromatography [silica gel (12 g), eluting with CMA80 in CHCl₃ 0 to 30%] 2-(3-acetyl-5-(pyridin-3-yl)-1H-indol-1-yl)-N-(2-((3-chloro-2-fluorobenzyl)amino)-2-oxoethyl)-N-isopropylacetamide (105a) (75 mg, 0.14 mmol, 50% yield) as a white solid as a mixture of rotamers in 2:1 ratio; $^1$H NMR (300 MHz, DMSO-$d_6$) δ 8.91-8.87 (m, 1H), 8.84 (t, J=5.7 Hz) and 8.39-8.27 (m) (2H), 8.61-8.53 (m, 1H), 8.45 (s, 1H), 8.14-8.05 (m, 1H), 7.67-7.57 (m, 2H), 7.57-7.47 (m, 2H), 7.46-7.36 (m, 1H), 7.26-6.94 (m, 1H), 5.41 and 5.22 (s, 2H), 4.66-4.53 and 4.32-4.21 (m, 1H), 4.49 and 4.34 (d, J=5.8 Hz, 2H), 4.20 and 3.86 (s, 2H), 2.47 and 2.45 (s, 3H), 1.27 and 1.01 (2d, J=6.4 Hz, 6H); $^{19}$F NMR (282 MHz, DMSO-$d_6$) δ −121.18, −121.77; MS (ES+) 535.6 (M+1), MS (ES−): 569.5, 571.5 (M+Cl).

Scheme 106

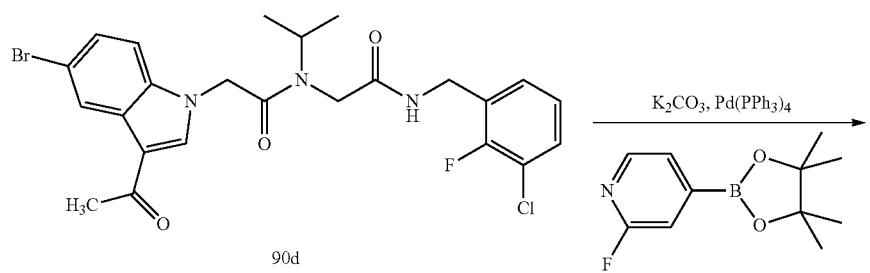

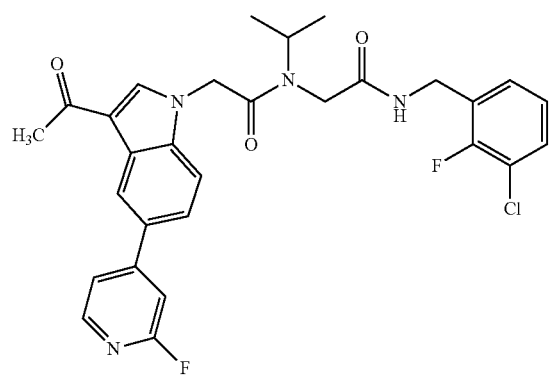

Preparation of 2-(3-acetyl-5-(2-fluoropyridin-4-yl)-1H-indol-1-yl)-N-(2-((3-chloro-2-fluorobenzyl)amino)-2-oxoethyl)-N-isopropylacetamide (106a)

Reaction of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol) with 2-fluoropyridin-4-ylboronic acid (39 mg, 0.28 mmol) according the procedure reported in Scheme 100 gave after workup and purification by flash column chromatography [silica gel (12 g), eluting with CMA80 in CHCl$_3$ 0 to 30%] 2-(3-acetyl-5-(2-fluoropyridin-4-yl)-1H-indol-1-yl)-N-(2-((3-chloro-2-fluorobenzyl)amino)-2-oxoethyl)-N-isopropylacetamide (106a) (52 mg, 0.094 mmol, 34% yield) as a white solid as a mixture of rotamers in 2:1 ratio; $^1$H NMR (300 MHz, DMSO-d$_6$) δ 8.84 (t, J=5.7 Hz) and 8.42-8.23 (m) (3H), 8.58 (bs, 1H), 7.81-6.89 (m, 7H), 5.42 and 5.23 (2s, 2H), 4.66-4.53 and 4.30-4.22 (m, 1H), 4.49 and 4.34 (2d, J=5.8 Hz, 2H), 4.20 and 3.86 (s, 2H), 2.48 and 2.46 (s, 3H), 1.27 and 1.00 (2d, J=6.8 Hz, 6H); $^{19}$F NMR (282 MHz, DMSO-d$_6$) δ −69.06, −69.09, −121.18, −121.77; MS (ES+): 553.6 (M+1), MS (ES−): 587.5 (M+Cl).

Scheme 107

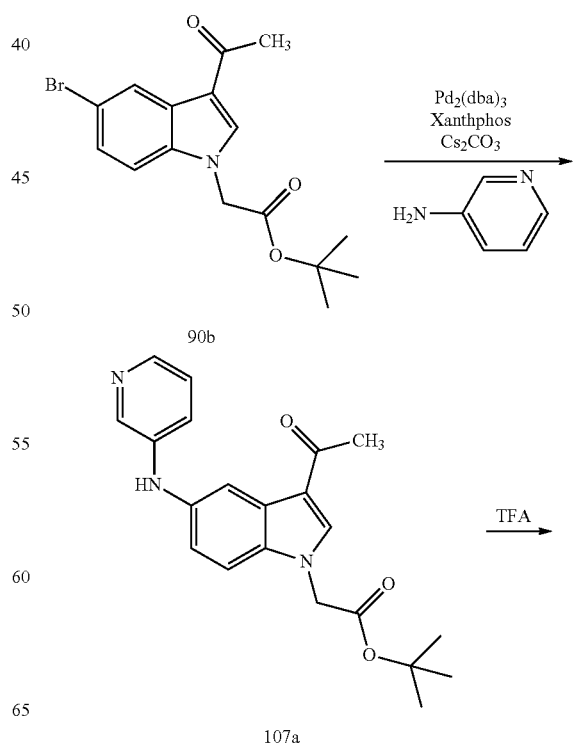

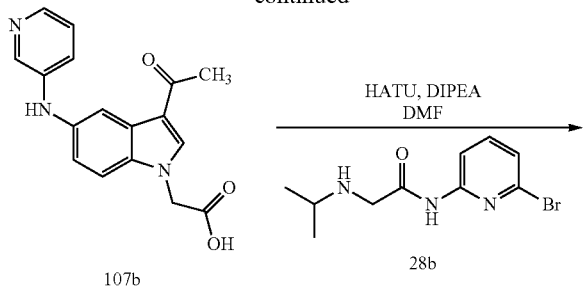

107b

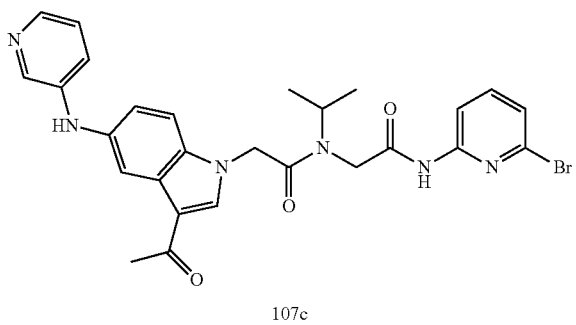

107c

Preparation of 2-(3-acetyl-5-(pyridin-3-ylamino)-1H-indol-1-yl)-N-(2-((6-bromopyridin-2-yl)amino)-2-oxoethyl)-N-isopropylacetamide (107c)

Step-1: Preparation of tert-butyl 2-(3-acetyl-5-(pyridin-3-ylamino)-1H-indol-1-yl)acetate (107a)

Reaction of tert-butyl 2-(3-acetyl-5-bromo-1H-indol-1-yl)acetate (90b) (1.05 g, 2.98 mmol) with pyridin-3-amine (310 mg, 3.28 mmol), according to the procedure reported in step-1 of Scheme 97 gave after workup and purification by column chromatography [silica gel (40 g), eluting with CMA80 in CHCl₃ 0 to 20%] tert-butyl 2-(3-acetyl-5-(pyridin-3-ylamino)-1H-indol-1-yl)acetate (107a) (250 g, 0.7 mmol, 23% yield) as light yellow solid; $^1$H NMR (300 MHz, DMSO-$d_6$) δ 8.35-8.23 (m, 3H), 8.02-7.91 (m, 2H), 7.43-7.31 (m, 2H), 7.18 (dd, J=8.3, 4.6 Hz, 1H), 7.07 (dd, J=8.8, 2.2 Hz, 1H), 5.08 (s, 2H), 2.41 (s, 3H), 1.44 (s, 9H); MS (ES+): 366.5 (M+1), MS (ES−): 400.4 (M+Cl).

Step-2: Preparation of 2-(3-acetyl-5-(pyridin-3-ylamino)-1H-indol-1-yl)acetic acid (107b)

Reaction of tert-butyl 2-(3-acetyl-5-(pyridin-3-ylamino)-1H-indol-1-yl)acetate (107a) (250 mg, 0.68 mmol) with TFA (1.58 mL, 20.52 mmol) according to the procedure reported in step-2 of Scheme 2 gave after workup and trituration of crude with EtOAc-hexane (10 mL) 2-(3-acetyl-5-(pyridin-3-ylamino)-1H-indol-1-yl)acetic acid (107b) (0.2 g, 0.647 mmol, 95% yield) as light orange solid; $^1$H NMR (300 MHz, DMSO-$d_6$) δ 13.31 (bs, 1H, D₂O exchangeable), 9.09 (s, 1H), 8.36 (s, 1H), 8.28 (s, 1H), 8.14 (s, 1H), 8.05 (s, 1H), 7.82 (s, 1H), 7.70 (s, 1H), 7.55 (d, J=8.7 Hz, 1H), 7.18 (d, J=8.6 Hz, 1H), 5.14 (s, 2H), 2.42 (s, 3H); MS (ES−): 308.3 (M−1).

Step-3: Preparation of 2-(3-acetyl-5-(pyridin-3-ylamino)-1H-indol-1-yl)-N-(2-((6-bromopyridin-2-yl)amino)-2-oxoethyl)-N-isopropylacetamide (107c)

Reaction of 2-(3-acetyl-5-(pyridin-3-ylamino)-1H-indol-1-yl)acetic acid (107b) (60 mg, 0.19 mmol) with N-(6-bromopyridin-2-yl)-2-(isopropylamino)acetamide (28b) (53 mg, 0.19 mmol) according to the procedure reported in step-3 of Scheme 2 gave after workup and purification by flash column [silica gel (12 g), eluting with CMA-80 in CHCl₃ 0-100%] 2-(3-acetyl-5-(pyridin-3-ylamino)-1H-indol-1-yl)-N-(2-((6-bromopyridin-2-yl)amino)-2-oxoethyl)-N-isopropylacetamide (107c) (57 mg, 0.101 mmol, 52% yield) as a off-white solid as a mixture of rotamers in 2:1 ratio; $^1$H NMR (300 MHz, DMSO-$d_6$) (a mixture of two rotamers) δ 11.20 and 10.82 (2s, 1H), 8.33-8.24 (m, 2H), 8.22 and 8.21 (2s, 1H), 8.05-7.91 (m, 3H), 7.81 and 7.70 (2t, J=8.0 Hz, 1H), 7.44-7.28 (m, 3H), 7.23-7.11 (m, 1H), 7.12-7.01 (m, 1H), 5.35 and 5.16 (2s, 2H), 4.72-4.57 and 4.47-4.20 (2m, 1H), 4.43 and 4.05 (2s, 2H), 2.41 and 2.40 (2s, 3H), 1.26 and 1.04 (2d, J=6.8 Hz, 6H); MS (ES+): 563.5, 565.5 (M+1); MS (ES−): 561.5, 563.5 (M−1), 597.5, 599.5 (M+Cl).

Scheme 108

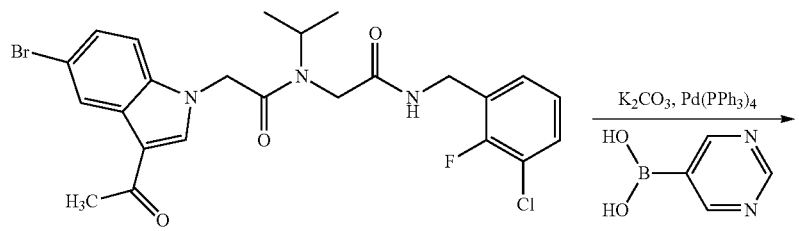

90d

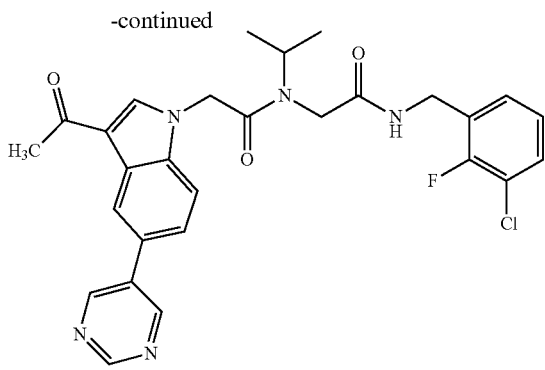

108a

Preparation of 2-(3-acetyl-5-(pyrimidin-5-yl)-1H-indol-1-yl)-N-(2-((3-chloro-2-fluorobenzyl)amino)-2-oxoethyl)-N-isopropylacetamide (108a)

Reaction of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol) with pyrimidin-5-ylboronic acid (35 mg, 0.28 mmol) according the procedure reported in Scheme 100 gave after workup and purification by flash column chromatography [silica gel (12 g), eluting with CMA80 in CHCl₃ 0 to 30%] 2-(3-acetyl-5-(pyrimidin-5-yl)-1H-indol-1-yl)-N-(2-((3-chloro-2-fluorobenzyl)amino)-2-oxoethyl)-N-isopropylacetamide (108a) (85 mg, 0.159 mmol, 57% yield) as a white solid; as a mixture of rotamers in 2:1 ratio; $^1$H NMR (300 MHz, DMSO-d$_6$) (a mixture of two rotamers) δ 9.19 and 9.18 (2s, 1H), 9.12 and 9.11 (2s, 2H), 8.89-8.79 and 8.40-8.28 (2m, 2H), 8.48 (s, 1H), 7.71-6.95 (m, 5H), 5.42 and 5.23 (2s, 2H), 4.65-4.54 and 4.32-4.21 (2m, 1H), 4.49 and 4.34 (2d, J=5.6 Hz, 2H), 4.20 and 3.86 (2s, 2H), 2.48 and 2.46 (2s, 3H), 1.27 and 1.01 (d, J=6.8 Hz, 6H); $^{19}$F NMR (282 MHz, DMSO-d$_6$) (a mixture of two rotamers) δ −121.18 and −121.79; MS (ES+): 536.5 (M+1), MS (ES−): 534.5 (M−1), 570.5 (M+Cl).

Scheme 109

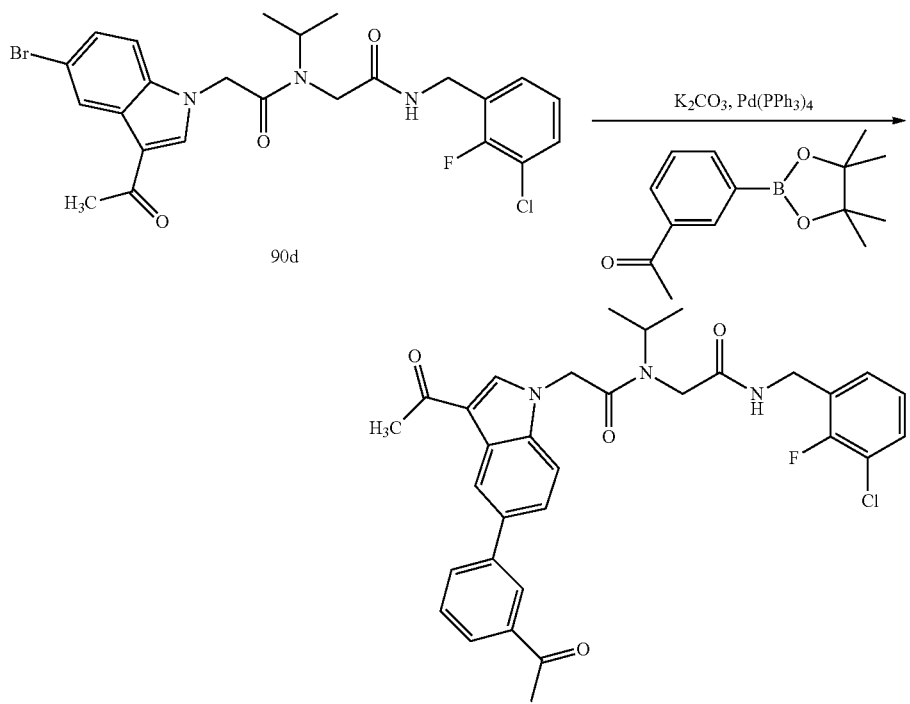

Preparation of 2-(3-acetyl-5-(3-acetylphenyl)-1H-indol-1-yl)-N-(2-((3-chloro-2-fluorobenzyl)amino)-2-oxoethyl)-N-isopropylacetamide (109a)

Reaction of 2-(3-acetyl-5-bromo-1H-indol-1-yl)-N-(2-((3-chloro-2-fluorobenzyl)amino)-2-oxoethyl)-N-isopropylacetamide (90d) (150 mg, 0.28 mmol) with 1-(3-(4,4,5,5-tetramethyl-1,3,2-dioxaborolan-2-yl)phenyl)ethanone (70 mg, 0.28 mmol) according the procedure reported in Scheme 100 gave after workup and purification by flash column chromatography [silica gel (12 g), eluting with CMA80 in CHCl₃ 0 to 30%] 2-(3-acetyl-5-(3-acetylphenyl)-1H-indol-1-yl)-N-(2-((3-chloro-2-fluorobenzyl)amino)-2-oxoethyl)-N-isopropylacetamide (109a) (80 mg, 0.14 mmol, 50% yield) as a white solid as mixture of rotamers in 2:1 ratio; $^1$H NMR (300 MHz, DMSO-$d_6$) δ 8.84 and 8.35 (2t, J=5.7 Hz, 1H), 8.47 (bs, 1H), 8.35 and 8.34 (s, 1H), 8.21-8.13 (m, 1H), 8.01-7.88 (m, 2H), 7.70-6.95 (m, 6H), 5.41 and 5.22 (s, 2H), 4.68-4.51 and 4.32-4.20 (m, 1H), 4.49 and 4.34 (d, J=5.8 Hz, 2H), 4.20 and 3.86 (s, 2H), 2.668 and 2.666 (2s, 3H), 2.47, 2.45 (s, 3H), 1.27 and 1.01 (2d, J=6.8 Hz, 6H); $^{19}$F NMR (282 MHz, DMSO-$d_6$) δ −121.18, −121.76; MS (ES+): 576.6 (M+1), 598.6 (M+Na); MS (ES−): 574.6 (M−1).

Preparation of 1-(2-((2-((3-chloro-2-fluorobenzyl)amino)-2-oxoethyl)((trans)-3-hydroxycyclobutyl)amino)-2-oxoethyl)-1H-indazole-3-carboxamide (110b)

Step-1: Preparation of N-(3-chloro-2-fluorobenzyl)-2-(((trans)-3-hydroxycyclobutyl)amino)acetamide (110a)

Reaction of 2-chloro-N-(3-chloro-2-fluorobenzyl)acetamide (35b) (350 mg, 1.48 mmol) with (trans)-3-aminocyclobutanol hydrochloride (458 mg, 3.71 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-(((trans)-3-hydroxycyclobutyl)amino)acetamide (110a) (200 mg, 0.7 mmol, 47%) as a yellow oil; MS (ES+): 287.4 (M+1); (ES−): 285.3 (M−1).

Step-2: Preparation of 1-(2-((2-((3-chloro-2-fluorobenzyl)amino)-2-oxoethyl)((trans)-3-hydroxycyclobutyl)amino)-2-oxoethyl)-1H-indazole-3-carboxamide (110b)

Reaction of N-(3-chloro-2-fluorobenzyl)-2-(((trans)-3-hydroxycyclobutyl)amino)acetamide (110a) (200 mg, 0.7 mmol) with 2-(3-carbamoyl-1H-indazol-1-yl)acetic acid (2e) (168 mg, 0.77 mmol) according to the procedure reported in step-3 of Scheme 2 gave after workup and purification by flash column chromatography [silica (12 g), eluting with CMA-80 in CHCl₃ 0 to 60%] 1-(2-((2-((3-chloro-2-fluorobenzyl)amino)-2-oxoethyl)((trans)-3-hydroxycyclobutyl)amino)-2-oxoethyl)-1H-indazole-3-carboxamide (110b) (92 mg, 27%) as a white solid; $^1$H NMR (300 MHz, DMSO-$d_6$) δ 8.86 (t, J=5.5 Hz) and 8.43 (t, J=5.7 Hz) (2t, 1H), 8.18 (d, J=8.1 Hz, 1H), 7.78-7.64 (m, 1H), 7.63-7.00 (m, 7H), 5.53 and 5.42 (2s, 2H), 5.12 (d, J=4.0 Hz) and 5.00 (d, J=4.3 Hz) (2d, 1H), 4.96-4.79 (m, 1H), 4.47 (d, J=5.2 Hz) and 4.33 (d, J=5.5 Hz) (2d, 2H), 4.28 and 4.00 (2s, 2H), 4.23-4.05 (m, 1H), 2.46-2.30 (m, 1H), 2.28-2.09 (m, 2H), 2.02-1.85 (m, 1H); $^{19}$F NMR (282 MHz, DMSO-$d_6$) δ −121.23, −121.62; MS (ES+): 488.5 (M+1); (ES−): 486.5 (M−1); [based on NMR, this compound is a mixture of rotamers 4:5 ratio].

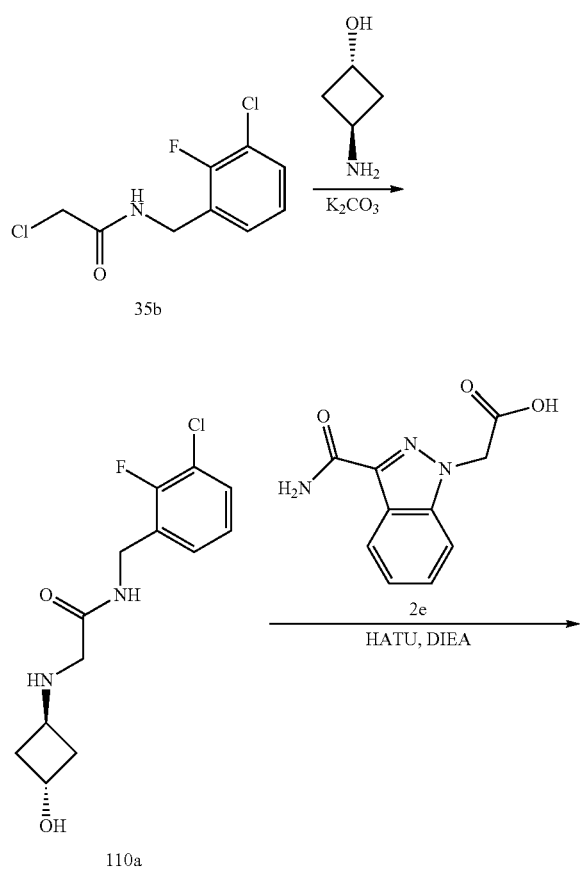

Scheme 110

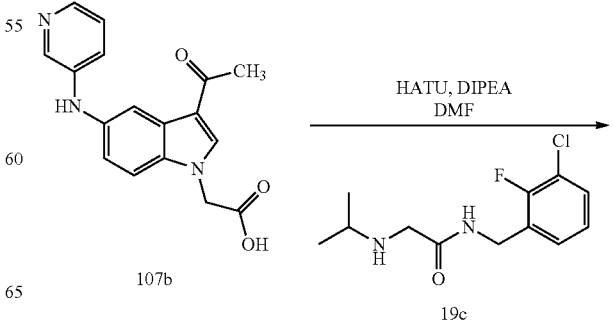

Scheme 111

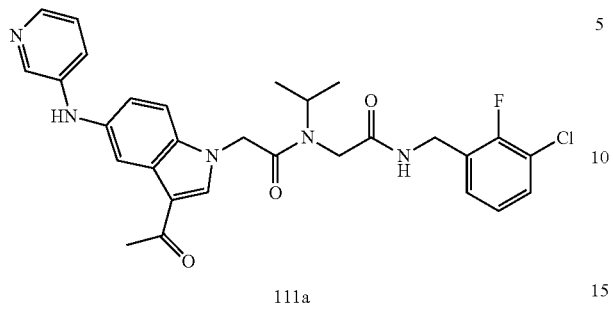

111a

Preparation of 2-(3-acetyl-5-(pyridin-3-ylamino)-1H-indol-1-yl)-N-(2-((3-chloro-2-fluorobenzyl)amino)-2-oxoethyl)-N-isopropylacetamide (111a)

Reaction of N-(3-chloro-2-fluorobenzyl)-2-(isopropylamino)acetamide (19c) (50 mg, 0.19 mmol) with 2-(3-acetyl-5-(pyridin-3-ylamino)-1H-indol-1-yl)acetic acid (107b) (60 mg, 0.19 mmol) according to the procedure reported in step-3 of Scheme 2 gave after workup and purification by flash column chromatography [silica gel (12 g), eluting with CMA80 in CHCl$_3$ 0 to 30%] 2-(3-acetyl-5-(pyridin-3-ylamino)-1H-indol-1-yl)-N-(2-((3-chloro-2-fluorobenzyl)amino)-2-oxoethyl)-N-isopropylacetamide (111a) (40 mg, 0.073 mmol, 38% yield) as an off-white solid as mixture of rotamers in 2:1 ratio; $^1$H NMR (300 MHz, DMSO-d$_6$) (a mixture of two rotamers) δ 8.82 and 8.34 (2t, J=5.7 Hz, 1H), 8.32-8.23 (m, 2H), 8.21 and 8.16 (2s, 1H), 7.98 (d, J=2.2 Hz, 1H), 7.96-7.90 (m, 1H), 7.56-6.96 (m, 7H), 5.32 and 5.13 (2s, 2H), 4.67-4.51 and 4.31-4.18 (2m, 1H), 4.47 and 4.34 (2d, J=5.8 Hz, 2H), 4.18 and 3.85 (2s, 2H), 2.40 and 2.39 (2s, 3H), 1.25 and 1.00 (2d, J=6.8 Hz, 6H); $^{19}$F NMR (282 MHz, DMSO-d$_6$) (a mixture of two rotamers) δ −121.18, −121.77; MS (ES+): 550.6 (M+1); MS (ES−): 584.6 (M+Cl).

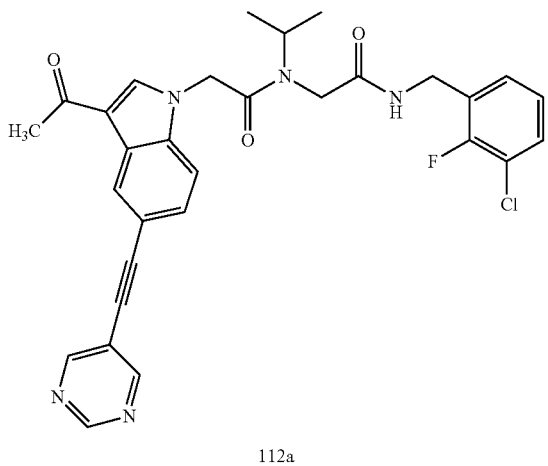

112a

Preparation of 2-(3-acetyl-5-(pyrimidin-5-ylethynyl)-1H-indol-1-yl)-N-(2-((3-chloro-2-fluorobenzyl)amino)-2-oxoethyl)-N-isopropylacetamide (112a)

Reaction of 2-(3-acetyl-5-bromo-1H-indol-1-yl)-N-(2-((3-chloro-2-fluorobenzyl)amino)-2-oxoethyl)-N-isopropylacetamide (90d) (300 mg, 0.56 mmol) with 5-ethynylpyrimidine (58 mg, 0.56 mmol) according to the procedure reported in Scheme 92 gave after workup and purification by flash column chromatography [First column: silica gel (24 g), eluting with MeOH in CHCl$_3$ 0 to 20%; Second column: silica gel (12 g), eluting with MeOH/EtOAc (9:1) in hexanes 0 to 100%] 2-(3-acetyl-5-(pyrimidin-5-ylethynyl)-1H-indol-1-yl)-N-(2-((3-chloro-2-fluorobenzyl)amino)-2-oxoethyl)-N-isopropylacetamide (112a) (13 mg, 0.023 mmol, 4% yield) as a yellow solid as a mixture of two rotamers; $^1$H NMR (300 MHz, DMSO-d$_6$) δ 9.183 and 9.180 (2s, 1H), 9.054 and 9.052 (2s, 2H), 8.84 (t, J=5.8 Hz) and 8.36 (t) (2t, 1H), 8.45 (d, J=1.5 Hz, 1H), 8.38 and 8.34 (2s, 1H), 7.68-6.93 (m, 5H), 5.41 and 5.22 (2s, 2H), 4.65-4.53 and 4.28-4.20 (2m, 1H), 4.52-4.30 (m, 2H), 4.19 and 3.85 (2s, 2H), 2.46 and 2.45 (2s, 3H), 1.26 (d, J=6.5 Hz) and 1.00 (d, J=6.8 Hz) (2t, 6H); $^{19}$F NMR (282 MHz, DMSO-d$_6$) δ −121.18, −121.77; MS (ES+): 560.61 (M+1); MS (ES−): 594.5 & 596.5 (M+Cl).

Scheme 112

Scheme 113

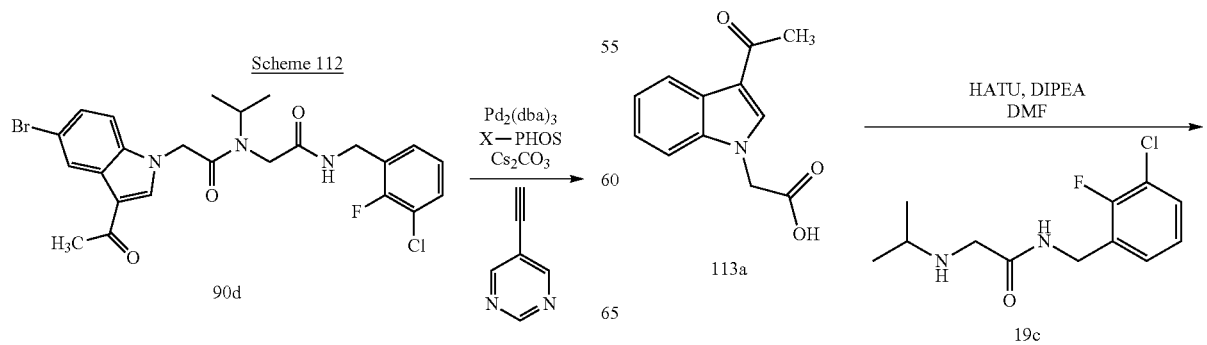

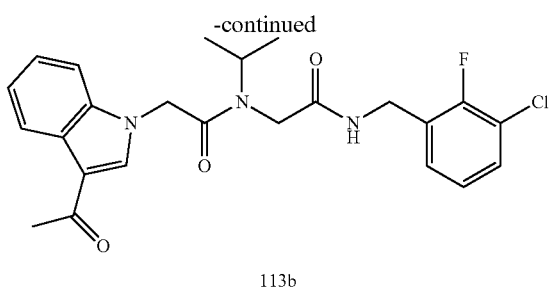

113b

Preparation of 2-(3-acetyl-1H-indol-1-yl)-N-(2-((3-chloro-2-fluorobenzyl)amino)-2-oxoethyl)-N-isopropylacetamide (113b)

Reaction of N-(3-chloro-2-fluorobenzyl)-2-(isopropylamino)acetamide (19c) (400 mg, 1.55 mmol) with 2-(3-acetyl-1H-indol-1-yl)acetic acid (113a) (403 mg, 1.86 mmol) according to the procedure reported in step-3 of Scheme 2 gave after workup and purification by flash column chromatography [silica gel (24 g), eluting with CMA80 in $CHCl_3$, 0 to 10%] 2-(3-acetyl-1H-indol-1-yl)-N-(2-((3-chloro-2-fluorobenzyl)amino)-2-oxoethyl)-N-isopropylacetamide (113b) (279 mg, 0.609 mmol, 39% yield) as a pale yellow solid in the form of mixture of two rotamers; $^1$H NMR (300 MHz, DMSO-$d_6$) δ 8.82 and 8.35 (t, J=5.4 Hz) (2t, 1H), 8.32 and 8.27 (2s, 1H), 8.22 (s, 1H), 8.18 (d, J=7.0 Hz, 1H), 7.57-7.34 (m, 2H), 7.29-7.14 (m, 2H, another triplet was overlapped in this region), 7.00 (t, J=7.9 Hz, 1H), 5.36 and 5.17 (2s, 2H), 4.65-4.52 and 4.30-4.22 (2m, 1H), 4.48 (d, J=5.6 Hz) and 4.33 (d, J=5.8 Hz) (2d, 2H), 4.19 (s) and 3.85 (2s, 2H), 2.43 and 2.42 (2s, 3H), 1.25 (d, J=6.3 Hz) and 1.00 (d, J=6.8 Hz) (2d, 6H); $^{19}$F NMR (282 MHz, DMSO-$d_6$) δ −121.19, −121.82; MS (ES+): 458.5 (M+1), 480.5 (M+Na); MS (ES−): 456.5 (M−1), 492.5 (M+Cl).

Scheme 114

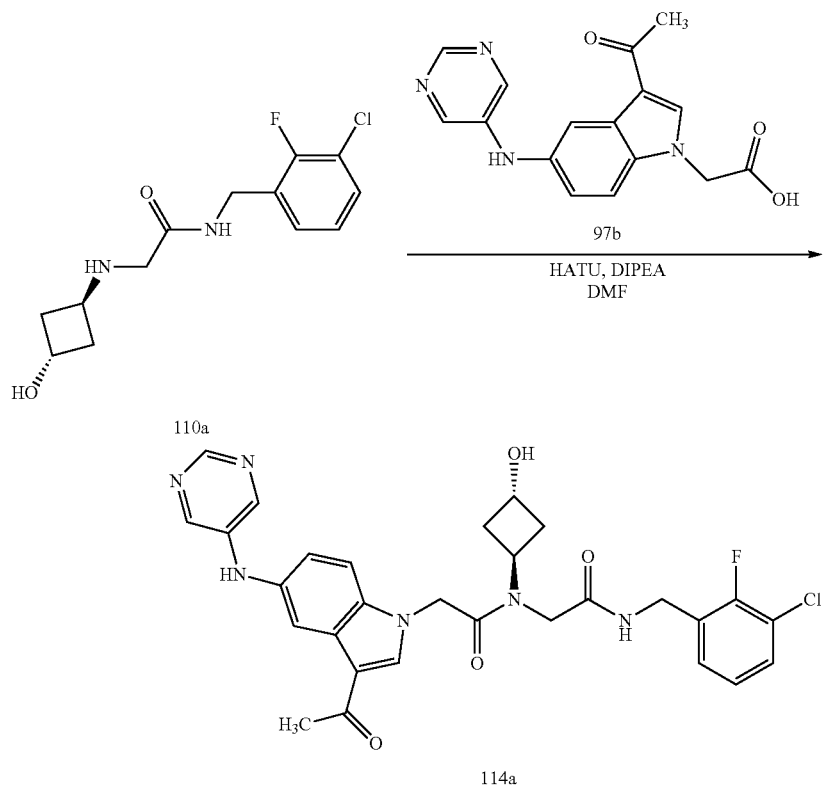

Preparation of 2-(3-acetyl-5-(pyrimidin-5-ylamino)-1H-indol-1-yl)-N-(2-((3-chloro-2-fluorobenzyl)amino)-2-oxoethyl)-N-((trans)-3-hydroxycyclobutyl)acetamide (114a)

Reaction of N-(3-chloro-2-fluorobenzyl)-2-(((trans)-3-hydroxycyclobutyl)amino)acetamide (110a) (55 mg, 0.19 mmol) with 2-(3-acetyl-5-(pyrimidin-5-ylamino)-1H-indol-1-yl)acetic acid (97b) (60 mg, 0.19 mmol) according to the procedure reported in step-3 of Scheme 2 gave after workup and purification by flash column chromatography [silica gel (12 g), eluting with CMA80 in $CHCl_3$ 0 to 100%] 2-(3-acetyl-5-(pyrimidin-5-ylamino)-1H-indol-1-yl)-N-(2-((3-chloro-2-fluorobenzyl)amino)-2-oxoethyl)-N-((trans)-3-hydroxycyclobutyl)acetamide (114a) (12 mg, 0.021 mmol, 11% yield) as a white solid as a mixture of rotamers in 2:1 ratio; $^1$H NMR (300 MHz, DMSO-$d_6$) δ 8.85 and 8.42 (2t, J=5.6 Hz, 1H), 8.563 and 8.559 (2s, 1H), 8.49 (s, 1H), 8.46 (s, 2H), 8.22 and 8.17 (2s, 1H), 8.004 and 7.997 (2s, 1H), 7.58-7.01 (m, 5H), 5.29 (s) and 5.17-4.79 (m) (s & m, 4H), 4.47 and 4.35 (2d, J=5.8 Hz, 2H), 4.27 and 4.02 (2s, 2H), 4.24-4.09 (m, 1H), 2.41 and 2.40 (2s, 3H), 2.28-2.11 (m, 2H), 2.00-1.84 (m, 2H); $^{19}$F NMR (282 MHz, DMSO-$d_6$) δ −121.20, −121.62; MS (ES+): 579.6 (M+1), MS (ES−): 613.5, 615.5 (M+Cl).

Scheme 115

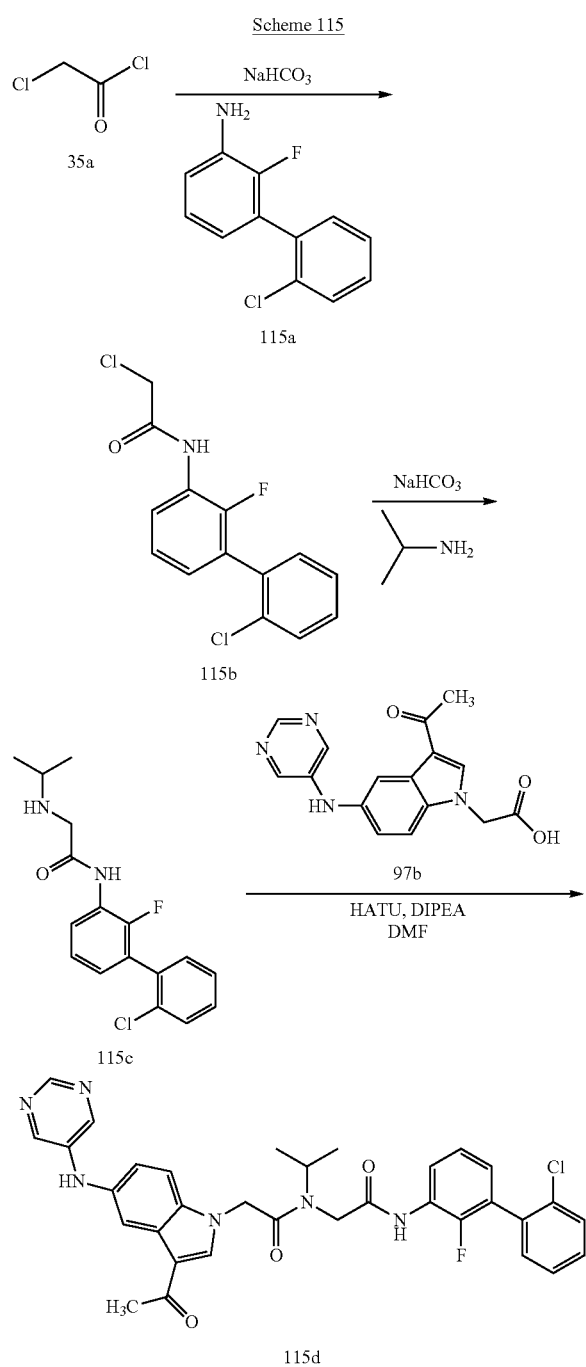

Preparation of 2-(3-acetyl-5-(pyrimidin-5-ylamino)-1H-indol-1-yl)-N-(2-((2'-chloro-2-fluoro-[1,1'-biphenyl]-3-yl)-amino)-2-oxoethyl)-N-isopropylacetamide (115d)

Step-1: Preparation of 2-chloro-N-(2'-chloro-2-fluoro-[1,1'-biphenyl]-3-yl)acetamide (115b)

To a biphasic solution of 2'-chloro-2-fluorobiphenyl-3-amine (115a) (0.8 g, 3.61 mmol, prepared according to procedure reported by Altmann, Eva et al, in PCT Int. Appl., WO 2012/093101) in EtOAc (20 mL), Saturated aqueous NaHCO₃ (20 mL) was added 2-chloroacetyl chloride (35a) (0.58 mL, 7.22 mmol) and stirred at RT for 2 h. The layers were separated and aqueous layer was extracted with EtOAc (40 mL). The organic layers were combined washed with brine, dried, filtered and concentrated in vacuum to afford 2-chloro-N-(2'-chloro-2-fluoro-[1,1'-biphenyl]-3-yl)acetamide (115b) (1 gm, 93% yield) as a white solid; ¹H NMR (300 MHz, DMSO-d₆) δ 10.24 (s, 1H), 8.00 (t, J=7.9 Hz, 1H), 7.64-7.57 (m, 1H), 7.53-7.39 (m, 3H), 7.28 (td, J=8.0, 1.0 Hz, 1H), 7.19-7.07 (m, 1H), 4.37 (s, 2H); MS (ES+): 298.3, 300.3 (M+1), 320.3, 322.3 (M+Na); MS (ES−): 296.3, 298.3 (M−1).

Step-2: Preparation of N-(2'-chloro-2-fluoro-[1,1'-biphenyl]-3-yl)-2-(isopropylamino)acetamide (115c)

To a solution of 2-chloro-N-(2'-chloro-2-fluorobiphenyl-3-yl)acetamide (115b) (1.00 g, 3.35 mmol) in THF (30 mL) was added isopropylamine (0.86 mL, 10.06 mmol) and stirred at RT for 24 h. Reaction mixture was poured into saturated aqueous NaHCO₃ solution (60 mL) and extracted with EtOAc (2×50 mL). The organics layers were combined washed with brine, dried, filtered, concentrated and purified by flash column chromatography [silica gel (24 g), eluting with EtOAc in Hexane 0 to 100%] to afford N-(2'-chloro-2-fluorobiphenyl-3-yl)-2-(isopropylamino)acetamide (115c) (520 mg, 1.62 mmol, 48% yield) as a white solid; ¹H NMR (300 MHz, DMSO-d₆) (major rotamer) δ 8.25 (td, J=7.8, 1.7 Hz, 1H), 7.65-7.56 (m, 1H), 7.53-7.37 (m, 4H), 7.27 (td, J=8.0, 1.1 Hz, 1H), 7.11-7.02 (m, 1H), 3.30 (s, 2H), 2.79-2.66 (m, 1H), 1.04-0.94 (m, 6H); MS (ES+) 321.4, 323.4 (M+1), MS (ES−): 355.3, 357.3 (M+Cl).

Step-3: Preparation of 2-(3-acetyl-5-(pyrimidin-5-ylamino)-1H-indol-1-yl)-N-(2-((2'-chloro-2-fluoro-[1,1'-biphenyl]-3-yl)amino)-2-oxoethyl)-N-isopropylacetamide (115d)

Reaction of N-(2'-chloro-2-fluoro-[1,1'-biphenyl]-3-yl)-2-(isopropylamino)acetamide (115c) (62 mg, 0.19 mmol) with 2-(3-acetyl-5-(pyrimidin-5-ylamino)-1H-indol-1-yl) acetic acid (97b) (60 mg, 0.19 mmol) according to the procedure reported in step-3 of Scheme 2 gave after workup and purification by flash column chromatography [silica gel (12 g), eluting with CMA80 in CHCl₃ 0 to 30%] 2-(3-acetyl-5-(pyrimidin-5-ylamino)-1H-indol-1-yl)-N-(2-((2'-chloro-2-fluoro-[1,1'-biphenyl]-3-yl)-amino)-2-oxoethyl)-N-isopropylacetamide (115d) (21m g, 0.034 mmol, 18% yield) as a white solid as a mixture of rotamers in 2:1 ratio; ¹H NMR (300 MHz, DMSO-d₆) (a mixture of two rotamers) δ 10.25 and 9.74 (2s, 1H), 8.56 (s, 1H), 8.52-8.43 (m, 3H), 8.26 and 8.24 (s, 1H), 8.15-7.91 (m, 2H), 7.66-7.36 (m, 4H), 7.32 and 7.22 (2t, J=8.0 Hz, 1H), 7.18-7.02 (m, 2H), 5.38 and 5.21 (2s, 2H), 4.75-4.59 and 4.38-4.23 (2m, 1H), 4.47 and 4.10 (2s, 2H), 2.42 and 2.40 (2s, 3H), 1.28 and 1.07 (2d, J=6.8 Hz, 6H); MS (ES+); 613.5, 615.7 (M+1), MS (ES−); 611.6, 613.6 (M−1).

Scheme 116

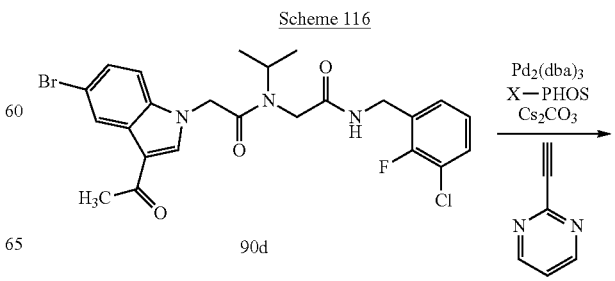

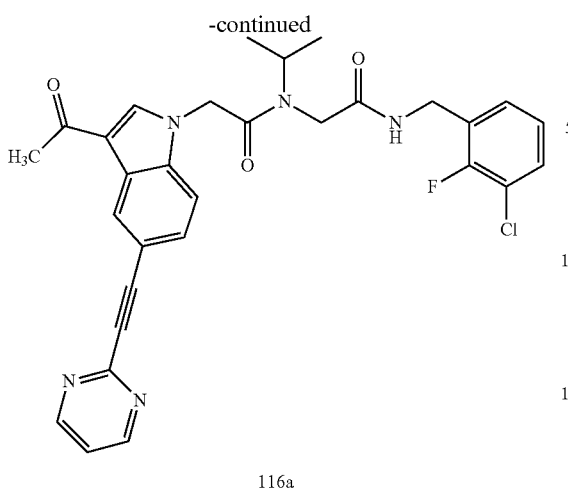

116a

Preparation of 2-(3-acetyl-5-(pyrimidin-2-ylethynyl)-1H-indol-1-yl)-N-(2-((3-chloro-2-fluorobenzyl)amino)-2-oxoethyl)-N-isopropylacetamide (116a)

Reaction of 2-(3-acetyl-5-bromo-1H-indol-1-yl)-N-(2-((3-chloro-2-fluorobenzyl)amino)-2-oxoethyl)-N-isopropylacetamide (90d) (325 mg, 0.61 mmol) with 2-ethynylpyrimidine (63 mg, 0.61 mmol) according to the procedure reported in scheme 92 gave after workup and purification by flash column chromatography [silica gel (12 g), eluting with EtOAc/MeOH (9:1) in hexanes 0 to 100%] 2-(3-acetyl-5-(pyrimidin-2-ylethynyl)-1H-indol-1-yl)-N-(2-((3-chloro-2-fluorobenzyl)amino)-2-oxoethyl)-N-isopropylacetamide (116a) (14 mg, 0.025 mmol, 4% yield) as a dark-yellow solid in the form of mixture of two rotamers; $^1$H NMR (300 MHz, DMSO-$d_6$) δ 8.92-8.80 (m, 2H), 8.59 (t, J=5.0 Hz) and 8.42-8.29 (m) (t & m, 2H), 8.51-8.45 (m, 1H), 7.66-6.93 (m, 6H), 5.42 and 5.24 (2s, 2H), 4.67-4.55 and 4.29-4.24 (2m, 1H), 4.52-4.31 (m, 2H), 4.19 and 3.86 (2s, 2H), 2.47 and 2.46 (2s, 3H), 1.27 (d, J=6.4 Hz) and 1.01 (d, J=6.8 Hz) (2d, 6H); $^{19}$F NMR (282 MHz, DMSO-$d_6$) δ −121.17, −121.75; MS (ES+): 560.6 (M+1); MS (ES−): 558.5 & 560.6 (M−1).

Scheme 117

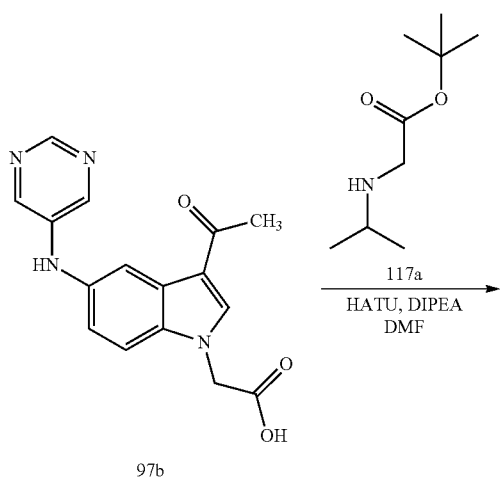

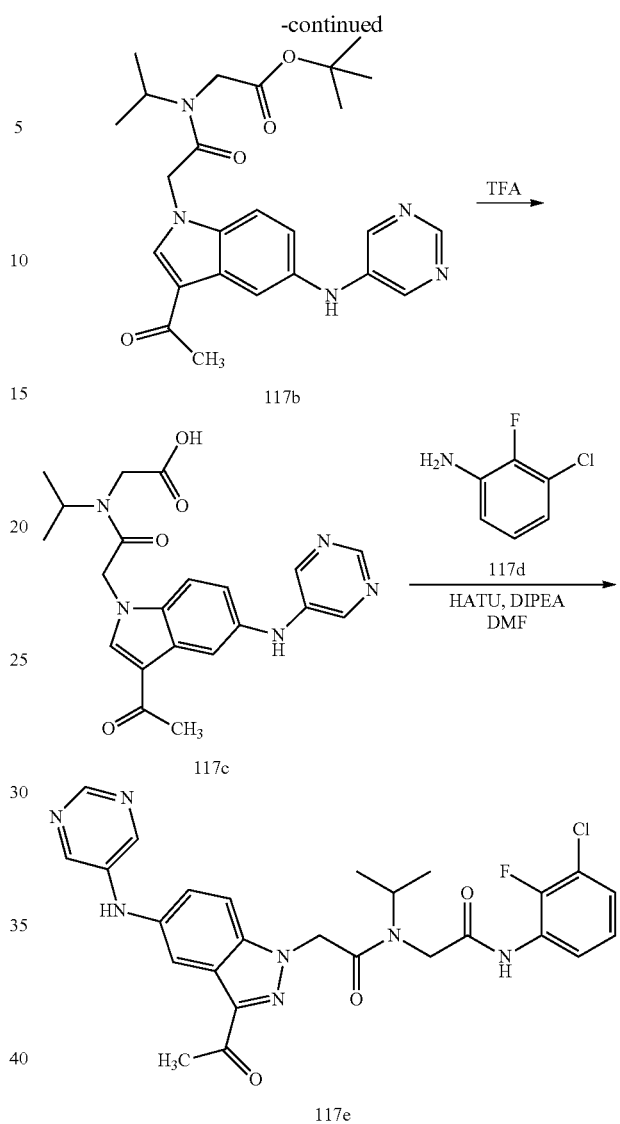

Preparation of 2-(3-acetyl-5-(pyrimidin-5-ylamino)-1H-indol-1-yl)-N-(2-((3-chloro-2-fluorophenyl)amino)-2-oxoethyl)-N-isopropylacetamide (117e)

Step-1: Preparation of tert-butyl 2-(2-(3-acetyl-5-(pyrimidin-5-ylamino)-1H-indol-1-yl)-N-isopropylacetamido)acetate (117b)

Reaction of tert-butyl 2-(isopropylamino)acetate (117a) (134 mg, 0.77 mmol, prepared according to the procedure reported by Brotherton-Pleiss, Christine E. et al; in PCT Int. Appl., 2014049047) with 2-(3-acetyl-5-(pyrimidin-5-ylamino)-1H-indol-1-yl)acetic acid (97b) (160 mg, 0.52 mmol) according to the procedure reported in step-3 of Scheme 2 gave after workup and purification by flash column chromatography [silica gel (12 g), eluting with CMA80 in CHCl$_3$ 0 to 30%] tert-butyl 2-(2-(3-acetyl-5-(pyrimidin-5-ylamino)-1H-indol-1-yl)-N-isopropylacetamido)acetate (117b) (120 mg, 0.26 mmol, 50% yield) as an off-white solid; $^1$H NMR (300 MHz, DMSO-$d_6$) δ 8.56 (d, J=0.9 Hz, 1H), 8.49 (s, 1H), 8.47 (s, 1H), 8.46 (s, 1H), 8.24 (s, 1H), 8.01 (d, J=2.1 Hz, 1H), 7.33 (t, J=8.2 Hz, 1H), 7.16-7.06 (m, 1H), 5.36 and 5.05 (2s, 2H), 4.67-4.52 and 4.34-4.27 (m, 1H), 4.26 and 3.84 (2s, 2H), 2.42 and 2.41 (2s, 3H), 1.51 and 1.36 (2s, 9H), 1.22 and 1.04 (2d, J=6.8 Hz, 6H); MS (ES−) 464.5 (M−1).

Step-2: Preparation of 2-(2-(3-acetyl-5-(pyrimidin-5-ylamino)-1H-indol-1-yl)-N-isopropylacetamido)acetic acid (117c)

Reaction of tert-butyl 2-(2-(3-acetyl-5-(pyrimidin-5-ylamino)-1H-indol-1-yl)-N-isopropylacetamido)acetate (117b) (120 mg, 0.26 mmol) with TFA (0.4 mL, 5.16 mmol) according to the procedure reported in step-2 of Scheme 2 gave after workup 2-(2-(3-acetyl-5-(pyrimidin-5-ylamino)-1H-indol-1-yl)-N-isopropylacetamido)acetic acid (117c) (120 mg, 0.29 mmol, 114% yield) light orange gummy solid; $^1$H NMR (300 MHz, DMSO-d$_6$) δ 8.57 (s, 1H), 8.48 (s, 2H), 8.25 (d, J=1.3 Hz, 1H), 8.01 (t, J=2.2 Hz, 1H), 7.36 and 7.34 (2s, 1H), 7.12 and 7.09 (2t, J=1.9 Hz, 1H), 5.35 and 5.07 (s, 2H), 4.66-4.54 (m, 1H), 4.35-4.18 (m, 1H), 3.87 (s, 1H), 2.41 and 2.41 (2s, 3H), 1.23 and 1.04 (2d, J=6.8 Hz, 6H); MS (ES+) 410.5 (M+1); MS (ES−) 408.5 (M−1).

Step-3: Preparation of 2-(3-acetyl-5-(pyrimidin-5-ylamino)-1H-indol-1-yl)-N-(2-((3-chloro-2-fluorophenyl)amino)-2-oxoethyl)-N-isopropylacetamide (117e)

Reaction of 2-(2-(3-acetyl-5-(pyrimidin-5-ylamino)-1H-indol-1-yl)-N-isopropylacetamido)acetic acid (117c) (50 mg, 0.12 mmol) with 3-chloro-2-fluoroaniline (117d) (0.018 g, 0.122 mmol) according to the procedure reported in step-3 of Scheme 2 gave after workup and purification by flash column chromatography [silica gel (12 g), eluting with CMA80 in CHCl$_3$ 0 to 30%] 2-(3-acetyl-5-(pyrimidin-5-ylamino)-1H-indol-1-yl)-N-(2-((3-chloro-2-fluorophenyl)amino)-2-oxoethyl)-N-isopropylacetamide (117e) (25 mg, 0.047 mmol, 38% yield) as an off-white solid as a mixture of two rotamers; $^1$H NMR (300 MHz, DMSO-d$_6$) δ 10.33 and 9.84 (2s, 1H), 8.56 (s, 1H), 8.49 (s, 1H), 8.47 and 8.46 (2s, 2H), 8.25 and 8.23 (2s, 1H), 8.03-8.00 (m, 1H), 7.97 and 7.79 (2t, J=7.6 Hz, 1H), 7.49-7.06 (m, 4H), 5.38 and 5.19 (2s, 2H), 4.75-4.58 and 4.37-4.25 (2m, 1H), 4.46 and 4.09 (2s, 2H), 2.42 and 2.41 (2s, 3H), 1.28 and 1.07 (2d, J=6.8 Hz, 6H); $^{19}$F NMR (282 MHz, DMSO-d$_6$) (a mixture of two rotamers) δ −126.50, −126.67; MS (ES+): 537.6 (M+1); MS (ES−): 535.5 (M−1).

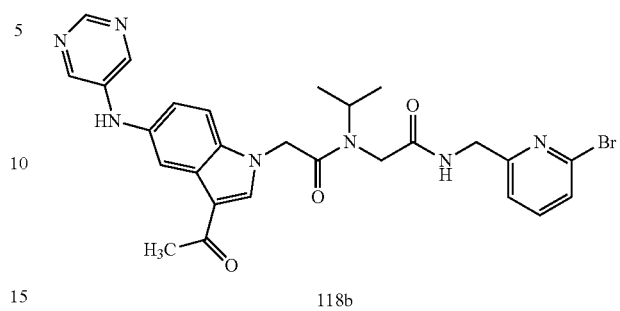

118b

Preparation of 2-(3-acetyl-5-(pyrimidin-5-ylamino)-1H-indol-1-yl)-N-(2-(((6-bromopyridin-2-yl)methyl)amino)-2-oxoethyl)-N-isopropylacetamide (118b)

Reaction of 2-(2-(3-acetyl-5-(pyrimidin-5-ylamino)-1H-indol-1-yl)-N-isopropylacetamido)acetic acid (117c) (60 mg, 0.15 mmol) with (6-bromopyridin-2-yl)methanamine (118a) (27 mg, 0.15 mmol) according to the procedure reported in step-3 of Scheme 2 gave after workup and purification by flash column chromatography [silica gel (12 g), eluting with CMA80 in CHCl$_3$ 0 to 30%] 2-(3-acetyl-5-(pyrimidin-5-ylamino)-1H-indol-1-yl)-N-(2-(((6-bromopyridin-2-yl)methyl)amino)-2-oxoethyl)-N-isopropylacetamide (118b) (5 mg, 0.086 mmol, 59% yield) as an off-white solid as a mixture of two rotamers; $^1$H NMR (300 MHz, DMSO-d$_6$) δ 8.92 (t, J=6.0 Hz, 1H), 8.56 and 8.55 (2s, 1H), 8.48 (s, 1H), 8.464 and 8.458 (2s, 2H), 8.24 and 8.19 (2s, 1H), 8.00 (t, 1H), 7.74 (t, J=7.7 Hz, 1H), 7.62-7.19 (m, 3H), 7.13-7.00 (m, 1H), 5.34 and 5.17 (2s, 2H), 4.67-4.54 and 4.28-4.24 (2m, 1H), 4.48 and 4.34 (2d, J=6.0 Hz, 2H), 4.22 and 3.87 (2s, 2H), 2.40 and 2.39 (2s, 3H), 1.28 and 1.04 (d, J=6.8 Hz, 6H); MS (ES+): 578.6, 580.6 (M+1); MS (ES−): 576.6, 578.5 (M−1).

Scheme 118

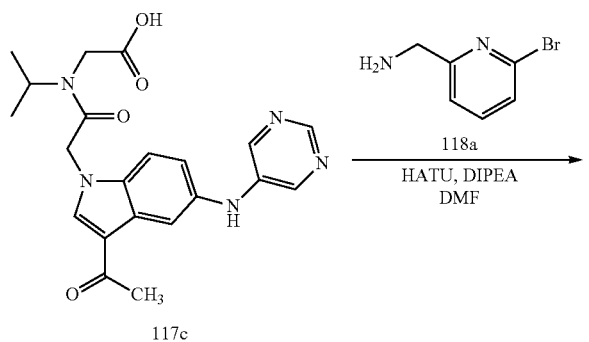

117c

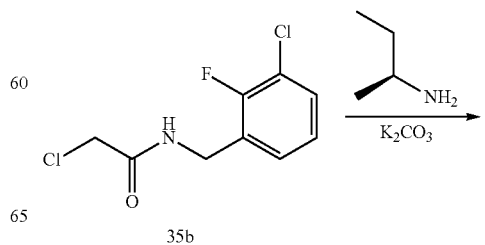

Scheme 119

35b

-continued

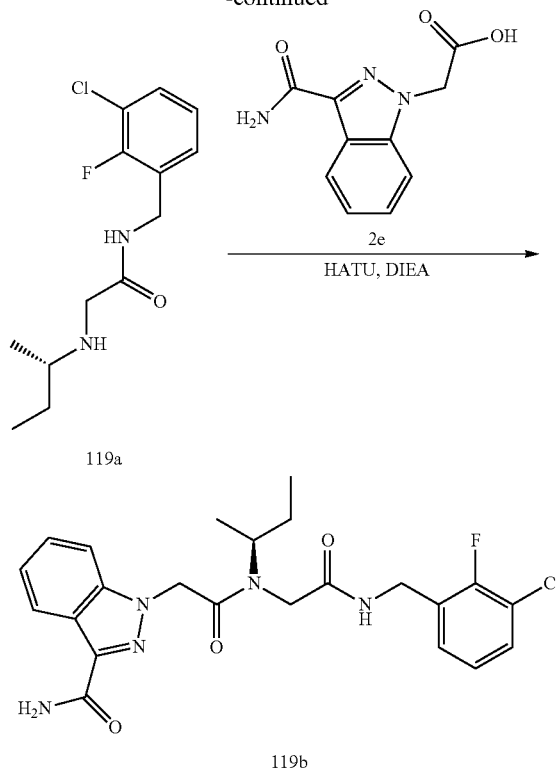

119a

119b

Preparation of (S)-1-(2-(sec-butyl(2-((3-chloro-2-fluorobenzyl)amino)-2-oxoethyl)amino)-2-oxo-ethyl)-1H-indazole-3-carboxamide (119b)

Step-1: Preparation of (S)-2-(sec-butylamino)-N-(3-chloro-2-fluorobenzyl)acetamide (119a)

Reaction of 2-chloro-N-(3-chloro-2-fluorobenzyl)acetamide (35b) (350 mg, 1.48 mmol) with (S)-butan-2-amine (271 mg, 3.71 mmol) according to the procedure reported in step-2 of Scheme 35 gave after workup (S)-2-(sec-butylamino)-N-(3-chloro-2-fluorobenzyl)acetamide (119a) (402 mg, 1.47 mmol, 99% yield) as a yellow oil, which was used in the next step without further purification; $^1$H NMR (300 MHz, DMSO-$d_6$) δ 8.35 (t, J=5.8 Hz, 1H), 7.52-7.38 (m, 1H), 7.33-7.23 (m, 1H), 7.23-7.09 (m, 1H), 4.37 (d, J=5.9 Hz, 2H), 3.13 (s, 2H), 2.46-2.31 (m, 1H), 2.07 (s, 1H), 1.55-1.30 (m, 1H), 1.30-1.08 (m, 1H), 0.92 (d, J=6.3 Hz, 3H), 0.81 (t, J=7.4 Hz, 3H); $^{19}$F NMR (282 MHz, DMSO-$d_6$) δ −121.65; MS (ES$^+$) 273.4 (M+1); MS (ES$^-$) 271.3 (M−1);

Step-2: Preparation of (S)-1-(2-(sec-butyl(2-((3-chloro-2-fluorobenzyl)amino)-2-oxoethyl)amino)-2-oxoethyl)-1H-indazole-3-carboxamide (119b)

Reaction of (S)-2-(sec-butylamino)-N-(3-chloro-2-fluorobenzyl)acetamide (119a) (180 mg, 0.66 mmol) with 2-(3-carbamoyl-1H-indazol-1-yl)acetic acid (2e) (159 mg, 0.73 mmol) according to the procedure reported in step-3 of Scheme 2 gave after workup and purification by flash column chromatography [silica (12 g), eluting with CMA-80 in CHCl$_3$ 0 to 60%] (S)-1-(2-(sec-butyl(2-((3-chloro-2-fluorobenzyl)amino)-2-oxo ethyl)-1H-indazole-3-carboxamide (119b) (220 mg, 0.46 mmol, 70% yield) as a white solid; $^1$H NMR (300 MHz, DMSO-$d_6$) δ 8.82 (t, J=5.7 Hz) and 8.35 (t, J=5.9 Hz) (2t, 1H), 8.18 (d, J=8.1 Hz, 1H), 7.75-7.67 (m, 1H), 7.61-7.00 (m, 7H), 5.68-5.39 (m, 2H), 4.51-3.70 (m, 5H), 1.63-0.50 (m, 8H); $^{19}$F NMR (282 MHz, DMSO) δ −121.19, −121.76; MS (ES+): 474.5 (M+1), 496.5 (M+Na); (ES−): 472.5 (M−1); 518.5 (M+Cl); [based on NMR, this compound is a mixture of two rotamers 2:1 ratio].

Scheme 120

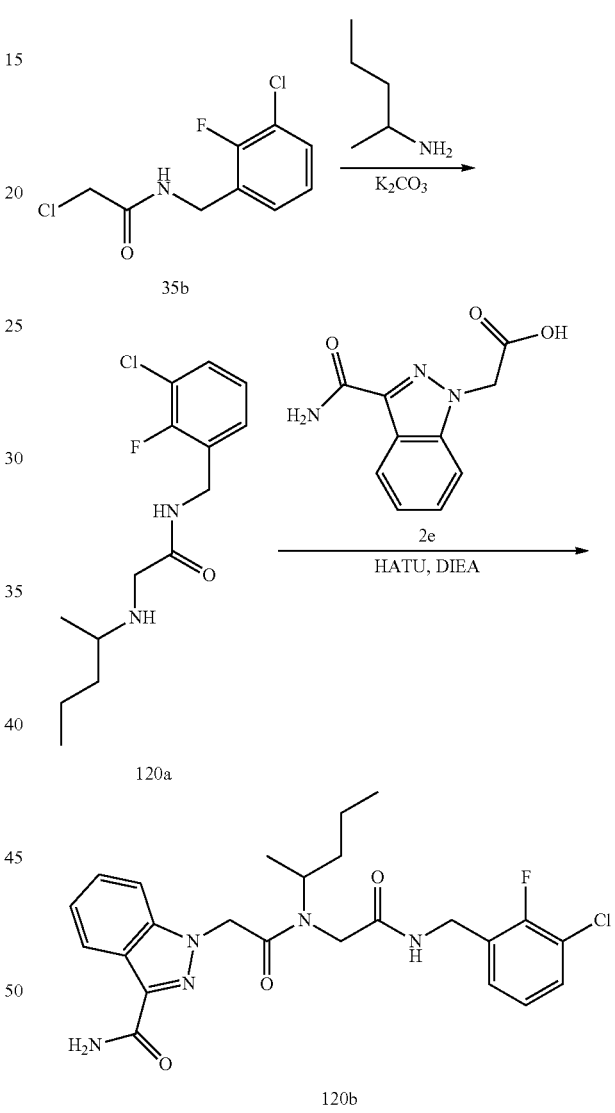

120a

120b

Preparation of 1-(2-((2-((3-chloro-2-fluorobenzyl)amino)-2-oxoethyl)(pentan-2-yl)-amino)-2-oxo-ethyl)-1H-indazole-3-carboxamide (120b)

Step-1: Preparation of N-(3-chloro-2-fluorobenzyl)-2-(pentan-2-ylamino)acetamide (120a)

Reaction of 2-chloro-N-(3-chloro-2-fluorobenzyl)acetamide (35b) (350 mg, 1.48 mmol) with pentan-2-amine (323 mg, 3.71 mmol) according to the procedure reported in step-2 of Scheme 35 gave after workup N-(3-chloro-2-fluorobenzyl)-2-(pentan-2-ylamino)acetamide (120a) (400 mg, 1.4 mmol, 94% yield) as a yellow oil, which was used in the next step without further purification; $^1$H NMR (300 MHz, DMSO-d$_6$) δ 8.36 (t, J=6.0 Hz, 1H), 7.53-7.42 (m, 1H), 7.34-7.24 (m, 1H), 7.22-7.11 (m, 1H), 4.37 (d, J=5.8 Hz, 2H), 3.14 (d, J=2.6 Hz, 2H), 2.50-2.42 (m, 1H), 2.06 (s, 1H), 1.40-1.14 (m, 4H), 0.93 (d, J=6.3 Hz, 3H), 0.84 (t, J=7.0 Hz, 3H); $^{19}$F NMR (282 MHz, DMSO) δ −121.65; MS (ES+) 287.4 (M+1); MS (ES−) 285.4 (M−1);

Step-2: Preparation of 1-(2-((2-((3-chloro-2-fluorobenzyl)amino)-2-oxoethyl)(pentan-2-yl)amino)-2-oxoethyl)-1H-indazole-3-carboxamide (120b)

Reaction of N-(3-chloro-2-fluorobenzyl)-2-(pentan-2-ylamino)acetamide (120a) (146 mg, 0.51 mmol) with 2-(3-carbamoyl-1H-indazol-1-yl)acetic acid (2e) (123 mg, 0.56 mmol) according to the procedure reported in step-3 of Scheme 2 gave after workup and purification by flash column chromatography [silica (12 g), eluting with CMA-80 in CHCl$_3$ 0 to 60%] 1-(2-((2-((3-chloro-2-fluorobenzyl)amino)-2-oxoethyl)(pentan-2-yl)amino)-2-oxoethyl)-1H-indazole-3-carboxamide (120b) (174 mg, 0.36 mmol, 70% yield) as a white solid; $^1$H NMR (300 MHz, DMSO-d$_6$) δ 8.81 (t, J=5.7 Hz) and 8.35 (t, J=5.9 Hz) (2t, 1H), 8.18 (d, J=8.1 Hz, 1H), 7.71 (s, 1H), 7.57-7.10 (m, 7H), 5.66-5.35 (m, 2H), 4.63-3.67 (m, 5H), 1.45-0.69 (m, 10H); $^{19}$F NMR (282 MHz, DMSO) δ −121.19, −121.75; MS (ES+): 488.5 (M+1), 510.5 (M+Na); (ES−): 486.5 (M−1). [based on NMR, this compound is a mixture of two rotamers with 3:1 ratio]

Scheme 121

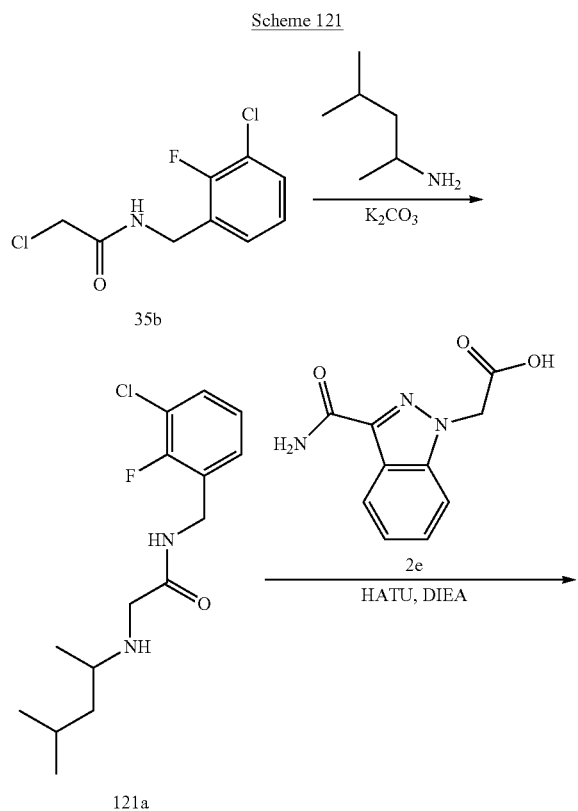

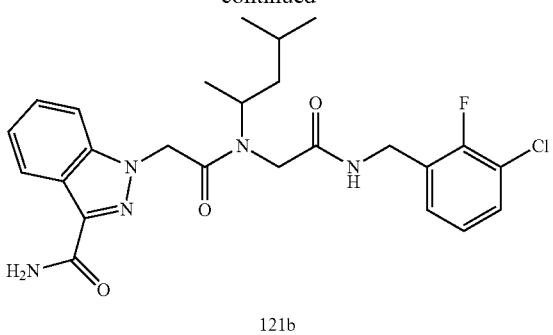

Preparation of 1-(2-((2-((3-chloro-2-fluorobenzyl)amino)-2-oxoethyl)(4-methylpentan-2-yl)amino)-2-oxoethyl)-1H-indazole-3-carboxamide (121b)

Step-1: Preparation of N-(3-chloro-2-fluorobenzyl)-2-((4-methylpentan-2-yl)amino)acetamide (121a)

Reaction of 2-chloro-N-(3-chloro-2-fluorobenzyl)acetamide (35b) (350 mg, 1.48 mmol) with 4-methylpentan-2-amine (375 mg, 3.71 mmol) according to the procedure reported in step-2 of Scheme 35 gave after workup and purification by flash column chromatography [silica (12 g), eluting with EtOAc/MeOH (9:1) in hexane 0 to 60%] to give N-(3-chloro-2-fluorobenzyl)-2-(4-methylpentan-2-ylamino)acetamide (121a) (235 mg, 0.78 mmol, 53% yield) as a yellow oil; $^1$H NMR (300 MHz, DMSO-d$_6$) δ 8.35 (t, J=6.0 Hz, 1H), 7.55-7.41 (m, 1H), 7.37-7.25 (m, 1H), 7.22-7.12 (m, 1H), 4.45-4.29 (m, 2H), 3.14 (d, J=3.9 Hz, 2H), 2.54-2.49 (m, 1H), 2.06 (s, 1H), 1.75-1.51 (m, 1H), 1.35-1.13 (m, 1H), 1.13-0.98 (m, 1H), 0.92 (d, J=6.2 Hz, 3H), 0.86-0.77 (m, 6H); $^{19}$F NMR (282 MHz, DMSO) δ −121.63; MS (ES+): 301.4 (M+1); MS (ES−): 299.4 (M−1);

Step-2: Preparation of 1-(2-((2-((3-chloro-2-fluorobenzyl)amino)-2-oxoethyl)(4-methylpentan-2-yl)amino)-2-oxoethyl)-1H-indazole-3-carboxamide (121b)

Reaction of N-(3-chloro-2-fluorobenzyl)-2-(4-methylpentan-2-ylamino)acetamide (121a) (120 mg, 0.4 mmol) with 2-(3-carbamoyl-1H-indazol-1-yl)acetic acid (2e) (96 mg, 0.44 mmol) according to the procedure reported in step-3 of Scheme 2 gave after workup and purification by flash column chromatography [silica (12 g), eluting with CMA-80 in CHCl$_3$ 0 to 60%] 1-(2-((2-((3-chloro-2-fluorobenzyl)amino)-2-oxoethyl)(4-methylpentan-2-yl)amino)-2-oxoethyl)-1H-indazole-3-carboxamide (121b) (142 mg, 0.28 mmol, 71% yield) as a white solid; $^1$H NMR (300 MHz, DMSO-d$_6$) δ 8.81 (t, J=5.7 Hz) and 8.36 (t, J=6.2 Hz) (2t, 1H), 8.25-8.11 (m, 1H), 7.72 (s, 1H), 7.57-7.17 (m, 7H), 5.78-5.25 (m, 2H), 4.66-4.02 (m, 5H), 1.56-0.63 (m, 12H); $^{19}$F NMR (282 MHz, DMSO) δ −121.17, −121.72; MS (ES+) 524.6 (M+Na); (ES−): 500.5 (M−1); [based on NMR, this compound is a mixture of two rotamers 4:1 ratio].

Scheme 122

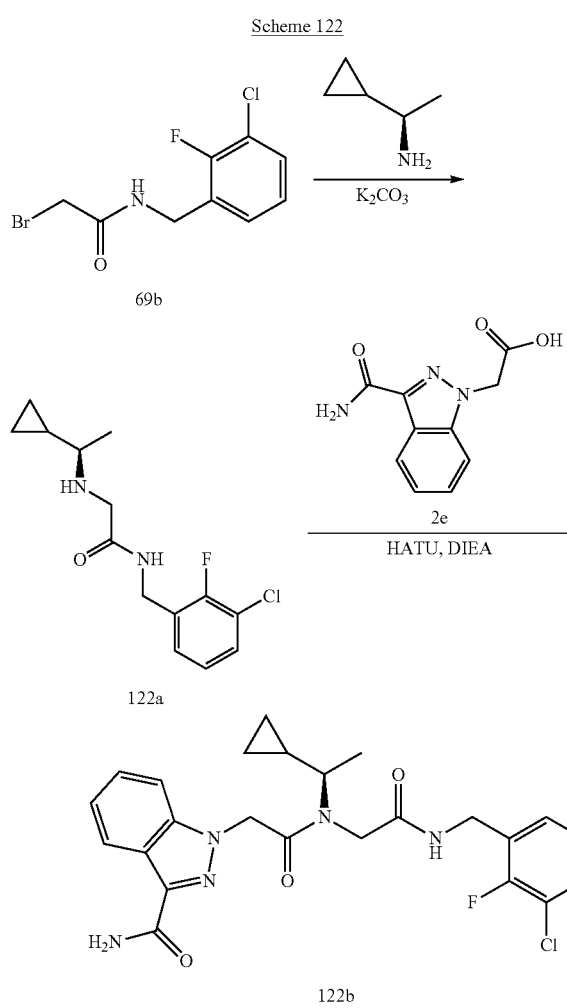

reported in step-3 of Scheme 2 gave after workup and purification by flash column chromatography [silica (40 g), eluting with MeOH in CHCl₃ 0 to 10%] (R)-1-(2-((2-((3-chloro-2-fluorobenzyl)amino)-2-oxoethyl)(1-cyclopropyl-ethyl)amino)-2-oxoethyl)-1H-indazole-3-carboxamide (122b) (0.251 g, 0.517 mmol, 47.4% yield) as a white solid as a mixture two rotamers; $^1$H NMR (300 MHz, DMSO-d₆) δ 8.82 (t, J=5.7 Hz) and 8.29 (t, J=5.9 Hz) (2t, 1H), 8.23-8.12 (m, 1H), 7.73 and 7.69 (2s, 1H), 7.59-6.96 (m, 7H), 5.68-5.39 (m, 2H), 4.46 (d, J=5.5 Hz) and 4.39-4.26 (m) and 3.96 (s) (d & m & s, 4H), 3.80-3.62 and 3.60-3.46 (2m, 1H), 1.27 (d, J=6.4 Hz) and 1.03 (d, J=6.8 Hz) (2d, 3H), 1.15-0.79 (m, 1H), 0.61-0.00 (m, 4H); $^{19}$F NMR (282 MHz, DMSO-d₆) δ −121.19, −121.75; MS (ES+): 486.5, 488.5 (M+1), 508.5, 510.5 (M+Na); MS (ES−): 484.5 (M−1), 520.5, 522.5 (M+Cl).

Scheme 123

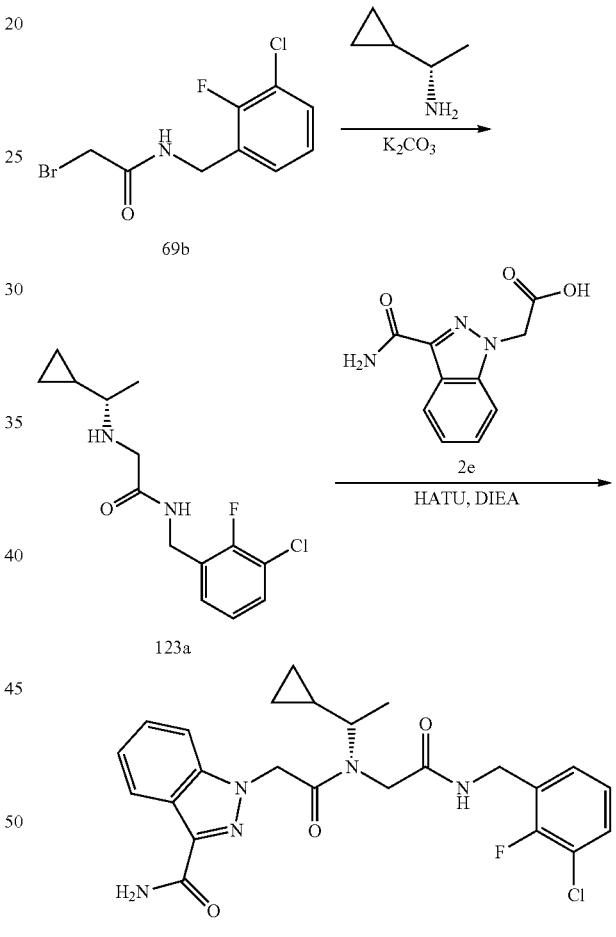

Preparation of (R)-1-(2-((2-((3-chloro-2-fluorobenzyl)amino)-2-oxoethyl)(1-cyclopropylethyl)amino)-2-oxoethyl)-1H-indazole-3-carboxamide (122b)

Step-1: Preparation of (R)—N-(3-chloro-2-fluorobenzyl)-2-((1-cyclopropylethyl)amino)acetamide (122a)

Reaction of 2-bromo-N-(3-chloro-2-fluorobenzyl)acetamide (69b) (323 mg, 1.16 mmol) with (R)-1-cyclopropylethanamine (99 mg, 1.16 mmol) according to the procedure reported in step-2 of Scheme 35 gave after workup (R)—N-(3-chloro-2-fluorobenzyl)-2-((1-cyclopropylethyl)amino)acetamide (122a) (310 mg, 1.09 mmol, 94% yield) as a yellow oil which was used as such without further purification; MS (ES+): 285.4 (M+1).

Step-2: Preparation of (R)-1-(2-((2-((3-chloro-2-fluorobenzyl)amino)-2-oxoethyl)(1-cyclopropylethyl)amino)-2-oxoethyl)-1H-indazole-3-carboxamide (122b)

Reaction of (R)—N-(3-chloro-2-fluorobenzyl)-2-((1-cyclopropylethyl)amino)acetamide (122a) (310 mg, 1.09 mmol) with 2-(3-carbamoyl-1H-indazol-1-yl)acetic acid (2e) (286 mg, 1.31 mmol) according to the procedure Preparation of (S)-1-(2-((2-((3-chloro-2-fluorobenzyl)amino)-2-oxoethyl)(1-cyclopropylethyl)amino)-2-oxoethyl)-1H-indazole-3-carboxamide (123b)

Step-1: Preparation of (S)—N-(3-chloro-2-fluorobenzyl)-2-((1-cyclopropylethyl)amino)acetamide (123a)

Reaction of 2-bromo-N-(3-chloro-2-fluorobenzyl)acetamide (69b) (355 mg, 1.27 mmol) with (S)-1-cyclopropylethanamine (108 mg, 1.27 mmol) according to the procedure reported in step-2 of Scheme 35 gave after workup (S)—N-(3-chloro-2-fluorobenzyl)-2-((1-cyclopropylethyl)amino) acetamide (123a) (354 mg, 1.24 mmol, 98% yield) as a thick yellow oil which was used as such in the next step; MS (ES+): 285.4 (M+1); MS (ES−): 319.3 (M+Cl)

Step-2: Preparation of (S)-1-(2-((2-((3-chloro-2-fluorobenzyl)amino)-2-oxoethyl)(1-cyclopropylethyl)amino)-2-oxoethyl)-1H-indazole-3-carboxamide (123b)

Reaction of (S)—N-(3-chloro-2-fluorobenzyl)-2-((1-cyclopropylethyl)amino)acetamide (123a) (350 mg, 1.23 mmol) with 2-(3-carbamoyl-1H-indazol-1-yl)acetic acid (2e) (323 mg, 1.48 mmol) according to the procedure reported in step-3 of Scheme 2 gave after workup and purification by flash column chromatography [First column: Silica gel, (24 g) eluting with MeOH in DCM from 0-20%; Second column silica gel, (24 g) eluting with MeOH in CHCl₃ from 0-10%)] (S)-1-(2-((2-((3-chloro-2-fluorobenzyl)amino)-2-oxoethyl)(1-cyclopropylethyl)amino)-2-oxoethyl)-1H-indazole-3-carboxamide (123b) (0.079 g, 0.163 mmol, 13% yield) as a white solid in the form of mixture two rotamers; $^1$H NMR (300 MHz, DMSO-$d_6$) δ 8.83 (t, J=5.7 Hz) and 8.30 (t, J=5.9 Hz) (2t, 1H), 8.21-8.15 (m, 1H), 7.73 and 7.70 (2s, 1H), 7.62-6.96 (m, 7H), 5.70-5.36 (m, 2H), 4.46 (d, J=5.5 Hz) and 4.36-4.26 (m) and 3.97 (s) (d & m & s, 4H), 3.80-3.63 and 3.59-3.45 (2m, 1H), 1.28 (d, J=6.5 Hz) and 1.03 (d, J=6.8 Hz)(2d, 3H), 1.15-0.79 (m, 1H), 0.60 to −0.02 (m, 4H); $^{19}$F NMR (282 MHz, DMSO-$d_6$) δ −121.19, −121.75. MS (ES+): 486.5 (M+1), 508.5 (M+Na); MS (ES−): 484.5 & 486.5 (M−1), 520.5 (M+Cl).

Scheme 124

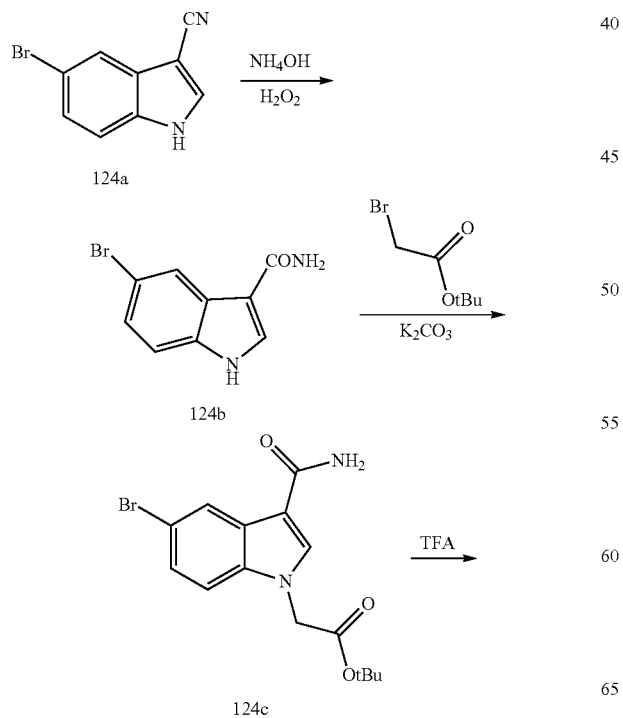

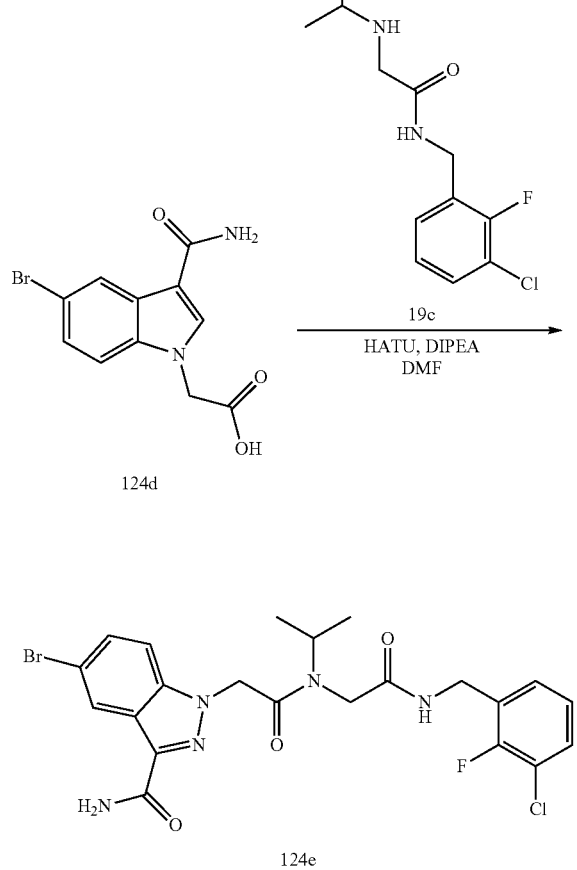

Preparation of 5-bromo-1-(2-((2-((3-chloro-2-fluorobenzyl)amino)-2-oxoethyl)(isopropyl)amino)-2-oxoethyl)-1H-indole-3-carboxamide (124e)

Step-1: Preparation of 5-bromo-1H-indole-3-carboxamide (124b)

Reaction of 5-bromo-1H-indole-3-carbonitrile (124a) (1.38 g, 6.22 mmol) with ammonium hydroxide (4.85 mL, 124 mmol) and hydrogen peroxide (1.9 mL, 62.2 mmol) according to the procedure reported Scheme 65 gave after workup 5-bromo-1H-indole-3-carboxamide (124b) (1.2 g, 5.02 mmol, 81% yield) as an off-white solid; MS (ES+): 239.2, 241.2 (M+2), MS (ES−): 237.1, 239.1 (M−2).

Step-2: Preparation of tert-butyl 2-(5-bromo-3-carbamoyl-1H-indol-1-yl)acetate (124c)

Reaction of 5-bromo-1H-indole-3-carboxamide (124b) (1.2 g, 5.02 mmol) with tert-butyl 2-bromoacetate (1.11 mL, 7.53 mmol) using potassium carbonate (1.39 g, 10.04 mmol) as base according to the procedure reported step-1 of Scheme 45 gave after workup and purification by flash column chromatography [silica gel (40 g), eluting with CMA80 in CHCl$_3$ 0 to 15%] tert-butyl 2-(5-bromo-3-carbamoyl-1H-indol-1-yl)acetate (124c) (970 mg, 2.75 mmol, 55% yield) as off-white solid; $^1$H NMR (300 MHz, DMSO-d$_6$) δ 8.36-8.27 (m, 1H), 8.00 (s, 1H), 7.54 (brs, 1H), 7.43 (dd, J=8.8, 0.6 Hz, 1H), 7.33 (dd, J=8.7, 2.0 Hz, 1H), 6.96 (brs, 1H), 5.10 (s, 2H), 1.42 (s, 9H); MS (ES+): 353.4, 355.4 (M+2), MS (ES−): 351.3, 353.3 (M−1).

Step-3: Preparation of 2-(5-bromo-3-carbamoyl-1H-indol-1-yl)acetic acid (124d)

Reaction of tert-butyl 2-(5-bromo-3-carbamoyl-1H-indol-1-yl)acetate (124c) (500 mg, 1.42 mmol) with TFA (2.18 mL, 28.3 mmol) according to the procedure reported in step-2 of Scheme 2 gave after workup and trituration of crude product with 30% EtOAc-hexane (10 mL) 2-(5-bromo-3-carbamoyl-1H-indol-1-yl)acetic acid (124d) (420 mg, 1.41 mmol, 100% yield) as light orange solid; $^1$H NMR (300 MHz, DMSO-d$_6$) δ 13.24 (bs, 1H), 8.31 (d, J=1.9 Hz, 1H), 8.01 (s, 1H), 7.65-7.38 (m, 2H), 7.32 (dd, J=8.7, 2.0 Hz, 1H), 6.97 (s, 1H), 5.10 (s, 2H); MS (ES+): 297.2, 299.3 (M+2); MS (ES−); 295.2, 297.2 (M−2).

Step-4: Preparation of 5-bromo-1-(2-((2-((3-chloro-2-fluorobenzyl)amino)-2-oxoethyl)(isopropyl)amino)-2-oxoethyl)-1H-indole-3-carboxamide (124e)

Reaction of 2-(5-bromo-3-carbamoyl-1H-indol-1-yl)acetic acid (124d) (400 mg, 1.35 mmol) with N-(3-chloro-2-fluorobenzyl)-2-(isopropylamino)acetamide (19c) (348 mg, 1.35 mmol) according to the procedure reported in step-3 of Scheme 2 gave after workup 5-bromo-1-(2-((2-(3-chloro-2-fluorobenzylamino)-2-oxoethyl)(isopropyl)amino)-2-oxoethyl)-1H-indole-3-carboxamide (124e) (0.52 g, 0.967 mmol, 71.8% yield) as a white solid as a mixture of two rotamers; $^1$H NMR (300 MHz, DMSO-d$_6$) (a mixture of two rotamers) δ 8.81 (t, J=5.7 Hz) and 8.34-8.27 (m) (t & m, 2H), 7.97 (s, 1H), 7.59-6.76 (m, 7H), 5.32 and 5.14 (2s, 2H), 4.62-4.51 and 4.28-4.21 (2m, 1H), 4.46 and 4.32 (2d, J=5.6 Hz, 2H), 4.15 and 3.83 (2s, 2H), 1.23 and 0.98 (2d, J=6.8 Hz, 6H); $^{19}$F NMR (282 MHz, DMSO-d$_6$) (a mixture of two rotamers) δ −121.22 and −121.76; MS (ES+): 561.4 (M+23), MS (ES−): 571.4, 573.3 (M+Cl).

Scheme 125

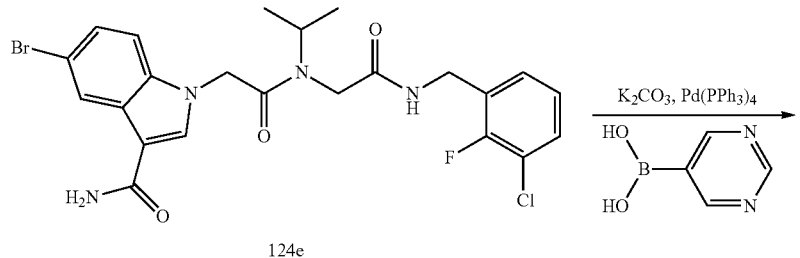

124e

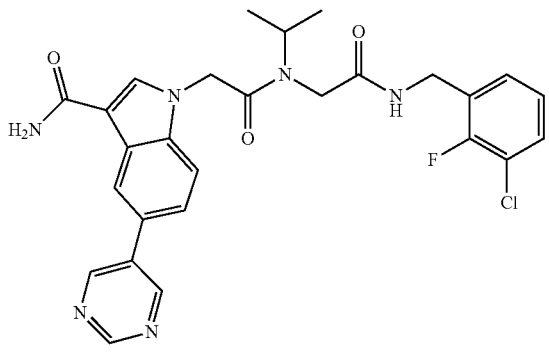

125a

Preparation of 1-(2-((2-((3-chloro-2-fluorobenzyl)amino)-2-oxoethyl)(isopropyl)amino)-2-oxoethyl)-5-(pyrimidin-5-yl)-1H-indole-3-carboxamide (125a)

Reaction of 5-bromo-1-(2-((2-((3-chloro-2-fluorobenzyl)amino)-2-oxoethyl)(isopropyl)amino)-2-oxoethyl)-1H-indole-3-carboxamide (124e) (120 mg, 0.22 mmol) with pyrimidin-5-ylboronic acid (33 mg, 0.27 mmol) according the procedure reported in Scheme 100 gave after workup and purification by flash column chromatography [silica gel (12 g), eluting with CMA80 in CHCl$_3$ 0 to 30%] 1-(2-((2-((3-chloro-2-fluorobenzyl)amino)-2-oxoethyl)(isopropyl)amino)-2-oxoethyl)-5-(pyrimidin-5-yl)-1H-indole-3-carboxamide (125a) as a white solid as a mixture of rotamers in 2:1 ratio; $^1$H NMR (300 MHz, DMSO-d$_6$) δ 9.167 and 9.161 (2s, 1H), 9.138 and 9.131 (2s, 2H), 8.83 and 8.33 (2t, J=5.7 Hz, 1H), 8.45 (s, 1H), 8.01 and 7.99 (2s, 1H), 7.74-6.80 (m, 7H), 5.37 and 5.19 (2s, 2H), 4.65-4.53 and 4.31-4.20 (2m, 1H), 4.48 and 4.33 (2d, J=5.6 Hz, 2H), 4.18 and 3.85 (2s, 2H), 1.25 and 1.00 (2d, J=6.6 Hz, 6H); NMR (282 MHz, DMSO-d$_6$) δ −121.21 and −121.79; MS (ES+) 537.5 (M+1), 559.5 (M+23), MS (ES−) 571.5 (M+Cl).

Scheme 126

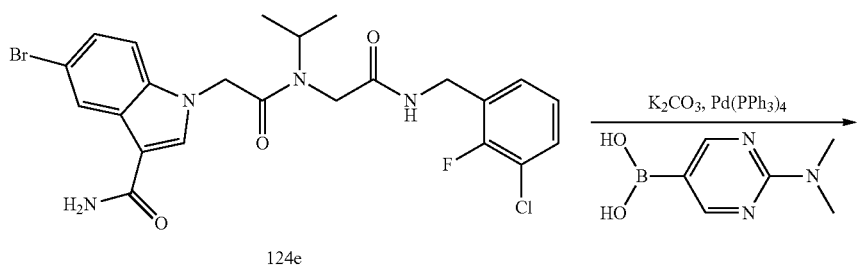

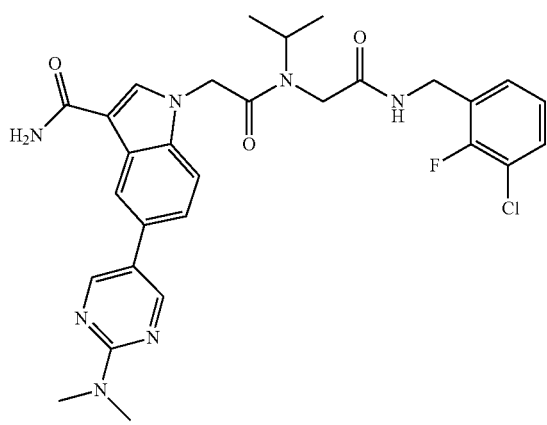

Preparation of 1-(2-((2-((3-chloro-2-fluorobenzyl)amino)-2-oxoethyl)(isopropyl)amino)-2-oxoethyl)-5-(2-(dimethylamino)pyrimidin-5-yl)-1H-indole-3-carboxamide (126a)

Reaction of 5-bromo-1-(2-((2-((3-chloro-2-fluorobenzyl)amino)-2-oxoethyl)(isopropyl)amino)-2-oxoethyl)-1H-indole-3-carboxamide (124e) (120 mg, 0.22 mmol) with 2-(dimethylamino)pyrimidin-5-ylboronic acid (45 mg, 0.27 mmol) according the procedure reported in Scheme 100 gave after workup and purification by flash column chromatography [silica gel (12 g), eluting with CMA80 in CHCl$_3$ 0 to 40%]1-(2-((2-((3-chloro-2-fluorobenzyl)amino)-2-oxoethyl)(isopropyl)amino)-2-oxoethyl)-5-(2-(dimethylamino)pyrimidin-5-yl)-1H-indole-3-carboxamide (126a) (85 mg, 0.15 mmol, 66% yield) as a white solid as a mixture of rotamers in 2:1 ratio; $^1$H NMR (300 MHz, DMSO-d$_6$) δ 8.82 (t, J=5.8 Hz, 1H), 8.66 (s, 2H), 8.37-8.23 (m, 1H), 7.99-7.90 (m, 2H), 7.66-6.72 (m, 6H), 5.33 and 5.15 (2s, 2H), 4.64-4.51 and 4.28-4.22 (2m, 1H), 4.48 and 4.32 (2d, J=5.8 Hz, 2H), 4.17 and 3.84 (2s, 2H), 3.178 and 3.172 (2s, 6H), 1.24 and 0.99 (2d, J=6.8 Hz, 6H); $^{19}$F NMR (282 MHz, DMSO-d$_6$) δ -121.21 and -121.77; MS (ES+): 580.6 (M+1); MS (ES-): 614.6 (M+Cl).

Scheme 127

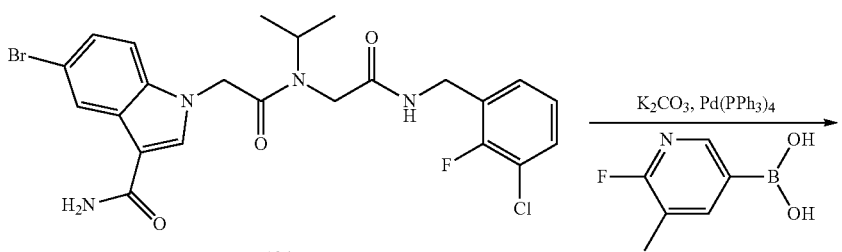

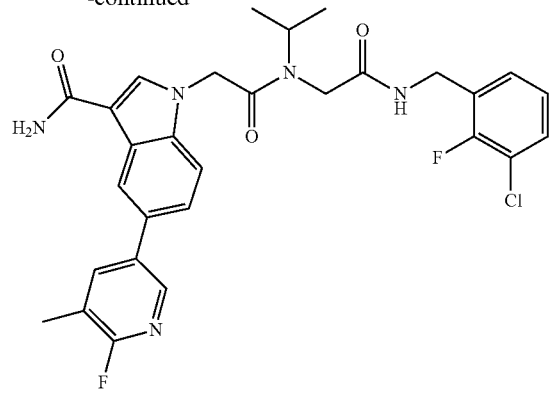

127a

Preparation of 1-(2-((2-((3-chloro-2-fluorobenzyl)amino)-2-oxoethyl)(isopropyl)amino)-2-oxoethyl)-5-(6-fluoro-5-methylpyridin-3-yl)-1H-indole-3-carboxamide (127a)

Reaction of 5-bromo-1-(2-((2-((3-chloro-2-fluorobenzyl)amino)-2-oxoethyl)(isopropyl)amino)-2-oxoethyl)-1H-indole-3-carboxamide (124e) (120 mg, 0.22 mmol) with 6-fluoro-5-methylpyridin-3-ylboronic acid (0.041 g, 0.268 mmol) according the procedure reported in Scheme 100 gave after workup and purification by flash column chromatography [silica gel (12 g), eluting with CMA80 in CHCl$_3$ 0 to 30%]1-(2-((2-((3-chloro-2-fluorobenzyl)amino)-2-oxoethyl)(isopropyl)amino)-2-oxoethyl)-5-(6-fluoro-5-methylpyridin-3-yl)-1H-indole-3-carboxamide (127a) (95 mg, 0.17 mmol, 75% yield) as a white solid as a mixture of rotamers in 2:1 ratio; $^1$H NMR (300 MHz, DMSO-d$_6$) δ 8.83 (t, J=5.7 Hz, 1H), 8.40-8.29 (m, 2H), 8.17-8.08 (m, 1H), 7.98 and 7.97 (2s, 1H), 7.61-7.34 (m, 5H), 7.22 and 7.03 (2t, J=7.8 Hz, 1H), 6.94 (bs, 1H), 5.35 and 5.18 (2s, 2H), 4.66-4.52 and 4.30-4.22 (2m, 1H), 4.48 and 4.33 (d, J=5.6 Hz, 2H), 4.18 and 3.85 (2s, 2H), 2.34 (s, 3H), 1.24 and 1.00 (d, J=6.8 Hz, 6H); $^{19}$F NMR (282 MHz, DMSO-d$_6$) (a mixture of two rotamers) δ −76.98, −121.21 and −121.78; MS (ES+): 568.6 (M+1), 590.5 (M+23), MS (ES−): 602.5 (M+Cl).

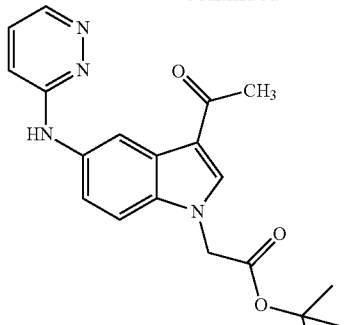

128a

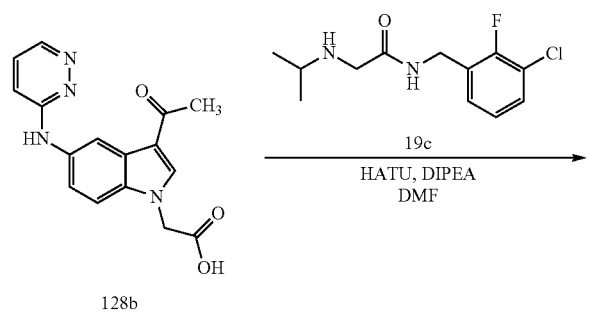

128b

Scheme 128

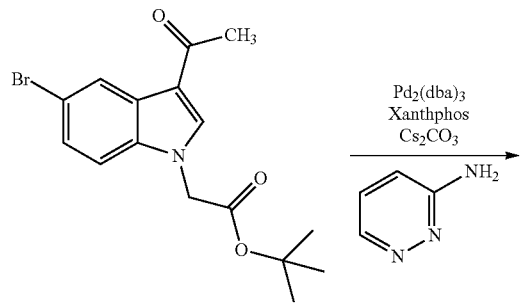

90b

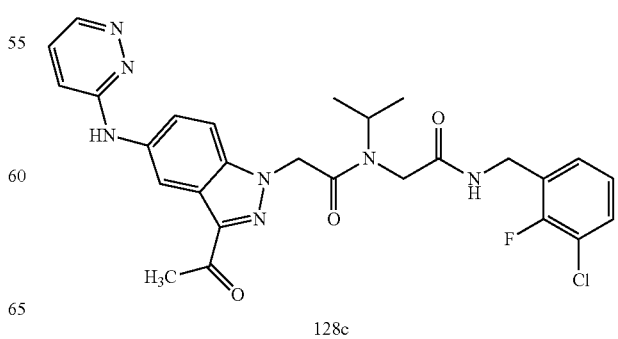

128c

271

Preparation of 2-(3-acetyl-5-(pyridazin-3-ylamino)-1H-indol-1-yl)-N-(2-((3-chloro-2-fluorobenzyl)amino)-2-oxoethyl)-N-isopropylacetamide (128c)

Step-1: Preparation of tert-butyl 2-(3-acetyl-5-(pyridazin-3-ylamino)-1H-indol-1-yl)acetate (128a)

Reaction of tert-butyl 2-(3-acetyl-5-bromo-1H-indol-1-yl)acetate (90b) (1.0 g, 2.84 mmol) with pyridazin-3-amine (0.41 g, 4.26 mmol) according to the procedure reported in step-1 of Scheme 97 gave after workup and purification by flash column chromatography [silica gel (40 g), eluting with CMA80 in CHCl$_3$ 0 to 20%] tert-butyl 2-(3-acetyl-5-(pyridazin-3-ylamino)-1H-indol-1-yl)acetate (128a) (180 mg, 0.49 mmol, 17% yield) as light yellow solid; $^1$H NMR (300 MHz, DMSO-d$_6$) δ 9.22 (s, 1H), 8.61 (d, J=4.6 Hz, 1H), 8.45-8.35 (m, 1H), 8.27 (s, 1H), 7.73 (dd, J=8.9, 2.1 Hz, 1H), 7.47-7.32 (m, 2H), 7.12-7.02 (m, 1H), 5.09 (s, 2H), 2.43 (s, 3H), 1.44 (s, 9H); MS (ES+): 367.5 (M+1); 389.5 (M+Na); (ES−): 365.4 (M−1).

Step-2: Preparation of 2-(3-acetyl-5-(pyridazin-3-ylamino)-1H-indol-1-yl)acetic acid (128b)

Reaction of tert-butyl 2-(3-acetyl-5-(pyridazin-3-ylamino)-1H-indol-1-yl)acetate (128a) (120 mg, 0.33 mmol) with TFA (0.63 mL, 8.19 mmol) according to the procedure reported in step-2 of Scheme 2 gave after workup 2-(3-acetyl-5-(pyridazin-3-ylamino)-1H-indol-1-yl)acetic acid (128b) (0.12 g, 0.28 mmol, 88% yield) as light orange solid; $^1$H NMR (300 MHz, DMSO-d$_6$) δ 13.45 (brs, 1H), 10.24 (s, 1H), 8.76 (d, J=4.7 Hz, 1H), 8.38 (d, J=2.3 Hz, 2H), 7.81 (dd, J=9.3, 4.5 Hz, 1H), 7.62-7.43 (m, 2H), 7.32-7.10 (m, 1H), 5.15 (s, 2H), 2.44 (s, 3H); MS (ES+): 311.4 (M+1); (ES−): 309.4 (M−1).

Step-3: Preparation of 2-(3-acetyl-5-(pyridazin-3-ylamino)-1H-indol-1-yl)-N-(2-((3-chloro-2-fluorobenzyl)amino)-2-oxoethyl)-N-isopropylacetamide (128c)

Reaction of 2-(3-acetyl-5-(pyridazin-3-ylamino)-1H-indol-1-yl)acetic acid (128b) (60 mg, 0.19 mmol) with N-(3-chloro-2-fluorobenzyl)-2-(isopropylamino)acetamide (19c) (50 mg, 0.19 mmol) according to the procedure reported in step-3 of Scheme 2 gave after workup and purification by flash column [silica gel (12 g), eluting with CMA-80 in CHCl$_3$ 0-100%] 2-(3-acetyl-5-(pyridazin-3-ylamino)-1H-indol-1-yl)-N-(2-((3-chloro-2-fluorobenzyl)amino)-2-oxoethyl)-N-isopropylacetamide (128c) (54 mg, 0.098 mmol, 51% yield) as an off-white solid as a mixture of two rotamers; $^1$H NMR (300 MHz, DMSO-d$_6$) δ 9.20 (s, 1H), 8.82 and 8.34 (2t, J=5.7 Hz, 1H), 8.65-8.55 (m, 1H), 8.40 (m, 1H), 8.23 and 8.17 (2s, 1H), 7.65 (dd, J=8.8, 2.2 Hz, 1H), 7.57-7.34 (m, 4H), 7.27-7.17 (m, 1H), 7.12-7.02 (m, 1H), 5.33 and 5.15 (2s, 2H), 4.65-4.53 and 4.31-4.21 (2m, 1H), 4.48 and 4.35 (2d, J=5.8 Hz, 2H), 4.19 and 3.86 (2s, 2H), 2.42 and 2.41 (2s, 3H), 1.26 and 1.00 (2d, J=6.8 Hz, 6H); $^{19}$F NMR (282 MHz, DMSO-d$_6$) δ −121.18 and −121.86; MS (ES+): 551.6 (M+1), MS (ES−): 585.5 (M+Cl).

272

Scheme 129

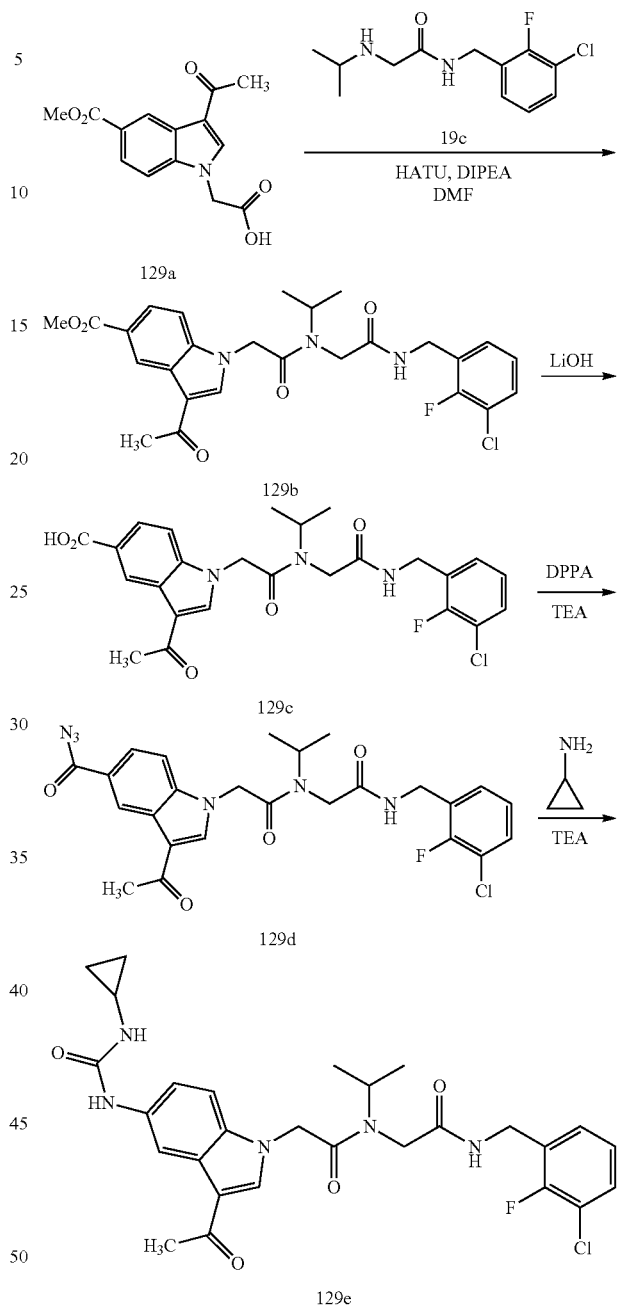

Preparation of 2-(3-acetyl-5-(3-cyclopropylureido)-1H-indol-1-yl)-N-(2-((3-chloro-2-fluorobenzyl)amino)-2-oxoethyl)-N-isopropylacetamide (129e)

Step-1: Preparation of methyl 3-acetyl-1-(2-((2-((3-chloro-2-fluorobenzyl)amino)-2-oxoethyl)(isopropyl)amino)-2-oxoethyl)-1H-indole-5-carboxylate (129b)

Reaction of 2-(3-acetyl-5-(methoxycarbonyl)-1H-indol-1-yl)acetic acid (129a) (154 mg, 0.56 mmol, prepared according to the procedure reported by Altmann, Eva et al, in PCT Int. Appl., WO 2012/093101) with N-(3-chloro-2- fluorobenzyl)-2-(isopropylamino)acetamide (19c) (174 mg, 0.67 mmol) according to the procedure reported in step-3 of Scheme 2 gave after workup and purification by flash column [silica gel (12 g), eluting with MeOH in CHCl$_3$ 0-10%] methyl 3-acetyl-1-(2-((2-((3-chloro-2-fluorobenzyl) amino)-2-oxoethyl)(isopropyl)amino)-2-oxoethyl)-1H-indole-5-carboxylate (129b) (261 mg, 0.51 mmol, 90% yield) as a light brown gum; $^1$H NMR (300 MHz, DMSO-d$_6$) δ 8.87 (d, J=0.6 Hz) and 8.86 (d, J=0.6 Hz) (2d, 1H), 8.82 (t, J=5.7 Hz) and 8.34 (2t, 1H), 8.40 and 8.36 (2s, 1H), 7.85 (dd, J=8.7, 1.7 Hz) and 7.79 (dd, J=8.7, 1.7 Hz) (2dd, 1H), 7.63-6.93 (m, 4H), 5.42 and 5.23 (2s, 2H), 4.68-4.51 and 4.28-4.18 (2m, 1H), 4.33 (d, J=6.1 Hz) and 4.25 (d, J=6.3 Hz) (2d, 2H), 4.19 and 3.85 (2s, 2H), 3.884 and 3.878 (2s, 3H), 2.47 and 2.45 (2s, 3H), 1.27 (d, J=6.4 Hz) and 1.00 (d, J=6.8 Hz) (2d, 6H); $^{19}$F NMR (282 MHz, DMS O-d$_6$) δ −121.19, −121.76; MS (ES+): 516.5 (M+1), MS (ES−): 514.5 (M−1).

Step-2: Preparation of 3-acetyl-1-(2-((2-((3-chloro-2-fluorobenzyl)amino)-2-oxoethyl)(isopropyl) amino)-2-oxoethyl)-1H-indole-5-carboxylic acid (129c)

To a solution of methyl 3-acetyl-1-(2-((2-((3-chloro-2-fluorobenzyl)amino)-2-oxoethyl)(isopropyl)amino)-2-oxoethyl)-1H-indole-5-carboxylate (129b) (560 mg, 1.09 mmol) in THF (8 mL) and MeOH (8 mL) was added a solution of lithium hydroxide hydrate (279 mg, 6.51 mmol) in water (8 mL) and stirred at room temperature for 3 days. The reaction mixture was concentrated to remove THF and MeOH, diluted with water (4 mL), acidified with 4 N HCl and solid obtained was collected by filtration, dried under vacuum to give 3-acetyl-1-(2-((2-((3-chloro-2-fluorobenzyl)amino)-2-oxoethyl)(isopropyl)amino)-2-oxoethyl)-1H-indole-5-carboxylic acid (129c) (360 mg, 0.72 mmol, 66% yield) as a yellow solid, which was used in the next step without further purification; $^1$H NMR (300 MHz, DMSO-d$_6$, a mixture of two rotamers) δ 8.88-8.79 and 8.40-8.31 (2m, 3H), 7.82 (dd, J=8.6, 1.7 Hz) and 7.78 (dd, J=8.6, 1.7 Hz) (2dd, 1H), 7.62-6.88 (m, 4H), 5.41 and 5.22 (2s, 2H), 4.64-4.51 and 4.29-4.20 (2m, 1H), 4.47 (d, J=5.5 Hz) and 4.33 (d, J=6.0 Hz) (2d, 2H), 4.19 and 3.85 (2s, 2H), 2.46 and 2.44 (2s, 3H), 1.26 (d, J=6.4 Hz) and 1.00 (d, J=6.8 Hz) (2d, 6H); $^{19}$F NMR (282 MHz, DMSO-d$_6$) δ −121.19, −121.76; MS (ES+): 524.5 & 526.5 (M+Na); MS (ES−): 536.5 & 538.5 (M+Cl).

Step-3: Preparation of 3-acetyl-1-(2-((2-((3-chloro-2-fluorobenzyl)amino)-2-oxoethyl)(isopropyl) amino)-2-oxoethyl)-1H-indole-5-carbonyl azide (129d)

A suspension of 3-acetyl-1-(2-((2-((3-chloro-2-fluorobenzyl)amino)-2-oxoethyl)(isopropyl)amino)-2-oxoethyl)-1H-indole-5-carboxylic acid (129c) (139 mg, 0.28 mmol) in THF (10 mL) was treated with triethylamine (0.039 μL, 0.28 mmol) and stirred at room temperature for 15 min. The mixture was then treated with diphenyl phosphorazidate (0.062 mL, 0.277 mmol) and stirred at room temperature for 15 h. The reaction mixture was concentrated in vacuum to dryness, solid obtained was triturated with DCM, collected by filtration, dried under vacuum to afford 3-acetyl-1-(2-((2-((3-chloro-2-fluorobenzyl)amino)-2-oxoethyl)(isopropyl) amino)-2-oxoethyl)-1H-indole-5-carbonyl azide (129d); MS (ES−): 525.5 (M−1)

Step-4: Preparation of 2-(3-acetyl-5-(3-cyclopropylureido)-1H-indol-1-yl)-N-(2-((3-chloro-2-fluorobenzyl)amino)-2-oxoethyl)-N-isopropylacetamide (129e)

A suspension of 3-acetyl-1-(2-((2-((3-chloro-2-fluorobenzyl)amino)-2-oxoethyl)(isopropyl)amino)-2-oxoethyl)-1H-indole-5-carbonyl azide (129d) (75 mg, 0.14 mmol) in THF/Tol (24 mL, Ratio: 1:2) was heated at reflux for 4 h, cooled to room temperature and concentrated in vacuum to dryness. The residue obtained was dissolved in THF (20 mL) and ACN (10 mL) followed by the addition of cyclopropanamine (16.25 mg, 0.29 mmol) and triethylamine (0.060 μL, 0.427 mmol). The reaction mixture was stirred at room temperature overnight, diluted with EtOAc (100 mL), washed with water (3×), dried, filtered and concentrated in vacuum. The residue was purified by column chromatography [silica (12 g), eluting with CMA80 in CHCl$_3$ 0 to 40%] followed by preparative HPLC with water/ACN to give 2-(3-acetyl-5-(3-cyclopropylureido)-1H-indol-1-yl)-N-(2-((3-chloro-2-fluorobenzyl)amino)-2-oxoethyl)-N-isopropylacetamide (129e) (6 mg, 10.79 μma 6% yield) as a white solid after lyophilization; $^1$H NMR (300 MHz, DMSO-d$_6$) (a mixture of two rotamers) δ 8.84-8.13 (m, 4H), 7.60-6.90 (m, 5H), 6.27 (d, J=2.3 Hz, 1H), 5.29 and 5.11 (2s, 2H), 4.66-4.50 and 4.28-4.20 (2m, 1H), 4.47 (d, J=5.4 Hz) and 4.34 (d, J=5.8 Hz) (2d, 2H), 4.17 and 3.84 (2s, 2H), 2.40 and 2.39 (2s, 3H), 1.24 (d, J=6.3 Hz) and 1.00 (d, J=6.8 Hz) (2d, 6H), 0.71-0.55 (m, 2H), 0.50-0.31 (m, 2H); $^{19}$F NMR (282 MHz, DMSO-d$_6$) δ −73.45 (TFA peak), −121.20, −121.82; MS (ES+); 578.5 (M+Na); MS (ES$^-$): 554.5 (M−1).

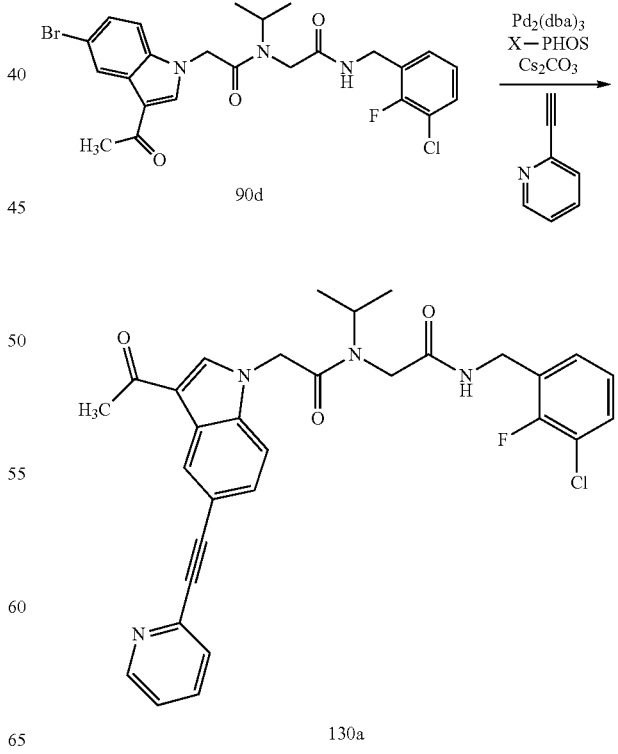

Scheme 130

90d

130a

Preparation of 2-(3-acetyl-5-(pyridin-2-ylethynyl)-1H-indol-1-yl)-N-(2-((3-chloro-2-fluorobenzyl) amino)-2-oxoethyl)-N-isopropylacetamide (130a)

Reaction of 2-(3-acetyl-5-bromo-1H-indol-1-yl)-N-(2-((3-chloro-2-fluorobenzyl)amino)-2-oxoethyl)-N-isopropylacetamide (90d) (301 mg, 0.56 mmol) with 2-ethynylpyridine (58 mg, 0.56 mmol) according to the procedure reported in scheme 92 gave after workup and purification by flash column chromatography [silica gel 12 g, eluting with EtOAc/MeOH (9:1) in hexanes 0 to 100%] 2-(3-acetyl-5-(pyridin-2-ylethynyl)-1H-indol-1-yl)-N-(2-((3-chloro-2-fluorobenzyl)amino)-2-oxoethyl)-N-isopropylacetamide (130a) (17 mg, 0.030 mmol, 5% yield) as a dark-yellow solid as a mixture of two rotamers; $^{1}$H NMR (300 MHz, DMSO-$d_6$) δ 8.84 (t, J=5.8 Hz, $D_2O$ exchangeable) and 8.39-8.31 (m) (2H) 8.65-8.57 (m, 1H), 8.43 (d, J=1.5 Hz, 1H), 7.92-7.81 (m, 1H), 7.69 and 7.67 (2s, 1H), 7.63-6.94 (m, 6H), 5.41 and 5.23 (2s, 2H), 4.65-4.55 and 4.29-4.24 (2m, 1H), 4.52-4.30 (m, 2H), 4.19 and 3.86 (2s, 2H), 2.47 and 2.45 (2s, 3H), 1.27 (d, J=6.4 Hz) and 1.01 (d, J=6.7 Hz) (2d, 6H); $^{19}$F NMR (282 MHz, DMSO-$d_6$) δ −121.17, −121.76; MS (ES+): 559.5, 561.6 (M+1); MS (ES−): 558.5, 557.5 (M−1), 593.5 (M+Cl).

nyl)-1H-indol-1-yl)-N-(2-((3-chloro-2-fluorobenzyl) amino)-2-oxoethyl)-N-isopropylacetamide (131a) (14 mg, 0.025 mmol, 5% yield) as a dark-yellow solid as a mixture of two rotamers; $^{1}$H NMR (300 MHz, DMSO-$d_6$) δ 8.84 (t, J=5.7 Hz) and 8.44-8.32 (t & m, 3H), 8.81-8.78 (m, 1H), 8.60-8.55 (m, 1H), 8.02 (dt, J=7.9, 1.9 Hz, 1H), 7.66-6.94 (m, 6H), 5.41 and 5.22 (2s, 2H), 4.68-4.54 and 4.30-4.22 (2m, 1H), 4.48 (d, J=5.6 Hz) and 4.34 (d, J=6.5 Hz) (2d, 2H), 4.19 and 3.86 (2s, 2H), 2.46 and 2.45 (2s, 3H), 1.27 (d, J=6.4 Hz) and 1.01 (d, J=6.8 Hz) (2d, 6H); $^{19}$F NMR (282 MHz, DMSO-$d_6$) δ −121.18, −121.77; MS (ES+): 559.61, 561.58 (M+1); MS (ES−): 559.5, 557.5 (M−1), 593.5 (M+Cl).

Scheme 132

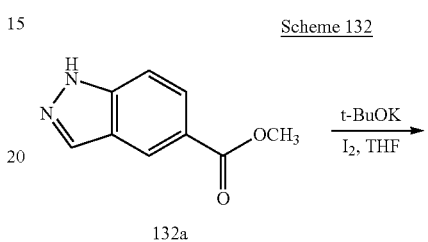

132a

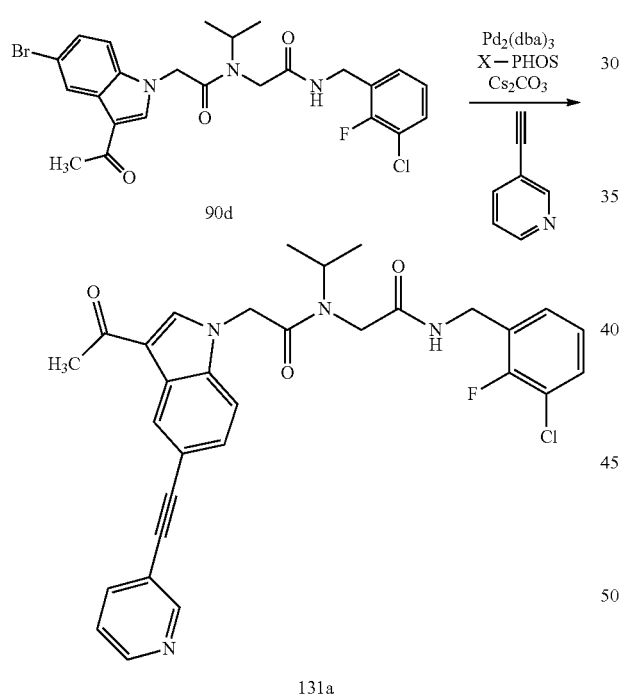

Preparation of 2-(3-acetyl-5-(pyridin-3-ylethynyl)-1H-indol-1-yl)-N-(2-((3-chloro-2-fluorobenzyl) amino)-2-oxoethyl)-N-isopropylacetamide (131a)

Reaction of 2-(3-acetyl-5-bromo-1H-indol-1-yl)-N-(2-((3-chloro-2-fluorobenzyl)amino)-2-oxoethyl)-N-isopropylacetamide (90d) (301 mg, 0.56 mmol) with 3-ethynylpyridine (58 mg, 0.56 mmol) according to the procedure reported in scheme 92 gave after workup and purification by flash column chromatography [silica gel 12 g, eluting with MeOH in CHCl$_3$ 0 to 20%] 2-(3-acetyl-5-(pyridin-3-ylethy-

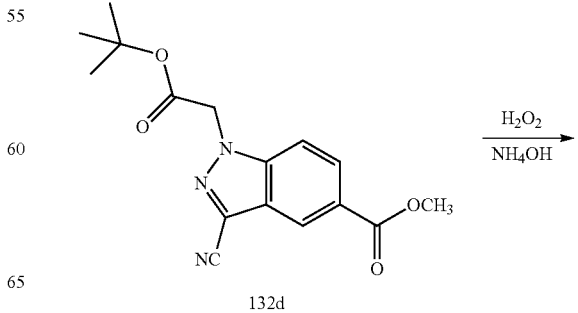

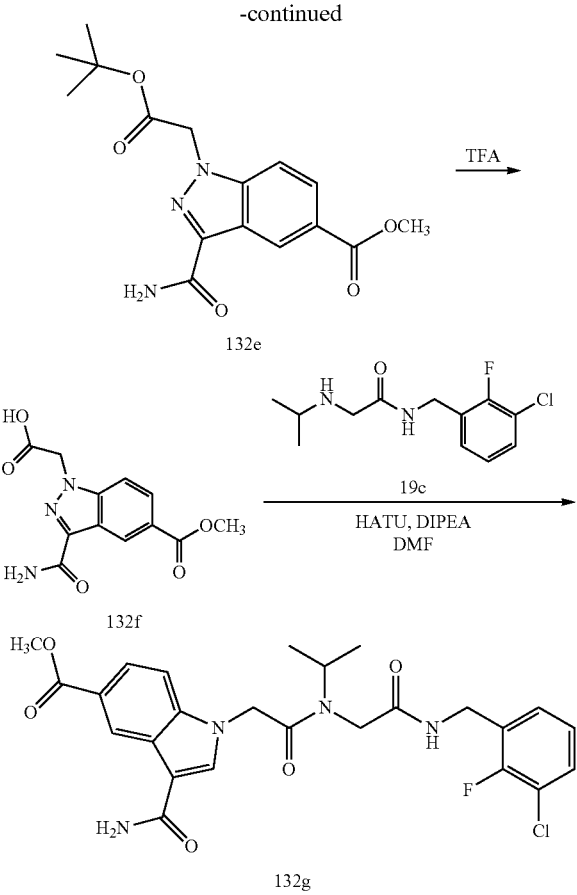

Preparation of methyl 3-carbamoyl-1-(2-((2-((3-chloro-2-fluorobenzyl)amino)-2-oxoethyl)(isopropyl)amino)-2-oxoethyl)-1H-indazole-5-carboxylate (132 g)

Step-1: Preparation of methyl 3-iodo-1H-indazole-5-carboxylate (132b)

To a solution of methyl 1H-indazole-5-carboxylate (132a) (5 g, 28.4 mmol) in THF (40 mL) was added I2 (10.81 g, 42.6 mmol) and KOtBu (7.96 g, 71.0 mmol) at 0° C., the resulting mixture was stirred for 3 h at room temperature. The reaction mixture was diluted with 10% aqueous sodium thiosulfate and extracted with EtOAc (3×40 mL). The combined organic layers were washed with water, brine, dried and concentrated in vacuum. The obtained solid was washed with MeOH (20 mL) to give methyl 3-iodo-1H-indazole-5-carboxylate (132b) (5.6 g, 18.54 mmol, 65% yield) as a yellow solid; $^1$H NMR (300 MHz, DMSO-$d_6$) δ13.87 (s, 1H), 8.08-8.03 (m, 1H), 7.97 (dd, J=8.8, 1.6 Hz, 1H), 7.65 (dd, J=8.8, 0.7 Hz, 1H), 3.88 (s, 3H); MS (ES+): 303.2 (M+1); MS (ES−): 301.2 (M−1).

Step-2: Preparation of methyl 1-(2-(tert-butoxy)-2-oxoethyl)-3-iodo-1H-indazole-5-carboxylate (132c)

Reaction of methyl 3-iodo-1H-indazole-5-carboxylate (132b) (5 g, 16.55 mmol) with tert-butyl 2-bromoacetate (4.84 g, 24.83 mmol) according to the procedure reported in step-1 of Scheme 56 gave after workup and trituration of solid with hexane (50 mL) methyl 1-(2-tert-butoxy-2-oxoethyl)-3-iodo-1H-indazole-5-carboxylate (132c) (5.74 g, 13.79 mmol, 83% yield) as a yellow solid; $^1$H NMR (300 MHz, DMSO-$d_6$) δ 8.16-7.92 (m, 2H), 7.89-7.67 (m, 1H), 5.37 (s, 2H), 3.90 (s, 3H), 1.40 (s, 9H); MS (ES+): 439.4 (M+Na).

Step-3: Preparation of methyl 1-(2-(tert-butoxy)-2-oxoethyl)-3-cyano-1H-indazole-5-carboxylate (132d)

A mixture of Pd(Ph$_3$P)$_4$ (83 mg, 0.072 mmol), methyl 1-(2-tert-butoxy-2-oxoethyl)-3-iodo-1H-indazole-5-carboxylate (132c) (300 mg, 0.72 mmol), zinc cyanide (110 mg, 0.94 mmol) in DMF (5 mL) was heated at 120° C. for 30 min on microwave under argon atmosphere. The reaction was cooled to room temperature diluted with EtOAc (100 mL), washed with water, brine, dried, filtered and concentrated in vacuum. The residue was purified by column chromatography [silica (12 g), eluting with EtOAc in hexane 0 to 30%] to give methyl 1-(2-(tert-butoxy)-2-oxoethyl)-3-cyano-1H-indazole-5-carboxylate (132d) (125 mg, 0.4 mmol, 55% yield) as a white solid; $^1$H NMR (300 MHz, DMSO-$d_6$) δ 8.49 (s, 1H), 8.20-8.10 (m, 1H), 8.07-7.99 (m, 1H), 5.58 (s, 2H), 3.92 (s, 3H), 1.41 (s, 9H); MS (ES+): 316.4 (M+1); 338.4 (M+Na); MS (ES−): 314.4 (M−1).

Step-4: Preparation of methyl 1-(2-(tert-butoxy)-2-oxoethyl)-3-carbamoyl-1H-indazole-5-carboxylate (132e)

Reaction of methyl 1-(2-(tert-butoxy)-2-oxoethyl)-3-cyano-1H-indazole-5-carboxylate (132d) (795 mg, 2.52 mmol) in ethanol (16 mL) using conc. NH$_4$OH (8 mL, 54.4 mmol) and H$_2$O$_2$ (aq. 35%, 1.56 mL, 15.13 mmol) according to the procedure reported in Scheme 65 gave after workup and purification by flash column chromatography [silica (12 g), eluting with DMA80 in DCM 0 to 50%] methyl 1-(2-(tert-butoxy)-2-oxoethyl)-3-carbamoyl-1H-indazole-5-carboxylate (132e) (302 mg, 0.91 mmol, 36% yield) as a white solid; $^1$H NMR (300 MHz, DMSO-$d_6$) δ 8.93-8.83 (m, 1H), 8.03 (dd, J=8.9, 1.6 Hz, 1H), 7.92 (s, 1H), 7.89-7.79 (m, 1H), 7.61 (s, 1H), 5.41 (s, 2H), 3.91 (s, 3H), 1.41 (s, 9H); MS (ES+): 334.4 (M+1); 356.4 (M+Na); MS (ES−): 332.3 (M−1).

Step-5: Preparation of 2-(3-carbamoyl-5-(methoxycarbonyl)-1H-indazol-1-yl)acetic acid (132f)

Reaction of methyl 1-(2-(tert-butoxy)-2-oxoethyl)-3-carbamoyl-1H-indazole-5-carboxylate (132e) (3.05 g, 9.15 mmol) with TFA (7.05 mL, 91 mmol) according to the procedure reported in step-2 of Scheme 2 gave after workup 2-(3-carbamoyl-5-(methoxycarbonyl)-1H-indazol-1-yl)acetic acid (132f) (2.7 g, 6.9 mmol, 75% yield) as a white solid; $^1$H NMR (300 MHz, DMSO-$d_6$) δ 8.93-8.82 (m, 1H), 8.01 (dd, J=8.9, 1.6 Hz, 1H), 7.91 (s, 1H), 7.86 (dd, J=8.9, 0.7 Hz, 1H), 7.59 (s, 1H), 5.41 (s, 2H), 3.90 (s, 3H); MS (ES+): 278.3 (M+1).

Step-5: Preparation of methyl 3-carbamoyl-1-(2-((2-((3-chloro-2-fluorobenzyl)amino)-2-oxoethyl)(isopropyl)amino)-2-oxoethyl)-1H-indazole-5-carboxylate (132 g)

Reaction of 2-(3-carbamoyl-5-(methoxycarbonyl)-1H-indazol-1-yl)acetic acid (132f) (100 mg, 0.26 mmol) with N-(3-chloro-2-fluorobenzyl)-2-(isopropylamino)acetamide (19c) (66 mg, 0.26 mmol) according to the procedure reported in step-3 of Scheme 2 gave after workup and purification by flash column [silica (12 g), eluting with DMA80 in DCM 0 to 50%] to give methyl 3-carbamoyl-1-(2-((2-((3-chloro-2-fluorobenzyl)amino)-2-oxoethyl)(isopropyl)amino)-2-oxoethyl)-1H-indazole-5-carboxylate (132 g) (62 mg, 0.12 mmol, 47% yield) as an off white solid; $^1$H NMR (300 MHz, DMSO-$d_6$) δ 8.91-8.86 (m, 1H), 8.83 (t, J=5.7 Hz) and 8.36 (t, J=5.9 Hz) (2t, 1H), 8.06-6.97 (m, 7H), 5.65 and 5.52 (2s, 2H), 4.61-4.49 and 4.28-4.21 (2m, 1H), 4.46 (d, J=5.4 Hz) and 4.31 (d, J=5.6 Hz) (2d, 2H), 4.18 and 3.84 (2s, 2H), 3.91 and 3.9 (2s, 3H), 1.24 (d, J=6.4 Hz) and 0.99 (d, J=6.8 Hz) (2d, 6H); $^{19}$F NMR (282 MHz, DMSO-$d_6$) δ −121.22, −121.71; MS (ES+): 518.5 (M+1); MS (ES−): 516.5 (M−1).

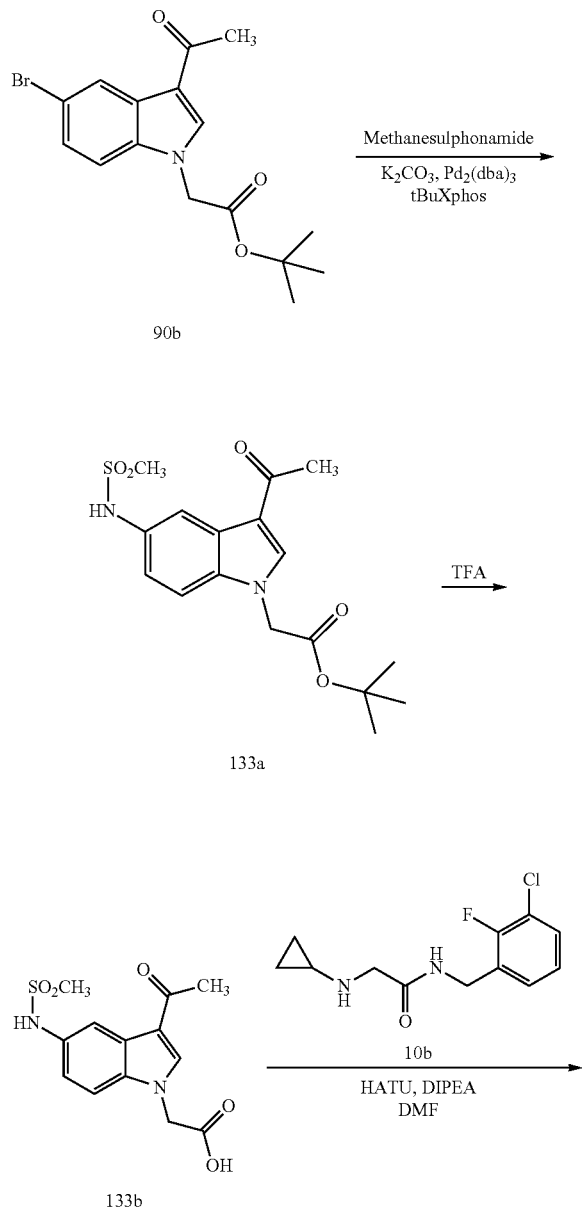

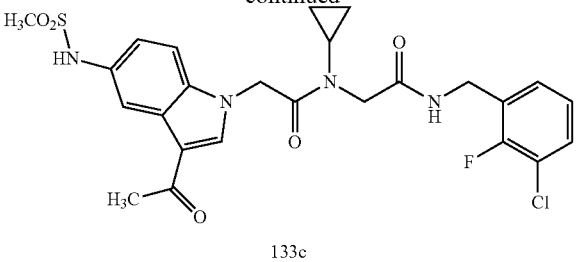

133c

Preparation of 2-(3-acetyl-5-(methylsulfonamido)-1H-indol-1-yl)-N-(2-((3-chloro-2-fluorobenzyl)amino)-2-oxoethyl)-N-cyclopropylacetamide (133c)

Step-1: Preparation of tert-butyl 2-(3-acetyl-5-(methylsulfonamido)-1H-indol-1-yl)acetate (133a)

To degassed Dioxane (4 mL) in a sealed reactor were added tert-butyl 2-(3-acetyl-5-bromo-1H-indol-1-yl)acetate (90b) (500 mg, 1.42 mmol), methanesulfonamide (162 mg, 1.70 mmol), potassium carbonate (392 mg, 2.84 mmol), di-tert-butyl(2',4',6'-triisopropylbiphenyl-2-yl)phosphine (tBuXphos, 30 mg, 0.071 mmol), Pd$_2$(dba)$_3$ (32 mg, 0.035 mmol) and heated at 90° C. for 16 h. Mixture was cooled to room temperature, filtered over Celite pad and pad was washed with EtOAc (2×10 mL). The combined filtrate was washed water (2×30 mL), dried, filtered and concentrated in vacuum. The residue obtained was purified by column chromatography [silica gel (24 g), eluting with MeOH-EtOAc (1:9) in hexane 0 to 80%] to afford tert-butyl 2-(3-acetyl-5-(methylsulfonamido)-1H-indol-1-yl)acetate (133a) (220 mg, 0.6 mmol, 42% yield) as an orange solid; $^1$H NMR (300 MHz, DMSO-$d_6$) δ 9.49 (s, 1H), 8.32 (s, 1H), 8.10 (d, J=2.1 Hz, 1H), 7.44 (d, J=8.8 Hz, 1H), 7.16 (dd, J=8.8, 2.2 Hz, 1H), 5.10 (s, 2H), 2.88 (s, 3H), 2.42 (s, 3H), 1.44 (s, 9H).

Step-2: Preparation of 2-(3-acetyl-5-(methylsulfonamido)-1H-indol-1-yl)acetic acid (133b)

Reaction of tert-butyl 2-(3-acetyl-5-(methylsulfonamido)-1H-indol-1-yl)acetate (133a) (220 mg, 0.6 mmol) with TFA (0.93 mL, 12.01 mmol) according to the procedure reported in step-2 of Scheme 2 gave after workup, trituration of residue with toluene (2×30 mL) and 30% EtOAc-hexane (10 mL) 2-(3-acetyl-5-(methylsulfonamido)-1H-indol-1-yl)acetic acid (133b) (230 mg, 0.74 mmol, 90% yield) as light orange solid; $^1$H NMR (300 MHz, DMSO-$d_6$) δ 13.26 (s, 1H D$_2$O exchangeable), 9.49 (s, 1H), 8.34 (s, 1H), 8.10 (d, J=2.1 Hz, 1H), 7.49 (d, J=8.9 Hz, 1H), 7.16 (dd, J=8.8, 2.2 Hz, 1H), 5.11 (s, 2H), 2.88 (s, 3H), 2.42 (s, 3H); MS (ES+): 311.3 (M+1), MS (ES−): 309.3 (M−1).

Step-3: Preparation of 2-(3-acetyl-5-(methylsulfonamido)-1H-indol-1-yl)-N-(2-((3-chloro-2-fluorobenzyl)amino)-2-oxoethyl)-N-cyclopropylacetamide (133c)

Reaction of 2-(3-acetyl-5-(methylsulfonamido)-1H-indol-1-yl)acetic acid (133b) (60 mg, 0.19 mmol) with N-(3-chloro-2-fluorobenzyl)-2-(cyclopropylamino)acetamide (10b) (60 mg, 0.23 mmol) according to the procedure reported in step-3 of Scheme 2 gave after workup and purification by flash column [silica (12 g), eluting with CMA80 in CHCl₃ 0 to 30%] 2-(3-acetyl-5-(methylsulfonamido)-1H-indol-1-yl)-N-(2-((3-chloro-2-fluorobenzyl) amino)-2-oxoethyl)-N-cyclopropylacetamide (133c) (46 mg, 0.084 mmol, 43% yield) as a white solid; $^1$H NMR (300 MHz, DMSO-$d_6$) δ 9.47 (s, 1H), 8.47 (t, J=5.9 Hz, 1H), 8.29 (s, 1H), 8.10 (d, J=2.1 Hz, 1H), 7.52-7.36 (m, 2H), 7.23 (t, J=7.1 Hz, 1H), 7.17-7.04 (m, 2H), 5.42 (s, 2H), 4.35 (d, J=5.7 Hz, 2H), 3.99 (s, 2H), 3.08 (d, J=4.4 Hz, 1H), 2.89 (s, 3H), 2.41 (s, 3H), 1.08-0.94 (m, 2H), 0.95-0.82 (m, 2H); $^{19}$F NMR (282 MHz, DMSO-$d_6$) δ −121.61; MS (ES+): 549.5 (M+1), MS (ES−): 547.5 (M−1), 583.5 (M+Cl).

Scheme 134

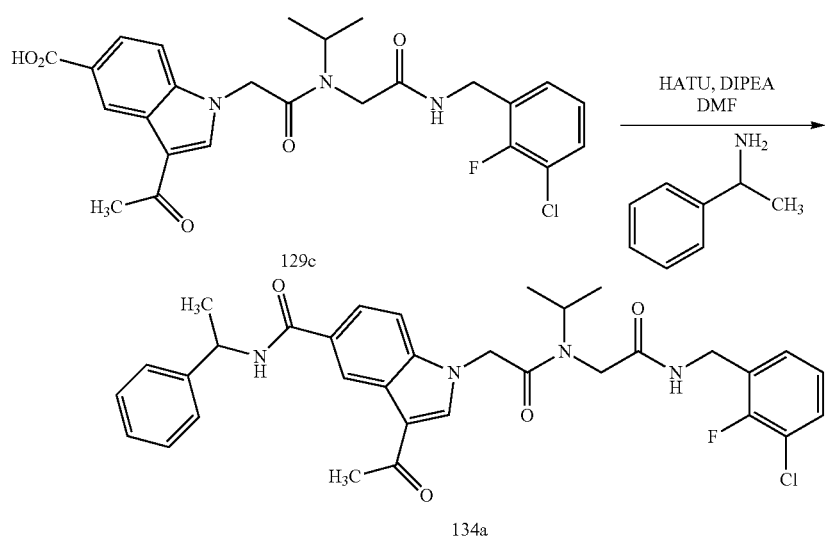

Preparation of 3-acetyl-1-(2-((2-((3-chloro-2-fluorobenzyl)amino)-2-oxoethyl)(isopropyl)amino)-2-oxoethyl)-N-(1-phenylethyl)-1H-indole-5-carboxamide (134a)

Reaction of 3-acetyl-1-(2-((2-((3-chloro-2-fluorobenzyl)amino)-2-oxoethyl)(isopropyl)amino)-2-oxoethyl)-1H-indole-5-carboxylic acid (129c) (50 mg, 0.1 mmol) with 1-phenylethanamine (20 mg, 0.15 mmol) according to the procedure reported in step-3 of Scheme 2 gave after workup and purification by flash column [silica (4 g), eluting with MeOH in CHCl₃ 0 to 10%] 3-acetyl-1-(2-((2-((3-chloro-2-fluorobenzyl)amino)-2-oxoethyl)(isopropyl)amino)-2-oxoethyl)-N-(1-phenylethyl)-1H-indole-5-carboxamide (134a) (34 mg, 56%) as a white solid; $^1$H NMR (300 MHz, DMSO-$d_6$) (a mixture of two rotamers) δ 8.87-8.78 and 8.38-8.27 (2m, 2H), 8.72 (d, J=1.7 Hz) and 8.71 (2d, 1H), 8.35 and 8.30 (2s, 1H), 7.77 (dd, J=8.6, 1.8 Hz), and 7.72 (2dd, 1H), 7.56-6.92 (m, 9H), 5.39 and 5.20 (2s, 2H), 5.27-5.12 (m, 1H), 4.65-4.51 and 4.29-4.20 2 (m, 1H) 4.48 (d, J=5.5 Hz) and 4.33 (d, J=5.8 Hz) (2d, 2H), 4.19 and 3.85 (2s, 2H), 2.46 and 2.45 2 (s, 3H), 1.51 (d, J=3.0 Hz) and 1.49 (d, J=3.1 Hz) (2d, 3H), 1.26 (d, J=6.5 Hz) and 1.00 (d, J=6.8 Hz) (2d, 6H); $^{19}$F NMR (282 MHz, DMSO-$d_6$) δ −121.20, −121.79; MS (ES+): 627.6 & 629.6 (M+Na); MS (ES⁻): 639.6 & 641.5 (M+Cl).

Scheme 135

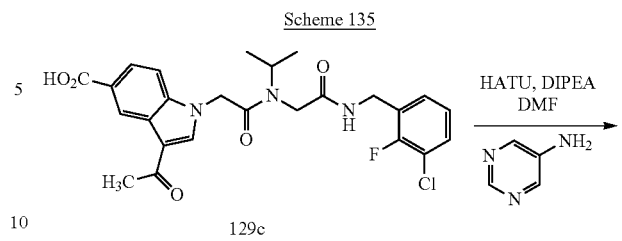

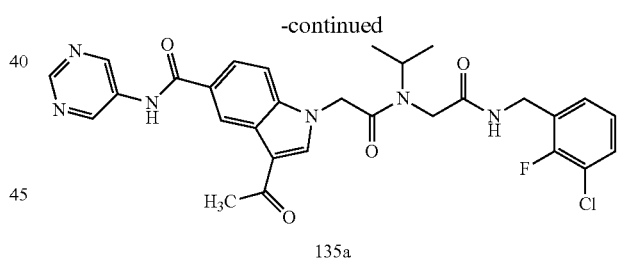

Preparation of 3-acetyl-1-(2-((2-((3-chloro-2-fluorobenzyl)amino)-2-oxoethyl)(isopropyl)amino)-2-oxoethyl)-N-(pyrimidin-5-yl)-1H-indole-5-carboxamide (135a)

Reaction of 3-acetyl-1-(2-((2-((3-chloro-2-fluorobenzyl) amino)-2-oxoethyl)(isopropyl)amino)-2-oxoethyl)-1H-indole-5-carboxylic acid (129c) (50 mg, 0.1 mmol) with pyrimidin-5-amine (14.80 mg, 0.15 mmol) according to the procedure reported in step-3 of Scheme 2 gave after workup and purification by flash column [silica (4 g), eluting with MeOH in CHCl₃ 0 to 10%] 3-acetyl-1-(2-((2-((3-chloro-2-fluorobenzyl)amino)-2-oxoethyl)(isopropyl)amino)-2-oxoethyl)-N-(pyrimidin-5-yl)-1H-indole-5-carboxamide (135a) (31 mg, 54%); $^1$H NMR (300 MHz, DMSO-$d_6$) δ 9.20-9.17 (m, 1H), 8.91-8.82 and 8.40-8.33 (2m, 2H), 8.79 (t, J=1.4 Hz) and 8.77 (t, J=1.5 Hz) (2t, 1H), 8.55 and 8.52 (2s, 1H), 8.13 (dd, J=8.8, 1.8 Hz) and 8.04 (dd, J=8.8, 1.8 Hz) (2dd, 1H), 7.82 (d, J=8.8 Hz) and 7.77 (d, J=8.8 Hz) (2d, 1H), 7.70 (dd, J=4.5, 1.8 Hz) and 7.68 (dd, J=4.5, 1.8 Hz) (2dd, 1H), 7.59-6.91 (m, 4H), 5.52 (s) and 5.46-5.17 (m) (2H), 4.67-4.51 and 4.30-4.15 (2m, 1H), 4.49 (d, J=5.4 Hz) and 4.34 (d, J=5.7 Hz) (2d, 2H), 4.21 and 3.87 (2s, 2H), 1.29 (d, J=6.5 Hz) and 1.01 (d, J=6.7 Hz) (2d, 6H); $^{19}$F NMR (282 MHz, DMSO-$d_6$) δ -121.18, -121.75.

Scheme 136

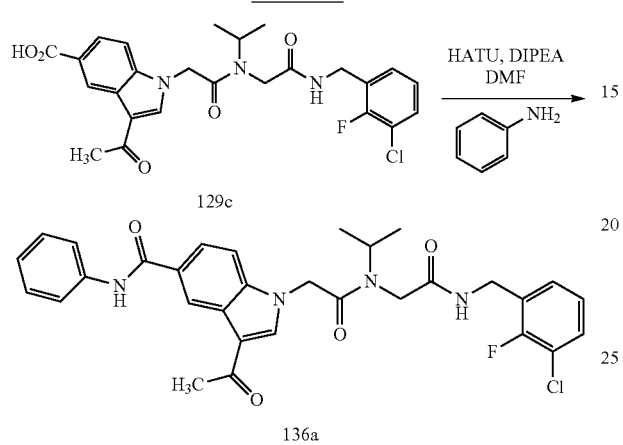

Preparation of 3-acetyl-1-(2-((2-((3-chloro-2-fluorobenzyl)amino)-2-oxoethyl)(isopropyl)amino)-2-oxoethyl)-N-phenyl-1H-indole-5-carboxamide (136a)

Reaction of 3-acetyl-1-(2-((2-((3-chloro-2-fluorobenzyl)amino)-2-oxoethyl)(isopropyl)amino)-2-oxoethyl)-1H-indole-5-carboxylic acid (129c) (50 mg, 0.1 mmol) with aniline (0.014 mL, 0.15 mmol) according to the procedure reported in step-3 of Scheme 2 gave after workup and purification by flash column [silica (4 g), eluting with MeOH in CHCl$_3$ 0 to 10%] 3-acetyl-1-(2-((2-((3-chloro-2-fluorobenzyl)amino)-2-oxoethyl)(isopropyl)amino)-2-oxoethyl)-N-phenyl-1H-indole-5-carboxamide (136a) (33 mg, 57%) as a white solid; $^1$H NMR (300 MHz, DMSO-$d_6$) δ 10.30 and 10.27 (2s, 1H), 8.84 (t, J=5.8 Hz) and 8.35 (2t, 1H), 8.80-8.77 (m, 1H), 8.39 and 8.35 (2s, 1H), 7.86-7.77 (m, 3H), 7.60 (d, J=3.7 Hz) and 7.57 (d, J=3.7 Hz) (2d, 1H), 7.55-6.97 (m, 6H), 5.42 and 5.24 (2s, 2H), 4.65-4.51 and 4.30-4.22 (2m, 1H), 4.49 (d, J=5.6 Hz) and 4.34 (d, J=5.8 Hz) (2d, 2H), 4.20 and 3.86 (2s, 2H), 1.27 (d, J=6.4 Hz) and 1.01 (d, J=6.8 Hz) (2d, 6H); $^{19}$F NMR (282 MHz, DMSO-$d_6$) δ -121.18, -121.75; MS (ES-): 611.5 & 613.5 (M+Cl).

Scheme 137

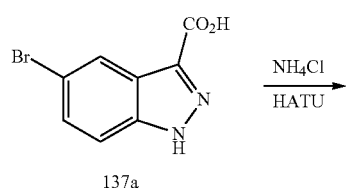

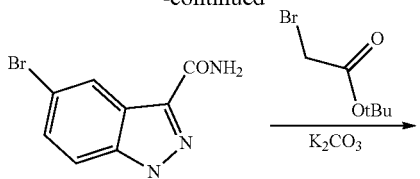

Preparation of 5-bromo-1-(2-((2-((3-chloro-2-fluorobenzyl)amino)-2-oxoethyl)(isopropyl)amino)-2-oxoethyl)-1H-indazole-3-carboxamide (137e)

Step-1: Preparation of 5-bromo-1H-indazole-3-carboxamide (137b)

To a solution of 5-bromo-1H-indazole-3-carboxylic acid (137a) (3.00 g, 12.45 mmol, prepared according to the procedure reported by Hood, John and Sunil Kumar in PCT Int. Appl., 2013040215) in DMF (60 mL) was added ammonium chloride (1.997 g, 37.3 mmol), HATU (7.10 g, 18.67 mmol) followed by the drop-wise addition of DIPEA (21.74 mL, 124 mmol). The reaction mixture was stirred at room temperature for 3 h, quenched with water (100 mL) and extracted with EtOAc (2×100 mL). The organic layers were combined washed with brine (50 mL), dried, filtered and evaporated to dryness. The solid obtained was washed with MeOH (3×10 mL) and dried to afford 5-bromo-1H-indazole-3-carboxamide (137b) (1.33 g, 5.54 mmol, 44% yield) as an off-white solid; $^1$H NMR (300 MHz, DMSO-d$_6$) δ 13.77 (s, 1H, D$_2$O exchangeable), 8.31 (dd, J=1.9, 0.8 Hz, 1H), 7.84 (s, 1H), 7.64-7.58 (m, 1H), 7.53 (dd, J=8.8, 1.9 Hz, 1H), 7.46 (s, 1H); MS (ES−): 240.1, 238.1 (M−2).

Step-2: Preparation of tert-butyl 2-(5-bromo-3-carbamoyl-1H-indazol-1-yl)acetate (137c)

Reaction of 5-bromo-1H-indazole-3-carboxamide (137b) (1.2 g, 5.0 mmol) with tert-butyl 2-bromoacetate (0.89 mL, 6.0 mmol) using potassium carbonate (1.73 g, 12.5 mmol) as base according to the procedure reported step-1 of Scheme 45 gave after workup tert-butyl 2-(5-bromo-3-carbamoyl-1H-indazol-1-yl)acetate (137c) (1.55 g, 4.38 mmol, 88% yield) as a light green solid; $^1$H NMR (300 MHz, DMSO-d$_6$) δ 8.33 (dd, J=1.9, 0.7 Hz, 1H), 7.84 (s, 1H, D$_2$O exchangeable), 7.75 (dd, J=9.0, 0.7 Hz, 1H), 7.65-7.59 (m, 1H), 7.53 (s, 1H, D$_2$O exchangeable), 5.37 (s, 2H), 1.41 (s, 9H); MS (ES+): 376.3, 378.3 (M+Na); MS (ES−): 354.3, 352.2 (M−2).

Step-3: Preparation of 2-(5-bromo-3-carbamoyl-1H-indazol-1-yl)acetic acid (137d)

Reaction of tert-butyl 2-(5-bromo-3-carbamoyl-1H-indazol-1-yl)acetate (137c) (1.0 g, 2.82 mmol) with TFA (4.35 mL, 56.5 mmol) according to the procedure reported in step-2 of Scheme 2 gave after workup 2-(5-bromo-3-carbamoyl-1H-indazol-1-yl)acetic acid (137d) (806 mg, 2.70 mmol, 96% yield) as a yellow solid in the form of TFA adduct; $^1$H NMR (300 MHz, DMSO-d$_6$) δ 13.34 (s, 1H, D$_2$O exchangeable), 8.33 (d, J=1.8 Hz, 1H), 7.84 (s, 1H), 7.78 (d, J=8.9 Hz, 1H), 7.61 (dd, J=9.0, 1.9 Hz, 1H), 7.52 (s, 1H), 5.37 (s, 2H); MS (ES+): 298.3, 300.2 (M+2); MS (ES−): 595.3, 597.3 (2M−1).

Step-4: Preparation of 5-bromo-1-(2-((2-((3-chloro-2-fluorobenzyl)amino)-2-oxoethyl)(isopropyl)amino)-2-oxoethyl)-1H-indazole-3-carboxamide (137e)

Reaction of 2-(5-bromo-3-carbamoyl-1H-indazol-1-yl)acetic acid (137d) (100 mg, 0.34 mmol) with N-(3-chloro-2-fluorobenzyl)-2-(isopropylamino)acetamide (19c) (104 mg, 0.4 mmol) according to the procedure reported in step-3 of Scheme 2 gave after workup and purification by flash column chromatography [Silica gel, (24 g) eluting with MeOH in DCM 0-30%), 5-bromo-1-(2-((2-((3-chloro-2-fluorobenzyl)amino)-2-oxoethyl)(isopropyl)amino)-2-oxoethyl)-1H-indazole-3-carboxamide (137e) (34 mg, 0.063 mmol, 19% yield) as a white solid as a mixture two rotamers; $^1$H NMR (300 MHz, DMSO-d$_6$) δ 8.83 and 8.36 (J=5.7 Hz, 1H) (2t, 1H), 8.32 (dd, J=1.8, 0.8 Hz, 1H), 7.82 and 7.79 (2s, 1H), 7.68-6.95 (m, 6H), 5.61 and 5.47 (2s, 2H), 4.62-4.48 and 4.28-4.21 (2m, 1H), 4.46 (d, J=5.6 Hz) and 4.31 (d, J=5.9 Hz)(2d, 2H), 4.17 and 3.83 (2s, 2H), 1.23 (d, J=6.4 Hz) and 0.98 (d, J=6.8 Hz) (2d, 6H); $^{19}$F NMR (282 MHz, DMSO-d$_6$) δ −121.22, −121.71; MS (ES+): 538.5 & 540.5 (M+1); MS (ES−): 538.4 & 536.4 (M−1).

Scheme 138

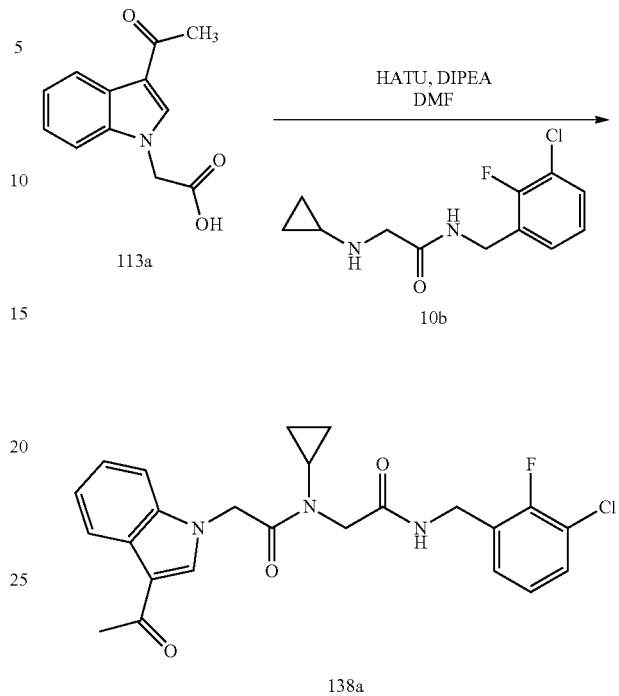

Preparation of 2-(3-acetyl-1H-indol-1-yl)-N-(2-((3-chloro-2-fluorobenzyl)amino)-2-oxoethyl)-N-cyclopropylacetamide (138a)

Reaction of N-(3-chloro-2-fluorobenzyl)-2-(cyclopropylamino)acetamide (10b) (100 mg, 0.39 mmol) with 2-(3-acetyl-1H-indol-1-yl)acetic acid (113a) (85 mg, 0.39 mmol) according to the procedure reported in step-3 of Scheme 2 gave after workup and purification by flash column chromatography [silica gel (24 g), eluting with CMA80 in CHCl$_3$ 0 to 20%] 2-(3-acetyl-1H-indol-1-yl)-N-(2-((3-chloro-2-fluorobenzyl)amino)-2-oxoethyl)-N-cyclopropylacetamide (138a) (115 mg, 0.25 mmol, 65% yield) as a white solid; $^1$H NMR (300 MHz, DMSO-d$_6$) δ 8.46 (t, J=5.8 Hz, 1H), 8.28 (s, 1H), 8.21-8.14 (m, 1H), 7.52-7.40 (m, 2H), 7.28-7.16 (m, 3H), 7.10 (t, J=7.9 Hz, 1H), 5.44 (s, 2H), 4.34 (d, J=5.8 Hz, 2H), 3.99 (s, 2H), 3.16-3.02 (m, 1H), 2.43 (s, 3H), 1.04-0.96 (m, 2H), 0.96-0.87 (m, 2H); $^{19}$F NMR (282 MHz, DMSO-d$_6$) δ −121.62; MS (ES+): 456.5 (M+1), 478.5 (M+Na), MS (ES−): 454.4 (M−1), 490.4 (M+Cl).

Scheme 139

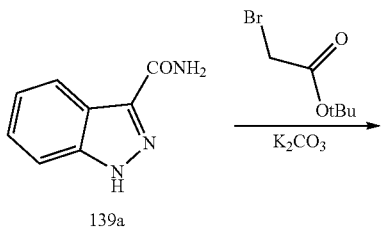

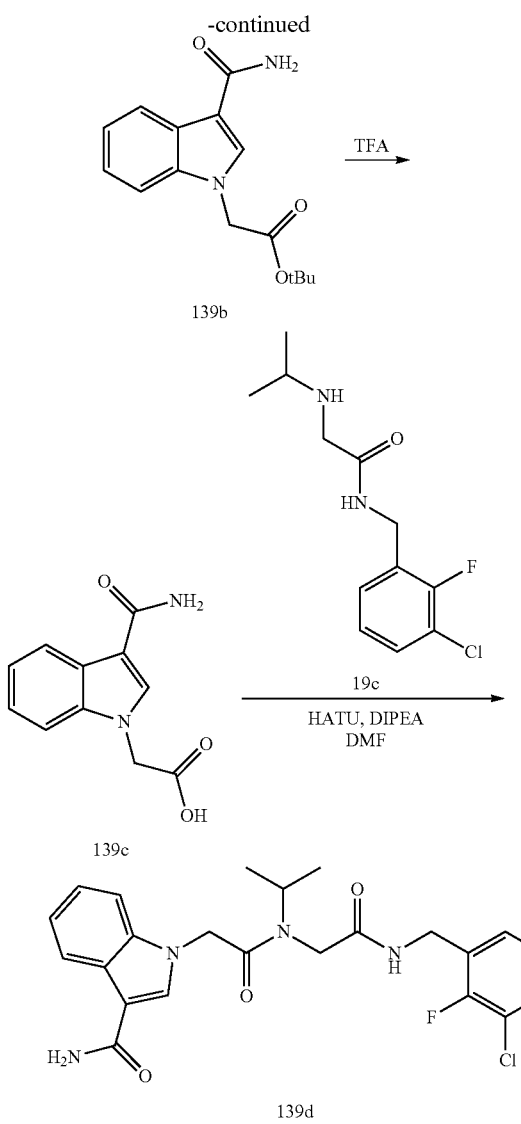

2-(3-carbamoyl-1H-indol-1-yl)acetic acid (139c) (1.18 g, 3.55 mmol, 87% yield) as a yellow solid in the form of TFA adduct; MS (ES+): 219.3 (M+1).

Step-3: Preparation of 1-(2-((2-((3-chloro-2-fluorobenzyl)amino)-2-oxoethyl)(isopropyl)amino)-2-oxoethyl)-1H-indole-3-carboxamide (139d)

Reaction of 2-(3-carbamoyl-1H-indol-1-yl)acetic acid (139c) (150 mg, 0.69 mmol) with N-(3-chloro-2-fluorobenzyl)-2-(isopropylamino)acetamide (19c) (213 mg, 0.83 mmol) according to the procedure reported in step-3 of Scheme 2 gave after workup and purification by flash column chromatography [Silica gel, (24 g) eluting with MeOH in DCM 0-30%] 1-(2-((2-((3-chloro-2-fluorobenzyl)amino)-2-oxoethyl)(isopropyl)amino)-2-oxoethyl)-1H-indole-3-carboxamide (139d) (43 mg, 0.094 mmol, 14% yield) as a white solid as a mixture two rotamers; $^1$H NMR (300 MHz, DMSO-d$_6$) δ 8.81 (t, J=5.7 Hz) and 8.34 (t, J=5.9 Hz) (2t, 1H), 8.20-8.11 (m, 1H), 7.93 and 7.92 (2s, 1H), 7.59-6.63 (m, 8H), 5.30 and 5.13 (2s, 2H), 4.68-4.52 and 4.30-4.23 (2m, 1H), 4.47 (d, J=5.6 Hz) and 4.33 (d, J=5.9 Hz) (2d, 2H), 4.17 and 3.84 (2s, 2H), 1.23 (d, J=6.5 Hz) and 0.99 (d, J=6.8 Hz) (2d, 6H); $^{19}$F NMR (282 MHz, DMSO-d$_6$) δ −121.22, −121.81; MS (ES+): 481.5, 483.5 (M+Na), 939.9, 941.9 (2M+Na); (ES−): 457.5 (M−1), 493.4, 495.5 (M+Cl).

Scheme 140

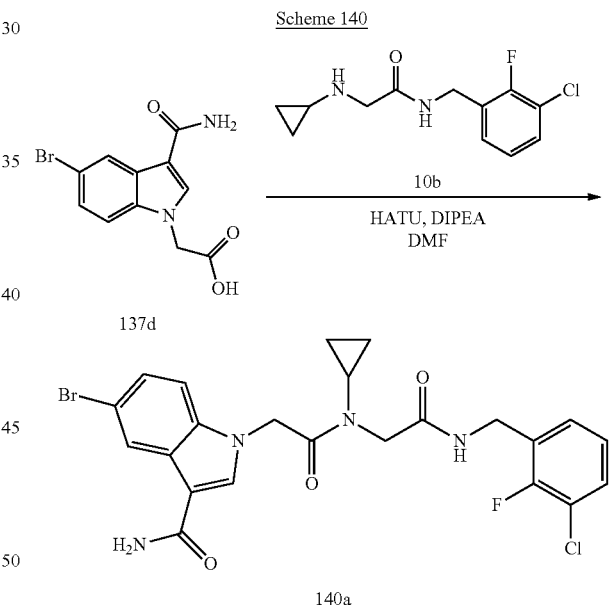

Preparation of 1-(2-((2-((3-chloro-2-fluorobenzyl)amino)-2-oxoethyl)(isopropyl)amino)-2-oxoethyl)-1H-indole-3-carboxamide (139d)

Step-1: Preparation of tert-butyl 2-(3-carbamoyl-1H-indol-1-yl)acetate (139b)

Reaction of 1H-indole-3-carboxamide (139a) (1.0 g, 6.24 mmol) with tert-butyl 2-bromoacetate (1.11 mL, 7.49 mmol) using potassium carbonate (2.16 g, 15.61 mmol) as base according to the procedure reported step-1 of Scheme 45 gave after workup tert-butyl 2-(3-carbamoyl-1H-indol-1-yl)acetate (139b) (1.55 g, 5.65 mmol, 91% yield) as a yellow white solid; MS (ES+): 275.4 (M+1), 294.7 (M+Na); MS (ES−): 273.3 (M−1)

Step-2: Preparation of 2-(3-carbamoyl-1H-indol-1-yl)acetic acid (139c)

Reaction of tert-butyl 2-(3-carbamoyl-1H-indol-1-yl)acetate (139b) (1.12 g, 4.08 mmol) with TFA (6.29 mL, 82 mmol) according to the procedure reported in step-2 of Scheme 2 gave after workup Preparation of 5-bromo-1-(2-((2-((3-chloro-2-fluorobenzyl)amino)-2-oxoethyl)(cyclopropyl)amino)-2-oxoethyl)-1H-indazole-3-carboxamide (140a)

Reaction of N-(3-chloro-2-fluorobenzyl)-2-(cyclopropylamino)acetamide (10b) (517 mg, 2.01 mmol) with 2-(5-bromo-3-carbamoyl-1H-indazol-1-yl)acetic acid (137d) (500 mg, 1.68 mmol) according to the procedure reported in step-3 of Scheme 2 gave after workup and purification by flash column chromatography [silica gel (40 g), eluting with MeOH in DCM 0 to 30%] 5-bromo-1-(2-((2-((3-chloro-2-fluorobenzyl)amino)-2-oxoethyl)(cyclopropyl)amino)-2-oxoethyl)-1H-indazole-3-carboxamide (140a) (329 mg, 0.613 mmol, 37% yield) as a light brown solid; $^1$H NMR (300 MHz, DMSO-$d_6$) δ 8.50 (t, J=5.8 Hz, 1H), 8.32 (dd, J=1.9, 0.7 Hz, 1H), 7.83 (s, 1H), 7.72-7.64 (m, 1H), 7.56 (dd, J=8.9, 1.9 Hz, 1H), 7.52-7.42 (m, 2H), 7.28-7.18 (m, 1H), 7.17-7.06 (m, 1H), 5.68 (s, 2H), 4.33 (d, J=5.7 Hz, 2H), 3.98 (s, 2H), 3.13-3.00 (m, 1H), 1.03-0.95 (m, 2H), 0.95-0.86 (m, 2H). $^{19}$F NMR (282 MHz, DMSO-$d_6$) δ −121.56; MS (ES+): 560.4, 558.4 (M+Na); MS (ES−): 534.3, 536.4 (M−1).

Scheme 141

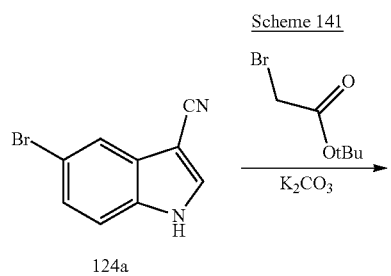

124a

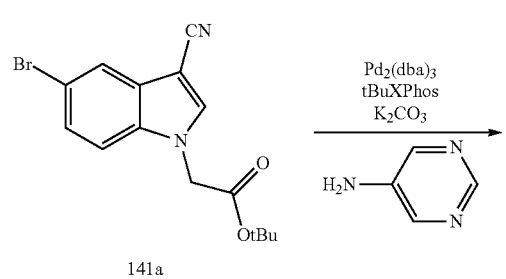

141a

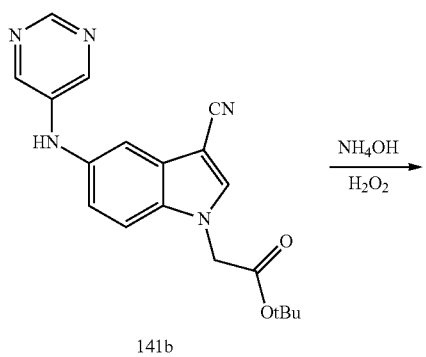

141b

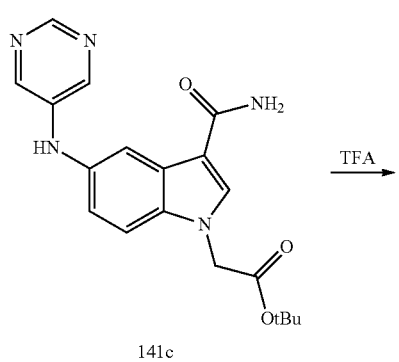

141c

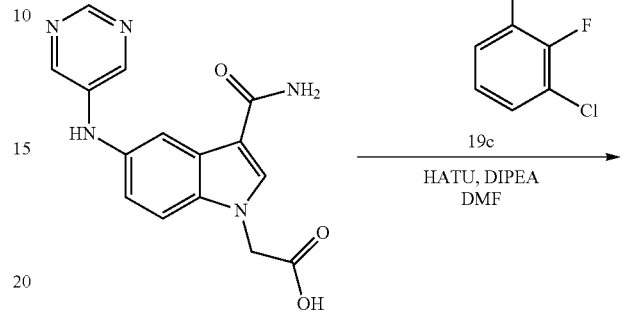

141d

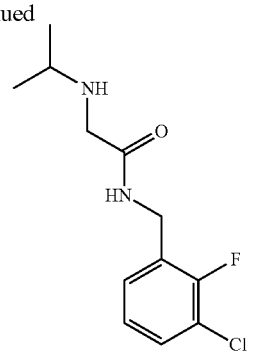

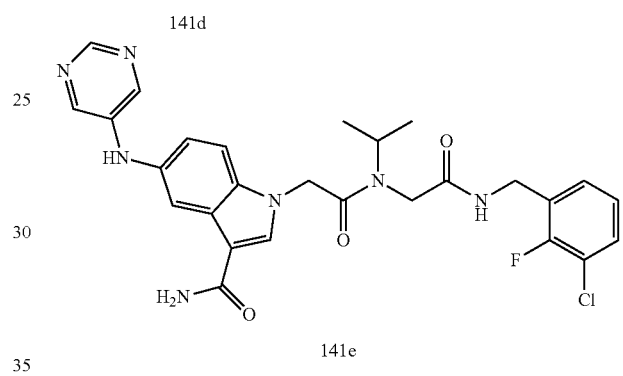

141e

Preparation of 1-(2-((2-((3-chloro-2-fluorobenzyl)amino)-2-oxoethyl)(isopropyl)amino)-2-oxoethyl)-5-(pyrimidin-5-ylamino)-1H-indole-3-carboxamide (141e)

Step-1: Preparation of tert-butyl 2-(5-bromo-3-cyano-1H-indol-1-yl)acetate (141a)

Reaction of 5-bromo-1H-indole-3-carbonitrile (124a) (2.2 g, 9.95 mmol) with tert-butylbromoacetate (2.06 mL, 13.93 mmol) in acetonitrile (50 mL) using potassium carbonate (2.75 g, 19.90 mmol) as base, according to the procedure reported in step-1 of Scheme 43 gave after workup and purification by column chromatography [silica gel (40 g), eluting with EtOAc in hexane 0 to 80%] tert-butyl 2-(5-bromo-3-cyano-1H-indol-1-yl)acetate (141a) (1.4 g, 4.18 mmol, 42% yield) as an off-white solid; MS (ES+): 335.3, 337.3 (M+2), MS (ES−): 369.2, 371.2 (M+Cl).

Step-2: Preparation of 2-(3-carbamoyl-5-(pyrimidin-5-ylamino)-1H-indol-1-yl)acetic acid (141b)

Reaction of tert-butyl 2-(5-bromo-3-cyano-1H-indol-1-yl)acetate (141a) (1.3 g, 3.88 mmol), with pyrimidin-5-amine (369 mg, 3.88 mmol) using potassium carbonate (1.07 g, 7.76 mmol), di-tert-butyl(2',4',6'-triisopropylbiphenyl-2-yl)phosphine (165 mg, 0.389 mmol), Pd$_2$(dba)$_3$ (178 mg, 0.19 mmol) according to the procedure reported in step-1 of Scheme 97 gave after workup and purification by flash column chromatography [silica gel (40 g), eluting with MeOH/EtOAc (1:9) in Hexane 0 to 100%] 2-(3-carbamoyl-5-(pyrimidin-5-ylamino)-1H-indol-1-yl)acetic acid (141b) (320 mg, 0.92 mmol, 24% yield) as light colorless foam; $^1$H NMR (300 MHz, DMSO-$d_6$) δ 8.61 (s, 1H), 8.54 (s, 1H), 8.51 (s, 2H), 8.19 (s, 1H), 7.55 (d, J=8.8 Hz, 1H), 7.35 (d, J=2.0 Hz, 1H), 7.19 (dd, J=8.8, 2.1 Hz, 1H), 5.13 (s, 2H), 1.43 (s, 9H); MS (ES+): 350.4 (M+1), MS (ES−): 348.3 (M−1), 384.4 (M+Cl).

Step-3: Preparation of tert-butyl 2-(3-carbamoyl-5-(pyrimidin-5-ylamino)-1H-indol-1-yl)acetate (141c)

Reaction of 2-(3-carbamoyl-5-(pyrimidin-5-ylamino)-1H-indol-1-yl)acetic acid (141b) (320 mg, 0.92 mmol) in EtOH (10 mL) with conc. NH$_4$OH (0.71 mL, 18.32 mmol) and Hydrogen peroxide (35% aqueous, 0.42 mL, 13.74 mmol) according to the procedure reported in step-1 of Scheme 97 gave after workup tert-butyl 2-(3-carbamoyl-5-(pyrimidin-5-ylamino)-1H-indol-1-yl)acetate (141c) (300 mg, 0.82 mmol, 89% yield) as an off-white solid; $^1$H NMR (300 MHz, DMSO-$d_6$) δ 10.22 (s, 1H), 8.54 (s, 1H), 8.44 (s, 2H), 7.99 (d, J=2.2 Hz, 1H), 7.94 (s, 1H), 7.40 (d, J=8.8 Hz, 1H), 7.06 (dd, J=8.7, 2.2 Hz, 1H), 6.85 (brs, 1H), 5.06 (s, 2H), 1.43 (d, J=2.6 Hz, 9H); MS (ES+): 368.5 (M+1), 390.5 (M+Na); MS (ES−): 366.4 (M−1), 402.4 (M+Cl).

Step-4: Preparation of 2-(3-carbamoyl-5-(pyrimidin-5-ylamino)-1H-indol-1-yl)acetic acid (141d)

Reaction of tert-butyl 2-(3-carbamoyl-5-(pyrimidin-5-ylamino)-1H-indol-1-yl)acetate (141c) (300 mg, 0.82 mmol) with TFA (1.26 mL, 16.33 mmol) according to the procedure reported in step-2 of Scheme 2 gave after workup and trituration of crude with toluene (2×30 mL) and 30% EtOAc-hexane (10 mL), 2-(3-carbamoyl-5-(pyrimidin-5-ylamino)-1H-indol-1-yl)acetic acid (141d) (250 mg, 0.8 mmol, 98% yield) as light orange solid; $^1$H NMR (300 MHz, DMSO-$d_6$) δ 13.54 (brs, 1H, D$_2$O exchangeable) 8.54 (s, 1H), 8.45 (s, 2H), 8.00 (d, J=2.2 Hz, 1H), 7.96 (s, 1H), 7.43 (d, J=8.8 Hz, 1H), 7.11-7.01 (m, 1H), 5.07 (s, 2H); MS (ES+): 312.4 (M+1); MS (ES−): 310.3 (M−1).

Step-5: Preparation of 1-(2-((2-(((3-chloro-2-fluorobenzyl)amino)-2-oxoethyl)(isopropyl)amino)-2-oxoethyl)-5-(pyrimidin-5-ylamino)-1H-indole-3-carboxamide (141e)

Reaction of 2-(3-carbamoyl-5-(pyrimidin-5-ylamino)-1H-indol-1-yl)acetic acid (141d) (70 mg, 0.23 mmol) with N-(3-chloro-2-fluorobenzyl)-2-(isopropylamino)acetamide (19c) (64 mg, 0.25 mmol) according to the procedure reported in step-3 of Scheme 2 gave after workup and purification by flash column [silica gel (12 g), eluting with CMA-80 in CHCl$_3$ 0-50%] 1-(2-((2-(((3-chloro-2-fluorobenzyl)amino)-2-oxoethyl)(isopropyl)amino)-2-oxoethyl)-5-(pyrimidin-5-ylamino)-1H-indole-3-carboxamide (141e) (33 mg, 0.06 mmol, 27% yield) as a white solid as a mixture of rotamers in 2:1; $^1$H NMR (300 MHz, DMSO-$d_6$) δ 8.82 and 8.34 (2t, J=5.9 Hz, 1H), 8.531 and 8.538 (2s, 1H), 8.44 (s, 2H), 8.39 (s, 1H), 8.00 and 7.99 (2s, 1H), 7.91 (s, 1H), 7.62-6.65 (m, 6H), 5.29 and 5.12 (2s, 2H), 4.67-4.52 and 4.30-4.18 (m, 1H), 4.47 and 4.33 (2d, J=5.6 Hz, 2H), 4.16 and 3.85 (2s, 2H), 1.23 and 0.99 (2d, J=6.8 Hz, 6H); $^{19}$F NMR (282 MHz, DMSO-$d_6$) δ −121.20 and −121.77; MS (ES+): 552.6 (M+1), 574.6 (M+Na); MS (ES−): 586.5 (M+Cl).

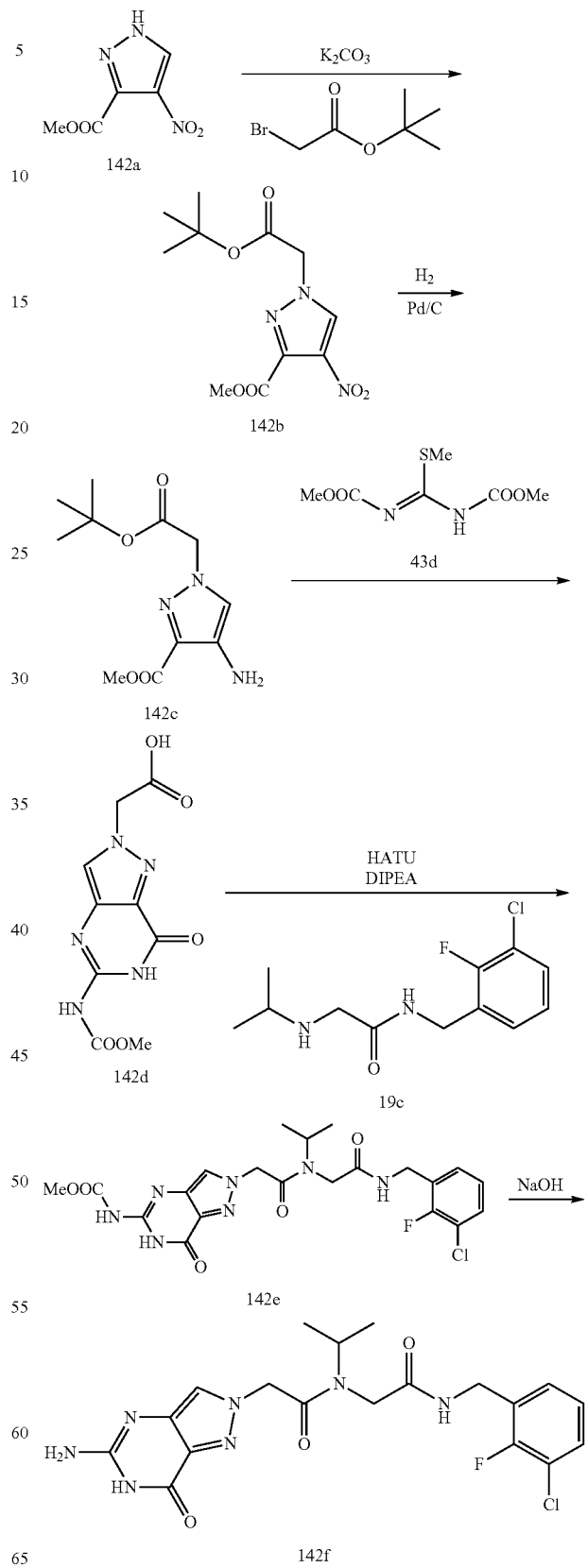

Scheme 142

Preparation of 2-(5-amino-7-oxo-6,7-dihydro-2H-pyrazolo[4,3-d]pyrimidin-2-yl)-N-(2-((3-chloro-2-fluorobenzyl)amino)-2-oxoethyl)-N-isopropylacetamide (142f)

Step-1: Preparation of methyl 1-(2-(tert-butoxy)-2-oxoethyl)-4-nitro-1H-pyrazole-3-carboxylate (142b)

Reaction of methyl 4-nitro-1H-pyrazole-3-carboxylate (142a) (3 g, 17.53 mmol) and tert-butyl 2-bromoacetate (3.11 mL, 21.04 mmol) in DMF (10 mL) using potassium carbonate (3.63 g, 26.3 mmol) according to the procedure reported in step-1 of Scheme 43 gave after workup and purification by flash column chromatography [silica gel eluting with hexanes/EtOAc (1:0 to 4:1)] methyl 1-(2-(tert-butoxy)-2-oxoethyl)-4-nitro-1H-pyrazole-3-carboxylate (142b) (3.35 g, 67%) as a colorless gum; $^1$H NMR (300 MHz, DMSO-$d_6$) δ 8.98 (s, 1H), 5.14 (s, 2H), 3.89 (s, 3H), 1.44 (s, 9H); MS (ES+): 308.3 (M+Na).

Step-2: Preparation of methyl 4-amino-1-(2-(tert-butoxy)-2-oxoethyl)-1H-pyrazole-3-carboxylate (142c)

Hydrogenation of methyl 1-(2-(tert-butoxy)-2-oxoethyl)-4-nitro-1H-pyrazole-3-carboxylate (142b) (3.19 g, 11.18 mmol) in MeOH (100 mL) using palladium (0.595 g, 0.559 mmol) (Pd/C, 10%) as catalyst according to procedure reported in Scheme 79 gave after workup 4-amino-1-(2-(tert-butoxy)-2-oxoethyl)-1H-pyrazole-3-carboxylate (142c) (2.65 g, 93%) as an off white solid which was used as such in next step without further purification; $^1$H NMR (300 MHz, DMSO-$d_6$) δ 7.17 (s, 1H), 4.87 (s, 2H), 4.71 (s, 2H), 3.75 (s, 3H), 1.42 (s, 9H); MS (ES+): 278.4 (M+Na).

Step-3: Preparation of 2-(5-((methoxycarbonyl)amino)-7-oxo-6,7-dihydro-2H-pyrazolo[4,3-d]pyrimidin-2-yl)acetic acid (142d)

Reaction of methyl 4-amino-1-(2-(tert-butoxy)-2-oxoethyl)-1H-pyrazole-3-carboxylate (142c) (530 mg, 2.08 mmol) with (methoxycarbonylamino)(methylthio)methylenecarbamic acid methyl ester (43d) (646 mg) in acetic acid according to the procedure reported in step-2 of Scheme 43 gave after workup and trituration with CHCl$_3$ 2-(5-((methoxycarbonyl)amino)-7-oxo-6,7-dihydro-2H-pyrazolo[4,3-d]pyrimidin-2-yl)acetic acid (142d) (223 mg, 40%) as an off-white solid; $^1$H NMR (300 MHz, DMSO-$d_6$) δ 13.35 (bs, 1H), 11.29 (s, 1H), 11.05 (s, 1H), 8.14 (s, 1H), 5.18 (s, 2H), 3.74 (s, 3H); MS (ES-): 266.3 (M-1).

Step-4: Preparation of methyl (2-(2-((2-((3-chloro-2-fluorobenzyl)amino)-2-oxoethyl)(isopropyl)amino)-2-oxoethyl)-7-oxo-6,7-dihydro-2H-pyrazolo[4,3-d]pyrimidin-5-yl)carbamate (142e)

Reaction of 2-(5-((methoxycarbonyl)amino)-7-oxo-6,7-dihydro-2H-pyrazolo[4,3-d]pyrimidin-2-yl)acetic acid (142d) (36 mg, 0.14 mmol) with N-(3-chloro-2-fluorobenzyl)-2-(isopropylamino)acetamide (19c) (35 mg, 0.14 mmol) according to the procedure reported in step-3 of Scheme 2 gave after workup and purification by flash column [silica gel (12 g), eluting with CHCl$_3$/MeOH (1:0 to 9:1)] methyl (2-(2-((2-((3-chloro-2-fluorobenzyl)amino)-2-oxoethyl)(isopropyl)amino)-2-oxoethyl)-7-oxo-6,7-dihydro-2H-pyrazolo[4,3-d]pyrimidin-5-yl)carbamate (142e) (35 mg, 61% yield) as a white solid; $^1$H NMR (300 MHz, DMSO-$d_6$) δ 11.29 (s, 1H), 11.08 (s, 1H), 8.77 (t, J=5.8 Hz) and 8.36 (t, J=5.9 Hz) (2t, 1H), 8.05 and 8.04 (2s, 1H), 7.56-7.08 (m, 3H), 5.44 and 5.27 (2s, 2H), 4.64-4.49 and 4.20-4.08 (2m, 1H), 4.42 (d, J=5.6 Hz) and 4.33 (d, J=5.9 Hz) (2d, 2H), 4.12 and 3.84 (2s, 2H), 3.73 (s, 3H), 1.18 (d, J=6.4 Hz) and 0.98 (d, J=6.8 Hz) (2d, 6H); $^{19}$F NMR (282 MHz, DMSO-$d_6$) δ −121.32, −121.72; MS (ES+): 508.6 (M+1) and 530.5 (M+Na).

Step-5: Preparation of 2-(5-amino-7-oxo-6,7-dihydro-2H-pyrazolo[4,3-d]pyrimidin-2-yl)-N-(2-((3-chloro-2-fluorobenzyl)amino)-2-oxoethyl)-N-isopropylacetamide (142f)

Reaction of methyl (2-(2-((2-((3-chloro-2-fluorobenzyl)amino)-2-oxoethyl)(isopropyl)amino)-2-oxoethyl)-7-oxo-6,7-dihydro-2H-pyrazolo[4,3-d]pyrimidin-5-yl)carbamate (142e) (32 mg, 0.063 mmol) with 2 N aqueous sodium hydroxide (0.32 mL, 0.63 mmol) in MeOH according to the procedure reported in step-4 of scheme 43 gave after workup and purification by flash column [silica gel (12 g), eluting with CHCl$_3$/CMA80 (1:0 to 0:1)] 2-(5-amino-7-oxo-6,7-dihydro-2H-pyrazolo[4,3-d]pyrimidin-2-yl)-N-(2-((3-chloro-2-fluorobenzyl)amino)-2-oxoethyl)-N-isopropylacetamide (142f) (6 mg, 32%) as a white solid; $^1$H NMR (300 MHz, DMSO-$d_6$) δ 8.76 (t, J=5.8 Hz) & 8.36 (t, J=5.9 Hz) (2t, 1H), 7.67 & 7.63 (2s, 1H), 7.55-7.08 (m, 3H), 5.93 (bs, 2H), 5.33 & 5.16 (2s, 2H), 4.41 (d, J=5.6 Hz) & 4.34 (d, J=6.0 Hz) (2d, 2H), 4.63-4.52 & 4.19-4.04 (2m, 1H), 4.10 & 3.83 (s) (2s, 2H), 1.15 (d, J=6.4 Hz) & 0.98 (d, J=6.8 Hz) (2d, 6H); $^{19}$F NMR (282 MHz, DMSO-$d_6$) δ −121.34, −121.74; MS (ES+): 472.5 (M+Na).

Scheme 143

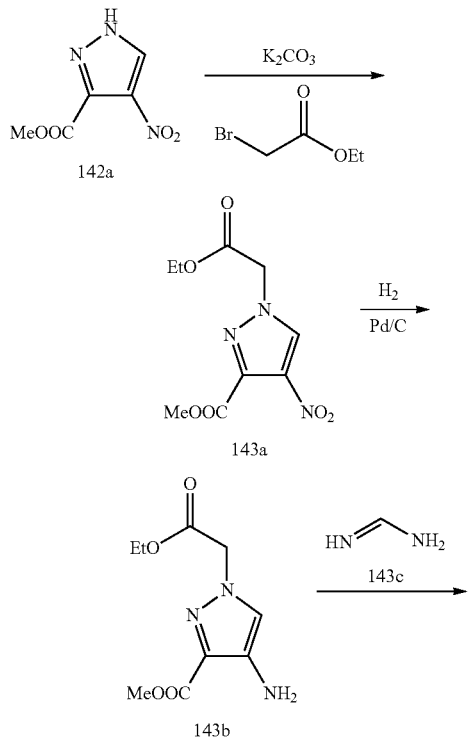

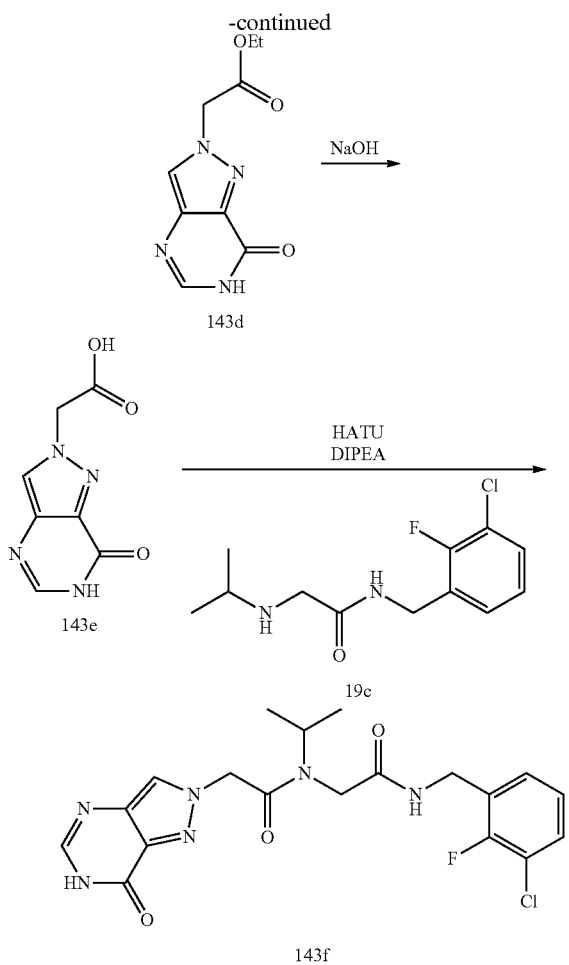

Preparation of N-(2-((3-chloro-2-fluorobenzyl)amino)-2-oxoethyl)-N-isopropyl-2-(7-oxo-6,7-dihydro-2H-pyrazolo[4,3-d]pyrimidin-2-yl)acetamide (143f)

Step-1: Preparation of methyl 1-(2-ethoxy-2-oxoethyl)-4-nitro-1H-pyrazole-3-carboxylate (143a)

Reaction of methyl 4-nitro-1H-pyrazole-3-carboxylate (142a) (1.9 g, 11.1 mmol) and 2-bromoacetate (1.508 mL, 13.32 mmol) in DMF (7 mL) using potassium carbonate (2.3 g, 16.66 mmol) according to the procedure reported in step-1 of Scheme 43 gave after workup and purification by flash column chromatography [silica gel eluting with hexanes/EtOAc (1:0 to 2:1)] methyl 1-(2-ethoxy-2-oxoethyl)-4-nitro-1H-pyrazole-3-carboxylate (143a) (2.28 g, 80%) as a yellow oil; $^1$H NMR (300 MHz, DMSO-d$_6$) δ 8.99 (s, 1H), 5.26 (s, 2H), 4.19 (q, J=7.1 Hz, 2H), 3.89 (s, 3H), 1.22 (t, J=7.1 Hz, 3H); MS (ES+): 258.3 (M+Na).

Step-2: Preparation of methyl 4-amino-1-(2-ethoxy-2-oxoethyl)-1H-pyrazole-3-carboxylate (143b)

Hydrogenation of methyl 1-(2-ethoxy-2-oxoethyl)-4-nitro-1H-pyrazole-3-carboxylate (143a) (2.19 g, 8.5 mmol) in MeOH (80 mL) using palladium (0.45 g, Pd/C, 10%) as catalyst according to procedure reported in Scheme 79 gave after workup methyl 4-amino-1-(2-ethoxy-2-oxoethyl)-1H-pyrazole-3-carboxylate (143b) as an off white solid which was used as such in next step without further purification; MS (ES+): 228.3 (M+Na).

Step-3: Preparation of ethyl 2-(7-oxo-6,7-dihydro-2H-pyrazolo[4,3-d]pyrimidin-2-yl)acetate (143d)

A mixture of methyl 4-amino-1-(2-ethoxy-2-oxoethyl)-1H-pyrazole-3-carboxylate (143b) (1.75 g of the above crude product from step-2) and formimidamide acetate (143c) (8.08 g, 77 mmol) in ethanol (75 mL) was refluxed for 12 h. The reaction mixture was cooled to room temperature and solid obtained was collected by filtration, washed with ethanol, and dried under vacuum to give ethyl 2-(7-oxo-6,7-dihydro-2H-pyrazolo[4,3-d]pyrimidin-2-yl)acetate (143d) (1.49 g, 82% for two steps) as an off-white solid; $^1$H NMR (300 MHz, DMSO-d$_6$) δ 11.92 (s, 1H), 8.36 (s, 1H), 7.79 (d, J=2.6 Hz, 1H), 5.34 (s, 2H), 4.18 (d, J=7.1 Hz, 2H), 1.22 (t, J=7.1 Hz, 3H); MS (ES+): 245.3 (M+Na).

Step-4: Preparation of 2-(7-oxo-6,7-dihydro-2H-pyrazolo[4,3-d]pyrimidin-2-yl)acetic acid (143e)

Reaction of ethyl 2-(7-oxo-6,7-dihydro-2H-pyrazolo[4,3-d]pyrimidin-2-yl)acetate (143d) (200 mg, 0.9 mmol) with 2 N aqueous sodium hydroxide (2.7 mL, 5.4 mmol) in MeOH according to the procedure reported in step-4 of scheme 43 gave after workup 2-(7-oxo-6,7-dihydro-2H-pyrazolo[4,3-d]pyrimidin-2-yl)acetic acid (143e) (165 mg, 94%) as a white solid; $^1$H NMR (300 MHz, DMSO-d$_6$) δ 13.40 (s, 1H), 11.90 (s, 1H), 8.34 (s, 1H), 7.79 (d, J=3.4 Hz, 1H), 5.22 (s, 2H); MS (ES-): 193.1 (M-1), Step-5: Preparation of N-(2-((3-chloro-2-fluorobenzyl)amino)-2-oxoethyl)-N-isopropyl-2-(7-oxo-6,7-dihydro-2H-pyrazolo[4,3-d]pyrimidin-2-yl)acetamide (143f)

Reaction of 2-(7-oxo-6,7-dihydro-2H-pyrazolo[4,3-d]pyrimidin-2-yl)acetic acid (143e) (70 mg, 0.36 mmol) with N-(3-chloro-2-fluorobenzyl)-2-(isopropylamino)acetamide (19c) (112 mg, 0.43 mmol) according to the procedure reported in step-3 of Scheme 2 gave after workup and purification by flash column [silica gel (4 g), eluting with CHCl$_3$/MeOH (1:0 to 9:1)] N-(2-((3-chloro-2-fluorobenzyl)amino)-2-oxoethyl)-N-isopropyl-2-(7-oxo-6,7-dihydro-2H-pyrazolo[4,3-d]pyrimidin-2-yl)acetamide (143f) (85 mg, 54% yield) as a white solid; $^1$H NMR (300 MHz, DMSO-d$_6$) δ 11.86 (bs, 1H), 8.77 (t, J=5.7 Hz) & 8.35 (2t, 1H), 8.25 & 8.24 (2s, 1H), 7.78 (t, J=3.1 Hz, 1H), 7.55-7.09 (m, 3H), 5.48 & 5.31 (2s, 2H), 4.68-4.48 & 4.22-4.10 (2m, 1H), 4.42 (d, J=5.6 Hz) & 4.33 (d, J=5.7 Hz) (2d, 2H), 4.13 & 3.85 (2s, 2H), 1.19 (d, J=6.4 Hz) & 0.99 (d, J=6.8 Hz) (2d, 6H); $^{19}$F NMR (282 MHz, DMSO-d$_6$) δ -121.32, -121.71; MS (ES+): 435.4 (M+1).

Scheme 144

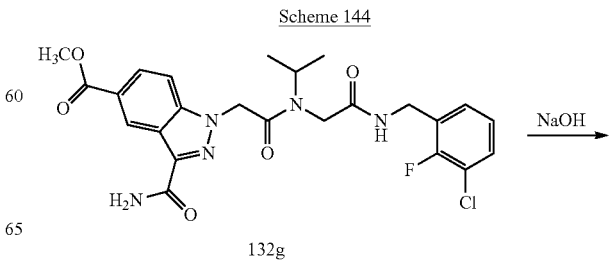

297

-continued

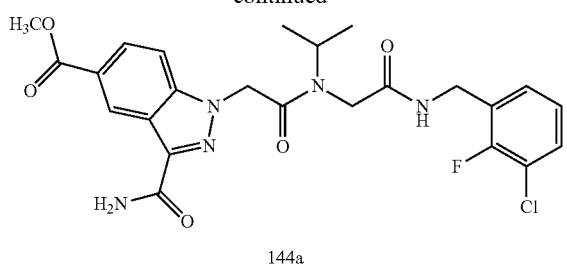

144a

Preparation of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a)

Reaction of methyl 3-carbamoyl-1-(2-((2-((3-chloro-2-fluorobenzyl)amino)-2-oxoethyl)(isopropyl)amino)-2-oxoethyl)-1H-indazole-5-carboxylate (132 g) (3.2 g, 6.18 mmol) in MeOH/water (50 mL, 5:2, v/v) using NaOH (1.24 g, 30.9 mmol) in water (10 mL), according to the procedure reported in step-4 of scheme 43 gave after workup 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (3.04 g, 6.03 mmol, 98% yield) as a white solid; $^1$H NMR (300 MHz, DMSO-$d_6$) δ 12.95 (s, 1H), 8.96-8.30 (m, 2H), 7.98 (dd, J=8.9, 1.5 Hz) and 7.93 (dd, J=8.9, 1.5 Hz) (2dd, 1H), 7.86 and 7.84 (2s, 1H), 7.69 (d, J=9.0 Hz) and 7.61 (d, J=8.9 Hz) (2d, 1H), 7.57-6.92 (m, 4H), 5.64 and 5.51 (2s, 2H), 4.63-4.49 and 4.27-4.20 (2m, 1H), 4.46 (d, J=5.4 Hz) and 4.31 (d, J=5.7 Hz) (2d, 2H), 4.18 and 3.83 (2s, 2H), 1.23 (d, J=6.4 Hz) and 0.99 (d, J=6.8 Hz) (2d, 6H); $^{19}$F NMR (282 MHz, DMSO-$d_6$) δ −121.22, −121.70; MS (ES+): 504.5 (M+1), 526.5 (M+Na); MS (ES−): 502.5 (M−1).

Scheme 145

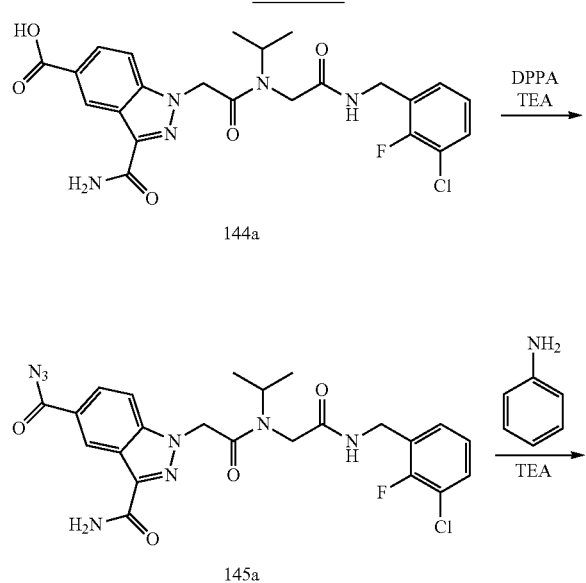

298

-continued

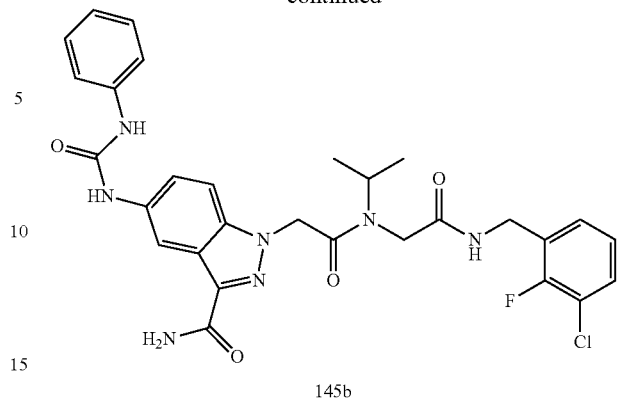

145b

Preparation of 1-(2-((2-((3-chloro-2-fluorobenzyl)amino)-2-oxoethyl)(isopropyl)amino)-2-oxoethyl)-5-(3-phenylureido)-1H-indazole-3-carboxamide (145b)

Step-1: Preparation of 3-carbamoyl-1-(2-((2-((3-chloro-2-fluorobenzyl)amino)-2-oxoethyl)(isopropyl)amino)-2-oxoethyl)-1H-indazole-5-carbonyl azide (145a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (800 mg, 1.588 mmol) according to the procedure reported in step-3 of Scheme 129 gave after workup 3-carbamoyl-1-(2-((2-(3-chloro-2-fluorobenzylamino)-2-oxoethyl)(isopropyl)amino)-2-oxoethyl)-1H-indazole-5-carbonyl azide (145a) (1.32 g, 2.5 mmol), which was used directly in the next step without further purification.

Step-2: Preparation of 1-(2-((2-((3-chloro-2-fluorobenzyl)amino)-2-oxoethyl)(isopropyl)amino)-2-oxoethyl)-5-(3-phenylureido)-1H-indazole-3-carboxamide (145b)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (112 mg, 0.212 mmol) in toluene (15 mL) with aniline (39.4 mg, 0.424 mmol) using TEA (0.059 mL, 0.424 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(3-phenylureido)-1H-indazole-3-carboxamide (145b) (9 mg, 0.015 mmol, 7% yield) as a white solid; $^1$H NMR (300 MHz, DMSO-$d_6$) (a mixture of two rotamers) δ 8.83 8.77 and 8.42-8.28 (2m, 3H), 8.63 (s, 1H), 7.65-6.91 (m, 12H), 5.55 and 5.41 (2s, 2H), 4.62-4.50 and 4.30-4.21 (2m, 1H), 4.46 (d, J=4.9 Hz) and 4.32 (d, J=5.2 Hz) (2d, 2H), 4.18 and 3.83 (2s, 2H), 1.22 (d, J=6.4 Hz) and 0.99 (d, J=6.7 Hz) (2d, 6H); $^{19}$F NMR (282 MHz, DMSO-$d_6$) δ −121.22, −121.74; MS (ES+): 594.6 (M+1) MS (ES−): 628.6 (M+Cl).

299

Scheme 146

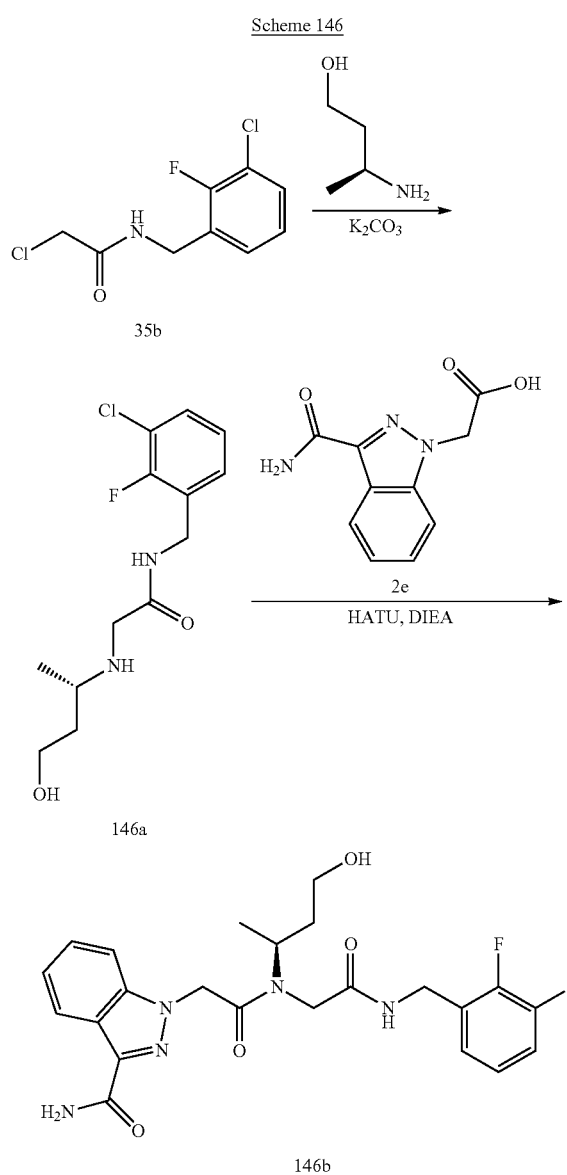

146a

146b

Preparation of (S)-1-(2-((2-((3-chloro-2-fluoroben-zyl)amino)-2-oxoethyl)(4-hydroxybutan-2-yl)amino)-2-oxoethyl)-1H-indazole-3-carboxamide (146b)

Step-1: Preparation of (S)—N-(3-chloro-2-fluorobenzyl)-2-((4-hydroxybutan-2-yl)amino)acetamide (146a)

Reaction of 2-chloro-N-(3-chloro-2-fluorobenzyl)acetamide (35b) (350 mg, 1.48 mmol) with (S)-3-aminobutan-1-ol (264 mg, 2.97 mmol) according to the procedure reported in step-2 of Scheme 35 gave after workup (S)—N-(3-chloro-2-fluorobenzyl)-2-((4-hydroxybutan-2-yl)amino)acetamide (146a) (112, 26%) as a yellow oil, which was used in the next step without further purification; MS (ES+): 289.4 (M+1); MS (ES−): 287.3 (M−1).

300

Step-2: Preparation of (S)-1-(2-((2-((3-chloro-2-fluorobenzyl)amino)-2-oxoethyl)(4-hydroxybutan-2-yl)amino)-2-oxoethyl)-1H-indazole-3-carboxamide (146b)

Reaction of (S)—N-(3-chloro-2-fluorobenzyl)-2-((4-hydroxybutan-2-yl)amino)acetamide (146a) (112 mg, 0.39 mmol) with 2-(3-carbamoyl-1H-indazol-1-yl)acetic acid (2e) (94 mg, 0.43 mmol) according to the procedure reported in step-3 of Scheme 2 gave after workup and purification by flash column chromatography [silica (12 g), eluting with DMA-80 in DCM 0 to 40%] (S)-1-(2-((2-((3-chloro-2-fluorobenzyl)amino)-2-oxoethyl)(4-hydroxybutan-2-yl)amino)-2-oxoethyl)-1H-indazole-3-carboxamide (146b) (40 mg, 0.082 mmol, 21% yield) as a white solid; $^1$H NMR (300 MHz, DMSO-$d_6$) δ 8.83 (t, J=5.7 Hz) and 8.40 (t, J=5.9 Hz) (2t, 1H), 8.24-8.12 (m, 1H), 7.71 (d, J=6.3 Hz, 1H), 7.56-6.99 (m, 7H), 5.83-5.35 (m, 2H), 4.95-3.65 (m, 6H), 3.62-3.19 (m, 2H), 1.83-1.38 (m, 2H), 1.25 (d, J=6.5 Hz) and 0.98 (d, J=6.8 Hz) (2d, 3H); $^{19}$F NMR (282 MHz, DMSO-$d_6$) δ −121.25, −121.76; MS (ES+): 490.5 (M+1), 512.5 (M+Na); MS (ES−): 488.5 (M−1); [based on NMR, this compound is a mixture of rotamer 1:1 ratio].

Scheme 147

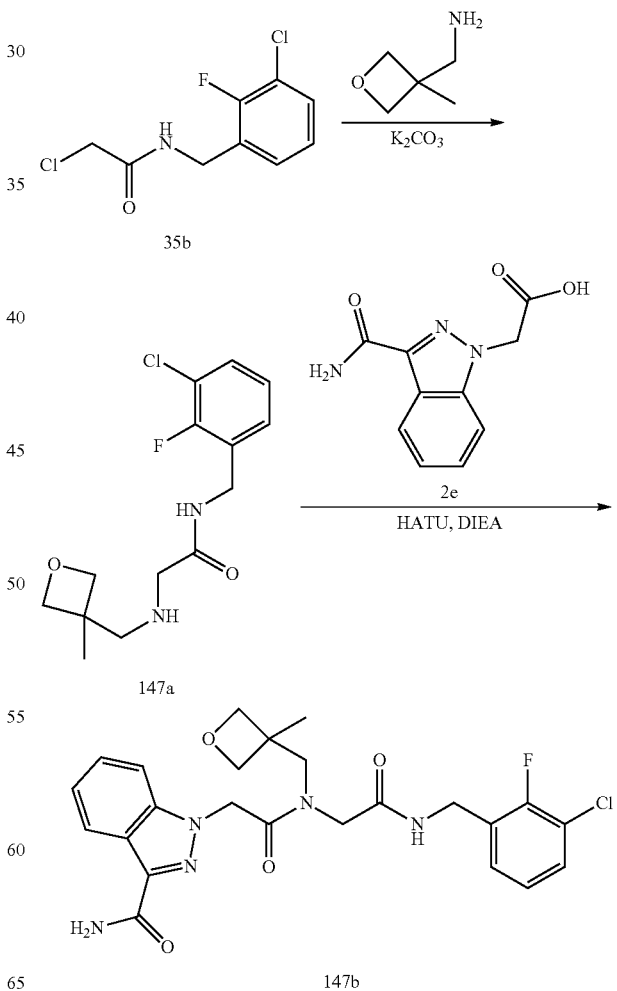

147a

147b

Preparation of (1-(2-((2-((3-chloro-2-fluorobenzyl)amino)-2-oxoethyl)((3-methyloxetan-3-yl)methyl)amino)-2-oxoethyl)-1H-indazole-3-carboxamide (147b)

Step-1: Preparation of N-(3-chloro-2-fluorobenzyl)-2-((2-(3-methyloxetan-3-yl)ethyl)amino)acetamide (147a)

Reaction of 2-chloro-N-(3-chloro-2-fluorobenzyl)acetamide (35b) (292 mg, 1.24 mmol) with (3-methyloxetan-3-yl)methanamine (250 mg, 2.47 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((2-(3-methyloxetan-3-yl)ethyl)amino)acetamide (147a) (113 mg, 30%) as a colorless oil; MS (ES+): 301.3 (M+1), 323.3 (M+Na); MS (ES−): 299.3 (M−1).

Step-2: Preparation of (1-(2-((2-((3-chloro-2-fluorobenzyl)amino)-2-oxoethyl)((3-methyloxetan-3-yl)methyl)amino)-2-oxoethyl)-1H-indazole-3-carboxamide (147b)

Reaction of N-(3-chloro-2-fluorobenzyl)-2-((2-(3-methyloxetan-3-yl)ethyl)amino)acetamide (147a) (113 mg, 0.38 mmol) with 2-(3-carbamoyl-1H-indazol-1-yl)acetic acid (2e) (91 mg, 0.4 mmol) according to the procedure reported in step-3 of Scheme 2 gave after workup and purification by flash column chromatography [silica (12 g), eluting with DMA-80 in DCM 0 to 40%] (1-(2-((2-((3-chloro-2-fluorobenzyl)amino)-2-oxoethyl)((3-methyloxetan-3-yl)methyl)amino)-2-oxoethyl)-1H-indazole-3-carboxamide (147b) (76 mg, 0.15 mmol, 40% yield) as a white solid; $^1$H NMR (300 MHz, DMSO-$d_6$) δ 8.83 (t, J=5.6 Hz) and 8.50 (t, J=5.8 Hz) (2t, 1H), 8.19 (d, J=8.1 Hz, 1H), 7.82-7.65 (m, 1H), 7.57-7.10 (m, 7H), 5.54 and 5.49 (2s, 2H), 4.54-3.03 (m, 10H), 1.24 and 1.22 (2s, 3H); $^{19}$F NMR (282 MHz, DMSO-$d_6$) δ −121.16, −121.55; MS (ES+): 524.5 (M+Na); [based on NMR, this compound is a mixture of two rotamers 4:1 ratio].

Preparation of 1-(2-((2-((3-chloro-2-fluorobenzyl)amino)-2-oxoethyl)(isopropyl)amino)-2-oxoethyl)-5-(3,3-difluoropiperidine-1-carboxamido)-1H-indazole-3-carboxamide (148a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (200 mg, 0.38 mmol) in toluene (15 mL) with 3,3-difluoropiperidine hydrochloride (119 mg, 0.756 mmol) using TEA (0.21 mL, 1.51 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(3,3-difluoropiperidine-1-carboxamido)-1H-indazole-3-carboxamide (148a) (36 mg, 0.058 mmol, 15% yield) as a white solid; $^1$H NMR (300 MHz, DMSO-$d_6$) (as a mixture of two rotamers) δ 8.82 (t, J=5.8 Hz) and 8.36 (t, J=5.8 Hz) (2t, 1H), 8.78 (s, 1H), 8.19 (s, 1H), 7.71-7.04 (m, 7H), 5.54 and 5.41 (2s, 2H), 4.65-4.50 and 4.29-4.21 (2m, 1H), 4.46 (d, J=5.3 Hz) and 4.32 (d, J=5.6 Hz) (2d, 2H), 4.21-3.70 (m, 4H), 3.52 (t, 2H), 2.17-1.95 (m, 2H), 1.82-1.60 (m, 2H), 1.22 (d, J=6.4 Hz) and 0.99 (d, J=6.8 Hz)(2d, 6H); $^{19}$F NMR (282 MHz, DMSO-$d_6$) δ −101.17, −121.22, −121.78; MS (ES+): 622.6 (M+1), 644.6 (M+Na); MS (ES−): 620.5 (M−1).

Scheme 149

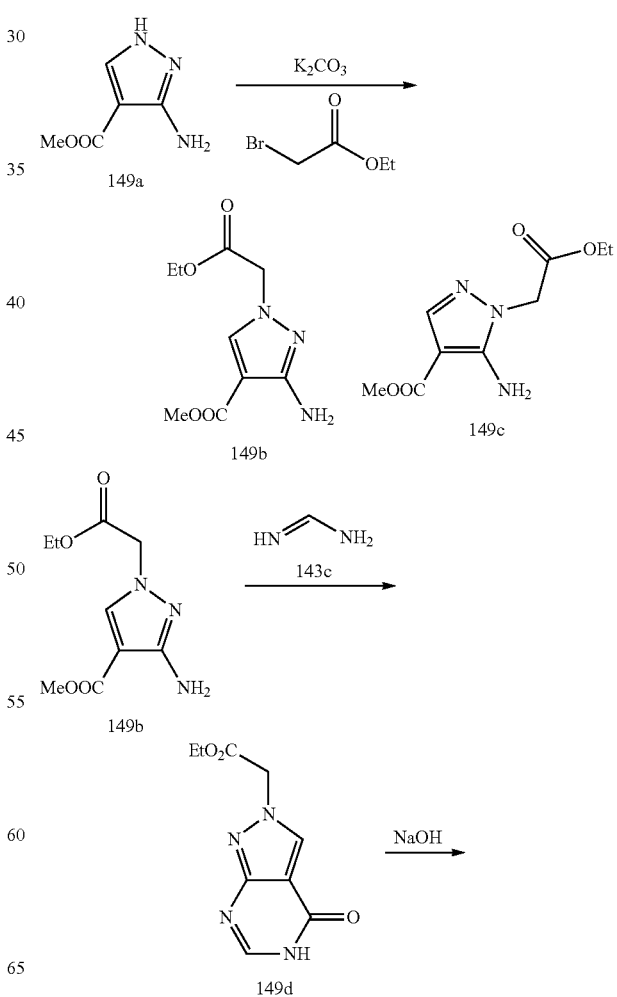

Scheme 148

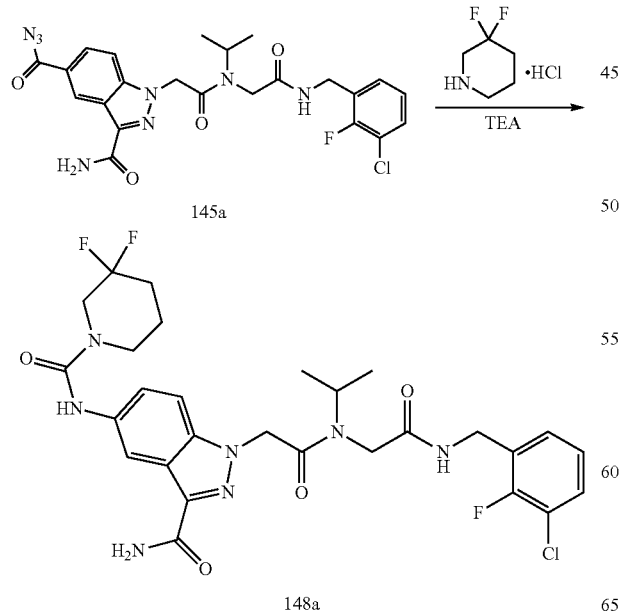

-continued

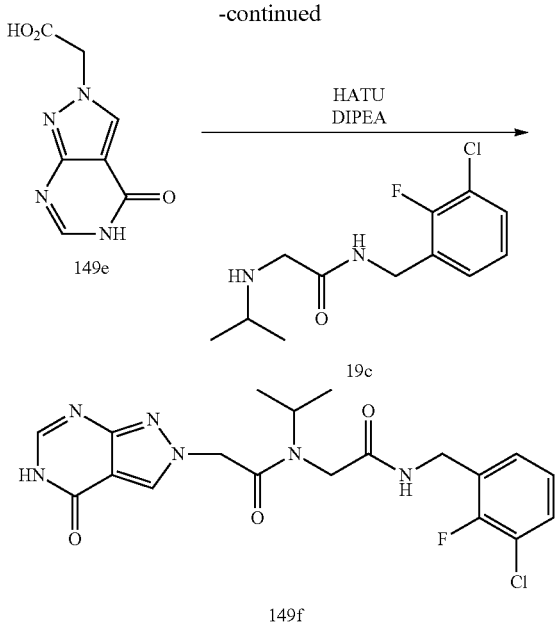

Preparation of N-(2-(3-chloro-2-fluorobenzy-lamino)-2-oxoethyl)-N-isopropyl-2-(4-oxo-4,5-dihydro-2H-pyrazolo[3,4-d]pyrimidin-2-yl)acetamide (149f)

Step-1: Preparation of methyl 3-amino-1-(2-ethoxy-2-oxoethyl)-1H-pyrazole-4-carboxylate (149b)

Reaction of methyl 3-amino-1H-pyrazole-4-carboxylate (149a) (4.9 g, 33.0 mmol) and 2-bromoacetate (4.48 mL, 39.6 mmol) in DMF (20 mL) using potassium carbonate (6.91 g, 49.5 mmol) according to the procedure reported in step-1 of Scheme-43 gave after workup and purification by flash column chromatography [silica gel eluting with hexanes/EtOAc (1:0 to 1:1)] methyl 5-amino-1-(2-ethoxy-2-oxoethyl)-1H-pyrazole-4-carboxylate (149b) (3.98 g, 53%) as a yellow oil; $^1$H NMR (300 MHz, DMSO-$d_6$) δ 7.97 (s, 1H), 5.41 (s, 2H), 4.82 (s, 2H), 4.14 (q, J=7.1 Hz, 2H), 3.70 (s, 3H), 1.20 (t, J=7.2 Hz, 3H); MS (ES+): 228.3 (M+1); and methyl 5-amino-1-(2-ethoxy-2-oxoethyl)-1H-pyrazole-4-carboxylate (149c) (2.73 g, 36%) as a yellow solid; $^1$H NMR (300 MHz, DMSO-$d_6$) δ 7.48 (s, 1H), 6.42 (s, 2H), 4.82 (s, 2H), 4.13 (q, J=7.1 Hz, 2H), 3.68 (s, 3H), 1.20 (t, J=7.1 Hz, 3H); MS (ES+): 228.3 (M+1).

Step-2: Preparation of ethyl 2-(4-oxo-4,5-dihydro-2H-pyrazolo[3,4-d]pyrimidin-2-yl)acetate (149d)

Reaction of methyl 3-amino-1-(2-ethoxy-2-oxoethyl)-1H-pyrazole-4-carboxylate (149b) (3.44 g, 15.15 mL) with formimidamide acetate (143c) (15.93 g, 151 mmol) in ethanol (120 mL) according to the procedure reported in step-3 of Scheme-143 gave after workup and purification by flash column chromatography [silica gel eluting with CHCl$_3$/MeOH (1:0 to 9:1)] ethyl 2-(4-oxo-4,5-dihydro-2H-pyrazolo[3,4-d]pyrimidin-2-yl)acetate (149d) (979 mg, 29%) as a white solid; %). $^1$H NMR (300 MHz, DMSO-$d_6$) δ 11.80 (s, 1H), 8.53 (s, 1H), 7.95 (s, 1H), 5.25 (s, 2H), 4.18 (q, J=7.1 Hz, 2H), 1.22 (t, J=7.1 Hz, 3H); MS (ES+): 223.3 (M+1).

Step-3: Preparation of 2-(4-oxo-4,5-dihydro-2H-pyrazolo[3,4-d]pyrimidin-2-yl)acetic acid (149e)

Reaction of ethyl 2-(4-oxo-4,5-dihydro-2H-pyrazolo[3,4-d]pyrimidin-2-yl)acetate (149d) (200 mg, 0.9 mmol) with 2 N aqueous sodium hydroxide (2.7 mL, 5.4 mmol) in MeOH according to the procedure reported in step-4 of scheme 43 gave after workup 2-(4-oxo-4,5-dihydro-2H-pyrazolo[3,4-d]pyrimidin-2-yl)acetic acid (149e) (162 mg, 93%) as a white solid; $^1$H NMR (300 MHz, DMSO-$d_6$) δ 13.40 (s, 1H), 11.77 (s, 1H), 8.51 (s, 1H), 7.94 (d, J=3.7 Hz, 1H), 5.13 (s, 2H); MS (ES$^-$): 193.1 (M−1).

Step-4: Preparation of N-(2-(3-chloro-2-fluorobenzylamino)-2-oxoethyl)-N-isopropyl-2-(4-oxo-4,5-dihydro-2H-pyrazolo [3,4-d]pyrimidin-2-yl)acetamide (149f)

Reaction of 2-(4-oxo-4,5-dihydro-2H-pyrazolo[3,4-d]pyrimidin-2-yl)acetic acid (149e) (70 mg, 0.36 mmol) with N-(3-chloro-2-fluorobenzyl)-2-(isopropylamino)acetamide (19c) (112 mg, 0.43 mmol) according to the procedure reported in step-3 of Scheme-2 gave after workup and purification by flash column [silica gel (4 g), eluting with CHCl$_3$/MeOH (1:0 to 9:1)] N-(2-(3-chloro-2-fluorobenzylamino)-2-oxoethyl)-N-isopropyl-2-(4-oxo-4,5-dihydro-2H-pyrazolo[3,4-d]pyrimidin-2-yl)acetamide (149f) (81 mg, 52% yield) as an off-white solid; $^1$H NMR (300 MHz, DMSO-$d_6$) δ 11.74 (bs, 1H), 8.76 (t, J=5.8 Hz) & 8.36 (t, J=5.9 Hz) (2t, 1H) 8.43 & 8.42 (2s, 1H), 7.93 (t, J=2.7 Hz, 1H), 7.54-7.10 (m, 3H), 5.40 & 5.23 (2s, 2H), 4.65-4.49 & 4.23-4.10 (2m, 1H), 4.42 (d, J=5.8 Hz) & 4.32 (d, J=5.8 Hz) (2d, 2H), 4.13 & 3.84 (2s, 2H), 1.18 (d, J=6.5 Hz) & 0.98 (d, J=6.8 Hz) (2d, 6H); $^{19}$F NMR (282 MHz, DMSO-$d_6$) δ −121.32, −121.71; MS (ES−): 433.5 & 435.3 (M−1); 469.5 & 471.5 (M+Cl).

Scheme 150

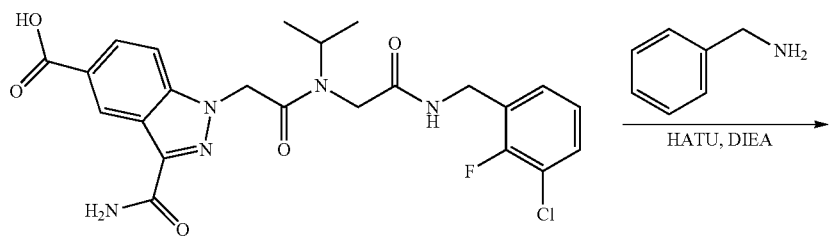

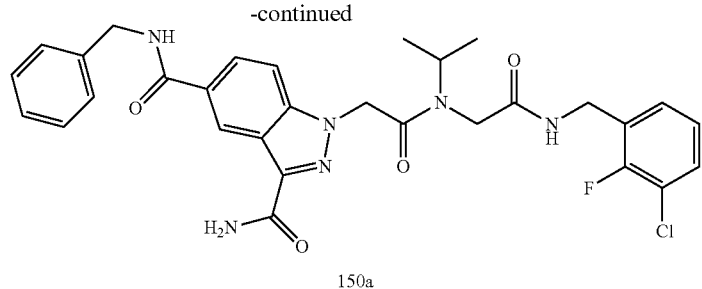

150a

Preparation of N5-benzyl-1-(2-((2-((3-chloro-2-fluorobenzyl)amino)-2-oxoethyl)(isopropyl)amino)-2-oxoethyl)-1H-indazole-3,5-dicarboxamide (150a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with phenylmethanamine (0.016 mL, 0.149 mmol) according to the procedure reported in step-3 of Scheme 2 gave after workup and purification by flash column chromatography [silica (4 g), eluting with MeOH in DCM (1:0 to 19:1)] N5-benzyl-1-(2-((2-((3-chloro-2-fluorobenzyl)amino)-2-oxoethyl)(isopropyl)amino)-2-oxoethyl)-1H-indazole-3,5-dicarboxamide (150a) (25 mg, 43%) as a white solid; $^1$H NMR (300 MHz, DMSO-$d_6$) δ 9.20 (t, J=6.0 Hz) and 8.88-8.68 (m) and 8.36 (t, J=5.8 Hz) (3H), 7.98-7.88 (m, 1H), 7.81 and 7.79 (2s, 1H), 7.67 (d, J=8.9 Hz) and 7.60 (dd, J=8.9, 0.8 Hz) (d & dd, 1H), 7.55-6.96 (m, 9H), 5.63 and 5.49 (2s, 2H), 4.60-4.48 and 4.28-4.21 (2m, 3H), 4.46 (d, J=5.7 Hz) and 4.31 (d, J=5.8 Hz) (2d, 2H), 4.18 and 3.83 (2s, 2H), 1.23 (d) and 0.99 (d, J=6.8 Hz) (2d, 6H); $^{19}$F NMR (282 MHz, DMSO-$d_6$) δ −121.22, −121.73; MS (ES+): 615.6 & 617.6 (M+Na); MS (ES−): 627.5 & 629.5 (M+Cl).

ethyl)-1H-indazole-5-carboxylic acid (144a) (50 mg, 0.1 mmol) with aniline (0.016 mL, 0.18 mmol) according to the procedure reported in step-3 of Scheme 2 gave after workup and purification by flash column chromatography [silica (4 g), eluting with MeOH in DCM (1:0 to 19:1)] 1-(2-((2-((3-chloro-2-fluorobenzyl)amino)-2-oxoethyl)(isopropyl)amino)-2-oxoethyl)-N5-phenyl-1H-indazole-3,5-dicarboxamide (151a) (17 mg, 30%) as a white solid; $^1$H NMR (300 MHz, DMSO-$d_6$) δ 10.44 and 10.43 (2s, 1H), 8.89-8.79 (m) and 8.38 (t, J=5.9 Hz) (2H), 8.02-7.92 (m, 1H), 7.87-7.77 (m, 3H), 7.75-7.64 (m, 1H), 7.57-6.98 (m, 7H), 5.65 and 5.52 2 (s, 2H), 4.61-4.50 and 4.31-4.21 (2m, 1H), 4.47 (d, J=5.5 Hz) and 4.32 (d, J=6.0 Hz (2d, 2H), 4.19 and 3.85 (2s, 2H), 1.24 (d, J=6.2 Hz) and 1.00 (d, J=6.8 Hz) (2d, 6H); $^{19}$F NMR (282 MHz, DMSO-$d_6$) δ −121.21, −121.70; MS (ES+): 601.6 & 603.6 (M+Na).

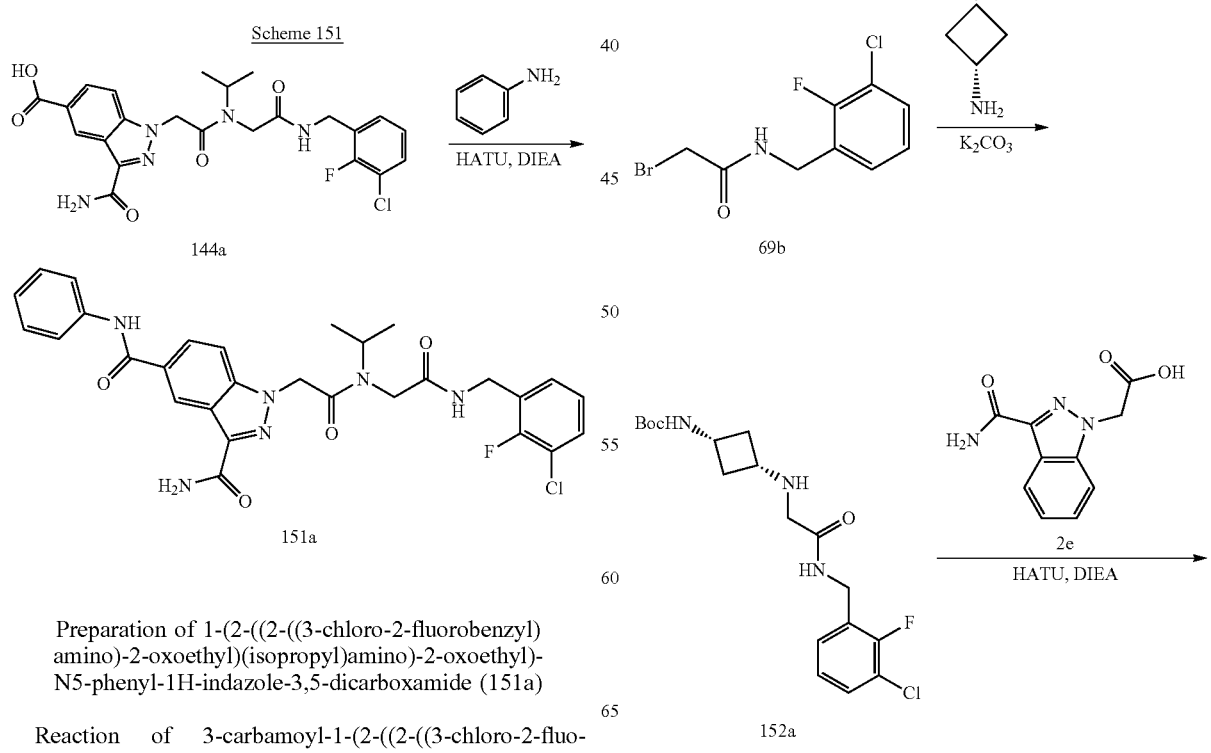

Preparation of 1-(2-((2-((3-chloro-2-fluorobenzyl)amino)-2-oxoethyl)(isopropyl)amino)-2-oxoethyl)-N5-phenyl-1H-indazole-3,5-dicarboxamide (151a)

Reaction of 3-carbamoyl-1-(2-((2-((3-chloro-2-fluorobenzyl)amino)-2-oxoethyl)(isopropyl)amino)-2-oxo-

307

-continued

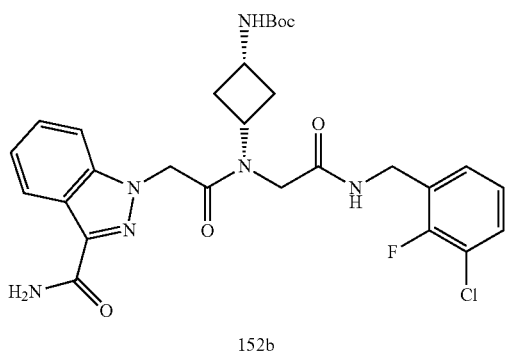

152b

Preparation of tert-butyl ((cis)-3-(2-(3-carbamoyl-1H-indazol-1-yl)-N-(2-((3-chloro-2-fluorobenzyl)amino)-2-oxoethyl)acetamido)cyclobutyl)carbamate (152b)

Step-1: Preparation of tert-butyl ((cis)-3-((2-((3-chloro-2-fluorobenzyl)amino)-2-oxoethyl)amino)cyclobutyl)carbamate (152a)

Reaction of 2-bromo-N-(3-chloro-2-fluorobenzyl)acetamide (69b) (250 mg, 0.89 mmol) with tert-butyl (cis)-3-aminocyclobutylcarbamate (250 mg, 1.34 mmol) according to the procedure reported in step-2 of Scheme 35 gave after workup and purification by flash column chromatography [silica gel 12 g, eluting with MeOH in DCM 0 to 50%] tert-butyl ((cis)-3-((2-((3-chloro-2-fluorobenzyl)amino)-2-oxoethyl)amino)cyclobutyl)carbamate (152a) (243 mg, 0.63 mmol, 71% yield) as a thick yellow oil. MS (ES+): 386.5 (M+1); MS (ES−): 384.4 (M−1).

Step-2: Preparation of tert-butyl ((cis)-3-((2-((3-chloro-2-fluorobenzyl)amino)-2-oxoethyl)amino)cyclobutyl)carbamate (152a)

Reaction of tert-butyl ((cis)-3-((2-((3-chloro-2-fluorobenzyl)amino)-2-oxoethyl)amino)cyclobutyl)carbamate (152a) (114 mg, 0.3 mmol) with 2-(3-carbamoyl-1H-indazol-1-yl)acetic acid (2e) (78 mg, 0.36 mmol) according to the procedure reported in step-3 of Scheme 2 gave after workup and purification by flash column chromatography [Silica gel, (12 g) eluting with MeOH in DCM from 0-20%] tert-butyl ((cis)-3-((2-((3-chloro-2-fluorobenzyl)amino)-2-oxoethyl)amino)cyclobutyl)carbamate (152a) (122 mg, 0.21 mmol, 70% yield) as a white solid as a mixture two rotamers; $^1$H NMR (300 MHz, DMSO-d$_6$) δ 8.80 and 8.40 (2t, J=5.9 Hz, 1H), 8.20-8.15 (m, 1H), 7.69 (bs, 1H), 7.59 and 7.57 (2s, 1H), 7.53-6.99 (m, 6H), 5.56 and 5.36 (2s, 2H), 4.47 (d, J=5.6 Hz) and 4.37-4.25 (m) and 4.04 (s) (5H), 3.82-3.55 (m, 1H), 2.60-2.53 and 2.36-1.82 (2m, 4H), 1.38 and 1.37 (2s, 9H); $^{19}$F NMR (282 MHz, DMSO-d$_6$) δ −121.25, −121.60. MS (ES−): 621.5, 623.5 (M+Cl).

308

Scheme 153

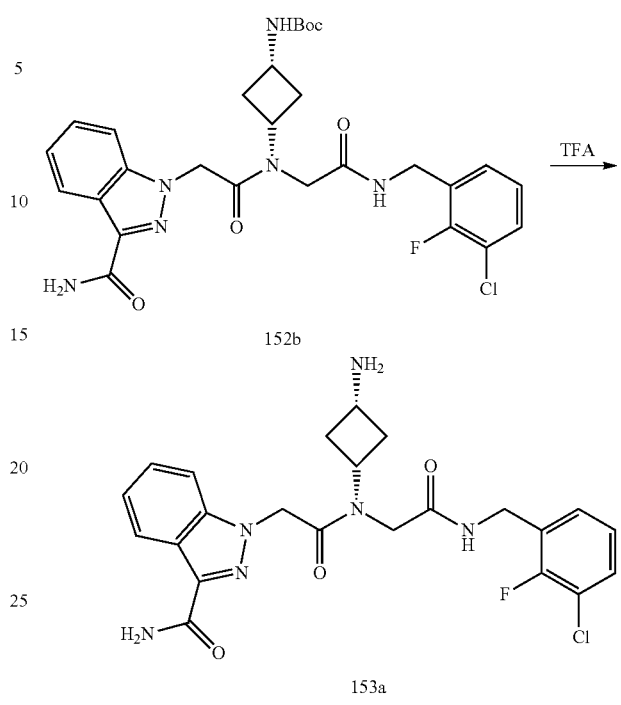

Preparation of 1-(2-(((cis)-3-aminocyclobutyl)(2-((3-chloro-2-fluorobenzyl)amino)-2-oxoethyl)amino)-2-oxoethyl)-1H-indazole-3-carboxamide (153a)

Reaction of tert-butyl ((cis)-3-((2-((3-chloro-2-fluorobenzyl)amino)-2-oxoethyl)amino)cyclobutyl)carbamate (152a) (109 mg, 0.19 mmol) with TFA (0.286 mL, 3.71 mmol) according to the procedure reported in step-2 of Scheme 2 gave after workup and purification by flash column chromatography [Silica gel, (8 g) eluting with DMA80 in DCM 0-30%)] 1-(2-(((cis)-3-aminocyclobutyl)(2-((3-chloro-2-fluorobenzyl)amino)-2-oxoethyl)amino)-2-oxoethyl)-1H-indazole-3-carboxamide (153a) (15 mg, 0.031 mmol, 17% yield) as a white solid as a mixture of two rotamers; $^1$H NMR (300 MHz, DMSO-d$_6$) δ 8.96-8.89 and 8.41 (t, J=6.0 Hz), (m & t, 1H, D$_2$O exchangeable), 8.21-8.13 (m, 1H), 7.68 (s, 1H, D$_2$O exchangeable), 7.61-7.00 (m, 7H), 5.53 and 5.40 (2s, 2H), 4.47 (d, J=5.6 Hz) and 4.38-3.97 (m) (5H), 3.03-2.85 (m, 1H), 2.32-1.47 (m, 4H); $^{19}$F NMR (282 MHz, DMSO-d$_6$) δ −121.23, −121.62; MS (ES+): 487.5 (M+1); MS (ES−): 485.5 (M−1), 521.4, 523.4 (M+Cl).

Scheme 154

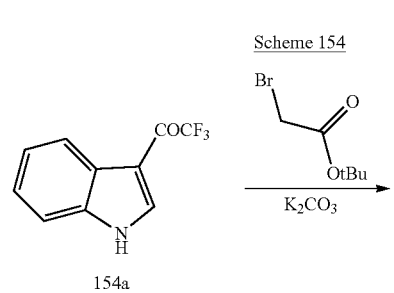

154a

309

-continued

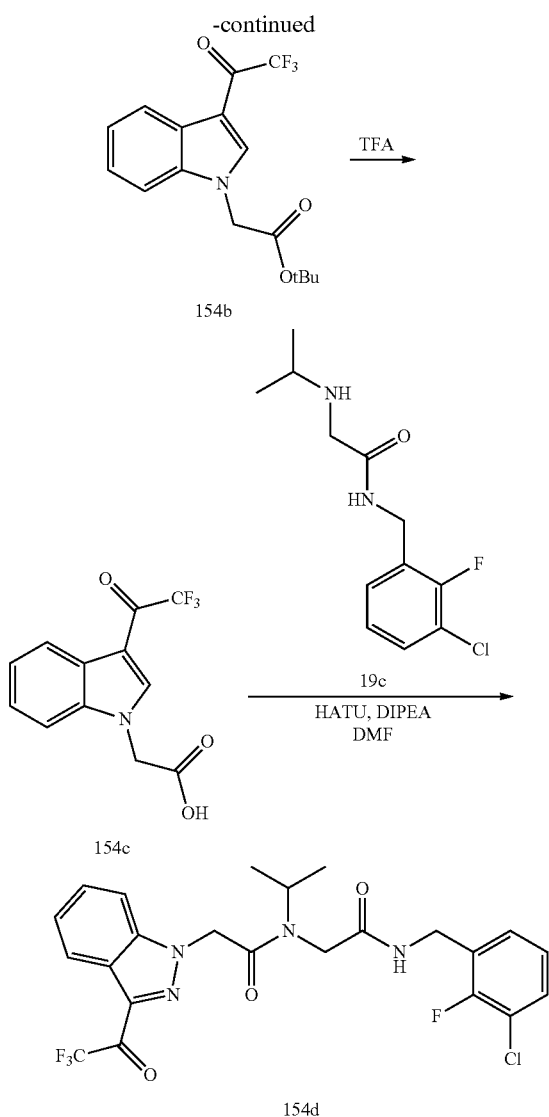

Preparation of N-(2-((3-chloro-2-fluorobenzyl)amino)-2-oxoethyl)-N-isopropyl-2-(3-(2,2,2-trifluoroacetyl)-1H-indol-1-yl)acetamide (154d)

Step-1: Preparation of tert-butyl 2-(3-(2,2,2-trifluoroacetyl)-1H-indol-1-yl)acetate (154b)

Reaction of 2,2,2-trifluoro-1-(1H-indol-3-yl)ethanone (154a) (800 mg, 3.75 mmol) with tert-butyl 2-bromoacetate (1.46 g, 7.51 mmol) using Potassium carbonate (1.03 g, 7.51 mmol) as base in acetonitrile (50 mL) according to the procedure reported step-1 of Scheme 43 gave after workup and purification by flash column chromatography [silica gel (24 g), eluting with EtOAc-hexane 0 to 60%] tert-butyl 2-(3-(2,2,2-trifluoroacetyl)-1H-indol-1-yl)acetate (154b) (1.15 g, 3.51 mmol, 94% yield) as a white solid; $^1$H NMR (300 MHz, DMSO-$d_6$) δ 8.60 (q, J=1.9 Hz, 1H), 8.23-8.17 (m, 1H), 7.63-7.57 (m, 1H), 7.44-7.35 (m, 2H), 5.27 (s, 2H), 1.43 (s, 9H); MS (ES+) 328.4 (M+1), MS (ES-): 326.4, (M-1), 362.3 (M+Cl).

310

Step-2: Preparation of 2-(3-(2,2,2-trifluoroacetyl)-1H-indol-1-yl)acetic acid (154c)

Reaction of tert-butyl 2-(3-(2,2,2-trifluoroacetyl)-1H-indol-1-yl)acetate (154b) (1.1 g, 3.36 mmol) with TFA (3.88 mL, 50.4 mmol) according to the procedure reported in step-2 of Scheme 2 gave after workup and trituration of crude product with 30% EtOAc-hexane (10 mL) 2-(3-(2,2,2-trifluoroacetyl)-1H-indol-1-yl)acetic acid (154c) (650 mg, 2.4 mmol, 71% yield) as a white solid; $^1$H NMR (300 MHz, DMSO-$d_6$) δ 13.38 (s, 1H, D$_2$O exchangeable), 8.64-8.55 (m, 1H), 8.26-8.14 (m, 1H), 7.70-7.58 (m, 1H), 7.44-7.30 (m, 2H), 5.28 (s, 2H); MS (ES+) 272.3 (M+1), 294.3 (M+Na), MS (ES-); 270.2, (M-1).

Step-3: Preparation of N-(2-((3-chloro-2-fluorobenzyl)amino)-2-oxoethyl)-N-isopropyl-2-(3-(2,2,2-trifluoroacetyl)-1H-indol-1-yl)acetamide (154d)

Reaction of 2-(3-(2,2,2-trifluoroacetyl)-1H-indol-1-yl)acetic acid (154c) (80 mg, 0.3 mmol) with N-(3-chloro-2-fluorobenzyl)-2-(isopropylamino)acetamide (19c) (76 mg, 0.3 mmol) according to the procedure reported in step-3 of Scheme 2 gave after workup and purification by flash column chromatography [silica gel (12 g), eluting with DMA80-DCM 0 to 20%] N-(2-((3-chloro-2-fluorobenzyl)amino)-2-oxoethyl)-N-isopropyl-2-(3-(2,2,2-trifluoroacetyl)-1H-indol-1-yl)acetamide (154d) (115 mg, 0.23 mmol, 76% yield) as a white solid; $^1$H NMR (300 MHz, DMSO-$d_6$) (a mixture of two rotamers) δ 8.83 and 8.34 (2t, J=5.7 Hz, 1H), 8.56 and 8.47 (2d, J=2.0 Hz, 1H), 8.23-8.17 (m, 1H), 7.67-6.92 (m, 6H), 5.51 and 5.30 (2s, 2H), 4.64-4.54 and 4.29-4.19 (2m, 1H), 4.48 and 4.33 (2d, J=5.6 Hz, 2H), 4.18 and 3.85 (2s, 2H), 1.27 and 1.00 (2d, J=6.8 Hz, 6H); $^{19}$F NMR (282 MHz, DMSO-$d_6$) (a mixture of two rotamers) δ -71.30 and -71.33, -121.19 and -121.86; MS (ES+) 512.5 (M+1), 534.5 (M+Na), MS (ES-): 510.5 (M-1), 546.5 (M+Cl).

Scheme 155

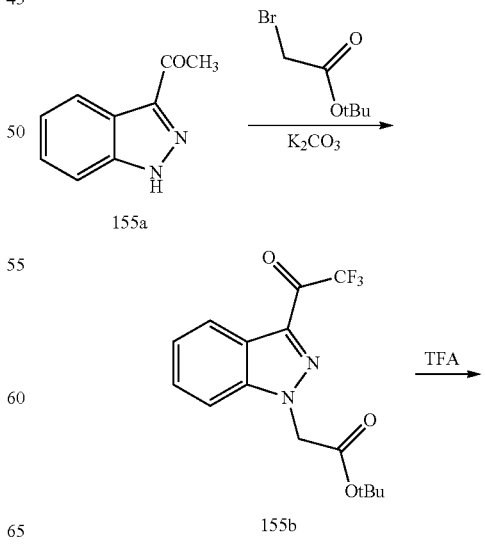

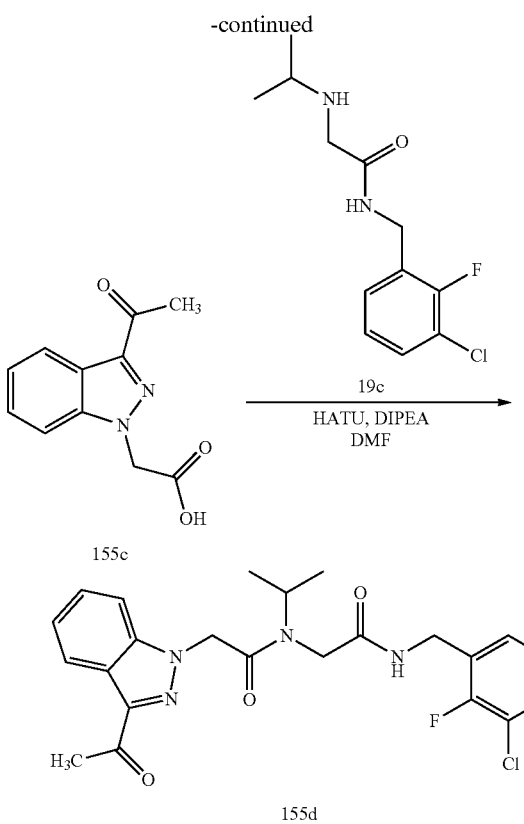

Preparation of 2-(3-acetyl-1H-indazol-1-yl)-N-(2-((3-chloro-2-fluorobenzyl)amino)-2-oxoethyl)-N-isopropylacetamide (155d)

Step-1: Preparation of tert-butyl 2-(3-acetyl-1H-indazol-1-yl)acetate (155b)

Reaction of 1-(1H-indazol-3-yl)ethanone (155a) (800 mg, 5.0 mmol) with tert-butyl 2-bromoacetate (1.47 g, 10 mmol) using Potassium carbonate (1.38 g, 10 mmol) as base in acetonitrile (50 mL) according to the procedure reported step-1 of Scheme 43 gave after workup and purification by flash column chromatography [silica gel (24 g), eluting with EtOAC-hexane 0 to 60%] tert-butyl 2-(3-acetyl-1H-indazol-1-yl)acetate (155b) (1.3 g, 4.74 mmol, 95% yield) as a white solid; $^1$H NMR (300 MHz, DMSO-$d_6$) δ 8.19 (dt, J=8.1, 1.0 Hz, 1H), 7.75 (dt, J=8.5, 0.9 Hz, 1H), 7.51 (ddd, J=8.4, 6.9, 1.2 Hz, 1H), 7.36 (ddd, J=7.9, 6.9, 0.9 Hz, 1H), 5.45 (s, 2H), 2.62 (s, 3H), 1.42 (s, 9H); MS (ES+) 297.4 (M+Na); MS (ES−): 273.4 (M−1).

Step-2: Preparation of 2-(3-acetyl-1H-indazol-1-yl)acetic acid (155c)

Reaction of tert-butyl 2-(3-acetyl-1H-indazol-1-yl)acetate (155b) (1 g, 3.65 mmol) with TFA (5.62 mL, 72.9 mmol) according to the procedure reported in step-2 of Scheme 2 gave after workup and trituration of crude product with 30% EtOAc-hexane (10 mL) 2-(3-acetyl-1H-indazol-1-yl)acetic acid (155c) (800 mg, 3.67 mmol, 101% yield) as a white solid; $^1$H NMR (300 MHz, DMSO-$d_6$) δ 13.35 (s, 1H), 8.19 (dt, J=8.1, 1.0 Hz, 1H), 7.79 (dt, J=8.5, 0.9 Hz, 1H), 7.50 (ddd, J=8.4, 6.9, 1.2 Hz, 1H), 7.36 (ddd, J=8.0, 6.9, 0.9 Hz, 1H), 5.46 (s, 2H), 2.62 (s, 3H); MS (ES+) 219.3 (M+1), 241.3 (M+Na), MS (ES−): 217.2 (M−1).

Step-3: Preparation of 2-(3-acetyl-1H-indazol-1-yl)-N-(2-((3-chloro-2-fluorobenzyl)amino)-2-oxoethyl)-N-isopropylacetamide (155d)

Reaction of 2-(3-acetyl-1H-indazol-1-yl)acetic acid (155c) (65 mg, 0.3 mmol) with N-(3-chloro-2-fluorobenzyl)-2-(isopropylamino)acetamide (19c) (77 mg, 0.3 mmol) according to the procedure reported in step-3 of Scheme 2 gave after workup and purification by flash column chromatography [silica gel (12 g), eluting with DMA80-DCM; 0 to 20%] 2-(3-acetyl-1H-indazol-1-yl)-N-(2-((3-chloro-2-fluorobenzyl)amino)-2-oxoethyl)-N-isopropylacetamide (155d) (120 mg, 0.26 mmol, 88% yield) as a white solid as a mixture of two rotamers; $^1$H NMR (300 MHz, DMSO-$d_6$) δ 8.83 and 8.34 (t, J=5.7 Hz) (2t, 1H), 8.21-8.16 (m, 1H), 7.72-6.96 (m, 6H), 5.70 and 5.53 (2s, 2H), 4.62-4.50 and 4.32-4.19 (2m, 1H), 4.47 and 4.32 (2d, J=5.6 Hz, 2H), 4.18 and 3.84 (s, 2H), 2.69 and 2.61 (2s, 3H), 1.25 and 1.00 (d, J=6.8 Hz, 6H). $^{19}$F NMR (282 MHz, DMSO-$d_6$) δ −121.21, −121.76; MS (ES+) 458.4, 459.5 (M+1), 481.5 (M+Na), MS (ES−): 493.4 (M+Cl).

Scheme 156

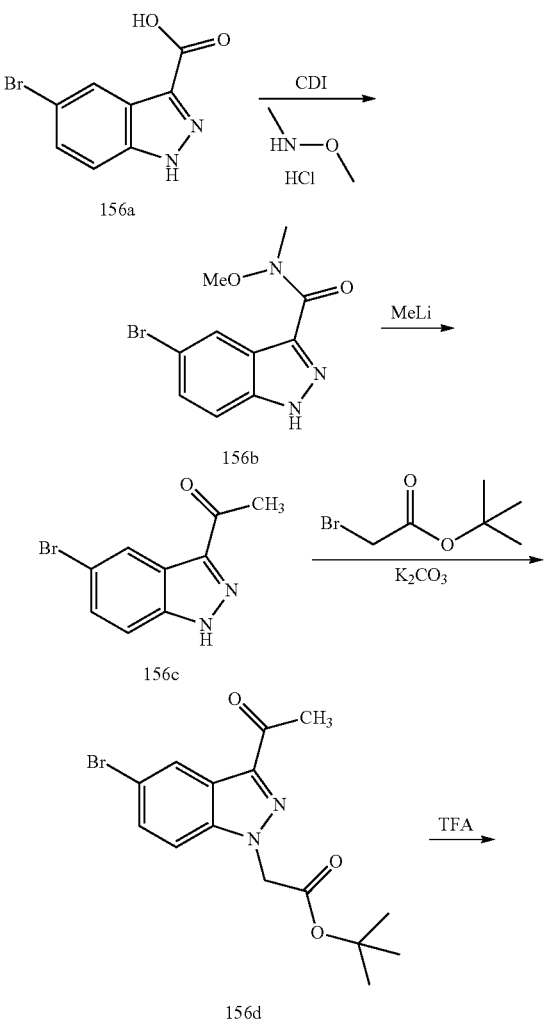

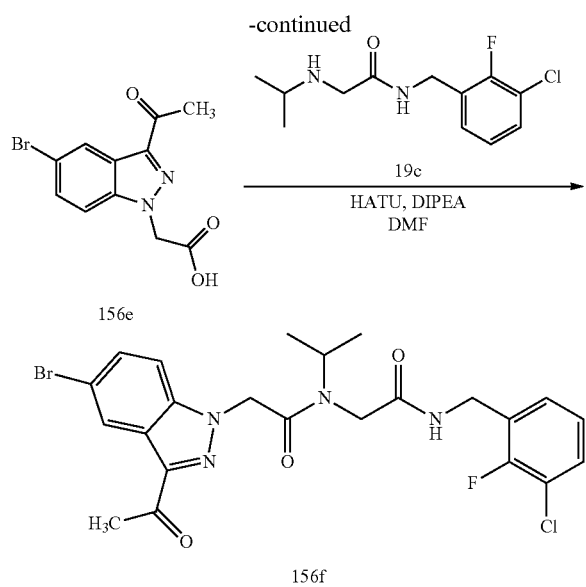

Preparation of 2-(3-acetyl-5-bromo-1H-indazol-1-yl)-N-(2-((3-chloro-2-fluorobenzyl)amino)-2-oxoethyl)-N-isopropylacetamide (156f)

Step-1: Preparation of 5-bromo-N-methoxy-N-methyl-1H-indazole-3-carboxamide (156b)

To a solution of 5-bromo-1H-indazole-3-carboxylic acid (156a) (1 g, 4.15 mmol) in DMF (20 mL) was added CDI (0.81 g, 4.98 mmol) and stirred at 65° C. for 15 min. The resultant clear solution was cooled to RT, added N,O-dimethylhydroxylamine hydrochloride (0.49 g, 5 mmol) and continued stirring at 65° C. for 3 h. Mixture was cooled to RT, concentrated under vacuum and resultant solution was diluted with water (100 mL) and stirred for 10 min. The solid obtained was collected by filtration, washed with water (3×5 mL) and dried to afford 5-bromo-N-methoxy-N-methyl-1H-indazole-3-carboxamide (156b) (830 mg, 2.92 mmol, 70% yield) as an off-white solid; $^1$H NMR (300 MHz, DMSO-$d_6$) δ 13.85 (s, 1H), 8.18 (d, J=1.8 Hz, 1H), 7.69-7.49 (m, 2H), 3.78 (s, 3H), 3.45 (s, 3H); MS (ES+) 284.3, 286.2 (M+2), 306.3, 308.3 (M+Na); MS (ES−): 318.2, 320.2 (M+Cl).

Step-2: Preparation of 1-(5-bromo-1H-indazol-3-yl)ethanone (156c)

To a solution of 5-bromo-N-methoxy-N-methyl-1H-indazole-3-carboxamide (156b) (820 mg, 2.89 mmol) in THF (30 mL) at 0° C. under argon atmosphere was added MeLi (8.66 mL, 8.66 mmol). The mixture was slowly warmed to RT and continued to stir for 3 h at RT. Mixture was poured into 1 N aqueous KHSO$_4$ solution (50 mL) and then diluted with EtOAc (40 mL). Layers were separated, aqueous layer was extracted with EtOAc (1×40 mL) and the combined organics were washed with brine, dried, filtered and concentrated to afford crude product as a dark green solid. This solid was suspended in 30% EtOAc-hexane (10 mL) and sonicated for few minutes. The solid obtained was collected by filtration, washed with 30% EtOAc-hexane (2×2 mL) to afford 1-(5-bromo-1H-indazol-3-yl)ethanone (156c) (470 mg, 1.97 mmol, 68% yield) as light green solid; $^1$H NMR (300 MHz, DMSO-$d_6$) δ 14.06 (s, 1H), 8.30 (dd, J=1.8, 0.8 Hz, 1H), 7.68 (dd, J=8.8, 0.7 Hz, 1H), 7.58 (dd, J=8.9, 1.9 Hz, 1H), 2.63 (s, 3H); MS (ES+) 239.2, 241.2 (M+2), MS (ES−): 237.1, 239.1 (M−2), 273.2, 275.1 (M+Cl).

Step-3: Preparation of tert-butyl 2-(3-acetyl-5-bromo-1H-indazol-1-yl)acetate (156d)

Reaction of 1-(5-bromo-1H-indazol-3-yl)ethanone (156c) (400 mg, 1.67 mmol) with tert-butyl 2-bromoacetate (0.49 mL, 3.35 mmol) using Potassium carbonate (0.46 g, 3.35 mmol) as base in acetonitrile (20 mL) according to the procedure reported step-1 of Scheme 43 gave after workup and purification by flash column chromatography [silica gel (12 g), eluting with EtOAc-hexane 0 to 100%] tert-butyl 2-(3-acetyl-5-bromo-1H-indazol-1-yl)acetate (156d) (480 mg, 1.36 mmol, 81% yield) as a white solid; $^1$H NMR (300 MHz, DMSO-$d_6$) δ 8.32 (dd, J=1.9, 0.7 Hz, 1H), 7.79 (dd, J=9.0, 0.7 Hz, 1H), 7.67 (dd, J=8.9, 1.9 Hz, 1H), 5.48 (s, 2H), 2.62 (s, 3H), 1.42 (s, 9H); MS (ES+): 375.3, 377.3 (M+2), MS (ES−): 387.3, 389.3 (M+Cl).

Step-4: Preparation of 2-(3-acetyl-5-bromo-1H-indazol-1-yl)acetic acid (156e)

Reaction of tert-butyl 2-(3-acetyl-5-bromo-1H-indazol-1-yl)acetate (156d) (480 mg, 1.36 mmol) with TFA (2.09 mL, 27.2 mmol) according to the procedure reported in step-2 of Scheme 2 gave after workup and trituration of crude product with 20% EtOAc-hexane (10 mL) 2-(3-acetyl-5-bromo-1H-indazol-1-yl)acetic acid (156e) (400 mg, 1.35 mmol, 99% yield) as an off-white solid; $^1$H NMR (300 MHz, DMSO-$d_6$) δ 13.42 (s, 1H), 8.32 (d, J=1.9, 0.7 Hz, 1H), 7.82 (dd, J=9.0, 0.7 Hz, 1H), 7.66 (dd, J=9.0, 1.9 Hz, 1H), 5.48 (s, 2H), 2.62 (s, 3H); MS (ES+): 297.2, 299.2 (M+2), 319.2, 321.2 (M+Na); MS (ES−): 295.2, 297.2 (M−2).

Step-5: Preparation of 2-(3-acetyl-5-bromo-1H-indazol-1-yl)-N-(2-((3-chloro-2-fluorobenzyl)amino)-2-oxoethyl)-N-isopropylacetamide (156f)

Reaction of 2-(3-acetyl-5-bromo-1H-indazol-1-yl)acetic acid (156e) (70 mg, 0.24 mmol) with N-(3-chloro-2-fluorobenzyl)-2-(isopropylamino)acetamide (19c) (61 mg, 0.24 mmol) according to the procedure reported in step-3 of Scheme 2 gave after workup and purification by flash column chromatography [silica gel (12 g), eluting with DMA80-DCM; 0 to 20%] 2-(3-acetyl-5-bromo-1H-indazol-1-yl)-N-(2-((3-chloro-2-fluorobenzyl)amino)-2-oxoethyl)-N-isopropylacetamide (156f) (93 mg, 0.173 mmol, 73% yield) as a white solid as a mixture of two rotamers; $^1$H NMR (300 MHz, DMSO-$d_6$) δ 8.83 and 8.34 (2t, J=5.7 Hz, 1H), 8.32-8.30 (m, 1H), 7.74-6.91 (m, 5H), 5.72 and 5.55 (2s, 2H), 4.62-4.50 and 4.30-4.19 (2m, 1H), 4.46 and 4.31 (2d, J=5.6 Hz, 2H), 4.17 and 3.84 (2s, 2H), 2.69 and 2.61 (2s, 3H), 1.24 and 0.99 (2d, J=6.8 Hz, 6H); $^{19}$F NMR (282 MHz, DMSO-$d_6$) δ −121.22, −121.72; MS(ES−) 535.4, 537.4 (M−2), 571.4, 573.4; (M+Cl).

Scheme 157

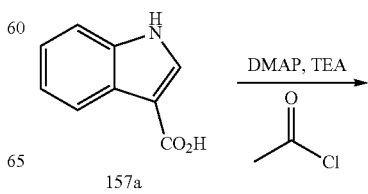

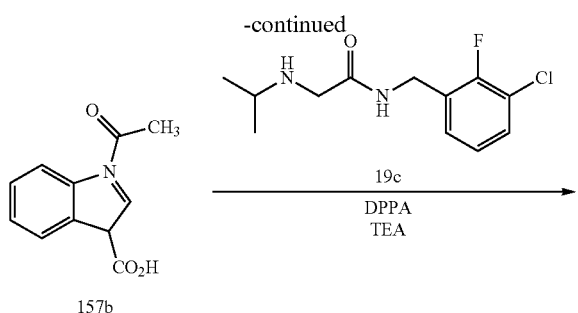

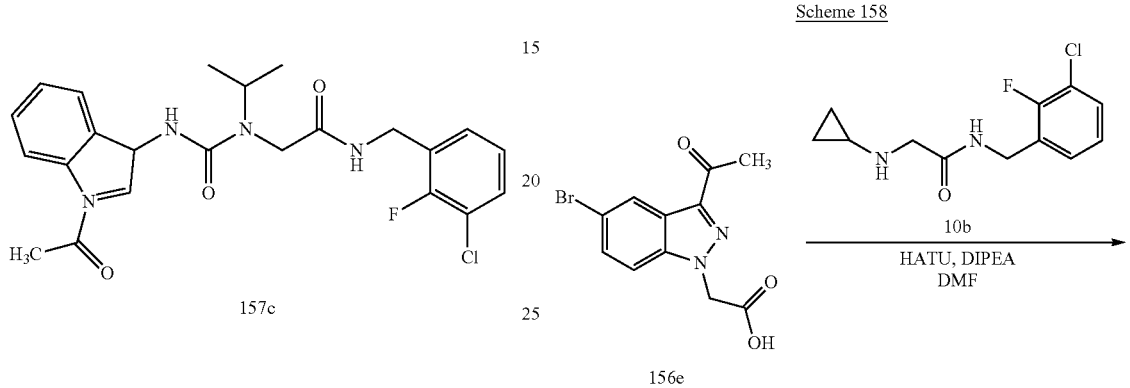

EtOAc in hexanes 0 to 100%] to afford 2-(3-(1-acetyl-1H-indol-3-yl)-1-isopropylureido)-N-(3-chloro-2-fluorobenzyl)acetamide (157c) (95 mg, 0.21 mmol, 42% yield) as a white solid; $^1$H NMR (300 MHz, DMSO-d$_6$) δ 9.10 (s, 1H), 8.78 (t, J=5.8 Hz, 1H), 8.33 (d, J=8.1 Hz, 1H), 7.84 (s, 1H), 7.70 (d, J=7.6 Hz, 1H), 7.54-7.44 (m, 1H), 7.42-7.23 (m, 3H), 7.18-7.10 (m, 1H), 4.56-4.34 (m, 3H), 3.98 (s, 2H), 2.58 (s, 3H), 1.10 (d, J=6.7 Hz, 6H); $^{19}$F NMR (282 MHz, DMSO-d$_6$) δ −121.32; MS (ES+): 459.5 (M+1), 481.5 (M+Na); MS (ES−): 457.5 (M−1), 493.4 (M+Cl).

Scheme 158

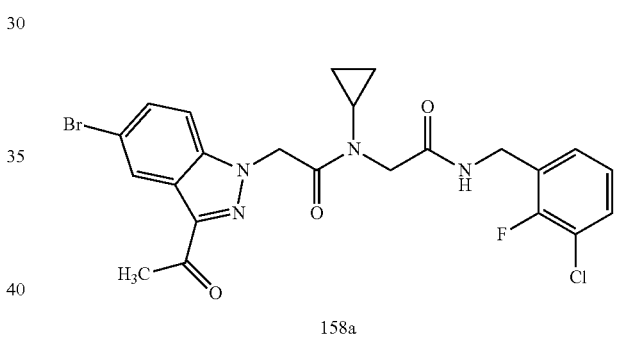

Preparation of 2-(3-(1-acetyl-1H-indol-3-yl)-1-isopropylureido)-N-(3-chloro-2-fluorobenzyl)acetamide (157c)

Step-1: Preparation of 1-acetyl-1H-indole-3-carboxylic acid (157b)

To a solution of 1H-indole-3-carboxylic acid (157a) (10 g, 62.1 mmol), TEA (19.03 mL, 137 mmol) and DMAP (1.516 g, 12.41 mmol) in DCM (100 mL) cooled to 0° C. was added drop-wise acetyl chloride (4.41 mL, 62.1 mmol) and stirred for 3 h at RT. The reaction mixture was poured into an aqueous 1 N HCl solution, the solid obtained was collected by filtration, washed with water, MeOH and dried to give 1-acetyl-1H-indole-3-carboxylic acid (157b) (10.2 g, 50.2 mmol, 81% yield) as an off white solid; $^1$H NMR (300 MHz, DMSO-d$_6$) δ 12.83 (s, 1H), 8.44 (s, 1H), 8.39-8.31 (m, 1H), 8.13-8.05 (m, 1H), 7.43-7.32 (m, 2H), 2.74 (s, 3H); MS (ES+): 204.2 (M+1); (ES−) 202.2 (M−1).

Step-2: Preparation of 2-(3-(1-acetyl-1H-indol-3-yl)-1-isopropylureido)-N-(3-chloro-2-fluorobenzyl)acetamide (157c)

To a solution of 1-acetyl-1H-indole-3-carboxylic acid (157b) (0.1 g, 0.49 mmol) in dioxane (10 mL) was added triethylamine (0.2 mL, 1.4 mmol), diphenylphospharyl azide (0.21 mL, 0.984 mmol) and stirred at RT for 2 h. To the mixture added N-(3-chloro-2-fluorobenzyl)-2-(isopropylamino)acetamide (19c) (127 mg, 0.49 mmol) and mixture was heated at 90° C. for 4 h. Mixture was cooled to RT, partitioned between saturated aqueous NaHCO$_3$ (60 mL) and EtOAc (60 mL). Layers were separated and aqueous layer was extracted with EtOAc (50 mL). The combined organics were washed with brine, dried, filtered, concentrated in vacuum and the residue obtained was purified by flash column chromatography [silica gel, (12 g) eluting with Preparation of 2-(3-acetyl-5-bromo-1H-indazol-1-yl)-N-(2-((3-chloro-2-fluorobenzyl)amino)-2-oxoethyl)-N-cyclopropylacetamide (158a)

Reaction of N-(3-chloro-2-fluorobenzyl)-2-(cyclopropylamino)acetamide (10b) (332 mg, 1.29 mmol) with 2-(3-acetyl-5-bromo-1H-indazol-1-yl)acetic acid (156e) (320 mg, 1.06 mmol) according to the procedure reported in step-3 of Scheme 2 gave after workup and purification by [silica (12 g), eluting with DMA80 in DCM from 0 to 20%] 2-(3-acetyl-5-bromo-1H-indazol-1-yl)-N-(2-((3-chloro-2-fluorobenzyl)amino)-2-oxoethyl)-N-cyclopropylacetamide (158a) (0.48 g, 0.9 mmol, 83% yield) as a colorless foam; $^1$H NMR (300 MHz, DMSO-d$_6$) δ 8.48 (t, J=5.9 Hz, 1H), 8.31 (dd, J=1.8, 0.7 Hz, 1H), 7.73 (dd, J=9.0, 0.7 Hz, 1H), 7.60 (dd, J=8.9, 1.9 Hz, 1H), 7.51-7.41 (m, 1H), 7.26-7.18 (m, 1H), 7.14-7.05 (m, 1H), 5.77 (s, 2H), 4.33 (d, J=5.8 Hz, 2H), 3.98 (s, 2H), 3.18-3.02 (m, 1H), 2.62 (s, 3H), 1.09-0.95 (m, 2H), 0.95-0.79 (m, 2H); $^{19}$F NMR (282 MHz, DMSO-d$_6$) δ −121.57; MS (ES+): 535.4 (M+1), 557.5 (M+Na), MS (ES−): 533.4 (M−1), 569.4 (M+Cl).

Scheme 159

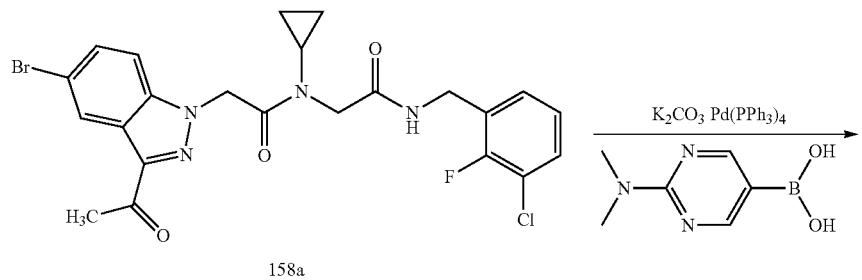

158a

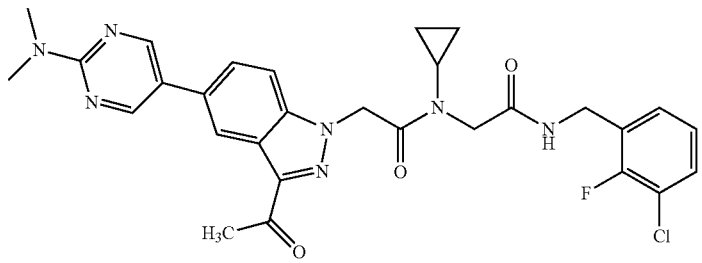

159a

Preparation of 2-(3-acetyl-5-(2-(dimethylamino)pyrimidin-5-yl)-1H-indazol-1-yl)-N-(2-((3-chloro-2-fluorobenzyl)amino)-2-oxoethyl)-N-cyclopropylacetamide (159a)

Reaction of 2-(3-acetyl-5-bromo-1H-indazol-1-yl)-N-(2-((3-chloro-2-fluorobenzyl)amino)-2-oxoethyl)-N-cyclopropylacetamide (158a) (125 mg, 0.23 mmol) with 2-(dimethylamino)pyrimidin-5-ylboronic acid (0.047 g, 0.280 mmol) according to the procedure reported in Scheme 100 gave after workup and purification by flash column chromatography [silica gel (12 g), eluting with CMA80 in CHCl$_3$ 0 to 20%] 2-(3-acetyl-5-(2-(dimethylamino)pyrimidin-5-yl)-1H-indazol-1-yl)-N-(2-((3-chloro-2-fluorobenzyl)amino)-2-oxoethyl)-N-cyclopropylacetamide (159a) (93 mg, 0.16 mmol, 69% yield) as a white solid; $^1$H NMR (300 MHz, DMSO-d$_6$) δ 8.71 (s, 2H), 8.48 (t, J=5.9 Hz, 1H), 8.29 (dd, J=1.7, 0.9 Hz, 1H), 7.79 (dd, J=8.8, 0.9 Hz, 1H), 7.72 (dd, J=8.8, 1.7 Hz, 1H), 7.50-7.41 (m, 1H), 7.28-7.18 (m, 1H), 7.15-7.06 (m, 1H), 5.78 (s, 2H), 4.34 (d, J=5.7 Hz, 2H), 4.00 (s, 2H), 3.19 (s, 6H), 3.16-3.08 (m, 1H), 2.63 (s, 3H), 1.09-0.99 (m, 2H), 0.96-0.88 (m, 2H); $^{19}$F NMR (282 MHz, DMSO-d$_6$) δ −121.58; MS (ES+): 578.7 (M+1), 600.6 (M+Na); MS (ES−) 576.5 (M−1), 612.5 (M+Cl).

Scheme 160

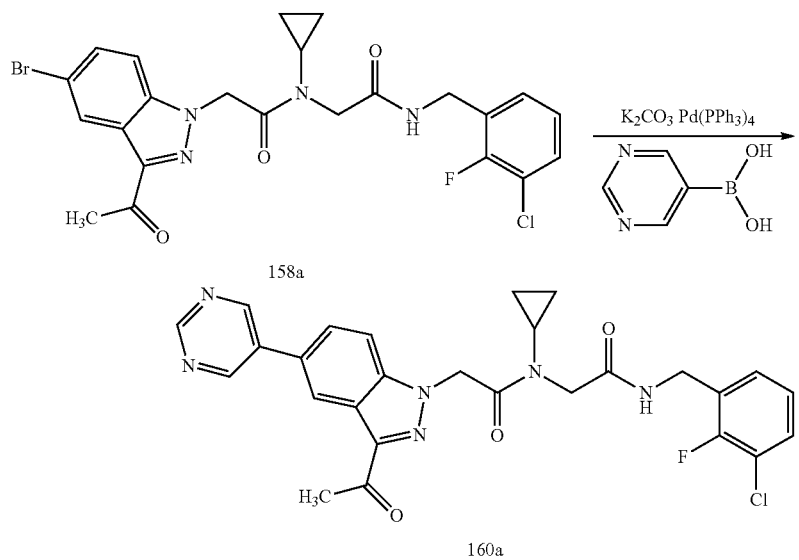

319

Preparation of 2-(3-acetyl-5-(pyrimidin-5-yl)-1H-indazol-1-yl)-N-(2-((3-chloro-2-fluorobenzyl)amino)-2-oxoethyl)-N-cyclopropylacetamide (160a)

Reaction of 2-(3-acetyl-5-bromo-1H-indazol-1-yl)-N-(2-((3-chloro-2-fluorobenzyl)amino)-2-oxoethyl)-N-cyclopropylacetamide (158a) (125 mg, 0.23 mmol) with pyrimidin-5-ylboronic acid (0.035 g, 0.280 mmol) according the procedure reported in Scheme 100 gave after workup and purification by flash column chromatography [silica gel (12 g), eluting with CMA80 in CHCl₃ 0 to 20%] 2-(3-acetyl-5-(pyrimidin-5-yl)-1H-indazol-1-yl)-N-(2-((3-chloro-2-fluorobenzyl)amino)-2-oxoethyl)-N-cyclopropylacetamide (160a) (96 mg, 0.18 mmol, 77% yield) as a white solid; $^1$H NMR (300 MHz, DMSO-d₆) δ 9.22 (s, 1H), 9.19 (s, 2H), 8.52-8.43 (m, 2H), 7.89 (bs, 2H), 7.51-7.39 (m, 1H), 7.29-7.18 (m, 1H), 7.16-7.06 (m, 1H), 5.82 (s, 2H), 4.35 (d, J=5.8 Hz, 2H), 4.00 (s, 2H), 3.20-3.09 (m, 1H), 2.66 (s, 3H), 1.10-1.00 (m, 2H), 0.97-0.88 (m, 2H); $^{19}$F NMR (282 MHz, DMSO-d₆) δ −121.58; MS (ES+): 535.6 (M+1), 557.6 (M+Na); MS (ES−): 569.5 (M+Cl).

Scheme 161

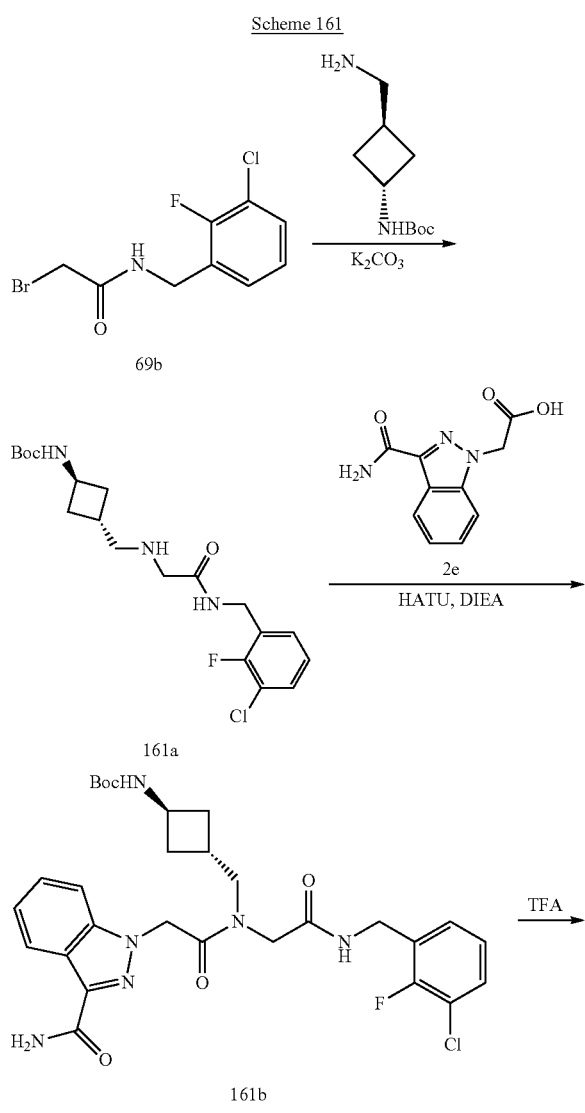

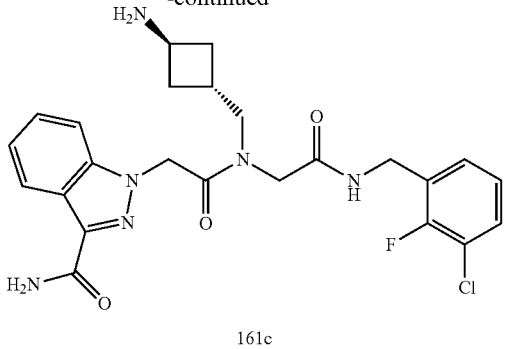

161c

Preparation of 1-(2-(((((trans)-3-aminocyclobutyl)methyl)(2-((3-chloro-2-fluorobenzyl)amino)-2-oxoethyl)amino)-2-oxoethyl)-1H-indazole-3-carboxamide (161c)

Step-1: Preparation of tert-butyl (trans-3-(((2-((3-chloro-2-fluorobenzyl)amino)-2-oxoethyl)amino)methyl)cyclobutyl)carbamate (161a)

Reaction of 2-bromo-N-(3-chloro-2-fluorobenzyl)acetamide (69b) (250 mg, 0.89 mmol) tert-butyl (trans)-3-(aminomethyl)cyclobutylcarbamate (268 mg, 1.34 mmol) according to the procedure reported in step-2 of Scheme 35 gave after workup and purification by flash column chromatography [silica gel 12 g, eluting with MeOH in DCM 0 to 20%] tert-butyl ((trans)-3-(((2-((3-chloro-2-fluorobenzyl)amino)-2-oxoethyl)amino)methyl)cyclobutyl)carbamate (161a) (152 mg, 0.38 mmol, 43% yield) as a white solid; MS (ES+): 400.5 (M+1), 799.8 (2M+1), 422.5 (M+Na); MS (ES−): 434.5 (M+Cl).

Step-2: Preparation of tert-butyl ((trans)-3-((2-(3-carbamoyl-1H-indazol-1-yl)-N-(2-((3-(161b)

Reaction tert-butyl ((trans)-3-(((2-((3-chloro-2-fluorobenzyl)amino)-2-oxoethyl)amino)methyl)cyclobutyl)carbamate (161a) (85 mg, 0.21 mmol) with 2-(3-carbamoyl-1H-indazol-1-yl)acetic acid (2e) (56 mg, 0.26 mmol) according to the procedure reported in step-3 of Scheme 2 gave after workup and purification by flash column chromatography [Silica gel, (24 g) eluting with MeOH in CHCl₃ 0-10%] tert-butyl ((trans)-3-((2-(3-carbamoyl-1H-indazol-1-yl)-N-(2-((3-chloro-2-fluorobenzyl)amino)-2-oxoethyl)acetamido)methyl)cyclobutyl)carbamate (161b) (59 mg, 0.1 mmol, 46% yield) as a white solid as a mixture two rotamers; $^1$H NMR (300 MHz, DMSO-d₆) δ 8.81 & 8.48 (t, J=5.6 Hz) (2t, 1H), 8.19 & 8.17 (2s, 1H), 7.73 (bs, 1H), 7.64-7.00 (m, 7H), 5.59 & 5.46 (s, 2H), 4.46 (d, J=5.6 Hz) & 4.32 (d, J=5.8 Hz) (2d, 2H), 4.29-3.88 (m, 3H), 3.62 (d, J=7.7 Hz, 1H), 2.27 (s, 1H), 2.05 (t, J=7.0 Hz, 1H), 1.97-1.75 (m, 3H), 1.38 & 1.35 (2s, 9H); $^{19}$F NMR (282 MHz, DMSO-d₆) δ −121.30, −121.67; MS (ES+): 601.7 (M+1), 623.7, 625.7 (M+Na); MS (ES−): 600.6 (M−1), 635.7, 637.6 (M+Cl).

Step-3: Preparation of 1-(2-((((trans)-3-aminocyclobutyl)methyl)(2-((3-chloro-2-fluorobenzyl)amino)-2-oxoethyl)amino)-2-oxoethyl)-1H-indazole-3-carboxamide (161c)

Reaction of tert-butyl ((trans)-3-((2-(3-carbamoyl-1H-indazol-1-yl)-N-(2-((3-chloro-2-fluorobenzyl)amino)-2-oxoethyl)acetamido)methyl)cyclobutyl)carbamate (161b) (56 mg, 0.09 mmol) with TFA (0.144 mL, 1.863 mmol) according to the procedure reported in step-2 of Scheme 2 gave after workup and purification by flash column chromatography [Silica gel, (8 g) eluting with CMA50 in DCM 0-100%) 1-(2-((((trans)-3-aminocyclobutyl)methyl)(2-((3-chloro-2-fluorobenzyl)amino)-2-oxoethyl)amino)-2-oxoethyl)-1H-indazole-3-carboxamide (161c) (24 mg, 0.048 mmol, 51% yield) as an off-white solid; $^1$H NMR (300 MHz, DMSO-$d_6$) δ 8.81 (t, J=5.7 Hz) and 8.45 (t, J=5.8 Hz) (2t, 1H), 8.21-8.15 (m, 1H), 7.73 (s, 1H), 7.60-7.00 (m, 7H), 5.57 and 5.47 (2s, 2H), 4.45 (d, J=5.5 Hz) and 4.32 (d, J=5.7 Hz) (2d, 2H), 4.22 and 3.93 (2s, 2H), 2.36-1.44 (m, 5H); $^1$H NMR (300 MHz, DMSO-$d_6$, $D_2O$ exchange) δ 8.22-8.14 (m, 1H), 7.61-7.01 (m, 7H), 5.59 & 5.45 (2s, 2H), 4.46 and 4.34 and 4.23 (3s, 3H), 3.67-3.20 (m, 3H), 2.40-1.56 (m, 5H); $^{19}$F NMR (282 MHz, DMSO-$d_6$) δ −121.24, −121.64; MS (ES+): 501.6 (M+1), 523.6 (M+Na); MS (ES−): 499.5 (M−1), 535.5 (M+Cl).

Scheme 162

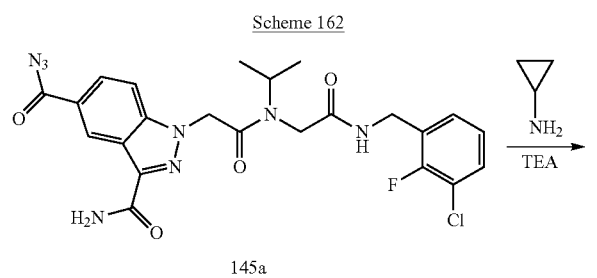

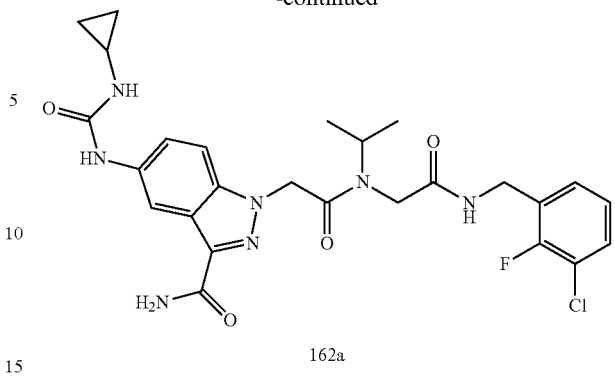

162a

Preparation of 1-(2-((2-((3-chloro-2-fluorobenzyl)amino)-2-oxoethyl)(isopropyl)amino)-2-oxoethyl)-5-(3-cyclopropylureido)-1H-indazole-3-carboxamide (162a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (270 mg, 0.51 mmol) in toluene (15 mL) with cyclopropanamine (58.3 mg, 1.02 mmol) using TEA (0.29 mL, 2.04 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(3-cyclopropylureido)-1H-indazole-3-carboxamide (162a) (29 mg, 0.052 mmol, 11% yield) as a white solid; $^1$H NMR (300 MHz, DMSO-$d_6$) (a mixture of two rotamers) δ 8.82 (t, J=5.7 Hz) and 8.36 (t, J=6.0 Hz) (2t, 1H), 8.46 and 8.45 (2s, 1H), 8.23-8.17 (m, 1H), 7.67-7.03 (m, 7H), 6.44-6.30 (m, 1H), 5.52 and 5.38 (2s, 2H), 4.62-4.22 (m, 3H), 4.17 and 3.83 (2s, 2H), 2.59-2.53 (m, 1H), 1.21 (d, J=6.8 Hz) and 0.98 (d, J=6.8 Hz) (2d, 6H), 0.68-0.59 (m, 2H), 0.47-0.37 (m, 2H); $^{19}$F NMR (282 MHz, DMSO) δ −121.22, −121.76; MS (ES+): 580.6 (M+Na); MS (ES−): 558.5 (M−1).

Scheme 163

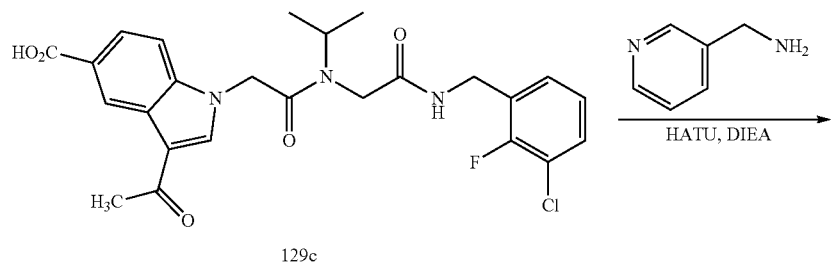

129c

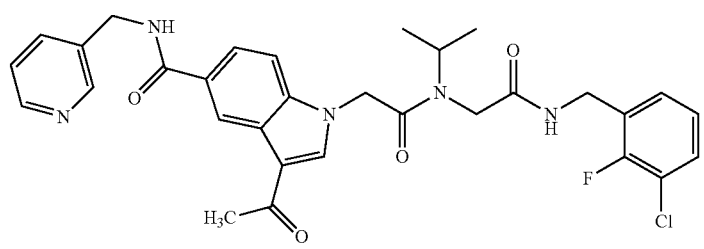

163a

323

Preparation of 3-acetyl-1-(2-((2-((3-chloro-2-fluorobenzyl)amino)-2-oxoethyl)(isopropyl)amino)-2-oxoethyl)-N-(pyridin-3-ylmethyl)-1H-indole-5-carboxamide (163a)

Reaction of 3-acetyl-1-(2-((2-((3-chloro-2-fluorobenzyl)amino)-2-oxoethyl)(isopropyl)amino)-2-oxoethyl)-1H-indole-5-carboxylic acid (129c) (50 mg, 0.1 mmol) with pyridin-3-ylmethanamine (0.015 mL, 0.15 mmol) according to the procedure reported in step-3 of Scheme 2 gave after workup and purification by flash column chromatography [silica (4 g), eluting with MeOH in DCM (1:0 to 19:1)] 3-acetyl-1-(2-((2-((3-chloro-2-fluorobenzyl)amino)-2-oxoethyl)(isopropyl)amino)-2-oxoethyl)-N-(pyridin-3-ylmethyl)-1H-indole-5-carboxamide (163a) (42 mg, 71%) as a white solid; $^1$H NMR (300 MHz, DMSO-d$_6$) (a mixture of two rotamers) δ 9.16-9.06 (m, 1H), 8.83 (t, J=5.7 Hz) and 8.34 (t) (2t, 1H), 8.78-8.71 (m, 1H), 8.57 (bs, 1H), 8.49-8.43 (m, 1H), 8.35 and 8.31 (2s, 1H), 7.83-6.91 (m, 7H), 5.40 and 5.21 (2s, 2H), 4.63-4.54 and 4.29-4.21 (2m, 1H), 4.53 and 4.51 (2s, 2H), 4.47 (d, J=5.3 Hz) and 4.33 (d, J=5.8 Hz) (2d, 2H), 4.19 and 3.85 (2s, 2H), 2.46 and 2.45 (2s, 3H), 1.26 (d, J=6.4 Hz) and 1.00 (d, J=6.7 Hz) (2d, 6H); $^{19}$F NMR (282 MHz, DMSO-d$_6$) δ −121.19, −121.79; MS (ES+): 592.6 & 594.6 (M+1).

Scheme 164

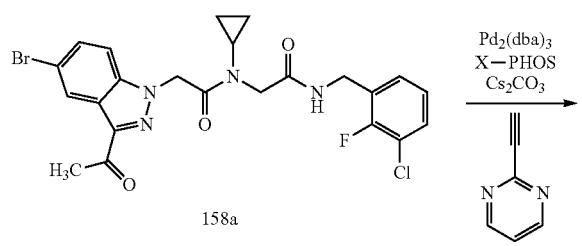

324

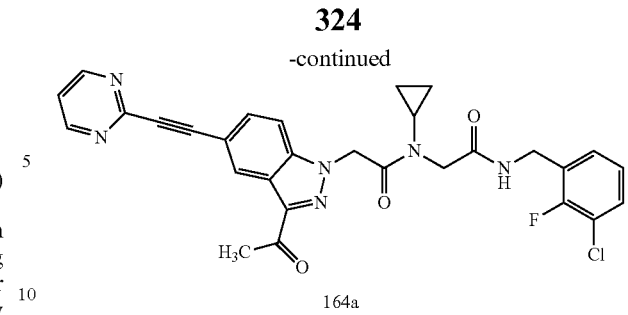

164a

Preparation of 2-(3-acetyl-5-(pyrimidin-2-ylethynyl)-1H-indazol-1-yl)-N-(2-((3-chloro-2-fluorobenzyl)amino)-2-oxoethyl)-N-cyclopropylacetamide (164a)

Reaction of 2-(3-acetyl-5-bromo-1H-indazol-1-yl)-N-(2-((3-chloro-2-fluorobenzyl)amino)-2-oxoethyl)-N-cyclopropylacetamide (158a) (300 mg, 0.56 mmol) using Cs$_2$CO$_3$ (365 mg, 1.12 mmol), dicyclohexyl(2',4',6'-triisopropylbiphenyl-2-yl)phosphine (X-PHOS, 53 mg, 0.112 mmol), Pd$_2$(dba)$_3$ (51 mg, 0.056 mmol) according to procedure reported in Scheme 92 gave after workup and purification by flash column chromatography [silica gel (8 g), eluting with MeOH in DCM from 0 to 30%] 2-(3-acetyl-5-(pyrimidin-2-ylethynyl)-1H-indazol-1-yl)-N-(2-((3-chloro-2-fluorobenzyl)amino)-2-oxoethyl)-N-cyclopropylacetamide (164a) (21 mg, 0.038 mmol, 7% yield) as a dark-yellow solid; $^1$H NMR (300 MHz, DMSO-d$_6$) δ 8.87 (d, J=4.9 Hz, 2H), 8.49 (t, J=6.0 Hz, 1H), 8.46-8.43 (m, 1H), 7.89-7.80 (m, 1H), 7.70 (dd, J=8.8, 1.5 Hz, 1H), 7.54 (t, J=5.0 Hz, 1H), 7.46 (td, J=7.6, 1.7 Hz, 1H), 7.27-7.19 (m, 1H), 7.14-7.07 (m, 1H), 5.81 (s, 2H), 4.34 (d, J=5.8 Hz, 2H), 4.00 (s, 2H), 3.21-3.05 (m, 1H), 2.65 (s, 3H), 1.09-0.83 (m, 4H); $^{19}$F NMR (282 MHz, DMSO-d$_6$) δ −121.57; MS (ES+): 581.6, 583.6 (M+Na); MS (ES−): 593.5, 595.6 (M+Cl).

Scheme 165

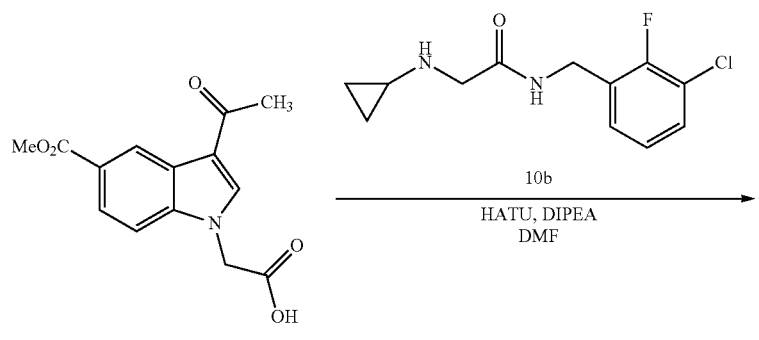

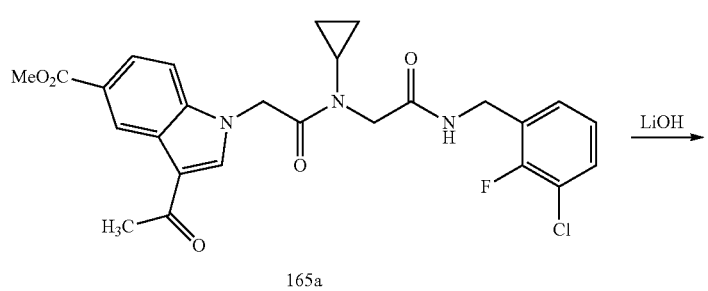

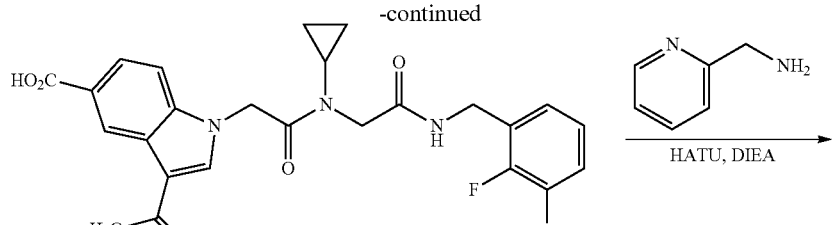

165b

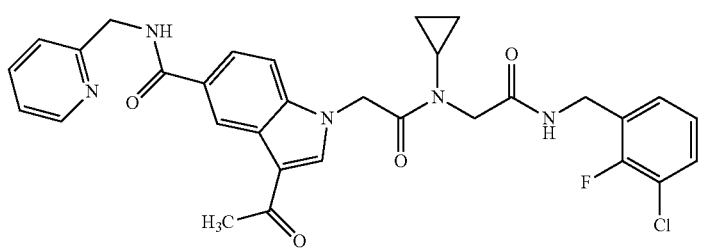

165c

Preparation of 3-acetyl-1-(2-((2-((3-chloro-2-fluorobenzyl)amino)-2-oxoethyl)(cyclopropyl)amino)-2-oxoethyl)-N-(pyridin-2-ylmethyl)-1H-indole-5-carboxamide (165c)

Step-1: Preparation of methyl 3-acetyl-1-(2-((2-((3-chloro-2-fluorobenzyl)amino)-2-oxoethyl)(cyclopropyl)amino)-2-oxoethyl)-1H-indole-5-carboxylate (165a)

Reaction of 2-(3-acetyl-5-(methoxycarbonyl)-1H-indol-1-yl)acetic acid (129a) (5.91 mmol, prepared according to the procedure reported by Altmann, Eva et al, in PCT Int. Appl., WO 2012/093101) with N-(3-chloro-2-fluorobenzyl)-2-(cyclopropylamino)acetamide (10b) (1.82 g, 7.09 mmol) according to the procedure reported in step-3 of Scheme 2 gave after workup and purification by flash column [silica gel, eluting with hexanes/10% MeOH in EtOAc (1:0 to 1:2)] methyl 3-acetyl-1-(2-((2-((3-chloro-2-fluorobenzyl)amino)-2-oxoethyl)(cyclopropyl)amino)-2-oxoethyl)-1H-indole-5-carboxylate (165a) (1.89 g, 62%) as a light brown solid. $^1$H NMR (300 MHz, DMSO-$d_6$) δ 8.87 (dd, J=1.7, 0.6 Hz, 1H), 8.47 (t, J=5.9 Hz, 1H), 8.42 (s, 1H), 7.81 (dd, J=8.7, 1.8 Hz, 1H), 7.58 (dd, J=8.7, 0.7 Hz, 1H), 7.49-7.41 (m, 1H), 7.26-7.18 (m, 1H), 7.12-7.05 (m, 1H), 5.50 (s, 2H), 4.34 (d, J=5.8 Hz, 2H), 3.99 (s, 2H), 3.88 (s, 3H), 3.16-3.04 (m, 1H), 2.46 (s, 3H), 1.05-0.85 (m, 4H); $^{19}$F NMR (282 MHz, DMSO-$d_6$) δ -121.59; MS (ES+): 536.5 & 538.5 (M+Na).

Step-2: Preparation of 3-acetyl-1-(2-((2-((3-chloro-2-fluorobenzyl)amino)-2-oxoethyl)(cyclopropyl)amino)-2-oxoethyl)-1H-indole-5-carboxylic acid (165b)

Reaction of methyl 3-acetyl-1-(2-((2-((3-chloro-2-fluorobenzyl)amino)-2-oxoethyl)(cyclopropyl)amino)-2-oxoethyl)-1H-indole-5-carboxylate (165a) (1.83 g, 3.56 mmol) in THF (30 mL) and MeOH (30 mL) was added a solution of lithium hydroxide hydrate (911 mg, 21.28 mmol) in water (30 mL) according to the procedure reported in step-2 of Scheme 129 gave after workup 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (1.51 g, 85%) as a light brown solid; $^1$H NMR (300 MHz, DMSO-$d_6$) δ 8.83 (d, J=1.6 Hz, 1H), 8.48 (t, J=5.9 Hz, 1H), 8.38 (s, 1H), 7.80 (dd, J=8.6, 1.7 Hz, 1H), 7.52 (d, J=8.7 Hz, 1H), 7.45 (td, J=7.6, 1.7 Hz, 1H), 7.27-7.18 (m, 1H), 7.12-7.05 (m, 1H), 5.48 (s, 2H), 4.34 (d, J=5.7 Hz, 2H), 3.99 (s, 2H), 3.15-3.03 (m, 1H), 2.45 (s, 3H), 1.06-0.82 (m, 4H); $^{19}$F NMR (282 MHz, DMSO-$d_6$) δ -121.59; MS (ES+): 522.5 (M+Na); MS (ES-): 534.5 & 536.5 (M+Cl).

Step-3: Preparation of 3-acetyl-1-(2-((2-((3-chloro-2-fluorobenzyl)amino)-2-oxoethyl)(cyclopropyl)amino)-2-oxoethyl)-N-(pyridin-2-ylmethyl)-1H-indole-5-carboxamide (165c)

Reaction of 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (50 mg, 0.1 mmol) with pyridin-2-ylmethanamine (0.015 mL, 0.15 mmol) according to the procedure reported in step-3 of Scheme 2 gave after workup and purification by flash column chromatography [silica (4 g), eluting with MeOH in DCM (1:0 to 19:1)] 3-acetyl-1-(2-((2-((3-chloro-2-fluorobenzyl)amino)-2-oxoethyl)(cyclopropyl)amino)-2-oxoethyl)-N-(pyridin-2-ylmethyl)-1H-indole-5-carboxamide (165c) (45 mg, 76%) as a light yellow solid; $^1$H NMR (300 MHz, DMSO-$d_6$) (a mixture of two rotamers) δ 9.13 (t, J=5.9 Hz, 1H), 8.80-8.78 (m, 1H), 8.53-8.50 (m, 1H), 8.47 (t, J=5.9 Hz, 1H), 8.38 (s, 1H), 7.83-7.70 (m, 2H), 7.54 (d, J=8.7 Hz, 1H), 7.48-7.41 (m, 1H), 7.32 (d, J=7.9 Hz, 1H), 7.29-7.19 (m, 2H), 7.09 (t, J=7.9 Hz, 1H), 5.49 (s, 2H), 4.59 (d, J=5.8 Hz, 2H), 4.35 (d, J=5.7 Hz, 2H), 4.00 (s, 2H), 3.15-3.06 (m, 1H), 2.46 (s, 3H), 1.05-0.88 (m, 4H); $^{19}$F NMR (282 MHz, DMSO-$d_6$) δ -121.60; MS (ES+): 590.6 (M+1) & 612.6 (M+Na).

Scheme 166

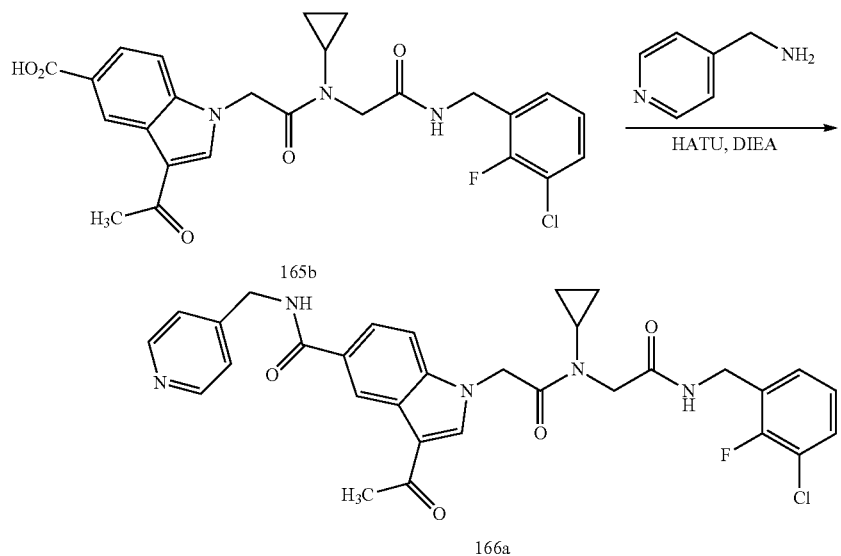

Preparation of 3-acetyl-1-(2-((2-((3-chloro-2-fluorobenzyl)amino)-2-oxoethyl)(cyclopropyl)amino)-2-oxoethyl)-N-(pyridin-4-ylmethyl)-1H-indole-5-carboxamide (166a)

Reaction of 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (50 mg, 0.1 mmol) with pyridin-4-ylmethanamine (0.016 mL, 0.15 mmol) according to the procedure reported in step-3 of Scheme 2 gave after workup and purification by flash column chromatography [silica (4 g), eluting with MeOH in DCM (1:0 to 19:1)] 3-acetyl-1-(2-((2-((3-chloro-2-fluorobenzyl)amino)-2-oxoethyl)(cyclopropyl)amino)-2-oxoethyl)-N-(pyridin-4-ylmethyl)-1H-indole-5-carboxamide (166a) (27 mg, 46%) as an off-white solid; $^1$H NMR (300 MHz, DMSO-$d_6$) (a mixture of two rotamers) δ 9.15 (t, J=5.9 Hz, 1H), 8.79-8.77 (m, 1H), 8.54-8.43 (m, 3H), 8.38 (s, 1H), 7.78 (dd, J=8.7, 1.8 Hz, 1H), 7.55 (d, J=8.6 Hz, 1H), 7.49-7.41 (m, 1H), 7.34-7.29 (m, 2H), 7.27-7.18 (m, 1H), 7.14-7.02 (m, 1H), 5.49 (s, 2H), 4.52 (d, J=5.9 Hz, 2H), 4.35 (d, J=5.8 Hz, 2H), 4.00 (s, 2H), 3.17-3.03 (m, 1H), 2.46 (s, 3H), 1.08-0.74 (m, 4H); $^{19}$F NMR (282 MHz, DMSO-$d_6$) δ −121.59; MS (ES+): 590.7 & 592.7 (M+1).

Scheme 167

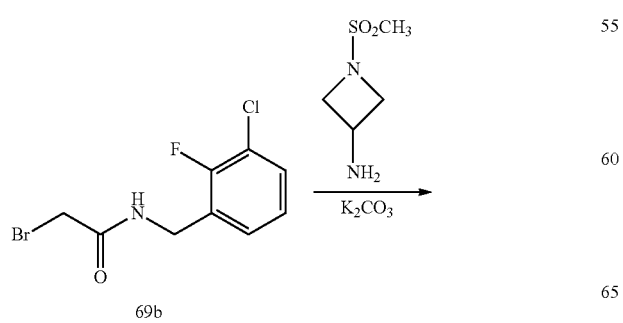

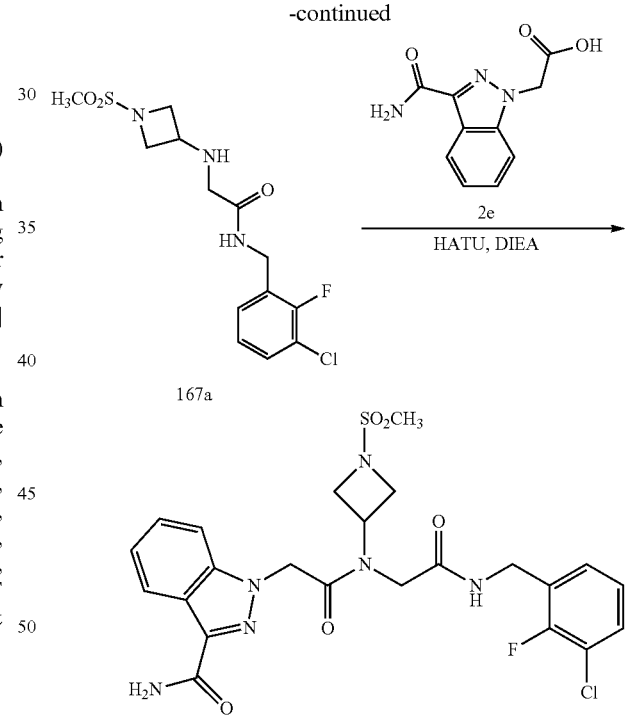

Preparation of 1-(2-((2-((3-chloro-2-fluorobenzyl)amino)-2-oxoethyl)(1-(methylsulfonyl)azetidin-3-yl)amino)-2-oxoethyl)-1H-indazole-3-carboxamide (167b)

Step-1: Preparation of N-(3-chloro-2-fluorobenzyl)-2-((1-(methylsulfonyl)azetidin-3-yl)amino)acetamide (167a)

Reaction of 2-bromo-N-(3-chloro-2-fluorobenzyl)acetamide (69b) (250 mg, 0.89 mmol) with 1-(methylsulfonyl)

azetidin-3-amine (241 mg, 1.60 mmol) according to the procedure reported in step-2 of Scheme 35 gave after workup and purification by flash column chromatography [Silica gel, (12 g) eluting with MeOH in DCM, 0-30%) to afford N-(3-chloro-2-fluorobenzyl)-2-((1-(methylsulfonyl)azetidin-3-yl)-amino)acetamide (167a) (68 mg, 0.194 mmol, 22% yield) as a thick yellow oil which was used as such in the next step; MS (ES+): 350.4 (M+1), 372.4 (M+Na); MS (ES−): 348.3 (M−1), 384.3, 386.3 (M+Cl)

Step-2: Preparation of 1-(2-((2-((3-chloro-2-fluorobenzyl)amino)-2-oxoethyl)(1-(methylsulfonyl)azetidin-3-yl)-amino)-2-oxoethyl)-1H-indazole-3-carboxamide (167b)

Reaction of N-(3-chloro-2-fluorobenzyl)-2-((1-(methylsulfonyl)azetidin-3-yl)amino)acetamide (167a) (30 mg, 0.086 mmol) with 2-(3-carbamoyl-1H-indazol-1-yl)acetic acid (2e) (19 mg, 0.086 mmol) according to the procedure reported in step-3 of Scheme 2 gave after workup and purification by flash column chromatography [Silica gel, (8 g) eluting with MeOH in DCM from 0-30%] 1-(2-((2-((3-chloro-2-fluorobenzyl)amino)-2-oxoethyl)(1-(methylsulfonyl)azetidin-3-yl)amino)-2-oxoethyl)-1H-indazole-3-carboxamide (167b) (8 mg, 0.015 mmol, 17% yield) as a white solid as a mixture of two rotamers; $^1$H NMR (300 MHz, DMSO-$d_6$) δ 8.99 (t, J=5.7 Hz) & 8.64 (t, J=5.8 Hz) (2t, 1H), 8.22-8.12 (m, 1H), 7.74-7.66 (m, 2H), 7.62-6.95 (m, 6H), 5.64 & 5.42 (s, 2H), 5.19-4.76 (m, 1H), 4.49 (d, J=5.6 Hz) & 4.34 (d, J=5.8 Hz) (2d, 2H), 4.42 (s) and 4.23-3.78 (m) (6H), 3.08 & 2.99 (s, 3H); $^{19}$F NMR (282 MHz, DMSO-$d_6$) δ −121.32, −121.65; MS (ES+): 551.52 (M+1), 573.5 (M+Na); MS (ES−): 549.5 (M−1), 585.3 (M+Cl).

Scheme 168

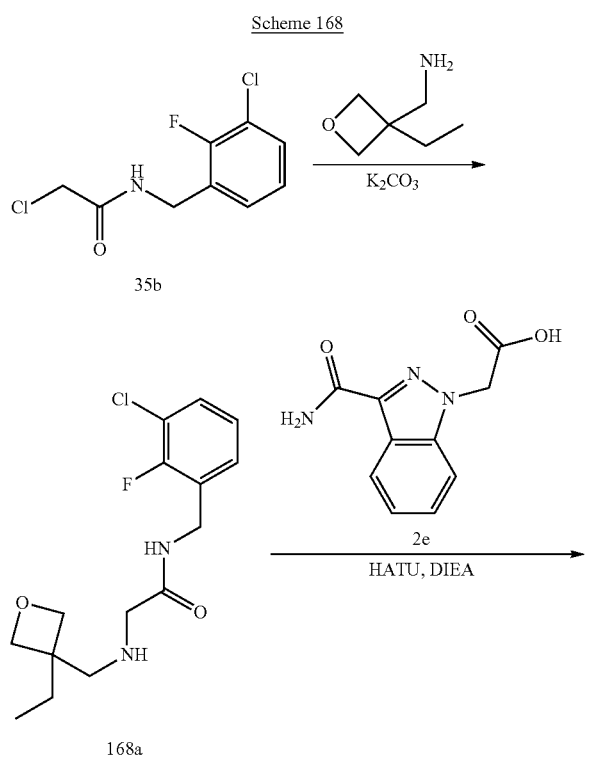

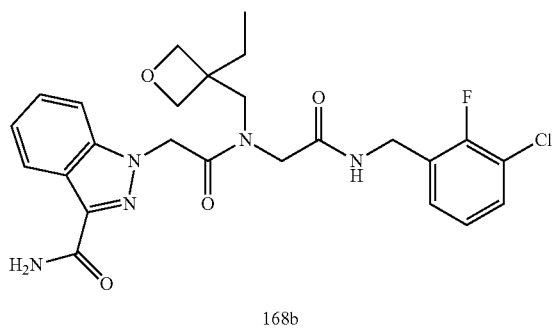
168b

Preparation of 1-(2-((2-((3-chloro-2-fluorobenzyl)amino)-2-oxoethyl)((3-ethyloxetan-3-yl)methyl)amino)-2-oxoethyl)-1H-indazole-3-carboxamide (168b)

Step-1: Preparation of N-(3-chloro-2-fluorobenzyl)-2-((2-(3-ethyloxetan-3-yl)methyl)amino)acetamide (168a)

Reaction of 2-chloro-N-(3-chloro-2-fluorobenzyl)acetamide (35b) (205 mg, 0.87 mmol) with (3-ethyloxetan-3-yl)methanamine (250 mg, 2.47 mmol) according to the procedure reported in step-2 of Scheme 35 gave after workup N-(3-chloro-2-fluorobenzyl)-2-((2-(3-ethyloxetan-3-yl)methyl)amino)acetamide (168a) as a colorless oil which was used in the next step without further purification; MS (ES+) 315.4 (M+1); (ES−) 313.4 (M−1).

Step-2: Preparation of 1-(2-((2-((3-chloro-2-fluorobenzyl)amino)-2-oxoethyl)((3-ethyloxetan-3-yl)methyl)amino)-2-oxoethyl)-1H-indazole-3-carboxamide (168b)

Reaction of N-(3-chloro-2-fluorobenzyl)-2-((2-(3-ethyloxetan-3-yl)methyl)amino)acetamide (168a) (51 mg, 0.162 mmol) with 2-(3-carbamoyl-1H-indazol-1-yl)acetic acid (2e) (43 mg, 0.19 mmol) according to the procedure reported in step-3 of Scheme 2 gave after workup and purification by flash column chromatography [silica (12 g), eluting with DMA-80 in DCM 0 to 100%] 1-(2-((2-((3-chloro-2-fluorobenzyl)amino)-2-oxoethyl)((3-ethyloxetan-3-yl)methyl)amino)-2-oxoethyl)-1H-indazole-3-carboxamide (168b) (26 mg, 0.05 mmol, 31% yield) as a white solid; $^1$H NMR (300 MHz, DMSO-$d_6$) δ 8.84 (t, J=5.7 Hz) and 8.51 (t) (1H), 8.18 (dt, J=8.1, 1.0 Hz, 1H), 7.79-7.00 (m, 8H), 5.51 and 5.50 (2s, 2H), 4.47 (d, J=5.5 Hz) and 4.40-3.73 (m) (8H), 1.74 (q) and 1.61 (q, J=7.3 Hz, 2H), 1.09 (t, J=7.3 Hz) and 0.84 (t, J=7.4 Hz) (3H); $^{19}$F NMR (282 MHz, DMSO-$d_6$) δ −121.17, −121.55; MS (ES+): 516.5 (M+1); MS (ES−): 514.5 (M−1).

Scheme 169

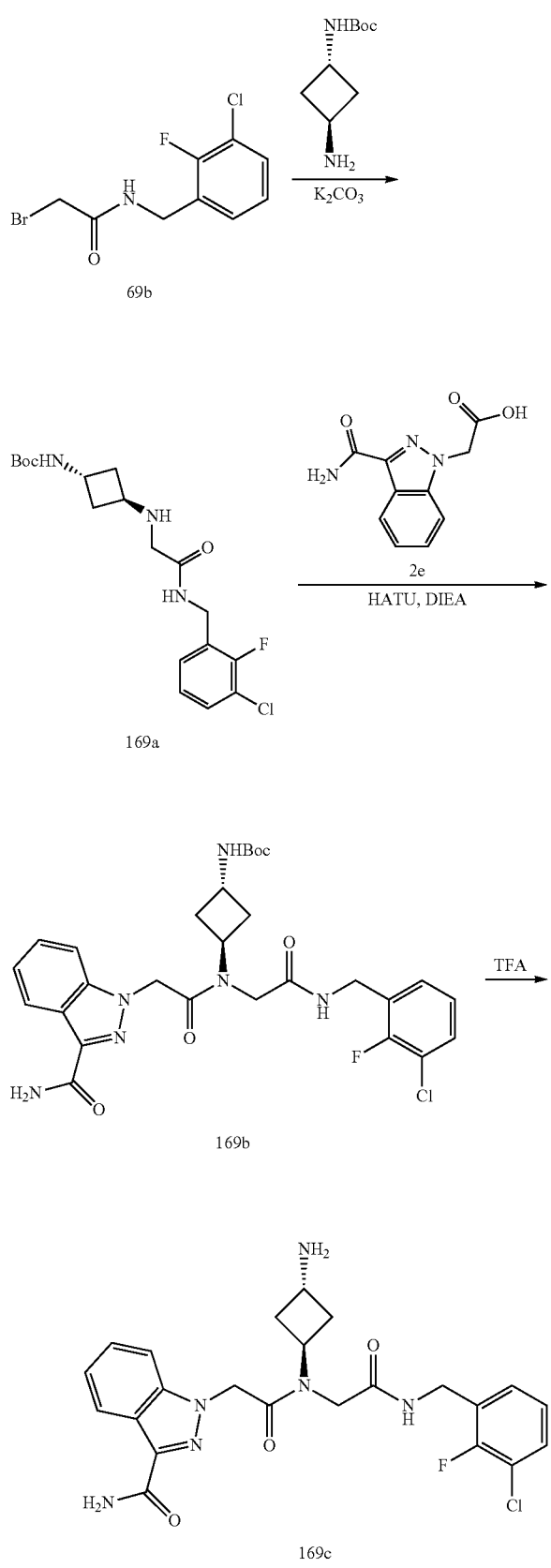

Preparation of 1-(2-(((trans)-3-aminocyclobutyl)(2-((3-chloro-2-fluorobenzyl)amino)-2-oxoethyl)amino)-2-oxoethyl)-1H-indazole-3-carboxamide (169c)

Step-1: Preparation of tert-butyl ((trans)-3-((2-((3-chloro-2-fluorobenzyl)amino)-2-oxoethyl)amino)cyclobutyl)carbamate (169a)

Reaction of 2-bromo-N-(3-chloro-2-fluorobenzyl)acetamide (69b) (250 mg, 0.89 mmol) with tert-butyl (trans)-3-aminocyclobutylcarbamate (250 mg, 1.34 mmol) according to the procedure reported in step-2 of Scheme 35 gave tert-butyl ((trans)-3-((2-((3-chloro-2-fluorobenzyl)amino)-2-oxoethyl)amino)cyclobutyl)carbamate (169a) (173 mg, 0.45 mmol, 50% yield) as a thick yellow oil; MS (ES+): 386.5 (M+1), 408.5 (M+Na); MS (ES−): 384.4 (M−1), 420.4, 422.4 (M+Cl).

Step-2: Preparation of tert-butyl ((trans)-3-(2-(3-carbamoyl-1H-indazol-1-yl)-N-(2-((3-chloro-2-fluorobenzyl)amino)-2-oxoethyl)acetamido)cyclobutyl)carbamate (169b)

Reaction of tert-butyl ((trans)-3-((2-((3-chloro-2-fluorobenzyl)amino)-2-oxoethyl)amino)cyclobutyl)carbamate (169a) (108 mg, 0.28 mmol) with 2-(3-carbamoyl-1H-indazol-1-yl)acetic acid (2e) (74 mg, 0.34 mmol) according to the procedure reported in step-3 of Scheme 2 gave after workup and purification by flash column chromatography [Silica gel, (24 g) eluting with MeOH in $CHCl_3$ 0-10%] tert-butyl ((trans)-3-(2-(3-carbamoyl-1H-indazol-1-yl)-N-(2-((3-chloro-2-fluorobenzyl)amino)-2-oxoethyl)acetamido)cyclobutyl)carbamate (169b) (0.101 g, 0.172 mmol, 61.5% yield) as an off-white solid in the form of mixture two rotamers; MS (ES+): 587.6 (M+1), 609.6, 611.6 (M+Na); MS (ES−): 585.6 (M−1), 621.6, 623.6 (M+Cl).

Step-3: Preparation of 1-(2-(((trans)-3-aminocyclobutyl)(2-((3-chloro-2-fluorobenzyl)amino)-2-oxoethyl)amino)-2-oxoethyl)-1H-indazole-3-carboxamide (169c)

Reaction of tert-butyl((trans)-3-(2-(3-carbamoyl-1H-indazol-1-yl)-N-(2-((3-chloro-2-fluorobenzyl)amino)-2-oxoethyl)acetamido)cyclobutyl)carbamate (169b) (91 mg, 0.16 mmol) with TFA (0.24 mL, 3.1 mmol) according to the procedure reported in step-2 of Scheme 2 gave after workup and purification by flash column chromatography [Silica gel, (12 g) eluting with DMA80 in DCM 0-100%)] 1-(2-(((trans)-3-aminocyclobutyl)(2-((3-chloro-2-fluorobenzyl)amino)-2-oxoethyl)amino)-2-oxoethyl)-1H-indazole-3-carboxamide (169c) (17 mg, 22% yield) as a white solid as a mixture of two isomers; $^1$H NMR (300 MHz, DMSO-$d_6$) δ 8.88 (t, J=5.8 Hz) & 8.43 (t, J=5.9 Hz) (2t, 1H, $D_2O$ exchangeable), 8.21-8.14 (m, 1H), 7.72 (s, 1H), 7.63-7.02 (m, 7H), 5.53 & 5.42 (2s, 2H), 5.06-4.81 (m, 1H), 4.47 (d, J=5.6 Hz) & 4.33 (d, J=5.8 Hz) (2d, 2H), 4.29 & 4.01 (2s, 2H), 2.42-1.69 (m, 4H); $^{19}$F NMR (282 MHz, DMSO-$d_6$) δ −121.25, −121.64; MS (ES+): 487.5 (M+1), 509.5 (M+Na); MS (ES−): 485.5 (M−1), 521.43 (M+Cl).

Scheme 170

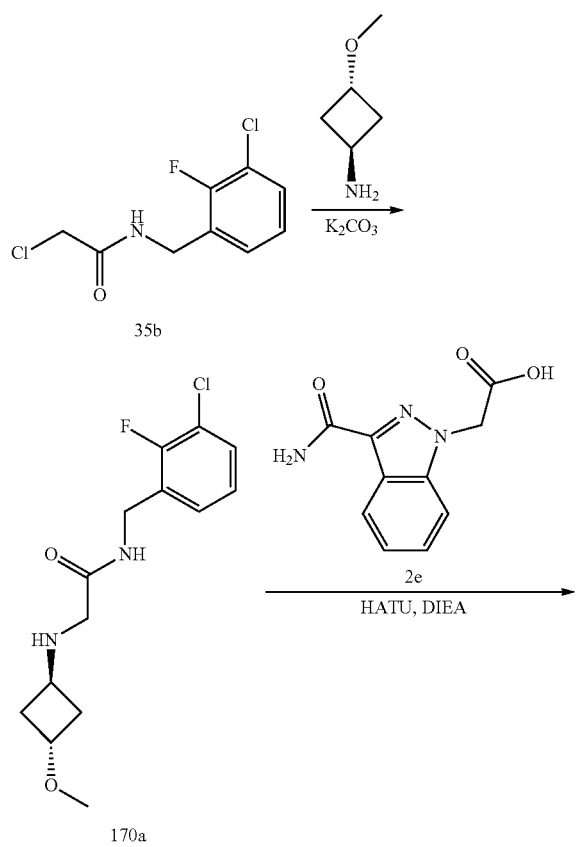

(((trans)-3-methoxycyclobutyl)amino)acetamide (170a) (122 mg, 0.41 mmol, 50%) as a colorless oil; MS (ES+) 301.4 (M+1); MS (ES−): 299.3 (M−1).

Step-2: Preparation of 1-(2-((2-((3-chloro-2-fluorobenzyl)amino)-2-oxoethyl)((trans)-3-methoxycyclobutyl)amino)-2-oxoethyl)-1H-indazole-3-carboxamide (170b)

Reaction of N-(3-chloro-2-fluorobenzyl)-2-(((trans)-3-methoxycyclobutyl)amino)acetamide (170a) (122 mg, 0.41 mmol) with 2-(3-carbamoyl-1H-indazol-1-yl)acetic acid (2e) (122 mg, 0.41 mmol) according to the procedure reported in step-3 of Scheme 2 gave after workup and purification by flash column chromatography [silica (12 g), eluting with CMA-80 in CHCl$_3$ 0 to 60%] 1-(2-((2-((3-chloro-2-fluorobenzyl)amino)-2-oxoethyl)((trans)-3-methoxycyclobutyl)amino)-2-oxoethyl)-1H-indazole-3-carboxamide (170b) (137 mg, 0.27 mmol, 67% yield) as an off white solid; $^1$H NMR (300 MHz, DMSO-d$_6$) δ 8.87 (t, J=5.7 Hz) and 8.44 (t, J=5.9 Hz) (2t, 1H), 8.17 (d, J=8.1 Hz, 1H), 7.72-7.01 (m, 8H), 5.55 and 5.42 (2s, 2H), 4.85-4.69 (m, 1H), 4.47 (d, J=5.6 Hz) and 4.33 (d, J=5.7 Hz) (2d, 2H), 4.29 and, 4.02 (2s, 2H), 3.92-3.78 (m, 1H), 3.17 and 3.10 (2s, 3H), 2.43-1.93 (m, 4H); $^{19}$F NMR (282 MHz, DMSO) δ −121.18, −121.60; MS (ES+) 502.5 (M+1); 524.5 (M+Na); (ES−) 500.5 (M−1); (Based on NMR, this compound is a mixture of rotamers 4:5 ratio).

Scheme 171

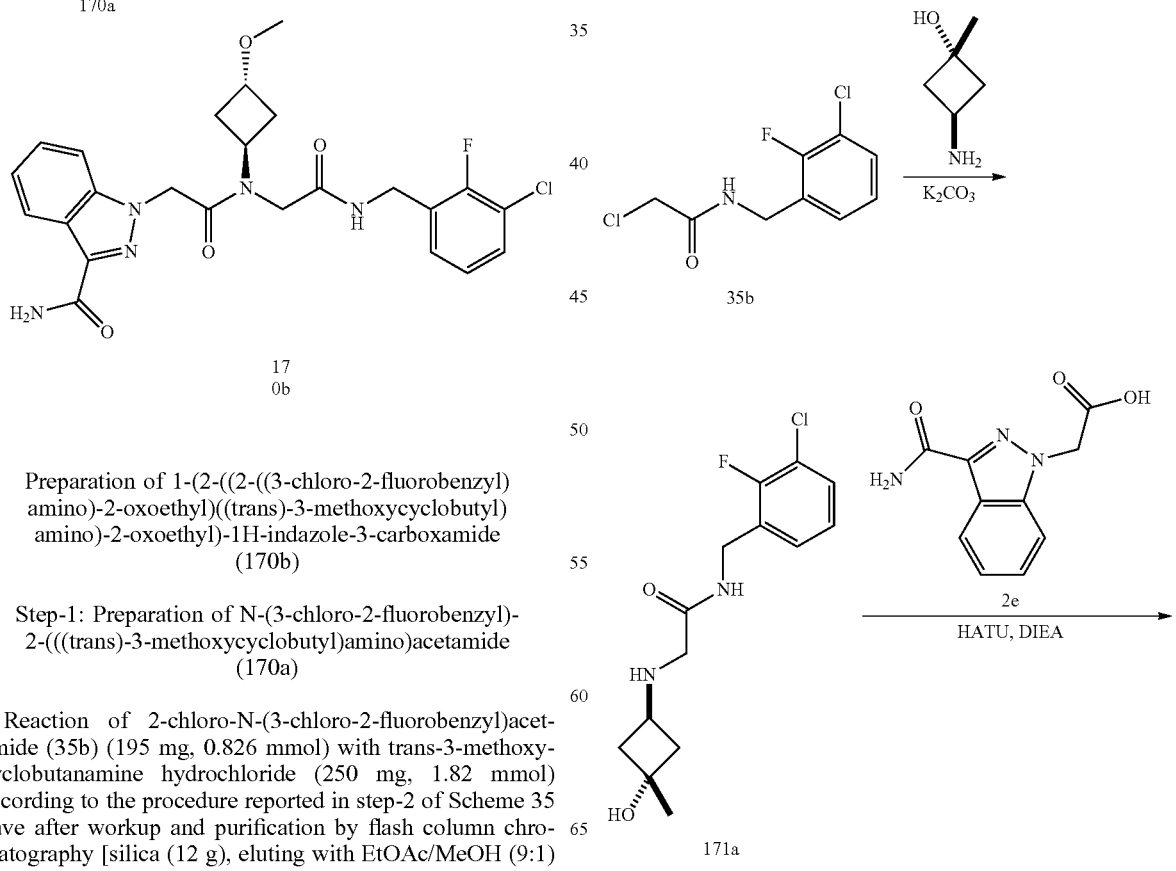

Preparation of 1-(2-((2-((3-chloro-2-fluorobenzyl)amino)-2-oxoethyl)((trans)-3-methoxycyclobutyl)amino)-2-oxoethyl)-1H-indazole-3-carboxamide (170b)

Step-1: Preparation of N-(3-chloro-2-fluorobenzyl)-2-(((trans)-3-methoxycyclobutyl)amino)acetamide (170a)

Reaction of 2-chloro-N-(3-chloro-2-fluorobenzyl)acetamide (35b) (195 mg, 0.826 mmol) with trans-3-methoxycyclobutanamine hydrochloride (250 mg, 1.82 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-

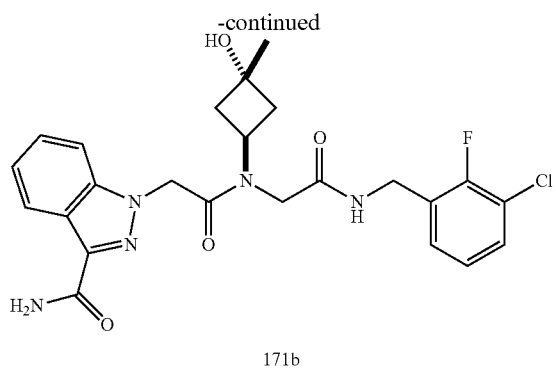

171b

Preparation of 1-(2-((2-((3-chloro-2-fluorobenzyl)amino)-2-oxoethyl)((trans)-3-hydroxy-3-(cis)-methylcyclobutyl)amino)-2-oxoethyl)-1H-indazole-3-carboxamide (171b)

Step-1: Preparation of N-(3-chloro-2-fluorobenzyl)-2-(((trans)-3-hydroxy-3-(cis)-methylcyclobutyl)amino)acetamide (171a)

Reaction of 2-chloro-N-(3-chloro-2-fluorobenzyl)acetamide (35b) (195 mg, 0.83 mmol) with (trans)-3-amino-1-methylcyclobutanol hydrochloride (250 mg, 1.82 mmol) according to the procedure reported in step-2 of Scheme 35 gave after workup and purification by flash column chromatography [silica (12 g), eluting with EtOAc/MeOH (9:1) in hexane 0 to 60%] of N-(3-chloro-2-fluorobenzyl)-2-(((trans)-3-hydroxy-3-(cis)-methylcyclobutyl)amino)acetamide (171a) (108 mg, 0.36 mmol, 43%) as a colorless oil; $^1$H NMR (300 MHz, DMSO-$d_6$) δ 8.33 (t, J=6.1 Hz, 1H), 7.48 (td, J=7.6, 1.9 Hz, 1H), 7.31-7.24 (m, 1H), 7.23-7.15 (m, 1H), 4.69 (s, 1H), 4.36 (d, J=5.9 Hz, 2H), 3.17 (d, J=4.7 Hz, 2H), 3.03 (s, 2H), 2.14-2.03 (m, 2H), 1.70-1.58 (m, 2H), 1.23 (s, 3H); $^{19}$F NMR (282 MHz, DMSO-$d_6$) δ −121.65; MS (ES+) 3001.4 (M+1), 323.4 (M+Na); (ES−) 299.3 (M−1).

Step-2: Preparation of 1-(2-((2-((3-chloro-2-fluorobenzyl)amino)-2-oxoethyl)((trans)-3-hydroxy-3-(cis)-methylcyclobutyl)amino)-2-oxoethyl)-1H-indazole-3-carboxamide (171b)

Reaction of N-(3-chloro-2-fluorobenzyl)-2-(((trans)-3-hydroxy-3-(cis)-methylcyclobutyl)amino)acetamide (171a) (108 mg, 0.36 mmol) with 2-(3-carbamoyl-1H-indazol-1-yl)acetic acid (2e) (87 mg, 0.4 mmol) according to the procedure reported in step-3 of Scheme 2 gave after workup and purification by flash column chromatography [silica (12 g), eluting with CMA-80 in CHCl$_3$ 0 to 60%] 1-(2-((2-((3-chloro-2-fluorobenzyl)amino)-2-oxoethyl)((trans)-3-hydroxy-3-(cis)-methylcyclobutyl)amino)-2-oxoethyl)-1H-indazole-3-carboxamide (171b) (65 mg, 0.13 mmol, 36% yield) as a white solid; $^1$H NMR (300 MHz, DMSO-$d_6$) δ 8.88 (t, J=5.7 Hz) and 8.42 (t, J=5.9 Hz) (2t, 1H), 8.17 (m, 1H), 7.69 (m, 1H), 7.31-7.01 (m, 7H), 5.53 and 5.42 (2s, 2H), 5.01-4.67 (m, 2H), 4.46 (d, J=5.5 Hz) and 4.33 (d, J=5.8 Hz) (2d, 2H), 4.24 and 3.99 (2s, 2H), 2.32-1.83 (m, 4H), 1.26 and 1.17 (2s, 3H); $^{19}$F NMR (282 MHz, DMSO) δ −121.09, −121.56; MS (ES+) 524.5 (M+Na); (ES−): 500.5 (M−1); (Based on NMR, this compound is a mixture of rotamers 1:1 ratio).

Scheme 172

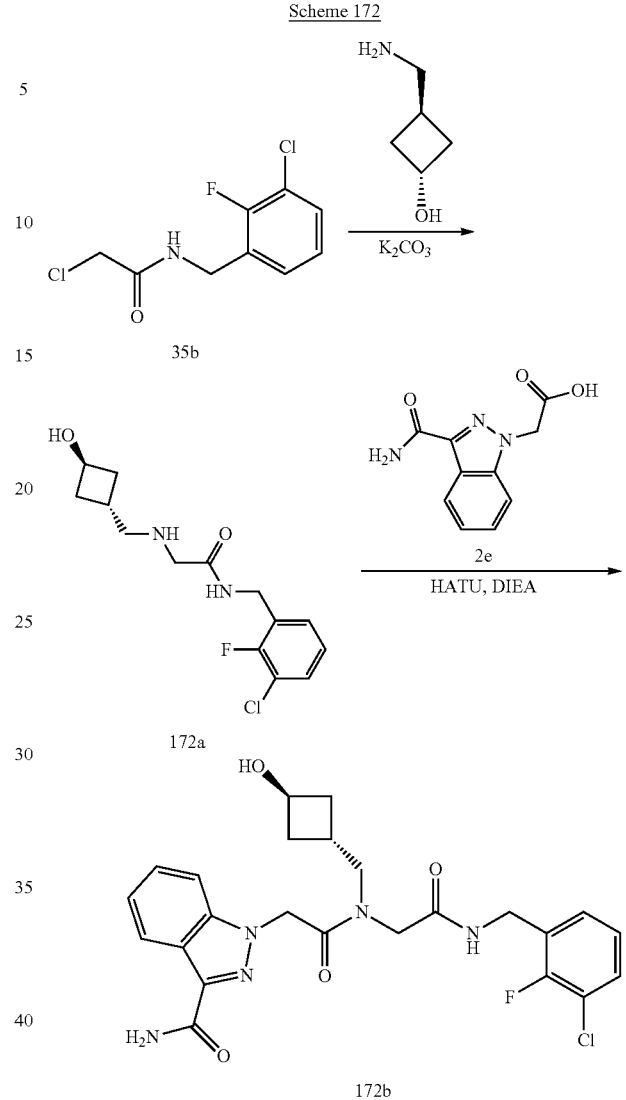

Preparation of 1-(2-((2-((3-chloro-2-fluorobenzyl)amino)-2-oxoethyl)(((trans)-3-hydroxycyclobutyl)methyl)amino)-2-oxoethyl)-1H-indazole-3-carboxamide (172b)

Step-1: Preparation of N-(3-chloro-2-fluorobenzyl)-2-(((((trans)-3-hydroxycyclobutyl)methyl)amino)acetamide (172a)

Reaction of 2-chloro-N-(3-chloro-2-fluorobenzyl)acetamide (35b) (254 mg, 1.08 mmol) with (trans)-3-(aminomethyl)cyclobutanol hydrochloride (370 mg, 2.69 mmol) according to the procedure reported in step-2 of Scheme 35 gave after workup and purification by flash column chromatography [silica (12 g), eluting with EtOAc/MeOH (9:1) in hexane 0 to 60%] of N-(3-chloro-2-fluorobenzyl)-2-((((trans)-3-hydroxycyclobutyl)methyl)amino)acetamide (172a) (130 mg, 0.43 mmol, 40%) as a colorless oil; MS (ES+): 301.4, 303.4 (M+1, M+2), 323.3 (M+Na); MS (ES−) 299.3 (M−1).

Step-2: Preparation of 1-(2-((2-((3-chloro-2-fluo-robenzyl)amino)-2-oxoethyl)(((trans)-3-hydroxycy-clobutyl)methyl)amino)-2-oxoethyl)-1H-indazole-3-carboxamide (172b)

Reaction of N-(3-chloro-2-fluorobenzyl)-2-(((((trans)-3-hydroxycyclobutyl)methyl)amino)acetamide (172a) (130 mg, 0.43 mmol) with 2-(3-carbamoyl-1H-indazol-1-yl)acetic acid (2e) (104 mg, 0.48 mmol) according to the procedure reported in step-3 of Scheme 2 gave after workup and purification by flash column chromatography [silica (12 g), eluting with CMA-80 in CHCl$_3$ 0 to 60%] 1-(2-((2-((3-chloro-2-fluorobenzyl)amino)-2-oxoethyl)(((trans)-3-hydroxycyclobutyl)methyl)amino)-2-oxoethyl)-1H-indazole-3-carboxamide (172b) (32 mg, 0.064 mmol, 15% yield) as a white solid; $^1$H NMR (300 MHz, DMSO-d$_6$) δ 8.81 (t, J=5.8 Hz) and 8.45 (t, J=6.0 Hz) (2t, 1H), 8.21-8.13 (m, 1H), 7.73 (bs, 1H), 7.58-7.07 (m, 7H), 5.57 and 5.47 (2s, 2H), 5.05 (d, J=6.1 Hz) and 4.93 (d, J=6.0 Hz) (2d, 1H), 4.45 (d, J=5.5 Hz) and 4.32 (d, J=6.0 Hz) (2d, 2H), 4.23 and 3.93 (2s, 2H), 4.41-4.25 and 4.19-4.07 (2m, 1H), 3.56 (d, J=8.0 Hz) and 3.31 (d, J=7.9 Hz) (2d, 2H), 2.32-1.76 (m, 5H); $^{19}$F NMR (282 MHz, DMSO) δ −121.27, −121.65; MS (ES+) 524.5 (M+Na); (ES−) 500.5 (M−1). (Based on NMR, this compound is a mixture of rotamers 2:1 ratio)

Scheme 173

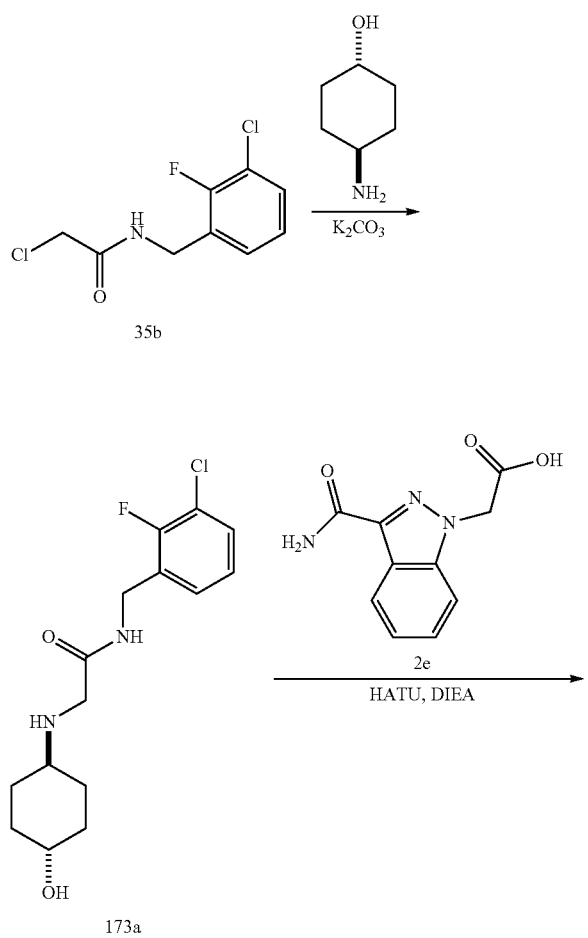

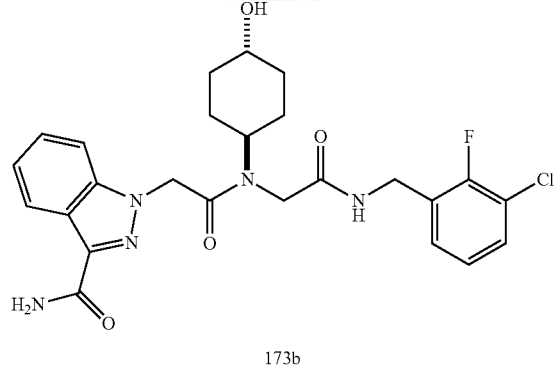

Preparation of 1-(2-((2-((3-chloro-2-fluorobenzyl)amino)-2-oxoethyl)((tran)-4-hydroxycyclohexyl)amino)-2-oxoethyl)-1H-indazole-3-carboxamide (173b)

Step-1: Preparation of N-(3-chloro-2-fluorobenzyl)-2-(((trans)-4-hydroxycyclohexyl)amino)acetamide (173a)

Reaction of 2-chloro-N-(3-chloro-2-fluorobenzyl)acetamide (35b) (342 mg, 1.45 mmol) with (trans)-4-aminocyclohexanol (500 mg, 4.34 mmol) according to the procedure reported in step-2 of Scheme 35 gave after workup and purification by flash column chromatography [silica (12 g), eluting with EtOAc/MeOH (9:1) in hexane 0 to 60%] of N-(3-chloro-2-fluorobenzyl)-2-(((trans)-4-hydroxycyclohexyl)amino)acetamide (173a) (445 mg, 1.41 mmol, 98%) as a colorless oil; MS (ES+): 315.4, 317.4 (M+1, M+3); (ES−): 313.3.

Step-2: Preparation of 1-(2-((2-((3-chloro-2-fluorobenzyl)amino)-2-oxoethyl)((tran)-4-hydroxycyclohexyl)amino)-2-oxoethyl)-1H-indazole-3-carboxamide (173b)

Reaction of N-(3-chloro-2-fluorobenzyl)-2-(((trans)-4-hydroxycyclohexyl)amino)acetamide (173a) (320 mg, 1.02 mmol) with 2-(3-carbamoyl-1H-indazol-1-yl)acetic acid (2e) (245 mg, 1.12 mmol) according to the procedure reported in step-3 of Scheme 2 gave after workup and purification by flash column chromatography [silica (12 g), eluting with CMA80 in CHCl$_3$ 0 to 60%] 1-(2-((2-((3-chloro-2-fluorobenzyl)amino)-2-oxoethyl)((tran)-4-hydroxycyclohexyl)amino)-2-oxoethyl)-1H-indazole-3-carboxamide (173b) (110 mg, 0.21 mmol, 21% yield) as a white solid; $^1$H NMR (300 MHz, DMSO-d$_6$) δ 8.80 (t, J=5.7 Hz) and 8.33 (t, J=6.0 Hz) (2t, 1H), 8.21-8.14 (m, 1H), 7.75-7.64 (m, 1H), 7.63-7.00 (m, 7H), 5.61 and 5.45 (2s, 2H), 4.60 (d, J=4.2 Hz) and 4.55 (d, J=4.6 Hz) (2d, 1H), 4.45 (d, J=5.6 Hz) and 4.31 (d, J=5.8 Hz) (2d, 2H), 4.24-3.72 (m, 3H), 3.45-3.19 (m, 1H), 1.94-0.98 (m, 8H); $^{19}$F NMR (282 MHz, DMSO-d$_6$) δ −121.13, −121.69; MS (ES+): 516.5 (M+1), 538.5 (M+Na); (ES−): 514.5 (M−1), 550.5 (M+Cl); (Based on NMR, this compound is a mixture of rotamers 3:2 ratio).

Scheme 174

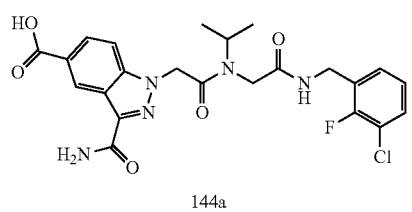

144a

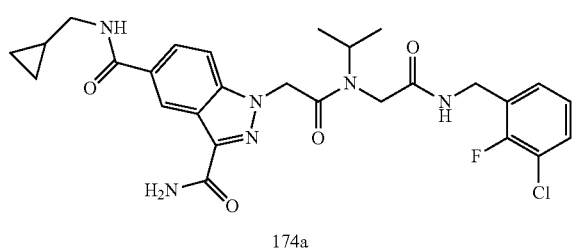

174a

Preparation of 1-(2-((2-((3-chloro-2-fluorobenzyl)amino)-2-oxoethyl)(isopropyl)amino)-2-oxoethyl)-N5-(cyclopropylmethyl)-1H-indazole-3,5-dicarboxamide)amino)-2-oxoethyl)(isopropyl)amino)-2-oxoethyl)-N-(pyridin-3-ylmethyl)-1H-indole-5-carboxamide (174a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with cyclopropylmethanamine (0.013 mL, 0.15 mmol) according to the procedure reported in step-3 of Scheme 2 gave after workup and purification by flash column chromatography [silica (4 g), eluting with MeOH in DCM (1:0 to 19:1)] 1-(2-((2-((3-chloro-2-fluorobenzyl)amino)-2-oxoethyl)-N5-(cyclopropylmethyl)-1H-indazole-3,5-dicarboxamide)amino)-2-oxoethyl)(isopropyl)amino)-2-oxoethyl)-N-(pyridin-3-ylmethyl)-1H-indole-5-carboxamide (174a) (31 mg, 56%) as a white solid; $^1$H NMR (300 MHz, DMSO-d$_6$) (a mixture of two rotamers) δ 8.83 (t, J=5.7 Hz) and 8.37 (t, J=5.9 Hz) (2t, 1H), 8.77-8.62 (m, 2H), 7.93-6.94 (m, 7H), 5.62 and 5.48 (2s, 2H), 4.61-4.48 and 4.29-4.20 2 (m, 1H), 4.46 (d, J=5.6 Hz) and 4.31 (d, J=5.8 Hz) (2d, 2H), 4.18 and 3.83 (2s, 2H), 3.17 (t, J=6.3 Hz, 2H), 1.23 (d, J=6.3 Hz) and 0.99 (d, J=6.8 Hz) (2d, 6H), 1.13-1.01 (m, 1H), 0.51-0.37 (m, 2H), 0.32-0.18 (m, 2H); $^{19}$F NMR (282 MHz, DMSO-d$_6$) δ −121.22, −121.73; MS (ES+): 557.6 (M+1) & 579.6 (M+Na); MS (ES−): 591.5 & 593.5 (M+Cl).

Scheme 175

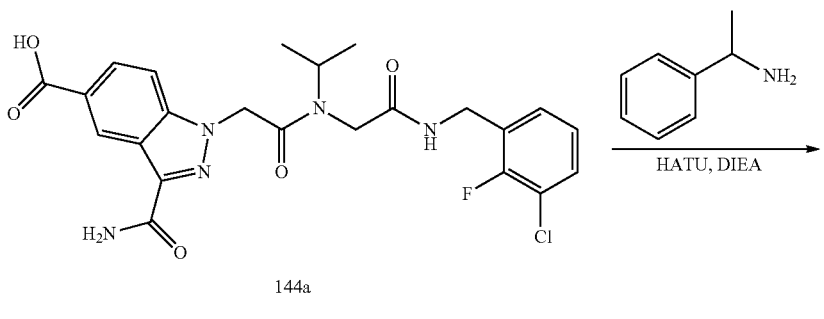

144a

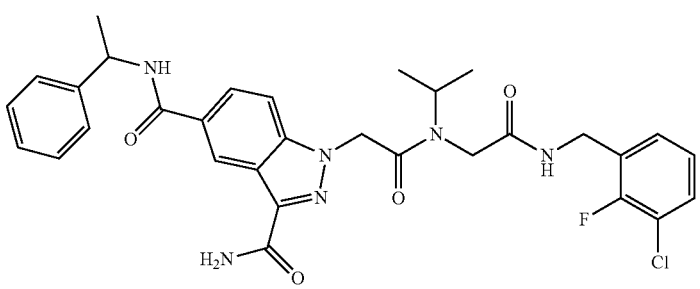

175a

Preparation of 1-(2-((2-((3-chloro-2-fluorobenzyl) amino)-2-oxoethyl)(isopropyl)amino)-2-oxoethyl)- N5-(1-phenylethyl)-1H-indazole-3,5-dicarboxamide (175a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with 1-phenylethanamine (0.02 mL, 0.15 mmol) according to the procedure reported in step-3 of Scheme 2 gave after workup and purification by flash column chromatography [silica (4 g), eluting with MeOH in DCM (1:0 to 19:1)] 1-(2-((2-((3-chloro-2-fluorobenzyl)amino)-2-oxoethyl)(isopropyl)amino)-2-oxoethyl)-N5-(1-phenylethyl)-1H-indazole-3,5-dicarboxamide (175a) (49 mg, 81%) as a white solid; $^1$H NMR (300 MHz, DMSO-$d_6$) (a mixture of two rotamers) δ 9.02 (d, J=3.6 Hz) and 8.99 (d, J=3.8 Hz) (2d, 1H), 8.83 (t, J=5.7 Hz) and 8.36 (t, J=5.9 Hz) (2t, 1H), 8.77-8.71 (m, 1H), 7.97-6.94 (m, 12H), 5.62 and 5.48 (2s, 2H), 5.29-5.09 (m, 1H), 4.62-4.49 and 4.28-4.21 (2m, 1H), 4.46 (d, J=5.6 Hz) and 4.31 (d, J=5.9 Hz) (2d, 2H), 4.18 and 3.83 (2s, 2H), 1.55-1.46 (m, 3H), 1.23 (d, J=6.3 Hz) and 0.99 (d, J=6.9 Hz) (2d, 6H); $^{19}$F NMR (282 MHz, DMSO-$d_6$) δ −121.22, −121.73; MS (ES+): 607.7 (M+1) & 629.7 (M+Na); MS (ES−): 641.6 & 643.6 (M+Cl).

Scheme 176

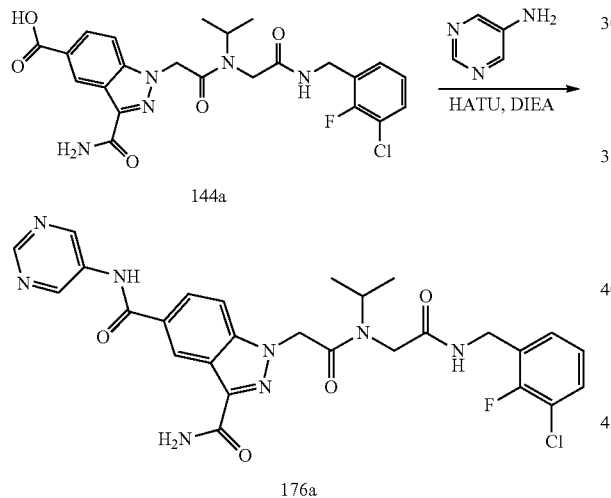

144a

176a

Preparation of 1-(2-((2-((3-chloro-2-fluorobenzyl) amino)-2-oxoethyl)(isopropyl)amino)-2-oxoethyl)- N5-(pyrimidin-5-yl)-1H-indazole-3,5-dicarboxamide (176a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with pyrimidin-5-amine (15 mg, 0.15 mmol) according to the procedure reported in step-3 of Scheme 2 gave after workup and purification by flash column chromatography [silica (4 g), eluting with MeOH in DCM (1:0 to 9:1)] 1-(2-((2-((3-chloro-2-fluorobenzyl)amino)-2-oxoethyl)(isopropyl)amino)-2-oxoethyl)-N5-(pyrimidin-5-yl)-1H-indazole-3,5-dicarboxamide (176a) (10 mg, 17%) as an off-white solid; $^1$H NMR (300 MHz, DMSO-$d_6$) (a mixture of two rotamers) δ 10.863 and 10.857 (2s, 1H), 9.213 and 9.209 (2s, 2H), 8.941 and 8.938 (2s, 1H), 8.93-8.82 (m, 2H), 8.49-6.91 (m, 7H), 5.67 and 5.53 (2s, 2H), 4.66-4.50 and 4.29-4.22 (2m, 1H), 4.47 (d, J=5.5 Hz) and 4.32 (d, J=6.0 Hz) (2d, 2H), 4.20 and 3.85 (2s, 2H), 1.24 (d, J=6.6 Hz) and 1.00 (d, J=6.8 Hz) (2d, 6H); $^{19}$F NMR (282 MHz, DMSO-$d_6$) δ −121.21, −121.70; MS (ES+): 581.6 (M+1); 603.6 (M+Na).

Scheme 177

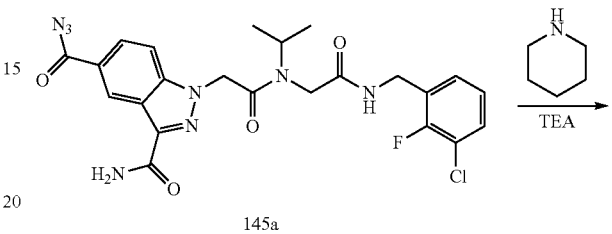

145a

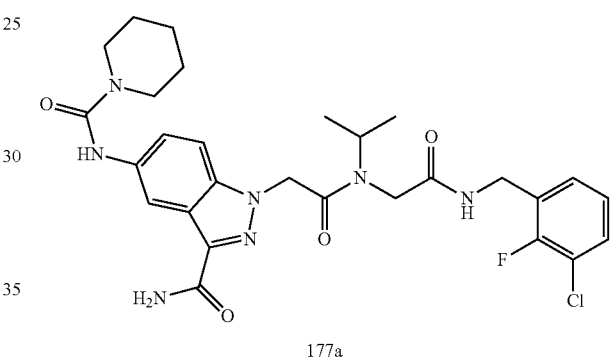

177a

Preparation of 1-(2-((2-((3-chloro-2-fluorobenzyl) amino)-2-oxoethyl)(isopropyl)amino)-2-oxoethyl)-5- (piperidine-1-carboxamido)-1H-indazole-3-carboxamide (177a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (420 mg, 0.79 mmol) in toluene (15 mL) with piperidine (135 mg, 1.59 mmol) using TEA (0.44 mL, 3.18 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl) amino)-2-oxoethyl)-5-(piperidine-1-carboxamido)-1H-indazole-3-carboxamide (177a) (179 mg, 0.31 mmol, 39% yield) as a white solid; $^1$H NMR (300 MHz, DMSO-$d_6$) δ 8.82 (t, J=5.7 Hz) and 8.37 (t, J=5.9 Hz) (2t, 1H), 8.58 (s, 1H), 8.22-8.15 (m, 1H), 7.66-7.06 (m, 7H), 5.53 and 5.40 (2s, 2H), 4.63-4.23 (m, 3H), 4.17 and, 3.83 (2s, 2H), 3.48-3.39 (m, 4H), 1.65-1.42 (m, 6H), 1.21 (d, J=6.5 Hz) and 0.99 (d, J=6.8 Hz) (2d, 6H); $^{19}$F NMR (282 MHz, DMSO-$d_6$) δ −121.22, −121.78; MS (ES+) 586.6 (M+1); MS (ES−) 584.5 (M−1).

Scheme 178

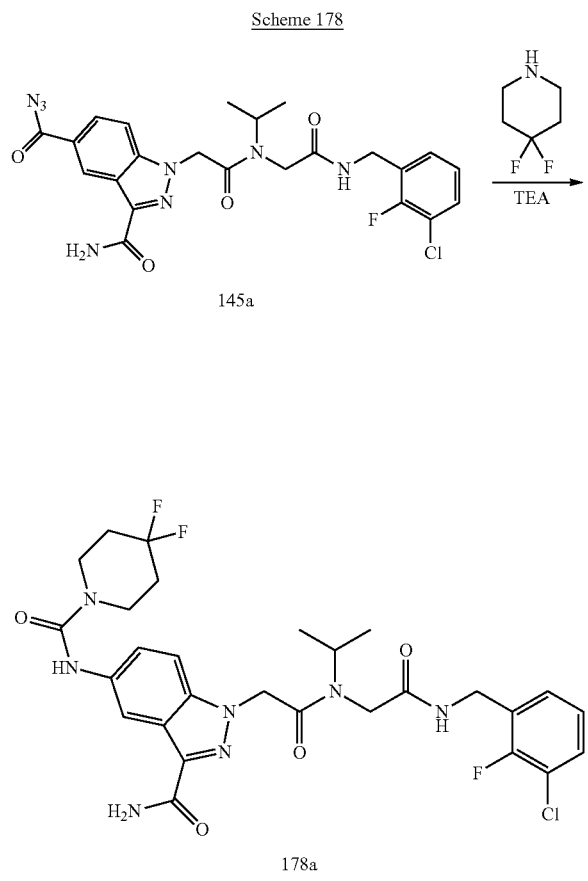

Preparation of 1-(2-((2-((3-chloro-2-fluorobenzyl) amino)-2-oxoethyl)(isopropyl)amino)-2-oxoethyl)-5-(4,4-difluoropiperidine-1-carboxamido)-1H-indazole-3-carboxamide (178a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (150 mg, 0.28 mmol) in toluene (10 mL) with 4,4-difluoropiperidine hydrochloride (134 mg, 0.85 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(4,4-difluoropiperidine-1-carboxamido)-1H-indazole-3-carboxamide (178a) (43 mg, 0.069 mmol, 24% yield) as a white solid; $^1$H NMR (300 MHz, DMSO-$d_6$) δ 8.91-8.32 (m, 2H), 8.23-8.14 (m, 1H), 7.66-7.06 (m, 7H), 5.53 and 5.40 (2s, 2H), 4.62-4.23 (m, 3H), 4.17 and 3.83 (2s, 2H), 3.66-3.56 (m, 4H), 2.09-1.87 (m, 4H), 1.21 (d, J=6.5 Hz) and 0.99 (d, J=6.8 Hz) (2d, 6H); $^{19}$F NMR (282 MHz, DMSO-$d_6$) δ −95.19, −121.22, −121.78; MS (ES+): 622.6 (M+1); MS (ES−): 620.5 (M−1).

Scheme 179

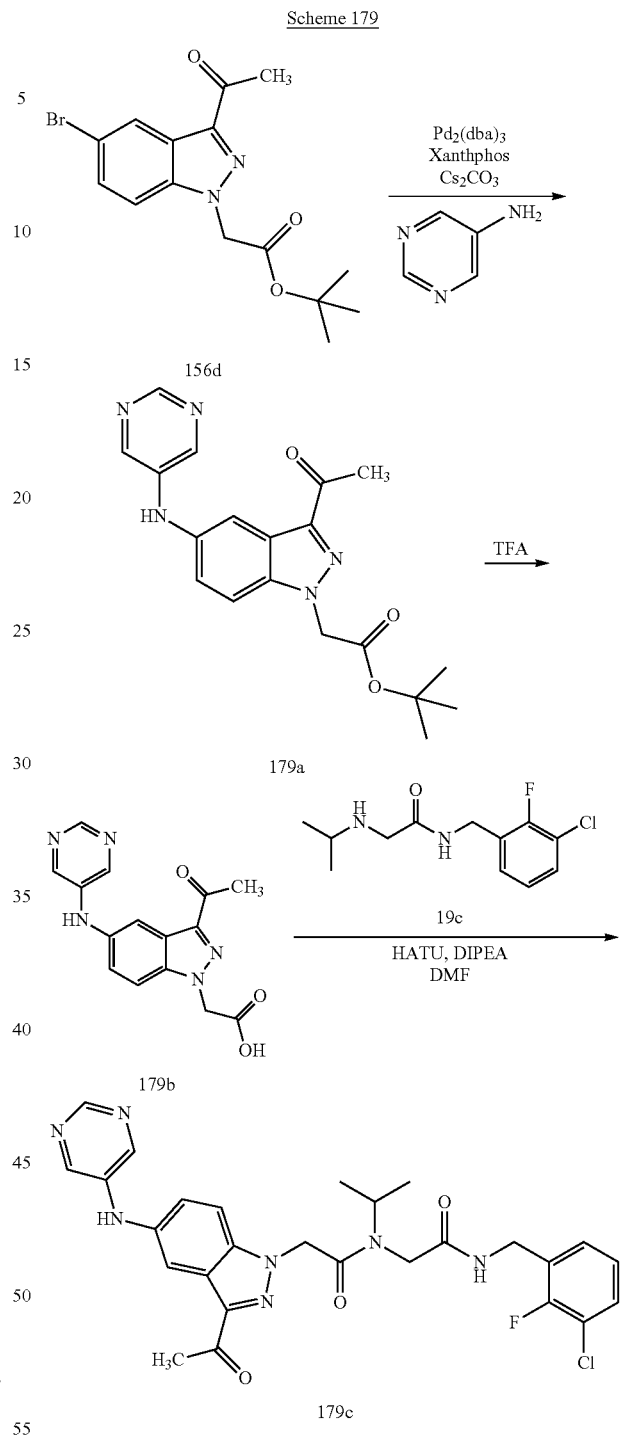

Preparation of 2-(3-acetyl-5-(pyrimidin-5-ylamino)-1H-indazol-1-yl)-N-(2-((3-chloro-2-fluorobenzyl)amino)-2-oxoethyl)-N-isopropylacetamide (179c)

Step-1: Preparation of tert-butyl 2-(3-acetyl-5-(pyrimidin-5-ylamino)-1H-indazol-1-yl)acetate (179a)

Reaction of tert-butyl 2-(3-acetyl-5-bromo-1H-indazol-1-yl)acetate (156d) (1.0 g, 2.83 mmol) with pyrimidin-5-amine (0.539 g, 5.66 mmol) according to the procedure reported in step-1 of Scheme 97 gave after workup and purification by flash column chromatography [silica gel (40 g), eluting with DMA80 in DCM 0 to 20%] tert-butyl 2-(3-acetyl-5-(pyrimidin-5-ylamino)-1H-indazol-1-yl)acetate (179a) (720 mg, 1.96 mmol, 69% yield) as an off-white solid; $^1$H NMR (300 MHz, DMSO-$d_6$) δ 8.73 (s, 1H), 8.65 (s, 1H), 8.56 (s, 2H), 7.93-7.88 (m, 1H), 7.72 (dd, J=9.0, 0.7 Hz, 1H), 7.37 (dd, J=9.1, 2.2 Hz, 1H), 5.42 (s, 2H), 2.59 (s, 3H), 1.44 (s, 9H); MS (ES+): 368.5 (M+1), 390.5 (M+Na); MS (ES−): 366.5 (M−1), 402.4 (M+Cl).

Step-2: Preparation of 2-(3-acetyl-5-(pyrimidin-5-ylamino)-1H-indazol-1-yl)acetic acid (179b)

Reaction of tert-butyl 2-(3-acetyl-5-(pyrimidin-5-ylamino)-1H-indazol-1-yl)acetate (179a) (700 mg, 1.91 mmol) with TFA (1.47 mL, 19.05 mmol) according to the procedure reported in step-2 of Scheme 2 gave after workup and trituration with 30% EtOAc-hexane (10 mL) 2-(3-acetyl-5-(pyrimidin-5-ylamino)-1H-indazol-1-yl)acetic acid (179b) (400 mg, 1.35 mmol, 99% yield) as an off-white solid; $^1$H NMR (300 MHz, DMSO-$d_6$) δ 13.37 (s, 1H, $D_2O$ exchangeable), 8.74 (s, 1H), 8.66 (s, 1H), 8.56 (s, 2H), 7.90 (dd, J=2.2, 0.7 Hz, 1H), 7.76 (dd, J=9.0, 0.7 Hz, 1H), 7.36 (dd, J=9.0, 2.2 Hz, 1H), 5.43 (s, 2H), 2.59 (s, 3H); MS (ES+): 312.4 (M+1), 334.4 (M+Na), MS (ES−): 310.4 (M−1).

Step-3: Preparation of 2-(3-acetyl-5-(pyrimidin-5-ylamino)-1H-indazol-1-yl)-N-(2-((3-chloro-2-fluorobenzyl)amino)-2-oxoethyl)-N-isopropylacetamide (179c)

Reaction of 2-(3-acetyl-5-(pyrimidin-5-ylamino)-1H-indazol-1-yl)acetic acid (179b) (70 mg, 0.23 mmol) with N-(3-chloro-2-fluorobenzyl)-2-(isopropylamino)acetamide (19c) (58 mg, 0.23 mmol) according to the procedure reported in step-3 of Scheme 2 gave after workup and purification by flash column [silica gel (12 g), eluting with DMA-80 in DCM 0-20%] 2-(3-acetyl-5-(pyrimidin-5-ylamino)-1H-indazol-1-yl)-N-(2-((3-chloro-2-fluorobenzyl)amino)-2-oxoethyl)-N-isopropylacetamide (179c) (105 mg, 0.19 mmol, 85% yield) as a very light orange solid as a mixture of two rotamers; $^1$H NMR (300 MHz, DMSO-$d_6$) δ 8.84 and 8.36 (2t, J=5.6 Hz, 1H), 8.72 (s, 1H), 8.65 and 8.64 (2s, 1H), 8.55 (s, 2H), 7.908 and 7.902 (2s, 1H), 7.70-7.00 (m, 5H), 5.67 and 5.51 (2s, 2H), 4.63-4.52 and 4.33-4.20 (2m, 1H), 4.47 and 4.33 (2d, J=6.0 Hz, 2H), 4.18 and 3.85 (2s, 2H), 2.59 (s, 3H), 1.25 and 1.00 (2d, J=6.8 Hz, 6H); $^{19}$F NMR (282 MHz, DMSO-$d_6$) δ −121.21, −121.72; MS (ES+): 552.6 (M+1); MS (ES−): 586.5, 588.5 (M+Cl).

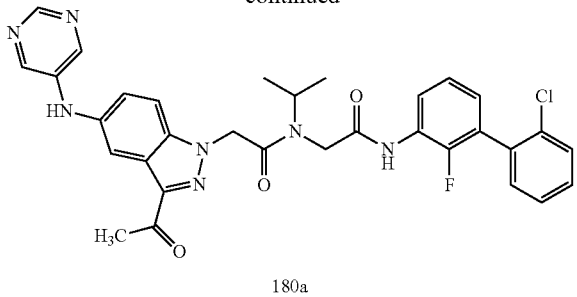

180a

Preparation of 2-(3-acetyl-5-(pyrimidin-5-ylamino)-1H-indazol-1-yl)-N-(2-((2'-chloro-2-fluoro-[1,1'-biphenyl]-3-yl)-amino)-2-oxoethyl)-N-isopropylacetamide (180a)

Reaction of 2-(3-acetyl-5-(pyrimidin-5-ylamino)-1H-indazol-1-yl)acetic acid (179b) (70 mg, 0.23 mmol) with N-(2'-chloro-2-fluoro-[1,1'-biphenyl]-3-yl)-2-(isopropylamino)acetamide (115c) (72 mg, 0.23 mmol) according to the procedure reported in step-3 of scheme-2 gave after workup and purification by flash column [silica gel (12 g), eluting with DMA-80 in DCM 0-20%] 2-(3-acetyl-5-(pyrimidin-5-ylamino)-1H-indazol-1-yl)-N-(2-((2'-chloro-2-fluoro-[1,1'-biphenyl]-3-yl)-amino)-2-oxoethyl)-N-isopropylacetamide (180a) (61 mg, 0.099 mmol, 44% yield) as an off-white solid as a mixture of two rotamers; $^1$H NMR (300 MHz, DMSO-$d_6$) δ 10.27 and 9.76 (2s, 1H), 8.73 and 8.72 (2s, 1H), 8.65 (s, 1H), 8.55 and 8.54 (2s, 2H), 8.11 and 7.95 (2t, J=7.4 Hz, 1H), 7.90 and 7.89 (2d, J=2.1 Hz, 1H), 7.68-7.00 (m, 6H), 5.73 and 5.55 (2s, 2H), 4.73-4.57 and 4.40-4.26 (2m, 1H), 4.47 and 4.09 (2s, 2H), 2.59 and 2.58 (2s, 3H), 1.28 and 1.07 (2d, J=6.8 Hz, 6H); $^{19}$F NMR (282 MHz, DMSO-$d_6$) δ −126.81, −126.96; MS (ES+): 614.6 (M+1); MS (ES−): 648.6 (M+Cl).

Scheme 181

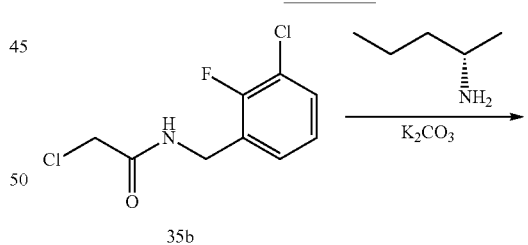

35b

Scheme 180

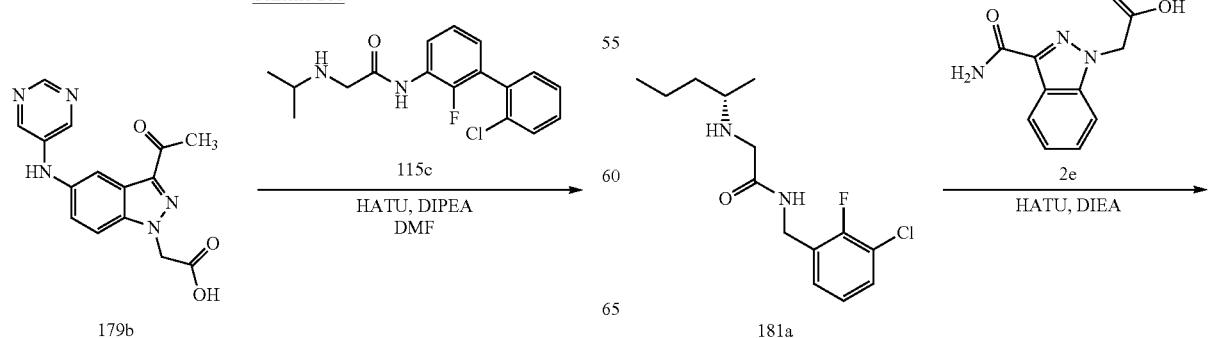

179b     115c     181a     2e

HATU, DIPEA DMF

HATU, DIEA

-continued

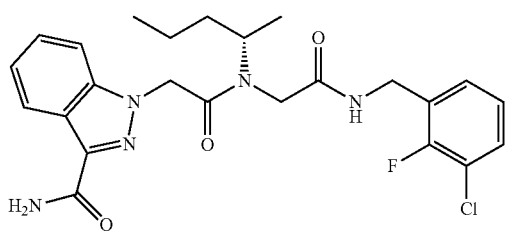

181b

Preparation of (S)-1-(2-((2-((3-chloro-2-fluorobenzyl)amino)-2-oxoethyl)(pentan-2-yl)amino)-2-oxoethyl)-1H-indazole-3-carboxamide (181b)

Step-1: Preparation of (S)—N-(3-chloro-2-fluorobenzyl)-2-(pentan-2-ylamino)acetamide (181a)

Reaction of 2-chloro-N-(3-chloro-2-fluorobenzyl)acetamide (35b) (267 mg, 1.13 mmol) with (S)-pentan-2-amine hydrochloride (350 mg, 2.83 mmol) according to the procedure reported in step-2 of Scheme 35 gave after workup and purification by flash column chromatography [silica (12 g), eluting with EtOAc/MeOH (9:1) in hexane 0 to 60%] (S)—N-(3-chloro-2-fluorobenzyl)-2-(pentan-2-ylamino)acetamide (181a) (112 mg, 0.39 mmol, 35%) as a colorless oil; MS (ES+): 287.4, 289.4 (M+1, M+3); (ES−): 285.4.

Step-2: Preparation of (S)-1-(2-((2-((3-chloro-2-fluorobenzyl)amino)-2-oxoethyl)(pentan-2-yl)amino)-2-oxoethyl)-1H-indazole-3-carboxamide (181b)

Reaction of (S)—N-(3-chloro-2-fluorobenzyl)-2-(pentan-2-ylamino)acetamide (181a) (112 mg, 0.39 mmol) with 2-(3-carbamoyl-1H-indazol-1-yl)acetic acid (2e) (94 mg, 0.43 mmol) according to the procedure reported in step-3 of Scheme 2 gave after workup and purification by flash column chromatography [silica (12 g), eluting with DMA80 in DCM 0 to 60%] (S)-1-(2-((2-((3-chloro-2-fluorobenzyl)amino)-2-oxoethyl)(pentan-2-yl)-amino)-2-oxoethyl)-1H-indazole-3-carboxamide (181b) (141 mg, 0.29 mmol, 74% yield) as a white solid; $^1$H NMR (300 MHz, DMSO-$d_6$) (a mixture of two rotamers) δ 8.81 (t, J=5.6 Hz) and 8.34 (t, J=6.2 Hz) (2t, 1H), 8.22-8.13 (m, 1H), 7.70 (bs, 1H), 7.59-7.04 (m, 7H), 5.63-5.40 (m, 2H), 4.56-3.70 (m, 5H), 1.62-0.58 (m, 10H); $^{19}$F NMR (282 MHz, DMSO-$d_6$) δ −121.19, −121.73; MS (ES+): 488.5 (M+1); MS (ES−): 486.5 (M−1).

Scheme 182

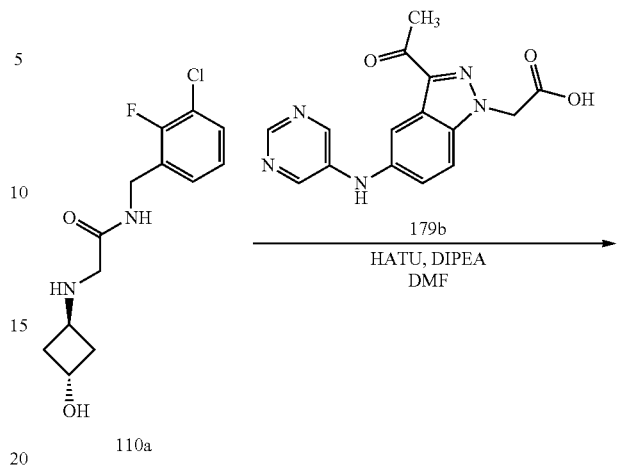

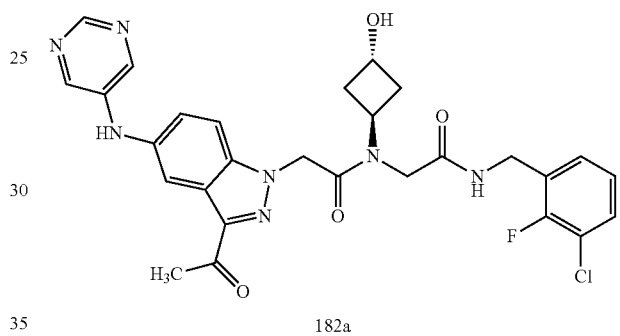

182a

Preparation of 2-(3-acetyl-5-(pyrimidin-5-ylamino)-1H-indazol-1-yl)-N-(2-((3-chloro-2-fluorobenzyl)amino)-2-oxoethyl)-N-(trans-3-hydroxycyclobutyl)acetamide (182a)

Reaction of 2-(3-acetyl-5-(pyrimidin-5-ylamino)-1H-indazol-1-yl)acetic acid (179b) (70 mg, 0.23 mmol) with N-(3-chloro-2-fluorobenzyl)-2-(((trans)-3-hydroxycyclobutyl)amino)acetamide (110a) (64 mg, 0.23 mmol) according to the procedure reported in step-3 of scheme-2 gave after workup and purification by flash column [silica gel (12 g), eluting with DMA-80 in DCM 0-50%] 2-(3-acetyl-5-(pyrimidin-5-ylamino)-1H-indazol-1-yl)-N-(2-((3-chloro-2-fluorobenzyl)amino)-2-oxoethyl)-N-(trans-3-hydroxycyclobutyl)acetamide (182a) (65 mg, 0.11 mmol, 50% yield) as a off-white solid; $^1$H NMR (300 MHz, DMSO-$d_6$) (a mixture of two rotamers) δ 8.87 and 8.43 (2t, J=5.7 Hz, 1H), 8.728 and 8.72 (2s, 1H), 8.657 and 8.65 (2s, 1H), 8.55 (s, 2H), 7.90 and 7.89 (2s, 1H), 7.67-7.03 (m, 5H), 5.61 and 5.48 (2s, 2H), 5.10 and 5.02 (2d, J=4.0 Hz, 1H), 4.96 and 4.86 (2t, J=8.2 Hz, 1H), 4.47 and 4.34 (2d, J=5.6 Hz, 2H), 4.27 and 4.02 (2s, 2H), 4.24-4.09 (m, 1H), 2.587 and 2.58 (2s, 3H), 2.46-2.33 (m, 1H), 2.29-2.12 (m, 2H), 2.02-1.88 (m, 1H); 19F NMR (282 MHz, DMSO-$d_6$) (a mixture of two rotamers) δ −121.22, −121.59; MS (ES+): 580.6 (M+1), 602.5 (M+Na); MS (ES−): 614.5 (M+Cl).

Scheme 183

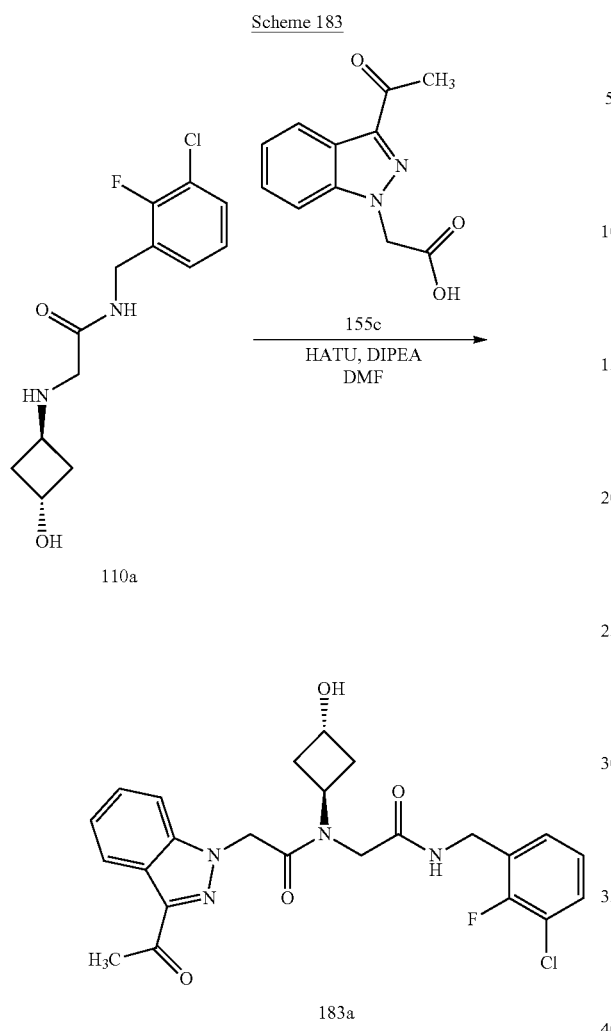

Scheme 184

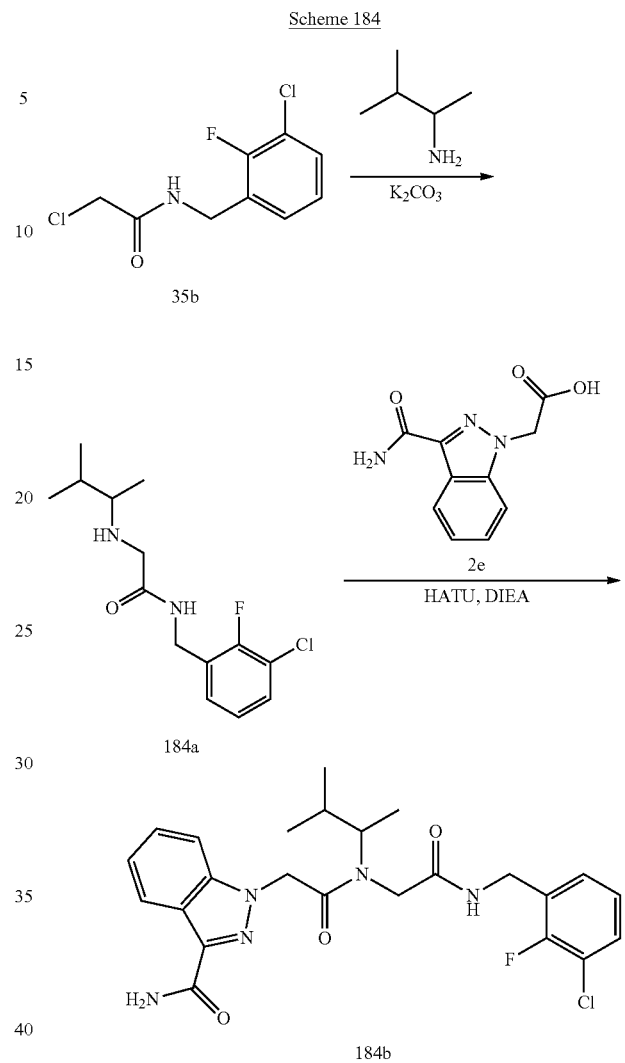

Preparation of 2-(3-acetyl-1H-indazol-1-yl)-N-(2-((3-chloro-2-fluorobenzyl)amino)-2-oxoethyl)-N-(trans-3-hydroxycyclobutyl)acetamide (183a)

Reaction of 2-(3-acetyl-1H-indazol-1-yl)acetic acid (155c) (70 mg, 0.32 mmol) with N-(3-chloro-2-fluorobenzyl)-2-(((trans)-3-hydroxycyclobutyl)amino)acetamide (110a) (92 mg, 0.32 mmol) according to the procedure reported in step-3 of scheme-2 gave after workup and purification by flash column [silica gel (12 g), eluting with DMA-80 in DCM 0-40%] 2-(3-acetyl-1H-indazol-1-yl)-N-(2-((3-chloro-2-fluorobenzyl)amino)-2-oxoethyl)-N-(trans-3-hydroxycyclobutyl)acetamide (183a) (70 mg, 0.14 mmol, 45% yield) as a off-white solid; $^1$H NMR (300 MHz, DMSO-$d_6$) (mixture of two rotamers) δ 8.87 and 8.42 (2t, J=5.9 Hz, 1H), 8.20 and 8.17 (2d, J=1.0 Hz, 1H), 7.72-6.99 (m, 6H), 5.63 and 5.50 (2s, 2H), 5.10 and 5.01 (2d, J=4.4 Hz, 1H), 4.98-4.80 (m, 1H), 4.47 and 4.33 (2d, J=5.8 Hz, 2H), 4.28 and 4.01 (2s, 2H) 4.24-4.09 (m, 1H), 2.61 (s, 3H), 2.46-2.34 (m, 1H), 2.29-2.13 (m, 2H), 2.00-1.88 (m, 1H); $^{19}$F NMR (282 MHz, DMSO-$d_6$) (mixture of two rotamers) δ −121.23, −121.63; MS (ES+): 487.5 (M+1): MS (ES−): 521.4 (M+Cl).

Preparation of 1-(2-((2-((3-chloro-2-fluorobenzyl)amino)-2-oxoethyl)(3-methylbutan-2-yl)amino)-2-oxoethyl)-1H-indazole-3-carboxamide (184b)

Step-1: Preparation of N-(3-chloro-2-fluorobenzyl)-2-((3-methylbutan-2-yl)amino)acetamide (184a)

Reaction of 2-chloro-N-(3-chloro-2-fluorobenzyl)acetamide (35b) (316 mg, 1.34 mmol) with 3-methylbutan-2-amine (350 mg, 4.02 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((3-methylbutan-2-yl)amino)acetamide (184a) (145 mg, 0.51 mmol, 38%) as a colorless oil; $^1$H NMR (300 MHz, DMSO-$d_6$) δ 8.32 (t, J=6.1 Hz, 1H), 7.46 (ddd, J=7.9, 7.2, 1.8 Hz, 1H), 7.32-7.23 (m, 1H), 7.22-7.12 (m, 1H), 4.48-4.29 (m, 2H), 3.22-3.05 (m, 2H), 2.40-2.24 (m, 1H), 1.99 (s, 1H), 1.68-1.53 (m, 1H), 0.86-0.77 (m, 9H); $^{19}$F NMR (282 MHz, DMSO-$d_6$) δ −121.62; MS (ES+): 287.4 (M+1); MS (ES−): 285.3 (M−1).

Step-2: Preparation of 1-(2-((2-((3-chloro-2-fluorobenzyl)amino)-2-oxoethyl)(3-methylbutan-2-yl)amino)-2-oxoethyl)-1H-indazole-3-carboxamide (184b)

Reaction of N-(3-chloro-2-fluorobenzyl)-2-((3-methylbutan-2-yl)amino)acetamide (184a) (145 mg, 0.51 mmol) with 2-(3-carbamoyl-1H-indazol-1-yl)acetic acid (2e) (122 mg, 0.56 mmol) according to the procedure reported in step-3 of Scheme 2 gave after workup and purification by flash column chromatography [silica (12 g), eluting with DMA80 in DCM 0 to 60%] 1-(2-((2-((3-chloro-2-fluorobenzyl)amino)-2-oxoethyl)(3-methylbutan-2-yl)amino)-2-oxoethyl)-1H-indazole-3-carboxamide (184b) (113 mg, 0.23 mmol, 46% yield) as a white solid; $^1$H NMR (300 MHz, DMSO-$d_6$) (mixture of two rotamers) δ 8.81 (t, J=5.7 Hz) and 8.34 (t, J=6.0 Hz) (2t, 1H), 8.23-8.13 (m, 1H), 7.77-7.66 (m, 1H), 7.58-7.15 (m, 7H), 5.72-5.36 (m, 2H), 4.54-3.63 (m, 5H), 1.82-1.55 (m, 1H), 1.26 (d, J=6.4 Hz) and 1.01-0.93 (m) and 0.84 (d, J=6.5 Hz) and 0.74 (d, J=6.5 Hz (9H); $^{19}$F NMR (282 MHz, DMSO-$d_6$) δ −121.20, −121.80; MS (ES+) 488.5 (M+1); MS (ES−) 486.5 (M−1).

Preparation of (S)-1-(2-((2-((3-chloro-2-fluorobenzyl)amino)-2-oxoethyl)(tetrahydrofuran-3-yl)amino)-2-oxoethyl)-1H-indazole-3-carboxamide (185b)

Step-1: Preparation of (S)—N-(3-chloro-2-fluorobenzyl)-2-((tetrahydrofuran-3-yl)amino)acetamide (185a)

Reaction of 2-chloro-N-(3-chloro-2-fluorobenzyl)acetamide (35b) (325 mg, 1.38 mmol) with (S)-tetrahydrofuran-3-amine (300 mg, 3.44 mmol) according to the procedure reported in step-2 of Scheme 35 gave after workup and purification by flash column chromatography [silica (12 g), eluting with EtOAc/MeOH (9:1) in hexane 0 to 60%] (S)—N-(3-chloro-2-fluorobenzyl)-2-((tetrahydrofuran-3-yl)-amino)acetamide (185a) (112 mg, 0.39 mmol, 28%) as a colorless oil; MS (ES+): 287.4 (M+1), 309.3 (M+Na); MS (ES−): 285.3

Step-2: Preparation of (S)-1-(2-((2-((3-chloro-2-fluorobenzyl)amino)-2-oxoethyl)(tetrahydrofuran-3-yl)-amino)-2-oxoethyl)-1H-indazole-3-carboxamide (185b)

Reaction of (S)—N-(3-chloro-2-fluorobenzyl)-2-((tetrahydrofuran-3-yl)amino)acetamide (185a) (112 mg, 0.39 mmol) with 2-(3-carbamoyl-1H-indazol-1-yl)acetic acid (2e) (94 mg, 0.43 mmol) according to the procedure reported in step-3 of Scheme 2 gave after workup and purification by flash column chromatography [silica (12 g), eluting with DMA80 in DCM 0 to 60%] (S)-1-(2-((2-((3-chloro-2-fluorobenzyl)amino)-2-oxoethyl)(tetrahydrofuran-3-yl)amino)-2-oxoethyl)-1H-indazole-3-carboxamide (185b) (103 mg, 0.21 mmol, 54% yield) as a white solid; $^1$H NMR (300 MHz, DMSO-$d_6$) (mixture of two rotamers) δ 8.89 (t, J=5.8 Hz and, 8.49 (t, J=5.9 Hz) (2t, 1H), 8.22-8.13 (m, 1H), 7.74-7.64 (m, 1H), 7.63-7.00 (m, 7H), 5.81-5.29 (m, 2H), 4.97-4.74 (m, 1H), 4.47 (d, J=5.6 Hz) and 4.31 (d, J=5.9 Hz) (2d, 2H), 4.25 (s) and 4.00-3.43 (m) (s & m, 6H), 2.42-1.54 (m, 2H); $^{19}$F NMR (282 MHz, DMSO-$d_6$) δ −121.27, −121.73; MS (ES+): 488.5 (M+1); MS (ES−): 486.5 (M−1).

Scheme 185

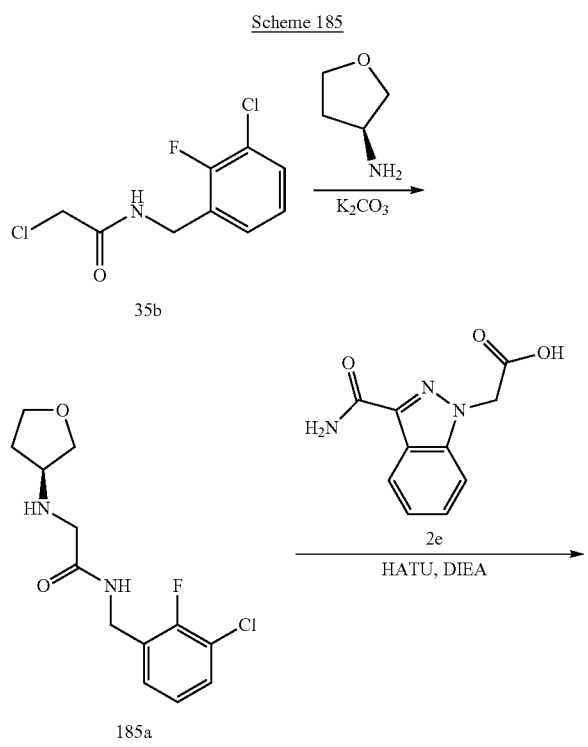

Scheme 186

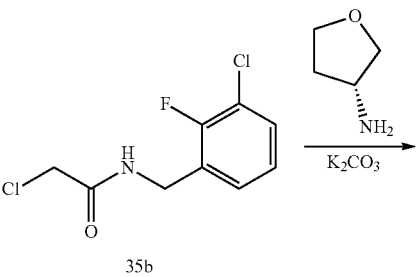

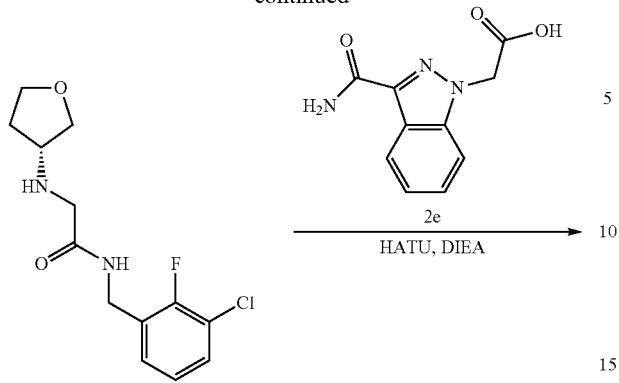

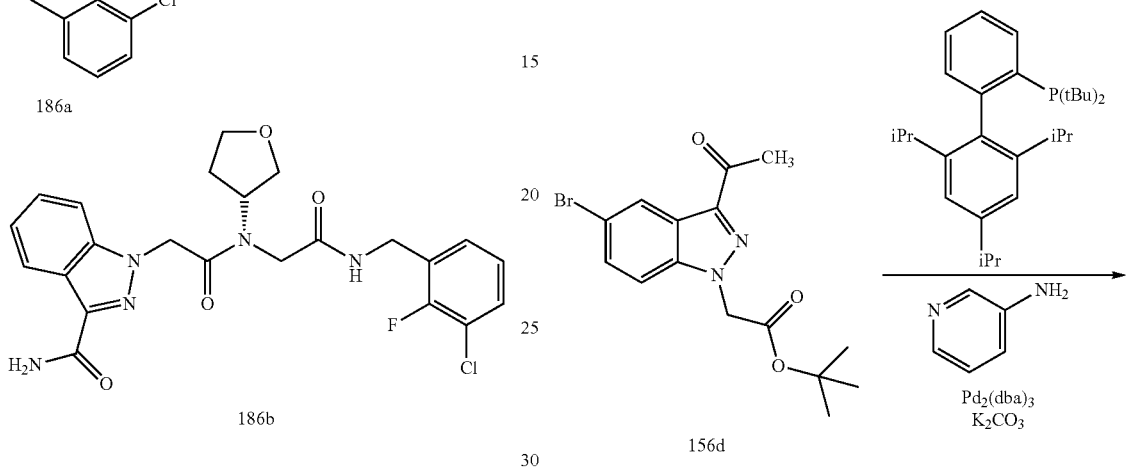

Preparation of (R)-1-(2-((2-((3-chloro-2-fluorobenzyl)amino)-2-oxoethyl)(tetrahydrofuran-3-yl)-amino)-2-oxoethyl)-1H-indazole-3-carboxamide (186b)

Step-1: Preparation of (R)—N-(3-chloro-2-fluorobenzyl)-2-((tetrahydrofuran-3-yl)-amino)acetamide (186a)

Reaction of 2-chloro-N-(3-chloro-2-fluorobenzyl)acetamide (35b) (339 mg, 1.44 mmol) with (R)-tetrahydrofuran-3-amine (250 mg, 2.87 mmol) according to the procedure reported in step-2 of Scheme 35 gave after workup and purification by flash column chromatography [silica (12 g), eluting with EtOAc/MeOH (9:1) in hexane 0 to 60%] (R)—N-(3-chloro-2-fluorobenzyl)-2-((tetrahydrofuran-3-yl)amino)acetamide (186a) (109 mg, 0.38 mmol, 27%) as a colorless oil; MS (ES+): 287.4 (M+1), 309.3 (M+Na); MS (ES−): 285.3

Step-2: Preparation of (R)-1-(2-((2-((3-chloro-2-fluorobenzyl)amino)-2-oxoethyl)(tetrahydrofuran-3-yl)amino)-2-oxo ethyl)-1H-indazole-3-carboxamide (186b)

Reaction of (R)—N-(3-chloro-2-fluorobenzyl)-2-((tetrahydrofuran-3-yl)amino)acetamide (186a) (109 mg, 0.38 mmol) with 2-(3-carbamoyl-1H-indazol-1-yl)acetic acid (2e) (92 mg, 0.42 mmol) according to the procedure reported in step-3 of Scheme 2 gave after workup and purification by flash column chromatography [silica (12 g), eluting with DMA80 in DCM 0 to 60%] (R)-1-(2-((2-((3-chloro-2-fluorobenzyl)amino)-2-oxoethyl)(tetrahydrofuran-3-yl)amino)-2-oxoethyl)-1H-indazole-3-carboxamide (186b) (23 mg, 0.047 mmol, 12% yield) as a white solid; $^1$H NMR (300 MHz, DMSO-$d_6$) δ 8.95-8.43 (m, 1H), 8.23-8.13 (m, 1H), 7.74-7.64 (m, 1H), 7.63-6.95 (m, 7H), 5.76-5.54 (m) and 5.40 (s) (2H), 5.00-4.73 (m, 1H), 4.47 (d, J=5.5 Hz) and 4.32 (d, J=5.9 Hz) (2d, 2H), 4.25 (s) and 4.02-3.51 (m) (6H), 2.16-1.61 (m, 2H); $^{19}$F NMR (282 MHz, DMSO-$d_6$) δ −121.28, −121.74; MS (ES+): 488.5 (M+1); MS (ES−): 486.5 (M−1).

Scheme 187

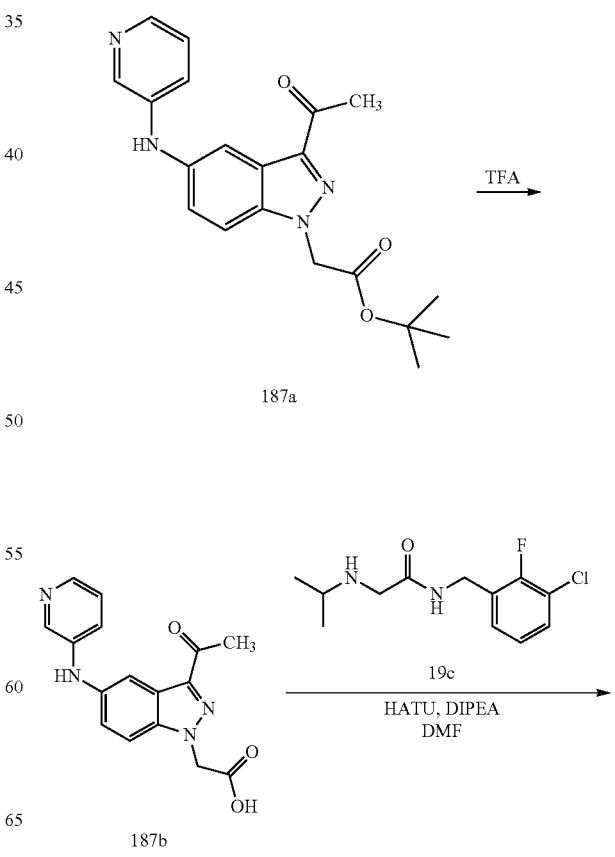

-continued

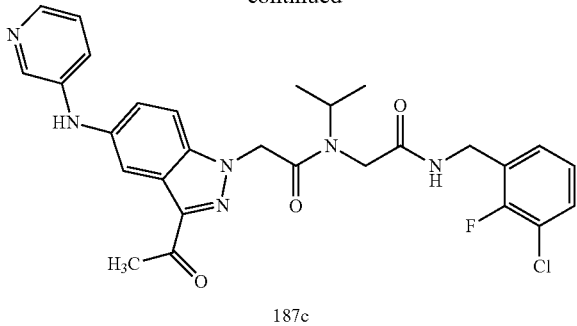

187c

Preparation of 2-(3-acetyl-5-(pyridin-3-ylamino)-1H-indazol-1-yl)-N-(2-((3-chloro-2-fluorobenzyl)amino)-2-oxoethyl)-N-isopropylacetamide (187c)

Step-1: Preparation of tert-butyl 2-(3-acetyl-5-(pyridin-3-ylamino)-1H-indazol-1-yl)acetate (187a)

Reaction of tert-butyl 2-(3-acetyl-5-bromo-1H-indazol-1-yl)acetate (156d) (935 mg, 2.65 mmol) with pyridin-3-amine (0.498 g, 5.29 mmol), using potassium carbonate (732 mg, 5.29 mmol), di-tert-butyl(2',4',6'-triisopropylbiphenyl-2-yl)phosphine (135 mg, 0.32 mmol), Pd$_2$(dba)$_3$ (145 mg, 0.16 mmol) according to the procedure reported in step-1 of Scheme 97 gave after workup and purification by flash column chromatography [silica gel (40 g), eluting with DMA80 in DCM 0 to 50] tert-butyl 2-(3-acetyl-5-(pyridin-3-ylamino)-1H-indazol-1-yl)acetate (187a) (722 mg, 1.97 mmol, 74% yield) as a yellow solid; $^1$H NMR (300 MHz, DMSO-d$_6$) δ 8.54 (s, 1H), 8.37 (d, J=2.8 Hz, 1H), 8.05 (dd, J=4.6, 1.4 Hz, 1H), 7.88 (d, J=2.1 Hz, 1H), 7.68 (d, J=9.0 Hz, 1H), 7.56-7.41 (m, 1H), 7.38-7.22 (m, 2H), 5.41 (s, 2H), 2.59 (s, 3H), 1.44 (s, 9H); MS (ES+): 367.5 (M+1), 389.5 (M+Na); MS (ES−): 365.4 (M−1).

Step-2: Preparation of 2-(3-acetyl-5-(pyridin-3-ylamino)-1H-indazol-1-yl)acetic acid (187b)

Reaction of tert-butyl 2-(3-acetyl-5-(pyridin-3-ylamino)-1H-indazol-1-yl)acetate (187a) (115 mg, 0.31 mmol) with TFA (0.73 mL, 9.42 mmol) according to the procedure reported in step-2 of Scheme 2 gave after workup and trituration with hexane (10 mL) 2-(3-acetyl-5-(pyridin-3-ylamino)-1H-indazol-1-yl)acetic acid (187b) (129 mg, 0.3 mmol, 97% yield) as a yellow solid in the form of TFA adduct; $^1$H NMR (300 MHz, DMSO-d$_6$) δ 13.44 (bs, 1H, D$_2$O exchangeable), 9.34 (s, 1H, D$_2$O exchangeable), 8.41 (s, 1H), 8.24 (d, J=5.3 Hz, 1H), 8.05-7.92 (m, 2H), 7.85 (d, J=9.0 Hz, 1H), 7.78 (dd, J=8.7, 5.2 Hz, 1H), 7.44 (dd, J=9.0, 2.1 Hz, 1H), 5.47 (s, 2H), 2.61 (s, 3H); MS (ES+): 311.4 (M+1); MS (ES−): 619.5 (2M−1).

Step-3: Preparation of 2-(3-acetyl-5-(pyridin-3-ylamino)-1H-indazol-1-yl)-N-(2-((3-chloro-2-fluorobenzyl)amino)-2-oxoethyl)-N-isopropylacetamide (187c)

Reaction of 2-(3-acetyl-5-(pyridin-3-ylamino)-1H-indazol-1-yl)acetic acid (187b) (234 mg, 0.754 mmol) with N-(3-chloro-2-fluorobenzyl)-2-(isopropylamino)acetamide (19c) (234 mg, 0.91 mmol) according to the procedure reported in step-3 of Scheme 2 gave after workup and purification by flash column [silica gel (12 g), eluting with DMA-80 in DCM 0-100%] 2-(3-acetyl-5-(pyridin-3-ylamino)-1H-indazol-1-yl)-N-(2-((3-chloro-2-fluorobenzyl)amino)-2-oxoethyl)-N-isopropylacetamide (187c) (38 mg, 0.069 mmol, 9% yield) as a yellow solid; $^1$H NMR (300 MHz, DMSO-d$_6$) δ 8.84 (t, J=5.8 Hz) and 8.42-8.29 (m) (t & m, 2H), 8.52 (s, 1H), 8.10-8.00 (m, 1H), 7.88 (d, J=2.0 Hz, 1H), 7.63-6.99 (m, 6H), 5.66 & 5.49 (2s, 2H), 4.66-4.52 & 4.30-4.22 (2m, 1H), 4.47 (d, J=5.6 Hz) and 4.33 (d, J=5.9 Hz) (2d, 2H), 4.18 & 3.86 (2s, 2H), 2.58 (s, 3H), 1.25 (d, J=6.5 Hz) & 1.01 (d, J=6.8 Hz) (2d, 6H); $^{19}$F NMR (282 MHz, DMSO-d$_6$) δ −121.21, −121.72; MS (ES+): 573.5, 575.5 (M+Na); MS (ES−): 549.4 (M−1);

Scheme 188

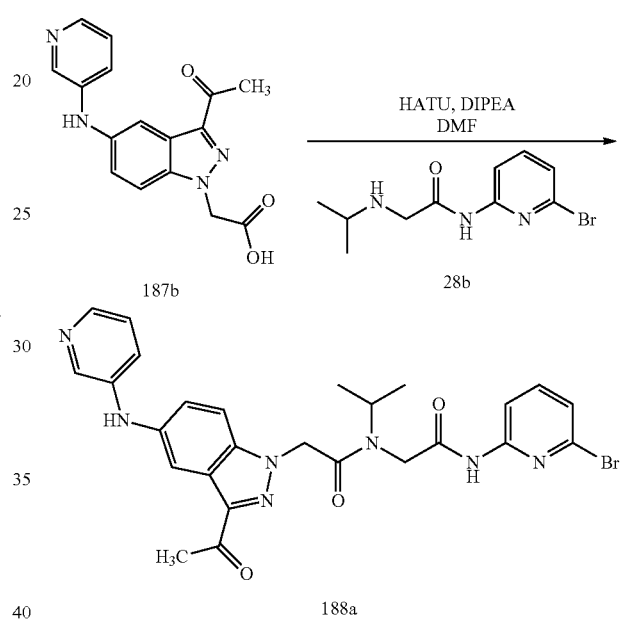

Preparation of 2-(3-acetyl-5-(pyridin-3-ylamino)-1H-indazol-1-yl)-N-(2-((6-bromopyridin-2-yl)amino)-2-oxoethyl)-N-isopropylacetamide (188a)

Reaction of 2-(3-acetyl-5-(pyridin-3-ylamino)-1H-indazol-1-yl)acetic acid (187b) (210 mg, 0.68 mmol) with N-(6-bromopyridin-2-yl)-2-(isopropylamino)acetamide (28b) (221 mg, 0.81 mmol) according to the procedure reported in step-3 of Scheme 2 gave after workup and purification by flash column [silica gel (24 g), eluting with DMA-80 in DCM 0-100%] 2-(3-acetyl-5-(pyridin-3-ylamino)-1H-indazol-1-yl)-N-(2-((6-bromopyridin-2-yl)amino)-2-oxoethyl)-N-isopropylacetamide (188a) (139 mg, 0.25 mmol, 36% yield) as a light green solid as a mixture of two rotamers; $^1$H NMR (300 MHz, DMSO-d$_6$) δ 11.21 & 10.82 (2s, 1H, D$_2$O exchangeable), 8.53 & 8.51 (2s, 1H), 8.36 (t, J=3.3 Hz, 1H), 8.23-7.97 (m, 2H), 7.88 (d, J=2.0 Hz) & 7.86 (d, J=2.1 Hz) (2d, 1H), 7.81 (t, J=8.0 Hz) & 7.70 (t, J=8.0 Hz) (2t, 1H), 7.61 (d, J=3.4 Hz) & 7.58 (d, J=3.4 Hz) (2d, 1H), 7.50-7.21 (m, 4H), 5.70 & 5.51 (2s, 2H), 4.71-4.57 & 4.38-4.26 (2m, 1H), 4.43 & 4.05 (2s, 2H), 2.59 & 2.58 (2s, 3H), 1.26 (d, J=6.4 Hz) &, 1.05 (d, J=6.8 Hz) (2d, 6H); MS (ES+): 564.5 & 566.5 (M+1), 586.5 & 588.5 (M+Na); MS (ES−): 562.4 & 564.4 (M−1).

Scheme 189

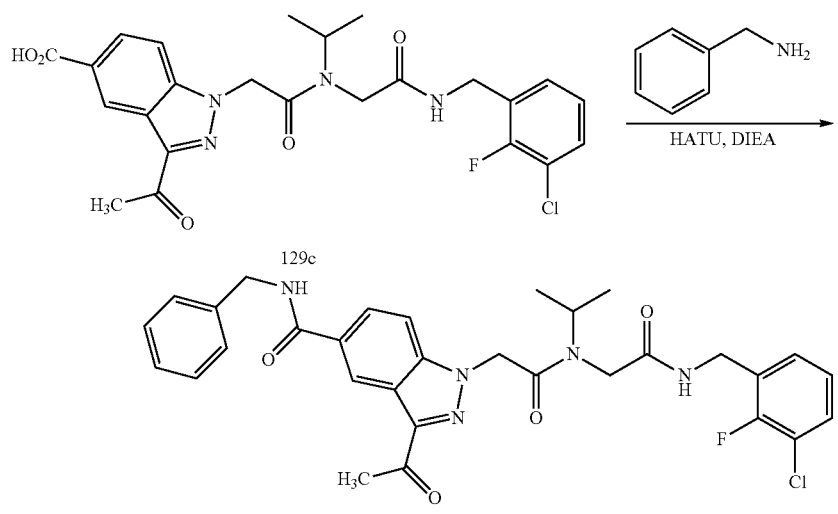

Preparation of 3-acetyl-N-benzyl-1-(2-((2-((3-chloro-2-fluorobenzyl)amino)-2-oxoethyl)(isopropyl)amino)-2-oxoethyl)-1H-indole-5-carboxamide (189a)

Reaction of 3-acetyl-1-(2-((2-((3-chloro-2-fluorobenzyl)amino)-2-oxoethyl)(isopropyl)amino)-2-oxoethyl)-1H-indole-5-carboxylic acid (129c) (50 mg, 0.1 mmol) with phenylmethanamine (0.016 mL, 0.15 mmol) according to the procedure reported in step-3 of Scheme 2 gave after workup and purification by flash column [silica gel (4 g), eluting with CHCl$_3$/MeOH (1:0 to 19:1)] 3-acetyl-N-benzyl-1-(2-((2-((3-chloro-2-fluorobenzyl)amino)-2-oxoethyl)(isopropyl)amino)-2-oxoethyl)-1H-indole-5-carboxamide (189a) (47 mg, 80%) as a light brown solid; $^1$H NMR (300 MHz, DMSO-d$_6$) δ 9.09-8.79 (m, 1H), 8.77-8.73 (m, 1H), 8.35 and 8.31 (2s, 1H), 7.82-6.93 (m, 11H), 5.40 and 5.21 (2s, 2H), 4.62-4.21 (m, 5H), 4.19 and 3.85 (2s, 2H), 2.46 and 2.45 (2s, 3H), 1.26 (d, J=6.5 Hz) and 1.00 (d, J=6.8 Hz (2d, 6H); $^{19}$F NMR (282 MHz, DMSO-d$_6$) δ -121.19, -121.80; MS (ES-): 589.9 & 591.6 (M-1), 625.5 & 627.6 (M+Cl).

Scheme 190

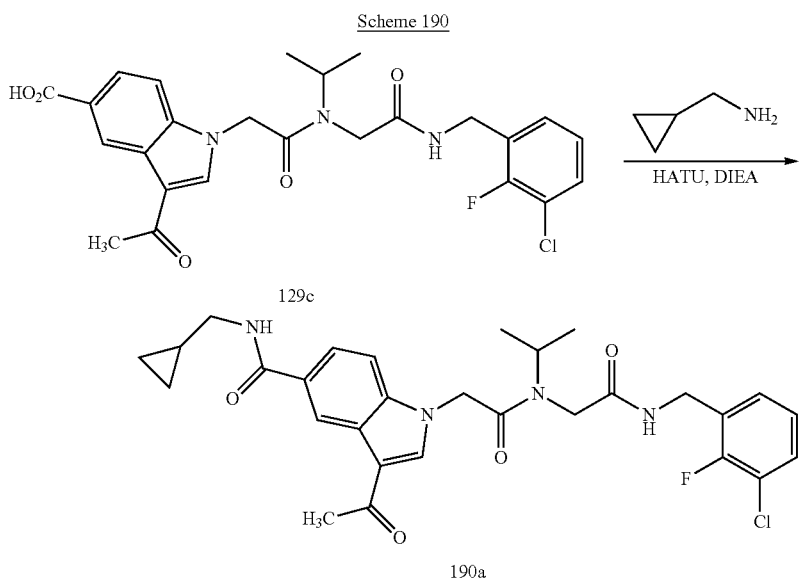

Preparation of 3-acetyl-1-(2-((2-((3-chloro-2-fluorobenzyl)amino)-2-oxoethyl)(isopropyl)amino)-2-oxoethyl)-N-(cyclopropylmethyl)-1H-indole-5-carboxamide (190a)

Reaction of 3-acetyl-1-(2-((2-((3-chloro-2-fluorobenzyl)amino)-2-oxoethyl)(isopropyl)amino)-2-oxoethyl)-1H-indole-5-carboxylic acid (129c) (50 mg, 0.1 mmol) with cyclopropylmethanamine (0.013 mL, 0.149 mmol) according to the procedure reported in step-3 of Scheme 2 gave after workup and purification by flash column [silica gel (4 g), eluting with CHCl$_3$/MeOH (1:0 to 19:1)] 3-acetyl-1-(2-((2-((3-chloro-2-fluorobenzyl)amino)-2-oxoethyl)(isopropyl)amino)-2-oxoethyl)-N-(cyclopropylmethyl)-1H-indole-5-carboxamide (190a) (39 mg, 71%) as an off-white solid; $^1$H NMR (300 MHz, DMSO-d$_6$) (mixture of two rotamers) δ 8.89-8.48 (m, 2H), 8.34 and 8.30 (2s, 1H), 7.79-6.91 (m, 6H), 5.39 and 5.20 (2s, 2H), 4.65-4.51 and 4.29-4.20 (2m, 1H), 4.48 (d, J=5.5 Hz) and 4.33 (d, J=5.8 Hz) (2d, 2H), 4.19 and 3.85 (2s, 2H), 3.16 (t, J=6.1 Hz, 2H), 2.46 and 2.45 (2s, 3H), 1.26 (d, J=6.5 Hz) and 1.00 (d, J=6.8 Hz) (2d, 6H), 1.12-1.01 (m, 1H), 0.48-0.38 (m, 2H), 0.29-0.19 (m, 2H); $^{19}$F NMR (282 MHz, DMSO-d$_6$) δ -121.19, -121.79; MS (ES+): 555.6 (M+1) and 577.6 (M+Na), MS (ES-): 589.6 & 591.5 (M+Cl).

NMR (282 MHz, DMSO-d$_6$) δ -121.22, -121.73; MS (ES+): 594.6 & 596.6 (M+1); 628.5 & 630.6 (M+Na).

Scheme 192

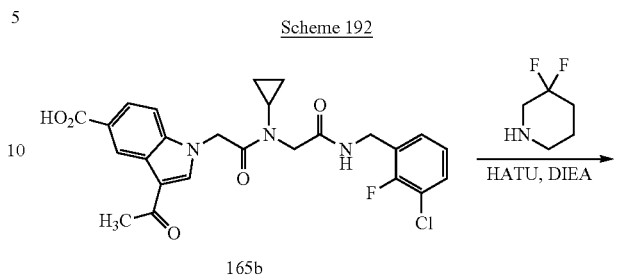

165b

Scheme 191

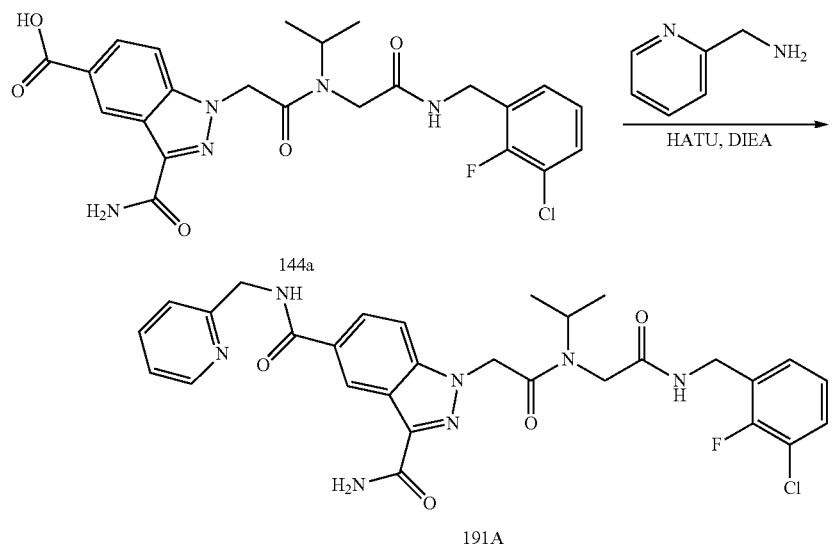

144a

191A

Preparation of 1-(2-((2-((3-chloro-2-fluorobenzyl)amino)-2-oxoethyl)(isopropyl)amino)-2-oxoethyl)-N5-(pyridin-2-ylmethyl)-1H-indazole-3,5-dicarboxamide (191a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with pyridin-2-ylmethanamine (0.015 mL, 0.15 mmol) according to the procedure reported in step-3 of Scheme 2 gave after workup and purification by flash column chromatography [silica (4 g), eluting with MeOH in DCM (1:0 to 9:1)] 1-(2-((2-((3-chloro-2-fluorobenzyl)amino)-2-oxoethyl)(isopropyl)amino)-2-oxoethyl)-N5-(pyridin-2-ylmethyl)-1H-indazole-3,5-dicarboxamide (191a) (27 mg, 46%) as a white solid; $^1$H NMR (300 MHz, DMSO-d$_6$) (mixture of two rotamers) δ 9.28 (t, J=5.8 Hz, 1H), 8.84 (t, J=5.7 Hz) and 8.37 (t, J=5.9 Hz)(2t, 1H), 8.81-8.78 (m, 1H), 8.55-8.50 (m, 1H), 8.01-7.90 (m, 1H), 7.86-7.73 (m, 2H), 7.69 (d, J=8.9 Hz) and 7.62 (d, J=8.8 Hz) (2d, 1H), 7.55-6.94 (m, 6H), 5.64 and 5.50 (2s, 2H), 4.60 (d, J=5.8 Hz, 2H), 4.58-4.49 and 4.29-4.21 (2m, 1H), 4.46 (d, J=5.6 Hz) and 4.31 (d, J=5.8 Hz) (2d, 2H), 4.19 and 3.84 (2s, 2H), 1.23 (d, J=6.3 Hz) and 0.99 (d, J=6.8 Hz) (2d, 6H); $^{19}$F -continued

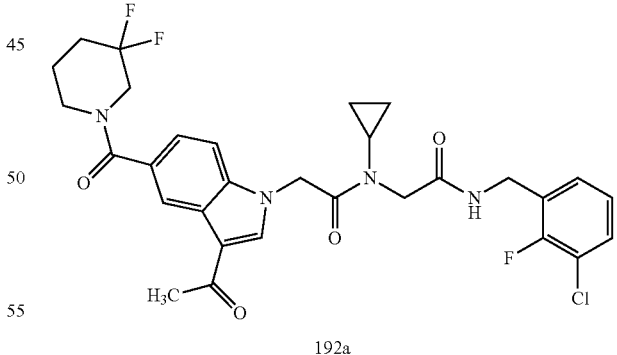

192a

Preparation of 2-(3-acetyl-5-(3,3-difluoropiperidine-1-carbonyl)-1H-indol-1-yl)-N-(2-((3-chloro-2-fluorobenzyl)amino)-2-oxoethyl)-N-cyclopropylacetamide (192a)

Reaction of 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (50 mg, 0.1 mmol) with 3,3-difluoropiperidine hydrochloride (24 mg, 0.15 mmol) according to the procedure reported in step-3 of Scheme 2 gave after workup and purification by flash column chromatography [silica (4 g), eluting with MeOH in DCM (1:0 to 19:1)] 2-(3-acetyl-5-(3,3-difluoropiperidine-1-carbonyl)-1H-indol-1-yl)-N-(2-((3-chloro-2-fluorobenzyl)amino)-2-oxoethyl)-N-cyclopropylacetamide (192a) (39 mg, 65%) as a white solid; $^1$H NMR (300 MHz, DMSO-$d_6$) δ 8.47 (t, J=5.8 Hz, 1H), 8.39 (s, 1H), 8.22 (d, J=1.6 Hz, 1H), 7.54 (d, J=8.5 Hz, 1H), 7.45 (td, J=7.7, 1.7 Hz, 1H), 7.28-7.16 (m, 2H), 7.09 (td, J=7.9, 1.0 Hz, 1H), 5.48 (s, 2H), 4.34 (d, J=5.7 Hz, 2H), 4.00 (s, 2H), 3.96-3.42 (m, 4H), 3.17-3.04 (m, 1H), 2.44 (s, 3H), 2.20-1.98 (m, 2H), 1.70 (bs, 2H), 1.05-0.82 (m, 4H); MS (ES+): 603.6 (M+1); MS (ES−): 601.6 (M−1), 637.6, 639.6 (M+Cl).

lacetamide (156f) (150 mg, 0.28 mmol) with 2-(dimethylamino)pyrimidin-5-ylboronic acid (47 mg, 0.28 mmol) according the procedure reported in Scheme 100 gave after workup and purification by flash column chromatography [silica gel (12 g), eluting with CMA80 in CHCl$_3$ 0 to 20%] 2-(3-acetyl-5-(2-(dimethylamino)pyrimidin-5-yl)-1H-indazol-1-yl)-N-(2-((3-chloro-2-fluorobenzyl)amino)-2-oxoethyl)-N-isopropylacetamide (193a) (50 mg, 0.093 mmol, 33% yield) as a white solid as a mixture of two rotamers; $^1$H NMR (300 MHz, DMSO-$d_6$) (mixture of two rotamers) δ 8.84 and 8.36 (2t, J=5.8 Hz, 1H), 8.71 (s, 2H), 8.31-8.26 (m,

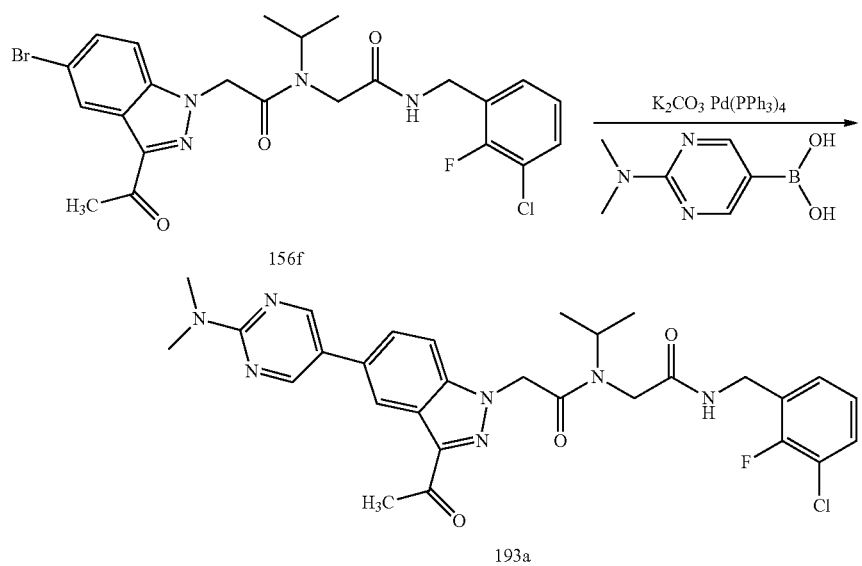

Preparation of 2-(3-acetyl-5-(2-(dimethylamino)pyrimidin-5-yl)-1H-indazol-1-yl)-N-(2-((3-chloro-2-fluorobenzyl)amino)-2-oxoethyl)-N-isopropylacetamide (193a)

Reaction of 2-(3-acetyl-5-bromo-1H-indazol-1-yl)-N-(2-((3-chloro-2-fluorobenzyl)amino)-2-oxoethyl)-N-isopropy- 1H), 7.82-6.92 (m, 5H), 5.73 and 5.55 (2s, 2H), 4.64-4.51 and 4.30-4.22 (2m, 1H), 4.48 and 4.32 (2d, J=5.6 Hz, 2H), 4.19 and 3.85 (2s, 2H), 3.199 and 3.19 (2s, 6H), 2.63 (s, 3H), 1.25 and 1.00 (2d, J=6.7 Hz, 6H); $^{19}$F NMR (282 MHz, DMSO-$d_6$) (mixture of two rotamers) δ −121.20, −121.74; MS (ES+): 580.6 (M+1), MS (ES−): 614.5 (M+Cl).

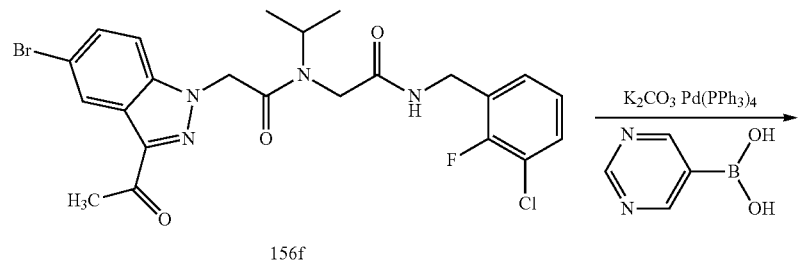

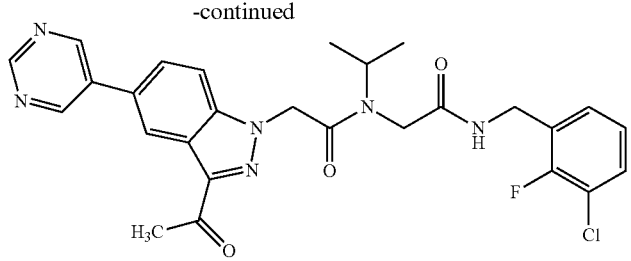

194a

Preparation of 2-(3-acetyl-5-(pyrimidin-5-yl)-1H-indazol-1-yl)-N-(2-((3-chloro-2-fluorobenzyl)amino)-2-oxoethyl)-N-isopropylacetamide (194a)

Reaction of 2-(3-acetyl-5-bromo-1H-indazol-1-yl)-N-(2-((3-chloro-2-fluorobenzyl)amino)-2-oxoethyl)-N-isopropylacetamide (156f) (150 mg, 0.28 mmol) with pyrimidin-5ylboronic acid (0.035 g, 0.28 mmol) according the procedure reported in Scheme 100 gave after workup and purification by flash column chromatography [silica gel (12 g), eluting with CMA80 in $CHCl_3$ 0 to 20%] 2-(3-acetyl-5-(pyrimidin-5-yl)-1H-indazol-1-yl)-N-(2-((3-chloro-2-fluorobenzyl)amino)-2-oxoethyl)-N-isopropylacetamide (194a) (98 mg, 0.18 mmol, 65% yield) as a white solid as a mixture of two rotamers; $^1$H NMR (300 MHz, DMSO-$d_6$) (a mixture of two rotamers) δ 9.228 and 9.22 (2s, 1H), 9.187 and 9.18 (2s, 2H), 8.85 and 8.36 (2t, J=5.6 Hz, 1H), 8.51-8.44 (m, 1H), 7.97-7.75 (m, 2H), 7.57-6.96 (m, 3H), 5.77 and 5.59 (2s, 2H), 4.65-4.52 and 4.30-4.17 (2m, 1H), 4.48 and 4.32 (2d, J=5.8 Hz, 2H), 4.20 and 3.86 (2s, 2H), 2.65 (s, 3H), 1.27 and 1.01 (2d, J=6.8 Hz, 6H); $^{19}$F NMR (282 MHz, DMSO-$d_6$) (mixture of two rotamers) δ −121.20, −121.74; MS (ES+): 537.5 (M+1), 559.6 (M+Na); MS (ES−): 571.5 (M+Cl).

Scheme 195

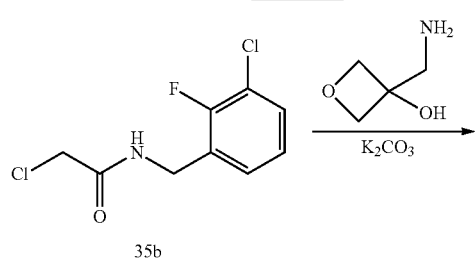

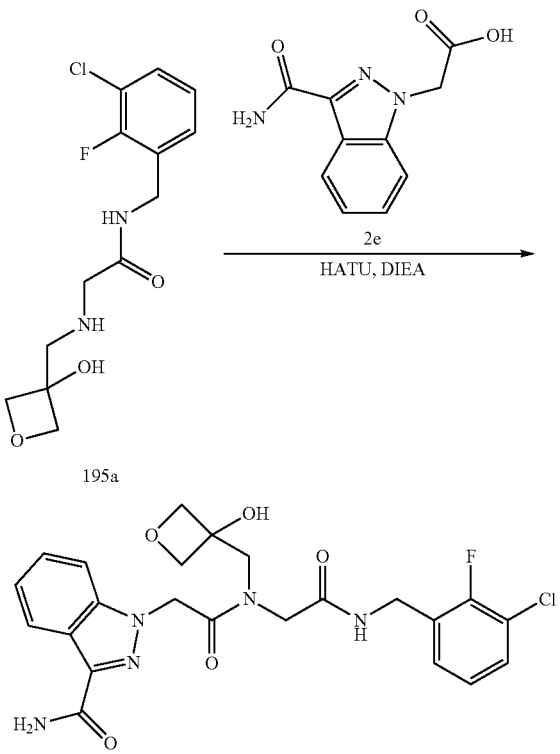

Preparation of 1-(2-((2-((3-chloro-2-fluorobenzyl)amino)-2-oxoethyl)((3-hydroxyoxetan-3-yl)methyl)amino)-2-oxoethyl)-1H-indazole-3-carboxamide (195b)

Step-1: Preparation of N-(3-chloro-2-fluorobenzyl)-2-((2-(3-hydroxyoxetan-3-yl)ethyl)amino)acetamide (195a)

Reaction of 2-chloro-N-(3-chloro-2-fluorobenzyl)acetamide (35b) (410 mg, 1.74 mmol) with 3-(aminomethyl)oxetan-3-ol (269 mg, 2.61 mmol) according to the procedure reported in step-2 of Scheme 35 gave after workup N-(3-chloro-2-fluorobenzyl)-2-((3-hydroxyoxetan-3-yl)methyl-amino)acetamide (195a) (250 mg, 0.83 mmol, 48%) as an oil which was used in the next step without further purification; MS (ES+) 303.4 (M+1); (ES−) 301.3 (M−1).

Step-2: Preparation of 1-(2-((2-((3-chloro-2-fluorobenzyl)amino)-2-oxoethyl)((3-hydroxyoxetan-3-yl)methyl)amino)-2-oxoethyl)-1H-indazole-3-carboxamide (195b)

Reaction of N-(3-chloro-2-fluorobenzyl)-2-((2-(3-hydroxy oxetan-3-yl)ethyl)amino)acetamide (195a) (250 mg, 0.83 mmol) with 2-(3-carbamoyl-1H-indazol-1-yl)acetic acid (2e) (181 mg, 0.83 mmol) according to the procedure reported in step-3 of Scheme 2 gave after workup and purification by flash column chromatography [silica (12 g), eluting with MeOH in DCM 0 to 50%] 1-(2-((2-((3-chloro-2-fluorobenzyl)amino)-2-oxo ethyl)((3-hydroxy oxetan-3-yl)methyl)amino)-2-oxoethyl)-1H-indazole-3-carboxamide (195b) (85 mg, 0.17 mmol, 20% yield) as a white solid as a mixture as a rotamers; $^1$H NMR (300 MHz, DMSO-$d_6$) δ 8.81 (t, J=5.7 Hz) & 8.58 (t, J=5.8 Hz) (2t, 1H, $D_2O$ exchangeable), 8.21-8.16 (m, 1H), 7.74 & 7.71 (2s, 1H), 7.59-7.02 (m, 7H), 6.52 & 6.05 (2s, 1H, $D_2O$ exchangeable), 5.63 & 5.45 (2s, 2H), 4.61-4.29 (m, 8H), 4.04 & 3.94 (2s, 2H); $^{19}$F NMR (282 MHz, DMSO-$d_6$) δ −121.39, −121.56; MS (ES+): 526.5 (M+Na); MS (ES−): 502.4 (M−1).

7.98-6.94 (m, 9H), 5.63 and 5.49 (2s, 2H), 4.60-4.45 and 4.30-4.20 (2m, 1H), 4.53 (d, J=6.0 Hz, 2H), 4.46 (d, J=5.6 Hz) and 4.31 (d, J=5.9 Hz) (2d, 2H), 4.18 and 3.83 (2s, 2H), 1.23 (d, J=6.3 Hz) and 0.99 (d, J=6.8 Hz) (2d, 6H); $^{19}$F NMR (282 MHz, DMSO-$d_6$) δ −121.22, −121.73; MS (ES+): 594.6 (M+1); MS (ES−): 628.6 & 630.6 (M+Cl).

Scheme 197

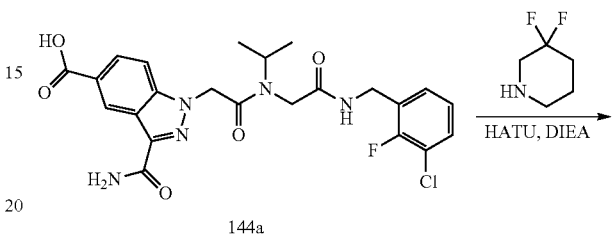

144a

Scheme 196

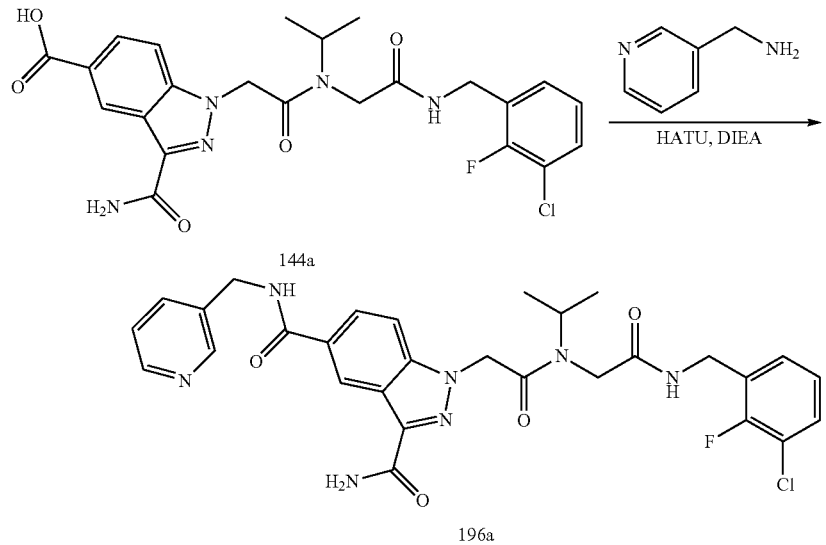

Preparation of 1-(2-((2-((3-chloro-2-fluorobenzyl)amino)-2-oxoethyl)(isopropyl)amino)-2-oxoethyl)-N5-(pyridin-3-ylmethyl)-1H-indazole-3,5-dicarboxamide (196a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with pyridin-3-ylmethanamine (0.015 mL, 0.15 mmol) according to the procedure reported in step-3 of Scheme 2 gave after workup and purification by flash column chromatography [silica (4 g), eluting with MeOH in DCM (1:0 to 9:1)] 1-(2-((2-((3-chloro-2-fluorobenzyl)amino)-2-oxoethyl)(isopropyl)amino)-2-oxoethyl)-N5-(pyridin-3-ylmethyl)-1H-indazole-3,5-dicarboxamide (196a) (32 mg, 54%) as a white solid; $^1$H NMR (300 MHz, DMSO-$d_6$) (mixture of two rotamers) δ 9.30-9.21 (m, 1H), 8.83 (t, J=5.7 Hz) and 8.36 (t, J=6.0 Hz) (2t, 1H) 8.78-8.74 (m, 1H), 8.61-8.55 (m, 1H), 8.46 (dt, J=4.8, 1.6 Hz, 1H), -continued

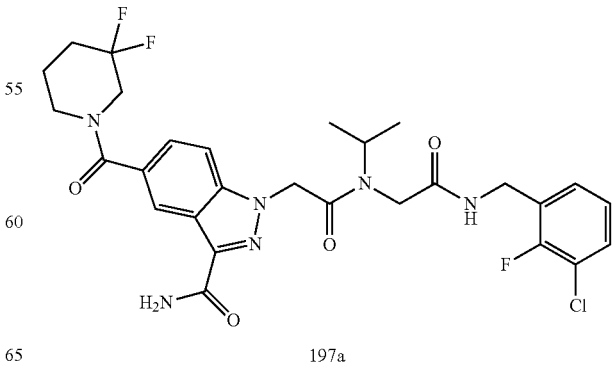

197a

Preparation of 1-(2-((2-((3-chloro-2-fluorobenzyl)amino)-2-oxoethyl)(isopropyl)amino)-2-oxoethyl)-5-(3,3-difluoropiperidine-1-carbonyl)-1H-indazole-3-carboxamide (197a)

Reaction of 3-carbamoyl-1-(2-((2-((3-chloro-2-fluorobenzyl)amino)-2-oxoethyl)(isopropyl)amino)-2-oxoethyl)-1H-indazole-5-carboxylic acid (144a) (50 mg, 0.1 mmol) with 3,3-difluoropiperidine hydrochloride (24 mg, 0.15 mmol) according to the procedure reported in step-3 of Scheme 2 gave after workup and purification by flash column chromatography [silica (8 g), eluting with MeOH in DCM (1:0 to 19:1)] 1-(2-((2-((3-chloro-2-fluorobenzyl)amino)-2-oxoethyl)(isopropyl)amino)-2-oxoethyl)-5-(3,3-difluoropiperidine-1-carbonyl)-1H-indazole-3-carboxamide (197a) (43 mg, 71%) as a white solid; $^1$H NMR (300 MHz, DMSO-$d_6$) δ 8.84 (t, J=5.8 Hz) and 8.37 (t, J=5.9 Hz) (2t, 1H), 8.21 (bs, 1H), 7.82 and 7.80 (2s, 1H), 7.74-7.58 (m, 1H), 7.55-6.96 (m, 5H), 5.64 and 5.50 (2s, 2H), 4.63-4.49 and 4.29-4.212 (m, 1H), 4.46 (d, J=5.6 Hz) and 4.31 (d, J=5.8 Hz) (2d, 2H), 4.18 and 3.84 (2s, 2H), 4.10-3.20 (m, 4H), 2.21-2.02 (m, 2H), 1.71 (bs, 2H), 1.24 (d, J=6.4 Hz) and 0.99 (d, J=6.8 Hz) (2d, 6H); MS (ES+): 607.6 & 609.6 (M+1).

workup and purification by flash column [silica (40 g), eluting with DMA80 in DCM 0 to 30%] methyl 3-carbamoyl-1-(2-((2-((3-chloro-2-fluorobenzyl)amino)-2-oxoethyl)(cyclopropyl)amino)-2-oxoethyl)-1H-indazole-5-carboxylate (198a) (4.23 g, 8.20 mmol, 73% yield) as a white solid; $^1$H NMR (300 MHz, DMSO-$d_6$) δ 8.91-8.84 (m, 1H), 8.50 (t, J=5.8 Hz, 1H), 7.97 (dd, J=8.9, 1.6 Hz, 1H), 7.90 (s, 1H), 7.80-7.73 (m, 1H), 7.60-7.53 (m, 1H), 7.50-7.41 (m, 1H), 7.26-7.17 (m, 1H), 7.15-7.05 (m, 1H), 5.72 (s, 2H), 4.33 (d, J=5.7 Hz, 2H), 3.98 (s, 2H), 3.90 (s, 3H), 3.14-3.01 (m, 1H), 1.06-0.97 (m, 2H), 0.96-0.86 (m, 2H); $^{19}$F NMR (282 MHz, DMSO-$d_6$) δ −121.56; MS (ES+) 516.4 (M+1); (ES−) 514.3 (M−1).

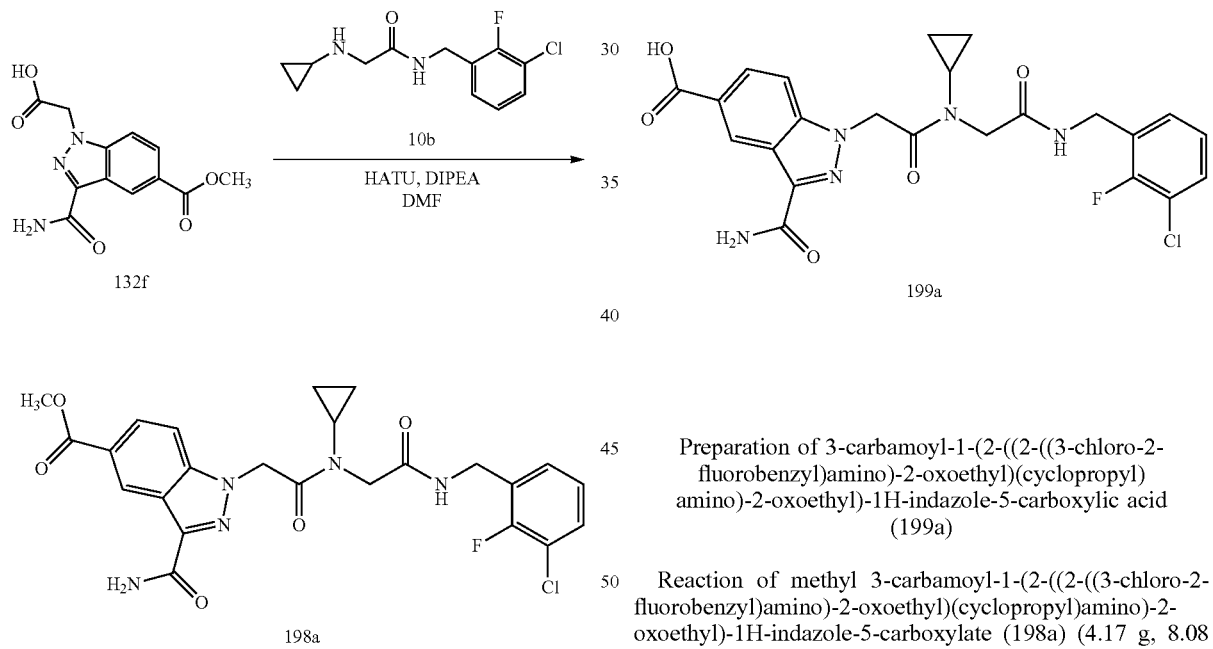

Preparation of methyl 3-carbamoyl-1-(2-((2-((3-chloro-2-fluorobenzyl)amino)-2-oxoethyl)(cyclopropyl)amino)-2-oxoethyl)-1H-indazole-5-carboxylate (198a)

Reaction of 2-(3-carbamoyl-5-(methoxycarbonyl)-1H-indazol-1-yl)acetic acid, TFA adduct (132f) (4.38 g, 11.19 mmol) with N-(3-chloro-2-fluorobenzyl)-2-(isopropylamino)acetamide (19c) (3.22 g, 12.54 mmol) according to the procedure reported in step-3 of Scheme 2 gave after Preparation of 3-carbamoyl-1-(2-((2-((3-chloro-2-fluorobenzyl)amino)-2-oxoethyl)(cyclopropyl)amino)-2-oxoethyl)-1H-indazole-5-carboxylic acid (199a)

Reaction of methyl 3-carbamoyl-1-(2-((2-((3-chloro-2-fluorobenzyl)amino)-2-oxoethyl)(cyclopropyl)amino)-2-oxoethyl)-1H-indazole-5-carboxylate (198a) (4.17 g, 8.08 mmol) in THF (50 mL) and water (50 mL) using a solution of lithium hydroxide hydrate (2.37 g, 56.6 mmol) in water (20 mL) according to the procedure reported in step-2 of Scheme 29 gave after workup 3-carbamoyl-1-(2-((2-((3-chloro-2-fluorobenzyl)amino)-2-oxoethyl)(cyclopropyl)amino)-2-oxoethyl)-1H-indazole-5-carboxylic acid (199a) (4.06 g, 8.09 mmol, 100% yield) as a white solid, which was used in the next step without further purification; $^1$H NMR (300 MHz, DMSO-$d_6$) δ 12.84 (s, 1H), 8.89-8.81 (m, 1H), 8.56 (t, J=5.9 Hz, 1H), 8.01-7.91 (m, 1H), 7.87 (s, 1H), 7.79-7.70 (m, 1H), 7.53 (s, 1H), 7.50-7.41 (m, 1H), 7.28-7.19 (m, 1H), 7.14-7.05 (m, 1H), 5.72 (s, 2H), 4.33 (d, J=5.7 Hz, 2H), 3.99 (s, 2H), 3.12-2.99 (m, 1H), 1.11-0.98 (m, 2H), 0.98-0.84 (m, 2H); $^{19}$F NMR (282 MHz, DMSO-$d_6$) δ −121.58; MS (ES+): 502.5 (M+1); (ES−): 501.5 (M−1).

Scheme 200
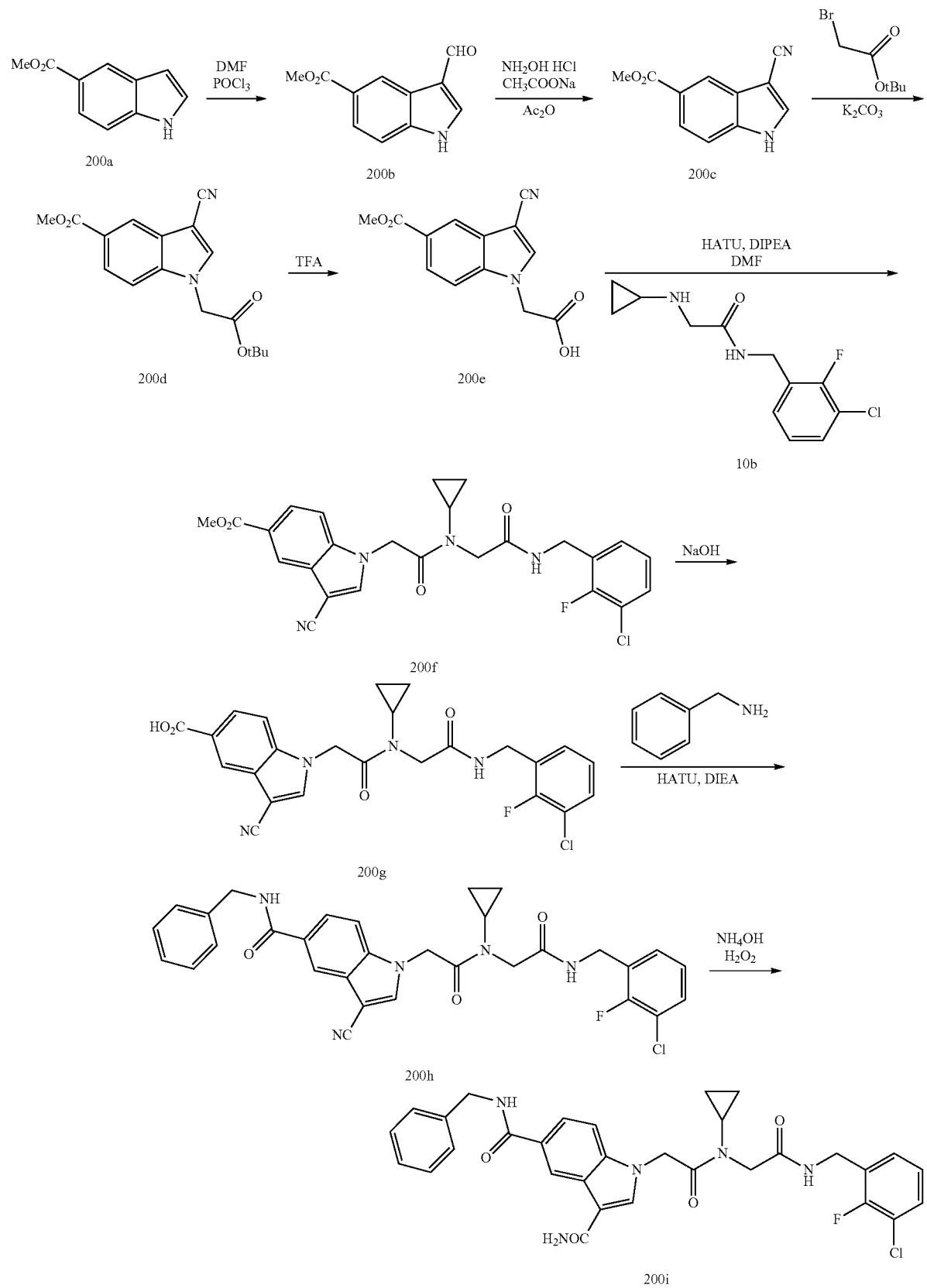

Preparation of N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200i)

Step-1: Preparation of methyl 3-formyl-1H-indole-5-carboxylate (200b)

To a solution of methyl 1H-indole-5-carboxylate (200a) (4 g, 22.83 mmol) in DMF (36 mL) cooled to 0° C. was added phosphoryl trichloride (2.87 mL, 31.1 mmol) and stirred at RT for 2 h. The reaction mixture was quenched with water (130 mL) refluxed for 15 min, cooled to RT and solid obtained was collected by filtration, washed with water, hexanes, dried under vacuum to give methyl 3-formyl-1H-indole-5-carboxylate (200b) (4.38 g, 94%) as a light brown solid; $^1$H NMR (300 MHz, DMSO-$d_6$) δ 12.45 (s, 1H), 9.98 (s, 1H), 8.77 (dd, J=1.7, 0.7 Hz, 1H), 8.45 (s, 1H), 7.88 (dd, J=8.6, 1.8 Hz, 1H), 7.61 (dd, J=8.6, 0.7 Hz, 1H), 3.87 (s, 3H); MS (ES+): 204.2 (M+1).

Step-2: Preparation of methyl 3-cyano-1H-indole-5-carboxylate (200c)

To a solution of methyl 3-formyl-1H-indole-5-carboxylate (200b) (1.02 g, 5 mmol), hydroxylamine hydrochloride (556 mg, 8 mmol), and sodium acetate (451 mg, 5.5 mmol) in acetic acid (7.5 mL) was added acetic anhydride (1.0 mL, 10.6 mmol) and heated at reflux for 6.5 h. The reaction mixture was diluted with ice-water, solid separated was collected by filtration, washed with water, dried under vacuum to give methyl 3-cyano-1H-indole-5-carboxylate (200c) (856 mg, 86%) as a brown solid; $^1$H NMR (300 MHz, DMSO-$d_6$) δ 12.57 (s, 1H), 8.42 (s, 1H), 8.25 (dd, J=1.7, 0.7 Hz, 1H), 7.89 (dd, J=8.6, 1.6 Hz, 1H), 7.66 (dd, J=8.6, 0.7 Hz, 1H), 3.88 (s, 3H); MS (ES+): 223.3 (M+Na).

Step-3: Preparation of methyl 1-(2-(tert-butoxy)-2-oxoethyl)-3-cyano-1H-indole-5-carboxylate (200d)

Reaction of methyl 3-cyano-1H-indole-5-carboxylate (200c) (800 mg, 4.0 mmol) with tert-butyl 2-bromoacetate (0.89 mL, 5.99 mmol) according to the procedure reported in step-1 of Scheme 56 gave after workup methyl 1-(2-(tert-butoxy)-2-oxoethyl)-3-cyano-1H-indole-5-carboxylate (200d) (1.29 g, 4 mmol) which was used as such for next step; MS (ES$^+$): 337.4 (M+Na).

Step-4: Preparation of 2-(3-cyano-5-(methoxycarbonyl)-1H-indol-1-yl)acetic acid (200e)

Reaction of methyl 1-(2-(tert-butoxy)-2-oxoethyl)-3-cyano-1H-indole-5-carboxylate (200d) from above (1.27 g) with TFA (4.55 mL, 59.1 mmol) according to the procedure reported in step-2 of Scheme 2 gave after workup 2-(3-cyano-5-(methoxycarbonyl)-1H-indol-1-yl)acetic acid (200e) which was used as such in next step; MS (ES+): 281.3 (M+Na).

Step-5: Preparation of methyl 1-(2-((2-((3-chloro-2-fluorobenzyl)amino)-2-oxoethyl)(cyclopropyl)amino)-2-oxoethyl)-3-cyano-1H-indole-5-carboxylate (200f)

Reaction of 2-(3-cyano-5-(methoxycarbonyl)-1H-indol-1-yl)acetic acid (200e) (crude from above, 4 mmol) with N-(3-chloro-2-fluorobenzyl)-2-(cyclopropylamino)acetamide (10b) (1.21 g, 4.73 mmol) according to the procedure reported in step-3 of Scheme 2 gave after workup and purification by flash column [silica (12 g), eluting with hexanes/10% MeOH in EtOAc (1:0 to 1:1)] methyl 1-(2-((2-((3-chloro-2-fluorobenzyl)amino)-2-oxoethyl)(cyclopropyl)amino)-2-oxoethyl)-3-cyano-1H-indole-5-carboxylate (200f) (446 mg, 23% yield for three steps) as an off white solid; $^1$H NMR (300 MHz, DMSO-$d_6$) δ 8.46 (t, J=5.8 Hz, 1H), 8.34 (s, 1H), 8.26-8.23 (m, 1H), 7.87 (dd, J=8.8, 1.6 Hz, 1H), 7.72-7.66 (m, 1H), 7.50-7.41 (m, 1H), 7.25-7.18 (m, 1H), 7.12-7.04 (m, 1H), 5.53 (s, 2H), 4.34 (d, J=5.7 Hz, 2H), 3.98 (s, 2H), 3.89 (s, 3H), 3.18-3.00 (m, 1H), 1.03-0.85 (m, 4H); $^{19}$F NMR (282 MHz, DMSO-$d_6$) δ −121.57; MS (ES+): 497.5 (M+1); MS (ES−): 495.5 & 497.5 (M−1).

Step-6: Preparation of 1-(2-((2-((3-chloro-2-fluorobenzyl)amino)-2-oxoethyl)(cyclopropyl)amino)-2-oxoethyl)-3-cyano-1H-indole-5-carboxylic acid (200 g)

Reaction of methyl 1-(2-((2-((3-chloro-2-fluorobenzyl)amino)-2-oxoethyl)(cyclopropyl)amino)-2-oxoethyl)-3-cyano-1H-indole-5-carboxylate (200f) (429 mg, 0.863 mmol) in MeOH (30 mL) using 2 N aqueous NaOH (2.59 mL, 5.18 mmol) according to the procedure reported in step-4 of scheme 43 gave after workup 1-(2-((2-((3-chloro-2-fluorobenzyl)amino)-2-oxoethyl)(cyclopropyl)amino)-2-oxoethyl)-3-cyano-1H-indole-5-carboxylic acid (200 g) (371 mg, 89% yield) as an off-white solid; $^1$H NMR (300 MHz, DMSO-$d_6$) δ 8.46 (t, J=5.8 Hz, 1H), 8.31 (s, 1H), 8.24-8.21 (m, 1H), 7.86 (dd, J=8.7, 1.6 Hz, 1H), 7.67 (d, J=8.7 Hz, 1H), 7.45 (td, J=7.6, 1.8 Hz, 1H), 7.27-7.17 (m, 1H), 7.09 (td, J=7.9, 1.0 Hz, 1H), 5.52 (s, 2H), 4.34 (d, J=5.7 Hz, 2H), 3.98 (s, 2H), 3.18-3.00 (m, 1H), 1.09-0.79 (m, 4H); $^{19}$F NMR (282 MHz, DMSO-$d_6$) δ −121.56; MS (ES−): 517.4 & 519.5 (M+Cl).

Step-7: Preparation of N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200 h)

Reaction of 1-(2-((2-((3-chloro-2-fluorobenzyl)amino)-2-oxoethyl)(cyclopropyl)amino)-2-oxoethyl)-3-cyano-1H-indole-5-carboxylic acid (200 g) (100 mg, 0.21 mmol) with phenylmethanamine (0.034 mL, 0.31 mmol) according to the procedure reported in step-3 of Scheme 2 gave after workup and purification by flash column [silica (12 g), eluting DCM/MeOH (1:0 to 19:1)] N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200 h) as a light brown gum; MS (ES−): 606.6 (M+Cl).

Step-8: Preparation of N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200i)

Reaction of N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200 h) (132 mg) in ethanol (4 mL) using conc. NH$_4$OH (1.5 mL) and H$_2$O$_2$ (aq. 35%, 0.066 mL, 0.74 mmol) according to the procedure reported in Scheme 65 gave after workup and purification by flash column chromatography [silica (4 g), eluting with DCM/MeOH (1:0 to 19:1)] N-benzyl-1-(2-((2-((3-chloro-2-fluorobenzyl)amino)-2-oxoethyl)(cyclopropyl)amino)-2-oxoethyl)-3-cyano-1H-indole-5-carboxamide (200i) (56 mg, 51% for two steps) as a white solid; $^1$H NMR (300 MHz, DMSO-d$_6$) δ 8.99 (t, J=6.0 Hz, 1H), 8.71 (d, J=1.8 Hz, 1H), 8.47 (t, J=5.8 Hz, 1H), 8.01 (s, 1H), 7.71 (dd, J=8.7, 1.7 Hz, 1H), 7.54-6.87 (m, 11H), 5.42 (s, 2H), 4.50 (d, J=6.0 Hz, 2H), 4.34 (d, J=5.7 Hz, 2H), 3.99 (s, 2H), 3.15-3.02 (m, 1H), 1.06-0.82 (m, 4H); $^{19}$F NMR (282 MHz, DMSO-d$_6$) δ −121.61; MS (ES+): 590.7 & 592.6 (M+1); MS (ES−): 624.5 & 626.6 (M+Cl).

Prepared according to the procedure reported by Altmann, Eva et al; in PCT Int. Appl., WO 2012/093101) with N-(3-chloro-2-fluorobenzyl)-2-(cyclopropylamino)acetamide (10b) (7.10 g, 27.7 mmol) according to the procedure reported in step-3 of Scheme 2 gave after workup and trituration of crude with EtOAc, methyl 3-acetyl-1-(2-((2-((3-chloro-2-fluorobenzyl)amino)-2-oxoethyl)(cyclopropyl)amino)-2-oxoethyl)-1H-indole-6-carboxylate (201b) (8.17 g, 57%) as an off-white; $^1$H NMR (300 MHz, DMSO-d$_6$) δ 8.55-8.43 (m, 2H), 8.27 (dd, J=8.4, 0.7 Hz, 1H), 8.15 (dd, J=1.5, 0.7 Hz, 1H), 7.82 (dd, J=8.4, 1.4 Hz, 1H), 7.48-7.36 (m, 1H), 7.26-7.16 (m, 1H), 7.04 (td, J=7.9, 1.1 Hz, 1H), 5.57 (s, 2H), 4.35 (d, J=5.8 Hz, 2H), 3.99 (s, 2H), 3.82 (s, 3H), 3.20-3.05 (m, 1H), 2.45 (s, 3H), 1.08-0.80 (m, 4H); $^{19}$F NMR (282 MHz, DMSO-d$_6$) δ −121.72; MS (ES+): 514.5 & 516.5 (M+1).

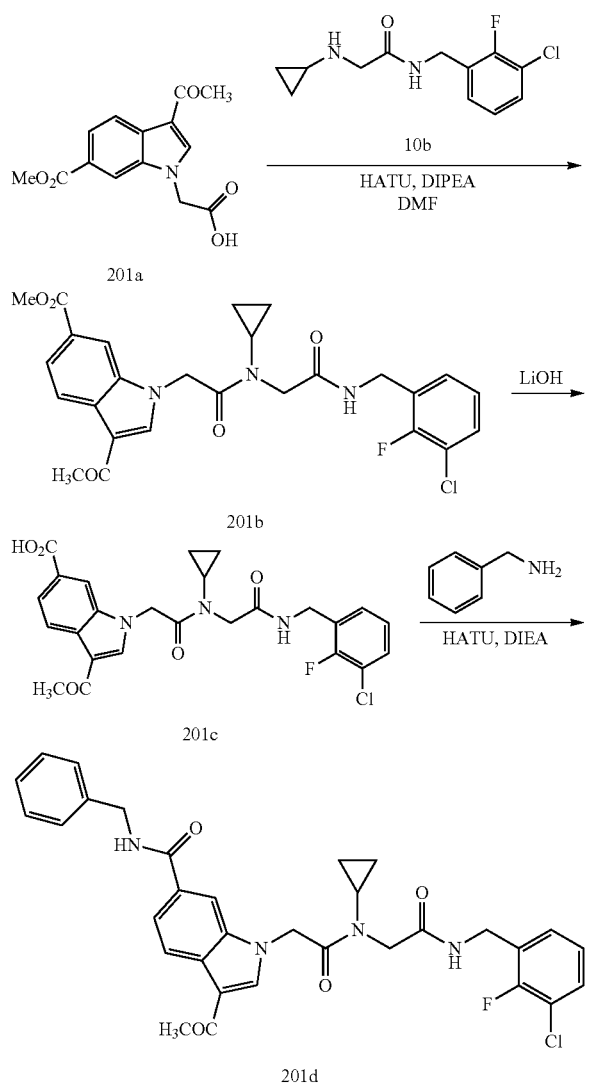

Scheme 201

Preparation of 3-acetyl-N-benzyl-1-(2-((2-((3-chloro-2-fluorobenzyl)amino)-2-oxoethyl)(cyclopropyl)amino)-2-oxoethyl)-1H-indole-6-carboxamide (201d)

Step-1: Preparation of methyl 3-acetyl-1-(2-((2-((3-chloro-2-fluorobenzyl)amino)-2-oxoethyl)(cyclopropyl)amino)-2-oxoethyl)-1H-indole-6-carboxylate (201b)

Reaction of 2-(3-acetyl-6-(methoxycarbonyl)-1H-indol-1-yl)acetic acid (201a) TFA adduct (10.77 g, 27.7 mmol, Step-2: Preparation of 3-acetyl-1-(2-((2-((3-chloro-2-fluorobenzyl)amino)-2-oxoethyl)(cyclopropyl)amino)-2-oxoethyl)-1H-indole-6-carboxylic acid (201c)

Reaction of methyl 3-acetyl-1-(2-((2-((3-chloro-2-fluorobenzyl)amino)-2-oxoethyl)(cyclopropyl)amino)-2-oxoethyl)-1H-indole-6-carboxylate (201b) (8 g, 15.57 mmol) in THF (100 mL) and MeOH (100 mL) using a solution of lithium hydroxide hydrate (4 g, 93 mmol) in water (100 mL) according to the procedure reported in step-2 of Scheme 129 gave after workup 3-acetyl-1-(2-((2-((3-chloro-2-fluorobenzyl)amino)-2-oxoethyl)(cyclopropyl)amino)-2-oxoethyl)-1H-indole-6-carboxylic acid (201c) (8.012 g) as a light brown solid. $^1$H NMR (300 MHz, DMSO-d$_6$) δ 12.80 (s, 1H), 8.53-8.41 (m, 2H), 8.24 (dd, J=8.4, 0.6 Hz, 1H), 8.15-8.11 (m, 1H), 7.81 (dd, J=8.3, 1.4 Hz, 1H), 7.45 (td, J=7.7, 7.2, 1.7 Hz, 1H), 7.27-7.17 (m, 1H), 7.08 (td, J=7.9, 1.0 Hz, 1H), 5.55 (s, 2H), 4.34 (d, J=5.8 Hz, 2H), 3.99 (s, 2H), 3.20-3.06 (m, 1H), 2.45 (s, 3H), 1.08-0.82 (m, 4H); $^{19}$F NMR (282 MHz, DMSO-d$_6$) δ −121.66; MS (ES+): 522.5 & 524.5 (M+Na).

Step-3: Preparation of 3-acetyl-N-benzyl-1-(2-((2-((3-chloro-2-fluorobenzyl)amino)-2-oxoethyl)(cyclopropyl)amino)-2-oxoethyl)-1H-indole-6-carboxamide (201d)

Reaction of 3-acetyl-1-(2-((2-((3-chloro-2-fluorobenzyl)amino)-2-oxoethyl)(cyclopropyl)amino)-2-oxoethyl)-1H-indole-6-carboxylic acid (201c) (50 mg, 0.1 mmol) with phenylmethanamine (0.017 mL, 0.15 mmol) according to the procedure reported in step-3 of Scheme 2 gave after workup and purification by flash column [silica (4 g), eluting DCM/MeOH (1:0 to 19:1)] 3-acetyl-N-benzyl-1-(2-((2-((3-chloro-2-fluorobenzyl)amino)-2-oxoethyl)(cyclopropyl)amino)-2-oxoethyl)-1H-indole-6-carboxamide (201d) (31 mg, 53%) as a light yellow solid. $^1$H NMR (300 MHz, DMSO-d$_6$) δ 8.96 (t, J=6.0 Hz, 1H), 8.54 (t, J=5.8 Hz, 1H), 8.42 (s, 1H), 8.22 (d, J=8.3 Hz, 1H), 8.02 (s, 1H), 7.78 (dd, J=8.4, 1.4 Hz, 1H), 7.47-7.39 (m, 1H), 7.34-7.15 (m, 6H), 7.04 (t, J=7.9 Hz, 1H), 5.52 (s, 2H), 4.50 (d, J=5.9 Hz, 2H), 4.30 (d, J=5.8 Hz, 2H), 4.01 (s, 2H), 3.22-3.02 (m, 1H), 2.45 (s, 3H), 1.05-0.80 (m, 4H); $^{19}$F NMR (282 MHz, DMSO-d$_6$) δ −121.58; MS (ES+): 589.6 (M+1); MS (ES−): 623.5 & 625.5 (M+Cl).

Scheme 202

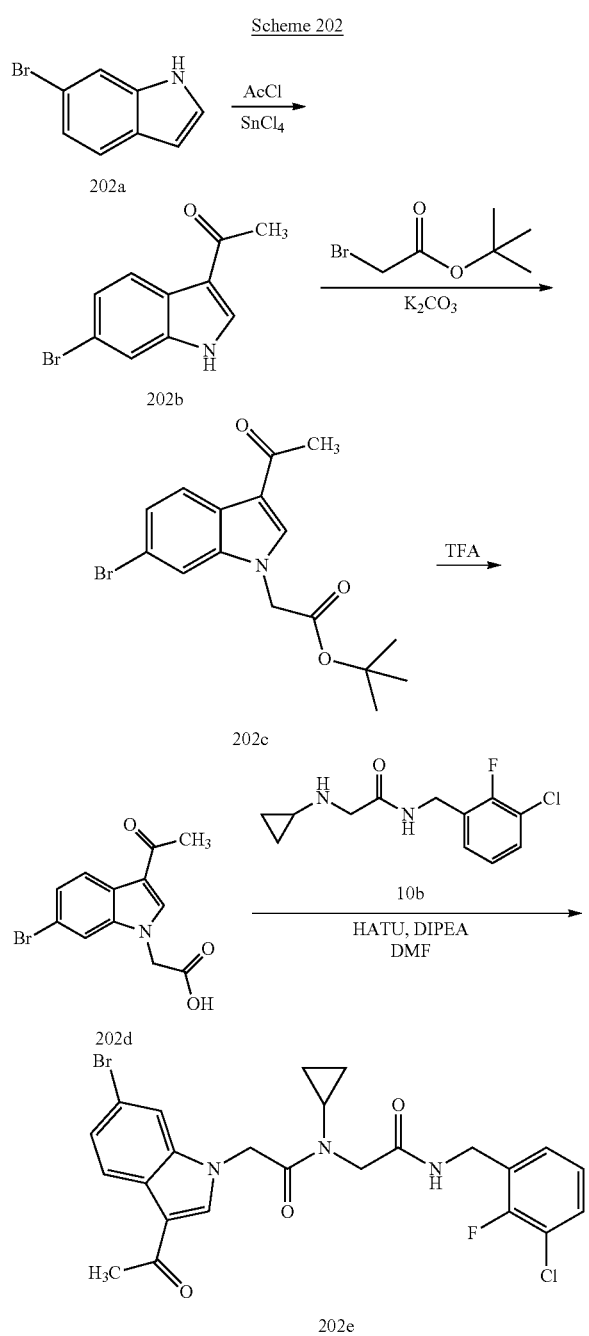

Preparation of 2-(3-acetyl-6-bromo-1H-indol-1-yl)-
N-(2-((3-chloro-2-fluorobenzyl)amino)-2-oxoethyl)-
N-cyclopropylacetamide (202e)

Step-1: Preparation of 1-(6-bromo-1H-indol-3-yl)
ethanone (202b)

To a solution of 6-bromo-1H-indole (202a) (5 g, 25.5 mmol) in toluene (80 mL) at 0° C. under inert atmosphere was added acetyl chloride (2.72 mL, 38.3 mmol), stirred for 10 mins followed by dropwise addition of Tin(IV) chloride (4.49 mL, 38.3 mmol) in toluene (20 mL). The reaction mixture was stirred at 0° C. for 3 h in ice-water bath and the pink fine suspension was poured into a bi-phasic layer of aqueous saturated NaHCO$_3$ (600 mL) and EtOAc (400 mL). The mixture was stirred vigorously for 15 min and filtered over Celite pad to remove inorganic impurities. The organic layer was separated washed with brine, dried, filtered and concentrated in vacuum to afford 1-(6-bromo-1H-indol-3-yl)ethanone (202b) (4.15 g, 17.43 mmol, 68% yield) as a white solid; $^1$H NMR (300 MHz, DMSO-d$_6$) δ 12.04 (s, 1H), 8.34 (d, J=1.6 Hz, 1H), 8.10 (dd, J=8.5, 0.6 Hz, 1H), 7.65 (dd, J=1.8, 0.6 Hz, 1H), 7.31 (dd, J=8.5, 1.8 Hz, 1H), 2.44 (s, 3H); MS (ES+): 238.2, 240.2 (M+2); MS (ES−): 236.1, 238.1 (M−2).

Step-2: Preparation of tert-butyl 2-(3-acetyl-6-
bromo-1H-indol-1-yl)acetate (202c)

Reaction of 1-(6-bromo-1H-indol-3-yl)ethanone (202b) (4 g, 16.8 mmol) with tert-butyl 2-bromoacetate (4.97 mL, 33.6 mmol) according to the procedure reported in step-1 of Scheme 56 gave after workup and trituration of crude with 20% EtOAc-hexane (40 mL), tert-butyl 2-(3-acetyl-6-bromo-1H-indol-1-yl)acetate (202c) (4.49 g, 12.75 mmol, 76% yield) as a white solid; $^1$H NMR (300 MHz, DMSO-d$_6$) δ 8.34 (s, 1H), 8.11 (dd, J=8.5, 0.5 Hz, 1H), 7.82 (dd, J=1.8, 0.5 Hz, 1H), 7.36 (dd, J=8.5, 1.7 Hz, 1H), 5.14 (s, 2H), 2.43 (s, 3H), 1.44 (s, 9H); MS (ES+): 352.3, 354.3 (M+2), MS (ES−): 386.2, 388.2 (M+Cl).

Step-3: Preparation of 2-(3-acetyl-6-bromo-1H-
indol-1-yl)acetic acid (202d)

Reaction of tert-butyl 2-(3-acetyl-6-bromo-1H-indol-1-yl)acetate (202c) (1.5 g, 4.26 mmol) with TFA (6.56 mL, 85 mmol) according to the procedure reported in step-2 of Scheme 2 gave after workup and trituration of crude with 20% EtOAc-hexane (10 mL), 2-(3-acetyl-6-bromo-1H-indol-1-yl)acetic acid (202d) TFA adduct (1.25 g, 4.22 mmol, 99% yield) as an off-white solid; III NMR (300 MHz, DMSO-d$_6$) δ 13.26 (s, 1H, D$_2$O exchangeable), 8.36 (s, 1H), 8.10 (dd, J=8.5, 0.5 Hz, 1H), 7.86 (dd, J=1.8, 0.5 Hz, 1H), 7.36 (dd, J=8.5, 1.7 Hz, 1H), 5.15 (s, 2H), 2.43 (s, 3H); MS (ES+): 296.2, 298.3 (M+2); MS (ES−); 294.2, 296.2 (M−2).

Step-4: Preparation of 2-(3-acetyl-6-bromo-1H-
indol-1-yl)-N-(2-((3-chloro-2-fluorobenzyl)amino)-
2-oxoethyl)-N-cyclopropylacetamide (202e)

Reaction of 2-(3-acetyl-6-bromo-1H-indol-1-yl)acetic acid (202d) (600 mg, 2.03 mmol) with N-(3-chloro-2-fluorobenzyl)-2-(cyclopropylamino)acetamide (10b) (572 mg, 2.23 mmol) according to the procedure reported in step-3 of Scheme 2 gave after workup and purification by flash column [silica gel (24 g), eluting with DMA80-DCM 0 to 20%] 2-(3-acetyl-6-bromo-1H-indol-1-yl)-N-(2-((3-chloro-2-fluorobenzyl)amino)-2-oxoethyl)-N-cyclopropylacetamide (202e) (0.78 g, 1.46 mmol, 72% yield) as a white solid; $^1$H NMR (300 MHz, DMSO-d$_6$) δ 8.47 (t, J=5.9 Hz, 1H), 8.30 (s, 1H), 8.10 (d, J=8.4 Hz, 1H), 7.80 (d, J=1.7 Hz, 1H), 7.49-7.41 (m, 1H), 7.34 (dd, J=8.5, 1.7 Hz, 1H), 7.28-7.19 (m, 1H), 7.09 (td, J=7.9, 1.1 Hz, 1H), 5.45 (s, 2H), 4.35 (d, J=5.8 Hz, 2H), 3.99 (s, 2H), 3.16-3.04 (m, 1H), 2.42 (s, 3H), 1.05-0.96 (m, 2H), 0.95-0.85 (m, 2H); $^{19}$F NMR (282 MHz, DMSO-d$_6$) δ −121.66; MS (ES+) 534.4, 536.4 (M+1); MS (ES−): 570.3 (M+Cl).

Scheme 203

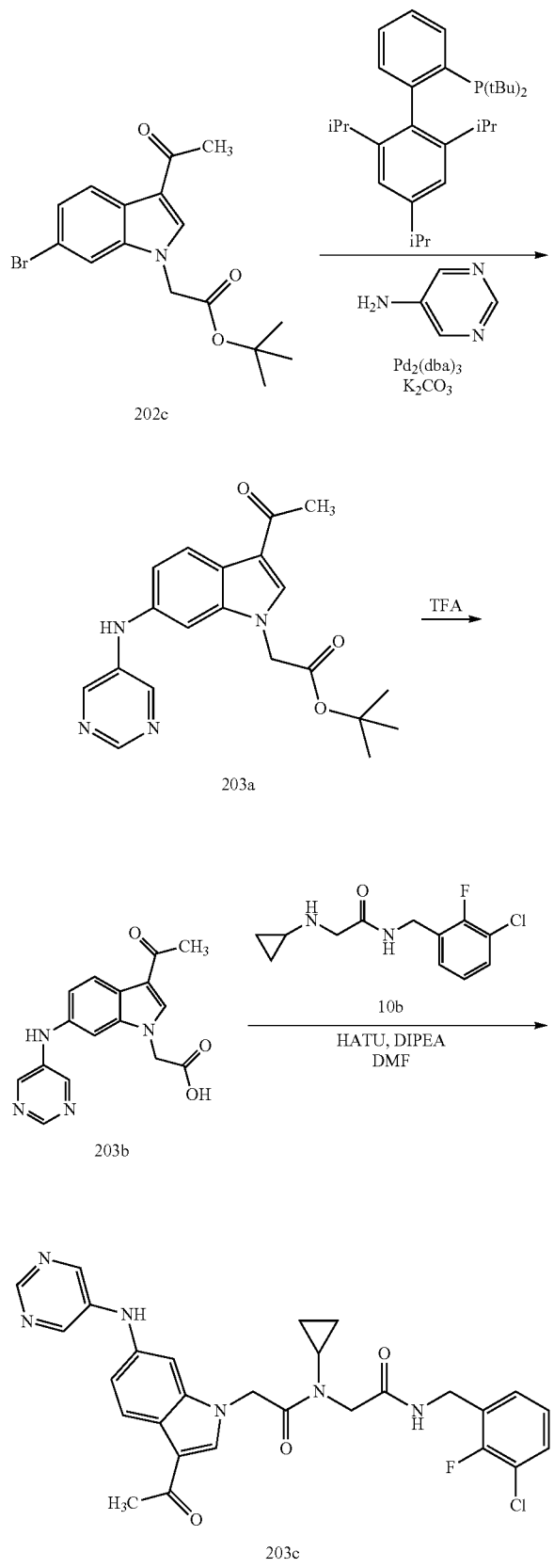

Preparation of 2-(3-acetyl-6-(pyrimidin-5-ylamino)-1H-indol-1-yl)-N-(2-((3-chloro-2-fluorobenzyl)amino)-2-oxoethyl)-N-cyclopropylacetamide (203c)

Step-1: Preparation of tert-butyl 2-(3-acetyl-6-(pyrimidin-5-ylamino)-1H-indol-1-yl)acetate (203a)

Reaction of tert-butyl 2-(3-acetyl-6-bromo-1H-indol-1-yl)acetate (202c) (1.0 g, 2.84 mmol) with pyrimidin-5-amine (351 mg, 3.69 mmol) using potassium carbonate (785 mg, 5.68 mmol), di-tert-butyl(2',4',6'-triisopropylbiphenyl-2-yl)phosphine (169 mg, 0.4 mmol), $Pd_2(dba)_3$ (182 mg, 0.2 mmol) according to the procedure reported in step-1 of Scheme 97 gave after workup and purification by flash column [silica gel (40 g), eluting with DMA80-DCM 0 to 20%] tert-butyl 2-(3-acetyl-6-(pyrimidin-5-ylamino)-1H-indol-1-yl)acetate (203a) (72 mg, 1.96 mmol, 69% yield) as an off-white solid; $^1$H NMR (300 MHz, DMSO-$d_6$) δ 8.60 (s, 1H), 8.59 (s, 1H), 8.55 (s, 2H), 8.21 (s, 1H), 8.09 (d, J=8.5 Hz, 1H), 7.26 (d, J=1.9 Hz, 1H), 7.02 (dd, J=8.5, 1.9 Hz, 1H), 5.76 (s, 1H), 5.10 (s, 2H), 2.42 (s, 3H), 1.43 (s, 9H); MS (ES+) 367.5 (M+1); MS (ES−): 365.4 (M−1).

Step-2: Preparation of 2-(3-acetyl-6-(pyrimidin-5-ylamino)-1H-indol-1-yl)acetic acid (203b)

Reaction of tert-butyl 2-(3-acetyl-6-(pyrimidin-5-ylamino)-1H-indol-1-yl)acetate (203a) (530 mg, 1.45 mmol) with TFA (1.47 mL, 19.05 mmol) according to the procedure reported in step-2 of Scheme 2 gave after workup and trituration of crude with 30% EtOAc-hexane (10 mL), 2-(3-acetyl-6-(pyrimidin-5-ylamino)-1H-indol-1-yl)acetic acid (203b) TFA adduct (470 mg, 1.11 mmol, 77% yield) as an orange solid; $^1$H NMR (300 MHz, DMSO-$d_6$) δ 8.60 (s, 1H), 8.55 (s, 2H), 8.23 (s, 1H), 8.09 (d, J=8.5 Hz, 1H), 7.30 (d, J=1.9 Hz, 1H), 7.03 (dd, J=8.5, 2.0 Hz, 1H), 5.11 (s, 2H), 2.42 (s, 3H).

Step-3: Preparation of 2-(3-acetyl-6-(pyrimidin-5-ylamino)-1H-indol-1-yl)-N-(2-((3-chloro-2-fluorobenzyl)amino)-2-oxoethyl)-N-cyclopropylacetamide (203c)

Reaction of N-(3-chloro-2-fluorobenzyl)-2-(cyclopropylamino)acetamide (10b) (66 mg, 0.26 mmol) with 2-(3-acetyl-6-(pyrimidin-5-ylamino)-1H-indol-1-yl)acetic acid (203b) (80 mg, 0.26 mmol) according to the procedure reported in step-3 of Scheme 2 gave after workup and purification by flash column chromatography [silica gel (12 g), eluting with DMA80-DCM 0 to 30%] 2-(3-acetyl-6-(pyrimidin-5-ylamino)-1H-indol-1-yl)-N-(2-((3-chloro-2-fluorobenzyl)amino)-2-oxoethyl)-N-cyclopropylacetamide (203c) (65 mg, 0.12 mmol, 46% yield) as an off-white solid; $^1$H NMR (300 MHz, DMSO-$d_6$) δ 8.56 (s, 1H), 8.53 (s, 1H), 8.51 (s, 2H), 8.44 (t, J=5.9 Hz, 1H), 8.21 (s, 1H), 8.09 (d, J=8.5 Hz, 1H), 7.43 (td, J=7.7, 7.2, 1.7 Hz, 1H), 7.27-7.17 (m, 2H), 7.14-6.98 (m, 2H), 5.41 (s, 2H), 4.31 (d, J=5.7 Hz, 2H), 3.98 (s, 2H), 3.12-2.98 (m, 1H), 2.41 (s, 3H), 1.01-0.94 (m, 2H), 0.94-0.86 (m, 2H); 19F NMR (282 MHz, DMSO-$d_6$) δ −121.62; MS (ES+): 549.5 (M+1), 571.5 (M+Na), MS (ES−): 547.5 (M−1).

Scheme 204

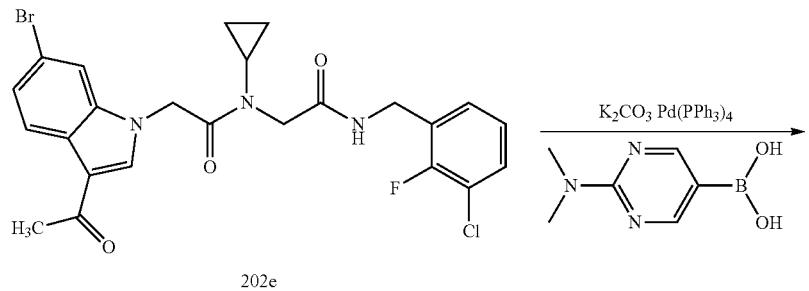

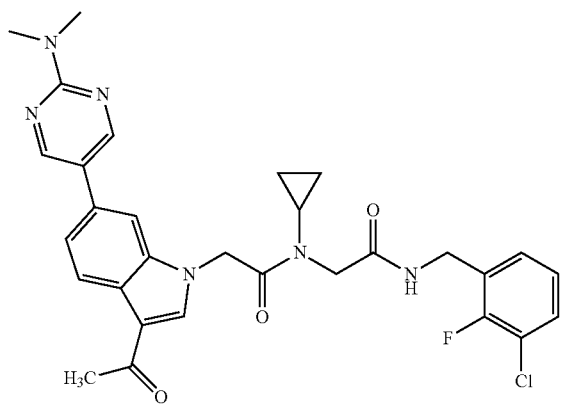

Preparation of 2-(3-acetyl-6-(2-(dimethylamino)pyrimidin-5-yl)-1H-indol-1-yl)-N-(2-((3-chloro-2-fluorobenzyl)amino)-2-oxoethyl)-N-cyclopropylacetamide (204a)

Reaction of 2-(3-acetyl-6-bromo-1H-indol-1-yl)-N-(2-((3-chloro-2-fluorobenzyl)amino)-2-oxoethyl)-N-cyclopropylacetamide (202e) (150 mg, 0.28 mmol) with 2-(dimethylamino)pyrimidin-5-ylboronic acid (56 mg, 0.34 mmol) according the procedure reported in Scheme 100 gave after workup and purification by flash column chromatography [silica gel (12 g), eluting with CMA80 in CHCl$_3$ 0 to 20%] 2-(3-acetyl-6-(2-(dimethylamino)pyrimidin-5-yl)-1H-indol-1-yl)-N-(2-((3-chloro-2-fluorobenzyl)amino)-2-oxoethyl)-N-cyclopropylacetamide (204a) (85 mg, 0.15 mmol, 53% yield) as a white solid; $^1$H NMR (300 MHz, DMSO-d$_6$) δ 8.73 (s, 2H), 8.51 (t, J=5.9 Hz, 1H), 8.29 (s, 1H), 8.19 (d, J=8.3 Hz, 1H), 7.69 (bs, 1H), 7.49 (dd, J=8.3, 1.5 Hz, 1H), 7.39-7.30 (m, 1H), 7.24-7.16 (m, 1H), 6.97-6.86 (m, 1H), 5.49 (s, 2H), 4.36 (d, J=5.8 Hz, 2H), 4.01 (s, 2H), 3.19-3.11 (m, 7H), 2.44 (s, 3H), 1.03-0.96 (m, 2H), 0.96-0.88 (m, 2H); $^{19}$F NMR (282 MHz, DMSO-d$_6$) δ -121.72; MS (ES+): 577.5 (M+1); MS (ES-): 611.4 (M+Cl).

Scheme 205

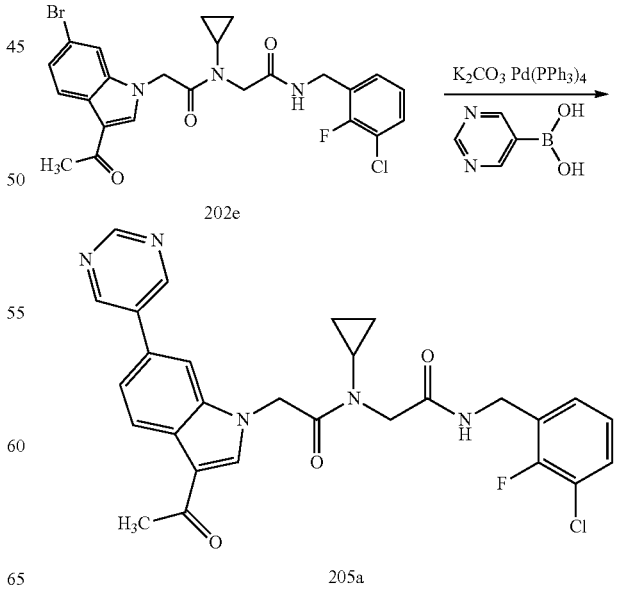

Preparation of 2-(3-acetyl-6-(pyrimidin-5-yl)-1H-indol-1-yl)-N-(2-((3-chloro-2-fluorobenzyl)amino)-2-oxoethyl)-N-cyclopropylacetamide (205a)

Reaction of 2-(3-acetyl-6-bromo-1H-indol-1-yl)-N-(2-((3-chloro-2-fluorobenzyl)amino)-2-oxoethyl)-N-cyclopropylacetamide (202e) (150 mg, 0.28 mmol) with pyrimidin-5-ylboronic acid (42 mg, 0.34 mmol) according the procedure reported in Scheme 100 gave after workup and purification by flash column chromatography [silica gel (12 g), eluting with CMA80 in CHCl$_3$ 0 to 20%] 2-(3-acetyl-6-(pyrimidin-5-yl)-1H-indol-1-yl)-N-(2-((3-chloro-2-fluorobenzyl)amino)-2-oxoethyl)-N-cyclopropylacetamide (205a) (60 mg, 0.11 mmol, 40% yield) as a white solid; $^1$H NMR (300 MHz, DMSO-d$_6$) δ 9.18 (s, 2H), 9.12 (s, 1H), 8.51 (t, J=5.9 Hz, 1H), 8.38 (s, 1H), 8.29 (d, J=8.3 Hz, 1H), 7.92 (d, J=1.6 Hz, 1H), 7.67 (dd, J=8.3, 1.6 Hz, 1H), 7.34 (td, J=7.7, 7.2, 1.7 Hz, 1H), 7.21-7.12 (m, 1H), 6.88 (td, J=7.9, 1.1 Hz, 1H), 5.54 (s, 2H), 4.35 (d, J=5.7 Hz, 2H), 4.01 (s, 2H), 3.23-3.11 (m, 1H), 2.46 (s, 3H), 1.05-0.97 (m, 2H), 0.97-0.90 (m, 2H); $^{19}$F NMR (282 MHz, DMSO-d$_6$) δ −121.60; MS (ES+): 534.5 (M+1), MS (ES−): 532.4 (M−1), 568.4 (M+Cl).

Scheme 206

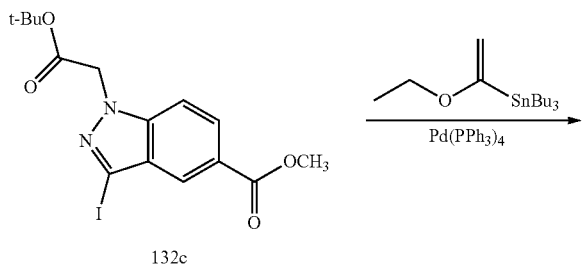

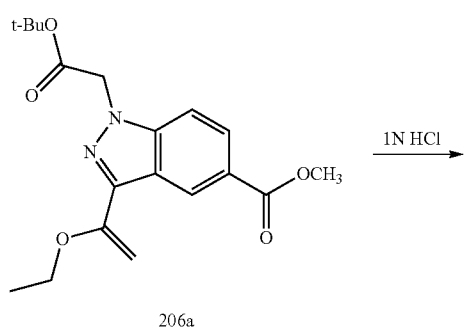

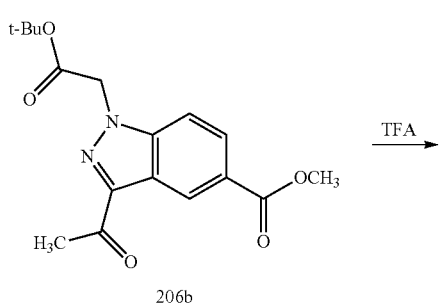

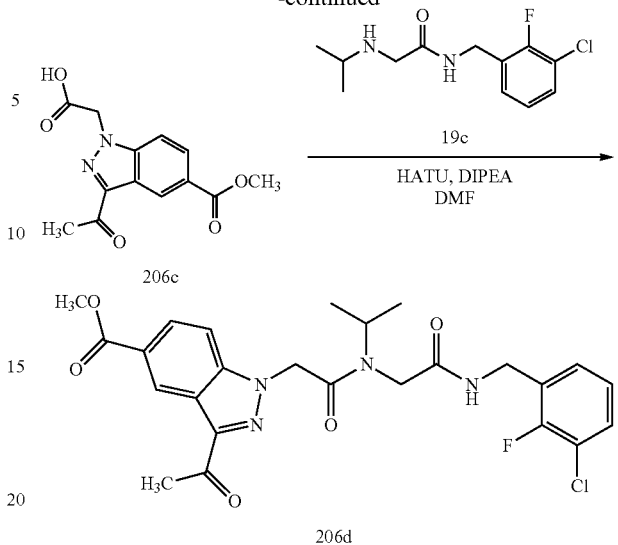

Preparation of methyl 3-acetyl-1-(2-((2-((3-chloro-2-fluorobenzyl)amino)-2-oxoethyl)(isopropyl)amino)-2-oxoethyl)-1H-indazole-5-carboxylate (206d)

Step-1: Preparation of methyl 1-(2-(tert-butoxy)-2-oxoethyl)-3-(1-ethoxyvinyl)-1H-indazole-5-carboxylate (206a)

To a solution of methyl 1-(2-(tert-butoxy)-2-oxoethyl)-3-iodo-1H-indazole-5-carboxylate (132c) (9.2 g, 22.10 mmol) in toluene (75 mL) under Argon atmosphere was added tributyl(1-ethoxyvinyl)stannane (9.98 g, 27.6 mmol), Pd(Ph$_3$P)$_4$ (2.55 g, 2.210 mmol) and heated at 120° C. for 15 h. The reaction mixture was cooled to room temperature, diluted with EtOAc (200 mL), filtered through a Celite pad. The filtrate was washed with water, brine, dried and concentrated in vacuum. The residue obtained was purified by chromatography [silica (40 g), eluting with EtOAc in hexane 0 to 40%] to afford methyl 1-(2-(tert-butoxy)-2-oxoethyl)-3-(1-ethoxyvinyl)-1H-indazole-5-carboxylate (206a) (7.5 g, 19.31 mmol, 87% yield) as a yellow oil; $^1$H NMR (300 MHz, DMSO-d$_6$) δ 8.67 (dd, J=1.6, 0.8 Hz, 1H), 7.97 (dd, J=8.9, 1.6 Hz, 1H), 7.73 (dd, J=8.9, 0.8 Hz, 1H), 5.34 (s, 2H), 4.97 (d, J=2.3 Hz, 1H), 4.46 (d, J=2.3 Hz, 1H), 4.03 (q, J=6.9 Hz, 2H), 3.88 (s, 3H), 1.45 (m, 3H), 1.40 (s, 9H), 0.85 (t, J=7.2 Hz, 3H); MS (ES+): 361.5 (M+1), 383.5 (M+Na); MS (ES−): 359.3 (M−1).

Step-2: Preparation of methyl 3-acetyl-1-(2-(tert-butoxy)-2-oxoethyl)-1H-indazole-5-carboxylate (206b)

To a solution of methyl 1-(2-(tert-butoxy)-2-oxoethyl)-3-(1-ethoxyvinyl)-1H-indazole-5-carboxylate (206a) from step-1 in EtOAc (200 mL) was added HCl (1 N, 120 mL) and sonicated for 10 min. The organic phase was separated, dried, concentrated in vacuum to afford methyl 3-acetyl-1-(2-(tert-butoxy)-2-oxoethyl)-1H-indazole-5-carboxylate (206b) (6.2 g, 18.65 mmol, 84% yield over 2 steps) as a white solid, which was used in the next step without further purification; $^1$H NMR (300 MHz, DMSO-d$_6$) δ 8.84 (dd, J=1.6, 0.8 Hz, 1H), 8.06 (dd, J=8.9, 1.6 Hz, 1H), 7.89 (dd, J=8.9, 0.9 Hz, 1H), 5.51 (s, 2H), 3.91 (s, 3H), 2.65 (s, 3H), 1.42 (s, 9H); MS (ES+), 355.4 (M+Na); 331.4 (M−1).

Step-3: Preparation of 2-(3-acetyl-5-(methoxycarbonyl)-1H-indazol-1-yl)acetic acid (206c)

Reaction of methyl 3-acetyl-1-(2-(tert-butoxy)-2-oxoethyl)-1H-indazole-5-carboxylate (206b) (6.1 g, 18.35 mmol) with TFA (7.07 mL, 92 mmol) in DCM (50 mL) according to the procedure reported in step-2 of Scheme 2 gave after workup 2-(3-acetyl-5-(methoxycarbonyl)-1H-indazol-1-yl)acetic acid (206c) (5.8 g, 14.86 mmol, 81% yield) TFA salt as an off white solid, which was used in the next step without further purification; $^1$H NMR (300 MHz, DMSO-$d_6$) δ 13.00 (s, 1H), 8.83 (dd, J=1.7, 0.8 Hz, 1H), 8.08-7.99 (m, 1H), 7.91 (dd, J=8.9, 0.8 Hz, 1H), 5.51 (s, 2H), 3.91 (s, 3H), 2.65 (s, 3H); MS (ES−): 275.3 (M−1)

Step-4: Preparation of methyl 3-acetyl-1-(2-((2-((3-chloro-2-fluorobenzyl)amino)-2-oxoethyl)(isopropyl)amino)-2-oxoethyl)-1H-indazole-5-carboxylate (206d)

Reaction of 2-(3-acetyl-5-(methoxycarbonyl)-1H-indazol-1-yl)acetic acid (206c) TFA adduct (1.9 g, 4.87 mmol) with N-(3-chloro-2-fluorobenzyl)-2-(isopropylamino)acetamide (19c) (1.51 g, 5.84 mmol) according to the procedure reported in step-3 of Scheme 2 gave after workup and purification by flash column [silica (12 g), eluting with DMA80 in DCM 0 to 40%] methyl 3-acetyl-1-(2-((2-((3-chloro-2-fluorobenzyl)amino)-2-oxoethyl)(isopropyl)amino)-2-oxoethyl)-1H-indazole-5-carboxylate (206d) (2.24 g, 4.33 mmol, 89% yield) as a white solid; $^1$H NMR (300 MHz, DMSO-$d_6$) δ 8.89-8.29 (m, 2H), 8.04 (dd, J=8.9, 1.7 Hz) and 7.97 (dd, J=8.9, 1.7 Hz) (2dd, 1H), 7.77 (dd, J=8.9, 0.8 Hz) and 7.70 (dd, J=8.9, 0.8 Hz) (2dd, 1H), 7.56-6.95 (m, 3H), 5.76 and 5.59 (2s, 2H), 4.69-4.23 (m, 3H), 4.18 and 3.85 (2s, 2H), 3.913 and 3.908 (2s, 3H), 2.64 (s, 3H), 1.26 (d, J=6.7 Hz) and 1.00 (d, J=6.8 Hz) (2d, 6H); $^{19}$F NMR (282 MHz, DMSO) δ −121.21, −121.72; MS (ES+): 517.5 (M+1), 539.5 (M+Na); MS (ES−): 515.5 (M−1).

Scheme 207

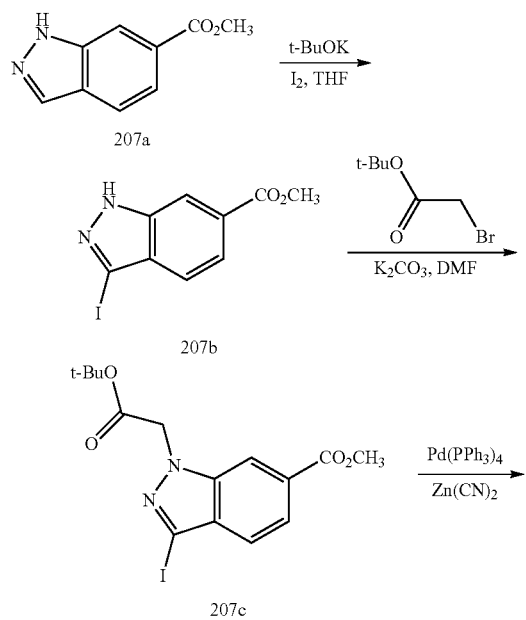

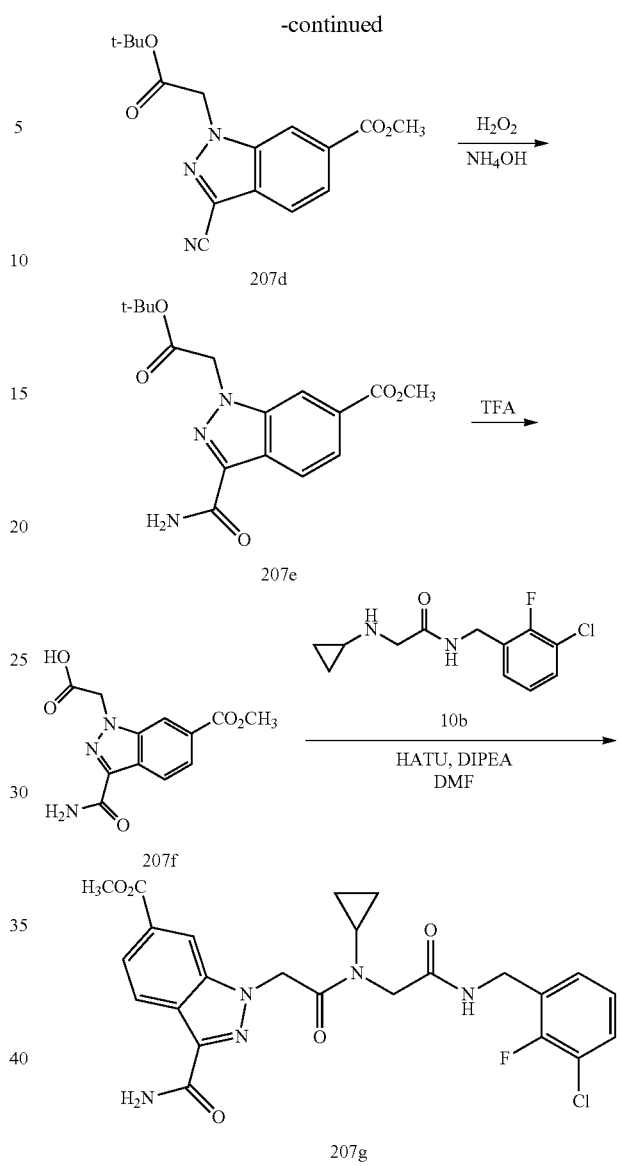

Preparation of methyl 3-carbamoyl-1-(2-((2-((3-chloro-2-fluorobenzyl)amino)-2-oxoethyl)(cyclopropyl)amino)-2-oxoethyl)-1H-indazole-6-carboxylate (207 g)

Step-1: Preparation of methyl 3-iodo-1H-indazole-6-carboxylate (207b)

Compound methyl 3-iodo-1H-indazole-6-carboxylate (207b) was prepared from methyl 1H-indazole-6-carboxylate (15 g, 85 mmol) according to the procedure reported in step-1 of Scheme 132 to furnish product (22 g, 72.8 mmol, 86% yield) as a white solid; $^1$H NMR (300 MHz, DMSO-$d_6$) δ 13.82 (s, 1H, D$_2$O exchangeable), 8.16-8.08 (m, 1H), 7.71 (dd, J=8.6, 1.4 Hz, 1H), 7.53 (dd, J=8.6, 0.8 Hz, 1H), 3.88 (s, 3H); MS (ES+); 303.2 (M+1); MS (ES−): 301.2 (M−1).

Step-2: Preparation of methyl 1-(2-(tert-butoxy)-2-oxoethyl)-3-iodo-1H-indazole-6-carboxylate (207c)

Reaction of methyl 3-iodo-1H-indazole-6-carboxylate (207b) (12 g, 39.7 mmol) with tert-butyl 2-bromoacetate (11.62 g, 59.6 mmol) according to the procedure reported in step-1 of Scheme 56 gave after workup methyl 1-(2-tert-butoxy-2-oxoethyl)-3-iodo-1H-indazole-6-carboxylate (207c) (11.7 g, 28.1 mmol, 71% yield) as an off white solid; $^1$H NMR (300 MHz, DMSO-$d_6$) δ 8.37 (t, J=1.1 Hz, 1H), 7.78 (dd, J=8.5, 1.3 Hz, 1H), 7.56 (dd, J=8.5, 0.8 Hz, 1H), 5.44 (s, 2H), 3.91 (s, 3H), 1.40 (s, 9H); MS (ES+): 439.4 (M+Na).

Step-3: Preparation of methyl 1-(2-(tert-butoxy)-2-oxoethyl)-3-cyano-1H-indazole-6-carboxylate (207d)

A mixture of methyl 1-(2-tert-butoxy-2-oxoethyl)-3-iodo-1H-indazole-6-carboxylate (207c) (10.7 g, 25.7 mmol), zinc (0.336 g, 5.14 mmol), zinc cyanide (3.62 g, 30.8 mmol), Pd$_2$(dba)$_3$, (1.883 g, 2.06 mmol), Xantphos (1.488 g, 2.57 mmol), TMEDA (0.776 mL, 5.14 mmol) in DMF (75 mL) was purged with Argon for 5 mins and heated at 100° C. for 6 h. The reaction mixture was cooled to room temperature, diluted with EtOAc (250 mL), and filtered through Celite, rinsing with EtOAc (2×100 mL). The filtrate was concentrated to dryness and the residue was triturated with MeOH (10 mL). The solid obtained was collected by filtration washed with MeOH (2×3 mL), dried to give methyl 1-(2-tert-butoxy-2-oxoethyl)-3-cyano-1H-indazole-6-carboxylate (207d) (5.28 g, 16.74 mmol, 65.1% yield) as a white solid; $^1$H NMR (300 MHz, DMSO-$d_6$) δ 8.61 (t, J=1.1 Hz, 1H), 8.05 (dd, J=8.6, 0.8 Hz, 1H), 7.95 (dd, J=8.6, 1.3 Hz, 1H), 5.65 (s, 2H), 3.93 (s, 3H), 1.41 (s, 9H); MS (ES+): 338.4 (M+Na); MS (ES−): 314.3 (M−1).

Step-4: Preparation of methyl 1-(2-(tert-butoxy)-2-oxoethyl)-3-carbamoyl-1H-indazole-6-carboxylate (207e)

Reaction of methyl 1-(2-(tert-butoxy)-2-oxoethyl)-3-cyano-1H-indazole-6-carboxylate (207d) (5.18 g, 16.42 mmol) in ethanol (50 mL) using conc. NH$_4$OH (30 mL) and H$_2$O$_2$ (aq. 35%, 10.16 mL, 99 mmol) according to the procedure reported in Scheme 65 gave after workup methyl 1-(2-tert-butoxy-2-oxoethyl)-3-carbamoyl-1H-indazole-6-carboxylate (207e) (3.4 g, 10.18 mmol, 62% yield) as a white solid; $^1$H NMR (300 MHz, DMSO-$d_6$) δ 8.43 (t, J=1.1 Hz, 1H), 8.30 (dd, J=8.6, 0.8 Hz, 1H), 7.90-7.81 (m, 2H), 7.54 (s, 1H), 5.49 (s, 2H), 3.92 (s, 3H), 1.41 (s, 9H); MS (ES+): 333.4 (M+1)

Step-5: Preparation of 2-(3-carbamoyl-6-(methoxycarbonyl)-1H-indazol-1-yl)acetic acid (207f)

Reaction of methyl 1-(2-(tert-butoxy)-2-oxoethyl)-3-carbamoyl-1H-indazole-5-carboxylate (207e) (3.3 g, 9.9 mmol) with TFA (3.81 mL, 49.5 mmol) in DCM (50 mL) according to the procedure reported in step-2 of Scheme 2 gave after workup 2-(3-carbamoyl-6-(methoxycarbonyl)-1H-indazol-1-yl)acetic acid (207f) TFA salt (2.8 g, 7.16 mmol, 72% yield) as a white solid, which was used in the next step without further purification; $^1$H NMR (300 MHz, DMSO-$d_6$) δ 13.37 (s, 1H), 8.47-8.41 (m, 1H), 8.35-8.24 (m, 1H), 7.90-7.80 (m, 2H), 7.54 (s, 1H), 5.50 (s, 2H), 3.91 (s, 3H); MS (ES+): 278.3 (M+1); MS (ES−): 276.2 (M−1).

Step-6: Preparation of methyl 3-carbamoyl-1-(2-((2-((3-chloro-2-fluorobenzyl)amino)-2-oxoethyl)(cyclopropyl)amino)-2-oxoethyl)-1H-indazole-6-carboxylate (207 g)

Reaction of 2-(3-carbamoyl-6-(methoxycarbonyl)-1H-indazol-1-yl)acetic acid (207f) TFA adduct (1.82 g, 4.65 mmol) with N-(3-chloro-2-fluorobenzyl)-2-(cyclopropylamino)acetamide (10b) (1.43 g, 5.58 mmol) according to the procedure reported in step-3 of Scheme 2 gave after workup and purification by flash column [silica (40 g), eluting with DMA80 in DCM 0 to 40%] methyl 3-carbamoyl-1-(2-((2-((3-chloro-2-fluorobenzyl)amino)-2-oxoethyl)(cyclopropyl)amino)-2-oxoethyl)-1H-indazole-6-carboxylate (207 g) (1.6 g, 3.10 mmol, 67% yield) as a yellow solid; $^1$H NMR (300 MHz, DMSO-$d_6$) δ 8.52 (t, J=5.9 Hz, 1H), 8.38 (t, J=1.1 Hz, 1H), 8.29 (dd, J=8.5, 0.8 Hz, 1H), 7.87 (s, 1H), 7.83 (dd, J=8.6, 1.3 Hz, 1H), 7.50 (s, 1H), 7.44 (ddd, J=8.8, 7.3, 1.7 Hz, 1H), 7.21 (td, J=7.3, 6.8, 1.7 Hz, 1H), 7.06 (td, J=7.9, 1.1 Hz, 1H), 5.80 (s, 2H), 4.33 (d, J=5.7 Hz, 2H), 3.99 (s, 2H), 3.88 (s, 3H), 3.17-3.04 (m, 1H), 1.07-0.99 (m, 2H), 0.97-0.88 (m, 2H); $^{19}$F NMR (282 MHz, DMSO-$d_6$) δ −121.65; MS (ES+): 538.5 (M+Na); (ES−): 514.4 (M−1).

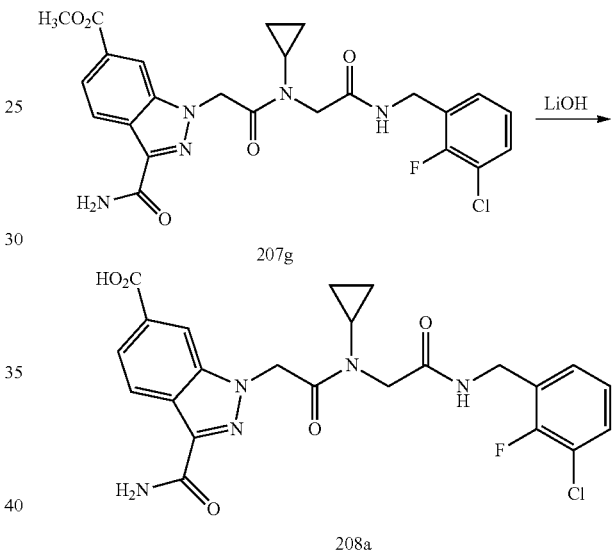

Scheme 208

207g

208a

Preparation of 3-carbamoyl-1-(2-((2-((3-chloro-2-fluorobenzyl)amino)-2-oxoethyl)(cyclopropyl)amino)-2-oxoethyl)-1H-indazole-6-carboxylic acid (208a)

Reaction of methyl 3-carbamoyl-1-(2-((2-((3-chloro-2-fluorobenzyl)amino)-2-oxoethyl)(cyclopropyl)amino)-2-oxoethyl)-1H-indazole-6-carboxylate (207 g) (1.6 g, 3.10 mmol) in MeOH (25 mL) and water (25 mL) with lithium hydroxide hydrate (0.78 g, 18.61 mmol) according to the procedure reported in step-2 of Scheme 129 gave after workup 3-carbamoyl-1-(2-((2-((3-chloro-2-fluorobenzyl)amino)-2-oxoethyl)(cyclopropyl)amino)-2-oxoethyl)-1H-indazole-6-carboxylic acid (208a) (1.3 g, 2.59 mmol, 84% yield) as an off white solid, which was used in the next step without further purification; $^1$H NMR (300 MHz, DMSO-$d_6$) δ 13.18 (s, 1H), 8.52 (t, J=5.8 Hz, 1H), 8.36 (s, 1H), 8.26 (d, J=8.5 Hz, 1H), 7.95-7.76 (m, 2H), 7.58-7.39 (m, 2H), 7.34-7.18 (m, 1H), 7.09 (t, J=7.9 Hz, 1H), 5.79 (s, 2H), 4.33 (d, J=5.7 Hz, 2H), 3.99 (s, 2H), 3.14-2.98 (m, 1H), 1.09-0.97 (m, 2H), 0.97-0.83 (m, 2H); $^{19}$F NMR (282 MHz, DMSO-$d_6$) δ −121.60; MS (ES+): 502.4 (M+1); MS (ES−) 500.4 (M−1).

Scheme 209

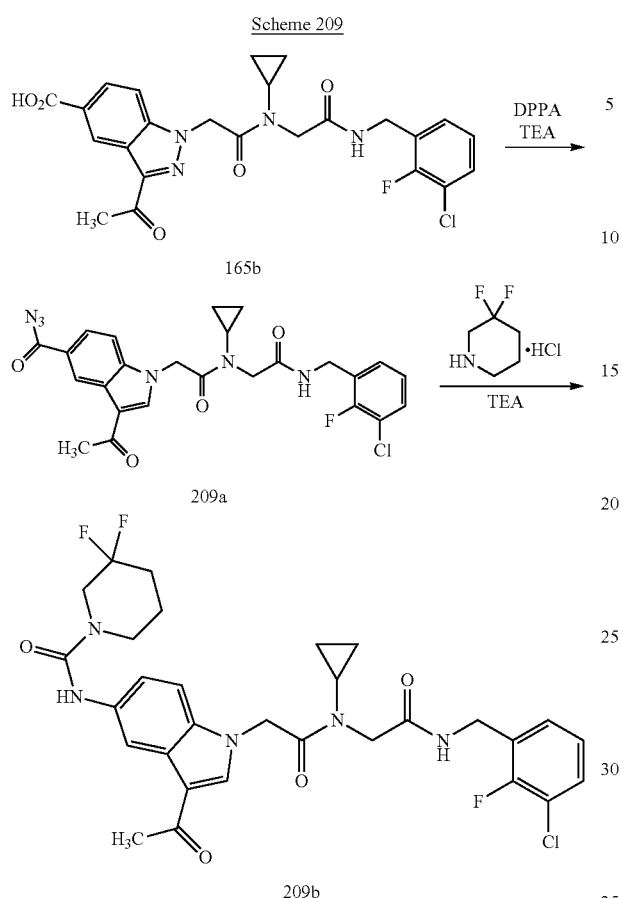

Preparation of N-(3-acetyl-1-(2-((2-((3-chloro-2-fluorobenzyl)amino)-2-oxoethyl)(cyclopropyl)amino)-2-oxoethyl)-1H-indol-5-yl)-3,3-difluoropiperidine-1-carboxamide (209b)

Step-1: Preparation of 3-acetyl-1-(2-((2-((3-chloro-2-fluorobenzyl)amino)-2-oxoethyl)(cyclopropyl)amino)-2-oxoethyl)-1H-indole-5-carbonyl azide (209a)

Compound 3-acetyl-1-(2-((2-((3-chloro-2-fluorobenzyl)amino)-2-oxoethyl)(cyclopropyl)amino)-2-oxoethyl)-1H-indole-5-carbonyl azide (209a) was prepared from 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (1.8 g, 3.60 mmol) according to the procedure reported in step-3 of Scheme 129 to afford product; MS (ES−): 523.4 (M−1).

Step-2: Preparation of N-(3-acetyl-1-(2-((2-((3-chloro-2-fluorobenzyl)amino)-2-oxoethyl)(cyclopropyl)amino)-2-oxoethyl)-1H-indol-5-yl)-3,3-difluoropiperidine-1-carboxamide (209b)

Compound (209b) was prepared from 3-acetyl-1-(2-((2-((3-chloro-2-fluorobenzyl)amino)-2-oxoethyl)(cyclopropyl)amino)-2-oxoethyl)-1H-indole-5-carbonyl azide (209a) (200 mg, 0.38 mmol) and 3,3-difluoropiperidine hydrochloride (120 mg, 0.76 mmol) using TEA (0.21 mL, 1.51 mmol) as base according to the procedure reported in step-4 of Scheme 129 to afford after workup and purification by column chromatography [silica gel (12 g), eluting with DMA80 in DCM 0 to 40%] (45 mg, 0.073 mmol, 19%) as a white solid; $^1$H NMR (300 MHz, DMSO-$d_6$) δ 8.65 (s, 1H), 8.47 (t, J=5.8 Hz, 1H), 8.21 (s, 1H), 8.19 (s, 1H), 7.45 (t, J=7.6 Hz, 1H), 7.41-7.28 (m, 2H), 7.24 (t, J=7.1 Hz, 1H), 7.12 (t, J=7.9 Hz, 1H), 5.39 (s, 2H), 4.35 (d, J=5.7 Hz, 2H), 4.00 (s, 2H), 3.81 (t, J=12.1 Hz, 2H), 3.52 (t, J=5.3 Hz, 2H), 3.17-2.97 (m, 1H), 2.41 (s, 3H), 2.16-1.94 (m, 2H), 1.79-1.59 (m, 2H), 1.04-0.88 (m, 4H); $^{19}$F NMR (282 MHz, DMSO-$d_6$) δ −101.12, −121.63; MS (ES+): 618.6 (M+1); MS (ES−): 616.5 (M−1).

Scheme 210

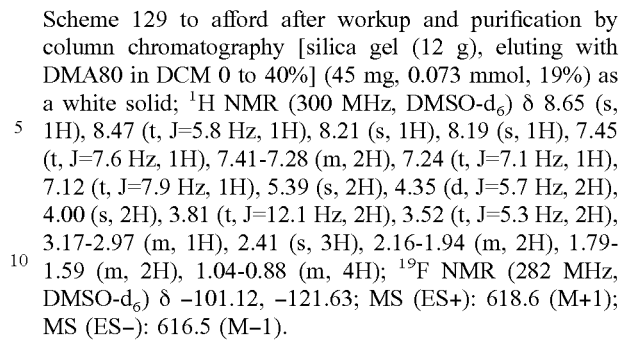

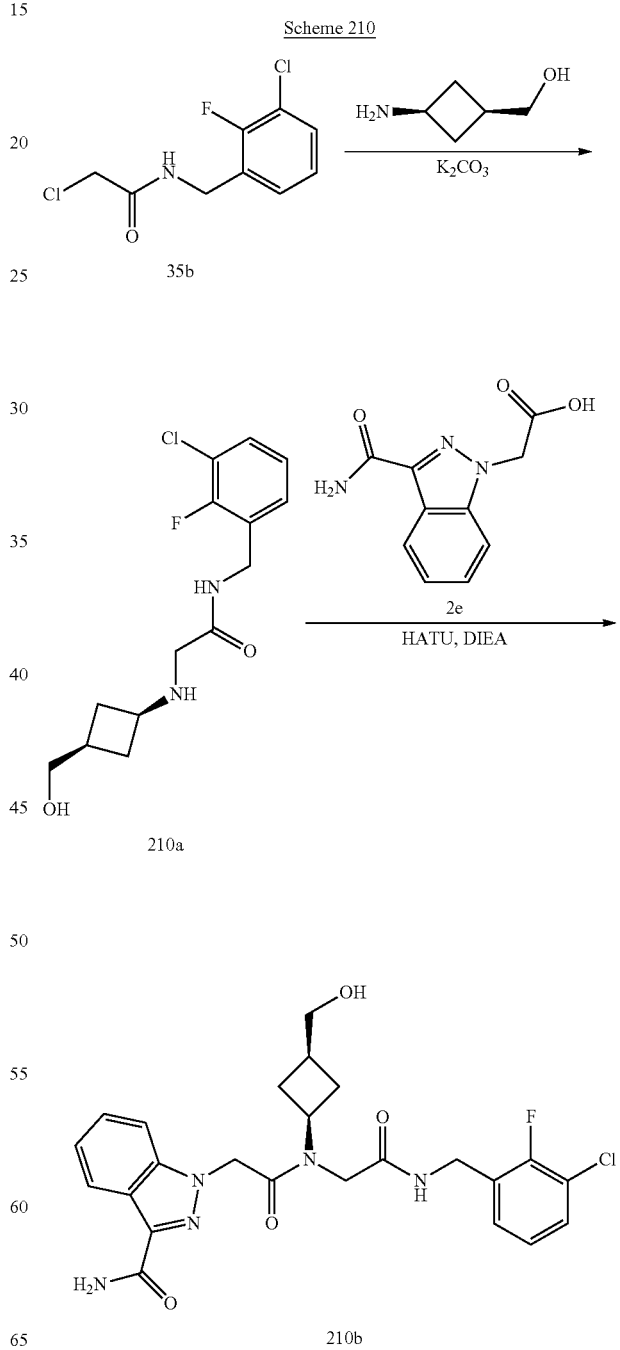

389

Preparation of 1-(2-((2-((3-chloro-2-fluorobenzyl)amino)-2-oxoethyl)((cis)-3-(hydroxymethyl)cyclobutyl)amino)-2-oxoethyl)-1H-indazole-3-carboxamide (210b)

Step-1: Preparation of N-(3-chloro-2-fluorobenzyl)-2-(((cis)-3-(hydroxymethyl)cyclobutyl)amino)acetamide (210a)

Reaction of 2-chloro-N-(3-chloro-2-fluorobenzyl)acetamide (35b) (300 mg, 1.27 mmol) with ((cis)-3-aminocyclobutyl)methanol hydrochloride (262 mg, 1.91 mmol) according to the procedure reported in step-2 of Scheme 35 gave after workup N-(3-chloro-2-fluorobenzyl)-2-(((cis)-3-(hydroxymethyl)cyclobutyl)amino)acetamide (210a) a an oil which was used in the next step without further purification; MS (ES+): 301.4 (M+1); MS (ES−): 299.4 (M−1).

Step-2: Preparation of 1-(2-((2-((3-chloro-2-fluorobenzyl)amino)-2-oxoethyl)((cis)-3-(hydroxymethyl)cyclobutyl)amino)-2-oxoethyl)-1H-indazole-3-carboxamide (210b)

Reaction of N-(3-chloro-2-fluorobenzyl)-2-(((cis)-3-(hydroxymethyl)cyclobutyl)amino)acetamide (210a) (169 mg, 0.56 mmol) with 2-(3-carbamoyl-1H-indazol-1-yl)acetic acid (2e) (123 mg, 0.56 mmol) according to the procedure reported in step-3 of Scheme 2 gave after workup and purification by flash column chromatography [silica (12 g), eluting with MeOH in DCM 0 to 30%] 1-(2-((2-((3-chloro-2-fluorobenzyl)amino)-2-oxoethyl)((cis)-3-(hydroxymethyl)cyclobutyl)amino)-2-oxoethyl)-1H-indazole-3-carboxamide (210b) (53 mg, 0.11 mmol, 19% yield) as a white solid as a mixture of two rotamers; $^1$H NMR (300 MHz, DMSO-$d_6$) δ 8.89 (t, J=5.8 Hz) & 8.42 (t, J=5.9 Hz) (2t, 1H), 8.23-8.13 (m, 1H), 7.70 (s, 1H), 7.62-7.00 (m, 7H), 5.56 & 5.40 (2s, 2H), 4.59 & 4.52 (t, J=5.2 Hz) (2t, 1H, D$_2$O exchangeable), 4.55-4.37 (m, 1H), 4.47 (d, J=6.2 Hz) & 4.34 (d, J=5.9 Hz) (2d, 2H), 4.28 & 4.01 (2s, 2H), 3.43-3.28 (m, 2H), 2.34-1.66 (m, 5H); $^{19}$F NMR (282 MHz, DMSO-$d_6$) δ −121.25, −121.66; MS (ES+): 502.5 (M+1), 524.5, 526.5 (M+Na); MS (ES−): 500.4 (M−1), 536.4 (M+Cl).

390

-continued

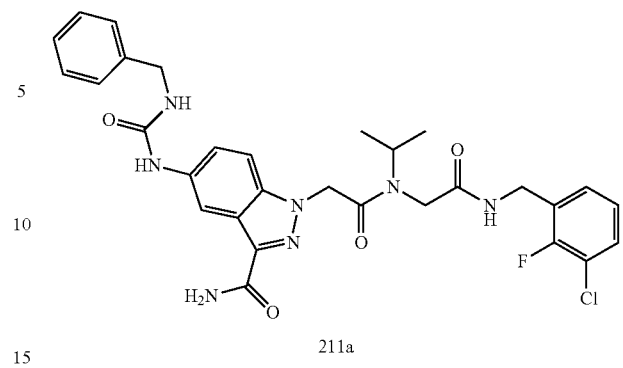

211a

Preparation of 5-(3-benzylureido)-1-(2-((2-((3-chloro-2-fluorobenzyl)amino)-2-oxoethyl)(isopropyl)amino)-2-oxoethyl)-1H-indazole-3-carboxamide (211a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (150 mg, 0.284 mmol) in toluene (15 mL) with phenylmethanamine (60.8 mg, 0.567 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] 5-(3-benzylureido)-1-(2-((2-((3-chloro-2-fluorobenzyl)amino)-2-oxoethyl)(isopropyl)amino)-2-oxoethyl)-1H-indazole-3-carboxamide (211a) (11 mg, 0.018 mmol, 6% yield) as a white solid; $^1$H NMR (300 MHz, DMSO-$d_6$) (a mixture of two rotamers) δ 8.81 (t, J=5.7 Hz) and 8.36 (t, J=5.9 Hz) (2t, 1H), 8.74-8.64 (m, 1H), 8.24 and 8.20 (2s, 1H), 7.63-7.54 (m, 1H), 7.52-6.99 (m, 11H), 6.58 (t, J=5.7 Hz, 1H), 5.52 and 5.39 (2s, 2H), 4.61-4.23 (m, 5H), 4.17 and 3.83 (2s, 2H), 1.21 (d, J=6.5 Hz) and 0.98 (d, J=6.8 Hz) (2d, 6H); $^{19}$F NMR (282 MHz, DMSO-$d_6$) δ −121.23, −121-76; MS (ES+): 608.6 (M+1); MS (ES−): 606.6 (M−1).

Scheme 212

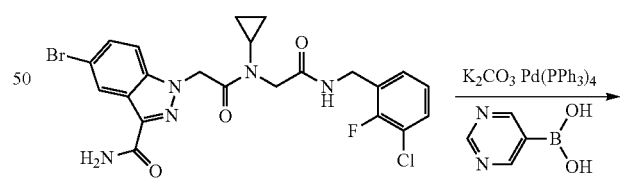

140a

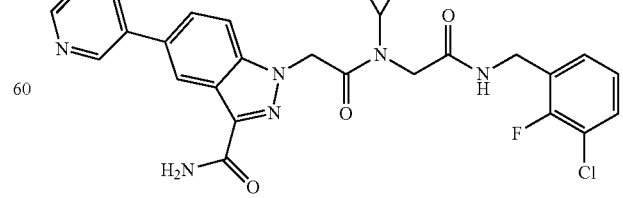

212a

Scheme 211

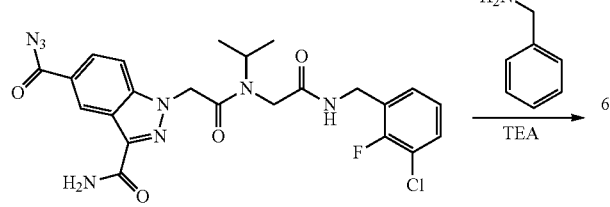

145a

Preparation of 1-(2-((2-((3-chloro-2-fluorobenzyl)amino)-2-oxoethyl)(cyclopropyl)amino)-2-oxoethyl)-5-(pyrimidin-5-yl)-1H-indazole-3-carboxamide (212a)

Reaction of 5-bromo-1-(2-((2-((3-chloro-2-fluorobenzyl)amino)-2-oxoethyl)(cyclopropyl)amino)-2-oxoethyl)-1H-indazole-3-carboxamide (140a) (125 mg, 0.23 mmol) with pyrimidin-5-ylboronic acid (32 mg, 0.256 mmol) according the procedure reported in Scheme 100 gave after workup and purification by flash column chromatography [silica gel (12 g), eluting with DMA80-DCM 0 to 30%] 1-(2-((2-((3-chloro-2-fluorobenzyl)amino)-2-oxoethyl)(cyclopropyl)amino)-2-oxoethyl)-5-(pyrimidin-5-yl)-1H-indazole-3-carboxamide (212a) (69 mg, 0.13 mmol, 55% yield) as a white solid; $^1$H NMR (300 MHz, DMSO-$d_6$) δ 9.21 (s, 1H), 9.17 (s, 2H), 8.56-8.44 (m, 2H), 7.89-7.78 (m, 3H), 7.54-7.39 (m, 2H), 7.27-7.19 (m, 1H), 7.17-7.07 (m, 1H), 5.73 (s, 2H), 4.34 (d, J=5.7 Hz, 2H), 4.00 (s, 2H), 3.15-3.02 (m, 1H), 1.08-0.96 (m, 2H), 0.99-0.86 (m, 2H); 19F NMR (282 MHz, DMSO-$d_6$) δ −121.57; MS (ES+): 536.6 (M+1), 558.5 (M+Na); MS (ES−): 534.5 (M−1), 570.5 (M+Cl).

boxamido)-1H-indazole-3-carboxamide (213a) (31 mg, 0.052 mmol, 18% yield) as a white solid; $^1$H NMR (300 MHz, DMSO-$d_6$) (mixture of two rotamers) δ 8.82 (t, J=5.7 Hz) and 8.36 (t, J=5.8 Hz) (2t, 1H), 8.65 (s, 1H), 8.19-8.15 (m, 1H), 7.64-7.01 (m, 7H), 5.53 and 5.39 (2s, 2H), 4.60-4.25 (m, 3H), 4.17 and 3.83 (2s, 2H), 3.50-3.43 (m, 4H), 2.39-2.31 (m, 4H), 2.23 (s, 3H), 1.21 (d, J=6.6 Hz) and 0.98 (d, J=6.8 Hz) (2d, 6H); $^{19}$F NMR (282 MHz, DMSO-$d_6$) δ −121.22, −121.79; MS (ES+): 601.5 (M+1); MS (ES): 599.5 (M−1).

Scheme 213

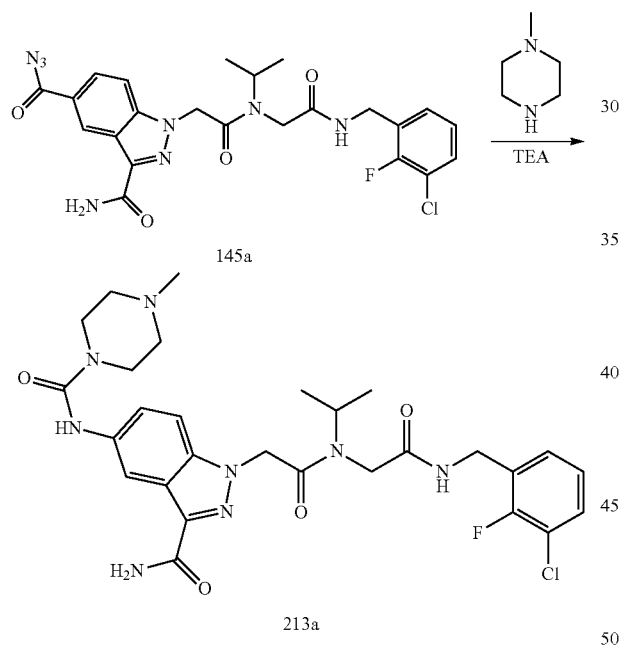

145a

213a

Preparation of 1-(2-((2-((3-chloro-2-fluorobenzyl)amino)-2-oxoethyl)(isopropyl)amino)-2-oxoethyl)-5-(4-methylpiperazine-1-carboxamido)-1H-indazole-3-carboxamide (213a)

Reaction of 3-carbamoyl-1-(2-((2-((3-chloro-2-fluorobenzylamino)-2-oxoethyl)(isopropyl)amino)-2-oxoethyl)-1H-indazole-5-carbonyl azide (145a) (150 mg, 0.284 mmol) in toluene (15 mL) with 1-methylpiperazine (56.8 mg, 0.567 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(4-methylpiperazine-1-car-

Scheme 214

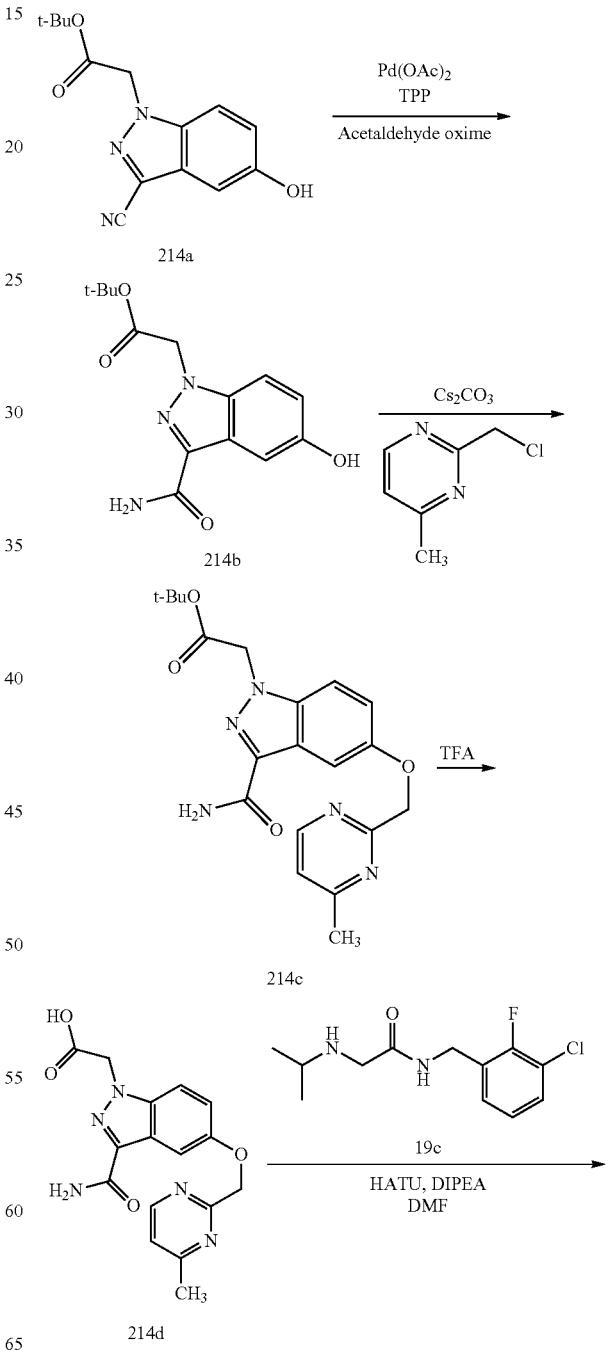

214a

214b

214c

214d

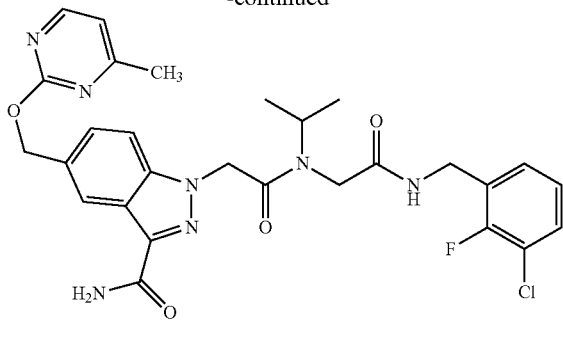

214e

Preparation of 1-(2-((2-((3-chloro-2-fluorobenzyl)amino)-2-oxoethyl)(isopropyl)amino)-2-oxoethyl)-5-((4-methylpyrimidin-2-yl)methoxy)-1H-indazole-3-carboxamide (214e)

Step-1: Preparation of tert-butyl 2-(3-carbamoyl-5-hydroxy-1H-indazol-1-yl)acetate (214b)

A mixture of tert-butyl 2-(3-cyano-5-hydroxy-1H-indazol-1-yl)acetate (214a) (Prepared according to the procedure reported by Altmann, Eva et al; in PCT Int. Appl., WO 2014/002053, 360 mg, 1.32 mmol), palladium(II) acetate (30 mg, 0.13 mmol), triphenylphosphine (69 mg, 0.26 mmol) acetaldehyde oxime (0.16 mL, 2.63 mmol) in ethanol (8 mL) and water (2 mL) was heated to 90° C. for 2 h. The reaction mixture was cooled to room temperature, diluted with EtOAc (50 mL), filtered through a Celite pad and evaporated to dryness. The residue obtained was purified by flash column chromatography [Silica gel, (12 g) eluting with EtOAc in hexanes 0-100%] to afford tert-butyl 2-(3-carbamoyl-5-hydroxy-1H-indazol-1-yl)acetate (214b) (351 mg, 1.21 mmol, 91% yield) as a white solid; $^1$H NMR (300 MHz, DMSO-d$_6$) δ 9.41 (s, 1H), 7.67-7.47 (m, 3H), 7.28 (s, 1H), 6.97 (dd, J=8.9, 2.4 Hz, 1H), 5.26 (s, 2H), 1.41 (s, 9H); MS (ES+): 292.1 (M+1), MS (ES−): 290.3 (M−1).

Step-2: Preparation of tert-butyl 2-(3-carbamoyl-5-((4-methylpyrimidin-2-yl)methoxy)-1H-indazol-1-yl)acetate (214c)

To a solution of tert-butyl 2-(3-carbamoyl-5-hydroxy-1H-indazol-1-yl)acetate (214b) (201 mg, 0.69 mmol) in DMF (5 mL) was added cesium carbonate (0.28 g, 0.863 mmol) and 2-(chloromethyl)-4-methylpyrimidine (108 mg, 0.759 mmol). The reaction mixture was stirred at room temperature for 13 h and quenched with cold water (50 mL). The solid obtained was collected by filtration, washed with water (2×25 mL), dried under reduced pressure over P$_2$O$_5$ to furnish tert-butyl 2-(3-carbamoyl-5-((4-methylpyrimidin-2-yl)methoxy)-1H-indazol-1-yl)acetate (214c) (152 mg, 0.38 mmol, 55% yield) as a white solid; $^1$H NMR (300 MHz, DMSO-d$_6$) δ 8.66 (d, J=5.1 Hz, 1H), 7.67-7.60 (m, 2H), 7.59 (d, J=2.4 Hz, 1H), 7.38-7.32 (m, 2H), 7.20 (dd, J=9.1, 2.4 Hz, 1H), 5.30 (s, 2H), 5.25 (s, 2H), 2.49 (s, 3H), 1.41 (s, 9H); MS (ES+): 398.5 (M+1), 795.9 (2M+1); MS (ES−): 396.4 (M−1).

Step-3: Preparation of 2-(3-carbamoyl-5-((4-methylpyrimidin-2-yl)methoxy)-1H-indazol-1-yl)acetic acid (214d)

Reaction of tert-butyl 2-(3-carbamoyl-5-((4-methylpyrimidin-2-yl)methoxy)-1H-indazol-1-yl)acetate (214c) (138 mg, 0.35 mmol) with TFA (0.54 mL, 6.94 mmol) in DCM (10 mL) according to the procedure reported in step-2 of Scheme 2 gave after workup and trituration with hexanes, 2-(3-carbamoyl-5-((4-methylpyrimidin-2-yl)methoxy)-1H-indazol-1-yl)acetic acid (214d) (148 mg, 0.33 mmol, 94% yield) TFA salt as an off white solid; $^1$H NMR (300 MHz, DMSO-d$_6$) δ 13.4 (bs, 1H), 8.67 (d, J=5.1 Hz, 1H), 7.68-7.62 (m, 2H), 7.58 (d, J=2.4 Hz, 1H), 7.39-7.29 (m, 2H), 7.19 (dd, J=9.1, 2.4 Hz, 1H), 5.31 (s, 2H), 5.26 (s, 2H), 2.49 (s, 3H); MS (ES+): 342.4 (M+1).

Step-4: Preparation of 1-(2-((2-((3-chloro-2-fluorobenzyl)amino)-2-oxoethyl)(isopropyl)amino)-2-oxoethyl)-5-((4-methylpyrimidin-2-yl)methoxy)-1H-indazole-3-carboxamide (214e)

Reaction of 2-(3-carbamoyl-5-((4-methylpyrimidin-2-yl)methoxy)-1H-indazol-1-yl)acetic acid (214d) TFA (103 mg, 0.23 mmol with N-(3-chloro-2-fluorobenzyl)-2-(isopropylamino)acetamide (19c) (70 mg, 0.27 mmol) according to the procedure reported in step-3 of Scheme 2 gave after workup and purification by flash column [silica (12 g), eluting with DMA80 in DCM, 0 to 100%] 1-(2-((2-((3-chloro-2-fluorobenzyl)amino)-2-oxoethyl)(isopropyl)amino)-2-oxoethyl)-5-((4-methylpyrimidin-2-yl)methoxy)-1H-indazole-3-carboxamide (214e) (94 mg, 0.16 mmol, 71% yield) as an off-white solid as a mixture of two rotamers; $^1$H NMR (300 MHz, DMSO-d$_6$) δ 8.82 (t, J=5.7 Hz) & 8.36 (t, J=6.1 Hz) (2t, 1H), 8.67 (d, J=5.1 Hz, 1H), 7.61-6.98 (m, 9H), 5.54 & 5.40 (2s, 2H), 5.26 & 5.25 (2s, 2H), 4.60-4.49 & 4.28-4.22 (2m, 1H), 4.46 (d, J=5.5 Hz) & 4.32 (d, J=5.8 Hz) (2d, 2H), 4.16 & 3.83 (2s, 2H), 2.49 (s, 3H), 1.25 (d) & 0.98 (d, J=6.8 Hz) (2d, 6H); $^{19}$F NMR (282 MHz, DMSO-d$_6$) δ −121.22, −121.76; MS (ES+): 582.6 & 584.6 (M+1), 604.6, 606.6 (M+Na); MS (ES−): 580.5 (M−1).

Scheme 215

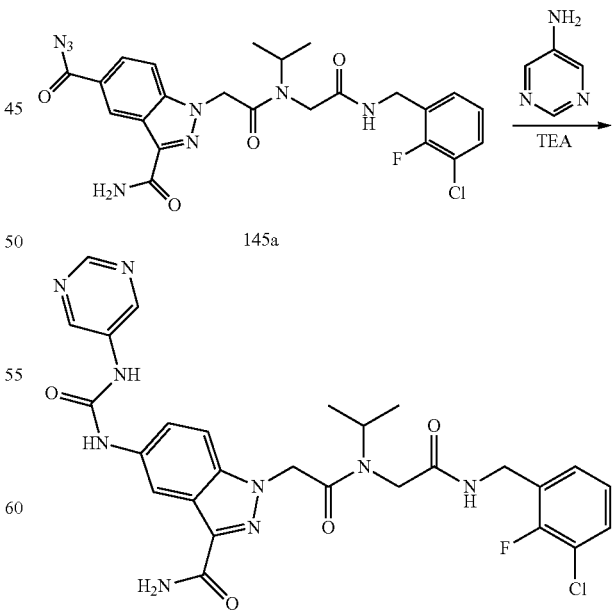

145a

215a

Preparation of 1-(2-((2-((3-chloro-2-fluorobenzyl)amino)-2-oxoethyl)(isopropyl)amino)-2-oxoethyl)-5-(3-(pyrimidin-5-yl)ureido)-1H-indazole-3-carboxamide (215a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (150 mg, 0.284 mmol) in toluene (15 mL) with pyrimidin-5-amine (54 mg, 0.57 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(3-(pyrimidin-5-yl)ureido)-1H-indazole-3-carboxamide (215a) (14 mg, 0.023 mmol, 8% yield) as a white solid; $^1$H NMR (300 MHz, DMSO-$d_6$) δ 9.36-9.09 (m, 2H), 8.044 and 8.935 (2s, 2H), 8.88-8.29 (m, 3H), 7.71-7.59 (m, 1H), 7.57-6.99 (m, 6H), 5.56 and 5.42 (2s, 2H), 4.64-4.25 (m, 3H), 4.18 and 3.84 (2s, 2H), 1.22 (d, J=6.3 Hz) and 0.99 (d, J=6.7 Hz) (2d, 6H); $^{19}$F NMR (282 MHz, DMSO-$d_6$) δ −121.22, −121-75; MS (ES+) 596.6 (M+1); (ES−) 594.5 (M−1).

Scheme 216

Preparation of 3-acetyl-1-(2-((2-((3-chloro-2-fluorobenzyl)amino)-2-oxoethyl)(isopropyl)amino)-2-oxoethyl)-1H-indazole-5-carboxylic acid (216a)

Reaction of methyl 3-acetyl-1-(2-((2-((3-chloro-2-fluorobenzyl)amino)-2-oxoethyl)(isopropyl)amino)-2-oxoethyl)-1H-indazole-5-carboxylate (206d) (2.24 g, 4.33 mmol) in MeOH (25 mL) and water (25 mL) with lithium hydroxide hydrate (1.091 g, 26.0 mmol) according to the procedure reported in step-2 of Scheme 129 gave after workup 3-acetyl-1-(2-((2-((3-chloro-2-fluorobenzyl)amino)-2-oxoethyl)(isopropyl)amino)-2-oxoethyl)-1H-indazole-5-carboxylic acid (216a) (2.1 g, 4.18 mmol, 96% yield) as an off white solid, which was used in the next step without further purification; $^1$H NMR (300 MHz, DMSO-$d_6$) (a mixture of two rotamers) δ 13.07 (s, 1H), 9.21 (t, J=5.8 Hz) and 8.62 (t, J=6.0 Hz) (2t, 1H), 8.86-8.77 (m, 1H)), 8.05-7.64 (m, 2H), 7.55-6.88 (m, 3H), 5.81 and 5.60 (2s, 2H), 4.64-4.20 (m, 3H), 4.26 and 3.84 (2s, 2H), 2.64 and 2.29 (2s, 3H), 1.26 (d, J=6.4 Hz) and 1.00 (d, J=6.8 Hz) (2d, 6H); $^{19}$F NMR (282 MHz, DMSO-$d_6$) δ −121.29, −121.81; MS (ES+): 502.4 (M+1); (ES−): 500.4 (M−1).

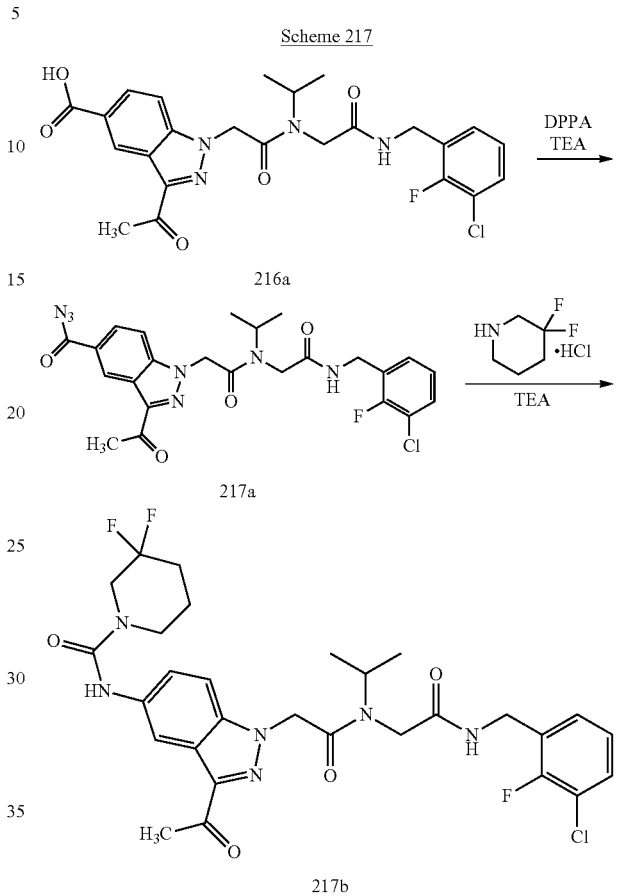

Scheme 217

Preparation of N-(3-acetyl-1-(2-((2-((3-chloro-2-fluorobenzyl)amino)-2-oxoethyl)(isopropyl)amino)-2-oxoethyl)-1H-indazol-5-yl)-3,3-difluoropiperidine-1-carboxamide (217b)

Step-1: Preparation of 3-acetyl-1-(2-((2-((3-chloro-2-fluorobenzyl)amino)-2-oxoethyl)(isopropyl)amino)-2-oxoethyl)-1H-indazole-5-carbonyl azide (217a)

Compound 3-acetyl-1-(2-((2-((3-chloro-2-fluorobenzyl)amino)-2-oxoethyl)(isopropyl)amino)-2-oxoethyl)-1H-indazole-5-carbonyl azide (217a) was prepared from 3-acetyl-1-(2-((2-((3-chloro-2-fluorobenzyl)amino)-2-oxoethyl)(isopropyl)amino)-2-oxoethyl)-1H-indazole-5-carboxylic acid (216a) (950 mg, 1.889 mmol) according to the procedure reported in step-3 of Scheme 129 to afford product (1.4 g, 2.65 mmol, 140% yield), which was used in the next step without further purification. MS (ES+): 528.5 (M+1).

Step-2: Preparation of N-(3-acetyl-1-(2-((2-((3-chloro-2-fluorobenzyl)amino)-2-oxoethyl)(isopropyl)amino)-2-oxoethyl)-1H-indazol-5-yl)-3,3-difluoropiperidine-1-carboxamide (217b)

Compound (217b) was prepared from 3-acetyl-1-(2-((2-((3-chloro-2-fluorobenzyl)amino)-2-oxoethyl)(isopropyl)

amino)-2-oxoethyl)-1H-indazole-5-carbonyl azide (217a) (220 mg, 0.42 mmol) and 3,3-difluoropiperidine hydrochloride (131 mg, 0.83 mmol) using TEA (0.23 mL, 1.67 mmol) as base according to the procedure reported in step-4 of Scheme 129 to afford after workup and purification by column chromatography [silica gel (12 g), eluting with DMA80 in DCM 0 to 40%] (32 mg, 0.052 mmol, 12.36% yield) product as a white solid; $^1$H NMR (300 MHz, DMSO-$d_6$) (mixture of two rotamers) δ 8.93-8.31 (m, 2H), 8.24 (bs, 1H), 7.65-7.00 (m, 5H), 5.64 and 5.48 (2s, 2H), 4.66-4.23 (m, 3H), 4.17 and 3.78 (2s, 2H), 3.88-3.80 (m, 2H), 3.61-3.47 (m, 2H), 2.59 (s, 3H), 2.19-1.95 (m, 2H), 1.84-1.60 (m, 2H), 1.24 (d, J=6.4 Hz) and 1.00 (d, J=6.8 Hz) (2d, 6H); $^{19}$F NMR (282 MHz, DMSO-$d_6$) δ −101.15, −121.22, −121.78; MS (ES+): 621.7 (M+1); (ES−): 619.6 (M−1).

gave after workup and purification by flash column chromatography [silica gel (12 g), eluting with DMA80-DCM 0 to 30%] 1-(2-((2-((3-chloro-2-fluorobenzyl)amino)-2-oxoethyl)(cyclopropyl)amino)-2-oxoethyl)-5-(2-(dimethylamino)pyrimidin-5-yl)-1H-indazole-3-carboxamide (218a) (42 mg, 0.073 mmol, 31% yield) as a white solid; $^1$H NMR (300 MHz, DMSO-$d_6$) δ 8.69 (s, 2H), 8.50 (t, J=5.9 Hz, 1H), 8.28 (dd, J=1.7, 0.9 Hz, 1H), 7.80-7.62 (m, 3H), 7.51-7.39 (m, 2H), 7.28-7.19 (m, 1H), 7.12 (td, J=7.9, 1.0 Hz, 1H), 5.69 (s, 2H), 4.33 (d, J=5.7 Hz, 2H), 3.99 (s, 2H), 3.18 (s, 6H), 3.13-3.02 (m, 1H), 1.05-0.96 (m, 2H), 0.97-0.86 (m, 2H); $^{19}$F NMR (282 MHz, DMSO-$d_6$) δ −121.57; MS (ES+): 579.6 (M+1), 601.6 (M+Na); MS (ES−): 577.5 (M−1), 613.6 (M+Cl).

Scheme 218

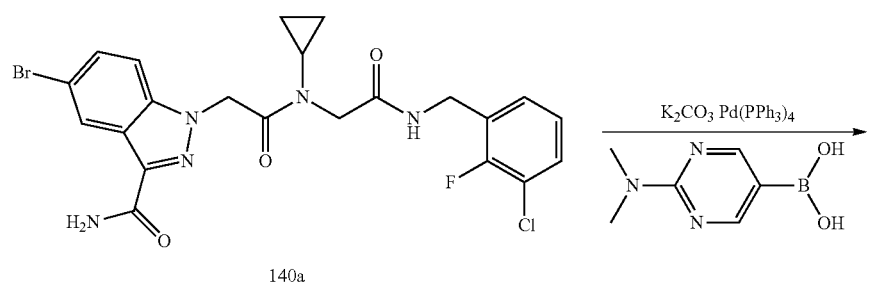

140a

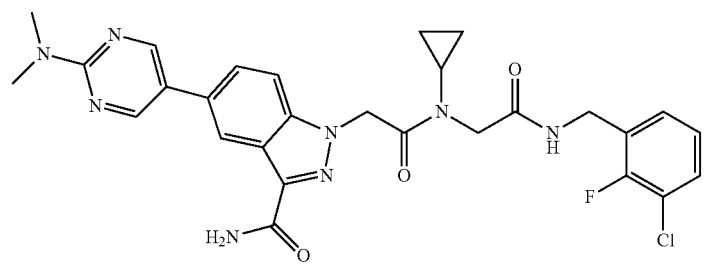

218a

Preparation of 1-(2-((2-((3-chloro-2-fluorobenzyl)amino)-2-oxoethyl)(cyclopropyl)amino)-2-oxoethyl)-5-(2-(dimethylamino)pyrimidin-5-yl)-1H-indazole-3-carboxamide (218a)

Reaction of 5-bromo-1-(2-((2-((3-chloro-2-fluorobenzyl)amino)-2-oxoethyl)(cyclopropyl)amino)-2-oxoethyl)-1H-indazole-3-carboxamide (140a) (125 mg, 0.23 mmol) with 2-(dimethylamino)pyrimidin-5-ylboronic acid (43 mg, 0.26 mmol) according the procedure reported in Scheme 100

Scheme 219

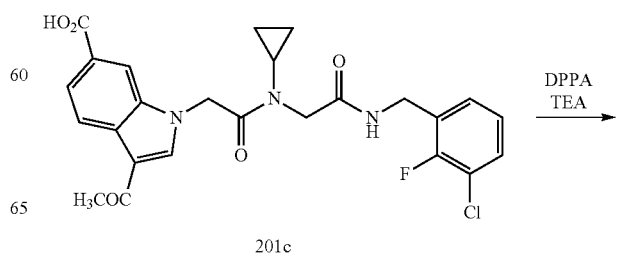

201c

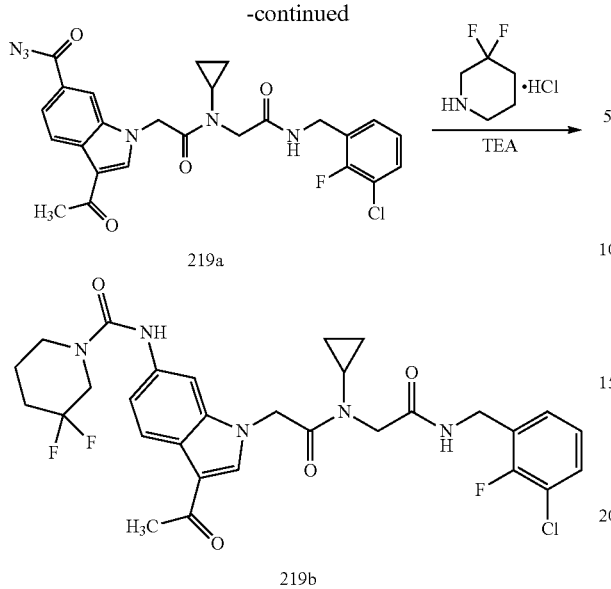

219a

219b

Preparation of N-(3-acetyl-1-(2-((2-((3-chloro-2-fluorobenzyl)amino)-2-oxoethyl)(cyclopropyl)amino)-2-oxoethyl)-1H-indol-6-yl)-3,3-difluoropiperidine-1-carboxamide (219b)

Step-1: Preparation of 3-acetyl-1-(2-((2-((3-chloro-2-fluorobenzyl)amino)-2-oxoethyl)(cyclopropyl)amino)-2-oxoethyl)-1H-indole-6-carbonyl azide (219a)

Compound (219a) was prepared from 3-acetyl-1-(2-((2-((3-chloro-2-fluorobenzyl)amino)-2-oxoethyl)(cyclopropyl)amino)-2-oxoethyl)-1H-indole-6-carboxylic acid (201a) (1.98 g, 3.96 mmol) according to the procedure reported in step-3 of Scheme 129 to afford product (219a) (2.2 g, 4.19 mmol, 106% yield) which was used in the next step without further purification; MS (ES−): 523.5 (M−1).

Step-2: Preparation of N-(3-acetyl-1-(2-((2-((3-chloro-2-fluorobenzyl)amino)-2-oxoethyl)(cyclopropyl)amino)-2-oxoethyl)-1H-indol-6-yl)-3,3-difluoropiperidine-1-carboxamide (219b)

Compound (219b) was prepared from 3-acetyl-1-(2-((2-((3-chloro-2-fluorobenzyl)amino)-2-oxoethyl)(cyclopropyl)amino)-2-oxoethyl)-1H-indole-6-carbonyl azide (219a) (200 mg, 0.38 mmol) and 3,3-difluoropiperidine hydrochloride (120 mg, 0.76 mmol) using TEA (0.21 mL, 1.51 mmol) as base according to the procedure reported in step-4 of Scheme 129 to afford after workup and purification by column chromatography [silica gel (12 g), eluting with DMA80 in DCM 0 to 40%] (17 mg, 0.028 mmol, 7% yield) as a white solid; $^1$H NMR (300 MHz, DMSO-d$_6$) δ 8.66 (s, 1H), 8.47 (t, J=5.8 Hz, 1H), 8.19 (s, 1H), 8.01 (d, J=8.6 Hz, 1H), 7.58 (d, J=1.8 Hz, 1H), 7.50-7.41 (m, 1H), 7.28-7.20 (m, 2H), 7.17-7.09 (m, 1H), 5.35 (s, 2H), 4.34 (d, J=5.7 Hz, 2H), 4.00 (s, 2H), 3.79 (t, J=12.1 Hz, 2H), 3.56-3.46 (m, 2H), 3.13-3.01 (m, 1H), 2.40 (s, 3H), 2.16-1.95 (m, 2H), 1.78-1.59 (m, 2H), 1.02-0.98 (m, 2H), 0.97-0.90 (m, 2H); $^{19}$F NMR (282 MHz, DMSO-d$_6$) δ −101.11, −121.65; MS (ES+): 618.6 (M+1); MS (ES−): 616.6 (M−1).

Scheme 220

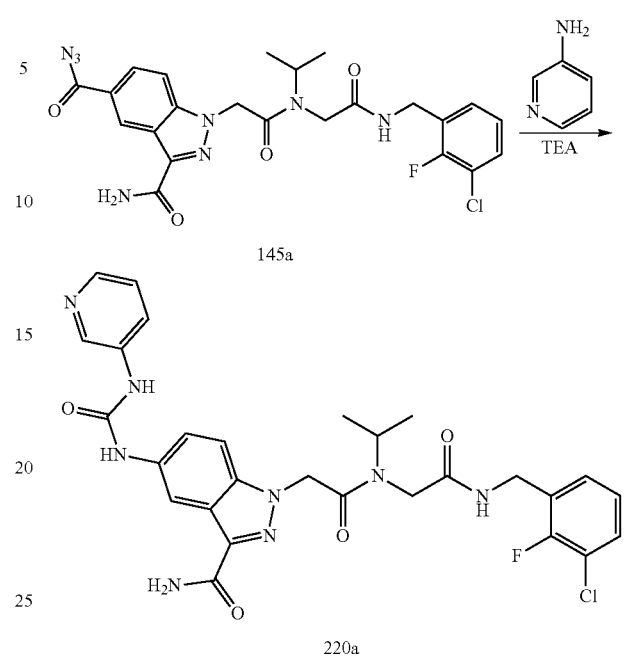

145a

220a

Preparation of 1-(2-((2-((3-chloro-2-fluorobenzyl)amino)-2-oxoethyl)(isopropyl)amino)-2-oxoethyl)-5-(3-(pyridin-3-yl)ureido)-1H-indazole-3-carboxamide (220a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (150 mg, 0.28 mmol) in toluene (15 mL) with pyridin-3-amine (53 mg, 0.57 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] 1-(2-((2-((3-chloro-2-fluorobenzyl)amino)-2-oxoethyl)(isopropyl)amino)-2-oxoethyl)-5-(3-(pyridin-3-yl)ureido)-1H-indazole-3-carboxamide (220a) (22 mg, 0.037 mmol, 13.04% yield) as a white solid; $^1$H NMR (300 MHz, DMSO-d$_6$) (mixture of two rotamers) δ 8.98 and 8.96 (2s, 1H), 8.90-8.77 and 8.41-8.30 (2m, 3H), 8.66-8.56 (m, 1H), 8.22-8.13 (m, 1H), 8.02-7.91 (m, 1H), 7.67-6.99 (m, 8H), 5.55 and 5.42 (2s, 2H), 4.64-4.23 (m, 3H), 4.18 and 3.83 (2s, 2H), 1.22 (d, J=6.3 Hz) and 0.99 (d, J=6.7 Hz) (2d, 6H); $^{19}$F NMR (282 MHz, DMSO-d$_6$) δ −121.21, −121.74; MS (ES+): 595.6 (M+1); (ES−): 593.5 (M−1)

Scheme 221

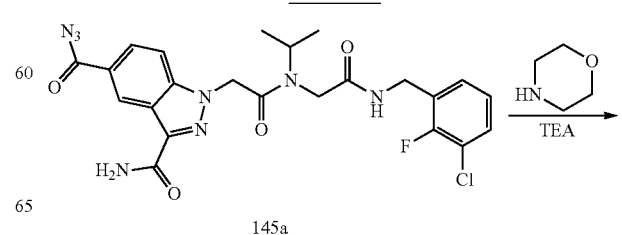

145a

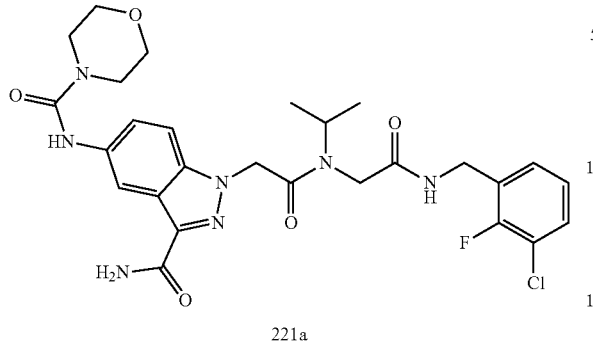

221a

Preparation of N-(3-carbamoyl-1-(2-((2-((3-chloro-2-fluorobenzyl)amino)-2-oxoethyl)(isopropyl)amino)-2-oxoethyl)-1H-indazol-5-yl)morpholine-4-carboxamide (221a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (150 mg, 0.28 mmol) in toluene (15 mL) with morpholine (49.4 mg, 0.57 mmol) using TEA (0.16 mL, 1.13 mmol) as base according to the procedure reported in step-4 of Scheme 129 gave after workup and purification by column chromatography [silica gel (12 g), eluting with DMA80 in DCM 0 to 40%] N-(3-carbamoyl-1-(2-((2-((3-chloro-2-fluorobenzyl)amino)-2-oxoethyl)(isopropyl)amino)-2-oxo ethyl)-1H-indazol-5-yl)morpholine-4-carboxamide (221a) (33 mg, 0.056 mmol, 20% yield) as a white solid; $^1$H NMR (300 MHz, DMSO-d$_6$) δ 8.81 and 8.36 (2t, J=5.7 Hz, 1H), 8.67 (s, 1H), 8.22-8.15 (m, 1H), 7.65-7.00 (m, 7H), 5.53 and 5.40 (2s, 2H), 4.61-4.23 (m, 3H), 4.17 and 3.83 (2s, 2H), 3.66-3.56 (m, 4H), 3.47-3.39 (m, 4H), 1.21 (d, J=6.6 Hz) and 0.98 (d, J=6.8 Hz) (2d, 6H); $^{19}$F NMR (282 MHz, DMSO) δ −121.22, −121.78; MS (ES+): 588.6 (M+1); MS (ES−): 586.5 (M−1).

Scheme 222

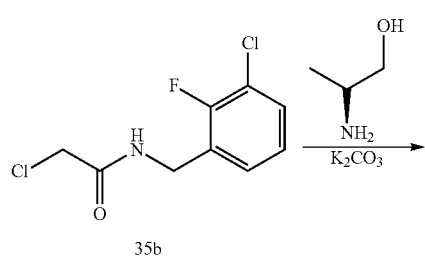

35b

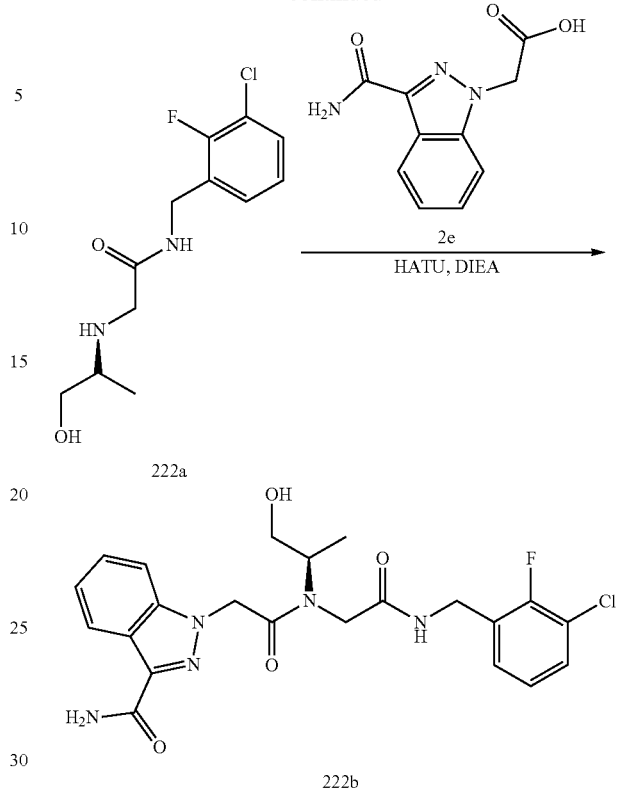

Preparation of (R)-1-(2-((2-((3-chloro-2-fluorobenzyl)amino)-2-oxoethyl)(1-hydroxypropan-2-yl)amino)-2-oxoethyl)-1H-indazole-3-carboxamide (222b)

Step-1: Preparation of (R)—N-(3-chloro-2-fluorobenzyl)-2-((1-hydroxypropan-2-yl)amino)acetamide (222a)

Reaction of 2-chloro-N-(3-chloro-2-fluorobenzyl)acetamide (35b) (500 mg, 2.12 mmol) with (R)-2-aminopropan-1-ol (318 mg, 4.24 mmol) according to the procedure reported in step-2 of Scheme 35 gave after workup (R)—N-(3-chloro-2-fluorobenzyl)-2-(1-hydroxypropan-2-ylamino)acetamide (222a) (582 mg, 2.12 mmol, 100%) which was used as such in the next step; MS (ES+): 275.3 (M+1); MS (ES−): 273.3 (M−1).

Step-2: Preparation of (R)-1-(2-((2-((3-chloro-2-fluorobenzyl)amino)-2-oxoethyl)(1-hydroxypropan-2-yl)amino)-2-oxoethyl)-1H-indazole-3-carboxamide (222b)

Reaction of (R)—N-(3-chloro-2-fluorobenzyl)-2-((1-hydroxy propan-2-yl)-amino)acetamide (222a) (200 mg, 0.73 mmol) with 2-(3-carbamoyl-1H-indazol-1-yl)acetic acid (2e) (251 mg, 0.91 mmol) according to the procedure reported in step-3 of Scheme 2 gave after workup and purification by flash column chromatography [silica (12 g), eluting with CMA80 in CHCl$_3$ 0 to 60%] (R)-1-(2-((2-((3-chloro-2-fluorobenzyl)amino)-2-oxoethyl)(1-hydroxypropan-2-yl)amino)-2-oxoethyl)-1H-indazole-3-carboxamide (222b) (39 mg, 0.082 mmol, 9% yield) as an off-white solid as a mixture of two rotamers; ¹H NMR (300 MHz, DMSO-$d_6$) δ 8.88 (t, J=5.7 Hz) & 8.61 (t, J=5.9 Hz) (2t, 1H, $D_2O$ exchangeable), 8.24-8.13 (m, 1H), 7.71 (s, 1H), 7.60-6.94 (m, 7H), 5.63 (d, J=3.6 Hz) & 5.42 (d, J=2.9 Hz) (2d, 2H), 5.51 (t, J=6.0 Hz) & 4.81 (t, J=5.7 Hz) (2t, 1H, $D_2O$ exchangeable), 4.59-3.74 (m, 5H), 3.55-3.24 (m, 2H), 1.15 (d, J=6.6 Hz) & 0.96 (d, J=6.9 Hz) (2d, 3H); ¹⁹F NMR (282 MHz, DMSO-$d_6$) δ −121.26, −121.65; MS (ES+): 498.5 (M+Na); MS (ES−): 474.4 (M−1), 510.4 (M+Cl).
Scheme 223
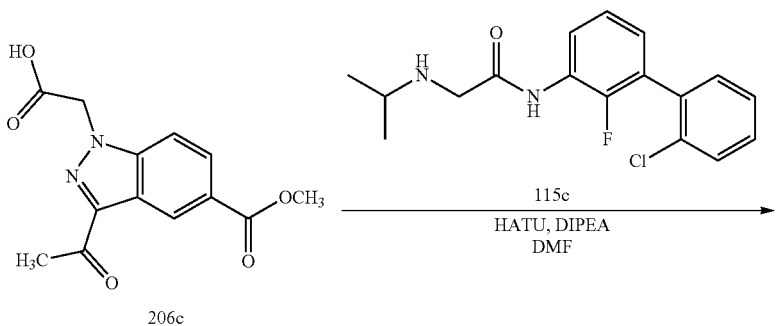
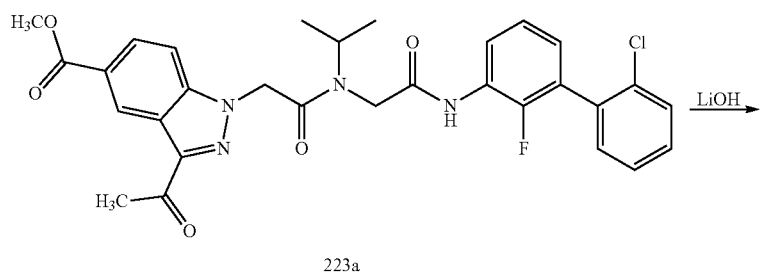
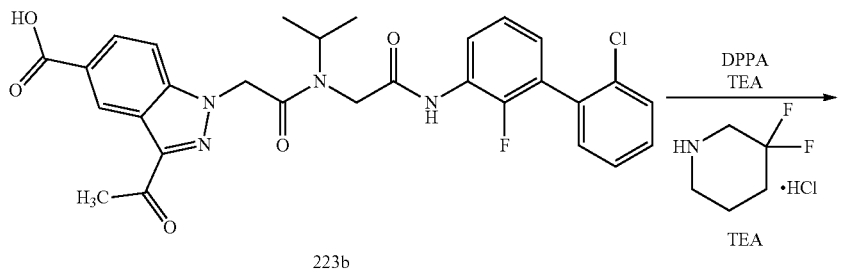
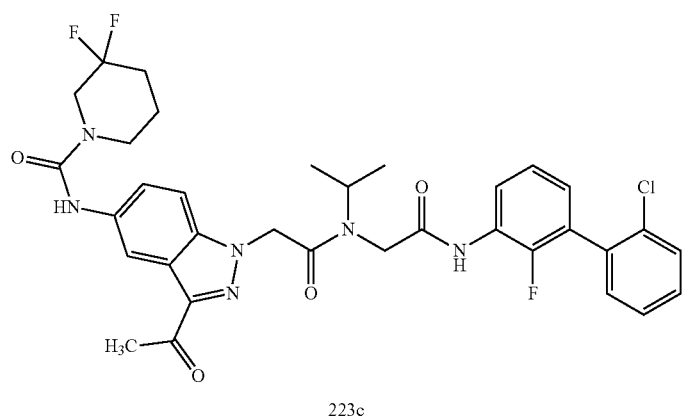

Preparation of N-(3-acetyl-1-(2-((2-((2'-chloro-2-fluoro-[1,1'-biphenyl]-3-yl)amino)-2-oxoethyl)(isopropyl)amino)-2-oxoethyl)-1H-indazol-5-yl)-3,3-difluoropiperidine-1-carboxamide (223c)

Step-1: Preparation of methyl 3-acetyl-1-(2-((2-((2'-chloro-2-fluoro-[1,1'-biphenyl]-3-yl)amino)-2-oxoethyl)(isopropyl)amino)-2-oxoethyl)-1H-indazole-5-carboxylate (223a)

Reaction of 2-(3-acetyl-5-(methoxycarbonyl)-1H-indazol-1-yl)acetic acid (206c) TFA adduct (237 g, 0.86 mmol) with N-(2'-chloro-2-fluorobiphenyl-3-yl)-2-(isopropylamino)acetamide (115c) (250 mg, 0.78 mmol) according to the procedure reported in step-3 of scheme-2 gave after workup and purification by flash column [silica (24 g), eluting with DMA80 in DCM 0 to 20%] methyl 3-acetyl-1-(2-((2-((2'-chloro-2-fluoro-[1,1'-biphenyl]-3-yl)amino)-2-oxoethyl)(isopropyl)amino)-2-oxoethyl)-1H-indazole-5-carboxylate (223a) (280 mg, 0.48 mmol, 62% yield) as a off-white solid; $^1$H NMR (300 MHz, DMSO-d$_6$) (mixture of two rotamers) δ 10.27 and 9.74 (2s, 1H), 8.85 and 8.83 (dd, J=1.6, 0.8 Hz, 1H), 8.18-6.97 (m, 9H), 5.83 and 5.64 (2s, 2H), 4.69-4.57 and 4.38-4.26 (2m, 1H), 4.47 and 4.09 (2s, 2H), 3.918 and 3.91 (s, 3H), 2.657 and 2.65 (2s, 3H), 1.29 and 1.07 (2d, J=6.8 Hz, 6H); MS (ES+): 579.6 (M+1), 601.6 (M+Na); MS (ES−): 577.5 (M−1), 613.5 (M+Cl).

Step-2: Preparation 3-acetyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (223b)

Reaction of methyl 3-acetyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylate (223a) (280 mg, 0.48 mmol) in THF (25 mL) with a solution of lithium hydroxide hydrate (23 mg, 0.97 mmol) in water (1 mL) according to the procedure reported in step-2 of scheme-29 gave after workup 3-acetyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (223b) (250 mg, 0.44 mmol, 92% yield) as a white solid; $^1$H NMR (300 MHz, DMSO-d$_6$) (mixture of two rotamers) δ 13.01 (s, 1H), 10.27 and 9.74 (2s, 1H), 8.83 and 8.82 (2s, 1H), 8.19-6.97 (m, 9H), 5.81 and 5.63 (2s, 2H), 4.70-4.57 and 4.38-4.27 (2m, 1H), 4.47 and 4.09 (s, 2H), 2.65 and 2.64 (2s, 3H), 1.29 and 1.07 (2d, J=6.7 Hz, 6H); 19F NMR (282 MHz, DMSO-d$_6$) δ −126.85, −126.96; MS (ES−): 563.6 & 565.4 (M−1).

Step-3: Preparation of N-(3-acetyl-1-(2-((2-((2'-chloro-2-fluoro-[1,1'-biphenyl]-3-yl)-amino)-2-oxoethyl)(isopropyl)amino)-2-oxoethyl)-1H-indazol-5-yl)-3,3-difluoropiperidine-1-carboxamide (223c)

To a solution of 3-acetyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (223b) (150 mg, 0.27 mmol) in toluene (4 mL) was added triethylamine (0.19 mL, 1.33 mmol), diphenyl phosphorazidate (110 mg, 0.4 mmol) and stirred at RT for 2 h. Dioxane (2 ml) was added to the reaction mixture and heated at 90° C. for 2 h. The reaction mixture was cooled to RT, added 3,3-difluoropiperidine hydrochloride (84 mg, 0.53 mmol) and continued stirring at 90° C. for 20 h. The reaction mixture was cooled to RT, partitioned between 0.5 M aq. HCl (40 ml) and EtOAc (50 ml). The aqueous layer was separated and extracted with EtOAc (40 ml). The organic layers were combined washed with saturated aqueous NaHCO$_3$ solution (40 ml), brine, dried, filtered and concentrated in vacuum. The residue obtained was purified by flash column chromatography [silica gel (12 g), eluting with MeOH:EtOAc (9:1) in hexanes 0 to 70%] to afford N-(3-acetyl-1-(2-((2-((2'-chloro-2-fluoro-[1,1'-biphenyl]-3-yl)-amino)-2-oxoethyl)(isopropyl)amino)-2-oxoethyl)-1H-indazol-5-yl)-3,3-difluoropiperidine-1-carboxamide (223c) (32 mg, 0.047 mmol, 18% yield) as white solid; $^1$H NMR (300 MHz, DMSO-d$_6$) (mixture of two rotamers) δ 10.26 and 9.75 (2s, 1H), 8.84 and 8.82 (2s, 1H), 8.24 and 8.23 (2s, 1H), 8.11 and 7.95 (2t, J=7.8 Hz, 1H), 7.67-7.01 (m, 8H), 5.69 and 5.53 (2s, 2H), 4.72-4.56 and 4.38-4.27 (2m, 1H), 4.46 and 4.09 (2s, 2H), 3.82 (t, J=12.0 Hz, 2H), 3.58-3.48 (m, 2H), 2.595 and 2.588 (2s, 3H), 2.17-1.95 (m, 2H), 1.78-1.64 (m, 2H), 1.27 and 1.07 (2d, J=6.8 Hz, 6H); $^{19}$F NMR (282 MHz, DMSO-d$_6$) (mixture of two rotamers) δ −101.15, −126.86 and −126.99; MS (ES+): 683.7 (M+1), 705.7 (M+Na), MS (ES−): 717.6 (M+Cl).

Scheme 224

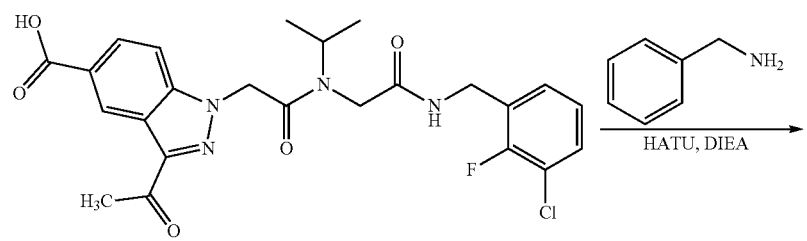

216a

-continued

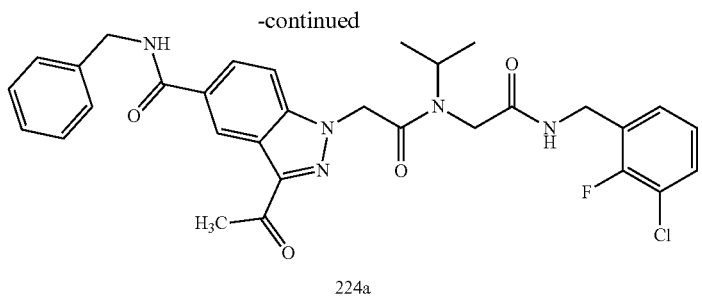

224a

Preparation of 3-acetyl-N-benzyl-1-(2-((2-((3-chloro-2-fluorobenzyl)amino)-2-oxoethyl)(isopropyl)amino)-2-oxoethyl)-1H-indazole-5-carboxamide (224a)

Reaction of 3-acetyl-1-(2-((2-((3-chloro-2-fluorobenzyl)amino)-2-oxoethyl)(isopropyl)amino)-2-oxoethyl)-1H-indazole-5-carboxylic acid (216a) (50 mg, 0.1 mmol) with phenylmethanamine (0.017 mL, 0.15 mmol) according to the procedure reported in step-3 of Scheme 2 gave after workup and purification by flash column [silica (8 g), eluting DCM/MeOH (1:0 to 19:1)] 3-acetyl-N-benzyl-1-(2-((2-((3-chloro-2-fluorobenzyl)amino)-2-oxoethyl)(isopropyl)amino)-2-oxoethyl)-1H-indazole-5-carboxamide (224a) (35 mg, 60%) as a white solid as mixture of two rotamers; $^1$H NMR (300 MHz, DMSO-d$_6$) δ 9.25 (t, J=5.9 Hz, 1H), 8.85 (t, J=5.6 Hz) and 8.36 (t, J=5.9 Hz) (2t, 1H), 8.79-8.75 (m, 1H), 8.00 (dd, J=8.9, 1.6 Hz) and 7.95 (dd, J=8.9, 1.6 Hz) (2dd, 1H), 7.72 (d) and 7.66 (d, J=8.9 Hz) (2d, 1H), 7.58-6.86 (m, 8H), 5.74 and 5.57 (2s, 2H), 4.64-4.22 (m, 5H), 4.19 and 3.85 (2s, 2H), 2.69 and 2.64 (s, 3H), 1.26 (d, J=6.5 Hz) and 1.00 (d, J=6.7 Hz) (2d, 6H); $^{19}$F NMR (282 MHz, DMSO-d$_6$) δ −121.21, −121.74; MS (ES+): 614.7 (M+Na); MS (ES−): 590.6 (M−1), 626.5 (M+Cl).

Preparation of 3-acetyl-1-(2-((2-((3-chloro-2-fluorobenzyl)amino)-2-oxoethyl)(isopropyl)amino)-2-oxoethyl)-N-(1-phenylethyl)-1H-indazole-5-carboxamide (225a)

Reaction of 3-acetyl-1-(2-((2-((3-chloro-2-fluorobenzyl)amino)-2-oxoethyl)(isopropyl)amino)-2-oxoethyl)-1H-indazole-5-carboxylic acid (216a) (50 mg, 0.1 mmol) with 1-phenylethanamine (0.02 mL, 0.15 mmol) according to the procedure reported in step-3 of Scheme 2 gave after workup and purification by flash column [silica (8 g), eluting EtOAc/MeOH (1:0 to 19:1)] 3-acetyl-1-(2-((2-((3-chloro-2-fluorobenzyl)amino)-2-oxoethyl)(isopropyl)amino)-2-oxoethyl)-N-(1-phenylethyl)-1H-indazole-5-carboxamide (225a) (37 mg, 61%) as a white solid as mixture of two rotamers; $^1$H NMR (300 MHz, DMSO-d$_6$) δ 9.08-9.00 (m, 1H), 8.85 (t, J=5.8 Hz) and 8.36 (t, J=5.9 Hz) (2t, 1H), 8.77-8.72 (m, 1H), 7.98 (dd, J=8.9, 1.6 Hz) and 7.92 (dd, J=8.9, 1.6 Hz) (2dd, 1H), 7.70 (d) and 7.66 (d, J=8.9 Hz) (2d, 1H), 7.55-6.90 (m, 8H), 5.73 and 5.56 (2s, 2H), 5.30-5.12 (m, 1H), 4.64-4.50 and 4.29-4.21 (2m, 1H), 4.47 (d, J=5.6 Hz) and 4.32 (d, J=5.9 Hz) (2d, 2H), 4.19 and 3.85 (2s, 2H), 2.69 and 2.64 (2s, 3H), 1.55-1.46 (m, 3H), 1.25 (d, J=6.6 Hz)

Scheme 225

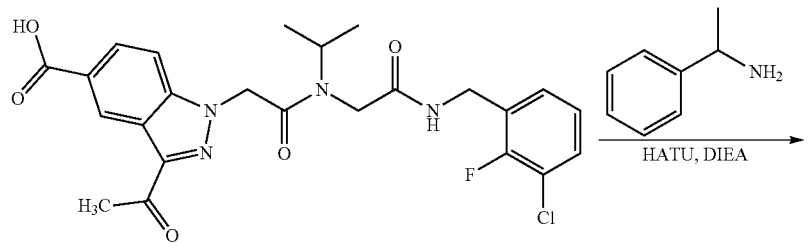

216a

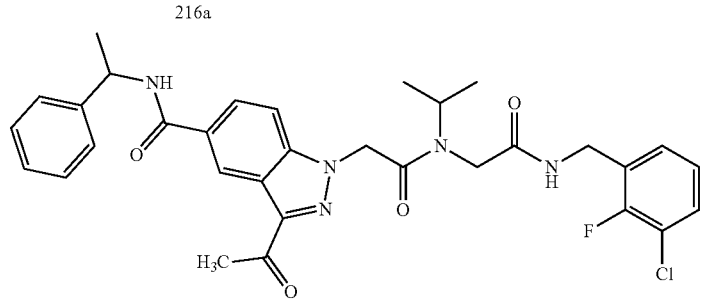

225a and 1.00 (d, J=6.7 Hz) (2d, 6H); ¹⁹F NMR (282 MHz, DMSO-d₆) δ −121.22, −121.73; MS (ES−): 604.2 (M−1).

Scheme 226

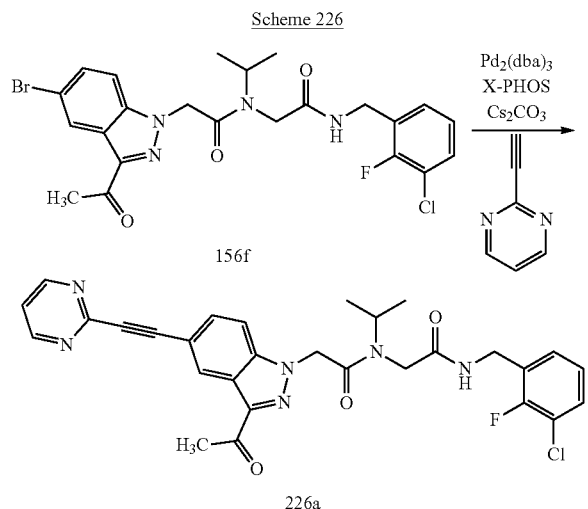

156f

226a

Preparation of 2-(3-acetyl-5-(pyrimidin-2-ylethynyl)-1H-indazol-1-yl)-N-(2-((3-chloro-2-fluorobenzyl)amino)-2-oxoethyl)-N-isopropylacetamide (226a)

Reaction of 2-(3-acetyl-5-bromo-1H-indazol-1-yl)-N-(2-(3-chloro-2-fluorobenzylamino)-2-oxoethyl)-N-isopropylacetamide (156f) (300 mg, 0.56 mmol) using Cs₂CO₃ (365 mg, 1.12 mmol), dicyclohexyl(2',4',6'-triisopropylbiphenyl-2-yl)phosphine (X-PHOS, 53 mg, 0.112 mmol), Pd₂(dba)₃ (51 mg, 0.056 mmol) according to procedure reported in Scheme 92 gave after workup and purification by flash column chromatography [silica gel (12 g), eluting with MeOH in DCM from 0 to 100%] 2-(3-acetyl-5-(pyrimidin-2-ylethynyl)-1H-indazol-1-yl)-N-(2-((3-chloro-2-fluorobenzyl)amino)-2-oxoethyl)-N-isopropylacetamide (226a) (16 mg, 0.029 mmol, 5% yield) as a dark-yellow solid as a mixture of two rotamers; ¹H NMR (300 MHz, DMSO-d₆) δ 8.93-8.80 (m) and 8.36 (t, J=5.8 Hz) (3H), 8.49-8.42 (m, 1H), 7.82-6.98 (m, 6H), 5.76 & 5.59 (2s, 2H), 4.64-4.52 & 4.29-4.21 (2m, 1H), 4.48 (d, J=5.6 Hz) & 4.32 (d, J=5.8 Hz) (2d, 2H), 4.19 & 3.85 (2s, 2H), 2.64 (s, 3H), 1.26 (d, J=6.4 Hz) & 1.00 (d, J=6.8 Hz (2d, 6H); ¹⁹F NMR (282 MHz, DMSO-d₆) δ −121.20, −121.71; MS (ES+): 561.5 (M+1), 583.5 (M+Na); MS (ES−): 559.4 (M−1), 595.4 (M+Cl).

Scheme 227

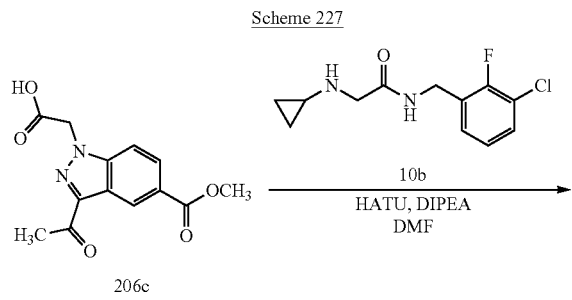

206c

227a

Preparation of methyl 3-acetyl-1-(2-((2-((3-chloro-2-fluorobenzyl)amino)-2-oxoethyl)(cyclopropyl)amino)-2-oxoethyl)-1H-indazole-5-carboxylate (227a)

Reaction of 2-(3-acetyl-5-(methoxycarbonyl)-1H-indazol-1-yl)acetic acid (206c) TFA adduct (2.09 g, 5.36 mmol) with N-(3-chloro-2-fluorobenzyl)-2-(cyclopropylamino)acetamide (10b) (1.65 g, 6.43 mmol) according to the procedure reported in step-3 of Scheme 2 gave after workup and purification by flash column [silica (40 g), eluting with DMA80 in DCM 0 to 40%] methyl 3-acetyl-1-(2-((2-((3-chloro-2-fluorobenzyl)amino)-2-oxoethyl)(cyclopropyl)amino)-2-oxoethyl)-1H-indazole-5-carboxylate (227a) (2.3 g, 4.47 mmol, 83% yield) as a white solid; ¹H NMR (300 MHz, DMSO-d₆) δ 8.87-8.81 (m, 1H), 8.48 (t, J=5.9 Hz, 1H), 7.99 (dd, J=8.9, 1.6 Hz, 1H), 7.88-7.77 (m, 1H), 7.50-7.39 (m, 1H), 7.28-7.18 (m, 1H), 7.14-7.03 (m, 1H), 5.80 (s, 2H), 4.34 (d, J=5.7 Hz, 2H), 3.99 (s, 2H), 3.91 (s, 3H), 3.20-3.05 (m, 1H), 2.65 (s, 3H), 1.10-0.99 (m, 2H), 0.96-0.82 (m, 2H); ¹⁹F NMR (282 MHz, DMSO-d₆) δ −121.57; MS (ES+): 515.5 (M+1); MS (ES−): 513.4 (M−1).

Scheme 228

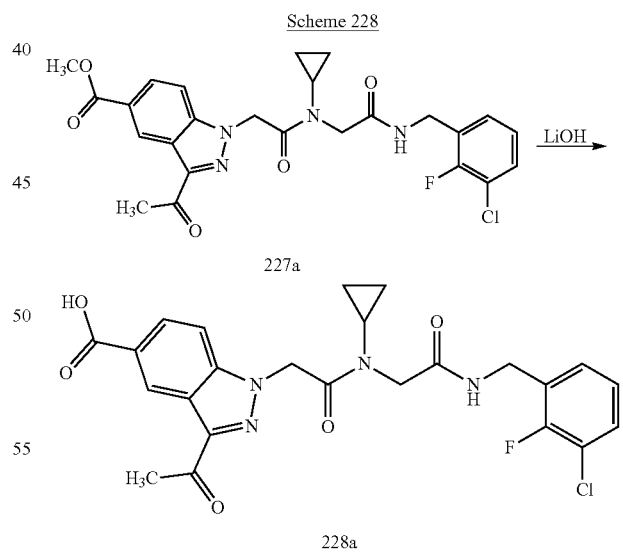

227a

228a

Preparation of 3-acetyl-1-(2-((2-((3-chloro-2-fluorobenzyl)amino)-2-oxoethyl)(cyclopropyl)amino)-2-oxoethyl)-1H-indazole-5-carboxylic acid (228a)

Reaction of methyl 3-acetyl-1-(2-((2-((3-chloro-2-fluorobenzyl)amino)-2-oxoethyl)(cyclopropyl)amino)-2-oxoethyl)-1H-indazole-5-carboxylate (227a) (2.3 g, 4.47 mmol) in MeOH (25 mL) and water (25 mL) with a solution of lithium hydroxide hydrate (1.31 g, 31.3 mmol) in water (10 mL) according to the procedure reported in step-2 of Scheme 129 gave after workup 3-acetyl-1-(2-((2-(((3-chloro-2-fluorobenzyl)amino)-2-oxoethyl)(cyclopropyl)amino)-2-oxoethyl)-1H-indazole-5-carboxylic acid (228a) (2.2 g, 4.39 mmol, 98% yield) as a white solid; $^1$H NMR (300 MHz, DMSO-d$_6$) δ 13.05 (s, 1H), 8.88-8.80 (m, 1H), 8.50 (t, J=5.9 Hz, 1H), 8.04-7.95 (m, 1H), 7.84-7.75 (m, 1H), 7.51-7.40 (m, 1H), 7.29-7.19 (m, 1H), 7.14-7.04 (m, 1H), 5.80 (s, 2H), 4.34 (d, J=5.7 Hz, 2H), 4.00 (s, 2H), 3.20-3.07 (m, 1H), 2.65 (s, 3H), 1.09-0.99 (m, 2H), 0.98-0.83 (m, 2H); $^{19}$F NMR (282 MHz, DMSO-d$_6$) δ −121.57; MS (ES+): 501.5 (M+1); (ES−): 499.4 (M−1).

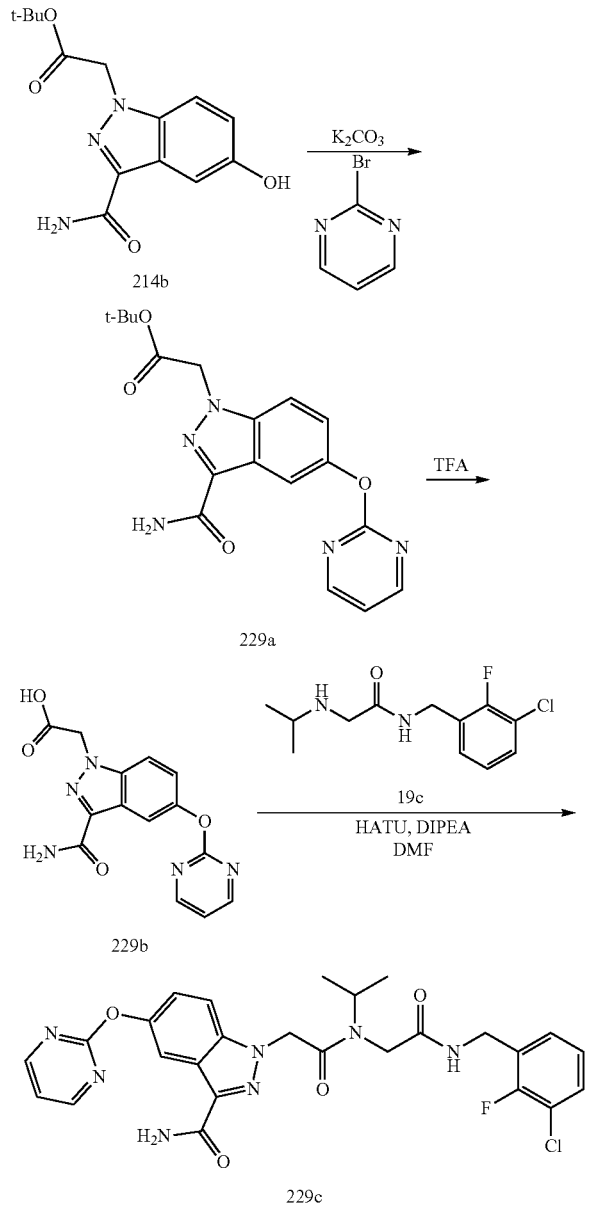

Scheme 229

Preparation of 1-(2-((2-(((3-chloro-2-fluorobenzyl)amino)-2-oxoethyl)(isopropyl)amino)-2-oxoethyl)-5-(pyrimidin-2-yloxy)-1H-indazole-3-carboxamide (229c)

Step-1: Preparation of tert-butyl 2-(3-carbamoyl-5-(pyrimidin-2-yloxy)-1H-indazol-1-yl)acetate (229a)

To a solution of tert-butyl 2-(3-carbamoyl-5-hydroxy-1H-indazol-1-yl)acetate (214b) (115 mg, 0.4 mmol) in acetonitrile (5 mL) was added 2-bromopyrimidine (78 mg, 0.49 mmol), potassium carbonate (164 mg, 1.18 mmol) and heated at reflux for 16 h. The reaction mixture was concentrated in vacuum and residue was suspended in brine (50 mL) and extracted with EtOAc (2×50 mL). The organic layers were combined dried, filtered and evaporated to dryness. The residue was purified by flash column chromatography [silica gel (12 g), eluting with EtOAc/MeOH (9:1) in hexanes from 0 to 100%] to afford tert-butyl 2-(3-carbamoyl-5-(pyrimidin-2-yloxy)-1H-indazol-1-yl)acetate (229a) (130 mg, 0.35 mmol, 89% yield) as an orange solid; $^1$H NMR (300 MHz, DMSO-d$_6$) δ 8.65 (s, 1H), 8.64 (s, 1H), 7.86 (dd, J=2.3, 0.7 Hz, 1H), 7.81-7.75 (m, 2H), 7.46 (s, 1H), 7.34 (dd, J=9.0, 2.3 Hz, 1H), 7.28 (t, J=4.8 Hz, 1H), 5.39 (s, 2H), 1.44 (s, 9H); MS (ES+): 370.4 (M+1), 739.7 (2M+1), 392.4 (M+Na); MS (ES−): 368.4 (M−1).

Step-2: Preparation of 2-(3-carbamoyl-5-(pyrimidin-2-yloxy)-1H-indazol-1-yl)acetic acid (229b)

Reaction of tert-butyl 2-(3-carbamoyl-5-(pyrimidin-2-yloxy)-1H-indazol-1-yl)acetate (229a) (118 mg, 0.32 mmol) with TFA (0.74 mL, 9.58 mmol) in DCM (5 mL) according to the procedure reported in step-2 of Scheme 2 gave after workup and trituration with hexanes, 2-(3-carbamoyl-5-(pyrimidin-2-yloxy)-1H-indazol-1-yl)acetic acid (229b) (0.129 g, 0.302 mmol, 95% yield) as a yellow solid in the form of TFA adduct; MS (ES+): 314.3 (M+1).

Step-3: Preparation of 1-(2-((2-(((3-chloro-2-fluorobenzyl)amino)-2-oxoethyl)(isopropyl)amino)-2-oxoethyl)-5-(pyrimidin-2-yloxy)-1H-indazole-3-carboxamide (229c)

Reaction of 2-(3-carbamoyl-5-(pyrimidin-2-yloxy)-1H-indazol-1-yl)acetic acid (229b) TFA adduct (119 mg, 0.38 mmol with N-(3-chloro-2-fluorobenzyl)-2-(isopropylamino)acetamide (19c) (118 mg, 0.46 mmol) according to the procedure reported in step-3 of Scheme 2 gave after workup and purification by flash column [silica (12 g), eluting with MeOH in DCM, 0 to 50%] 1-(2-((2-(((3-chloro-2-fluorobenzyl)amino)-2-oxoethyl)(isopropyl)amino)-2-oxoethyl)-5-(pyrimidin-2-yloxy)-1H-indazole-3-carboxamide (229c) (85 mg, 0.15 mmol, 40% yield) as an off-white solid as a mixture of two rotamers; $^1$H NMR (300 MHz, DMSO-d$_6$) δ 8.83 (t, J=5.7 Hz) & 8.38 (t, J=5.9 Hz) (2t, 1H), 8.67-8.62 (m, 2H), 7.88-7.83 (m, 1H), 7.75 and 7.73 (2s, 1H), 7.68 (dd, J=9.1, 0.7 Hz) and 7.62 (dd, J=9.1, 0.7 Hz) (2dd, 1H), 7.55-7.01 (m, 6H), 5.63 & 5.49 (2s, 2H), 4.65-4.50 & 4.39-4.24 (2m, 1H), 4.46 (d, J=5.6 Hz) & 4.32 (d, J=5.8 Hz) (2d, 2H), 4.19 & 3.85 (2s, 2H), 1.24 (d, J=6.4 Hz) & 1.00 (d, J=6.7 Hz) (2d, 6H); $^{19}$F NMR (282 MHz, DMSO-d$_6$) δ −121.21, −121.77; MS (ES+): 554.5 (M+1), 576.5 (M+Na); MS (ES−): 588.4 (M+Cl).

Scheme 230

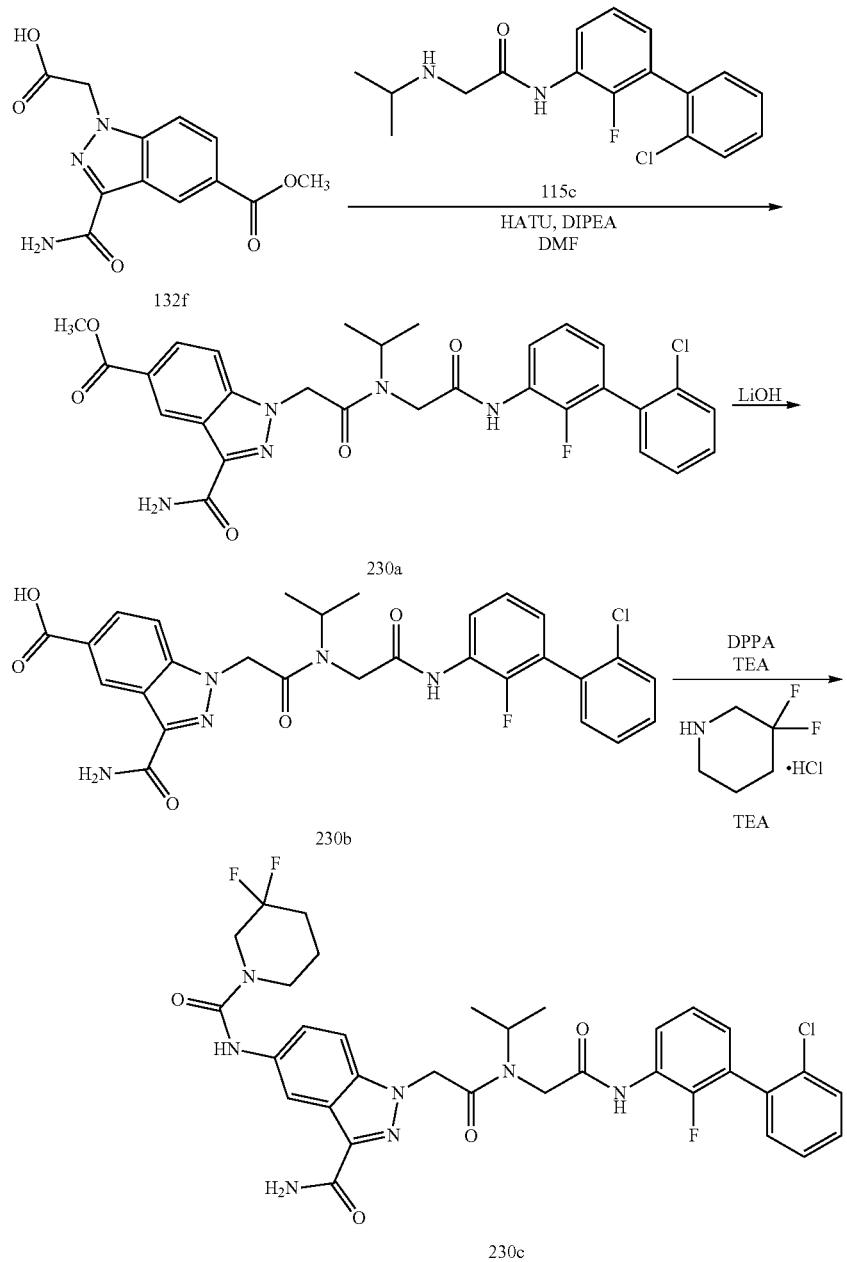

Preparation of 1-(2-((2-((2'-chloro-2-fluoro-[1,1'-biphenyl]-3-yl)-amino)-2-oxoethyl)(isopropyl)amino)-2-oxoethyl)-5-(3,3-difluoropiperidine-1-carboxamido)-1H-indazole-3-carboxamide (230c)

Step-1: Preparation of methyl 3-carbamoyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylate (230a)

Reaction of 2-(3-carbamoyl-5-(methoxycarbonyl)-1H-indazol-1-yl)acetic acid (132f) TFA adduct (300 g, 0.94 mmol) with N-(2'-chloro-2-fluorobiphenyl-3-yl)-2-(isopropylamino)acetamide (115c) (300 mg, 0.94 mmol) according to the procedure reported in step-3 of scheme-2 gave after workup and purification by flash column [silica (24 g), eluting with DMA80 in DCM 0 to 20%] methyl 3-carbamoyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylate (230a) (310 mg, 0.53 mmol, 57% yield) as an off-white solid; $^1$H NMR (300 MHz, DMSO-$d_6$) (mixture of two rotamers) δ 10.27 and 9.76 (2s, 1H), 8.91-8.86 (m, 1H), 8.16-6.96 (m, 11H), 5.71 and 5.56 (2s, 2H), 4.68-4.55 and 4.38-4.26 (2m, 1H), 4.47 and 4.08 (2s, 2H), 3.909 and 3.90 (2s, 3H), 1.27 and 1.06 (2d, J=6.8 Hz, 6H); $^{19}$F NMR (282 MHz, DMSO-$d_6$) δ −126.77, −126.94; MS (ES+): 580.5 (M+1), 602.5 (M+Na), MS (ES−): 578.5 (M−1), 614.6 (M+Cl).

Step-2: Preparation 3-carbamoyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (230b)

Reaction of methyl 3-carbamoyl-1-(2-((2-((2'-chloro-2-fluoro-[1,1'-biphenyl]-3-yl)amino)-2-oxoethyl)(isopropyl)amino)-2-oxoethyl)-1H-indazole-5-carboxylate (230a) (300 mg, 0.52 mmol) in THF (5 mL) with a solution of lithium hydroxide hydrate (25 mg, 1.03 mmol) in water (1 mL) according to the procedure reported in step-2 of scheme-29 gave after workup 3-carbamoyl-1-(2-((2-((2'-chloro-2-fluoro-[1,1'-biphenyl]-3-yl)amino)-2-oxoethyl)(isopropyl)amino)-2-oxoethyl)-1H-indazole-5-carboxylic acid (230b) (270 mg, 0.48 mmol, 92% yield) as a white solid; $^1$H NMR (300 MHz, DMSO-$d_6$) (mixture of two rotamers) δ 12.94 (s, 1H), 10.26 and 9.76 (2s, 1H), 8.86 and 8.85 (2dd, J=1.6, 0.8 Hz, 1H), 8.16-6.96 (m, 11H), 5.69 and 5.55 (2s, 2H), 4.68-4.56 and 4.37-4.28 (m, 1H), 4.47 and 4.08 (2s, 2H), 1.27 and 1.06 (2d, J=6.8 Hz, 6H); MS (ES−): 564.4 & 566.4 (M−1).

Step-3: Preparation of 1-(2-((2-((2'-chloro-2-fluoro-[1,1'-biphenyl]-3-yl)amino)-2-oxoethyl)(isopropyl)amino)-2-oxoethyl)-5-(3,3-difluoropiperidine-1-carboxamido)-1H-indazole-3-carboxamide (230c)

Compound 230c was prepared from 3-carbamoyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (230b) (150 mg, 0.27 mmol) according to the procedure reported in step-3 of scheme-223. This gave after work up and purification by flash column chromatography [silica gel (12 g), eluting with MeOH:EtOAc (9:1) in hexanes 0 to 70%] (120 mg, 0.18 mmol, 66% yield) of compound 230c as white solid; $^1$H NMR (300 MHz, DMSO-$d_6$) (mixture of two rotamers) δ 10.25 and 9.77 (2s, 1H), 8.78 and 8.77 (2s, 1H), 8.188 and 8.183 (2s, 1H), 8.19-8.05 and 7.99-7.90 (2m, 1H), 7.69-6.99 (m, 10H), 5.58 and 5.45 (2s, 2H), 4.70-4.56 and 4.38-4.27 (2m, 1H), 4.46 and 4.08 (2s, 2H), 3.81 (t, J=12.1 Hz, 2H), 3.58-3.47 (m, 2H), 2.18-1.95 (m, 2H), 1.79-1.64 (m, 2H), 1.25 and 1.06 (2d, J=6.8 Hz, 6H); 19F NMR (282 MHz, DMSO-$d_6$) (mixture of two rotamers) δ −101.16, −126.79 and −126.98; MS (ES+): 684.6 (M+1).

Scheme 231

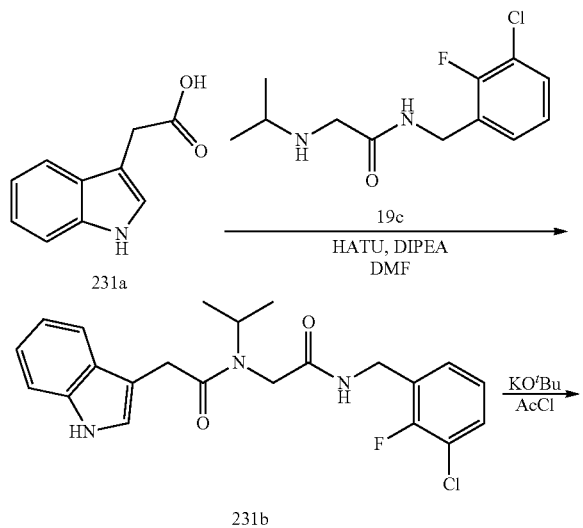

231a

HATU, DIPEA
DMF

231b

KO$^t$Bu
AcCl

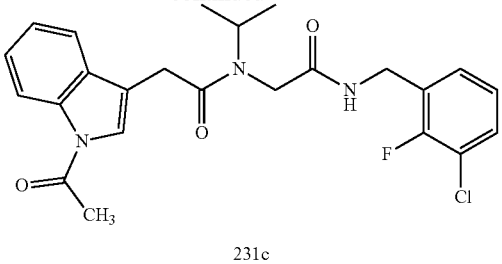

231c

Preparation of 2-(1-acetyl-1H-indol-3-yl)-N-(2-((3-chloro-2-fluorobenzyl)amino)-2-oxoethyl)-N-isopropylacetamide (231c)

Step-1: Preparation of N-(2-((3-chloro-2-fluorobenzyl)amino)-2-oxoethyl)-2-(1H-indol-3-yl)-N-isopropylacetamide (231b)

Reaction of N-(3-chloro-2-fluorobenzyl)-2-(isopropylamino)acetamide (19c) (795 mg, 3.07 mmol) with 2-(1H-indol-3-yl)acetic acid (231a) (359 mg, 2.05 mmol) according to the procedure reported in step-3 of Scheme 2 gave after workup and trituration of crude with EtOAc N-(2-((3-chloro-2-fluorobenzyl)amino)-2-oxoethyl)-2-(1H-indol-3-yl)-N-isopropylacetamide (231b) (583 mg, 1.40 mmol, 68% yield) as a white solid as a mixture of two rotamers; $^1$H NMR (300 MHz, DMSO-$d_6$) δ 10.89 (s, 1H), 8.63 (t, J=5.7 Hz) & 8.32 (t, J=5.9 Hz) (2t, 1H), 7.58-6.90 (m, 8H), 4.73-4.57 & 4.29-4.16 (2m, 1H), 4.41 (d, J=5.7 Hz) & 4.34 (d, J=5.9 Hz) (2d, 2H), 3.94 & 3.60 (2s, 2H), 3.81 & 3.80 (2s, 2H), 1.00 (d, J=6.5 Hz) & 0.96 (d, J=6.8 Hz) (2d, 6H); $^{19}$F NMR (282 MHz, DMSO-$d_6$) δ −121.31, −121.81; MS (ES+): 416.5 (M+1), 438.5 (M+Na); MS (ES−): 414.4 (M−1), 450.4 (M+Cl).

Step-2: Preparation of 2-(1-acetyl-1H-indol-3-yl)-N-(2-((3-chloro-2-fluorobenzyl)amino)-2-oxoethyl)-N-isopropylacetamide (231c)

To a solution of N-(2-((3-chloro-2-fluorobenzyl)amino)-2-oxoethyl)-2-(1H-indol-3-yl)-N-isopropylacetamide (231b) (0.15 g, 0.360 mmol) in THF (5 mL) at 0° C. under Argon atmosphere was added potassium tert-butoxide (40 mg, 0.361 mmol) and stirred for 10 mins. To the resulting suspension was added acetyl chloride (0.023 mL, 0.325 mmol) and stirred at 0° C. for 30 mins. The reaction mixture quenched with saturated aqueous NH$_4$C$_1$ solution (30 mL) and extracted with EtOAc (2×30 mL). The combined organic layers were washed with brine, dried, filtered and concentrated in vacuum. The residue obtained was purified by flash column chromatography [silica gel (12 g), eluting with EtOAc in hexanes o to 100%] to afford 2-(1-acetyl-1H-indol-3-yl)-N-(2-((3-chloro-2-fluorobenzyl)amino)-2-oxoethyl)-N-isopropylacetamide (231c) (42 mg, 0.092 mmol, 25% yield) as a white solid; $^1$H NMR (300 MHz, DMSO-$d_6$) (mixture of two rotamers) δ 8.70 and 8.40 (2t, J=5.9 Hz, 1H), 8.33-8.27 (m, 1H), 7.90 and 7.63 (2s, 1H), 7.61-7.09 (m, 6H), 4.71-4.59 and 4.29-4.18 (2m, 1H), 4.42 and 4.35 (2d, J=5.8 Hz, 2H), 4.09 and 3.69 (2s, 2H), 3.85 (s, 2H), 2.60 and 2.59 (2s, 3H), 1.10 (d, J=6.5 Hz) and 0.99 (d, J=6.8 Hz) (2d, 6H); $^{19}$F NMR (282 MHz, DMSO-$d_6$) (a mixture of two rotamers) δ −121.29, −121.75; MS (ES+) 480.4 & 482.5 (M+Na); MS (ES−): 456.4 & 458.4 (M−1).

Scheme 232

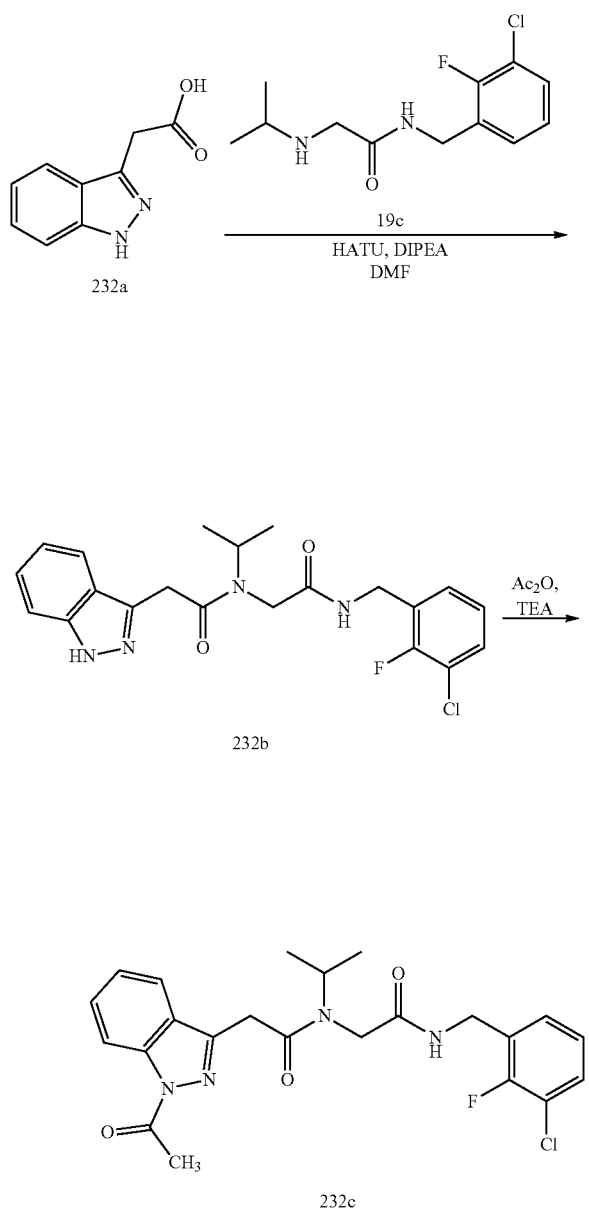

Preparation of 2-(1-acetyl-1H-indazol-3-yl)-N-(2-((3-chloro-2-fluorobenzyl)amino)-2-oxoethyl)-N-isopropylacetamide (232c)

Step-1: Preparation of N-(2-((3-chloro-2-fluorobenzyl)amino)-2-oxoethyl)-2-(1H-indazol-3-yl)-N-isopropylacetamide (232b)

Reaction of N-(3-chloro-2-fluorobenzyl)-2-(isopropylamino)acetamide (19c) (257 mg, 0.99 mmol) with 2-(1H-indazol-3-yl)acetic acid (232a) (175 mg, 0.99 mmol) according to the procedure reported in step-3 of Scheme 2 gave after workup and purification by flash column chromatography [silica gel (12 g), eluting with EtOAc in hexane 0 to 100%] N-(2-((3-chloro-2-fluorobenzyl)amino)-2-oxoethyl)-2-(1H-indazol-3-yl)-N-isopropylacetamide (232b) (310 mg, 0.74 mmol, 75% yield); $^1$H NMR (300 MHz, DMSO-$d_6$) (a mixture of two rotamers) δ 12.85 and 12.76 (2s, 1H), 8.70 and 8.48 (2t, J=6.0 Hz, 1H), 7.70 and 7.65 (2d, J=8.1 Hz, 1H), 7.54-6.99 (m, 6H), 4.68-4.57 and 4.33-4.23 (2m, 1H), 4.42 and 4.37 (2d, J=6.0 Hz, 2H), 4.11 and 4.09 (2s, 2H), 3.90 and 3.81 (2s, 2H), 1.03 and 0.95 (2d, J=6.8 Hz, 6H); MS (ES+): 417.4 (M+1), 439.4 (M+Na): MS (ES−): 415.3 (M−1).

Step-2: Preparation of 2-(1-acetyl-1H-indazol-3-yl)-N-(2-((3-chloro-2-fluorobenzyl)amino)-2-oxoethyl)-N-isopropylacetamide (232c)

To a solution of N-(2-((3-chloro-2-fluorobenzyl)amino)-2-oxoethyl)-2-(1H-indazol-3-yl)-N-isopropylacetamide (232b) (150 mg, 0.36 mmol) in DCM (5 mL) was added at room temperature triethylamine (0.15 mL, 1.08 mmol), DMAP (8.79 mg, 0.072 mmol), acetic anhydride (0.068 mL, 0.72 mmol) and stirred at RT for 48 h. The reaction mixture was concentrated to dryness and purified by flash column chromatography [silica gel (12 g), eluting with EtOAc in hexane 0 to 100%] to afford 2-(1-acetyl-1H-indazol-3-yl)-N-(2-((3-chloro-2-fluorobenzyl)amino)-2-oxoethyl)-N-isopropylacetamide (232c) (82 mg, 0.18 mmol, 50% yield) as a white solid; $^1$H NMR (300 MHz, DMSO-$d_6$) (mixture of two rotamers) δ 8.75 and 8.34 (2t, J=5.7 Hz, 1H), 8.30 and 8.27 (2dt, J=2.7, 0.9 Hz, 1H), 7.82-7.74 (m, 1H), 7.64-7.57 (m, 1H), 7.52-7.02 (m, 4H), 4.69-4.57 and 4.40-4.36 (2m, 1H), 4.43 and 4.33 (2d, J=6.0 Hz, 2H), 4.24 and 4.15 (2s, 2H), 4.05 and 3.83 (2s, 2H), 2.68 and 2.67 (2s, 3H), 1.17 and 1.00 (2d, J=6.8 Hz, 6H); $^{19}$FNMR (282 MHz, DMSO-$d_6$) (a mixture of two rotamers) δ −121.28, −121.81; MS (ES+) 459.5 (M+1), 481.4 (M+23), MS (ES−) 493.4 (M+Cl).

Scheme 233

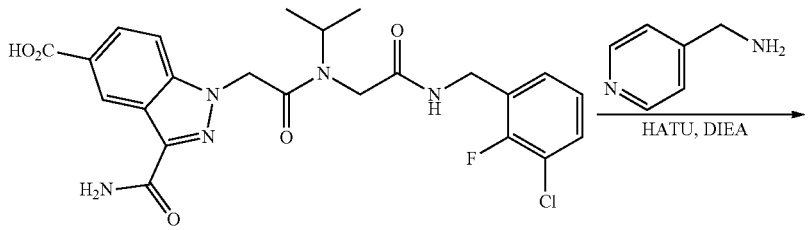

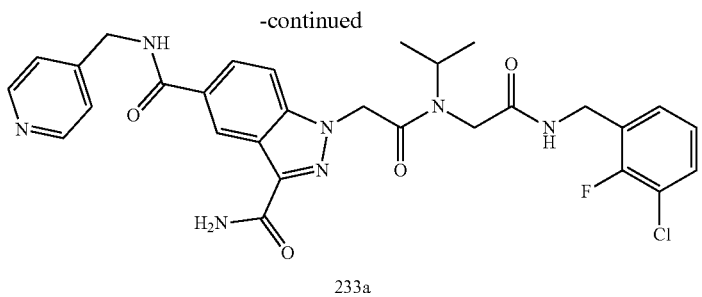

233a

Preparation of 1-(2-((2-(((3-chloro-2-fluorobenzyl)amino)-2-oxoethyl)(isopropyl)amino)-2-oxoethyl)-N5-(pyridin-4-ylmethyl)-1H-indazole-3,5-dicarboxamide (233a)

Reaction of 3-carbamoyl-1-(2-((2-(((3-chloro-2-fluorobenzyl)amino)-2-oxoethyl)(isopropyl)amino)-2-oxoethyl)-1H-indazole-5-carboxylic acid (144a) (50 mg, 0.1 mmol) with pyridin-4-ylmethanamine (0.015 mL, 0.15 mmol) according to the procedure reported in step-3 of Scheme 2 gave after workup and purification by flash column chromatography [silica (4 g), eluting with MeOH in DCM (1:0 to 9:1)] 1-(2-((2-(((3-chloro-2-fluorobenzyl)amino)-2-oxoethyl)(isopropyl)amino)-2-oxoethyl)-N5-(pyridin-4-ylmethyl)-1H-indazole-3,5-dicarboxamide (233a) (26 mg, 44%) as a white solid; $^1$H NMR (300 MHz, DMSO-$d_6$) (mixture of two rotamers) δ 9.32-9.26 (m, 1H), 8.83 (t, J=5.9 Hz) and 8.36 (t, J=5.9 Hz) (2t, 1H), 8.80-8.77 (m, 1H), 8.53-8.47 (m, 2H), 7.94 (ddd, J=10.8, 8.9, 1.7 Hz, 1H), 7.83 and 7.80 (2s, 1H), 7.72-7.60 (m, 1H), 7.56-6.95 (m, 6H), 5.64 and 5.50 (2s, 2H), 4.62-4.22 (m, 5H), 4.19 and 3.84 (2s, 2H), 1.23 (d, J=6.4 Hz) and 0.99 (d, J=6.8 Hz) (2d, 6H); $^{19}$F NMR (282 MHz, DMSO-$d_6$) δ −121.22, −121.72; MS (ES+): 594.6 & 596.6 (M+1); MS (ES−): 628.6 & 630.5 (M+Cl).

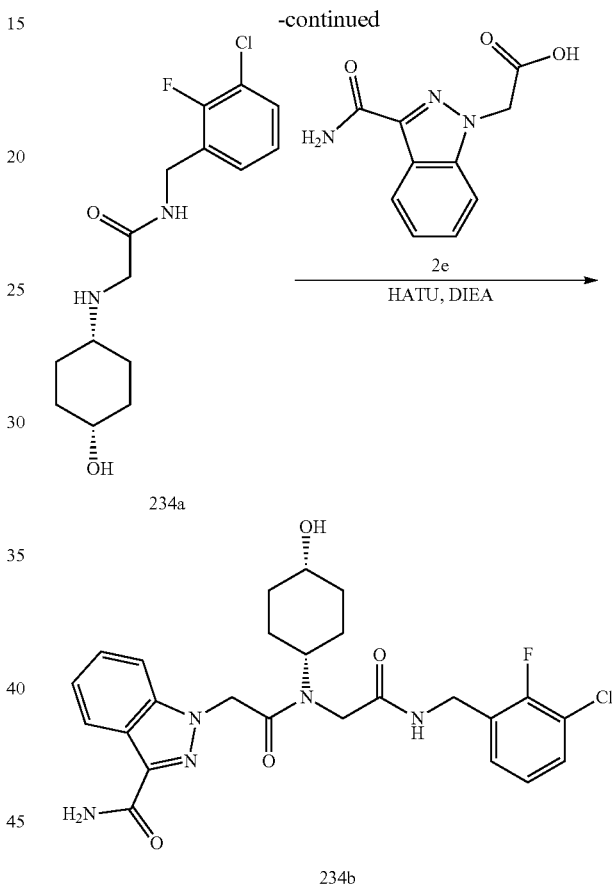

234a

234b

Preparation of 1-(2-((2-(((3-chloro-2-fluorobenzyl)amino)-2-oxoethyl)((1s,4s)-4-hydroxycyclohexyl)amino)-2-oxoethyl)-1H-indazole-3-carboxamide (234b)

Step-1: Preparation of N-(3-chloro-2-fluorobenzyl)-2-(((cis)-4-hydroxycyclohexyl)amino)acetamide (234a)

Reaction of 2-chloro-N-(3-chloro-2-fluorobenzyl)acetamide (35b) (500 mg, 2.12 mmol) with (1s,4s)-4-aminocyclohexanol (244 mg, 2.12 mmol) according to the procedure reported in step-2 of Scheme 35 gave after workup N-(3-chloro-2-fluorobenzyl)-2-(((cis)-4-hydroxycyclohexyl)amino)acetamide (234a) as a colorless oil which was used as such in the next step; MS (ES+): 315.4 (M+1); MS (ES−): 313.4 (M−1).

Scheme 234

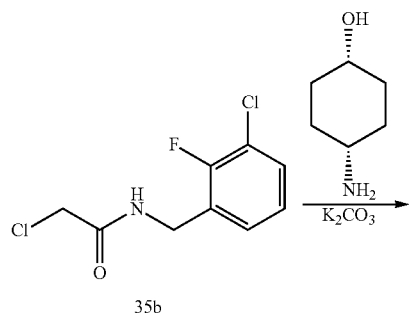

35b

421

Step-2: Preparation of 1-(2-((2-((3-chloro-2-fluorobenzyl)amino)-2-oxoethyl)((cis)-4-hydroxycyclohexyl)amino)-2-oxoethyl)-1H-indazole-3-carboxamide (234b)

Reaction of N-(3-chloro-2-fluorobenzyl)-2-(((1 s,4s)-4-hydroxy cy clohexyl)amino)acetamide (234a) (360 mg, 1.14 mmol) with 2-(3-carbamoyl-1H-indazol-1-yl)acetic acid (2e) (301 mg, 1.37 mmol) according to the procedure reported in step-3 of Scheme 2 gave after workup 1-(2-((2-((3-chloro-2-fluorobenzyl)amino)-2-oxoethyl)((cis)-4-hydroxycyclohexyl)amino)-2-oxoethyl)-1H-indazole-3-carboxamide (234b) (163 mg, 0.32 mmol, 28% yield) as a white solid as a mixture of two rotamers; $^1$H NMR (300 MHz, DMSO-$d_6$) δ 8.89 (t, J=5.7 Hz) & 8.36 (t, J=6.0 Hz) (2t, 1H), 8.23-8.11 (m, 1H), 7.79-6.98 (m, 8H), 5.61 & 5.45 (2s, 2H), 4.52-3.73 (m, 7H), 1.88-1.13 (m, 8H); $^{19}$F NMR (282 MHz, DMSO-$d_6$) δ −121.25, −121.69; MS (ES+): 516.5 (M+1), 538.4 (M+Na); MS (ES−): 514.4 (M−1), 550.5 (M+Cl).

422

Preparation of 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-indazole-3-carboxamide (235b)

Step-1: Preparation of 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a)

Compound 235a was prepared from 3-carbamoyl-1-(2-((2-((3-chloro-2-fluorobenzyl)amino)-2-oxoethyl)(cyclopropyl)amino)-2-oxoethyl)-1H-indazole-5-carboxylic acid (199a) (4 g, 7.97 mmol) according to the procedure reported in step-3 of Scheme 129 to afford product as a white solid (6.6 g, 12.53 mmol, 157% yield), which was used in the next step without further purification; MS (ES−): 525.4 (M−1).

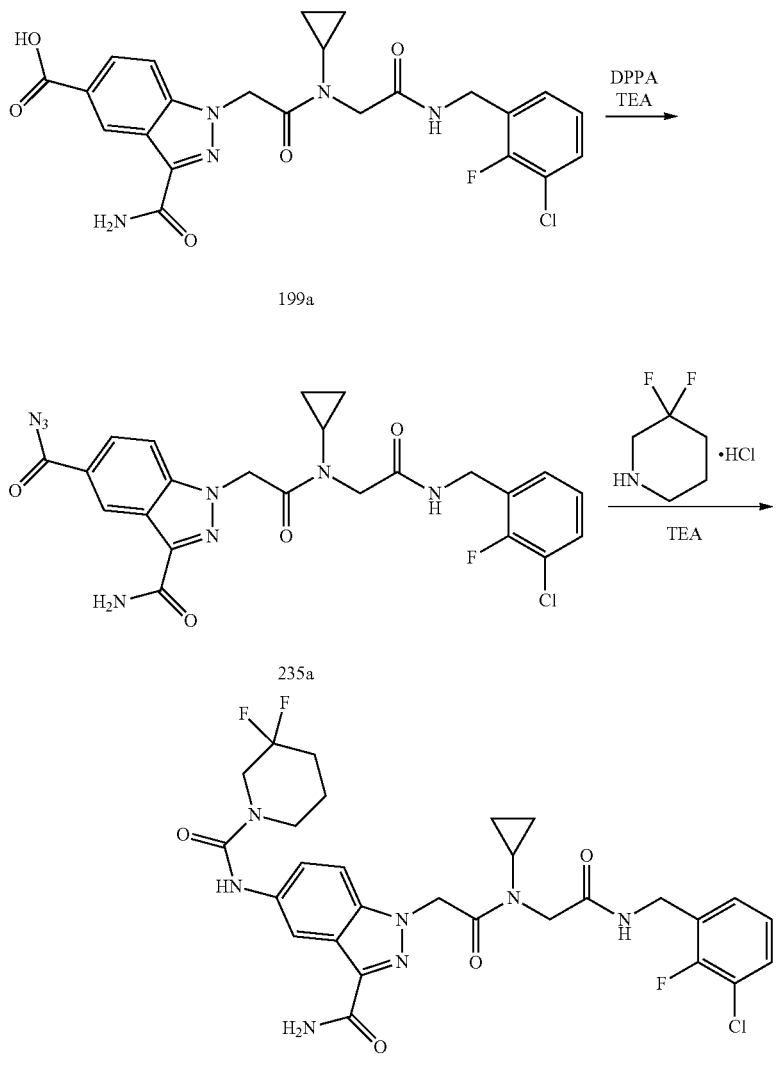

Scheme 235

423

Step-2: Preparation of 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-indazole-3-carboxamide (235b)

Compound 235b was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (500 mg, 0.47 mmol) and 3,3-difluoropiperidine hydrochloride (150 mg, 0.95 mmol) using TEA (0.27 mL, 1.9 mmol) as base according to the procedure reported in step-4 of Scheme 129 to afford after workup and purification by column chromatography [silica gel (12 g), eluting with DMA80 in DCM 0 to 40%] 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-indazole-3-carboxamide (235b) (86 mg, 0.14 mmol, 29% yield) as a white solid; $^1$H NMR (300 MHz, DMSO-$d_6$) δ 8.78 (s, 1H), 8.50 (t, J=5.8 Hz, 1H), 8.25-8.13 (m, 1H), 7.65 (s, 1H), 7.59-7.42 (m, 3H), 7.33 (s, 1H), 7.28-7.19 (m, 1H), 7.17-7.08 (m, 1H), 5.61 (s, 2H), 4.33 (d, J=5.7 Hz, 2H), 3.99 (s, 2H), 3.82 (t, J=12.0 Hz, 2H), 3.60-3.46 (m, 2H), 3.13-2.94 (m, 1H), 2.18-1.96 (m, 2H), 1.81-1.63 (m, 2H), 1.04-0.84 (m, 4H); $^{19}$F NMR (282 MHz, DMSO-$d_6$) δ −101.17, −121.60; MS (ES$^+$): 620.6 (M+1); MS (ES$^−$): 618.5 (M−1).

Scheme 236

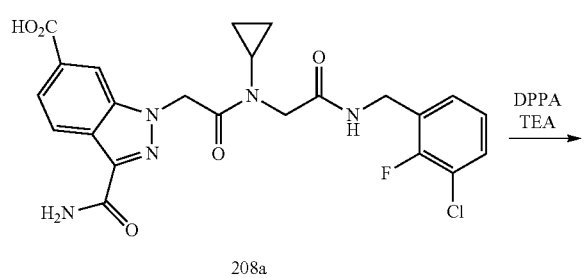

208a

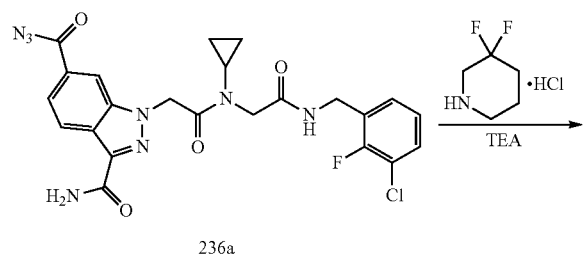

236a

424

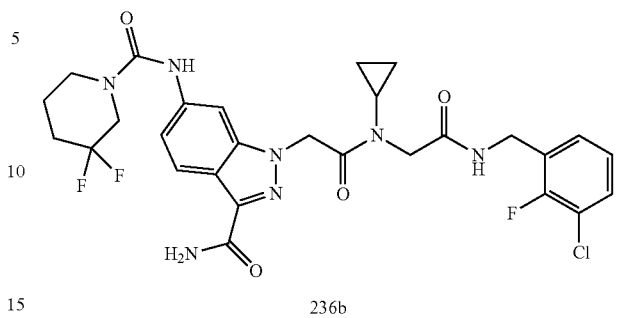

236b

Preparation of 1-(2-((2-((3-chloro-2-fluorobenzyl)amino)-2-oxoethyl)(cyclopropyl)amino)-2-oxoethyl)-6-(3,3-difluoropiperidine-1-carboxamido)-1H-indazole-3-carboxamide (236b)

Step-1: Preparation of 3-carbamoyl-1-(2-((2-((3-chloro-2-fluorobenzyl)amino)-2-oxoethyl)(cyclopropyl)amino)-2-oxoethyl)-1H-indazole-6-carbonyl azide (236a)

Compound 236a was prepared from 3-carbamoyl-1-(2-((2-((3-chloro-2-fluorobenzyl)amino)-2-oxoethyl)(cyclopropyl)amino)-2-oxoethyl)-1H-indazole-6-carboxylic acid (208a) (800 mg, 1.6 mmol) according to the procedure reported in step-3 of Scheme 129 to afford product; MS (ES+) 549.5 (M+Na).

Step-2: Preparation of 1-(2-((2-((3-chloro-2-fluorobenzyl)amino)-2-oxoethyl)(cyclopropyl)amino)-2-oxoethyl)-6-(3,3-difluoropiperidine-1-carboxamido)-1H-indazole-3-carboxamide (236b)

Compound 236b was prepared from 3-carbamoyl-1-(2-((2-((3-chloro-2-fluorobenzyl)amino)-2-oxoethyl)(cyclopropyl)amino)-2-oxoethyl)-1H-indazole-6-carbonyl azide (236a) (200 mg, 0.38 mmol) and 3,3-difluoropiperidine hydrochloride (120 mg, 0.76 mmol) using TEA (0.21 mL, 1.51 mmol) as base according to the procedure reported in step-4 of Scheme 129 to afford after workup and purification by column chromatography [silica gel (12 g), eluting with DMA80 in DCM 0 to 40%] (26 mg, 0.042 mmol, 11.05% yield) product as a white solid; $^1$H NMR (300 MHz, DMSO-$d_6$) δ 8.93 (s, 1H), 8.58 (t, J=5.8 Hz, 1H), 8.01 (d, J=8.6 Hz, 1H), 7.77 (s, 1H), 7.74-7.61 (m, 1H), 7.49-7.43 (m, 1H), 7.36-7.31 (m, 2H), 7.27-7.21 (m, 1H), 7.17-7.12 (m, 1H), 5.57 (s, 2H), 4.33 (d, J=5.5 Hz, 2H), 4.00 (s, 2H), 3.82 (t, J=11.9 Hz, 2H), 3.55-3.51 (m, 2H), 3.15-2.97 (m, 1H), 2.13-1.97 (m, 2H), 1.81-1.64 (m, 2H), 1.34-1.20 (m, 2H), 1.00-0.92 (m, 2H); $^{19}$F NMR (282 MHz, DMSO-$d_6$) δ −101.18, −121.66; MS (ES+) 620.6 (M+1); MS (ES−): 654.5, 656.5 (M+Cl).

Scheme 237

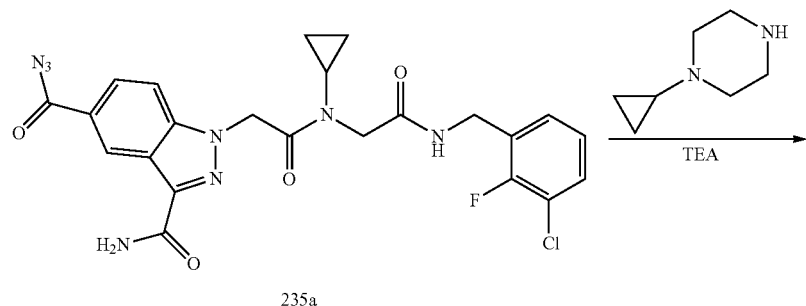

235a

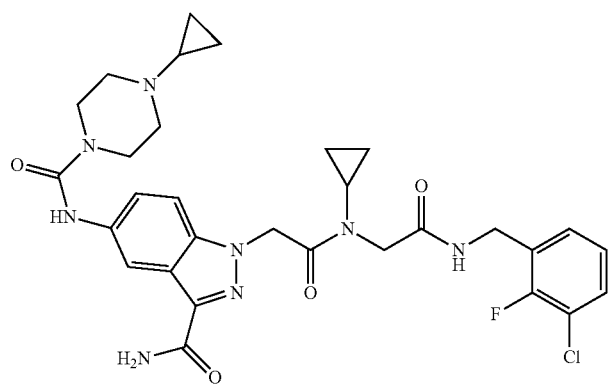

237a

Preparation of 1-(2-((2-((3-chloro-2-fluorobenzyl)amino)-2-oxoethyl)(cyclopropyl)amino)-2-oxoethyl)-5-(4-cyclopropylpiperazine-1-carboxamido)-1H-indazole-3-carboxamide (237a)

Compound 237a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (200 mg, 0.19 mmol) and 1-cyclopropylpiperazine (48 mg, 0.38 mmol) using TEA (0.11 mL, 0.76 mmol) as base according to the procedure reported in step-4 of Scheme 129. This gave after workup and purification by flash column chromatography [silica gel (12 g), eluting with DMA80 in DCM 0 to 40%] 1-(2-((2-((3-chloro-2-fluorobenzyl)amino)-2-oxoethyl)(cyclopropyl)amino)-2-oxoethyl)-5-(4-cyclopropylpiperazine-1-carboxamido)-1H-indazole-3-carboxamide (237a) (30 mg, 0.048 mmol, 25% yield) as a white solid; $^1$H NMR (300 MHz, DMSO-d$_6$) δ 8.65 (s, 1H), 8.50 (t, J=5.9 Hz, 1H), 8.21-8.15 (m, 1H), 7.67-7.60 (m, 1H), 7.60-7.42 (m, 3H), 7.35-7.28 (m, 1H), 7.27-7.20 (m, 1H), 7.18-7.09 (m, 1H), 5.61 (s, 2H), 4.33 (d, J=5.7 Hz, 2H), 3.99 (s, 2H), 3.42 (t, J=4.9 Hz, 4H), 3.10-3.01 (m, 1H), 2.58-2.52 (m, 4H), 1.71-1.61 (m, 1H), 1.02-0.96 (m, 2H), 0.95-0.89 (m, 2H), 0.46-0.40 (m, 2H), 0.38-0.33 (m, 2H); $^{19}$F NMR (282 MHz, DMSO) δ −121.60; MS (ES+) 625.7 (M+1), 647.7 (M+Na); (ES−) 623.6 (M−1).

Scheme 238

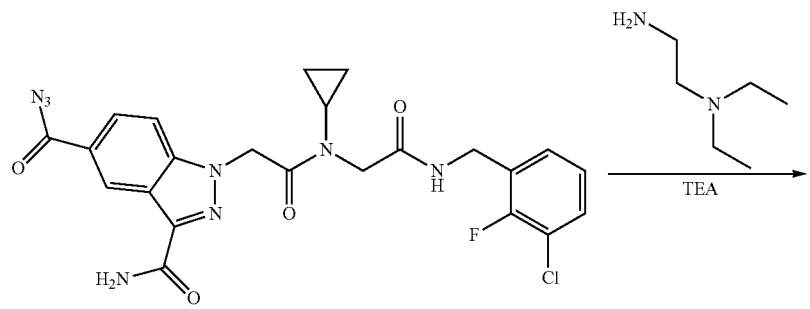

235a

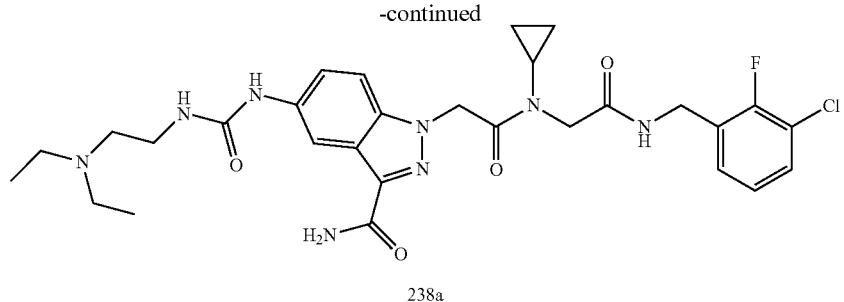

238a

Preparation of 1-(2-((2-(((3-chloro-2-fluorobenzyl)amino)-2-oxoethyl)(cyclopropyl)amino)-2-oxoethyl)-5-(3-(2-(diethylamino)ethyl)ureido)-1H-indazole-3-carboxamide (238a)

Compound 238a was prepared from 3-carbamoyl-1-(2-((2-(((3-chloro-2-fluorobenzyl)amino)-2-oxoethyl)(cyclopropyl)amino)-2-oxoethyl)-1H-indazole-5-carbonyl azide (235a) (150 mg, 0.14 mmol) and $N^1,N^1$-diethylethane-1,2-diamine (33 mg, 0.29 mmol) using TEA (0.08 mL, 0.57 mmol) as base according to the procedure reported in step-4 of Scheme 129. This gave after workup, purification by flash column chromatography [silica gel (12 g), eluting with DMA80 in DCM 0 to 40%] and prep-HPLC [eluting with CH$_3$CN in water (contains 0.1% TFA) from 0-100%] 1-(2-((2-(((3-chloro-2-fluorobenzyl)amino)-2-oxoethyl)(cyclopropyl)amino)-2-oxoethyl)-5-(3-(2-(diethylamino)ethyl)ureido)-1H-indazole-3-carboxamide (238a) (16 mg, 0.026 mmol, 18% yield) as an off white solid; $^1$H NMR (300 MHz, DMSO-d$_6$) δ 8.81 (s, 1H), 8.50 (t, J=5.9 Hz, 1H), 8.24-8.13 (m, 1H), 7.60 (s, 1H), 7.53-7.41 (m, 3H), 7.33-7.27 (m, 1H), 7.27-7.19 (m, 1H), 7.17-7.07 (m, 1H), 6.00 (t, J=5.4 Hz, 1H), 5.60 (s, 2H), 4.33 (d, J=5.7 Hz, 2H), 3.98 (s, 2H), 3.16 (q, J=6.2 Hz, 2H), 3.09-2.95 (m, 1H), 2.57-2.50 (m, 6H), 1.07-0.83 (m, 10H); $^{19}$F NMR (282 MHz, DMSO-d$_6$) δ −73.45 (TFA peak), −121.60; MS (ES+) 615.7 (M+1); MS (ES−): 614.6 (M−1).

Scheme 239

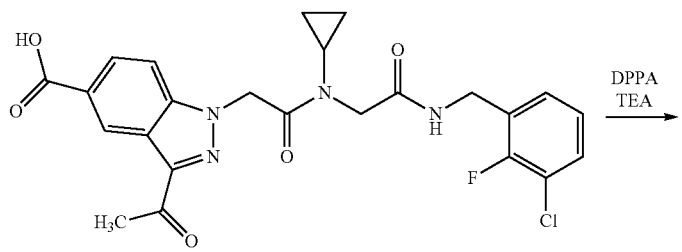

228a

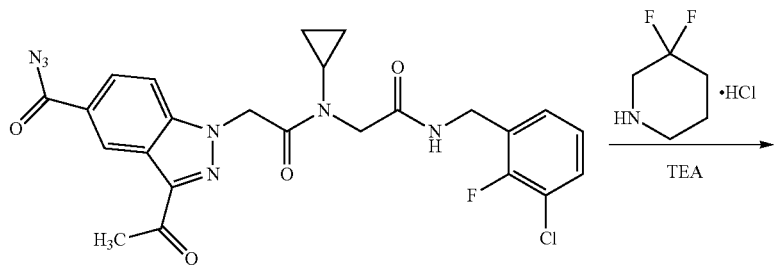

239a

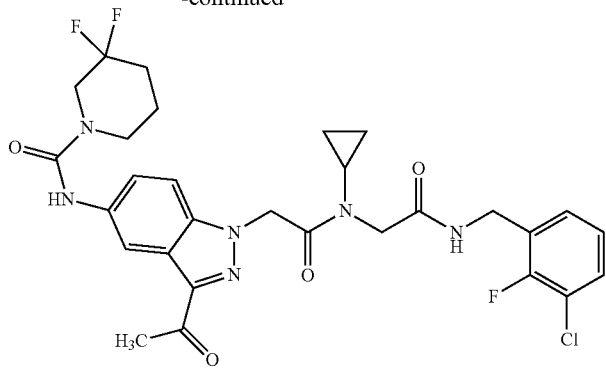

239b

Preparation of N-(3-acetyl-1-(2-((2-((3-chloro-2-fluorobenzyl)amino)-2-oxoethyl)(cyclopropyl)amino)-2-oxoethyl)-1H-indazol-5-yl)-3,3-difluoropiperidine-1-carboxamide (239b)

Step-1: Preparation of 3-acetyl-1-(2-((2-((3-chloro-2-fluorobenzyl)amino)-2-oxoethyl)(cyclopropyl)amino)-2-oxoethyl)-1H-indazole-5-carbonyl azide (239a)

Compound 235a was prepared from 3-acetyl-1-(2-((2-((3-chloro-2-fluorobenzyl)amino)-2-oxoethyl)(cyclopropyl)amino)-2-oxoethyl)-1H-indazole-5-carboxylic acid (228a) (630 mg, 1.26 mmol) according to the procedure reported in step-3 of Scheme 129 to afford product as a white solid (750 mg, 1.426 mmol, 113% yield), which was used in the next step without further purification. MS (ES+): 526.5 (M+1).

Step-2: Preparation of N-(3-acetyl-1-(2-((2-((3-chloro-2-fluorobenzyl)amino)-2-oxoethyl)(cyclopropyl)amino)-2-oxoethyl)-1H-indazol-5-yl)-3,3-difluoropiperidine-1-carboxamide (239b)

Compound 239b was prepared from 3-acetyl-1-(2-((2-((3-chloro-2-fluorobenzyl)amino)-2-oxoethyl)(cyclopropyl)amino)-2-oxoethyl)-1H-indazole-5-carbonyl azide (239a) (350 mg, 0.67 mmol) and 3,3-difluoropiperidine hydrochloride (210 mg, 1.33 mmol) using TEA (0.37 mL, 2.66 mmol) as base according to the procedure reported in step-4 of Scheme 129. This gave after workup and purification by flash column chromatography [silica gel (12 g), eluting with DMA80 in DCM 0 to 40%] N-(3-acetyl-1-(2-((2-((3-chloro-2-fluorobenzyl)amino)-2-oxoethyl)(cyclopropyl)amino)-2-oxoethyl)-1H-indazol-5-yl)-3,3-difluoropiperidine-1-carboxamide (239b) (190 mg, 0.31 mmol, 46% yield) as a white solid; $^1$H NMR (300 MHz, DMSO-$d_6$) δ 8.83 (s, 1H), 8.48 (t, J=5.8 Hz, 1H), 8.28-8.19 (m, 1H), 7.63-7.52 (m, 2H), 7.45 (td, J=7.6, 1.7 Hz, 1H), 7.23 (td, J=7.3, 6.8, 1.7 Hz, 1H), 7.15-7.07 (m, 1H), 5.70 (s, 2H), 4.34 (d, J=5.7 Hz, 2H), 3.99 (s, 2H), 3.82 (t, J=12.0 Hz, 2H), 3.61-3.47 (m, 2H), 3.19-3.01 (m, 1H), 2.60 (s, 3H), 2.17-1.97 (m, 2H), 1.80-1.64 (m, 2H), 1.07-0.96 (m, 2H), 0.96-0.80 (m, 2H); $^{19}$F NMR (282 MHz, DMSO-$d_6$) δ −101.17, −121.61; MS (ES+) 619.7 (M+1); (ES−): 617.6 (M−1).

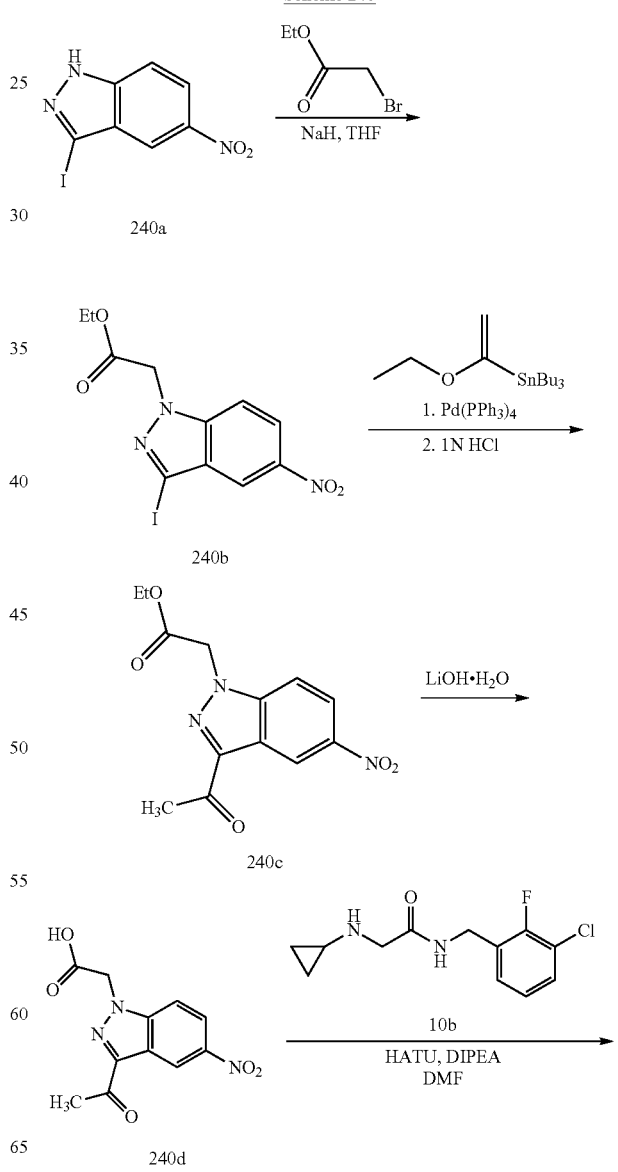

Scheme 240

-continued

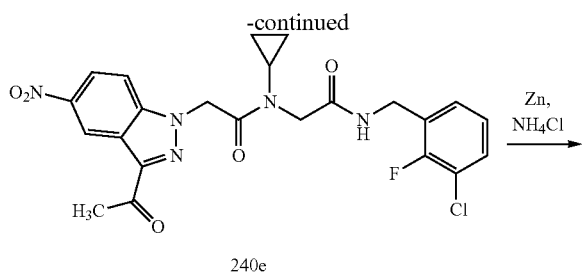

240e

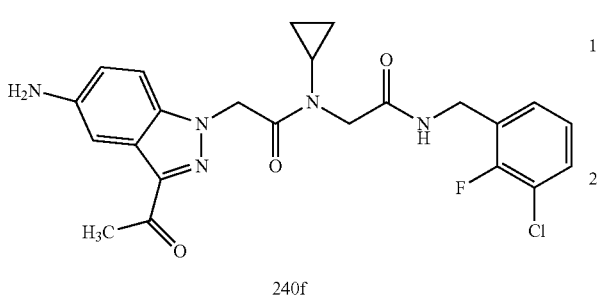

240f

Preparation of 2-(3-acetyl-5-amino-1H-indazol-1-yl)-N-(2-((3-chloro-2-fluorobenzyl)amino)-2-oxoethyl)-N-cyclopropylacetamide (240f)

Step-1: Preparation of ethyl 2-(3-iodo-5-nitro-1H-indazol-1-yl)acetate (240b)

Reaction of 3-iodo-5-nitro-1H-indazole (240a) (3 g, 10.38 mmol) with ethyl 2-bromoacetate (1.38 mL, 12.46 mmol) using sodium hydride (0.46 g, 11.42 mmol) as base according to the procedure reported in step-1 of Scheme 57 gave after workup and purification by flash column chromatography [silica (40 g), eluting with EtOAc in hexane 0 to 30%] ethyl 2-(3-iodo-5-nitro-1H-indazol-1-yl)acetate (240b) (2.52 g, 6.72 mmol, 64.7% yield) as an orange solid; $^1$H NMR (300 MHz, DMSO-d$_6$) δ 8.38-8.30 (m, 2H), 7.95 (d, J=9.9 Hz, 1H), 5.56 (s, 2H), 4.16 (q, J=7.1 Hz, 2H), 1.21 (t, J=7.1 Hz, 3H); MS (ES+): 376.3 (M+1), 398.3 (M+Na).

Step-2: Preparation of ethyl 2-(3-acetyl-5-nitro-1H-indazol-1-yl)acetate (240c)

Reaction of ethyl 2-(3-iodo-5-nitro-1H-indazol-1-yl)acetate (240b) (1.5 g, 4.00 mmol) in Toluene (40 mL) using tributyl(1-ethoxyvinyl)stannane (1.62 mL, 4.80 mmol) and Pd(PPh$_3$)$_4$ according to the procedure reported in step-1 and step-2 of Scheme 206 gave after workup and purification by flash column chromatography [silica gel (24 g), eluting with EtOAc in DCM 0 to 20%] ethyl 2-(3-acetyl-5-nitro-1H-indazol-1-yl)acetate (240c) (0.83 g, 2.85 mmol, 71% yield) as dark orange solid; $^1$H NMR (300 MHz, DMSO-d$_6$) δ 9.01 (dd, J=2.3, 0.7 Hz, 1H), 8.37 (dd, J=9.3, 2.2 Hz, 1H), 8.06 (dd, J=9.3, 0.7 Hz, 1H), 5.70 (s, 2H), 4.19 (q, J=7.1 Hz, 2H), 2.67 (s, 3H), 1.22 (t, J=7.1 Hz, 3H); MS (ES+): 292.3 (M+1), MS (ES−): 326.3 (M+Cl).

Step-3: Preparation of 2-(3-acetyl-5-nitro-1H-indazol-1-yl)acetic acid (240d)

Reaction of ethyl 2-(3-acetyl-5-nitro-1H-indazol-1-yl)acetate (240c) (0.8 g, 2.75 mmol) in THF (20 mL) using a solution of lithium hydroxide hydrate (0.13 g, 5.49 mmol) in water (5 mL) according to the procedure reported in step-2 of Scheme 129 gave after workup 2-(3-acetyl-5-nitro-1H-indazol-1-yl)acetic acid (240d) (0.71 g, 2.7 mmol, 98% yield) as off-white solid; $^1$H NMR (300 MHz, DMSO-d$_6$) δ 13.52 (s, 1H), 9.00 (dd, J=2.2, 0.6 Hz, 1H), 8.36 (dd, J=9.3, 2.2 Hz, 1H), 8.06 (dd, J=9.4, 0.7 Hz, 1H), 5.58 (s, 2H), 2.67 (s, 3H); MS (ES+): 264.3 (M+1); MS (ES−): 262.2 (M−1).

Step-4: Preparation of 2-(3-acetyl-5-nitro-1H-indazol-1-yl)-N-(2-((3-chloro-2-fluorobenzyl)amino)-2-oxoethyl)-N-cyclopropylacetamide (240e)

Reaction of 2-(3-acetyl-5-nitro-1H-indazol-1-yl)acetic acid (240d) (0.65 g, 2.47 mmol) with N-(3-chloro-2-fluorobenzyl)-2-(cyclopropylamino)acetamide (10b) (0.7 g, 2.72 mmol) according to the procedure reported in step-3 of Scheme 2 gave after workup and purification by flash column [silica (12 g), eluting with DMA80 in DCM 0 to 40%] 2-(3-acetyl-5-nitro-1H-indazol-1-yl)-N-(2-((3-chloro-2-fluorobenzyl)amino)-2-oxoethyl)-N-cyclopropylacetamide (240e) (820 mg, 1.63 mmol, 66% yield) as a light orange solid; $^1$H NMR (300 MHz, DMSO-d$_6$) δ 9.00 (dd, J=2.3, 0.6 Hz, 1H), 8.49 (t, J=5.9 Hz, 1H), 8.30 (dd, J=9.3, 2.2 Hz, 1H), 7.95 (dd, J=9.3, 0.7 Hz, 1H), 7.45 (td, J=7.6, 1.7 Hz, 1H), 7.26-7.17 (m, 1H), 7.09 (td, J=7.9, 1.0 Hz, 1H), 5.87 (s, 2H), 4.34 (d, J=5.7 Hz, 2H), 3.99 (s, 2H), 3.19-3.07 (m, 1H), 2.67 (s, 3H), 1.09-0.99 (m, 2H), 0.96-0.86 (m, 2H); $^{19}$F NMR (282 MHz, DMSO-d$_6$) δ −121.56; MS (ES+): 524.4 (M+Na), MS (ES−): 536.3 (M+Cl).

Step-5: Preparation of 2-(3-acetyl-5-amino-1H-indazol-1-yl)-N-(2-((3-chloro-2-fluorobenzyl)amino)-2-oxoethyl)-N-cyclopropylacetamide (240f)

To a solution of 2-(3-acetyl-5-nitro-1H-indazol-1-yl)-N-(2-((3-chloro-2-fluorobenzyl)amino)-2-oxoethyl)-N-cyclopropylacetamide (240e) (800 mg, 1.59 mmol) in THF (20 mL) and MeOH (5 mL) was added NH$_4$Cl (1.71 g, 31.9 mmol), Zinc (1.04 g, 15.94 mmol) and stirred at RT for 3 h. The reaction mixture was filtered over a Celite pad, washed with 20% MeOH in EtOAc (2×8 mL). The filtrate was concentrated in vacuum to dryness and the resultant residue was suspended in brine (60 mL) and EtOAc (80 mL). The organic layer was separated dried, filtered and concentrated in vacuum to afford 2-(3-acetyl-5-amino-1H-indazol-1-yl)-N-(2-((3-chloro-2-fluorobenzyl)amino)-2-oxoethyl)-N-cyclopropylacetamide (240f) (650 mg, 1.378 mmol, 86% yield) as a light orange solid; $^1$H NMR (300 MHz, DMSO-d$_6$) δ 8.47 (t, J=5.4 Hz, 1H), 7.53-7.41 (m, 1H), 7.35 (d, J=8.9 Hz, 1H), 7.30-7.07 (m, 3H), 6.81 (dd, J=8.9, 2.1 Hz, 1H), 5.60 (s, 2H), 5.21 (s, 2H), 4.34 (d, J=5.8 Hz, 2H), 3.98 (s, 2H), 3.14-3.03 (m, 1H), 2.53 (s, 3H), 1.04-0.95 (m, 2H), 0.93-0.84 (m, 2H); $^{19}$F NMR (282 MHz, DMSO-d$_6$) δ −121.62; MS (ES+): 472.4 (M+1), 494.4 (M+Na), MS (ES−): 506.4 (M+Cl).

Scheme 241

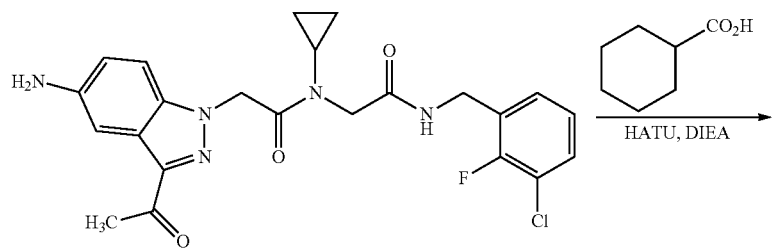

240f

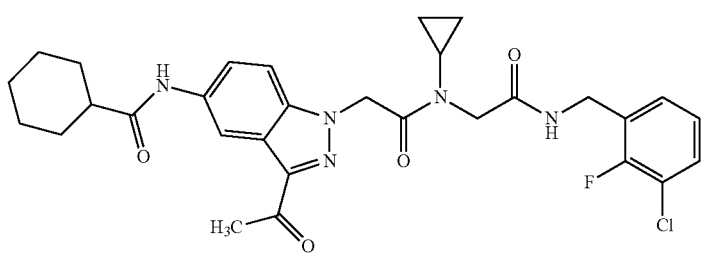

241a

Preparation of N-(3-acetyl-1-(2-((2-((3-chloro-2-fluorobenzyl)amino)-2-oxoethyl)(cyclopropyl)amino)-2-oxoethyl)-1H-indazol-5-yl)cyclohexanecarboxamide (241a)

Reaction of 2-(3-acetyl-5-amino-1H-indazol-1-yl)-N-(2-((3-chloro-2-fluorobenzyl)amino)-2-oxoethyl)-N-cyclopropylacetamide (240f) (100 mg, 0.21 mmol) with cyclohexanecarboxylic acid (33 mg, 0.25 mmol) according to the procedure reported in step-3 of Scheme 2 gave after workup and purification by flash column chromatography [silica (12 g), eluting with EtOAc in hexane 0 to 100%] N-(3-acetyl-1-(2-((2-((3-chloro-2-fluorobenzyl)amino)-2-oxoethyl)(cyclopropyl)amino)-2-oxoethyl)-1H-indazol-5-yl)cyclohexanecarboxamide (241a) (85 mg, 0.15 mmol, 69% yield) as a white solid; $^1$H NMR (300 MHz, DMSO-$d_6$) δ 9.97 (s, 1H), 8.54-8.51 (m, 1H), 8.48 (t, J=5.9 Hz, 1H), 7.67-7.56 (m, 2H), 7.50-7.42 (m, 1H), 7.27-7.17 (m, 1H), 7.10 (td, J=7.9, 1.0 Hz, 1H), 5.71 (s, 2H), 4.34 (d, J=5.8 Hz, 2H), 3.98 (s, 2H), 3.18-3.04 (m, 1H), 2.60 (s, 3H), 2.41-2.28 (m, 1H), 1.91-1.58 (m, 6H), 1.52-1.14 (m, 4H), 1.07-0.97 (m, 2H), 0.95-0.84 (m, 2H); $^{19}$F NMR (282 MHz, DMSO-$d_6$) δ −121.60; MS (ES+): 604.6 (M+Na); MS (ES−): 580.5 (M−1), 616.5 (M+Cl).

Scheme 242

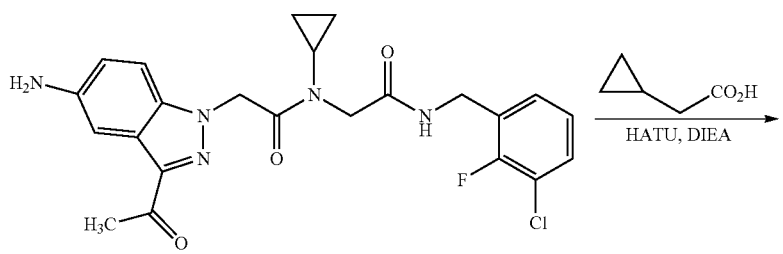

240f

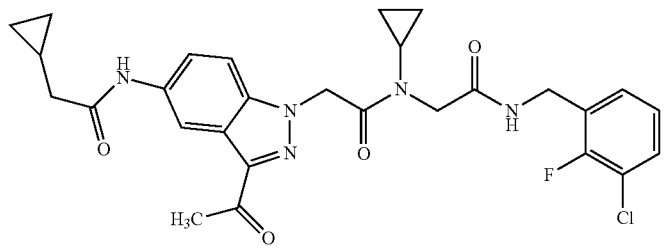

242a

Preparation of 2-(3-acetyl-5-(2-cyclopropylacetamido)-1H-indazol-1-yl)-N-(2-((3-chloro-2-fluorobenzyl)amino)-2-oxoethyl)-N-cyclopropylacetamide (242a)

Reaction of 2-(3-acetyl-5-amino-1H-indazol-1-yl)-N-(2-((3-chloro-2-fluorobenzyl)amino)-2-oxoethyl)-N-cyclopropylacetamide (240f) (100 mg, 0.21 mmol) with 2-cyclopropylacetic acid (25 mg, 0.25 mmol) according to the procedure reported in step-3 of Scheme 2 gave after workup and purification by flash column chromatography [silica (12 g), eluting with EtOAc in hexane 0 to 100%] 2-(3-acetyl-5-(2-cyclopropylacetamido)-1H-indazol-1-yl)-N-(2-((3-chloro-2-fluorobenzyl)amino)-2-oxoethyl)-N-cyclopropylacetamide (242a) (80 g, 0.14 mmol, 68% yield) as a white solid; $^1$H NMR (300 MHz, DMSO-d$_6$) δ 9.98 (s, 1H), 8.56-8.43 (m, 2H), 7.68-7.57 (m, 2H), 7.50-7.42 (m, 1H), 7.10 (td, J=7.9, 1.0 Hz, 1H), 7.15-7.06 (m, 1H), 5.72 (s, 2H), 4.34 (d, J=5.8 Hz, 2H), 3.99 (s, 2H), 3.17-3.05 (m, 1H), 2.60 (s, 3H), 2.23 (d, J=7.0 Hz, 2H), 1.14-0.97 (m, 3H), 0.96-0.85 (m, 2H), 0.55-0.44 (m, 2H), 0.26-0.16 (m, 2H); $^{19}$F NMR (282 MHz, DMSO-d$_6$) δ −121.60; MS (ES+): 576.6 (M+Na); MS (ES−): 588.5 (M+Cl).

Scheme 243

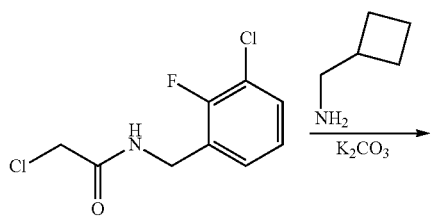

35b

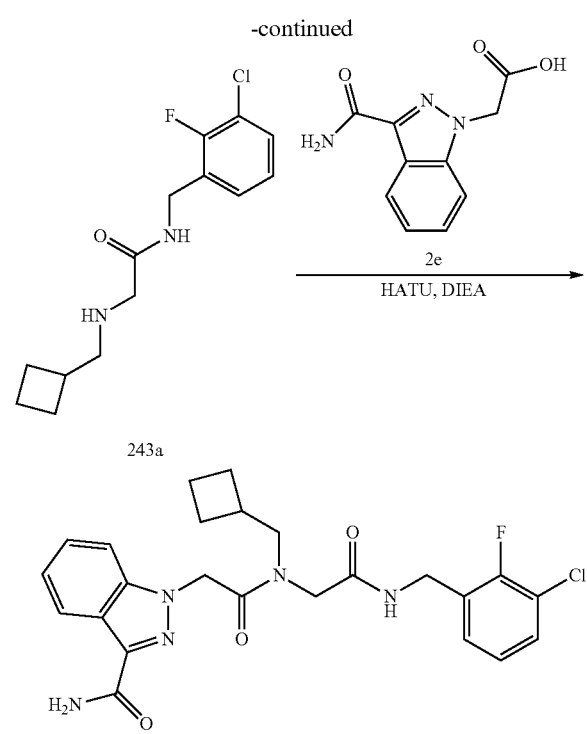

243a

243b

Preparation of 1-(2-((2-((3-chloro-2-fluorobenzyl)amino)-2-oxoethyl)(cyclobutylmethyl)amino)-2-oxoethyl)-1H-indazole-3-carboxamide (243b)

Step-1: Preparation of N-(3-chloro-2-fluorobenzyl)-2-((cyclobutylmethyl)amino)acetamide (243a)

Reaction of 2-chloro-N-(3-chloro-2-fluorobenzyl)acetamide (35b) (243 mg, 1.03 mmol) with cyclobutylmethanamine hydrochloride (250 mg, 2.056 mmol) according to the procedure reported in step-2 of Scheme 35 gave after workup and purification by flash column chromatography [silica (12 g), eluting with EtOAc/MeOH (9:1) in hexane 0 to 60%] N-(3-chloro-2-fluorobenzyl)-2-((cyclobutylmethyl)

amino)acetamide (243a) (203 mg, 0.71 mmol, 69% yield) as a clear oil which was used as such in the next step; MS (ES+) 285.4 (M+1); (ES−) 283.3 (M−1).

Step-2: Preparation of 1-(2-((2-((3-chloro-2-fluorobenzyl)amino)-2-oxoethyl)(cyclobutylmethyl)amino)-2-oxo ethyl)-1H-indazole-3-carboxamide (243b)

Reaction of N-(3-chloro-2-fluorobenzyl)-2-((cyclobutylmethyl)amino)acetamide (243a) (109 mg, 0.38 mmol) with 2-(3-carbamoyl-1H-indazol-1-yl)acetic acid (2e) (92 mg, 0.42 mmol) according to the procedure reported in step-3 of Scheme 2 gave after workup and purification by flash column chromatography [silica (12 g), eluting with DMA80 in DCM 0 to 40%] 1-(2-((2-((3-chloro-2-fluorobenzyl)amino)-2-oxoethyl)(cyclobutylmethyl)amino)-2-oxo ethyl)-1H-indazole-3-carboxamide (243b) (48 mg, 0.1 mmol, 26% yield) as a white solid as a mixture of two rotamers; $^1$H NMR (300 MHz, DMSO-d$_6$) δ 8.83 (t, J=5.7 Hz) and 8.46 (t, J=5.8 Hz) (2t, 1H), 8.18 (d, J=8.1 Hz, 1H), 7.79-7.65 (m, 1H), 7.58-7.05 (m, 7H), 5.57 and 5.46 2 (s, 2H), 4.45 (d, J=5.5 Hz) and 4.33 (d, J=5.7 Hz) (2d, 2H), 4.22 and 3.92 (2s, 2H), 3.53 and, 3.29 (2d, J=7.2 Hz, 2H), 2.73-2.60 and 2.47-2.32 (m, 1H), 2.07-1.50 (m, 6H); $^{19}$F NMR (282 MHz, DMSO-d$_6$) δ −121.18, −121.60; MS (ES+) 486.5 (M+1); (ES−) 484.5 (M−1).

Scheme 244

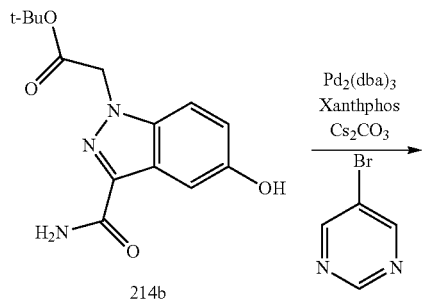

214b

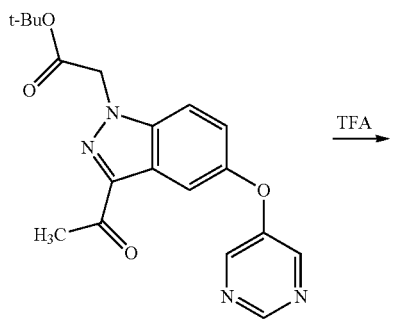

244a

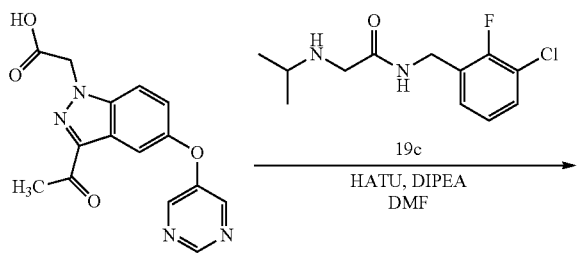

244b

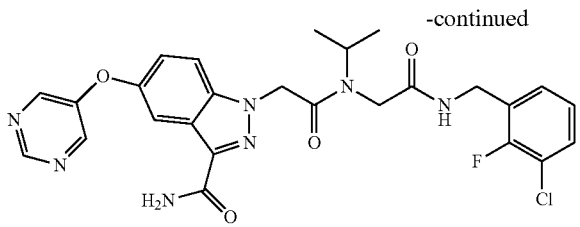

244c

Preparation of 1-(2-((2-(((3-chloro-2-fluorobenzyl) amino)-2-oxoethyl)(isopropyl)amino)-2-oxoethyl)-5-(pyrimidin-5-yloxy)-1H-indazole-3-carboxamide (244c)

Step-1: Preparation of tert-butyl 2-(3-carbamoyl-5-(pyrimidin-5-yloxy)-1H-indazol-1-yl)acetate (229a)

Reaction of tert-butyl 2-(3-carbamoyl-5-hydroxy-1H-indazol-1-yl)acetate (214b) (164 mg, 0.56 mmol) with 5-bromopyrimidine (107 mg, 0.68 mmol) using cesium carbonate (367 mg, 1.13 mmol), Pd$_2$(dba)$_3$ (26 mg, 0.03 mmol) and (9,9-dimethyl-9H-xanthene-4,5-diyl)bis(diphenylphosphine) (Xantphos, 33 mg, 0.06 mmol) according to the procedure reported in step-1 of Scheme 97 gave after workup and purification by flash column chromatography [silica gel (12 g), eluting with methanol in DCM 0 to 100%] tert-butyl 2-(3-carbamoyl-5-(pyrimidin-5-yloxy)-1H-indazol-1-yl)acetate (229a) (39 mg, 0.11 mmol, 19% yield) as an off-white solid; MS (ES+): 370.4 (M+1); MS (ES−): 368.3 (M−1).

Step-2: Preparation 2-(3-carbamoyl-5-(pyrimidin-5-yloxy)-1H-indazol-1-yl)acetic acid (244b)

Reaction of tert-butyl 2-(3-carbamoyl-5-(pyrimidin-5-yloxy)-1H-indazol-1-yl)acetate (244a) (39 mg, 0.11 mmol) with TFA (0.24 mL, 3.17 mmol) in DCM (10 mL) according to the procedure reported in step-2 of Scheme 2 gave after workup 2-(3-carbamoyl-5-(pyrimidin-5-yloxy)-1H-indazol-1-yl)acetic acid (244b) (33 mg, 0.11 mmol, 100% yield) as a yellow solid in the form of TFA adduct; MS (ES+): 314.3 (M+1); MS (ES−): 312.3 (M−1).

Step-3: Preparation of 1-(2-((2-(((3-chloro-2-fluorobenzyl)amino)-2-oxoethyl)(isopropyl)amino)-2-oxoethyl)-5-(pyrimidin-5-yloxy)-1H-indazole-3-carboxamide (244c)

Reaction of 2-(3-carbamoyl-5-(pyrimidin-5-yloxy)-1H-indazol-1-yl)acetic acid (244b) TFA adduct (33 mg, 0.11 mmol with N-(3-chloro-2-fluorobenzyl)-2-(isopropylamino)acetamide (19c) (33 mg, 0.13 mmol) according to the procedure reported in step-3 of Scheme 2 gave after workup and purification by flash column [silica (12 g), eluting with DMA-80 in DCM, 0 to 100%] 1-(2-((2-(((3-chloro-2-fluorobenzyl)amino)-2-oxo ethyl)(isopropyl)amino)-2-oxoethyl)-5-(pyrimidin-5-yloxy)-1H-indazole-3-carboxamide (244c) (8 mg, 0.014 mmol, 14% yield) as an off-white solid as a mixture of two rotamers; $^1$H NMR (300 MHz, DMSO-d$_6$) δ 10.83 & 10.78 (2s, 1H), 9.57 & 9.56 (2s, 1H), 9.29 & 9.28 (2s, 2H), 8.91 & 8.90 (2s, 1H), 8.85 (t, J=5.8 Hz) & 8.40 (t, J=5.9 Hz) (2t, 1H), 7.60-6.94 (m, 6H), 5.62 & 5.50 (2s, 2H), 4.63-3.78 (m, 5H), 1.23 (d, J=6.1 Hz) & 0.99 (d, J=6.8 Hz) (2d, 6H); $^{19}$F NMR (282 MHz, DMSO-d$_6$) δ −121.20, −121.69; MS (ES+): 554.5 (M+1), 576.5 (M+Na); MS (ES−): 552.5 (M−1), 588.5 (M+Cl).

Scheme 245

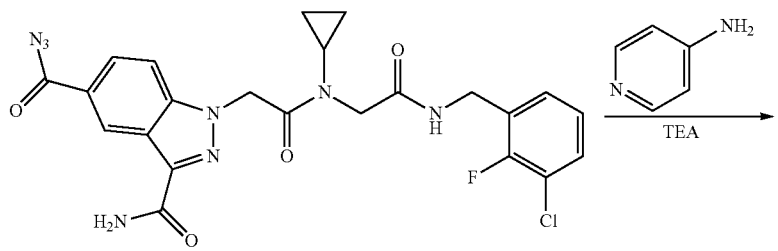

235a

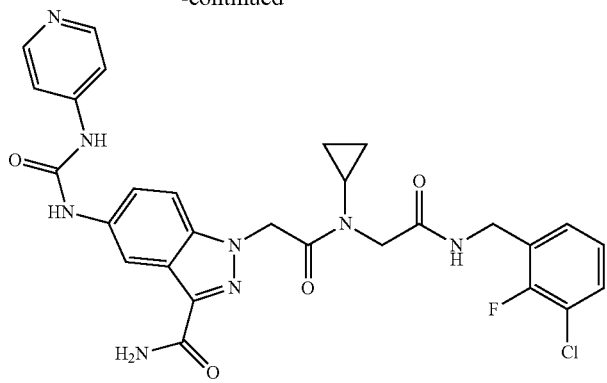

245a

Preparation of 1-(2-((2-((3-chloro-2-fluorobenzyl)amino)-2-oxoethyl)(cyclopropyl)amino)-2-oxoethyl)-5-(3-(pyridin-4-yl)ureido)-1H-indazole-3-carboxamide (245a)

Compound 245a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (300 mg, 0.29 mmol) and pyridin-4-amine (53.6 mg, 0.569 mmol) using TEA (0.16 mL, 1.14 mmol) as base according to the procedure reported in step-4 of Scheme 129. This gave after workup, purification by flash column chromatography [silica gel (12 g), eluting with DMA80 in DCM 0 to 40%] and prep-HPLC [eluting with CH$_3$CN in water (contains 0.1% TFA) from 0-100%] 1-(2-((2-((3-chloro-2-fluorobenzyl)amino)-2-oxoethyl)(cyclopropyl)amino)-2-oxoethyl)-5-(3-(pyridin-4-yl)ureido)-1H-indazole-3-carboxamide (245a) (9 mg, 0.015 mmol, 5% yield) as a white solid; $^1$H NMR (300 MHz, DMSO-d$_6$) δ 10.75 (s, 1H), 9.87 (s, 1H), 8.60 (d, J=6.8 Hz, 2H), 8.51 (t, J=5.9 Hz, 1H), 8.44 (d, J=1.9 Hz, 1H), 7.94 (d, J=6.6 Hz, 2H), 7.73-7.68 (m, 1H), 7.62 (d, J=9.0 Hz, 1H), 7.51-7.41 (m, 2H), 7.40-7.31 (m, 1H), 7.30-7.19 (m, 1H), 7.18-7.06 (m, 1H), 5.65 (s, 2H), 4.33 (d, J=5.7 Hz, 2H), 3.99 (s, 2H), 3.13-2.97 (m, 1H), 1.08-0.95 (m, 2H), 0.95-0.82 (m, 2H); $^{19}$F NMR (282 MHz, DMSO-d$_6$) δ −73.66 (TFA peak), −121.58; MS (ES+): 593.5 (M+1).

Scheme 246

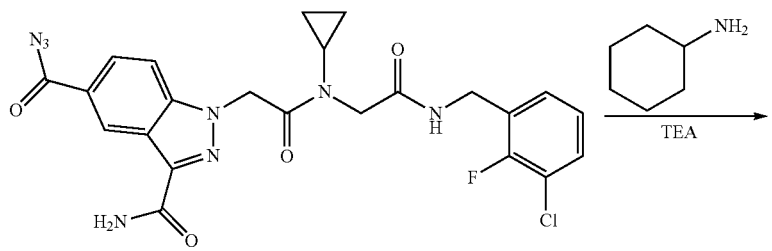

235a

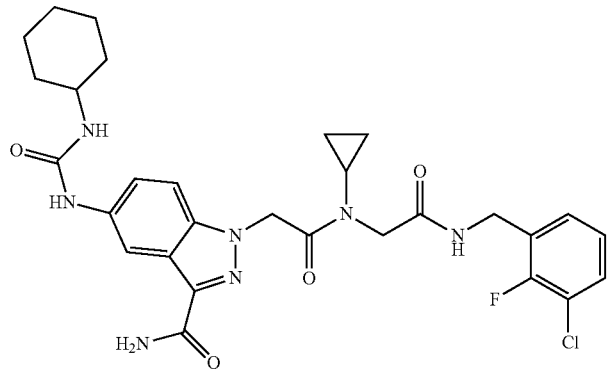

246a

443

Preparation of 1-(2-((2-((3-chloro-2-fluorobenzyl)amino)-2-oxoethyl)(cyclopropyl)amino)-2-oxoethyl)-5-(3-cyclohexylureido)-1H-indazole-3-carboxamide (246a)

Compound 246a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (300 mg, 0.29 mmol) and cyclohexanamine (57 mg, 0.57 mmol) using TEA (0.16 mL, 1.14 mmol) as base according to the procedure reported in step-4 of Scheme 129. This gave after workup, purification by flash column chromatography [silica gel (12 g), eluting with DMA80 in DCM 0 to 40%] 1-(2-((2-((3-chloro-2-fluorobenzyl)amino)-2-oxoethyl)(cyclopropyl)amino)-2-oxoethyl)-5-(3-cyclohexylureido)-1H-indazole-3-carboxamide (246a) (15 mg, 0.025 mmol, 9% yield) as a white solid; $^1$H NMR (300 MHz, DMSO-$d_6$) δ 8.50 (t, J=6.0 Hz, 1H), 8.42 (s, 1H), 8.24-8.12 (m, 1H), 7.60 (s, 1H), 7.55-7.37 (m, 3H), 7.30 (s, 1H), 7.26-7.18 (m, 1H), 7.12 (t, J=7.8 Hz, 1H), 5.99 (d, J=7.8 Hz, 1H), 5.60 (s, 2H), 4.33 (d, J=5.8 Hz, 2H), 3.98 (s, 2H), 3.58-3.42 (m, 1H), 3.14-2.97 (m, 1H), 1.93-1.75 (m, 2H), 1.75-1.61 (m, 2H), 1.61-1.44 (m, 1H), 1.36-1.13 (m, 5H), 1.03-0.95 (m, 2H), 0.95-0.84 (m, 2H); $^{19}$F NMR (282 MHz, DMSO-$d_6$) δ −121.59; MS (ES+): 598.6 (M+1).

Scheme 247

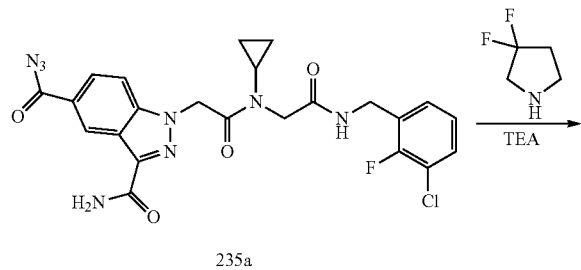

235a

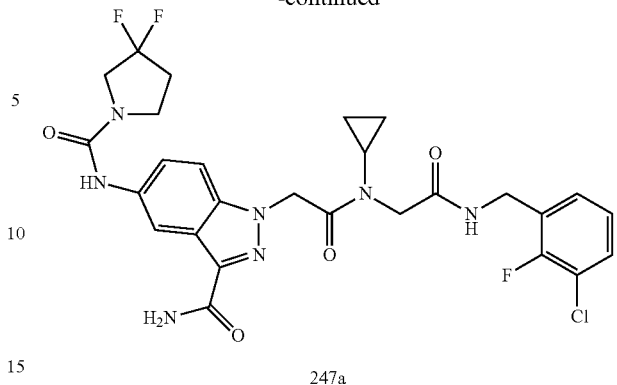

247a

Preparation of 1-(2-((2-((3-chloro-2-fluorobenzyl)amino)-2-oxoethyl)(cyclopropyl)amino)-2-oxoethyl)-5-(3,3-difluoropyrrolidine-1-carboxamido)-1H-indazole-3-carboxamide (247a)

Compound 247a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (300 mg, 0.29 mmol) and 3,3-difluoropyrrolidine hydrochloride (102 mg, 0.712 mmol) using TEA (0.16 mL, 1.14 mmol) as base according to the procedure reported in step-4 of Scheme 129. This gave after workup, purification by flash column chromatography [silica gel (12 g), eluting with DMA80 in DCM 0 to 40%] 1-(2-((2-((3-chloro-2-fluorobenzyl)amino)-2-oxoethyl)(cyclopropyl)amino)-2-oxoethyl)-5-(3,3-difluoropyrrolidine-1-carboxamido)-1H-indazole-3-carboxamide (247a) (26 mg, 0.043 mmol, 15% yield) as a white solid; $^1$H NMR (300 MHz, DMSO-$d_6$) δ 8.58-8.45 (m, 2H), 8.25-8.20 (m, 1H), 7.69-7.63 (m, 1H), 7.61 (d, J=2.0 Hz, 1H), 7.56-7.42 (m, 2H), 7.36-7.30 (m, 1H), 7.26-7.18 (m, 1H), 7.13 (td, J=7.8, 1.0 Hz, 1H), 5.62 (s, 2H), 4.33 (d, J=5.8 Hz, 2H), 3.99 (s, 2H), 3.84 (t, J=13.3 Hz, 2H), 3.65 (t, J=7.4 Hz, 2H), 3.14-2.96 (m, 1H), 2.49-2.38 (m, 2H), 1.06-0.96 (m, 2H), 0.93-0.83 (m, 2H); $^{19}$F NMR (282 MHz, DMSO-$d_6$) δ −100.42, −121.60; MS (ES+) 606.5 (M+1).

Scheme 248

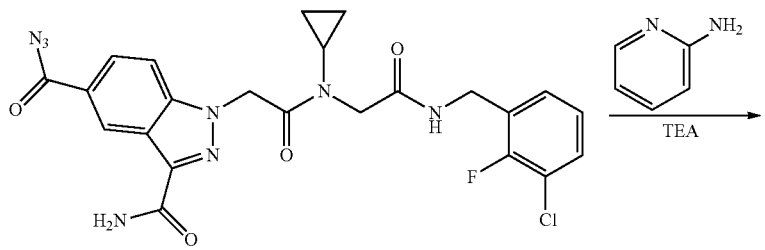

235a

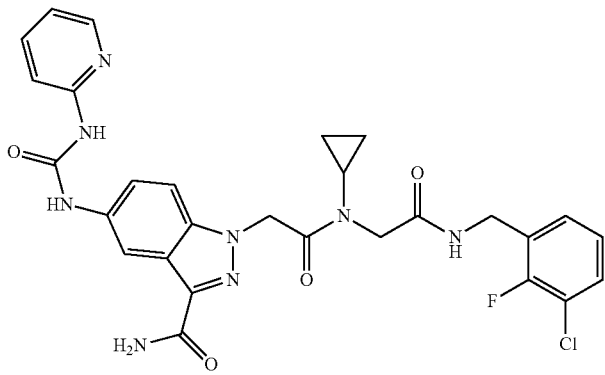

248a

Preparation of 1-(2-((2-((3-chloro-2-fluorobenzyl)amino)-2-oxoethyl)(cyclopropyl)amino)-2-oxoethyl)-5-(3-(pyridin-2-yl)ureido)-1H-indazole-3-carboxamide (248a)

Compound 248a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (286 mg, 0.27 mmol) and pyridin-2-amine (51 mg, 0.54 mmol) using TEA (0.15 mL, 1.11 mmol) as base according to the procedure reported in step-4 of Scheme 129. This gave after workup, purification by flash column chromatography [silica gel (12 g), eluting with DMA80 in DCM 0 to 40%] 1-(2-((2-((3-chloro-2-fluorobenzyl)amino)-2-oxoethyl)(cyclopropyl)amino)-2-oxoethyl)-5-(3-(pyridin-2-yl)ureido)-1H-indazole-3-carboxamide (248a) (11 mg, 0.02 mmol, 7% yield) as a white solid; $^1$H NMR (300 MHz, DMSO-$d_6$) δ 10.61 (s, 1H), 9.45 (s, 1H), 8.51 (t, J=5.9 Hz, 1H), 8.40 (d, J=2.0 Hz, 1H), 8.34-8.24 (m, 1H), 7.80-7.71 (m, 1H), 7.70-7.64 (m, 1H), 7.60 (d, J=9.0 Hz, 1H), 7.55-7.42 (m, 3H), 7.36 (s, 1H), 7.27-7.19 (m, 1H), 7.16-7.08 (m, 1H), 7.05-6.97 (m, 1H), 5.64 (s, 2H), 4.34 (d, J=5.7 Hz, 2H), 3.99 (s, 2H), 3.13-2.97 (m, 1H), 1.05-0.97 (m, 2H), 0.96-0.83 (m, 2H); $^{19}$F NMR (282 MHz, DMSO-$d_6$) δ −121.58; MS (ES+); 593.5 (M+1); (ES−): 591.5 (M−1).

Scheme 249

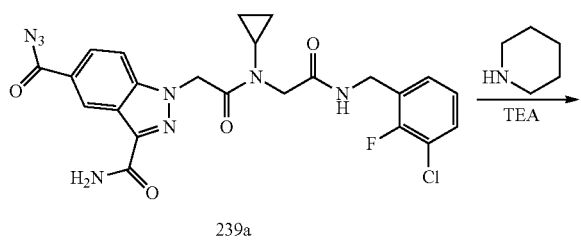

239a

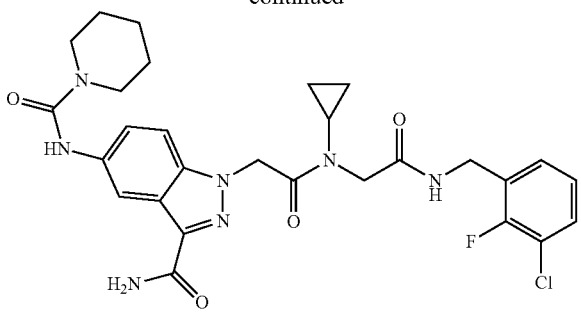

249a

Preparation of N-(3-acetyl-1-(2-((2-((3-chloro-2-fluorobenzyl)amino)-2-oxoethyl)(cyclopropyl)amino)-2-oxoethyl)-1H-indazol-5-yl)piperidine-1-carboxamide (249a)

Compound 249a was prepared from 3-acetyl-1-(2-((2-((3-chloro-2-fluorobenzyl)amino)-2-oxoethyl)(cyclopropyl)amino)-2-oxoethyl)-1H-indazole-5-carbonyl azide (239a) (300 mg, 0.57 mmol) and piperidine (97 mg, 1.14 mmol) using TEA (0.32 mL, 2.28 mmol) as base according to the procedure reported in step-4 of Scheme 129. This gave after workup and purification by flash column chromatography [silica gel (12 g), eluting with DMA80 in DCM 0 to 40%] N-(3-acetyl-1-(2-((2-((3-chloro-2-fluorobenzyl)amino)-2-oxoethyl)(cyclopropyl)amino)-2-oxoethyl)-1H-indazol-5-yl)piperidine-1-carboxamide (249a) (42 mg, 0.07 mmol, 13% yield) as a white solid; $^1$H NMR (300 MHz, DMSO-$d_6$) δ 8.63 (s, 1H), 8.48 (t, J=5.9 Hz, 1H), 8.25 (d, J=1.8 Hz, 1H), 7.67-7.50 (m, 2H), 7.50-7.40 (m, 1H), 7.28-7.16 (m, 1H), 7.11 (t, J=7.8 Hz, 1H), 5.69 (s, 2H), 4.35 (d, J=5.6 Hz, 2H), 4.00 (s, 2H), 3.56-3.40 (m, 4H), 3.21-3.03 (m, 1H), 2.59 (s, 3H), 1.66-1.43 (m, 6H), 1.09-0.98 (m, 2H), 0.97-0.80 (m, 2H); $^{19}$F NMR (282 MHz, DMSO-$d_6$) δ −121.61; MS (ES+): 583.6 (M+1); (ES−): 581.6 (M−1).

Scheme 250

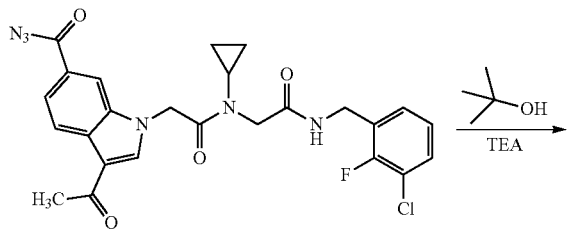

Preparation of tert-butyl (3-acetyl-1-(2-((2-((3-chloro-2-fluorobenzyl)amino)-2-oxoethyl)(cyclopropyl)amino)-2-oxoethyl)-1H-indol-6-yl)carbamate (250a)

Compound (250a) was prepared from 3-acetyl-1-(2-((2-((3-chloro-2-fluorobenzyl)amino)-2-oxoethyl)(cyclopropyl)amino)-2-oxoethyl)-1H-indole-6-carbonyl azide (219a) (210 mg, 0.4 mmol) and 2-methylpropan-2-ol (0.23 mL, 2.4 mmol) using TEA (0.11 mL, 0.8 mmol) as base according to the procedure reported in step-4 of Scheme 129 to afford after workup and purification by column chromatography [silica gel, eluting with dichloromethane/methanol (1:0 to 9:1)] tert-butyl (3-acetyl-1-(2-((2-((3-chloro-2-fluorobenzyl)amino)-2-oxoethyl)(cyclopropyl)amino)-2-oxoethyl)-1H-indol-6-yl)carbamate (250a) (55 mg, 24% for two steps) as a white solid; $^1$H NMR (300 MHz, DMSO-$d_6$) δ 9.32 (s, 1H), 8.48 (t, J=5.8 Hz, 1H), 8.19 (s, 1H), 7.99 (d, J=8.6 Hz, 1H), 7.57 (s, 1H), 7.51-7.39 (m, 1H), 7.27-7.18 (m, 2H), 7.17-7.05 (m, 1H), 5.35 (s, 2H), 4.34 (d, J=5.8 Hz, 2H), 4.00 (s, 2H), 3.11-2.99 (m, 1H), 2.40 (s, 3H), 1.47 (s, 9H), 1.09-0.85 (m, 4H); $^{19}$F NMR (282 MHz, DMSO-$d_6$) δ −121.67; MS (ES+): 593.5 & 595.5 (M+Na).

Scheme 251

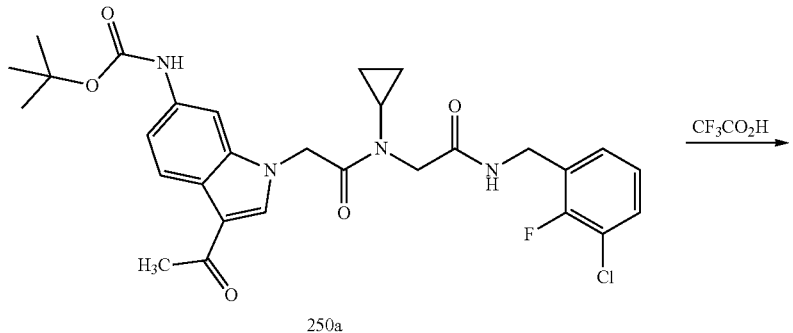

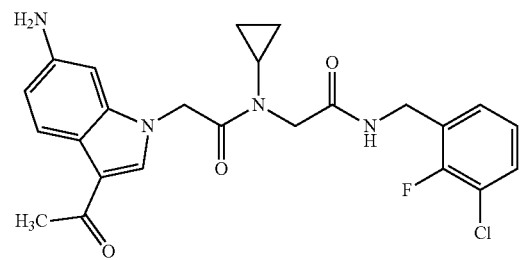

449

Preparation of 2-(3-acetyl-6-amino-1H-indol-1-yl)-N-(2-((3-chloro-2-fluorobenzyl)amino)-2-oxoethyl)-N-cyclopropylacetamide (251a)

Compound (251a) was prepared by hydrolysis of Boc protecting group of tert-butyl (3-acetyl-1-(2-((2-((3-chloro-2-fluorobenzyl)amino)-2-oxoethyl)(cyclopropyl)amino)-2-oxoethyl)-1H-indol-6-yl)carbamate (250a) (47 mg, 0.08 mmol) using 2,2,2-trifluoroacetic acid (0.127 mL, 1.646 mmol) in DCM (10 mL). This gave after workup and purification by flash column chromatography [silica gel, eluting with dichloromethane/DMA 80 (1:0 to 3:1)] 2-(3-acetyl-6-amino-1H-indol-1-yl)-N-(2-((3-chloro-2-fluorobenzyl)amino)-2-oxoethyl)-N-cyclopropylacetamide (251a) (26 mg, 67%) as a light brown solid; $^1$H NMR (300 MHz, DMSO-$d_6$) δ 8.48 (t, J=5.8 Hz, 1H), 7.95 (s, 1H), 7.80 (d, J=8.4 Hz, 1H), 7.47 (td, J=7.6, 1.8 Hz, 1H), 7.25 (td, J=7.3, 6.8, 1.8 Hz, 1H), 7.15 (td, J=7.9, 1.0 Hz, 1H), 6.54 (dd, J=8.4, 1.9 Hz, 1H), 6.46 (d, J=1.8 Hz, 1H), 5.23 (s, 2H), 4.94 (s, 2H), 4.34 (d, J=5.7 Hz, 2H), 4.00 (s, 2H), 3.10-2.97 (m, 1H), 2.35 (s, 3H), 1.04-0.88 (m, 4H); $^{19}$F NMR (282 MHz, DMSO-$d_6$) δ −121.61; MS (ES+): 493.5 & 495.5 (M+Na); MS (ES−): 505.4 & 507.4 (M+Cl).

450 hexane 0 to 100%]N-(2-((3-chloro-2-fluorobenzyl)amino)-2-oxoethyl)-N-isopropyl-2-(1-(methylsulfonyl)-1H-indazol-3-yl)acetamide (252a) (21 mg, 0.042 mmol, 18% yield) as a white solid as a mixture of rotamers; $^1$H NMR (300 MHz, DMSO-$d_6$) δ 8.70 and 8.48 (2t, J=5.7 Hz, 1H), 7.74-7.68 and 7.68-7.61 (2m, 1H), 7.53-7.00 (m, 6H), 4.69-4.57 and 4.34-4.24 (2m, 1H), 4.42 and 4.37 (2d, J=5.9 Hz, 2H), 4.12 and 4.09 (2s, 2H), 3.91 and 3.81 (2s, 2H), 2.37 (s, 3H), 1.03 and 0.95 (2d, J=6.8 Hz, 6H); 19F NMR (282 MHz, DMSO-$d_6$) δ −121.35 and −121.77; MS (ES−): 529.5 (M+Cl).

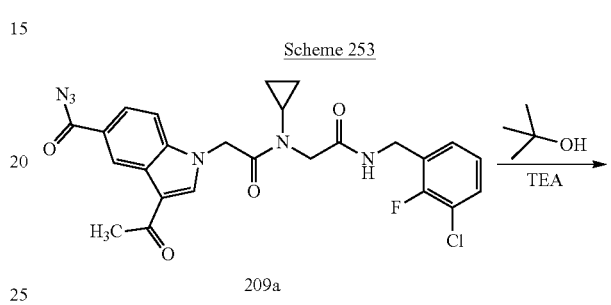

Scheme 253

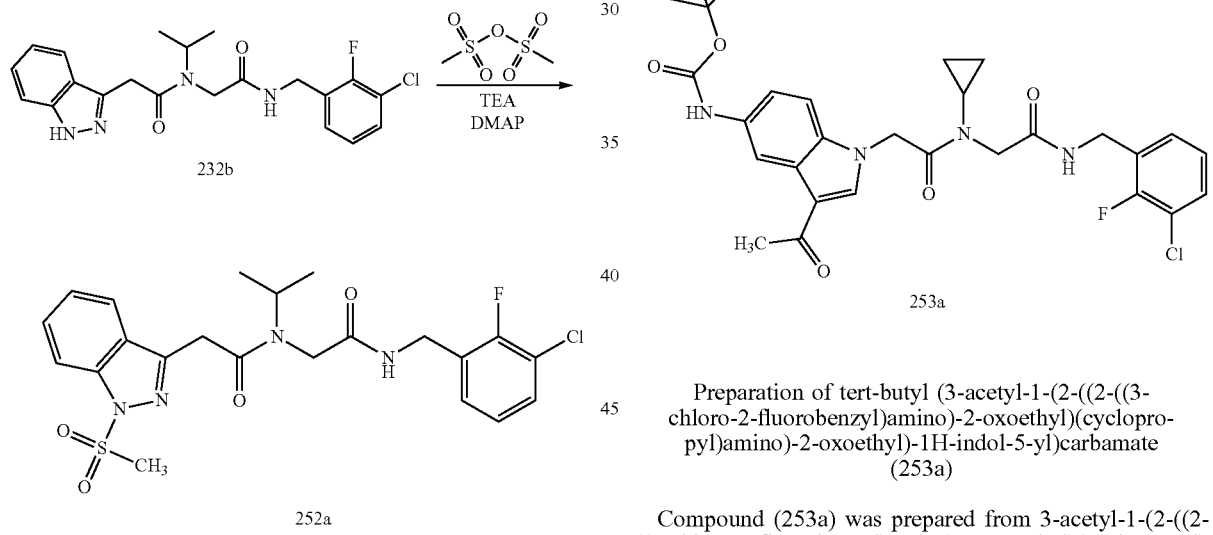

Scheme 252

Preparation of N-(2-((3-chloro-2-fluorobenzyl)amino)-2-oxoethyl)-N-isopropyl-2-(1-(methylsulfonyl)-1H-indazol-3-yl)acetamide (252a)

Compound (252a) was prepared from N-(2-((3-chloro-2-fluorobenzyl)amino)-2-oxoethyl)-2-(1H-indazol-3-yl)-N-isopropylacetamide (232b) (100 mg, 0.24 mmol) using methanesulphonic anhydride (84 mg, 0.48 mmol), triethylamine (0.1 mL, 0.72 mmol), DMAP (6 mg, 0.048 mmol) according to the procedure reported in step-2 of Scheme 232.

This gave after workup and purification by flash column chromatography [silica gel (12 g), eluting with EtOAc in Preparation of tert-butyl (3-acetyl-1-(2-((2-((3-chloro-2-fluorobenzyl)amino)-2-oxoethyl)(cyclopropyl)amino)-2-oxoethyl)-1H-indol-5-yl)carbamate (253a)

Compound (253a) was prepared from 3-acetyl-1-(2-((2-((3-chloro-2-fluorobenzyl)amino)-2-oxoethyl)(cyclopropyl)amino)-2-oxoethyl)-1H-indole-5-carbonyl azide (209a) (210 mg, 0.4 mmol) and 2-methylpropan-2-ol (0.23 mL, 2.4 mmol) using TEA (0.11 mL, 0.8 mmol) as base according to the procedure reported in step-4 of Scheme 129 to afford after workup and purification by column chromatography [silica gel, eluting with hexanes/10% methanol in ethyl acetate (1:0 to 1:1)] tert-butyl (3-acetyl-1-(2-((2-((3-chloro-2-fluorobenzyl)amino)-2-oxoethyl)(cyclopropyl)amino)-2-oxoethyl)-1H-indol-5-yl)carbamate (253a) (42 mg, 18%) as a white solid; $^1$H NMR (300 MHz, DMSO-$d_6$) δ 9.22 (s, 1H), 8.47 (t, J=5.9 Hz, 1H), 8.35 (d, J=1.9 Hz, 1H), 8.20 (s, 1H), 7.49-7.42 (m, 1H), 7.33-7.18 (m, 3H), 7.11 (td, J=7.9, 1.0 Hz, 1H), 5.38 (s, 2H), 4.35 (d, J=5.7 Hz, 2H), 3.99 (s, 2H), 3.14-2.97 (m, 1H), 2.40 (s, 3H), 1.49 (s, 9H), 1.03-0.81 (m, 4H); $^{19}$F NMR (282 MHz, DMSO-$d_6$) δ −121.63; MS (ES+): 593.6 & 595.6 (M+Na); MS (ES−): 569.6 & 571.5 (M−1).

Scheme 254
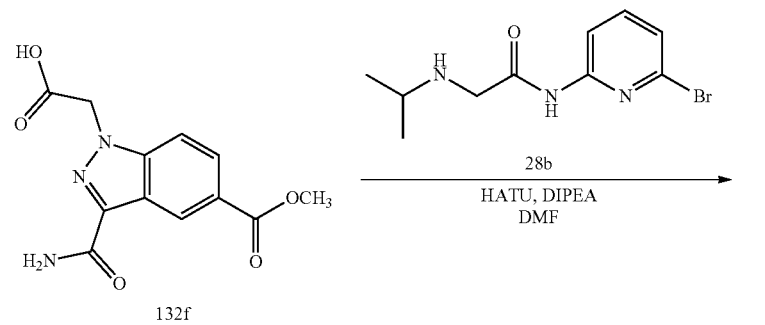
132f
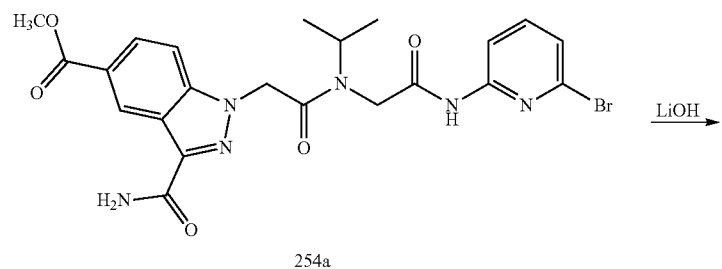
254a
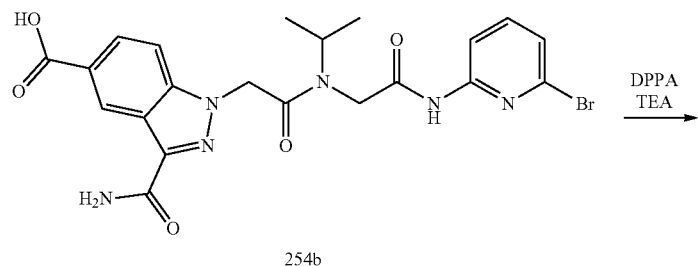
254b
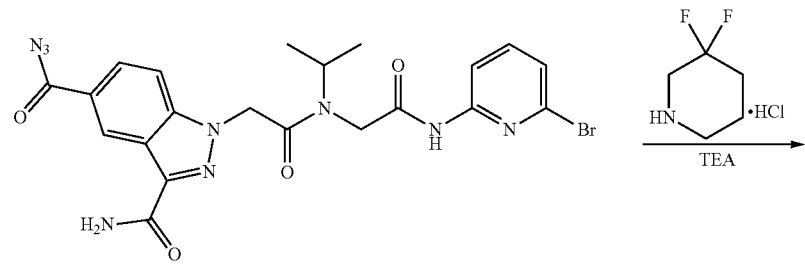
254c
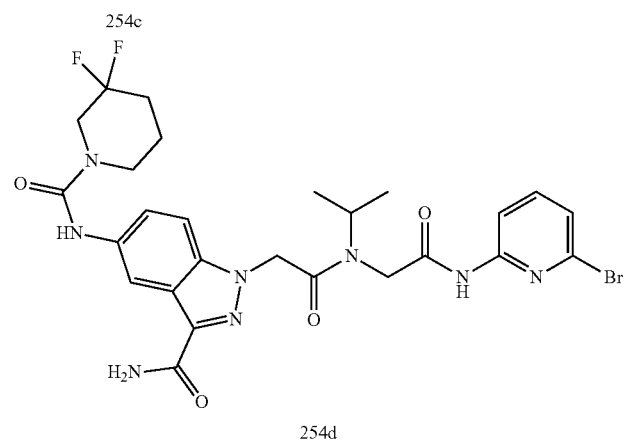
254d Preparation of 1-(2-((2-((6-bromopyridin-2-yl)amino)-2-oxoethyl)(isopropyl)amino)-2-oxoethyl)-5-(3,3-difluoropiperidine-1-carboxamido)-1H-indazole-3-carboxamide (254d)

Step-1: Preparation of methyl 1-(2-((2-((6-bromopyridin-2-yl)amino)-2-oxoethyl)(isopropyl)amino)-2-oxoethyl)-3-carbamoyl-1H-indazole-5-carboxylate (254a)

Reaction of 2-(3-carbamoyl-5-(methoxycarbonyl)-1H-indazol-1-yl)acetic acid (132f) TFA adduct (719 mg, 1.84 mmol) with N-(6-bromopyridin-2-yl)-2-(isopropylamino)acetamide (28b) (500 mg, 1.84 mmol) according to the procedure reported in step-3 of Scheme 2 gave after workup and purification by flash column [silica (12 g), eluting with DMA80 in DCM 0 to 30%] methyl 1-(2-((2-((6-bromopyridin-2-yl)amino)-2-oxoethyl)(isopropyl)amino)-2-oxoethyl)-3-carbamoyl-1H-indazole-5-carboxylate (254a) (865 mg, 1.63 mmol, 89% yield) as an off white solid; $^1$H NMR (300 MHz, DMSO-$d_6$) δ 11.21 and 10.82 (2s, 1H), 8.94-8.84 (m, 1H), 8.19-7.28 (m, 7H), 5.70 and, 5.52 (2s, 2H), 4.67-4.54 and 4.37-4.27 (2m, 1H), 4.43 and 4.03 (s, 1H), 3.90 (d, J=3.3 Hz, 3H), 1.26 (d, J=6.4 Hz) and 1.03 (d, J=6.8 Hz) (2d, 6H); MS (ES$^+$) 533.4 (M+2); 529.4 (M−1).

Step-2: Preparation of 1-(2-((2-((6-bromopyridin-2-yl)amino)-2-oxoethyl)(isopropyl)amino)-2-oxoethyl)-3-carbamoyl-1H-indazole-5-carboxylic acid (254b)

Reaction of methyl 1-(2-((2-((6-bromopyridin-2-yl)amino)-2-oxoethyl)(isopropyl)amino)-2-oxoethyl)-3-carbamoyl-1H-indazole-5-carboxylate (254a) (860 mg, 1.62 mmol) in MeOH/water (50 mL) with a solution of lithium hydroxide hydrate (679 mg, 16.18 mmol) in water (10 mL) according to the procedure reported in step-2 of Scheme 129 gave after workup 1-(2-((2-((6-bromopyridin-2-yl)amino)-2-oxoethyl)(isopropyl)amino)-2-oxoethyl)-3-carbamoyl-1H-indazole-5-carboxylic acid (254b) (736 g, 1.43 mmol, 88% yield) as a white solid; $^1$H NMR (300 MHz, DMSO-$d_6$) δ 12.95 (s, 1H), 11.21 and 10.82 (2s, 1H), 8.93-8.78 (m, 1H), 8.26-7.16 (m, 7H), 5.67 and 5.51 (2s, 2H), 4.73-4.54 and 4.34-4.25 (2m, 1H), 4.43 and 4.03 (2s, 2H), 1.25 (d, J=6.6 Hz) and 1.03 (d, J=6.7 Hz) (2d, 6H); MS (ES$^-$) 515.3 (M−1).

Step-3: Preparation of 1-(2-((2-((6-bromopyridin-2-yl)amino)-2-oxoethyl)(isopropyl)amino)-2-oxoethyl)-3-carbamoyl-1H-indazole-5-carbonyl azide (254c)

Compound 254c was prepared from 1-(2-((2-((6-bromopyridin-2-yl)amino)-2-oxoethyl)(isopropyl)amino)-2-oxoethyl)-3-carbamoyl-1H-indazole-5-carboxylic acid (254b) (400 mg, 0.77 mmol) according to the procedure reported in step-3 of Scheme 129 to afford product (600 mg, 143% yield), which was used in the next step without further purification.

Step-4: Preparation of 1-(2-((2-((6-bromopyridin-2-yl)amino)-2-oxoethyl)(isopropyl)amino)-2-oxoethyl)-5-(3,3-difluoropiperidine-1-carboxamido)-1H-indazole-3-carboxamide (254d)

Compound (254d) was prepared from 1-(2-((2-((6-bromopyridin-2-yl)amino)-2-oxoethyl)(isopropyl)amino)-2-oxoethyl)-3-carbamoyl-1H-indazole-5-carbonyl azide (254c) (300 mg, 0.55 mmol) and 3,3-difluoropiperidine hydrochloride (174 mg, 1.106 mmol) using TEA (0.31 mL, 2.2 mmol) as base according to the procedure reported in step-4 of Scheme 129 to afford after workup and purification by column chromatography [silica (12 g), eluting with DMA80 in DCM 0 to 40%] 1-(2-((2-((6-bromopyridin-2-yl)amino)-2-oxoethyl)(isopropyl)amino)-2-oxoethyl)-5-(3,3-difluoropiperidine-1-carboxamido)-1H-indazole-3-carboxamide (254d) (32 mg, 0.05 mmol, 9% yield) as a white solid; $^1$H NMR (300 MHz, DMSO-$d_6$) δ 11.20 and 10.83 (2s, 1H), 8.78 (d, J=5.6 Hz, 1H), 8.28-7.95 (m, 2H), 7.86-7.23 (m, 6H), 5.57 and 5.41 (2s, 2H), 4.71-4.52 and 4.38-4.20 (m, 1H), 4.42 and 4.03 (2s, 2H), 3.81 (t, J=11.6 Hz, 2H), 3.52 (bs, 2H), 2.16-1.91 (m, 2H), 1.71 (bs, 2H), 1.24 (d, J=6.3 Hz) and 1.03 (d, J=6.7 Hz) (2d, 6H); $^{19}$F NMR (282 MHz, DMSO-$d_6$) δ −101.17; MS (ES+): 635.6 (M+1); (ES−): 633.5 (M−1).

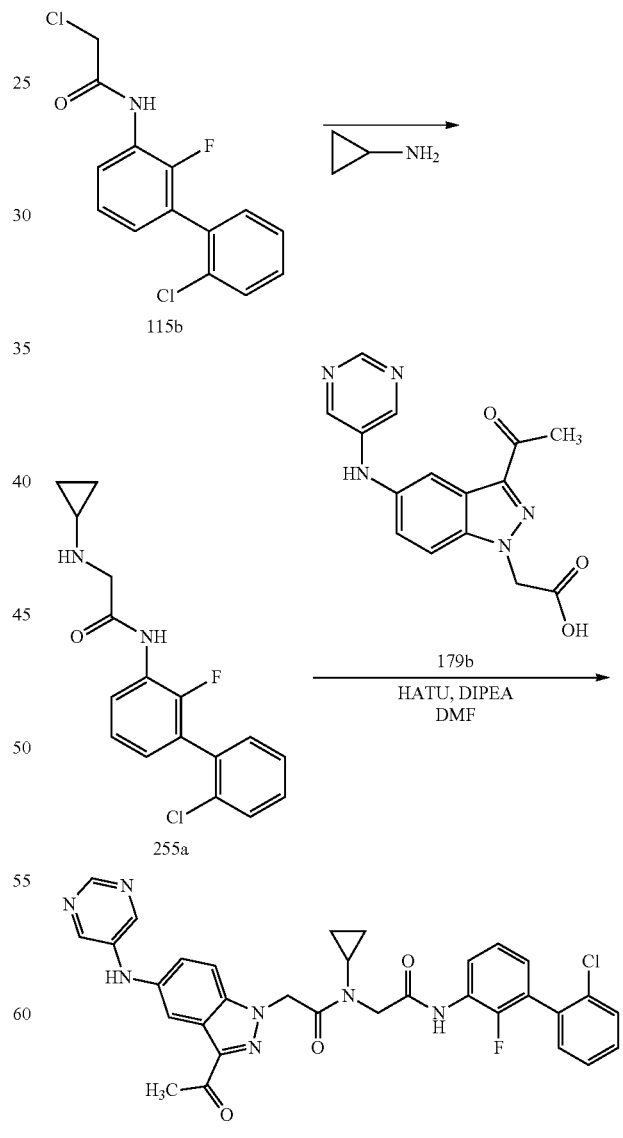

Scheme 255

Preparation of 2-(3-acetyl-5-(pyrimidin-5-ylamino)-1H-indazol-1-yl)-N-(2-((2'-chloro-2-fluoro-[1,1'-biphenyl]-3-yl)-amino)-2-oxoethyl)-N-cyclopropylacetamide (255b)

Step-1: Preparation of N-(2'-chloro-2-fluorobiphenyl-3-yl)-2-(cyclopropylamino)acetamide (255a)

Compound (255a) was prepared from 2-chloro-N-(2'-chloro-2-fluoro-[1,1'-biphenyl]-3-yl)acetamide (115b) (2 g, 6.71 mmol) and cyclopropylamine (1.18 mL, 16.77 mmol) according to the procedure reported in step-2 of scheme-115. This gave after workup and purification by flash column chromatography [silica gel 24 g, eluting with EtOAc-Hexane 10 to 100%] N-(2'-chloro-2-fluorobiphenyl-3-yl)-2-(cyclopropylamino)acetamide (255a) (1.8 g, 5.65 mmol, 84% yield) as a thick syrup; $^1$H NMR (300 MHz, DMSO-d$_6$) δ 9.73 (s, 1H), 8.20-8.10 (m, 1H), 7.64-7.57 (m, 1H), 7.53-7.38 (m, 3H), 7.26 (td, J=7.9, 1.0 Hz, 1H), 7.11-7.04 (m, 1H), 3.38 (bs, 2H), 3.11 (bs, 1H), 2.24-2.12 (m, 1H), 0.43-0.34 (m, 2H), 0.32-0.23 (m, 2H); MS (ES+): 319.4 (M+1), MS (ES−): 353.3 (M+Cl).

Step-2: Preparation of 2-(3-acetyl-5-(pyrimidin-5-ylamino)-1H-indazol-1-yl)-N-(2-((2'-chloro-2-fluoro-[1,1'-biphenyl]-3-yl)-amino)-2-oxoethyl)-N-cyclopropylacetamide (255b)

Reaction of N-(2'-chloro-2-fluorobiphenyl-3-yl)-2-(cyclopropylamino)acetamide (255a) (70 mg, 0.22 mmol) with 2-(3-acetyl-5-(pyrimidin-5-ylamino)-1H-indazol-1-yl)acetic acid (179b) (68 mg, 0.22 mmol) according to the procedure reported in step-3 of scheme-2 gave after workup and purification by flash column [silica gel (12 g), eluting with DMA-80 in DCM 0-40%] 2-(3-acetyl-5-(pyrimidin-5-ylamino)-1H-indazol-1-yl)-N-(2-((2'-chloro-2-fluoro-[1,1'-biphenyl]-3-yl)-amino)-2-oxoethyl)-N-cyclopropylacetamide (255b) (90 mg, 0.15 mmol, 67% yield) as an off-white solid; $^1$H NMR (300 MHz, DMSO-d$_6$) δ 9.94 (s, 1H), 8.72 (s, 1H), 8.65 (s, 1H), 8.55 (s, 2H), 7.98 (t, J=7.7 Hz, 1H), 7.90 (d, J=2.1 Hz, 1H), 7.69 (d, J=8.9 Hz, 1H), 7.63-7.54 (m, 1H), 7.52-7.30 (m, 4H), 7.24 (t, J=7.9 Hz, 1H), 7.14-7.03 (m, 1H), 5.77 (s, 2H), 4.24 (s, 2H), 3.22-3.10 (m, 1H), 2.60 (s, 3H), 1.12-1.01 (m, 2H), 1.00-0.90 (m, 2H); 19F NMR (282 MHz, DMSO-d$_6$) δ −126.70; MS (ES+): 612.6 (M+1); MS (ES−): 610.6 (M−1).

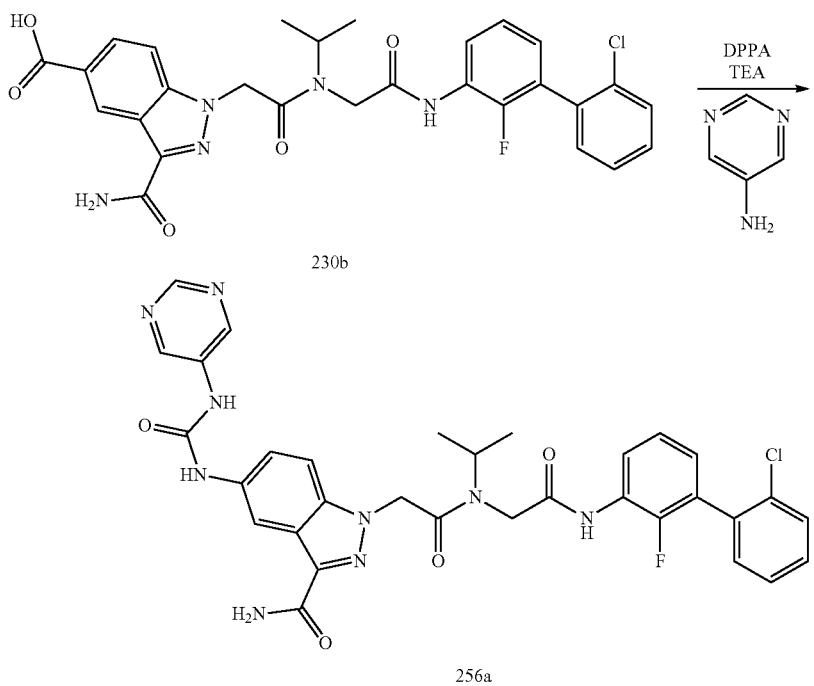

Scheme 256

Preparation of 1-(2-((2-((2'-chloro-2-fluoro-[1,1'-biphenyl]-3-yl)-amino)-2-oxoethyl)(isopropyl)amino)-2-oxoethyl)-5-(3-(pyrimidin-5-yl)ureido)-1H-indazole-3-carboxamide (256a)

Compound (256a) was prepared from 3-carbamoyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (230b) (85 mg, 0.15 mmol) and pyrimidin-5-amine (29 mg, 0.3 mmol) according to the procedure reported in step-3 of scheme-223 to afford after workup and purification by column chromatography [silica gel, (4 g) eluting with DMA80 in DCM 0 to 50%] 1-(2-((2-((2'-chloro-2-fluoro-[1,1'-biphenyl]-3-yl)-amino)-2-oxoethyl)(isopropyl)amino)-2-oxoethyl)-5-(3-(pyrimidin-5-yl)ureido)-1H-indazole-3-carboxamide (256a) (27 mg, 0.041 mmol, 27% yield) as a white solid; $^1$H NMR (300 MHz, DMSO-d$_6$) (as a mixture of two rotamers) δ 10.26 and 9.77 (2s, 1H), 9.15 (s, 1H), 8.99 and 8.97 (2s, 1H), 8.94 and 8.93 (2s, 2H), 8.810 and 8.808 (2s, 1H), 8.35 and 8.32 (2d, J=1.4 Hz, 1H), 8.10 and 7.95 (2t, J=7.8 Hz, 1H), 7.76-7.00 (m, 10H), 5.61 and 5.47 (2s, 2H), 4.72-4.57 and 4.41-4.26 (2m, 1H), 4.47 and 4.08 (2s, 2H) 1.26 and 1.06 (2d, J=6.7 Hz, 6H); 19F NMR (282 MHz, DMSO-d$_6$) δ −126.77 and −126.97; MS (ES−): 692.5 & 694.5 (M+Cl).

Scheme 257

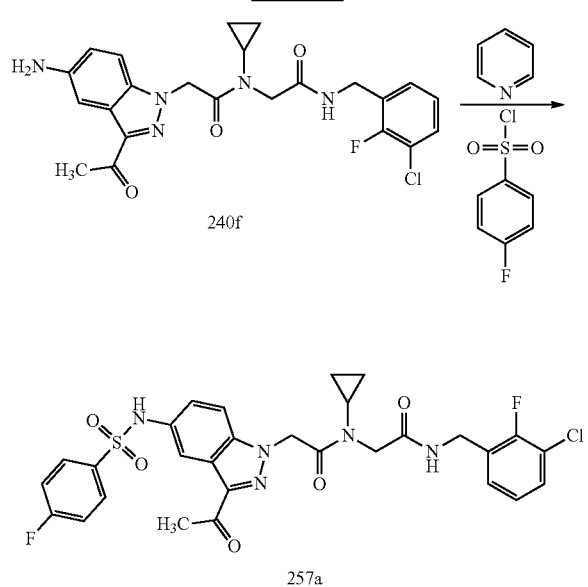

Preparation of 2-(3-acetyl-5-(4-fluorophenylsulfonamido)-1H-indazol-1-yl)-N-(2-((3-chloro-2-fluorobenzyl)amino)-2-oxoethyl)-N-cyclopropylacetamide (257a)

To a solution of 2-(3-acetyl-5-amino-1H-indazol-1-yl)-N-(2-((3-chloro-2-fluorobenzyl)amino)-2-oxoethyl)-N-cyclopropylacetamide (240f) (8 mg, 0.17 mmol) in DCM (3 mL) was added Pyridine (0.069 mL, 0.85 mmol), 4-fluorobenzene-1-sulfonyl chloride (49 mg, 0.25 mmol) and stirred at RT for 3 h. The reaction mixture was quenched with methanol (0.5 mL), concentrated in vacuum to dryness and the residue was purified by flash column chromatography [silica gel (12 g), eluting with DMA80 in DCM 0 to 20%] to afford 2-(3-acetyl-5-(4-fluorophenylsulfonamido)-1H-indazol-1-yl)-N-(2-((3-chloro-2-fluorobenzyl)amino)-2-oxoethyl)-N-cyclopropylacetamide (257a) (70 mg, 0.11 mmol, 66% yield) as a white solid; $^1$H NMR (300 MHz, DMSO-$d_6$) δ 10.36 (s, 1H), 8.46 (t, J=5.9 Hz, 1H), 7.90-7.85 (m, 1H), 7.82-7.74 (m, 2H), 7.58 (d, J=8.9 Hz, 1H), 7.52-7.31 (m, 3H), 7.27-7.16 (m, 2H), 7.14-7.02 (m, 1H), 5.69 (s, 2H), 4.33 (d, J=5.7 Hz, 2H), 3.96 (s, 2H), 3.15-3.01 (m, 1H), 2.56 (s, 3H), 1.07-0.95 (m, 2H), 0.94-0.82 (m, 2H); $^{19}$F NMR (282 MHz, DMSO-$d_6$) δ −105.97, −121.58; MS (ES+): 630.5 (M+1), 652.6 (M+Na); MS (ES−): 628.5 (M−1), 664.5 (M+Cl).

Scheme 258

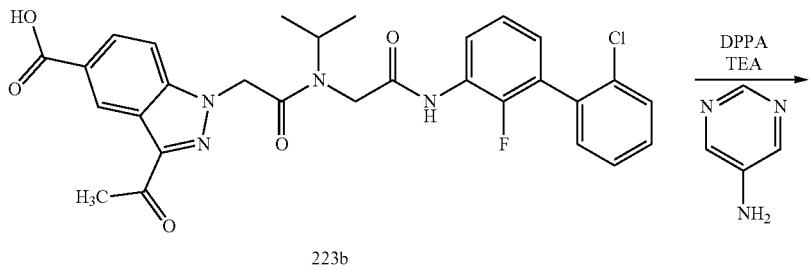

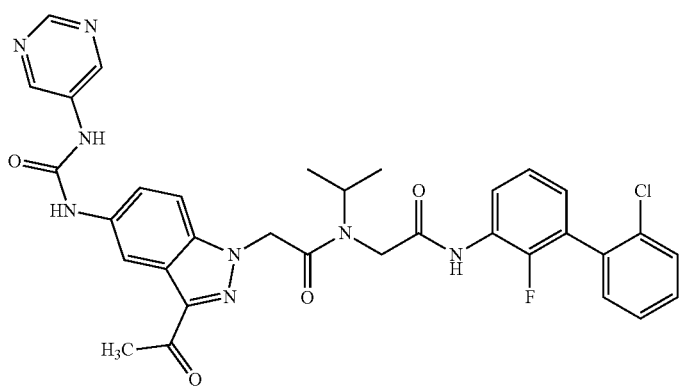

Preparation of 2-(3-acetyl-5-(3-(pyrimidin-5-yl)ureido)-1H-indazol-1-yl)-N-(2-((2'-chloro-2-fluoro-[1,1'-biphenyl]-3-yl)-amino)-2-oxoethyl)-N-isopropylacetamide (258a)

Compound (256a) was prepared from 3-acetyl-1-(2-((2-((2'-chloro-2-fluoro-[1,1'-biphenyl]-3-yl)-amino)-2-oxoethyl)(isopropyl)amino)-2-oxoethyl)-1H-indazole-5-carboxylic acid (223b) (110 mg, 0.2 mmol) and pyrimidin-5-amine (37 mg, 0.4 mmol) according to the procedure reported in step-3 of scheme-223 to afford after workup and purification by column chromatography [silica gel, (4 g) eluting with DMA80 in DCM 0 to 30%] 2-(3-acetyl-5-(3-(pyrimidin-5-yl)ureido)-1H-indazol-1-yl)-N-(2-((2'-chloro-2-fluoro-[1,1'-biphenyl]-3-yl)-amino)-2-oxoethyl)-N-isopropylacetamide (258a) (26 mg, 0.04 mmol, 20% yield) as a white solid as a mixture of rotamers; $^1$H NMR (300 MHz, DMSO-$d_6$) δ 10.27 and 9.76 (2s, 1H), 9.23 (s, 1H), 9.02 and 9.01 (2s, 1H), 8.94 (s, 2H), 8.82 (s, 1H), 8.41 and 8.37 (2s, 1H), 8.12 and 7.96 (2t, J=8.0 Hz, 1H), 7.71-6.99 (m, 8H), 5.72 and 5.55 (2s, 2H), 4.72-4.57 and 4.41-4.26 (2m, 1H), 4.47 and 4.09 (2s, 2H), 2.61 and 2.60 (2s, 3H), 1.28 and 1.07 (2d, J=6.8 Hz, 6H); $^{19}$F NMR (282 MHz, DMSO-$d_6$) δ −126.85 and −126.99; MS (ES+): 657.5 (M+1), MS (ES−): 655.5 (M−1), 691.5 (M+Cl).

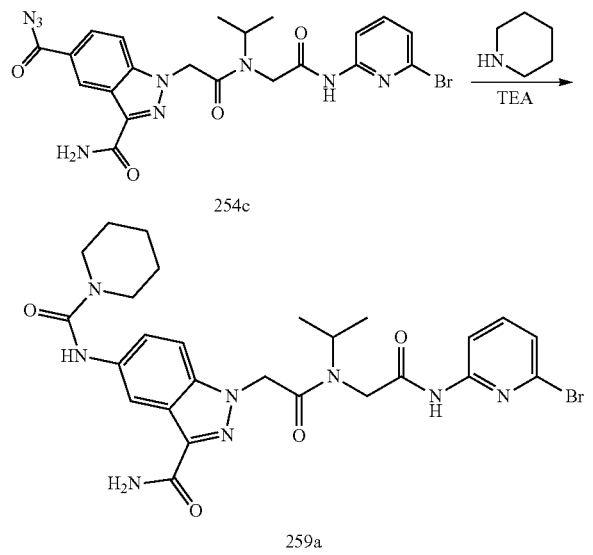

Preparation of 1-(2-((2-((6-bromopyridin-2-yl)amino)-2-oxoethyl)(isopropyl)amino)-2-oxoethyl)-5-(piperidine-1-carboxamido)-1H-indazole-3-carboxamide (259a)

Compound (259a) was prepared from 1-(2-((2-((6-bromopyridin-2-yl)amino)-2-oxoethyl)(isopropyl)amino)-2-oxoethyl)-3-carbamoyl-1H-indazole-5-carbonyl azide (254c) (300 mg, 0.55 mmol) and piperidine (94 mg, 1.11 mmol) using TEA (0.31 mL, 2.2 mmol) as base according to the procedure reported in step-4 of Scheme 129 to afford after workup and purification by column chromatography [silica (12 g), eluting with DMA80 in DCM 0 to 40%] 1-(2-((2-((6-bromopyridin-2-yl)amino)-2-oxoethyl)(isopropyl)amino)-2-oxoethyl)-5-(piperidine-1-carboxamido)-1H-indazole-3-carboxamide (259a) (61 mg, 0.1 mmol, 18% yield) as a white solid; $^1$H NMR (300 MHz, DMSO-$d_6$) δ 11.20 and 10.82 (2s, 1H), 8.57 (d, J=5.1 Hz, 1H), 8.24-7.94 (m, 2H), 7.86-7.27 (m, 6H), 5.56 and 5.40 (2s, 2H), 4.66-4.52 and 4.35-4.26 (2m, 1H), 4.42 and 4.02 (2s, 2H), 3.52-3.38 (m, 4H), 1.62-1.46 (m, 6H), 1.23 (d, J=6.4 Hz) and 1.03 (d, J=6.7 Hz) (2d, 6H); MS (ES+): 599.6 (M+1); (ES−): 597.5 (M−1).

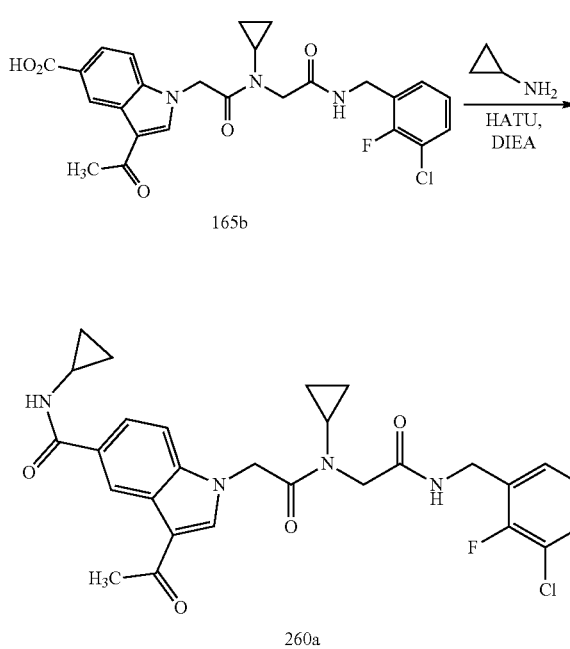

Preparation of 3-acetyl-1-(2-((2-((3-chloro-2-fluorobenzyl)amino)-2-oxoethyl)(cyclopropyl)amino)-2-oxoethyl)-N-cyclopropyl-1H-indole-5-carboxamide (260a)

Reaction of 3-acetyl-1-(2-((2-((3-chloro-2-fluorobenzyl)amino)-2-oxoethyl)(cyclopropyl)amino)-2-oxoethyl)-1H-indole-5-carboxylic acid (165b) (50 mg, 0.1 mmol) with cyclopropanamine (10.40 μL, 0.150 mmol) according to the procedure reported in step-3 of Scheme 2 gave after workup and purification by flash column [silica (8 g), eluting dichloromethane/methanol (1:0 to 19:1)] 3-acetyl-1-(2-((2-((3-chloro-2-fluorobenzyl)amino)-2-oxoethyl)(cyclopropyl)amino)-2-oxoethyl)-N-cyclopropyl-1H-indole-5-carboxamide (260a) (30 mg, 56%) as a white solid; $^1$H NMR (300 MHz, DMSO-$d_6$) δ 8.67-8.64 (m, 1H), 8.50-8.41 (m, 2H), 8.35 (s, 1H), 7.67 (dd, J=8.7, 1.8 Hz, 1H), 7.52-7.41 (m, 2H), 7.27-7.19 (m, 1H), 7.09 (td, J=7.8, 1.0 Hz, 1H), 5.47 (s, 2H), 4.34 (d, J=5.7 Hz, 2H), 3.99 (s, 2H), 3.17-3.03 (m, 1H), 2.96-2.79 (m, 1H), 2.45 (s, 3H), 1.05-0.82 (m, 4H), 0.75-0.55 (m, 4H); $^{19}$F NMR (282 MHz, DMSO-$d_6$) δ −121.59; MS (ES+): 539.5 & 541.5 (M+1).

Scheme 261

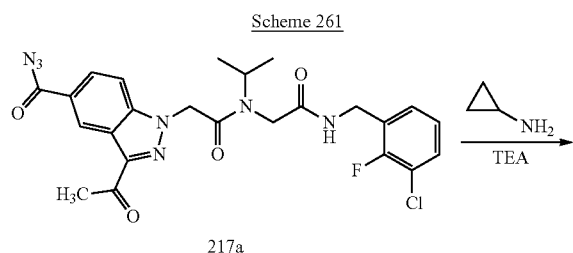

217a

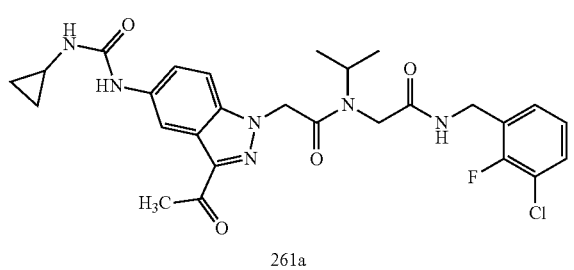

261a

Preparation of 2-(3-acetyl-5-(3-cyclopropylureido)-1H-indazol-1-yl)-N-(2-((3-chloro-2-fluorobenzyl)amino)-2-oxoethyl)-N-isopropylacetamide (261a)

Compound (261a) was prepared from 3-acetyl-1-(2-((2-((3-chloro-2-fluorobenzyl)amino)-2-oxoethyl)(isopropyl)amino)-2-oxoethyl)-1H-indazole-5-carbonyl azide (217a) (105 mg, 0.2 mmol) and cyclopropanamine (0.028 mL, 0.4 mmol) using TEA (0.055 mL, 0.4 mmol) as base according to the procedure reported in step-4 of Scheme 129 to afford after workup and purification by column chromatography [silica gel (8 g), eluting with dichloromethane/methanol (1:0 to 19:1)] 2-(3-acetyl-5-(3-cyclopropylureido)-1H-indazol-1-yl)-N-(2-((3-chloro-2-fluorobenzyl)amino)-2-oxoethyl)-N-isopropylacetamide (261a) (16 mg, 14%) as an off-white solid; $^1$H NMR (300 MHz, DMSO-d$_6$) δ 8.83 (t, J=5.9 Hz) and 8.39-8.09 (m) (2H), 8.60 and 8.58 (2s, 1H), 7.58-6.94 (m, 5H), 6.49-6.30 (m, 1H), 5.63 and 5.46 (2s, 2H), 4.64-4.50 and 4.29-4.20 (2m, 1H), 4.46 (d, J=5.5 Hz) and 4.32 (d, J=6.0 Hz) (2d, 2H), 4.17 and 3.84 (2s, 2H), 2.58 and 2.41 (2s, 3H), 1.23 (d, J=6.5 Hz) and 0.99 (d, J=6.8 Hz) (2d, 6H), 0.71-0.55 (m, 2H), 0.49-0.34 (m, 2H); MS (ES-): 591.5 & 593.5 (M+Cl).

Scheme 262

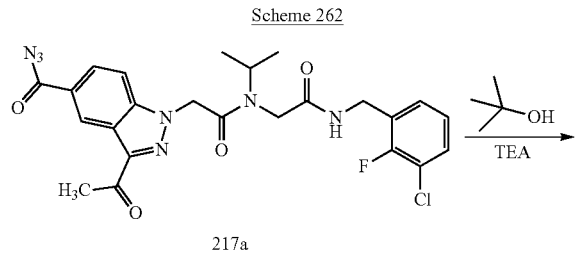

217a

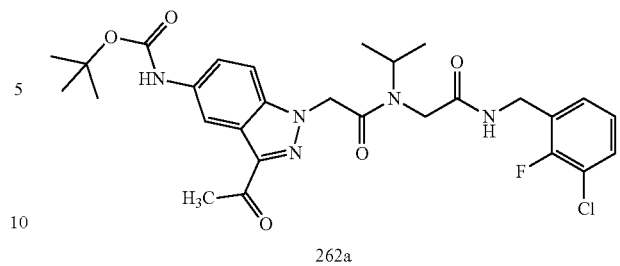

262a

Preparation of tert-butyl (3-acetyl-1-(2-((2-((3-chloro-2-fluorobenzyl)amino)-2-oxoethyl)(isopropyl)amino)-2-oxoethyl)-1H-indazol-5-yl)carbamate (262a)

Compound (262a) was prepared from 3-acetyl-1-(2-((2-((3-chloro-2-fluorobenzyl)amino)-2-oxoethyl)(isopropyl)amino)-2-oxoethyl)-1H-indazole-5-carbonyl azide (217a) (105 mg, 0.2 mmol) and 2-methylpropan-2-ol (0.114 mL, 1.19 mmol) using TEA (0.055 mL, 0.4 mmol) as base according to the procedure reported in step-4 of Scheme 129 to afford after workup and purification by column chromatography [silica gel, eluting with dichloromethane/methanol (1:0 to 19:1)] tert-butyl (3-acetyl-1-(2-((2-((3-chloro-2-fluorobenzyl)amino)-2-oxoethyl)(isopropyl)amino)-2-oxoethyl)-1H-indazol-5-yl)carbamate (262a) (8 mg, 7%) as an off-white solid as a mixture of rotamers; $^1$H NMR (300 MHz, DMSO-d$_6$) δ 9.47 (s, 1H), 8.83 and 8.35 (2t, 1H) 8.42 (s, 1H), 7.58-6.67 (m, 5H), 5.63 and 5.46 (2s, 2H), 4.62-4.22 (m, 3H), 4.16 and 3.84 (2s, 2H), 2.58 and 2.53 (2s, 3H), 1.50 and 1.49 (2s, 9H), 1.23 and 0.99 (2d, J=6.8 Hz, 6H); MS (ES-): 608.6 & 610.6 (M+Cl).

Scheme 263

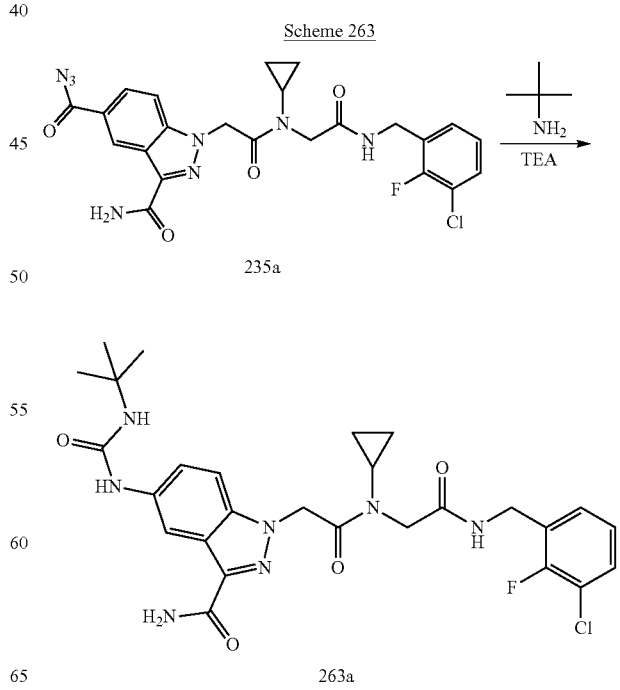

463

Preparation of 5-(3-tert-butylureido)-1-(2-((2-(3-chloro-2-fluorobenzylamino)-2-oxoethyl)(cyclopropyl)amino)-2-oxoethyl)-1H-indazole-3-carboxamide (263a)

Compound 263a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (300 mg, 0.29 mmol) and 3,3-difluoropyrrolidine hydrochloride (102 mg, 0.712 mmol) using TEA (0.16 mL, 1.14 mmol) as base according to the procedure reported in step-4 of Scheme 129. This gave after workup, purification by flash column chromatography [silica gel (12 g), eluting with DMA80 in DCM 0 to 40%] 5-(3-tert-butylureido)-1-(2-((2-(3-chloro-2-fluorobenzylamino)-2-oxoethyl)(cyclopropyl)amino)-2-oxoethyl)-1H-indazole-3-carboxamide (263a) (30 mg, 0.052 mmol, 14% yield) as a white solid; $^1$H NMR (300 MHz, DMSO-$d_6$) δ 8.46 (t, J=5.8 Hz, 1H), 8.33 (s, 1H), 8.23-8.18 (m, 1H), 7.54 (s, 1H), 7.51-7.41 (m, 2H), 7.33 (dd, J=9.0, 2.0 Hz, 1H), 7.30-7.19 (m, 2H), 7.17-7.07 (m, 1H), 5.88 (s, 1H), 5.59 (s, 2H), 4.33 (d, J=5.7 Hz, 2H), 3.98 (s, 2H), 3.14-2.97 (m, 1H), 1.31 (s, 9H), 1.02-0.95 (m, 2H), 0.95-0.85 (m, 2H); $^{19}$F NMR (282 MHz, DMSO-$d_6$) δ −121.59; MS (ES−) 570.4 (M−1).

Scheme 264

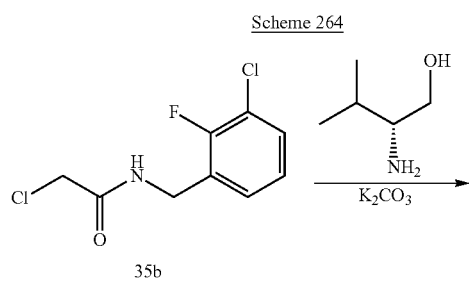

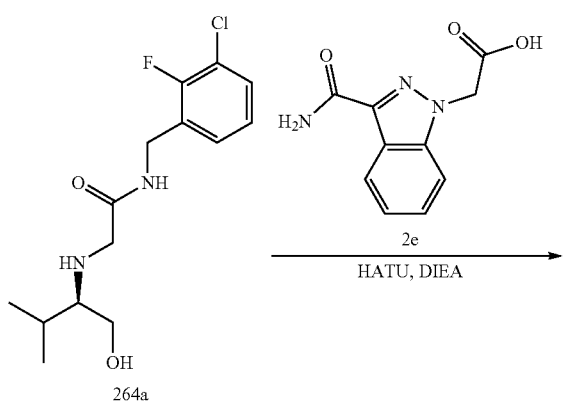

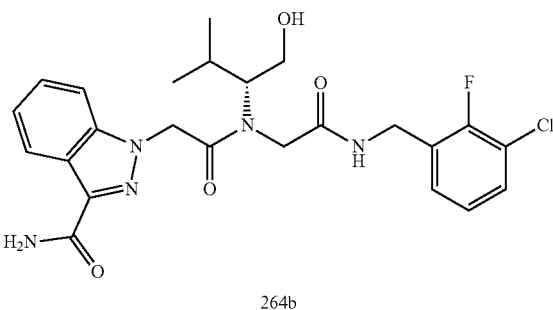

264b

Preparation of (R)-1-(2-((2-((3-chloro-2-fluorobenzyl)amino)-2-oxoethyl)(1-hydroxy-3-methylbutan-2-yl)-amino)-2-oxoethyl)-1H-indazole-3-carboxamide (264b)

Step-1: Preparation of (R)—N-(3-chloro-2-fluorobenzyl)-2-((1-hydroxy-3-methylbutan-2-yl)amino)acetamide (264a)

Reaction of 2-chloro-N-(3-chloro-2-fluorobenzyl)acetamide (35b) (500 mg, 2.12 mmol) with (R)-2-amino-3-methylbutan-1-ol (437 mg, 4.24 mmol) according to the procedure reported in step-2 of Scheme 35 gave after workup (R)—N-(3-chloro-2-fluorobenzyl)-2-(1-hydroxy-3-methylbutan-2-ylamino)acetamide (264a) (641 mg, 2.12 mmol, 100% yield) which was used as such in the next step; MS (ES+): 303.4 (M+1), 325.4 (M+Na); MS (ES−): 337.3 (M+Cl).

Step-2: Preparation of (R)-1-(2-((2-((3-chloro-2-fluorobenzyl)amino)-2-oxoethyl)(1-hydroxy-3-methylbutan-2-yl)amino)-2-oxoethyl)-1H-indazole-3-carboxamide (264b)

Reaction of (R)—N-(3-chloro-2-fluorobenzyl)-2-(1-hydroxy-3-methylbutan-2-ylamino)acetamide (264a) (360 mg, 1.19 mmol) with 2-(3-carbamoyl-1H-indazol-1-yl)acetic acid (2e) (261 mg, 1.19 mmol) according to the procedure reported in step-3 of Scheme 2 gave after workup and purification by flash column chromatography [silica (12 g), eluting with DMA80 in DCM 0 to 50%] (R)-1-(2-((2-((3-chloro-2-fluorobenzyl)amino)-2-oxoethyl)(1-hydroxy-3-methylbutan-2-yl)amino)-2-oxoethyl)-1H-indazole-3-carboxamide (264b) (0.016 g, 0.032 mmol, 3% yield) as a white solid in the form of mixture of rotamers. $^1$H NMR (300 MHz, DMSO-$d_6$) δ 8.95 (t, J=5.7 Hz) & 8.82 (t, J=5.8 Hz) (2t, 1H), 8.27-8.12 (m, 1H), 7.79 and 7.71 (2s, 1H), 7.67-6.85 (m, 7H), 5.75 (bs, 1H, D$_2$O exchangeable), 5.70-5.39 (m, 2H), 4.59-3.37 (m, 7H), 1.92-1.65 (m, 1H), 1.00 (d, J=6.4 Hz) and 0.94 (d, J=6.5 Hz) and 0.87 (d, J=6.5 Hz) and 0.76 (d, J=6.6 Hz) (4d, 6H); $^{19}$F NMR (282 MHz, DMSO-$d_6$) δ −121.32, −121.55; MS (ES+): 504.5 (M+1), 526.5 (M+Na); MS (ES−): 502.5 (M−1).

Scheme 265

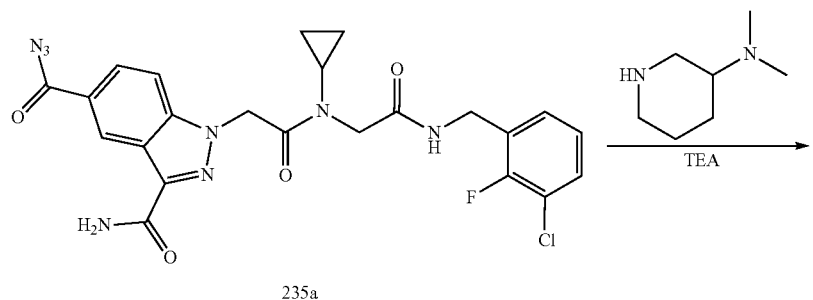

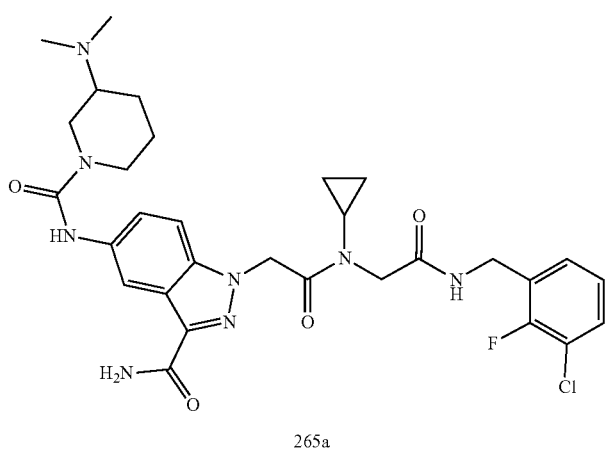

Preparation of 1-(2-((2-((3-chloro-2-fluorobenzyl)amino)-2-oxoethyl)(cyclopropyl)amino)-2-oxoethyl)-5-(3-(dimethylamino)piperidine-1-carboxamido)-1H-indazole-3-carboxamide (265a)

Compound 265a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (400 mg, 0.38 mmol) and N,N-dimethylpiperidin-3-amine (97 mg, 0.76 mmol) using TEA (0.21 mL, 1.52 mmol) as base according to the procedure reported in step-4 of Scheme 129. This gave after workup, purification by flash column chromatography [silica gel (12 g), eluting with DMA80 in DCM 0 to 40%] followed by preparative HPLC [Cis column, eluting with CH$_3$CN in water (containing 0.1% TFA) 0-100%] 1-(2-((2-((3-chloro-2-fluorobenzyl)amino)-2-oxoethyl)(cyclopropyl)amino)-2-oxoethyl)-5-(3-(dimethylamino)piperidine-1-carboxamido)-1H-indazole-3-carboxamide (265a) (32 mg, 0.051 mmol, 13% yield) white solid as a TFA salt; $^1$H NMR (300 MHz, DMSO-d$_6$) δ 9.60-9.46 (m, 1H), 8.77 (s, 1H), 8.50 (t, J=5.8 Hz, 1H), 8.25-8.18 (m, 1H), 7.66 (s, 1H), 7.56-7.50 (m, 2H), 7.50-7.42 (m, 1H), 7.32 (s, 1H), 7.27-7.19 (m, 1H), 7.19-7.08 (m, 1H), 5.61 (s, 2H), 4.33 (d, J=5.7 Hz, 2H), 4.24 (d, J=13.0 Hz, 2H), 3.98 (s, 2H), 3.94-3.88 (m, 1H), 3.33-3.22 (m, 1H), 3.10-2.97 (m, 2H), 2.86 and 2.85 and 2.82 and 2.81 (4s, 6H), 2.13-2.03 (m, 1H), 1.86-1.65 (m, 2H), 1.61-1.39 (m, 1H), 1.03-0.95 (m, 2H), 0.95-0.85 (m, 2H); $^{19}$F NMR (282 MHz, DMSO-d$_6$) δ −73.92 (TFA peak), −121.58; MS (ES+): 627.5 (M+1).

Scheme 266

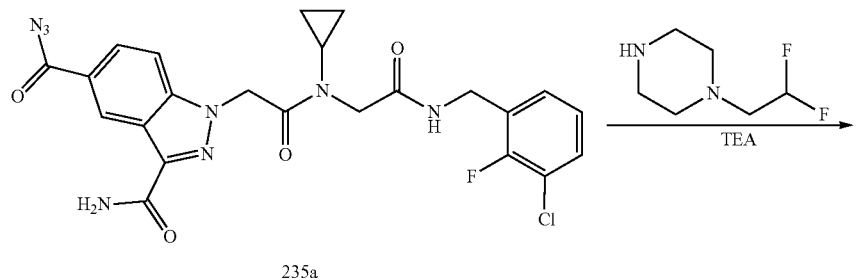

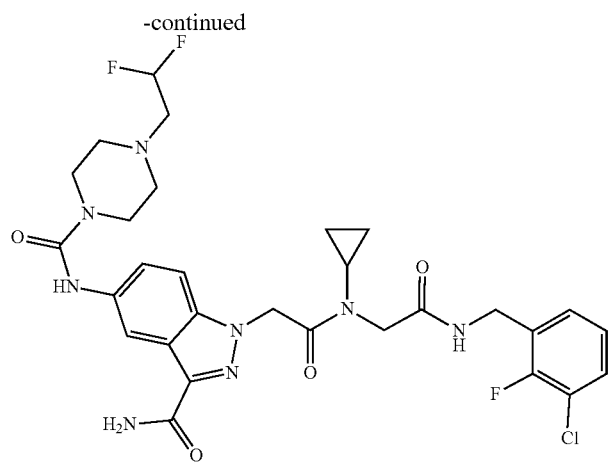

266a

Preparation of 1-(2-((2-((3-chloro-2-fluorobenzyl)amino)-2-oxoethyl)(cyclopropyl)amino)-2-oxoethyl)-5-(4-(2,2-difluoroethyl)piperazine-1-carboxamido)-1H-indazole-3-carboxamide (266a)

Compound 266a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (400 mg, 0.38 mmol) and 1-(2,2-difluoroethyl)piperazine hydrochloride (163 mg, 0.87 mmol) using TEA (0.24 mL, 1.75 mmol) as base according to the procedure reported in step-4 of Scheme 129. This gave after workup, purification by flash column chromatography [silica gel (12 g), eluting with DMA80 in DCM 0 to 40%] followed by preparative HPLC [C$_{18}$ column, eluting with CH$_3$CN in water (containing 0.1% TFA) 0-100%] 1-(2-((2-((3-chloro-2-fluorobenzyl)amino)-2-oxoethyl)(cyclopropyl)amino)-2-oxoethyl)-5-(4-(2,2-difluoroethyl)piperazine-1-carboxamido)-1H-indazole-3-carboxamide (266a) (32 mg, 0.042 mmol, 10% yield) white solid as a TFA salt; $^1$H NMR (300 MHz, DMSO-d$_6$) δ 8.80 (s, 1H), 8.50 (t, J=5.9 Hz, 1H), 8.21-8.15 (m, 1H), 7.65 (s, 1H), 7.58-7.43 (m, 3H), 7.36-7.29 (m, 1H), 7.28-7.20 (m, 1H), 7.19-7.07 (m, 2H), 5.61 (s, 2H), 4.33 (d, J=5.6 Hz, 2H), 3.98 (s, 2H), 3.78-2.71 (m, 12H), 1.03-0.95 (m, 2H), 0.95-0.86 (m, 2H); $^{19}$F NMR (282 MHz, DMSO-d$_6$) δ -74.40 (TFA peak), -119.35, -121.59; MS (ES+) 649.5 (M+1).

Scheme 267

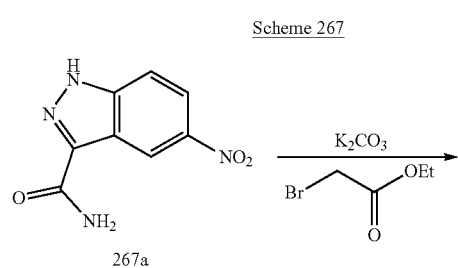

267a

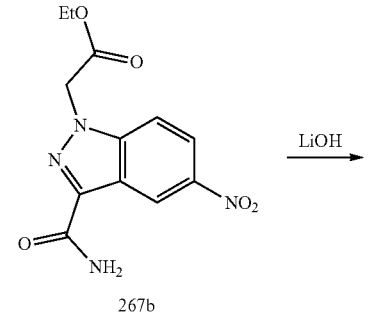

267b

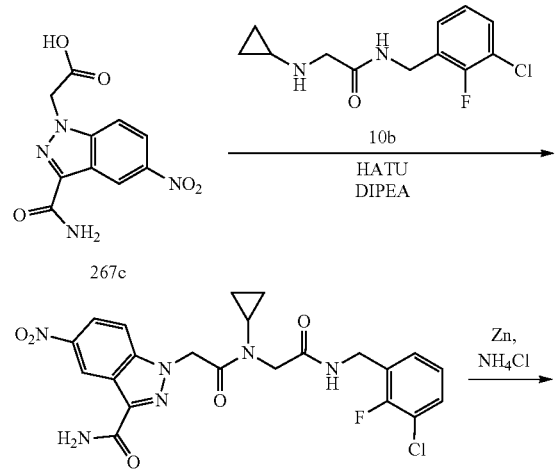

267c

267d

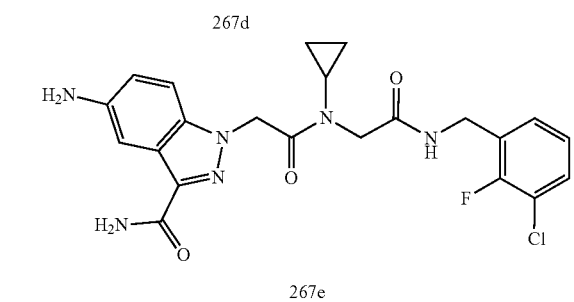

267e

Preparation of 5-amino-1-(2-((2-((3-chloro-2-fluorobenzyl)amino)-2-oxoethyl)(cyclopropyl)amino)-2-oxoethyl)-1H-indazole-3-carboxamide (267e)

Step-1: Preparation of ethyl 2-(3-carbamoyl-5-nitro-1H-indazol-1-yl)acetate (267b)

Compound 267b was prepared from 5-nitro-1H-indazole-3-carboxamide (267a) (1.85 g, 8.97 mmol, prepared according to the procedure reported by Ochs, Raymond S. and Talele; Tanaji T; in U S. Pai. Appl Publ., 20120130078) and ethyl 2-bromoacetate (1.985 mL, 17.95 mmol), using Potassium carbonate (2.480 g, 17.95 mmol) as base according to the procedure reported in step-1 of Scheme 56. This gave after workup ethyl 2-(3-carbamoyl-5-nitro-1H-indazol-1-yl)acetate (267b) (2 g, 6.84 mmol, 76% yield) as a white solid; $^1$H NMR (300 MHz, DMSO-$d_6$) δ 9.06 (dd, J=2.3, 0.7 Hz, 1H), 8.33 (dd, J=9.3, 2.3 Hz, 1H), 8.09-7.97 (m, 2H), 7.73 (s, 1H), 5.60 (s, 2H), 4.18 (q, J=7.1 Hz, 2H), 1.21 (t, J=7.1 Hz, 3H); MS (ES+) 293.4 (M+1), MS (ES−): 327.3 (M+Cl).

Step-2: Preparation of 2-(3-carbamoyl-5-nitro-1H-indazol-1-yl)acetic acid (267c)

Compound 267c was prepared from ethyl 2-(3-carbamoyl-5-nitro-1H-indazol-1-yl)acetate (267b) (2 g, 6.84 mmol) using a solution of LiOH (0.49 g, 20.53 mmol) in Water (10 mL) as base, according to the procedure reported in step-2 of Scheme 129. This gave after workup 2-(3-carbamoyl-5-nitro-1H-indazol-1-yl)acetic acid (267c) (1.6 g, 6.06 mmol, 88% yield) as a white solid; $^1$H NMR (300 MHz, DMSO-$d_6$) δ 13.48 (s, 1H), 9.05 (dd, J=2.3, 0.7 Hz, 1H), 8.32 (dd, J=9.3, 2.3 Hz, 1H), 8.04 (s, 1H), 8.01 (dd, J=9.3, 0.7 Hz, 1H), 7.72 (s, 1H), 5.48 (s, 2H); MS (ES−): 263.2 (M−1).

Step-3: Preparation of 1-(2-((2-((3-chloro-2-fluorobenzyl)amino)-2-oxoethyl)(cyclopropyl)amino)-2-oxoethyl)-5-nitro-1H-indazole-3-carboxamide (267d)

Compound 267d was prepared from 2-(3-carbamoyl-5-nitro-1H-indazol-1-yl)acetic acid (267c) (800 mg, 3.03 mmol) and N-(3-chloro-2-fluorobenzyl)-2-(cyclopropylamino)acetamide (10b) (933 mg, 3.63 mmol) according to the procedure reported in step-3 of Scheme 2. This gave after workup and trituration with ethyl acetate/hexanes (20 mL, 1:1) 1-(2-((2-((3-chloro-2-fluorobenzyl)amino)-2-oxoethyl)(cyclopropyl)amino)-2-oxoethyl)-5-nitro-1H-indazole-3-carboxamide (267d) (1.3 g, 2.59 mmol, 85% yield) as a off-white solid; $^1$H NMR (300 MHz, DMSO-$d_6$) δ 9.05 (dd, J=2.3, 0.6 Hz, 1H), 8.52 (t, J=5.8 Hz, 1H), 8.27 (dd, J=9.3, 2.3 Hz, 1H), 8.04 (s, 1H), 7.91 (dd, J=9.3, 0.7 Hz, 1H), 7.69 (s, 1H), 7.50-7.42 (m, 1H), 7.27-7.18 (m, 1H), 7.14-7.07 (m, 1H), 5.78 (s, 2H), 4.33 (d, J=5.7 Hz, 2H), 3.99 (s, 2H), 3.14-3.01 (m, 1H), 1.05-0.96 (m, 2H), 0.96-0.87 (m, 2H); $^{19}$F NMR (282 MHz, DMSO-$d_6$) δ −121.55; MS (ES+): 525.5 (M+Na), MS (ES−); 537.4 (M+Cl).

Step-4: Preparation of 5-amino-1-(2-((2-((3-chloro-2-fluorobenzyl)amino)-2-oxoethyl)(cyclopropyl)amino)-2-oxoethyl)-1H-indazole-3-carboxamide (267e)

To a solution of 1-(2-((2-((3-chloro-2-fluorobenzyl)amino)-2-oxoethyl)(cyclopropyl)amino)-2-oxoethyl)-5-nitro-1H-indazole-3-carboxamide (267d) (1.2 g, 2.39 mmol) in THF/methanol (80 mL, 1:1) was added ammonium Chloride (2.55 g, 47.7 mmol), Zinc (1.56 g, 23.86 mmol) and stirred at RT for 3 h. The mixture was filtered over a Celite pad, pad was washed with 20% methanol in EtOAc (2×10 mL) and concentrated partially in vacuum. The resultant residue was partitioned between brine (60 mL) and EtOAc (80 mL). The organic layer was separated, dried, filtered and concentrated in vacuum. The residue obtained was purified by flash column chromatography [silica gel (24 g), eluting with DMA80 in DCM, 0 to 25%] to afford 5-amino-1-(2-((2-((3-chloro-2-fluorobenzyl)amino)-2-oxoethyl)(cyclopropyl)amino)-2-oxoethyl)-1H-indazole-3-carboxamide (267e) (1.05 g, 2.22 mmol, 93% yield) as light orange solid; $^1$H NMR (300 MHz, DMSO-$d_6$) δ 8.49 (t, J=5.8 Hz, 1H), 7.52-7.41 (m, 2H), 7.35-7.07 (m, 5H), 6.79 (dd, J=8.9, 2.1 Hz, 1H), 5.52 (s, 2H), 5.04 (s, 2H), 4.33 (d, J=5.7 Hz, 2H), 3.97 (s, 2H), 3.09-2.98 (m, 1H), 1.02-0.93 (m, 2H), 0.93-0.85 (m, 2H); $^{19}$F NMR (282 MHz, DMSO-$d_6$) δ −121.61; MS (ES+): 473.5 (M+1), 495.4 (M+Na); MS (ES−): 507.4 (M+Cl).

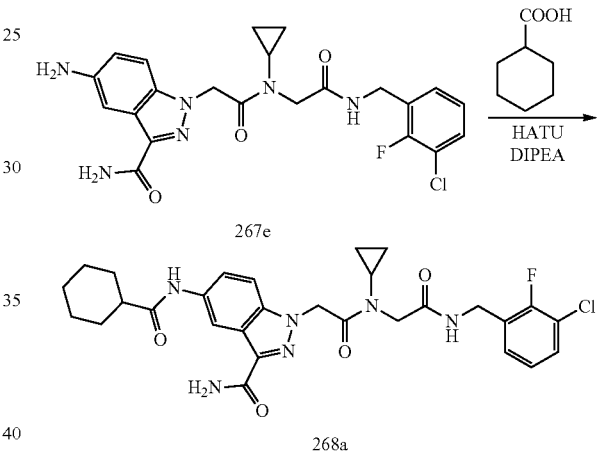

Scheme 268

Preparation of 1-(2-((2-((3-chloro-2-fluorobenzyl)amino)-2-oxoethyl)(cyclopropyl)amino)-2-oxoethyl)-5-(cyclohexanecarboxamido)-1H-indazole-3-carboxamide (268a)

Compound 268a was prepared from 5-amino-1-(2-((2-((3-chloro-2-fluorobenzyl)amino)-2-oxoethyl)(cyclopropyl)amino)-2-oxoethyl)-1H-indazole-3-carboxamide (267e) (120 mg, 0.25 mmol) and cyclohexanecarboxylic acid (33 mg, 0.25 mmol) according to the procedure reported in step-3 of Scheme 2. This gave after workup and purification by flash column chromatography [silica (12 g), eluting with DMA80 in DCM 0 to 30%] 1-(2-((2-((3-chloro-2-fluorobenzyl)amino)-2-oxoethyl)(cyclopropyl)amino)-2-oxoethyl)-5-(cyclohexanecarboxamido)-1H-indazole-3-carboxamide (268a) (70 mg, 0.12 mmol, 47% yield) as a white solid; $^1$H NMR (300 MHz, DMSO-$d_6$) δ 9.91 (s, 1H), 8.50 (t, J=6.0 Hz, 1H), 8.45 (s, 1H), 7.71-7.51 (m, 3H), 7.46 (td, J=7.6, 1.7 Hz, 1H), 7.35 (s, 1H), 7.28-7.18 (m, 1H), 7.12 (t, J=7.9 Hz, 1H), 5.62 (s, 2H), 4.33 (d, J=5.7 Hz, 2H), 3.98 (s, 2H), 3.12-2.99 (m, 1H), 2.34 (t, J=11.4 Hz, 1H), 1.91-1.11 (m, 10H), 1.04-0.94 (m, 2H), 0.94-0.85 (m, 2H); $^{19}$F NMR (282 MHz, DMSO-$d_6$) δ −121.59; MS (ES+): 584.5 (M+1), MS (ES−): 617.5 (M+Cl).

Scheme 269

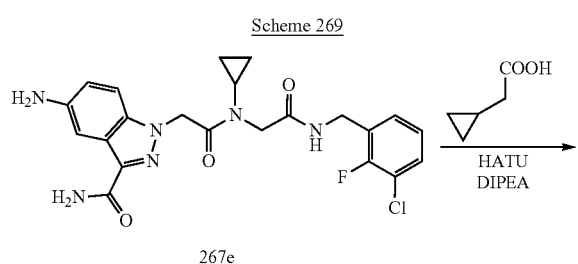

267e

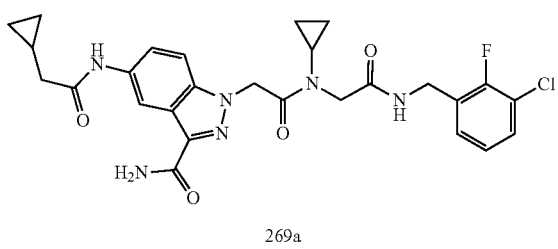

269a

Preparation of 1-(2-((2-((3-chloro-2-fluorobenzyl)amino)-2-oxoethyl)(cyclopropyl)amino)-2-oxo-ethyl)-5-(2-cyclopropylacetamido)-1H-indazole-3-carboxamide (269a)

Compound 269a was prepared from 5-amino-1-(2-((2-((3-chloro-2-fluorobenzyl)amino)-2-oxoethyl)(cyclopropyl)amino)-2-oxoethyl)-1H-indazole-3-carboxamide (267e) (120 mg, 0.25 mmol) and 2-cyclopropylacetic acid (25 mg, 0.25 mmol) according to the procedure reported in step-3 of Scheme 2. This gave after workup and purification by flash column chromatography [silica (12 g), eluting with DMA80 in DCM 0 to 30%] 1-(2-((2-((3-chloro-2-fluorobenzyl)amino)-2-oxoethyl)(cyclopropyl)amino)-2-oxoethyl)-5-(2-cyclopropylacetamido)-1H-indazole-3-carboxamide (269a) (95 mg, 0.17 mmol, 68% yield) as a white solid; $^1$H NMR (300 MHz, DMSO-$d_6$) δ 9.92 (s, 1H), 8.50 (t, J=5.8 Hz, 1H), 8.44 (d, J=1.8 Hz, 1H), 7.72-7.52 (m, 3H), 7.51-7.41 (m, 1H), 7.35 (s, 1H), 7.28-7.17 (m, 1H), 7.12 (t, J=7.8 Hz, 1H), 5.63 (s, 2H), 4.33 (d, J=5.7 Hz, 2H), 3.98 (s, 2H), 3.13-2.99 (m, 1H), 2.22 (d, J=7.0 Hz, 2H), 1.15-0.84 (m, 5H), 0.55-0.43 (m, 2H), 0.26-0.16 (m, 2H); $^{19}$F NMR (282 MHz, DMSO-$d_6$) δ -121.59; MS (ES+): 555.5 (M+1), 577.4 (M+Na); MS (ES−): 589.4 (M+Cl).

Scheme 270

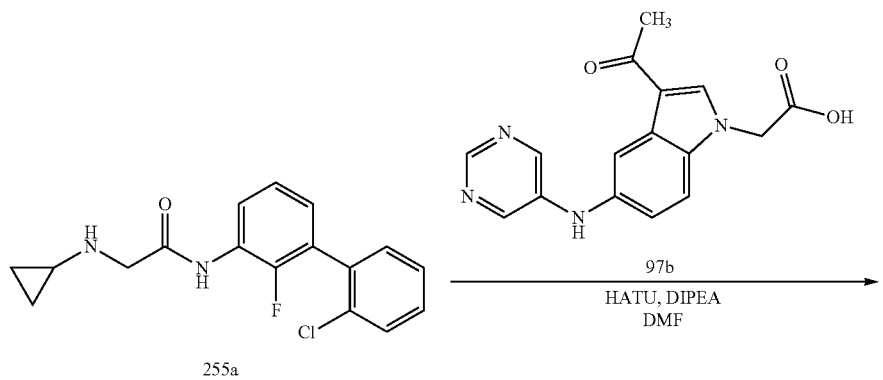

255a

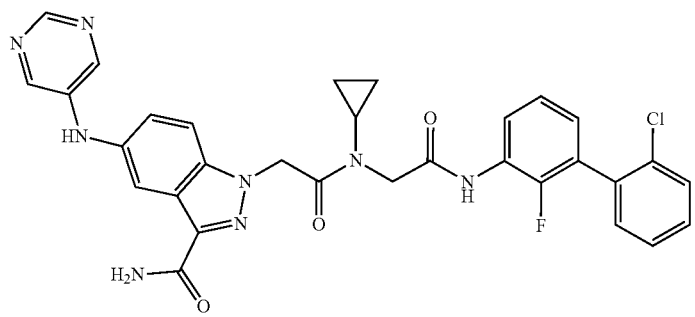

270a

473

Preparation of 2-(3-acetyl-5-(pyrimidin-5-ylamino)-1H-indol-1-yl)-N-(2-((2'-chloro-2-fluoro-[1,1'-biphenyl]-3-yl)-amino)-2-oxoethyl)-N-cyclopropylacetamide (270a)

Compound 270a was prepared from N-(2'-chloro-2-fluorobiphenyl-3-yl)-2-(cyclopropylamino)acetamide (255a) (80 mg, 0.25 mmol) and 2-(3-acetyl-5-(pyrimidin-5-ylamino)-1H-indol-1-yl)acetic acid (97b) (78 mg, 0.25 mmol) according to the procedure reported in step-3 of Scheme 2. This gave after workup and purification by flash column chromatography [silica gel (12 g), eluting with DMA-80 in DCM 0 to 40%] 2-(3-acetyl-5-(pyrimidin-5-ylamino)-1H-indol-1-yl)-N-(2-((2'-chloro-2-fluoro-[1,1'-biphenyl]-3-yl)-amino)-2-oxoethyl)-N-cyclopropylacetamide (270a) (35 mg, 0.06 mmol, 23% yield) as an off-white solid; $^{1}$H NMR (300 MHz, DMSO-$d_6$) δ 9.94 (s, 1H), 8.56 (s, 1H), 8.49 (s, 1H), 8.47 (s, 2H), 8.28 (s, 1H), 8.06-7.93 (m, 2H), 7.62-7.55 (m, 1H), 7.50-7.36 (m, 4H), 7.24 (t, J=7.9 Hz, 1H), 7.15-7.03 (m, 2H), 5.46 (s, 2H), 4.24 (s, 2H), 3.20-3.08 (m, 1H), 2.41 (s, 3H), 1.07-0.99 (m, 2H), 0.99-0.92 (m, 2H); $^{19}$F NMR (282 MHz, DMSO-$d_6$) δ −126.77; MS (ES+): 611.6 (M+1); MS(ES−): 645.5 (M+Cl).

474

Preparation of 2-(3-acetyl-5-(pyridin-3-ylamino)-1H-indazol-1-yl)-N-(2-((2'-chloro-2-fluoro-[1,1'-biphenyl]-3-yl)-amino)-2-oxoethyl)-N-cyclopropylacetamide (271a)

Compound 271a was prepared from N-(2'-chloro-2-fluorobiphenyl-3-yl)-2-(cyclopropylamino)acetamide (255a) (65 mg, 0.2 mmol) and 2-(3-acetyl-5-(pyridin-3-ylamino)-1H-indazol-1-yl)acetic acid (187b) (63 mg, 0.2 mmol) according to the procedure reported in step-3 of Scheme 2. This gave after workup and purification by flash column chromatography [silica gel (12 g), eluting with DMA-80 in DCM 0 to 40%] 2-(3-acetyl-5-(pyridin-3-ylamino)-1H-indazol-1-yl)-N-(2-((2'-chloro-2-fluoro-[1,1'-biphenyl]-3-yl)-amino)-2-oxoethyl)-N-cyclopropylacetamide (271a) (40 mg, 0.07 mmol, 32% yield) as an off-white solid; $^{1}$H NMR (300 MHz, DMSO-$d_6$) δ 9.95 (s, 1H), 8.52 (s, 1H), 8.36 (d, J=2.7 Hz, 1H), 8.04 (dd, J=4.6, 1.4 Hz, 1H), 8.02-7.94 (m, 1H), 7.87 (d, J=2.0 Hz, 1H), 7.65 (d, J=9.0 Hz, 1H), 7.61-7.56 (m, 1H), 7.51-7.37 (m, 4H), 7.31-7.20 (m, 3H), 7.13-7.02 (m, 1H), 5.76 (s, 2H), 4.24 (s, 2H), 3.22-3.11 (m, 1H), 2.59 (s, 3H), 1.11-1.00 (m, 2H), 1.00-0.88 (m, 2H); $^{19}$F NMR (282 MHz, DMSO-$d_6$) δ −126.71; MS (ES+): 611.6 (M+1), MS (ES−): 645.5 (M+Cl).

Scheme 271

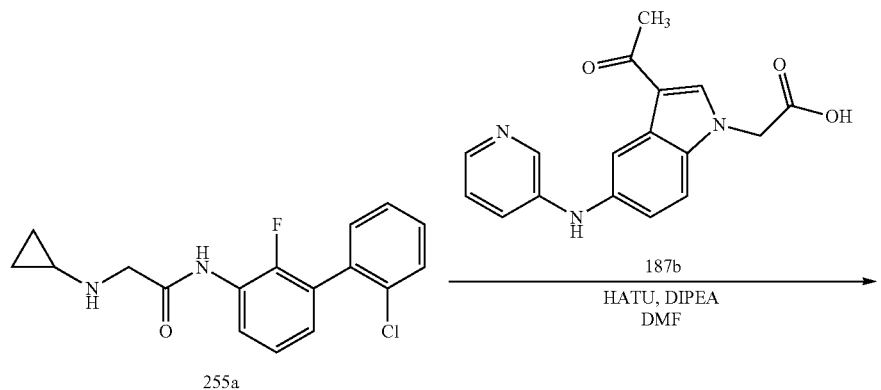

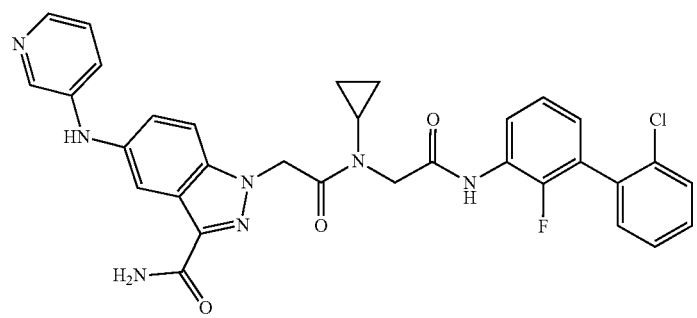

271a

Scheme 272

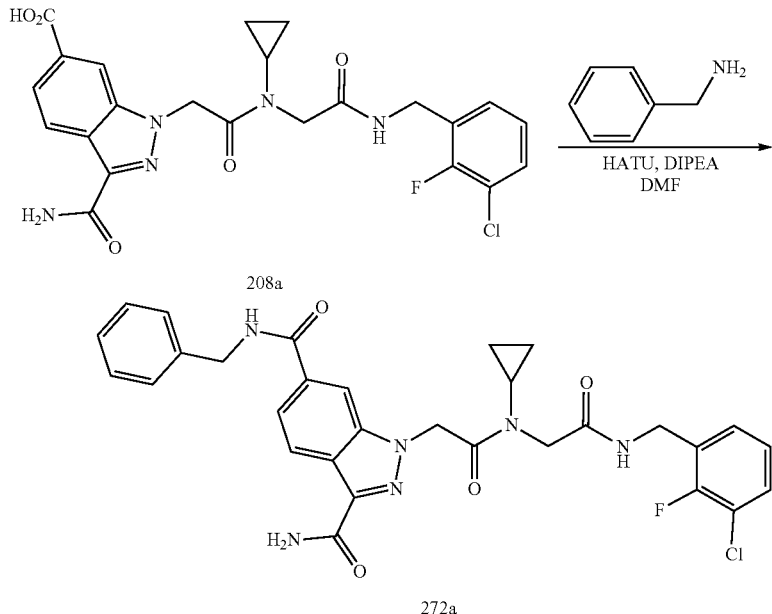

Preparation of N6-benzyl-1-(2-((2-((3-chloro-2-fluorobenzyl)amino)-2-oxoethyl)(cyclopropyl)amino)-2-oxoethyl)-1H-indazole-3,6-dicarboxamide (272a)

Compound 272a was prepared from 3-carbamoyl-1-(2-((2-((3-chloro-2-fluorobenzyl)amino)-2-oxoethyl)(cyclopropyl)amino)-2-oxoethyl)-1H-indazole-6-carboxylic acid (208a) (50 mg, 0.1 mmol) and phenylmethanamine (0.016 mL, 0.15 mmol) according to the procedure reported in step-3 of Scheme 2. This gave after workup and purification by flash column chromatography [silica gel (8 g), eluting with dichloromethane/methanol (1:0 to 19:1)] N6-benzyl-1-(2-((2-((3-chloro-2-fluorobenzyl)amino)-2-oxoethyl)(cyclopropyl)amino)-2-oxoethyl)-1H-indazole-3,6-dicarboxamide (272a) (36 mg, 61% yield) as a white solid; $^1$H NMR (300 MHz, DMSO-$d_6$) δ 9.14 (t, J=6.0 Hz, 1H), 8.55 (t, J=5.8 Hz, 1H), 8.26-8.19 (m, 2H), 7.83 (s, 1H), 7.79 (dd, J=8.5, 1.4 Hz, 1H), 7.51-7.16 (m, 8H), 7.08 (td, J=7.9, 1.0 Hz, 1H), 5.74 (s, 2H), 4.52 (d, J=5.9 Hz, 2H), 4.30 (d, J=5.7 Hz, 2H), 4.00 (s, 2H), 3.19-2.98 (m, 1H), 1.06-0.87 (m, 4H); $^{19}$F NMR (282 MHz, DMSO-$d_6$) δ -121.57; MS (ES-): 625.5 & 627.6 (M+Cl).

Scheme 273

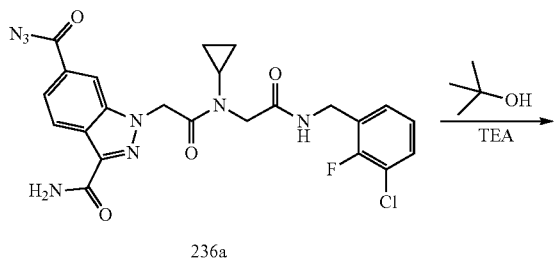

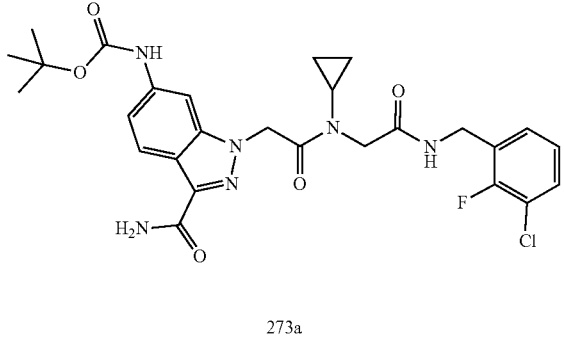

Preparation of tert-butyl (3-carbamoyl-1-(2-((2-((3-chloro-2-fluorobenzyl)amino)-2-oxoethyl)(cyclopropyl)amino)-2-oxoethyl)-1H-indazol-6-yl)carbamate (273a)

Compound 273a was prepared from 3-carbamoyl-1-(2-((2-((3-chloro-2-fluorobenzyl)amino)-2-oxoethyl)(cyclopropyl)amino)-2-oxoethyl)-1H-indazole-6-carbonyl azide (236a) (210 mg, 0.4 mmol) and 2-methylpropan-2-ol (0.23 mL, 2.4 mmol) using TEA (0.11 mL, 0.8 mmol) as base according to the procedure reported in step-4 of Scheme 129 to afford after workup and purification by column chromatography [silica gel, eluting with hexanes/10% methanol in ethyl acetate (1:0 to 1:1)] tert-butyl (3-carbamoyl-1-(2-((2-((3-chloro-2-fluorobenzyl)amino)-2-oxoethyl)(cyclopropyl)amino)-2-oxoethyl)-1H-indazol-6-yl)carbamate (273a) (96 mg, 42%) as a white solid; $^1$H NMR (300 MHz, DMSO-$d_6$) δ 9.61 (s, 1H), 8.53 (t, J=5.8 Hz, 1H), 7.99 (dd, J=8.8, 0.7 Hz, 1H), 7.81 (s, 1H), 7.68 (s, 1H), 7.45 (td, J=7.5, 1.7 Hz, 1H), 7.34 (s, 1H), 7.27-7.07 (m, 3H), 5.58 (s, 2H), 4.33 (d, J=5.7 Hz, 2H), 3.99 (s, 2H), 3.16-2.99 (m, 1H), 1.49 (s, 9H), 1.07-0.83 (m, 4H); ¹⁹F NMR (282 MHz, DMSO-d₆) δ −121.65; MS (ES+): 595.5 & 597.5 (M+Na); MS (ES−): 607.4 & 609.4 (M+Cl).

Scheme 274

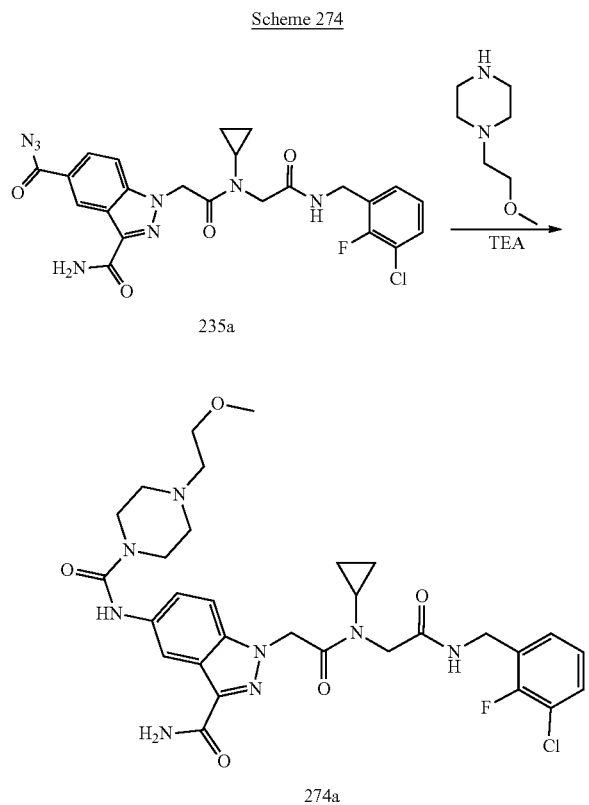

Preparation of 1-(2-((2-((3-chloro-2-fluorobenzyl) amino)-2-oxoethyl)(cyclopropyl)amino)-2-oxo-ethyl)-5-(4-(2-methoxyethyl)piperazine-1-carbox-amido)-1H-indazole-3-carboxamide (274a)

Compound 274a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (460 mg, 0.44 mmol) and 1-(2-methoxyethyl)piperazine (126 mg, 0.87 mmol) using TEA (0.24 mL, 1.75 mmol) as base according to the procedure reported in step-4 of Scheme 129. This gave after workup, purification by flash column chromatography [silica gel (12 g), eluting with DMA80 in DCM 0 to 40%] followed by preparative HPLC [C₁₈ column, eluting with CH₃CN in water (containing 0.1% TFA) 0-100%] 1-(2-((2-((3-chloro-2-fluorobenzyl)amino)-2-oxoethyl)(cyclopropyl)amino)-2-oxoethyl)-5-(4-(2-methoxyethyl)piperazine-1-carboxamido)-1H-indazole-3-carboxamide (274a) (25 mg, 0.04 mmol, 9% yield) white solid as a TFA salt; ¹H NMR (300 MHz, DMSO-d₆) δ 8.64 (s, 1H), 8.50 (t, J=5.8 Hz, 1H), 8.23-8.12 (m, 1H), 7.63 (s, 1H), 7.58-7.41 (m, 3H), 7.32 (s, 1H), 7.27-7.19 (m, 1H), 7.18-7.07 (m, 1H), 5.61 (s, 2H), 4.33 (d, J=5.7 Hz, 2H), 3.98 (s, 2H), 3.49-3.42 (m, 5H), 3.35 (s, 3H), 3.24 (s, 3H), 3.14-2.97 (m, 1H), 2.47-2.38 (m, 4H), 1.04-0.94 (m, 2H), 0.94-0.81 (m, 2H); ¹⁹F NMR (282 MHz, DMSO) δ −73.44 (TFA peak), −121.60; MS (ES+): 643.6 (M+1).

Scheme 275

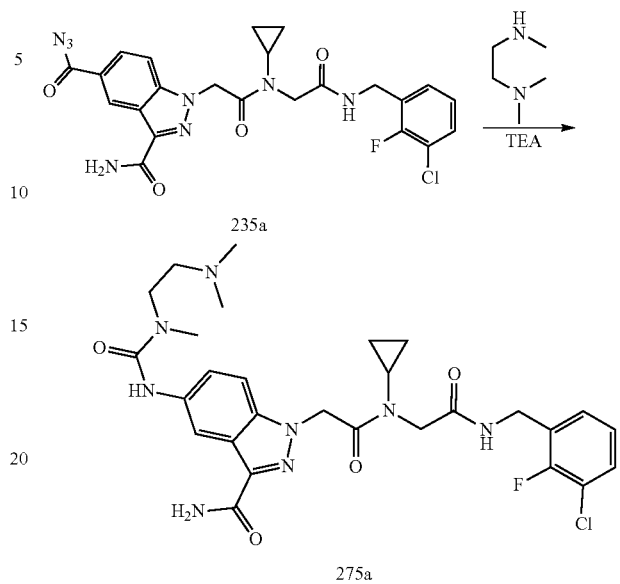

Preparation of 1-(2-((2-((3-chloro-2-fluorobenzyl) amino)-2-oxoethyl)(cyclopropyl)amino)-2-oxo-ethyl)-5-(3-(2-(dimethylamino)ethyl)-3-methylu-reido)-1H-indazole-3-carboxamide (275a)

Compound 275a was prepared from 3-carbamoyl-1-(2-((2-((3-chloro-2-fluorobenzyl)amino)-2-oxoethyl)(cyclo-propyl)amino)-2-oxoethyl)-1H-indazole-5-carbonyl azide (235a) (500 mg, 0.47 mmol) and N1,N1,N2-trimethyl-ethane-1,2-diamine (97 mg, 0.95 mmol) using TEA (0.27 mL, 1.9 mmol) as base according to the procedure reported in step-4 of Scheme 129. This gave after workup, purification by flash column chromatography [silica gel (12 g), eluting with DMA80 in DCM 0 to 40%] followed by preparative HPLC [C₁₈ column, eluting with CH₃CN in water (containing 0.1% TFA) 0-100%] 1-(2-((2-((3-chloro-2-fluorobenzyl)amino)-2-oxoethyl)(cyclopropyl)amino)-2-oxo ethyl)-5-(3-(2-(dimethylamino)ethyl)-3-methylureido)-1H-indazole-3-carboxamide (275a) (22 mg, 0.04 mmol, 8% yield) white solid as a TFA salt; ¹H NMR (300 MHz, DMSO-d₆) δ 8.93 (s, 1H), 8.50 (t, J=5.8 Hz, 1H), 8.21-8.13 (m, 1H), 7.61 (bs, 1H), 7.53-7.41 (m, 3H), 7.30 (s, 1H), 7.26-7.18 (m, 1H), 7.18-7.08 (m, 1H), 5.61 (s, 2H), 4.33 (d, J=5.7 Hz, 2H), 3.98 (s, 2H), 3.41 (t, J=6.3 Hz, 2H), 3.12-3.01 (m, 1H), 2.96 (s, 3H), 2.47-2.41 (m, 2H), 2.23 (s, 6H), 1.03-0.95 (m, 2H), 0.95-0.87 (m, 2H); ¹⁹F NMR (282 MHz, DMSO) δ −73.44 (TFA peak), −121.61; MS (ES+): 601.6 (M+1); MS (ES−): 599.5 (M−1).

Scheme 276

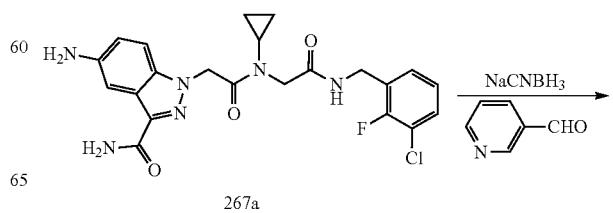

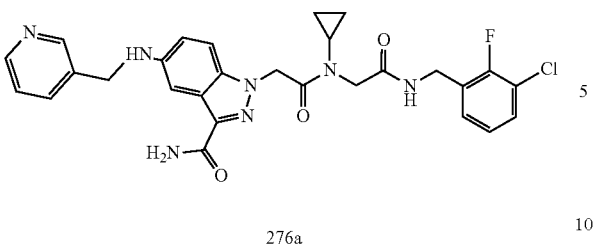

276a

Preparation of 1-(2-((2-((3-chloro-2-fluorobenzyl)amino)-2-oxoethyl)(cyclopropyl)amino)-2-oxoethyl)-5-((pyridin-3-ylmethyl)amino)-1H-indazole-3-carboxamide (276a)

To a solution of 5-amino-1-(2-((2-((3-chloro-2-fluorobenzyl)amino)-2-oxoethyl)(cyclopropyl)amino)-2-oxoethyl)-1H-indazole-3-carboxamide (267e) (100 mg, 0.21 mmol) in DMF (2 mL) and acetic acid (1 mL) was added nicotinaldehyde (230 mg, 0.21 mmol) and stirred at RT for 1 h. To the red colored solution was added in portion wise sodium cyanoborohydride (130 mg, 0.21 mmol) and continued stirring at RT for 16 h. The reaction mixture was diluted with saturated aqueous NaHCO$_3$ solution (50 mL) and extracted with EtOAc (2×50 mL). The organic layers were combined washed with brine, dried, filtered and concentrated in vacuum. The residue obtained was purified by flash column chromatography [silica gel (24 g), eluting with DMA80 in DCM 0 to 40%] to afford 1-(2-((2-((3-chloro-2-fluorobenzyl)amino)-2-oxoethyl)(cyclopropyl)amino)-2-oxoethyl)-5-((pyridin-3-ylmethyl)amino)-1H-indazole-3-carboxamide (276a) (40 mg, 0.07 mmol, 34% yield) as white solid; $^1$H NMR (300 MHz, DMSO-d$_6$) δ 8.64 (d, 1H), 8.54-8.43 (m, 2H), 7.90-7.81 (m, 1H), 7.51-7.33 (m, 5H), 7.27-7.06 (m, 4H), 6.93 (dd, J=9.1, 2.2 Hz, 1H), 5.53 (s, 2H), 4.39-4.28 (m, 4H), 3.97 (s, 2H), 3.10-2.98 (m, 1H), 1.01-0.93 (m, 2H), 0.93-0.84 (m, 2H); $^{19}$F NMR (282 MHz, DMSO-d$_6$) δ −121.60; MS (ES+): 564.5 (M+1), 586.5 (M+Na), MS (ES−): 598.4, 600.4 (M+Cl).

Scheme 277

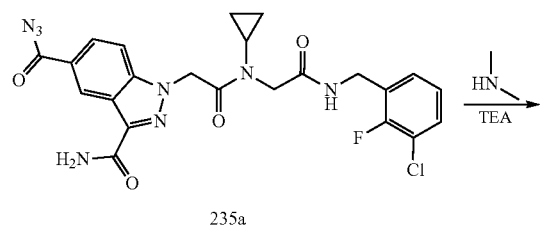

235a

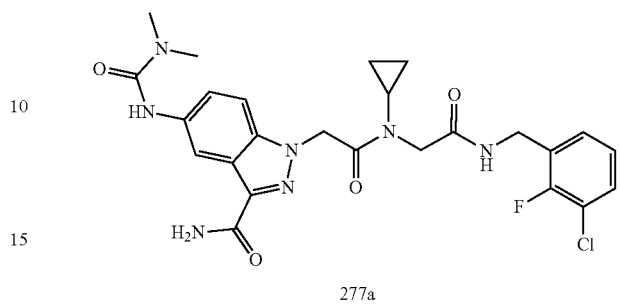

277a

Preparation of 1-(2-((2-((3-chloro-2-fluorobenzyl)amino)-2-oxoethyl)(cyclopropyl)amino)-2-oxoethyl)-5-(3,3-dimethylureido)-1H-indazole-3-carboxamide (277a)

Compound 277a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (500 mg, 0.47 mmol) and dimethylamine (2M in THF) (0.47 mL, 0.95 mmol) using TEA (0.27 mL, 1.9 mmol) as base according to the procedure reported in step-4 of Scheme 129. This gave after workup, purification by flash column chromatography [silica gel (12 g), eluting with DMA80 in DCM 0 to 40%] followed by preparative HPLC [C$_{18}$ column, eluting with CH$_3$CN in water (containing 0.1% TFA) 0-100%] 1-(2-((2-((3-chloro-2-fluorobenzyl)amino)-2-oxoethyl)(cyclopropyl)amino)-2-oxoethyl)-5-(3,3-dimethylureido)-1H-indazole-3-carboxamide (277a) (26 mg, 0.048 mmol, 11% yield) white solid as a TFA salt; $^1$H NMR (300 MHz, DMSO-d$_6$) δ 8.51 (t, J=5.8 Hz, 1H), 8.43 (s, 1H), 8.21-8.15 (m, 1H), 7.63 (s, 1H), 7.60-7.53 (m, 1H), 7.52-7.42 (m, 2H), 7.31 (s, 1H), 7.27-7.19 (m, 1H), 7.18-7.09 (m, 1H), 5.61 (s, 2H), 4.33 (d, J=5.7 Hz, 2H), 3.98 (s, 2H), 3.10-3.00 (m, 1H), 2.94 (s, 6H), 1.04-0.95 (m, 2H), 0.95-0.85 (m, 2H); $^{19}$F NMR (282 MHz, DMSO-d$_6$) δ −73.47 (TFA peak), −121.61; MS (ES+) 544.5 (M+1); (ES−) 542.5 (M−1).

Scheme 278

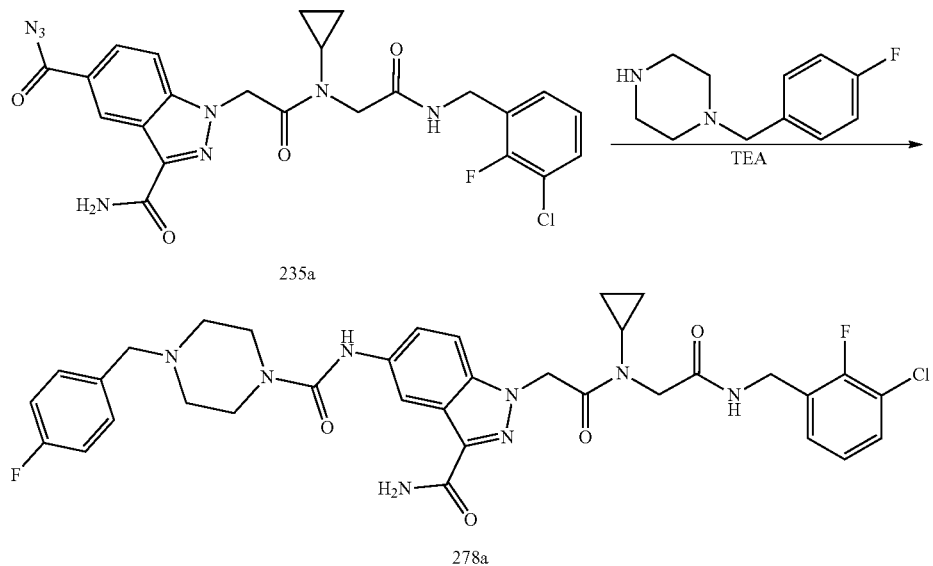

Preparation of 1-(2-((2-(((3-chloro-2-fluorobenzyl)amino)-2-oxoethyl)(cyclopropyl)amino)-2-oxoethyl)-5-(4-(4-fluorobenzyl)piperazine-1-carboxamido)-1H-indazole-3-carboxamide (278a)

Compound 278a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (750 mg, 0.71 mmol) and 1-(4-fluorobenzyl)piperazine (276 mg, 1.423 mmol) using TEA (0.4 mL, 2.85 mmol) as base according to the procedure reported in step-4 of Scheme 129. This gave after workup, purification by flash column chromatography [silica gel (12 g), eluting with DMA80 in DCM 0 to 40%] followed by preparative HPLC [$C_{18}$ column, eluting with $CH_3CN$ in water (containing 0.1% TFA) 0-100%] 1-(2-((2-(((3-chloro-2-fluorobenzyl)amino)-2-oxoethyl)(cyclopropyl)amino)-2-oxoethyl)-5-(4-(4-fluorobenzyl)piperazine-1-carboxamido)-1H-indazole-3-carboxamide (278a) (35 mg, 6% yield) white solid as a TFA salt; $^1$H NMR (300 MHz, DMSO-$d_6$) δ 10.13 (s, 1H), 8.92 (s, 1H), 8.52 (t, J=5.9 Hz, 1H), 8.25-8.12 (m, 1H), 7.67 (s, 1H), 7.62-7.51 (m, 4H), 7.46 (td, J=7.6, 1.8 Hz, 1H), 7.40-7.30 (m, 3H), 7.28-7.18 (m, 1H), 7.18-7.08 (m, 1H), 5.62 (s, 2H), 4.38 (s, 2H), 4.36-4.17 (m, 4H), 3.98 (s, 2H), 3.45-2.98 (m, 7H), 1.07-0.96 (m, 2H), 0.96-0.85 (m, 2H); $^{19}$F NMR (282 MHz, DMSO-$d_6$) δ −74.05 (TFA peak), −111.72, −121.59; MS (ES+) 693.6 (M+1).

Scheme 279

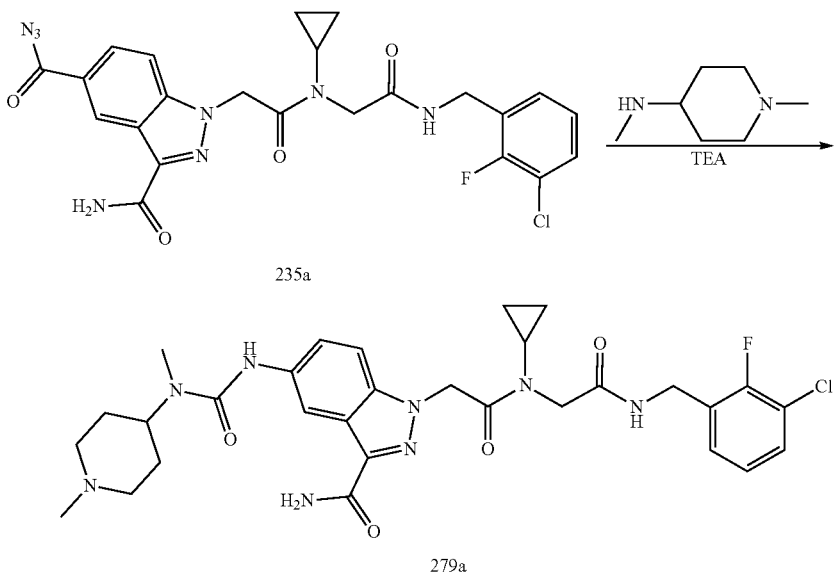

483

Preparation of 1-(2-((2-((3-chloro-2-fluorobenzyl)amino)-2-oxoethyl)(cyclopropyl)amino)-2-oxoethyl)-5-(3-methyl-3-(1-methylpiperidin-4-yl)ureido)-1H-indazole-3-carboxamide (279a)

Compound 279a was prepared from 3-carbamoyl-1-(2-((2-((3-chloro-2-fluorobenzyl)amino)-2-oxoethyl)(cyclopropyl)amino)-2-oxoethyl)-1H-indazole-5-carbonyl azide (235a) (500 mg, 0.47 mmol) and N,1-dimethylpiperidin-4-amine (122 mg, 0.95 mmol), using TEA (0.13 mL, 0.95 mmol) as base according to the procedure reported in step-4 of Scheme 129. This gave after workup, purification by flash column chromatography [silica gel (12 g), eluting with DMA80 in DCM 0 to 40%] followed by preparative HPLC [$C_{18}$ column, eluting with $CH_3CN$ in water (containing 0.1% TFA) 0-100%] 1-(2-((2-((3-chloro-2-fluorobenzyl)amino)-2-oxoethyl)(cyclopropyl)amino)-2-oxoethyl)-5-(3-methyl-3-(1-methylpiperidin-4-yl)ureido)-1H-indazole-3-carboxamide (279a) (68 mg, 19% yield) white solid as a TFA salt; $^1$H NMR (300 MHz, DMSO-$d_6$) δ 9.51 (s, 1H), 8.55-8.44 (m, 2H), 8.22-8.16 (m, 1H), 7.65 (s, 1H), 7.57-7.51 (m, 2H), 7.51-7.41 (m, 1H), 7.35-7.27 (m, 1H), 7.27-7.19 (m, 1H), 7.18-7.09 (m, 1H), 5.61 (s, 2H), 4.36-4.29 (m, 3H), 3.98 (s, 2H), 3.56-3.40 (m, 2H), 3.16-2.98 (m, 3H), 2.84 (s, 3H), 2.79 and 2.78 (2s, 3H), 2.04-1.86 (m, 2H), 1.86-1.74 (m, 2H), 1.02-0.94 (m, 2H), 0.94-0.85 (m, 2H); $^{19}$F NMR (282 MHz, DMSO-$d_6$) δ −73.93 (TFA peak), −121.60; MS (ES+): 627.6 (M+1).

484

Preparation of 2-(3-acetyl-5-(pyrimidin-5-yl)-1H-indazol-1-yl)-N-(2-((2'-chloro-2-fluoro-[1,1'-biphenyl]-3-yl)-amino)-2-oxoethyl)-N-isopropylacetamide (280b)

Step-1: Preparation of 2-(3-acetyl-5-bromo-1H-indazol-1-yl)-N-(2-((2'-chloro-2-fluoro-[1,1'-biphenyl]-3-yl)-amino)-2-oxoethyl)-N-isopropylacetamide (280a)

Compound 280a was prepared from N-(2'-chloro-2-fluoro-[1,1'-biphenyl]-3-yl)-2-(isopropylamino)acetamide (115c) (190 mg, 0.59 mmol) and 2-(3-acetyl-5-bromo-1H-indazol-1-yl)acetic acid (156e) (160 mg, 0.54 mmol) according to the procedure reported in step-3 of Scheme 2. This gave after workup and purification by flash column chromatography [silica (12 g), eluting with DMA80 in DCM from 0 to 30%] 2-(3-acetyl-5-bromo-1H-indazol-1-yl)-N-(2-((2'-chloro-2-fluoro-[1,1'-biphenyl]-3-yl)-amino)-2-oxoethyl)-N-isopropylacetamide (280a) (280 mg, 0.47 mmol, 87% yield) as an off white solid; $^1$H NMR (300 MHz, DMSO-$d_6$) δ 10.26 and 9.74 (2s, 1H), 8.11 and 7.94 (2t, J=7.8 Hz, 1H), 7.72-7.54 (m, 4H), 7.54-7.36 (m, 3H), 7.36-7.01 (m, 2H), 5.78 and 5.60 (2s, 2H), 4.70-4.55 and 4.38-4.23 (2m, 1H), 4.46 and 4.08 (2s, 2H), 2.62 and 2.61 (2s, 3H), 1.28 and 1.07 (2d, J=6.8 Hz, 6H); MS (ES−): 635.3, 637.3 (M+Cl).

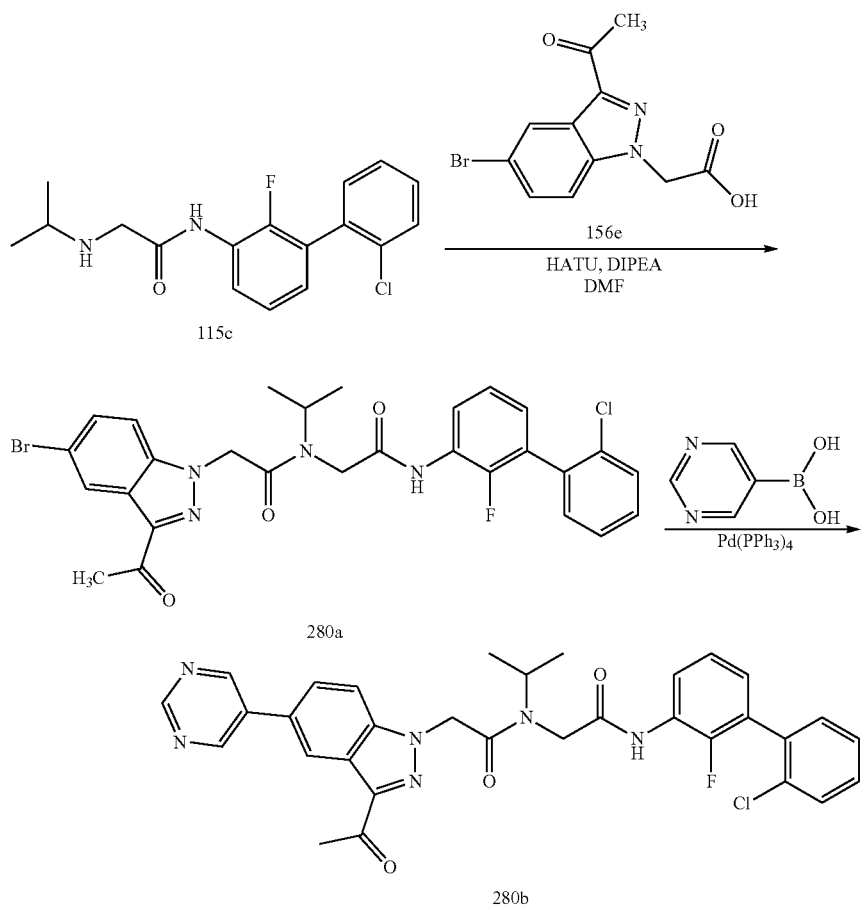

Scheme 280

280a

280b

485

Step-2: Preparation of 2-(3-acetyl-5-(pyrimidin-5-yl)-1H-indazol-1-yl)-N-(2-((2'-chloro-2-fluoro-[1,1'-biphenyl]-3-yl)-amino)-2-oxoethyl)-N-isopropylacetamide (280b)

Compound 280b was prepared from 2-(3-acetyl-5-bromo-1H-indazol-1-yl)-N-(2-((2'-chloro-2-fluoro-[1,1'-biphenyl]-3-yl)-amino)-2-oxoethyl)-N-isopropylacetamide (280a) (120 mg, 0.20 mmol), and pyrimidin-5-ylboronic acid (0.025 g, 0.200 mmol) according to the procedure reported in Scheme 100. This gave after workup and purification by flash column chromatography [silica (12 g), eluting with DMA80 in DCM from 0 to 30%] 2-(3-acetyl-5-(pyrimidin-5-yl)-1H-indazol-1-yl)-N-(2-((2'-chloro-2-fluoro-[1,1'-biphenyl]-3-yl)-amino)-2-oxoethyl)-N-isopropylacetamide (280b) (55 mg, 0.09 mmol, 46% yield) as a white solid; $^1$H NMR (300 MHz, DMSO-$d_6$) δ 10.28 and 9.75 (2s, 1H), 9.23 and 9.22 (2s, 1H), 9.19 and 9.17 (2s, 2H), 8.50-8.48 and 8.50-8.43 (2m, 1H), 8.18-7.80 (m, 3H), 7.67-7.00 (m, 6H), 5.83 and 5.64 (2s, 2H), 4.72-4.58 and 4.41-4.28 (2m, 1H), 4.49 and 4.10 (2s, 2H), 2.66 and 2.65 (2s, 3H), 1.30 and 1.08 (2d, J=6.8 Hz, 6H); $^{19}$F NMR (282 MHz, DMSO-$d_6$) δ −126.91; MS (ES−): 597.4 (M−1), 633.5 (M+Cl).

486

Preparation of 2-(3-acetyl-5-(2-oxopyrrolidin-1-yl)-1H-indol-1-yl)-N-(2-((2'-chloro-2-fluoro-[1,1'-biphenyl]-3-yl)-amino)-2-oxoethyl)-N-cyclopropylacetamide (281c)

Step-1: Preparation of tert-butyl 2-(3-acetyl-5-(2-oxopyrrolidin-1-yl)-1H-indol-1-yl)acetate (281a)

Compound 281a was prepared from tert-butyl 2-(3-acetyl-5-bromo-1H-indol-1-yl)acetate (90b) (500 mg, 1.42 mmol) and pyrrolidin-2-one (121 mg, 1.42 mmol), according to the procedure reported in Scheme 92. This gave after workup and purification by flash column chromatography [silica (24 g), eluting with methanol in DCM from 0 to 100%] tert-butyl 2-(3-acetyl-5-(2-oxopyrrolidin-1-yl)-1H-indol-1-yl)acetate (281a) (256 mg, 0.72 mmol, 51% yield) as a brown wax; MS (ES+): 357.4 (M+1), 379.4 (M+Na); MS (ES−): 391.3 (M+Cl).

Step-2: Preparation of 2-(3-acetyl-5-(2-oxopyrrolidin-1-yl)-1H-indol-1-yl)acetic acid (281b)

Compound 281b was prepared from tert-butyl 2-(3-acetyl-5-(2-oxopyrrolidin-1-yl)-1H-indol-1-yl)acetate

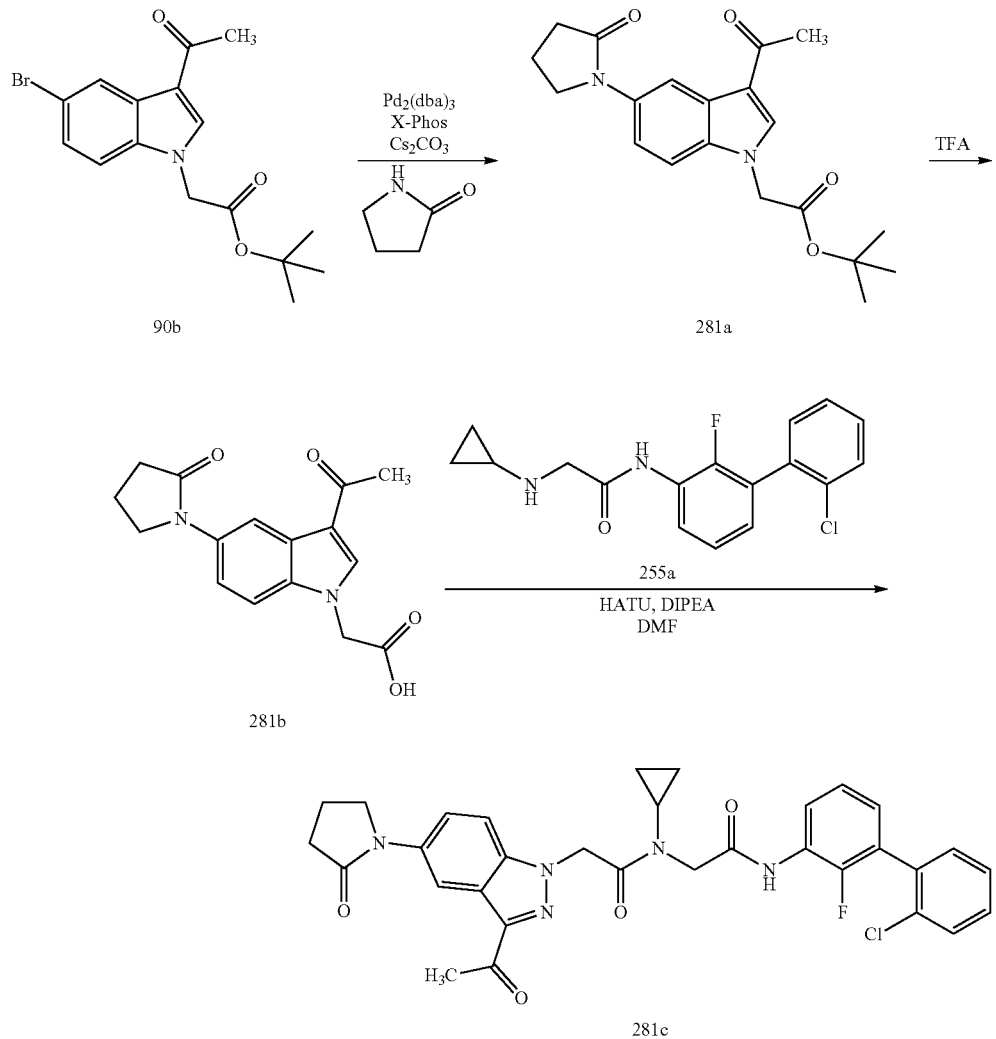

Scheme 281

(281a) (256 mg, 0.72 mmol) using TFA (1.66 mL, 21.55 mmol), according to the procedure reported in step-2 of Scheme 2. This gave after workup 2-(3-acetyl-5-(2-oxopyrrolidin-1-yl)-1H-indol-1-yl)acetic acid (281b) (298 mg, 0.72 mmol, 100% yield) yellow solid as a TFA salt; MS (ES+): 323.4 (M+Na); MS (ES−): 299.3 (M−1).

Step-3: Preparation of 2-(3-acetyl-5-(2-oxopyrrolidin-1-yl)-1H-indol-1-yl)-N-(2-((2'-chloro-2-fluoro-[1,1'-biphenyl]-3-yl)-amino)-2-oxoethyl)-N-cyclopropylacetamide (281c)

Compound 281c was prepared from 2-(3-acetyl-5-(2-oxopyrrolidin-1-yl)-1H-indol-1-yl)acetic acid (281b) (150 mg, 0.36 mmol) and N-(2'-chloro-2-fluoro-[1,1'-biphenyl]-3-yl)-2-(cyclopropylamino)acetamide (255a) (138 mg, 0.43 mmol) according to the procedure reported in step-3 of Scheme 2. This gave after workup and purification by flash column chromatography [First Column: silica gel (24 g), eluting with methanol in DCM 0-20%; second column: Silica gel (24 g), eluting with ethyl acetate/methanol (9:1) in hexanes 0-100%]] 2-(3-acetyl-5-(2-oxopyrrolidin-1-yl)-1H-indol-1-yl)-N-(2-((2'-chloro-2-fluoro-[1,1'-biphenyl]-3-yl)-amino)-2-oxoethyl)-N-cyclopropylacetamide (281c) (25 mg, 0.042 mmol, 12% yield) as a white solid; $^1$H NMR (300 MHz, DMSO-$d_6$) δ 9.94 (s, 1H), 8.31 (s, 1H), 8.28-8.22 (m, 1H), 8.03-7.96 (m, 1H), 7.65-7.53 (m, 2H), 7.52-7.36 (m, 4H), 7.25 (t, J=7.9 Hz, 1H), 7.12-7.05 (m, 1H), 5.48 (s, 2H), 4.24 (s, 2H), 3.87 (t, J=7.0 Hz, 2H), 3.20-3.07 (m, 1H), 2.52-2.43 (m, 2H), 2.42 (s, 3H), 2.17-2.01 (m, 2H), 1.07-0.91 (m, 4H); $^{19}$F NMR (282 MHz, DMSO-$d_6$) δ −126.79; MS (ES+): 601.5 (M+1), 623.5 (M+Na); MS (ES−): 599.5 (M−1).

Scheme 282

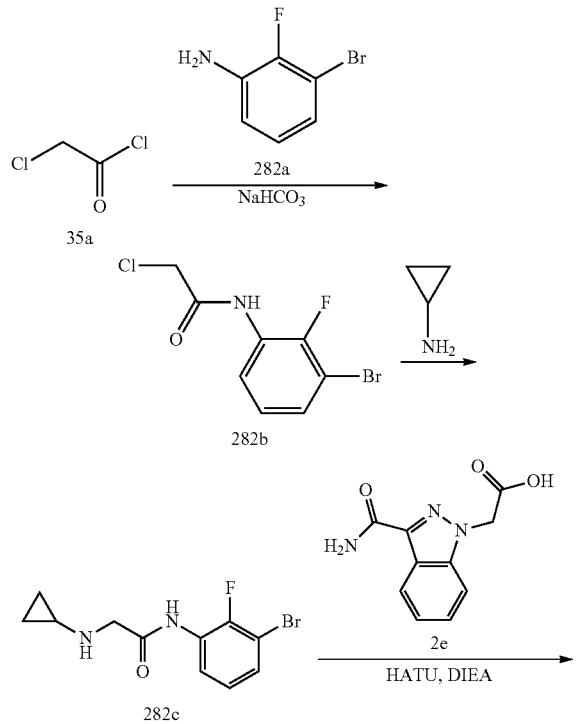

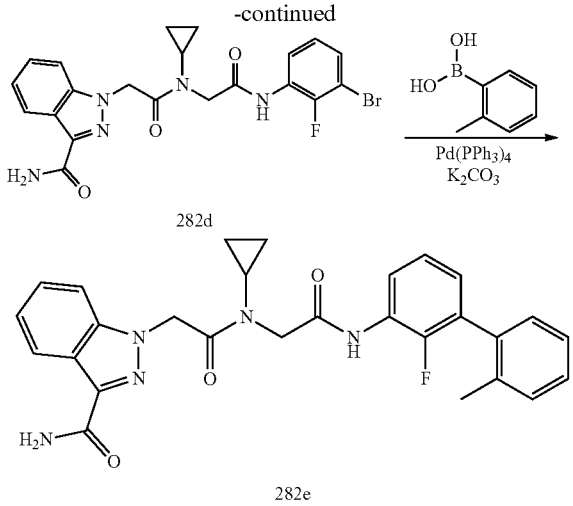

Preparation of 1-(2-(cyclopropyl(2-((2-fluoro-2'-methyl-[1,1'-biphenyl]-3-yl)-amino)-2-oxoethyl)amino)-2-oxoethyl)-1H-indazole-3-carboxamide (282e)

Step-1: Preparation of N-(3-bromo-2-fluorophenyl)-2-chloroacetamide (282b)

To a biphasic solution of 3-bromo-2-fluoroaniline (282a) (5 g, 26.3 mmol) in EtOAc (100 mL), saturated aqueous NaHCO$_3$ (100 mL) was added chloroacetyl chloride (35a) (2.11 mL, 26.3 mmol) and stirred at RT for 2 h. The organic layer was separated washed with brine, dried, filtered and concentrated in vacuum to afford N-(3-bromo-2-fluorophenyl)-2-chloroacetamide (282b) (7 g, 26.3 mmol, 100% yield) as a white solid; $^1$H NMR (300 MHz, DMSO-$d_6$) δ 10.27 (s, 1H), 7.85 (ddd, J=8.5, 7.2, 1.6 Hz, 1H), 7.50 (ddd, J=8.1, 6.4, 1.6 Hz, 1H), 7.16 (td, J=8.1, 1.4 Hz, 1H), 4.37 (s, 2H); MS (ES−): 264.1, 266.1 (M−1).

Step-2: Preparation of N-(3-bromo-2-fluorophenyl)-2-(cyclopropylamino)acetamide (282c)

Compound 282c was prepared from N-(3-bromo-2-fluorophenyl)-2-chloroacetamide (282b) (5.0 g, 18.76 mmol) and cyclopropylamine (3.31 mL, 46.9 mmol) according to the procedure reported in step-1 of Scheme 35. This gave after workup N-(3-bromo-2-fluorophenyl)-2-(cyclopropylamino)acetamide (282c) (5.3 g, 18.46 mmol, 98% yield) as a thick syrup which was used as such without any purification; $^1$H NMR (300 MHz, DMSO-$d_6$) δ 9.87 (bs, 1H), 7.99 (ddd, J=8.2, 7.2, 1.6 Hz, 1H), 7.43 (ddd, J=8.1, 6.5, 1.6 Hz, 1H), 7.14 (td, J=8.2, 1.5 Hz, 1H), 3.35 (s, 2H), 2.18 (m, 1H), 0.43-0.35 (m, 2H), 0.35-0.26 (m, 2H).

Step-3: Preparation of 1-(2-((2-((3-bromo-2-fluorophenyl)amino)-2-oxoethyl)(cyclopropyl)amino)-2-oxoethyl)-1H-indazole-3-carboxamide (282d)

Compound 282d was prepared from 2-(3-carbamoyl-1H-indazol-1-yl)acetic acid (2e) (2.52 g, 11.5 mmol) and N-(3-bromo-2-fluorophenyl)-2-(cyclopropylamino)acetamide (282c) (3 g, 10.45 mmol) according to the procedure reported in step-3 of Scheme 2. This gave after workup 1-(2-((2-((3-bromo-2-fluorophenyl)amino)-2-oxoethyl)(cyclopropyl)amino)-2-oxoethyl)-1H-indazole-3-carboxamide (282d) (4 g, 79% yield) as a white solid which was used as such without further purification; $^1$H NMR (300 MHz, DMSO-d$_6$) δ 10.02 (s, 1H), 8.18 (dt, J=8.2, 1.0 Hz, 1H), 7.89-7.80 (m, 1H), 7.72 (s, 1H), 7.66 (dt, J=8.6, 0.9 Hz, 1H), 7.49-7.35 (m, 3H), 7.30-7.22 (m, 1H), 7.12 (td, J=8.2, 1.4 Hz, 1H), 5.70 (s, 2H), 4.22 (s, 2H), 3.18-3.05 (m, 1H), 1.08-0.99 (m, 2H), 0.99-0.92 (m, 2H); $^{19}$F NMR (282 MHz, DMSO-d$_6$) δ −118.11; MS (ES+) 488.4, 490.4 (M+1), 510.3, 512.3 (M+Na), MS (ES−): 522.3, 524.3 (M+Cl).

Step-4: Preparation of 1-(2-(cyclopropyl(2-((2-fluoro-2′-methyl-[1,1′-biphenyl]-3-yl)-amino)-2-oxoethyl)amino)-2-oxoethyl)-1H-indazole-3-carboxamide (282e)

Compound 282e was prepared from 1-(2-((2-((3-bromo-2-fluorophenyl)amino)-2-oxoethyl)(cyclopropyl)amino)-2-oxoethyl)-1H-indazole-3-carboxamide (282d) (150 mg, 0.31 mmol), and o-tolylboronic acid (50 mg, 0.37 mmol) according to the procedure reported in Scheme 100. This gave after workup and purification by flash column chromatography [silica (12 g), eluting with DMA80 in DCM from 0 to 20%] 1-(2-(cyclopropyl(2-((2-fluoro-2′-methyl-[1,1′-biphenyl]-3-yl)amino)-2-oxoethyl)amino)-2-oxoethyl)-1H-indazole-3-carboxamide (282e) (85 mg, 0.17 mmol, 55% yield) as a white solid; $^1$H NMR (300 MHz, DMSO-d$_6$) δ 9.91 (s, 1H), 8.18 (dt, J=8.1, 1.1 Hz, 1H), 7.91 (t, J=7.3 Hz, 1H), 7.74 (bs, 1H), 7.67 (dt, J=8.6, 1.0 Hz, 1H), 7.48-7.36 (m, 2H), 7.35-7.15 (m, 6H), 7.06-6.99 (m, 1H), 5.71 (s, 2H), 4.23 (s, 2H), 3.19-3.07 (m, 1H), 2.12 (s, 3H), 1.03 (s, 2H), 1.00-0.91 (m, 2H); 19F NMR (282 MHz, DMSO-d$_6$) δ −127.47; MS (ES+) 500.5 (M+1), MS (ES−): 498.5 (M−1), 534.4 (M+Cl).

0.31 mmol), and 2-chlorophenylboronic acid (62 mg, 0.38 mmol) according to the procedure reported in Scheme 100. This gave after workup and purification by flash column chromatography [silica gel (12 g), eluting with DMA80 in DCM 0 to 20%] 1-(2-((2-((2′-chloro-2-fluoro-[1,1′-biphenyl]-3-yl)-amino)-2-oxoethyl)(cyclopropyl)amino)-2-oxoethyl)-1H-indazole-3-carboxamide (283a) (95 mg, 0.18 mmol, 60% yield) as a white solid; $^1$H NMR (300 MHz, DMSO-d$_6$) δ 9.95 (s, 1H), 8.18 (dt, J=8.1, 1.0 Hz, 1H), 8.04-7.91 (m, 1H), 7.74 (s, 1H), 7.70-7.63 (m, 1H), 7.62-7.55 (m, 1H), 7.52-7.34 (m, 5H), 7.30-7.19 (m, 2H), 7.12-7.03 (m, 1H), 5.71 (s, 2H), 4.23 (s, 2H), 3.19-3.06 (m, 1H), 1.07-1.00 (m, 2H), 1.00-0.92 (m, 2H); $^{19}$F NMR (282 MHz, DMSO-d$_6$) δ −126.75; MS (ES+): 520.4 (M+1), 542.4 (M+Na); MS (ES−): 518.4 (M−1).

Scheme 284

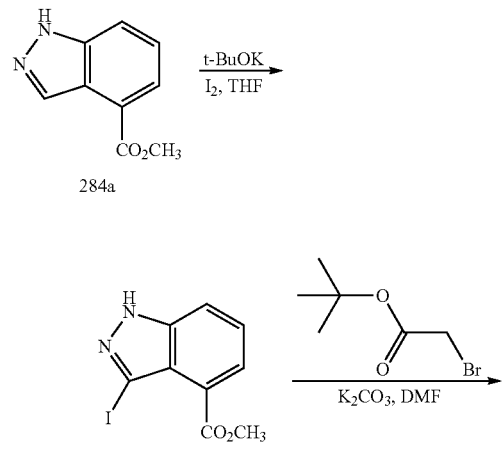

Scheme 283

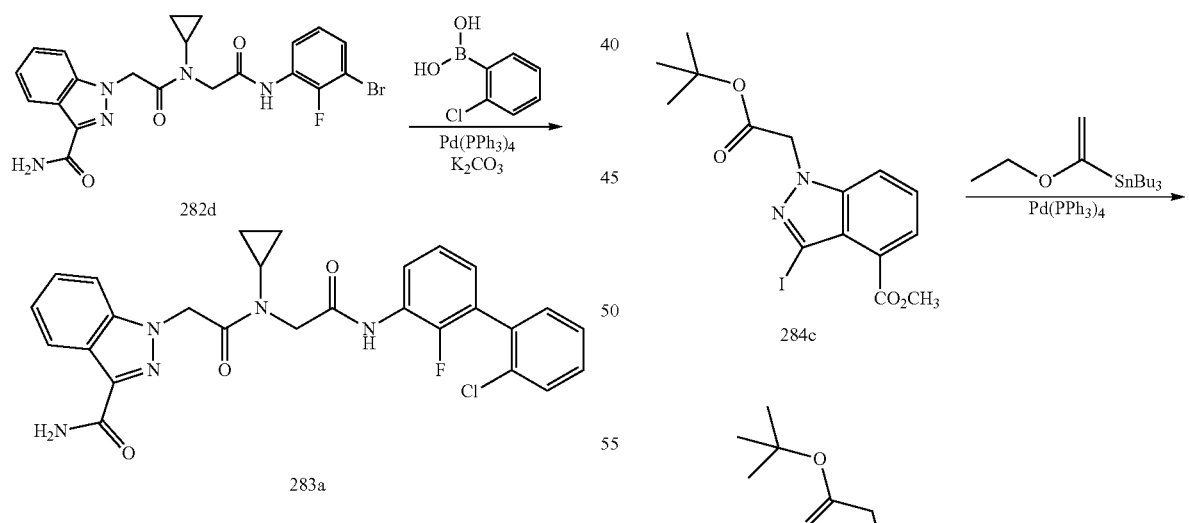

Preparation of 1-(2-((2-((2′-chloro-2-fluoro-[1,1′-biphenyl]-3-yl)-amino)-2-oxoethyl)(cyclopropyl) amino)-2-oxoethyl)-1H-indazole-3-carboxamide (283a)

Compound 283a was prepared from 1-(2-((2-((3-bromo-2-fluorophenyl)amino)-2-oxoethyl)(cyclopropyl)amino)-2-oxoethyl)-1H-indazole-3-carboxamide (282d) (150 mg,

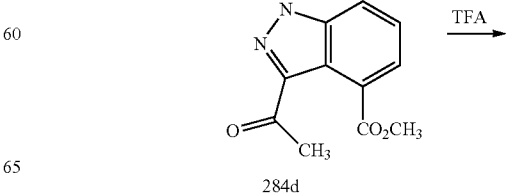

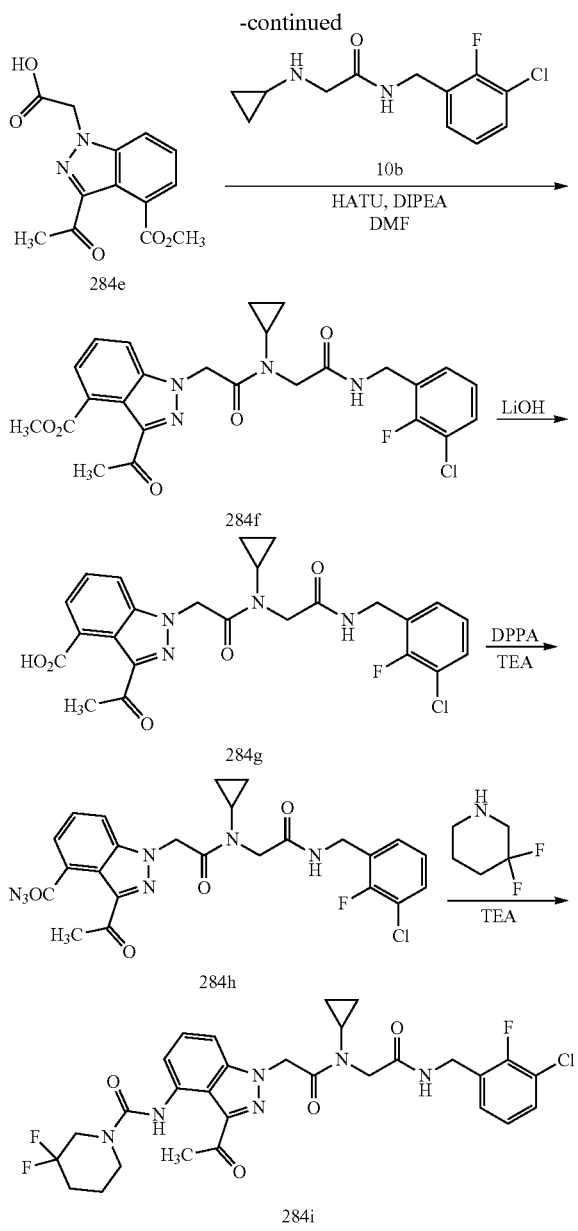

Preparation of N-(3-acetyl-1-(2-((2-((3-chloro-2-fluorobenzyl)amino)-2-oxoethyl)(cyclopropyl)amino)-2-oxoethyl)-1H-indazol-4-yl)-3,3-difluoropiperidine-1-carboxamide (284i)

Step-1: Preparation of methyl 3-iodo-1H-indazole-4-carboxylate (284b)

Compound 284b was prepared from methyl 1H-indazole-4-carboxylate (284a) (5 g, 28.4 mmol) according to the procedure reported in step-1 of Scheme 132. This gave after work up and purification by flash chromatography [silica gel, (40 g) eluting with EtOAc in hexane 0-60%] methyl 3-iodo-1H-indazole-4-carboxylate (284b) (6.6 g, 21.85 mmol, 77% yield) as an off white solid. $^1$H NMR (300 MHz, DMSO-$d_6$) δ 13.89 (s, 1H), 7.87-7.74 (m, 1H), 7.53-7.44 (m, 2H), 4.00 (s, 3H); MS (ES+) 303.2 (M+1); (ES−) 301.2 (M−1).

Step-2: Preparation methyl 1-(2-(tert-butoxy)-2-oxoethyl)-3-iodo-1H-indazole-4-carboxylate (284c)

Compound 284c was prepared from methyl 3-iodo-1H-indazole-4-carboxylate (132b) (6.6 g, 21.85 mmol) and tert-butyl 2-bromoacetate (6.39 g, 32.8 mmol) according to the procedure reported in step-1 of Scheme 56. This gave after workup and trituration of solid with methanol (5 mL) methyl 1-(2-tert-butoxy-2-oxoethyl)-3-iodo-1H-indazole-4-carboxylate (284c) (6.6 g, 15.86 mmol, 73% yield) as a white solid; $^1$H NMR (300 MHz, DMSO-$d_6$) δ 7.92 (dd, J=7.9, 1.5 Hz, 1H), 7.64-7.43 (m, 2H), 5.38 (s, 2H), 3.95 (s, 3H), 1.41 (s, 9H); MS (ES+) 417.4 (M+1), 439.3 (M+Na).

Step-3: Preparation of methyl 3-acetyl-1-(2-(tert-butoxy)-2-oxoethyl)-1H-indazole-4-carboxylate (284d)

Compound 284d was prepared from methyl 1-(2-(tert-butoxy)-2-oxoethyl)-3-iodo-1H-indazole-4-carboxylate (284c) (2.05 g, 4.91 mmol) according to the procedure reported in step-1 and step-2 of Scheme 206. This gave after work up and purification by flash chromatography [silica gel, (40 g) eluting with EtOAc in hexane 0-50%] methyl 3-acetyl-1-(2-(tert-butoxy)-2-oxoethyl)-1H-indazole-4-carboxylate (284d) (1.44 g, 4.33 mmol, 88% yield) as a yellow solid; $^1$H NMR (300 MHz, DMSO-$d_6$) δ 7.94 (dd, J=8.4, 0.9 Hz, 1H), 7.62-7.54 (m, 1H), 7.49 (dd, J=7.1, 0.9 Hz, 1H), 5.50 (s, 2H), 3.83 (s, 3H), 2.62 (s, 3H), 1.42 (s, 9H); MS (ES+) 333.3 (M+1); 355.3 (M+Na); (ES−) 331.3 (M−1).

Step-4: Preparation of 2-(3-acetyl-4-(methoxycarbonyl)-1H-indazol-1-yl)acetic acid (284e)

Compound 284e was prepared from methyl 3-acetyl-1-(2-(tert-butoxy)-2-oxoethyl)-1H-indazole-4-carboxylate (284d) (1.44 g, 4.33 mmol) and TFA (2.0 mL, 26.0 mmol), according to the procedure reported in step-2 of Scheme 2. This gave after work up 2-(3-acetyl-4-(methoxycarbonyl)-1H-indazol-1-yl)acetic acid (284e) (1.11 g, 4.02 mmol, 93% yield) as a brown solid, which was used as such in the next step without further purification. MS (ES+) 277.3 (M+1).

Step-5: Preparation of methyl 3-acetyl-1-(2-((2-((3-chloro-2-fluorobenzyl)amino)-2-oxoethyl)(cyclopropyl)amino)-2-oxoethyl)-1H-indazole-4-carboxylate (284f)

Compound 284f was prepared from 2-(3-acetyl-4-(methoxycarbonyl)-1H-indazol-1-yl)acetic acid (284e) (788 mg, 2.85 mmol) and N-(3-chloro-2-fluorobenzyl)-2-(cyclopropylamino)acetamide (10b) (769 mg, 3.00 mmol) according to the procedure reported in step-3 of Scheme 2. This gave after workup and purification by flash column [silica (12 g), eluting with DMA80 in DCM 0 to 30%] methyl 3-acetyl-1-(2-((2-((3-chloro-2-fluorobenzyl)amino)-2-oxoethyl)(cyclopropyl)amino)-2-oxoethyl)-1H-indazole-4-carboxylate (284f) (950 mg, 1.85 mmol, 65% yield) as a yellow solid. MS (ES−) 513.5 (M−1).

Step-6: Preparation of 3-acetyl-1-(2-((2-((3-chloro-2-fluorobenzyl)amino)-2-oxoethyl)(cyclopropyl)amino)-2-oxoethyl)-1H-indazole-4-carboxylic acid (284 g)

Compound 284g was prepared from methyl 3-acetyl-1-(2-((2-((3-chloro-2-fluorobenzyl)amino)-2-oxoethyl)(cyclopropyl)amino)-2-oxoethyl)-1H-indazole-4-carboxylate (284f) (850 mg, 1.651 mmol) and lithium hydroxide monohydride (416 mg, 9.90 mmol) in water (10 mL) according to the procedure reported in step-2 of Scheme 129. This gave after work up 3-acetyl-1-(2-((2-((3-chloro-2-fluorobenzyl)amino)-2-oxoethyl)(cyclopropyl)amino)-2-oxoethyl)-1H-indazole-4-carboxylic acid (284 g) (827 mg, 1.65 mmol, 100% yield) as a white solid, which was used as such in the next step without further purification. $^1$H NMR (300 MHz, DMSO-$d_6$) δ 8.48 (t, J=5.8 Hz, 1H), 7.86-7.78 (m, 1H), 7.53-7.41 (m, 3H), 7.27-7.18 (m, 1H), 7.10 (td, J=7.8, 1.0 Hz, 1H), 5.78 (s, 2H), 4.34 (d, J=5.7 Hz, 2H), 3.99 (s, 2H), 3.19-3.03 (m, 1H), 2.60 (s, 3H), 1.12-0.99 (m, 2H), 0.98-0.83 (m, 2H); $^{19}$F NMR (282 MHz, DMSO-$d_6$) δ −74.96 (TFA peak), −121.61; MS (ES+): 501.4 (M+1), (ES−): 499.3 (M−1).

Step-7: Preparation of 3-acetyl-1-(2-((2-((3-chloro-2-fluorobenzyl)amino)-2-oxoethyl)(cyclopropyl)amino)-2-oxoethyl)-1H-indazole-4-carbonyl azide (284 h)

Compound 284h was prepared from 3-acetyl-1-(2-((2-((3-chloro-2-fluorobenzyl)amino)-2-oxoethyl)(cyclopropyl)amino)-2-oxoethyl)-1H-indazole-4-carboxylic acid (284 g) (320 mg, 0.639 mmol) according to the procedure reported in step-3 of Scheme 129. This gave after work up 3-acetyl-1-(2-((2-((3-chloro-2-fluorobenzyl)amino)-2-oxoethyl)(cyclopropyl)amino)-2-oxoethyl)-1H-indazole-4-carbonyl azide (284 h) (300 mg, 0.57 mmol, 89% yield) which was used as such in the next step without further purification; MS (ES−): 560.3 (M+Cl).

Step-8: Preparation of N-(3-acetyl-1-(2-((2-((3-chloro-2-fluorobenzyl)amino)-2-oxoethyl)(cyclopropyl)amino)-2-oxoethyl)-1H-indazol-4-yl)-3,3-difluoropiperidine-1-carboxamide (284i)

Compound 284i was prepared from 3-acetyl-1-(2-((2-((3-chloro-2-fluorobenzyl)amino)-2-oxoethyl)(cyclopropyl)amino)-2-oxoethyl)-1H-indazole-4-carbonyl azide (284 h) (150 mg, 0.285 mmol) and 3,3-difluoropiperidine hydrochloride (90 mg, 0.57 mmol) using TEA (0.16 mL, 1.14 mmol) as base according to the procedure reported in step-4 of Scheme 129 to afford after workup and purification by column chromatography [First column: silica gel (12 g), eluting with DMA80 in DCM 0 to 40%, second column: silica gel (12 g), eluting with ethyl acetate/methanol (9:1) in hexanes 0 to 100%] N-(3-acetyl-1-(2-((2-((3-chloro-2-fluorobenzyl)amino)-2-oxoethyl)(cyclopropyl)amino)-2-oxoethyl)-1H-indazol-4-yl)-3,3-difluoropiperidine-1-carboxamide (284i) (20 mg, 0.032 mmol, 11.33% yield) as a white solid; $^1$H NMR (300 MHz, DMSO-$d_6$) δ 10.84 (s, 1H), 8.48 (t, J=5.8 Hz, 1H), 8.14-8.02 (m, 1H), 7.50-7.43 (m, 1H), 7.37 (t, J=8.1 Hz, 1H), 7.28-7.17 (m, 2H), 7.15-7.05 (m, 1H), 5.74 (s, 2H), 4.34 (d, J=5.7 Hz, 2H), 3.99 (s, 2H), 3.91 (t, J=12.0 Hz, 2H), 3.72-3.56 (m, 2H), 3.19-3.07 (m, 1H), 2.74 (s, 3H), 2.20-2.02 (m, 2H), 1.86-1.75 (m, 2H), 1.09-0.96 (m, 2H), 0.96-0.82 (m, 2H); $^{19}$F NMR (282 MHz, DMSO) δ −101.19; −121.60; MS (ES+): 641.5 (M+Na); (ES−): 617.4 (M−1).

Scheme 285

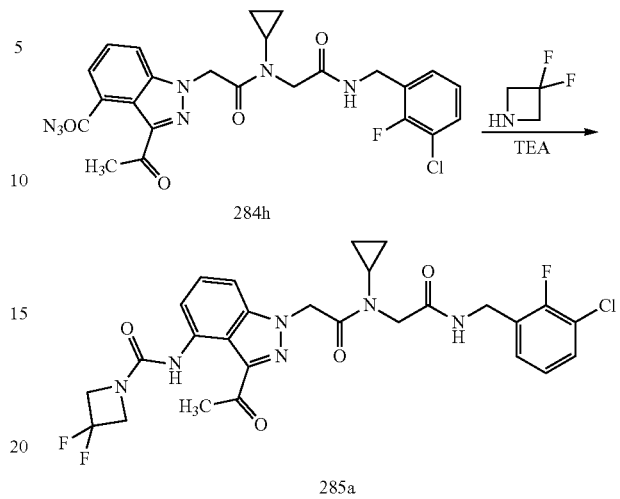

Preparation of N-(3-acetyl-1-(2-((2-((3-chloro-2-fluorobenzyl)amino)-2-oxoethyl)(cyclopropyl)amino)-2-oxoethyl)-1H-indazol-4-yl)-3,3-difluoroazetidine-1-carboxamide (285a)

Compound 285a was prepared from 3-acetyl-1-(2-((2-((3-chloro-2-fluorobenzyl)amino)-2-oxoethyl)(cyclopropyl)amino)-2-oxoethyl)-1H-indazole-4-carbonyl azide (284 h) (150 mg, 0.285 mmol) and 3,3-difluoroazetidine hydrochloride (73.9 mg, 0.570 mmol) using TEA (0.16 mL, 1.14 mmol) as base according to the procedure reported in step-4 of Scheme 129 to afford after workup and purification twice by column chromatography [silica gel (12 g), eluting with DMA80 in DCM 0 to 40%] N-(3-acetyl-1-(2-((2-((3-chloro-2-fluorobenzyl)amino)-2-oxoethyl)(cyclopropyl)amino)-2-oxoethyl)-1H-indazol-4-yl)-3,3-difluoroazetidine-1-carboxamide (285a) (25 mg, 0.042 mmol, 15% yield) as a yellow solid; $^1$H NMR (300 MHz, DMSO-$d_6$) δ 10.92 (s, 1H), 8.48 (t, J=5.8 Hz, 1H), 8.11 (d, J=7.7 Hz, 1H), 7.52-7.43 (m, 1H), 7.43-7.33 (m, 1H), 7.31-7.18 (m, 2H), 7.16-7.03 (m, 1H), 5.73 (s, 2H), 4.54 (t, J=12.6 Hz, 4H), 4.34 (d, J=5.7 Hz, 2H), 3.99 (s, 2H), 3.19-3.06 (m, 1H), 2.73 (s, 3H), 1.09-0.97 (m, 2H), 0.97-0.84 (m, 2H); $^{19}$F NMR (282 MHz, DMSO) δ −99.58; −121.59; MS (ES+): 591.5 (M+1); MS (ES−): 589.4 (M−1); 625.5 (M+Cl).

Scheme 286

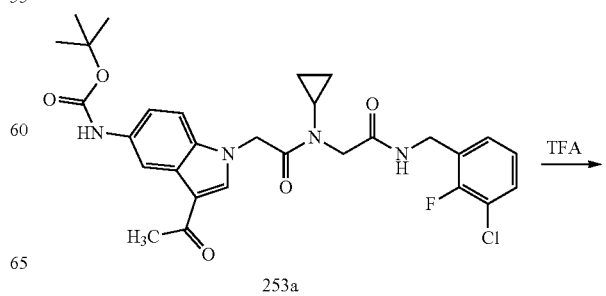

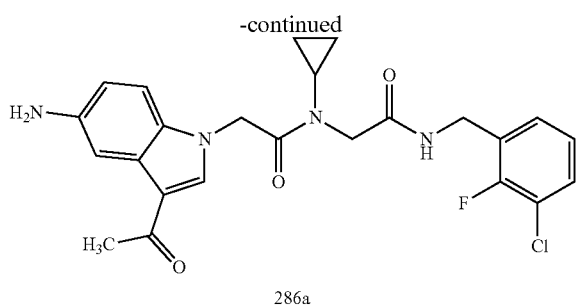

286a

Preparation of 2-(3-acetyl-5-amino-1H-indol-1-yl)-N-(2-((3-chloro-2-fluorobenzyl)amino)-2-oxoethyl)-N-cyclopropylacetamide (286a)

Compound 286a was prepared from tert-butyl (3-acetyl-1-(2-((2-((3-chloro-2-fluorobenzyl)amino)-2-oxoethyl)(cyclopropyl)amino)-2-oxoethyl)-1H-indol-5-yl)carbamate (253a) (20 mg, 0.035 mmol) and 2,2,2-trifluoroacetic acid (0.16 mL, 2.1 mmol) according to the procedure reported in step-2 of Scheme 2. This gave after workup and purification by flash column chromatography [silica gel (4 g), eluting with dichloromethane/DMA 80 (1:0 to 3:1)] 2-(3-acetyl-5-amino-1H-indol-1-yl)-N-(2-((3-chloro-2-fluorobenzyl)amino)-2-oxoethyl)-N-cyclopropylacetamide (286a) (12 mg, 73%) as a white solid; $^1$H NMR (300 MHz, DMSO-$d_6$) δ 8.46 (t, J=5.9 Hz, 1H), 8.03 (s, 1H), 7.50-7.43 (m, 1H), 7.40 (d, J=2.1 Hz, 1H), 7.27-7.20 (m, 1H), 7.16-7.07 (m, 2H), 6.54 (dd, J=8.7, 2.2 Hz, 1H), 5.29 (s, 2H), 4.81 (s, 2H), 4.34 (d, J=5.7 Hz, 2H), 3.98 (s, 2H), 3.15-2.96 (m, 1H), 2.35 (s, 3H), 1.04-0.79 (m, 4H); $^{19}$F NMR (282 MHz, DMSO-$d_6$) δ −121.63; MS (ES+): 471.4 (M+1); MS (ES−): 505.3 & 507.2 (M+Cl).

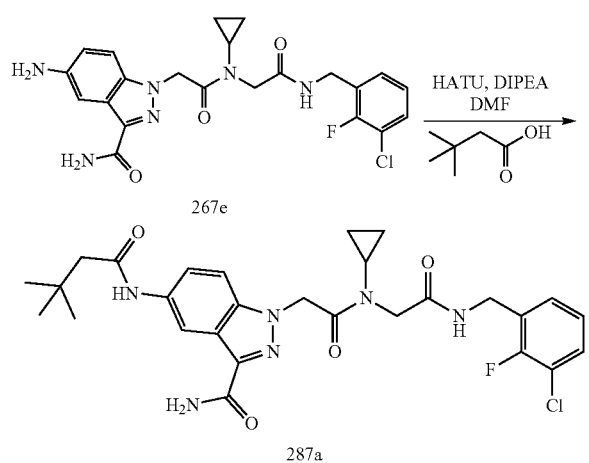

Scheme 287

Preparation of 1-(2-((2-((3-chloro-2-fluorobenzyl)amino)-2-oxoethyl)(cyclopropyl)amino)-2-oxoethyl)-5-(3,3-dimethylbutanamido)-1H-indazole-3-carboxamide (287a)

Compound 287a was prepared from 5-amino-1-(2-((2-((3-chloro-2-fluorobenzyl)amino)-2-oxoethyl)(cyclopropyl)amino)-2-oxoethyl)-1H-indazole-3-carboxamide (267e) (50 mg, 0.11 mmol) and 3,3-dimethylbutanoic acid (0.016 mL, 0.12 mmol) according to the procedure reported in step-3 of Scheme 2. This gave after workup and purification by flash column chromatography [silica gel (4 g), eluting with dichloromethane/methanol (1:0 to 19:1)] 1-(2-((2-((3-chloro-2-fluorobenzyl)amino)-2-oxoethyl)(cyclopropyl)amino)-2-oxoethyl)-5-(3,3-dimethylbutanamido)-1H-indazole-3-carboxamide (287a) (50 mg, 83%). $^1$H NMR (300 MHz, DMSO-$d_6$) δ 9.91 (s, 1H), 8.50 (t, J=5.8 Hz, 1H), 8.45-8.44 (m, 1H), 7.66 (s, 1H), 7.64-7.53 (m, 2H), 7.45 (td, J=7.6, 1.7 Hz, 1H), 7.35 (s, 1H), 7.23 (td, J=7.2, 6.7, 1.7 Hz, 1H), 7.11 (td, J=7.8, 1.0 Hz, 1H), 5.62 (s, 2H), 4.33 (d, J=5.7 Hz, 2H), 3.98 (s, 2H), 3.13-2.97 (m, 1H), 2.20 (s, 2H), 1.04 (s, 9H), 1.02-0.85 (m, 4H); $^{19}$F NMR (282 MHz, DMSO-$d_6$) δ −121.59; MS (ES+): 571.5 (M+1); 593.5 & 595.5 (M+Na).

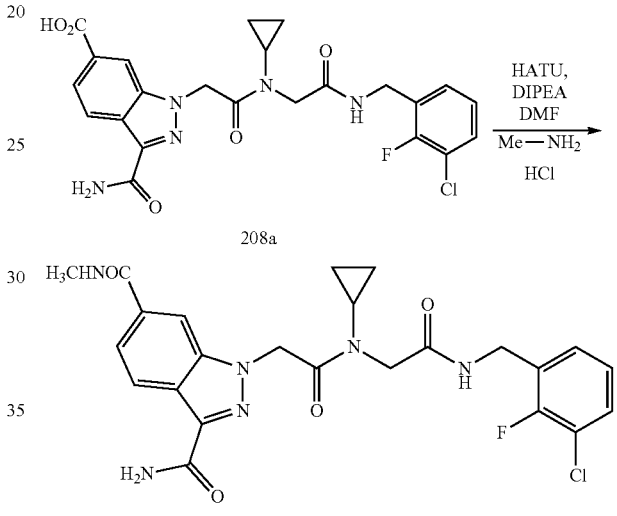

Scheme 288

Preparation of 1-(2-((2-((3-chloro-2-fluorobenzyl)amino)-2-oxoethyl)(cyclopropyl)amino)-2-oxoethyl)-N6-methyl-1H-indazole-3,6-dicarboxamide (288a)

Compound 288a was prepared from 3-carbamoyl-1-(2-((2-((3-chloro-2-fluorobenzyl)amino)-2-oxoethyl)(cyclopropyl)amino)-2-oxoethyl)-1H-indazole-6-carboxylic acid (208a) (50 mg, 0.1 mmol) and methanamine hydrochloride (10 mg, 0.15 mmol) according to the procedure reported in step-3 of Scheme 2. This gave after workup and purification by flash column chromatography [silica gel (4 g), eluting with dichloromethane/methanol (1:0 to 19:1)] 1-(2-((2-((3-chloro-2-fluorobenzyl)amino)-2-oxoethyl)(cyclopropyl)amino)-2-oxoethyl)-N6-methyl-1H-indazole-3,6-dicarboxamide (288a) (12 mg, 23%) as a white solid; $^1$H NMR (300 MHz, DMSO-$d_6$) δ 8.56 (t, J=5.7 Hz, 1H), 8.50 (d, J=4.6 Hz, 1H), 8.20 (dd, J=8.5, 0.8 Hz, 1H), 8.14-8.12 (m, 1H), 7.80 (s, 1H), 7.70 (dd, J=8.6, 1.3 Hz, 1H), 7.49-7.38 (m, 2H), 7.25-7.17 (m, 1H), 7.10-7.04 (m, 1H), 5.73 (s, 2H), 4.33 (d, J=5.7 Hz, 2H), 4.00 (s, 2H), 3.18-3.03 (m, 1H), 2.80 (d, J=4.5 Hz, 3H), 1.09-0.78 (m, 4H); $^{19}$F NMR (282 MHz, DMSO-$d_6$) δ −121.62; MS (ES−): 549.3 & 551.5 (M+Cl).

Scheme 289

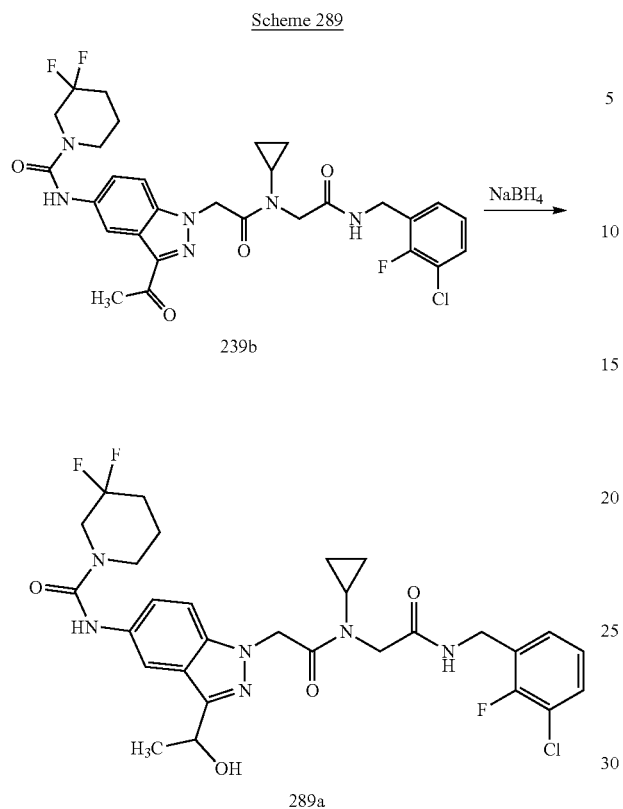

Preparation of N-(1-(2-((2-((3-chloro-2-fluorobenzyl)amino)-2-oxoethyl)(cyclopropyl)amino)-2-oxoethyl)-3-(1-hydroxy ethyl)-1H-indazol-5-yl)-3,3-difluoropiperidine-1-carboxamide (289a)

To a suspension of N-(3-acetyl-1-(2-((2-(3-chloro-2-fluorobenzylamino)-2-oxoethyl)(cyclopropyl)amino)-2-oxoethyl)-1H-indazol-5-yl)-3,3-difluoropiperidine-1-carboxamide (239b) (50 mg, 0.08 mmol) in MeOH (10 mL) was added sodium borohydride (12 mg, 0.32 mmol) and stirred for 1 h at room temperature. The mixture was extracted with ethyl acetate (3×30 mL), the organic layer were combined, dried, filtered and concentrated in vacuum. The residue obtained was purified by flash column chromatography [silica (12 g), eluting with DMA80 in DCM from 0 to 40%] to afford N-(1-(2-((2-((3-chloro-2-fluorobenzyl)amino)-2-oxoethyl)(cyclopropyl)amino)-2-oxoethyl)-3-(1-hydroxyethyl)-1H-indazol-5-yl)-3,3-difluoropiperidine-1-carboxamide (289a) (30 mg, 0.048 mmol, 60% yield) as a white solid; $^1$H NMR (300 MHz, DMSO-$d_6$) δ 8.64 (s, 1H), 8.45 (t, J=5.9 Hz, 1H), 7.95-7.85 (m, 1H), 7.54-7.42 (m, 1H), 7.42-7.32 (m, 2H), 7.28-7.19 (m, 1H), 7.18-7.08 (m, 1H), 5.46 (s, 2H), 5.33 (d, J=4.0 Hz, 1H), 5.10-4.96 (m, 1H), 4.34 (d, J=5.7 Hz, 2H), 3.97 (s, 2H), 3.81 (t, J=12.1 Hz, 2H), 3.52 (t, J=5.3 Hz, 2H), 3.12-2.97 (m, 1H), 2.17-1.94 (m, 2H), 1.79-1.63 (m, 2H), 1.52 (d, J=6.5 Hz, 3H), 1.04-0.93 (m, 2H), 0.93-0.83 (m, 2H); $^{19}$F NMR (282 MHz, DMSO-$d_6$) δ −101.13, −121.65; MS (ES+): 643.5 (M+Na); (ES−): 619.5 (M−1).

Scheme 290

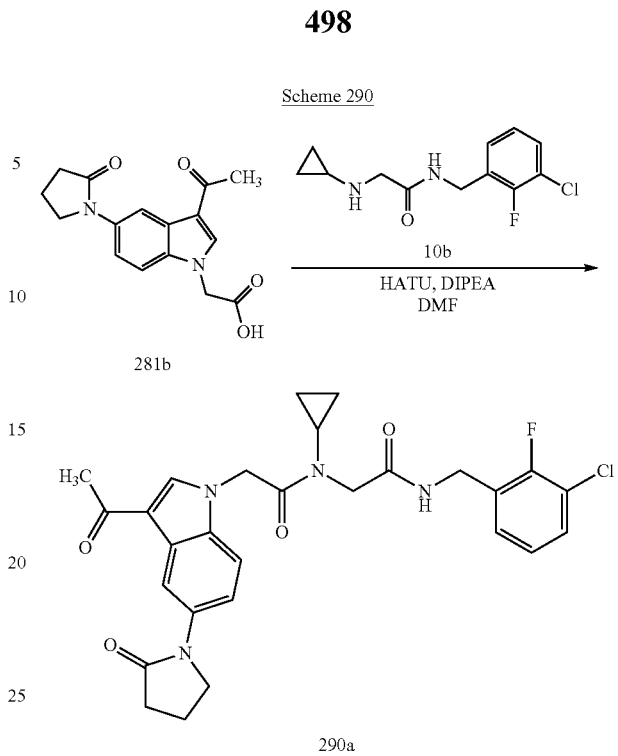

Preparation of 2-(3-acetyl-5-(2-oxopyrrolidin-1-yl)-1H-indol-1-yl)-N-(2-((3-chloro-2-fluorobenzyl)amino)-2-oxoethyl)-N-cyclopropylacetamide (290a)

Compound 290a was prepared from 2-(3-acetyl-5-(2-oxopyrrolidin-1-yl)-1H-indol-1-yl)acetic acid (281b) (138 mg, 0.33 mmol) and N-(3-chloro-2-fluorobenzyl)-2-(cyclopropylamino)acetamide (10b) (128 mg, 0.5 mmol) according to the procedure reported in step-3 of Scheme 2. This gave after workup and purification by flash column chromatography [silica gel (24 g), eluting with ethyl acetate/methanol (9:1) in hexanes 0-100%]] 2-(3-acetyl-5-(2-oxopyrrolidin-1-yl)-1H-indol-1-yl)-N-(2-((3-chloro-2-fluorobenzyl)amino)-2-oxoethyl)-N-cyclopropylacetamide (290a) (26 mg, 0.05 mmol, 14% yield) as an off-white solid; $^1$H NMR (300 MHz, DMSO-$d_6$) δ 8.47 (t, J=5.8 Hz, 1H), 8.29 (s, 1H), 8.25 (d, J=2.1 Hz, 1H), 7.54 (dd, J=8.9, 2.1 Hz, 1H), 7.50-7.39 (m, 2H), 7.28-7.18 (m, 1H), 7.15-7.04 (m, 1H), 5.43 (s, 2H), 4.35 (d, J=5.7 Hz, 2H), 3.99 (s, 2H), 3.87 (t, J=7.0 Hz, 2H), 3.17-3.00 (m, 1H), 2.54-2.46 (m, 2H), 2.42 (s, 3H), 2.09 (p, J=7.6 Hz, 2H), 1.02-0.85 (m, 4H); $^{19}$F NMR (282 MHz, DMSO-$d_6$) δ −121.63; MS (ES+): 539.5 (M+1), 561.5 (M+Na); MS (ES−): 537.4 (M−1); 573.4 (M+Cl).

Scheme 291

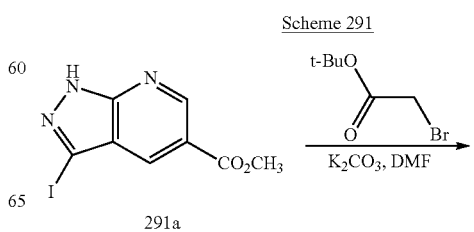

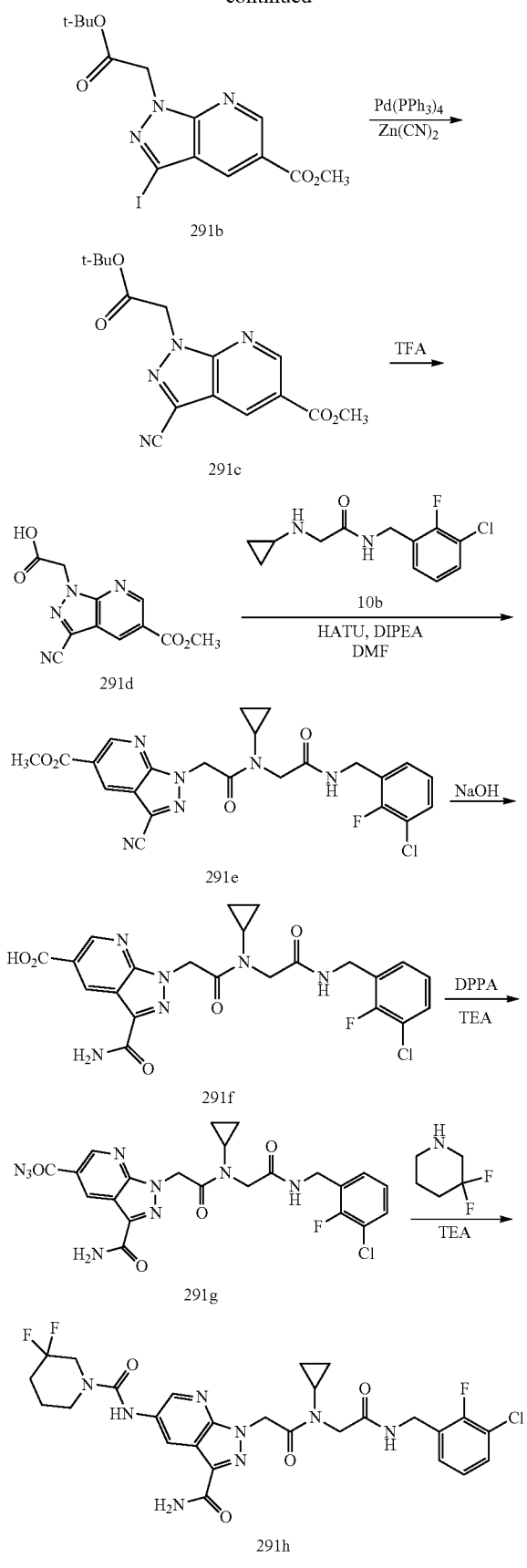

Preparation of 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-pyrazolo[3,4-b]pyridine-3-carboxamide (291 h)

Step-1: Preparation of methyl 1-(2-(tert-butoxy)-2-oxoethyl)-3-iodo-1H-pyrazolo[3,4-b]pyridine-5-carboxylate (291b)

Compound 291b was prepared from methyl 3-iodo-1H-pyrazolo[3,4-b]pyridine-5-carboxylate (291a) (950 mg, 3.13 mmol) according to the procedure reported in step-1 of Scheme 56. This gave after workup and purification by flash column chromatography [silica (24 g), eluting with hexanes/EtOAc (1:0 to 2:1)] methyl 1-(2-(tert-butoxy)-2-oxoethyl)-3-iodo-1H-pyrazolo[3,4-b]pyridine-5-carboxylate (291b) (595 mg, 46% yield) as a white solid; $^1$H NMR (300 MHz, DMSO-$d_6$) δ 9.11 (d, J=2.0 Hz, 1H), 8.42 (d, J=2.0 Hz, 1H), 5.32 (s, 2H), 3.93 (s, 3H), 1.40 (s, 9H); MS (ES+); 440.3 (M+Na).

Step-2: Preparation of methyl 1-(2-(tert-butoxy)-2-oxoethyl)-3-cyano-1H-pyrazolo[3,4-b]pyridine-5-carboxylate (291c)

Compound 291c was prepared from methyl 1-(2-(tert-butoxy)-2-oxoethyl)-3-iodo-1H-pyrazolo[3,4-b]pyridine-5-carboxylate (291b) (341 mg, 0.82 mmol) according to the procedure reported in step-3 of Scheme 207. This gave after workup and purification by flash column chromatography [silica (24 g), eluting with hexanes/EtOAc (1:0 to 3:1)] methyl 1-(2-(tert-butoxy)-2-oxoethyl)-3-cyano-1H-pyrazolo[3,4-b]pyridine-5-carboxylate (291c) (188 mg, 73% yield) as a yellow solid; $^1$H NMR (300 MHz, DMSO-$d_6$) δ 9.23 (d, J=1.9 Hz, 1H), 9.01 (d, J=1.9 Hz, 1H), 5.52 (s, 2H), 3.95 (s, 3H), 1.40 (s, 9H); MS (ES+): 339.3 (M+Na).

Step-3: Preparation of 2-(3-cyano-5-(methoxycarbonyl)-1H-pyrazolo[3,4-b] pyridin-1-yl)acetic acid (291d)

Compound 291d was prepared from methyl 1-(2-(tert-butoxy)-2-oxoethyl)-3-cyano-1H-pyrazolo[3,4-b]pyridine-5-carboxylate (291c) (293 mg, 0.93 mmol), according to the procedure reported in step-2 of Scheme 2. This gave after workup 2-(3-cyano-5-(methoxycarbonyl)-1H-pyrazolo[3,4-b]pyridin-1-yl)acetic acid (291d) as a brown gum which was used as such without further purification.

Step-4: Preparation of methyl 1-(2-((2-((3-chloro-2-fluorobenzyl)amino)-2-oxoethyl)(cyclopropyl)amino)-2-oxoethyl)-3-cyano-1H-pyrazolo[3,4-b]pyridine-5-carboxylate (291e)

Compound 291e was prepared from 2-(3-cyano-5-(methoxycarbonyl)-1H-pyrazolo[3,4-b]pyridin-1-yl)acetic acid (291d) (241 mg, 0.93 mmol) and N-(3-chloro-2-fluorobenzyl)-2-(cyclopropylamino)acetamide (10b) (285 mg, 1.11 mmol) according to the procedure reported in step-3 of Scheme 2. This gave after workup and purification by flash column [silica (24 g), eluting with hexanes/10% methanol in ethyl acetate (1:0 to 1:1)] methyl 1-(2-((2-((3-chloro-2-fluorobenzyl)amino)-2-oxoethyl)(cyclopropyl)amino)-2-oxoethyl)-3-cyano-1H-pyrazolo[3,4-b]pyridine-5-carboxylate (291e) (338 mg, 73% yield) as a brown gum; $^1$H NMR (300 MHz, DMSO-$d_6$) δ 9.20 (d, J=1.9 Hz, 1H), 9.01 (d, J=1.9 Hz, 1H), 8.48 (t, J=5.8 Hz, 1H), 7.51-7.40 (m, 1H), 7.29-7.06 (m, 2H), 5.86 (s, 2H), 4.32 (d, J=5.8 Hz, 2H), 3.97 (s, 2H), 3.96 (s, 3H), 3.15-3.05 (m, 1H), 1.04-0.86 (m, 4H); $^{19}$F NMR (282 MHz, DMSO-d$_6$) δ −121.57; MS (ES+): 499.4 (M+1).

Step-5: Preparation of 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carboxylic acid (291f)

Compound 291f was prepared from methyl 1-(2-((2-((3-chloro-2-fluorobenzyl)amino)-2-oxoethyl)(cyclopropyl)amino)-2-oxoethyl)-3-cyano-1H-pyrazolo[3,4-b]pyridine-5-carboxylate (291e) (326 mg, 0.65 mmol) according to the procedure reported in step-4 of Scheme 43. This gave after workup 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carboxylic acid (291f) (200 mg, 61% yield) as a white solid; $^1$H NMR (300 MHz, DMSO-d$_6$) δ 9.09 (d, J=2.0 Hz, 1H), 9.06 (d, J=2.0 Hz, 1H), 8.51 (t, J=5.8 Hz, 1H), 8.05 (s, 1H), 7.68 (s, 1H), 7.49-7.42 (m, 1H), 7.26-7.18 (m, 1H), 7.12 (td, J=7.8, 1.0 Hz, 1H), 5.73 (s, 2H), 4.31 (d, J=5.5 Hz, 2H), 3.98 (s, 2H), 3.16-2.98 (m, 1H), 1.03-0.85 (m, 4H); $^{19}$F NMR (282 MHz, DMSO-d$_6$) δ −121.56; MS (ES+): 503.4 (M+1); 525.4 and 527.4 (M+Na).

Step-6: Preparation of 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carbonyl azide (291 g)

Compound 291g was prepared from 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carboxylic acid (291f) (100 mg, 0.2 mmol) according to the procedure reported in step-3 of Scheme 129. This gave after work up 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carbonyl azide (291 g) which was used as such without further purification.

Step-7: Preparation of 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-pyrazolo[3,4-b] pyridine-3-carboxamide (291 h)

Compound 291h was prepared from 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carbonyl azide (291 g) (105 mg, 0.2 mmol) and 3,3-difluoropiperidine hydrochloride (63 mg, 0.4 mmol) using TEA (0.11 mL, 0.8 mmol) as base according to the procedure reported in step-4 of Scheme 129 to afford after workup and purification by column chromatography [silica gel (8 g), eluting with DCM in methanol (1:0 to 9:1)] 1-(2-((2-((3-chloro-2-fluorobenzyl)amino)-2-oxoethyl)(cyclopropyl)amino)-2-oxoethyl)-5-(3,3-difluoropiperidine-1-carboxamido)-1H-pyrazolo[3,4-b]pyridine-3-carboxamide (291 h) (15 mg, 12% yield for two steps) as a white solid; $^1$H NMR (300 MHz, DMSO-d$_6$) δ 8.99 (s, 1H), 8.67 (d, J=2.4 Hz, 1H), 8.59 (d, J=2.4 Hz, 1H), 8.51 (t, J=5.8 Hz, 1H), 7.83 (s, 1H), 7.53-7.41 (m, 2H), 7.28-7.17 (m, 1H), 7.16-7.08 (m, 1H), 5.65 (s, 2H), 4.32 (d, J=5.7 Hz, 2H), 3.98 (s, 2H), 3.84 (t, J=12.1 Hz, 2H), 3.60-3.52 (m, 2H), 3.13-3.00 (m, 1H), 2.19-1.93 (m, 2H), 1.81-1.61 (m, 2H), 1.04-0.75 (m, 4H); $^{19}$F NMR (282 MHz, DMSO-d$_6$) δ −101.19, −121.59; MS (ES+): 643.5 (M+Na); (ES−): 655.5 and 657.5 (M+Cl).

Scheme 292

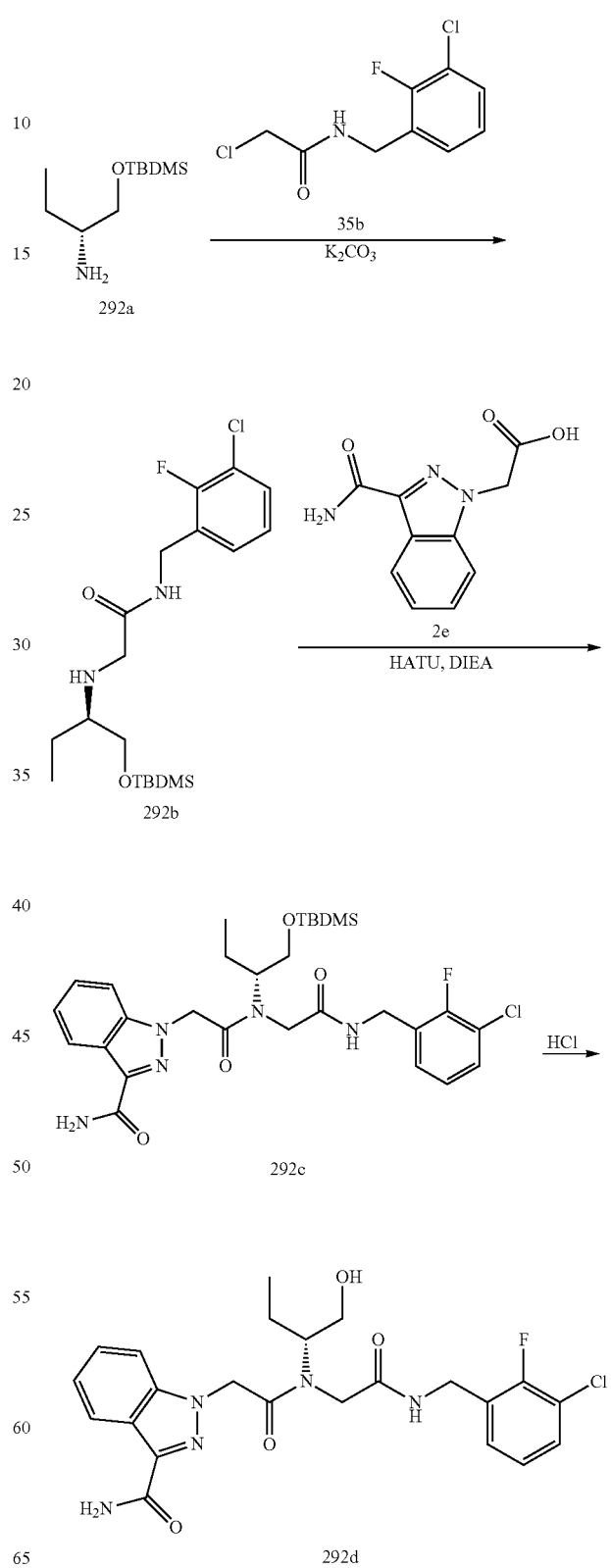

Preparation of (R)-1-(2-((2-((3-chloro-2-fluorobenzyl)amino)-2-oxoethyl)(1-hydroxybutan-2-yl)amino)-2-oxoethyl)-1H-indazole-3-carboxamide (292d)

Step-1: Preparation of (R)-2-((1-(((tert-butyldimethylsilyl)oxy)butan-2-yl)-amino)-N-(3-chloro-2-fluorobenzyl)acetamide (292b)

Compound 292b was prepared according to the procedure reported in step-2 of Scheme 35 from 2-chloro-N-(3-chloro-2-fluorobenzyl)acetamide (35b) (300 mg, 1.27 mmol) and (R)-1-((tert-butyldimethylsilyl)oxy)butan-2-amine (292a) (284 mg, 1.4 mmol, prepared according to the procedure reported by Gant, Thomas G. and Sarshar, Sepehr; in PCT Int. Appl., 2009032843). This gave gave after workup (R)-2-((1-((tert-butyldimethylsilyl)oxy)butan-2-yl)amino)-N-(3-chloro-2-fluorobenzyl)acetamide (292b) as a colorless oil which was used as such in the next step; MS (ES+): 403.4 (M+1); MS (ES−): 401.4 (M−1), 437.4 (M+Cl).

Step-2: Preparation of (R)-1-(2-((1-((tert-butyldimethylsilyl)oxy)butan-2-yl)(2-((3-chloro-2-fluorobenzyl)amino)-2-oxoethyl)amino)-2-oxoethyl)-1H-indazole-3-carboxamide (292c)

Compound 292c was prepared from (R)-2-((1-(((tert-butyldimethylsilyl)oxy)butan-2-yl)amino)-N-(3-chloro-2-fluorobenzyl)acetamide (292b) (300 mg, 0.74 mmol) with 2-(3-carbamoyl-1H-indazol-1-yl)acetic acid (2e) (163 mg, 0.74 mmol) according to the procedure reported in step-3 of Scheme 2. This gave after workup and purification by flash column chromatography [silica (24 g), eluting with methanol in DCM from 0-20%] (R)-1-(2-((1-(((tert-butyldimethylsilyl)oxy)butan-2-yl)(2-((3-chloro-2-fluorobenzyl)amino)-2-oxoethyl)amino)-2-oxoethyl)-1H-indazole-3-carboxamide (292c) (171 mg, 38% yield) as a white solid; MS (ES+): 604.5 (M+1); 626.5 (M+Na); MS (ES−): 602.5 (M−1).

Step-3: Preparation of (R)-1-(2-((2-((3-chloro-2-fluorobenzyl)amino)-2-oxoethyl)(1-hydroxybutan-2-yl)amino)-2-oxoethyl)-1H-indazole-3-carboxamide (292d)

To a stirred solution of (R)-1-(2-((1-(((tert-butyldimethylsilyl)oxy)butan-2-yl)(2-((3-chloro-2-fluorobenzyl)amino)-2-oxoethyl)amino)-2-oxoethyl)-1H-indazole-3-carboxamide (292c) (162 mg, 0.27 mmol) in MTBE (10 mL) was added at room temperature conc. HCl (0.223 mL, 2.68 mmol) and stirred for 1 h. The reaction was concentrated in vacuum to dryness basified with saturated aqueous NaHCO$_3$ and extracted with ethyl acetate (2×50 mL). The organic layers were combined dried, filtered and evaporated to dryness. The residue obtained was purified by flash column chromatography [First column, silica gel, (12 g) eluting with ethyl acetate/methanol (9:1) in hexanes from 0-100%; second column, Silica gel, (12 g) eluting with methanol in DCM from 0-10%)) to afford (R)-1-(2-((2-((3-chloro-2-fluorobenzyl)amino)-2-oxoethyl)(1-hydroxybutan-2-yl)amino)-2-oxoethyl)-1H-indazole-3-carboxamide (292d) (18 mg, 0.04 mmol, 14% yield) as a white solid; $^1$H NMR (300 MHz, DMSO-d$_6$) δ 8.92 (t, J=5.7 Hz) & 8.72 (t, J=5.9 Hz) (2t, 1H), 8.26-8.13 (m, 1H), 7.77 & 7.72 (2s, 1H), 7.56-6.93 (m, 7H), 5.71-3.89 (m) (6H), 4.24 and 3.86 (2s, 2H), 3.65-3.33 (m, 2H), 1.58-1.40 (m, 2H), 0.96 (t, J=7.3 Hz) & 0.75 (t, J=7.3 Hz) (2t, 3H); $^{19}$F NMR (282 MHz, DMSO-d$_6$) δ −121.27, −121.59; MS (ES+): 490.4, 492.4 (M+1); MS (ES−): 488.4, 490.3 (M−1), 524.4, 526.4 (M+Cl).

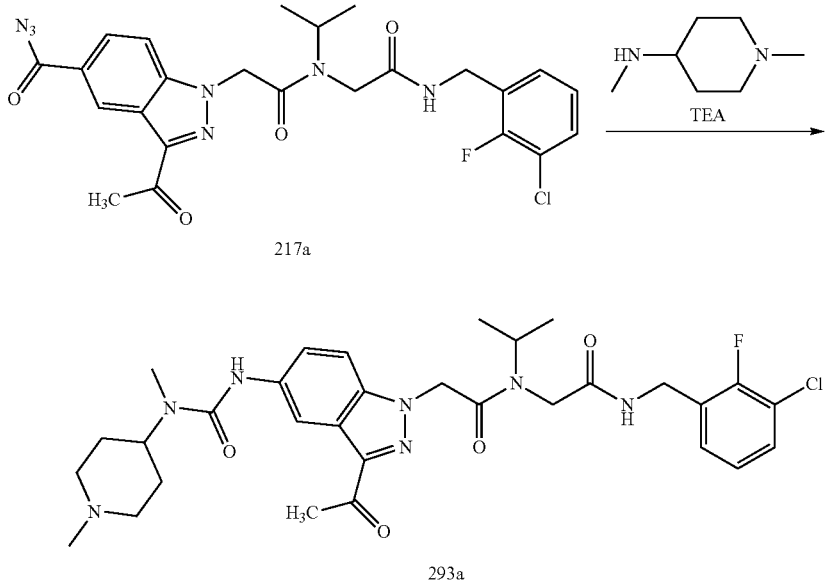

Scheme 293

Preparation of 2-(3-acetyl-5-(3-methyl-3-(1-methylpiperidin-4-yl)ureido)-1H-indazol-1-yl)-N-(2-((3-chloro-2-fluorobenzyl)amino)-2-oxoethyl)-N-isopropylacetamide (293a)

Compound 293a was prepared from 3-acetyl-1-(2-((2-((3-chloro-2-fluorobenzyl)amino)-2-oxoethyl)(isopropyl)amino)-2-oxoethyl)-1H-indazole-5-carbonyl azide (217a) (500 mg, 0.95 mmol) and N,1-dimethylpiperidin-4-amine (243 mg, 1.9 mmol), using TEA (0.26 mL, 1.9 mmol) as base according to the procedure reported in step-4 of Scheme 129. This gave after workup, purification by flash column chromatography [silica gel (12 g), eluting with DMA80 in DCM 0 to 40%] 2-(3-acetyl-5-(3-methyl-3-(1-methylpiperidin-4-yl)ureido)-1H-indazol-1-yl)-N-(2-((3-chloro-2-fluorobenzyl)amino)-2-oxoethyl)-N-isopropylacetamide (293a) (38 mg, 7% yield) white solid; $^1$H NMR (300 MHz, DMSO-$d_6$) δ 8.83 (t, J=5.7 Hz) and 8.35 (t, J=5.8 Hz) (2t, 1H), 8.44 (s, 1H), 8.26-8.20 (m, 1H), 7.64-7.55 (m, 1H), 7.54-7.00 (m, 4H), 5.63 and 5.47 (2s, 2H), 4.62-4.52 and 4.28-4.24 (2m, 1H), 4.47 (d, J=5.6 Hz) and 4.32 (d, J=5.9 Hz) (2d, 2H), 4.17 and 3.85 (2s, 2H), 4.13-3.96 (m, 1H), 2.59 (s, 3H), 2.17 (s, 3H), 2.87-2.79 and 2.01-1.90 and 1.80-1.64 and 1.56-1.46 (4m, 11H), 1.24 (d, J=6.3 Hz) and 1.00 (d, J=6.8 Hz) (2d, 6H); $^{19}$F NMR (282 MHz, DMSO-$d_6$) δ −121.22, −121.78; MS (ES+) 628.7 (M+1); (ES−) 626.6 (M−1).

propyl)amino)-2-oxoethyl)-1H-indazole-5-carbonyl azide (235a) (750 mg, 0.71 mmol) and (5)-tert-butyl piperidin-3-ylcarbamate (285 mg, 1.423 mmol), using TEA (0.2 mL, 1.4 mmol) as base according to the procedure reported in step-4 of Scheme 129. This gave after workup, purification by flash column chromatography [silica gel (12 g), eluting with DMA80 in DCM 0 to 40%] followed by preparative HPLC [$C_{18}$ column, eluting with $CH_3CN$ in water 0-100%] (S)-tert-butyl (1-((3-carbamoyl-1-(2-((2-((3-chloro-2-fluorobenzyl)amino)-2-oxoethyl)(cyclopropyl)amino)-2-oxoethyl)-1H-indazol-5-yl)carbamoyl)piperidin-3-yl)carbamate (294a) (86 mg, 17% yield) as a white solid; $^1$H NMR (300 MHz, DMSO-$d_6$) δ 8.65 (s, 1H), 8.50 (t, J=5.8 Hz, 1H), 8.20-8.14 (m, 1H), 7.63 (s, 1H), 7.59-7.42 (m, 3H), 7.31 (s, 1H), 7.28-7.19 (m, 1H), 7.19-7.07 (m, 1H), 6.97-6.85 (m,

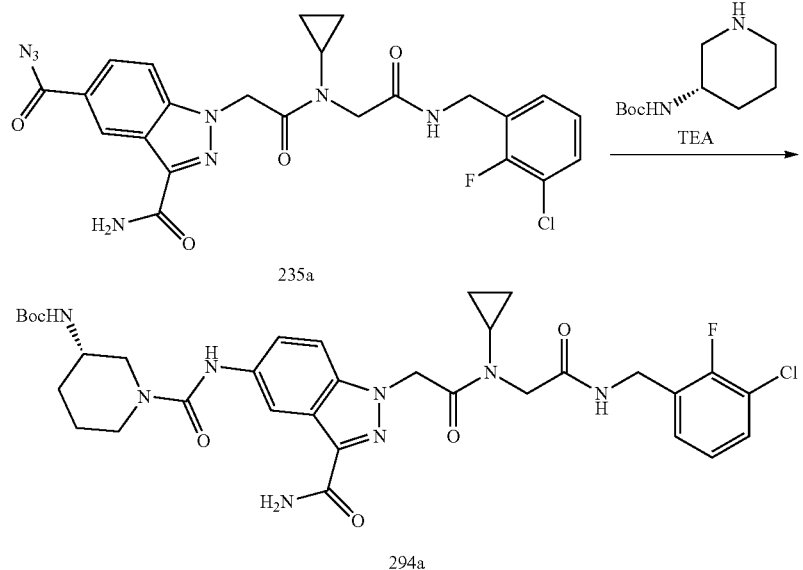

Scheme 294

235a

294a

Preparation of (5)-tert-butyl (1-((3-carbamoyl-1-(2-((2-((3-chloro-2-fluorobenzyl)amino)-2-oxoethyl)(cyclopropyl)amino)-2-oxoethyl)-1H-indazol-5-yl)carbamoyl)piperidin-3-yl)carbamate (294a)

Compound 294a was prepared from 3-carbamoyl-1-(2-((2-((3-chloro-2-fluorobenzyl)amino)-2-oxoethyl)(cyclo- 1H), 5.61 (s, 2H), 4.33 (d, J=5.7 Hz, 2H), 4.08-3.86 (m, 4H), 3.44-3.24 (m, 3H), 3.11-2.99 (m, 1H), 2.86-2.59 (m, 2H), 1.90-1.77 (m, 1H), 1.77-1.64 (m, 1H), 1.38 (s, 9H), 1.04-0.96 (m, 2H), 0.96-0.83 (m, 2H); $^{19}$F NMR (282 MHz, DMSO-$d_6$) δ −73.73 (TFA peak), −121.62; MS (ES+) 699.7 (M+1); (ES−) 697.7 (M−1).

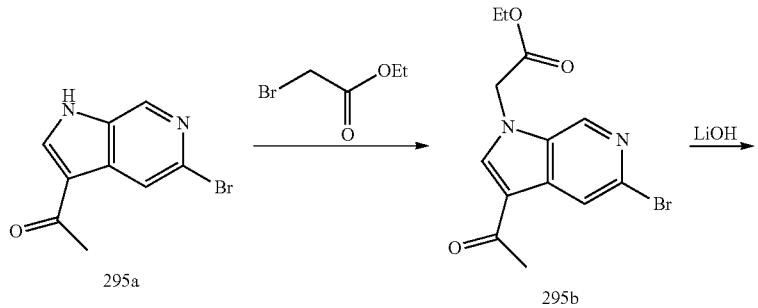

Scheme 295

295a

295b

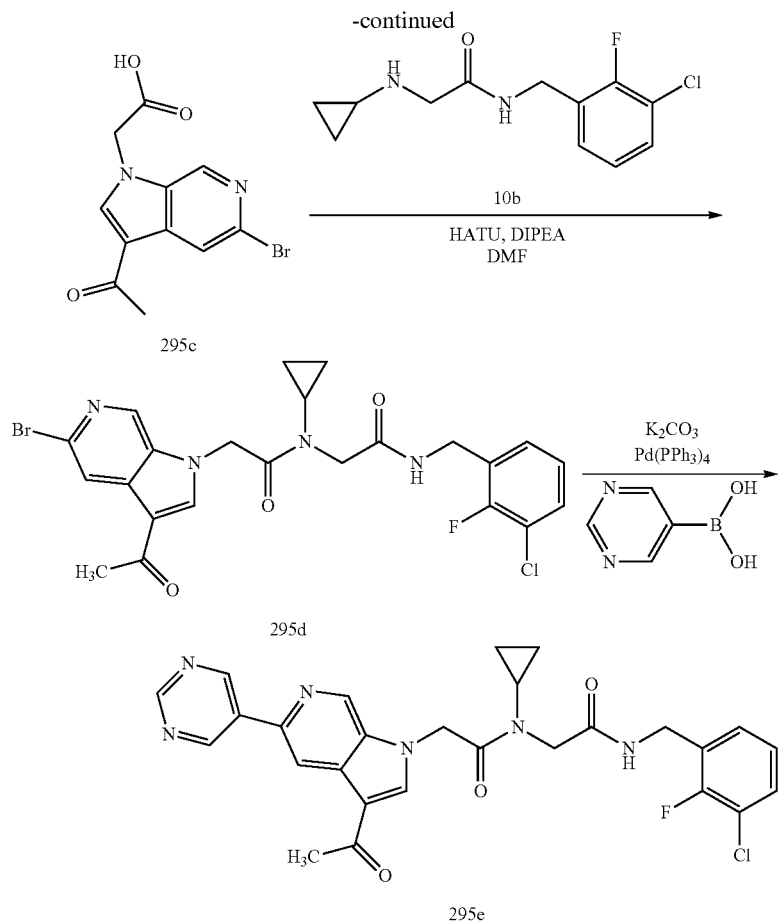

Preparation of 2-(3-acetyl-5-(pyrimidin-5-yl)-1H-pyrrolo[2,3-c] pyridin-1-yl)-N-(2-((3-chloro-2-fluorobenzyl)amino)-2-oxoethyl)-N-cyclopropylacetamide (295e)

Step-1: Preparation of ethyl 2-(3-acetyl-5-bromo-1H-pyrrolo[2,3-c]pyridin-1-yl)acetate (295b)

Compound 295b was prepared according to the procedure reported in step-1 of Scheme 56 from 1-(5-bromo-1H-pyrrolo[2,3-c]pyridin-3-yl)ethanone (295a) (1.2 g, 5.02 mmol, prepared according to procedure reported by Hynd, George et al: in PCT Int. Appl., 2014174021). This gave after workup and purification by flash column chromatography [silica (24 g), eluting with DMA80 in DCM 0 to 30%] ethyl 2-(3-acetyl-5-bromo-1H-pyrrolo[2,3-c]pyridin-1-yl) acetate (295b) (850 mg, 52% yield) as a light orange solid; $^1$H NMR (300 MHz, DMSO-$d_6$) δ 8.79 (d, J=1.0 Hz, 1H), 8.58 (s, 1H), 8.18 (d, J=0.9 Hz, 1H), 5.36 (s, 2H), 4.19 (q, J=7.1 Hz, 2H), 2.46 (s, 3H), 1.23 (t, J=7.1 Hz, 3H); MS (ES+) 325.3, 327.3 (M+1), 347.3, 349.3 (M+Na): MS (ES−): 359.2, 361.2 (M+Cl).

Step-2: Preparation of 2-(3-acetyl-5-bromo-1H-pyrrolo[2,3-c]pyridin-1-yl)acetic acid (295c)

Compound 295c was prepared from ethyl 2-(3-acetyl-5-bromo-1H-pyrrolo[2,3-c]pyridin-1-yl)acetate (295b) (500 mg, 1.54 mmol) according to the procedure reported in step-2 of Scheme 129. This gave after workup 2-(3-acetyl-5-bromo-1H-pyrrolo[2,3-c]pyridin-1-yl)acetic acid (295c) (260 mg, 0.88 mmol, 57% yield) as a light orange solid; $^1$H NMR (300 MHz, DMSO-$d_6$) δ 13.42 (s, 1H), 8.79 (d, J=0.9 Hz, 1H), 8.59 (s, 1H), 8.18 (d, J=0.9 Hz, 1H), 5.25 (s, 2H), 2.46 (s, 3H); MS (ES−): 295.1, 297.1 (M−1).

Step-3: Preparation of 2-(3-acetyl-5-bromo-1H-pyrrolo[2,3-c]pyridin-1-yl)-N-(2-((3-chloro-2-fluorobenzyl)amino)-2-oxoethyl)-N-cyclopropylacetamide (295d)

Compound 295d was prepared from 2-(3-acetyl-5-bromo-1H-pyrrolo[2,3-c]pyridin-1-yl)acetic acid (295c) (250 mg, 0.84 mmol) with N-(3-chloro-2-fluorobenzyl)-2-(cyclopropylamino)acetamide (10b) (259 mg, 1.01 mmol) according to the procedure reported in step-3 of Scheme 2. This gave after workup and purification by flash column [silica gel (12 g), eluting with DMA80-DCM 0 to 20%] 2-(3-acetyl-5-bromo-1H-pyrrolo[2,3-c]pyridin-1-yl)-N-(2-((3-chloro-2-fluorobenzyl)amino)-2-oxoethyl)-N-cyclopropylacetamide (295d) (70 mg, 15% yield) as a white solid; $^1$H NMR (300 MHz, DMSO-$d_6$) δ 8.68 (s, 1H), 8.53 (s, 1H), 8.47 (t, J=6.0 Hz, 1H), 8.18 (d, J=0.9 Hz, 1H), 7.52-7.41 (m, 1H), 7.27-7.18 (m, 1H), 7.14-7.04 (m, 1H), 5.57 (s, 2H), 4.34 (d, J=5.8 Hz, 2H), 3.99 (s, 2H), 3.14-3.03 (m, 1H), 2.46 (s, 3H), 1.05-0.94 (m, 2H), 0.95-0.86 (m, 2H); 19F NMR (282 MHz, DMSO-$d_6$) δ −121.59; MS (ES+) 535.4, 537.4 (M+1); MS (ES−): 569.3, 571.3 (M+Cl).

Step-4: Preparation of Preparation of 2-(3-acetyl-5-(pyrimidin-5-yl)-1H-pyrrolo[2,3-c]pyridin-1-yl)-N-(2-((3-chloro-2-fluorobenzyl)amino)-2-oxoethyl)-N-cyclopropylacetamide (295e)

Compound 295e was prepared according from to 2-(3-acetyl-5-bromo-1H-pyrrolo[2,3-c] pyridin-1-yl-N-(2-fluorobenzyl)amino)-2-oxoethyl)-N-cyclopropylacetamide (295d) (65 mg, 0.12 mmol) according to the procedure reported in Scheme 92. This gave after workup and purification by flash column [silica gel (12 g), eluting with DMA80-DCM 0 to 20%] 2-(3-acetyl-5-(pyrimidin-5-yl)-1H-pyrrolo[2,3-c]pyridin-1-yl)-N-(2-(3-chloro-2-fluorobenzylamino)-2-oxoethyl)-N-cyclopropylacetamide (295e) (55 mg, 0.1 mmol, 85% yield) as a white solid; $^1$H NMR (300 MHz, DMSO-$d_6$) 9.41 (s, 2H), 9.21 (s, 1H), 9.00 (d, J=1.1 Hz, 1H), 8.64 (d, J=1.1 Hz, 1H), 8.54 (s, 1H), 8.49 (t, J=5.8 Hz, 1H), 7.43 (td, J=7.7, 7.2, 1.7 Hz, 1H), 7.28-7.19 (m, 1H), 7.14-7.02 (m, 1H), 5.64 (s, 2H), 4.35 (d, J=5.7 Hz, 2H), 4.02 (s, 2H), 3.18-3.06 (m, 1H), 2.52 (s, 3H), 1.08-0.98 (m, 2H), 0.98-0.88 (m, 2H); 19F NMR (282 MHz, DMSO-$d_6$) δ −121.59; MS (ES+): 535.5 (M+1), MS (ES−): 569.4 (M+Cl).

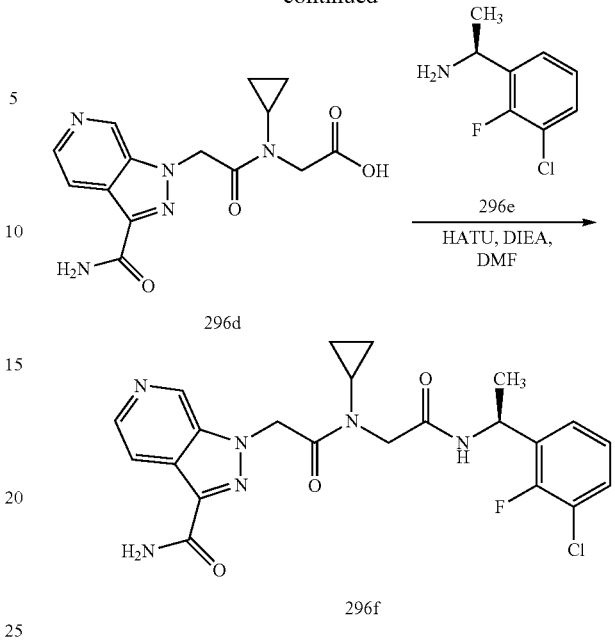

Scheme 296

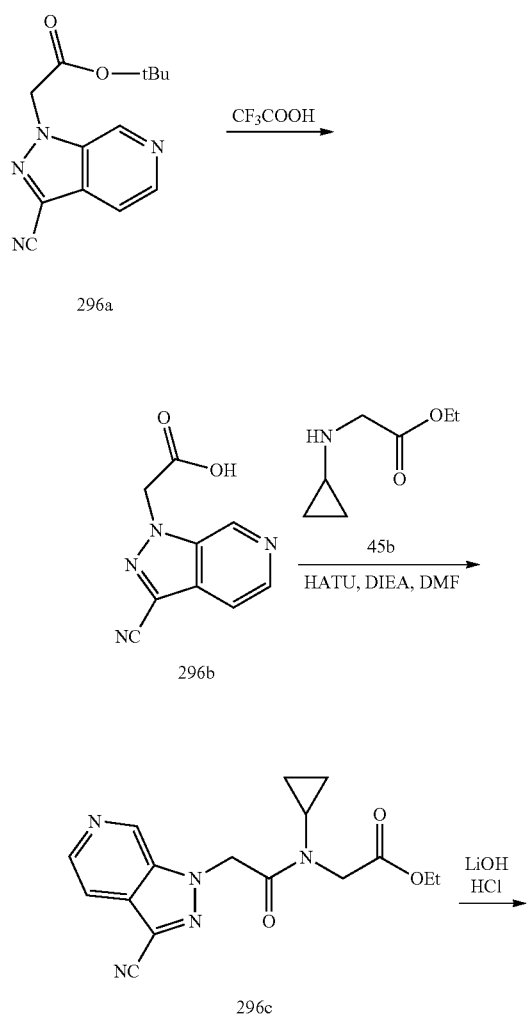

Preparation of (S)-1-(2-((2-(((1-(3-chloro-2-fluorophenyl)ethyl)amino)-2-oxoethyl)(cyclopropyl)amino)-2-oxoethyl)-1H-pyrazolo[3,4-c]pyridine-3-carboxamide (296f)

Step-1: Preparation of 2-(3-cyano-1H-pyrazolo[3,4-c]pyridin-1-yl)acetic acid (296b)

Compound 296b was prepared from tert-butyl 2-(3-cyano-1H-pyrazolo[3,4-c]pyridin-1-yl)acetate (296a) (995 mg, 3.85 mmol, prepared according to the procedure reported by Altmann, Eva et al; in PCT Int. Appl., 2014002058, 3 Jan. 2014) using TFA (2.5 mL, 2.66 mmol) in CH$_2$Cl$_2$ (30 mL) according to the procedure reported in step-2 of Scheme 2. This gave after workup 2-(3-cyano-1H-pyrazolo[3,4-c]pyridin-1-yl)acetic acid (296b) (1.78 g) as a brown gum which was used as such for next step.

Step-2: Preparation of ethyl 2-(2-(3-cyano-1H-pyrazolo[3,4-c]pyridin-1-yl)-N-cyclopropylacetamido)acetate (296c)

Reaction of 2-(3-cyano-1H-pyrazolo[3,4-c]pyridin-1-yl) acetic acid (296b) (389 mg, 1.93 mmol) with ethyl 2-(cyclopropylamino)acetate (45b) (413 mg, 2.89 mmol) according to the procedure reported in step-3 of Scheme 2 gave after workup and purification by flash column chromatography [silica gel, eluting with dichloromethane/methanol (1:0 to 19:1)] ethyl 2-(2-(3-cyano-1H-pyrazolo[3,4-c]pyridin-1-yl)-N-cyclopropylacetamido)acetate (296c) (317 mg, 50%) as a brown gum; $^1$H NMR (300 MHz, DMSO-$d_6$) δ 9.31 (s, 1H), 8.49 (d, J=5.8 Hz, 1H), 7.96 (d, J=5.7 Hz, 1H), 6.00 (s, 2H), 4.18-3.99 (m, 4H), 3.20-3.03 (m, 1H), 1.18 (t, J=7.2 Hz, 3H), 0.98 (dd, J=27.3, 5.5 Hz, 4H); MS (ES+): 350.2 (M+Na).

Step-3: Preparation of 2-(2-(3-carbamoyl-1H-pyrazolo[3,4-c]pyridin-1-yl)-N-cyclopropylacetamido)acetic acid (296d)

To a solution of ethyl 2-(2-(3-cyano-1H-pyrazolo[3,4-c]pyridin-1-yl)-N-cyclopropylacetamido)acetate (296c) (308 mg, 0.941 mmol) in THF (20 mL) and MeOH (20.00 mL) was added a solution of lithium hydroxide hydrate (242 mg, 5.65 mmol) in water (20 mL) and stirred at RT for 15 h. The reaction mixture was concentrated to remove THF and methanol. The residue was treated with water (15 mL) and acidified carefully with 4 N HCl followed by concentration to dryness to give 2-(2-(3-carbamoyl-1H-pyrazolo[3,4-c]pyridin-1-yl)-N-cyclopropylacetamido)acetic acid (296d) (660 mg) as a brown gum which was used as such for next step; MS (ES−): 316.2 (M−1).

Step-4: Preparation of (S)-1-(2-((2-(((1-(3-chloro-2-fluorophenyl)ethyl)amino)-2-oxoethyl)(cyclopropyl)amino)-2-oxoethyl)-1H-pyrazolo[3,4-c]pyridine-3-carboxamide (296f)

Reaction of 2-(2-(3-carbamoyl-1H-pyrazolo[3,4-c]pyridin-1-yl)-N-cyclopropylacetamido)acetic acid (296d) (102 mg, 0.32 mmol) with (S)-1-(3-chloro-2-fluorophenyl)ethanamine hydrochloride (296e) (70.8 mg, 0.320 mmol) according to the procedure reported in step-3 of Scheme 2 gave after workup and purification by flash column chromatography [silica gel, eluting with dichloromethane/methanol (1:0 to 9:1)] (S)-1-(2-((2-(((1-(3-chloro-2-fluorophenyl)ethyl)amino)-2-oxoethyl)(cyclopropyl)amino)-2-oxoethyl)-1H-pyrazolo[3,4-c]pyridine-3-carboxamide (296f) (24 mg, 16% for two steps) as a yellow solid; $^1$H NMR (300 MHz, DMSO-$d_6$) δ 9.15 (s, 1H), 8.59 (d, J=7.4 Hz, 1H), 8.35 (d, J=5.5 Hz, 1H), 8.05 (d, J=5.7 Hz, 1H), 7.95 (s, 1H), 7.54 (s, 1H), 7.44 (t, J=7.5 Hz, 1H), 7.28 (t, J=7.3 Hz, 1H), 7.14 (t, J=7.9 Hz, 1H), 5.79 (s, 2H), 5.15-4.96 (m, 1H), 3.99 (s, 2H), 3.08-2.94 (m, 1H), 1.33 (d, J=7.0 Hz, 3H), 1.04-0.82 (m, 4H); $^{19}$F NMR (282 MHz, DMSO-$d_6$) δ −122.71; MS (ES+): 495.1 & 497.1 (M+Na); MS (ES−): 471.2 (M−1) & 507.1 (M+Cl).

Scheme 297

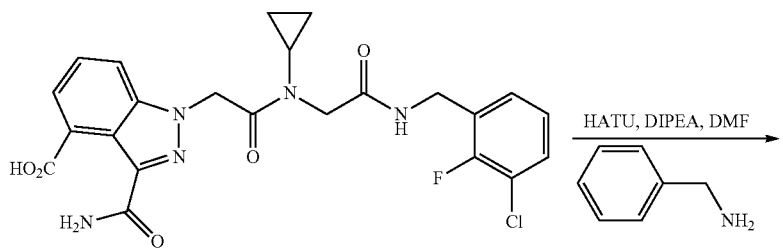

284g

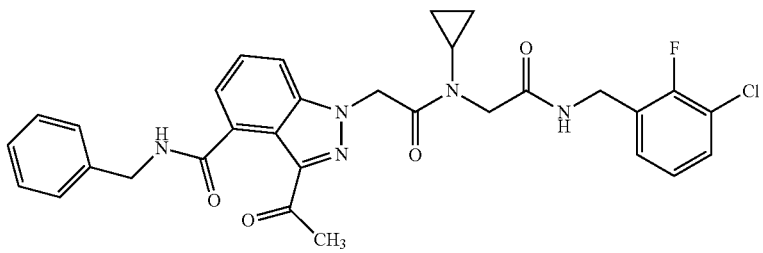

297a

Preparation of 3-acetyl-N-benzyl-1-(2-((2-(3-chloro-2-fluorobenzylamino)-2-oxoethyl)(cyclopropyl)amino)-2-oxoethyl)-1H-indazole-4-carboxamide (297a)

Reaction of 3-acetyl-1-(2-((2-(3-chloro-2-fluorobenzylamino)-2-oxoethyl)(cyclopropyl)amino)-2-oxoethyl)-1H-indazole-4-carboxylic acid (284 g) (50 mg, 0.10 mmol) with phenylmethanamine (0.017 mL, 0.15 mmol) according to the procedure reported in step-3 of Scheme 2 gave after workup and purification by flash column chromatography [silica gel, eluting with hexanes/10% methanol in ethyl acetate, 1:0 to 1:2] 3-acetyl-N-benzyl-1-(2-((2-(3-chloro-2-fluorobenzylamino)-2-oxoethyl)(cyclopropyl)amino)-2-oxoethyl)-1H-indazole-4-carboxamide as a white solid (297a) (21 mg, 36%). $^1$H NMR (300 MHz, DMSO-d$_6$) δ 8.73 (t, J=5.9 Hz, 1H), 8.48 (t, J=5.9 Hz, 1H), 7.75 (dd, J=8.6, 0.9 Hz, 1H), 7.52-7.18 (m, 9H), 7.10 (td, J=7.9, 1.0 Hz, 1H), 5.77 (s, 2H), 4.50 (d, J=5.9 Hz, 2H), 4.34 (d, J=5.7 Hz, 2H), 3.99 (s, 2H), 3.19-3.05 (m, 1H), 2.58 (s, 3H), 1.09-0.84 (m, 4H); $^{19}$F NMR (282 MHz, DMSO-d$_6$) δ −121.61; MS(ES+): 612.5 & 614.5 (M+Na); MS (ES−): 624.5 & 626.5 (M+Cl).

Scheme 298

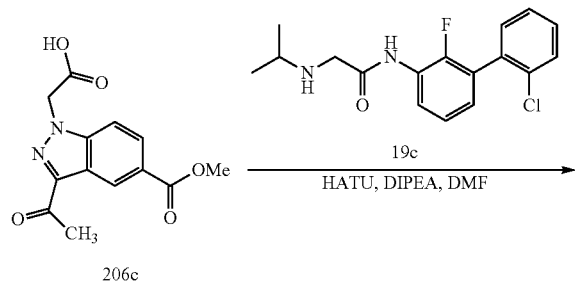

206c

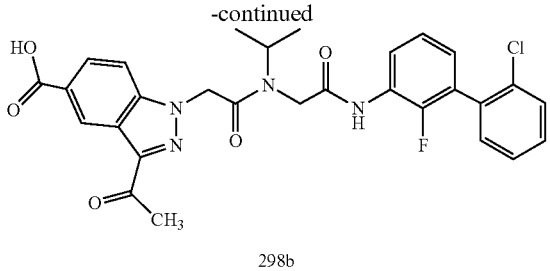

19c

HATU, DIPEA, DMF

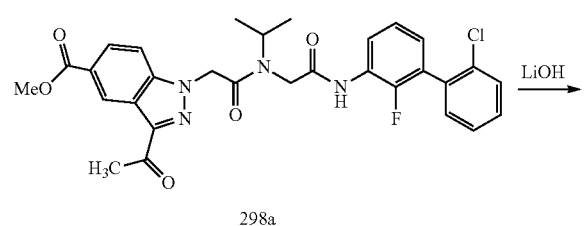

298a

LiOH

-continued

298b

Preparation of 3-acetyl-1-(2-((2-(2'-chloro-2-fluorobiphenyl-3-ylamino)-2-oxoethyl)(isopropyl)-amino)-2-oxoethyl)-1H-indazole-5-carboxylic acid (298b)

Step 1: Preparation of methyl 3-acetyl-1-(2-((2-(2'-chloro-2-fluorobiphenyl-3-ylamino)-2-oxoethyl)(isopropyl)amino)-2-oxoethyl)-1H-indazole-5-carboxylate (298a)

Reaction of 2-(3-acetyl-5-(methoxycarbonyl)-1H-indazol-1-yl)acetic acid (206c) (2.35 g, 8.51 mmol) with N-(2'-chloro-2-fluorobiphenyl-3-yl)-2-(isopropylamino)acetamide (19c) (2.1 g, 6.55 mmol according to the procedure reported in step-3 of Scheme 2 gave crude product. The crude product was stirred with 50% EtOAc-hexane (50 mL) and solid obtained was collected by filtration, washed with EtOAc (2×1 mL) to afford methyl 3-acetyl-1-(2-((2-(2'-chloro-2-fluorobiphenyl-3-ylamino)-2-oxoethyl)(isopropyl)amino)-2-oxoethyl)-1H-indazole-5-carboxylate (298a) (3.0 g, 79% yield) as an off-white solid. $^1$H NMR (300 MHz, DMSO-d$_6$) (a mixture of rotamers) δ 10.27 and 9.74 (2s, 1H), 8.85 and 8.83 (2dd, J=1.6, 0.8 Hz, 1H), 8.16-8.09 and 7.98-7.90 (2m, 1H), 8.07 and 8.02 (2dd, J=8.9, 1.6 Hz, 1H), 7.83-6.99 (m, 7H), 5.82 and 5.64 (2s, 2H), 4.69-4.57 and 4.38-4.27 (2m, 1H), 4.47 and 4.09 (2s, 2H), 3.912 and 3.906 (2s, 3H), 2.65 and 2.64 (2s, 3H), 1.29 and 1.07 (2d, J=6.8 Hz, 6H); MS (ES+) 579.5 (M+1), MS(ES−) 613.6 (M+Cl).

Step 2: preparation of 3-acetyl-1-(2-((2-(2'-chloro-2-fluorobiphenyl-3-ylamino)-2-amino)-2-oxoethyl)-1H-indazole-5-carboxylic acid (298b)

Reaction of methyl 3-acetyl-1-(2-((2-(2'-chloro-2-fluorobiphenyl-3-ylamino)-2-oxoethyl)(isopropyl) amino)-2-oxoethyl)-1H-indazole-5-carboxylate (298a) (3 g, 5.18 mmol) with lithium hydroxide (0.37 g, 15.54 mmol) according to the procedure reported in step-2 of Scheme 129 gave after workup and purification 3-acetyl-1-(2-((2-(2'-chloro-2-fluorobiphenyl-3-ylamino)-2-oxoethyl)(isopropyl)amino)-2-oxoethyl)-1H-indazole-5-carboxylic acid (298b) (2.75 g, 94% yield) as a white solid. $^1$H NMR (300 MHz, DMSO-d$_6$) δ 13.05 (s, 1H), 10.28 and 9.75 (2s, 1H), 8.83 and 8.81 (2dd, J=1.6, 0.8 Hz, 1H), 8.1-6.98 (m, 9H), 5.81 and 5.63 (2s, 2H), 4.70-4.57 and 4.39-4.26 (2m, 1H), 4.47 and 4.09 (2s, 2H), 2.65 and 2.64 (2s, 3H), 1.29 and 1.07 (2d, J=6.8 Hz, 6H); 19F NMR (282 MHz, DMSO-d$_6$) δ −126.84, −126.96; MS(ES−) 563.5 (M−1), 599.5 (M+Cl).

Scheme 299

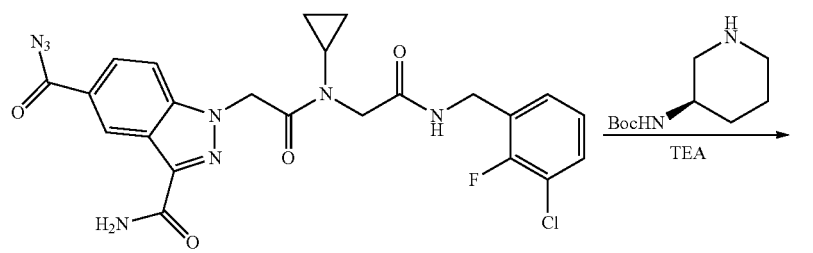

Preparation of (R)-tert-butyl 1-(3-carbamoyl-1-(2-((2-(3-chloro-2-fluorobenzylamino)-2-oxoethyl)(cyclopropyl)-amino)-2-oxoethyl)-1H-indazol-5-ylcarbamoyl)piperidin-3-ylcarbamate (299a)

Reaction of 3-carbamoyl-1-(2-((2-(3-chloro-2-fluorobenzylamino)-2-oxoethyl)(cyclopropyl)amino)-2-oxoethyl)-1H-indazole-5-carbonyl azide (235a) (750 mg, 0.712 mmol) with (R)-tert-butyl piperidin-3-ylcarbamate (285 mg, 1.42 mmol) according to the procedure reported in step-4 of Scheme 129 gave after workup and purification by flash column chromatography [silica (12 g), eluting with 0 to 40% DMA-80 in DCM] and preparative HPLC [C$_{18}$ column, eluting with CH$_3$CN in water from 0-100%] (R)-tert-butyl 1-(3-carbamoyl-1-(2-((2-(3-chloro-2-fluorobenzylamino)-2-oxoethyl)(cyclopropyl)amino)-2-oxoethyl)-1H-indazol-5-ylcarbamoyl)piperidin-3-ylcarbamate (299a) (75 mg, 15% yield) as a white solid. $^1$H NMR (300 MHz, DMSO-d$_6$) δ 8.65 (s, 1H), 8.50 (t, J=5.8 Hz, 1H), 8.23-8.12 (m, 1H), 7.63 (s, 1H), 7.58-7.42 (m, 3H), 7.31 (s, 1H), 7.27-7.23 (m, 1H), 7.13 (t, J=7.8 Hz, 1H), 6.91 (d, J=7.9 Hz, 1H), 5.61 (s, 2H), 4.33 (d, J=5.7 Hz, 2H), 4.12-3.84 (m, 4H), 3.42-3.21 (m, 1H), 3.12-2.99 (m, 1H), 2.87-2.58 (m, 2H), 1.90-1.59 (m, 2H), 1.48-1.28 (m, 11H), 1.09-0.96 (m, 2H), 0.96-0.81 (m, 2H); $^{19}$F NMR (282 MHz, DMSO-d$_6$) δ −74.22 (TFA peak), −121.62; MS (ES+) 699.7 (M+1); (ES−) 697.7 (M−1).

Scheme 300

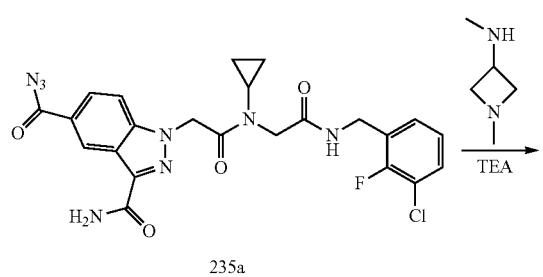

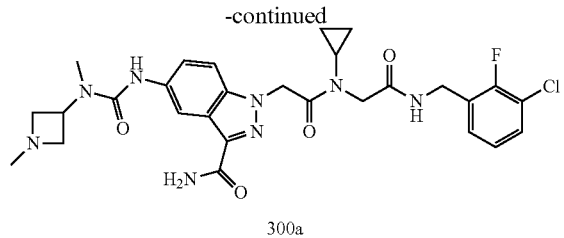

Preparation of 1-(2-((2-(3-chloro-2-fluorobenzylamino)-2-oxoethyl)(cyclopropyl)amino)-2-oxoethyl)-5-(3-methyl-3-(1-methylazetidin-3-yl)ureido)-1H-indazole-3-carboxamide (300a)

Reaction 3-carbamoyl-1-(2-((2-(3-chloro-2-fluorobenzylamino)-2-oxoethyl)(cyclopropyl)amino)-2-oxoethyl)-1H-indazole-5-carbonyl azide (235a) (500 mg, 0.47 mmol) with N,1-dimethylazetidin-3-amine (86 mg, 0.85 mmol) according to the procedure reported in step-4 of Scheme 129 gave after workup and purification by chromatography [silica (40 g), eluting with 0 to 40% DMA80 in DCM], then [silica (24 g), eluting with 0 to 90% EtOAc/MeOH (9:1) in hexane] and prep-HPLC [C$_{18}$ column, 5 injections, eluting with CH$_3$CN in water (containing 0.1% TFA) from 0-100%], followed by lyophilization 1-(2-((2-(3-chloro-2-fluorobenzylamino)-2-oxoethyl)(cyclopropyl)amino)-2-oxoethyl)-5-(3-methyl-3-(1-methylazetidin-3-yl)ureido)-1H-indazole-3-carboxamide (300a) (65 mg, 26% yield) as a white solid; $^1$H NMR (300 MHz, DMSO-d$_6$) δ 8.86 (s, 1H), 8.75 (s, 1H), 8.53 (t, J=5.8 Hz, 1H), 8.16 (s, 1H), 7.82 (s, 1H), 7.72 (d, J=9.0 Hz, 1H), 7.52-7.41 (m, 2H), 7.41-7.31 (m, 1H), 7.27-7.19 (m, 1H), 7.18-7.08 (m, 1H), 5.68 (s, 2H), 4.93-4.69 (m, 2H), 4.51-4.37 (m, 1H), 4.33 (d, J=5.7 Hz, 2H), 3.99 (s, 2H), 3.49-3.31 (m, 2H), 3.18 (s, 3H), 3.11-3.00 (m, 1H), 2.68 (s, 3H), 1.03-0.96 (m, 2H), 0.96-0.87 (m, 2H); $^{19}$F NMR (282 MHz, DMSO-d$_6$) δ −73.80 (TFA peak), −121.54; MS (ES$^+$) 599.6 (M+1); (ES−) 597.5 (M−1).

Scheme 301
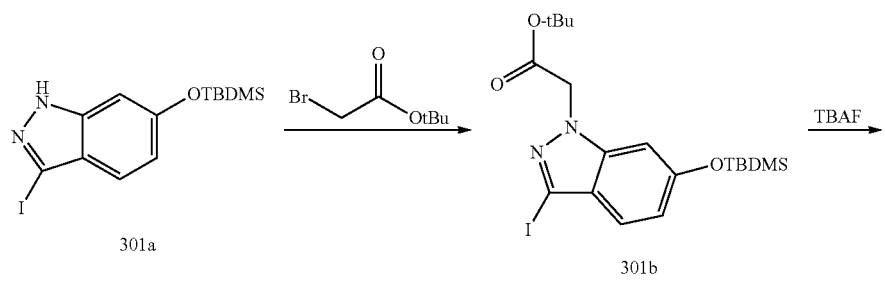
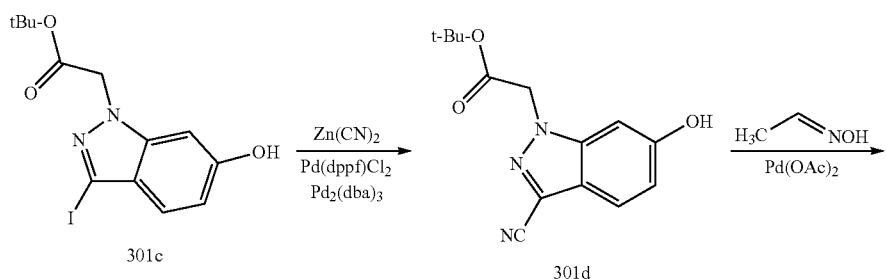
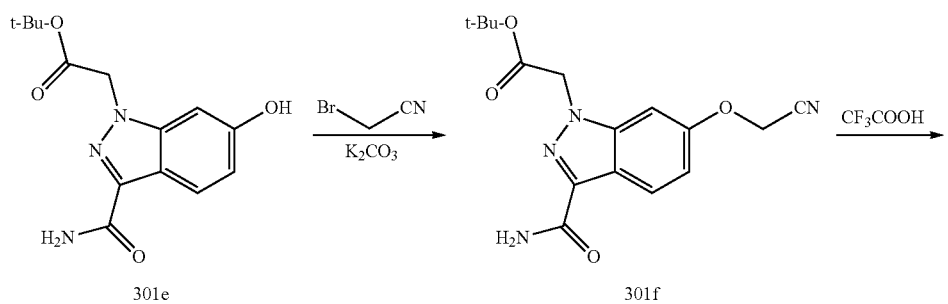
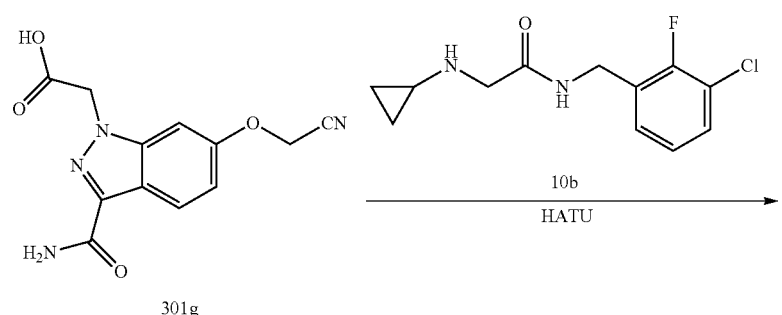
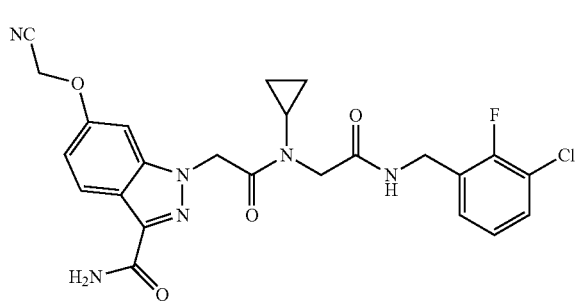

Preparation of 1-(2-((2-(3-chloro-2-fluorobenzylamino)-2-oxoethyl)(cyclopropyl)amino)-2-oxoethyl)-6-(cyanomethoxy)-1H-indazole-3-carboxamide (301 h)

Step 1: Preparation of tert-butyl 2-(6-(tert-butyldimethylsilyloxy)-3-iodo-1H-indazol-1-yl)acetate (301b)

Reaction of 6-(tert-butyldimethylsilyloxy)-3-iodo-1H-indazole (301a) (36.2 mmol, crude prepared according to the procedure reported by Atobe, Masakazu et al; in Bioorganic Medicinal Chemistry Letters, 24(5), 1327-1333; 201.4) with tert-butyl 2-bromoacetate (6.41 mL, 43.4 mmol) according to the procedure reported in step-1 of Scheme 43 gave after workup and purification tert-butyl 2-(6-(tert-butyldimethylsilyloxy)-3-iodo-1H-indazol-1-yl)acetate as a brown gum (301b) (17.25 g, used as such for next step). MS (ES+): 489.4 (M+1).

Step 2: Preparation of tert-butyl 2-(6-hydroxy-3-iodo-1H-indazol-1-yl)acetate (301c)

To a solution of tert-butyl 2-(6-(tert-butyldimethylsilyloxy)-3-iodo-1H-indazol-1-yl)acetate (301d) (17.68 g, crude) in THF (200 mL) cooled to 0° C. was added tetrabutylammonium fluoride (10.96 g, 39.8 mmol) and stirred at RT for 6 h. The reaction mixture was poured into ice-water (300 mL), extracted with ethyl acetate (300, 200 mL). The combined organic extracts were washed with brine (300 mL), dried, filtered and concentrated in vacuum. The crude product was purified by flash column chromatography [silica gel, eluting with hexanes/EtOAc (1:0 to 3:1)] to give tert-butyl 2-(6-hydroxy-3-iodo-1H-indazol-1-yl)acetate as a yellow solid (301c) (7.61 g, 56% for 4 steps). $^1$H NMR (300 MHz, DMSO-d$_6$) δ 9.94 (s, 1H), 7.21 (dd, J=8.6, 0.7 Hz, 1H), 6.80-6.79 (m, 1H), 6.76 (dd, J=8.6, 1.9 Hz, 1H), 5.13 (s, 2H), 1.41 (s, 9H); MS(ES+): 397.2 (M+Na).

Step 3: Preparation of tert-butyl 2-(3-cyano-6-hydroxy-1H-indazol-1-yl)acetate (301d)

A mixture of tert-butyl 2-(6-hydroxy-3-iodo-1H-indazol-1-yl)acetate (301c) (3.1 g, 8.28 mmol), dicyanozinc (1.07 g, 9.11 mmol), Pd$_2$(dba)$_3$ (0.76 g, 0.83 mmol), and [1,1'-Bis(diphenylphosphino)ferrocene]dichloropalladium(II), complex with dichloromethane (Pd(dppf)Cl$_2$.CH$_2$Cl$_2$) (0.68 g, 0.83 mmol) in DMF (35 mL) and water (3.5 mL) was stirred at 80° C. for 3 h. The reaction mixture was diluted with ethyl acetate (200 mL), washed with water (80 mL), Sat. NaHCO$_3$ (60 mL) and brine (50 mL), dried, filtered and concentrated in vacuum. The crude product was purified by flash column chromatography [silica gel, eluting with hexanes/ethyl acetate (1:0 to 3:1)] to give tert-butyl 2-(3-cyano-6-hydroxy-1H-indazol-1-yl)acetate as a yellow solid (301d) (880 mg, 39%); $^1$H NMR (300 MHz, DMSO-d$_6$) δ 10.27 (s, 1H), 7.69 (dd, J=8.7, 0.7 Hz, 1H), 7.00-6.98 (m, 1H), 6.96 (dd, J=8.7, 2.0 Hz, 1H), 5.34 (s, 2H), 1.41 (s, 9H); MS(ES+): 296.3 (M+Na).

Step 4: Preparation of tert-butyl 2-(3-carbamoyl-6-hydroxy-1H-indazol-1-yl)acetate (301e)

A mixture of tert-butyl 2-(3-cyano-6-hydroxy-1H-indazol-1-yl)acetate (301d) (858 mg, 3.14 mmol), palladium (II) acetate (71.9 mg, 0.31 mmol), triphenylphosphine (166 mg, 0.63 mmol), and acetaldehyde oxime (0.39 mL, 6.28 mmol) in ethanol (20 mL) and water (5 mL) was refluxed for 3 h. The reaction mixture was cooled to RT, diluted with ethyl acetate (60 mL), filtered and concentrated in vacuum. The crude product was purified by flash column chromatography [silica gel, eluting with hexanes/ethyl acetate (1:0 to 0:1)] to give tert-butyl 2-(3-carbamoyl-6-hydroxy-1H-indazol-1-yl)acetate as a white solid (301e) (749 mg, 82%). MS (ES–): 290.3 (M–1).

Step 5: Preparation of tert-butyl 2-(3-carbamoyl-6-(cyanomethoxy)-1H-indazol-1-yl)acetate (301f)

A suspension of tert-butyl 2-(3-carbamoyl-6-hydroxy-1H-indazol-1-yl)acetate (301e) (100 mg, 0.34 mmol) in DMF (5 mL) was treated with Potassium carbonate (96 mg, 0.69 mmol) and 2-bromoacetonitrile (0.025 mL, 0.34 mmol) followed by stirring at RT for 13 h. The reaction mixture was diluted with ethyl acetate (100 mL), washed with water (2×50 mL), brine (50 mL), dried, filtered and concentrated in vacuum to give tert-butyl 2-(3-carbamoyl-6-(cyanomethoxy)-1H-indazol-1-yl)acetate as a yellow solid (301f) (107 mg, used as such for next step). MS(ES+): 353.3 (M+Na).

Step 6: Preparation of 2-(3-carbamoyl-6-(cyanomethoxy)-1H-indazol-1-yl)acetic acid (301 g)

Reaction of tert-butyl 2-(3-carbamoyl-6-(cyanomethoxy)-1H-indazol-1-yl)acetate (301f) (0.113 g, 0.34 mmol, crude) with 2,2,2-trifluoroacetic acid (0.264 mL, 3.43 mmol) according to the procedure reported in step-2 of Scheme 2 gave after workup and purification 2-(3-carbamoyl-6-(cyanomethoxy)-1H-indazol-1-yl)acetic acid (301 g) which was used as such for next step.

Step 7: Preparation of 1-(2-((2-(3-chloro-2-fluorobenzylamino)-2-oxoethyl)(cyclopropyl)amino)-2-oxoethyl)-6-(cyanomethoxy)-1H-indazole-3-carboxamide (301 h)

Reaction of 2-(3-carbamoyl-6-(cyanomethoxy)-1H-indazol-1-yl)acetic acid (301 g) (0.094 g, 0.34 mmol, crude) with N-(3-chloro-2-fluorobenzyl)-2-(cyclopropylamino)acetamide (0.11 g, 0.41 mmol) (10b) according to the procedure reported in step-3 of Scheme 2 gave after workup and purification by flash column chromatography [silica gel, eluting with dichloromethane/methanol (1:0 to 19:1)] 1-(2-((2-(3-chloro-2-fluorobenzylamino)-2-oxoethyl)(cyclopropyl)amino)-2-oxoethyl)-6-(cyanomethoxy)-1H-indazole-3-carboxamide (301 h) (44 mg, 25% for 3 steps) as a light brown solid; $^1$H NMR (300 MHz, DMSO-d$_6$) δ 8.54 (t, J=5.8 Hz, 1H), 8.10 (d, J=8.9 Hz, 1H), 7.72 (s, 1H), 7.52-7.33 (m, 2H), 7.29 (d, J=2.2 Hz, 1H), 7.26-7.18 (m, 1H), 7.14-7.04 (m, 1H), 7.01 (dd, J=8.9, 2.2 Hz, 1H), 5.60 (s, 2H), 5.20 (s, 2H), 4.34 (d, J=5.7 Hz, 2H), 4.00 (s, 2H), 3.13-2.98 (m, 1H), 1.06-0.84 (m, 4H); $^{19}$F NMR (282 MHz, DMSO-d$_6$) δ –121.56; MS(ES+): 513.5 & 515.5 (M+1); MS (ES–): 547.4 & 549.4 (M+Cl).

Scheme 302

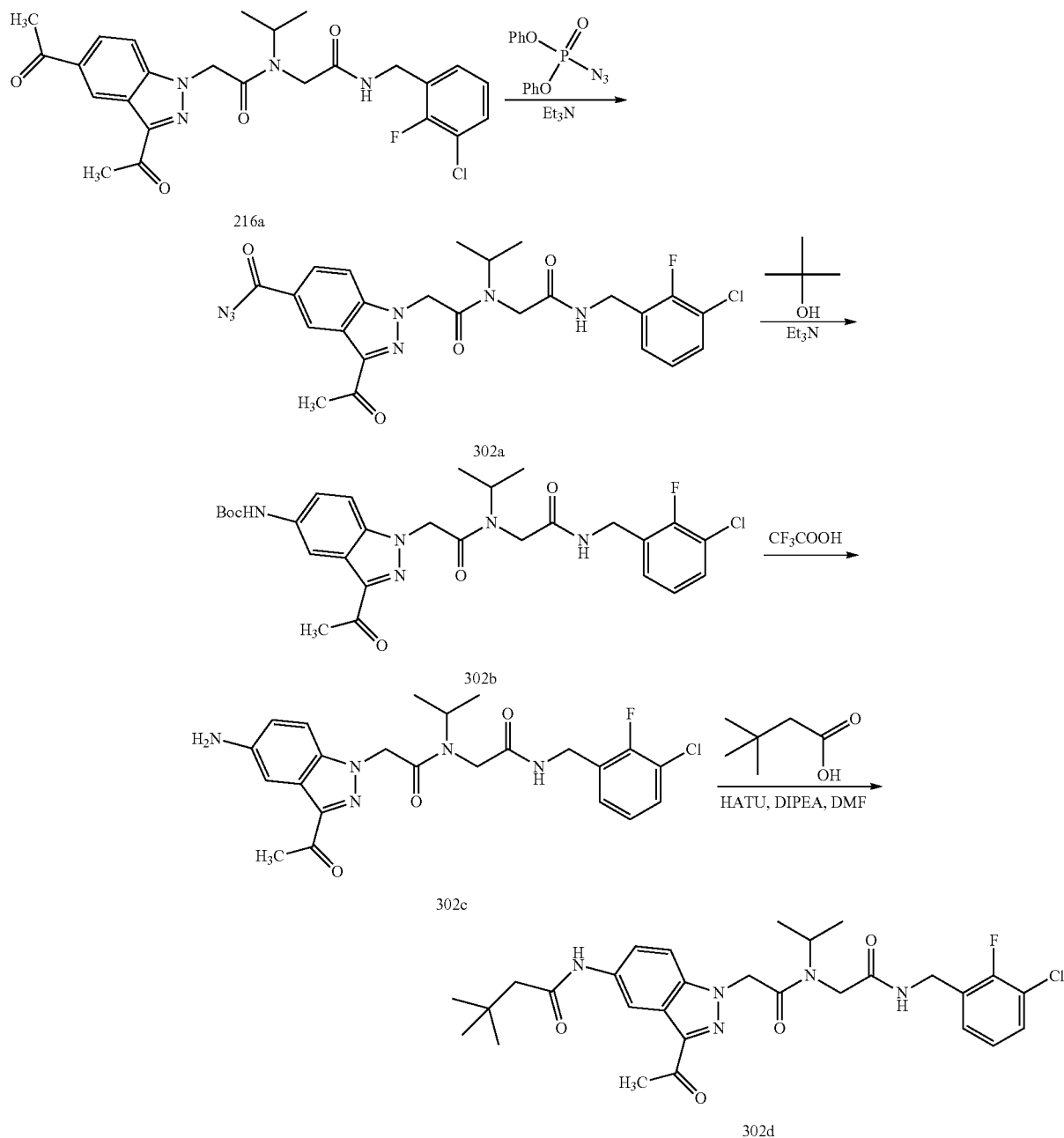

Preparation of N-(3-acetyl-1-(2-((2-(3-chloro-2-fluorobenzylamino)-2-oxoethyl)(isopropyl)-amino)-2-oxoethyl)-1H-indazol-5-yl)-3,3-dimethylbutanamide (302d)

Step-1: Preparation of 3-acetyl-1-(2-((2-(3-chloro-2-fluorobenzylamino)-2-oxoethyl)(isopropyl)-amino)-2-oxoethyl)-1H-indazole-5-carbonyl azide (302a)

Reaction of 3-acetyl-1-(2-((2-(3-chloro-2-fluorobenzylamino)-2-oxoethyl)(isopropyl)amino)-2-oxoethyl)-1H-indazole-5-carboxylic acid (216a) (200 mg, 0.4 mmol) with diphenyl phosphorazidate (0.088 mL, 0.4 mmol) according to the procedure reported in step-3 of Scheme 129 gave after workup crude 3-acetyl-1-(2-((2-(3-chloro-2-fluorobenzylamino)-2-oxoethyl)(isopropyl)-amino)-2-oxoethyl)-1H-indazole-5-carbonyl azide (302a), which was used as such for next step.

Step-2: Preparation of tert-butyl 3-acetyl-1-(2-((2-(3-chloro-2-fluorobenzylamino)-2-oxoethyl)(isopropyl)amino)-2-oxoethyl)-1H-indazol-5-ylcarbamate (302b)

Reaction of 3-acetyl-1-(2-((2-(3-chloro-2-fluorobenzylamino)-2-oxoethyl)(isopropyl)amino)-2-oxoethyl)-1H-indazole-5-carbonyl azide (302a) (210 mg, 0.4 mmol) with 2-methylpropan-2-ol (0.23 mL, 2.39 mmol) according to the procedure reported in step-4 of Scheme 129 gave after workup and purification by flash column chromatography tert-butyl 3-acetyl-1-(2-((2-(3-chloro-2-fluorobenzylamino)-2-oxoethyl)(isopropyl)amino)-2-oxoethyl)-1H-indazol-5-ylcarbamate (302b) (20 mg, 9% for two steps) as a white solid; MS (ES+) 574.6, 575.6 (M+1); (ES−) 572.6 (M−1); 608.5, 610.5 (M+Cl).

Step-3: Preparation of 2-(3-acetyl-5-amino-1H-indazol-1-yl)-N-(2-(3-chloro-2-fluorobenzylamino)-2-oxoethyl)-N-isopropylacetamide (302c)

Reaction of tert-butyl 3-acetyl-1-(2-((2-(3-chloro-2-fluorobenzylamino)-2-oxoethyl)(isopropyl)amino)-2-oxoethyl)-1H-indazol-5-ylcarbamate (302b) (18 mg, 0.03 mmol) with 2,2,2-trifluoroacetic acid (0.193 mL, 2.51 mmol) according to the procedure reported in step-2 of Scheme 2 gave after workup crude 2-(3-acetyl-5-amino-1H-indazol-1-yl)-N-(2-(3-chloro-2-fluorobenzylamino)-2-oxoethyl)-N-isopropylacetamide (302c), which was used as such for next step.

Step-4: Preparation of N-(3-acetyl-1-(2-((2-(3-chloro-2-fluorobenzylamino)-2-oxoethyl)(isopropyl)-amino)-2-oxoethyl)-1H-indazol-5-yl)-3,3-dimethylbutanamide (302d)

Reaction of 2-(3-acetyl-5-amino-1H-indazol-1-yl)-N-(2-(3-chloro-2-fluorobenzylamino)-2-oxoethyl)-N-isopropylacetamide (302c) (14.69 mg, 0.031 mmol) with 3,3-dimethylbutanoic acid (6.04 µL, 0.047 mmol) according to the procedure reported in step-3 of Scheme 2 gave after workup and purification by flash column chromatography [silica gel, eluting with hexanes/10% methanol in ethyl acetate (1:0 to 1:1)] N-(3-acetyl-1-(2-((2-(3-chloro-2-fluorobenzylamino)-2-oxoethyl)(isopropyl)amino)-2-oxoethyl)-1H-indazol-5-yl)-3,3-dimethylbutanamide (302d) (11 mg, 62% for two steps) as a light yellow solid; $^1$H NMR (300 MHz, DMSO-d$_6$) δ 9.97 (s, 1H), 8.83 (t, J=5.7 Hz) and 8.35 (t, J=5.8 Hz) (2t, 1H), 8.56-8.48 (m, 1H), 7.72-6.89 (m, 5H), 5.65 and 5.49 (2s, 2H), 4.64-4.49 and 4.30-4.18 (2m, 1H), 4.47 (d, J=5.5 Hz) and 4.32 (d, J=5.8 Hz) (2d, 2H), 4.17 and 3.84 (2s, 2H), 2.59 (s, 3H), 2.21 and 1.99 (2s, 2H), 1.24 (d, J=6.3 Hz) and 0.99 (d, J=6.8 Hz) (2d, 6H), 1.04 and 1.04 (2s, 9H); $^{19}$F NMR (282 MHz, DMSO-d$_6$) δ −121.22, −121.75; MS (ES+): 572.7 (M+1).

Scheme 303

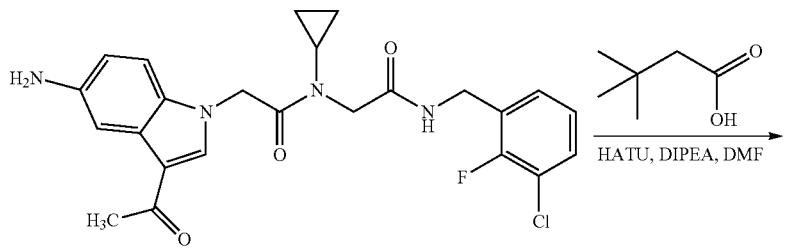

286a

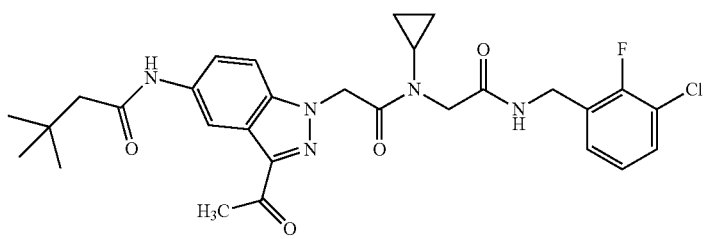

303a

525

Preparation of N-(3-acetyl-1-(2-((2-(3-chloro-2-fluorobenzylamino)-2-oxoethyl)(cyclopropyl)amino)-2-oxoethyl)-1H-indol-5-yl)-3,3-dimethylbutanamide (303a)

Reaction of 2-(3-acetyl-5-amino-1H-indol-1-yl)-N-(2-(3-chloro-2-fluorobenzylamino)-2-oxoethyl)-N-cyclopropylacetamide (286a) (14.36 mg, 0.031 mmol) with 3,3-dimethylbutanoic acid (5.95 μL, 0.046 mmol) according to the procedure reported in step-3 of Scheme 2 gave after workup and purification by flash column chromatography [silica gel, eluting with hexanes/10% methanol in ethyl acetate (1:0 to 1:2)] N-(3-acetyl-1-(2-((2-(3-chloro-2-fluorobenzylamino)-2-oxoethyl)(cyclopropyl)amino)-2-oxoethyl)-1H-indol-5-yl)-3,3-dimethylbutanamide (303a) (11 mg, 63%) as a white solid; $^1$H NMR (300 MHz, DMSO-$d_6$) δ 9.78 (s, 1H), 8.48 (t, J=5.8 Hz, 1H), 8.36 (d, J=2.0 Hz, 1H), 8.23 (s, 1H), 7.53 (dd, J=8.9, 2.1 Hz, 1H), 7.45 (td, J=7.6, 1.7 Hz, 1H), 7.34 (d, J=8.8 Hz, 1H), 7.26-7.19 (m, 1H), 7.14-7.06 (m, 1H), 5.40 (s, 2H), 4.34 (d, J=5.7 Hz, 2H), 3.99 (s, 2H), 3.14-2.99 (m, 1H), 2.41 (s, 3H), 2.19 (s, 2H), 1.03 (s, 9H), 1.00-0.87 (m, 4H); $^{19}$F NMR (282 MHz, DMSO-$d_6$) δ −121.63; MS (ES+): 591.6 (M+Na).

526

Preparation of 2-(3-acetyl-5-(2-cyclopropylacetamido)-1H-indol-1-yl)-N-(2-(3-chloro-2-fluorobenzylamino)-2-oxoethyl)-N-cyclopropylacetamide (304a)

Reaction of 2-(3-acetyl-5-amino-1H-indol-1-yl)-N-(2-(3-chloro-2-fluorobenzylamino)-2-oxoethyl)-N-cyclopropylacetamide (286a) (14.36 mg, 0.031 mmol) with 2-cyclopropylacetic acid (4.34 μL, 0.046 mmol) according to the procedure reported in step-3 of Scheme 2 gave after workup and purification by flash column chromatography [silica gel, eluting with hexanes/10% methanol in ethyl acetate (1:0 to 1:2)] 2-(3-acetyl-5-(2-cyclopropylacetamido)-1H-indol-1-yl)-N-(2-(3-chloro-2-fluorobenzylamino)-2-oxoethyl)-N-cyclopropylacetamide (304a) (11 mg, 65%) as a white solid; $^1$H NMR (300 MHz, DMSO-$d_6$) δ 9.80 (s, 1H), 8.47 (t, J=5.9 Hz, 1H), 8.36 (d, J=2.0 Hz, 1H), 8.23 (s, 1H), 7.55 (dd, J=8.9, 2.1 Hz, 1H), 7.46 (td, J=7.6, 1.7 Hz, 1H), 7.36 (d, J=8.9 Hz, 1H), 7.27-7.19 (m, 1H), 7.14-7.06 (m, 1H), 5.40 (s, 2H), 4.34 (d, J=5.8 Hz, 2H), 3.99 (s, 2H), 3.15-3.00 (m, 1H), 2.41 (s, 3H), 2.20 (d, J=7.0 Hz, 2H), 1.33-0.81 (m, 5H), 0.55-0.40 (m, 2H), 0.29-0.14 (m, 2H); $^{19}$F NMR (282 MHz, DMSO-$d_6$) δ −121.62; MS (ES+): 553.6 (M+1); MS (ES−): 551.4 & 553.6 (M−1).

Scheme 304

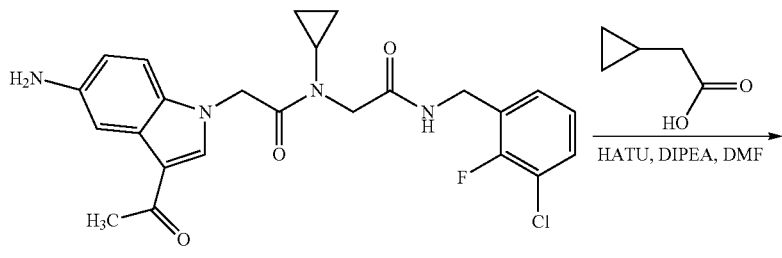

286a

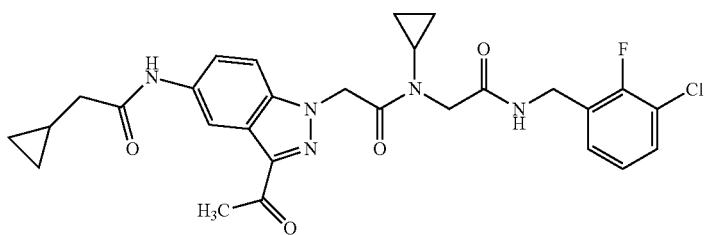

304a

Scheme 305

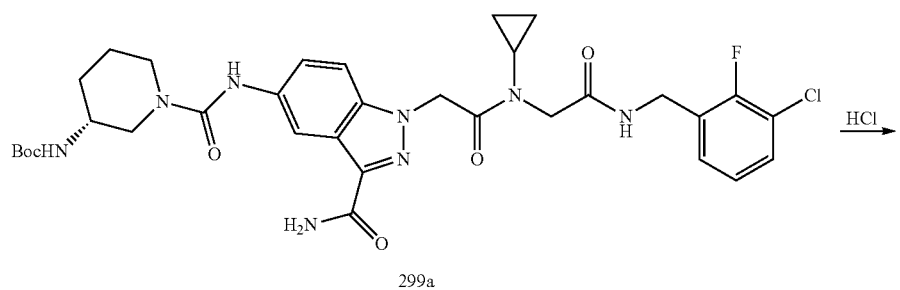

299a

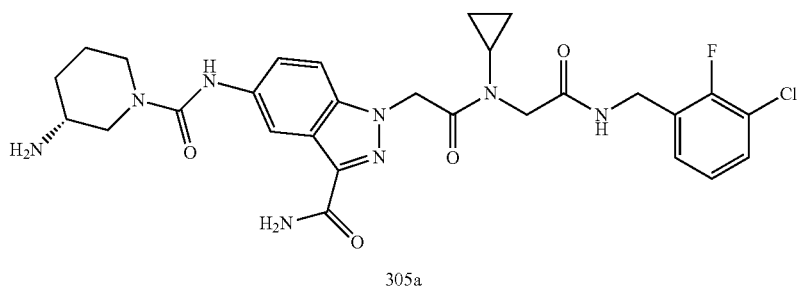

305a

Preparation of (R)-5-(3-aminopiperidine-1-carboxamido)-1-(2-((2-(3-chloro-2-fluorobenzylamino)-2-oxoethyl)(cyclopropyl)amino)-2-oxoethyl)-1H-indazole-3-carboxamide (305a)

To a solution of (R)-5-(3-aminopiperidine-1-carboxamido)-1-(2-((2-(3-chloro-2-fluorobenzylamino)-2-oxoethyl)(cyclopropyl)amino)-2-oxoethyl)-1H-indazole-3-carboxamide (299a) (40 mg, 0.067 mmol) in MeOH (15 mL) was added HCl (3N in MeOH) (0.19 mL, 0.57 mmol) and stirred at room temperature overnight. The reaction mixture was concentrated in vacuum and residue obtained was purified by flash chromatography [silica (12 g), eluting with 0 to 40% DMA-80 in DCM] and preparative HPLC [$C_{18}$ column, eluting with $CH_3CN$ in water from 0-100%]. The combined fractions were neutralized with $NaHCO_3$ (sat.) to afford (R)-5-(3-aminopiperidine-1-carboxamido)-1-(2-((2-(3-chloro-2-fluorobenzylamino)-2-oxoethyl)(cyclopropyl) amino)-2-oxoethyl)-1H-indazole-3-carboxamide (305a) (40 mg, 93% yield) as a white solid; $^1$H NMR (300 MHz, DMSO-$d_6$) δ 8.57 (s, 1H), 8.50 (t, J=5.9 Hz, 1H), 8.16 (dd, J=2.0, 0.8 Hz, 1H), 7.62 (s, 1H), 7.58-7.42 (m, 3H), 7.31 (s, 1H), 7.26-7.18 (m, 1H), 7.17-7.10 (m, 1H), 5.60 (s, 2H), 4.33 (d, J=5.7 Hz, 2H), 4.05-3.90 (m, 4H), 3.10-2.97 (m, 1H), 2.85-2.69 (m, 1H), 2.67-2.45 (m, 2H), 1.89-1.78 (m, 1H), 1.72-1.58 (m, 1H), 1.48-1.32 (m, 1H), 1.25-1.11 (m, 1H), 1.03-0.95 (m, 2H), 0.95-0.85 (m, 2H); $^{19}$F NMR (282 MHz, DMSO-$d_6$) δ −73.43 (TFA peak), −121.60; MS (ES+): 599.7 (M+1); (ES−): 597.6 (M−1).

Scheme 306

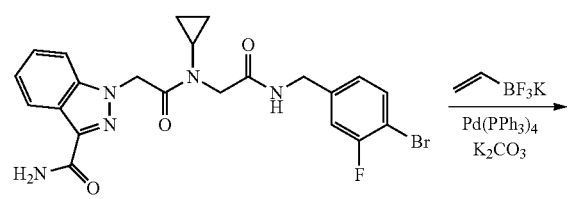

282d

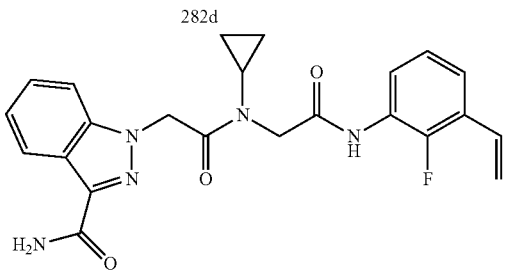

306a

Preparation of 1-(2-(cyclopropyl(2-(2-fluoro-3-vinylphenylamino)-2-oxoethyl)amino)-2-oxoethyl)-1H-indazole-3-carboxamide (306a)

Reaction of 1-(2-((2-(3-bromo-2-fluorophenylamino)-2-oxoethyl)(cyclopropyl)amino)-2-oxoethyl)-1H-indazole-3-carboxamide (282d) (0.3 g, 0.61 mmol) with Potassium Vinyltrifluoroborate (0.17 g, 1.23 mmol) according to the procedure reported in Scheme 78 gave after workup and purification by flash column chromatography [silica gel 12 g, eluting with 0 to 20% DMA-80 in DCM] 1-(2-(cyclopropyl(2-(2-fluoro-3-vinylphenylamino)-2-oxoethyl)amino)-2-oxoethyl)-1H-indazole-3-carboxamide (306a) (0.21 g, 78% yield) as a white solid; $^1$H NMR (300 MHz, DMSO-d$_6$) δ 9.86 (s, 1H), 8.18 (d, J=8.1 Hz, 1H), 7.89-7.31 (m, 6H), 7.31-7.21 (m, 1H), 7.17-7.06 (m, 1H), 6.84 (dd, J=17.7, 11.2 Hz, 1H), 5.92 (dd, J=17.7, 1.2 Hz, 1H), 5.70 (s, 2H), 5.44 (dd, J=11.2, 1.2 Hz, 1H), 4.21 (s, 2H), 3.19-3.05 (m, 1H), 1.07-1.00 (m, 2H), 0.99-0.92 (m, 2H); $^{19}$F NMR (282 MHz, DMSO-d$_6$) δ −131.22; MS (ES+): 436.5 (M+1), 458.5 (M+Na), MS (ES−): 434.5 (M−1).

Scheme 307

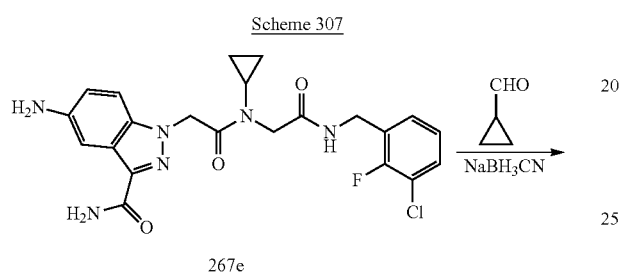

267e

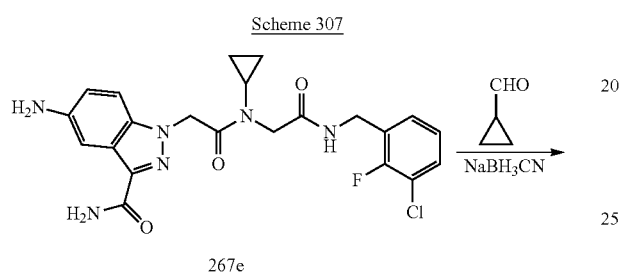

307a

Preparation of 5-(bis(cyclopropylmethyl)amino)-1-(2-((2-(3-chloro-2-fluorobenzylamino)-2-oxoethyl)(cyclopropyl)amino)-2-oxoethyl)-1H-indazole-3-carboxamide (307a)

Reaction of 5-amino-1-(2-((2-(3-chloro-2-fluorobenzylamino)-2-oxoethyl)(cyclopropyl)amino)-2-oxoethyl)-1H-indazole-3-carboxamide (267e) (0.08 g, 0.17 mmol) with cyclopropanecarbaldehyde (0.036 g, 0.51 mmol) according to the procedure reported in Scheme 276 gave after workup and purification by flash column chromatography [silica gel (24 g), eluting with 0 to 40% DMA-80 in DCM] 5-(bis(cyclopropylmethyl)amino)-1-(2-((2-(3-chloro-2-fluorobenzylamino)-2-oxoethyl)(cyclopropyl)amino)-2-oxoethyl)-1H-indazole-3-carboxamide (307a) (0.045 g, 46% yield) as white solid; $^1$H NMR (300 MHz, DMSO-d$_6$) δ 8.50 (t, J=5.9 Hz, 1H), 7.52 (s, 1H), 7.50-7.40 (m, 3H), 7.27-7.18 (m, 2H), 7.18-7.07 (m, 2H), 5.57 (s, 2H), 4.33 (d, J=5.7 Hz, 2H), 3.98 (s, 2H), 3.27 (d, J=6.3 Hz, 4H), 3.11-2.98 (m, 1H), 1.15-0.82 (m, 6H), 0.54-0.35 (m, 4H), 0.30-0.13 (m, 4H); 19F NMR (282 MHz, DMSO-d$_6$) δ −121.59; MS (ES+): 581.6 (M+1), MS (ES−): 615.5 (M+Cl).

Scheme 308

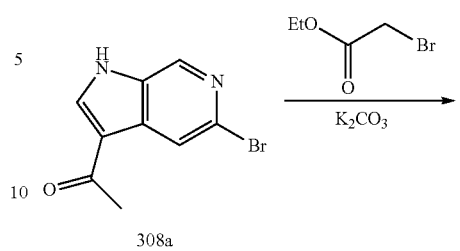

308a

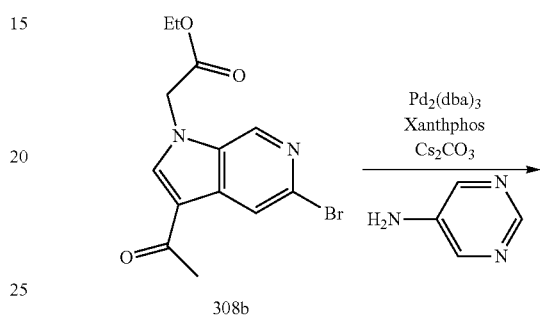

308b

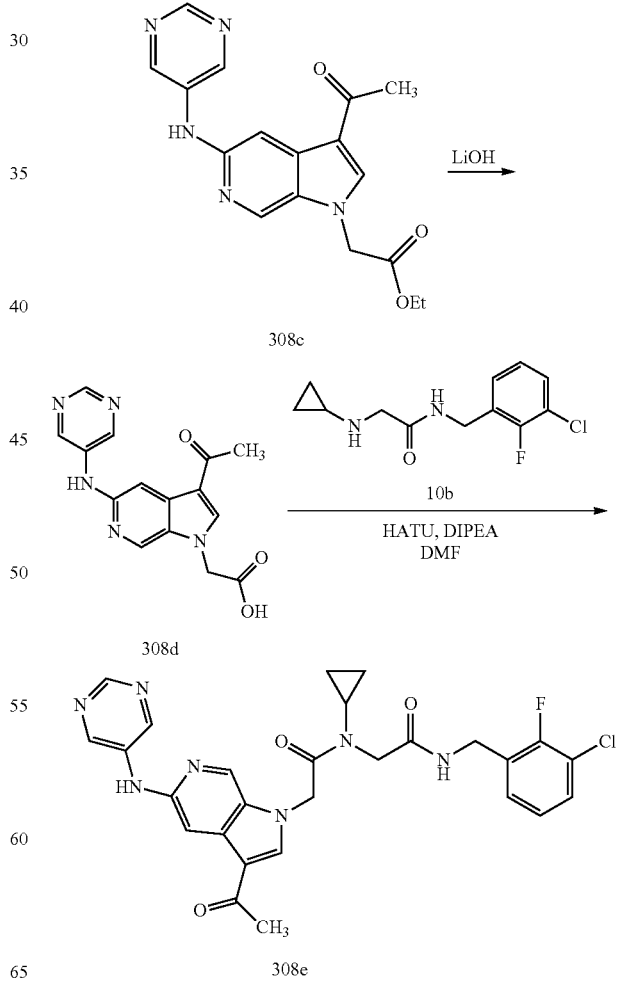

308c

308d

308e

Preparation of 2-(3-acetyl-5-(pyrimidin-5-ylamino)-1H-pyrrolo[2,3-c]pyridin-1-yl)-N-(2-((3-chloro-2-fluorobenzyl)amino)-2-oxoethyl)-N-cyclopropylacetamide (308e)

Step-1: Preparation of ethyl 2-(3-acetyl-5-bromo-1H-pyrrolo[2,3-c]pyridin-1-yl)acetate (308b)

Reaction of 1-(5-bromo-1H-pyrrolo[2,3-c]pyridin-3-yl)ethanone (308a) (1.2 g, 5.02 mmol; Prepared according to the procedure described by Hynd, George et al; in PCT Int. Appl., 2014174021, 30 Oct. 2014) with Ethyl bromoacetate (1.12 mL, 10.04 mmol), Potassium Carbonate (1.39 g, 10.04 mmol) in acetonitrile (40 mL) according to the procedure reported in step-1 of Scheme 56 gave after workup and purification by flash column chromatography [silica gel 24 g, DMA80 in DCM 0 to 30% as eluents] ethyl 2-(3-acetyl-5-bromo-1H-pyrrolo[2,3-c]pyridin-1-yl)acetate (308b) (0.85 g, 52% yield) as a light orange solid; $^1$H NMR (300 MHz, DMSO-$d_6$) δ 8.79 (d, J=1.0 Hz, 1H), 8.58 (s, 1H), 8.18 (d, J=0.9 Hz, 1H), 5.36 (s, 2H), 4.19 (q, J=7.1 Hz, 2H), 2.46 (s, 3H), 1.23 (t, J=7.1 Hz, 3H); MS (ES+) 325.3, 327.3 (M+1), 347.3, 349.3 (M+Na), MS (ES−) 359.2, 361.2 (M+Cl).

Step-2: Preparation of ethyl 2-(3-acetyl-5-(pyrimidin-5-ylamino)-1H-pyrrolo[2,3-c]pyridin-1-yl)acetate (308c)

Compound 308c was prepared from ethyl 2-(3-acetyl-5-bromo-1H-pyrrolo[2,3-c]pyridin-1-yl)acetate (308b) (0.2 g, 0.62 mmol) and pyrimidin-5-amine (0.088 g, 0.92 mmol) using di-tert-butyl(2',4',6'-triisopropylbiphenyl-2-yl)phosphine (0.052 g, 0.12 mmol), Potassium Carbonate (0.17 g, 1.23 mmol), Pd$_2$(dba)$_3$ (0.056 g, 0.062 mmol) according to the procedure reported in step-1 of Scheme 97. This gave after workup and purification by reverse phase chromatography [C18 60 g, acetonitrile in 0.1% TFA in water 0 to 70% as eluents] ethyl 2-(3-acetyl-5-(pyrimidin-5-ylamino)-1H-pyrrolo[2,3-c]pyridin-1-yl)acetate (308c) (0.02 g, 10% yield) as off-white solid; $^1$H NMR (300 MHz, MeOH-$d_4$) δ 9.12 (s, 2H), 8.59 (s, 1H), 8.50 (d, J=1.1 Hz, 1H), 8.31 (s, 1H), 7.72 (d, J=1.1 Hz, 1H), 5.20 (s, 2H), 4.27 (q, J=7.1 Hz, 2H), 2.52 (s, 3H), 1.30 (t, J=7.1 Hz, 4H).

Step-3: Preparation 2-(3-acetyl-5-(pyrimidin-5-ylamino)-1H-pyrrolo [2,3-c] pyridin-1-yl)acetic acid (308d)

Compound (308d) was prepared from ethyl 2-(3-acetyl-5-(pyrimidin-5-ylamino)-1H-pyrrolo[2,3-c]pyridin-1-yl)acetate (308c) (0.02 g, 0.059 mmol) using a solution of LiOH (2.82 mg, 0.118 mmol) in Water (0.3 mL) and THF (2 mL) according to the procedure reported in Scheme 129 step-2. This gave after workup 2-(3-acetyl-5-(pyrimidin-5-ylamino)-1H-pyrrolo[2,3-c]pyridin-1-yl)acetic acid (308d) (0.02 g, 0.059 mmol, 100% yield) as a white solid; $^1$H NMR (300 MHz, Methanol-$d_4$) δ 9.06 (s, 2H), 9.01 (s, 1H), 8.86 (s, 1H), 8.76 (s, 1H), 8.14 (s, 1H), 5.30 (s, 2H), 2.56 (s, 3H); MS (ES+) 312.3 (M+1), MS (ES−) 310.3 (M−1).

Step-4: Preparation of 2-(3-acetyl-5-(pyrimidin-5-ylamino)-1H-pyrrolo[2,3-c]pyridin-1-yl)-N-(2-((3-chloro-2-fluorobenzyl)amino)-2-oxoethyl)-N-cyclopropylacetamide (308e)

Reaction of 2-(3-acetyl-5-(pyrimidin-5-ylamino)-1H-pyrrolo[2,3-c] pyridin-1-yl)acetic acid (308d) (0.02 g, 0.064 mmol) with N-(3-chloro-2-fluorobenzyl)-2-(cyclopropylamino)acetamide (10b) (0.016 g, 0.064 mmol) according to the procedure reported in step-3 of Scheme 2 gave after workup and purification by column chromatography [silica gel 4 g, DMA-80 in DCM 0 to 40% as eluents] 2-(3-acetyl-5-(pyrimidin-5-ylamino)-1H-pyrrolo [2,3-c] pyridin-1-yl)-N-(2-(3-chloro-2-fluorobenzylamino)-2-oxoethyl)-N-cyclopropylacetamide (308e) (0.008 g, 23% yield) as a white solid; $^1$H NMR (300 MHz, DMSO-$d_6$) δ 9.35 (s, 1H), 9.10 (s, 2H), 8.62 (s, 1H), 8.53 (d, J=1.0 Hz, 1H), 8.48 (t, J=5.8 Hz, 1H), 8.41 (s, 1H), 7.68 (d, J=1.0 Hz, 1H), 7.47-7.38 (m, 1H), 7.23 (t, J=7.1 Hz, 1H), 7.13-7.04 (m, 1H), 5.50 (s, 2H), 4.35 (d, J=5.7 Hz, 2H), 4.00 (s, 2H), 3.16-3.03 (m, 1H), 2.43 (s, 3H), 1.06-0.95 (m, 2H), 0.98-0.86 (m, 2H); $^{19}$F NMR (282 MHz, DMSO-$d_6$) δ −121.60; MS (ES+): 550.5 (M+1); MS (ES−): 584.5 (M+Cl).

Scheme 309

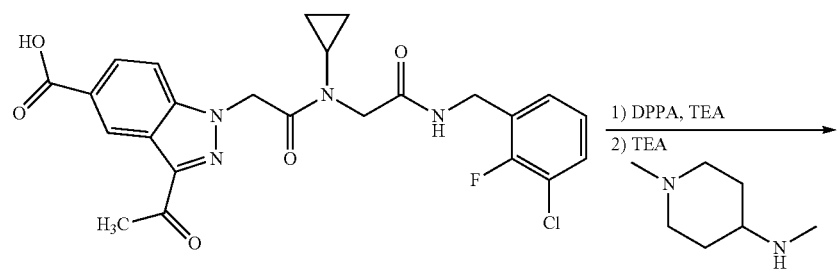

228a

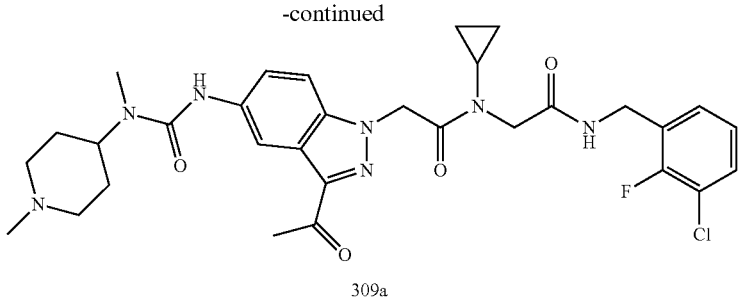

309a

Preparation of 2-(3-Acetyl-5-(3-methyl-3-(1-methylpiperidin-4-yl)ureido)-1H-indazol-1-yl)-N-(2-(3-chloro-2-fluorobenzylamino)-2-oxoethyl)-N-cyclopropylacetamide HCl salt (309a)

Reaction of 3-acetyl-1-(2-((2-(3-chloro-2-fluorobenzylamino)-2-oxoethyl)(cyclopropyl)amino)-2-oxoethyl)-1H-indazole-5-carboxylic acid (228a) (0.93 g, 1.85 mmol) with diphenyl phosphorazidate (0.41 mL, 1.85 mmol), then with N,1-dimethylpiperidin-4-amine (0.29 g, 2.22 mmol) according to the procedure reported in step-3 and step-4 of Scheme 129 gave after workup and purification by column chromatography [silica (12 g), eluting with DMA80 in DCM from 0 to 40%] and then reverse phase preparative column chromatography [C18 column, eluting with MeOH in water (containing 0.1% TFA) from 0 to 100%], followed by conversion to HCl salt using HCl (3 N HCl in MeOH, 10 mL) in methanol (10 mL) 2-(3-acetyl-5-(3-methyl-3-(1-methylpiperidin-4-yl)ureido)-1H-indazol-1-yl)-N-(2-(3-chloro-2-fluorobenzylamino)-2-oxoethyl)-N-cyclopropylacetamide (309a) (240 mg, 20% yield) HCl salt as a yellow solid; $^1$H NMR (300 MHz, DMSO-$d_6$) δ 10.82 (s, 1H), 8.66-8.49 (m, 2H), 8.27 (t, J=1.3 Hz, 1H), 7.60 (d, J=1.4 Hz, 2H), 7.51-7.39 (m, 1H), 7.27-7.19 (m, 1H), 7.18-7.05 (m, 1H), 5.71 (s, 2H), 4.42-4.26 (m, 3H), 3.99 (s, 2H), 3.47-3.35 (m, 2H), 3.19-3.00 (m, 3H), 2.86 (s, 3H), 2.71 (d, J=4.7 Hz, 3H), 2.59 (s, 3H), 2.26-2.04 (m, 2H), 1.83-1.66 (m, 2H), 1.09-0.96 (m, 2H), 0.97-0.83 (m, 2H); $^{19}$F NMR (282 MHz, DMSO-$d_6$) δ −121.64; MS (ES+): 626.7 (M+1); (ES−): 624.6 (M−1).

Scheme 310

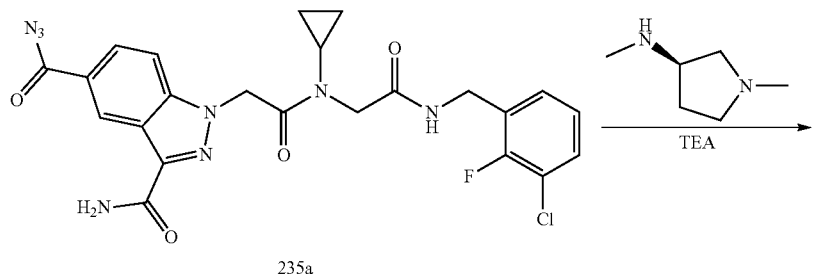

235a

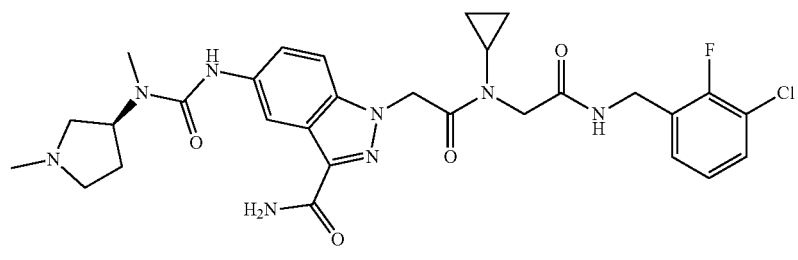

310a

535

Preparation of (R)-1-(2-((2-(3-chloro-2-fluorobenzylamino)-2-oxoethyl)(cyclopropyl)amino)-2-oxoethyl)-5-(3-methyl-3-(1-methylpyrrolidin-3-yl)ureido)-1H-indazole-3-carboxamide HCl salt (310a)

Reaction of 3-carbamoyl-1-(2-((2-(3-chloro-2-fluorobenzylamino)-2-oxoethyl)(cyclopropyl)-amino)-2-oxoethyl)-1H-indazole-5-carbonyl azide (235a) (500 mg, 0.47 mmol) with (R)—N,1-dimethylpyrrolidin-3-amine (98 mg, 0.85 mmol) according to the procedure reported in step-4 of Scheme 129 gave after workup, purification by chromatography [silica (40 g), eluting with DMA80 in DCM from 0 to 40%]; followed by [silica (24 g), eluting with EtOAc/MeOH (9:1) in hexane from 0 to 90%], then prep-HPLC [C18 column, 5 injections, eluting with CH$_3$CN in water (containing 0.1% TFA) from 0-100%]; followed by conversion to HCl salt using HCl (3 N in MeOH, 10 mL) in methanol (10 mL) (R)-1-(2-((2-(3-chloro-2-fluorobenzylamino)-2-oxoethyl)(cyclopropyl)amino)-2-oxoethyl)-5-(3-methyl-3-(1-methylpyrrolidin-3-yl)ureido)-1H-indazole-3-carboxamide (310a) (112 mg, 036% yield) HCl salt as a white solid. $^1$H NMR (300 MHz, DMSO-d$_6$) δ 10.90-10.56 (m, 1H), 8.67-8.49 (m, 2H), 8.20 (t, J=1.4 Hz, 1H), 7.71-7.60 (m, 1H), 7.59-7.52 (m, 2H), 7.48-7.40 (m, 1H), 7.37-7.29 (m, 1H), 7.28-7.19 (m, 1H), 7.17-7.08 (m, 1H), 5.63 (s, 2H), 5.05-4.89 (m, 1H), 4.33 (d, J=5.6 Hz, 2H), 3.98 (s, 2H), 3.69-3.41 (m, 2H), 3.31-3.15 (m, 1H), 3.12-2.94 (m, 5H), 2.84 (d, J=4.8 Hz) and 2.78 (d, J=4.9 Hz) (2d, 3H), 2.33-1.96 (m, 2H), 1.07-0.96 (m, 2H), 0.95-0.79 (m, 2H); $^{19}$F NMR (282 MHz, DMSO-d$_6$) δ −121.62; MS (ES+): 613.6 (M+1).

536

Preparation of (S)-5-(3-aminopiperidine-1-carboxamido)-1-(2-((2-(3-chloro-2-fluorobenzylamino)-2-oxoethyl)(cyclopropyl)amino)-2-oxoethyl)-1H-indazole-3-carboxamide TFA salt (311a)

Reaction of (5)-tert-butyl 1-(3-carbamoyl-1-(2-((2-(3-chloro-2-fluorobenzylamino)-2-oxoethyl)(cyclopropyl)amino)-2-oxoethyl)-1H-indazol-5-ylcarbamoyl)piperidin-3-ylcarbamate (294a) (185 mg, 0.27 mmol) with TFA (0.41 mL, 5.29 mmol) according to the procedure reported in step-2 of Scheme 2 gave after workup and purification by column chromatography [silica (12 g), eluting with DMA80 in DCM from 0 to 40%], then prep-HPLC [C18 column, eluting with CH$_3$CN in water (containing 0.1% TFA) from 0-100%] followed by lyophilization (S)-5-(3-aminopiperidine-1-carboxamido)-1-(2-((2-(3-chloro-2-fluorobenzylamino)-2-oxoethyl)(cyclopropyl)amino)-2-oxoethyl)-1H-indazole-3-carboxamide (311a) (112 mg, 59% yield) TFA salt as a white solid; $^1$H NMR (300 MHz, DMSO-d$_6$) δ 8.73 (s, 1H), 8.52 (t, J=5.8 Hz, 1H), 8.20 (t, J=1.3 Hz, 1H), 8.06-7.89 (m, 3H), 7.65 (s, 1H), 7.57-7.51 (m, 2H), 7.46 (td, J=7.6, 1.8 Hz, 1H), 7.31 (s, 1H), 7.27-7.19 (m, 1H), 7.18-7.09 (m, 1H), 5.61 (s, 2H), 4.33 (d, J=5.7 Hz, 2H), 4.10-4.03 (m, 1H), 3.98 (s, 2H), 3.84-3.72 (m, 1H), 3.24-3.12 (m, 2H), 3.11-3.00 (m, 2H), 2.05-1.91 (m, 1H), 1.82-1.69 (m, 1H), 1.60-1.43 (m, 2H), 1.04-0.95 (m, 2H), 0.95-0.85 (m, 2H); $^{19}$F NMR (282 MHz, DMSO-d$_6$) δ −73.79 (TFA peak), −121.60; MS (ES+): 599.5 (M+1); (ES−): 597.5 (M−1).

Scheme 311

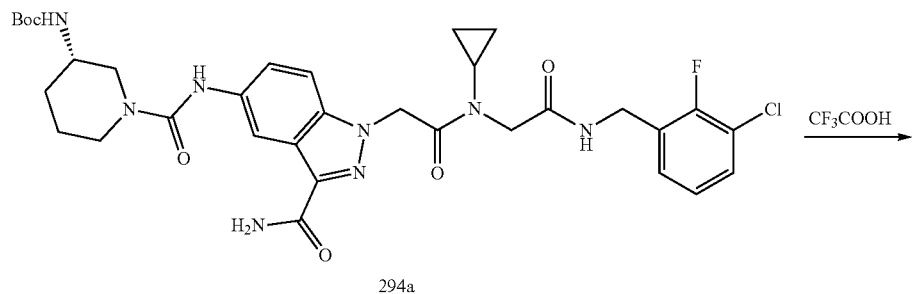

294a

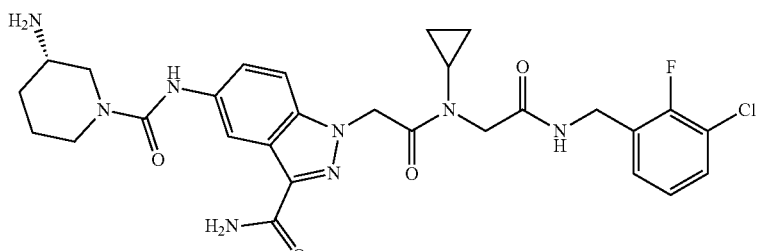

311a

Scheme 312

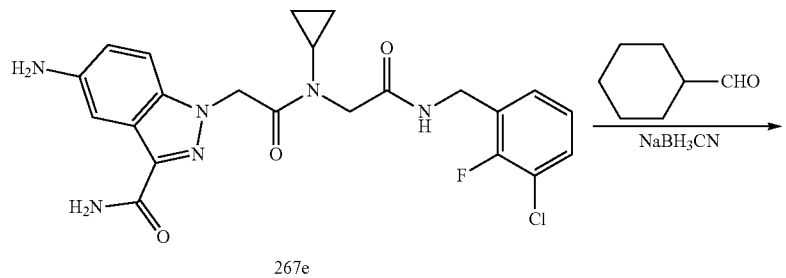

Preparation of 1-(2-((2-((3-chloro-2-fluorobenzyl) amino)-2-oxoethyl)(cyclopropyl)amino)-2-oxo-ethyl)-5-((cyclohexylmethyl)amino)-1H-indazole-3-carboxamide (312a)

Reaction of 5-amino-1-(2-((2-(3-chloro-2-fluorobenzy-lamino)-2-oxoethyl)(cyclopropyl)amino)-2-oxoethyl)-1H-indazole-3-carboxamide (267e) (0.1 g, 0.21 mmol) with cyclohexanecarbaldehyde (0.036 g, 0.32 mmol) according to the procedure reported in Scheme 276 gave after workup and purification by flash column chromatography [silica gel (12 g), eluting with 0 to 30% DMA-80 in DCM] 1-(2-((2-(3-chloro-2-fluorobenzylamino)-2-oxoethyl)(cyclopropyl) amino)-2-oxoethyl)-5-(cyclohexylmethylamino)-1H-indazole-3-carboxamide (312a) (0.018 g, 15% yield) as a white solid; $^1$H NMR (300 MHz, DMSO-$d_6$) δ 8.49 (t, J=5.8 Hz, 1H), 7.55-7.40 (m, 2H), 7.34 (d, J=8.9 Hz, 1H), 7.29-7.01 (m, 5H), 6.97-6.83 (m, 1H), 5.53 (s, 2H), 4.33 (d, J=5.7 Hz, 2H), 3.97 (s, 2H), 3.11-2.96 (m, 1H), 2.88 (d, J=6.5 Hz, 2H), 1.93-1.78 (m, 2H), 1.78-1.50 (m, 3H), 1.33-0.80 (m, 10H); $^{19}$F NMR (282 MHz, DMSO-$d_6$) δ −121.60; MS (ES+): 569.5 (M+1), MS (ES−): 603.5 (M+Cl).

Scheme 313

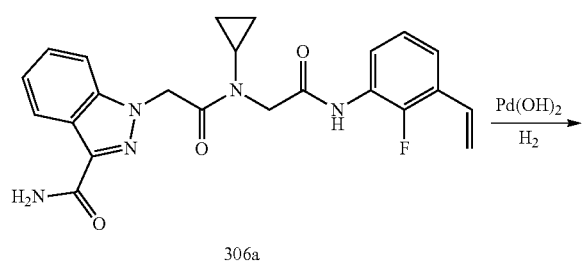

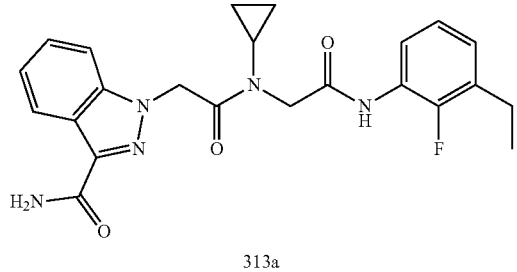

Preparation of 1-(2-(cyclopropyl(2-((3-ethyl-2-fluo-rophenyl)amino)-2-oxoethyl)amino)-2-oxoethyl)-1H-indazole-3-carboxamide (313a)

Compound (313a) was prepared according to the procedure reported in Scheme 79 from 1-(2-(cyclopropyl(2-(2-fluoro-3-vinylphenylamino)-2-oxoethyl)amino)-2-oxo-ethyl)-1H-indazole-3-carboxamide (306a) (0.07 g, 0.161 mmol) in EtOAc (5 mL) using dihydroxypalladium (0.113 mg, 0.804 μmop. This gave after workup and purification by flash chromatography [silica gel 4 g, DMA-80 DCM, 0 to 20% as eluents] to afford 1-(2-(cyclopropyl(2-((3-ethyl-2-fluorophenyl)amino)-2-oxoethyl)amino)-2-oxoethyl)-1H-indazole-3-carboxamide (313a) (0.03 g, 43% yield) as a white solid; 1H NMR (300 MHz, DMSO-$d_6$) δ 9.78 (s, 1H), 8.18 (dt, J=8.2, 1.0 Hz, 1H), 7.90-6.91 (m, 8H), 5.70 (s, 2H), 4.20 (s, 2H), 3.18-3.04 (m, 1H), 2.61 (q, J=7.4 Hz, 2H), 1.15 (t, J=7.5 Hz, 3H), 1.06-0.95 (m, 2H), 1.00-0.89 (m, 2H); 19F NMR (282 MHz, DMSO-$d_6$) δ −131.78; MS (ES+): 438.5 (M+1), 460.4 (M+Na), MS (ES−): 472.4 (M+Cl).

Scheme 314
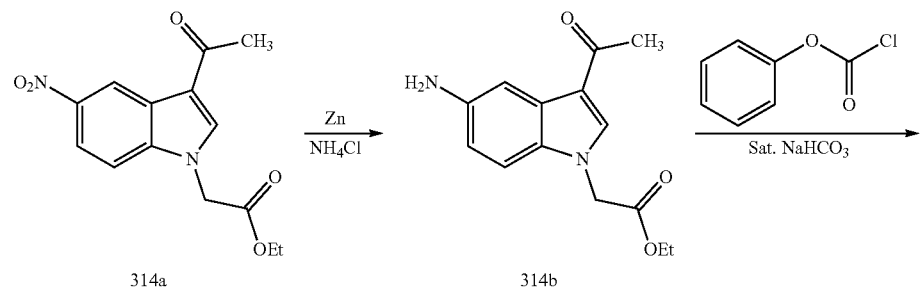
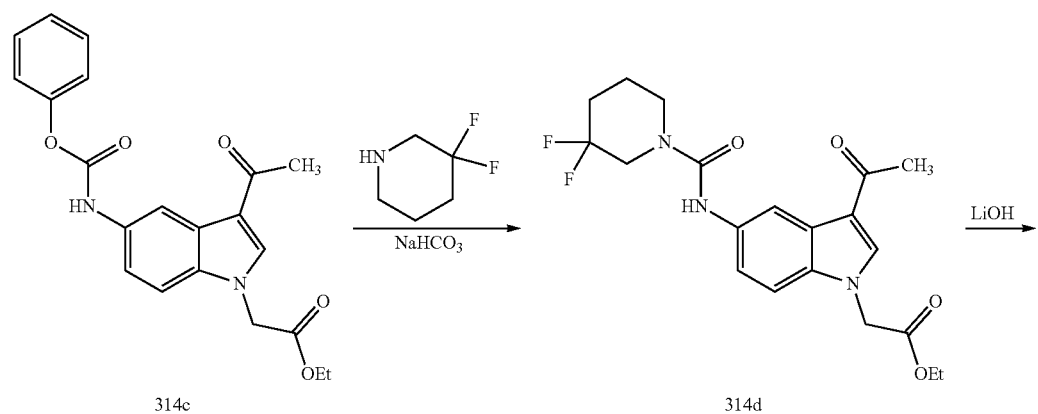
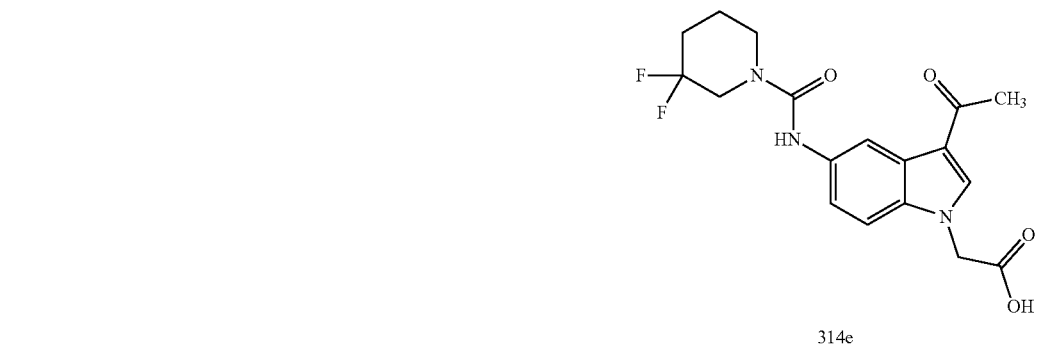
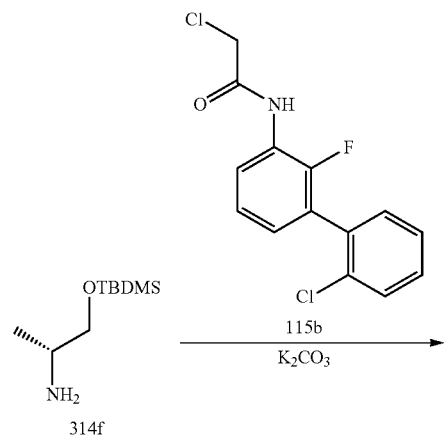

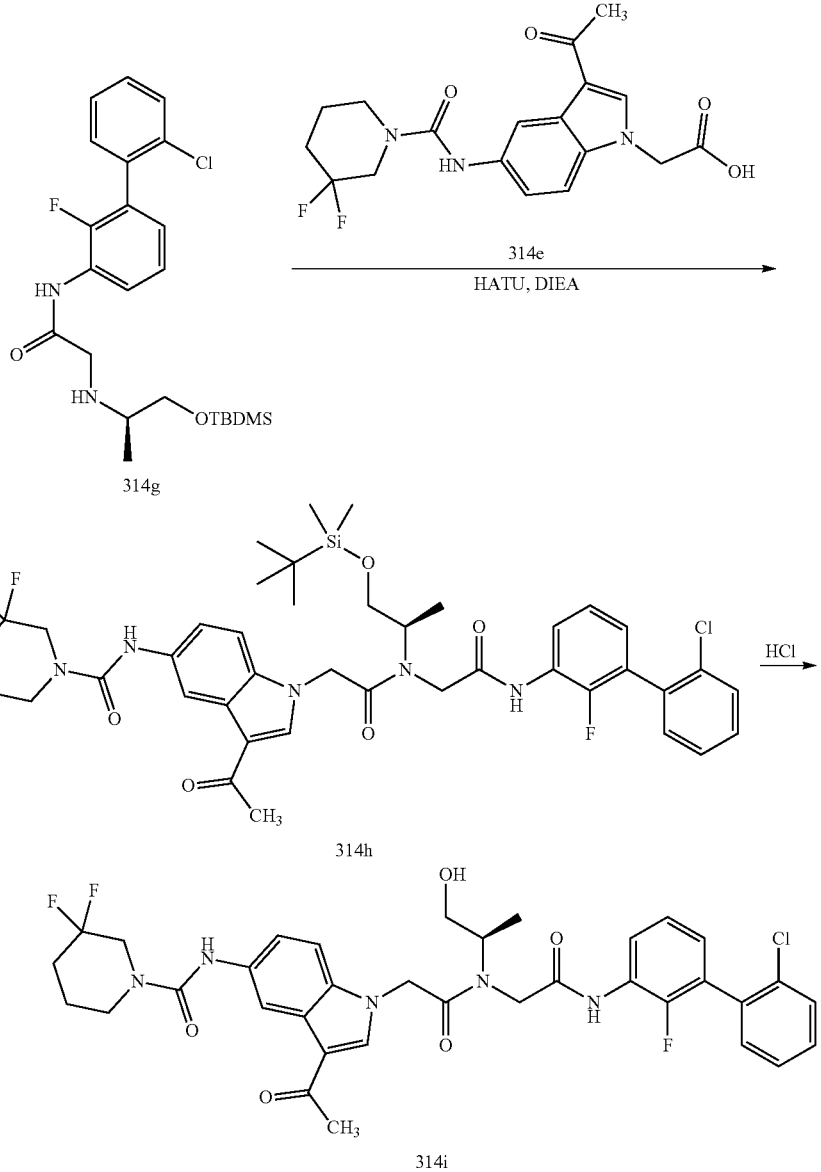

Preparation of (R)—N-(3-acetyl-1-(2-((2-((2'-chloro-2-fluoro-[1,1'-biphenyl]-3-yl)-amino)-2-oxo-ethyl)(1-hydroxy propan-2-yl)-amino)-2-oxoethyl)-1H-indol-5-yl)-3,3-difluoropiperidine-1-carboxamide (314i)

Step-1: Preparation of ethyl 2-(3-acetyl-5-amino-1H-indol-1-yl)acetate (314b)

Compound 314b was prepared from ethyl 2-(3-acetyl-5-nitro-1H-indol-1-yl)acetate (314a) (6.00 g, 20.67 mmol, prepared according to procedure reported by Venkatanarayana, Muvvala and Dubey, Pramod K. in Letters in Organic Chemistry, 9(3), 192-197; 2012) using ammonium chloride (17.69 g, 331 mmol), zinc powder (10.82 g, 165 mmol) in THF (120 mL), methanol (30 mL); according to the procedure reported in step-4 of Scheme 267. This gave after workup and purification by flash column chromatography [Silica gel 120 g, eluting with ethyl acetate/methanol (9:1) in hexanes from 0-100%] ethyl 2-(3-acetyl-5-amino-1H-indol-1-yl)acetate (314b) (4.28 g, 80% yield) as a yellow solid; $^1$H NMR (300 MHz, DMSO-d$_6$) δ 8.08 (s, 1H), 7.41 (d, J=2.2 Hz, 1H), 7.12 (d, J=8.7 Hz, 1H), 6.57 (dd, J=8.6, 2.2 Hz, 1H), 5.09 (s, 2H), 4.89 (s, 2H, D$_2$O exchangeable), 4.16 (q, J=7.0 Hz, 2H), 2.36 (s, 3H), 1.22 (t, J=7.1 Hz, 3H); MS (ES+): 261.4 (M+1).

Step-2: Preparation of ethyl 2-(3-acetyl-5-(phenoxycarbonylamino)-1H-indol-1-yl)acetate (314c)

To a biphasic solution of ethyl 2-(3-acetyl-5-amino-1H-indol-1-yl)acetate (314b) (1.00 g, 3.84 mmol) in EtOAc (10 mL) and sat. NaHCO$_3$ (5 mL) was added phenyl chloroformate (0.627 mL, 4.99 mmol) and stirred at room temperature for 13 h. The organic layer was separated and aqueous layer was extracted with EtOAc (2×50 mL). The combined organics were washed with brine, dried, filtered, and concentrated in vacuum to afford ethyl 2-(3-acetyl-5-(phenoxycarbonylamino)-1H-indol-1-yl)acetate (314c) (1.41 g, 96% yield) as a brown solid; ¹H NMR (300 MHz, DMSO-d₆) δ 10.16 (s, 1H), 8.31 (s, 1H), 7.47-7.40 (m, 3H), 7.27-7.21 (m, 3H), 7.19-7.12 (m, 1H), 6.87-6.66 (m, 1H), 5.21 (s, 2H), 4.18 (q, J=7.1 Hz, 2H), 2.42 (s, 3H), 1.23 (t, J=7.1 Hz, 3H); MS (ES+): 381.4 (M+1).

Step-3: Preparation of ethyl 2-(3-acetyl-5-(3,3-difluoropiperidine-1-carboxamido)-1H-indol-1-yl)acetate (314d)

To a solution of ethyl 2-(3-acetyl-5-(phenoxycarbonylamino)-1H-indol-1-yl)acetate (314c) (1.39 g, 3.65 mmol) in THF (40 mL) was added 3,3-difluoropiperidine hydrochloride (0.576 g, 3.65 mmol), a solution of sodium bicarbonate (1.535 g, 18.27 mmol) in water (5 mL) and stirred at 65° C. for 4.5 h. The reaction mixture was cooled to room temperature and partitioned between water (100 mL) and EtOAc (100 mL). The aqueous layer was separated, extracted with EtOAc (100 mL). The combined organics were washed with brine, dried, filtered and evaporated to dryness. The crude product was purified by flash column chromatography [Silica gel, 24 g eluting with ethyl acetate/methanol (9:1) in hexanes from 0-100%] to afford ethyl 2-(3-acetyl-5-(3,3-difluoropiperidine-1-carboxamido)-1H-indol-1-yl)acetate (314d) (0.991 g, 67% yield) as a yellow solid; ¹H NMR (300 MHz, DMSO-d₆) δ 8.66 (s, 1H), 8.26 (s, 1H), 8.19 (dd, J=2.0, 0.7 Hz, 1H), 7.47-7.32 (m, 2H), 5.19 (s, 2H), 4.17 (q, J=7.1 Hz, 2H), 3.80 (t, J=12.1 Hz, 2H), 3.51 (t, J=5.5 Hz, 2H), 2.42 (s, 3H), 2.15-1.96 (m, 2H), 1.79-1.64 (m, 2H), 1.22 (t, J=7.1 Hz, 3H); MS (ES+): 408.5 (M+1), 815.8 (2M+1), 834.8 (2M+Na); MS (ES−): 406.4 (M−1).

Step-4: Preparation of 2-(3-Acetyl-5-(3,3-difluoropiperidine-1-carboxamido)-1H-indol-1-yl)acetic acid (314e)

Compound (314e) was prepared from ethyl 2-(3-acetyl-5-(3,3-difluoropiperidine-1-carboxamido)-1H-indol-1-yl)acetate (314d) (0.956 g, 2.347 mmol) using a solution of LiOH (0.169 g, 7.04 mmol) in Water (3 mL) and THF (15 mL) according to the procedure reported in Scheme 129 step-2. This gave after workup 2-(3-acetyl-5-(3,3-difluoropiperidine-1-carboxamido)-1H-indol-1-yl)acetic acid (314e) (0.557 g, 63% yield) as a brick-red solid; ¹H NMR (300 MHz, DMSO-d₆) δ 13.22 (s, 1H), 8.66 (s, 1H), 8.26 (s, 1H), 8.22-8.13 (m, 1H), 7.50-7.28 (m, 2H), 5.07 (s, 2H), 3.80 (t, J=12.1 Hz, 2H), 3.51 (t, J=5.4 Hz, 2H), 2.41 (s, 3H), 2.17-1.92 (m, 2H), 1.71 (s, 2H); MS (ES−): 378.3 (M−1), 757.5 (2M−1).

Step-5: Preparation of (R)-2-((1-((tert-butyldimethylsilyl)oxy)propan-2-yl)-amino)-N-(2'-chloro-2-fluoro-[1,1'-biphenyl]-3-yl)acetamide (314 g)

Compound 314f was prepared according to the procedure reported in step-2 of Scheme 35 from 2-chloro-N-(2'-chloro-2-fluoro-[1,1'-biphenyl]-3-yl)acetamide (115b) (2.00 g, 6.71 mmol) and (R)-1-((tert-butyldimethylsilyl)oxy)propan-2-amine (314f) (1.65 g, 8.72 mmol, prepared according to the procedure reported by Chen, Yi et al, in U S. Pat. Appl. Publ., 20040204427, 14 Oct. 2004). This gave after workup and purification by flash column chromatography [Silica gel, 40 g eluting with ethyl acetate in hexanes from 0-20%] (R)-2-((1-((tert-butyldimethylsilyl)oxy)propan-2-yl)-amino)-N-(2'-chloro-2-fluoro-[1,1'-biphenyl]-3-yl)acetamide (314 g) (1.64 g, 54% yield) as a thick colorless oil; ¹H NMR (300 MHz, DMSO-d₆) δ 9.99 (s, 1H), 8.22 (td, J=7.9, 1.7 Hz, 1H), 7.64-7.56 (m, 1H), 7.52-7.37 (m, 3H), 7.26 (td, J=7.9, 1.0 Hz, 1H), 7.10-7.03 (m, 1H), 3.45 (d, J=5.6 Hz, 2H), 3.37 (d, J=1.6 Hz, 2H), 3.16 (d, J=5.2 Hz, 1H), 2.77-2.61 (m, 1H), 0.95 (d, J=6.3 Hz, 3H), 0.83 (s, 9H), 0.00 (s, 3H), −0.00 (s, 3H); ¹⁹F NMR (282 MHz, DMSO-d₆) δ −130.68; MS (ES+): 451.5, 453.5 (M+1); MS (ES−): 449.4, 451.4 (M−1).

Step-6: Preparation of (R)—N-(3-acetyl-1-(2-((1-(tert-butyldimethylsilyloxy)propan-2-yl)(2-(2'-chloro-2-fluorobiphenyl-3-ylamino)-2-oxoethyl)amino)-2-oxoethyl)-1H-indol-5-yl)-3,3-difluoropiperidine-1-carboxamide (314 h)

Compound 314h was prepared from (R)-2-(1-(tert-butyldimethylsilyloxy)propan-2-ylamino)-N-(2'-chloro-2-fluorobiphenyl-3-yl)acetamide (314 g) (297 mg, 0.66 mmol) by reaction with 2-(3-Acetyl-5-(3,3-difluoropiperidine-1-carboxamido)-1H-indol-1-yl)acetic acid (314e) (250 mg, 0.766 mmol) according to the procedure reported in step-3 of Scheme 2. This gave after workup and purification by flash column chromatography [Silica gel, 12 g eluting with methanol in DCM from 0-10%] (R)—N-(3-acetyl-1-(2-((1-(tert-butyldimethylsilyloxy)propan-2-yl)(2-(2'-chloro-2-fluorobiphenyl-3-ylamino)-2-oxoethyl)amino)-2-oxoethyl)-1H-indol-5-yl)-3,3-difluoropiperidine-1-carboxamide (314 h) (0.27 g, 51% yield) as a yellow solid; MS (ES+): 812.6 (M+1); MS (ES−): 846.6 (M+Cl).

Step-7: Preparation of (R)—N-(3-acetyl-1-(2-((2-((2'-chloro-2-fluoro-[1,1'-biphenyl]-3-yl)amino)-2-oxoethyl)(1-hydroxypropan-2-yl)amino)-2-oxoethyl)-1H-indol-5-yl)-3,3-difluoropiperidine-1-carboxamide (314i)

Compound 314i was prepared from (R)—N-(3-acetyl-1-(2-((1-(tert-butyldimethylsilyloxy)propan-2-yl)(2-(2'-chloro-2-fluorobiphenyl-3-ylamino)-2-oxoethyl)amino)-2-oxoethyl)-1H-indol-5-yl)-3,3-difluoropiperidine-1-carboxamide (314 h) (204 mg, 0.25 mmol) by reaction with 12N aq. HCl (0.209 mL, 2.51 mmol) in MTBE (5.00 mL) according to the procedure reported in step-3 of Scheme 292. This gave after workup and purification by flash column chromatography [Silica gel, 24 g eluting with methanol in DCM from 0-20%) (R)—N-(3-acetyl-1-(2-((2-((2'-chloro-2-fluoro-[1,1'-biphenyl]-3-yl)-amino)-2-oxoethyl)(1-hydroxypropan-2-yl)amino)-2-oxoethyl)-1H-indol-5-yl)-3,3-difluoropiperidine-1-carboxamide (314i) (50 mg, 29% yield) as a white solid; ¹H NMR (300 MHz, DMSO-d₆) δ 10.27 & 9.97 (2s, 1H, D₂O exchangeable), 8.635 & 8.645 (s, 1H), 8.29-7.84 (m, 4H), 7.66-7.57 (m, 1H), 7.55-7.26 (m, 4H), 7.27-7.02 (m, 2H), 5.48 (t, J=5.7 Hz) & 4.88-4.81 (m, 1H), 5.36 & 5.17 (2s, 2H), 4.59-4.43 (m, 1H), 4.28-4.13 (m, 1H), 4.00 & 3.94 (2s, 1H), 3.80 (t, J=12.1 Hz, 2H), 3.58-3.48 (m, 4H), 2.41 (s, 1H), 2.38 (s, 2H), 2.17-1.94 (m, 2H), 1.81-1.59 (m, 2H), 1.19 (d, J=6.6 Hz) & 1.05 (d, J=6.9 Hz) (2d, 3H); ¹⁹F NMR (282 MHz, DMSO-d₆) δ −101.10, −127.32; MS (ES+): 720.5 (M+Na); MS (ES−): 696.6 (M−1).

Scheme 315

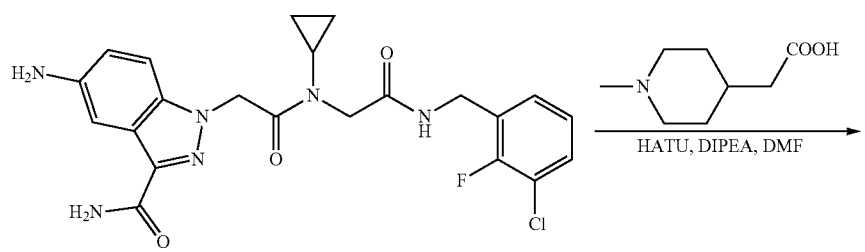

Preparation of 1-(2-((2-(3-chloro-2-fluorobenzylamino)-2-oxoethyl)(cyclopropyl)amino)-2-oxoethyl)-5-(2-(1-methylpiperidin-4-yl)acetamido)-1H-indazole-3-carboxamide (315a)

Reaction of 5-amino-1-(2-((2-(3-chloro-2-fluorobenzylamino)-2-oxoethyl)(cyclopropyl)amino)-2-oxoethyl)-1H-indazole-3-carboxamide (267e) (0.15 g, 0.317 mmol) with 2-(1-methylpiperidin-4-yl)acetic acid (0.055 g, 0.349 mmol) according to the procedure reported in step-3 of Scheme 2 gave after workup and purification by flash column chromatography [silica gel 12 g, DMA80 in DCM 0 to 100% as eluents] 1-(2-((2-(3-chloro-2-fluorobenzylamino)-2-oxoethyl)(cyclopropyl)amino)-2-oxoethyl)-5-(2-(1-methylpiperidin-4-yl)acetamido)-1H-indazole-3-carboxamide (315a) (0.053 g, 27% yield) as an off-white solid; $^1$H NMR (300 MHz, DMSO-$d_6$) δ 9.99 (s, 1H), 8.49 (t, J=5.8 Hz, 1H), 8.46-8.43 (m, 1H), 7.66 (s, 1H), 7.64-7.52 (m, 2H), 7.50-7.41 (m, 1H), 7.35 (s, 1H), 7.23 (t, J=6.9 Hz, 1H), 7.16-7.07 (m, 1H), 5.62 (s, 2H), 4.33 (d, J=5.7 Hz, 2H), 3.98 (s, 2H), 3.13-2.99 (m, 1H), 2.84-2.73 (m, 2H), 2.24 (d, J=7.0 Hz, 2H), 2.18 (s, 3H), 2.02-1.82 (m, 2H), 1.81-1.58 (m, 3H), 1.35-1.17 (m, 2H), 1.03-0.95 (m, 2H), 0.95-0.85 (m, 2H); $^{19}$F NMR (282 MHz, DMSO-$d_6$) δ −121.59; MS (ES+): 612.6 (M+1), MS (ES−): 646.5 (M+Cl).

Scheme 316

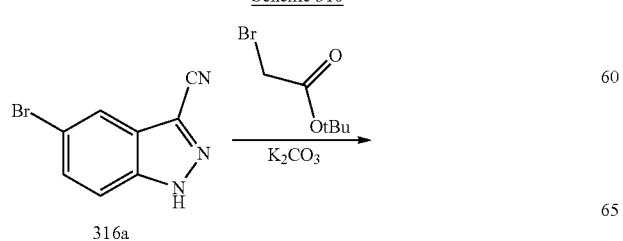

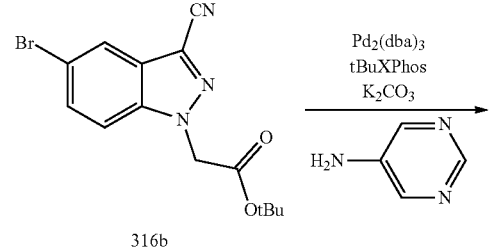

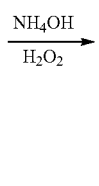

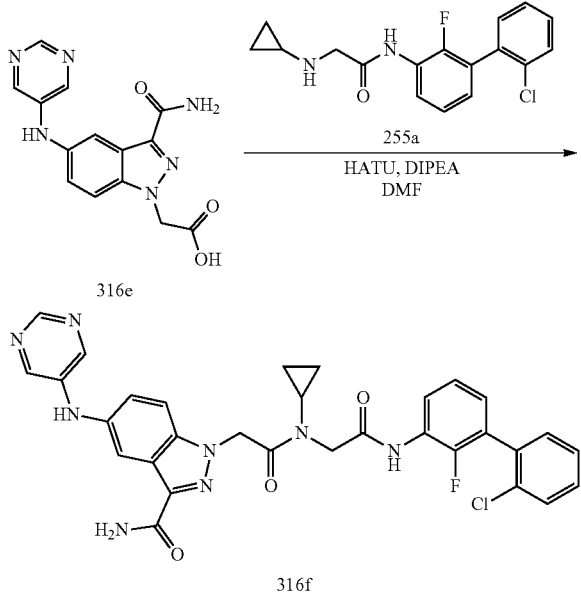

Preparation of 1-(2-((2-((2'-chloro-2-fluoro-[1,1'-biphenyl]-3-yl)-amino)-2-oxoethyl)(cyclopropyl) amino)-2-oxoethyl)-5-(pyrimidin-5-ylamino)-1H-indazole-3-carboxamide (316f)

Step-1: Preparation of tert-butyl 2-(5-bromo-3-cyano-1H-indazol-1-yl)acetate (316b)

Reaction of 5-bromo-1H-indazole-3-carbonitrile (316a) (0.85 g, 3.83 mmol, prepared according to the procedure reported By Boyd, Scott et al; in Journal of Medicinal Chemistry, 58(8), 3611-3625; 2015) with tert-butylbromoacetate (1.13 mL, 7.66 mmol) in acetonitrile (40 mL) using potassium carbonate (1.06 g, 7.66 mmol) as base, according to the procedure reported in step-1 of Scheme 43 gave after workup and purification by column chromatography [silica gel (24 g), eluting with EtOAc in hexane 0 to 60%] tert-butyl 2-(5-bromo-3-cyano-1H-indazol-1-yl)acetate (316b) (0.95 g, 74% yield) as an off-white solid; $^1$H NMR (300 MHz, DMSO-$d_6$) δ 8.21 (dd, J=1.8, 0.7 Hz, 1H), 7.94-7.88 (m, 1H), 7.76 (dd, J=9.0, 1.8 Hz, 1H), 5.53 (s, 2H), 1.40 (s, 9H).

Step-2: Preparation of tert-butyl 2-(3-cyano-5-(pyrimidin-5-ylamino)-1H-indazol-1-yl)acetate (316c)

Reaction of tert-butyl 2-(5-bromo-3-cyano-1H-indazol-1-yl)acetate (316b) (0.5 g, 1.49 mmol), with pyrimidin-5-amine (212 mg, 2.23 mmol) using Potassium carbonate (0.41 g, 2.97 mmol), di-tert-butyl(2',4',6'-triisopropylbiphenyl-2-yl)phosphine (95 mg, 0.223 mmol), Pd$_2$(dba)$_3$ (95 mg, 0.104 mmol) according to the procedure reported in step-1 of Scheme 97 gave after workup and purification by flash column chromatography [silica gel (12 g), eluting with EtOAc in Hexane 0 to 100%] tert-butyl 2-(3-cyano-5-(pyrimidin-5-ylamino)-1H-indazol-1-yl)acetate (316c) (0.375 g, 72% yield) as an off-white solid; $^1$H NMR (300 MHz, DMSO-$d_6$) δ 8.78 (s, 1H), 8.70 (s, 1H), 8.64 (s, 2H), 7.84 (dd, J=9.1, 0.7 Hz, 1H), 7.49 (dd, J=2.1, 0.7 Hz, 1H), 7.42 (dd, J=9.1, 2.1 Hz, 1H), 5.46 (s, 2H), 1.42 (s, 9H); MS (ES+): 351.4 (M+1), MS (ES-): 349.3 (M-1).

Step-3: Preparation of tert-butyl 2-(3-carbamoyl-5-(pyrimidin-5-ylamino)-1H-indazol-1-yl)acetate (316d)

Reaction of tert-butyl 2-(3-cyano-5-(pyrimidin-5-ylamino)-1H-indazol-1-yl)acetate (316c) (350 mg, 1.0 mmol) in EtOH (10 mL) with conc. NH$_4$OH Ammonium hydroxide (0.78 mL, 19.98 mmol) and Hydrogen peroxide (35% aqueous, 0.46 mL, 14.98 mmol) according to the procedure reported in Scheme 65 gave after workup tert-butyl 2-(3-carbamoyl-5-(pyrimidin-5-ylamino)-1H-indazol-1-yl)acetate (316d) (0.32 g, 87% yield) as a off-white solid; $^1$H NMR (300 MHz, DMSO-$d_6$) δ 8.64 (s, 1H), 8.63 (s, 1H), 8.52 (s, 2H), 7.94-7.89 (m, 1H), 7.73-7.66 (m, 2H), 7.39 (s, 1H), 7.33 (dd, J=9.0, 2.2 Hz, 1H), 5.32 (s, 2H), 1.42 (s, 9H); MS (ES-): 403.3 (M-1).

Step-4: Preparation of 2-(3-carbamoyl-5-(pyrimidin-5-ylamino)-1H-indazol-1-yl)acetic acid (316e)

Reaction of tert-butyl 2-(3-carbamoyl-5-(pyrimidin-5-ylamino)-1H-indazol-1-yl)acetate (316d) (320 mg, 0.87 mmol) with TFA (1.00 mL, 13.03 mmol) according to the procedure reported in step-2 of Scheme 2 gave after workup and trituration of crude with toluene (2×15 mL) and 30% EtOAc-hexane (10 mL), 2-(3-carbamoyl-5-(pyrimidin-5-ylamino)-1H-indazol-1-yl)acetic acid (316e) (0.31 g, 84% yield) as a dark brown solid; MS (ES+): 313.3 (M+1).

Step-5: Preparation of 1-(2-((2-((2'-chloro-2-fluoro-[1,1'-biphenyl]-3-yl)-amino)-2-oxoethyl)(cyclopropyl)amino)-2-oxoethyl)-5-(pyrimidin-5-ylamino)-1H-indazole-3-carboxamide (316f)

Reaction of 2-(3-carbamoyl-5-(pyrimidin-5-ylamino)-1H-indazol-1-yl)acetic acid (316e) (94 mg, 0.30 mmol) with N-(2'-chloro-2-fluoro-[1,1'-biphenyl]-3-yl)-2-(cyclopropylamino)acetamide (255a) (60 mg, 0.19 mmol) according to the procedure reported in step-3 of Scheme 2 gave after workup and purification by flash column [silica gel (12 g), eluting with CMA-80 in CHCl$_3$ 0-50%] 1-(2-((2-((2'-chloro-2-fluoro-[1,1'-biphenyl]-3-yl)-amino)-2-oxoethyl)(cyclopropyl)amino)-2-oxoethyl)-5-(pyrimidin-5-ylamino)-1H-indazole-3-carboxamide (316f) (0.018 g, 16% yield) as an off-white solid; $^1$H NMR (300 MHz, DMSO-$d_6$) δ 9.96 (s, 1H), 8.62 (d, J=1.6 Hz, 2H), 8.52 (s, 2H), 7.98 (t, J=7.9 Hz, 1H), 7.92 (d, J=2.1 Hz, 1H), 7.75-7.54 (m, 3H), 7.52-7.19 (m, 6H), 7.13-7.03 (m, 1H), 5.68 (s, 2H), 4.24 (s, 2H), 3.19-3.05 (m, 1H), 1.09-0.99 (m, 2H), 1.00-0.90 (m, 2H); $^{19}$F NMR (282 MHz, DMSO-$d_6$) δ -126.71; MS (ES+) 613.5 (M+1), MS (ES-): 647.5 (M+Cl).

Scheme 317

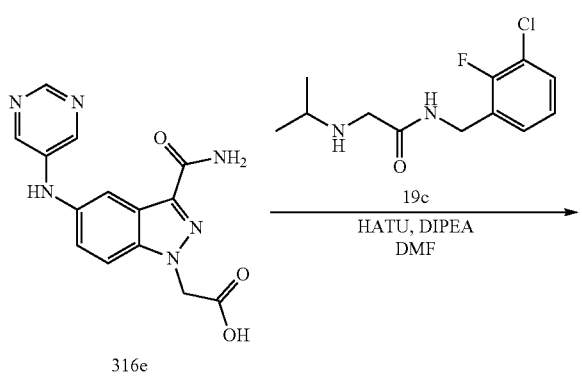

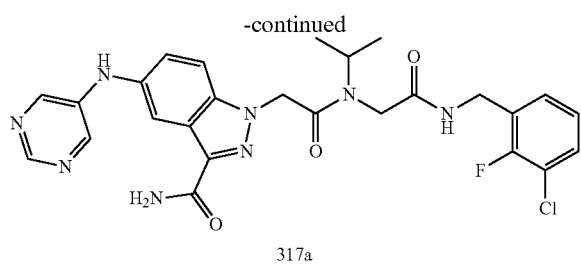

317a

Preparation of 1-(2-((2-((3-chloro-2-fluorobenzyl)amino)-2-oxoethyl)(isopropyl)amino)-2-oxoethyl)-5-(pyrimidin-5-ylamino)-1H-indazole-3-carboxamide (317a)

Reaction of 2-(3-carbamoyl-5-(pyrimidin-5-ylamino)-1H-indazol-1-yl)acetic acid (316e) (87 mg, 0.28 mmol) with N-(3-chloro-2-fluorobenzyl)-2-(isopropylamino)acetamide (19c) (60 mg, 0.23 mmol) according to the procedure reported in step-3 of Scheme 2 gave after workup and purification by flash column [silica gel (4 g), eluting with DMA-80 in DCM 0-40%] 1-(2-((2-((3-chloro-2-fluorobenzyl)amino)-2-oxoethyl)(isopropyl)amino)-2-oxoethyl)-5-(pyrimidin-5-ylamino)-1H-indazole-3-carboxamide (317a) (0.015 g, 12% yield) as an off-white solid; $^1$H NMR (300 MHz, DMSO-$d_6$) (a mixture of two rotamers) δ 8.83 and 8.37 (2t, J=5.7 Hz, 1H), 8.62 and 8.61 (2s, 1H), 8.52 (s, 2H), 7.929 and 7.92 (2s, 1H), 7.73-7.01 (m, 8H), 5.57 and 5.43 (2s, 2H), 4.63-4.50 and 4.32-4.20 (2m, 1H), 4.46 and 4.32 (2d, J=5.8 Hz, 2H), 4.18 and 3.84 (2s, 2H), 1.22 and 0.99 (2d, J=6.8 Hz, 6H); $^{19}$F NMR (282 MHz, DMSO-$d_6$) (a mixture of two rotamers) δ −121.21, −121.72; MS (ES+): 553.5 (M+1), MS (ES−): 587.4 (M+Cl).

Scheme 318

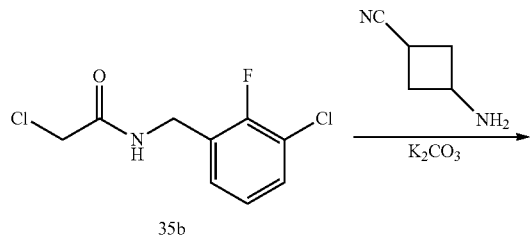

35b

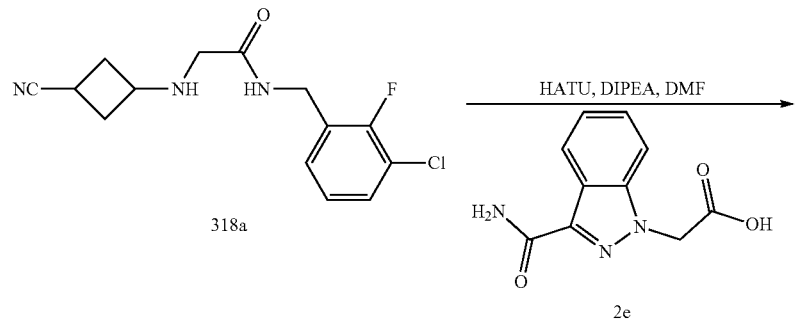

318a

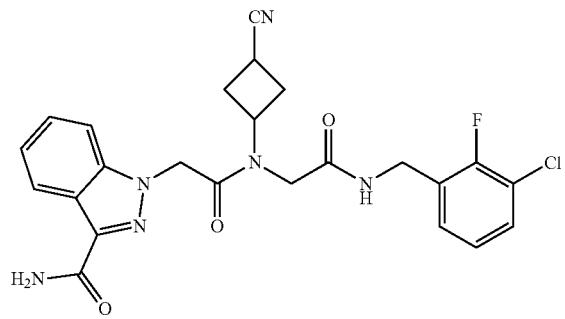

318b

Preparation of 1-(2-((2-((3-chloro-2-fluorobenzyl)amino)-2-oxoethyl)(3-cyanocyclobutyl)amino)-2-oxoethyl)-1H-indazole-3-carboxamide (318b)

Step-1: Preparation of N-(3-chloro-2-fluorobenzyl)-2-((3-cyanocyclobutyl)amino)acetamide (318a)

Reaction of 2-chloro-N-(3-chloro-2-fluorobenzyl)acetamide (35b) (410 mg, 1.74 mmol) with 3-aminocyclobutanecarbonitrile (250 mg, 2.61 mmol) according to the procedure reported in step-2 of Scheme 35 gave after workup N-(3-chloro-2-fluorobenzyl)-2-((3-cyanocyclobutyl)amino)acetamide (318a) (0.514 g, 100% yield) as a yellow wax; MS (ES+): 296.3 (M+1); MS (ES−): 294.3 (M−1).

Step-2: Preparation of 1-(2-((2-((3-chloro-2-fluorobenzyl)amino)-2-oxoethyl)(3-cyanocyclobutyl)amino)-2-oxoethyl)-1H-indazole-3-carboxamide (318b)

Reaction of N-(3-chloro-2-fluorobenzyl)-2-((3-cyanocyclobutyl)amino)acetamide (318a) (514 mg, 1.74 mmol) with 2-(3-carbamoyl-1H-indazol-1-yl)acetic acid (2e) (381 mg, 1.74 mmol) according to the procedure reported in step-3 of Scheme 2 gave after workup and purification by flash column chromatography [Silica gel, (24 g) eluting with ethyl acetate/methanol (9:1) in hexanes from 0-100%] 1-(2-((2-((3-chloro-2-fluorobenzyl)amino)-2-oxoethyl)(3-cyanocyclobutyl)amino)-2-oxoethyl)-1H-indazole-3-carboxamide (318b) (0.257 g, 30% yield) as a white solid; $^1$H NMR (300 MHz, DMSO-$d_6$) δ 8.91 (t, J=5.8 Hz) & 8.50 (t, J=5.8 Hz) (t, 1H), 8.19 & 8.16 (2s, 1H), 7.71 (bs, 1H), 7.62-7.36 (m, 4H), 7.33-7.04 (m, 3H), 5.57 & 5.41 (2s, 2H), 4.71-4.06 (m, 5H), 3.13-2.90 (m, 1H), 2.74-2.53 (m, 2H), 2.46-2.30 (m, 2H); $^{19}$F NMR (282 MHz, DMSO-$d_6$) δ −121.23, −121.59; MS (ES+): 519.4 (M+Na); MS (ES−): 495.4 (M−1).

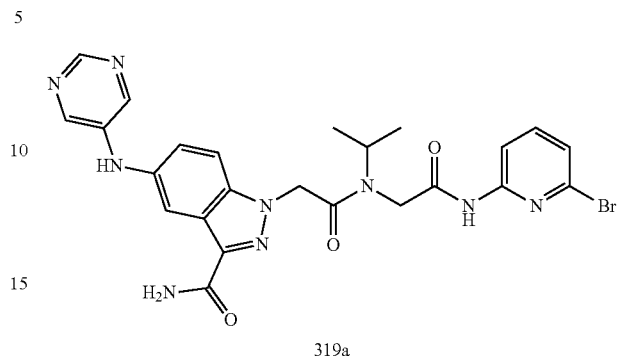

319a

Preparation of 1-(2-((2-(((6-bromopyridin-2-yl)amino)-2-oxoethyl)(isopropyl)amino)-2-oxoethyl)-5-(pyrimidin-5-ylamino)-1H-indazole-3-carboxamide (319a)

Reaction of 2-(3-carbamoyl-5-(pyrimidin-5-ylamino)-1H-indazol-1-yl)acetic acid (316e) (96 mg, 0.31 mmol) with N-(6-bromopyridin-2-yl)-2-(isopropylamino)acetamide (28b) (60 mg, 0.22 mmol) according to the procedure reported in step-3 of Scheme 2 gave after workup and purification by flash column [silica gel (4 g), eluting with DMA-80 in DCM 0-50%] 1-(2-((2-(((6-bromopyridin-2-yl)amino)-2-oxoethyl)(isopropyl)amino)-2-oxoethyl)-5-(pyrimidin-5-ylamino)-1H-indazole-3-carboxamide (319a) (0.014 g, 11% yield) as an off-white solid; $^1$H NMR (300 MHz, DMSO-$d_6$) (a mixture of two rotamers) δ 11.20 and 10.82 (2s, 1H), 8.64-8.60 (m, 2H), 8.52 and 8.51 (2s, 2H), 8.16 and 8.01 (2d, J=8.2 Hz, 1H), 7.92 and 7.90 (2d, J=2.1 Hz, 1H), 7.87-7.53 (m, 3H), 7.46-7.23 (m, 3H), 5.61 and 5.44 (2s, 2H), 4.69-4.55 and 4.38-4.26 (2m, 1H), 4.43 and 4.03 (2s, 2H), 1.24 and 1.03 (2d, J=6.8 Hz, 6H); MS (ES+): 566.4, 568.4 (M+1), MS (ES−): 600.3, 602.3 (M+Cl).

Scheme 319

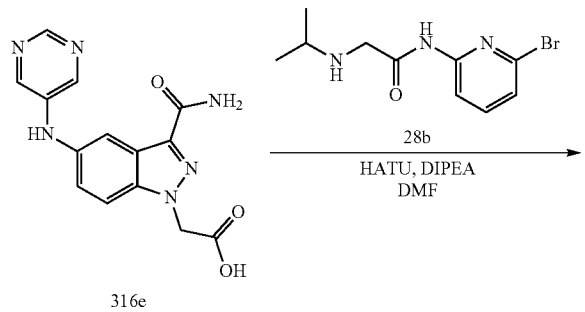

316e

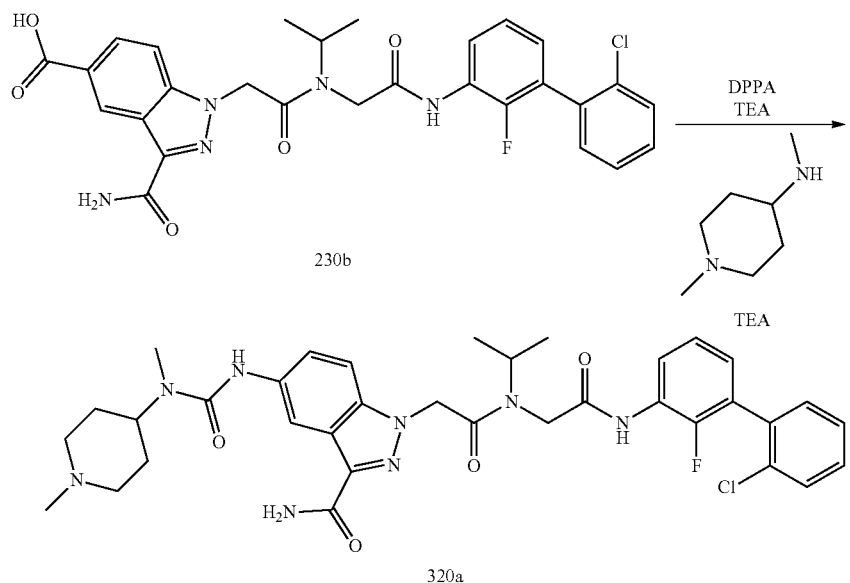

Scheme-320

Preparation of 1-(2-((2-(((2'-chloro-2-fluoro-[1,1'-biphenyl]-3-yl)-amino)-2-oxoethyl)(isopropyl)amino)-2-oxoethyl)-5-(3-methyl-3-(1-methylpiperidin-4-yl)ureido)-1H-indazole-3-carboxamide (320a)

Compound 320a was prepared from 3-carbamoyl-1-(2-((2-(((2'-chloro-2-fluoro-[1,1'-biphenyl]-3-yl)-amino)-2-oxoethyl)(isopropyl)amino)-2-oxoethyl)-1H-indazole-5-carboxylic acid (230b) (200 mg, 0.353 mmol) according to the procedure reported in step-3 of scheme-223. This gave after work up and purification by flash column chromatography [silica gel (4 g), eluting with DMA80 in DCM 0 to 100%] 1-(2-((2-(((2'-chloro-2-fluoro-[1,1'-biphenyl]-3-yl)-amino)-2-oxoethyl)(isopropyl)amino)-2-oxoethyl)-5-(3-methyl-3-(1-methylpiperidin-4-yl)ureido)-1H-indazole-3-carboxamide (320a) (0.023 g, 9% yield) as a white solid; $^1$H NMR (300 MHz, DMSO-d$_6$) (a mixture of two rotamers) δ 10.25 and 9.77 (2s, 1H), 8.417 and 8.41 (2s, 1H), 8.175 and 8.17 (2s, 1H), 8.09 and 7.95 (t, J=7.8 Hz, 1H), 7.70-7.53 (m, 2H), 7.51-7.36 (m, 3H), 7.36-6.90 (m, 5H), 5.57 and 5.44 (2s, 2H), 4.71-4.55 and 4.39-4.25 (2m, 1H), 4.46 (s, 1H) and 4.18-4.01 (m, 2H), 3.06-2.90 (m, 2H), 2.83 and 2.83 (2s, 3H), 2.40-2.14 (m, 5H), 1.87-1.68 (m, 2H), 1.64-1.51 (m, 2H), 1.25 and 1.06 (2d, J=6.7 Hz, 6H); $^{19}$F NMR (282 MHz, DMSO-d$_6$) (a mixture of two rotamers) δ –126.78, –126.98; MS (ES+): 691.5 (M+1).

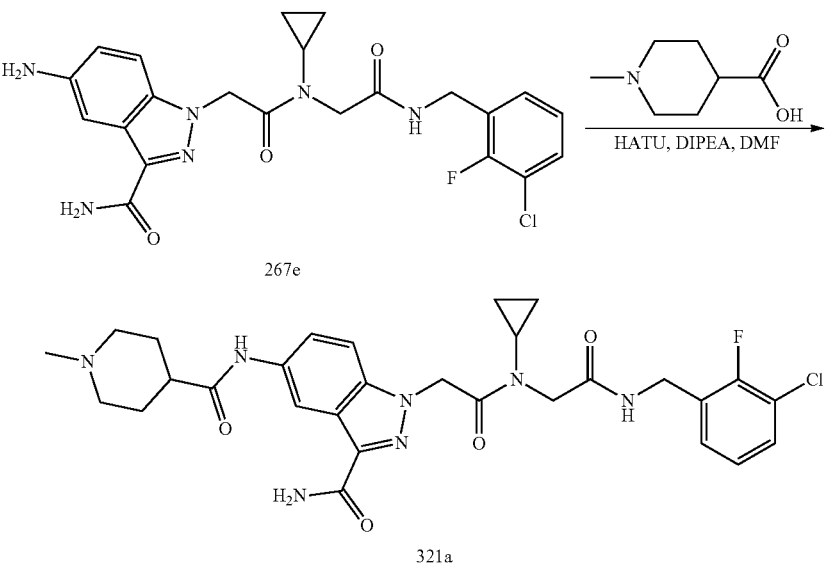

Scheme 321

Preparation of 1-(2-((2-((3-chloro-2-fluorobenzyl)amino)-2-oxoethyl)(cyclopropyl)amino)-2-oxoethyl)-5-(1-methylpiperidine-4-carboxamido)-1H-indazole-3-carboxamide (321a)

Reaction of 5-amino-1-(2-((2-(3-chloro-2-fluorobenzylamino)-2-oxoethyl)(cyclopropyl)amino)-2-oxoethyl)-1H-indazole-3-carboxamide (267e) (170 mg, 0.36 mmol) with 1-methylpiperidine-4-carboxylic acid (62 mg, 0.43 mmol) according to the procedure reported in step-3 of Scheme 2 gave after workup and purification by flash column chromatography [silica (12 g), eluting with DMA80 in DCM from 0 to 70%], followed by conversion of freebase to HCl salt using HCl (3N in MeOH, 3 mL) in MeOH (10 mL) 1-(2-((2-(3-chloro-2-fluorobenzylamino)-2-oxoethyl)(cyclopropyl)amino)-2-oxoethyl)-5-(1-methylpiperidine-4-carboxamido)-1H-indazole-3-carboxamide (321a) (85 mg, 37% yield) HCl salt as a white solid; $^1$H NMR (300 MHz, DMSO-$d_6$) δ 10.22 (s, 1H), 9.75 (brs, 1H), 8.53 (t, J=5.8 Hz, 1H), 8.49-8.42 (m, 1H), 7.68 (s, 1H), 7.63-7.57 (m, 2H), 7.49-7.42 (m, 1H), 7.35 (s, 1H), 7.27-7.19 (m, 1H), 7.15-7.08 (m, 1H), 5.63 (s, 2H), 4.33 (d, J=5.7 Hz, 2H), 3.98 (s, 2H), 3.52-3.44 (m, 2H), 3.13-2.91 (m, 3H), 2.84-2.70 (m, 4H), 2.09-1.99 (m, 2H), 1.98-1.82 (m, 2H), 1.02-0.96 (m, 2H), 0.95-0.87 (m, 2H); $^{19}$F NMR (282 MHz, DMSO-$d_6$) δ −121.58; MS (ES+): 598.6 (M+1); (ES−): 632.5 (M+Cl).

Preparation of 1-(2-((2-((3-chloro-2-fluorobenzyl)amino)-2-oxoethyl)(cyclopropyl)amino)-2-oxoethyl)-6-(3,3-dimethylbutanamido)-1H-indazole-3-carboxamide (322b)

Step-1: Preparation of 6-amino-1-(2-((2-((3-chloro-2-fluorobenzyl)amino)-2-oxoethyl)(cyclopropyl)amino)-2-oxoethyl)-1H-indazole-3-carboxamide (322a)

Reaction of tert-butyl (3-carbamoyl-1-(2-((2-((3-chloro-2-fluorobenzyl)amino)-2-oxoethyl)(cyclopropyl)amino)-2-oxoethyl)-1H-indazol-6-yl)carbamate (273a) (15 mg, 0.026 mmol) with 2,2,2-trifluoroacetic acid (0.121 mL, 1.57 mmol) according to the procedure reported in step-2 of Scheme-2 gave after workup and purification by flash column chromatography [silica gel, eluting with hexanes/10% methanol in ethyl acetate (1:0 to 0:1)] 6-amino-1-(2-((2-((3-chloro-2-fluorobenzyl)amino)-2-oxoethyl)(cyclopropyl)amino)-2-oxoethyl)-1H-indazole-3-carboxamide (322a) (8 mg, 65%) as a light pink solid; $^1$H NMR (300 MHz, Methanol-$d_4$) δ 7.88 (d, J=8.7 Hz, 1H), 7.38-7.28 (m, 1H), 7.27-7.20 (m, 1H), 7.07-6.99 (m, 1H), 6.73 (dd, J=8.7, 1.8 Hz, 1H), 6.62-6.59 (m, 1H), 5.49 (s, 2H), 4.44 (s, 2H), 4.13 (s, 2H), 3.12-2.98 (m, 1H), 1.09-0.94 (m, 4H); MS (ES+): 495.3 & 497.2 (M+Na).

Step-2: Preparation of 1-(2-((2-((3-chloro-2-fluorobenzyl)amino)-2-oxoethyl)(cyclopropyl)amino)-2-oxoethyl)-6-(3,3-dimethylbutanamido)-1H-indazole-3-carboxamide (322b)

Reaction of 6-amino-1-(2-((2-((3-chloro-2-fluorobenzyl)amino)-2-oxoethyl)(cyclopropyl)amino)-2-oxoethyl)-1H-indazole-3-carboxamide (322a) (26.5 mg, 0.056 mmol) with 3,3-dimethylbutanoic acid (10.92 μL, 0.084 mmol) according to the procedure reported in step-3 of Scheme-2 gave after workup and purification by flash column chromatography [silica gel, eluting with hexanes/10% methanol in ethyl acetate (1:0 to 1:1)] 1-(2-((2-((3-chloro-2-fluorobenzyl)amino)-2-oxoethyl)(cyclopropyl)amino)-2-oxoethyl)-6-(3,3-dimethylbutanamido)-1H-indazole-3-carboxamide (322b) (11 mg, 34% yield) as an off-white solid; $^1$H NMR (300 MHz, DMSO-$d_6$) δ 10.03 (s, 1H), 8.52 (t, J=5.7 Hz, 1H), 8.09-7.99 (m, 2H), 7.70 (s, 1H), 7.49-7.40 (m, 1H), 7.35 (s, 1H), 7.30-7.18 (m, 2H), 7.12 (t, J=7.8 Hz, 1H), 5.59 (s, 2H), 4.32 (d, J=5.8 Hz, 2H), 3.99 (s, 2H), 3.14-2.97 (m, 1H), 2.22 (s, 2H), 1.03 (s, 9H), 1.08-0.87 (m, 4H); $^{19}$F NMR (282 MHz, DMSO-$d_6$) δ −121.63; MS (ES+): 571.5 (M+1), 593.5 & 595.5 (M+Na); MS (ES−): 569.4 & 571.4 (M−1).

Scheme 322

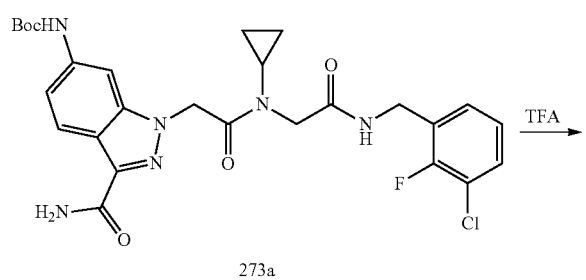

273a

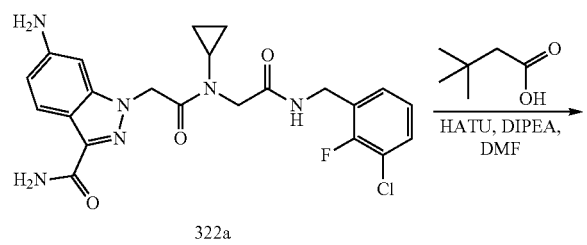

322a

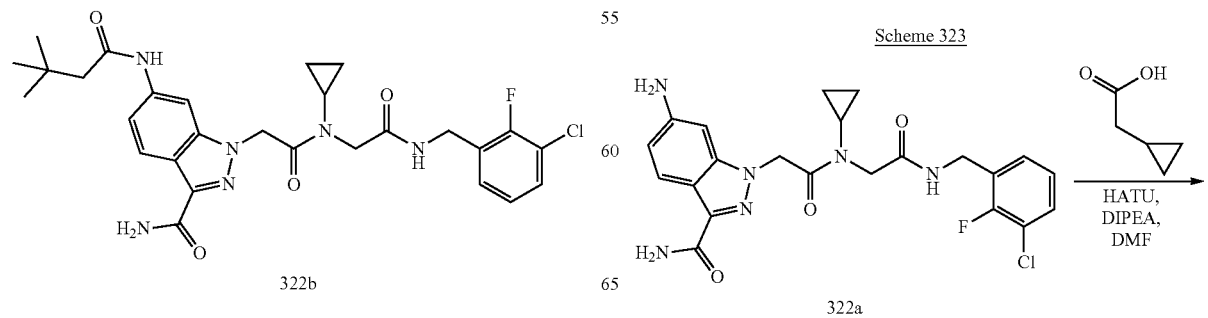

322b

Scheme 323

322a

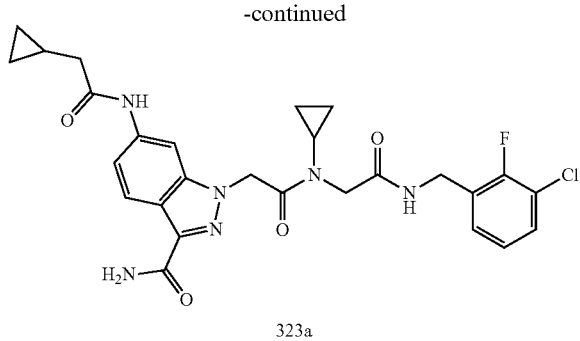

323a

Preparation of 1-(2-((2-((3-chloro-2-fluorobenzyl)amino)-2-oxoethyl)(cyclopropyl)amino)-2-oxo-ethyl)-6-(2-cyclopropylacetamido)-1H-indazole-3-carboxamide (323a)

Reaction of 6-amino-1-(2-((2-((3-chloro-2-fluorobenzyl)amino)-2-oxoethyl)(cyclopropyl)amino)-2-oxoethyl)-1H-indazole-3-carboxamide (322a) (26.5 mg, 0.056 mmol) with 2-cyclopropylacetic acid (7.98 μL, 0.084 mmol) according to the procedure reported in step-3 of Scheme-2 gave after workup and purification by flash column chromatography [silica gel, eluting with hexanes/10% methanol in ethyl acetate (1:0 to 1:2)] 1-(2-((2-((3-chloro-2-fluorobenzyl)amino)-2-oxoethyl)(cyclopropyl)amino)-2-oxoethyl)-6-(2-cyclopropylacetamido)-1H-indazole-3-carboxamide (323a) (14 mg, 45% yield) as a light brown solid; $^1$H NMR (300 MHz, DMSO-$d_6$) δ 10.07 (s, 1H), 8.52 (t, J=5.9 Hz, 1H), 8.13-7.96 (m, 2H), 7.70 (s, 1H), 7.53-7.40 (m, 1H), 7.35 (s, 1H), 7.29-7.18 (m, 2H), 7.13 (t, J=7.9 Hz, 1H), 5.59 (s, 2H), 4.33 (d, J=5.7 Hz, 2H), 3.99 (s, 2H), 3.12-2.92 (m, 1H), 2.23 (d, J=7.0 Hz, 2H), 1.14-0.78 (m, 5H), 0.56-0.35 (m, 2H), 0.29-0.10 (m, 2H); $^{19}$F NMR (282 MHz, DMSO-$d_6$) δ −121.63; MS (ES+): 555.5 (M+1), 577.5 & 579.5 (M+Na); MS (ES−): 589.5 & 591.4 (M+Cl).

Scheme 324

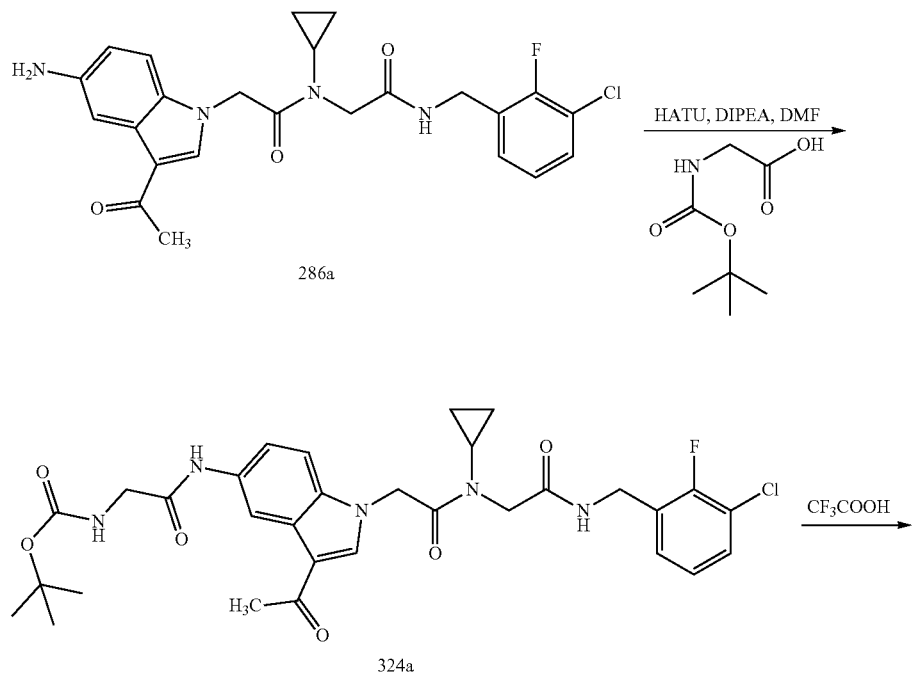

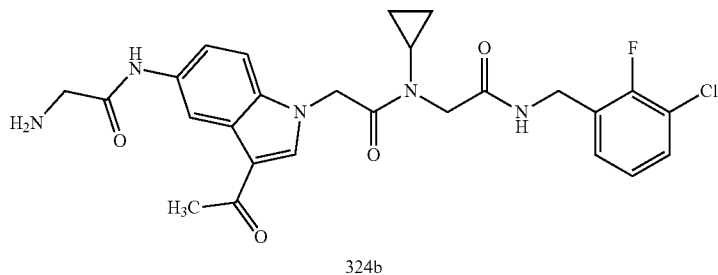

324b

Preparation of 2-(3-acetyl-5-(2-aminoacetamido)-1H-indol-1-yl)-N-(2-((3-chloro-2-fluorobenzyl)amino)-2-oxoethyl)-N-cyclopropylacetamide (324b)

Step-1: Preparation of tert-butyl (2-((3-acetyl-1-(2-((2-((3-chloro-2-fluorobenzyl)amino)-2-oxoethyl)(cyclopropyl)amino)-2-oxoethyl)-1H-indol-5-yl)-amino)-2-oxoethyl)carbamate (324a)

Reaction of 2-(3-acetyl-5-amino-1H-indol-1-yl)-N-(2-((3-chloro-2-fluorobenzyl)amino)-2-oxoethyl)-N-cyclopropylacetamide (286a) (54 mg, 0.12 mmol) with 2-(tert-butoxycarbonylamino)acetic acid (30.7 mg, 0.172 mmol) according to the procedure reported in step-3 of Scheme 2 gave after workup and purification by flash column chromatography [silica gel, eluting with hexanes/10% methanol in ethyl acetate (1:0 to 0:1)] tert-butyl (2-((3-acetyl-1-(2-((2-((3-chloro-2-fluorobenzyl)amino)-2-oxoethyl)(cyclopropyl)amino)-2-oxoethyl)-1H-indol-5-yl)-amino)-2-oxoethyl)carbamate (324a) (63 mg, 87% yield) as a light brown solid; $^1$H NMR (300 MHz, DMSO-$d_6$) δ 9.90 (s, 1H), 8.50-8.34 (m, 2H), 8.25 (s, 1H), 7.56-7.34 (m, 3H), 7.27-6.99 (m, 3H), 5.41 (s, 2H), 4.35 (d, J=5.9 Hz, 2H), 3.99 (s, 2H), 3.73 (d, J=6.0 Hz, 2H), 3.15-3.01 (m, 1H), 2.41 (s, 3H), 1.40 (s, 9H), 1.04-0.86 (m, 4H); $^{19}$F NMR (282 MHz, DMSO-$d_6$) δ −121.63; MS (ES−): 626.5 & 628.5 (M−1).

Step-2: Preparation of 2-(3-acetyl-5-(2-aminoacetamido)-1H-indol-1-yl)-N-(2-((3-chloro-2-fluorobenzyl)amino)-2-oxoethyl)-N-cyclopropylacetamide (324b)

Reaction of tert-butyl (2-((3-acetyl-1-(2-((2-((3-chloro-2-fluorobenzyl)amino)-2-oxoethyl)(cyclopropyl)amino)-2-oxoethyl)-1H-indol-5-yl)-amino)-2-oxoethyl)carbamate (324a) (55 mg, 0.088 mmol) with 2,2,2-trifluoroacetic acid (0.10 mL, 1.31 mmol) according to the procedure reported in step-2 of Scheme 2 gave after workup and purification by flash column chromatography [silica gel, eluting with dichloromethane/DMA80 (1:0 to 2:1)] 2-(3-acetyl-5-(2-aminoacetamido)-1H-indol-1-yl)-N-(2-((3-chloro-2-fluorobenzyl)amino)-2-oxoethyl)-N-cyclopropylacetamide (324b) (37 mg, 80%) as an off-white solid; $^1$H NMR (300 MHz, DMSO-$d_6$) δ 9.83 (s, 1H), 8.47 (t, J=5.8 Hz, 1H), 8.41 (d, J=2.0 Hz, 1H), 8.24 (s, 1H), 7.53 (dd, J=8.8, 2.1 Hz, 1H), 7.46 (td, J=7.6, 1.7 Hz, 1H), 7.37 (d, J=8.8 Hz, 1H), 7.27-7.20 (m, 1H), 7.16-7.07 (m, 1H), 5.41 (s, 2H), 4.35 (d, J=5.7 Hz, 2H), 3.99 (s, 2H), 3.27 (s, 2H), 3.13-2.99 (m, 1H), 2.41 (s, 3H), 2.07 (bs, 2H), 1.08-0.78 (m, 4H); $^{19}$F NMR (282 MHz, DMSO-$d_6$) δ −121.62; MS (ES+): 528.5 & 530.5 (M+1).

Scheme 325

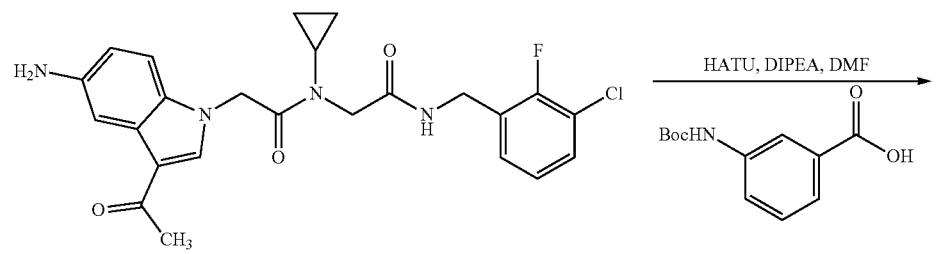

286a

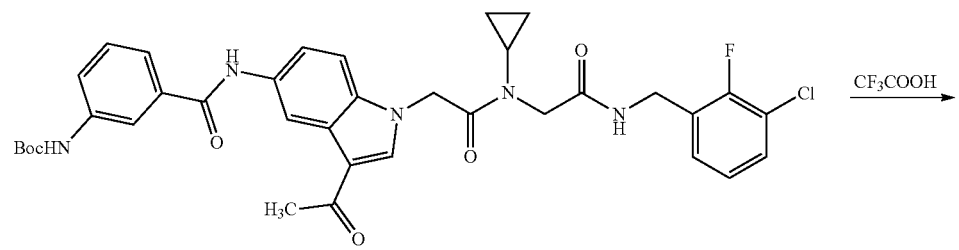

325a

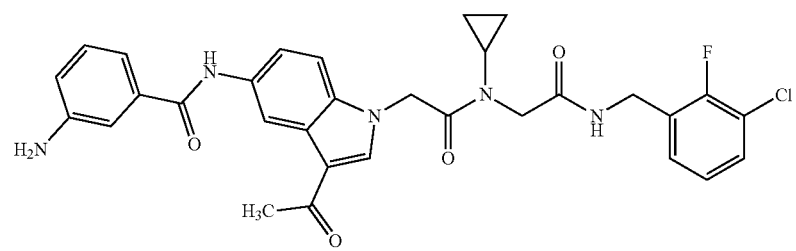

325b

Preparation of N-(3-acetyl-1-(2-((2-((3-chloro-2-fluorobenzyl)amino)-2-oxoethyl)(cyclopropyl)amino)-2-oxoethyl)-1H-indol-5-yl)-3-aminobenzamide (325b)

Step-1: Preparation of tert-butyl (3-((3-acetyl-1-(2-((2-((3-chloro-2-fluorobenzyl)amino)-2-oxoethyl)(cyclopropyl)amino)-2-oxoethyl)-1H-indol-5-yl)carbamoyl)phenyl)carbamate (325a)

Reaction of 2-(3-acetyl-5-amino-1H-indol-1-yl)-N-(2-((3-chloro-2-fluorobenzyl)amino)-2-oxoethyl)-N-cyclopropylacetamide (286a) (54 mg, 0.12 mmol) with 3-(tert-butoxycarbonylamino)benzoic acid (40.8 mg, 0.172 mmol) according to the procedure reported in step-3 of Scheme 2 gave after workup tert-butyl (3-((3-acetyl-1-(2-((2-((3-chloro-2-fluorobenzyl)amino)-2-oxoethyl)(cyclopropyl)amino)-2-oxoethyl)-1H-indol-5-yl)carbamoyl)phenyl)carbamate (325a) which was used as such for next step. MS (ES+): 690.6 (M+1); 712.5 (M+Na).

Step-2: Preparation of N-(3-acetyl-1-(2-((2-((3-chloro-2-fluorobenzyl)amino)-2-oxoethyl)(cyclopropyl)amino)-2-oxoethyl)-1H-indol-5-yl)-3-aminobenzamide (325b)

Reaction of tert-butyl (3-((3-acetyl-1-(2-((2-((3-chloro-2-fluorobenzyl)amino)-2-oxoethyl)(cyclopropyl)amino)-2-oxoethyl)-1H-indol-5-yl)carbamoyl)phenyl)carbamate (325a) (crude from step-1) with 2,2,2-trifluoroacetic acid (0.13 mL, 1.73 mmol) according to the procedure reported in step-2 of Scheme 2 gave after workup and purification by flash column chromatography [silica gel, eluting with dichloromethane/DMA80 (1:0 to 2:1)] N-(3-acetyl-1-(2-((2-((3-chloro-2-fluorobenzyl)amino)-2-oxoethyl)(cyclopropyl)amino)-2-oxoethyl)-1H-indol-5-yl)-3-aminobenzamide (325b) (19 mg, 28% for 2 steps) as a light brown solid; $^1$H NMR (300 MHz, DMSO-d$_6$) δ 10.07 (s, 1H), 8.55 (d, J=2.1 Hz, 1H), 8.47 (t, J=5.8 Hz, 1H), 8.25 (s, 1H), 7.62 (dd, J=8.9, 2.1 Hz, 1H), 7.46 (td, J=7.6, 1.7 Hz, 1H), 7.39 (d, J=8.9 Hz, 1H), 7.29-7.20 (m, 1H), 7.18-7.08 (m, 4H), 6.73 (dt, J=7.0, 2.3 Hz, 1H), 5.42 (s, 2H), 5.30 (s, 2H), 4.35 (d, J=5.7 Hz, 2H), 4.00 (s, 2H), 3.13-3.01 (m, 1H), 2.43 (d, J=2.2 Hz, 3H), 1.04-0.87 (m, 4H); $^{19}$F NMR (282 MHz, DMSO-d$_6$) δ −121.62; MS (ES+): 590.5 & 592.5 (M+1); MS (ES−): 624.5 & 626.4 (M+Cl).

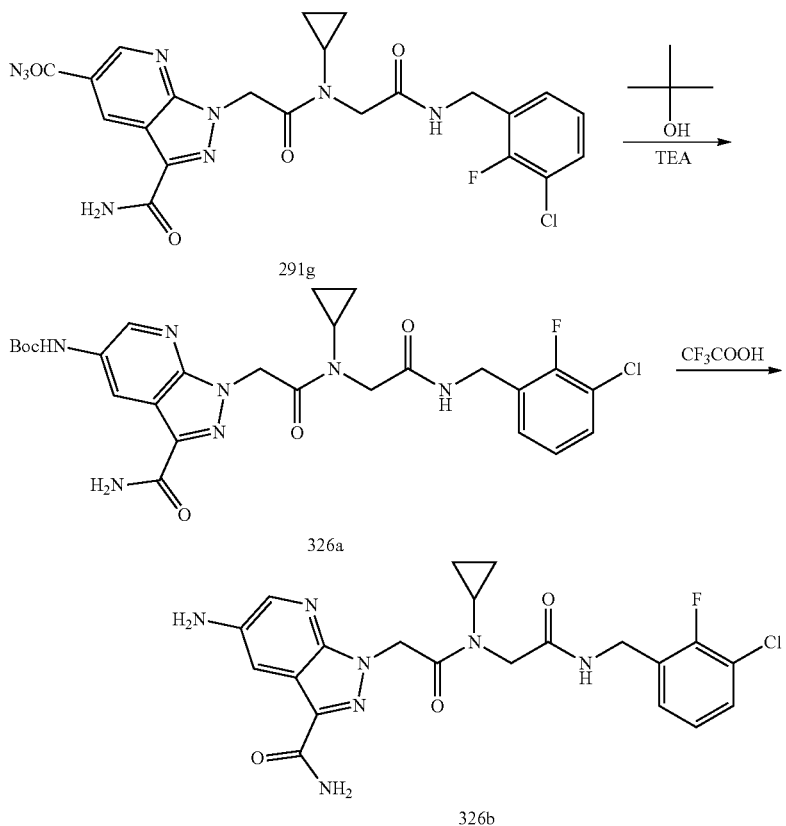

Scheme 326

Preparation of 5-amino-1-(2-((2-((3-chloro-2-fluorobenzyl)amino)-2-oxoethyl)(cyclopropyl)amino)-2-oxoethyl)-1H-pyrazolo[3,4-b]pyridine-3-carboxamide (326b)

Step-1: Preparation of tert-butyl(3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridin-5-yl)carbamate (326a)

Compound 326a was prepared from 3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridine-5-carbonyl azide (291 g) (0.183 mmol) and 2-methylpropan- 2-ol (0.105 mL, 1.1 mmol) using TEA (0.051 mL, 0.37 mmol) as base according to the procedure reported in step-4 of Scheme 129 to afford after workup and purification by column chromatography [silica gel, eluting with DCM in methanol (1:0 to 19:1)] tert-butyl (3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridin-5-yl)carbamate (326a) (12 mg, 11% yield for two steps) as a white solid; MS (ES+): 574.6 (M+1); 596.6 (M+Na).

Step-2: Preparation of 5-amino-1-(2-((2-((3-chloro-2-fluorobenzyl)amino)-2-oxoethyl)(cyclopropyl)amino)-2-oxoethyl)-1H-pyrazolo[3,4-b]pyridine-3-carboxamide (326b)

Compound 326b was prepared from tert-butyl (3-carbamoyl-1-(2-((2-((3-chloro-2-fluorobenzyl)amino)-2-oxoethyl)(cyclopropyl)amino)-2-oxoethyl)-1H-pyrazolo[3,4-b]pyridin-5-yl)carbamate (326a) (12 mg, 0.02 mmol), according to the procedure reported in step-2 of Scheme 2. This gave after workup and purification by column chromatography [silica gel, eluting with DCM in DMA-80 (1:0 to 2:1)] 5-amino-1-(2-((2-((3-chloro-2-fluorobenzyl)amino)-2-oxoethyl)(cyclopropyl)amino)-2-oxoethyl)-1H-pyrazolo[3,4-b]pyridine-3-carboxamide (326b) (6 mg, 61%); $^1$H NMR (300 MHz, DMSO-$d_6$) δ 8.50 (t, J=5.6 Hz, 1H), 8.07 (d, J=2.6 Hz, 1H), 7.64 (s, 1H), 7.61 (d, J=2.6 Hz, 1H), 7.52-7.41 (m, 1H), 7.30 (s, 1H), 7.26-7.19 (m, 1H), 7.19-7.09 (m, 1H), 5.55 (s, 2H), 5.35 (s, 2H), 4.32 (d, J=5.7 Hz, 2H), 3.97 (s, 2H), 3.12-2.92 (m, 1H), 1.01-0.81 (m, 4H); $^{19}$F NMR (282 MHz, DMSO-$d_6$) δ −121.59; MS (ES+): 474.4 & 476.4 (M+1); MS (ES−): 508.3 & 510.3 (M+Cl).

Scheme 327

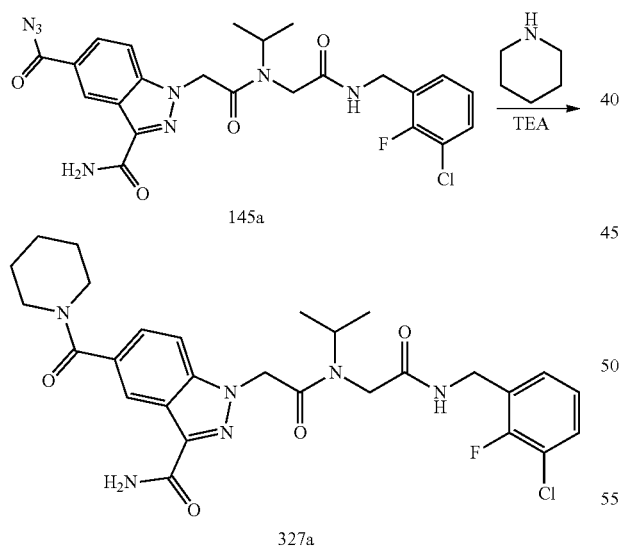

Preparation of 1-(2-((2-((3-chloro-2-fluorobenzyl)amino)-2-oxoethyl)(isopropyl)amino)-2-oxoethyl)-5-(piperidine-1-carbonyl)-1H-indazole-3-carboxamide (327a)

Reaction of 3-carbamoyl-1-(2-((2-(3-chloro-2-fluorobenzylamino)-2-oxoethyl)(isopropyl)amino)-2-oxoethyl)-1H-indazole-5-carbonyl azide (145a) (200 mg, 0.378 mmol) in toluene (20 mL) with piperidine (0.064 g, 0.756 mmol) using TEA (0.153 g, 1.42 mmol) as base according to the procedure reported in step-4 of Scheme 129 gave after workup 1-(2-((2-((3-chloro-2-fluorobenzyl)amino)-2-oxoethyl)(isopropyl)amino)-2-oxo ethyl)-5-(piperidine-1-carbonyl)-1H-indazole-3-carboxamide (327a)

(70 mg, 33% yield) as an off-white solid; $^1$H NMR (300 MHz, DMSO-$d_6$); δ 8.89-8.82 (m, 1H). 8.17 (s, 1H), 7.81-7.77 (s, 1H), 7.72-7.68 (m, 1H), 7.45-7.42 (m, 3H), 7.21-7.18 (m, 2H), 5.48-5.47 (s, 2H), 4.47-4.45 (m, 2H), 4.18-4.12 (m, 3H), 3.69-3.51 (m, 4H), 1.62-1.52 (m, 6H), 1.24-1.22 (s, 3H), 1.00-0.98 (s, 3H); MS (ES+): 571 (M+1).

Scheme 328

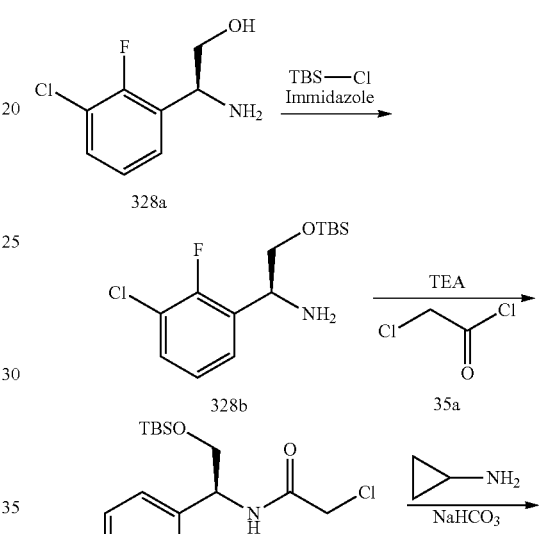

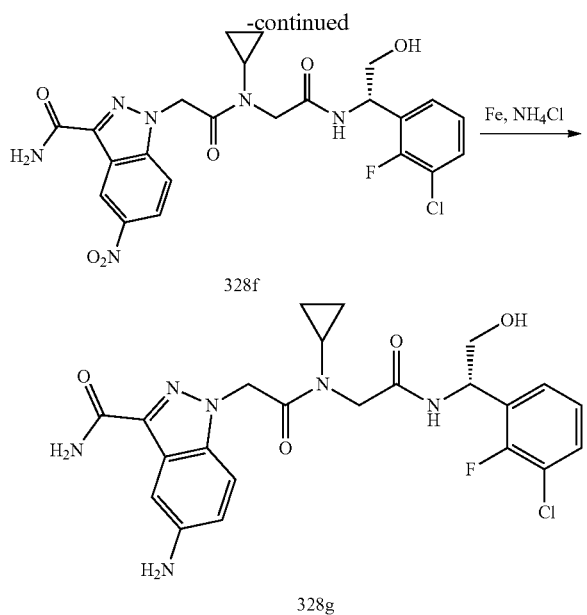

Preparation of (S)-5-amino-1-(2-((2-((1-(3-chloro-2-fluorophenyl)-2-hydroxyethyl)amino)-2-oxoethyl)(cyclopropyl)amino)-2-oxoethyl)-1H-indazole-3-carboxamide (328 g)

Step-1: Preparation of (S)-2-((tert-butyldimethylsilyl)oxy)-1-(3-chloro-2-fluorophenyl)ethanamine (328b)

To a solution of (S)-2-amino-2-(3-chloro-2-fluorophenyl)ethanol (328a) (1.05 g, 5.54 mmol) in DCM (50 mL) and DMF (5 mL) was added TBS-C$_l$ (1.002 g, 6.65 mmol), Imidazole (0.528 g, 7.75 mmol) and stirred at RT for 3 h. The solid obtained was collected by filtration washed with DCM (2×4 mL) and dried under vacuum to afford (S)-2-((tert-butyldimethylsilyl)oxy)-1-(3-chloro-2-fluorophenyl)ethanamine (328b) (1.3 g, 77% yield) as a white solid; MS (ES+): 304.4 (M+1).

Step-2: Preparation of (S)—N-(2-((tert-butyldimethylsilyl)oxy)-1-(3-chloro-2-fluorophenyl)ethyl)-2-chloroacetamide (328c)

To a biphasic solution of (S)-2-(tert-butyldimethylsilyloxy)-1-(3-chloro-2-fluorophenyl)ethanamine (328b) (1.3 g, 4.28 mmol) in EtOAc (80 mL) and sat. NaHCO$_3$ solution (80 mL) was added Chloroacetyl chloride (0.514 mL, 6.42 mmol) and stirred at RT for 16 h. Layers were separated, aqueous layer was extracted with EtOAc (40 mL) and combined organics were washed with brine, dried, filtered, concentrated and purified by flash chromatography [silica gel 24 g, EtOAc in hexanes 0 to 60% as eluents] to afford (S)—N-(2-(tert-butyldimethylsilyloxy)-1-(3-chloro-2-fluorophenyl)ethyl)-2-chloroacetamide (328c) (1.3 g, 80% yield) as a colorless thick syrup; $^1$H NMR (300 MHz, DMSO-d$_6$) δ 8.75 (d, J=8.1 Hz, 1H), 7.51 (ddd, J=7.9, 7.1, 1.7 Hz, 1H), 7.38 (ddd, J=8.1, 6.5, 1.7 Hz, 1H), 7.23 (td, J=7.9, 1.0 Hz, 1H), 5.18 (q, J=6.7 Hz, 1H), 4.13 (s, 2H), 3.85-3.68 (m, 2H), 0.77 (s, 9H), −0.06 (s, 3H), −0.10 (s, 3H); MS (ES+): 380.4 (M+1), 402.4 (M+Na), MS (ES−): 414.3, 416.5 (M+Cl).

Step-3: Preparation of (S)—N-(2-((tert-butyldimethylsilyl)oxy)-1-(3-chloro-2-fluorophenyl)ethyl)-2-(cyclopropylamino)acetamide (328d)

To a solution of (S)—N-(2-(tert-butyldimethylsilyloxy)-1-(3-chloro-2-fluorophenyl)ethyl)-2-chloroacetamide (328c) in THF (30 mL) was added Cyclopropyl amine (0.723 mL, 10.25 mmol) and stirred at RT for 2 days. Mixture was poured into sat. NaHCO$_3$ solution (60 mL) and resultant suspension extracted with EtOAc (2×50 mL). The combined organics were washed with brine, dried (MgSO$_4$), filtered, concentrated and purified by column chromatography [silica gel 24 g, EtOAc in hexane as eluents 0 to 100%] to afford (S)—N-(2-(tert-butyldimethylsilyloxy)-1-(3-chloro-2-fluorophenyl)ethyl)-2-(cyclopropylamino)acetamide (328d) (0.7 g, 51% yield) as a thick syrup; $^1$H NMR (300 MHz, DMSO-d$_6$) δ 8.28 (d, J=8.3 Hz, 1H), 7.53-7.44 (m, 1H), 7.39-7.30 (m, 1H), 7.25-7.17 (m, 1H), 5.25-5.14 (m, 1H), 3.76 (d, J=5.8 Hz, 2H), 3.17 (d, J=1.2 Hz, 2H), 2.14-2.06 (m, 1H), 0.77 (s, 9H), 0.39-0.30 (m, 2H), 0.29-0.22 (m, 2H), −0.09 (s, 3H), −0.10 (s, 3H); MS (ES+): 401.5 (M+1), MS (ES−): 435.4 (M+Cl).

Step-4: Preparation of (S)-1-(6-(3-chloro-2-fluorophenyl)-10-cyclopropyl-2,2,3,3-tetramethyl-8,11-dioxo-4-oxa-7,10-diaza-3-siladodecan-12-yl)-5-nitro-1H-indazole-3-carboxamide (328e)

Reaction of (S)—N-(2-(tert-butyldimethylsilyloxy)-1-(3-chloro-2-fluorophenyl)ethyl)-2-(cyclopropylamino)acetamide (328d) (200 mg, 0.50 mmol) with 2-(3-carbamoyl-5-nitro-1H-indazol-1-yl)acetic acid (267c) (145 mg, 0.55 mmol) according to the procedure reported in step-3 of Scheme 2 gave after workup and purification by flash column chromatography [silica gel 12 g, DMA80 in DCM 0 to 30% as eluents] (S)-1-(6-(3-chloro-2-fluorophenyl)-10-cyclopropyl-2,2,3,3-tetramethyl-8,11-dioxo-4-oxa-7,10-diaza-3-siladodecan-12-yl)-5-nitro-1H-indazole-3-carboxamide (328e) (0.216 g, 67% yield) as white solid; $^1$H NMR (300 MHz, DMSO-d$_6$) δ 9.05 (dd, J=2.3, 0.6 Hz, 1H), 8.54 (d, J=8.1 Hz, 1H), 8.26 (dd, J=9.3, 2.3 Hz, 1H), 8.06 (s, 1H), 7.89 (dd, J=9.3, 0.7 Hz, 1H), 7.67 (s, 1H), 7.51-7.41 (m, 1H), 7.36-7.27 (m, 1H), 7.16 (t, J=7.9 Hz, 1H), 5.84-5.66 (m, 2H), 5.16 (q, J=7.0 Hz, 1H), 4.11-3.91 (m, 2H), 3.79-3.59 (m, 2H), 3.09-2.95 (m, 1H), 1.03-0.92 (m, 2H), 0.92-0.83 (m, 2H), 0.74 (s, 9H), −0.08 (s, 3H), −0.13 (s, 3H); $^{19}$F NMR (282 MHz, DMSO-d$_6$) δ −121.35; MS (ES−): 681.5 (M−1).

Step-5: Preparation of (S)-1-(2-((2-((1-(3-chloro-2-fluorophenyl)-2-hydroxyethyl)amino)-2-oxoethyl)(cyclopropyl)amino)-2-oxoethyl)-5-nitro-1H-indazole-3-carboxamide (328f)

Compound 328f was prepared from (5)-1-(6-(3-chloro-2-fluorophenyl)-10-cyclopropyl-2,2,3,3-tetramethyl-8,11-dioxo-4-oxa-7,10-diaza-3-siladodecan-12-yl)-5-nitro-1H-indazole-3-carboxamide (328e) (0.21 g, 0.324 mmol) and TBAF (0.127 g, 0.487 mmol) according to the procedure reported in step-2 of Scheme 301. This gave after workup and purification by flash chromatography [silica gel 4 g, DMA80 in DCM, 0 to 20% as eluents] (S)-1-(2-((2-((1-(3-chloro-2-fluorophenyl)-2-hydroxyethyl)amino)-2-oxoethyl)(cyclopropyl)amino)-2-oxoethyl)-5-nitro-1H-indazole-3-carboxamide (328f) (0.15 g, 87% yield) as a white solid; $^1$H NMR (300 MHz, DMSO-d$_6$) δ 9.05 (dd, J=2.3, 0.6 Hz, 1H), 8.54 (d, J=7.9 Hz, 1H), 8.26 (dd, J=9.3, 2.3 Hz, 1H), 8.07 (s, 1H), 7.89 (dd, J=9.3, 0.7 Hz, 1H), 7.66 (s, 1H), 7.49-7.40 (m, 1H), 7.32-7.23 (m, 1H), 7.17-7.10 (m, 1H), 5.84-5.65 (m, 2H), 5.12-5.02 (m, 2H), 4.02 (s, 2H), 3.54 (t, J=6.0 Hz, 2H), 3.07-2.94 (m, 1H), 1.03-0.92 (m, 2H), 0.92-0.82 (m, 2H); 19F NMR (282 MHz, DMSO-$d_6$) δ −121.91; MS (ES−): 531.4 (M−1), 567.5 (M+Cl).

Step-6: Preparation of (S)-5-amino-1-(2-((2-((1-(3-chloro-2-fluorophenyl)-2-hydroxyethyl)amino)-2-oxoethyl)(cyclopropyl)amino)-2-oxoethyl)-1H-indazole-3-carboxamide (328 g)

To a solution of (S)-1-(2-((2-((1-(3-chloro-2-fluorophenyl)-2-hydroxyethyl)amino)-2-oxoethyl)(cyclopropyl) amino)-2-oxoethyl)-5-nitro-1H-indazole-3-carboxamide (328f) (0.12 g, 0.225 mmol) in EtOH (3 mL) was added a solution of Ammonium chloride (0.241 g, 4.50 mmol) in Water (3 mL) followed by Iron (0.126 g, 2.252 mmol) and mixture was stirred at 60° C. for 4 h. Mixture was filtered over Celite pad, washed with EtOH (3×5 mL) and water (3×5 mL). The combined filtrate was concentrated partially and resultant residue was partitioned between brine (60 mL) and EtOAc (80 mL), layers were separated, aqueous layer was extracted with EtOAc (40 mL). The combined organics were washed with brine, dried, filtered, concentrated and purified by column chromatography [silica gel 4 g, DMA80 in DCM 0 to 30% as eluents] to afford (S)-5-amino-1-(2-((2-((1-(3-chloro-2-fluorophenyl)-2-hydroxyethyl)amino)-2-oxoethyl)(cyclopropyl)amino)-2-oxoethyl)-1H-indazole-3-carboxamide (328 g) (0.015 g, 13% yield) as a white solid; $^1$H NMR (300 MHz, DMSO-$d_6$) δ 8.52 (d, J=7.8 Hz, 1H), 7.54-7.40 (m, 2H), 7.34-7.22 (m, 3H), 7.21-7.08 (m, 2H), 6.78 (dd, J=8.8, 2.1 Hz, 1H), 5.57-5.39 (m, 2H), 5.14-4.99 (m, 4H), 4.00 (s, 2H), 3.54 (t, J=6.0 Hz, 2H), 3.04-2.90 (m, 1H), 1.01-0.77 (m, 4H); $^{19}$F NMR (282 MHz, DMSO-$d_6$) δ −121.91; MS (ES+): 503.4 (M+1), 525.4 (M+Na), MS (ES−): 501.4 (M−1), 537.5 (M+Cl).

Scheme 329

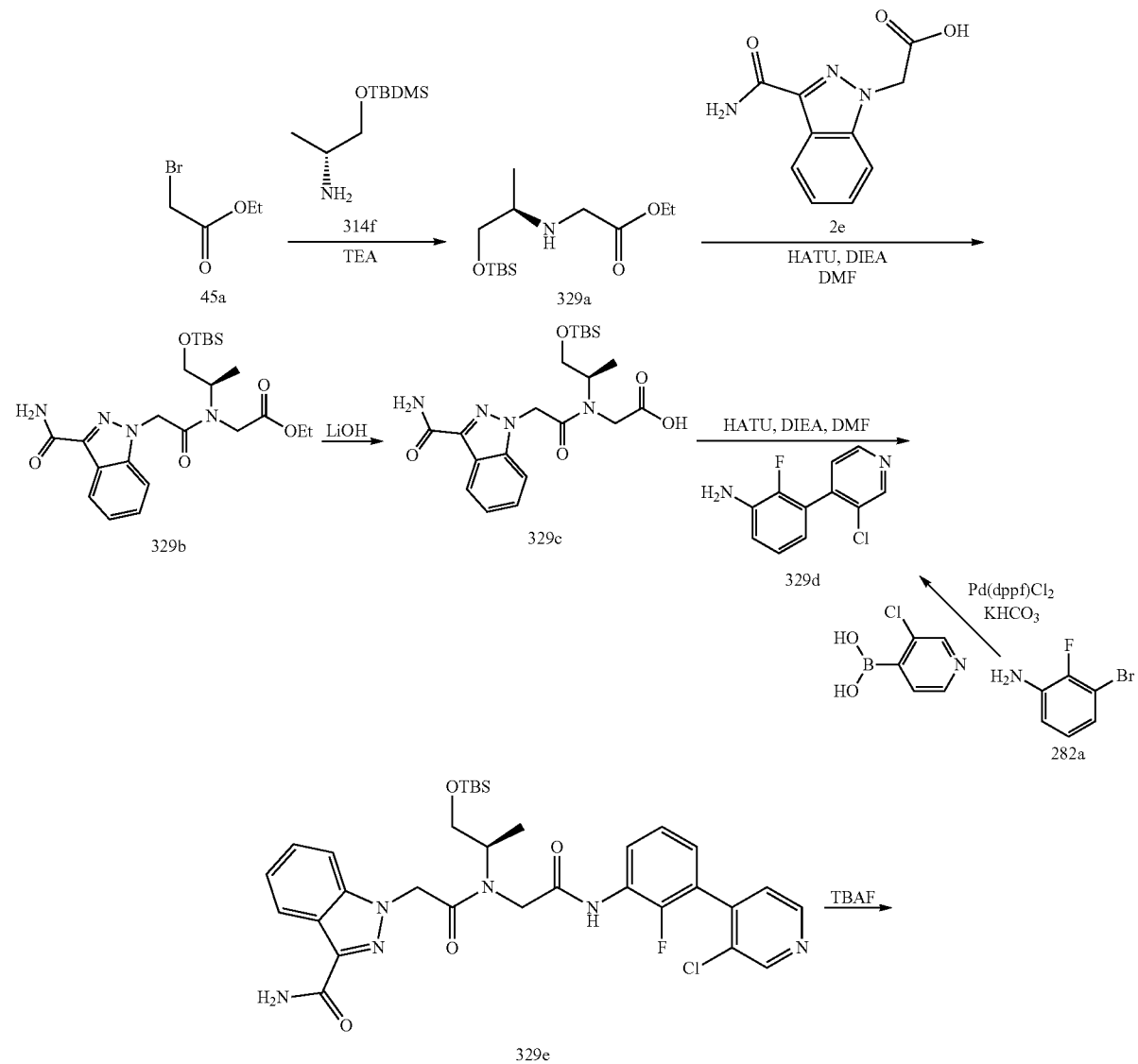

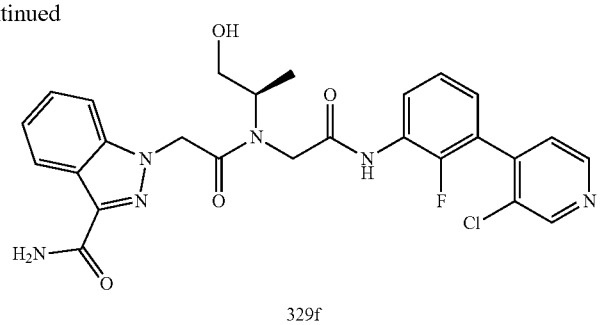

329f

Preparation of (R)-1-(2-((2-((3-(3-chloropyridin-4-yl)-2-fluorophenyl)amino)-2-oxoethyl)(1-hydroxypropan-2-yl)amino)-2-oxoethyl)-1H-indazole-3-carboxamide (329f)

Step-1: Preparation of (R)-ethyl 2-((1-((tert-butyldimethylsilyl)oxy)propan-2-yl)-amino)acetate (329a)

To a solution of (R)-1-((tert-butyldimethylsilyl)oxy)propan-2-amine (314f) (8 g, 42.2 mmol) in THF (50 mL) added ethyl 2-bromoacetate (45a) (7.06 g, 42.2 mmol), TEA (7.07 mL, 50.7 mmol) and mixture was stirred at RT for 20 h. Mixture was poured into sat. NaHCO$_3$ solution (100 mL) and resultant mixture was extracted with EtOAc (2×80 mL). The combined organics were washed with brine, dried, filtered, concentrated to afford (R)-ethyl 2-((1-((tert-butyldimethylsilyl)oxy)propan-2-yl)amino)acetate (329a) (11 g, 95% yield) as a colorless liquid; $^1$H NMR (300 MHz, CDCl$_3$) δ 4.18 (qd, J=7.2, 1.1 Hz, 2H), 3.58-3.33 (m, 4H), 2.83-2.68 (m, 1H), 2.16 (s, 1H), 1.27 (t, J=7.1 Hz, 3H), 0.98 (d, J=6.4 Hz, 3H), 0.90 (s, 9H), 0.05 (d, J=1.4 Hz, 6H).

Step-2: Preparation of (R)-ethyl 2-(N-(1-((tert-butyldimethylsilyl)oxy)propan-2-yl)-2-(3-carbamoyl-1H-indazol-1-yl)acetamido)acetate (329b)

Reaction of (R)-ethyl 2-((1-((tert-butyldimethylsilyl)oxy)propan-2-yl)-amino)acetate (329a) (2.0 g, 7.26 mmol) with 2-(3-carbamoyl-1H-indazol-1-yl)acetic acid (2e) (1.91 g, 8.71 mmol) according to the procedure reported in step-3 of Scheme 2 gave after workup and purification by flash column chromatography [silica gel 40 g, EtOAc in hexanes 0 to 100% as eluents] (R)-ethyl 2-(N-(1-((tert-butyldimethylsilyl)oxy)propan-2-yl)-2-(3-carbamoyl-1H-indazol-1-yl)acetamido)acetate (329b) (1.5 g, 3.15 mmol, 43.3% yield) as colorless foam; MS (ES+): 477.5 (M+1), 499.5 (M+Na), MS (ES−): 511.5 (M+Cl).

Step-3: Preparation of (R)-2-(N-(1-((tert-butyldimethylsilyl)oxy)propan-2-yl)-2-(3-carbamoyl-1H-indazol-1-yl)acetamido)acetic acid (329c)

Hydrolysis of ester of (R)-ethyl 2-(N-(1-((tert-butyldimethylsilyl)oxy)propan-2-yl)-2-(3-carbamoyl-1H-indazol-1-yl)acetamido)acetate (329b) (1.5 g, 3.15 mmol) according to the procedure reported in step-2 of Scheme 129 gave after workup (R)-2-(N-(1-((tert-butyldimethylsilyl)oxy)propan-2-yl)-2-(3-carbamoyl-1H-indazol-1-yl)acetamido)acetic acid (329c) (1.1 g, 78% yield) as a white solid; MS (ES+): 471.5 (M+Na), MS (ES−): 447.4 (M−1)

Step-4: Preparation of 3-(3-chloropyridin-4-yl)-2-fluoroaniline (329d)

To a degassed solution of 3-bromo-2-fluoroaniline (282a) (2.415 g, 12.71 mmol), 3-chloropyridin-4-ylboronic acid (2.00 g, 12.71 mmol) in ethylene glycol dimethyl ether (50 mL) was added a solution of potassium bicarbonate (4.45 g, 44.5 mmol) in water (2.00 mL) followed by (Pd(dppf)Cl$_2$ (0.930 g, 1.271 mmol) and mixture was stirred at 80° C. for 17 h. The reaction mixture was cooled to room temperature, diluted with water (100 mL) and extracted with ethyl acetate (2×100 mL). The combined organics were dried, filtered, concentrated and purified by chromatography [silica gel 24 g, eluting with EtOAc in hexanes from 0 to 50%] to afford 3-(3-chloropyridin-4-yl)-2-fluoroaniline (329d) (0.189 g, 7% yield) as a white solid; $^1$H NMR (300 MHz, DMSO-d$_6$) δ 8.75 (d, J=0.6 Hz, 1H), 8.59 (d, J=4.9 Hz, 1H), 7.46 (dd, J=5.0, 0.6 Hz, 1H), 6.99 (td, J=7.7, 0.7 Hz, 1H), 6.93-6.80 (m, 1H), 6.54-6.41 (m, 1H), 5.36 (s, 2H, D$_2$O exchangeable); $^{19}$F NMR (282 MHz, DMSO-d$_6$) δ −137.11; MS (ES+): 223.2 (M+1).

Step-5: Preparation of (R)-1-(2-((1-((tert-butyldimethylsilyl)oxy)propan-2-yl)(2-((3-(3-chloropyridin-4-yl)-2-fluorophenyl)amino)-2-oxoethyl)amino)-2-oxoethyl)-1H-indazole-3-carboxamide (329e)

Reaction of (R)-2-(N-(1-((tert-butyldimethylsilyl)oxy)propan-2-yl)-2-(3-carbamoyl-1H-indazol-1-yl)acetamido)acetic acid (329c) (0.13 g, 0.29 mmol) with 3-(3-chloropyridin-4-yl)-2-fluoroaniline (329d) (0.065 g, 0.29 mmol) (45e) (54 mg, 0.379 mmol), according to the procedure reported in step-3 of Scheme 2 gave after workup and purification by flash column chromatography [Silica gel, 4 g eluting with EtOAc in hexanes 0 to 100% as eluents] of (R)-1-(2-((1-((tert-butyldimethyl silyl)oxy)propan-2-yl)(2-((3-(3-chloropyridin-4-yl)-2-fluorophenyl)amino)-2-oxoethyl)amino)-2-oxoethyl)-1H-indazole-3-carboxamide (329e) (0.06 g, 32% yield) as colorless foam; MS (ES+): 653.6 (M+1), 675.5 (M+Na).

Step-6: Preparation of (R)-1-(2-((2-((3-(3-chloropyridin-4-yl)-2-fluorophenyl)amino)-2-oxoethyl)(1-hydroxypropan-2-yl)amino)-2-oxoethyl)-1H-indazole-3-carboxamide (329f)

Compound 329f was prepared from (R)-1-(2-((1-((tert-butyldimethylsilyl)oxy)propan-2-yl)(2-((3-(3-chloropyridin-4-yl)-2-fluorophenyl)amino)-2-oxoethyl)amino)-2-oxoethyl)-1H-indazole-3-carboxamide (329e) (0.06 g, 0.092 mmol) and TBAF (0.072 g, 0.276 mmol) according to the procedure reported in step-2 of Scheme 301. This gave after workup and purification by flash chromatography [silica gel 4 g, DMA80 in DCM, 0 to 40% as eluents] (R)-1-(2-((2-((3-(3-chloropyridin-4-yl)-2-fluorophenyl)amino)-2-oxoethyl)(1-hydroxypropan-2-yl)amino)-2-oxoethyl)-1H-indazole-3-carboxamide (329f) (0.035 g, 71% yield) as a white solid; $^1$H NMR (300 MHz, DMSO-$d_6$) (a mixture of two rotamers) δ 10.35 and 10.02 (2s, 1H), 8.81 and 8.79 (2s, 1H), 8.69-8.59 (m, 1H), 8.21-8.12 (m, 1H), 8.02 (t, J=7.7 Hz, 1H), 7.72 and 7.68 (2s, 1H), 7.62-7.09 (m, 7H), 5.75-5.57 and 5.53-5.46 (2m, 2H), 5.43 and 4.83 (2t, J=5.4 Hz, 1H) 4.61-4.40 and 4.30-4.18 (2m, 1H), 4.19 and 3.97 (2d, J=16.6 Hz, 2H), 3.58-3.42 (m, 2H), 1.19 and 1.04 (2d, J=6.9 Hz, 3H); $^{19}$F NMR (282 MHz, DMSO-$d_6$) δ −126.30, −126.74; MS (ES+): 539.4 (M+1), 561.5 (M+Na), MS (ES−): 537.5 (M−1), 573.5 (M+Cl).

Step 2: Preparation of 1-(2-((2-((3-chloro-2-fluorobenzyl)amino)-2-oxoethyl)(cyclopropyl)amino)-2-oxoethyl)-6-hydroxy-1H-indazole-3-carboxamide (330b)

Reaction of 2-(3-carbamoyl-6-hydroxy-1H-indazol-1-yl)acetic acid (330a) (0.172 mmol, crude) with N-(3-chloro-2-fluorobenzyl)-2-(cyclopropylamino)acetamide (0.066 g, 0.26 mmol) (10b) according to the procedure reported in step-3 of Scheme 2 gave after workup and purification by flash column chromatography [silica gel, eluting with dichloromethane/methanol (1:0 to 92:8)] 1-(2-((2-((3-chloro-2-fluorobenzyl)amino)-2-oxoethyl)(cyclopropyl)amino)-2-oxoethyl)-6-hydroxy-1H-indazole-3-carboxamide (330b) (26 mg, 32% for two steps) as an off-white solid; $^1$H NMR (300 MHz, DMSO-$d_6$) δ 9.80 (s, 1H), 8.50 (t, J=5.8 Hz, 1H), 7.96-7.87 (m, 1H), 7.59 (s, 1H), 7.50-7.38 (m, 1H), 7.32-7.19 (m, 2H), 7.13 (t, J=7.9 Hz, 1H), 6.84-6.75 (m, 2H), 5.50 (s, 2H), 4.33 (d, J=5.7 Hz, 2H), 3.98 (s, 2H), 3.11-2.96 (m, 1H), 1.00-0.85 (m, 4H); $^{19}$F NMR (282 MHz, DMSO-$d_6$) δ −121.62; MS (ES−): 472.4 & 474.5 (M−1).

Scheme 330

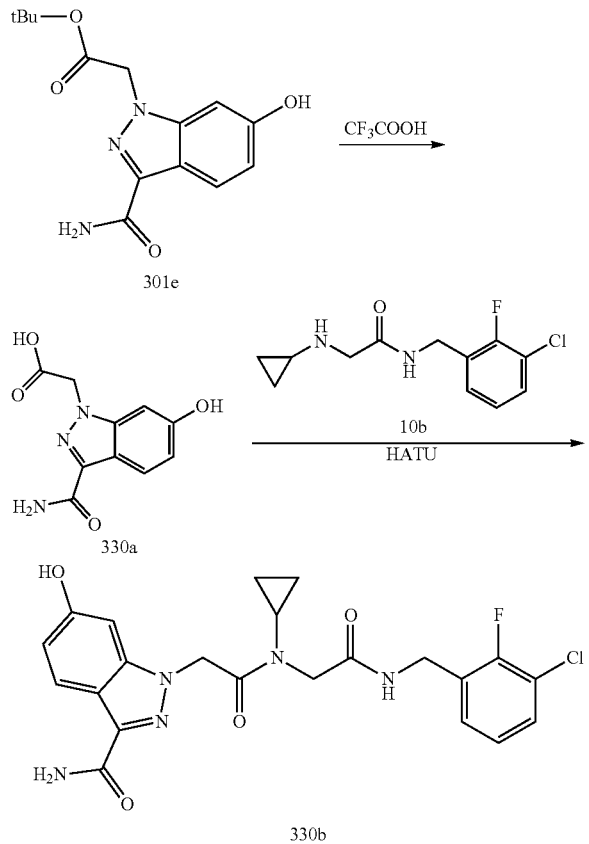

Preparation of 1-(2-((2-((3-chloro-2-fluorobenzyl)amino)-2-oxoethyl)(cyclopropyl)amino)-2-oxoethyl)-6-hydroxy-1H-indazole-3-carboxamide (330b)

Step 1: Preparation of 2-(3-carbamoyl-6-hydroxy-1H-indazol-1-yl)acetic acid (330a)

Reaction of tert-butyl 2-(3-carbamoyl-6-hydroxy-1H-indazol-1-yl)acetate (301e) (50 mg, 0.172 mmol, crude) with 2,2,2-trifluoroacetic acid (0.2 mL, 2.57 mmol) according to the procedure reported in step-2 of Scheme 2 gave after workup 2-(3-carbamoyl-6-hydroxy-1H-indazol-1-yl)acetic acid (330a) which was used as such for next step.

Scheme 331

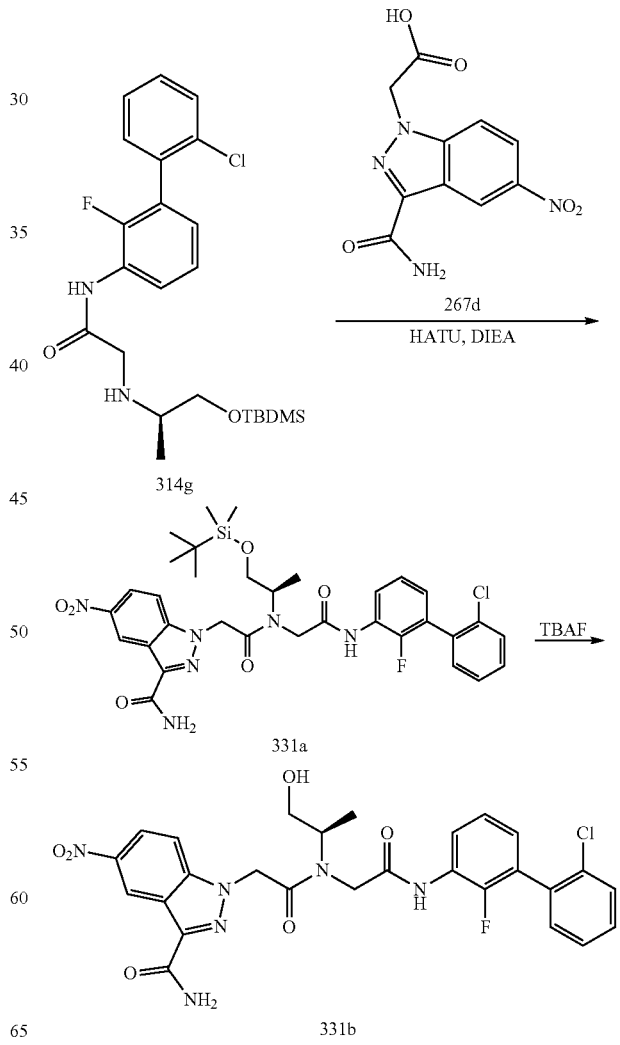

Preparation of (R)-1-(2-((2-((2'-chloro-2-fluoro-[1,1'-biphenyl]-3-yl)-amino)-2-oxoethyl)(1-hydroxy-propan-2-yl)amino)-2-oxoethyl)-5-nitro-1H-indazole-3-carboxamide (331b)

Step-1: Preparation of (R)-1-(2-((1-(((tert-butyldimethylsilyl)oxy)propan-2-yl)(2-((2'-chloro-2-fluoro-[1,1'-biphenyl]-3-yl)-amino)-2-oxoethyl)amino)-2-oxoethyl)-5-nitro-1H-indazole-3-carboxamide (331a)

Compound 331b was prepared from (R)-2-(1-(tert-butyldimethylsilyloxy)propan-2-ylamino)-N-(2'-chloro-2-fluorobiphenyl-3-yl)acetamide (314 g) (1.00 g, 2.22 mmol) by reaction with 2-(3-carbamoyl-5-nitro-1H-indazol-1-yl)acetic acid (267d) (703 mg, 2.66 mmol) according to the procedure reported in step-3 of Scheme 2. This gave after workup and purification by flash column chromatography [Silica gel, 24 g eluting with ethyl acetate/methanol (9:1) in hexanes from 0-100%] (R)-1-(2-((1-((tert-butyldimethylsilyl)oxy)propan-2-yl)(2-((2'-chloro-2-fluoro-[1,1'-biphenyl]-3-yl)-amino)-2-oxoethyl)amino)-2-oxoethyl)-5-nitro-1H-indazole-3-carboxamide (331a) (494 mg, 32% yield) as a yellow solid; MS (ES+): 697.7 (M+1), 719.5 (M+Na); MS (ES−): 695.5 (M−1).

Step-2: Preparation of (R)-1-(2-((2-((2'-chloro-2-fluoro-[1,1'-biphenyl]-3-yl)amino)-2-oxoethyl)(1-hydroxypropan-2-yl)amino)-2-oxoethyl)-5-nitro-1H-indazole-3-carboxamide (331b)

Compound 331b was prepared from (R)-1-(2-((1-((tert-butyldimethylsilyl)oxy)propan-2-yl)(2-((2'-chloro-2-fluoro-[1,1'-biphenyl]-3-yl)-amino)-2-oxoethyl)amino)-2-oxoethyl)-5-nitro-1H-indazole-3-carboxamide (331a) (106 mg, 0.15 mmol) and TBAF (60 mg, 0.228 mmol) according to the procedure reported in step-2 of Scheme 301. This gave after workup and purification by flash chromatography [First column; silica gel 12 g, eluting with methanol in DCM from 0-100%; second column, silica gel 12 g, eluting with ethyl acetate/methanol (9:1) in hexanes from 0-100%] (R)-1-(2-((2-((2'-chloro-2-fluoro-[1,1'-biphenyl]-3-yl)-amino)-2-oxoethyl)(1-hydroxypropan-2-yl)amino)-2-oxoethyl)-5-nitro-1H-indazole-3-carboxamide (331b) (61 mg, 69% yield) as a white solid; $^1$H NMR (300 MHz, DMSO-$d_6$, mixture of two rotamers) δ 10.30 & 9.95 (2s, 1H, D$_2$O exchangeable), 9.08-9.03 (m, 1H), 8.33 (dd, J=9.3, 2.3 Hz) & 8.22 (dd, J=9.3, 2.3 Hz) (2dd, 1H), 8.15-7.91 (m, 2H, D$_2$O exchangeable 1H), 7.82 (d, J=9.3 Hz) & 7.73 (d, J=9.3 Hz) (2d, 1H), 7.68 (bs, 1H, D$_2$O exchangeable), 7.64-7.56 (m, 1H), 7.54-7.37 (m, 3H), 7.32 (t, J=7.9 Hz) & 7.23 (t, J=7.9 Hz) (2t, 1H), 7.19-7.03 (m, 1H), 5.92-5.69 (m, 1H), 5.61 (s, 1H), 5.42 (t, J=5.6 Hz) & 4.83 (t, J=5.5 Hz) (2t, 1H, D$_2$O exchangeable), 4.61-3.90 (m, 3H), 3.65-3.45 (m, 2H), 1.21 (d, J=6.5 Hz) & 1.04 (d, J=6.9 Hz) (2d, 3H); $^{19}$F NMR (282 MHz, DMSO-$d_6$) δ −126.53, −126.90; MS (ES+): 583.4 (M+1), 606.4, 607.4 (M+Na); MS (ES−): 581.5, 583.5 (M−1).

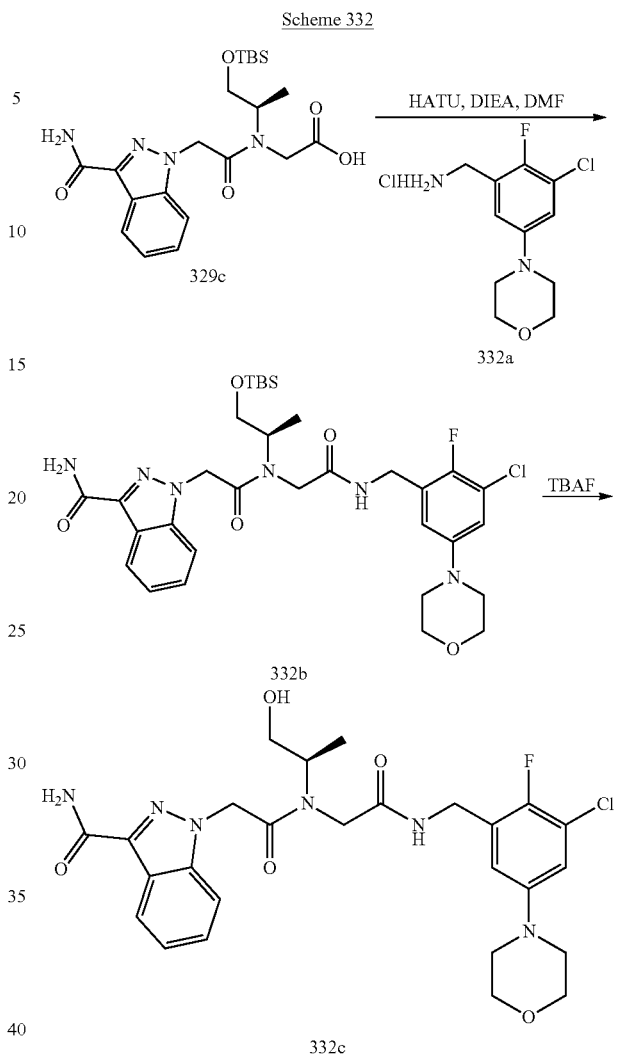

Scheme 332

Preparation of (R)-1-(2-((2-((3-chloro-2-fluoro-5-morpholinobenzyl)amino)-2-oxoethyl)(1-hydroxy-propan-2-yl)amino)-2-oxoethyl)-1H-indazole-3-carboxamide (332c)

Step-1: Preparation of (R)-1-(2-((1-(((tert-butyldimethylsilyl)oxy)propan-2-yl)(2-((3-chloro-2-fluoro-5-morpholinobenzyl)amino)-2-oxoethyl)amino)-2-oxoethyl)-1H-indazole-3-carboxamide (332b)

Reaction of (R)-2-(N-(1-(((tert-butyldimethylsilyl)oxy)propan-2-yl)-2-(3-carbamoyl-1H-indazol-1-yl)acetamido)acetic acid (329c) (100 mg, 0.223 mmol) with (3-chloro-2-fluoro-5-morpholinophenyl)methanamine hydrochloride (332a) (0.063 g, 0.223 mmol, prepared according to the procedure reported by Altmann, Eva et al; in PCT Int. Appl. (2012), WO 2012093101) according to the procedure reported in step-3 of Scheme 2 gave after workup and purification by flash column chromatography [Silica gel, 4 g eluting with DMA80 in DCM 0 to 30% as eluents] (R)-1-(2-((1-(((tert-butyldimethylsilyl)oxy)propan-2-yl)(2-((3-chloro-2-fluoro-5-morpholinobenzyl)amino)-2-oxoethyl)

amino)-2-oxoethyl)-1H-indazole-3-carboxamide (332b) (100 mg, 66% yield) as colorless foam; MS (ES−): 673.6 (M−1).

Step-2: Preparation of (R)-1-(2-((2-((3-chloro-2-fluoro-5-morpholinobenzyl)amino)-2-oxoethyl)(1-hydroxy propan-2-yl)-amino)-2-oxo ethyl)-1H-indazole-3-carboxamide (332c)

Compound 332c was prepared from of (R)-1-(2-((1-(((tert-butyldimethylsilyl)oxy)propan-2-yl)(2-((3-chloro-2-fluoro-5-morpholinobenzyl)amino)-2-oxoethyl)amino)-2-oxoethyl)-1H-indazole-3-carboxamide (332b) (100 mg, 0.148 mmol) and TBAF (0.077 g, 0.296 mmol) according to the procedure reported in step-2 of Scheme 301. This gave after workup and purification by flash chromatography [silica gel 4 g, DMA80 in DCM, 0 to 40% as eluents] (R)-1-(2-((2-((3-chloro-2-fluoro-5-morpholinobenzyl)amino)-2-oxo ethyl)(1-hydroxy propan-2-yl)amino)-2-oxoethyl)-1H-indazole-3-carboxamide (332c) (66 mg, 79% yield) as a white solid; $^1$H NMR (300 MHz, DMSO-$d_6$) (a mixture of two rotamers) δ 8.82 and 8.58 (2t, J=5.9 Hz, 1H), 8.21-8.14 (m, 1H), 7.76-7.17 (m, 5H), 7.03-6.63 (m, 2H), 5.70-5.55 and 5.44-5.34 (2m, 2H), 5.50 and 4.81 (2t, J=6.0 Hz, 1H), 4.49-3.12 (m, 11H), 3.05-2.94 and 2.81-2.71 (2m, 4H), 1.17 (d, J=6.5 Hz) and 1.00-0.94 (m) (3H); $^{19}$F NMR (282 MHz, DMSO-$d_6$) (a mixture of two rotamers) δ −134.26, −135.26; MS (ES−): 595.5 (M+Cl).

Preparation of 2-(3-acetyl-5-(6-morpholinopyridin-3-yl)-1H-indazol-1-yl)-N-(2-((3-chloro-2-fluorobenzyl)amino)-2-oxoethyl)-N-cyclopropylacetamide (333a)

Reaction of 2-(3-acetyl-5-bromo-1H-indazol-1-yl)-N-(2-((3-chloro-2-fluorobenzyl)amino)-2-oxoethyl)-N-cyclopropylacetamide (158a) (0.12 g, 0.224 mmol) with 6-morpholinopyridin-3-ylboronic acid (0.056 g, 0.269 mmol) according to the procedure reported in Scheme 78 gave after workup and purification by reverse phase column chromatography [silica gel 50 g, Acetonitrile in water (0.1% TFA) 0 to 50% as eluents] 2-(3-acetyl-5-(6-morpholinopyridin-3-yl)-1H-indazol-1-yl)-N-(2-((3-chloro-2-fluorobenzyl)amino)-2-oxoethyl)-N-cyclopropylacetamide (333a) (0.055 g, 40% yield) as a white solid; $^1$H NMR (300 MHz, DMSO-$d_6$) δ 8.53-8.45 (m, 2H), 8.31-8.29 (m, 1H), 7.93 (dd, J=8.8, 2.6 Hz, 1H), 7.81-7.70 (m, 2H), 7.49-7.41 (m, 1H), 7.27-7.18 (m, 1H), 7.14-7.05 (m, 1H), 6.97 (d, J=8.9 Hz, 1H), 5.78 (s, 2H), 4.34 (d, J=5.7 Hz, 2H), 4.00 (s, 2H), 3.78-3.68 (m, 4H), 3.55-3.46 (m, 4H), 3.20-3.07 (m, 1H), 2.63 (s, 3H), 1.10-0.98 (m, 2H), 0.98-0.85 (m, 2H); $^{19}$F NMR (282 MHz, DMSO-$d_6$) δ −121.58; MS (ES+): 619.0 (M+1), 641.5 (M+Na).

Scheme 333

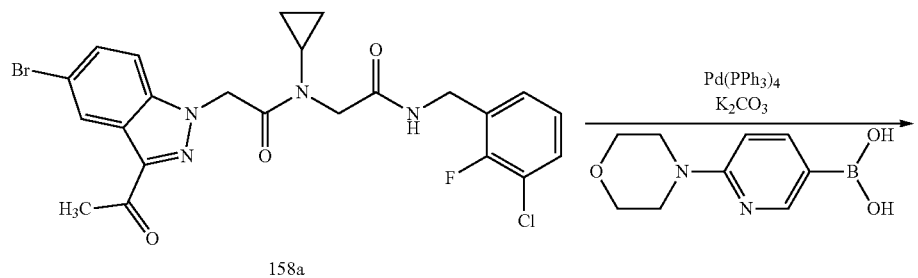

158a

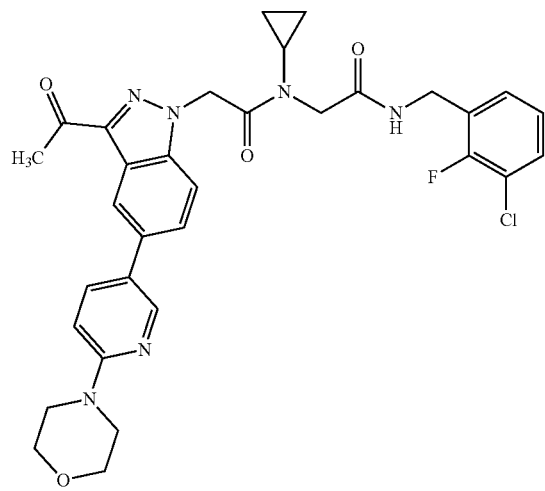

333a

Scheme 334

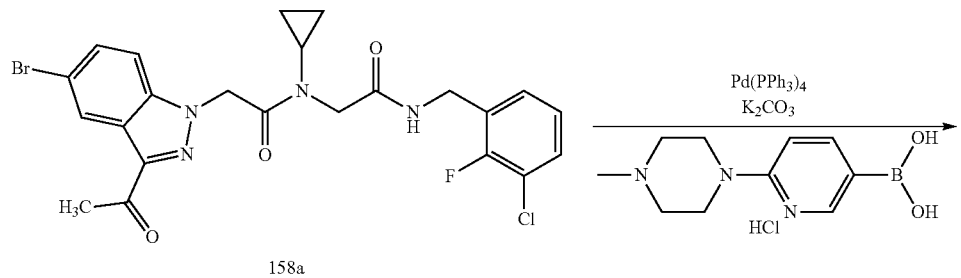

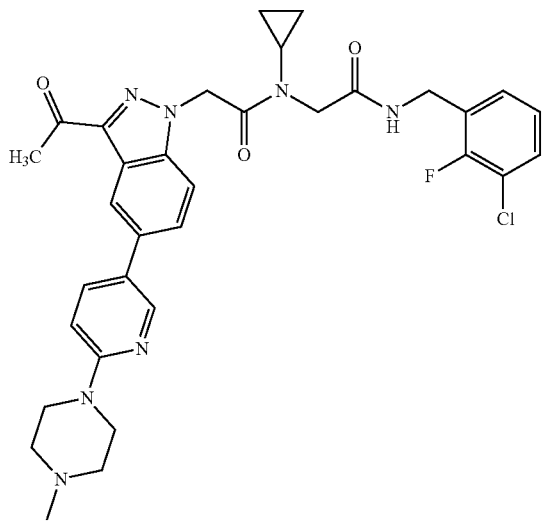

334a

Preparation of 2-(3-acetyl-5-(6-(4-methylpiperazin-1-yl)pyridin-3-yl)-1H-indazol-1-yl)-N-(2-((3-chloro-2-fluorobenzyl)amino)-2-oxoethyl)-N-cyclopropylacetamide (334a)

Reaction of 2-(3-acetyl-5-bromo-1H-indazol-1-yl)-N-(2-((3-chloro-2-fluorobenzyl)amino)-2-oxoethyl)-N-cyclopropylacetamide (158a) (0.12 g, 0.224 mmol) 6-(4-methylpiperazin-1-yl)pyridin-3-ylboronic acid hydrochloride (0.058 g, 0.224 mmol) according to the procedure reported in Scheme 78 gave after workup and purification by reverse phase column chromatography [silica gel 50 g, Acetonitrile in water (0.1% TFA) 0 to 50% as eluents] 2-(3-acetyl-5-(6-(4-methylpiperazin-1-yl)pyridin-3-yl)-1H-indazol-1-yl)-N-(2-((3-chloro-2-fluorobenzyl)amino)-2-oxoethyl)-N-cyclopropylacetamide (334a) (0.033 g, 23% yield) as a white solid; $^1$H NMR (300 MHz, DMSO-$d_6$) δ 8.54-8.45 (m, 2H), 8.33-8.27 (m, 1H), 7.90 (dd, J=8.9, 2.5 Hz, 1H), 7.80-7.69 (m, 2H), 7.50-7.41 (m, 1H), 7.27-7.19 (m, 1H), 7.15-7.06 (m, 1H), 6.98 (d, J=8.8 Hz, 1H), 5.78 (s, 2H), 4.34 (d, J=5.7 Hz, 2H), 4.00 (s, 2H), 3.58 (td, J=12.7, 11.0, 4.4 Hz, 4H), 3.21-3.07 (m, 1H), 2.63 (s, 3H), 2.53 (brs, 4H), 2.30 (s, 3H), 1.10-0.98 (m, 2H), 0.98-0.85 (m, 2H); $^{19}$F NMR (282 MHz, DMSO-$d_6$) δ -121.58; MS (ES+): 632.6 (M+1), 654.6 (M+Na); MS (ES-): 666.6 (M+Cl).

Scheme 335

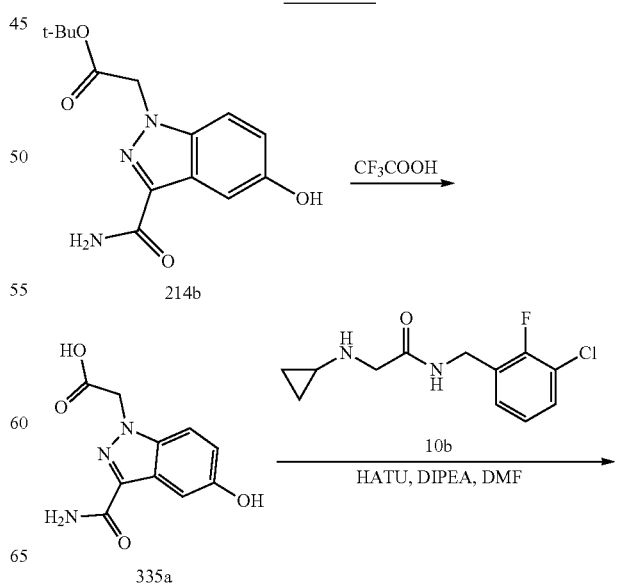

335a

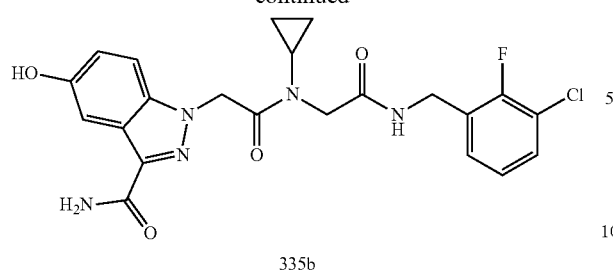

335b

Preparation of 1-(2-((2-(((3-chloro-2-fluorobenzyl)amino)-2-oxoethyl)(cyclopropyl)amino)-2-oxo-ethyl)-5-hydroxy-1H-indazole-3-carboxamide (335b)

Step-1: Preparation of 2-(3-carbamoyl-5-hydroxy-1H-indazol-1-yl)acetic acid (335a)

Reaction of tert-butyl 2-(3-carbamoyl-5-hydroxy-1H-indazol-1-yl)acetate (214b) (260 mg, 0.89 mmol) with 2,2,2-trifluoroacetic acid (1.03 mL, 13.39 mmol) according to the procedure reported in step-2 of Scheme 2 gave after workup 2-(3-carbamoyl-5-hydroxy-1H-indazol-1-yl)acetic acid (335a), which was used as such for next step.

Step 2 Preparation of 1-(2-((2-(3-chloro-2-fluorobenzylamino)-2-oxoethyl)(cyclopropyl)amino)-2-oxoethyl)-5-hydroxy-1H-indazole-3-carboxamide (335b)

Reaction of 2-(3-carbamoyl-5-hydroxy-1H-indazol-1-yl) acetic acid (335a) (210 mg, 0.89 mmol, crude) with N-(3-chloro-2-fluorobenzyl)-2-(cyclopropylamino)acetamide (10b) (344 mg, 1.34 mmol according to the procedure reported in step-3 of Scheme 2 gave after workup and purification by flash column chromatography [silica gel, eluting with dichloromethane/methanol (1:0 to 19:1)] 1-(2-((2-(3-chloro-2-fluorobenzylamino)-2-oxoethyl)(cyclopropyl)amino)-2-oxoethyl)-5-hydroxy-1H-indazole-3-carboxamide (335b) (101 mg, 24%) as a white solid; $^1$H NMR (300 MHz, DMSO-$d_6$) δ 9.36 (s, 1H), 8.49 (t, J=5.9 Hz, 1H), 7.57 (s, 1H), 7.51-7.42 (m, 3H), 7.28-7.18 (m, 2H), 7.12 (td, J=7.9, 1.0 Hz, 1H), 6.92 (dd, J=9.0, 2.4 Hz, 1H), 5.57 (s, 2H), 4.33 (d, J=5.7 Hz, 2H), 3.98 (s, 2H), 3.13-2.92 (m, 1H), 1.03-0.80 (m, 4H); $^{19}$F NMR (282 MHz, DMSO-$d_6$) δ −121.58; MS (ES+): 496.3 & 498.3 (M+Na); MS (ES−): 472.4 & 474.4 (M−1).

Scheme 336

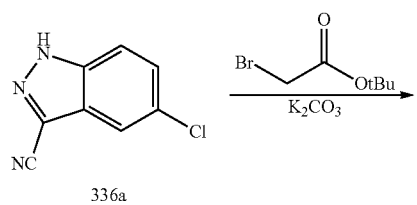

336a

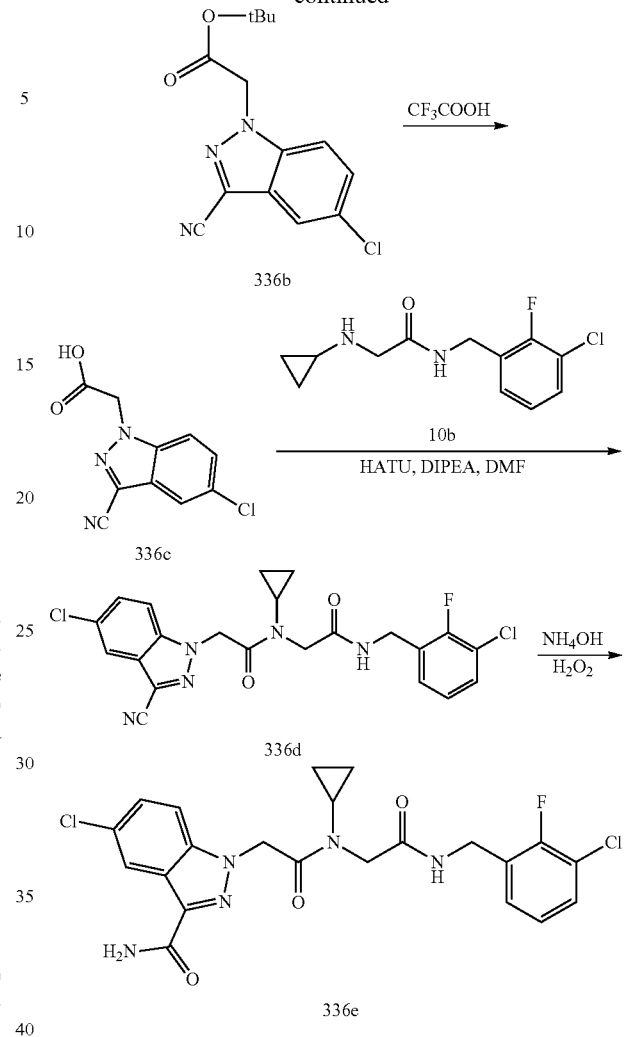

Preparation of 5-chloro-1-(2-((2-(3-chloro-2-fluorobenzylamino)-2-oxoethyl)(cyclopropyl)-amino)-2-oxoethyl)-1H-indazole-3-carboxamide (336b)

Step 1: Preparation of tert-butyl 2-(5-chloro-3-cyano-1H-indazol-1-yl)acetate (336b)

Reaction of 5-chloro-1H-indazole-3-carbonitrile (336a) (500 mg, 2.67 mmol) with tert-butyl 2-bromoacetate (0.474 mL, 3.21 mmol) according to the procedure reported in step-1 of Scheme 43 gave after workup tert-butyl 2-(5-chloro-3-cyano-1H-indazol-1-yl)acetate (336b) (1.013 g) as a brown semi-solid, which was used as such for next step. MS (ES−): 290.4 & 292.3 (M−1).

Step 2: Preparation of 2-(5-chloro-3-cyano-1H-indazol-1-yl)acetic acid (336c)

Reaction of tert-butyl 2-(5-chloro-3-cyano-1H-indazol-1-yl)acetate (336b) (0.779 g, 2.67 mmol, crude) with 2,2,2-trifluoroacetic acid (2.06 mL, 26.7 mmol) according to the procedure reported in step-2 of Scheme 2 gave after workup 2-(5-chloro-3-cyano-1H-indazol-1-yl)acetic acid (336c), which was used as such for next step.

Step 3: Preparation of N-(2-(3-chloro-2-fluorobenzylamino)-2-oxoethyl)-2-(5-chloro-3-cyano-1H-indazol-1-yl)-N-cyclopropylacetamide (336d)

Reaction of 2-(5-chloro-3-cyano-1H-indazol-1-yl)acetic acid (336c) (0.629 g, 2.67 mmol, crude) with N-(3-chloro-2-fluorobenzyl)-2-(cyclopropylamino)acetamide (10b) (0.82 g, 3.20 mmol) according to the procedure reported in step-3 of Scheme 2 gave after workup and purification by flash column chromatography [silica gel with hexanes/10% methanol in ethyl acetate (1:0 to 1:1)] N-(2-(3-chloro-2-fluorobenzylamino)-2-oxoethyl)-2-(5-chloro-3-cyano-1H-indazol-1-yl)-N-cyclopropylacetamide (336d) (479 mg, 38% for three steps) as a yellow solid; $^1$H NMR (300 MHz, DMSO-$d_6$) δ 8.47 (t, J=5.9 Hz, 1H), 8.06 (dd, J=1.9, 0.7 Hz, 1H), 7.89 (dd, J=9.1, 0.8 Hz, 1H), 7.60 (dd, J=9.0, 1.9 Hz, 1H), 7.50-7.42 (m, 1H), 7.25-7.18 (m, 1H), 7.13-7.07 (m, 1H), 5.81 (s, 2H), 4.33 (d, J=5.7 Hz, 2H), 3.97 (s, 2H), 3.16-2.98 (m, 1H), 1.08-0.82 (m, 4H); $^{19}$F NMR (282 MHz, DMSO-$d_6$) δ −121.57; MS (ES+): 474.4 (M+1).

Step 4: Preparation of 5-chloro-1-(2-((2-(3-chloro-2-fluorobenzylamino)-2-oxoethyl)-(cyclopropyl)amino)-2-oxoethyl)-1H-indazole-3-carboxamide (336e)

Reaction of N-(2-(3-chloro-2-fluorobenzylamino)-2-oxoethyl)-2-(5-chloro-3-cyano-1H-indazol-1-yl)-N-cyclopropylacetamide (336d) (369 mg, 0.778 mmol) with hydrogen peroxide (0.275 mL, 3.11 mmol) according to the procedure reported in Scheme 65 gave after workup and purification by flash column chromatography [silica gel with hexanes/10% methanol in ethyl acetate (1:0 to 1:1)] 5-chloro-1-(2-((2-(3-chloro-2-fluorobenzylamino)-2-oxoethyl)-(cyclopropyl)amino)-2-oxoethyl)-1H-indazole-3-carboxamide (336e) (197 mg, 51%) as a white solid; $^1$H NMR (300 MHz, DMSO-$d_6$) δ 8.50 (t, J=5.8 Hz, 1H), 8.16 (dd, J=2.1, 0.7 Hz, 1H), 7.82 (s, 1H), 7.73 (dd, J=9.0, 0.7 Hz, 1H), 7.50-7.42 (m, 3H), 7.26-7.17 (m, 1H), 7.11 (td, J=7.8, 1.0 Hz, 1H), 5.68 (s, 2H), 4.33 (d, J=5.7 Hz, 2H), 3.98 (s, 2H), 3.14-2.93 (m, 1H), 1.05-0.81 (m, 4H); $^{19}$F NMR (282 MHz, DMSO-$d_6$) δ −121.56; MS (ES+): 514.3 & 516.3 (M+Na); MS (ES−): 490.3 (M−1).

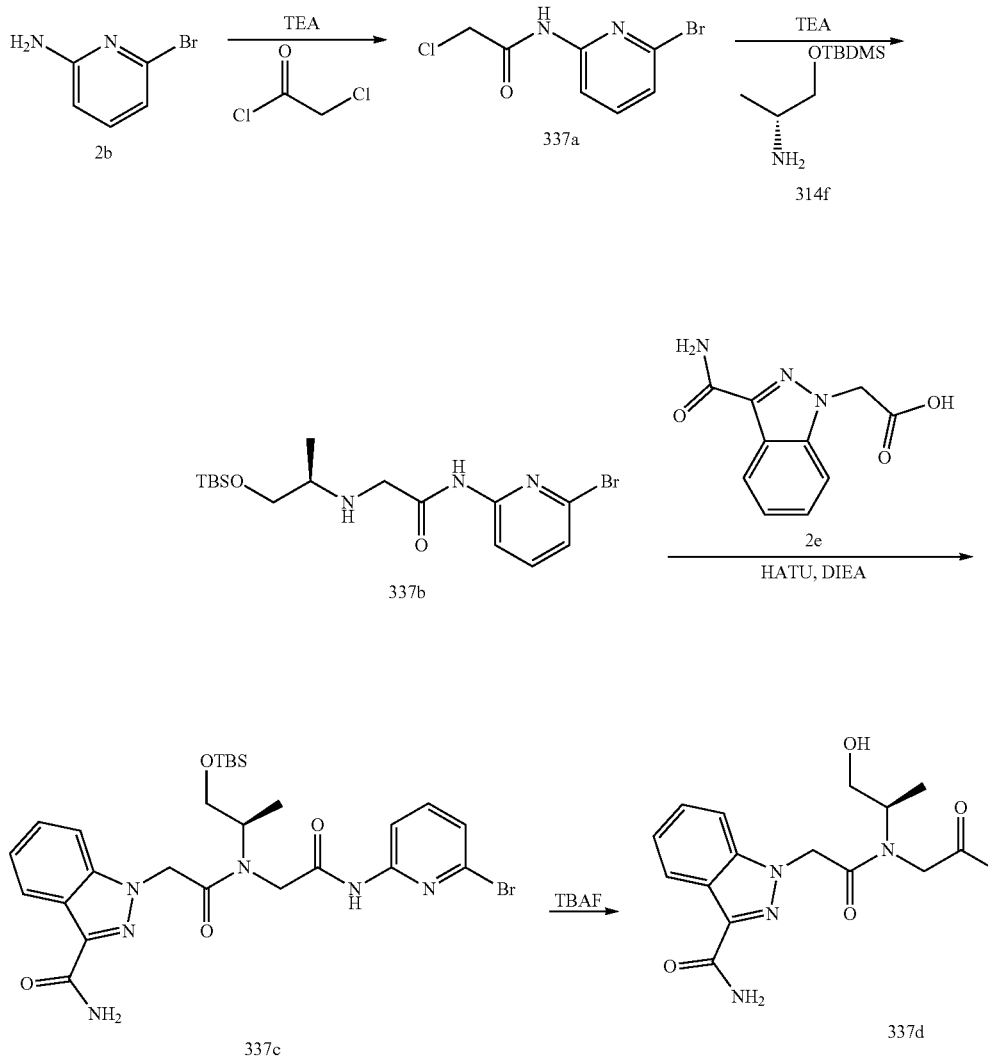

Scheme 337

Preparation of (R)-1-(2-((2-((6-bromopyridin-2-yl)amino)-2-oxoethyl)(1-hydroxypropan-2-yl)amino)-2-oxoethyl)-1H-indazole-3-carboxamide (337d)

Step-1: Preparation of N-(6-bromopyridin-2-yl)-2-chloroacetamide (337a)

Compound 337a was prepared from 6-bromopyridin-2-amine (2a) (2 g, 11.56 mmol) and Chloroacetyl chloride (1.852 mL, 23.12 mmol), according to the procedure reported in step-1 of Scheme 35. This gave after workup and purification by flash column chromatography [silica gel 40 g, EtOAc-hexane 0 to 40% as eluents] to afford N-(6-bromopyridin-2-yl)-2-chloroacetamide (337a) (2.3 g, 80% yield) as a white solid; $^1$H NMR (300 MHz, DMSO-$d_6$) δ 11.19 (s, 1H), 8.06 (dd, J=8.2, 0.7 Hz, 1H), 7.86-7.67 (m, 1H), 7.39 (dd, J=7.7, 0.7 Hz, 1H), 4.34 (s, 2H).

Step-2: Preparation of (R)—N-(6-bromopyridin-2-yl)-2-((1-((tert-butyldimethylsilyl)oxy)propan-2-yl)-amino)acetamide (337b)

Compound 337b was prepared from N-(6-bromopyridin-2-yl)-2-chloroacetamide (337a) (0.5 g, 2.0 mmol) and (R)-1-((tert-butyldimethylsilyl)oxy)propan-2-amine (314f) (0.38 g, 2.0 mmol) according to the procedure reported in step-1 of Scheme 35. This gave after workup and purification by flash column chromatography [silica gel 24 g, EtOAc-DCM 10 to 100% as eluents] (R)—N-(6-bromopyridin-2-yl)-2-((1-((tert-butyldimethylsilyl)oxy)propan-2-yl)-amino)acetamide (337b) (0.5 g, 62% yield) as thick syrup; $^1$H NMR (300 MHz, DMSO-$d_6$) δ 10.51 (s, 1H), 8.10 (dd, J=8.2, 0.7 Hz, 1H), 7.74 (t, J=7.9 Hz, 1H), 7.34 (dd, J=7.7, 0.7 Hz, 1H), 3.44 (d, J=5.8 Hz, 2H), 3.41-3.37 (m, 1H), 3.35 (s, 2H), 2.66 (q, J=6.1 Hz, 1H), 0.94 (d, J=6.4 Hz, 3H), 0.85 (s, 9H), 0.03 (s, 3H), −0.00 (s, 3H); MS (ES+): 402.4, 403.3 (M+1), MS (ES−): 436.3, 438.4 (M+Cl).

Step-3: Preparation of (R)-1-(2-((2-((6-bromopyridin-2-yl)amino)-2-oxoethyl)(1-((tert-butyldimethylsilyl)oxy)propan-2-yl)amino)-2-oxoethyl)-1H-indazole-3-carboxamide (337c)

Reaction of (R)—N-(6-bromopyridin-2-yl)-2-((1-((tert-butyldimethylsilyl)oxy)propan-2-yl)-amino)acetamide (337b) (200 mg, 0.50 mmol) with 2-(3-carbamoyl-1H-indazol-1-yl)acetic acid (2e) (163 mg, 0.75 mmol) according to the procedure reported in step-3 of Scheme 2 gave after workup and purification by flash column chromatography [silica gel 12 g, DMA80 in DCM 0 to 20% as eluents] (R)-1-(2-((2-((6-bromopyridin-2-yl)amino)-2-carboxamide (337c) (0.19 g, 63% yield) as a colorless foam; MS (ES+): 603.5, 605.5 (M+1), MS (ES+): 601.5, 603.5 (M−1).

Step-4: Preparation of (R)-1-(2-((2-((6-bromopyridin-2-yl)amino)-2-oxoethyl)(1-hydroxypropan-2-yl)amino)-2-oxoethyl)-1H-indazole-3-carboxamide (337d)

Compound 337d was prepared from (R)-1-(2-((2-((6-bromopyridin-2-yl)amino)-2-oxoethyl)(1-((tert-butyldimethylsilyl)oxy)propan-2-yl)-amino)-2-oxoethyl)-1H-indazole-3-carboxamide (337c) (0.07 g, 0.12 mmol) and TBAF (0.061 g, 0.232 mmol) according to the procedure reported in step-2 of Scheme 301. This gave after workup and purification by flash chromatography [silica gel 4 g, DMA80 in DCM, 0 to 30% as eluents] (R)-1-(2-((2-((6-bromopyridin-2-yl)amino)-2-oxoethyl)(1-hydroxypropan-2-yl)amino)-2-oxoethyl)-1H-indazole-3-carboxamide (337d) (0.038 g, 67% yield) as a white solid; $^1$H NMR (300 MHz, DMSO-$d_6$) (a mixture of two rotamers) δ 11.19 and 10.90 (2s, 1H), 8.21-8.12 (m, 1H), 8.02 and 7.99 (2s, 1H), 7.86-7.17 (m, 7H), 5.75-5.57 (m) and 5.45 (s, 2H), 5.35 and 4.77 (2t, J=5.5 Hz, 1H), 4.56-4.36 and 4.21 (2 m, 1H), 4.15 and 3.93 (2d, J=16.7 Hz, 2H), 3.59-3.39 (m, 2H), 1.17 and 1.00 (2d, J=6.9 Hz, 3H); MS (ES+): 489.3, 491.3 (M+1), 511.3, 513.3 (M+Na), MS (ES−): 487.3, 489.3 (M−1).

Scheme 338

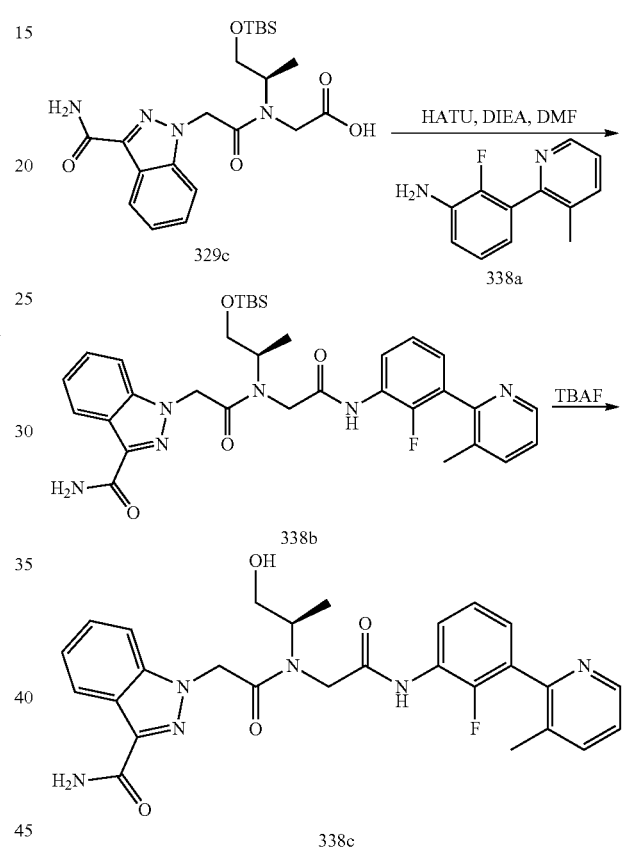

Preparation of (R)-1-(2-((2-((2-fluoro-3-(3-methylpyridin-2-yl)phenyl)amino)-2-oxoethyl)(1-hydroxypropan-2-yl)amino)-2-oxoethyl)-1H-indazole-3-carboxamide (338c)

Step-1: Preparation of (R)-1-(2-((1-((tert-butyldimethylsilyl)oxy)propan-2-yl)(2-((2-fluoro-3-(3-methylpyridin-2-yl)phenyl)amino)-2-oxoethyl)amino)-2-oxoethyl)-1H-indazole-3-carboxamide (338b)

Reaction of (R)-2-(N-(1-((tert-butyldimethylsilyl)oxy)propan-2-yl)-2-(3-carbamoyl-1H-indazol-1-yl)acetamido)acetic acid (329c) (0.1 g, 0.22 mmol) with 2-fluoro-3-(3-methylpyridin-2-yl)aniline (338a) (0.045 g, 0.22 mmol; prepared according to the procedure reported by Altmann, Eva et al; in PCT Int. Appl., 2012093101, 12 Jul. 2012) according to the procedure reported in step-3 of Scheme 2 gave after workup and purification by flash column chromatography [Silica gel, 12 g eluting with DMA80 in DCM 0 to 20% as eluents] to afford (R)-1-(2-((1-((tert-butyldimethylsilyl)oxy)propan-2-yl)(2-((2-fluoro-3-(3-methylpyridin-2-yl)phenyl)amino)-2-oxoethyl)amino)-2-oxoethyl)-1H-indazole-3-carboxamide (338b) (0.045 g, 32% yield) as a colorless foam; MS (ES+): 633.5 (M+1), 655.5 (M+Na).

Step-2: Preparation of (R)-1-(2-((1-((tert-butyldimethylsilyl)oxy)propan-2-yl)(2-((2-fluoro-3-(3-methylpyridin-2-yl)phenyl)amino)-2-oxoethyl)amino)-2-oxoethyl)-1H-indazole-3-carboxamide (338c)

Compound 338c was prepared from (R)-1-(2-((1-((tert-butyldimethylsilyl)oxy)propan-2-yl)(2-((2-fluoro-3-(3-methylpyridin-2-yl)phenyl)amino)-2-oxoethyl)amino)-2-oxoethyl)-1H-indazole-3-carboxamide (338b) (0.045 g, 0.071 mmol) and TBAF (0.037 g, 0.142 mmol) according to the procedure reported in step-2 of Scheme 301. This gave after workup and purification by flash chromatography [silica gel 4 g, DMA80 in DCM, 0 to 30% as eluents] (R)-1-(2-((1-((tert-butyldimethylsilyl)oxy)propan-2-yl)(2-((2-fluoro-3-(3-methylpyridin-2-yl)phenyl)amino)-2-oxoethyl)amino)-2-oxoethyl)-1H-indazole-3-carboxamide (338c) (0.028 g, 76% yield) as a white solid; $^1$H NMR (300 MHz, DMSO-$d_6$) (a mixture of two rotamers) δ 10.28 and 9.95 (2s, 1H), 8.53-8.47 (m, 1H), 8.21-8.14 (m, 1H), 8.06-7.97 (m, 1H), 7.81-7.06 (m, 9H), 5.74-5.59 (m) and 5.49 (s) (2H), 5.45 and 4.84 (t, J=5.5 Hz, 1H), 4.59-3.86 (m, 3H), 3.62-3.38 (m, 2H), 2.20 and 2.14 (2s, 3H), 1.19 and 1.04 (2d, J=6.9 Hz, 3H); $^{19}$F NMR (282 MHz, DMSO-$d_6$) (a mixture of two rotamers) δ −127.76, −128.34; MS (ES+) 519.4 (M+1), 541.4 (M+Na), MS (ES−) 517.5 (M−1).

Scheme 339

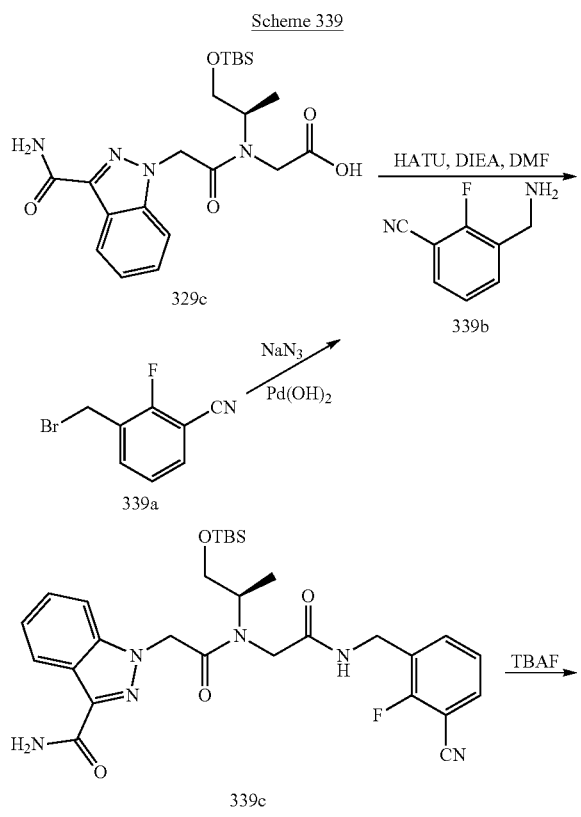

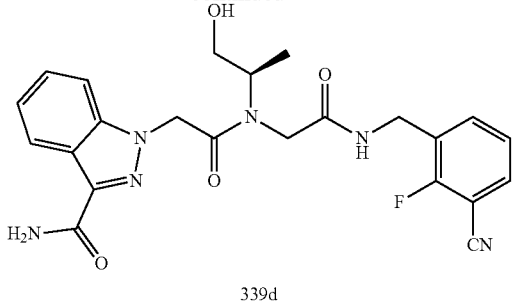

339d

Preparation of (R)-1-(2-((2-((3-cyano-2-fluorobenzyl)amino)-2-oxoethyl)(1-hydroxypropan-2-yl)amino)-2-oxoethyl)-1H-indazole-3-carboxamide (339d)

Step-1: Preparation of 3-(aminomethyl)-2-fluorobenzonitrile (339b)

To a solution of 3-(bromomethyl)-2-fluorobenzonitrile (339a) (0.25 g, 1.168 mmol) in DMSO (5 mL) was added Sodium azide (0.114 g, 1.752 mmol) and stirred at 50° C. for 16 h. Mixture was partitioned between water (50 mL) and EtOAc (60 mL) and Layers were separated. The aqueous layer was extracted with EtOAc (40 mL) and the combined organics were washed with water (50 mL), brine, dried, filtered and concentrated to afford azide as a pasty mass. This pasty mass was dissolved in Ethyl acetate (10 mL), added Palladium hydroxide on carbon (0.016 g, 0.117 mmol) and mixture was stirred under Hydrogen atmosphere for 2 h. Mixture was filtered over a Celite pad, washed with EtOAc (2×5 mL) and filtrate was concentrated in vacuum to afford 3-(aminomethyl)-2-fluorobenzonitrile (339b) (0.13 g, 74% yield) as off-white foam; $^1$H NMR (300 MHz, DMSO-$d_6$) δ 7.92-7.83 (m, 1H), 7.82-7.72 (m, 1H), 7.39 (t, J=7.7 Hz, 1H), 3.78 (s, 2H), 1.92 (d, J=30.5 Hz, 2H); $^{19}$F NMR (282 MHz, DMSO-$d_6$) δ −115.06.

Step-2: Preparation of (R)-1-(2-((1-((tert-butyldimethylsilyl)oxy)propan-2-yl)(2-((3-cyano-2-fluorobenzyl)amino)-2-oxoethyl)amino)-2-oxoethyl)-1H-indazole-3-carboxamide (339c)

Reaction of (R)-2-(N-(1-((tert-butyldimethylsilyl)oxy)propan-2-yl)-2-(3-carbamoyl-1H-indazol-1-yl)acetamido) acetic acid (329c) (0.12 g, 0.268 mmol) with 3-(aminomethyl)-2-fluorobenzonitrile (339b) (0.060 g, 0.401 mmol) according to the procedure reported in step-3 of Scheme 2 gave after workup and purification by flash column chromatography [Silica gel, 4 g eluting with EtOAc in DCM 0 to 100% as eluents] (R)-1-(2-((1-((tert-butyldimethylsilyl)oxy)propan-2-yl)(2-((3-cyano-2-fluorobenzyl)amino)-2-oxoethyl)amino)-2-oxoethyl)-1H-indazole-3-carboxamide (339c) (0.07 g, 45% yield) as a colorless foam; MS (ES+) 603.5 (M+Na).

Step-3: Preparation of (R)-1-(2-((2-((3-cyano-2-fluorobenzyl)amino)-2-oxoethyl)(1-hydroxy propan-2-yl)amino)-2-oxo ethyl)-1H-indazole-3-carboxamide (339d)

Compound 339d was prepared from (R)-1-(2-((1-((tert-butyldimethylsilyl)oxy)propan-2-yl)(2-((3-cyano-2-fluorobenzyl)amino)-2-oxoethyl)amino)-2-oxoethyl)-1H-indazole-3-carboxamide (339c) (0.07 g, 0.121) and TBAF (0.063 g, 0.241 mmol) according to the procedure reported in step-2 of Scheme 301. This gave after workup and purification by flash chromatography [silica gel 4 g, DMA80 in DCM, 0 to 30% as eluents] (R)-1-(2-((2-((3-cyano-2-fluorobenzyl)amino)-2-oxoethyl)(1-hydroxypropan-2-yl)amino)-2-oxoethyl)-1H-indazole-3-carboxamide (339d) (0.025 g, 45% yield) as a white solid; $^1$H NMR (300 MHz, DMSO-d$_6$) (a mixture of two rotamers) δ 8.91 and 8.65 (2t, J=5.9 Hz, 1H), 8.21-8.18 and 8.18-8.14 (2m, 1H), 7.89-7.73 (m, 1H), 7.69 (s, 1H), 7.61-7.08 (m, 6H), 5.66-5.55 (m) and 5.41 (s) (2H), 5.48 and 4.80 (2t, J=5.7 Hz, 1H), 4.55-3.69 (m, 5H), 3.51-3.40 (m, 2H), 1.15 and 0.95 (2d, J=6.9 Hz, 3H); $^{19}$F NMR (282 MHz, DMSO-d$_6$) (a mixture of two rotamers) δ −113.49, −113.84; MS (ES+): 467.5 (M+1), 489.5 (M+Na), MS (ES−): 465.5 (M−1), 501.5 (M+Cl).

Preparation of (R)-1-(2-((2-((2-fluoro-2'-methyl-[1,1'-biphenyl]-3-yl)amino)-2-oxoethyl)(1-hydroxypropan-2-yl)amino)-2-oxoethyl)-1H-indazole-3-carboxamide (340c)

Step-1: Preparation of 2-fluoro-2'-methyl-[1,1'-biphenyl]-3-amine (340a)

Compound 340a was prepared from 3-bromo-2-fluoroaniline (282a) (0.5 g, 2.63 mmol) and o-tolylboronic acid (0.43 g, 3.16 mmol) according to the procedure reported in step-4 of Scheme 329. This gave after workup and purification by flash column chromatography [silica gel 12 g, EtOAc in hexanes 0 to 30% as eluents] 2-fluoro-2'-methyl-[1,1'-biphenyl]-3-amine (340a) (0.4 g, 76% yield) as a colorless liquid; $^1$H NMR (300 MHz, DMSO-d$_6$) δ 7.33-7.18 (m, 3H), 7.18-7.11 (m, 1H), 6.95-6.86 (m, 1H), 6.77 (td, J=8.3, 1.7 Hz, 1H), 6.36 (ddd, J=7.5, 6.5, 1.7 Hz, 1H), 5.18 (s, 2H), 2.13 (s, 3H).

Step-2: Preparation of (R)-1-(2-((1-((tert-butyldimethylsilyl)oxy)propan-2-yl)(2-((2-fluoro-2'-methyl-[1,1'-biphenyl]-3-yl)-amino)-2-oxoethyl)amino)-2-oxoethyl)-1H-indazole-3-carboxamide (340b)

Reaction of (R)-2-(N-(1-(((tert-butyldimethylsilyl)oxy)propan-2-yl)-2-(3-carbamoyl-1H-indazol-1-yl)acetamido) acetic acid (329c) (0.12 g, 0.27 mmol) with 2-fluoro-2'-methyl-[1,1'-biphenyl]-3-amine (340a) (0.065 g, 0.32 mmol) according to the procedure reported in step-3 of Scheme 2 gave after workup and purification by flash column chromatography [Silica gel, 4 g eluting with EtOAc in DCM 0 to 100% as eluents] (R)-1-(2-((1-((tert-butyldimethylsilyl)oxy)propan-2-yl)(2-((2-fluoro-2'-methyl-[1,1'-biphenyl]-3-yl)amino)-2-oxoethyl)amino)-2-oxoethyl)-1H-indazole-3-carboxamide (340b) (0.09 g, 53% yield) as a colorless foam; MS (ES+): 654.6 (M+Na).

Step-3: Preparation of (R)-1-(2-((2-((2-fluoro-2'-methyl-[1,1'-biphenyl]-3-yl)amino)-2-oxoethyl)(1-hydroxypropan-2-yl)amino)-2-oxoethyl)-1H-indazole-3-carboxamide (340c)

Compound 340c was prepared from (R)-1-(2-((1-((tert-butyldimethylsilyl)oxy)propan-2-yl)(2-((2-fluoro-2'-methyl-[1,1'-biphenyl]-3-yl)-amino)-2-oxoethyl)amino)-2-oxoethyl)-1H-indazole-3-carboxamide (340b) (0.09 g, 0.142 mmol) and TBAF (0.074 g, 0.285 mmol) according to the procedure reported in step-2 of Scheme 301. This gave after workup and purification by flash chromatography [silica gel 4 g, DMA80 in DCM, 0 to 30% as eluents] (R)-1-(2-((2-((2-fluoro-2'-methyl-[1,1'-biphenyl]-3-yl)amino)-2-oxoethyl)(1-hydroxy propan-2-yl)-amino)-2-oxoethyl)-1H-indazole-3-carboxamide (340c) (0.058 g, 79% yield) as a white solid; $^1$H NMR (300 MHz, DMSO-d$_6$) (a mixture of two rotamers) δ 10.25 and 9.92 (s, 1H), 8.21-8.13 (m, 1H), 8.05-7.97 and 7.95-7.86 (2m, 1H), 7.73 and 7.68 (2s, 1H), 7.62-7.14 (m, 9H), 7.14-7.06 and 7.05-6.97 (2m, 1H), 5.74-5.58 and 5.48 (m and s, 2H), 5.45 and 4.83 (2t, J=5.5 Hz, 1H), 4.59-3.86 (m, 3H), 3.60-3.38 (m, 2H), 2.16 and 2.11 (2s, 3H), 1.19 and 1.04 (2d, J=6.9 Hz, 3H); $^{19}$F NMR (282 MHz, DMSO-d$_6$) (a mixture of two rotamers) δ −127.21, −127.76; MS (ES+): 540.5 (M+Na): MS (ES−): 516.6 (M−1).

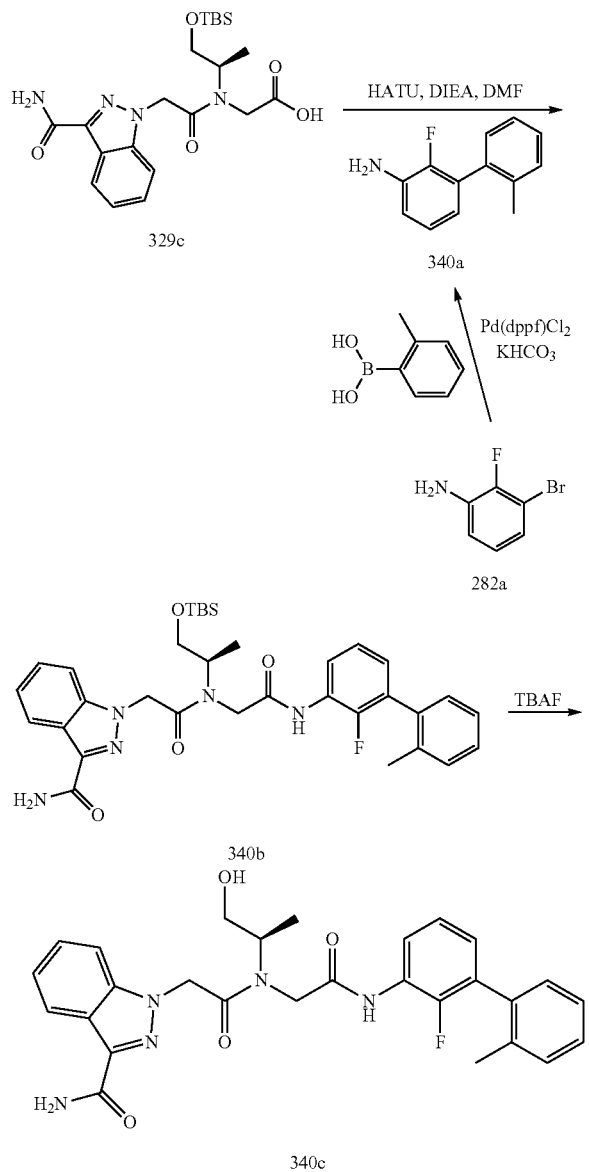

Scheme 340

Scheme 341

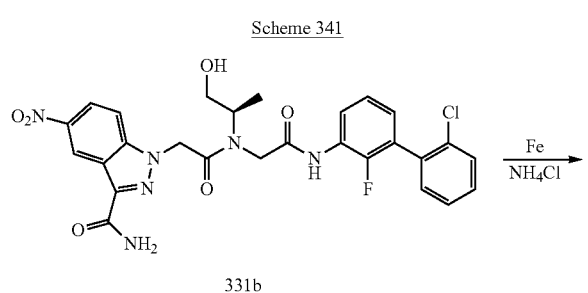

Preparation of (R)-5-amino-1-(2-((2-((2'-chloro-2-fluoro-[1,1'-biphenyl]-3-yl)amino)-2-oxoethyl)(1-hydroxypropan-2-yl)amino)-2-oxoethyl)-1H-indazole-3-carboxamide (341a)

Compound 341a was prepared from (R)-1-(2-((2-((2'-chloro-2-fluoro-[1,1'-biphenyl]-3-yl)amino)-2-oxoethyl)(1-hydroxypropan-2-yl)amino)-2-oxoethyl)-5-nitro-1H-indazole-3-carboxamide (331b) (0.05 g, 0.086 mmol) according to the procedure reported in step-6 of Scheme 328. This gave after workup and purification by flash chromatography [silica gel 4 g, DMA80 in DCM 0 to 30% as eluents] (R)-5-amino-1-(2-((2-((2'-chloro-2-fluoro-[1,1'-biphenyl]-3-yl)-amino)-2-oxoethyl)(1-hydroxypropan-2-yl)amino)-2-oxoethyl)-1H-indazole-3-carboxamide (341a) (0.025 g, 53% yield) as a white solid; $^1$H NMR (300 MHz, DMSO-$d_6$) (a mixture of two rotamers) δ 10.26 and 9.97 (2s, 1H), 8.10-8.04 and 8.01-7.93 (2m, 1H), 7.66-7.01 (m, 10H), 6.81 and 6.75 (2dd, J=8.9, 2.1 Hz, 1H), 5.59-5.43 (m) and 5.33 (s) (2H), 5.39 and 4.82 (2t, J=5.5 Hz, 1H), 5.03 and 5.02 (2s, 2H), 4.58-3.87 (m, 3H), 3.57-3.43 (m, 2H), 1.15 and 1.03 (2d, J=6.9 Hz, 3H); $^{19}$F NMR (282 MHz, DMSO-$d_6$) (a mixture of two rotamers) δ −126.49, −127.01; MS (ES+): 575.4 (M+Na), MS (ES−): 551.5 (M−1), 587.5 (M+Cl).

Scheme 342

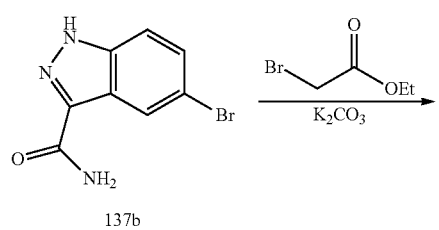

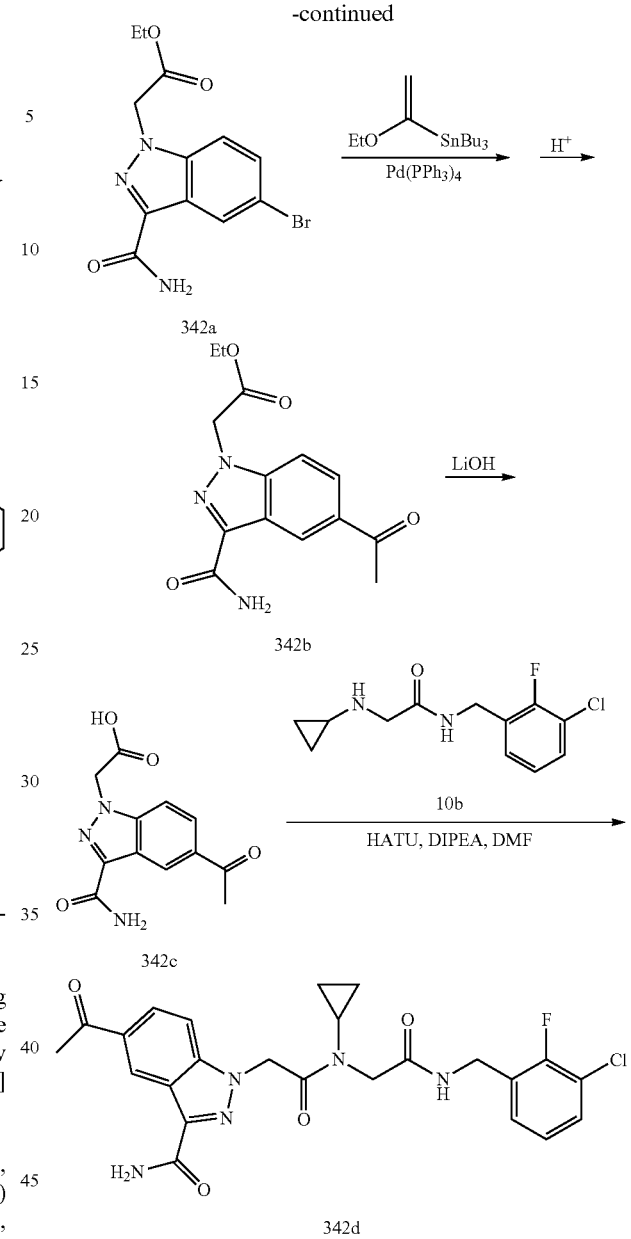

Preparation of 5-acetyl-1-(2-((2-(3-chloro-2-fluorobenzylamino)-2-oxoethyl)(cyclopropyl)-amino)-2-oxo-ethyl)-1H-indazole-3-carboxamide (342d)

Step 1: Preparation of ethyl 2-(5-bromo-3-carbamoyl-1H-indazol-1-yl)acetate (342a)

Reaction of 5-bromo-1H-indazole-3-carboxamide (137b) (4.4 g, 18.33 mmol) with ethylbromoacetate (3.06 mL, 27.5 mmol) according to the procedure reported in step-1 of Scheme 43 gave after workup ethyl 2-(5-bromo-3-carbamoyl-1H-indazol-1-yl)acetate (342a) (4.5 g, 75% yield) as a white solids; $^1$H NMR (300 MHz, DMSO-$d_6$) δ 8.33 (dd, J=2.0, 0.7 Hz, 1H), 7.84 (s, 1H), 7.78 (dd, J=9.0, 0.7 Hz, 1H), 7.62 (dd, J=9.0, 1.9 Hz, 1H), 7.54 (s, 1H), 5.49 (s, 2H), 4.16 (q, J=7.1 Hz, 2H), 1.20 (t, J=7.2 Hz, 3H).

Step 2: Preparation of ethyl 2-(5-acetyl-3-carbamoyl-1H-indazol-1-yl)acetate (342b)

Reaction of ethyl 2-(5-bromo-3-carbamoyl-1H-indazol-1-yl)acetate (342a) (200 mg, 0.613 mmol) with tributyl(1-ethoxyvinyl)stannane (0.267 mL, 0.767 mmol) according to the procedure reported in step-1 and step-2 of Scheme 206 gave after workup and purification by flash column chromatography [silica gel with hexanes/10% methanol in ethyl acetate (1:0 to 1:1)] ethyl 2-(5-acetyl-3-carbamoyl-1H-indazol-1-yl)acetate as a white solid (342b) (58 mg, 33%). $^1$H NMR (300 MHz, DMSO-d$_6$) δ 8.83 (dd, J=1.7, 0.8 Hz, 1H), 8.04 (dd, J=8.9, 1.6 Hz, 1H), 7.90 (s, 1H), 7.85 (dd, J=9.0, 0.8 Hz, 1H), 7.61 (s, 1H), 5.53 (s, 2H), 4.17 (q, J=7.1 Hz, 2H), 2.66 (s, 3H), 1.21 (t, J=7.1 Hz, 3H); MS (ES+): 312.4 (M+Na).

Step 3: Preparation of 2-(5-acetyl-3-carbamoyl-1H-indazol-1-yl)acetic acid (342c)

Reaction of ethyl 2-(5-acetyl-3-carbamoyl-1H-indazol-1-yl)acetate (342b) (54 mg, 0.187 mmol) with lithium hydroxide hydrate (47.0 mg, 1.120 mmol) according to the procedure reported in step-2 of Scheme 129 gave after workup and purification 2-(5-acetyl-3-carbamoyl-1H-indazol-1-yl)acetic acid (342c) (25 mg, 51%) as a white solid; $^1$H NMR (300 MHz, DMSO-d$_6$) δ 13.40 (s, 1H), 8.88-8.78 (m, 1H), 8.03 (dd, J=8.9, 1.7 Hz, 1H), 7.90 (s, 1H), 7.84 (d, J=9.0 Hz, 1H), 7.59 (s, 1H), 5.40 (s, 2H), 2.66 (s, 3H); MS (ES-): 260.3 (M-1).

Step 4: Preparation of 5-acetyl-1-(2-((2-(3-chloro-2-fluorobenzylamino)-2-oxoethyl)-(cyclopropyl)amino)-2-oxoethyl)-1H-indazole-3-carboxamide (342d)

Reaction of 2-(5-acetyl-3-carbamoyl-1H-indazol-1-yl)acetic acid (342c) (23 mg, 0.088 mmol) with N-(3-chloro-2-fluorobenzyl)-2-(cyclopropylamino)acetamide (10b) (33.9 mg, 0.132 mmol) according to the procedure reported in step-3 of Scheme 2 gave after workup and purification by flash column chromatography [silica gel with dichloromethane/methanol (1:0 to 19:1)] 5-acetyl-1-(2-((2-(3-chloro-2-fluorobenzylamino)-2-oxoethyl)-(cyclopropyl)amino)-2-oxoethyl)-1H-indazole-3-carboxamide (342d) (19 mg, 43%). $^1$H NMR (300 MHz, DMSO-d$_6$) δ 8.84-8.80 (m, 1H), 8.50 (t, J=5.8 Hz, 1H), 7.98 (dd, J=8.9, 1.6 Hz, 1H), 7.89 (s, 1H), 7.80-7.70 (m, 1H), 7.56 (s, 1H), 7.46 (td, J=7.6, 1.7 Hz, 1H), 7.28-7.18 (m, 1H), 7.10 (td, J=7.9, 1.0 Hz, 1H), 5.72 (s, 2H), 4.33 (d, J=5.7 Hz, 2H), 3.99 (s, 2H), 3.13-2.98 (m, 1H), 2.66 (s, 3H), 1.09-0.84 (m, 4H); $^{19}$F NMR (282 MHz, DMSO-d$_6$) δ -121.56; MS (ES+): 522.4 (M+Na); MS (ES-): 498.4 (M-1).

Scheme 343

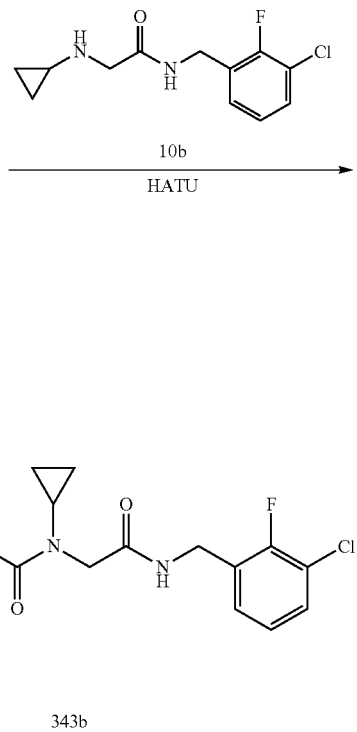

Preparation of 1-(2-((2-(3-chloro-2-fluorobenzylamino)-2-oxoethyl)(cyclopropyl)-amino)-2-oxoethyl)-5-fluoro-1H-indazole-3-carboxamide (343b)

Reaction of 2-(3-carbamoyl-5-fluoro-1H-indazol-1-yl)acetic acid (343a) (30 mg, 0.126 mmol; prepared according to the procedure reported by Altmann, Eva et al; in PCT Int. Appl., 2014002054, 3 Jan. 2014) with N-(3-chloro-2-fluorobenzyl)-2-(cyclopropylamino)acetamide (10b) (48.7 mg, 0.190 mmol) according to the procedure reported in step-3 of Scheme 2 gave after workup and purification by flash column chromatography [silica gel with dichloromethane/methanol (1:0 to 19:1) to give 1-(2-((2-(3-chloro-2-fluorobenzylamino)-2-oxoethyl)(cyclopropyl)amino)-2-oxoethyl)-5-fluoro-1H-indazole-3-carboxamide (343b) (25 mg, 42%) as a light brown solid; $^1$H NMR (300 MHz, DMSO-d$_6$) δ 8.50 (t, J=5.8 Hz, 1H), 7.83-7.75 (m, 2H), 7.72 (dd, J=9.2, 4.2 Hz, 1H), 7.51-7.40 (m, 2H), 7.34 (td, J=9.2, 2.5 Hz, 1H), 7.27-7.18 (m, 1H), 7.16-7.07 (m, 1H), 5.68 (s, 2H), 4.33 (d, J=5.7 Hz, 2H), 3.98 (s, 2H), 3.11-3.01 (m, 1H), 1.04-0.83 (m, 4H); $^{19}$F NMR (282 MHz, DMSO-d$_6$) δ -120.96, -121.57; MS (ES+): 498.4 & 500.3 (M+Na); MS (ES-): 510.4 (M+Cl).

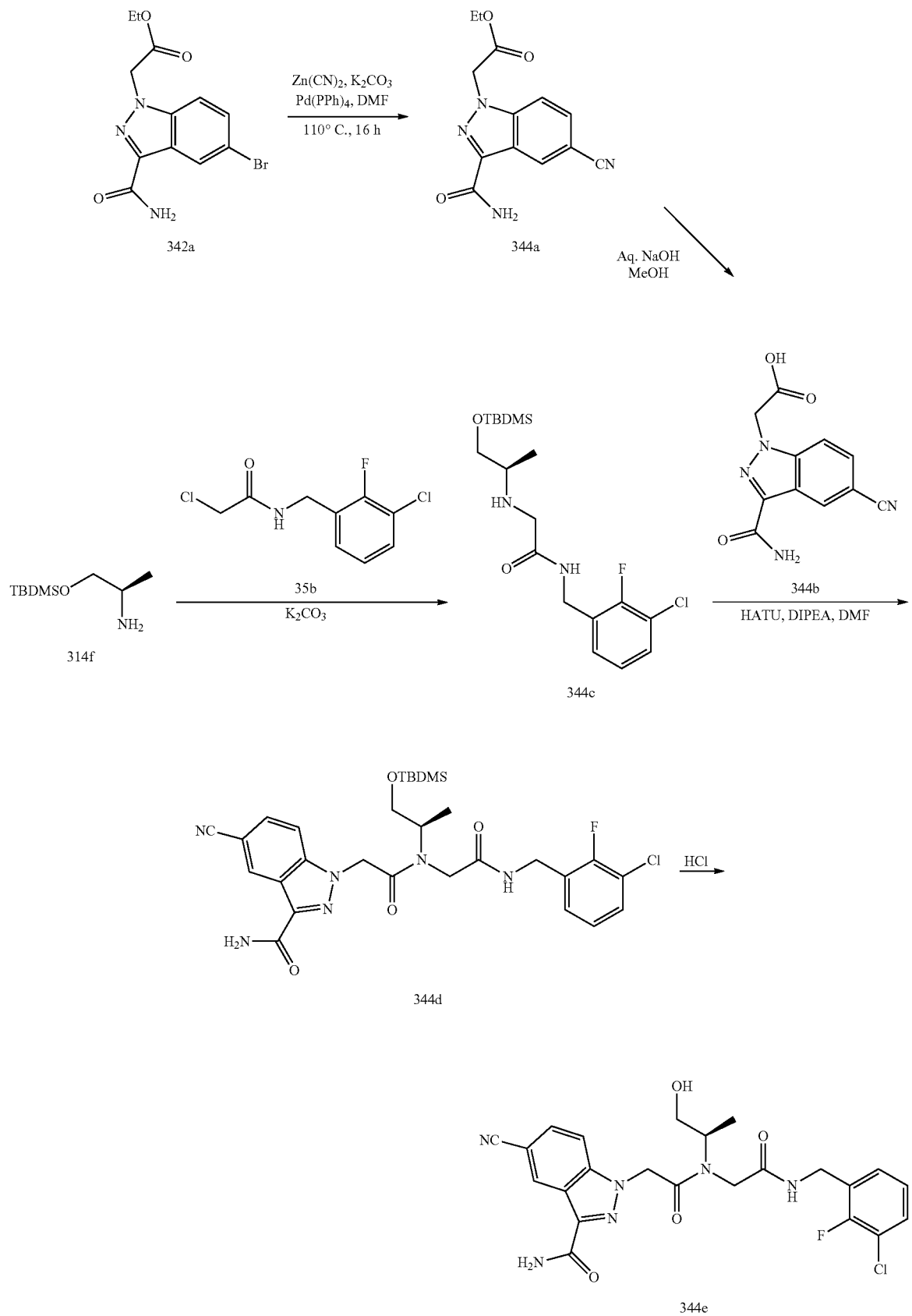

Preparation of (R)-1-(2-((2-((3-chloro-2-fluorobenzyl)amino)-2-oxoethyl)(1-hydroxypropan-2-yl)amino)-2-oxoethyl)-5-cyano-1H-indazole-3-carboxamide (344e)

Step-1: Preparation of ethyl 2-(3-carbamoyl-5-cyano-1H-indazol-1-yl)acetate (344a)

Compound 344a was prepared from ethyl 2-(5-bromo-3-carbamoyl-1H-indazol-1-yl)acetate (342a) (1.0 g, 3.06 mmol) in 1, 4 dioxane (20.0 mL) using zinc cyanide (3.66 g, 30.66 mmol), K$_2$CO$_3$ (1.05 g, 7.65 mmol) and tetrakis(triphenylphosphine)palladium(0) (1.41 g, 1.226 mmol) according to the procedure reported in step-3 of Scheme 301. This gave after workup ethyl 2-(3-carbamoyl-5-cyano-1H-indazol-1-yl)acetate (344a) (400.0 mg, 48%) as an off-white solid; $^1$H NMR (300 MHz, DMSO-d$_6$); δ 8.628-8.620 (s, 1H), 8.015-7.985 (m, 2H), 7.86-7.83 (d, 1H), 7.657 (s, 1H), 5.55 (s, 2H), 4.18-4.16 (m, 2H), 1.23-1.18 (m, 3H); MS (ES−): 271 (M−1).

Step-2: Preparation of 2-(3-carbamoyl-5-cyano-1H-indazol-1-yl)acetic acid (344b)

To a stirred solution of ethyl 2-(3-carbamoyl-5-cyano-1H-indazol-1-yl)acetate (344a) (400.0 mg, 1.47 mmol) in MeOH (20.0 mL) was added aq. NaOH (0.293 g, 7.30 mmol) and stirred for 12 h at RT. The reaction mixture was concentrated under reduced pressure and aqueous layer was acidified with HCl. The solid obtained was collected by filtration and dried to furnish 2-(3-carbamoyl-5-cyano-1H-indazol-1-yl)acetic acid (344b) (200.0 mg, 57%) as an off-white solid; $^1$H NMR (300 MHz, DMSO-d$_6$) δ 13.71-13.12 (m, 1H), 8.619-8.617 (s, 1H), 8.015-7.95 (m, 2H), 7.849-7.844 (d, 1H), 7.63 (s, 1H), 5.50-5.44 (s, 2H); MS (ES−): 243 (M−1).

Step-3: Preparation of (R)-2-((1-((tert-butyldimethylsilyl)oxy)propan-2-yl)-amino)-N-(3-chloro-2-fluorobenzyl)acetamide (344c)

To a stirred solution of 2-chloro-N-(3-chloro-2-fluorobenzyl) acetamide (35b) (500 mg, 2.13 mmol) in DCM (30 mL) were added (R)-1-((tert-butyldimethylsilyl)oxy)propan-2-amine (314f) (420.0 mg, 2.22 mmol) and DIPEA (1.36 mg, 10.54 mmol) at RT. The reaction mixture was stirred at room temperature for 48 h. The reaction mixture was concentrated in vacuum and purified by flash column chromatography [silica gel, eluting with ethyl acetate in n-hexane (0-90%)] to afford (R)-2-((1-((tert-butyldimethylsilyl)oxy)propan-2-yl)-amino)-N-(3-chloro-2-fluorobenzyl)acetamide (344c) (300.0 mg, 36.34%) as a brown solid; $^1$H NMR (300 MHz, DMSO-d$_6$) δ 8.36 (t, J=6.2 Hz, 1H), 7.53-7.38 (m, 1H), 7.32-7.21 (m, 1H), 7.21-7.10 (m, 1H), 4.35 (d, J=6.0 Hz, 2H), 3.46-3.31 (m, 2H), 3.18 (d, J=5.5 Hz, 2H), 2.67-2.55 (m, 1H), 0.90 (dd, J=6.4, 1.1 Hz, 3H), 0.84 (s, 9H), 0.00 (s, 6H); MS (ES+): 389.0 (M+1).

Step-4: Preparation of (R)-1-(2-((1-((tert-butyldimethylsilyl)oxy)propan-2-yl)(2-((3-chloro-2-fluorobenzyl)amino)-2-oxoethyl)amino)-2-oxoethyl)-5-cyano-1H-indazole-3-carboxamide (344d)

Compound 344d was prepared from (R)-2-((1-((tert-butyldimethylsilyl)oxy)propan-2-yl)-amino)-N-(3-chloro-2-fluorobenzyl)acetamide (344c) (382 mg, 0.98 mmol) by reaction with 2-(3-carbamoyl-5-cyano-1H-indazol-1-yl)acetic acid (344b) (200 mg, 0.82 mmol) according to the procedure reported in step-3 of Scheme 2. This gave after workup and purification by flash column chromatography [Silica gel, eluting with methanol in ethyl acetate from 0-10%] (R)-1-(2-((1-(((tert-butyldimethylsilyl)oxy)propan-2-yl)(2-((3-chloro-2-fluorobenzyl)amino)-2-oxoethyl)amino)-2-oxoethyl)-5-cyano-1H-indazole-3-carboxamide (344d) (400.0 mg, 20%) as an off-white solid.

Step-5: Preparation of (R)-1-(2-((2-((3-chloro-2-fluorobenzyl)amino)-2-oxo ethyl)(1-hydroxy propan-2-yl)amino)-2-oxo ethyl)-5-cyano-1H-indazole-3-carboxamide (344e)

Compound 344e was prepared from (R)-1-(2-((1-(((tert-butyldimethylsilyl)oxy)propan-2-yl)(2-((3-chloro-2-fluorobenzyl)amino)-2-oxoethyl)amino)-2-oxoethyl)-5-cyano-1H-indazole-3-carboxamide (344d) (100 mg, 0.162 mmol) by reaction with ethanolic HCl (10.0 mL) in ethanol (10 mL) according to the procedure reported in step-3 of Scheme 292. This gave after workup and purification by flash column chromatography [Silica gel, 24 g eluting with methanol in ethyl acetate from 0-5%) (R)-1-(2-((2-((3-chloro-2-fluorobenzyl)amino)-2-oxoethyl)(1-hydroxypropan-2-yl)amino)-2-oxoethyl)-5-cyano-1H-indazole-3-carboxamide (344e) (60.0 mg, 74%) as an off-white solid; $^1$H NMR (300 MHz, DMSO-d$_6$) (mixture of rotamers) δ 8.90 (t) and 8.67-8.55 (m) (2H), 7.96 (s, 1H), 7.86-7.69 (m, 2H), 7.61 (s, 1H), 7.55-7.12 (m, 2H), 6.99 (td, J=7.9, 1.0 Hz, 1H), 5.83-5.38 (m) and 4.89-4.71 (m) (3H), 4.51-3.72 (m, 5H), 3.54-3.37 (m, 2H), 1.16 (d, J=6.5 Hz) and 0.95 (d, J=6.9 Hz) (2d, 3H); $^{19}$F NMR (282 MHz, DMSO-d$_6$) δ −121.26, −121.60; MS (ES+): 501.4 & 503.4 (M+1); MS (ES−): 499.4 & 501.4 (M−1).

Scheme 345

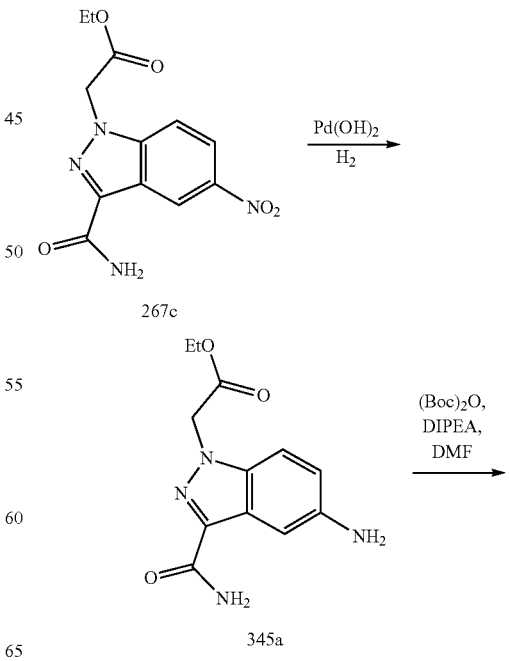

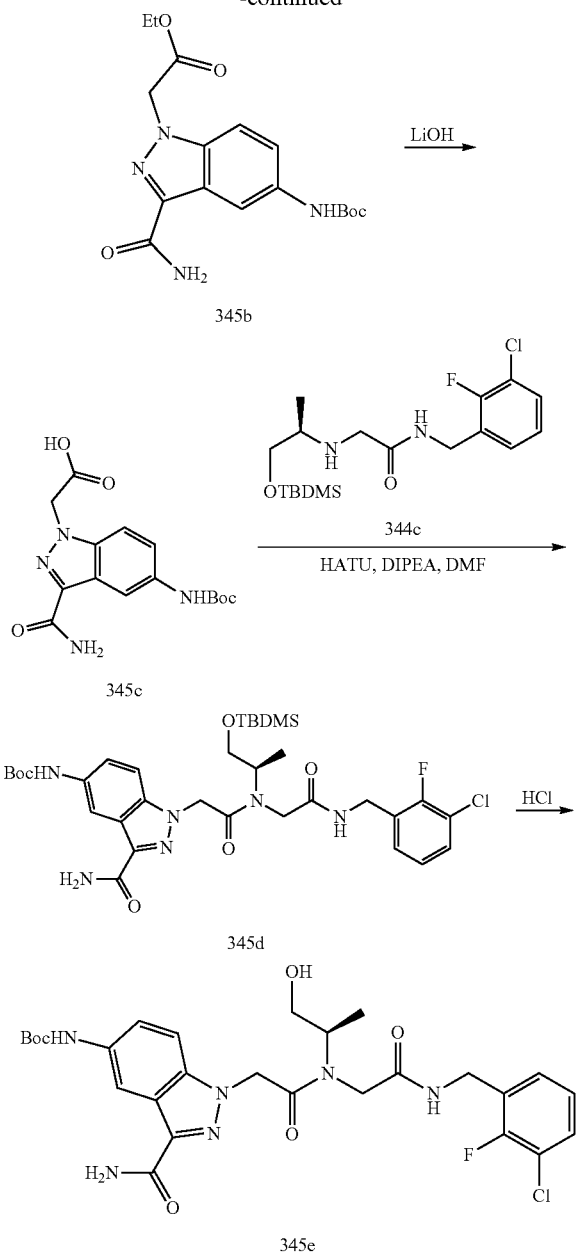

Preparation of (R)-tert-butyl(3-carbamoyl-1-(2-((2-((3-chloro-2-fluorobenzyl)amino)-2-oxoethyl)(1-hydroxypropan-2-yl)amino)-2-oxoethyl)-1H-indazol-5-yl)carbamate (345e)

Step-1: Preparation of ethyl 2-(5-amino-3-carbamoyl-1H-indazol-1-yl)acetate (345a)

Compound 345a was prepared from ethyl 2-(3-carbamoyl-5-nitro-1H-indazol-1-yl)acetate (267c) (2.0 g, 6.84 mmol) according to the procedure reported in Scheme 313. This gave after workup ethyl 2-(5-amino-3-carbamoyl-1H-indazol-1-yl)acetate (345a) (1.795 g) as a brown solid; MS (ES+): 263.3 (M+1).

Step-2: Preparation of ethyl 2-(5-(((tert-butoxycarbonyl)amino)-3-carbamoyl-1H-indazol-1-yl)acetate (345b)

To a stirred solution of ethyl 2-(5-amino-3-carbamoyl-1H-indazol-1-yl)acetate (345a) (3.0 g, 11.45 mmol) in DMF (15.0 mL) was added DIPEA (2.7 g, 20.86 mmol) and Boc anhydride (2.7 g, 12.37 mmol) and stirred at RT overnight. Water (50.0 mL) was poured into reaction mixture and extracted with EtOAc (3×50.0 mL). The combined organic layers were washed with brine, dried and concentrated under reduced pressure. The crude was purified by flash column chromatography [silica gel, eluting with ethyl acetate in n-hexane (0-50%)] to afford ethyl 2-(5-((tert-butoxy carbonyl)amino)-3-carbamoyl-1H-indazol-1-yl)acetate (345b) (1.3 g, 31.3%) as a white solid. Mass: MS (ES+): 363.0 (M+1); MS (ES−): 362.3 (M−1).

Step-3: Preparation of 2-(5-(((tert-butoxycarbonyl)amino)-3-carbamoyl-1H-indazol-1-yl)acetic acid (345c)

Compound 345c was prepared from ethyl 2-(5-((tert-butoxycarbonyl)amino)-3-carbamoyl-1H-indazol-1-yl)acetate (345b) (2.1 g, 5.8 mmol) according to the procedure reported in step-2 of Scheme 129. This gave after workup 2-(5-(tert-butoxycarbonylamino)-3-carbamoyl-1H-indazol-1-yl)acetic acid (345c) (1.68 g) as a white solid; $^1$H NMR (300 MHz, DMSO-$d_6$) δ 13.17 (s, 1H), 9.37 (s, 1H), 8.38 (s, 1H), 7.64-7.54 (m, 2H), 7.46-7.38 (m, 1H), 7.31 (s, 1H), 5.28 (s, 2H), 1.49 (s, 9H); MS (ES+): 357.2 (M+Na).

Step-4: Preparation of (R)-tert-butyl (1-(2-((1-((tert-butyldimethylsilyl)oxy)propan-2-yl)(2-((3-chloro-2-fluorobenzyl)amino)-2-oxoethyl)amino)-2-oxoethyl)-3-carbamoyl-1H-indazol-5-yl)carbamate (345d)

Compound 345d was prepared from (R)-2-((1-((tert-butyldimethylsilyl)oxy)propan-2-yl)-amino)-N-(3-chloro-2-fluorobenzyl)acetamide (344c) (174 mg, 0.45 mmol) by reaction with 2-(5-((tert-butoxycarbonyl)amino)-3-carbamoyl-1H-indazol-1-yl)acetic acid (345c) (150 mg, 0.45 mmol) according to the procedure reported in step-3 of Scheme 2. This gave after workup and purification by flash column chromatography [Silica gel, eluting with ethyl acetate in n-hexane (0-90%)] (R)-tert-butyl (1-(2-((1-((tert-butyldimethylsilyl)oxy)propan-2-yl)(2-((3-chloro-2-fluorobenzyl)amino)-2-oxoethyl)amino)-2-oxoethyl)-3-carbamoyl-1H-indazol-5-yl)carbamate (345d) (30 mg, 10%) as a white solid; MS (ES+): 704.0 (M+1): 705; MS (ES−): 703.3 (M−1).

Step-5: Preparation of (R)-tert-butyl (3-carbamoyl-1-(2-((2-((3-chloro-2-fluorobenzyl)amino)-2-oxoethyl)(1-hydroxy propan-2-yl)amino)-2-oxoethyl)-1H-indazol-5-yl)carbamate (345e)

Compound 345e was prepared from (R)-tert-butyl (1-(2-((1-((tert-butyldimethylsilyl)oxy)propan-2-yl)(2-((3-chloro-2-fluorobenzyl)amino)-2-oxoethyl)amino)-2-oxoethyl)-3-carbamoyl-1H-indazol-5-yl)carbamate (345d) (100 mg, 0.141 mmol) by reaction with ethanolic HCl (2 drops) in diethyl ether (10 mL) for 1 h. according to the procedure reported in step-3 of Scheme 292. This gave after workup (R)-tert-butyl (3-carbamoyl-1-(2-((2-((3-chloro-2-fluorobenzyl)amino)-2-oxo ethyl)(1-hydroxy propan-2-yl)

amino)-2-oxoethyl)-1H-indazol-5-yl)carbamate (345e) (30.0 mg, 36%) as an off-white solid; $^1$H NMR (300 MHz, DMSO-$d_6$) (a mixture of rotamers) δ 9.38 (s, 1H), 8.87 (t) & 8.60 (t, J=5.8 Hz) (2t, 1H), 8.38 (s, 1H), 8.01 (s, 1H), 7.60 (s, 1H), 7.56-7.28 (m, 3H), 7.27-7.15 (m, 1H), 7.08-6.96 (m, 1H), 5.67-5.25 (m, 2H), 5.48 & 4.80 (t, J=5.7 Hz) (2t, 1H), 4.52-3.71 (m, 5H), 3.52-3.37 (m, 2H), 1.49 (s, 9H), 1.13 (d, J=6.4 Hz) & 0.95 (d, J=7.0 Hz) (2d, 3H); $^{19}$F NMR (282 MHz, DMSO-$d_6$) δ −121.26, −121.66; MS (ES+): 613.5 & 615.4 (M+Na); MS (ES−): 589.5 (M−1).
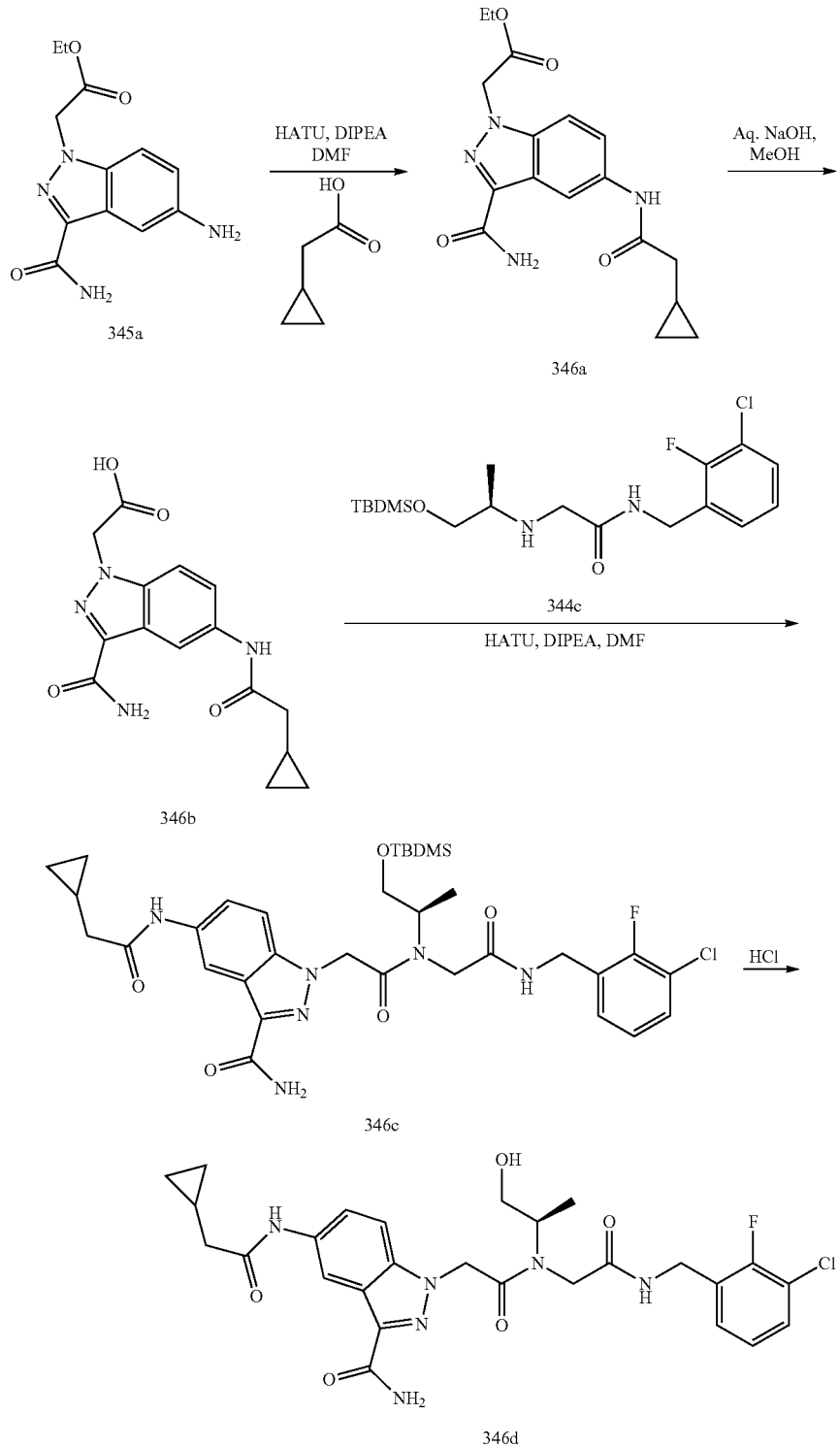
Scheme 346

Preparation of (R)-1-(2-((2-((3-chloro-2-fluorobenzyl)amino)-2-oxoethyl)(1-hydroxypropan-2-yl)amino)-2-oxoethyl)-5-(2-cyclopropylacetamido)-1H-indazole-3-carboxamide (346d)

Step-1: Preparation of ethyl 2-(3-carbamoyl-5-(2-cyclopropylacetamido)-1H-indazol-1-yl)acetate (346a)

Compound 346a was prepared from ethyl 2-(5-amino-3-carbamoyl-1H-indazol-1-yl)acetate (345a) (5.0 g, 19.06 mmol) according to the procedure reported in step-3 of Scheme 2. This gave after workup and purification by flash column chromatography [silica gel, eluting with ethyl acetate in n-hexane (0-50%)] ethyl 2-(3-carbamoyl-5-(2-cyclopropylacetamido)-1H-indazol-1-yl)acetate (346a) (1.0 gm, 15.23%) as a white solid; MS (ES+): 344.0 (M+1), MS (ES−): 343.0.0 (M−1).

Step-2: Preparation of 2-(3-carbamoyl-5-(2-cyclopropylacetamido)-1H-indazol-1-yl)acetic acid (346b)

Compound 346b was prepared from according to the procedure reported in step-2 of Scheme 344. This gave after workup and purification by flash column chromatography [silica gel, eluting with MeOH in EtOAc (0-10%)] 2-(3-carbamoyl-5-(2-cyclopropylacetamido)-1H-indazol-1-yl)acetic acid (346b) (240.0 mg, 65%) as an off-white solid; $^1$H NMR (300 MHz, DMSO-$d_6$) δ 10.14 (s, 1H), 8.04-8.03 (d, 1H), 7.97 (s, 2H), 6.93 (s, 2H), 6.74-6.73 (d, 1H), 4.97-4.80 (m, 1H), 4.12-4.10 (m, 2H), 2.0-1.87 (m, 4H); MS (ES−): 315.0 (M−1).

Step-3: Preparation of (R)-1-(2-((1-((tert-butyldimethylsilyl)oxy)propan-2-yl)(2-((3-chloro-2-fluorobenzyl)amino)-2-oxoethyl)amino)-2-oxoethyl)-5-(2-cyclopropylacetamido)-1H-indazole-3-carboxamide (346c)

Compound 346c was prepared from (R)-2-((1-((tert-butyldimethylsilyl)oxy)propan-2-yl)-amino)-N-(3-chloro-2-fluorobenzyl)acetamide (344c) (122 mg, 0.314 mmol) by reaction with 2-(3-carbamoyl-5-(2-cyclopropylacetamido)-1H-indazol-1-yl)acetic acid (346b) (100 mg, 0.32 mmol) according to the procedure reported in step-3 of Scheme 2. This gave after workup and purification by flash column chromatography [Silica gel, eluting with ethyl acetate in n-hexane (0-90%)] (R)-1-(2-((1-((tert-butyldimethylsilyl)oxy)propan-2-yl)(2-((3-chloro-2-fluorobenzyl)amino)-2-oxoethyl)amino)-2-oxoethyl)-5-(2-cyclopropylacetamido)-1H-indazole-3-carboxamide (346c) (70.0 mg, 32%) as a light brown solid; MS (ES−): 685 (M−1).

Step-4: Preparation of (R)-1-(2-((2-((3-chloro-2-fluorobenzyl)amino)-2-oxoethyl)(1-hydroxypropan-2-yl)amino)-2-oxoethyl)-5-(2-cyclopropylacetamido)-1H-indazole-3-carboxamide (346d)

Compound 346d was prepared from (R)-1-(2-((1-((tert-butyldimethylsilyl)oxy)propan-2-yl)(2-((3-chloro-2-fluorobenzyl)amino)-2-oxoethyl)amino)-2-oxoethyl)-5-(2-cyclopropylacetamido)-1H-indazole-3-carboxamide (346c) (160 mg, 0.232 mmol) by reaction with ethanolic HCl (8 mL) in ethanol (10 mL) according to the procedure reported in step-3 of Scheme 292. This gave after workup (R)-1-(2-((2-((3-chloro-2-fluorobenzyl)amino)-2-oxoethyl)(1-hydroxypropan-2-yl)amino)-2-oxoethyl)-5-(2-cyclopropylacetamido)-1H-indazole-3-carboxamide (346d) (17.0 mg, 13%) as a white solid; MS (ES+): 573 (M+1), MS (ES−): 571 (M−1).

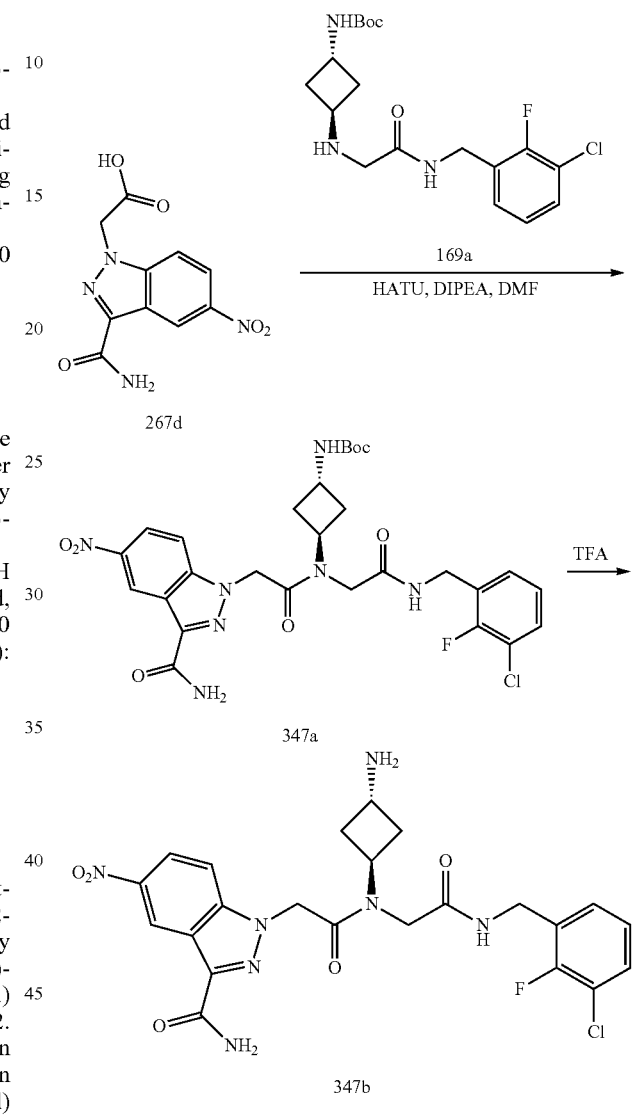

Scheme 347

Preparation of 1-(2-(((trans)-3-aminocyclobutyl)(2-((3-chloro-2-fluorobenzyl)amino)-2-oxoethyl)amino)-2-oxoethyl)-5-nitro-1H-indazole-3-carboxamide (347b)

Step-1: Preparation of tert-butyl ((trans)-3-(2-(3-carbamoyl-5-nitro-1H-indazol-1-yl)-N-(2-((3-chloro-2-fluorobenzyl)amino)-2-oxoethyl)acetamido)cyclobutyl)carbamate (347a)

Reaction of tert-butyl ((trans)-3-((2-((3-chloro-2-fluorobenzyl)amino)-2-oxoethyl)amino)cyclobutyl)carbamate (169a) (570 mg, 1.48 mmol) with 2-(3-carbamoyl-5-nitro-1H-indazol-1-yl)acetic acid (267d) (300 mg, 1.14 mmol) according to the procedure reported in step-3 of Scheme 2 gave after workup and purification by flash column chromatography [Silica gel, (12 g) eluting with EtOAc in DCM 0 to 100% as eluents] tert-butyl ((trans)-3-(2-(3-carbamoyl-5-nitro-1H-indazol-1-yl)-N-(2-((3-chloro-2-fluorobenzyl)amino)-2-oxoethyl)acetamido)cyclobutyl)carbamate (347a) (0.52 g, 73% yield) as a white powder; $^1$H NMR (300 MHz, DMSO-d$_6$) (a mixture of two rotamers) δ 9.06 and 9.05 (2s, 1H), 8.89 and 8.44 (2t, J=5.9 Hz, 1H), 8.33-8.22 (m, 1H), 8.03 and 7.69 (2s, 2H), 7.84 and 7.77 (2d, J=9.3 Hz, 1H), 7.57-7.29 (m, 2H), 7.26-6.99 (m, 1H), 5.65 and 5.54 (2s, 2H), 4.92-4.75 (m, 1H), 4.47 and 4.32 (2d, J=5.8 Hz, 2H), 4.32 and 4.04 (2s, 2H), 3.89-3.77 (m, 1H), 2.33-2.11 (m, 4H), 1.40 and 1.36 (2s, 9H); MS (ES+): 654.5 and 655.5 (M+Na); (ES−): 630.6 (M−1).

Step-2: Preparation of 1-(2-(((trans)-3-aminocyclobutyl)(2-((3-chloro-2-fluorobenzyl)amino)-2-oxoethyl)amino)-2-oxoethyl)-5-nitro-1H-indazole-3-carboxamide (347b)

Reaction of tert-butyl ((trans)-3-(2-(3-carbamoyl-5-nitro-1H-indazol-1-yl)-N-(2-((3-chloro-2-fluorobenzyl)amino)-2-oxoethyl)acetamido)cyclobutyl)carbamate (347a) (0.8 g, 1.266 mmol) with TFA (0.975 mL, 12.66 mmol) according to the procedure reported in step-2 of Scheme 2 gave after workup and purification by flash column chromatography [Silica gel, (12 g) eluting with DMA80 in DCM, 0 to 50% as eluents] 1-(2-(((trans)-3-aminocyclobutyl)(2-((3-chloro-2-fluorobenzyl)amino)-2-oxoethyl)amino)-2-oxoethyl)-5-nitro-1H-indazole-3-carboxamide (347b) (0.03 g, 5% yield) as a white solid; $^1$H NMR (300 MHz, DMSO-d$_6$) (a mixture of two rotamers) δ 9.058 and 9.05 (2s, 1H), 8.88 and 8.43 (2t, J=5.9 Hz, 1H), 8.31 and 8.25 (2dd, J=9.3, 2.3 Hz, 1H), 8.03 and 8.00 (2s, 2H), 7.85 and 7.77 (2d, J=9.3 Hz, 1H), 7.69 (s, 1H), 7.57-6.85 (m, 3H), 5.65 and 5.54 (2s, 2H), 4.99-4.83 (m, 1H), 4.47 and 4.32 (2d, J=5.9 Hz, 2H), 4.29 and, 4.02 (2s, 2H), 3.48-3.24 (m, 1H), 3.10-2.77 (m, 2H), 2.25-2.10 (m, 1H), 2.12-1.90 (m, 2H), 1.87-1.73 (m, 1H); $^{19}$F NMR (282 MHz, DMSO-d$_6$) (a mixture of two rotamers) δ −121.24, −121.59; MS (ES+): 532.4 (M+1).

Preparation of 1-(2-((2-(3-chloro-2-fluorobenzylamino)-2-oxoethyl)(cyclopropyl)-amino)-2-oxoethyl)-6-fluoro-1H-indazole-3-carboxamide (348b)

Reaction of 2-(3-carbamoyl-6-fluoro-1H-indazol-1-yl)acetic acid (348a) (202 mg, 0.853 mmol; prepared according to the procedure reported by Altmann, Eva et al; in PCT Int. Appl., 2014002058, 3 Jan. 2014) with N-(3-chloro-2-fluorobenzyl)-2-(cyclopropylamino)acetamide (10b) (328 mg, 1.28 mmol) according to the procedure reported in step-3 of Scheme 2 gave after workup and purification by flash column chromatography [silica gel with dichloromethane/methanol (1:0 to 19:1) to give 1-(2-((2-(3-chloro-2-fluorobenzylamino)-2-oxoethyl)(cyclopropyl)amino)-2-oxoethyl)-6-fluoro-1H-indazole-3-carboxamide (348b) (80 mg, 20%) as a light brown solid; $^1$H NMR (300 MHz, DMSO-d$_6$) δ 8.50 (t, J=5.8 Hz, 1H), 8.18 (dd, J=8.9, 5.4 Hz, 1H), 7.78 (s, 1H), 7.56 (dd, J=9.8, 2.2 Hz, 1H), 7.52-7.34 (m, 2H), 7.26-7.05 (m, 3H), 5.62 (s, 2H), 4.33 (d, J=5.7 Hz, 2H), 3.98 (s, 2H), 3.13-2.98 (m, 1H), 1.05-0.81 (m, 4H); $^{19}$F NMR (282 MHz, DMSO-d$_6$) δ −114.79, −121.60; MS (ES+): 498.4 & 500.4 (M+Na); MS (ES−): 510.4 (M+Cl).

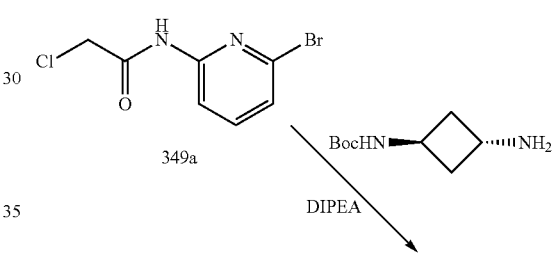

Scheme-349

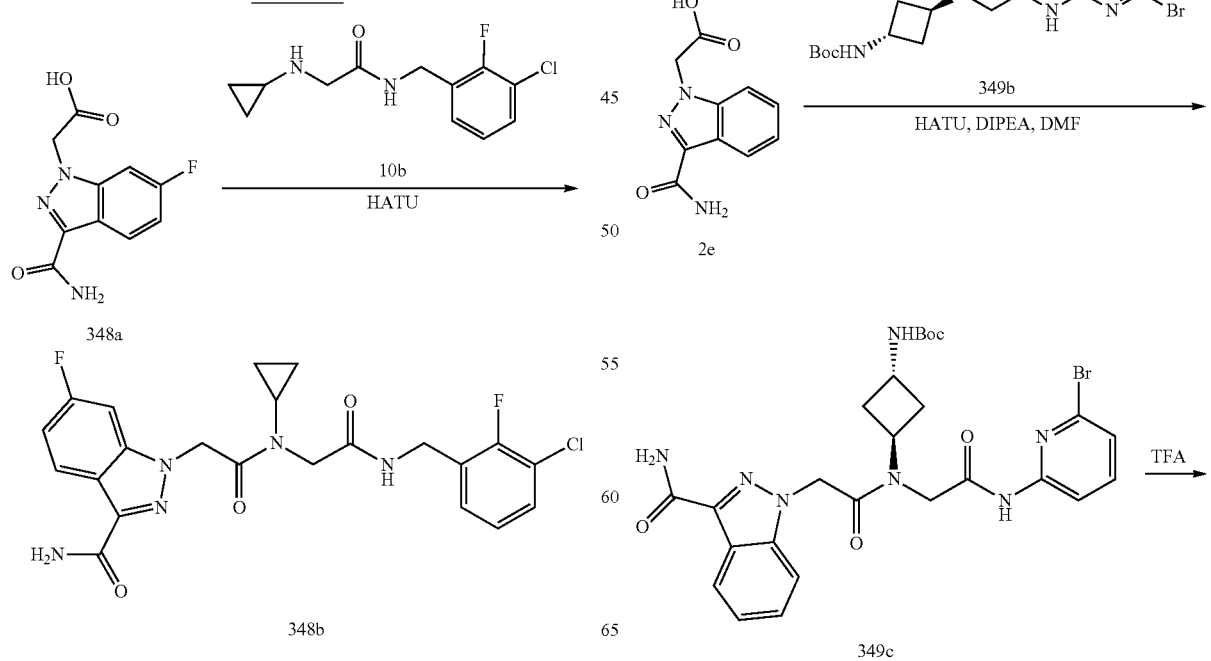

Scheme 348

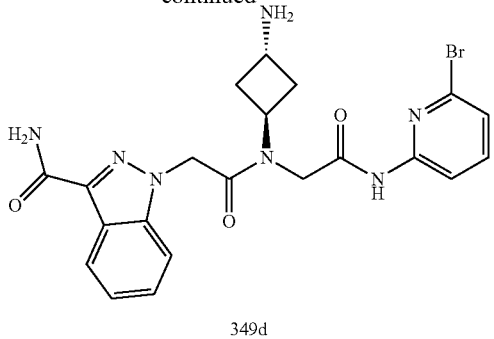

349d

Preparation of 1-(2-(((trans)-3-aminocyclobutyl)(2-((6-bromopyridin-2-yl)amino)-2-oxoethyl)amino)-2-oxoethyl)-1H-indazole-3-carboxamide (349d)

Step-1: Preparation of tert-butyl ((trans)-3-((2-((6-bromopyridin-2-yl)amino)-2-oxoethyl)amino)cyclobutyl)carbamate (349b)

To a solution of N-(6-bromopyridin-2-yl)-2-chloroacetamide (349a) (0.55 g, 2.204 mmol, prepared according to the procedure reported by Cheriard, Berland L. and Wu, Xinyuan; in PCI Int Appl., 2016044792, 24 Mar. 2016) in THF (10 mL) was added DIPEA (0.578 mL, 3.31 mmol), tert-butyl (trans)-3-aminocyclobutylcarbamate (0.452 g, 2.425 mmol) and stirred at 60° C. for 24 h. Mixture was poured into sat. NaHCO$_3$ solution (60 ml) and resultant suspension was extracted with EtOAc (2×80 ml). The combined organics were washed with brine, dried, filtered, concentrated and purified by flash column chromatography [silica gel 24 g, EtOAc in hexanes as eluents 0 to 100%] to afford tert-butyl ((trans)-3-((2-((6-bromopyridin-2-yl)amino)-2-oxoethyl)amino)cyclobutyl)carbamate (349b) (0.43 g, 49% yield) as off-white solid; $^1$H NMR (300 MHz, DMSO-d$_6$) δ 10.45 (s, 1H), 8.10 (dd, J=8.1, 0.7 Hz, 1H), 7.75 (t, J=8.0 Hz, 1H), 7.35 (dd, J=7.7, 0.7 Hz, 1H), 7.15 (d, J=7.6 Hz, 1H), 4.09-3.93 (m, 1H), 3.27-3.14 (m, 3H), 2.03-1.89 (m, 4H), 1.36 (s, 9H); MS (ES+): 421.3, 423.3 (M+Na), MS (ES−): 397.3, 399.3 (M−1).

Step-2: Preparation of tert-butyl ((trans)-3-(N-(2-((6-bromopyridin-2-yl)amino)-2-oxoethyl)-2-(3-carbamoyl-1H-indazol-1-yl)acetamido)cyclobutyl)carbamate (349c)

Reaction of tert-butyl ((trans)-3-((2-((6-bromopyridin-2-yl)amino)-2-oxoethyl)amino)cyclobutyl)carbamate (349b) (100 mg, 0.25 mmol) with 2-(3-carbamoyl-1H-indazol-1-yl) acetic acid (2e) (66 mg, 0.30 mmol) according to the procedure reported in step-3 of scheme-2 gave after workup and purification by flash column chromatography [Silica gel, (4 g) eluting with EtOAc in DCM 0 to 100% as eluents] tert-butyl ((trans)-3-(N-(2-((6-bromopyridin-2-yl)amino)-2-oxoethyl)-2-(3-carbamoyl-1H-indazol-1-yl)acetamido)cyclobutyl)carbamate (349c) (0.12 g, 80% yield) as a white powder; $^1$H NMR (300 MHz, DMSO-d$_6$) (a mixture of two rotamers) δ 11.25 and 10.90 (2s, 1H), 8.23-8.11 (m, 1H), 8.05-7.91 (m, 1H), 7.87-7.55 (m, 2H), 7.50-7.18 (m, 5H), 5.57 and 5.44 (2s, 2H), 4.98-4.81 (m, 1H), 4.55 and 4.22 (2s, 2H), 3.92-3.75 (m, 1H), 2.33-2.14 (m, 2H), 2.13-1.97 (m, 2H), 1.39 and 1.34 (2s, 9H).

Step-3: Preparation of 1-(2-(((trans)-3-aminocyclobutyl)(2-((6-bromopyridin-2-yl)amino)-2-oxoethyl)amino)-2-oxoethyl)-1H-indazole-3-carboxamide (349d)

Reaction of tert-butyl ((trans)-3-(N-(2-((6-bromopyridin-2-yl)amino)-2-oxoethyl)-2-(3-carbamoyl-1H-indazol-1-yl) acetamido)cyclobutyl)carbamate (349c) (0.12 g, 0.2 mmol) with TFA (0.15 mL, 2.0 mmol) according to the procedure reported in step-2 of scheme-2 gave after workup and purification by flash column chromatography [Silica gel, (12 g) eluting with DMA80 in DCM, 0 to 50% as eluents] 1-(2-(((trans)-3-aminocyclobutyl)(2-((6-bromopyridin-2-yl) amino)-2-oxoethyl)amino)-2-oxoethyl)-1H-indazole-3-carboxamide (349d) (0.075 g, 75% yield) as a white solid; $^1$H NMR (300 MHz, DMSO-d$_6$) (a mixture of two rotamers) δ 10.88 (s, 1H), 8.23-7.96 (m, 2H), 7.87-7.54 (m, 3H), 7.49-7.19 (m, 4H), 5.56 and 5.44 (2s, 2H), 5.03-4.86 (m, 1H), 4.53 and 4.21 (2s, 2H), 3.46-3.20 (m, 3H), 2.41-2.31 (m, 1H), 2.25-1.95 (m, 2H), 1.86-1.73 (m, 1H); MS (ES+): 500.4, 502.4 (M+1), MS (ES−): 498.4, 500.4 (M−1).

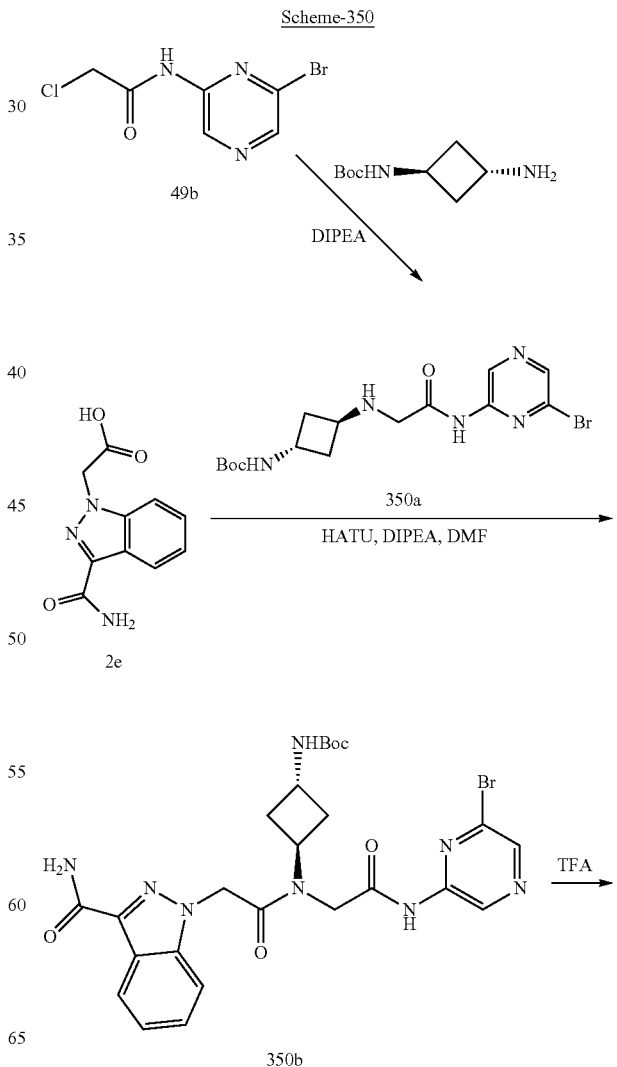

Scheme-350

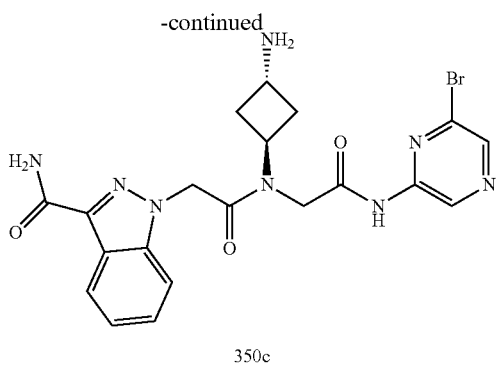

350c

Preparation of 1-(2-(((trans)-3-aminocyclobutyl)(2-((6-bromopyrazin-2-yl)amino)-2-oxoethyl)amino)-2-oxoethyl)-1H-indazole-3-carboxamide (350c)

Step-1: Preparation of tert-butyl ((trans)-3-((2-((6-bromopyrazin-2-yl)amino)-2-oxoethyl)amino)cyclobutyl)carbamate (350a)

Compound 350a was prepared from N-(6-bromopyrazin-2-yl)-2-chloroacetamide (49b) (0.5 g, 1.4 mmol) according to the procedure reported in step-1 of scheme-349. This gave after workup and purification by flash column chromatography [silica gel 24 g, EtOAc in hexanes as eluents 0 to 100%] tert-butyl ((trans)-3-((2-((6-bromopyrazin-2-yl)amino)-2-oxoethyl)amino)cyclobutyl)carbamate (350a) (0.08 g, 14% yield) as a white solid; $^1$H NMR (300 MHz, DMSO-$d_6$) δ 9.32 (d, J=0.6 Hz, 1H), 8.56 (d, J=0.6 Hz, 1H), 7.14 (d, J=7.6 Hz, 1H), 4.07-3.95 (m, 1H), 3.31-3.14 (m, 3H), 1.96 (t, J=6.5 Hz, 4H), 1.36 (s, 9H); MS (ES+): 400.4, 402.4 (M, M+2), 422.3, 424.4 (M+Na).

Step-2: Preparation of tert-butyl ((trans)-3-(N-(2-((6-bromopyrazin-2-yl)amino)-2-oxoethyl)-2-(3-carbamoyl-1H-indazol-1-yl)acetamido)cyclobutyl)carbamate (350b)

Reaction of tert-butyl ((trans)-3-((2-((6-bromopyrazin-2-yl)amino)-2-oxoethyl)amino)cyclobutyl)carbamate (350a) (80 mg, 0.2 mmol) with 2-(3-carbamoyl-1H-indazol-1-yl) acetic acid (2e) (53 mg, 0.24 mmol) according to the procedure reported in step-3 of scheme-2 gave after workup and purification by flash column chromatography [Silica gel, (4 g) eluting with DMA80 in DCM 0 to 30% as eluents] tert-butyl ((trans)-3-(N-(2-((6-bromopyrazin-2-yl)amino)-2-oxoethyl)-2-(3-carbamoyl-1H-indazol-1-yl)acetamido)cyclobutyl)carbamate (350b) (0.09 g, 75% yield) as a white solid; MS (ES+): 601.4, 603.4 (M, M+2).

Step-3: Preparation of 1-(2-(((trans)-3-aminocyclobutyl)(2-((6-bromopyrazin-2-yl)amino)-2-oxoethyl)amino)-2-oxoethyl)-1H-indazole-3-carboxamide (350c)

Reaction of tert-butyl ((trans)-3-(N-(2-((6-bromopyrazin-2-yl)amino)-2-oxoethyl)-2-(3-carbamoyl-1H-indazol-1-yl) acetamido)cyclobutyl)carbamate (350b) (0.09 g, 0.15 mmol) with TFA (0.23 mL, 3.0 mmol) according to the procedure reported in step-2 of scheme-2 gave after workup and purification by flash column chromatography [Silica gel, (12 g) eluting with DMA80 in DCM, 0 to 50% as eluents] 1-(2-(((trans)-3-aminocyclobutyl)(2-((6-bromopyrazin-2-yl)amino)-2-oxoethyl)amino)-2-oxoethyl)-1H-indazole-3-carboxamide (350c) (0.06 g, 80% yield) as a white solid; $^1$H NMR (300 MHz, DMSO-$d_6$) (a mixture of two rotamers) δ 9.38 and 9.24 (2s, 1H), 8.62 and 8.54 (2s, 1H), 8.21-8.13 (m, 1H), 7.71 (s, 1H), 7.62 and 7.60 (2d, J=3.4 Hz, 1H), 7.49-7.35 (m, 3H), 7.31-7.20 (m, 1H), 5.57 and 5.45 (2s, 2H), 4.96 (q, J=7.9 Hz, 1H), 4.55 and 4.25 (2s, 2H), 3.49-3.22 (m, 1H), 2.45-1.97 (m, 3H), 1.94-1.76 (m, 1H); MS (ES+): 501.2, 503.2 (M, M+2), 523.2, 525.2 (M+Na).

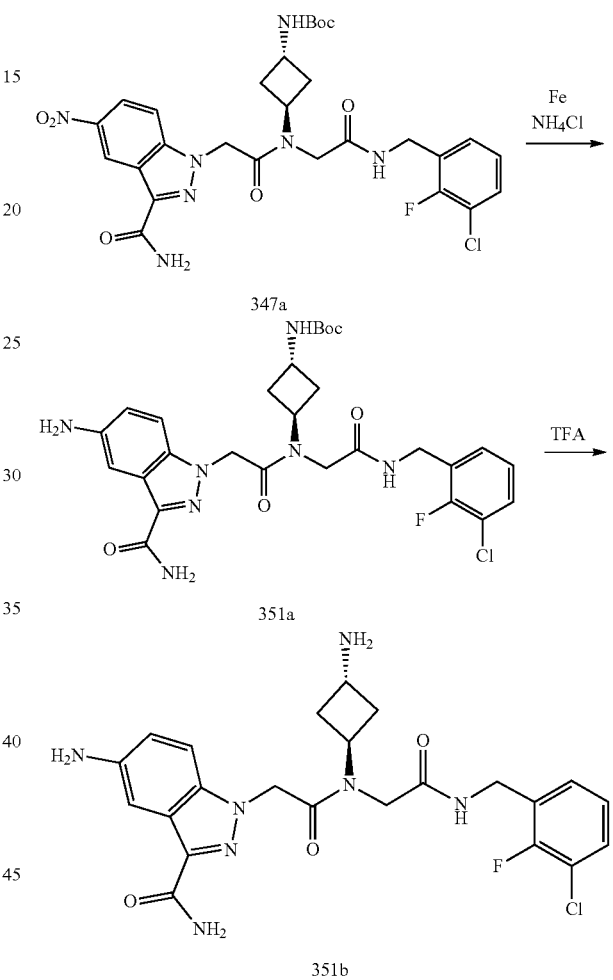

Scheme 351

Preparation of 5-amino-1-(2-(((trans)-3-aminocyclobutyl)(2-((3-chloro-2-fluorobenzyl)amino)-2-oxoethyl)amino)-2-oxoethyl)-1H-indazole-3-carboxamide (351b)

Step-1: Preparation of tert-butyl ((trans)-3-(2-(5-amino-3-carbamoyl-1H-indazol-1-yl)-N-(2-((3-chloro-2-fluorobenzyl)amino)-2-oxoethyl)acetamido)cyclobutyl)carbamate (351a)

Compound 351a was prepared from tert-butyl ((trans)-3-(2-(3-carbamoyl-5-nitro-1H-indazol-1-yl)-N-(2-((3-chloro-2-fluorobenzyl)amino)-2-oxoethyl)acetamido)cyclobutyl) carbamate (347a) (0.4 g, 0.63 mmol) according to the procedure reported in step-6 of Scheme 328. This gave after workup and purification by flash chromatography [silica gel 12 g, DMA80 in DCM 0 to 30% as eluents] tert-butyl ((trans)-3-(2-(5-amino-3-carbamoyl-1H-indazol-1-yl)-N-(2-((3-chloro-2-fluorobenzyl)amino)-2-oxoethyl)acetamido)cyclobutyl)carbamate (351a) (0.25 g, 66% yield) as a off-white solid; MS (ES+): 602.5 (M+1), MS (ES−): 636.5 (M+Cl).

Step-2: Preparation of 5-amino-1-(2-(((trans)-3-aminocyclobutyl)(2-((3-chloro-2-fluorobenzyl)amino)-2-oxoethyl)amino)-2-oxoethyl)-1H-indazole-3-carboxamide (351b)

Compound 351b was prepared from tert-butyl ((trans)-3-(2-(5-amino-3-carbamoyl-1H-indazol-1-yl)-N-(2-((3-chloro-2-fluorobenzyl)amino)-2-oxoethyl)acetamido)cyclobutyl)carbamate (351a) (0.08 g, 0.133 mmol) using TFA (0.205 mL, 2.66 mmol) according to the procedure reported in step-2 of Scheme 2. This gave after workup and purification by flash column chromatography [Silica gel, (4 g) eluting with DMA80 in DCM, 0 to 50% as eluents] 5-amino-1-(2-(((trans)-3-aminocyclobutyl)(2-((3-chloro-2-fluorobenzyl)amino)-2-oxoethyl)amino)-2-oxoethyl)-1H-indazole-3-carboxamide (351b) (0.053 g, 79% yield) as a white solid; $^1$H NMR (300 MHz, DMSO-$d_6$) δ 8.89 and 8.51 (2t, J=6.0 Hz, 1H), 8.10 and 8.01 (2s, 2H), 7.64-6.88 (m, 9H), 5.43 and 5.30 (2s, 2H), 5.14-4.91 (m, 1H), 4.46 (d, J=5.6 Hz, 1H), 4.36-4.28 (m, 2H), 4.05 (s, 1H), 3.74-3.15 (m, 2H), 2.68-2.58 and 2.46-2.30 (2m, 2H), 2.23-2.09 (m, 2H); $^{19}$F NMR (282 MHz, DMSO-$d_6$) (a mixture of two rotamers) δ −121.25, −121.59; MS (ES+) 502.4 (M+1).

Preparation of 1-(2-((2-((3-chloro-2-fluorobenzyl)amino)-2-oxoethyl)(cyclopropyl)amino)-2-oxoethyl)-5-(hydroxymethyl)-1H-indazole-3-carboxamide (352b)

Step 1 Preparation of 3-carbamoyl-1-(2-((2-(3-chloro-2-fluorobenzylamino)-2-oxoethyl)(cyclopropyl)amino)-2-oxoethyl)-1H-indazole-5-carboxylic (ethyl carbonic) anhydride (352a)

To a suspension of 3-carbamoyl-1-(2-((2-(3-chloro-2-fluorobenzylamino)-2-oxoethyl)(cyclopropyl)amino)-2-oxoethyl)-1H-indazole-5-carboxylic acid (199a) (100 mg, 0.199 mmol) in DCM (2 mL) was added triethylamine (0.083 mL, 0.598 mmol) followed by ethyl carbonochloridate (0.029 mL, 0.299 mmol) at 0° C. The reaction mixture was stirred at 0° C. and diluted with dichloromethane (100 mL). The reaction mixture was washed with water (50 mL) and brine (50 mL), dried, filtered and concentrated in vacuum to afford 3-carbamoyl-1-(2-((2-(3-chloro-2-fluorobenzylamino)-2-oxoethyl)(cyclopropyl)amino)-2-oxoethyl)-1H-indazole-5-carboxylic (ethyl carbonic) anhydride (352a) (108 mg) as an off-white solid, which was used as such for next step.

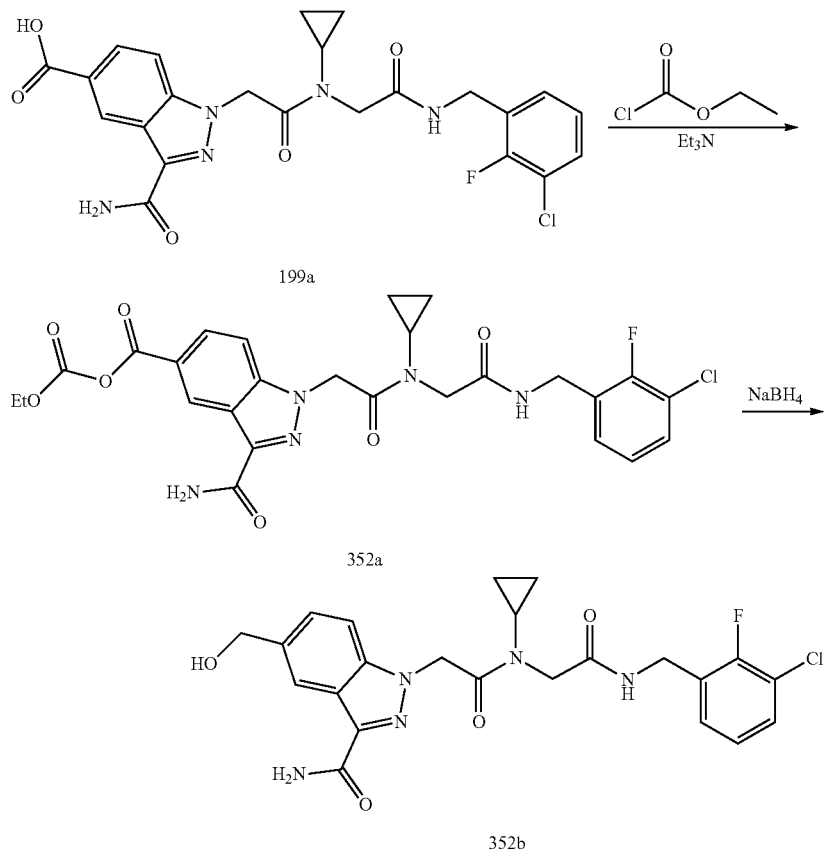

Scheme 352

Step 2 Preparation of 1-(2-((2-(3-chloro-2-fluorobenzylamino)-2-oxoethyl)(cyclopropyl)amino)-2-oxoethyl)-5-(hydroxymethyl)-1H-indazole-3-carboxamide (352b)

To a solution of 3-carbamoyl-1-(2-((2-(3-chloro-2-fluorobenzylamino)-2-oxoethyl)(cyclopropyl)amino)-2-oxoethyl)-1H-indazole-5-carboxylic (ethyl carbonic) anhydride (352a) (the above crude product, 93 mg, 0.162 mmol) in methanol (4 mL) was added sodium borohydride (12.51 mg, 0.324 mmol) and stirred at RT for 0.5 h. The reaction mixture was diluted with ethyl acetate (80 mL), neutralized with acetic acid, washed with water (40 mL), brine (40 mL), dried, filtered and concentrated in vacuum. The crude product was purified by flash column chromatography [silica gel, eluting with hexanes/10% methanol in ethyl acetate (1:0 to 0:1)] to afford 1-(2-((2-(3-chloro-2-fluorobenzylamino)-2-oxoethyl)(cyclopropyl)amino)-2-oxoethyl)-5-(hydroxymethyl)-1H-indazole-3-carboxamide (352b) (17 mg, 20% for two steps) as a white solid; $^1$H NMR (300 MHz, DMSO-$d_6$) δ 8.50 (t, J=5.9 Hz, 1H), 8.14 (s, 1H), 7.69 (s, 1H), 7.58 (d, J=8.8 Hz, 1H), 7.50-7.42 (m, 1H), 7.40-7.31 (m, 2H), 7.26-7.18 (m, 1H), 7.12 (t, J=7.8 Hz, 1H), 5.64 (s, 2H), 5.27 (t, J=5.7 Hz, 1H), 4.61 (d, J=5.6 Hz, 2H), 4.33 (d, J=5.6 Hz, 2H), 3.98 (s, 2H), 3.16-2.94 (m, 1H), 1.10-0.79 (m, 4H); $^{19}$F NMR (282 MHz, DMSO-$d_6$) δ −121.60; MS (ES+): 510.4 & 512.4 (M+Na); MS (ES−): 486.4 (M−1).

Preparation of 1-(2-((2-((3-chloro-2-fluorobenzyl)amino)-2-oxoethyl)(cyclopropyl)amino)-2-oxoethyl)-6-(hydroxymethyl)-1H-indazole-3-carboxamide (353b)

Step 1 Preparation of 3-carbamoyl-1-(2-((2-(3-chloro-2-fluorobenzylamino)-2-oxoethyl)(cyclopropyl)amino)-2-oxoethyl)-1H-indazole-6-carboxylic (ethyl carbonic) anhydride (353a)

Reaction of 3-carbamoyl-1-(2-((2-(3-chloro-2-fluorobenzylamino)-2-oxoethyl)(cyclopropyl)amino)-2-oxoethyl)-1H-indazole-6-carboxylic acid (208a) (100 mg, 0.199 mmol) with ethyl carbonochloridate (0.029 mL, 0.299 mmol) according to the procedure reported in step-1 of Scheme 352 gave after workup 3-carbamoyl-1-(2-((2-(3-chloro-2-fluorobenzylamino)-2-oxoethyl)(cyclopropyl)amino)-2-oxoethyl)-1H-indazole-6-carboxylic (ethyl carbonic) anhydride (353a) (107 mg) as a white solid, which was used as such for next step; MS (ES+): 510.4 & 596.4 (M+Na).

Step 2 Preparation of 1-(2-((2-(3-chloro-2-fluorobenzylamino)-2-oxoethyl)(cyclopropyl)amino)-2-oxoethyl)-6-(hydroxymethyl)-1H-indazole-3-carboxamide (353b)

Reaction of 3-carbamoyl-1-(2-((2-(3-chloro-2-fluorobenzylamino)-2-oxoethyl)(cyclopropyl)amino)-2-oxoethyl)-1H-indazole-6-carboxylic (ethyl carbonic) anhydride (353a) (97 mg, 0.169 mmol, crude) with sodium borohydride (13.05 mg, 0.338 mmol) according to the procedure reported in step-2 of Scheme 352 gave after workup and purification by flash column chromatography [silica gel with dichloromethane/methanol (1:0 to 19:1)] 1-(2-((2-(3-chloro-2-fluorobenzylamino)-2-oxoethyl)(cyclopropyl)amino)-2-oxoethyl)-6-(hydroxymethyl)-1H-indazole-3-carboxamide as a white solid (353b) (28 mg, 32% for two steps). $^1$H NMR (300 MHz, DMSO-$d_6$) δ 8.51 (t, J=5.9 Hz, 1H), 8.10 (d, J=8.4 Hz, 1H), 7.70 (s, 1H), 7.57 (s, 1H), 7.50-7.41 (m, 1H), 7.36 (s, 1H), 7.28-7.18 (m, 2H), 7.12 (t, J=7.8 Hz, 1H), 5.64 (s, 2H), 5.36 (t, J=5.6 Hz, 1H), 4.62 (d, J=5.6 Hz, 2H), 4.33 (d, J=5.7 Hz, 2H), 3.99 (s, 2H), 3.12-2.98 (m, 1H), 1.04-0.87 (m, 4H); $^{19}$F NMR (282 MHz, DMSO-$d_6$) δ −121.60; MS (ES+): 510.4 & 512.4 (M+Na); MS (ES−): 522.5 (M+Cl).

Scheme 353

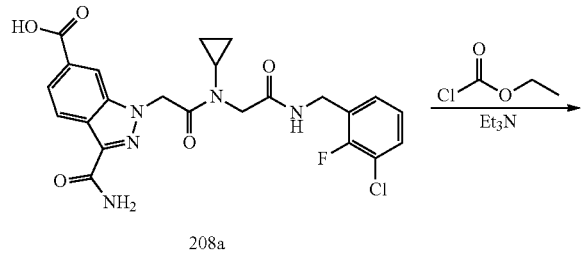

208a

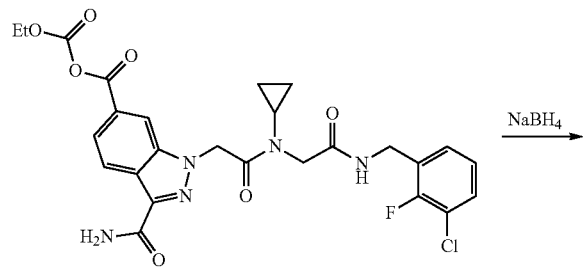

353a

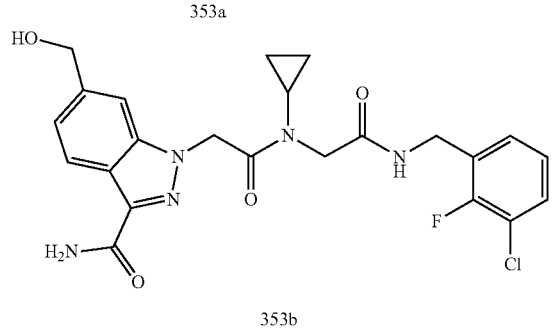

353b

Scheme 354

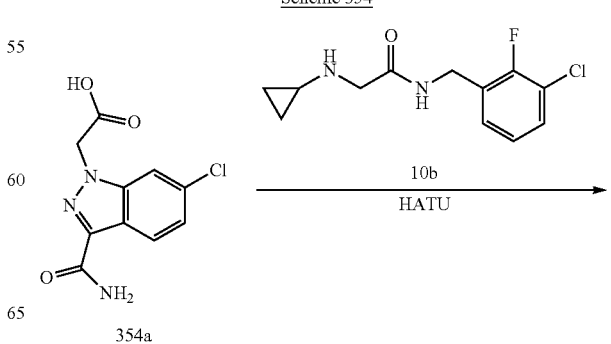

354a

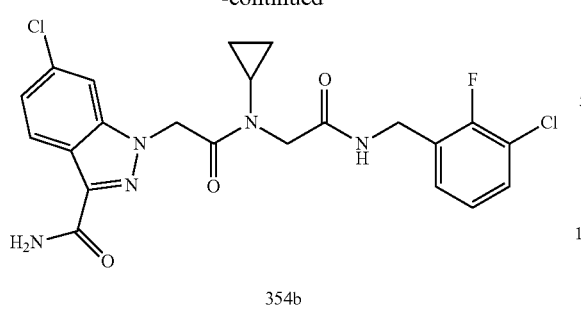

354b

Preparation of 6-chloro-1-(2-((2-(3-chloro-2-fluorobenzylamino)-2-oxoethyl)(cyclopropyl)-amino)-2-oxoethyl)-1H-indazole-3-carboxamide (354b)

Reaction of 2-(3-carbamoyl-6-chloro-1H-indazol-1-yl)acetic acid (300 mg, 1.183 mmol), prepared according to the procedure reported by Altmann; Eva et al; in PCI int. Appl 2014002058, 3 Jan. 2014), with N-(3-chloro-2-fluorobenzyl)-2-(cyclopropylamino)acetamide (10b) (455 mg, 1.774 mmol) according to the procedure reported in step-3 of Scheme 2 gave after workup and purification by flash column chromatography by flash column chromatography [silica gel with hexanes/10% methanol in ethyl acetate (1:0 to 1:1)] 6-chloro-1-(2-((2-(3-chloro-2-fluorobenzylamino)-2-oxoethyl)-(cyclopropyl)amino)-2-oxoethyl)-1H-indazole-3-carboxamide (108 mg, 19%) as a light brown solid. $^1$H NMR (300 MHz, DMSO-$d_6$) δ 8.51 (t, J=5.8 Hz, 1H), 8.17 (dd, J=8.7, 0.7 Hz, 1H), 7.90 (dd, J=1.8, 0.7 Hz, 1H), 7.82 (s, 1H), 7.51-7.42 (m, 2H), 7.28 (dd, J=8.7, 1.7 Hz, 1H), 7.26-7.19 (m, 1H), 7.14-7.07 (m, 1H), 5.66 (s, 2H), 4.33 (d, J=5.7 Hz, 2H), 3.98 (s, 2H), 3.17-2.94 (m, 1H), 1.05-0.84 (m, 4H); $^{19}$F NMR (282 MHz, DMSO-$d_6$) δ -121.62; MS (ES+): 514.4 & 516.4 (M+Na); MS (ES-): 490.4 (M-1).

Scheme 355

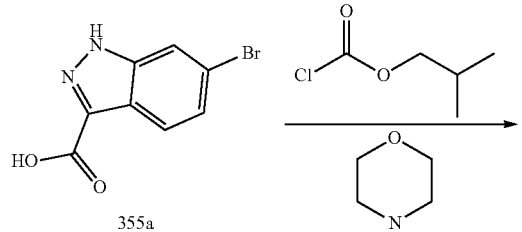

355a

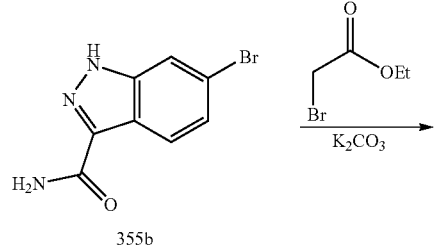

355b

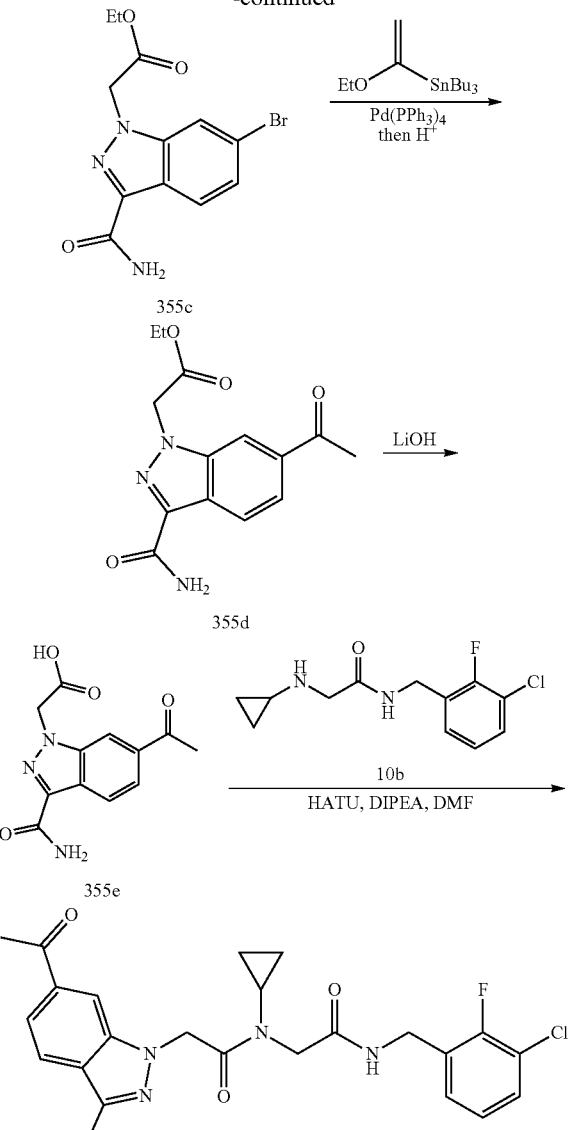

355c

355d

355e

355f

Preparation of 6-acetyl-1-(2-((2-(3-chloro-2-fluorobenzylamino)-2-oxoethyl)(cyclopropyl)-amino)-2-oxo-ethyl)-1H-indazole-3-carboxamide (355f)

Step 1: Preparation of 6-bromo-1H-indazole-3-carboxamide (355b)

To a solution of 6-bromo-1H-indazole-3-carboxylic acid (355a) (2 g, 8.30 mmol) in THF (40 mL) at -15° C. was added isobutyl chloroformate (1.77 mL, 13.28 mmol) and 4-methylmorpholine (1.47 mL, 13.28 mmol) and stirred at -15° C. for 2 h. The reaction mixture was treated with conc. ammonium hydroxide (5.61 mL, 83 mmol) at -15° C., stirred at -15° C. for 1 h and allowed to warm to RT overnight. The reaction mixture was diluted with ethyl acetate (200 mL) and water (100 mL). The solid obtained was collected by filtration dried in vacuum to afford 6-bromo-1H-indazole-3-carboxamide (355b) (1.148 g, 58%) as a light yellow solid; $^1$H NMR (300 MHz, DMSO-$d_6$) δ 13.52 (s, 1H), 8.10 (d, J=8.6 Hz, 1H), 7.88-7.80 (m, 2H), 7.43 (s, 1H), 7.39-7.33 (m, 1H).

Step 2: Preparation of ethyl 2-(6-bromo-3-carbamoyl-1H-indazol-1-yl)acetate (355c)

Reaction of 6-bromo-1H-indazole-3-carboxamide (355b) (1.1 g, 4.58 mmol) with ethylbromoacetate (0.73 mL, 6.42 mmol) according to the procedure reported in step-1 of Scheme 43 gave after workup ethyl 2-(6-bromo-3-carbamoyl-1H-indazol-1-yl)acetate (355c) (1.403 g, 94% yield) as an off-white solid, which was used as such for next step; MS (ES+): 348.2, 350.2 (M+Na).

Step 3: Preparation of ethyl 2-(6-acetyl-3-carbamoyl-1H-indazol-1-yl)acetate (355d)

Reaction of ethyl 2-(6-bromo-3-carbamoyl-1H-indazol-1-yl)acetate (355c) (300 mg, 0.92 mmol) with tributyl(1-ethoxyvinyl)stannane (0.4 mL, 1.15 mmol) according to the procedure reported in step-1 and step-2 of Scheme 206 gave after workup and purification by flash column chromatography [silica gel with hexanes/10% methanol in ethyl acetate (1:0 to 1:1)] ethyl 2-(6-acetyl-3-carbamoyl-1H-indazol-1-yl)acetate as a white solid (355d) 126 mg, 45% for two steps) as a light yellow solid; $^1$H NMR (300 MHz, DMSO-$d_6$) δ 8.53-8.51 (m, 1H), 8.27 (dd, J=8.6, 0.8 Hz, 1H), 7.87-7.80 (m, 2H), 7.54 (s, 1H), 5.61 (s, 2H), 4.18 (q, J=7.1 Hz, 2H), 2.68 (s, 3H), 1.22 (t, J=7.1 Hz, 3H); MS (ES+): 312.4 (M+Na).

Step 4: Preparation of 2-(6-acetyl-3-carbamoyl-1H-indazol-1-yl)acetic acid (355e)

Reaction of ethyl 2-(6-acetyl-3-carbamoyl-1H-indazol-1-yl)acetate (355d) (109 mg, 0.38 mmol) with lithium hydroxide hydrate (97.0 mg, 2.26 mmol) according to the procedure reported in step-2 of Scheme 129 gave after workup and purification 2-(6-acetyl-3-carbamoyl-1H-indazol-1-yl)acetic acid (355e) (75 mg, 76%) (75 mg, 76%) as a yellow solid; $^1$H NMR (300 MHz, DMSO-$d_6$) δ 13.36 (s, 1H), 8.51 (t, J=1.1 Hz, 1H), 8.26 (dd, J=8.6, 0.8 Hz, 1H), 7.89-7.76 (m, 2H), 7.52 (s, 1H), 5.49 (s, 2H), 2.68 (s, 3H); MS (ES−): 260.4 (M−1).

Step 5: Preparation of 6-acetyl-1-(2-((2-((2-(3-chloro-2-fluorobenzylamino)-2-oxoethyl)-(cyclopropyl)amino)-2-oxoethyl)-1H-indazole-3-carboxamide (355f)

Reaction of 2-(6-acetyl-3-carbamoyl-1H-indazol-1-yl)acetic acid (355e) (45 mg, 0.172 mmol) with N-(3-chloro-2-fluorobenzyl)-2-(cyclopropylamino)acetamide (10b) (66 mg, 0.26 mmol) according to the procedure reported in step-3 of Scheme 2 gave after workup and purification by flash column chromatography [silica gel with dichloromethane/methanol (1:0 to 19:1)] 6-acetyl-1-(2-((2-(3-chloro-2-fluorobenzylamino)-2-oxoethyl)-(cyclopropyl)amino)-2-oxoethyl)-1H-indazole-3-carboxamide (355f) (28 mg, 33%) as a light brown solid; $^1$H NMR (300 MHz, DMSO-$d_6$) δ 8.54 (t, J=5.8 Hz, 1H), 8.35-8.33 (m, 1H), 8.26 (dd, J=8.6, 0.8 Hz, 1H), 7.84 (s, 1H), 7.82 (dd, J=8.6, 1.3 Hz, 1H), 7.49 (s, 1H), 7.47-7.39 (m, 1H), 7.24-7.16 (m, 1H), 7.05 (td, J=7.8, 1.1 Hz, 1H), 5.79 (s, 2H), 4.33 (d, J=5.7 Hz, 2H), 4.00 (s, 2H), 3.16-3.01 (m, 1H), 2.64 (s, 3H), 1.05-0.88 (m, 4H); $^{19}$F NMR (282 MHz, DMSO-$d_6$) δ −121.63; MS (ES+): 522.4 (M+Na); MS (ES−): 498.6 (M−1), 534.4 & 536.5 (M+Cl).

Scheme 356

Preparation of 1-(2-((2-((3-chloro-2-fluorobenzyl)amino)-2-oxoethyl)(cyclopropyl)amino)-2-oxoethyl)-6-cyano-1H-indazole-3-carboxamide (356c)

Step 1: Preparation of ethyl 2-(3-carbamoyl-6-cyano-1H-indazol-1-yl)acetate (356a)

Compound 356a was prepared from ethyl 2-(6-bromo-3-carbamoyl-1H-indazol-1-yl)acetate (355c) (300 mg, 0.92 mmol) in 1, 4 dioxane (10.0 mL) using zinc cyanide (1.08 g, 9.2 mmol), $K_2CO_3$ (321 mg, 2.3 mmol) and tetrakis(triphenylphosphine)palladium(0) (425 mg, 0.368 mmol) according to the procedure reported in step-3 of Scheme 301. This gave after workup and purification by flash column chromatography [silica gel, eluting with hexanes/ 10% methanol in ethyl acetate (1:0 to 0:1)] to give ethyl 2-(3-carbamoyl-6-cyano-1H-indazol-1-yl)acetate (356a) (23 mg) as a white solid, which was used as such for next step. MS (ES−): 271.4 (M−1).

Step 2: Preparation of 2-(3-carbamoyl-6-cyano-1H-indazol-1-yl)acetic acid (356b)

Reaction of ethyl 2-(3-carbamoyl-6-cyano-1H-indazol-1-yl)acetate (356a) (20 mg, 0.073 mmol) with lithium hydroxide hydrate (19 mg, 0.44 mmol) according to the procedure reported in step-2 of Scheme 129 gave after workup 2-(3-carbamoyl-6-cyano-1H-indazol-1-yl)acetic acid (356b) (10 mg, 5% for 3 steps) as a white solid; MS (ES−): 243.4 (M−1).

Step 3: Preparation of 1-(2-((2-((3-chloro-2-fluorobenzyl)amino)-2-oxoethyl)(cyclopropyl)amino)-2-oxoethyl)-6-cyano-1H-indazole-3-carboxamide (356c)

Reaction of 2-(3-carbamoyl-6-cyano-1H-indazol-1-yl)acetic acid (356b) (10 mg, 0.041 mmol) with N-(3-chloro-2-fluorobenzyl)-2-(cyclopropylamino)acetamide (10b) (16 mg, 0.06 mmol) according to the procedure reported in step-3 of Scheme 2 gave after workup and purification by flash column chromatography [silica gel with dichloromethane/methanol (1:0 to 19:1)] 1-(2-((2-((3-chloro-2-fluorobenzyl)amino)-2-oxoethyl)(cyclopropyl)amino)-2-oxoethyl)-6-cyano-1H-indazole-3-carboxamide (356c) (6 mg, 30%) as a light yellow solid; $^1$H NMR (300 MHz, DMSO-$d_6$) δ 8.51 (t, J=5.8 Hz, 1H), 8.43 (t, J=1.1 Hz, 1H), 8.36-8.30 (m, 1H), 7.92 (s, 1H), 7.59 (dd, J=8.5, 1.3 Hz, 1H), 7.56 (s, 1H), 7.48-7.42 (m, 1H), 7.25-7.18 (m, 1H), 7.12-7.04 (m, 1H), 5.74 (s, 2H), 4.33 (d, J=5.8 Hz, 2H), 3.99 (s, 2H), 3.07 (s, 1H), 1.08-0.83 (m, 4H); $^{19}$F NMR (282 MHz, DMSO-$d_6$) δ −121.59; MS (ES+): 505.4 & 507.5 (M+Na).

Scheme 357

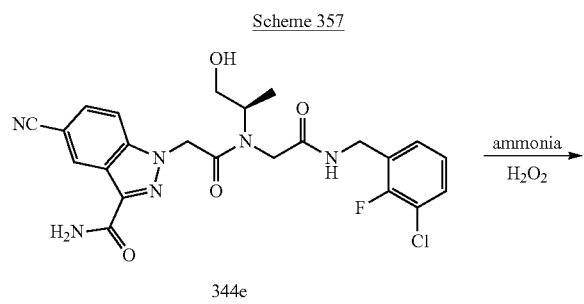

Preparation of (R)-1-(2-((2-((3-chloro-2-fluorobenzyl)amino)-2-oxoethyl)(1-hydroxypropan-2-yl)amino)-2-oxoethyl)-1H-indazole-3,5-dicarboxamide (357a)

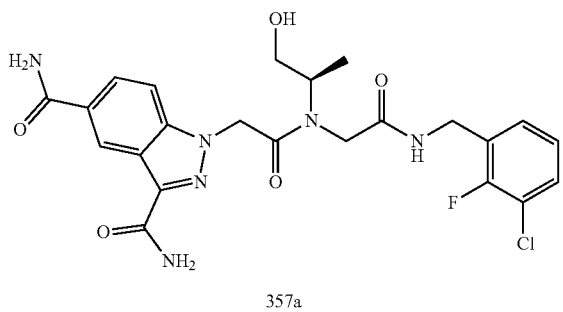

Reaction of (R)-1-(2-((2-((3-chloro-2-fluorobenzyl)amino)-2-oxoethyl)(1-hydroxypropan-2-yl)amino)-2-oxoethyl)-5-cyano-1H-indazole-3-carboxamide (344e) (17 mg, 0.034 mmol) with hydrogen peroxide (0.012 mL, 0.136 mmol) according to the procedure reported in Scheme 65 gave after workup and purification by flash column chromatography on silica gel with dichloromethane/methanol (1:0 to 4:1) to give (R)-1-(2-((2-((3-chloro-2-fluorobenzyl)amino)-2-oxoethyl)(1-hydroxypropan-2-yl)amino)-2-oxoethyl)-1H-indazole-3,5-dicarboxamide (357a) (5 mg, 28%). $^1$H NMR (300 MHz, DMSO-$d_6$, a mixture of two rotamers) δ 8.97-8.53 (m, 2H), 8.10 (s, 1H), 7.90 (t, J=9.5 Hz, 1H), 7.79 (s, 1H), 7.60-6.94 (m, 6H), 5.80-5.41 (m, 3H), 4.90-3.60 (m, 5H), 3.60-3.10 (m, 2H), 1.15 (d, J=6.5 Hz) and 0.96 (d, J=6.7 Hz) (2d, 3H); $^{19}$F NMR (282 MHz, DMSO-$d_6$) δ −121.27, −121.64; MS (ES+): 541.4 & 543.4 (M+Na).

Scheme 358

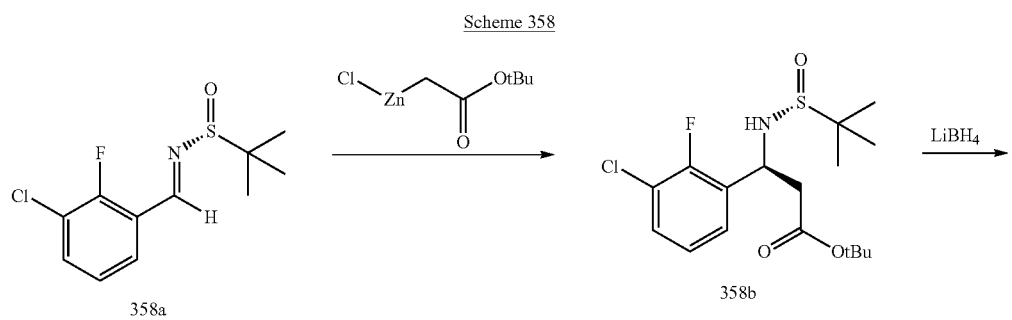

-continued
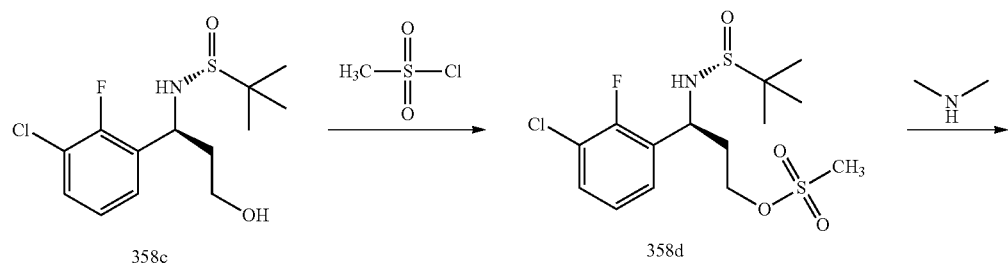
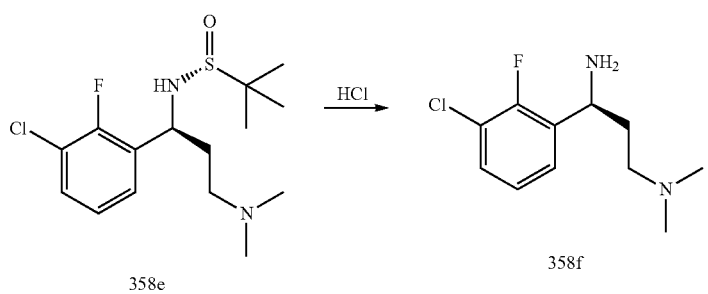
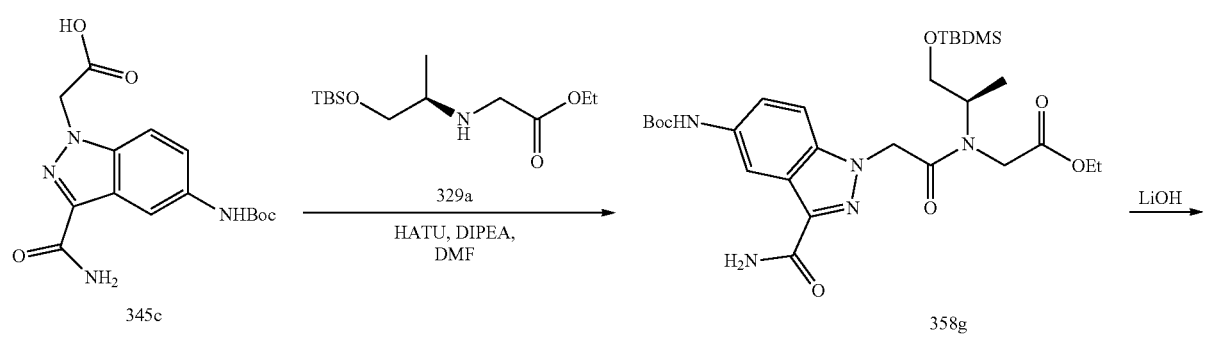
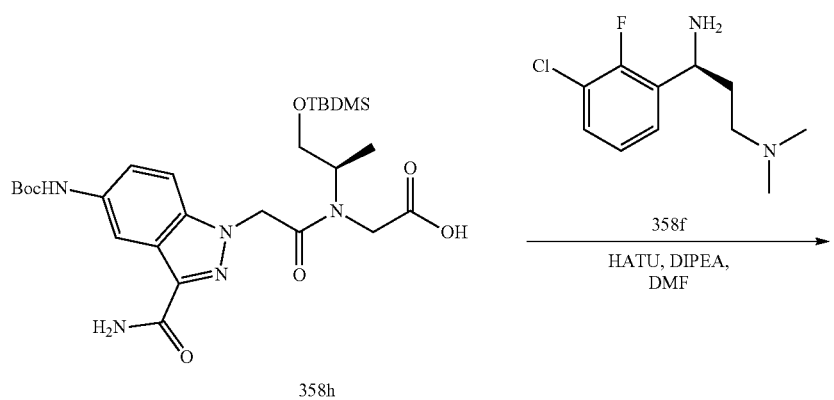
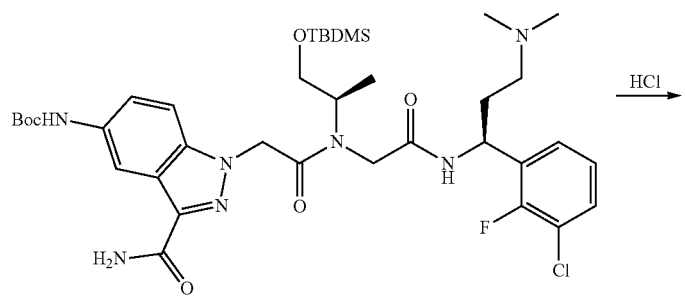

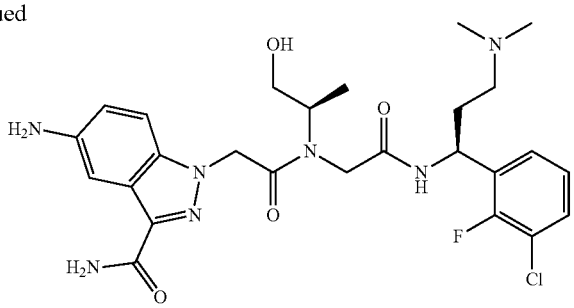

358j

Preparation of 5-amino-1-(2-((2-(((S)-1-(3-chloro-2-fluorophenyl)-3-(dimethylamino)propyl)amino)-2-oxoethyl)((R)-1-hydroxypropan-2-yl)-amino)-2-oxoethyl)-1H-indazole-3-carboxamide (358j)

Step-1: Preparation of (5)-tert-butyl 3-(3-chloro-2-fluorophenyl)-3-((R)-1,1-dimethylethyl-sulfinamido) propanoate (358b)

To a solution of (R,E)-N-(3-chloro-2-fluorobenzylidene)-2-methylpropane-2-sulfinamide (358a) (500 mg, 1.91 mmol; prepared according to the procedure reported by Lam, Patrick Y. S. et al; in PCI' flat. Appl., 2013022814, 14 Feb. 2013) in THF (12 mL) cooled with ice/water was added dropwise (2-tert-butoxy-2-oxoethyl)zinc(II) chloride (9.93 mL, 4.97 mmol) and stirred at 0° C. for 2 h. The reaction mixture was allowed to warm to RT over a period of 2 h, quenched with sat. NH$_4$Cl (50 mL), water (50 mL) and extracted with ethyl acetate (120 mL). The organic layer was separated washed with brine (60 mL), dried filtered and concentrated to give (5)-tert-butyl 3-(3-chloro-2-fluorophenyl)-3-((R)-1,1-dimethylethylsulfinamido)propanoate (358b) (775 mg) as a light yellow oil which was used as such for next step. MS (ES+): 400.4 & 402.4 (M+Na).

Step-2: Preparation of (R)—N—((S)-1-(3-chloro-2-fluorophenyl)-3-hydroxypropyl)-2-methylpropane-2-sulfinamide (358c)

To a solution of (S)-tert-butyl 3-(3-chloro-2-fluorophenyl)-3-((R)-1,1-dimethylethylsulfinamido)propanoate (358b) (600 mg, 1.59 mmol) in THF (9 mL) was added lithium borohydride (1.588 mL, 3.18 mmol, 2M in THF), MeOH (0.4 mL) and stirred at RT for 28.5 h. The reaction mixture was quenched with sat. NH$_4$Cl (20 mL), water (50 mL) and extracted with ethyl acetate (120 mL). The organic layer was washed with brine (60 mL), dried filtered, concentrated in vacuum and purified by flash column chromatography [silica gel, eluting with dichloromethane/methanol (1:0 to 19:1)] to give (R)—N—((S)-1-(3-chloro-2-fluorophenyl)-3-hydroxypropyl)-2-methylpropane-2-sulfinamide (358c) (133 mg, 27% for 2 steps) as a white solid; $^1$H NMR (300 MHz, DMSO-d$_6$) δ 7.53-7.38 (m, 2H), 7.23 (td, J=7.9, 1.1 Hz, 1H), 5.72 (d, J=5.7 Hz, 1H), 4.78-4.64 (m, 2H), 3.60-3.44 (m, 1H), 3.46-3.28 (m, 1H), 2.11-1.96 (m, 1H), 1.91-1.73 (m, 1H), 1.05 (d, J=1.4 Hz, 9H); $^{19}$F NMR (282 MHz, DMSO-d$_6$) δ −122.03; MS (ES+): 330.3 (M+Na).

Step-3: Preparation of (S)-3-(3-chloro-2-fluorophenyl)-3-((R)-1,1-dimethylethyl-sulfinamido)propyl methanesulfonate (358d)

To a solution of (R)—N—((S)-1-(3-chloro-2-fluorophenyl)-3-hydroxypropyl)-2-methylpropane-2-sulfinamide (358c) (162 mg, 0.526 mmol) and triethylamine (0.147 mL, 1.053 mmol) in CH$_2$C$_{12}$ (4 mL) was cooled to ~−10° C. was added methanesulfonyl chloride (0.045 mL, 0.579 mmol) and stirred at ~0° C. for 1.5 h. The reaction mixture was diluted with dichloromethane (75 mL), and (40 mL) at ~0° C. The organic layer was separated dried, filtered and concentrated in vacuum to give (S)-3-(3-chloro-2-fluorophenyl)-3-((R)-1,1-dimethylethyl-sulfinamido)propyl methanesulfonate (358d) (214 mg) as a colorless gum; MS (ES+): 408.3 & 410.2 (M+Na).

Step-4: Preparation of (R)—N—((S)-1-(3-chloro-2-fluorophenyl)-3-(dimethylamino)propyl)-2-methylpropane-2-sulfinamide (358e)

To a solution of (S)-3-(3-chloro-2-fluorophenyl)-3-((R)-1,1-dimethylethylsulfinamido)propyl methanesulfonate (358d) (0.095 g, 0.246 mmol) in ethanol (5 mL) was added dimethylamine (2M in THF, 2.71 mL, 5.41 mmol) and stirred at 80° C. in a sealed container for 2 h. The reaction mixture was cooled to RT and concentrated to dryness to give (R)—N—((S)-1-(3-chloro-2-fluorophenyl)-3-(dimethylamino)propyl)-2-methylpropane-2-sulfinamide (358e) (121 mg) as a yellow gum; MS (ES+): 357.4 & 359.4 (M+Na).

Step-5: Preparation of (S)-1-(3-chloro-2-fluorophenyl)-N3,N3-dimethylpropane-1,3-diamine (358f)

To a solution of (R)—N—((S)-1-(3-chloro-2-fluorophenyl)-3-(dimethylamino)propyl)-2-methylpropane-2-sulfinamide (358e) (0.076 g, 0.228 mmol) in MeOH (4 mL) was added hydrogen chloride (0.114 mL, 0.456 mmol, 4 N in 1,4-dioxane) and stirred at RT for 5 h. The reaction mixture was concentrated in vacuum to give (S)-1-(3-chloro-2-fluorophenyl)-N3,N3-dimethylpropane-1,3-diamine (358f) (105 mg) as a yellow gum; MS (ES+): 231.4 & 233.3 (M+Na).

Step-6: Preparation of (R)-ethyl 2-(2-(5-(tert-butoxycarbonylamino)-3-carbamoyl-1H-indazol-1-yl)-N-(1-(tert-butyldimethylsilyloxy)propan-2-yl)acetamido)acetate (358 g)

Reaction of 2-(5-((tert-butoxycarbonyl)amino)-3-carbamoyl-1H-indazol-1-yl)acetic acid (345c) (200 mg, 0.598 mmol) with (R)-ethyl 2-(1-(tert-butyldimethylsilyloxy)propan-2-ylamino)acetate (329a) (198 mg, 0.718 mmol) according to the procedure reported in step-3 of Scheme 2 gave after workup and purification by flash column chromatography [silica gel with dichloromethane/methanol (1:0 to 19:1)] (R)-ethyl 2-(2-(5-(tert-butoxycarbonylamino)-3- carbamoyl-1H-indazol-1-yl)-N-(1-(tert-butyldimethylsilyloxy)propan-2-yl)acetamido)acetate (358 g) (140 mg, 40%) as an off-white solid; $^1$H NMR (300 MHz, DMSO-d$_6$) δ 9.39 (s, 1H), 8.38 and 8.36 (2s, 1H), 7.98-7.23 (m, 4H), 5.78-5.19 (m, 2H), 4.48-3.55 (m, 7H), 1.49 (s, 9H), 1.27 (t, J=7.1 Hz) and 1.12 (t, J=7.1 Hz) (2t, 3H), 1.17 (d, J=6.7 Hz) and 1.04 (d, J=6.9 Hz) (2d, 3H), 0.90 and 0.86 (2s, 9H), 0.11-0.00 (m, 6H); MS (ES+): 614.6 (M+Na).

Step-7: Preparation of (R)-2-(2-(5-(tert-butoxycarbonylamino)-3-carbamoyl-1H-indazol-1-yl)-N-(1-(tert-butyldimethylsilyloxy)propan-2-yl)acetamido) acetic acid (358 h)

Reaction of (R)-ethyl 2-(2-(5-(tert-butoxycarbonylamino)-3-carbamoyl-1H-indazol-1-yl)-N-(1-(tert-butyldimethylsilyloxy)propan-2-yl)acetamido)acetate (358 g) (1.36 g, 2.298 mmol) with lithium hydroxide hydrate (0.59 g, 13.79 mmol) according to the procedure reported in step-2 of Scheme 129 gave after workup and purification (R)-2-(2-(5-(tert-butoxycarbonylamino)-3-carbamoyl-1H-indazol-1-yl)-N-(1-(tert-butyldimethylsilyloxy)propan-2-yl) acetamido)acetic acid (358 h) (350 mg, 27%) as a brown solid; $^1$H NMR (300 MHz, DMSO-d$_6$) δ 9.38 (s, 1H), 8.37 (s, 1H), 7.69-7.23 (m, 4H), 5.76-5.12 (m, 2H), 4.54-3.51 (m, 5H), 1.49 (s, 9H), 1.28-1.01 (m, 3H), 0.91 and 0.86 (2s, 9H), 0.10-0.01 (m, 6H); MS (ES−): 562.7 (M−1).

Step-8: Preparation of tert-butyl 1-(2-(((S)-1-(tert-butyldimethylsilyloxy)propan-2-yl)(2-((S)-1-(3-chloro-2-fluorophenyl)-3-(dimethylamino)propylamino)-2-oxoethyl)amino)-2-oxoethyl)-3-carbamoyl-1H-indazol-5-ylcarbamate (358i)

Reaction of (S)-2-(2-(5-(tert-butoxycarbonylamino)-3-carbamoyl-1H-indazol-1-yl)-N-(1-acid (358 h) (20 mg, 0.035 mmol) with (S)-1-(3-chloro-2-fluorophenyl)-N3,N3-dimethylpropane-1,3-diamine (358f) (24.56 mg, 0.106 mmol) according to the procedure reported in step-3 of Scheme 2 gave after workup and purification by flash column chromatography [silica gel eluting with dichloromethane/methanol (1:0 to 9:1)] tert-butyl 1-(2-(((S)-1-(tert-butyldimethylsilyloxy)propan-2-yl)(2-4S)-1-(3-chloro-2-fluorophenyl)-3-(dimethylamino)propylamino)-2-oxoethyl)amino)-2-oxoethyl)-3-carbamoyl-1H-indazol-5-ylcarbamate (358i) (10 mg, 36% for 4 steps) as a light yellow gum; MS (ES+): 776.7 & 778.8 (M+Na).

Step-9: Preparation of 5-amino-1-(2-((2-(((S)-1-(3-chloro-2-fluorophenyl)-3-(dimethylamino)propyl) amino)-2-oxoethyl)((R)-1-hydroxypropan-2-yl)-amino)-2-oxoethyl)-1H-indazole-3-carboxamide (358j)

Reaction of tert-butyl 1-(2-(((S)-1-(tert-butyldimethylsilyloxy)propan-2-yl)(2-((S)-1-(3-chloro-2-fluorophenyl)-3-(dimethylamino)propylamino)-2-oxoethyl)amino)-2-oxoethyl)-3-carbamoyl-1H-indazol-5-ylcarbamate ((358i)) (10 mg, 0.013 mmol) in Methanol (4 mL) with conc. HCl (0.032 mL, 0.386 mmol) at RT for 15.5 h, gave after workup and purification by flash column chromatography [silica gel eluting with chloroform/CMA80 (1:0 to 0:1)] 5-amino-1-(2-((2-((S)-1-(3-chloro-2-fluorophenyl)-3-(dimethylamino) propylamino)-2-oxoethyl)((S)-1-hydroxypropan-2-yl)-amino)-2-oxoethyl)-1H-indazole-3-carboxamide (358j) (1.3 mg, 18%) as a white solid; $^1$H NMR (300 MHz, DMSO-d$_6$) (a mixture of two rotamers) δ 8.91 (d, J=7.8 Hz) and 8.55 (d, J=8.0 Hz) (2d, 1H), 7.62-6.71 (m, 8H), 5.69-3.42 (m, 11H), 2.31-1.40 (m, 10H), 1.10 (d, J=6.5 Hz) and 0.99 (d, J=6.9 Hz) (2d, 3H); $^{19}$F NMR (282 MHz, Methanol-d$_4$) δ −122.46, −122.63; MS (ES+): 562.6 (M+1) and 584.6 (M+Na); MS (ES−): 560.6 (M−1).

Scheme 259

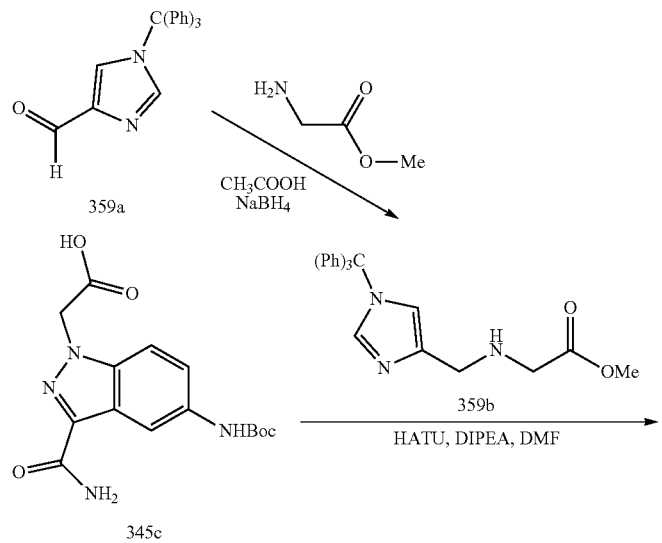

-continued
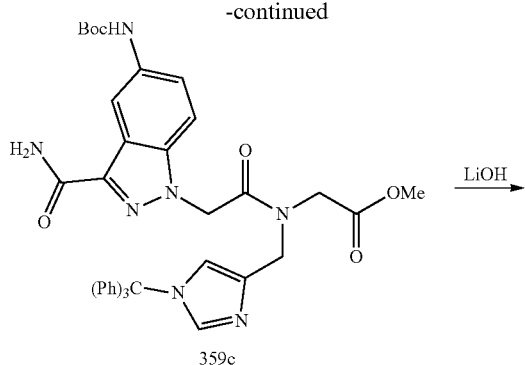
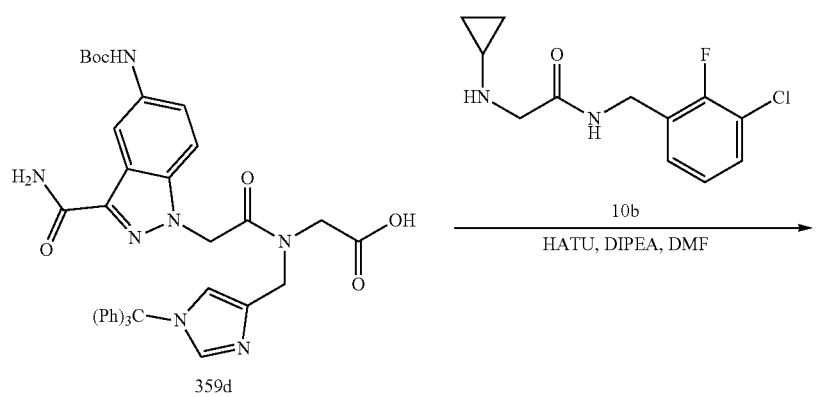
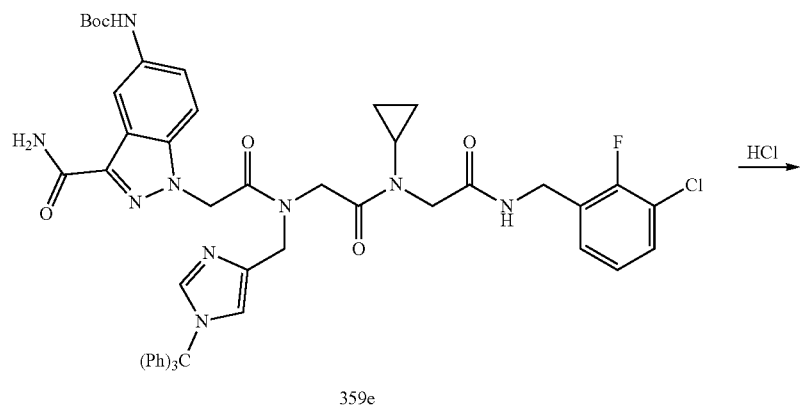
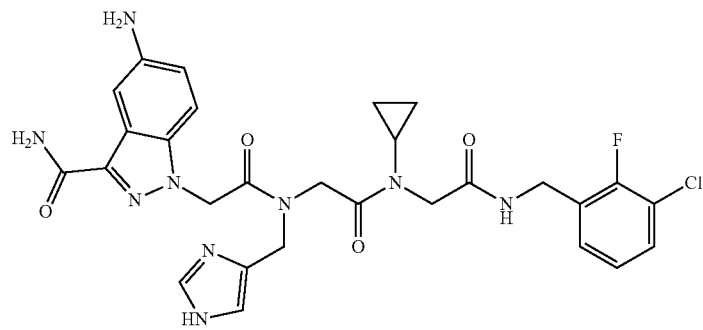

Preparation of 1-(2-(((1H-imidazol-4-yl)methyl)(2-((2-((3-chloro-2-fluorobenzyl)amino)-2-oxoethyl)(cyclopropyl)amino)-2-oxoethyl)amino)-2-oxoethyl)-5-amino-1H-indazole-3-carboxamide (359f)

Step-1: Preparation of methyl 2-(((1-trityl-1H-imidazol-4-yl)methyl)amino)acetate (359b)

Compound 359b was prepared from 1-trityl-1H-imidazole-4-carbaldehyde (359a) (1 g, 2.84 mmol) and methyl 2-aminoacetate hydrochloride (0.360 g, 2.84 mmol) According to the procedure reported in step-1 of Scheme 24. This gave after workup and purification by flash column chromatography [Silica gel, eluting with hexanes/ethyl acetate (1:0 to 1:1), then dichloromethane/methanol (1:0 to 9:1)] methyl 2-(41-trityl-1H-imidazol-4-yl)methyl)amino)acetate (359b) (84 mg, 7%) as a light brown gum, which was used as such for next step); MS (ES+): 434.5 (M+Na)

Step-2: Preparation of methyl 2-(2-(5-((tert-butoxycarbonyl)amino)-3-carbamoyl-1H-indazol-1-yl)-N-((1-trityl-1H-imidazol-4-yl)methyl)acetamido)acetate (359c)

Compound 359c was prepared from methyl 2-(41-trityl-1H-imidazol-4-yl)methyl)amino)acetate (359b) (82 mg, 0.199 mmol) and 2-(5-((tert-butoxycarbonyl)amino)-3-carbamoyl-1H-indazol-1-yl)acetic acid (345c) (44.4 mg, 0.133 mmol) according to the procedure reported in step-3 of Scheme 2. This gave after workup and purification by flash column chromatography [Silica gel, eluting with dichloromethane/methanol (1:0 to 19:1)] methyl 2-(2-(5-((tert-butoxycarbonyl)amino)-3-carbamoyl-1H-indazol-1-yl)-N-((l-trityl-1H-imidazol-4-yl)methyl)acetamido)acetate (359c) (73 mg, 76%) as a white solid; $^1$H NMR (300 MHz, DMSO-$d_6$) (a mixture of two rotamers) δ 9.39 (s, 1H), 8.38 (s, 1H), 7.61 (s, 1H), 7.54-6.75 (m, 20H), 5.86 and 5.39 (2s, 2H), 4.64-3.96 (m, 4H), 3.66 and 3.57 (2s, 3H), 1.50 and 1.49 (s, 9H); MS (ES+): 728.7 (M+1), 750.7, 751.8 (M+Na).

Step-3: Preparation of 2-(2-(5-((tert-butoxycarbonyl)amino)-3-carbamoyl-1H-indazol-1-yl)-N-((1-trityl-1H-imidazol-4-yl)methyl)acetamido)acetic acid (359d)

Compound 345d was prepared from methyl 2-(2-(5-((tert-butoxycarbonyl)amino)-3-carbamoyl-1H-indazol-1-yl)-N-((1-trityl-1H-imidazol-4-yl)methyl)acetamido)acetate (359c) (69 mg, 0.095 mmol) and lithium hydroxide hydrate (24.36 mg, 0.569 mmol) according to the procedure reported in step-2 of Scheme 129. This gave after workup 2-(2-(5-((tert-butoxy carbonyl)amino)-3-carbamoyl-1H-indazol-1-yl)-N-((1-trityl-1H-imidazol-4-yl)methyl)acetamido)acetic acid (359d) (55 mg, 81%) as a white solid; $^1$H NMR (300 MHz, DMSO-$d_6$)(a mixture of two rotamers) δ 12.70 (s, 1H), 9.39 (s, 1H), 8.38 (s, 1H), 7.70-6.76 (m, 21H), 5.81 and 5.36 (2s, 2H), 4.61-3.88 (m, 4H), 1.495 and 1.491 (2s, 9H); MS (ES+): 736.7 (M+Na).

Step-4: Preparation of (tert-butyl (3-carbamoyl-1-(2-((2-((2-((3-chloro-2-fluorobenzyl)amino)-2-oxoethyl)(cyclopropyl)amino)-2-oxo ethyl)((1-trityl-1H-imidazol-4-yl)methyl)amino)-2-oxoethyl)-1H-indazol-5-yl)carbamate (359e)

Compound 359e was prepared from 2-(2-(5-((tert-butoxycarbonyl)amino)-3-carbamoyl-1H-indazol-1-yl)-N-((1-trityl-1H-imidazol-4-yl)methyl)acetamido)acetic acid (359d) (45 mg, 0.063 mmol) by reaction with N-(3-chloro-2-fluorobenzyl)-2-(cyclopropylamino)acetamide (10b) (32 mg, 0.126 mmol) according to the procedure reported in step-3 of Scheme 2. This gave after workup and purification by flash column chromatography [Silica gel, eluting with dichloromethane/methanol (1:0 to 9:1)] (tert-butyl (3-carbamoyl-1-(2-((2-((2-((3-chloro-2-fluorobenzyl)amino)-2-oxoethyl)(cyclopropyl)amino)-2-oxoethyl)((1-trityl-1H-imidazol-4-yl)methyl)amino)-2-oxoethyl)-1H-indazol-5-yl)carbamate (359e) (38 mg, 63%), which used as such for next step; MS (ES+): 974.6 & 976.6 (M+Na).

Step-5: Preparation of 1-(2-(((1H-imidazol-4-yl)methyl)(2-((2-((3-chloro-2-fluorobenzyl)amino)-2-oxoethyl)(cyclopropyl)amino)-2-oxoethyl)amino)-2-oxoethyl)-5-amino-1H-indazole-3-carboxamide (359f)

Compound 359f was prepared from (tert-butyl (3-carbamoyl-1-(2-((2-((2-((3-chloro-2-fluorobenzyl)amino)-2-oxoethyl)(cyclopropyl)amino)-2-oxoethyl)((1-trityl-1H-imidazol-4-yl)methyl)amino)-2-oxoethyl)-1H-indazol-5-yl)carbamate (359e) (38 mg, 0.040 mmol) by reaction with conc. HCl (0.1 mL) in methanol (4 mL) according to the procedure reported in step-3 of Scheme 292. This gave after workup and purification by flash column chromatography [Silica gel, eluting with chloroform/CMA80 (1:0 to 0:1)] 1-(2-(((1H-imidazol-4-yl)methyl)(2-((2-((3-chloro-2-fluorobenzyl)amino)-2-oxoethyl)(cyclopropyl)amino)-2-oxoethyl)amino)-2-oxoethyl)-5-amino-1H-indazole-3-carboxamide (359f) (8 mg, 32%) as a white solid. $^1$H NMR (300 MHz, DMSO-$d_6$, a mixture of two rotamers) δ 8.61 and 8.44 (2t, 1H), 7.82-7.74 (m, 1H), 7.54-7.40 (m, 2H), 7.34-7.05 (m, 6H), 6.83-6.75 (m, 1H), 5.74 and 5.27 (2s, 2H), 4.61 and 4.56 (2s, 2H), 4.42-4.26 (m, 4H), 4.04 and 3.94 (2s, 2H), 2.97-2.67 (m, 1H), 0.93-0.57 (m, 4H); $^{19}$F NMR (282 MHz, DMSO-$d_6$) δ −121.52, −121.61; MS (ES+): 610.5 & 612.5 (M+1).

Scheme 360

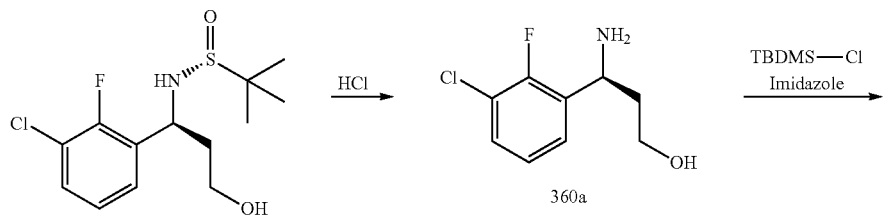

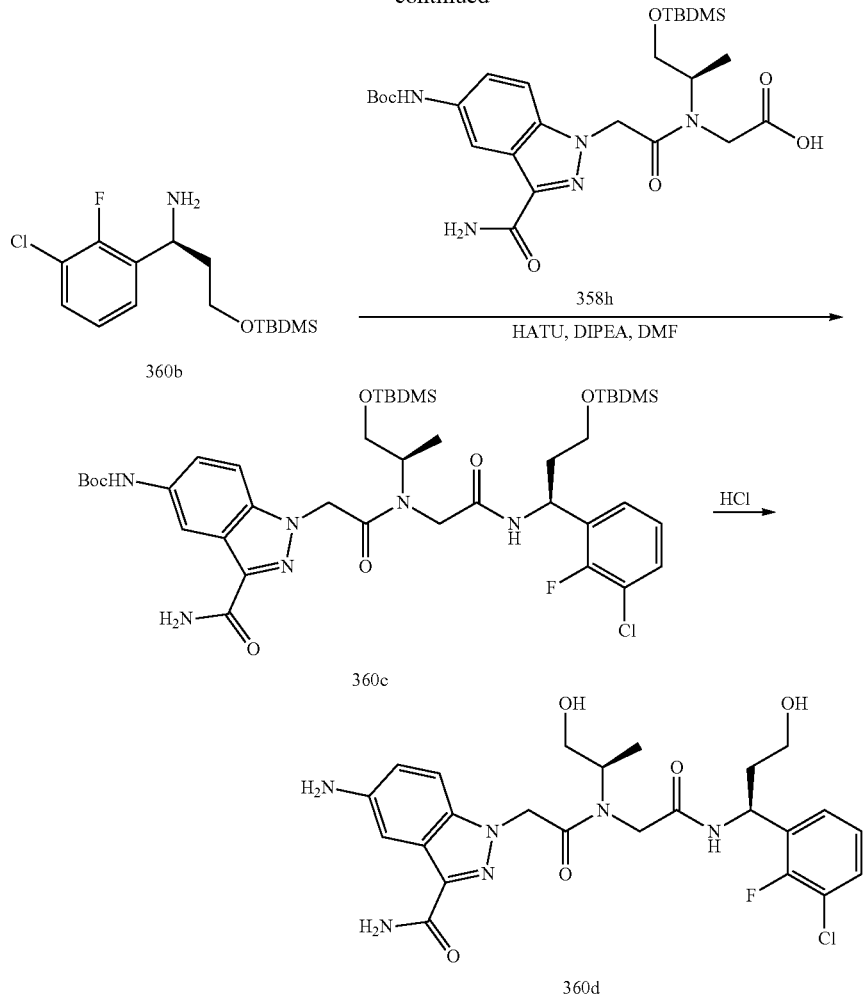

Preparation of 5-amino-1-(2-((2-(((S)-1-(3-chloro-2-fluorophenyl)-3-hydroxy propyl)amino)-2-oxoethyl)((R)-1-hydroxy propan-2-yl)amino)-2-oxoethyl)-1H-indazole-3-carboxamide (360d)

Step-1: Preparation of (S)-3-amino-3-(3-chloro-2-fluorophenyl)propan-1-ol (360a)

Reaction of (R)—N—((S)-1-(3-chloro-2-fluorophenyl)-3-hydroxy propyl)-2-methylpropane-2-sulfinamide (358c) (125 mg, 0.406 mmol) in MeOH (5 mL) with hydrogen chloride (0.203 mL, 0.812 mmol) (4 N in 1,4-dioxane) at RT for 1 h, followed by evaporation of reaction mixture under reduced pressure gave (S)-3-amino-3-(3-chloro-2-fluorophenyl)propan-1-ol (360a), which was used as such for next step; MS (ES+): 204.3 & 206.3 (M+1).

Step-2: Preparation of (S)-3-(tert-butyldimethylsilyloxy)-1-(3-chloro-2-fluorophenyl)propan-1-amine (360b)

Reaction of (S)-3-amino-3-(3-chloro-2-fluorophenyl)propan-1-ol (360a) (0.083 g, 0.406 mmol) in DMF (5 mL) with TBDMS-C$_1$ (0.092 g, 0.609 mmol) according to the procedure reported in step-1 of Scheme 328 gave after workup and purification (S)-3-(tert-butyldimethylsilyloxy)-1-(3-chloro-2-fluorophenyl)propan-1-amine (360b) (133 mg) as a yellow oil, which was used as such for next step; MS (ES+): 318.4 & 320.4 (M+Na).

Step-3: Preparation of tert-butyl 1-((S)-11-((S)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (360c)

Reaction of (S)-2-(2-(5-(tert-butoxycarbonylamino)-3-carbamoyl-1H-indazol-1-yl)-N-(1-(tert-butyldimethylsilyloxy)propan-2-yl)acetamido)acetic acid (358 h) (20 mg, 0.035 mmol) with (S)-3-(tert-butyldimethylsilyloxy)-1-(3-chloro-2-fluorophenyl)propan-1-amine (360b) (33.8 mg, 0.106 mmol) according to the procedure reported in step-3 of Scheme 2 gave after workup and purification by flash column chromatography [silica gel eluting with dichloromethane/methanol (1:0 to 19:1)] tert-butyl 1-((S)-11-((S)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (360c) (29 mg) as a colorless gum; MS (ES+): 885.7 (M+Na).

Step-4: Preparation of 5-amino-1-(2-((2-((S)-1-(3-chloro-2-fluorophenyl)-3-hydroxypropylamino)-2-oxoethyl)((S)-1-hydroxypropan-2-yl)amino)-2-oxoethyl)-1H-indazole-3-carboxamide (360d)

Reaction of tert-butyl 1-((S)-11-((S)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (360c) (29 mg, 0.034 mmol) in methanol (4 mL) with conc. HCl (0.028 mL, 0.336 mmol) at RT for 19 h gave after workup and purification by flash column chromatography [silica gel eluting with chloroform/CMA80 (1:0 to 0:1)] 5-amino-1-(2-((2-((S)-1-(3-chloro-2-fluorophenyl)-3-hydroxypropylamino)-2-oxoethyl)((S)-1-hydroxypropan-2-yl)-amino)-2-oxoethyl)-1H-indazole-3-carboxamide as a white solid (360d) (3 mg, 6% for 4 steps); $^1$H NMR (300 MHz, DMSO-$d_6$) (a mixture of two rotamers) δ 8.86 (d) and 8.50 (d, J=7.6 Hz) (2d, 1H), 7.56-6.71 (m, 8H), 5.60-3.20 (m, 14H), 2.03-1.65 (m, 2H), 1.10 (d, J=6.3 Hz) and 0.98 (d, J=6.8 Hz) (2d, 3H); $^{19}$F NMR (282 MHz, DMSO-$d_6$) δ −121.68, −121.87; MS (ES+): 557.2 (M+Na); MS (ES−): 533.6 (M−1).

Scheme 361

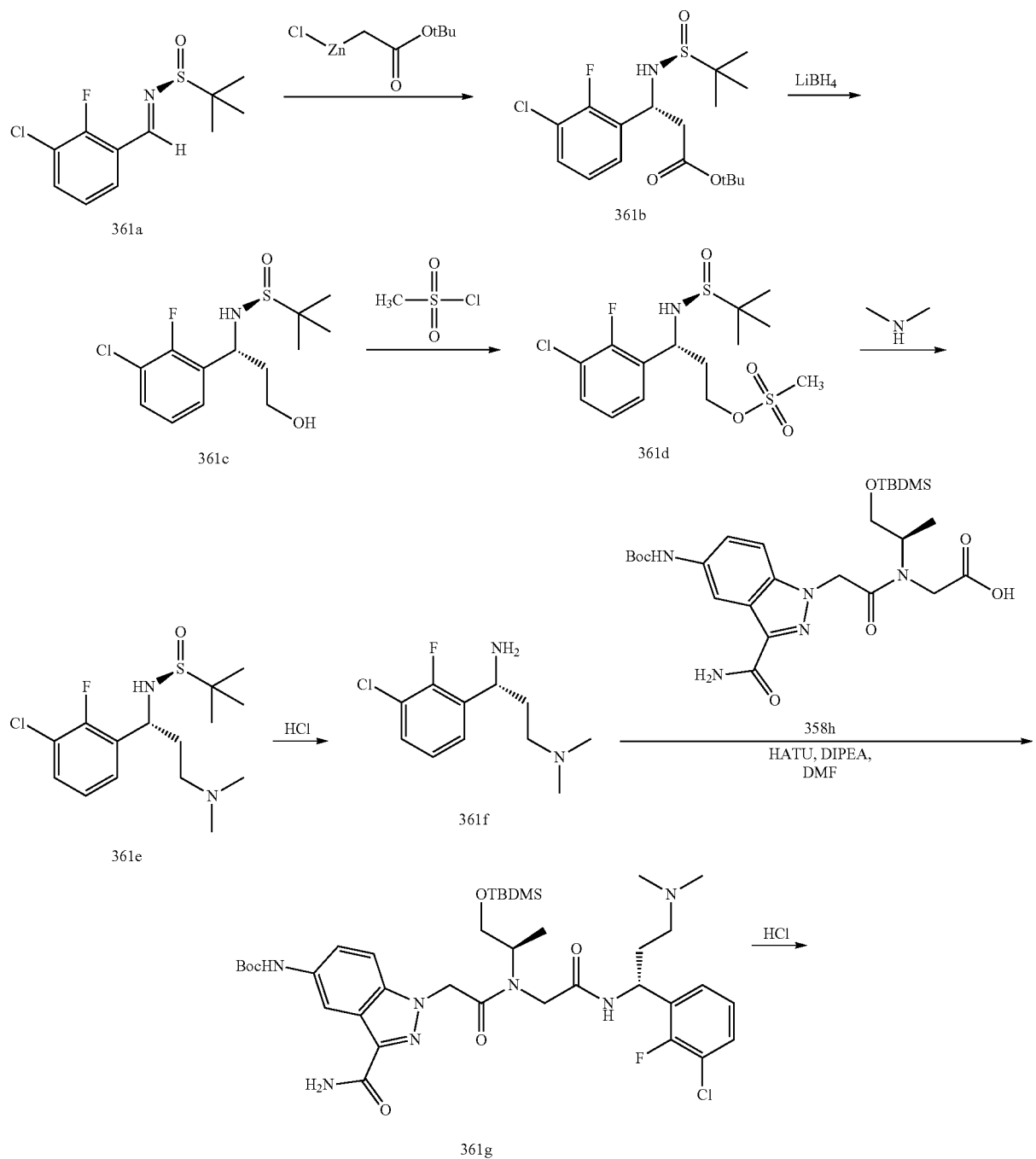

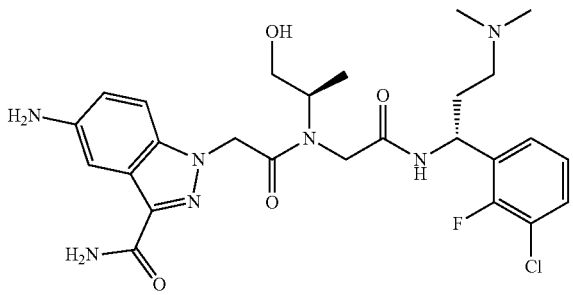

361h

Preparation of 5-amino-1-(2-((2-(((R)-1-(3-chloro-2-fluorophenyl)-3-(dimethylamino)propyl)amino)-2-oxoethyl)((R)-1-hydroxypropan-2-yl)-amino)-2-oxoethyl)-1H-indazole-3-carboxamide (361 h)

Step-1: Preparation of (S)-tert-butyl 3-(3-chloro-2-fluorophenyl)-3-((R)-1,1-dimethylethyl-sulfinamido)propanoate (361b)

Reaction of (S,E)-N-(3-chloro-2-fluorobenzylidene)-2-methylpropane-2-sulfinamide (361a) (500 mg, 1.91 mmol; prepared according to the procedure reported by Lain, Patrick Y. S. et al; in PCT 1111. Appl, 2013022814, 14 Feb. 2013) with (2-tert-butoxy-2-oxoethyl)zinc(II) chloride (9.93 mL, 4.97 mmol) according to the procedure reported in step-1 of Scheme 358 gave after workup and purification (R)-tert-butyl 3-(3-chloro-2-fluorophenyl)-3-((S)-1,1-dimethylethyl-sulfinamido)propanoate as a colorless gum (361b) (675 mg) as a colorless oil which was used as such for next step. MS (ES−): 412.4 & 414.5 (M+Cl).

Step-2: Preparation of (R)-3-(3-chloro-2-fluorophenyl)-3-((S)-1,1-dimethylethyl-sulfinamido)propyl methanesulfonate (361c)

Reaction of (S)—N—((R)-1-(3-chloro-2-fluorophenyl)-3-hydroxypropyl)-2-methylpropane-2-sulfinamide (360 mg, 1.17 mmol) (crude) with methanesulfonyl chloride (0.100 mL, 1.287 mmol) according to the procedure reported in step-2 of Scheme 358 gave after workup and purification (R)-3-(3-chloro-2-fluorophenyl)-3-((S)-1,1-dimethylethyl-sulfinamido)propyl methanesulfonate as a colorless gum (361c) (421 mg, used as such for next step). MS (ES+): 386.4 & 388.4 (M+1).

Step-3: Preparation of (R)-3-(3-chloro-2-fluorophenyl)-3-((S)-1,1-dimethylethyl-sulfinamido)propyl methanesulfonate (361d)

Reaction of (S)—N—((R)-1-(3-chloro-2-fluorophenyl)-3-hydroxypropyl)-2-methylpropane-2-sulfinamide (360 mg, 1.17 mmol, crude) with methanesulfonyl chloride (0.10 mL, 1.287 mmol) according to the procedure reported in step-3 of Scheme 358 gave after workup and purification (R)-3-(3-chloro-2-fluorophenyl)-3-((S)-1,1-dimethylethyl-sulfina-mido)propyl methanesulfonate (361d) (421 mg) as a colorless gum, which was used as such for next step; MS (ES+): 386.4 & 388.4 (M+1).

Step-4: Preparation of (S)—N—((R)-1-(3-chloro-2-fluorophenyl)-3-(dimethylamino)propyl)-2-methyl-propane-2-sulfinamide (361e)

Reaction of (R)-3-(3-chloro-2-fluorophenyl)-3-((S)-1,1-dimethylethylsulfinamido)propyl methanesulfonate (120 mg, 0.311 mmol) (361d) with dimethylamine (2M in THF, 3.42 mL, 6.84 mmol) according to the procedure reported in step-4 of Scheme 358 gave after workup and purification (S)—N—((R)-1-(3-chloro-2-fluorophenyl)-3-(dimethyl-amino)propyl)-2-methylpropane-2-sulfinamide (361e) (131 mg) as a yellow gum which was used as such for next step without further purification); MS (ES+): 335.4 & 337.4 (M+1).

Step-5: Preparation of (R)-1-(3-chloro-2-fluorophe-nyl)-N3,N3-dimethylpropane-1,3-diamine (361f)

Reaction of (S)—N—((R)-1-(3-chloro-2-fluorophenyl)-3-(dimethylamino)propyl)-2-methylpropane-2-sulfinamide (361e) (0.104 g, 0.311 mmol) with hydrogen chloride (0.156 mL, 0.622 mmol, 4 N in 1,4-dioxane) according to the procedure reported in step-5 of Scheme 358 gave after workup and purification (R)-1-(3-chloro-2-fluorophenyl)-N3,N3-dimethylpropane-1,3-diamine (361e), which was used as such for next step; MS (ES+): 231.4 & 333.3 (M+1).

Step-6: Preparation of tert-butyl 1-(2-(((R)-1-(tert-butyldimethylsilyloxy)propan-2-yl)(2-((R)-1-(3-chloro-2-fluorophenyl)-3-(dimethylamino)propy-lamino)-2-oxoethyl)amino)-2-oxoethyl)-3-carbamoyl-1H-indazol-5-ylcarbamate (361 g)

Reaction of (R)-2-(2-(5-(tert-butoxycarbonylamino)-3-carbamoyl-1H-indazol-1-yl)-N-(1-(tert-butyldimethylsily-loxy)propan-2-yl)acetamido)acetic acid (358 h) (58.4 mg, 0.104 mmol) with (R)-1-(3-chloro-2-fluorophenyl)-N3,N3-dimethylpropane-1,3-diamine (361f) (71.8 mg, 0.311 mmol) according to the procedure reported in step-3 of Scheme 2 gave after workup and purification by flash column chromatography [silica gel with dichloromethane/methanol (1:0 to 9:1)] tert-butyl 1-(2-(((R)-1-(tert-butyldimethylsilyloxy) propan-2-yl)(2-((R)-1-(3-chloro-2-fluorophenyl)-3-(dim-ethylamino)propylamino)-2-oxoethyl)amino)-2-oxoethyl)-3-carbamoyl-1H-indazol-5-ylcarbamate (361 g) (11 mg, 14% for 6 steps) as a white solid; MS (ES+): 776.6 & 778.6 (M+1).

635

Step-7: Preparation of 5-amino-1-(2-((2-(((R)-1-(3-chloro-2-fluorophenyl)-3-(dimethylamino)propyl)amino)-2-oxoethyl)((R)-1-hydroxypropan-2-yl)-amino)-2-oxoethyl)-1H-indazole-3-carboxamide (361 h)

Reaction of tert-butyl 1-(2-(((S)-1-(tert-butyldimethylsilyloxy)propan-2-yl)(2-((R)-1-(3-chloro-2-fluorophenyl)-3-(dimethylamino)propylamino)-2-oxoethyl)amino)-2-oxoethyl)-3-carbamoyl-1H-indazol-5-ylcarbamate (361 g) (11 mg, 0.014 mmol) with conc. HCl (0.071 mL, 0.850 mmol) according to the procedure reported in step-9 of Scheme 358 gave after workup and purification by flash column chromatography [silica gel with chloroform/CMA80 (1:0 to 0:1)] 5-amino-1-(2-((2-((R)-1-(3-chloro-2-fluorophenyl)-3-(dimethylamino)propylamino)-2-oxoethyl)((R)-1-hydroxypropan-2-yl)amino)-2-oxoethyl)-1H-indazole-3-carboxamide (361 h) (5 mg, 63%) as a white solid; $^1$H NMR (300 MHz, DMSO-$d_6$) (a mixture of two rotamers) δ 8.99 and 8.59 (2d, J=8.1 Hz, 1H), 7.61-6.67 (m, 8H), 5.61-3.40 (m, 11H), 2.48-1.76 (m, 10H), 1.11 (d, J=6.5 Hz) and 0.85 (d, J=6.9 Hz) (2d, 3H); MS (ES+): 562.6 & 564.7 (M+1).

Scheme 362

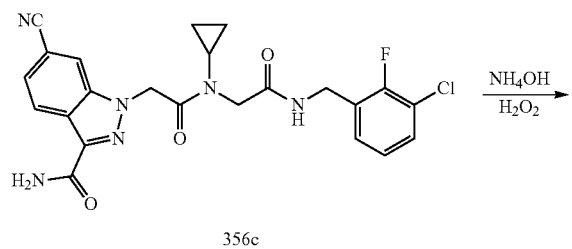

356c

636

-continued

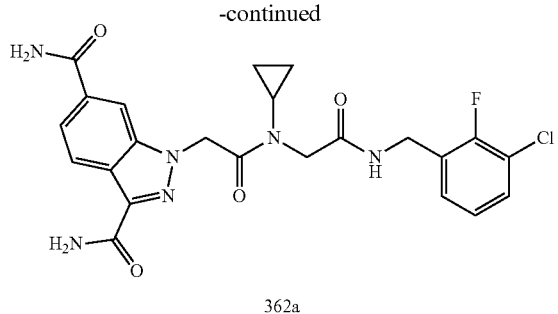

362a

Preparation of 1-(2-((2-((3-chloro-2-fluorobenzyl)amino)-2-oxoethyl)(cyclopropyl)amino)-2-oxoethyl)-1H-indazole-3,6-dicarboxamide (362a)

To a solution of 1-(2-((2-((3-chloro-2-fluorobenzyl)amino)-2-oxoethyl)(cyclopropyl)amino)-2-oxoethyl)-6-cyano-1H-indazole-3-carboxamide (356c) (37 mg, 0.077 mmol) in Ethanol (4 mL) was added conc. NH$_4$OH (1.5 mL), hydrogen peroxide (0.027 mL, 0.306 mmol) and stirred at RT for 15 h. The reaction mixture was concentrated to dryness. The crude product was purified by flash column chromatography [silica gel, eluting with dichloromethane/methanol (1:0 to 9:1)] to give 1-(2-((2-((3-chloro-2-fluorobenzyl)amino)-2-oxoethyl)(cyclopropyl)amino)-2-oxoethyl)-1H-indazole-3,6-dicarboxamide (362a) (34 mg, 89%); $^1$H NMR (300 MHz, DMSO-$d_6$) δ 8.55 (t, J=5.8 Hz, 1H), 8.28-8.13 (m, 2H), 8.06 (s, 1H), 7.85-7.71 (m, 2H), 7.53 (s, 1H), 7.49-7.38 (m, 2H), 7.26-7.19 (m, 1H), 7.13-7.06 (m, 1H), 5.72 (s, 2H), 4.32 (d, J=5.7 Hz, 2H), 4.00 (s, 2H), 3.14-2.99 (m, 1H), 1.08-0.85 (m, 4H); $^{19}$F NMR (282 MHz, DMSO-$d_6$) δ −121.55; MS (ES+): 523.4 & 525.4 (M+Na).

Scheme 363

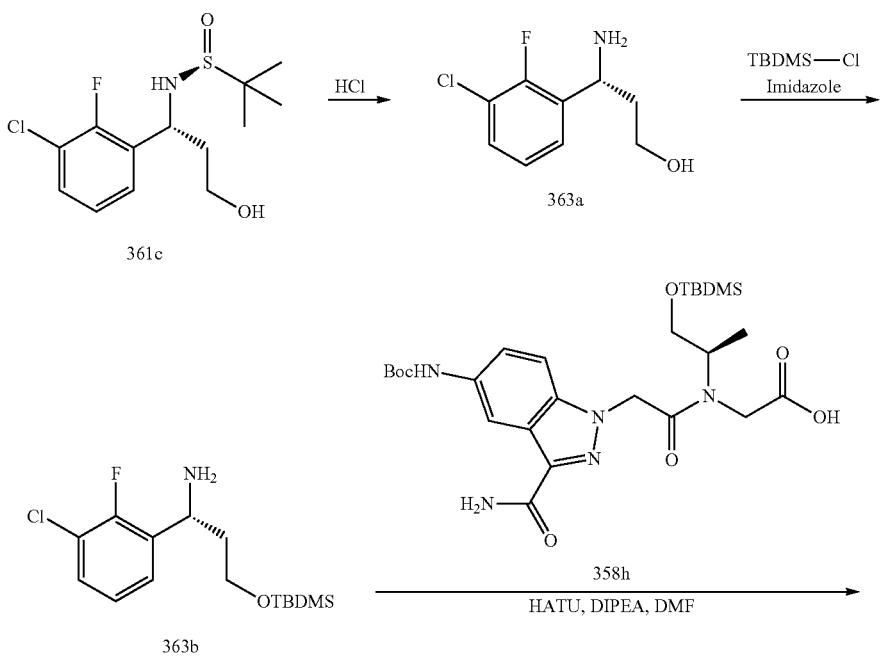

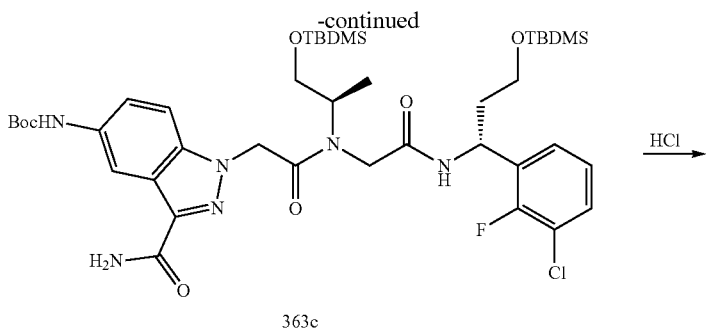

363c

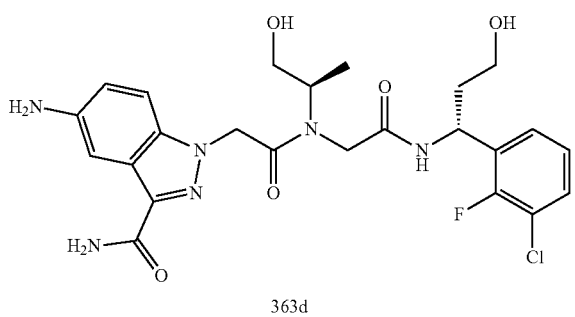

363d

Preparation of 5-amino-1-(2-((2-(((R)-1-(3-chloro-2-fluorophenyl)-3-hydroxypropyl)amino)-2-oxoethyl)((R)-1-hydroxypropan-2-yl)amino)-2-oxoethyl)-1H-indazole-3-carboxamide (363d)

Step-1: Preparation of (R)-3-amino-3-(3-chloro-2-fluorophenyl)propan-1-ol (363a)

Reaction of (S)—N—((R)-1-(3-chloro-2-fluorophenyl)-3-hydroxypropyl)-2-methylpropane-2-sulfinamide (361c) (150 mg, 0.487 mmol) with hydrogen chloride (0.244 mL, 0.975 mmol) (4 N in 1,4-dioxane) according to the procedure reported in step-1 of Scheme 360 gave after workup (R)-3-amino-3-(3-chloro-2-fluorophenyl)propan-1-ol (363a), which was used as such for next step without further purification; MS (ES+): 204.3 (M+1).

Step-2: Preparation of (R)-3-(tert-butyldimethylsilyloxy)-1-(3-chloro-2-fluorophenyl)propan-1-amine (363b)

Reaction of (R)-3-amino-3-(3-chloro-2-fluorophenyl)propan-1-ol (363a) (0.099 g, 0.487 mmol) in DMF (6 mL) with TBDMS-Cl (0.11 g, 0.731 mmol) according to the procedure reported in step-2 of Scheme 360 gave after workup (R)-3-(tert-butyldimethylsilyloxy)-1-(3-chloro-2-fluorophenyl)propan-1-amine as a yellow oil (363b) (139 mg), which was used as such for next step.

Step-3: Preparation of tert-butyl 1-((R)-11-((R)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (363c)

Reaction of (R)-2-(2-(5-(tert-butoxycarbonylamino)-3-carbamoyl-1H-indazol-1-yl)-N-(1-(tert-butyldimethylsilyloxy)propan-2-yl)acetamido)acetic acid (358 h) (80 mg, 0.142 mmol) with (R)-3-(tert-butyldimethylsilyloxy)-1-(3-chloro-2-fluorophenyl)propan-1-amine (363b) (135 mg, 0.425 mmol) (crude) according to the procedure reported in step-3 of Scheme 360 gave after workup and purification by flash column chromatography [silica gel, eluting with dichloromethane/methanol (1:0 to 19:1)] tert-butyl 1-((R)-11-((R)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (363c) (85 mg) as an off-white solid; MS (ES+): 885.8 & 887.9 (M+Na).

Step-4: Preparation of 5-amino-1-(2-((2-((R)-1-(3-chloro-2-fluorophenyl)-3-hydroxypropylamino)-2-oxoethyl)((R)-1-hydroxypropan-2-yl)-amino)-2-oxoethyl)-1H-indazole-3-carboxamide (363d)

Reaction of tert-butyl 1-((R)-11-((R)-1-(tert-butyldimethylsilyloxy)propan-2-yl)-7-(3-chloro-2-fluorophenyl)-2,2,3,3-tetramethyl-9,12-dioxo-4-oxa-8,11-diaza-3-silatridecan-13-yl)-3-carbamoyl-1H-indazol-5-ylcarbamate (363c) (71 mg, 0.082 mmol) with conc. HCl (0.206 mL, 2.466 mmol) according to the procedure reported in step-4 of Scheme 360 gave after workup and purification by flash column chromatography [silica gel, eluting with chloroform/CMA80 (1:0 to 0:1)] 5-amino-1-(2-((2-((R)-1-(3-chloro-2-fluorophenyl)-3-hydroxypropylamino)-2-oxoethyl)((R)-1-hydroxypropan-2-yl)-amino)-2-oxoethyl)-1H-indazole-3-carboxamide as a light brown solid (363d) (13 mg, 21% for 4 steps); $^1$H NMR (300 MHz, DMSO-$d_6$) (mixture of two rotamers) δ 8.89 (d, J=7.7 Hz) and 8.52 (d, J=7.7 Hz) (2d, 1H), 7.62-6.68 (m, 8H), 5.66-3.10 (m, 14H), 2.03-1.68 (m, 2H), 1.08 (d, J=6.4 Hz) and 0.83 (d, J=6.9 Hz) (2d, 3H); $^{19}$F NMR (282 MHz, DMSO-$d_6$) δ −121.75, −122.15; MS (ES+): 557.4 & 559.6 (M+Na); MS (ES−): 533.5 & 535.6 (M+Cl).

Scheme 364

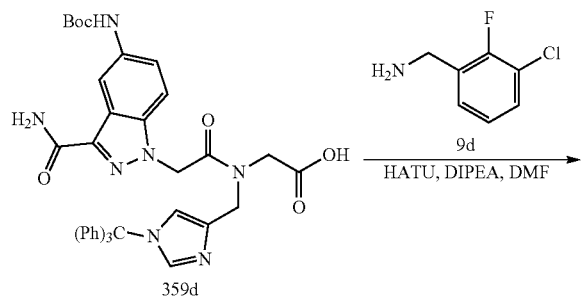

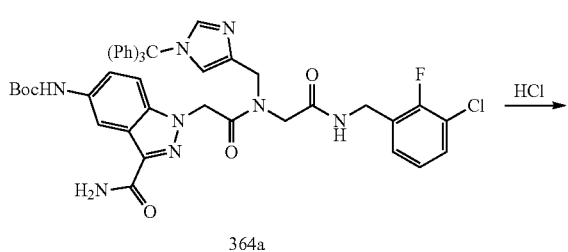

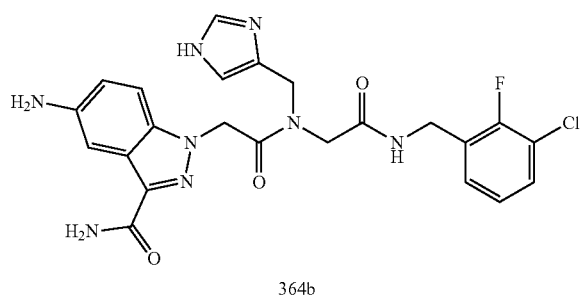

Preparation of 1-(2-(((1H-imidazol-4-yl)methyl)(2-((3-chloro-2-fluorobenzyl)amino)-2-oxoethyl)amino)-2-oxoethyl)-5-amino-1H-indazole-3-carboxamide (364b)

Step-1: Preparation of tert-butyl (3-carbamoyl-1-(2-((2-((3-chloro-2-fluorobenzyl)amino)-2-oxoethyl)((1-trityl-1H-imidazol-4-yl)methyl)amino)-2-oxoethyl)-1H-indazol-5-yl)carbamate (364a)

Compound 364a was prepared from 2-(2-(5-((tert-butoxycarbonyl)amino)-3-carbamoyl-1H-indazol-1-yl)-N-((1-trityl-1H-imidazol-4-yl)methyl)acetamido)acetic acid (359d) (40 mg, 0.056 mmol) by reaction with (3-chloro-2-fluorophenyl)methanamine (9d) (0.018 mL, 0.140 mmol) according to the procedure reported in step-3 of Scheme 2. This gave after workup and purification by flash column chromatography [Silica gel, eluting with dichloromethane/methanol (1:0 to 19:1)] tert-butyl (3-carbamoyl-1-(2-((2-((3-chloro-2-fluorobenzyl)amino)-2-oxoethyl)((1-trityl-1H-imidazol-4-yl)methyl)amino)-2-oxoethyl)-1H-indazol-5-yl)carbamate (364a) (60 mg) as an off-white solid; MS (ES+): 877.7 (M+Na).

Step-2: Preparation of 1-(2-(((1H-imidazol-4-yl)methyl)(2-((3-chloro-2-fluorobenzyl)amino)-2-oxoethyl)amino)-2-oxoethyl)-5-amino-1H-indazole-3-carboxamide (364b)

Compound 364b was prepared from tert-butyl (3-carbamoyl-1-(2-((2-((3-chloro-2-fluorobenzyl)amino)-2-oxoethyl)((1-trityl-1H-imidazol-4-yl)methyl)amino)-2-oxoethyl)-1H-indazol-5-yl)carbamate (364a) (55 mg, 0.064 mmol) by reaction with conc. HCl (0.214 mL, 2.57 mmol) in methanol (5 mL) according to the procedure reported in step-3 of Scheme 292. This gave after workup and purification by flash column chromatography [Silica gel, eluting with chloroform/CMA80 (1:0 to 1:2)] to give 1-(2-(((1H-imidazol-4-yl)methyl)(2-((3-chloro-2-fluorobenzyl)amino)-2-oxoethyl)amino)-2-oxoethyl)-5-amino-1H-indazole-3-carboxamide (364b) (15 mg, 57% for two steps) as a light brown solid; $^1$H NMR (300 MHz, DMSO-$d_6$, mixture of two rotamers) δ 12.11 & 11.97 (2s, 1H), 8.91 & 8.66 (2t, J=6.0 Hz, 1H), 7.87-6.71 (m, 10H), 5.80-4.94 (m, 4H), 4.71-3.82 (m, 6H); $^{19}$F NMR (282 MHz, DMSO-$d_6$) δ −121.41, −121.64; MS (ES+): 513.4 (M+1); MS (ES−): 511.5 (M−1).

Scheme 365

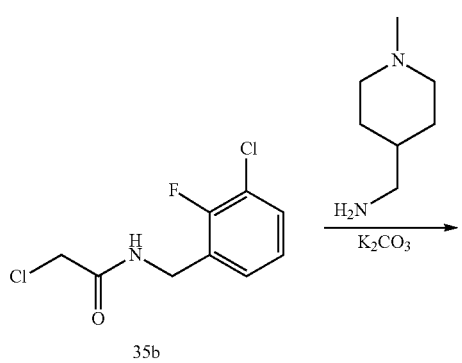

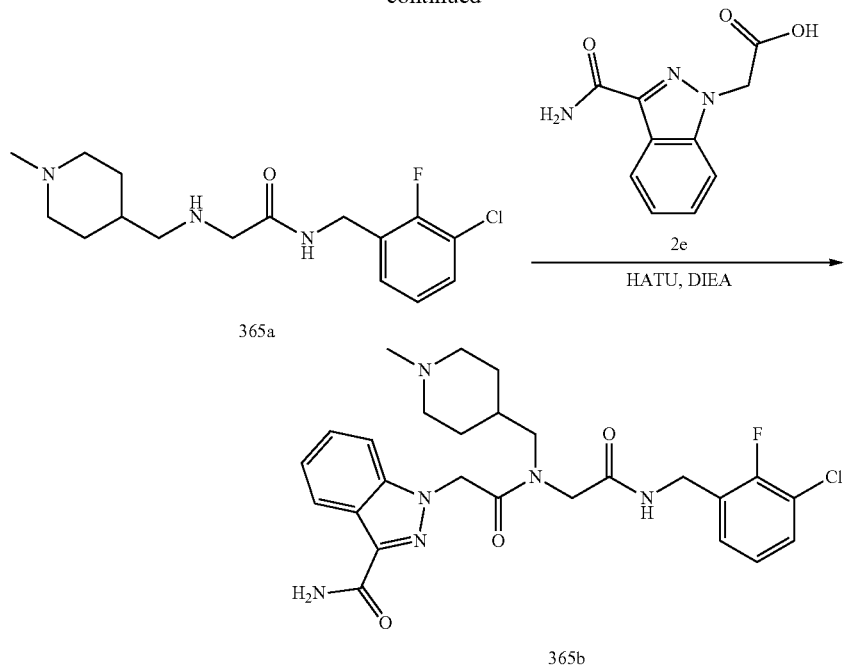

Preparation of 1-(2-((2-(((3-chloro-2-fluorobenzyl) amino)-2-oxoethyl)((1-methylpiperidin-4-yl)methyl) amino)-2-oxoethyl)-1H-indazole-3-carboxamide (365b)

Step 1: Preparation of N-(3-chloro-2-fluorobenzyl)-2-(((1-methylpiperidin-4-yl)methyl)amino)acetamide (365a)

Reaction of 2-chloro-N-(3-chloro-2-fluorobenzyl)acetamide (35b) (604 mg, 2.56 mmol) with (1-methylpiperidin-4-yl)methanamine (820 mg, 6.4 mmol) according to the procedure reported in step-2 of Scheme 35 gave after workup and purification by flash column chromatography [Silica gel, 12 g eluting with methanol in DCM from 0-30%] N-(3-chloro-2-fluorobenzyl)-2-(((1-methylpiperidin-4-yl)methyl)amino)acetamide (365a) (535 mg, 64% yield) as a clear oil. $^1$H NMR (300 MHz, DMSO-$d_6$) δ 8.30 (t, J=6.1 Hz, 1H, D$_2$O exchangeable), 7.47 (td, J=7.6, 1.8 Hz, 1H), 7.32-7.23 (m, 1H), 7.23-7.09 (m, 1H), 4.36 (d, J=6.0 Hz, 2H), 3.21-3.04 (m, 3H), 2.77-2.60 (m, 2H), 2.31 (d, J=6.5 Hz, 2H), 2.10 (s, 4H), 1.75 (td, J=11.5, 2.5 Hz, 2H), 1.68-1.55 (m, 2H), 1.18-0.94 (m, 2H); MS (ES+): 328.3 (M+1); (ES−): 326.4 (M−1).

Step 2: Preparation of 1-(2-((2-(((3-chloro-2-fluorobenzyl)amino)-2-oxoethyl)((1-methylpiperidin-4-yl)methyl)amino)-2-oxoethyl)-1H-indazole-3-carboxamide (365b)

Reaction of N-(3-chloro-2-fluorobenzyl)-2-(((1-methylpiperidin-4-yl)methyl)amino)acetamide (365a) (150 mg, 0.46 mmol) with 2-(3-carbamoyl-1H-indazol-1-yl)acetic acid (2e) (120 mg, 0.55 mmol) according to the procedure reported in step-3 of Scheme 2 gave after workup and purification by flash column chromatography [Silica gel, 12 g eluting with CMA80 in CHCl$_3$ from 0 to 60%] 1-(2-((2-((3-chloro-2-fluorobenzyl)amino)-2-oxoethyl)((1-methylpiperidin-4-yl)methyl)amino)-2-oxoethyl)-1H-indazole-3-carboxamide (365b) (65 mg, 27% yield) as a white solid, $^1$H NMR (300 MHz, DMSO-$d_6$) δ 10.24 (s, 1H, D$_2$O exchangeable), 9.04 (t, J=5.8 Hz, 1H, D$_2$O exchangeable), 8.18 (d, J=8.1 Hz, 1H), 7.71 (s, 1H), 7.62-7.34 (m, 5H), 7.30-7.06 (m, 2H), 5.62-5.38 (m, 2H), 4.71 (s, 2H), 4.53-4.23 (m, 4H), 3.41 (dd, J=30.9, 10.2 Hz, 2H), 3.17 (d, J=6.7 Hz, 1H), 2.81-2.63 (m, 4H), 2.05-1.88 (m, 1H), 1.80-1.63 (m, 2H), 1.48-1.28 (m, 1H); MS (ES+): 529.3 (M+1); (ES−): 563.3 (M+Cl).

Scheme 366

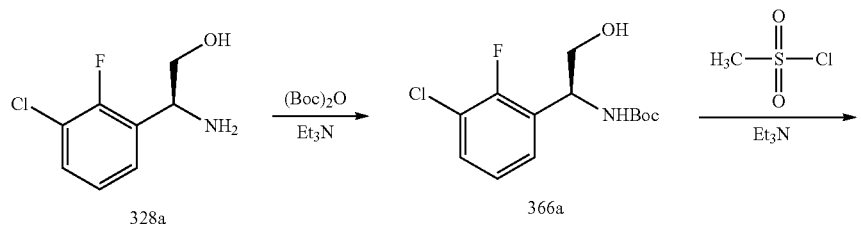

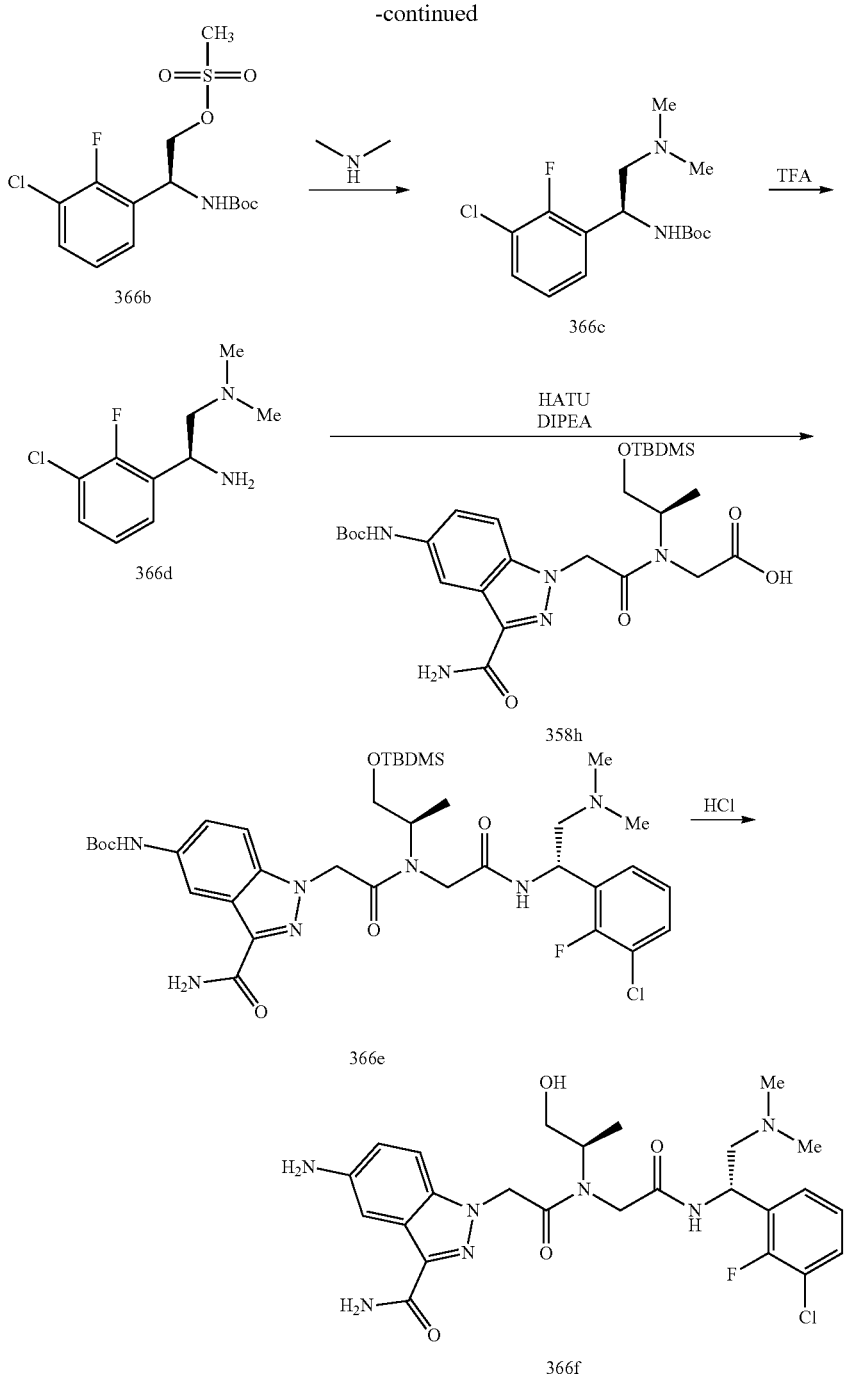

Preparation of 5-amino-1-(2-((2-(((S)-1-(3-chloro-2-fluorophenyl)-2-(dimethylamino)ethyl)amino)-2-oxoethyl)((R)-1-hydroxypropan-2-yl)-amino)-2-oxoethyl)-1H-indazole-3-carboxamide (366f)

Step-1: Preparation of (S)-tert-butyl 1-(3-chloro-2-fluorophenyl)-2-hydroxyethylcarbamate (366a)

To a solution of (S)-2-amino-2-(3-chloro-2-fluorophenyl) ethanol hydrochloride (328a) (800 mg, 3.54 mmol) in DCM (30 mL) and MeOH (15 mL) was added di-tert-butyl dicarbonate (946 mg, 4.25 mmol), triethylamine (0.986 mL, 7.08 mmol) and stirred at RT for 20 h. The reaction mixture was diluted with dichloromethane (100 mL), washed with water (50 mL), dried, filtered, concentrated in vacuum to give (S)-tert-butyl 1-(3-chloro-2-fluorophenyl)-2-hydroxyethylcarbamate (366a) (1.083 g) as a white solid which was used as such for next step. MS (ES+): 312.3 & 314.2 (M+Na).

Step-2: Preparation of (S)-2-(tert-butoxycarbonylamino)-2-(3-chloro-2-fluorophenyl)ethyl methanesulfonate (366b)

Reaction of (S)-tert-butyl 1-(3-chloro-2-fluorophenyl)-2-hydroxyethylcarbamate (366a) (1.026 g, 3.54 mmol) with methanesulfonyl chloride (0.303 mL, 3.89 mmol) according to the procedure reported in step-3 of Scheme 358 gave after workup (S)-2-(tert-butoxycarbonylamino)-2-(3-chloro-2-fluorophenyl)ethyl methanesulfonate (366b) (1.317 g) as a white solid which was used as such for next step. $^1$H NMR (300 MHz, DMSO-d$_6$) δ 7.87 (d, J=8.7 Hz, 1H), 7.56 (t, J=7.9 Hz, 1H), 7.44 (t, J=7.1 Hz, 1H), 7.27 (t, J=7.9 Hz, 1H), 5.25-5.09 (m, 1H), 4.35-4.19 (m, 2H), 3.19 (s, 3H), 1.37 (s, 9H); $^{19}$F NMR (282 MHz, DMSO-d$_6$) δ −121.15; MS (ES+): 390.2 & 392.2 (M+Na).

Step-3: Preparation of (5)-tert-butyl 1-(3-chloro-2-fluorophenyl)-2-(dimethyl-amino)ethylcarbamate (366c)

Reaction of (S)-2-(tert-butoxycarbonylamino)-2-(3-chloro-2-fluorophenyl)ethyl methanesulfonate (366b) (120 mg, 0.326 mmol) with dimethylamine (2M in THF, 3.59 mL, 7.18 mmol) according to the procedure reported in step-4 of Scheme 358 gave after workup and purification by flash column chromatography [silica gel, eluting with hexanes/ethyl acetate (1:0 to 1:1)] (5)-tert-butyl 1-(3-chloro-2-fluorophenyl)-2-(dimethyl-amino)ethylcarbamate as a brown gum (366c) (27 mg, 28% for 3 steps). MS (ES+): 317.3 (M+1). Another side product (S)-4-(3-chloro-2-fluorophenyl)oxazolidin-2-one was also formed from this reaction, MS (ES−): 214.2 & 216.1 (M−1).

Step-4: Preparation of (S)-1-(3-chloro-2-fluorophenyl)-N2,N2-dimethylethane-1,2-diamine (366d)

Reaction of (5)-tert-butyl 1-(3-chloro-2-fluorophenyl)-2-(dimethylamino)ethylcarbamate (366c) (22 mg, 0.069 mmol) with 2,2,2-trifluoroacetic acid (0.375 mL, 4.86 mmol) according to the procedure reported in step-2 of Scheme 2 gave after workup (S)-1-(3-chloro-2-fluorophenyl)-N2,N2-dimethylethane-1,2-diamine (366d), which used as such for next step.

Step-5: Preparation of tert-butyl 1-(2-(((R)-1-(tert-butyldimethylsilyloxy)propan-2-yl)(2-((S)-1-(3-chloro-2-fluorophenyl)-2-(dimethylamino)ethyl-amino)-2-oxoethyl)amino)-2-oxoethyl)-3-carbamoyl-1H-indazol-5-ylcarbamate (366e)

Reaction of (R)-2-(2-(5-(tert-butoxycarbonylamino)-3-carbamoyl-1H-indazol-1-yl)-N-(1-(tert-butyldimethylsilyloxy)propan-2-yl)acetamido)acetic acid (358 h) (0.051 g, 0.090 mmol) with (S)-1-(3-chloro-2-fluorophenyl)-N2,N2-dimethylethane-1,2-diamine (366d) (0.015 g, 0.069 mmol) according to the procedure reported in step-3 of Scheme 2 gave after workup and purification by flash column chromatography [silica gel, eluting with chloroform/CMA80 (1:0 to 1:1)] tert-butyl 1-(2-(((R)-1-(tert-butyldimethylsilyloxy)propan-2-yl)(2-((S)-1-(3-chloro-2-fluorophenyl)-2-(dimethylamino)ethylamino)-2-oxoethyl)amino)-2-oxoethyl)-3-carbamoyl-1H-indazol-5-ylcarbamate (366e) (17 mg) as a yellow solid; MS (ES+): 762.5 & 764.4 (M+1).

Step-6: Preparation of 5-amino-1-(2-((2-((S)-1-(3-chloro-2-fluorophenyl)-2-(dimethylamino)ethyl-amino)-2-oxoethyl)((R)-1-hydroxypropan-2-yl)amino)-2-oxoethyl)-1H-indazole-3-carboxamide (366f)

Reaction of tert-butyl 1-(2-(((R)-1-(tert-butyldimethylsilyloxy)propan-2-yl)(2-((S)-1-(3-chloro-2-fluorophenyl)-2-(dimethylamino)ethylamino)-2-oxoethyl)amino)-2-oxoethyl)-3-carbamoyl-1H-indazol-5-ylcarbamate (366f) (17 mg, 0.022 mmol) with conc. HCl (0.111 mL, 1.338 mmol) according to the procedure reported in step-4 of Scheme 360 gave after workup and purification by flash column chromatography [silica gel, eluting with chloroform/CMA80 (1:0 to 0:1)] 5-amino-1-(2-((2-((S)-1-(3-chloro-2-fluorophenyl)-2-(dimethylamino)ethylamino (366 g) (8 mg, 21% for 3 steps) as a light pink solid; $^1$H NMR (300 MHz, DMSO-d$_6$, a mixture of two rotamers) δ 7.71-6.74 (m, 8H), 5.63-3.40 (m, 11H), 2.80-2.00 (m, 8H), 1.10 (d, J=6.4 Hz) and 0.86 (d, J=6.8 Hz) (2d, 3H); $^{19}$F NMR (282 MHz, DMSO-d$_6$) δ −120.003, −120.009; MS (ES+): 548.4 (M+1) & 570.5 (M+Na).

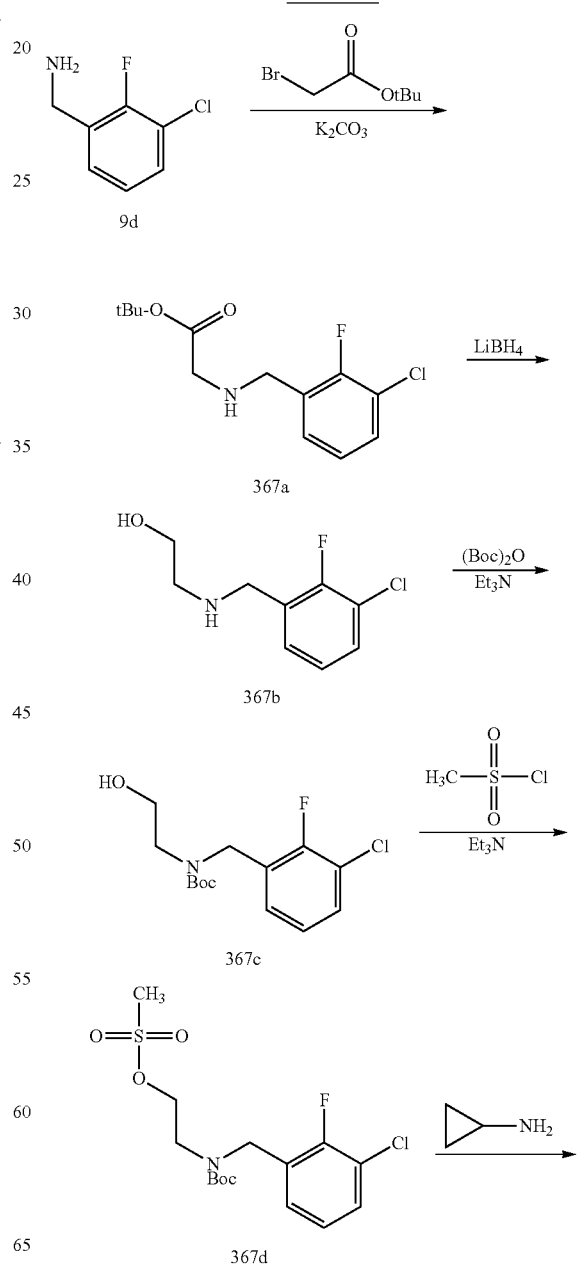

Scheme 367

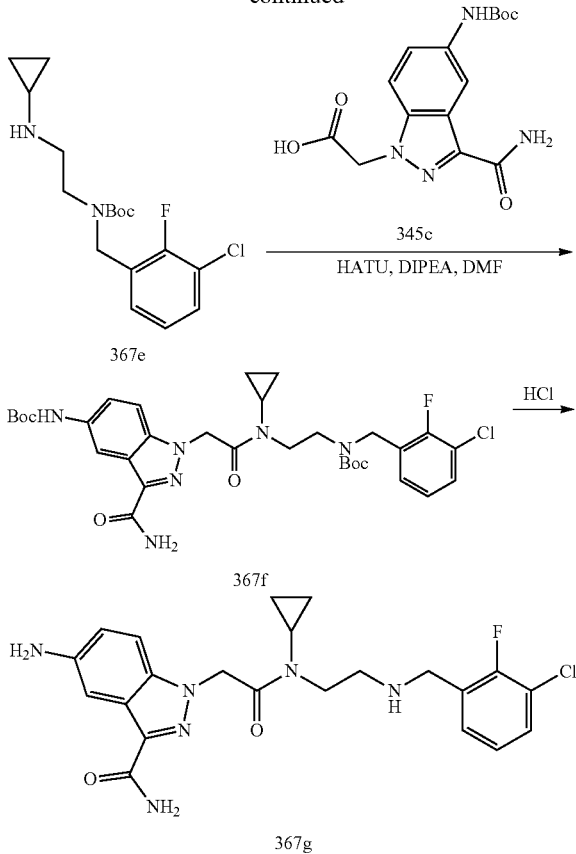

Preparation of 5-amino-1-(2-((2-((3-chloro-2-fluorobenzyl)amino)ethyl)(cyclopropyl)amino)-2-oxoethyl)-1H-indazole-3-carboxamide (367 g)

Step-1: Preparation of tert-butyl 2-((3-chloro-2-fluorobenzyl)amino)acetate (367a)

Compound 367a was prepared from (3-chloro-2-fluorophenyl)methanamine (9d) (4.06 g, 25.4 mmol) using $K_2CO_3$ (5.68 g, 40.7 mmol) and tert-butyl 2-chloroacetate (3 mL, 20.35 mmol) according to the procedure reported in step-1 of Scheme 43. This gave after workup and purification by flash column chromatography [silica gel, eluting with hexanes/ethyl acetate (1:0 to 4:1)] tert-butyl 2-((3-chloro-2-fluorobenzyl)amino)acetate (367a) (2.78 g, 50%) as a colorless oil; $^1H$ NMR (300 MHz, DMSO-$d_6$) δ 7.51-7.34 (m, 2H), 7.19 (td, J=7.8, 1.1 Hz, 1H), 3.78 (s, 2H), 3.20 (s, 2H), 1.40 (s, 9H); MS (ES+): 274.3 & 276.2 (M+1).

Step-2: Preparation of 2-((3-chloro-2-fluorobenzyl)amino)ethanol (367b)

Compound 367b was prepared from tert-butyl 2-((3-chloro-2-fluorobenzyl)amino)acetate (367a) (1.608 g, 5.87 mmol) and lithium borohydride (8.81 mL, 17.62 mmol, 2M in THF) according to the procedure reported in step-2 of Scheme 358. This gave after workup 2-((3-chloro-2-fluorobenzyl)amino)ethanol (367b) (1.175 g) as a colorless gum which was used as such for next step; MS (ES+): 204.2 & 206.2 (M+1).

Step-3: Preparation of tert-butyl 3-chloro-2-fluorobenzyl(2-hydroxyethyl)carbamate (367c)

To a solution of 2-(3-chloro-2-fluorobenzylamino)ethanol (367b) (1.1 g, 5.40 mmol) in DCM (40 mL) and MeOH (20 mL) was added di-tert-butyl dicarbonate (1.444 g, 6.48 mmol) triethylamine (1.506 mL, 10.80 mmol) and stirred at RT for 20 h. The reaction mixture was diluted with dichloromethane (120 mL), washed with water (60 mL), dried, filtered, concentrated in vacuum and purified by flash column chromatography [silica gel, eluting with dichloromethane/methanol (1:0 to 19:1)] to give tert-butyl 3-chloro-2-fluorobenzyl(2-hydroxyethyl)carbamate (367c) (713 mg) as a colorless oil which was used as such for next step; MS (ES+): 326.3 (M+Na).

Step-4: Preparation of 2-((tert-butoxycarbonyl)(3-chloro-2-fluorobenzyl)amino)ethyl methanesulfonate (367d)

Compound 367d was prepared from tert-butyl 3-chloro-2-fluorobenzyl(2-hydroxyethyl)carbamate (367c) (162 mg, 0.526 mmol) triethylamine (0.147 mL, 1.053 mmol) and methanesulfonyl chloride (0.045 mL, 0.579 mmol) according to the procedure reported in step-3 of Scheme 358. This gave after workup 2-((tert-butoxycarbonyl)(3-chloro-2-fluorobenzyl)amino)ethyl methanesulfonate (367d) (484 mg) as a colorless gum which was used as such for next step.

Step-5: Preparation of tert-butyl 3-chloro-2-fluorobenzyl(2-(cyclopropylamino)ethyl)carbamate (367e)

A solution of 2-((tert-butoxycarbonyl)(3-chloro-2-fluorobenzyl)amino)ethyl methanesulfonate (367d) (270 mg, 0.707 mmol) in DMF (10 mL) was added cyclopropanamine (1.084 mL, 15.56 mmol) and heated with stirring at 80° C. in a sealed tube for 2 h. The reaction mixture was cooled to RT, diluted with ethyl acetate (100 mL), washed with water (2×50 mL), brine (50 mL), dried, filtered, concentrated in vacuum and purified by flash column chromatography [silica gel, eluting with hexanes/ethyl acetate (1:0 to 1:1)] to give tert-butyl 3-chloro-2-fluorobenzyl(2-(cyclopropylamino)ethyl)-carbamate (367e) contaminated with 3-(3-chloro-2-fluorobenzyl)oxazolidin-2-one (90 mg, molar ratio: 1:5 based on $^1H$ NMR, 23% by weight of the desired product, 3.8% yield for 4 steps) as a colorless oil which was used as such for next step. MS (ES+): 343.3 & 345.3 (M+1).

Step-6: Preparation of tert-butyl (2-(2-(5-((tert-butoxycarbonyl)amino)-3-carbamoyl-1H-indazol-1-yl)-N-cyclopropylacetamido)ethyl)(3-chloro-2-fluorobenzyl)carbamate (367f)

Reaction of 2-(5-((tert-butoxycarbonyl)amino)-3-carbamoyl-1H-indazol-1-yl)acetic acid (345c) (35 mg, 0.11 mmol) with tert-butyl 3-chloro-2-fluorobenzyl(2-(cyclopropylamino)ethyl)carbamate (367e) (19 mg, 0.05 mmol) according to the procedure reported in step-3 of Scheme 2 gave after workup and purification by flash column chromatography [silica gel with dichloromethane/methanol (1:0 to 19:1)] tert-butyl (2-(2-(5-((tert-butoxycarbonyl)amino)-3-carbamoyl-1H-indazol-1-yl)-N-cyclopropylacetamido)

ethyl)(3-chloro-2-fluorobenzyl)carbamate (367f) (24 mg, 66%) as a colorless gum; MS (ES+): 681.3 & 683.4 (M+Na).

Step-7: Preparation of 5-amino-1-(2-((2-((3-chloro-2-fluorobenzyl)amino)ethyl)(cyclopropyl)amino)-2-oxoethyl)-1H-indazole-3-carboxamide (367 g)

Compound 367g was prepared from tert-butyl (2-(2-(5-((tert-butoxycarbonyl)amino)-3-carbamoyl-1H-indazol-1-yl)-N-cyclopropylacetamido)ethyl)(3-chloro-2-fluorobenzyl)carbamate (367f) (24 mg, 0.036 mmol) by reaction with conc. HCl (0.152 mL, 1.82 mmol) in methanol (4 mL) according to the procedure reported in step-3 of Scheme 292. This gave after workup and purification by flash column chromatography [Silica gel, eluting with chloroform/CMA80 (1:0 to 1:1) 5-amino-1-(2-((2-((3-chloro-2-fluorobenzyl)amino)ethyl)(cyclopropyl)amino)-2-oxoethyl)-1H-indazole-3-carboxamide (367 g) (9 mg, 54%) as a brown solid; $^1$H NMR (300 MHz, DMSO-d$_6$) δ 7.65-7.19 (m, 6H), 7.12 (s, 1H), 6.80 (dd, J=8.8, 2.1 Hz, 1H), 5.52 (s, 2H), 4.07 (s, 2H), 3.66-3.53 (m, 2H), 3.12-3.03 (m, 1H), 3.03-2.87 (m, 2H), 1.06-0.89 (m, 4H); $^{19}$F NMR (282 MHz, Methanol-d$_4$) δ −120.77; MS (ES+): 481.0 (M+Na).

zole-3-carboxamide (368a) (61 mg, 37%) as an off-white solid; $^1$H NMR (300 MHz, DMSO-d$_6$ (a mixture of two rotamers) δ 8.92 (t, J=5.6 Hz) and 8.60 (t, J=5.7 Hz ((2t, 1H), 8.14 (s, 1H), 7.75 (s, 1H), 7.67-6.92 (m, 6H), 5.74-5.37 (m, 2H), 4.58-3.68 (m, 5H), 3.60-3.10 (m, 2H), 1.16 (d, J=6.4 Hz) and 0.96 (d, J=6.9 Hz) (2d, 3H); $^{19}$F NMR (282 MHz, DMSO-d$_6$) δ −121.23, −121.64; MS (ES+): 513.3 & 515.3 (M+Na); MS (ES−): 525.2 & 527.3 (M+Cl); Analysis Calculated for $C_{22}H24ClFN_6O_4$.1.0 HCl.2.5H2O: C, 46.16; H, 5.28; N, 14.68; Cl, 12.39; Found: C, 45.98; H, 5.00; N, 14.50; Cl, 12.44.

Scheme 369

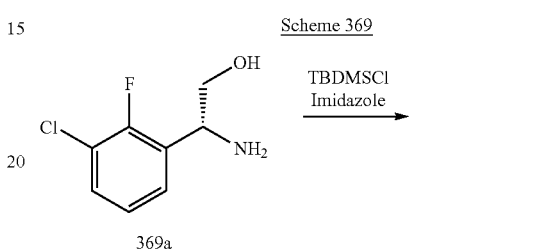

Scheme 368

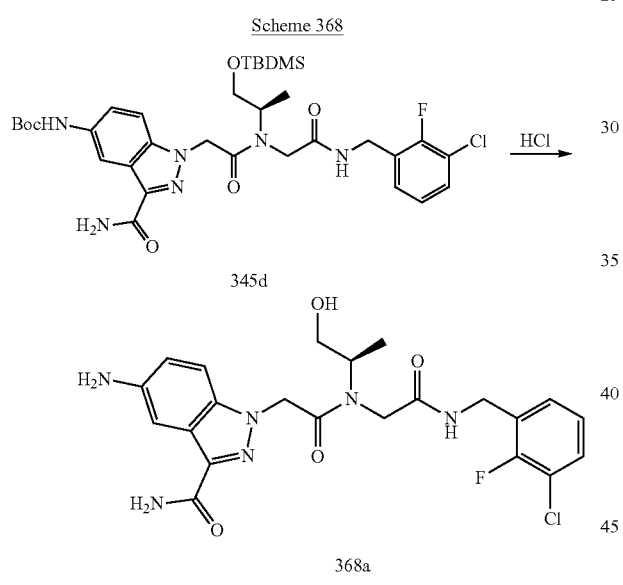

Preparation of (R)-5-amino-1-(2-((2-((3-chloro-2-fluorobenzyl)amino)-2-oxoethyl)(1-hydroxypropan-2-yl)amino)-2-oxoethyl)-1H-indazole-3-carboxamide (368a)

To a solution of (R)-tert-butyl (1-(2-((1-(((tert-butyldimethylsilyl)oxy)propan-2-yl)(2-((3-chloro-2-fluorobenzyl)amino)-2-oxoethyl)amino)-2-oxoethyl)-3-carbamoyl-1H-indazol-5-yl)carbamate (345d) (220 mg, 0.312 mmol) in MeOH (25 mL) was added hydrogen chloride (1.040 mL, 12.48 mmol) and stirring at RT for 15 h. The reaction mixture was concentrated to dryness and purified by flash column chromatography [silica gel, eluting with chloroform/DMA80 (1:0 to 1:1)] followed by reverse-phase combiflash column chromatography with water (0.1% HCl)/acetonitrile (1:0 to 1:1) to give (R)-5-amino-1-(2-((2-((3-chloro-2-fluorobenzyl)amino)-2-oxoethyl)(1-hydroxypropan-2-yl)amino)-2-oxoethyl)-1H-inda-

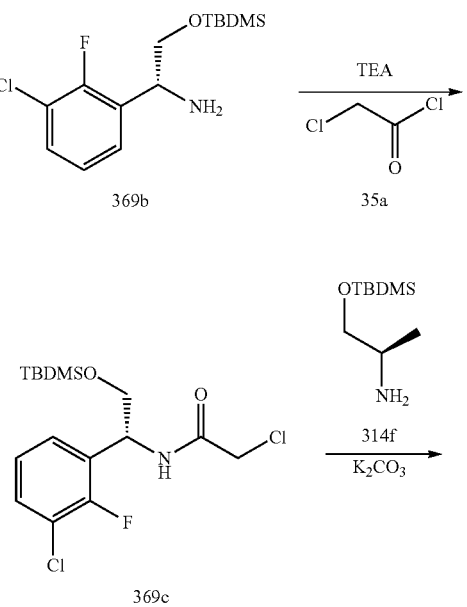

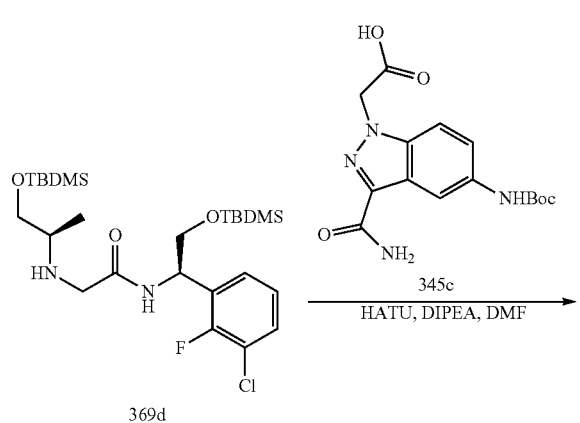

-continued

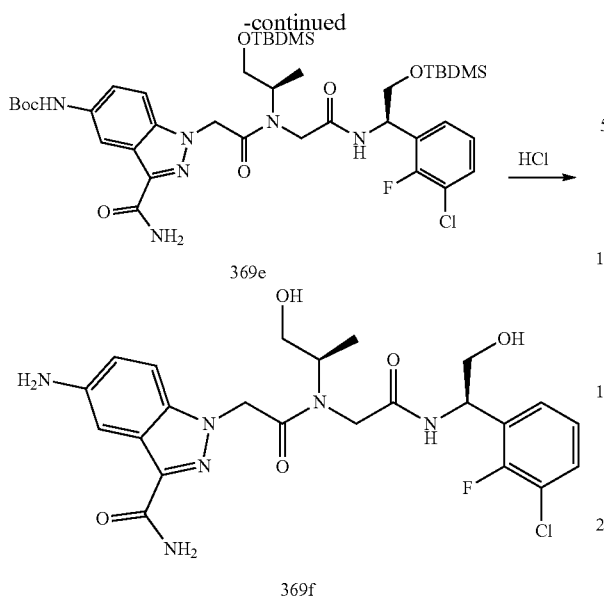

Preparation of 5-amino-1-(2-((2-((R)-1-(3-chloro-2-fluorophenyl)-2-hydroxyethylamino)-2-oxoethyl)((R)-1-hydroxypropan-2-yl)amino)-2-oxoethyl)-1H-indazole-3-carboxamide (369f)

Step-1: Preparation of (R)-2-(tert-butyldimethylsilyloxy)-1-(3-chloro-2-fluorophenyl)ethanamine (369b)

Reaction of (R)-2-amino-2-(3-chloro-2-fluorophenyl)ethanol (369a) (340 mg, 1.793 mmol with TBDMS-C₁ (324 mg, 2.152 mmol) according to the procedure reported in step-1 of Scheme 328 gave after workup (R)-2-(tert-butyldimethylsilyloxy)-1-(3-chloro-2-fluorophenyl)ethanamine (369b) (606 mg) as a white solid which was used as such for next step; MS (ES+): 304.2 & 306.3 (M+1).

Step-2: Preparation of (R)—N-(2-(tert-butyldimethylsilyloxy)-1-(3-chloro-2-fluorophenyl)ethyl)-2-chloroacetamide (369c)

Reaction of (R)-2-(tert-butyldimethylsilyloxy)-1-(3-chloro-2-fluorophenyl)ethanamine (369b) (590 mg, 1.942 mmol) with 2-chloroacetyl chloride (35a) (0.237 mL, 2.91 mmol) according to the procedure reported in step-2 of Scheme 328 gave after workup (R)—N-(2-(tert-butyldimethylsilyloxy)-1-(3-chloro-2-fluorophenyl)ethyl)-2-chloroacetamide (369c) (495 mg, 74% for two steps) as a colorless gum; $^1$H NMR (300 MHz, DMSO-d₆) δ 8.72 (d, J=7.9 Hz, 1H), 7.50 (td, J=7.6, 1.7 Hz, 1H), 7.42-7.34 (m, 1H), 7.23 (t, J=7.9 Hz, 1H), 5.18 (q, J=6.9 Hz, 1H), 4.12 (s, 2H), 3.85-3.65 (m, 2H), 0.77 (s, 9H), −0.06 (s, 3H), −0.09 (s, 3H); $^{19}$F NMR (282 MHz, DMSO-d₆) δ −121.13, −121.14; MS (ES+): 402.2 (M+Na).

Step-3: Preparation of N—((R)-2-(tert-butyldimethylsilyloxy)-1-(3-chloro-2-fluorophenyl)ethyl)-2-((R)-1-(tert-butyldimethylsilyloxy)propan-2-ylamino)acetamide (369d)

Reaction of (R)—N-(2-(tert-butyldimethylsilyloxy)-1-(3-chloro-2-fluorophenyl)ethyl)-2-chloroacetamide (369c) (480 mg, 1.262 mmol) with (R)-1-(tert-butyldimethylsilyloxy)propan-2-amine (314f) (311 mg, 1.641 mmol) according to the procedure reported in step-3 of Scheme 328 gave after workup and purification by flash column chromatography [silica gel, eluting with hexanes/ethyl acetate (1:0 to 2:1)] N—((R)-2-(tert-butyldimethylsilyloxy)-1-(3-chloro-2-fluorophenyl)ethyl)-2-((R)-1-(tert-butyldimethylsilyloxy)propan-2-ylamino)acetamide (369d) (376 mg, 56%) as a yellow oil; $^1$H NMR (300 MHz, DMSO-d₆) δ 8.36 (d, J=8.4 Hz, 1H), 7.56-7.42 (m, 1H), 7.33 (t, J=6.8 Hz, 1H), 7.19 (t, J=7.8 Hz, 1H), 5.27-5.13 (m, 1H), 3.77 (d, J=5.5 Hz, 2H), 3.52-3.34 (m, 2H), 3.18 (s, 2H), 2.69-2.55 (m, 1H), 0.94 (d, J=6.3 Hz, 3H), 0.86 (s, 9H), 0.78 (s, 9H), 0.03 (s, 3H), 0.02 (s, 3H), −0.08 (s, 3H), −0.11 (s, 3H); $^{19}$F NMR (282 MHz, DMSO-d₆) δ −121.43; MS (ES+): 533.4 & 535.4 (M+Na).

Step-4: Preparation of tert-butyl 1-((R)-10-((R)-1-(tert-butyldimethylsilyloxy)propan-2-yl)-6-(3-chloro-2-fluorophenyl)-2,2,3,3-tetramethyl-8,11-dioxo-4-oxa-7,10-diaza-3-siladodecan-12-yl)-3-carbamoyl-1H-indazol-5-ylcarbamate (369e)

Reaction of 2-(5-(tert-butoxycarbonylamino)-3-carbamoyl-1H-indazol-1-yl)acetic acid (345c) (150 mg, 0.449 mmol) with N—((R)-2-(tert-butyldimethylsilyloxy)-1-(3-chloro-2-fluorophenyl)ethyl)-2-((R)-1-(tert-butyldimethylsilyloxy)propan-2-ylamino)acetamide (369d) (299 mg, 0.561 mmol) according to the procedure reported in step-3 of Scheme 2 gave after workup and purification by flash column chromatography [silica gel, eluting with dichloromethane/methanol (1:0 to 19:1)] tert-butyl 1-((R)-10-((R)-1-(tert-butyldimethylsilyloxy)propan-2-yl)-6-(3-chloro-2-fluorophenyl)-2,2,3,3-tetramethyl-8,11-dioxo-4-oxa-7,10-diaza-3-siladodecan-12-yl)-3-carbamoyl-1H-indazol-5-ylcarbamate (369e) (342 mg, 90% yield) as an off-white solid; MS (ES+): 849.5 (M+1).

Step-5: Preparation of 5-amino-1-(2-((2-((R)-1-(3-chloro-2-fluorophenyl)-2-hydroxyethylamino)-2-oxoethyl)((R)-1-hydroxypropan-2-yl)amino)-2-oxoethyl)-1H-indazole-3-carboxamide (369f)

Reaction of tert-butyl 1-((R)-10-((R)-1-(tert-butyldimethylsilyloxy)propan-2-yl)-6-(3-chloro-2-fluorophenyl)-2,2,3,3-tetramethyl-8,11-dioxo-4-oxa-7,10-diaza-3-siladodecan-12-yl)-3-carbamoyl-1H-indazol-5-ylcarbamate (369e) (300 mg, 0.353 mmol) with conc. HCl (1.177 mL, 14.12 mmol) according to the procedure reported in step-4 of Scheme 360 gave after workup and purification by reverse-phase column chromatography eluting with water (0.1% HCl)/acetonitrile (1:0 to 1:1) 5-amino-1-(2-((2-((R)-1-(3-chloro-2-fluorophenyl)-2-hydroxyethylamino)-2-oxoethyl)((R)-1-hydroxypropan-2-yl)amino)-2-oxoethyl)-1H-indazole-3-carboxamide (369f) (9 mg, 5% yield) as an off-white solid; $^1$H NMR (300 MHz, DMSO-d₆) (a mixture of two rotamers) δ 9.02 (d, J=7.9 Hz) and 8.59 (d, J=7.8 Hz) (2d, 1H), 8.02 (s, 1H), 7.78 (s, 1H), 7.61-6.98 (m, 6H), 5.70-5.33 (m, 2H), 5.30-4.97 (m, 1H), 4.50-3.73 (m, 3H), 3.63 (d, J=6.4 Hz) and 3.53 (d, J=6.1 Hz) (2d, 2H), 1.14 (d, J=6.4 Hz) and 0.99 (d, J=6.9 Hz) (2d, 3H); $^{19}$F NMR (282 MHz, DMSO-d₆) δ −121.61, −121.76; MS (ES+): 543.2 & 545.3 (M+Na); MS (ES−): 555.3 & 557.1 (M+Cl).

Example 370

The IC₅₀ value of a compound (i.e., the concentration of the compound that inhibits 50% of the enzymatic activity)

was calculated according to the procedure reported in U.S. Pat. No. 6,653,340 B1, e.g., column 74 (incorporated by reference).

Specifically, the compounds were dissolved in a stock solution of DMSO at 10.0 or 100 mM. A portion of this stock solution was added to assay buffer in a final volume of 50 µL. Controls included buffer alone and enzyme solutions to which DMSO was added. Substrate was added to the reaction wells immediately or after incubation at room temperature. The reaction rates were measured spectrophotometrically by the generation of product at 405 nm for 200 sec. Background absorbance at 690 nm was measured and subtracted from the absorbance at 405 nm for each well.

The reaction rate for enzyme alone was compared to the rate of enzyme in the presence of inhibitor and the percent inhibition was calculated as shown below:

Percent Inhibition=[Rate without inhibitor−Rate with inhibitor)/(Rate without inhibitor)]×100

Factor D Esterolytic Assay:

An established esterolytic assay for the measurement of Factor D activity and inhibition of Factor D activity was used (Kam, C. M.; McRae, B. J.; Harper, J. W.; Niemann, M. A.; Volanakis, J. E.; Powers, J. C. Human complement proteins D, C2, and B Active site mapping with peptide thioester substrates. J Biol. Chem. 1987, 262, 3444-3451). For this assay Z-Lys-SBzl, 1.29 mM (Kim, S.; Narayana, S. V. L; Volanakis, J. E. Mutational analysis of the substrate binding site of human complement Factor D. Biochemistry. 1994, 33, 14393-14399) was used as the substrate for Factor D (104 mM). Hydrolysis of this compound by Factor D liberated a free sulfhydryl group which is then reacted with 5,5'-dithiobis(2nitrobenzoic acid) producing an intense yellow color (Habeeb, A. F. S. A. Reaction of protein sulfhydryl groups with Ellman's Reagent. Methods in Enzymol. 1976, 25, 457-464). The assays were performed in 96 well microtiter plates and rates of hydrolysis were monitored at 405 nm on a Biotek Synergy H1 plate reader. Hydrolysis rates were reported as change in mOD/min. The assay was conducted in 100 mM HEPES, 500 mM NaCl, pH 7.5 containing 10% DMSO in a final volume of 50 µL per well.

An $IC_{50}$, a compound concentration which inhibits 50% of the enzymatic activity, was calculated. Compounds in the examples were tested a minimum of three times. In the table below, three plus symbols (+++) are used to indicate compounds with an $IC_{50}$ value of less than 1 micromolar; two plus symbols (++) indicate compounds with an $IC_{50}$ value between 1 and 10 micromolar; and one plus symbol (+) indicates compounds with an $IC_{50}$ value greater than 10 micromolar.

TABLE 1

Measured Ki ($IC_{50}$) values for compounds.

| Compound | $IC_{50}$ |
|---|---|
| 2f | ++ |
| 3d | + |
| 4d | + |
| 5d | ++ |
| 6d | + |
| 7d | +++ |
| 8d | ++ |
| 9e | ++ |
| 10c | +++ |
| 11b | +++ |
| 12d | + |
| 13d | + |
| 14d | + |

TABLE 1-continued

Measured Ki ($IC_{50}$) values for compounds.

| Compound | $IC_{50}$ |
|---|---|
| 15d | + |
| 16d | ++ |
| 17a | +++ |
| 18d | + |
| 19d | +++ |
| 20d | + |
| 21d | + |
| 22d | + |
| 23b | + |
| 24b | ++ |
| 25a | +++ |
| 26d | ++ |
| 27d | ++ |
| 28c | +++ |
| 29b | ++ |
| 30b | ++ |
| 31d | ++ |
| 32b | + |
| 33b | +++ |
| 34d | + |
| 35d | +++ |
| 36b | +++ |
| 37b | +++ |
| 38b | +++ |
| 39f | + |
| 40b | ++ |
| 41b | +++ |
| 42b | +++ |
| 43g | + |
| 44f | ++ |
| 45f | ++ |
| 46b | + |
| 47d | + |
| 48b | +++ |
| 49b | +++ |
| 142f | + |
| 50d | + |
| 51b | ++ |
| 52b | + |
| 53b | +++ |
| 54b | ++ |
| 55a | ++ |
| 56d | ++ |
| 57d | + |
| 58b | +++ |
| 59d | +++ |
| 60a | ++ |
| 61b | +++ |
| 62b | +++ |
| 63a | ++ |
| 43f | + |
| 64b | +++ |
| 65a | ++ |
| 66d | + |
| 67a | + |
| 68a | ++ |
| 69d | +++ |
| 70b | +++ |
| 81b | +++ |
| 72b | +++ |
| 73b | +++ |
| 74b | ++ |
| 75b | + |
| 76b | ++ |
| 77b | ++ |
| 78a | + |
| 79a | +++ |
| 80b | +++ |
| 143e | + |
| 149f | + |
| 81b | +++ |
| 82e | + |
| 83d | + |
| 84e | + |
| 85b | ++ |
| 86d | + |

TABLE 1-continued

Measured Ki (IC$_{50}$) values for compounds.

| Compound | IC$_{50}$ |
|---|---|
| 87a | + |
| 88b | + |
| 89c | ++ |
| 90d | +++ |
| 91a | ++ |
| 92a | ++ |
| 93b | + |
| 94b | + |
| 95b | +++ |
| 96a | ++ |
| 97c | +++ |
| 98b | +++ |
| 99e | +++ |
| 100a | +++ |
| 101a | +++ |
| 102b | ++ |
| 103a | +++ |
| 104b | +++ |
| 105a | +++ |
| 106a | +++ |
| 107c | +++ |
| 108a | +++ |
| 109a | +++ |
| 110b | +++ |
| 111a | +++ |
| 112a | +++ |
| 113b | +++ |
| 114a | +++ |
| 115d | +++ |
| 116a | +++ |
| 117e | +++ |
| 118b | +++ |
| 119b | ++ |
| 120b | +++ |
| 121b | +++ |
| 122b | +++ |
| 123b | ++ |
| 189a | +++ |
| 190a | +++ |
| 124e | ++ |
| 125a | ++ |
| 126a | ++ |
| 127a | ++ |
| 128c | +++ |
| 129e | +++ |
| 130a | +++ |
| 131a | +++ |
| 132g | +++ |
| 133c | +++ |
| 134a | +++ |
| 135a | +++ |
| 136a | +++ |
| 137e | +++ |
| 138a | ++ |
| 139d | ++ |
| 140a | ++ |
| 141c | +++ |
| 144a | + |
| 145b | +++ |
| 146b | + |
| 147b | +++ |
| 148a | +++ |
| 150a | +++ |
| 151a | +++ |
| 152b | +++ |
| 154d | +++ |
| 155d | +++ |
| 156f | +++ |
| 157c | +++ |
| 153a | +++ |
| 151a | +++ |
| 160a | +++ |
| 161c | +++ |
| 129b | +++ |
| 129c | ++ |
| 164a | +++ |
| 162a | +++ |
| 163a | +++ |
| 165c | +++ |
| 166a | +++ |
| 167b | + |
| 214e | +++ |
| 168b | ++ |
| 169c | +++ |
| 170b | +++ |
| 171b | +++ |
| 172b | +++ |
| 158a | +++ |
| 173b | +++ |
| 174a | +++ |
| 175a | +++ |
| 176a | ++ |
| 177a | +++ |
| 178a | +++ |
| 179c | +++ |
| 180a | +++ |
| 181b | + |
| 182a | +++ |
| 183a | +++ |
| 184b | +++ |
| 185b | +++ |
| 186b | +++ |
| 187c | +++ |
| 200i | ++ |
| 191a | +++ |
| 192a | +++ |
| 193a | +++ |
| 194a | +++ |
| 195b | +++ |
| 196a | +++ |
| 197a | ++ |
| 201d | ++ |
| 202e | +++ |
| 203c | ++ |
| 204a | ++ |
| 205a | ++ |
| 229c | +++ |
| 206d | +++ |
| 207g | +++ |
| 209b | +++ |
| 210b | +++ |
| 211a | +++ |
| 212a | +++ |
| 213a | +++ |
| 215a | +++ |
| 217b | +++ |
| 218a | +++ |
| 219b | +++ |
| 208a | +++ |
| 220a | +++ |
| 221a | +++ |
| 216a | ++ |
| 222b | +++ |
| 223c | +++ |
| 224a | +++ |
| 225a | +++ |
| 226a | +++ |
| 227a | +++ |
| 230c | +++ |
| 231e | +++ |
| 232c | +++ |
| 233a | +++ |
| 234b | +++ |
| 235b | +++ |
| 236b | +++ |
| 237a | +++ |
| 238a | +++ |
| 161b | ++ |
| 198a | +++ |
| 228a | ++ |
| 231b | + |
| 199a | + |

TABLE 1-continued

Measured Ki (IC$_{50}$) values for compounds.

| Compound | IC$_{50}$ |
|---|---|
| 241a | +++ |
| 242a | +++ |
| 239b | +++ |
| 240f | +++ |
| 243f | +++ |
| 244c | +++ |
| 245a | +++ |
| 246a | +++ |
| 247a | +++ |
| 248a | +++ |
| 249a | +++ |
| 250a | +++ |
| 252a | + |
| 251a | +++ |
| 253a | +++ |
| 254d | +++ |
| 255b | +++ |
| 256a | +++ |
| 257a | +++ |
| 258a | +++ |
| 259a | +++ |
| 264b | ++ |
| 260a | +++ |
| 261a | +++ |
| 262a | +++ |
| 263a | +++ |
| 188a | +++ |
| 265a | +++ |
| 266a | +++ |
| 254a | +++ |
| 254b | + |
| 272a | +++ |
| 273a | +++ |
| 267c | +++ |
| 268c | +++ |
| 269a | +++ |
| 270a | +++ |
| 271a | +++ |
| 274a | +++ |
| 275a | +++ |
| 276a | +++ |
| 282e | +++ |
| 283a | +++ |
| 286a | +++ |
| 287a | +++ |
| 288a | +++ |
| 277a | +++ |
| 284i | +++ |
| 278a | +++ |
| 285a | ++ |
| 279a | +++ |
| 280b | +++ |
| 281c | +++ |
| 289a | ++ |
| 290a | +++ |
| 291h | +++ |
| 284g | + |
| 292d | +++ |
| 294a | +++ |
| 293a | +++ |
| 282d | +++ |
| 295e | +++ |
| 296f | +++ |
| 297a | + |
| 298b | +++ |
| 299a | +++ |
| 300a | +++ |
| 301h | +++ |
| 302d | +++ |
| 303a | +++ |
| 304a | +++ |
| 305a | +++ |
| 306a | ++ |
| 307a | +++ |
| 308e | +++ |
| 309a | +++ |
| 310a | +++ |
| 311a | +++ |
| 312a | +++ |
| 313a | +++ |
| 314i | +++ |
| 315a | +++ |
| 316f | +++ |
| 317a | +++ |
| 318b | +++ |
| 319a | +++ |
| 320a | +++ |
| 321a | +++ |
| 322b | +++ |
| 323a | +++ |
| 324b | +++ |
| 325b | +++ |
| 267d | +++ |
| 326b | ++ |
| 327a | +++ |
| 328f | +++ |
| 328g | +++ |
| 329f | +++ |
| 330b | +++ |
| 331b | +++ |
| 332c | ++ |
| 333a | +++ |
| 334a | +++ |
| 335b | +++ |
| 336e | +++ |
| 337d | +++ |
| 338c | +++ |
| 339d | ++ |
| 340c | +++ |
| 341a | +++ |
| 342d | +++ |
| 343b | +++ |
| 344e | +++ |
| 345e | +++ |
| 346d | +++ |
| 347b | +++ |
| 348b | +++ |
| 349d | +++ |
| 350c | +++ |
| 351b | +++ |
| 352b | +++ |
| 353b | +++ |
| 354b | +++ |
| 355f | +++ |
| 356c | +++ |
| 357a | +++ |
| 358f | ++ |
| 359f | + |
| 360d | ++ |
| 361h | +++ |
| 362a | +++ |
| 363d | +++ |
| 364b | ++ |
| 365b | +++ |
| 322a | +++ |
| 366f | +++ |
| 367g | ++ |
| 368a | +++ |
| 369f | ++ |

INCORPORATION BY REFERENCE

All of the U.S. patents, and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by Formula (I), or a pharmaceutically acceptable salt thereof:

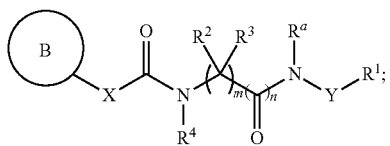

(I)

wherein, independently for each occurrence:
$R^1$ represents substituted aryl or heteroaryl;
$R^2$ and $R^3$ each independently represent H;
$R^4$ represents H or optionally substituted alkyl, cycloalkyl, (cycloalkyl)alkyl, heterocycloalkyl, (heterocycloalkyl)alkyl, aralkyl, heteroaralkyl, hydroxyalkyl, or haloalkyl;
X represents $CH_2$;
Y is absent or represents $CH_2$, $CR^{15}R^{16}$, or optionally substituted arylene;
$R^a$ represents H;
m is 1;
n is 0 or 1;
$R^{15}$ and $R^{16}$ are each independently selected from the group consisting of H alkyl, or hydroxyalkyl, wherein alkyl is optionally substituted with one or more substituents selected from the group consisting of —$OR^{17}$ and —$NR^{17}R^{18}$;
$R^{17}$ and $R^{18}$ are each independently selected from the group consisting of H and alkyl

represents

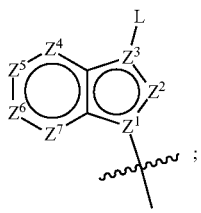

$Z^1$ represents N;
$Z^2$ represents CH;
$Z^3$ represents C;
$Z^4$ represents $CR^8$;
$Z^5$ represents $CR^5$;
$Z^6$ represents $CR^6$;
$Z^7$ represents $CR^9$;
$R^5$ and $R^6$ each independently represent H, halogen, —CN, —$NO_2$, —$OR^{13}$, —$NR^{13}R^{14}$, —$C(O)R^{13}$, —$C(O)OR^{13}$, —$C(O)NR^{13}R^{14}$, $NR^{13}C(O)R^{14}$, —$NR^{13}C(O)OR^{14}$, —$NR^{13}C(O)NR^{13}R^{14}$, —$NR^{13}S(O)_p(R^{14})$, or optionally substituted alkyl, alkynyl, heteroaryl, aryl, or heterocycloalkyl;
L represents —$C(O)R^7$;
$R^7$, independently for each occurrence, represents $NH_2$, $CH_3$, $CF_3$;
$R^8$ and $R^9$ each independently represent H, or —$C(O)NR^{13}R^{14}$;
$R^{13}$ and $R^{14}$, independently for each occurrence, represent H or optionally substituted alkyl, aryl, aralkyl, heteroaryl, heteroaralkyl, cycloalkyl, (cycloalkyl)alkyl, heterocycloalkyl, or (heterocycloalkyl)alkyl; or, when $R^{13}$ and $R^{14}$ are attached to the same atom, $R^{13}$ and $R^{14}$ taken together with the atom may form an optionally substituted heterocyclic ring; and
p is 0, 1, or 2.

2. The compound of claim 1, wherein n is 1.

3. The compound of claim 1, wherein $R^1$ represents aryl or heteroaryl, substituted by one or more substituents independently selected from the group consisting of halogen, —CN, alkoxy, haloalkoxy, haloalkyl, dialkylamino, heterocycloalkyl, aryl, and heteroaryl; or $R^1$ represents aryl or heteroaryl, substituted by one or more substituents, at least one of which is halogen.

4. The compound of claim 1, wherein Y is absent, Y is $CH_2$, or Y is $CR^{15}R^{16}$.

5. The compound of claim 4, wherein Y is $CR^{15}R^{16}$, and $R^{15}$ and $R^{16}$ are selected from the group consisting of H, alkyl, or hydroxyalkyl;
wherein alkyl is optionally substituted with $OR^{17}$, —$NR^{17}R^{18}$; and
further wherein $R^{17}$ and $R^{18}$ are each independently selected from the group consisting of H and alkyl.

6. The compound of claim 1, wherein $R^4$ represents H or optionally substituted alkyl, cycloalkyl, (cycloalkyl)alkyl, heterocycloalkyl, aralkyl, hydroxyalkyl, or haloalkyl.

7. The compound of claim 1, wherein $R^4$ represents H or optionally substituted alkyl or cycloalkyl.

8. The compound of claim 1, having the structure of Formula (Ib):

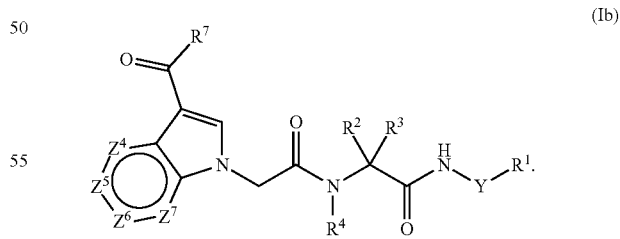

(Ib)

9. The compound of claim 8, wherein $Z^4$ and $Z^7$ each represent CH.

10. The compound of claim 8, wherein $Z^5$ represents $CR^5$; and $Z^6$ represents $CR^6$; and
$R^5$ and $R^6$ each independently represent H, halogen, —$NR^{13}R^{14}$, —$C(O)R^{13}$, —$C(O)OR^{13}$, —$C(O)NHR^{14}$, —$NHC(O)NR^{13}R^{14}$, —$NHS(O)_2(R^{14})$, or optionally substituted alkyl, alkynyl, heteroaryl, or aryl.

11. The compound of claim 10, wherein $R^5$ and $R^6$ each independently represent H or alkyl, alkynyl, heteroaryl, or aryl, optionally substituted with one or more substituents selected from the group consisting of aryl, heteroaryl, silyl, alkyl, amino, alkylamino, dialkylamino, —C(O)(alkyl), and halogen.

12. The compound of claim 10, wherein $R^{13}$ and $R^{14}$, independently for each occurrence, represent H or optionally substituted aryl, aralkyl, heteroaryl, heteroaralkyl, cycloalkyl, or (cycloalkyl)alkyl.

13. The compound of claim 1, wherein $R^7$ represents $NH_2$ or $CH_3$.

14. The compound of claim 1, wherein $R^7$ represents $CH_3$.

15. A pharmaceutical composition, comprising a compound of claim 1; and a pharmaceutically acceptable carrier.

16. The compound of claim 1, or a pharmaceutically acceptable salt thereof, selected from the following table:

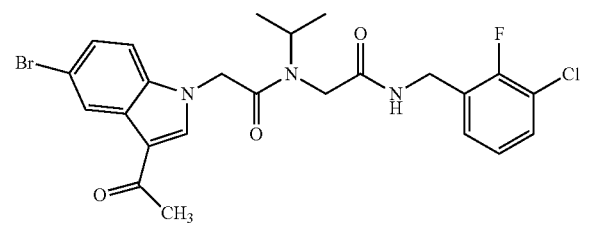

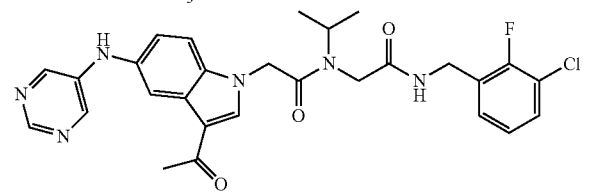

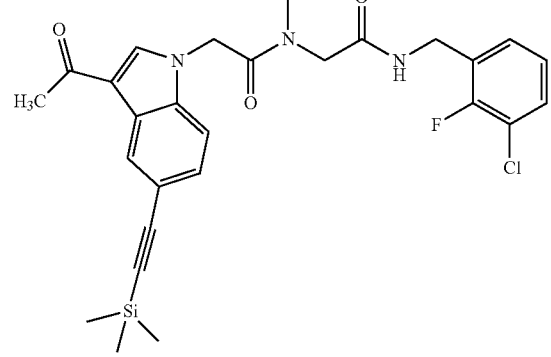

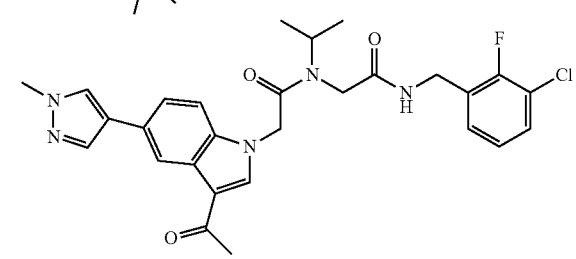

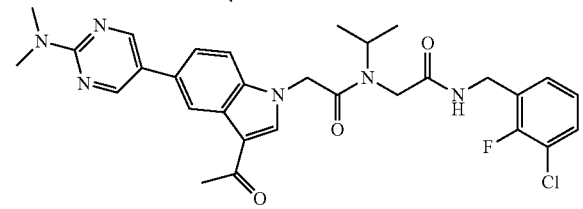

-continued

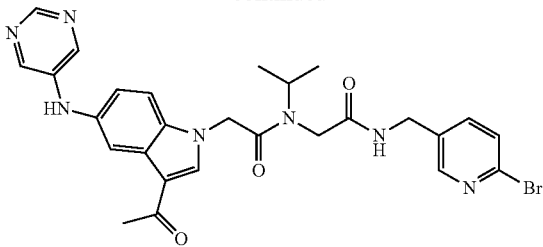

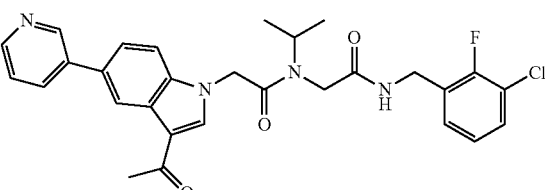

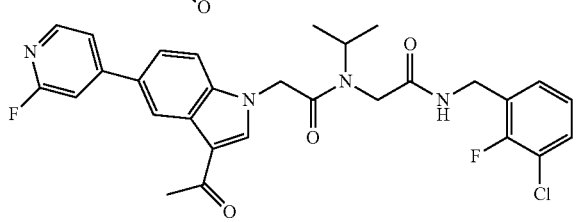

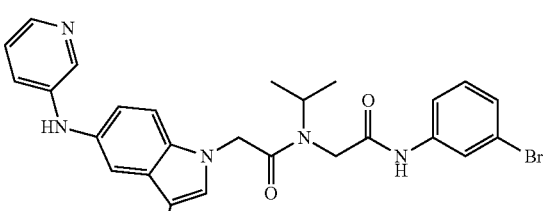

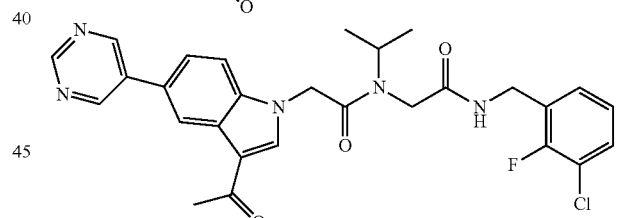

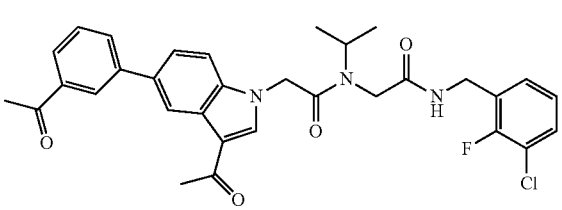

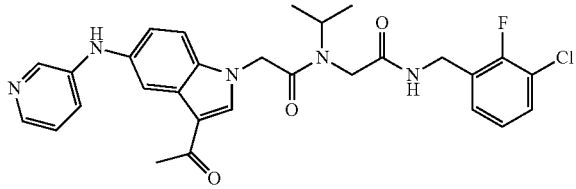

663
-continued
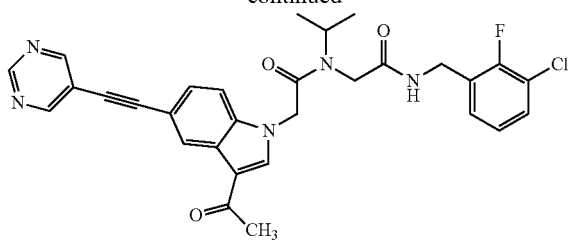
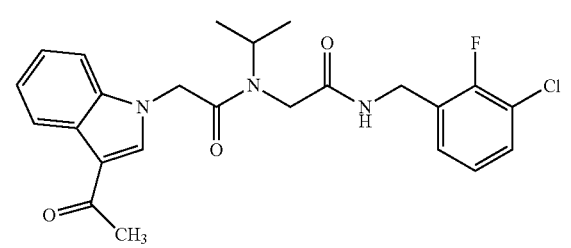
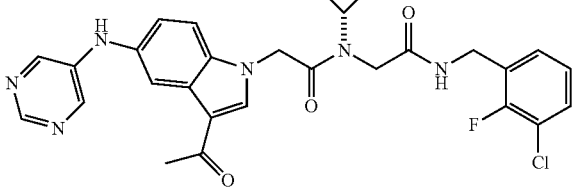
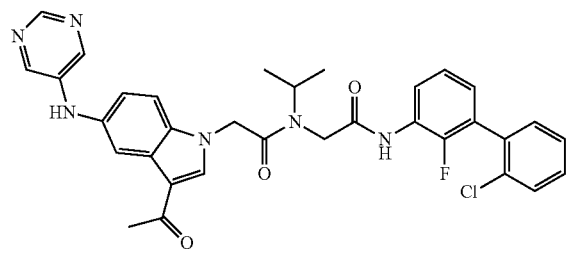
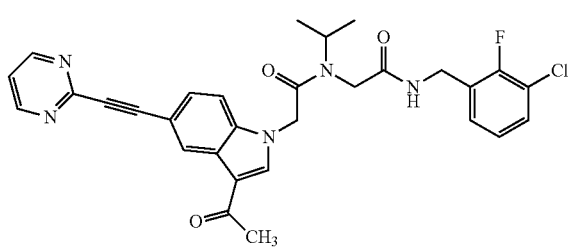
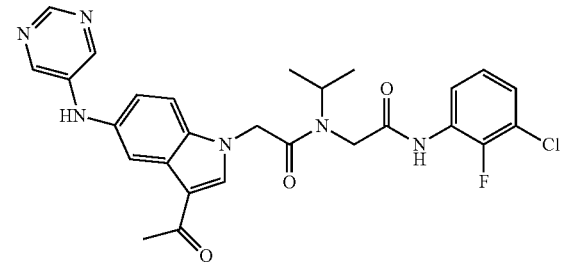
664
-continued
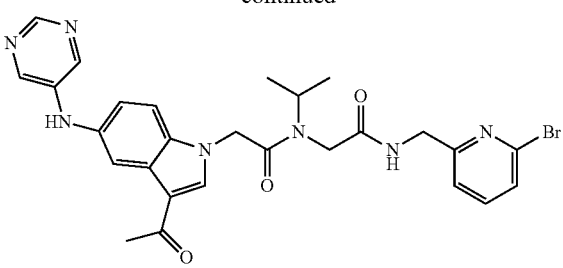
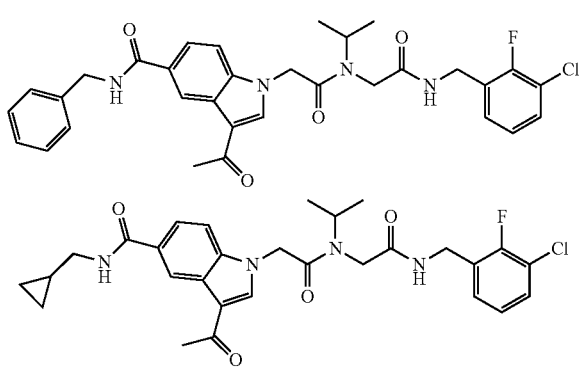
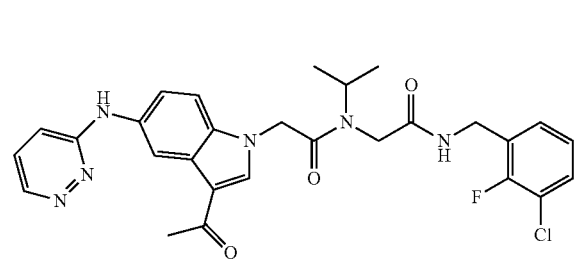
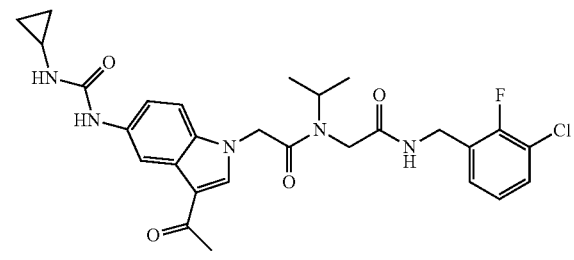
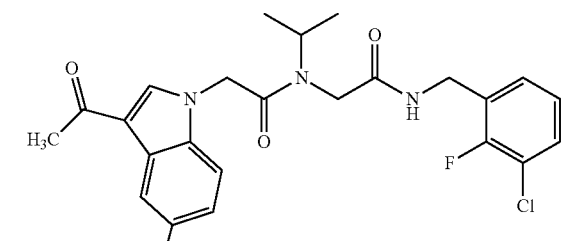
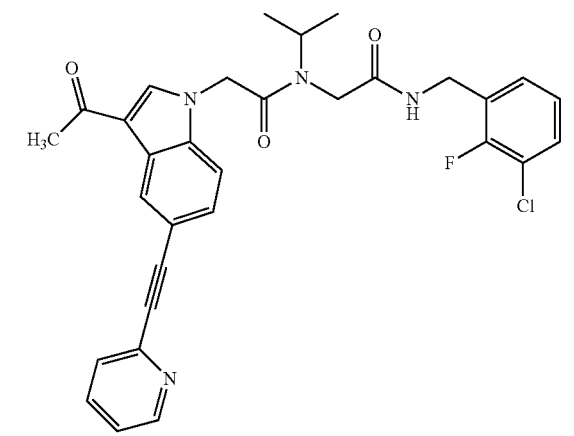

665 -continued
666 -continued
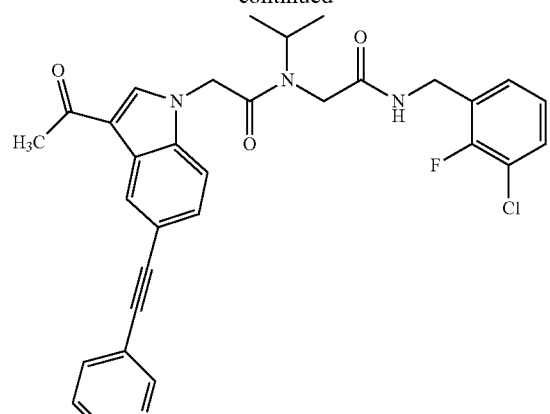
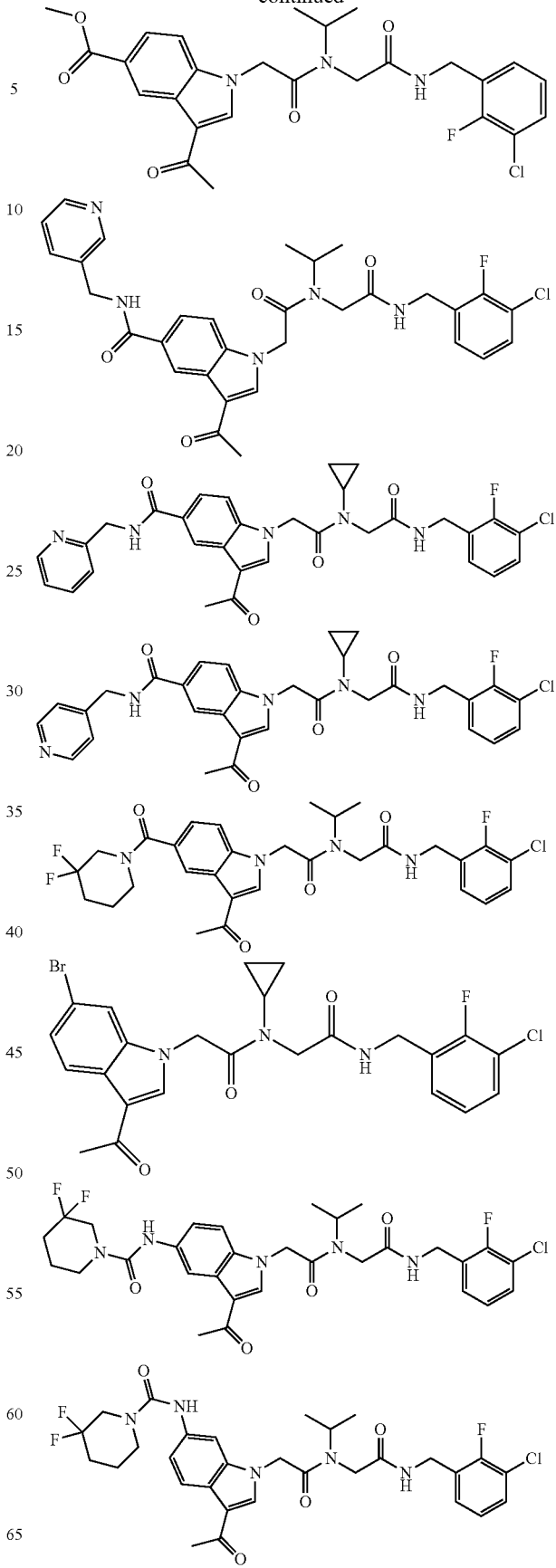

667
-continued
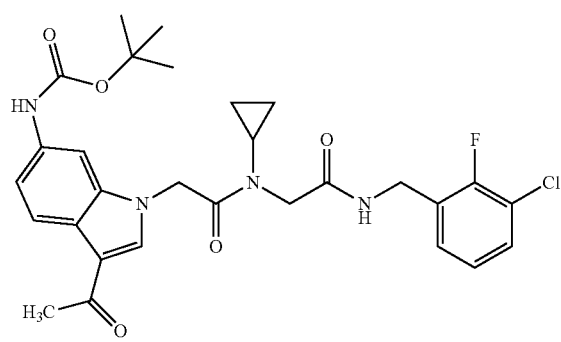
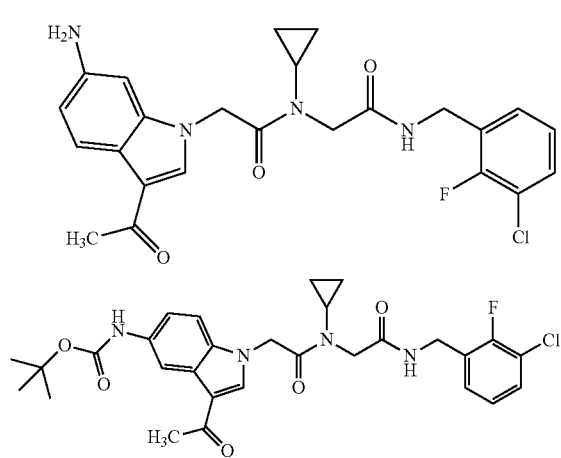
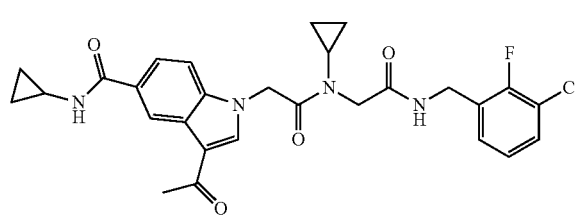
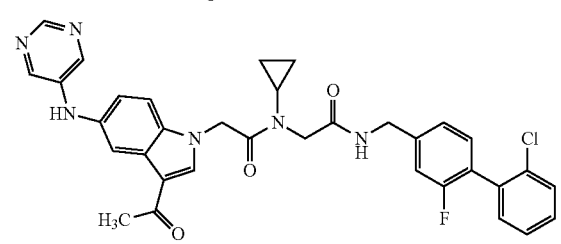
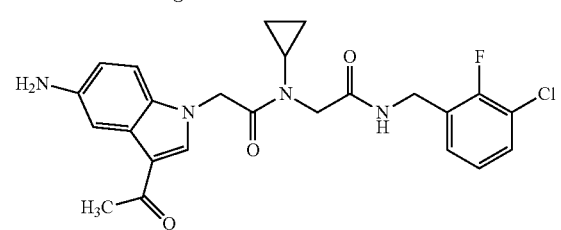
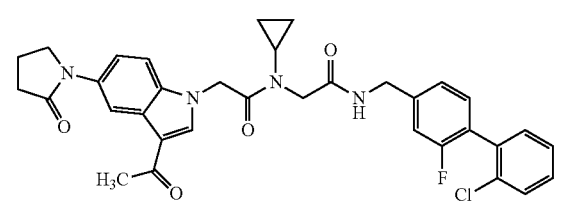
668
-continued
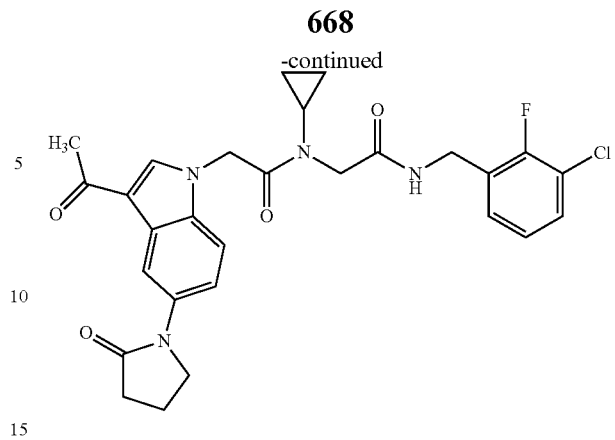
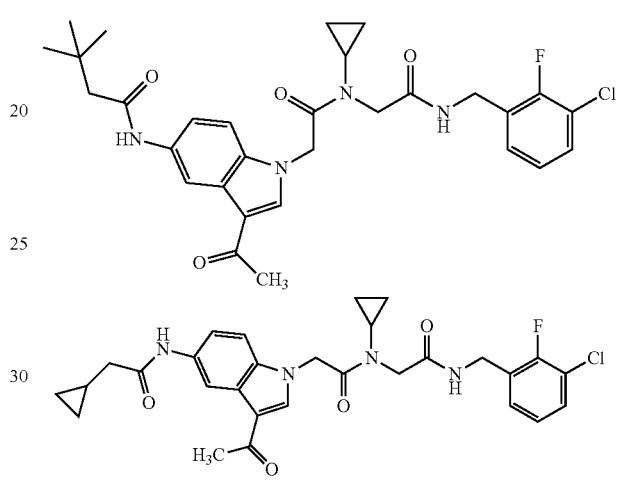
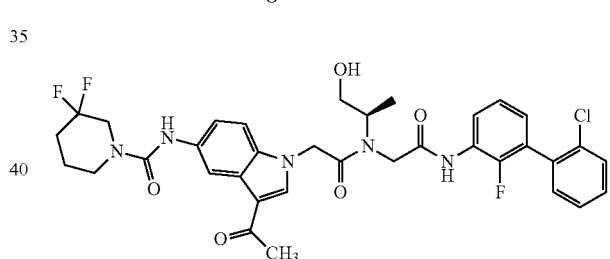
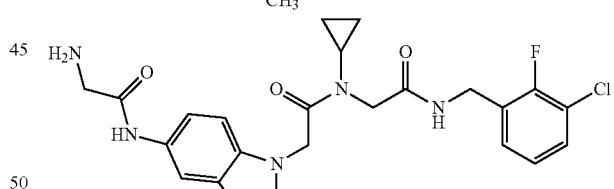
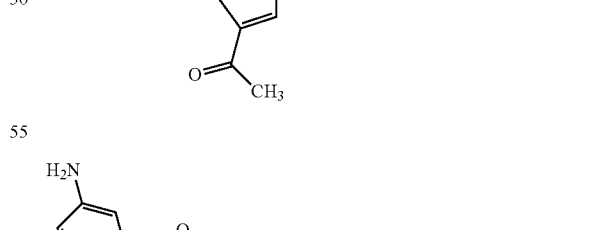
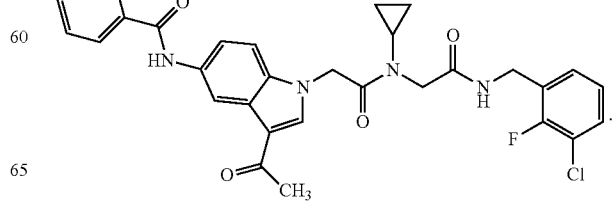

17. The compound of claim 1, wherein $R^4$ represents optionally substituted alkyl, cycloalkyl, or hydroxyalkyl.

18. The compound of claim 1, wherein Y is $CH_2$.

19. The compound of claim 1, wherein Y is optionally substituted arylene.

* * * * *